United States Patent
Czabaniuk et al.

(10) Patent No.: US 11,912,711 B2
(45) Date of Patent: Feb. 27, 2024

(54) HETEROCYCLIC COMPOUNDS AS TRIGGERING RECEPTOR EXPRESSED ON MYELOID CELLS 2 AGONISTS AND METHODS OF USE

(71) Applicants: AMGEN INC., Thousand Oaks, CA (US); Vigil Neuroscience, Inc., Cambridge, MA (US)

(72) Inventors: Lara C. Czabaniuk, Thousand Oaks, CA (US); Timothy Hopper, Thousand Oaks, CA (US); Jonathan B. Houze, Cambridge, MA (US); Jane Panteleev, Thousand Oaks, CA (US); Gwenaella Rescourio, Thousand Oaks, CA (US); Vincent Santora, Thousand Oaks, CA (US); Haoxuan Wang, Thousand Oaks, CA (US); Ryan D. White, Thousand Oaks, CA (US); Alice R. Wong, Thousand Oaks, CA (US); Yongwei Wu, Thousand Oaks, CA (US); Maxence Bos, Saint-Laurent (CA); John Mancuso, Saint-Laurent (CA); Ivan Franzoni, Saint-Laurent (CA)

(73) Assignees: AMGEN INC., Thousand Oaks, CA (US); VIGIL NEUROSCIENCE, INC., Cambridge, MA (US)

( * ) Notice: Subject to any disclaimer, the term of this patent is extended or adjusted under 35 U.S.C. 154(b) by 40 days.

(21) Appl. No.: 18/072,505

(22) Filed: Nov. 30, 2022

(65) Prior Publication Data
US 2023/0295170 A1    Sep. 21, 2023

Related U.S. Application Data

(63) Continuation of application No. 17/302,502, filed on May 4, 2021, now Pat. No. 11,608,344.

(60) Provisional application No. 63/019,772, filed on May 4, 2020.

(51) Int. Cl.
| | |
|---|---|
| *C07D 475/00* | (2006.01) |
| *A61P 25/28* | (2006.01) |
| *C07D 413/14* | (2006.01) |
| *C07D 471/04* | (2006.01) |
| *C07D 487/04* | (2006.01) |

(52) U.S. Cl.
CPC ............ *C07D 487/04* (2013.01); *A61P 25/28* (2018.01); *C07D 413/14* (2013.01); *C07D 471/04* (2013.01); *C07D 475/00* (2013.01)

(58) Field of Classification Search
CPC .......................... C07D 475/00; C07D 487/04
See application file for complete search history.

(56) References Cited

U.S. PATENT DOCUMENTS

| | | | |
|---|---|---|---|
| 2,940,972 A | 6/1960 | Roch | |
| 2,963,481 A | 12/1960 | Grannells et al. | |
| 5,620,978 A | 4/1997 | Cai et al. | |
| 7,582,366 B2 | 9/2009 | Hwang et al. | |
| 7,635,683 B2 | 12/2009 | Gai et al. | |
| 8,084,459 B2 | 12/2011 | Kok et al. | |
| 8,298,825 B1 | 10/2012 | Hochedlinger et al. | |
| 9,905,773 B2 | 2/2018 | Park et al. | |
| 10,403,826 B2 | 9/2019 | Dyatkin et al. | |
| 10,573,692 B2 | 2/2020 | Lim et al. | |
| 2005/0096327 A1 | 5/2005 | Caprathe et al. | |
| 2007/0225271 A1 | 9/2007 | Binggeli et al. | |
| 2009/0099174 A1 | 4/2009 | Smith et al. | |
| 2011/0124638 A1 | 5/2011 | Duggan et al. | |
| 2013/0012489 A1 | 1/2013 | Mederski et al. | |
| 2016/0272632 A1 | 9/2016 | Childers et al. | |
| 2019/0343838 A1 | 11/2019 | Allen et al. | |

(Continued)

FOREIGN PATENT DOCUMENTS

| | | |
|---|---|---|
| CN | 103374021 B | 10/2015 |
| CN | 102887895 B | 8/2016 |

(Continued)

OTHER PUBLICATIONS

"SID 378004572 Substance Record: 1265848-98-3," PubChem. Available Jan. 17, 2019: https://pubchem.ncbi.nlm.nih.gov/substance/378004572.

(Continued)

*Primary Examiner* — Alicia L Otton
(74) *Attorney, Agent, or Firm* — STERNE, KESSLER, GOLDSTEIN & FOX P.L.L.C.

(57) ABSTRACT

The present disclosure provides compounds of Formula I, useful for the activation of Triggering Receptor Expressed on Myeloid Cells 2 ("TREM2").

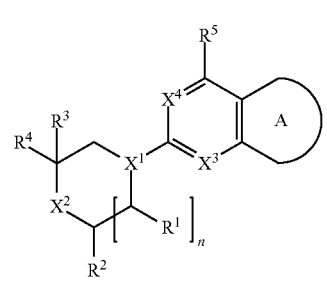

This disclosure also provides pharmaceutical compositions comprising the compounds, uses of the compounds, and compositions for treatment of, for example, a neurodegenerative disorder. Further, the disclosure provides intermediates useful in the synthesis of compounds of Formula I.

30 Claims, 3 Drawing Sheets

Specification includes a Sequence Listing.

(56) References Cited

U.S. PATENT DOCUMENTS

| | | | |
|---|---|---|---|
| 2020/0048207 | A1 | 2/2020 | Parham et al. |
| 2020/0075870 | A1 | 3/2020 | Boudreault et al. |
| 2020/0275661 | A1 | 9/2020 | Tamai et al. |
| 2021/0070792 | A1 | 3/2021 | Shih et al. |

FOREIGN PATENT DOCUMENTS

| | | |
|---|---|---|
| CN | 109265457 A | 1/2019 |
| CN | 110283171 A | 9/2019 |
| CN | 111454265 A | 7/2020 |
| CN | 108484680 B | 12/2020 |
| EP | 3229290 A1 | 10/2017 |
| IN | 2009MU01140 A | 11/2010 |
| JP | 2003005355 A | 1/2003 |
| KR | 2015080966 A | 7/2015 |
| KR | 2016060572 A | 5/2016 |
| KR | 2018107604 A | 10/2018 |
| KR | 2018116822 A | 10/2018 |
| WO | WO-1999021840 A1 | 5/1999 |
| WO | WO-2002058695 A1 | 8/2002 |
| WO | WO-2005007099 A2 | 1/2005 |
| WO | WO-2005039587 A1 | 5/2005 |
| WO | WO-2006039718 A2 | 4/2006 |
| WO | WO-2006128129 A2 | 11/2006 |
| WO | WO-2006128172 A2 | 11/2006 |
| WO | WO-2007038331 A2 | 4/2007 |
| WO | WO-2007103759 A2 | 9/2007 |
| WO | WO-2008003149 A2 | 1/2008 |
| WO | WO-2008130600 A2 | 10/2008 |
| WO | WO-2009100406 A2 | 8/2009 |
| WO | WO-2010033906 A2 | 3/2010 |
| WO | WO-2010042925 A2 | 4/2010 |
| WO | WO-2010107768 A1 | 9/2010 |
| WO | WO-2011014039 A1 | 2/2011 |
| WO | WO-2011037731 A1 | 3/2011 |
| WO | WO-2011119565 A1 | 9/2011 |
| WO | WO-2011156889 A1 | 12/2011 |
| WO | WO-2013117615 A1 | 8/2013 |
| WO | WO-2015017335 A1 | 2/2015 |
| WO | WO-2015086523 A1 | 6/2015 |
| WO | WO-2017025164 A1 | 2/2017 |
| WO | WO-2017031427 A1 | 2/2017 |
| WO | WO-2017181177 A1 | 10/2017 |
| WO | WO-2018066812 A1 | 4/2018 |
| WO | WO-2018067704 A1 | 4/2018 |
| WO | WO-2018108110 A1 | 6/2018 |
| WO | WO-2018169352 A1 | 9/2018 |
| WO | WO-2018183923 A1 | 10/2018 |
| WO | WO-2018195450 A1 | 10/2018 |
| WO | WO-2018204765 A1 | 11/2018 |
| WO | WO-2018227228 A1 | 12/2018 |
| WO | WO-2019079596 A1 | 4/2019 |
| WO | WO-2019079607 A1 | 4/2019 |
| WO | WO-2020231739 A2 | 11/2020 |
| WO | WO-2021226629 A1 | 11/2021 |

OTHER PUBLICATIONS

"SID 396338721 Substance Record," PubChem. Available Dec. 6, 2019: https://pubchem.ncbi.nlm.nih.gov/substance/396338721.
Bergner et al., "Microglia damage precedes major myelin breakdown in X-linked adrenoleukodystrophy and metachromatic leukodystrophy," Glia. Jun. 2019;67(6):1196-1209.
Bianchin et al., "Nasu-Hakola disease (polycystic lipomembranous osteodysplasia with sclerosing leukoencephalopathy—PLOSL): a dementia associated with bone cystic lesions. From clinical to genetic and molecular aspects," Cell Mol Neurobiol. Feb. 2004;24(1):1-24.
Bianchin et al., "Nasu-Hakola disease and primary microglial dysfunction," Nat Rev Neurol. Sep. 2010;6(9):2 p following 523.
Cantoni et al., "TREM2 regulates microglial cell activation in response to demyelination in vivo," Acta Neuropathol. Mar. 2015;129(3):429-47.
Colonna and Butovsky, "Microglia Function in the Central Nervous System During Health and Neurodegeneration" Annu Rev Immunol. Apr. 26, 2017;35:441-468.
Condello et al., "Microglia constitute a barrier that prevents neurotoxic protofibrillar A(beta)42 hotspots around plaques," Nat Commun. Jan. 29, 2015;6:6176.
Cserép et al., "Microglia monitor and protect neuronal function through specialized somatic purinergic junctions," Science. Jan. 31, 2020;367(6477):528-537.
Dardiotis et al., "A novel mutation in TREM2 gene causing Nasu-Hakola disease and review of the literature," Neurobiol Aging. May 2017;53:194.e13-194.e22.
Deming et al., "The MS4A gene cluster is a key modulator of soluble TREM2 and Alzheimer's disease risk," Sci Transl Med. Aug. 14, 2019;11(505):eaau2291.
Doens and Fernández, "Microglia receptors and their implications in the response to amyloid beta for Alzheimer's disease pathogenesis," J Neuroinflammation. Mar. 13, 2014;11:48.
Domingues et al., "Oligodendrocyte, Astrocyte, and Microglia Crosstalk in Myelin Development, Damage, and Repair," Front Cell Dev Biol. Jun. 28, 2016;4:71.
Ewers et al., "Increased soluble TREM2 in cerebrospinal fluid is associated with reduced cognitive and clinical decline in Alzheimer's disease," Sci Transl Med. Aug. 28, 2019;11(507):eaav6221.
Filipello et al., "The Microglial Innate Immune Receptor TREM2 Is Required for Synapse Elimination and Normal Brain Connectivity," Immunity. May 15, 2018;48(5):979-991.e8.
Golde et al., "Alzheimer's disease risk alleles in TREM2 illuminate innate immunity in Alzheimer's disease," Alzheimers Res Ther. May 21, 2013;5(3):24.
Gong et al., "Microglial dysfunction as a key pathological change in adrenomyeloneuropathy," Ann Neurol. Nov. 2017;82(5):813-27.
Guerreiro et al., "TREM2 variants in Alzheimer's disease," N Engl J Med. Jan. 10, 2013;368(2):117-27.
Guerreiro et al., "Using exome sequencing to reveal mutations in TREM2 presenting as a frontotemporal dementia-like syndrome without bone involvement," JAMA Neurol. Jan. 2013;70(1):78-84.
Guo et al., "TREM2 deficiency aggravates ?- synuclein-induced neurodegeneration and neuroinflammation in Parkinson's disease models," FASEB J. Nov. 2019;33(11):12164-12174.
Hickman and Khoury, "Analysis of the Microglial Sensome," Methods Mol Biol. 2019;2034:305-323.
Hickman et al., "Microglia in neurodegeneration," Nat Neurosci. Oct. 2018;21(10):1359-1369.
Hickman et al., "Microglia in neurodegeneration," Nat Neurosci. 2018;21(10):1359-1369.
Hickman et al., "The microglial sensome revealed by direct RNA sequencing," Nat Neurosci. Oct. 27, 2013;16(12):1896-1905.
Hollingworth et al., "Common variants at ABCA7, MS4A6A/MS4A4E, EPHA1, CD33 and CD2AP are associated with Alzheimer's disease," Nat Genet. May 2011;43(5):429-35.
Hong et al., "New insights on the role of microglia in synaptic pruning in health and disease," Curr Opin Neurobiol. Feb. 2016;36:128-34.
Hori et al., "Novel 4-phenoxy-2-(1-piperazinyl)quinazolines as potent anticonvulsive and antihypoxic agents," Chem Pharm Bull (Tokyo). Mar. 1990;38(3):681-7.
Huang and Pope, "The role of toll-like receptors in rheumatoid arthritis," Curr Rheumatol Rep. Oct. 2009;11(5):357-64.
Ikegami et al., "Microglia: Lifelong modulator of neural circuits," Neuropathology. Jun. 2019;39(3):173-180.
Jaitin et al., "Lipid-Associated Macrophages Control Metabolic Homeostasis in a Trem2-Dependent Manner," Cell. Jul. 2, 20195;178(3):686-698.e14.
Jay et al., "TREM2 deficiency eliminates TREM2+ inflammatory macrophages and ameliorates pathology in Alzheimer's disease mouse models," J Exp Med. Mar. 9, 2015;212(3):287-95.
Jay et al., "TREM2 in Neurodegenerative Diseases," Mol Neurodegener. Aug. 2, 2017;12(1):56.
Jonsson et al., "Variant of TREM2 associated with the risk of Alzheimer's disease," N Engl J Med. Jan. 10, 2013;368(2):107-16.

(56) References Cited

OTHER PUBLICATIONS

Kang et al., "Behavioral and transcriptomic analysis of Trem2-null mice: not all knockout mice are created equal," Hum Mol Genet. Jan. 15, 2018;27(2):211-223.
Keren-Shaul et al., "A Unique Microglia Type Associated with Restricting Development of Alzheimer's Disease," Cell. Jun. 15, 2017;169(7):1276-1290.e17.
Kim et al., "Deficient autophagy in microglia impairs synaptic pruning and causes social behavioral defects," Mol Psychiatry. Nov. 2017;22(11):1576-1584.
Kleinberger et al., "TREM2 mutations implicated in neurodegeneration impair cell surface transport and phagocytosis," Sci Transl Med. Jul. 2, 2014;6(243):243ra86.
Kobayashi et al., "TREM2/DAP12 Signal Elicits Proinflammatory Response in Microglia and Exacerbates Neuropathic Pain," J Neurosci. Oct. 26, 2016;36(43):11138-11150.
Kober and Brett, "TREM2-Ligand Interactions in Health and Disease," J Mol Biol. Jun. 2, 2017;429(11):1607-1629.
Konno et al., "CSF1R-related leukoencephalopathy: A major player in primary microgliopathies", Neurology, Dec. 11, 2018;91(24):1092-1104.
Lee et al., "Elevated TREM2 Gene Dosage Reprograms Microglia Responsivity and Ameliorates Pathological Phenotypes in Alzheimer's Disease Models," Neuron. Mar. 7, 2018;97(5):1032-1048.e5.
Leyns et al., "TREM2 function impedes tau seeding in neuritic plaques," Nat Neurosci. Aug. 2019;22(8):1217-1222.
Li and Barres, "Microglia and macrophages in brain homeostasis and disease," Nat Rev Immunol. Apr. 2018;18(4):225-242.
Liddelow et al., "Neurotoxic reactive astrocytes are induced by activated microglia," Nature. Jan. 26, 2017;541(7638):481-487.
Madry and Attwell, "Receptors, ion channels, and signaling mechanisms underlying microglial dynamics," J Biol Chem. May 15, 2015;290(20):12443-50.
Madry et al., "Nasu-Hakola disease (PLOSL): report of five cases and review of the literature," Clin Orthop Relat Res. Jan. 2007;454:262-9.
Oosterhof et al., "Colony-Stimulating Factor 1 Receptor (CSF1R) Regulates Microglia Density and Distribution, but Not Microglia Differentiation In Vivo," Cell Rep. Jul. 31, 2018;24(5):1203-1217.
Otero et al., "TREM2 and beta-catenin regulate bone homeostasis by controlling the rate of osteoclastogenesis," J Immunol. Mar. 15, 2012;188(6):2612-21.
Paloneva et al., "DAP12/TREM2 deficiency results in impaired osteoclast differentiation and osteoporotic features," J Exp Med. Aug. 18, 2003;198(4):669-75.
Paolicelli et al., "Synaptic pruning by microglia is necessary for normal brain development," Science. Sep. 9, 2011;333(6048):1456-8.
Parhizkar et al., "Loss of TREM2 function increases amyloid seeding but reduces plaque- associated ApoE," Nat Neurosci. Feb. 2019;22(2):191-204.
PCT International Search Report and Written Opinion from PCT/US2021/030719, dated Aug. 20, 2021.
PCT International Search Report and Written Opinion from PCT/US2021/070507 dated Jun. 30, 2021.
PCT International Search Report and Written Opinion from PCT/US2022/072095, dated Aug. 25, 2022.
Peng et al., "TREM2- and DAP12-dependent activation of PI3K requires DAP10 and is inhibited by SHIP1," Sci Signal. May 18, 2010;3(122):ra38.
Rademakers et al.,. "Mutations in the colony stimulating factor 1 receptor (CSF1R) gene cause hereditary diffuse leukoencephalopathy with spheroids," Nat Genet. 2012;44(2):200-5.
Schlepckow et al. "Enhancing Protective Microglial Activities With a Dual Function TREM2 Antibody to the Stalk Region," EMBO Mol Med. Apr. 7, 2020;12(4):e11227.
Sellgren et al., "Increased synapse elimination by microglia in schizophrenia patient-derived models of synaptic pruning," Nat Neurosci. Mar. 2019;22(3):374-385.
Shinozaki et al., "Transformation of Astrocytes to a Neuroprotective Phenotype by Microglia via P2Y1 Receptor Downregulation," Cell Rep. May 9, 2017;19(6):1151-1164.
Shirotani et al., "Aminophospholipids are signal-transducing TREM2 ligands on apoptotic cells," Sci Rep. May 17, 2019;9(1):7508.
Sims et al., "Rare coding variants in PLCG2, ABI3, and TREM2 implicate microglial-mediated innate immunity in Alzheimer's disease," Nat Genet. Sep. 2017;49(9):1373-1384.
Spangenberg et al., "Sustained microglial depletion with CSF1R inhibitor impairs parenchymal plaque development in an Alzheimer's disease model," Nat Commun. 2019;10:3758.
Suárez-Calvet et al., "Early increase of CSF sTREM2 in Alzheimer's disease is associated with tau related-neurodegeneration but not with amyloid-beta pathology," Mol Neurodegener. Jan. 10, 2019;14(1):1.
Tang et al., "Loss of mTOR-dependent macroautophagy causes autistic-like synaptic pruning deficits," Neuron. Sep. 3, 2014;83(5):1131-43.
U.S. Appl. No. 17/302,502, filed May 4, 2021.
U.S. Appl. No. 17/923,160, filed Nov. 3, 2022.
U.S. Appl. No. 18/072,497, filed Nov. 30, 2022.
U.S. Appl. No. 18/072,501, filed Nov. 30, 2022.
Ulland et al., "TREM2 Maintains Microglial Metabolic Fitness in Alzheimer's Disease," Cell. Aug. 10, 2017;170(4):649-663.e13.
Ulrich and Holtzman, "TREM2 Function in Alzheimer's Disease and Neurodegeneration," ACS Chem Neurosci. Apr. 20, 2016;7(4):420-7.
Ulrich et al., "Elucidating the Role of TREM2 in Alzheimer's Disease," Neuron. Apr. 19, 2017;94(2):237-248.
Wang et al., "TREM2 lipid sensing sustains the microglial response in an Alzheimer's disease model," Cell. Mar. 12, 2015;160(6):1061-71.
Wang et al., "Anti-human TREM2 induces microglia proliferation and reduces pathology in an Alzheimer's disease model", J Exp Med. Sep. 7, 2020;217(9):e20200785.
Weinhofer et al., "Impaired plasticity of macrophages in X-linked adrenoleukodystrophy," Brain. Aug. 1, 2018;141(8):2329-2342.
Wu et al., "TREM2 protects against cerebral ischemia/reperfusion injury," Mol Brain. Jun. 7, 2017;10(1):20.
Yeh et al., "TREM2 Binds to Apolipoproteins, Including APOE and CLU/APOJ, and Thereby Facilitates Uptake of Amyloid-Beta by Microglia," Neuron. Jul. 20, 2016;91(2):328-40.
Yuan et al., "TREM2 Haplodeficiency in Mice and Humans Impairs the Microglia Barrier Function Leading to Decreased Amyloid Compaction and Severe Axonal Dystrophy," Neuron. May 18, 2016,90(4):724-39.

SEQUENCE LISTING

```
Sequence total quantity: 10
SEQ ID NO: 1          moltype = AA  length = 5
FEATURE               Location/Qualifiers
source                1..5
                      mol_type = protein
                      note = anti-TREM2 antibody VH-CDR1
                      organism = synthetic construct
SEQUENCE: 1
SYWIG                                                                     5

SEQ ID NO: 2          moltype = AA  length = 17
FEATURE               Location/Qualifiers
source                1..17
                      mol_type = protein
                      note = anti-TREM2 antibody VH-CDR2
                      organism = synthetic construct
SEQUENCE: 2
```

```
IIYPGDADAR YSPSFQG                                                            17

SEQ ID NO: 3            moltype = AA  length = 12
FEATURE                 Location/Qualifiers
source                  1..12
                        mol_type = protein
                        note = anti-TREM2 antibody VH-CDR3
                        organism = synthetic construct
SEQUENCE: 3
RRQGIFGDAL DF                                                                 12

SEQ ID NO: 4            moltype = AA  length = 11
FEATURE                 Location/Qualifiers
source                  1..11
                        mol_type = protein
                        note = anti-TREM2 antibody VL-CDR1
                        organism = synthetic construct
SEQUENCE: 4
RASQSVSSNL A                                                                  11

SEQ ID NO: 5            moltype = AA  length = 7
FEATURE                 Location/Qualifiers
source                  1..7
                        mol_type = protein
                        note = anti-TREM2 antibody VL-CDR2
                        organism = synthetic construct
SEQUENCE: 5
GASTRAT                                                                        7

SEQ ID NO: 6            moltype = AA  length = 9
FEATURE                 Location/Qualifiers
source                  1..9
                        mol_type = protein
                        note = anti-TREM2 antibody VL-CDR3
                        organism = synthetic construct
SEQUENCE: 6
LQDNNFPPT                                                                      9

SEQ ID NO: 7            moltype = AA  length = 121
FEATURE                 Location/Qualifiers
source                  1..121
                        mol_type = protein
                        note = anti-TREM2 antibody VH Chain
                        organism = synthetic construct
SEQUENCE: 7
EVQLVQSGAE VKKPGESLKI SCKGSGYSFT SYWIGWVRQM PGKGLEWMGI IYPGDADARY    60
SPSFQGQVTI SADKSISTAY LQWSSLKASD TAMYFCARRR QGIFGDALDF WGQGTLVTVS   120
S                                                                            121

SEQ ID NO: 8            moltype = AA  length = 107
FEATURE                 Location/Qualifiers
source                  1..107
                        mol_type = protein
                        note = anti-TREM2 antibody VL Chain
                        organism = synthetic construct
SEQUENCE: 8
EIVMTQSPAT LSVSPGERAT LSCRASQSVS SNLAWFQQKP GQAPRLLIYG ASTRATGIPA    60
RFSGSGSGTE FTLTISSLQP EDFAVYYCLQ DNNFPPTFGQ GTKVDIK                  107

SEQ ID NO: 9            moltype = AA  length = 445
FEATURE                 Location/Qualifiers
source                  1..445
                        mol_type = protein
                        note = Ab-1 HC
                        organism = synthetic construct
SEQUENCE: 9
EVQLVQSGAE VKKPGESLKI SCKGSGYSFT SYWIGWVRQM PGKGLEWMGI IYPGDADARY    60
SPSFQGQVTI SADKSISTAY LQWSSLKASD TAMYFCARRR QGIFGDALDF WGQGTLVTVS   120
SAKTTPPSVY PLAPGSAAQT NSMVTLGCLV KGYFPEPVTV TWNSGSLSSG VHTFPAVLQS   180
DLYTLSSSVT VPSSTWPSET VTCNVAHPAS STKVDKKIVP RDCGCKPCIC TVPEVSSVFI   240
FPPKPKDVLT ITLTPKVTCV VVDISKDDPE VQFSWFVDDV EVHTAQTQPR EEQFGSTFRS   300
VSELPIMHQD WLNGKEFKCR VNSAAFPAPI EKTISKTKGR PKAPQVYTIP PKEQMAKDK    360
VSLTCMITDF FPEDITVEWQ WNGQPAENYK NTQPIMDTDG SYFVYSKLNV QKSNWEAGNT   420
FTCSVLHEGL HNHHTEKSLS HSPGK                                        445

SEQ ID NO: 10           moltype = AA  length = 214
FEATURE                 Location/Qualifiers
source                  1..214
                        mol_type = protein
```

```
                note = Ab-1 LC
                organism = synthetic construct
SEQUENCE: 10
EIVMTQSPAT LSVSPGERAT LSCRASQSVS SNLAWFQQKP GQAPRLLIYG ASTRATGIPA    60
RFSGSGSGTE FTLTISSLQP EDFAVYYCLQ DNNFPPTFGQ GTKVDIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214
```

HETEROCYCLIC COMPOUNDS AS TRIGGERING RECEPTOR EXPRESSED ON MYELOID CELLS 2 AGONISTS AND METHODS OF USE

CROSS REFERENCE TO RELATED APPLICATION

This application is a continuation application of U.S. patent application Ser. No. 17/302,502, filed May 4, 2021, which claims the benefit under 35 U.S.C. § 119(e) to U.S. Provisional Application No. 63/019,772, filed May 4, 2020, the entirety of each of which is incorporated herein by reference.

SUBMISSION OF SEQUENCE LISTING ON ASCII TEXT FILE

The instant application contains a Sequence Listing which has been submitted electronically in ASCII format and is hereby incorporated by reference in its entirety. Said ASCII copy, created on Apr. 24, 2023, is named 5258_0060004_SequenceListing_ST26 and is 12,511 bytes in size.

FIELD

The present disclosure provides compounds useful for the activation of Triggering Receptor Expressed on Myeloid Cells 2 ("TREM2"). This disclosure also provides pharmaceutical compositions comprising the compounds, uses of the compounds, and compositions for treatment of, for example, a neurodegenerative disorder. Further, the disclosure provides intermediates useful in the synthesis of compounds of Formula I.

BACKGROUND

Microglia are resident innate immune cells in the brain and are important for the maintenance of homeostatic conditions in the central nervous system. Hickman et al. 2018, Li and Barres 2018. These resident macrophages express a variety of receptors that allow them to sense changes in their microenvironment and alter their phenotypes to mediate responses to invading pathogens, proteotoxic stress, cellular injury, and other infarcts that can occur in health and disease. Id. Microglia reside in the parenchyma of the brain and spinal cord where they interact with neuronal cell bodies (Cserep et al. 2019), neuronal processes (Paolicelli et al. 2011, Ikegami et al. 2019) in addition to other types of glial cells (Domingues et al. 2016, Liddelow et al. 2017, Shinozaki et al. 2017), playing roles in a multitude of physiological processes. With the ability to rapidly proliferate in response to stimuli, microglia characteristically exhibit myeloid cell functions such as phagocytosis, cytokine/chemokine release, antigen presentation, and migration. Colonna and Butovsky 2017. More specialized functions of microglia include the ability to prune synapses from neurons and directly communicate with their highly arborized cellular processes that survey the area surrounding the neuronal cell bodies. Hong et al. 2016, Sellgren et al. 2019.

The plasticity of microglia and their diverse states as described through single-cells RNASeq profiling are thought to arise through the integration of signaling from a diverse array of cell surface receptors. Hickman et al. 2013. Collectively known as the microglial "sensome," these receptors are responsible for transducing activating or activation-suppressing intracellular signaling and include protein families such as Sialic acid-binding immunoglobulin-type lectins ("SIGLEC"), Toll-like receptors ("TLR"), Fc receptors, nucleotide-binding oligomerization domain ("NOD") and purinergic G protein-coupled receptors. Doens and Fernandez 2014, Madry and Attwell 2015, Hickman and El Khoury 2019. Similar to other cells of the myeloid lineage, the composition of microglial sensomes is dynamically regulated and acts to recognize molecular pattern that direct phenotypic responses to homeostatic changes in the central nervous system ("CNS"). Id. One of the receptors selectively expressed by brain microglia is TREM2, composed of a single-pass transmembrane domain, an extracellular stalk region, and extracellular immunoglobulin variable ("IgV")-like domain responsible for ligand interaction. Kleinberger et al. 2014. As TREM2 does not possess intracellular signal transduction-mediating domains, biochemical analysis has illustrated that interaction with adaptor proteins DAP10 and DAP12 mediate downstream signal transduction following ligand recognition. Peng et al. 2010, Jay et al. 2017. TREM2/DAP12 complexes in particular act as a signaling unit that can be characterized as pro-activation on microglial phenotypes in addition to peripheral macrophages and osteoclasts. Otero et al. 2012, Kobayashi et al. 2016, Jaitin et al. 2019. In the CNS, signaling through TREM2 has been studied in the context of ligands such as phospholipids, cellular debris, apolipoproteins, and myelin. Wang et al. 2015, Kober and Brett 2017, Shirotani et al. 2019). In mice lacking functional TREM2 expression or expressing a mutated form of the receptor, a core observation is blunted microglial responses to insults such as oligodendrocyte demyelination, stroke-induced tissue damage in the brain, and proteotoxic inclusions in vivo. Cantoni et al. 2015, Wu et al. 2017.

Coding variants in the TREM2 locus has been associated with late onset Alzheimer's disease ("LOAD") in human genome-wide association studies, linking a loss-of-receptor function to a gain in disease risk. Jonsson et al. 2013, Sims et al. 2017. Genetic variation of other genes selectively expressed by microglia in the CNS, for example, CD33, PLCg2 and MS4A4A/6A have reached genome-wide significance for their association with LOAD risk. Hollingworth et al. 2011, Sims et al. 2017, Deming et al. 2019. Together, these genetic findings link together in a putative biochemical circuit that highlights the importance of microglial innate immune function in LOAD. Additionally, increase or elevation in the soluble form of TREM2 ("sTREM2") in the cerebrospinal fluid (CSF) of human subjects is associated with disease progression and emergence of pathological hallmarks of LOAD including phosphorylated Tau. Suarez-Calvet et al. 2019. Furthermore, natural history and human biology studies indicate that baseline sTREM2 levels in the CSF can stratify the rate of temporal lobe volume loss and episodic memory decline in longitudinally monitored cohorts. Ewers et al. 2019.

In addition to human genetic evidence supporting a role of TREM2 in LOAD, homozygous loss-of-function mutations in TREM2 are causal for an early onset dementia syndrome known as Polycystic lipomembranous osteodysplasia with sclerosing leukoencephalopathy ("PLOSL") or Nasu-Hakola disease ("NHD"). Golde et al. 2013, Dardiotis et al. 2017. This progressive neurodegenerative disease typically manifests in the $3^{rd}$ decade of life and is pathologically characterized by loss of myelin in the brain concomitant with gliosis, unresolved neuroinflammation, and cerebral atrophy. Typical neuropsychiatric presentations are often preceded by osseous abnormalities, such as bone cysts and loss of peripheral bone density. Bianchin et al. 2004, Madry et al. 2007, Bianchin et al. 2010). Given that osteoclasts of the myeloid lineage are also known to express TREM2, the PLOSL-related symptoms of wrist and ankle pain, swelling, and fractures indicate that TREM2 may act to regulate bone homeostasis through defined signaling pathways that parallel the microglia in the CNS. Paloneva et al. 2003, Otero et al. 2012. The link between TREM2 function and PLOSL has illustrated the importance of the receptor in sustaining key physiological aspects of myeloid cell function in the human body.

Efforts have been made to model the biology of TREM2 in mice prompting the creation of TREM2 knock out ("KO") mice in addition to the LOAD-relevant TREM2 R47H loss-of-function mutant transgenic mice. Ulland et al. 2017, Kang et al. 2018. Although unable to recapitulate the neurological manifestations of PLOSL, TREM2 KO mice show abnormalities in bone ultrastructure. Otero et al. 2012. When the TREM2 KO or mutant mice have been crossed onto familial Alzheimer's disease transgenic mouse background such as the 5XFAD amyloidogenic mutation lines, marked phenotypes have been observed. Ulrich et al. 2017. These in vivo phenotypes of TREM2 loss-of-function in the CNS include elevated the plaque burden and lower levels of secreted microglial factors SPP1 and Osteopontin that are characteristic of the microglial response to amyloid pathology. Ulland, et al. 2017. Other rodent studies have demonstrated that loss of TREM2 leads to decreased microglial clustering around plaques and emergence of less compact plaque morphology in familial AD amyloid models. Parhizkar et al. 2019. With regards to the Tau protein pathology that is observed in LOAD, familial tauopathy models in mice demonstrated an enhanced spreading of pathological human Tau aggregates from point of injection into mouse brain in TREM2 KO mice. Leyns et al. 2019. Furthermore, single-cell RNASeq studies with the TREM2 KO mice in aged scenarios, 5XFAD familial Alzheimer's disease model mice, and Amyotrophic Lateral Sclerosis SOD1 mutant mouse backgrounds indicate that TREM2 receptor function is critical for a conserved set of phenotypic transformations within microglial populations in response to CNS pathology. Keren-Shaul et al. 2017.

In rodent models where TREM2 expression levels are elevated, brain amyloid pathology in the 5XFAD transgenic mice displayed reduced plaque volume and altered morphology. Lee et al. 2018). The changes in immunohistological markers relating to brain amyloid pathology were also accompanied by an attenuated presence of dystrophic neurites when TREM2 was overexpressed. Id. Therefore, the pharmacological activation of TREM2 is a target of interest for treating or preventing neurological, neurodegenerative and other diseases. Despite many attempts to alter disease progression by targeting the pathological hallmarks of LOAD through anti-amyloid and anti-Tau therapeutics, there is a need for activators of TREM2 to address the genetics-implicated neuroimmune aspects of, for example, LOAD. Such TREM2 activators may be suitable for use as therapeutic agents and remain in view of the significant continuing societal burden that remains unmitigated for diseases, such as Alzheimer's disease.

SUMMARY

First, provided herein is a compound of Formula I

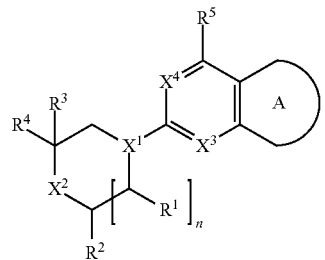

or a tautomer thereof, or a pharmaceutically acceptable salt of said compound or said tautomer, wherein Ring A together with the 6-membered ring system to which it is fused forms a bicyclic ring system of formula

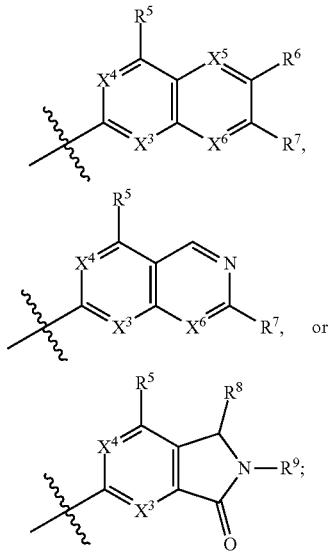

wherein
$X^1$ is CH or N;
$X^2$ is $CH_2$, CHF, $CF_2$, O, or NH;
$X^3$ is CH or N;
$X^4$ is CH or N;
$X^5$ is CH or N;
$X^6$ is CH or N;
$R^1$ is H or $C_{1-3}$alkyl;
$R^2$ is H or $C_{1-3}$alkyl;
$R^3$ is H or $C_{1-3}$alkyl;
$R^4$ is $C_{1-6}$alkyl, $C_{1-6}$haloalkyl, $diC_{1-3}$alkylamino, —C(=O)O($C_{1-6}$alkyl), $C_{3-6}$cycloalkyl, $C_{3-6}$heterocycloalkyl, phenyl, 5-membered heteroaryl, or 6-membered heteroaryl; wherein (1) the $C_{3-6}$cycloalkyl or the $C_{3-6}$heterocycloalkyl is optionally substituted with C=O;

(2) the phenyl, 5-membered heteroaryl, or 6-membered heteroaryl group is optionally substituted with 1 to 3 substituents independently selected from halogen, $C_{1-6}$alkyl, $C_{1-6}$haloalkyl, $C_{1-6}$alkoxy, $C_{1-6}$haloalkoxy, —($C_{1-3}$alkyl)O($C_{1-3}$alkyl), —CN, $C_{2-4}$alkenyl, $C_{3-6}$cycloalkyl, and $C_{3-6}$heterocycloalkyl; wherein the $C_{1-6}$alkyl and $C_{1-6}$haloalkyl of subsection (2) are optionally substituted with OH; and wherein the $C_{3-6}$heterocycloalkyl of subsection (2) is optionally substituted with 1 to 3 substituents selected from halogen, $C_{1-3}$alkyl, and —C(=O)O($C_{1-6}$alkyl);

$R^5$ is $C_{1-6}$alkyl, $C_{1-6}$haloalkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-($C_{3-6}$cycloalkyl), wherein the $C_{1-6}$alkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH$_2$-($C_{3-6}$cycloalkyl) is further substituted with 1 to 4 substituents independently selected from halogen, $C_{1-3}$alkyl, $C_{1-3}$haloalkyl, $C_{1-3}$alkoxy, and $C_{1-3}$haloalkoxy;

$R^6$ is H, halogen, or $C_{1-3}$alkyl;

$R^7$ is H, halogen, or $C_{1-3}$alkyl;

$R^8$ is H or $C_{1-3}$alkyl;

$R^9$ is H or $C_{1-5}$alkyl; and n is 0 or 1; provided that when $X^1$ is N and n is 0, $X^2$ is not NH or O.

Second, provided herein is a pharmaceutical composition comprising a compound of Formula I, or a tautomer thereof, or a pharmaceutically acceptable salt of said compound or said tautomer, and a pharmaceutically acceptable excipient.

Third, provided herein is a compound of Formula I, or a tautomer thereof, or a pharmaceutically acceptable salt of said compound or said tautomer, or a pharmaceutical composition as described hereinabove, for use in treating or preventing a condition associated with a loss of function of human TREM2.

Fourth, provided herein is a compound of Formula I, or a tautomer thereof, or a pharmaceutically acceptable salt of said compound or said tautomer, or a pharmaceutical composition described hereinabove, for use in treating or preventing Parkinson's disease, rheumatoid arthritis, Alzheimer's disease, Nasu-Hakola disease, frontotemporal dementia, multiple sclerosis, prion disease, or stroke.

BRIEF DESCRIPTION OF THE DRAWINGS

The drawings show embodiments of the disclosed subject matter for the purpose of illustrating the invention. However, it should be understood that the present application is not limited to the precise arrangements and embodiments shown in the drawings.

Figure 1:
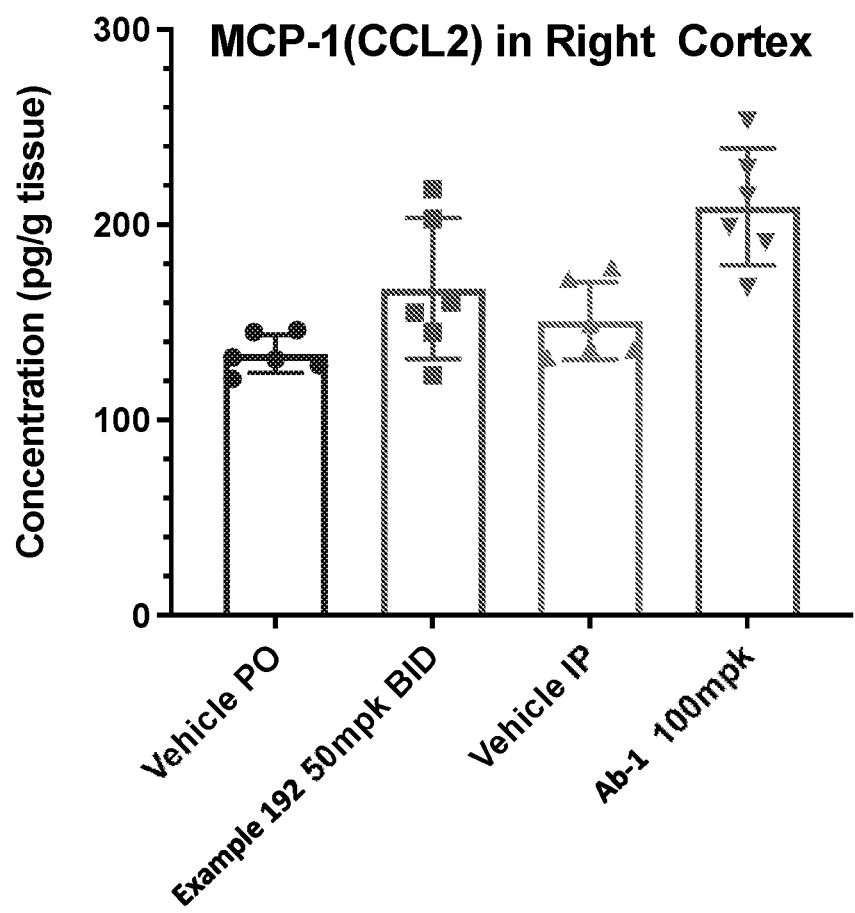
FIG. 1 is a graph showing the measured concentration of MCP-1 (CCL2) in the right cortex of mice 24 hours after administration of the compound of Example 192 or Antibody 13E7, as compared to controls. Error bars are shown as standard error of the mean (SEM).

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as Embodiment 1 is a compound of Formula I

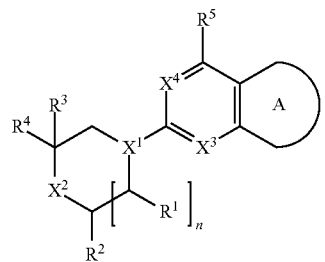

or a tautomer thereof, or a pharmaceutically acceptable salt of said compound or said tautomer, wherein Ring A together with the 6-membered ring system to which it is fused forms a bicyclic ring system of formula

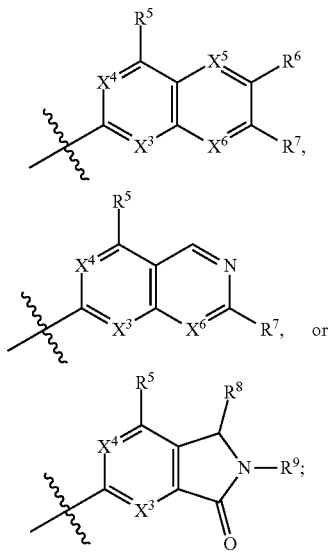

wherein $X^1$ is CH or N;

$X^2$ is CH$_2$, CHF, CF$_2$, O, or NH;

$X^3$ is CH or N;

$X^4$ is CH or N;

$X^5$ is CH or N;

$X^6$ is CH or N;

$R^1$ is H or $C_{1-3}$alkyl;

$R^2$ is H or $C_{1-3}$alkyl;

$R^3$ is H or $C_{1-3}$alkyl;

R⁴ is $C_{1-6}$alkyl, $C_{1-6}$haloalkyl, di$C_{1-3}$alkylamino, —C(=O)O($C_{1-6}$alkyl), $C_{3-6}$cycloalkyl, $C_{3-6}$heterocycloalkyl, phenyl, 5-membered heteroaryl, or 6-membered heteroaryl; wherein (1) the $C_{3-6}$cycloalkyl or the $C_{3-6}$heterocycloalkyl is optionally substituted with C=O;

(2) the phenyl, 5-membered heteroaryl, or 6-membered heteroaryl group is optionally substituted with 1 to 3 substituents independently selected from halogen, $C_{1-6}$alkyl, $C_{1-6}$haloalkyl, $C_{1-6}$alkoxy, $C_{1-6}$haloalkoxy, —($C_{1-3}$alkyl)O($C_{1-3}$alkyl), —CN, $C_{2-4}$alkenyl, $C_{3-6}$cycloalkyl, and $C_{3-6}$heterocycloalkyl; wherein the $C_{1-6}$alkyl and $C_{1-6}$haloalkyl of subsection (2) are optionally substituted with OH; and wherein the $C_{3-6}$heterocycloalkyl of subsection (2) is optionally substituted with 1 to 3 substituents selected from halogen, $C_{1-3}$alkyl, and —C(=O)O($C_{1-6}$alkyl);

R⁵ is $C_{1-6}$alkyl, $C_{1-6}$haloalkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-($C_{3-6}$cycloalkyl), wherein the $C_{1-6}$alkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH₂-($C_{3-6}$cycloalkyl) is further substituted with 1 to 4 substituents independently selected from halogen, $C_{1-3}$alkyl, $C_{1-3}$haloalkyl, $C_{1-3}$alkoxy, and $C_{1-3}$haloalkoxy;

R⁶ is H, halogen, or $C_{1-3}$alkyl;

R⁷ is H, halogen, or $C_{1-3}$alkyl;

R⁸ is H or $C_{1-3}$alkyl;

R⁹ is H or $C_{1-5}$alkyl; and n is 0 or 1; provided that when X¹ is N and n is 0, X² is not NH or O.

Provided herein as Embodiment 2 is the compound according to Embodiment 1, or a tautomer thereof, or a pharmaceutically acceptable salt of said compound or said tautomer, wherein the compound is not 4-(3-fluoro-1-azetidinyl)-6,7-dimethyl-2-((2S)-2-(1-methyl-1H-pyrazol-4-yl)-4-morpholinyl)pteridine;

4-(3,3-difluoro-1-piperidinyl)-6,7-dimethyl-2-((2S)-2-(1-methyl-1H-pyrazol-4-yl)-4-morpholinyl)pteridine;

2-((2S)-2-(1-cyclopropyl-1H-pyrazol-4-yl)-4-morpholinyl)-7-methyl-4-(3-(trifluoromethyl)bicyclo[1.1.1]pentan-1-yl)pyrido[2,3-d]pyrimidine;

6,7-dimethyl-2-((2S)-2-(1-methyl-1H-pyrazol-4-yl)-4-morpholinyl)-4-((cis-3-(trifluoromethyl)cyclobutyl)methoxy)pyrido[2,3-d]pyrimidine; or 2-methyl-6-((2S)-2-(1-methyl-1H-pyrazol-4-yl)-4-morpholinyl)-4-(cis-3-(trifluoromethyl)cyclobutyl)-2,3-dihydro-1H-pyrrolo[3,4-c]pyridin-1one.

Provided herein as Embodiment 3 is the compound according to Embodiment 1 or Embodiment 2, or a tautomer thereof, or a pharmaceutically acceptable salt of said compound or said tautomer, wherein the compound is a compound of Formula II

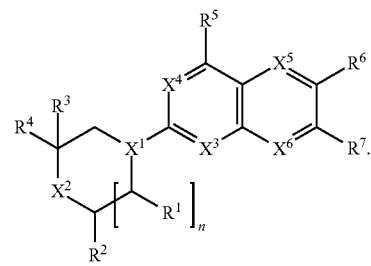

II

Provided herein as Embodiment 4 is the compound according to Embodiment 1 or Embodiment 2, or a tautomer thereof, or a pharmaceutically acceptable salt of said compound or said tautomer, wherein the compound is a compound of Formula IIA

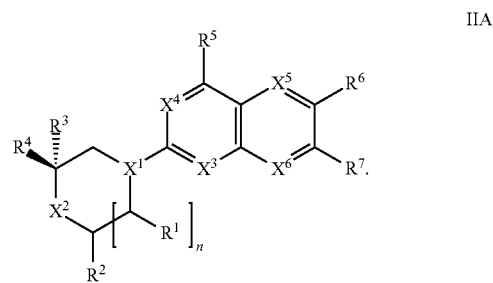

IIA

Provided herein as Embodiment 5 is the compound according to Embodiment 1 or Embodiment 2, or a tautomer thereof, or a pharmaceutically acceptable salt of said compound or said tautomer, wherein the compound is a compound of Formula IIB

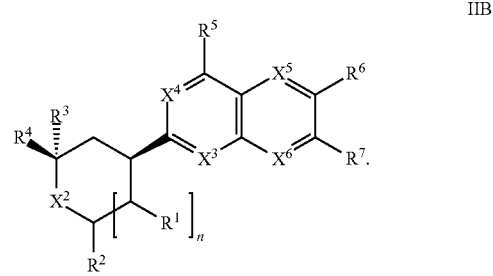

IIB

Provided herein as Embodiment 6 is the compound according to Embodiment 1 or Embodiment 2, or a tautomer thereof, or a pharmaceutically acceptable salt of said compound or said tautomer, wherein the compound is a compound of Formula IIC

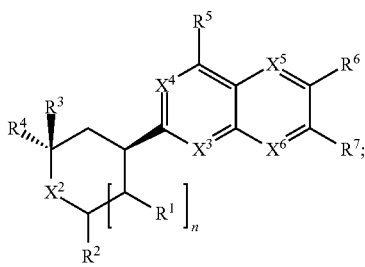

IIC

Provided herein as Embodiment 7 is the compound according to Embodiment 1 or Embodiment 2, or a tautomer thereof, or a pharmaceutically acceptable salt of said compound or said tautomer, wherein the compound is a compound of Formula IID

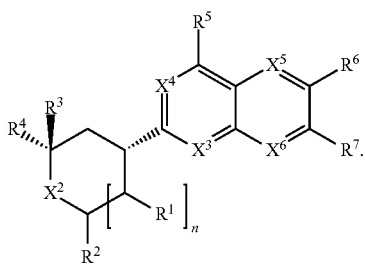

IID

Provided herein as Embodiment 8 is the compound according to Embodiment 1 or Embodiment 2, or a tautomer thereof, or a pharmaceutically acceptable salt of said compound or said tautomer, wherein the compound is a compound of Formula IIE

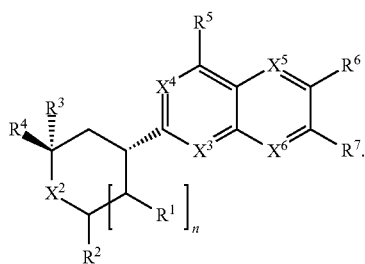

IIE

Provided herein as Embodiment 9 is the compound according to any one of Embodiments 1-4, or a tautomer thereof, or a pharmaceutically acceptable salt of said compound or said tautomer, wherein
$X^1$ is CH.

Provided herein as Embodiment 10 is the compound according to any one of Embodiments 1-4, or a tautomer thereof, or a pharmaceutically acceptable salt of said compound or said tautomer, wherein
$X^1$ is N.

Provided herein as Embodiment 11 is the compound according to any one of Embodiments 1-10, or a tautomer thereof, or a pharmaceutically acceptable salt of said compound or said tautomer, wherein
$X^2$ is $CH_2$, $CF_2$, or O.

Provided herein as Embodiment 12 is the compound according to any one of Embodiments 1-10, or a tautomer thereof, or a pharmaceutically acceptable salt of said compound or said tautomer, wherein
$X^2$ is O.

Provided herein as Embodiment 13 is the compound according to any one of Embodiments 1-12, or a tautomer thereof, or a pharmaceutically acceptable salt of said compound or said tautomer, wherein
$X^3$ is CH.

Provided herein as Embodiment 14 is the compound according to any one of Embodiments 1-12, or a tautomer thereof, or a pharmaceutically acceptable salt of said compound or said tautomer, wherein
$X^3$ is N.

Provided herein as Embodiment 15 is the compound according to any one of Embodiments 1-14, or a tautomer thereof, or a pharmaceutically acceptable salt of said compound or said tautomer, wherein
$X^4$ is CH.

Provided herein as Embodiment 16 is the compound according to any one of Embodiments 1-14, or a tautomer thereof, or a pharmaceutically acceptable salt of said compound or said tautomer, wherein
$X^4$ is N.

Provided herein as Embodiment 17 is the compound according to any one of Embodiments 1-16, or a tautomer thereof, or a pharmaceutically acceptable salt of said compound or said tautomer, wherein
$X^5$ is CH.

Provided herein as Embodiment 18 is the compound according to any one of Embodiments 1-16, or a tautomer thereof, or a pharmaceutically acceptable salt of said compound or said tautomer, wherein
$X^5$ is N.

Provided herein as Embodiment 19 is the compound according to any one of Embodiments 1-18, or a tautomer thereof, or a pharmaceutically acceptable salt of said compound or said tautomer, wherein
$X^6$ is CH.

Provided herein as Embodiment 20 is the compound according to any one of Embodiments 1-18, or a tautomer thereof, or a pharmaceutically acceptable salt of said compound or said tautomer, wherein
$X^6$ is N.

Provided herein as Embodiment 21 is the compound according to any one of Embodiments 1-20, or a tautomer thereof, or a pharmaceutically acceptable salt of said compound or said tautomer, wherein
$R^1$ is H or methyl.

Provided herein as Embodiment 22 is the compound according to any one of Embodiments 1-20, or a tautomer thereof, or a pharmaceutically acceptable salt of said compound or said tautomer, wherein
$R^1$ is H.

Provided herein as Embodiment 23 is the compound according to any one of Embodiments 1-22, or a tautomer thereof, or a pharmaceutically acceptable salt of said compound or said tautomer, wherein
$R^2$ is H or methyl.

Provided herein as Embodiment 24 is the compound according to any one of Embodiments 1-22, or a tautomer thereof, or a pharmaceutically acceptable salt of said compound or said tautomer, wherein
$R^2$ is H.

Provided herein as Embodiment 25 is the compound according to any one of Embodiments 1-24, or a tautomer thereof, or a pharmaceutically acceptable salt of said compound or said tautomer, wherein R³ is H or methyl.

Provided herein as Embodiment 26 is the compound according to any one of Embodiments 1-24, or a tautomer thereof, or a pharmaceutically acceptable salt of said compound or said tautomer, wherein R³ is H.

Provided herein as Embodiment 27 is the compound according to any one of Embodiments 1-26, or a tautomer thereof, or a pharmaceutically acceptable salt of said compound or said tautomer, wherein R⁴ is $C_{1-6}$alkyl, $C_{3-6}$heterocycloalkyl, 5-membered heteroaryl, or 6-membered heteroaryl; wherein the 5-membered heteroaryl or 6-membered heteroaryl group is optionally substituted with 1 to 3 substituents independently selected from $C_{1-6}$alkyl, $C_{1-6}$alkoxy, $C_{3-6}$cycloalkyl, and $C_{3-6}$heterocycloalkyl.

Provided herein as Embodiment 28 is the compound according to any one of Embodiments 1-26, or a tautomer thereof, or a pharmaceutically acceptable salt of said compound or said tautomer, wherein R⁴ is 5-membered heteroaryl or 6-membered heteroaryl; wherein the 5-membered heteroaryl or 6-membered heteroaryl group is optionally substituted with 1 to 3 substituents independently selected from $C_{1-6}$alkyl and $C_{3-6}$cycloalkyl.

Provided herein as Embodiment 29 is the compound according to any one of Embodiments 1-26, or a tautomer thereof, or a pharmaceutically acceptable salt of said compound or said tautomer, wherein R⁴ is methyl, tetrahydrofuran-3-yl,

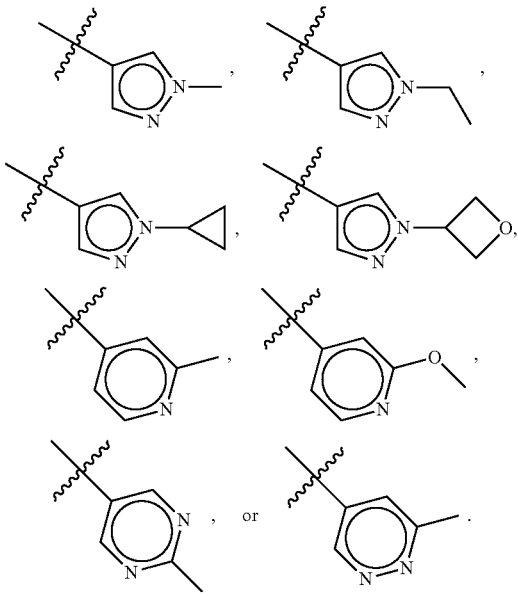

Provided herein as Embodiment 30 is the compound according to any one of Embodiments 1-26, or a tautomer thereof, or a pharmaceutically acceptable salt of said compound or said tautomer, wherein R⁴ is

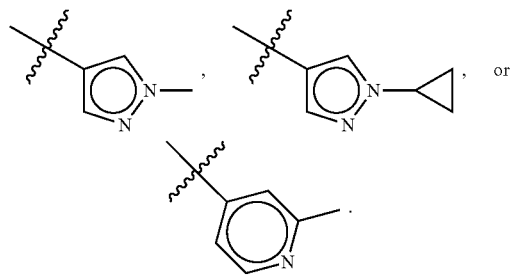

Provided herein as Embodiment 31 is the compound according to any one of Embodiments 1-30, or a tautomer thereof, or a pharmaceutically acceptable salt of said compound or said tautomer, wherein R⁵ is $C_{1-6}$haloalkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-($C_{3-6}$cycloalkyl), wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH₂-($C_{3-6}$cycloalkyl) is further substituted with 1 to 4 substituents independently selected from halogen, $C_{1-3}$alkyl, $C_{1-3}$haloalkyl, and $C_{1-3}$alkoxy.

Provided herein as Embodiment 32 is the compound according to any one of Embodiments 1-30, or a tautomer thereof, or a pharmaceutically acceptable salt of said compound or said tautomer, wherein R⁵ is —CH₂CH₂CF₃, optionally substituted $C_{3-6}$cycloalkyl, optionally substituted spiro[3.3]heptanyl, optionally substituted spiro[5.2]octanyl, optionally substituted

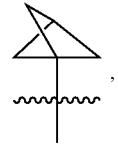 [SMILES: *C12CC(C1)C2]

optionally substituted cyclopent-1-en-1-yl, optionally substituted cyclohex-1-en-1-yl, optionally substituted phenyl, optionally substituted pyridinyl, substituted aziridine-1-yl, substituted pyrrolidine-1-yl, substituted azabicyclo[3.1.0]hexan-3-yl, substituted piperidine-1-yl, or substituted —OCH₂-($C_{3-4}$cycloalkyl).

Provided herein as Embodiment 33 is the compound according to any one of Embodiments 1-30, or a tautomer thereof, or a pharmaceutically acceptable salt of said compound or said tautomer, wherein R⁵ is —CH₂CH₂CF₃,

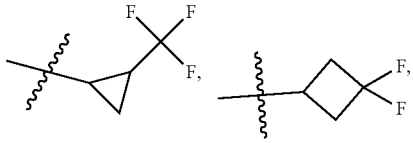

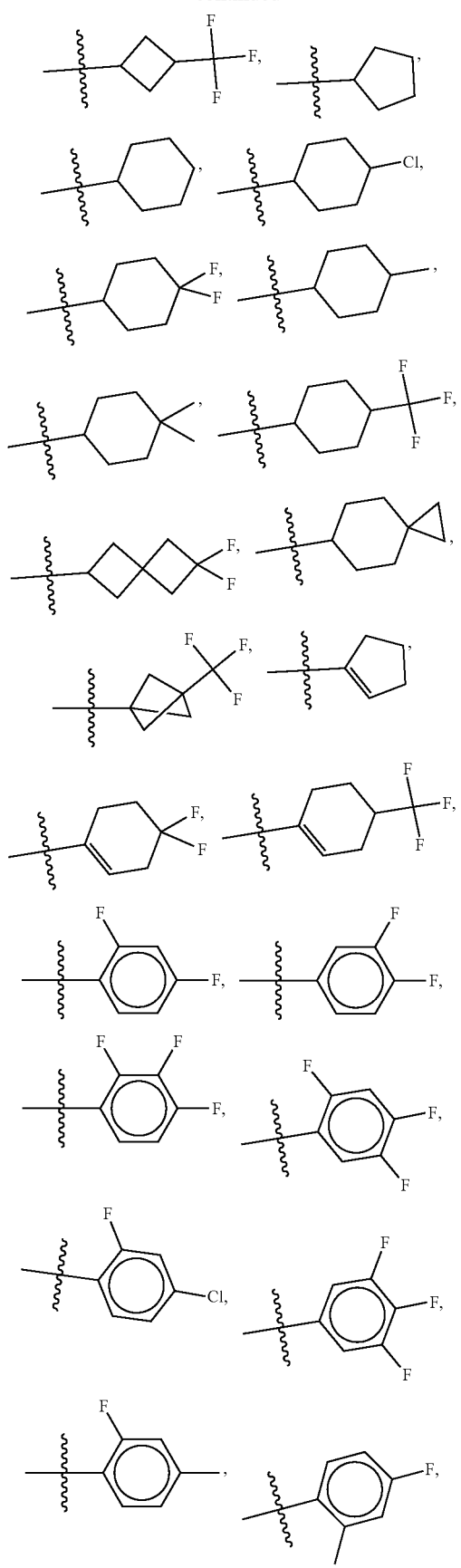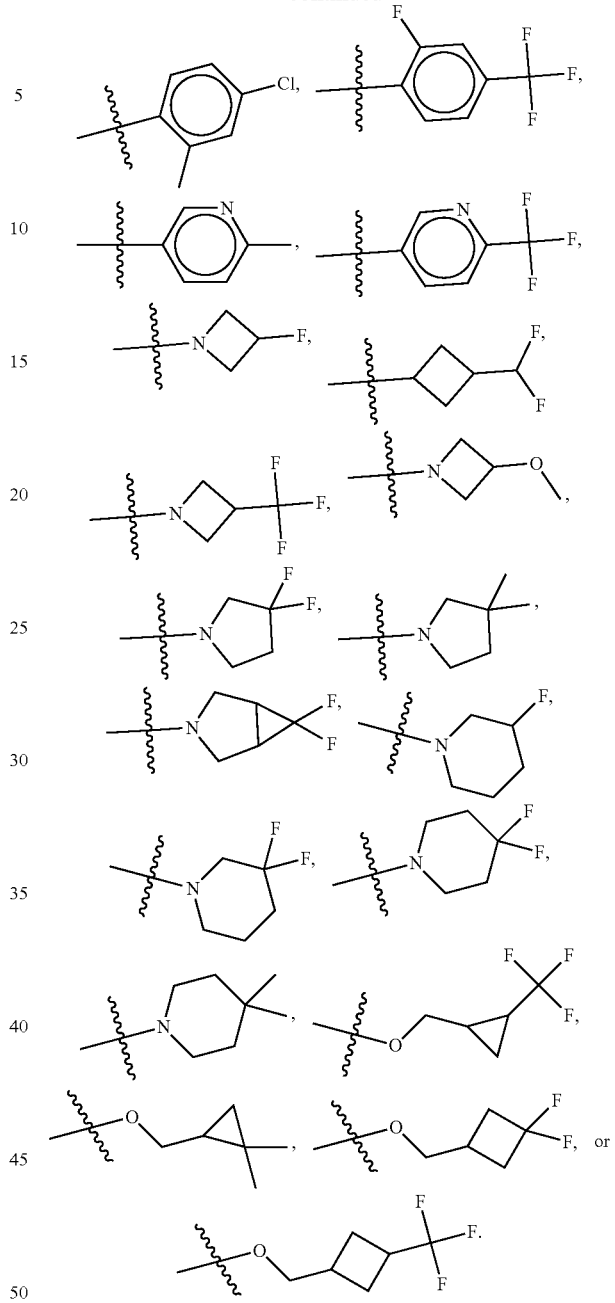

Provided herein as Embodiment 34 is the compound according to any one of Embodiments 1-33, or a tautomer thereof, or a pharmaceutically acceptable salt of said compound or said tautomer, wherein
$R^6$ is H, chlorine, or methyl.

Provided herein as Embodiment 35 is the compound according to any one of Embodiments 1-33, or a tautomer thereof, or a pharmaceutically acceptable salt of said compound or said tautomer, wherein
$R^6$ is H, chlorine, or methyl.

Provided herein as Embodiment 36 is the compound according to any one of Embodiments 1-33, or a tautomer thereof, or a pharmaceutically acceptable salt of said compound or said tautomer, wherein
$R^6$ is H or methyl.

Provided herein as Embodiment 37 is the compound according to any one of Embodiments 1-36, or a tautomer thereof, or a pharmaceutically acceptable salt of said compound or said tautomer, wherein $R^7$ is H, methyl, or ethyl.

Provided herein as Embodiment 38 is the compound according to any one of Embodiments 1-36, or a tautomer thereof, or a pharmaceutically acceptable salt of said compound or said tautomer, wherein $R^7$ is H or methyl.

Provided herein as Embodiment 39 is the compound according to any one of Embodiments 1-38, or a tautomer thereof, or a pharmaceutically acceptable salt of said compound or said tautomer, wherein $R^8$ is H or methyl.

Provided herein as Embodiment 40 is the compound according to any one of Embodiments 1-39, or a tautomer thereof, or a pharmaceutically acceptable salt of said compound or said tautomer, wherein $R^9$ is H, methyl, ethyl, or iso-propyl.

Provided herein as Embodiment 41 is the compound according to any one of Embodiments 1-40, or a tautomer thereof, or a pharmaceutically acceptable salt of said compound or said tautomer, wherein n is 0.

Provided herein as Embodiment 42 is the compound according to any one of Embodiments 1-40, or a tautomer thereof, or a pharmaceutically acceptable salt of said compound or said tautomer, wherein n is 1.

Provided herein as Embodiment 43 is the compound according to Embodiment 1, or a tautomer thereof, or a pharmaceutically acceptable salt of said compound or said tautomer, wherein the compound is 4-(4-chloro-2-fluorophenyl)-7-methyl-2-((2S)-2-(1-methyl-1H-pyrazol-4-yl)-4-morpholinyl)pteridine;

4-(4-chloro-2-fluorophenyl)-2-((2S)-2-(1-cyclopropyl-1H-pyrazol-4-yl)-4-morpholinyl)-7-methylpteridine;

4-(4-chloro-2-fluorophenyl)-7-methyl-2-((2S)-2-(2-methyl-4-pyridinyl)-4-morpholinyl)pteridine;

4-(4-chloro-2-fluorophenyl)-7-methyl-2-((2S)-2-(2-methyl-5-pyrimidinyl)-4-morpholinyl)pteridine;

4-(4-chloro-2-fluorophenyl)-7-methyl-2-(2-(tetrahydro-3-furanyl)-4-morpholinyl)pteridine;

4-(2,4-difluorophenyl)-7-methyl-2-((2S)-2-(1-methyl-1H-pyrazol-4-yl)-4-morpholinyl)pteridine;

2-((2S)-2-(1-cyclopropyl-1H-pyrazol-4-yl)-4-morpholinyl)-4-(2,4-difluorophenyl)-7-methylpteridine;

4-(2,4-difluorophenyl)-7-methyl-2-((2S)-2-(2-methyl-4-pyridinyl)-4-morpholinyl)pteridine;

2-((2S)-2-(1-cyclopropyl-1H-pyrazol-4-yl)-4-morpholinyl)-4-(2-fluoro-4-methylphenyl)-7-methylpteridine;

4-(2-fluoro-4-methylphenyl)-7-methyl-2-((2S)-2-(2-methyl-4-pyridinyl)-4-morpholinyl)pteridine;

7-methyl-2-((2S)-2-(1-methyl-1H-pyrazol-4-yl)-4-morpholinyl)-4-(trans-3-(trifluoromethyl)cyclobutyl)pteridine;

2-((2S)-2-(1-cyclopropyl-1H-pyrazol-4-yl)-4-morpholinyl)-7-methyl-4-(cis-3-(trifluoromethyl)cyclobutyl)pteridine;

2-((2S)-2-(1-cyclopropyl-1H-pyrazol-4-yl)-4-morpholinyl)-7-methyl-4-(trans-3-(trifluoromethyl)cyclobutyl)pteridine;

7-methyl-2-((2R)-2-(6-methyl-4-pyridazinyl)-4-morpholinyl)-4-(cis-3-(trifluoromethyl)cyclobutyl)pteridine;

7-methyl-2-((2S)-2-(2-methyl-4-pyridinyl)-4-morpholinyl)-4-(cis-3-(trifluoromethyl)cyclobutyl)pteridine;

7-methyl-2-((2S)-2-(2-methyl-4-pyridinyl)-4-morpholinyl)-4-(trans-3-(trifluoromethyl)cyclobutyl)pteridine;

4-(2-fluoro-4-(trifluoromethyl)phenyl)-6,7-dimethyl-2-((2S)-2-(1-methyl-1H-pyrazol-4-yl)-4-morpholinyl)pteridine;

6,7-dimethyl-2-((2S)-2-(1-methyl-1H-pyrazol-4-yl)-4-morpholinyl)-4-(3,4,5-trifluorophenyl)pteridine;

6,7-dimethyl-2-((2S)-2-(1-methyl-1H-pyrazol-4-yl)-4-morpholinyl)-4-(6-(trifluoromethyl)-3-pyridinyl)pteridine;

6,7-dimethyl-2-((2S)-2-(1-methyl-1H-pyrazol-4-yl)-4-morpholinyl)-4-(6-methyl-3-pyridinyl)pteridine;

4-(4-chloro-2-fluorophenyl)-6,7-dimethyl-2-((2S)-2-(1-methyl-1H-pyrazol-4-yl)-4-morpholinyl)pteridine;

4-(4-chloro-2-fluorophenyl)-2-((2S)-2-(1-cyclopropyl-1H-pyrazol-4-yl)-4-morpholinyl)-6,7-dimethylpteridine;

4-(4-chloro-2-fluorophenyl)-6,7-dimethyl-2-((2S)-2-(2-methyl-4-pyridinyl)-4-morpholinyl)pteridine;

4-(4-chloro-2-fluorophenyl)-6,7-dimethyl-2-((2R)-2-(2-methyl-5-pyrimidinyl)-4-morpholinyl)pteridine;

4-(4-chloro-2-fluorophenyl)-6,7-dimethyl-2-((2S)-2-(2-methyl-5-pyrimidinyl)-4-morpholinyl)pteridine;

4-(4-chloro-2-fluorophenyl)-6,7-dimethyl-2-(2-(tetrahydro-3-furanyl)-4-morpholinyl)pteridine;

4-((1R,5S)-6,6-difluoro-3-azabicyclo[3.1.0]hexan-3-yl)-6,7-dimethyl-2-((2S)-2-(1-methyl-1H-pyrazol-4-yl)-4-morpholinyl)pteridine;

4-(3-methoxy-1-azetidinyl)-6,7-dimethyl-2-((2S)-2-(1-methyl-1H-pyrazol-4-yl)-4-morpholinyl)pteridine;

6,7-dimethyl-2-((2S)-2-(1-methyl-1H-pyrazol-4-yl)-4-morpholinyl)-4-(3-(trifluoromethyl)-1-azetidinyl)pteridine;

4-(2,4-difluorophenyl)-6,7-dimethyl-2-((2S)-2-(1-methyl-1H-pyrazol-4-yl)-4-morpholinyl)pteridine;

2-((2S)-2-(1-cyclopropyl-1H-pyrazol-4-yl)-4-morpholinyl)-4-(2,4-difluorophenyl)-6,7-dimethylpteridine;

4-(2,4-difluorophenyl)-6,7-dimethyl-2-((2S)-2-(2-methyl-4-pyridinyl)-4-morpholinyl)pteridine;

4-(2,4-difluorophenyl)-6,7-dimethyl-2-((2S)-2-((3R)-tetrahydro-3-furanyl)-4-morpholinyl)pteridine;

4-(2,4-difluorophenyl)-6,7-dimethyl-2-((2R)-2-((3R)-tetrahydro-3-furanyl)-4-morpholinyl)pteridine;

4-(2,4-difluorophenyl)-6,7-dimethyl-2-((2R)-2-((3S)-tetrahydro-3-furanyl)-4-morpholinyl)pteridine;

4-(2-fluoro-4-methylphenyl)-6,7-dimethyl-2-((2S)-2-(1-methyl-1H-pyrazol-4-yl)-4-morpholinyl)pteridine;

2-((2S)-2-(1-cyclopropyl-1H-pyrazol-4-yl)-4-morpholinyl)-4-(2-fluoro-4-methylphenyl)-6,7-dimethylpteridine;

4-(2-fluoro-4-methylphenyl)-6,7-dimethyl-2-((2S)-2-(2-methyl-4-pyridinyl)-4-morpholinyl)pteridine;

6,7-dimethyl-2-((2S)-2-(1-methyl-1H-pyrazol-4-yl)-4-morpholinyl)-4-(3,3,3-trifluoropropyl)pteridine;

6,7-dimethyl-2-((2S)-2-(2-methyl-4-pyridinyl)-4-morpholinyl)-4-(3,3,3-trifluoropropyl)pteridine;

6,7-dimethyl-2-((2S)-2-(1-methyl-1H-pyrazol-4-yl)-4-morpholinyl)-4-(trans-3-(trifluoromethyl)cyclobutyl)pteridine;

6,7-dimethyl-2-((2S)-2-(1-methyl-1H-pyrazol-4-yl)-4-morpholinyl)-4-(cis-3-(trifluoromethyl)cyclobutyl)pteridine;

4-(cis-3-(difluoromethyl)cyclobutyl)-6,7-dimethyl-2-((2S)-2-(1-methyl-1H-pyrazol-4-yl)-4-morpholinyl)pteridine;

4-(trans-3-(difluoromethyl)cyclobutyl)-6,7-dimethyl-2-((2S)-2-(1-methyl-1H-pyrazol-4-yl)-4-morpholinyl)pteridine;

4-(6,6-difluorospiro[3.3]heptan-2-yl)-6,7-dimethyl-2-((2S)-2-(1-methyl-1H-pyrazol-4-yl)-4-morpholinyl)pteridine;

2-((2S)-2-(1-cyclopropyl-1H-pyrazol-4-yl)-4-morpholinyl)-4-(cis-3-(difluoromethyl)cyclobutyl)-6,7-dimethylpteridine;

2-((2S)-2-(1-cyclopropyl-1H-pyrazol-4-yl)-4-morpholinyl)-4-(trans-3-(difluoromethyl)cyclobutyl)-6,7-dimethylpteridine;

2-((2S)-2-(1-cyclopropyl-1H-pyrazol-4-yl)-4-morpholinyl)-4-(6,6-difluorospiro[3.3]heptan-2-yl)-6,7-dimethylpteridine;

2-((2S)-2-(1-cyclopropyl-1H-pyrazol-4-yl)-4-morpholinyl)-6,7-dimethyl-4-(trans-3-(trifluoromethyl)cyclobutyl)pteridine;

6,7-dimethyl-2-((2S)-2-(6-methyl-4-pyridazinyl)-4-morpholinyl)-4-(trans-3-(trifluoromethyl)cyclobutyl)pteridine;

6,7-dimethyl-2-((2R)-2-(6-methyl-4-pyridazinyl)-4-morpholinyl)-4-(trans-3-(trifluoromethyl)cyclobutyl)pteridine;

4-(cis-3-(difluoromethyl)cyclobutyl)-6,7-dimethyl-2-((2S)-2-(2-methyl-4-pyridinyl)-4-morpholinyl)pteridine;

4-(trans-3-(difluoromethyl)cyclobutyl)-6,7-dimethyl-2-((2S)-2-(2-methyl-4-pyridinyl)-4-morpholinyl)pteridine;

6,7-dimethyl-2-((2S)-2-(2-methyl-4-pyridinyl)-4-morpholinyl)-4-(trans-3-(trifluoromethyl)cyclobutyl)pteridine;

4-(6,6-difluorospiro[3.3]heptan-2-yl)-6,7-dimethyl-2-((2S)-2-(2-methyl-4-pyridinyl)-4-morpholinyl)pteridine;

6,7-dimethyl-2-((2S)-2-(1-methyl-1H-pyrazol-4-yl)-4-morpholinyl)-4-((1R,2R)-2-(trifluoromethyl)cyclopropyl)pteridine;

4-(4-chloro-2-methylphenyl)-6,7-dimethyl-2-((2S)-2-(1-methyl-1H-pyrazol-4-yl)-4-morpholinyl)pteridine;

4-(4-fluoro-2-methylphenyl)-6,7-dimethyl-2-((2S)-2-(1-methyl-1H-pyrazol-4-yl)-4-morpholinyl)pteridine;

4-(3,4-difluorophenyl)-6,7-dimethyl-2-((2S)-2-(1-methyl-1H-pyrazol-4-yl)-4-morpholinyl)pteridine;

6,7-dimethyl-2-((2S)-2-(1-methyl-1H-pyrazol-4-yl)-4-morpholinyl)-4-(2,3,4-trifluorophenyl)pteridine;

6,7-dimethyl-2-((2S)-2-(1-methyl-1H-pyrazol-4-yl)-4-morpholinyl)-4-(2,4,5-trifluorophenyl)pteridine;

6,7-dimethyl-2-((2S)-2-(1-methyl-1H-pyrazol-4-yl)-4-morpholinyl)-4-(3-(trifluoromethyl)bicyclo[1.1.1]pentan-1-yl)pteridine;

2-((2S)-2-(1-cyclopropyl-1H-pyrazol-4-yl)-4-morpholinyl)-6,7-dimethyl-4-(3-(trifluoromethyl)bicyclo[1.1.1]pentan-1-yl)pteridine;

6,7-dimethyl-2-((2S)-2-(2-methyl-4-pyridinyl)-4-morpholinyl)-4-(3-(trifluoromethyl)bicyclo[1.1.1]pentan-1-yl)pteridine;

4-(4,4-difluoro-1-piperidinyl)-6,7-dimethyl-2-((2S)-2-(1-methyl-1H-pyrazol-4-yl)-4-morpholinyl)pteridine;

4-(4,4-dimethyl-1-piperidinyl)-6,7-dimethyl-2-((2S)-2-(1-methyl-1H-pyrazol-4-yl)-4-morpholinyl)pteridine;

4-((3R)-3-fluoro-1-piperidinyl)-6,7-dimethyl-2-((2S)-2-(1-methyl-1H-pyrazol-4-yl)-4-morpholinyl)pteridine;

4-((3S)-3-fluoro-1-piperidinyl)-6,7-dimethyl-2-((2S)-2-(1-methyl-1H-pyrazol-4-yl)-4-morpholinyl)pteridine;

4-(3,3-difluoro-1-pyrrolidinyl)-6,7-dimethyl-2-((2S)-2-(1-methyl-1H-pyrazol-4-yl)-4-morpholinyl)pteridine;

4-(3,3-dimethyl-1-pyrrolidinyl)-6,7-dimethyl-2-((2S)-2-(1-methyl-1H-pyrazol-4-yl)-4-morpholinyl)pteridine;

5-(4-chloro-2-fluorophenyl)-2-methyl-7-((2S)-2-(1-methyl-1H-pyrazol-4-yl)-4-morpholinyl)pyrido[3,4-b]pyrazine;

5-(4-chloro-2-fluorophenyl)-3-methyl-7-((2S)-2-(1-methyl-1H-pyrazol-4-yl)-4-morpholinyl)pyrido[3,4-b]pyrazine;

5-(4-chloro-2-fluorophenyl)-7-((2S)-2-(1-ethyl-1H-pyrazol-4-yl)-4-morpholinyl)-2-methylpyrido[3,4-b]pyrazine;

5-(4-chloro-2-fluorophenyl)-7-((2S)-2-(1-cyclopropyl-1H-pyrazol-4-yl)-4-morpholinyl)-2-methylpyrido[3,4-b]pyrazine;

5-(4-chloro-2-fluorophenyl)-2-methyl-7-(2S)-2-(2-methyl-4-pyridinyl)-4-morpholinyl)pyrido[3,4-b]pyrazine;

5-(4-chloro-2-fluorophenyl)-7-((2S)-2-(2-methoxy-4-pyridinyl)-4-morpholinyl)-2-methylpyrido[3,4-b]pyrazine;

5-(4-chloro-2-fluorophenyl)-2,3-dimethyl-7-((2S)-2-(1-methyl-1H-pyrazol-4-yl)-4-morpholinyl)pyrido[3,4-b]pyrazine;

2,3-dimethyl-7-((2S)-2-(1-methyl-1H-pyrazol-4-yl)-4-morpholinyl)-5-(trans-3-(trifluoromethyl)cyclobutyl)pyrido[3,4-b]pyrazine;

7-((2S)-2-(1-cyclopropyl-1H-pyrazol-4-yl)-4-morpholinyl)-2,3-dimethyl-5-(trans-3-(trifluoromethyl)cyclobutyl)pyrido[3,4-b]pyrazine;

2,3-dimethyl-7-((2S)-2-(2-methyl-4-pyridinyl)-4-morpholinyl)-5-(trans-3-(trifluoromethyl)cyclobutyl)pyrido[3,4-b]pyrazine;

4-(4-chloro-2-fluorophenyl)-2-((2S)-2-(1-methyl-1H-pyrazol-4-yl)-4-morpholinyl)pyrido[2,3-d]pyrimidine;

4-(4-chloro-2-fluorophenyl)-7-methyl-2-((2S)-2-(1-methyl-1H-pyrazol-4-yl)-4-morpholinyl)pyrido[2,3-d]pyrimidine;

4-(4-chloro-2-fluorophenyl)-2-((2S)-2-(1-cyclopropyl-1H-pyrazol-4-yl)-4-morpholinyl)-7-methylpyrido[2,3-d]pyrimidine;

4-(4-chloro-2-fluorophenyl)-7-methyl-2-(2S)-2-(6-methyl-4-pyridazinyl)-4-morpholinyl)pyrido[2,3-d]pyrimidine;

4-(4-chloro-2-fluorophenyl)-7-methyl-2-((2R)-2-(6-methyl-4-pyridazinyl)-4-morpholinyl)pyrido[2,3-d]pyrimidine;

4-(4-chloro-2-fluorophenyl)-7-methyl-2-((2S)-2-(2-methyl-4-pyridinyl)-4-morpholinyl)pyrido[2,3-d]pyrimidine;

4-(4-chloro-2-fluorophenyl)-7-methyl-2-((2R)-2-(2-methyl-5-pyrimidinyl)-4-morpholinyl)pyrido[2,3-d]pyrimidine;

4-(4-chloro-2-fluorophenyl)-7-methyl-2-((2S)-2-(2-methyl-5-pyrimidinyl)-4-morpholinyl)pyrido[2,3-d]pyrimidine;

4-(2,4-difluorophenyl)-7-methyl-2-((2S)-2-(1-methyl-1H-pyrazol-4-yl)-4-morpholinyl)pyrido[2,3-d]pyrimidine;

2-((2S)-2-(1-cyclopropyl-1H-pyrazol-4-yl)-4-morpholinyl)-4-(2,4-difluorophenyl)-7-methylpyrido[2,3-d]pyrimidine;

4-(2,4-difluorophenyl)-7-methyl-2-((2S)-2-(2-methyl-4-pyridinyl)-4-morpholinyl)pyrido[2,3-d]pyrimidine;

4-(2-fluoro-4-methylphenyl)-7-methyl-2-((2S)-2-(1-methyl-1H-pyrazol-4-yl)-4-morpholinyl)pyrido[2,3-d]pyrimidine;

2-((2S)-2-(1-cyclopropyl-1H-pyrazol-4-yl)-4-morpholinyl)-4-(2-fluoro-4-methylphenyl)-7-methylpyrido[2,3-d]pyrimidine;

4-(2-fluoro-4-methylphenyl)-7-methyl-2-((2S)-2-(2-methyl-4-pyridinyl)-4-morpholinyl)pyrido[2,3-d]pyrimidine;

7-methyl-2-((2S)-2-(1-methyl-1H-pyrazol-4-yl)-4-morpholinyl)-4-(trans-3-(trifluoromethyl)cyclobutyl)pyrido[2,3-d]pyrimidine;

2-((2S)-2-(1-cyclopropyl-1H-pyrazol-4-yl)-4-morpholinyl)-7-methyl-4-(trans-3-(trifluoromethyl)cyclobutyl)pyrido[2,3-d]pyrimidine;

7-methyl-2-((2S)-2-(2-methyl-4-pyridinyl)-4-morpholinyl)-4-(trans-3-(trifluoromethyl)cyclobutyl)pyrido[2,3-d]pyrimidine;

7-methyl-2-((2S)-2-(1-methyl-1H-pyrazol-4-yl)-4-morpholinyl)-4-(3-(trifluoromethyl)bicyclo[1.1.1]pentan-1-yl)pyrido[2,3-d]pyrimidine;

7-methyl-2-((2S)-2-(2-methyl-4-pyridinyl)-4-morpholinyl)-4-(3-(trifluoromethyl)bicyclo[1.1.1]pentan-1-yl)pyrido[2,3-d]pyrimidine;

4-(4-chloro-2-fluorophenyl)-6,7-dimethyl-2-((2S)-2-(1-methyl-1H-pyrazol-4-yl)-4-morpholinyl)pyrido[2,3-d]pyrimidine;

4-(4-chloro-2-fluorophenyl)-6,7-dimethyl-2-((2S)-2-(6-methyl-4-pyridazinyl)-4-morpholinyl)pyrido[2,3-d]pyrimidine;

4-(4-chloro-2-fluorophenyl)-6,7-dimethyl-2-((2R)-2-(6-methyl-4-pyridazinyl)-4-morpholinyl)pyrido[2,3-d]pyrimidine;

4-(4-chloro-2-fluorophenyl)-6,7-dimethyl-2-((2R)-2-(2-methyl-5-pyrimidinyl)-4-morpholinyl)pyrido[2,3-d]pyrimidine;

4-(4-chloro-2-fluorophenyl)-6,7-dimethyl-2-((2S)-2-(2-methyl-5-pyrimidinyl)-4-morpholinyl)pyrido[2,3-d]pyrimidine;

4-((3,3-difluorocyclobutyl)methoxy)-6,7-dimethyl-2-((2S)-2-(1-methyl-1H-pyrazol-4-yl)-4-morpholinyl)pyrido[2,3-d]pyrimidine;

6,7-dimethyl-2-((2S)-2-(1-methyl-1H-pyrazol-4-yl)-4-morpholinyl)-4-(((1R,2R)-2-(trifluoromethyl)cyclopropyl)methoxy)pyrido[2,3-d]pyrimidine;

4-(((1S)-2,2-dimethylcyclopropyl)methoxy)-6,7-dimethyl-2-((2S)-2-(1-methyl-1H-pyrazol-4-yl)-4-morpholinyl)pyrido[2,3-d]pyrimidine;

6,7-dimethyl-2-((2S)-2-(1-methyl-1H-pyrazol-4-yl)-4-morpholinyl)-4-(trans-3-(trifluoromethyl)cyclobutyl)pyrido[2,3-d]pyrimidine;

2-((2S)-2-(1-cyclopropyl-1H-pyrazol-4-yl)-4-morpholinyl)-6,7-dimethyl-4-(trans-3-(trifluoromethyl)cyclobutyl)pyrido[2,3-d]pyrimidine;

6,7-dimethyl-2-((2S)-2-(6-methyl-4-pyridazinyl)-4-morpholinyl)-4-(trans-3-(trifluoromethyl)cyclobutyl)pyrido[2,3-d]pyrimidine;

6,7-dimethyl-2-((2S)-2-(2-methyl-4-pyridinyl)-4-morpholinyl)-4-(trans-3-(trifluoromethyl)cyclobutyl)pyrido[2,3-d]pyrimidine;

6-chloro-4-(4-chloro-2-fluorophenyl)-7-methyl-2-((2S)-2-(1-methyl-1H-pyrazol-4-yl)-4-morpholinyl)pyrido[2,3-d]pyrimidine;

4-(4-chloro-2-fluorophenyl)-2-methyl-6-((2S)-2-methyl-4-morpholinyl)-2,3-dihydro-1H-pyrrolo[3,4-c]pyridin-1-one;

4-(4-chloro-2-fluorophenyl)-2-methyl-6-((2S)-2-(1-methyl-1H-pyrazol-4-yl)-4-morpholinyl)-2,3-dihydro-1H-pyrrolo[3,4-c]pyridin-1-one;

4-(4-chloro-2-fluorophenyl)-6-((2S)-2-(1-cyclopropyl-1H-pyrazol-4-yl)-4-morpholinyl)-2-methyl-2,3-dihydro-1H-pyrrolo[3,4-c]pyridin-1-one;

4-(4-chloro-2-fluorophenyl)-2-ethyl-6-((2S)-2-(1-methyl-1H-pyrazol-4-yl)-4-morpholinyl)-2,3-dihydro-1H-pyrrolo[3,4-c]pyridin-1-one;

4-(4-chloro-2-fluorophenyl)-6-((2S)-2-(1-methyl-1H-pyrazol-4-yl)-4-morpholinyl)-2-(2-propanyl)-2,3-dihydro-1H-pyrrolo[3,4-c]pyridin-1-one;

4-(4-chloro-2-fluorophenyl)-2-((3S)-4,4-difluoro-3-(1-methyl-1H-pyrazol-4-yl)-1-piperidinyl)-6,7-dimethylpteridine;

4-(4-chloro-2-fluorophenyl)-2-((3R)-4,4-difluoro-3-(1-methyl-1H-pyrazol-4-yl)-1-piperidinyl)-6,7-dimethylpteridine;

4-(4,4-difluoro-1-cyclohexen-1-yl)-6,7-dimethyl-2-((2S)-2-(1-methyl-1H-pyrazol-4-yl)-4-morpholinyl)pteridine;

6,7-dimethyl-2-((2S)-2-(1-methyl-1H-pyrazol-4-yl)-4-morpholinyl)-4-((4R)-4-(trifluoromethyl)-1-cyclohexen-1-yl)pteridine;

6,7-dimethyl-2-((2S)-2-(1-methyl-1H-pyrazol-4-yl)-4-morpholinyl)-4-((4S)-4-(trifluoromethyl)-1-cyclohexen-1-yl)pteridine;

4-(1-cyclopenten-1-yl)-6,7-dimethyl-2-((2S)-2-(1-methyl-1H-pyrazol-4-yl)-4-morpholinyl)pteridine;

5-(4-chloro-2-fluorophenyl)-2-methyl-7-((2S)-2-(1-(3-oxetanyl)-1H-pyrazol-4-yl)-4-morpholinyl)pyrido[3,4-b]pyrazine;

4-(4,4-dimethylcyclohexyl)-6,7-dimethyl-2-((2S)-2-(1-methyl-1H-pyrazol-4-yl)-4-morpholinyl)pteridine;

6,7-dimethyl-2-((2S)-2-(1-methyl-1H-pyrazol-4-yl)-4-morpholinyl)-4-(cis-4-(trifluoromethyl)cyclohexyl)pteridine;

6,7-dimethyl-2-((2S)-2- (1-methyl-1H-pyrazol-4-yl)-4-morpholinyl)-4-(trans-4-(trifluoromethyl)cyclohexyl)pteridine;

4-(4,4-difluorocyclohexyl)-6,7-dimethyl-2-((2S)-2-(1-methyl-1H-pyrazol-4-yl)-4-morpholinyl)pteridine;

4-cyclohexyl-6,7-dimethyl-2-((2S)-2-(1-methyl-1H-pyrazol-4-yl)-4-morpholinyl)pteridine;

6,7-dimethyl-4-(cis-4-methylcyclohexyl)-2-((2S)-2-(1-methyl-1H-pyrazol-4-yl)-4-morpholinyl)pteridine;

6,7-dimethyl-4-(trans-4-methylcyclohexyl)-2-((2S)-2-(1-methyl-1H-pyrazol-4-yl)-4-morpholinyl)pteridine;

6,7-dimethyl-2-((2S)-2-(1-methyl-1H-pyrazol-4-yl)-4-morpholinyl)-4-(spiro[2.5]octan-6-yl)pteridine;

2-((2S)-2-(1-cyclopropyl-1H-pyrazol-4-yl)-4-morpholinyl)-4-(4,4-difluorocyclohexyl)-6,7-dimethylpteridine;

4-(4,4-difluorocyclohexyl)-6,7-dimethyl-2-((2S)-2-(2-methyl-4-pyridinyl)-4-morpholinyl)pteridine;

4-cyclopentyl-6,7-dimethyl-2-((2S)-2-(1-methyl-1H-pyrazol-4-yl)-4-morpholinyl)pteridine;

4-(4,4-difluorocyclohexyl)-7-methyl-2-((2S)-2-(1-methyl-1H-pyrazol-4-yl)-4-morpholinyl)pyrido[2,3-d]pyrimidine;

7-methyl-2-((2S)-2-(1-methyl-1H-pyrazol-4-yl)-4-morpholinyl)-4-(cis-4-(trifluoromethyl)cyclohexyl)pyrido[2,3-d]pyrimidine;

2-((2S)-2-(1-cyclopropyl-1H-pyrazol-4-yl)-4-morpholinyl)-4-(4,4-difluorocyclohexyl)-7-methylpyrido[2,3-d]pyrimidine;

2-((2S)-2-(1-cyclopropyl-1H-pyrazol-4-yl)-4-morpholinyl)-7-methyl-4-(cis-4-(trifluoromethyl)cyclohexyl)pyrido[2,3-d]pyrimidine;

2-((2S)-2-(1-cyclopropyl-1H-pyrazol-4-yl)-4-morpholinyl)-7-methyl-4-(trans-4-(trifluoromethyl)cyclohexyl)pyrido[2,3-d]pyrimidine;

4-(3,3-difluorocyclobutyl)-6,7-dimethyl-2-((2S)-2-(1-methyl-1H-pyrazol-4-yl)-4-morpholinyl)pteridine 1-(4-chloro-2-fluorophenyl)-6-methyl-3-((2S)-2-(1-methyl-1H-pyrazol-4-yl)-4-morpholinyl)isoquinoline;

5-(4-chloro-2-fluorophenyl)-2-methyl-7-((2S)-2-(1-methyl-1H-pyrazol-4-yl)-4-morpholinyl)-1,6-naphthyridine;

5-(4-chloro-2-fluorophenyl)-7-((2S)-2-(2-methoxy-4-pyridinyl)-4-morpholinyl)-2-methyl-1,6-naphthyridine;

5-(4-chloro-2-fluorophenyl)-7-((2S)-2-(1-cyclopropyl-1H-pyrazol-4-yl)-4-morpholinyl)-2-methyl-1,6-naphthyridine;

5-(4-chloro-2-fluorophenyl)-2-methyl-7-((2S)-2-(2-methyl-4-pyridinyl)-4-morpholinyl)-1,6-naphthyridine;

5-(4-chloro-2-fluorophenyl)-2,3-dimethyl-7-((2S)-2-(1-methyl-1H-pyrazol-4-yl)-4-morpholinyl)-1,6-naphthyridine;

5-(4-chloro-2-fluorophenyl)-2-methyl-7-((2S)-2-(1-methyl-1H-pyrazol-4-yl)-4-morpholinyl)quinazoline;

5-(2,4-difluorophenyl)-2-methyl-((2S)-2-(2-methyl-4-pyridinyl)-4-morpholinyl)quinazoline;

4-(4-chloro-2-fluorophenyl)-2-((2S)-2-(1-methyl-1H-pyrazol-4-yl)-4-morpholinyl)-1,8-naphthyridine;

4-(4-chloro-2-fluorophenyl)-7-methyl-2-((2S)-2-(1-methyl-1H-pyrazol-4-yl)-4-morpholinyl)-1,8-naphthyridine;

5-(4-chloro-2-fluorophenyl)-2,3-dimethyl-7-((2S)-2-(1-methyl-1H-pyrazol-4-yl)-4-morpholinyl)-1,8-naphthyridine;

8-(4-chloro-2-fluorophenyl)-2-methyl-((2S)-2-(1-methyl-1H-pyrazol-4-yl)-4-morpholinyl)pyrido[2,3-b]pyrazine;

8-(4-chloro-2-fluorophenyl)-3-methyl-6-((2S)-2-(1-methyl-1H-pyrazol-4-yl)-4-morpholinyl)pyrido[2,3-b]pyrazine;

8-(4-chloro-2-fluorophenyl)-2,3-dimethyl-6-((2S)-2-(1-methyl-1H-pyrazol-4-yl)-4-morpholinyl)pyrido[2,3-b]pyrazine;

8-(2,4-difluorophenyl)-2,3-dimethyl-6-((2S)-2-(1-methyl-1H-pyrazol-4-yl)-4-morpholinyl)pyrido[2,3-b]pyrazine;

5-(4-chloro-2-fluorophenyl)-2,3-dimethyl-7-((2S)-2-(1-methyl-1H-pyrazol-4-yl)-4-morpholinyl)quinoxaline;

5-(4-chloro-2-fluorophenyl)-2,3-dimethyl-7-((2S)-2-(2-methyl-4-pyridinyl)-4-morpholinyl)quinoxaline;

5-(2,4-difluorophenyl)-2,3-dimethyl-7-((2S)-2-(1-methyl-1H-pyrazol-4-yl)-4-morpholinyl)quinoxaline;

4-(trans-4-chlorocyclohexyl)-6,7-dimethyl-2-((2S)-2-(1-methyl-1H-pyrazol-4-yl)-4-morpholinyl)pteridine;

4-(2,4-difluorophenyl)-6,7-dimethyl-2-((2S)-2-(1-methyl-1H-pyrazol-4-yl)-4-morpholinyl)pyrido[2,3-d]pyrimidine;

4-(2,4-difluorophenyl)-7-ethyl-2-((2S)-2-(1-methyl-1H-pyrazol-4-yl)-4-morpholinyl)pyrido[2,3-d]pyrimidine;

4-(2,4-difluorophenyl)-6,7-dimethyl-2-((2S)-2-(2-methyl-4-pyridinyl)-4-morpholinyl)pyrido[2,3-d]pyrimidine;

2-((2S)-2-(1-cyclopropyl-1H-pyrazol-4-yl)-4-morpholinyl)-4-(2,4-difluorophenyl)-6,7-dimethylpyrido[2,3-d]pyrimidine;

4-(4-chloro-2-fluorophenyl)-2-((2R,4S)-2-(1-cyclopropyl-1H-pyrazol-4-yl)tetrahydro-2H-pyran-4-yl)-7-methylpteridine;

4-(4-chloro-2-fluorophenyl)-7-methyl-2-((2R,4S)-2-(2-methyl-4-pyridinyl)tetrahydro-2H-pyran-4-yl)pteridine;

4-(4-chloro-2-fluorophenyl)-7-methyl-2-((2S,4R)-2-(2-methyl-4-pyridinyl)tetrahydro-2H-pyran-4-yl)pteridine;

4-(4-chloro-2-fluorophenyl)-7-methyl-2-((2R,4S)-2-(2-methyl-5-pyrimidinyl)tetrahydro-2H-pyran-4-yl)pteridine;

4-(4-chloro-2-fluorophenyl)-7-methyl-2-((2S,4R)-2-(2-methyl-5-pyrimidinyl)tetrahydro-2H-pyran-4-yl)pteridine;

4-(4,4-difluorocyclohexyl)-6,7-dimethyl-2-((2S,4R)-2-(1-methyl-1H-pyrazol-4-yl)tetrahydro-2H-pyran-4-yl)pteridine;

4-(4,4-difluorocyclohexyl)-6,7-dimethyl-2-((2R,4S)-2-(1-methyl-1H-pyrazol-4-yl)tetrahydro-2H-pyran-4-yl)pteridine;

4-(4-chloro-2-fluorophenyl)-6,7-dimethyl-2-((2S,4R)-2-(1-methyl-1H-pyrazol-4-yl)tetrahydro-2H-pyran-4-yl)pteridine;

4-(4-chloro-2-fluorophenyl)-6,7-dimethyl-2-((2R,4S)-2-(1-methyl-1H-pyrazol-4-yl)tetrahydro-2H-pyran-4-yl)pteridine;

4-(4-chloro-2-fluorophenyl)-6,7-dimethyl-2-((2R,4R)-2-(1-methyl-1H-pyrazol-4-yl)tetrahydro-2H-pyran-4-yl)pteridine;

4-(4-chloro-2-fluorophenyl)-2-((2S,4R)-2-(1-cyclopropyl-1H-pyrazol-4-yl)tetrahydro-2H-pyran-4-yl)-6,7-dimethylpteridine;

4-(4-chloro-2-fluorophenyl)-2-((2R,4S)-2-(1-cyclopropyl-1H-pyrazol-4-yl)tetrahydro-2H-pyran-4-yl)-6,7-dimethylpteridine;

4-(2,4-difluorophenyl)-6,7-dimethyl-2-((2R,4S)-2-(1-methyl-1H-pyrazol-4-yl)tetrahydro-2H-pyran-4-yl)pteridine;

4-(2-fluoro-4-methylphenyl)-6,7-dimethyl-2-((2R,4S)-2-(1-methyl-1H-pyrazol-4-yl)tetrahydro-2H-pyran-4-yl)pteridine;

4-(2-fluoro-4-methylphenyl)-6,7-dimethyl-2-((2S,4R)-2-(1-methyl-1H-pyrazol-4-yl)tetrahydro-2H-pyran-4-yl)pteridine;

8-(4-chloro-2-fluorophenyl)-3-methyl-6-((2R,4S)-2-(1-methyl-1H-pyrazol-4-yl)tetrahydro-2H-pyran-4-yl)pyrido[2,3-b]pyrazine;

8-(4-chloro-2-fluorophenyl)-2,3-dimethyl-6-((2S,4S)-2-(1-methyl-1H-pyrazol-4-yl)tetrahydro-2H-pyran-4-yl)pyrido[2,3-b]pyrazine;

8-(4-chloro-2-fluorophenyl)-2,3-dimethyl-6-((2R,4S)-2-(1-methyl-1H-pyrazol-4-yl)tetrahydro-2H-pyran-4-yl)pyrido[2,3-b]pyrazine;

8-(2,4-difluorophenyl)-2,3-dimethyl-6-((2R,4S)-2-(1-methyl-1H-pyrazol-4-yl)tetrahydro-2H-pyran-4-yl)pyrido[2,3-b]pyrazine;

8-(2-fluoro-4-methylphenyl)-2,3-dimethyl-6-((2S,4R)-2-(1-methyl-1H-pyrazol-4-yl)tetrahydro-2H-pyran-4-yl)pyrido[2,3-b]pyrazine;

8-(2-fluoro-4-methylphenyl)-2,3-dimethyl-6-((2R,4S)-2-(1-methyl-1H-pyrazol-4-yl)tetrahydro-2H-pyran-4-yl)pyrido[2,3-b]pyrazine;

5-(4-chloro-2-fluorophenyl)-2-methyl-7-((2R,4S)-2-(1-methyl-1H-pyrazol-4-yl)tetrahydro-2H-pyran-4-yl)pyrido[3,4-b]pyrazine;

5-(4-chloro-2-fluorophenyl)-2,3-dimethyl-7-((2R,4S)-2-(1-methyl-1H-pyrazol-4-yl)tetrahydro-2H-pyran-4-yl)pyrido[3,4-b]pyrazine;

5-(4-chloro-2-fluorophenyl)-2,3-dimethyl-7-((2S,4R)-2-(1-methyl-1H-pyrazol-4-yl)tetrahydro-2H-pyran-4-yl)pyrido[3,4-b]pyrazine;

5-(4-chloro-2-fluorophenyl)-2,3-dimethyl-7-((2S,4S)-2-(1-methyl-1H-pyrazol-4-yl)tetrahydro-2H-pyran-4-yl)pyrido[3,4-b]pyrazine;

5-(2,4-difluorophenyl)-2,3-dimethyl-7-((2S,4S)-2-(1-methyl-1H-pyrazol-4-yl)tetrahydro-2H-pyran-4-yl)pyrido[3,4-b]pyrazine;

5-(2-fluoro-4-methylphenyl)-2,3-dimethyl-7-((2R,4S)-2-(1-methyl-1H-pyrazol-4-yl)tetrahydro-2H-pyran-4-yl)pyrido[3,4-b]pyrazine;

4-(4-chloro-2-fluorophenyl)-2-((2R,4S)-2-(1-cyclopropyl-1H-pyrazol-4-yl)tetrahydro-2H-pyran-4-yl)-7-methylpyrido[2,3-d]pyrimidine;

4-(4-chloro-2-fluorophenyl)-2-((2S,4R)-2-(1-cyclopropyl-1H-pyrazol-4-yl)tetrahydro-2H-pyran-4-yl)-6,7-dimethylpyrido[2,3-d]pyrimidine;

4-(4-chloro-2-fluorophenyl)-2-((2R,4S)-2-(1-cyclopropyl-1H-pyrazol-4-yl)tetrahydro-2H-pyran-4-yl)-6,7-dimethylpyrido[2,3-d]pyrimidine;

4-(2,4-difluorophenyl)-6,7-dimethyl-2-((2S,4R)-2-(1-methyl-1H-pyrazol-4-yl)tetrahydro-2H-pyran-4-yl)pyrido[2,3-d]pyrimidine;
4-(2,4-difluorophenyl)-6,7-dimethyl-2-((2R,4S)-2-(1-methyl-1H-pyrazol-4-yl)tetrahydro-2H-pyran-4-yl)pyrido[2,3-d]pyrimidine;
4-(2-fluoro-4-methylphenyl)-6,7-dimethyl-2-((2S,4R)-2-(1-methyl-1H-pyrazol-4-yl)tetrahydro-2H-pyran-4-yl)pyrido[2,3-d]pyrimidine;
4-(2-fluoro-4-methylphenyl)-6,7-dimethyl-2-((2R,4S)-2-(1-methyl-1H-pyrazol-4-yl)tetrahydro-2H-pyran-4-yl)pyrido[2,3-d]pyrimidine;
6,7-dimethyl-2-((2R,4R)-2-(1-methyl-1H-pyrazol-4-yl)tetrahydro-2H-pyran-4-yl)-4-(trans-3-(trifluoromethyl)cyclobutyl)pteridine;
6,7-dimethyl-2-((2R,4S)-2-(1-methyl-1H-pyrazol-4-yl)tetrahydro-2H-pyran-4-yl)-4-(trans-3-(trifluoromethyl)cyclobutyl)pteridine;
4-(4-chloro-2-fluorophenyl)-6,7-dimethyl-2-((2S,4R)-2-(2-methyl-4-pyridinyl)tetrahydro-2H-pyran-4-yl)pteridine;
4-(4-chloro-2-fluorophenyl)-6,7-dimethyl-2-((2R,4S)-2-(2-methyl-4-pyridinyl)tetrahydro-2H-pyran-4-yl)pteridine;
4-(4-chloro-2-fluorophenyl)-2-((2R,4S)-2-(2-methoxy-4-pyridinyl)tetrahydro-2H-pyran-4-yl)-6,7-dimethylpteridine;
4-(4-chloro-2-fluorophenyl)-6,7-dimethyl-2-((2R,4S)-2-(2-methyl-5-pyrimidinyl)tetrahydro-2H-pyran-4-yl)pteridine;
4-(2,4-difluorophenyl)-6,7-dimethyl-2-((2S,4R)-2-(2-methyl-4-pyridinyl)tetrahydro-2H-pyran-4-yl)pteridine;
4-(2,4-difluorophenyl)-6,7-dimethyl-2-((2R,4S)-2-(2-methyl-4-pyridinyl)tetrahydro-2H-pyran-4-yl)pteridine;
4-(2,4-difluorophenyl)-6,7-dimethyl-2-((2S,4S)-2-(2-methyl-4-pyridinyl)tetrahydro-2H-pyran-4-yl)pteridine;
4-(2,4-difluorophenyl)-6,7-dimethyl-2-((2R,4R)-2-(2-methyl-4-pyridinyl)tetrahydro-2H-pyran-4-yl)pteridine;
6,7-dimethyl-2-((2S,4R)-2-(2-methyl-4-pyridinyl)tetrahydro-2H-pyran-4-yl)-4-(trans-3-(trifluoromethyl)cyclobutyl)pteridine;
6,7-dimethyl-2-((2R,4S)-2-(2-methyl-4-pyridinyl)tetrahydro-2H-pyran-4-yl)-4-(trans-3-(trifluoromethyl)cyclobutyl)pteridine;
4-(4-chloro-2-fluorophenyl)-6,7-dimethyl-2-((2R,4S,6R)-2-methyl-6-(1-methyl-1H-pyrazol-4-yl)tetrahydro-2H-pyran-4-yl)pteridine;
5-(4-chloro-2-fluorophenyl)-2,3-dimethyl-7-((2S,4R)-2-(2-methyl-4-pyridinyl)tetrahydro-2H-pyran-4-yl)pyrido[3,4-b]pyrazine;
5-(4-chloro-2-fluorophenyl)-2,3-dimethyl-7-((2R,4S)-2-(2-methyl-4-pyridinyl)tetrahydro-2H-pyran-4-yl)pyrido[3,4-b]pyrazine;
4-(4-chloro-2-fluorophenyl)-7-methyl-2-((2R,4R)-2-(2-methyl-4-pyridinyl)tetrahydro-2H-pyran-4-yl)pyrido[2,3-d]pyrimidine;
4-(4-chloro-2-fluorophenyl)-7-methyl-2-((2S,4S)-2-(2-methyl-4-pyridinyl)tetrahydro-2H-pyran-4-yl)pyrido[2,3-d]pyrimidine;
4-(2,4-difluorophenyl)-7-methyl-2-((2S,4S)-2-(2-methyl-4-pyridinyl)tetrahydro-2H-pyran-4-yl)pyrido[2,3-d]pyrimidine;
4-(2-fluoro-4-methylphenyl)-6,7-dimethyl-2-((2R,4S)-2-(2-methyl-4-pyridinyl)tetrahydro-2H-pyran-4-yl)pyrido[2,3-d]pyrimidine;
4-(2-fluoro-4-methylphenyl)-6,7-dimethyl-2-((2S,4R)-2-(2-methyl-4-pyridinyl)tetrahydro-2H-pyran-4-yl)pyrido[2,3-d]pyrimidine;
4-(4-chloro-2-fluorophenyl)-6,7-dimethyl-2-((2R,4S)-2-(1-methyl-1H-pyrazol-4-yl)tetrahydro-2H-pyran-4-yl)pyrido[2,3-d]pyrimidine;
4-(4-chloro-2-fluorophenyl)-6,7-dimethyl-2-((2R,4R)-2-(1-methyl-1H-pyrazol-4-yl)tetrahydro-2H-pyran-4-yl)pyrido[2,3-d]pyrimidine;
4-(4-chloro-2-fluorophenyl)-6,7-dimethyl-2-((2S,4R)-2-(1-methyl-1H-pyrazol-4-yl)tetrahydro-2H-pyran-4-yl)pyrido[2,3-d]pyrimidine;
4-(2,4-difluorophenyl)-6,7-dimethyl-2-((2S,4S)-2-(2-methyl-4-pyridinyl)tetrahydro-2H-pyran-4-yl)pyrido[2,3-d]pyrimidine;
4-(2,4-difluorophenyl)-6,7-dimethyl-2-((2R,4R)-2-(2-methyl-4-pyridinyl)tetrahydro-2H-pyran-4-yl)pyrido[2,3-d]pyrimidine;
4-(4-chloro-2-fluorophenyl)-6,7-dimethyl-2-((2R,4S,6R)-2-methyl-6-(1-methyl-1H-pyrazol-4-yl)tetrahydro-2H-pyran-4-yl)pyrido[2,3-d]pyrimidine; or
5-(4-chloro-2-fluorophenyl)-2,3-dimethyl-7-((2R,4S,6R)-2-methyl-6-(1-methyl-1H-pyrazol-4-yl)tetrahydro-2H-pyran-4-yl)pyrido[3,4-b]pyrazine.

Provided herein as Embodiment 44 is the compound according to Embodiment 1, or a pharmaceutically acceptable salt thereof, wherein the compound is

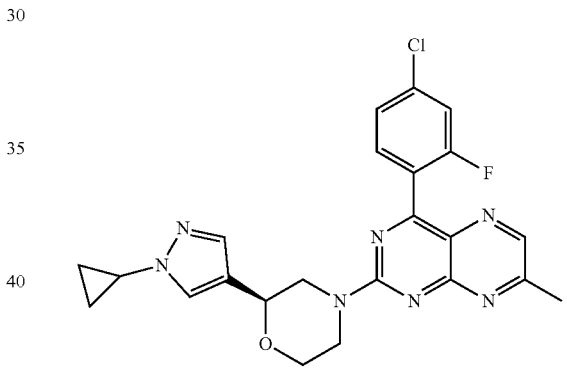

Provided herein as Embodiment 45 is the compound according to Embodiment 1, or a pharmaceutically acceptable salt thereof, wherein the compound is

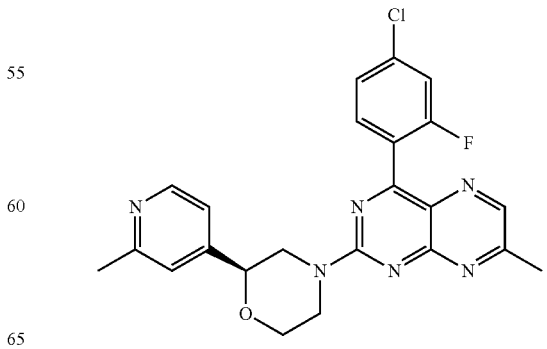

Provided herein as Embodiment 46 is the compound according to Embodiment 1, or a pharmaceutically acceptable salt thereof, wherein the compound is

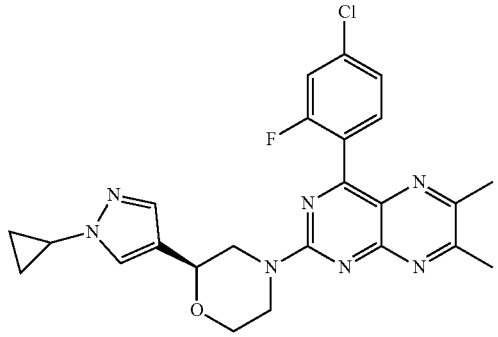

Provided herein as Embodiment 47 is the compound according to Embodiment 1, or a pharmaceutically acceptable salt thereof, wherein the compound is

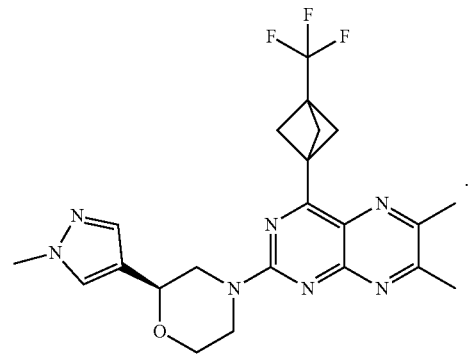

Provided herein as Embodiment 48 is the compound according to Embodiment 1, or a pharmaceutically acceptable salt thereof, wherein the compound is

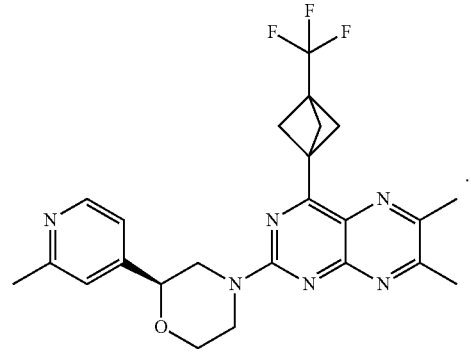

Provided herein as Embodiment 49 is the compound according to Embodiment 1, or a pharmaceutically acceptable salt thereof, wherein the compound is

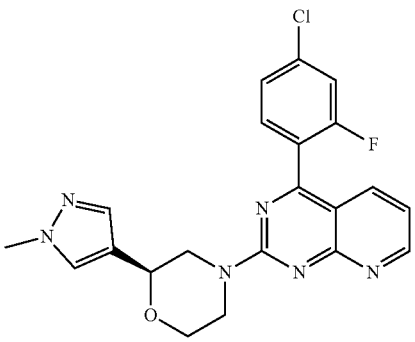

Provided herein as Embodiment 50 is the compound according to Embodiment 1, or a pharmaceutically acceptable salt thereof, wherein the compound is

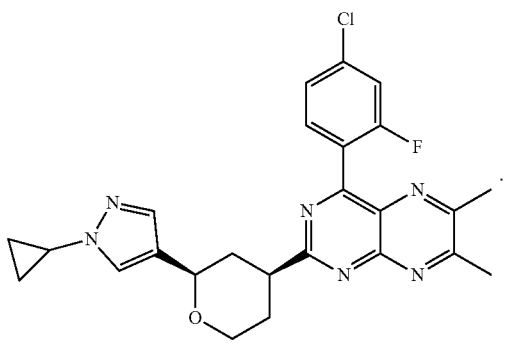 [SMILES: Cc1nc2nc([C@H]3CCO[C@@H](c4cnn(C5CC5)c4)C3)nc(-c3ccc(Cl)cc3F)c2nc1C]

Provided herein as Embodiment 51 is the compound according to Embodiment 1, or a pharmaceutically acceptable salt thereof, wherein the compound is

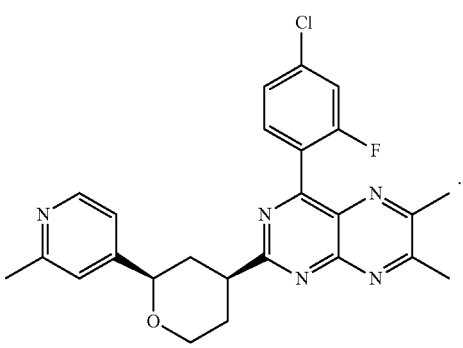

Provided herein as Embodiment 52 is the compound according to Embodiment 1, 2, or 3, or a tautomer thereof, or a pharmaceutically acceptable salt of said compound or said tautomer, wherein the compound is a compound of Formula IIIa:

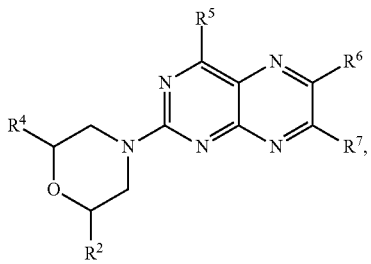

IIIa wherein each variable is as defined above and described in embodiments herein both singly and in combination.

Provided herein as Embodiment 53 is the compound according to Embodiment 1, 2, or 3, or a tautomer thereof, or a pharmaceutically acceptable salt of said compound or said tautomer, wherein the compound is a compound of Formula IIIb:

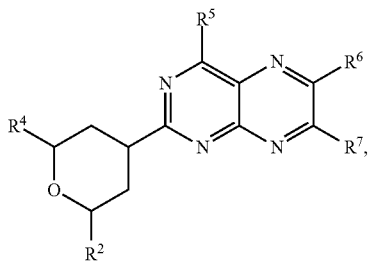

IIIb wherein each variable is as defined above and described in embodiments herein both singly and in combination.

Provided herein as Embodiment 54 is the compound according to Embodiment 1, 2, or 3, or a tautomer thereof, or a pharmaceutically acceptable salt of said compound or said tautomer, wherein the compound is a compound of Formula IIIc:

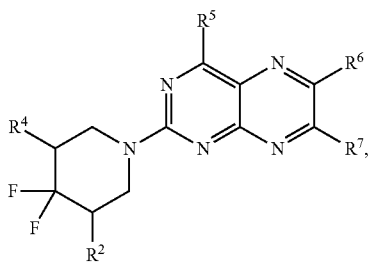

IIIc wherein each variable is as defined above and described in embodiments herein both singly and in combination.

Provided herein as Embodiment 55 is the compound according to Embodiment 1, 2, or 3, or a tautomer thereof, or a pharmaceutically acceptable salt of said compound or said tautomer, wherein the compound is a compound of Formula IIId:

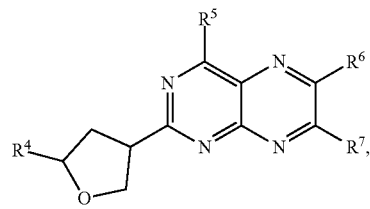

IIId wherein each variable is as defined above and described in embodiments herein both singly and in combination.

Provided herein as Embodiment 56 is the compound according to Embodiment 1, 2, or 3, or a tautomer thereof, or a pharmaceutically acceptable salt of said compound or said tautomer, wherein the compound is a compound of Formula IVa:

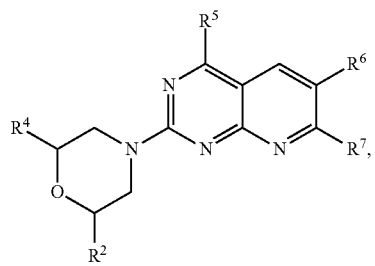

IVa wherein each variable is as defined above and described in embodiments herein both singly and in combination.

Provided herein as Embodiment 57 is the compound according to Embodiment 1, 2, or 3, or a tautomer thereof, or a pharmaceutically acceptable salt of said compound or said tautomer, wherein the compound is a compound of Formula IVb:

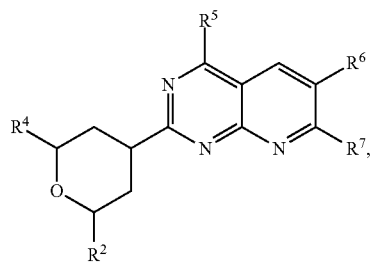

IVb wherein each variable is as defined above and described in embodiments herein both singly and in combination.

Provided herein as Embodiment 58 is the compound according to Embodiment 1, 2, or 3, or a tautomer thereof, or a pharmaceutically acceptable salt of said compound or said tautomer, wherein the compound is a compound of Formula IVc:

IVc

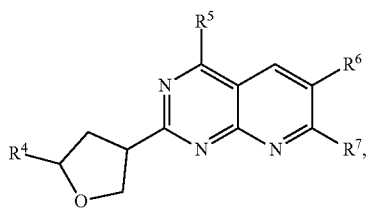

wherein each variable is as defined above and described in embodiments herein both singly and in combination.

Provided herein as Embodiment 59 is the compound according to Embodiment 1, 2, or 3, or a tautomer thereof, or a pharmaceutically acceptable salt of said compound or said tautomer, wherein the compound is a compound of Formula Va:

Va

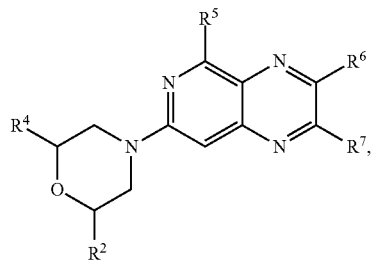

wherein each variable is as defined above and described in embodiments herein both singly and in combination.

Provided herein as Embodiment 60 is the compound according to Embodiment 1, 2, or 3, or a tautomer thereof, or a pharmaceutically acceptable salt of said compound or said tautomer, wherein the compound is a compound of Formula Vb:

Vb

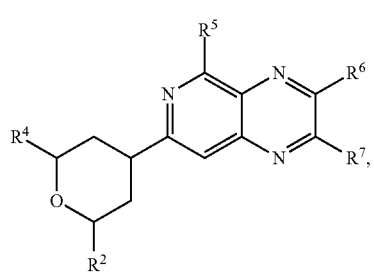

wherein each variable is as defined above and described in embodiments herein both singly and in combination.

Provided herein as Embodiment 61 is the compound according to Embodiment 1, 2, or 3, or a tautomer thereof, or a pharmaceutically acceptable salt of said compound or said tautomer, wherein the compound is a compound of Formula Vc:

Vc

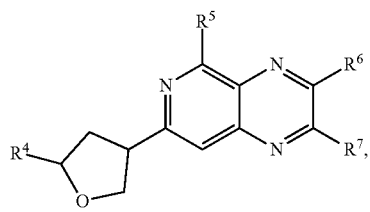

wherein each variable is as defined above and described in embodiments herein both singly and in combination.

Provided herein as Embodiment 62 is the compound according to Embodiment 1, 2, or 3, or a tautomer thereof, or a pharmaceutically acceptable salt of said compound or said tautomer, wherein the compound is a compound of Formula VIa:

VIa

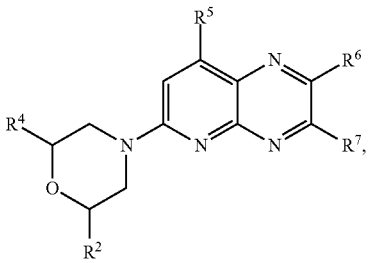

wherein each variable is as defined above and described in embodiments herein both singly and in combination.

Provided herein as Embodiment 63 is the compound according to Embodiment 1, 2, or 3, or a tautomer thereof, or a pharmaceutically acceptable salt of said compound or said tautomer, wherein the compound is a compound of Formula VIb:

VIb

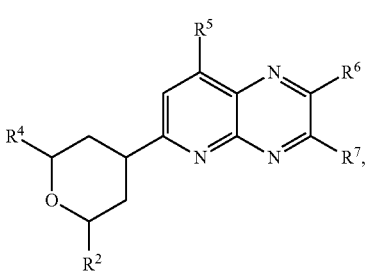

wherein each variable is as defined above and described in embodiments herein both singly and in combination.

Provided herein as Embodiment 64 is the compound according to Embodiment 1, 2, or 3, or a tautomer thereof, or a pharmaceutically acceptable salt of said compound or said tautomer, wherein the compound is a compound of Formula VIc:

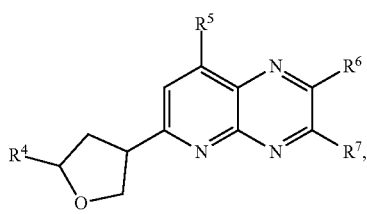

VIc wherein each variable is as defined above and described in embodiments herein both singly and in combination.

Provided herein as Embodiment 65 is the compound according to Embodiment 1, 2, or 3, or a tautomer thereof, or a pharmaceutically acceptable salt of said compound or said tautomer, wherein the compound is a compound of Formula VII:

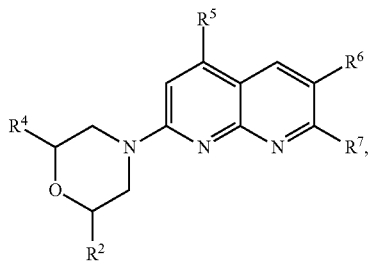

VII wherein each variable is as defined above and described in embodiments herein both singly and in combination.

Provided herein as Embodiment 66 is the compound according to Embodiment 1, 2, or 3, or a tautomer thereof, or a pharmaceutically acceptable salt of said compound or said tautomer, wherein the compound is a compound of Formula VIIIa:

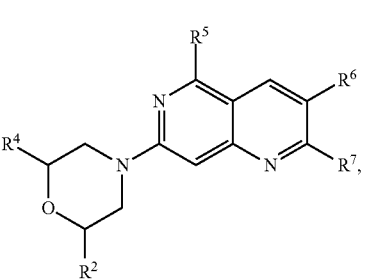

VIIIa wherein each variable is as defined above and described in embodiments herein both singly and in combination.

Provided herein as Embodiment 67 is the compound according to Embodiment 1, 2, or 3, or a tautomer thereof, or a pharmaceutically acceptable salt of said compound or said tautomer, wherein the compound is a compound of Formula VIIIb:

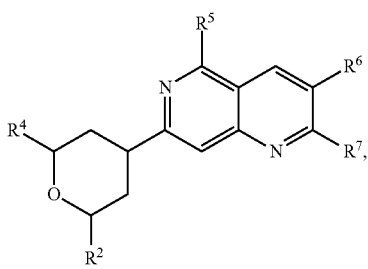

VIIIb wherein each variable is as defined above and described in embodiments herein both singly and in combination.

Provided herein as Embodiment 68 is the compound according to Embodiment 1, 2, or 3, or a tautomer thereof, or a pharmaceutically acceptable salt of said compound or said tautomer, wherein the compound is a compound of Formula VIIIc:

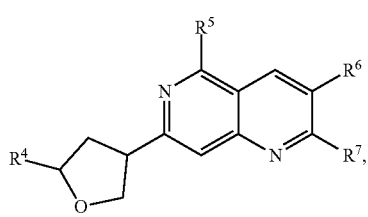

VIIIc wherein each variable is as defined above and described in embodiments herein both singly and in combination.

Provided herein as Embodiment 69 is the compound according to Embodiment 1, 2, or 3, or a tautomer thereof, or a pharmaceutically acceptable salt of said compound or said tautomer, wherein the compound is a compound of Formula IXa:

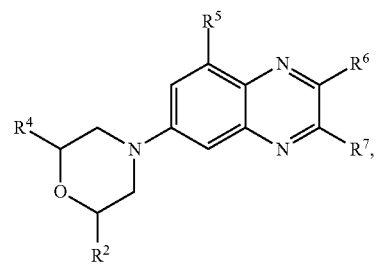

IXa wherein each variable is as defined above and described in embodiments herein both singly and in combination.

Provided herein as Embodiment 70 is the compound according to Embodiment 1, 2, or 3, or a tautomer thereof, or a pharmaceutically acceptable salt of said compound or said tautomer, wherein the compound is a compound of Formula IXb:

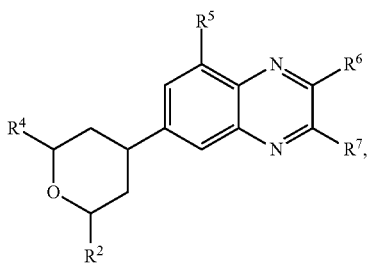

IXb wherein each variable is as defined above and described in embodiments herein both singly and in combination.

Provided herein as Embodiment 71 is the compound according to Embodiment 1, 2, or 3, or a tautomer thereof, or a pharmaceutically acceptable salt of said compound or said tautomer, wherein the compound is a compound of Formula IXc:

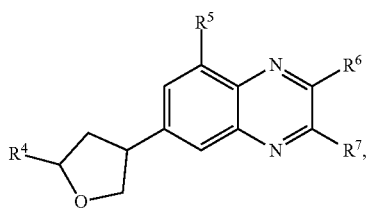

IXc wherein each variable is as defined above and described in embodiments herein both singly and in combination.

Provided herein as Embodiment 72 is the compound according to Embodiment 1 or 2, or a tautomer thereof, or a pharmaceutically acceptable salt of said compound or said tautomer, wherein the compound is a compound of Formula X:

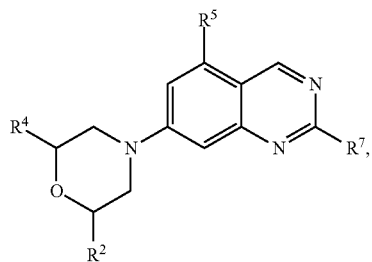

X wherein each variable is as defined above and described in embodiments herein both singly and in combination.

Provided herein as Embodiment 73 is the compound according to Embodiment 1, 2, or 3, or a tautomer thereof, or a pharmaceutically acceptable salt of said compound or said tautomer, wherein the compound is a compound of Formula XI:

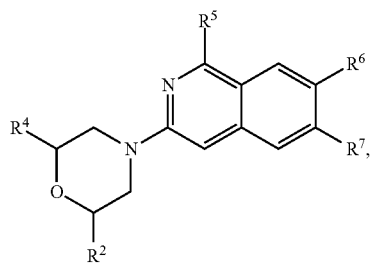

XI wherein each variable is as defined above and described in embodiments herein both singly and in combination.

Provided herein as Embodiment 74 is the compound according to Embodiment 1 or 2, or a tautomer thereof, or a pharmaceutically acceptable salt of said compound or said tautomer, wherein the compound is a compound of Formula XII:

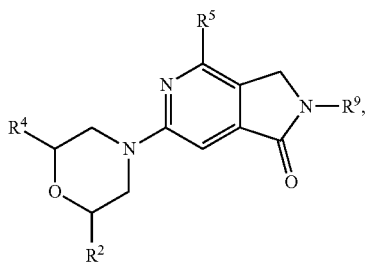

XII wherein each variable is as defined above and described in embodiments herein both singly and in combination.

Provided herein as Embodiment 75 is the compound according to any one of Embodiments 1-74, or a tautomer thereof, or a pharmaceutically acceptable salt of said compound or said tautomer, wherein $R^2$ is H or methyl.

Provided herein as Embodiment 76 is the compound according to any one of Embodiments 1-74, or a tautomer thereof, or a pharmaceutically acceptable salt of said compound or said tautomer, wherein $R^2$ is H.

Provided herein as Embodiment 77 is the compound according to any one of Embodiments 1-74, or a tautomer thereof, or a pharmaceutically acceptable salt of said compound or said tautomer, wherein $R^2$ is methyl.

Provided herein as Embodiment 78 is the compound according to any one of Embodiments 1-77, or a tautomer thereof, or a pharmaceutically acceptable salt of said compound or said tautomer, wherein $R^4$ is 5-membered heteroaryl or 6-membered heteroaryl; wherein the 5-membered heteroaryl or 6-membered heteroaryl group is optionally substituted with 1 to 3 substituents independently selected from $C_{1-6}$alkyl, $C_{1-6}$alkoxy, and $C_{3-6}$cycloalkyl.

Provided herein as Embodiment 79 is the compound according to any one of Embodiments 1-77, or a tautomer thereof, or a pharmaceutically acceptable salt of said compound or said tautomer, wherein $R^4$ is 5-membered heteroaryl or 6-membered heteroaryl; wherein the 5-membered heteroaryl or 6-membered heteroaryl group is optionally substituted with 1 to 3 substituents independently selected from $C_{1-6}$alkyl and $C_{3-6}$cycloalkyl. In some embodiments, $R^4$ is 5-membered heteroaryl optionally substituted with 1 to 3 substituents independently selected from $C_{1-6}$alkyl and $C_{3-6}$cycloalkyl. In some embodiments, $R^4$ is 6-membered heteroaryl optionally substituted with 1 to 3 substituents independently selected from $C_{1-6}$alkyl and $C_{3-6}$cycloalkyl.

Provided herein as Embodiment 80 is the compound according to any one of Embodiments 1-77, or a tautomer thereof, or a pharmaceutically acceptable salt of said compound or said tautomer, wherein $R^4$ is methyl, tetrahydrofuran-3-yl,

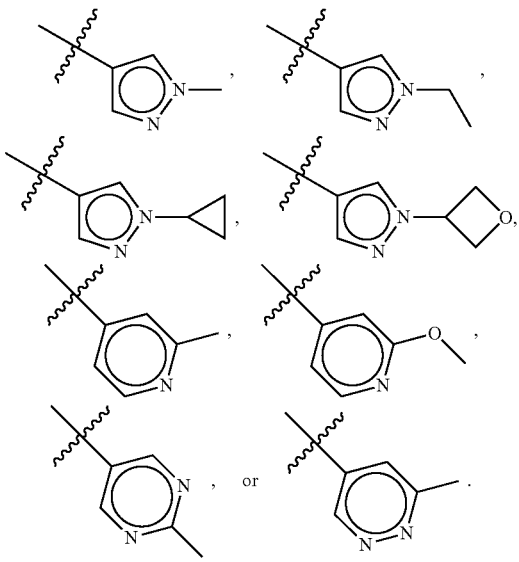

Provided herein as Embodiment 81 is the compound according to any one of Embodiments 1-77, or a tautomer thereof, or a pharmaceutically acceptable salt of said compound or said tautomer, wherein $R^4$ is methyl, tetrahydrofuran-3-yl,

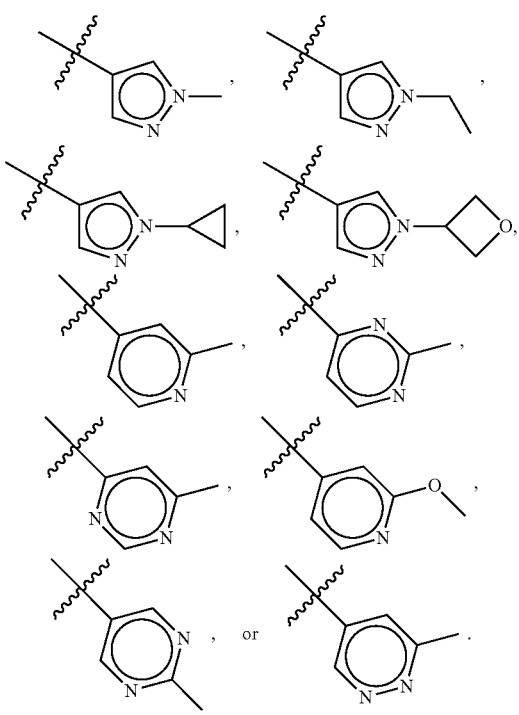

Provided herein as Embodiment 82 is the compound according to any one of Embodiments 1-77, or a tautomer thereof, or a pharmaceutically acceptable salt of said compound or said tautomer, wherein $R^4$ is

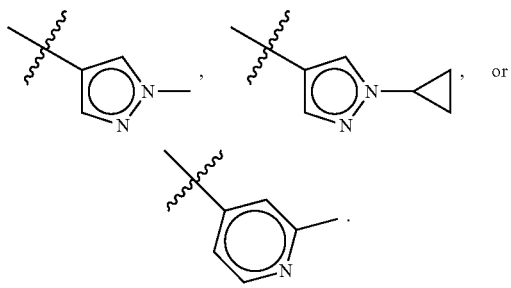

Provided herein as Embodiment 83 is the compound according to any one of Embodiments 1-77, or a tautomer thereof, or a pharmaceutically acceptable salt of said compound or said tautomer, wherein $R^4$ is

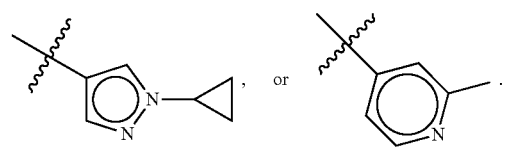

Provided herein as Embodiment 84 is the compound according to any one of Embodiments 1-77, or a tautomer thereof, or a pharmaceutically acceptable salt of said compound or said tautomer, wherein $R^4$ is

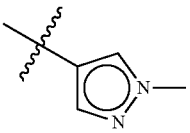

Provided herein as Embodiment 85 is the compound according to any one of Embodiments 1-77, or a tautomer thereof, or a pharmaceutically acceptable salt of said compound or said tautomer, wherein $R^4$ is

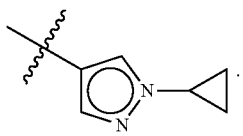

Provided herein as Embodiment 86 is the compound according to any one of Embodiments 1-77, or a tautomer thereof, or a pharmaceutically acceptable salt of said compound or said tautomer, wherein $R^4$ is

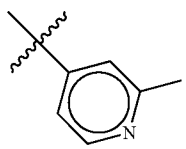

Provided herein as Embodiment 87 is the compound according to any one of Embodiments 1-86, or a tautomer thereof, or a pharmaceutically acceptable salt of said compound or said tautomer, wherein $R^5$ is $C_{1-6}$haloalkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-(C$_{3-6}$cycloalkyl), wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH$_2$-(C$_{3-6}$cycloalkyl) is further substituted with 1 to 4 substituents independently selected from halogen, $C_{1-3}$alkyl, $C_{1-3}$haloalkyl, and $C_{1-3}$alkoxy.

In some embodiments, $R^5$ is $C_{1-6}$haloalkyl. In some embodiments, $R^5$ is $C_{3-6}$cycloalkyl optionally substituted with 1 to 4 substituents independently selected from halogen, $C_{1-3}$alkyl, and $C_{1-3}$haloalkyl. In some embodiments, $R^5$ is $C_{5-8}$spiroalkyl optionally substituted with 1 to 4 substituents independently selected from halogen, $C_{1-3}$alkyl, and $C_{1-3}$haloalkyl. In some embodiments, $R^5$ is $C_{5-8}$tricycloalkyl optionally substituted with 1 to 4 substituents independently selected from halogen, $C_{1-3}$alkyl, and $C_{1-3}$haloalkyl. In some embodiments, $R^5$ is cyclopent-1-en-1-yl optionally substituted with 1 to 4 substituents independently selected from halogen, $C_{1-3}$alkyl, and $C_{1-3}$haloalkyl. In some embodiments, $R^5$ is cyclohex-1-en-1-yl optionally substituted with 1 to 4 substituents independently selected from halogen, $C_{1-3}$alkyl, and $C_{1-3}$haloalkyl. In some embodiments, $R^5$ is phenyl optionally substituted with 1 to 4 substituents independently selected from halogen, $C_{1-3}$alkyl, and $C_{1-3}$haloalkyl. In some embodiments, $R^5$ is 6-membered heteroaryl optionally substituted with 1 to 4 substituents independently selected from halogen, $C_{1-3}$alkyl, and $C_{1-3}$haloalkyl. In some embodiments, $R^5$ is aziridine-1-yl substituted with 1 to 4 substituents independently selected from halogen, $C_{1-3}$alkyl, $C_{1-3}$haloalkyl, and $C_{1-3}$alkoxy. In some embodiments, $R^5$ is pyrrolidine-1-yl substituted with 1 to 4 substituents independently selected from halogen, $C_{1-3}$alkyl, $C_{1-3}$haloalkyl, and $C_{1-3}$alkoxy. In some embodiments, $R^5$ is azabicyclo[3.1.0]hexan-3-yl substituted with 1 to 4 substituents independently selected from halogen, $C_{1-3}$alkyl, $C_{1-3}$haloalkyl, and $C_{1-3}$alkoxy. In some embodiments, $R^5$ is piperidine-1-yl substituted with 1 to 4 substituents independently selected from halogen, $C_{1-3}$alkyl, $C_{1-3}$haloalkyl, and $C_{1-3}$alkoxy. In some embodiments, $R^5$ is —OCH$_2$-(C$_{3-6}$cycloalkyl) substituted with 1 to 4 substituents independently selected from halogen, $C_{1-3}$alkyl, $C_{1-3}$haloalkyl, and $C_{1-3}$alkoxy.

Provided herein as Embodiment 88 is the compound according to any one of Embodiments 1-86, or a tautomer thereof, or a pharmaceutically acceptable salt of said compound or said tautomer, wherein $R^5$ is —CH$_2$CH$_2$CF$_3$, optionally substituted $C_{3-6}$cycloalkyl, optionally substituted spiro[3.3]heptanyl, optionally substituted spiro[5.2]octanyl, optionally substituted

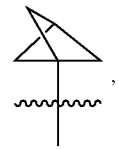 [SMILES: *C12CC(C1)C2]

optionally substituted cyclopent-1-en-1-yl, optionally substituted cyclohex-1-en-1-yl, optionally substituted phenyl, optionally substituted pyridinyl, substituted aziridine-1-yl, substituted pyrrolidine-1-yl, substituted azabicyclo[3.1.0]hexan-3-yl, substituted piperidine-1-yl, or substituted —OCH$_2$-(C$_{3-4}$cycloalkyl). In some embodiments, $R^5$ is —CH$_2$CH$_2$CF$_3$. In some embodiments, $R^5$ is optionally substituted $C_{3-6}$cycloalkyl. In some embodiments, $R^5$ is optionally substituted spiro[3.3]heptanyl. In some embodiments, $R^5$ is optionally substituted spiro[5.2]octanyl. In some embodiments, $R^5$ is optionally substituted

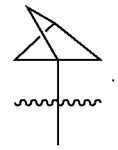 [SMILES: *C12CC(C1)C2]

. In some embodiments, $R^5$ is optionally substituted cyclopent-1-en-1-yl. In some embodiments, $R^5$ is optionally substituted cyclohex-1-en-1-yl. In some embodiments, $R^5$ is optionally substituted phenyl. In some embodiments, $R^5$ is optionally substituted pyridinyl. In some embodiments, $R^5$ is optionally substituted aziridine-1-yl. In some embodiments, $R^5$ is optionally substituted pyrrolidine-1-yl. In some embodiments, $R^5$ is optionally substituted azabicyclo[3.1.0]hexan-3-yl. In some embodiments, $R^5$ is optionally substituted piperidine-1-yl. In some embodiments, $R^5$ is optionally substituted —OCH$_2$-(C$_{3-4}$cycloalkyl).

Provided herein as Embodiment 89 is the compound according to any one of Embodiments 1-86, or a tautomer thereof, or a pharmaceutically acceptable salt of said compound or said tautomer, wherein $R^5$ is —CH$_2$CH$_2$CF$_3$,

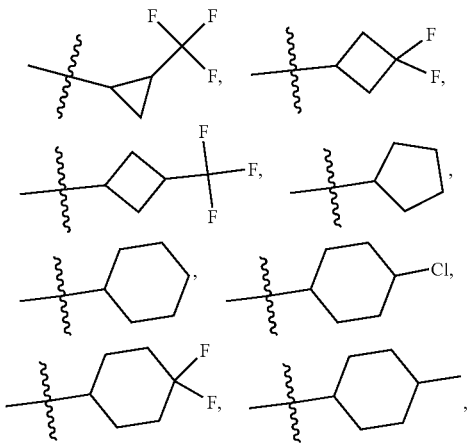

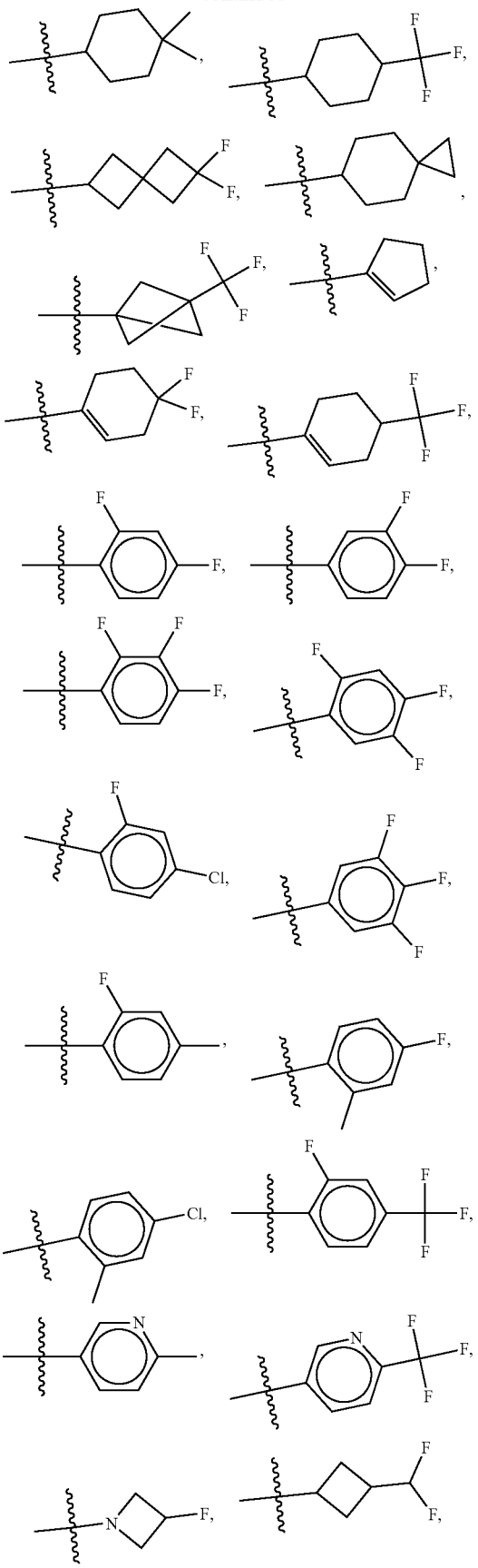
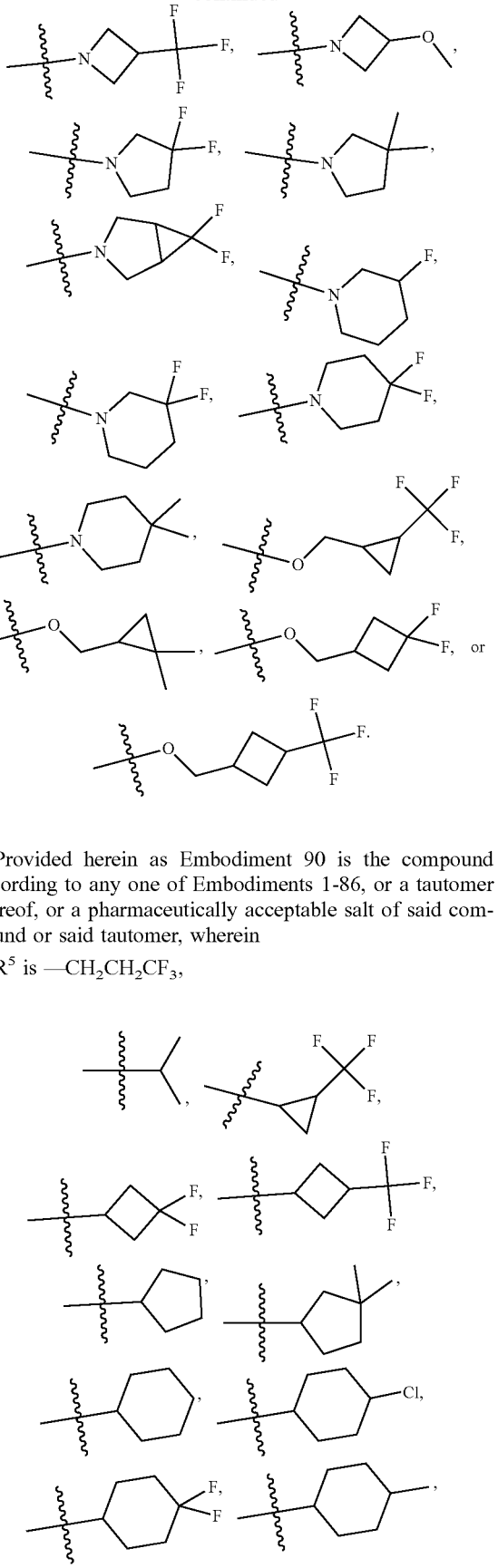
Provided herein as Embodiment 90 is the compound according to any one of Embodiments 1-86, or a tautomer thereof, or a pharmaceutically acceptable salt of said compound or said tautomer, wherein
$R^5$ is —$CH_2CH_2CF_3$,

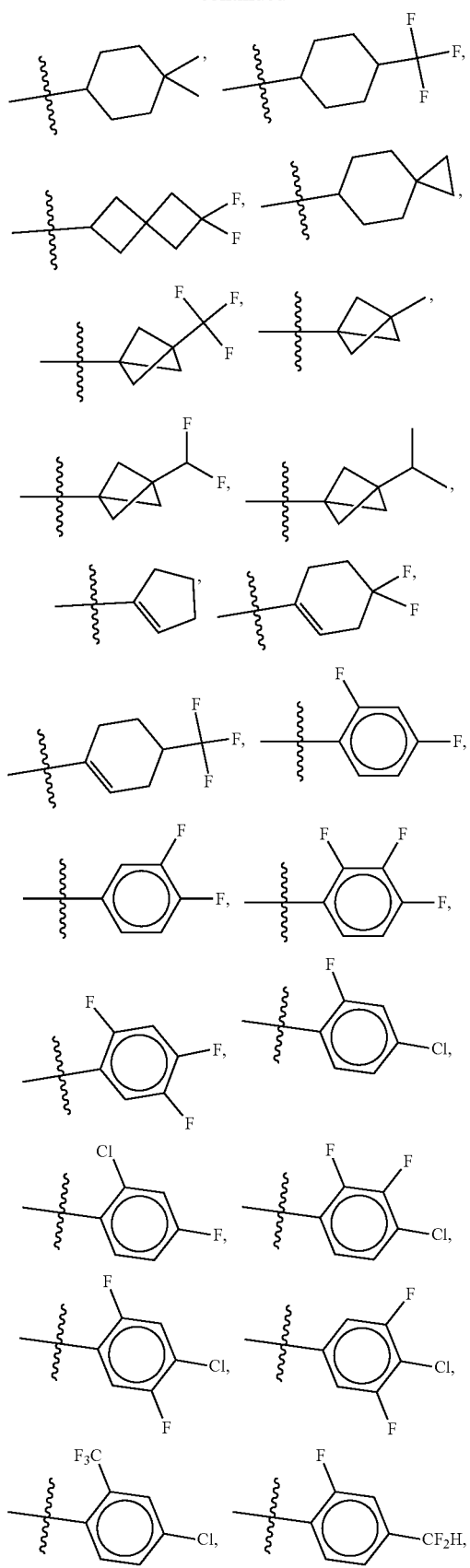
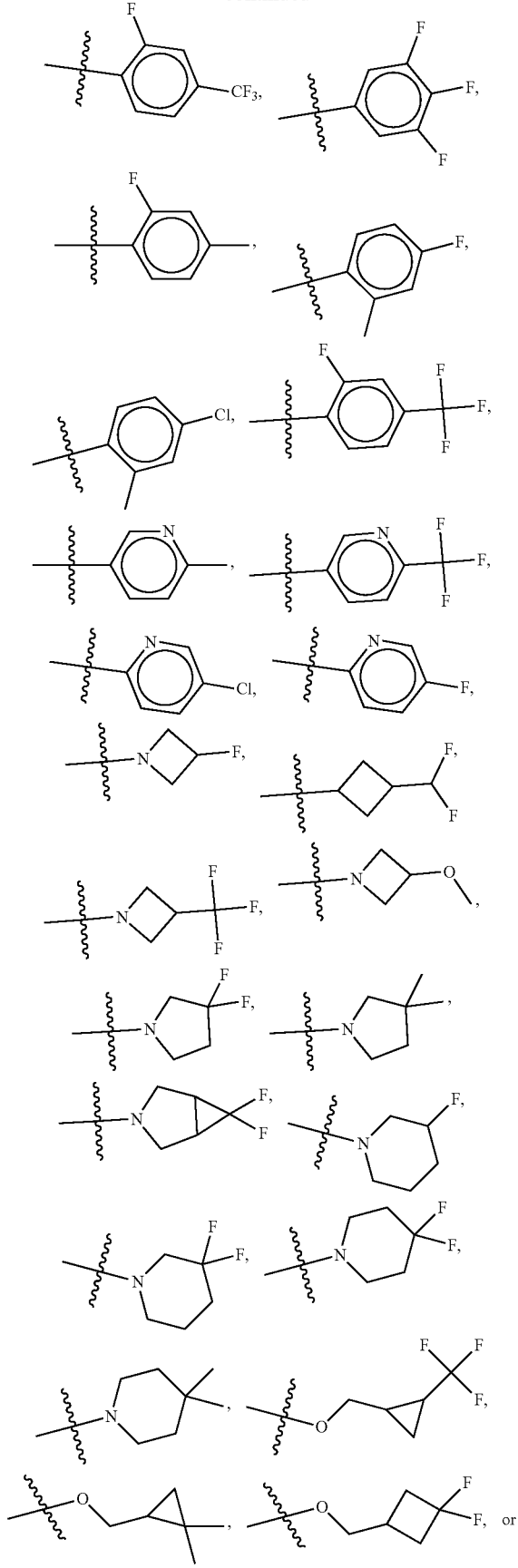

-continued

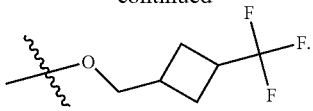

Provided herein as Embodiment 91 is the compound according to any one of Embodiments 1-86, or a tautomer thereof, or a pharmaceutically acceptable salt of said compound or said tautomer, wherein $R^5$ is optionally substituted phenyl.

Provided herein as Embodiment 92 is the compound according to any one of Embodiments 1-86, or a tautomer thereof, or a pharmaceutically acceptable salt of said compound or said tautomer, wherein $R^5$ is

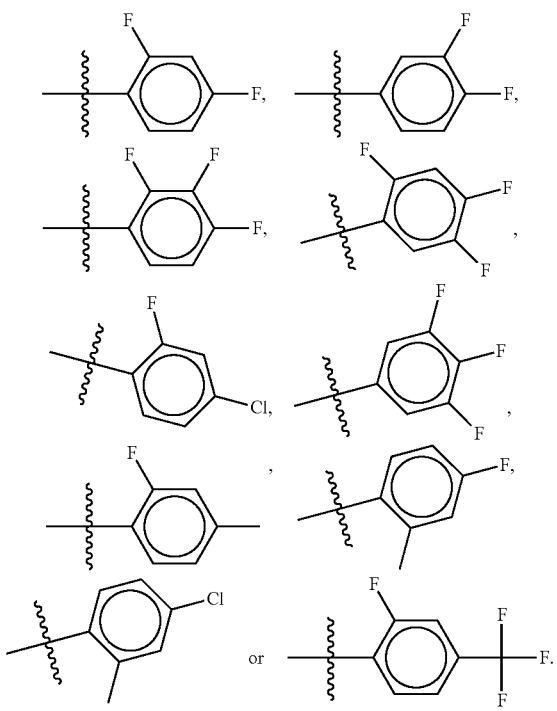

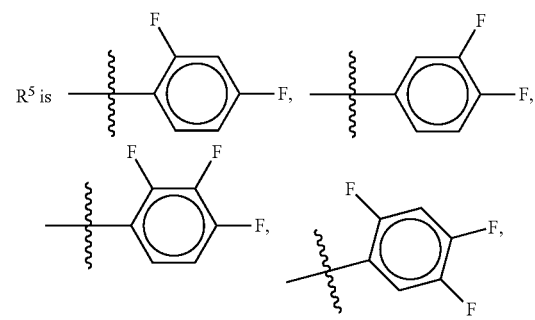

Provided herein as Embodiment 93 is the compound according to any one of Embodiments 1-86, or a tautomer thereof, or a pharmaceutically acceptable salt of said compound or said tautomer, wherein $R^5$ is -continued

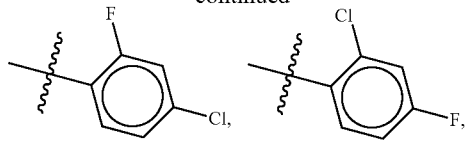

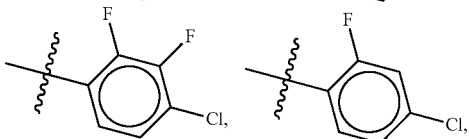


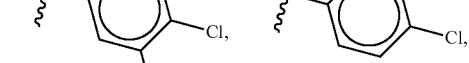

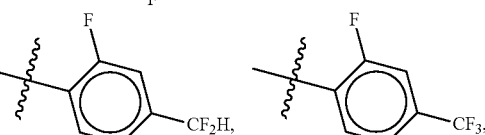

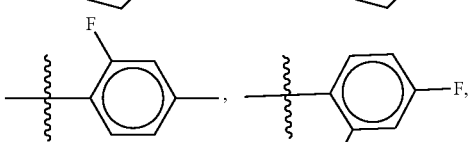

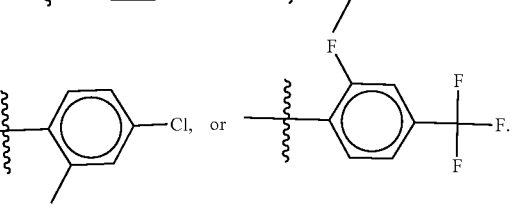

Provided herein as Embodiment 94 is the compound according to any one of Embodiments 1-86, or a tautomer thereof, or a pharmaceutically acceptable salt of said compound or said tautomer, wherein $R^5$ is

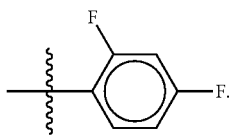

Provided herein as Embodiment 95 is the compound according to any one of Embodiments 1-86, or a tautomer thereof, or a pharmaceutically acceptable salt of said compound or said tautomer, $R^5$ is

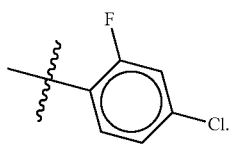

Provided herein as Embodiment 96 is the compound according to any one of Embodiments 1-86, or a tautomer thereof, or a pharmaceutically acceptable salt of said compound or said tautomer, wherein R⁵ is

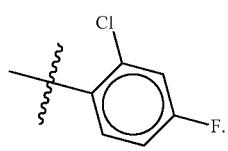

Provided herein as Embodiment 97 is the compound according to any one of Embodiments 1-86, or a tautomer thereof, or a pharmaceutically acceptable salt of said compound or said tautomer, wherein R⁵ is 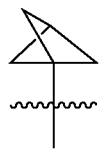.

Provided herein as Embodiment 98 is the compound according to any one of Embodiments 1-86, or a tautomer thereof, or a pharmaceutically acceptable salt of said compound or said tautomer, wherein R⁵ is optionally substituted $C_{3-6}$cycloalkyl, optionally substituted spiro[3.3]heptanyl, optionally substituted spiro[5.2]octanyl, or optionally substituted Provided herein as Embodiment 99 is the compound according to any one of Embodiments 1-86, or a tautomer thereof, or a pharmaceutically acceptable salt of said compound or said tautomer, wherein R⁵ is

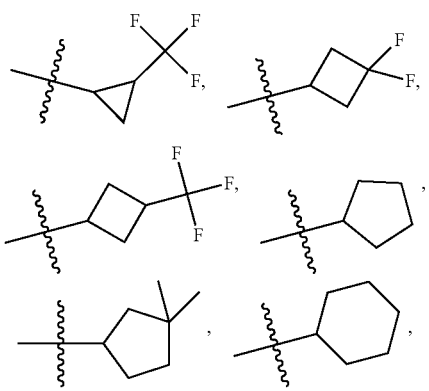

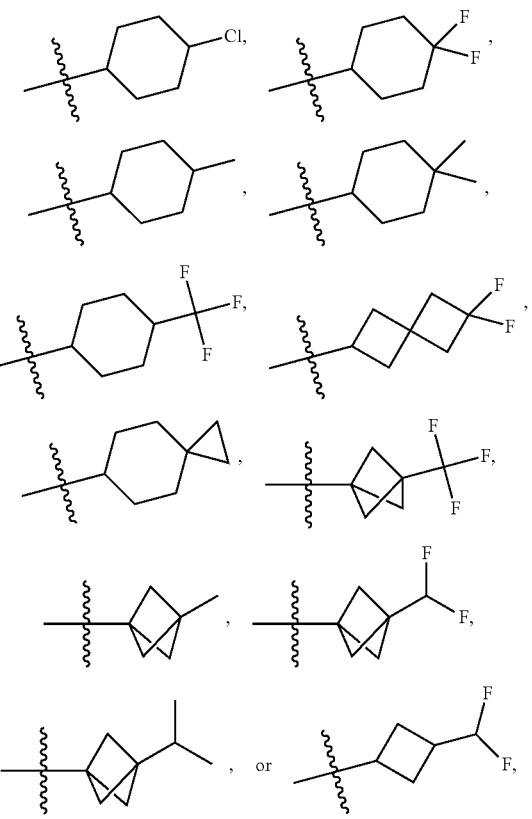

In some embodiments, R⁵ is

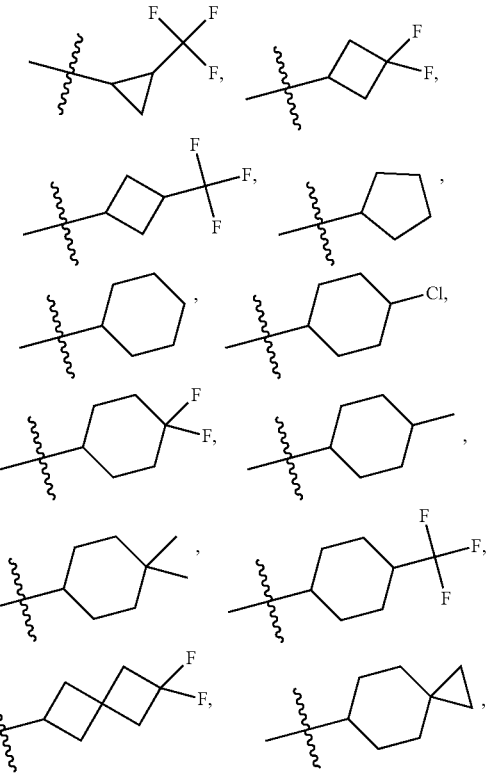

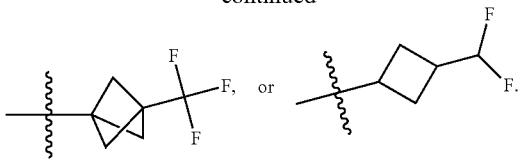

Provided herein as Embodiment 100 is the compound according to any one of Embodiments 1-86, or a tautomer thereof, or a pharmaceutically acceptable salt of said compound or said tautomer, wherein
$R^5$ is

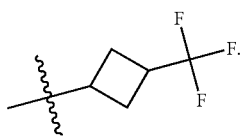 [SMILES: *C1CC(C(F)(F)F)C1]

Provided herein as Embodiment 101 is the compound according to any one of Embodiments 1-86, or a tautomer thereof, or a pharmaceutically acceptable salt of said compound or said tautomer, wherein
$R^5$ is

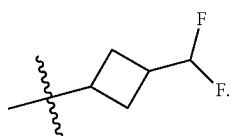 [SMILES: *C1CC(C(F)F)C1]

Provided herein as Embodiment 102 is the compound according to any one of Embodiments 1-86, or a tautomer thereof, or a pharmaceutically acceptable salt of said compound or said tautomer, wherein
$R^5$ is

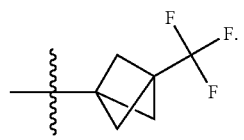

Provided herein as Embodiment 103 is the compound according to any one of Embodiments 1-86, or a tautomer thereof, or a pharmaceutically acceptable salt of said compound or said tautomer, wherein $R^5$ is optionally substituted cyclopent-1-en-1-yl, or optionally substituted cyclohex-1-en-1-yl.

Provided herein as Embodiment 104 is the compound according to any one of Embodiments 1-86, or a tautomer thereof, or a pharmaceutically acceptable salt of said compound or said tautomer, wherein
$R^5$ is

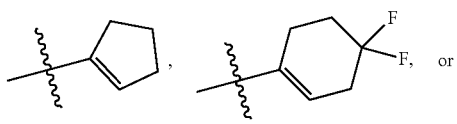

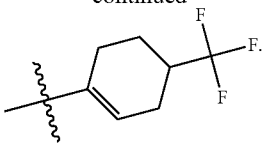

Provided herein as Embodiment 105 is the compound according to any one of Embodiments 1-86, or a tautomer thereof, or a pharmaceutically acceptable salt of said compound or said tautomer, wherein $R^5$ is optionally substituted pyridinyl.

Provided herein as Embodiment 106 is the compound according to any one of Embodiments 1-86, or a tautomer thereof, or a pharmaceutically acceptable salt of said compound or said tautomer, wherein
$R^5$ is

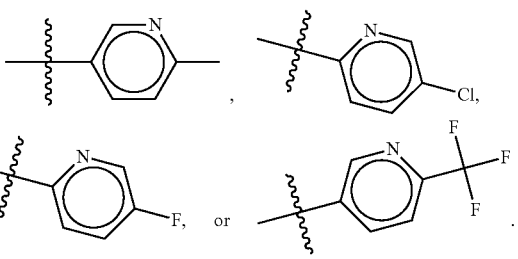

Provided herein as Embodiment 107 is the compound according to any one of Embodiments 1-86, or a tautomer thereof, or a pharmaceutically acceptable salt of said compound or said tautomer, wherein $R^5$ is substituted aziridine-1-yl, substituted pyrrolidine-1-yl, substituted azabicyclo[3.1.0]hexan-3-yl, or substituted piperidine-1-yl.

Provided herein as Embodiment 108 is the compound according to any one of Embodiments 1-86, or a tautomer thereof, or a pharmaceutically acceptable salt of said compound or said tautomer, wherein $R^5$ is 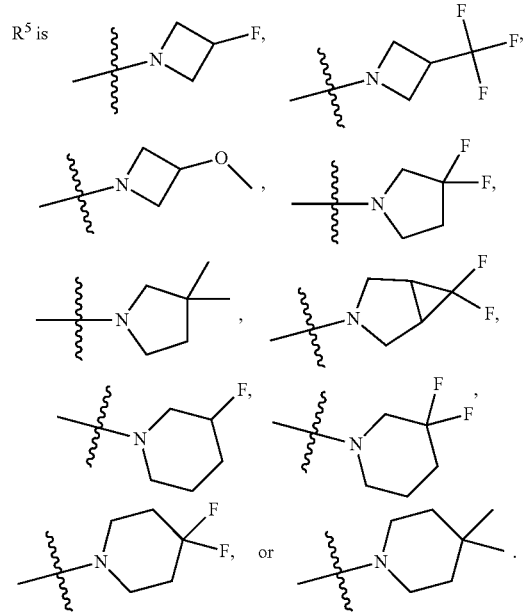

Provided herein as Embodiment 109 is the compound according to any one of Embodiments 1-86, or a tautomer thereof, or a pharmaceutically acceptable salt of said compound or said tautomer, wherein
$R^5$ is

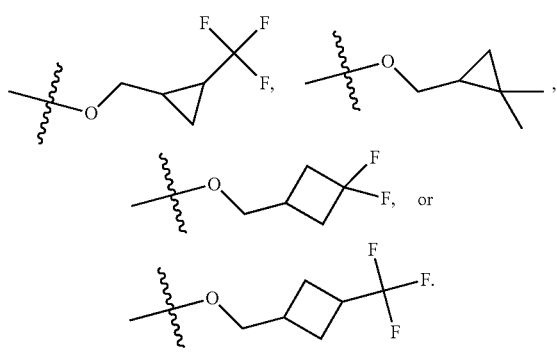

Provided herein as Embodiment 110 is the compound according to any one of Embodiments 1-109, or a tautomer thereof, or a pharmaceutically acceptable salt of said compound or said tautomer, wherein $R^6$ is H, chlorine, or methyl.

Provided herein as Embodiment 111 is the compound according to any one of Embodiments 1-109, or a tautomer thereof, or a pharmaceutically acceptable salt of said compound or said tautomer, wherein $R^6$ is H or methyl.

Provided herein as Embodiment 112 is the compound according to any one of Embodiments 1-109, or a tautomer thereof, or a pharmaceutically acceptable salt of said compound or said tautomer, wherein $R^6$ is H.

Provided herein as Embodiment 113 is the compound according to any one of Embodiments 1-109, or a tautomer thereof, or a pharmaceutically acceptable salt of said compound or said tautomer, wherein $R^6$ is methyl.

Provided herein as Embodiment 114 is the compound according to any one of Embodiments 1-113, or a tautomer thereof, or a pharmaceutically acceptable salt of said compound or said tautomer, wherein $R^7$ is H, methyl, or ethyl.

Provided herein as Embodiment 115 is the compound according to any one of Embodiments 1-113, or a tautomer thereof, or a pharmaceutically acceptable salt of said compound or said tautomer, wherein $R^7$ is H.

Provided herein as Embodiment 116 is the compound according to any one of Embodiments 1-113, or a tautomer thereof, or a pharmaceutically acceptable salt of said compound or said tautomer, wherein $R^7$ is methyl.

Provided herein as Embodiment 117 is the compound according to any one of Embodiments 1-113, or a tautomer thereof, or a pharmaceutically acceptable salt of said compound or said tautomer, wherein $R^7$ is ethyl.

Provided herein as Embodiment 118 is the compound according to any one of Embodiments 1-109, or a tautomer thereof, or a pharmaceutically acceptable salt of said compound or said tautomer, wherein $R^6$ is H or methyl and $R^7$ is H or methyl.

Provided herein as Embodiment 119 is the compound according to any one of Embodiments 1-109, or a tautomer thereof, or a pharmaceutically acceptable salt of said compound or said tautomer, wherein $R^6$ is H or methyl and $R^7$ is methyl.

Provided herein as Embodiment 120 is the compound according to any one of Embodiments 1-109, or a tautomer thereof, or a pharmaceutically acceptable salt of said compound or said tautomer, wherein $R^6$ is H and $R^7$ is methyl.

Provided herein as Embodiment 121 is the compound according to any one of Embodiments 1-109, or a tautomer thereof, or a pharmaceutically acceptable salt of said compound or said tautomer, wherein $R^6$ is methyl and $R^7$ is methyl.

Provided herein as Embodiment 122 is the compound according to any one of Embodiments 1-109, or a tautomer thereof, or a pharmaceutically acceptable salt of said compound or said tautomer, wherein $R^6$ is Cl and $R^7$ is methyl.

Provided herein as Embodiment 123 is the compound according to any one of Embodiments 1-109, or a tautomer thereof, or a pharmaceutically acceptable salt of said compound or said tautomer, wherein $R^6$ is H and $R^7$ is ethyl.

Provided herein as Embodiment 124 is the compound according to any one of Embodiments 1-109, or a tautomer thereof, or a pharmaceutically acceptable salt of said compound or said tautomer, wherein $R^9$ is H, methyl, ethyl, or iso-propyl.

Provided herein as Embodiment 125 is the compound according to any one of Embodiments 1-109, or a tautomer thereof, or a pharmaceutically acceptable salt of said compound or said tautomer, wherein $R^9$ is methyl, ethyl, or iso-propyl.

Provided herein as Embodiment 126 is the compound according to any one of Embodiments 1-125125, or a tautomer thereof, or a pharmaceutically acceptable salt of said compound or said tautomer, wherein $R^2$ is H or methyl; $R^4$ is

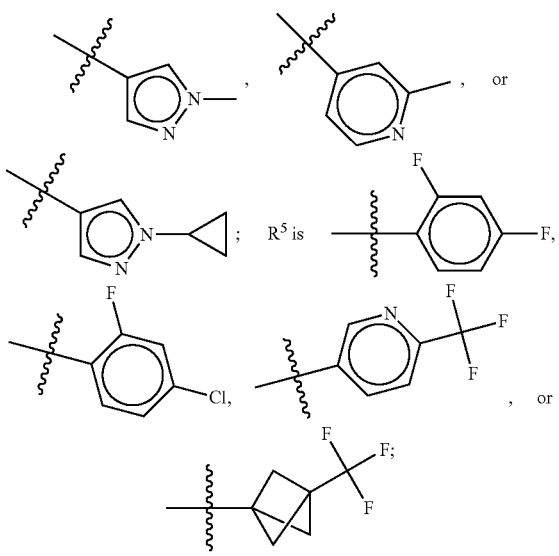

$R^6$ is H or methyl and $R^7$ is methyl.

Provided herein as Embodiment 127 is the compound according to any one of Embodiments 1-125, or a tautomer thereof, or a pharmaceutically acceptable salt of said compound or said tautomer, wherein $R^2$ is H or methyl; $R^4$ is

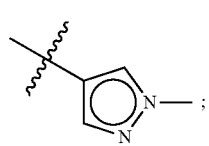

R⁵ is

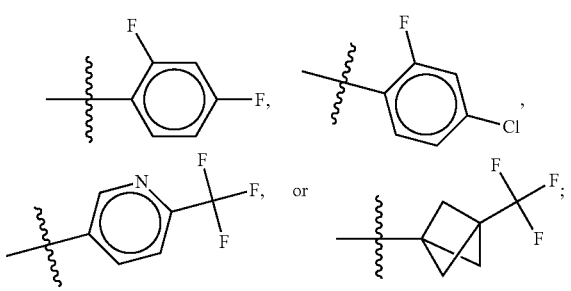

R⁶ is H or methyl and R⁷ is methyl.

Provided herein as Embodiment 128 is the compound according to any one of Embodiments 1-125, or a tautomer thereof, or a pharmaceutically acceptable salt of said compound or said tautomer, wherein R² is H or methyl; R⁴ is

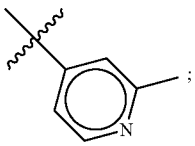

R⁵ is

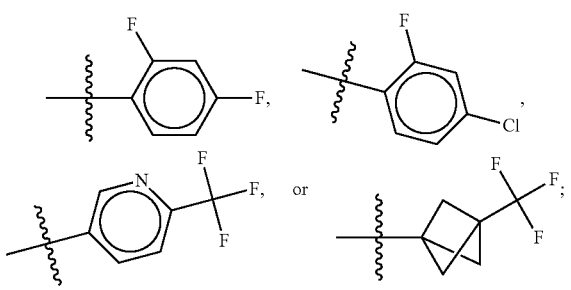

R⁶ is H or methyl and R⁷ is methyl.

Provided herein as Embodiment 129 is the compound according to any one of Embodiments 1-125, or a tautomer thereof, or a pharmaceutically acceptable salt of said compound or said tautomer, wherein R² is H or methyl; R⁴ is

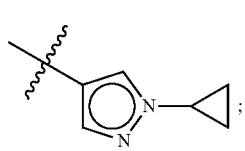

R⁵ is

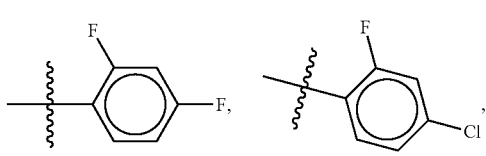

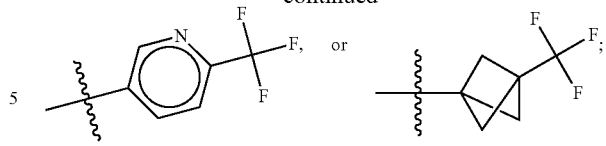

R⁶ is H or methyl and R⁷ is methyl.

Provided herein as Embodiment 130 is the compound according to any one of Embodiments 1-125, or a tautomer thereof, or a pharmaceutically acceptable salt of said compound or said tautomer, wherein R² is H or methyl; R⁴ is

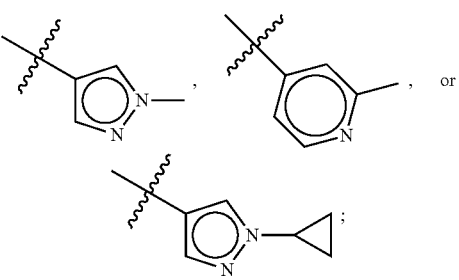

R⁵ is

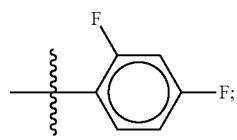

R⁶ is H or methyl and R⁷ is methyl.

Provided herein as Embodiment 131 is the compound according to any one of Embodiments 1-125, or a tautomer thereof, or a pharmaceutically acceptable salt of said compound or said tautomer, wherein R² is H or methyl; R⁴ is

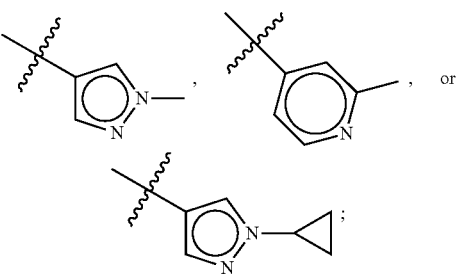

R⁵ is

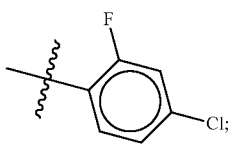

R⁶ is H or methyl and R⁷ is methyl.

Provided herein as Embodiment 132 is the compound according to any one of Embodiments 1-125, or a tautomer thereof, or a pharmaceutically acceptable salt of said compound or said tautomer, wherein $R^2$ is H or methyl; $R^4$ is

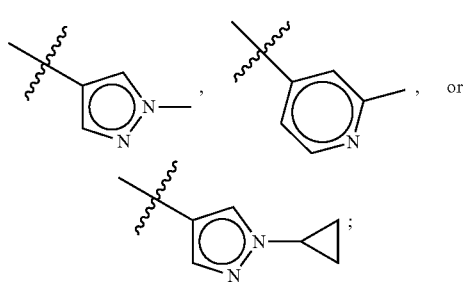

$R^5$ is

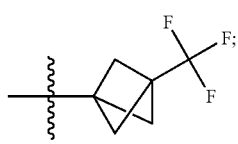 [SMILES: *C12CC(C(F)(F)F)(C1)C2]

$R^6$ is H or methyl and $R^7$ is methyl.

Provided herein as Embodiment 133 is the compound according to any one of Embodiments 1-125, or a tautomer thereof, or a pharmaceutically acceptable salt of said compound or said tautomer, wherein $R^2$ is H or methyl; $R^4$ is

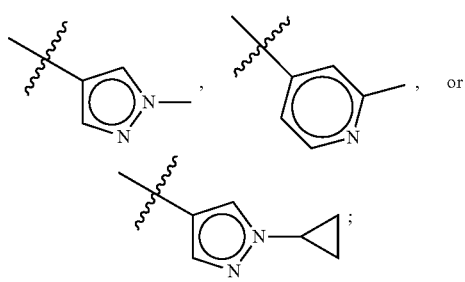

$R^5$ is

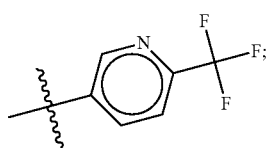

$R^6$ is H or methyl and $R^7$ is methyl.

Provided herein as Embodiment 134 is the compound according to any one of Embodiments 1-125, or a tautomer thereof, or a pharmaceutically acceptable salt of said compound or said tautomer, wherein $R^2$ is H or methyl; $R^4$ is

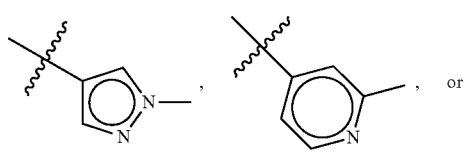

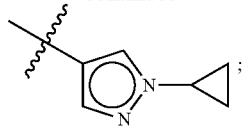

$R^5$ is

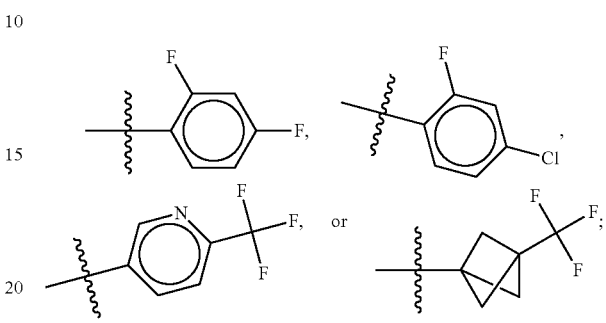

and $R^9$ is methyl, ethyl or iso-propyl.

Provided herein as Embodiment 135 is the compound according to any one of Embodiments 1-131, or a tautomer thereof, or a pharmaceutically acceptable salt of said compound or said tautomer, wherein at least one hydrogen atom of the compound is a deuterium atom.

Provided herein as Embodiment 136 is the compound according to any one of Embodiments 1-131, or a tautomer thereof, or a pharmaceutically acceptable salt of said compound or said tautomer, wherein at least one $C_1$-$C_6$alkyl group of the compound is substituted with at least one deuterium atom.

Provided herein as Embodiment 137 is the compound according to any one of Embodiments 1-109, or a tautomer thereof, or a pharmaceutically acceptable salt of said compound or said tautomer, wherein $R^6$ is —$CD_3$.

Provided herein as Embodiment 138 is the compound according to any one of Embodiments 1-109, or a tautomer thereof, or a pharmaceutically acceptable salt of said compound or said tautomer, wherein $R^7$ is —$CD_3$.

Provided herein as Embodiment 139 is the compound according to any one of Embodiments 1-109, or a tautomer thereof, or a pharmaceutically acceptable salt of said compound or said tautomer, wherein $R^6$ and $R^7$ are both —$CD_3$.

Provided herein as Embodiment 140 is the compound according to Embodiment 1, 2, or 3, or a tautomer thereof, or a pharmaceutically acceptable salt of said compound or said tautomer, wherein the compound is a compound of Formula IIIa

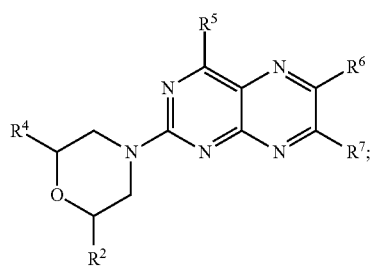

IIIa wherein
R² is H or methyl;
R⁴ is [structures: pyrazole-N-cyclopropyl; methylpyridine; methoxypyridine], or [continued: bicyclopentane-CF₃]; and when R⁴ is [pyridine structure]

and R² is H, R⁵ is not [structures: fluorochlorophenyl, fluoromethylphenyl, difluorophenyl, pyridine-CF₃, cyclobutyl-CF₃, cyclobutyl-CHF₂, spiro-difluoro, or bicyclopentane-CF₃].

R⁵ is C₃₋₆cycloalkyl, C₅₋₈spiroalkyl, C₅₋₈tricycloalkyl, cyclopent-1-en-1-yl, cyclohex-1-en-1-yl, phenyl, 6-membered heteroaryl, pyrrolidine-1-yl, 3-azabicyclo[3.1.0]hexan-3-yl, piperidine-1-yl, or —OCH₂-(C₃₋₆cycloalkyl),
wherein the C₃₋₆cycloalkyl, C₅₋₈spiroalkyl, C₅₋₈tricycloalkyl, cyclopent-1-en-1-yl, cyclohex-1-en-1-yl, phenyl, and 6-membered heteroaryl is further optionally substituted with 1 to 4 substituents independently selected from halogen, C₁₋₃alkyl, and C₁₋₃haloalkyl, and
wherein the aziridine-1-yl, pyrrolidine-1-yl, 3-azabicyclo[3.1.0]hexan-3-yl, piperidine-1-yl, and —OCH₂-(C₃₋₆cycloalkyl) is further substituted with 1 to 4 substituents independently selected from halogen, C₁₋₃alkyl, C₁₋₃haloalkyl, and C₁₋₃alkoxy;
R⁶ is H or methyl; and
R⁷ is methyl;
provided that:
when R⁴ is

[pyrazole-N-cyclopropyl structure]

and R² is H, R⁵ is not

[structures: fluorochlorophenyl, fluoromethylphenyl, difluorophenyl, pyridine-CF₃, cyclohexyl-CF₂, cyclobutyl-CF₃, cyclobutyl-CHF₂, spiro-difluoro], or Provided herein as Embodiment 141 is the compound according to Embodiment 1, 2, or 3, or a tautomer thereof, or a pharmaceutically acceptable salt of said compound or said tautomer, wherein the compound is a compound of Formula IIIa IIIa

[Morpholine-pyrimido-pyrazine structure with R², R⁴, R⁵, R⁶, R⁷ substituents]

wherein
R² is H or methyl;
R⁴ is

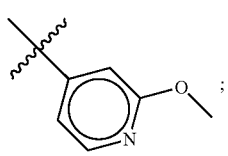

$R^5$ is $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-tl, pyrrolidine-1-yl, 3-azabicyclo[3.1.0]hexan-3-yl, piperidine-1-yl, or —OCH$_2$-(C$_{3-6}$cycloalkyl), wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH$_2$-(C$_{3-6}$cycloalkyl) is further substituted with 1 to 4 substituents independently selected from halogen, $C_{1-3}$alkyl, $C_{1-3}$haloalkyl, and $C_{1-3}$alkoxy;

$R^6$ is H or methyl; and $R^7$ is methyl.

Provided herein as Embodiment 142 is the compound according to Embodiment 1, 2, or 3, or a tautomer thereof, or a pharmaceutically acceptable salt of said compound or said tautomer, wherein the compound is a compound of Formula IIIa

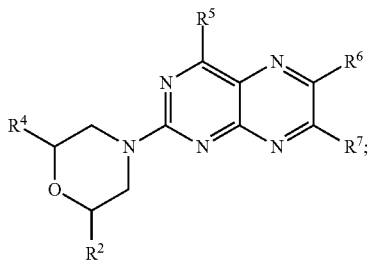

IIIa wherein $R^2$ is methyl;

$R^4$ is

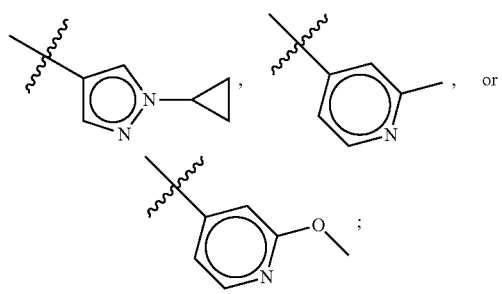

$R^5$ is $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-(C$_{3-6}$cycloalkyl), wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH$_2$-(C$_{3-6}$cycloalkyl) is further substituted with 1 to 4 substituents independently selected from halogen, $C_{1-3}$alkyl, $C_{1-3}$haloalkyl, and $C_{1-3}$alkoxy;

$R^6$ is H or methyl; and $R^7$ is methyl.

Provided herein as Embodiment 143 is the compound according to Embodiment 1, 2, or 3, or a tautomer thereof, or a pharmaceutically acceptable salt of said compound or said tautomer, wherein the compound is a compound of Formula IIIa

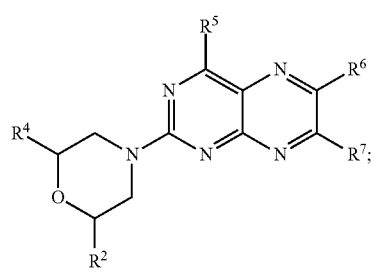

IIIa wherein $R^2$ is H or methyl;

$R^4$ is 5-membered heteroaryl or 6-membered heteroaryl; wherein the 5-membered heteroaryl or 6-membered heteroaryl group is optionally substituted with 1 to 3 substituents independently selected from $C_{1-6}$alkyl, $C_{1-6}$alkoxy, and $C_{3-6}$cycloalkyl;

$R^5$ is

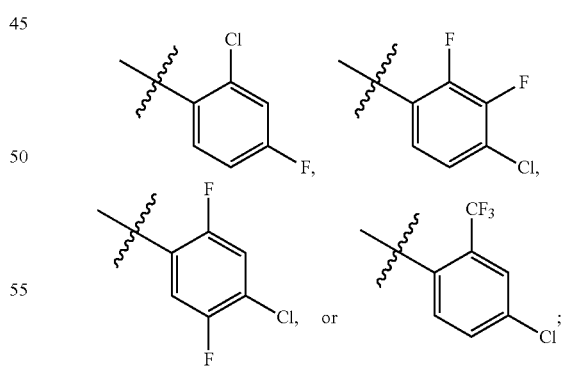

$R^6$ is H or methyl; and $R^7$ is methyl.

Provided herein as Embodiment 144 is the compound according to Embodiment 1, 2, or 3, or a tautomer thereof, or a pharmaceutically acceptable salt of said compound or said tautomer, wherein the compound is a compound of Formula IIIb

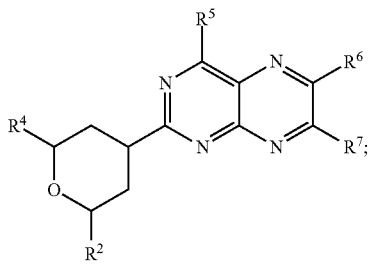

IIIb wherein
R² is H or methyl;
R⁴ is

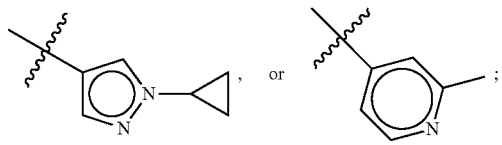

R⁵ is C₃₋₆cycloalkyl, C₅₋₈spiroalkyl, C₅₋₈tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-(C₃₋₆cycloalkyl),
  wherein the C₃₋₆cycloalkyl, C₅₋₈spiroalkyl, C₅₋₈tricycloalkyl, cyclopent-1-en-1-yl, cyclohex-1-en-1-yl, phenyl, and 6-membered heteroaryl is further optionally substituted with 1 to 4 substituents independently selected from halogen, C₁₋₃alkyl, and C₁₋₃haloalkyl, and
  wherein the aziridine-1-yl, pyrrolidine-1-yl, 3-azabicyclo[3.1.0]hexan-3-yl, piperidine-1-yl, and —OCH₂-(C₃₋₆cycloalkyl) is further substituted with 1 to 4 substituents independently selected from halogen, C₁₋₃alkyl, C₁₋₃haloalkyl, and C₁₋₃alkoxy;
R⁶ is H or methyl; and
R⁷ is methyl;
provided that:
when R⁴ is

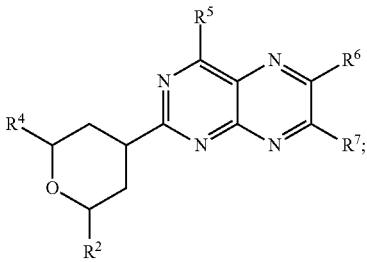

R⁵ is not

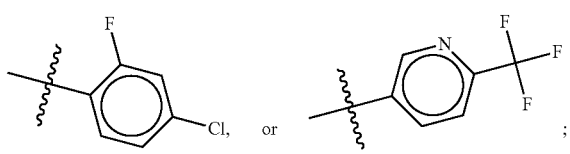

when R⁴ is

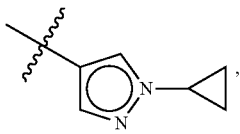

and R² is H, R⁵ is not

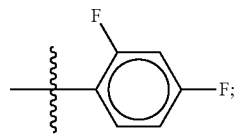

and
when R⁴ is

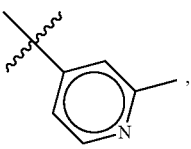

R⁵ is not

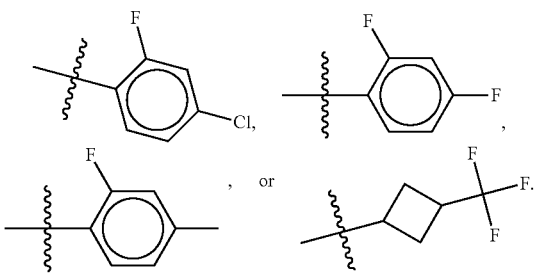

Provided herein as Embodiment 145 is the compound according to Embodiment 1, 2, or 3, or a tautomer thereof, or a pharmaceutically acceptable salt of said compound or said tautomer, wherein the compound is a compound of Formula IIIb IIIb wherein
R² is H or methyl;
R⁴ is 5-membered heteroaryl or 6-membered heteroaryl;
wherein the 5-membered heteroaryl or 6-membered heteroaryl group is optionally substituted with 1 to 3 substituents independently selected from $C_{1-6}$alkyl, $C_{1-6}$alkoxy, and $C_{3-6}$cycloalkyl;

$R^5$ is

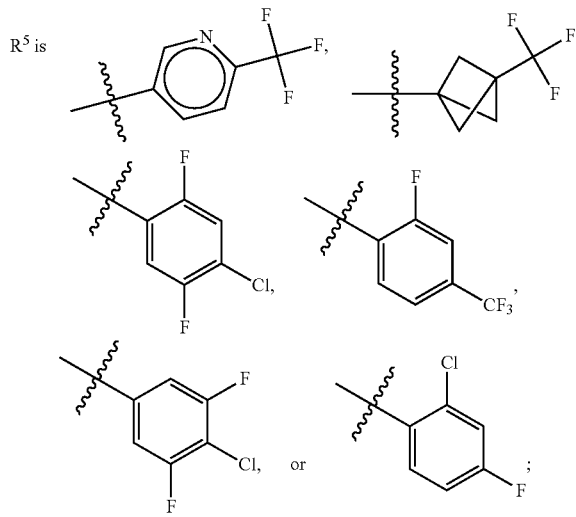

$R^6$ is H or methyl; and
$R^7$ is methyl;
provided that when $R^4$ is

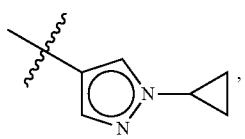

$R^5$ is not

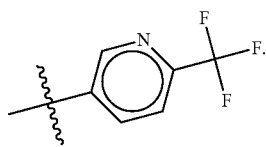

Provided herein as Embodiment 146 is the compound according to Embodiment 1, 2, or 3, or a tautomer thereof, or a pharmaceutically acceptable salt of said compound or said tautomer, wherein the compound is a compound of Formula IIIb

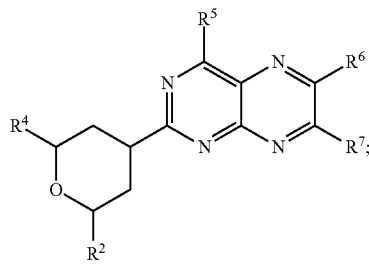

IIIb wherein
$R^2$ is H or methyl;
$R^4$ is

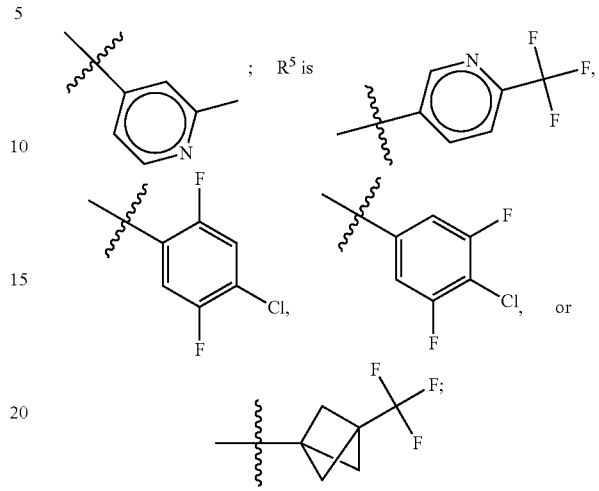

; $R^5$ is $R^6$ is H or methyl; and
$R^7$ is methyl.

Provided herein as Embodiment 147 is the compound according to Embodiment 1, 2, or 3, or a tautomer thereof, or a pharmaceutically acceptable salt of said compound or said tautomer, wherein the compound is a compound of Formula IIIb

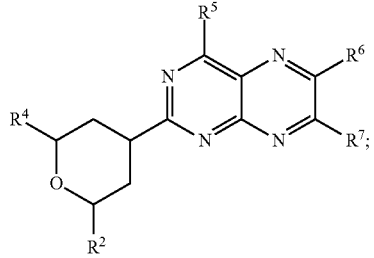

IIIb wherein
$R^2$ is H or methyl;
$R^4$ is

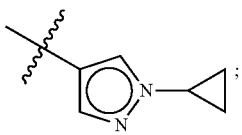

$R^5$ is

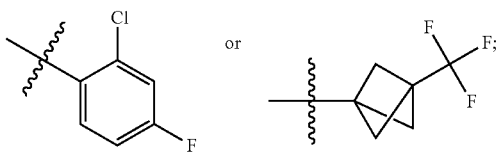 [SMILES: *c1ccc(F)cc1Cl ; *C12CC(C(F)(F)F)(C1)C2]

or R⁵ is

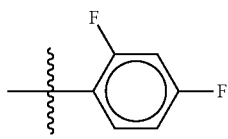

when R² is methyl;

R⁶ is H or methyl; and

R⁷ is methyl.

Provided herein as Embodiment 148 is the compound according to Embodiment 1, 2, or 3, or a tautomer thereof, or a pharmaceutically acceptable salt of said compound or said tautomer, wherein the compound is a compound of Formula Va

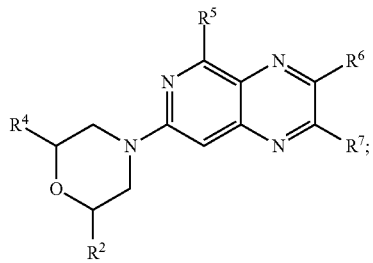

Va wherein
R² is H or methyl;
R⁴ is

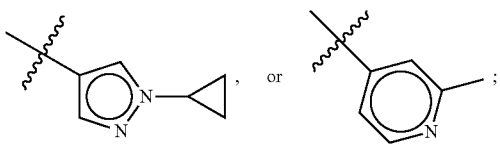

R⁵ is $C_{1-6}$haloalkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-($C_{3-6}$cycloalkyl),
  wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and
  wherein the aziridine-1-yl, pyrrolidine-1-yl, 3-azabicyclo[3.1.0]hexan-3-yl, piperidine-1-yl, and —OCH₂-($C_{3-6}$cycloalkyl) is further substituted with 1 to 4 substituents independently selected from halogen, $C_{1-3}$alkyl, $C_{1-3}$haloalkyl, and $C_{1-3}$alkoxy;

R⁶ is H or methyl; and
R⁷ is methyl;
provided that:
when R⁶ is Me and R² is H, R⁵ is not

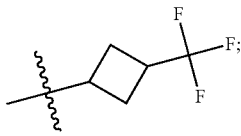

and
when both R² and R⁶ are H, R⁵ is not

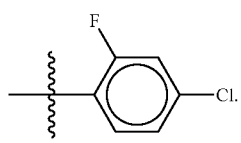

Provided herein as Embodiment 149 is the compound according to Embodiment 1, 2, or 3, or a tautomer thereof, or a pharmaceutically acceptable salt of said compound or said tautomer, wherein the compound is a compound of Formula Vb

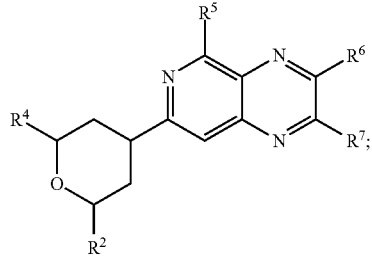

Vb wherein
R² is H or methyl;
R⁴ is

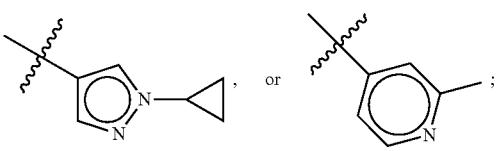

R⁵ is $C_{1-6}$haloalkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-($C_{3-6}$cycloalkyl),
  wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and
  wherein the aziridine-1-yl, pyrrolidine-1-yl, 3-azabicyclo[3.1.0]hexan-3-yl, piperidine-1-yl, and —OCH₂-

($C_{3-6}$cycloalkyl) is further substituted with 1 to 4 substituents independently selected from halogen, $C_{1-3}$alkyl, $C_{1-3}$haloalkyl, and $C_{1-3}$alkoxy;
$R^6$ is H or methyl; and
$R^7$ is methyl;
provided that when $R^2$ is H, $R^5$ is not

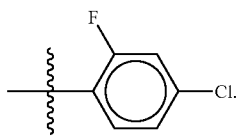

Provided herein as Embodiment 150 is the compound according to Embodiment 1, 2, or 3, or a tautomer thereof, or a pharmaceutically acceptable salt of said compound or said tautomer, wherein the compound is a compound of Formula Va or Vb

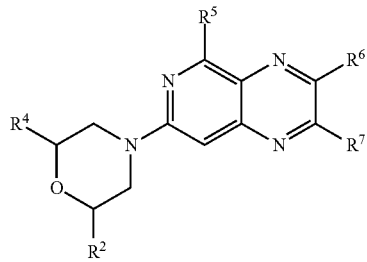

Va

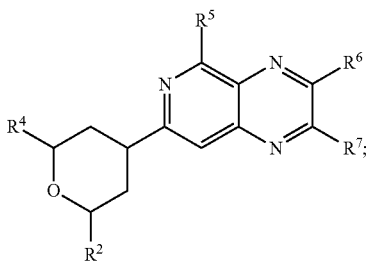

Vb wherein
$R^2$ is H or methyl;
$R^4$ is 5-membered heteroaryl or 6-membered heteroaryl; wherein the 5-membered heteroaryl or 6-membered heteroaryl group is optionally substituted with 1 to 3 substituents independently selected from $C_{1-6}$alkyl, $C_{1-6}$alkoxy, and $C_{3-6}$cycloalkyl;
$R^5$ is

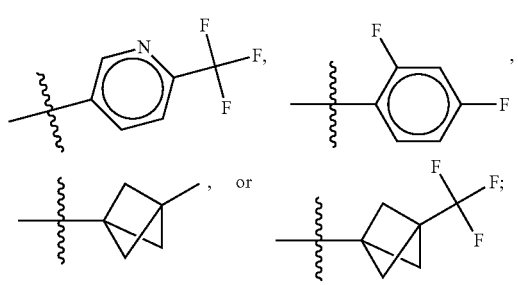

$R^6$ is H or methyl; and
$R^7$ is methyl.

Provided herein as Embodiment 151 is the compound according to Embodiment 1, 2, or 3, or a tautomer thereof, or a pharmaceutically acceptable salt of said compound or said tautomer, wherein the compound is a compound of Formula Va or Vb

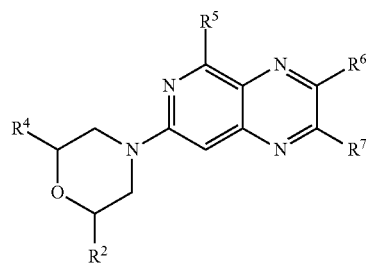

Va

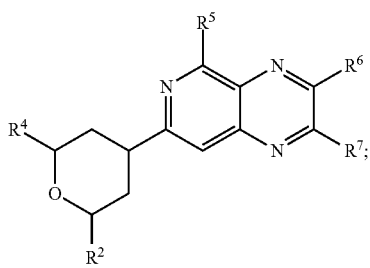

Vb wherein
$R^2$ is H or methyl;
$R^4$ is

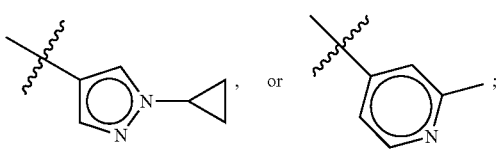

$R^5$ is

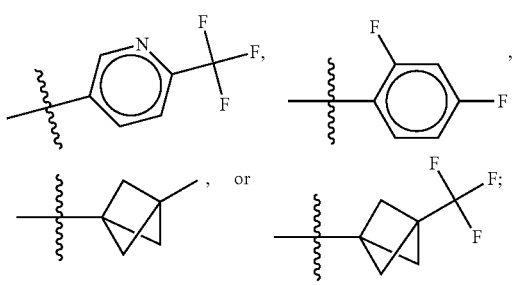

$R^6$ is H or methyl; and
$R^7$ is methyl.

Provided herein as Embodiment 152 is the compound according to Embodiment 1, 2, or 3, or a tautomer thereof, or a pharmaceutically acceptable salt of said compound or said tautomer, wherein the compound is a compound of Formula Va or Vb

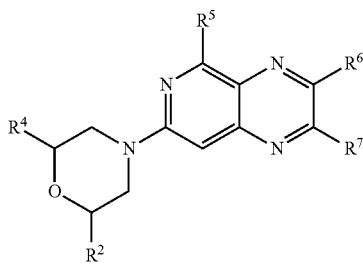

Va

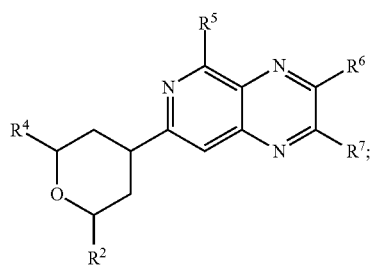

Vb

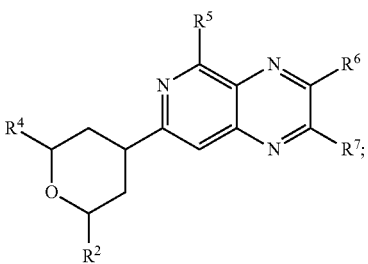

Vb wherein
R² is methyl;
R⁴ is

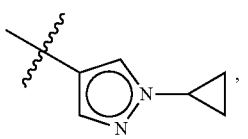, or 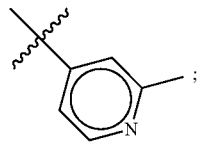;

R⁵ is C₁₋₆haloalkyl, C₃₋₆cycloalkyl, C₅₋₈spiroalkyl, C₅₋₈tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-(C₃₋₆cycloalkyl), wherein the C₃₋₆cycloalkyl, C₅₋₈spiroalkyl, C₅₋₈tricycloalkyl, cyclopent-1-en-1-yl, cyclohex-1-en-1-yl, phenyl, and 6-membered heteroaryl is further optionally substituted with 1 to 4 substituents independently selected from halogen, C₁₋₃alkyl, and C₁₋₃haloalkyl, and wherein the aziridine-1-yl, pyrrolidine-1-yl, 3-azabicyclo[3.1.0]hexan-3-yl, piperidine-1-yl, and —OCH₂-(C₃₋₆cycloalkyl) is further substituted with 1 to 4 substituents independently selected from halogen, C₁₋₃alkyl, C₁₋₃haloalkyl, and C₁₋₃alkoxy;

R⁶ is H or methyl; and
R⁷ is methyl.

Provided herein as Embodiment 153 is the compound according to Embodiment 1, 2, or 3, or a tautomer thereof, or a pharmaceutically acceptable salt of said compound or said tautomer, wherein the compound is a compound of Formula Vb wherein
R² is H or methyl;
R⁴ is

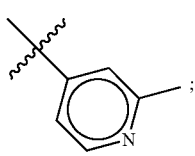;

R⁵ is

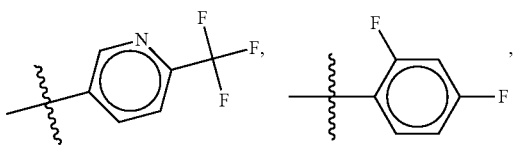

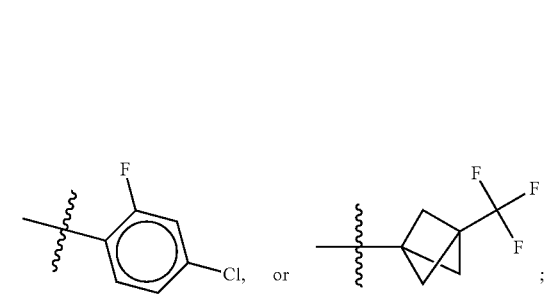

R⁶ is H or methyl; and
R⁷ is methyl;
provided that when R² is H, R⁵ is not

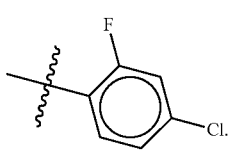

Provided herein as Embodiment 154 is the compound according to Embodiment 1, 2, or 3, or a tautomer thereof, or a pharmaceutically acceptable salt of said compound or said tautomer, wherein the compound is a compound of Formula VIIIa

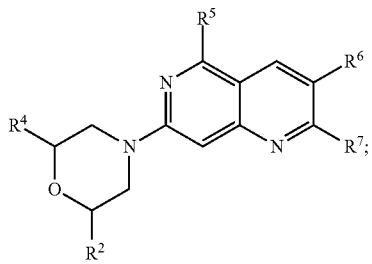

wherein
R² is H or methyl;
R⁴ is

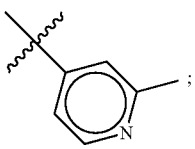

R⁵ is $C_{1-6}$haloalkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-($C_{3-6}$cycloalkyl),
  wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and
wherein the aziridine-1-yl, pyrrolidine-1-yl, 3-azabicyclo[3.1.0]hexan-3-yl, piperidine-1-yl, and —OCH₂-($C_{3-6}$cycloalkyl) is further substituted with 1 to 4 substituents independently selected from halogen, $C_{1-3}$alkyl, $C_{1-3}$haloalkyl, and $C_{1-3}$alkoxy;
R⁶ is H or methyl; and
R⁷ is Me
provided that R⁵ is not

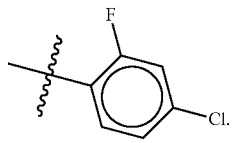

Provided herein as Embodiment 155 is the compound according to Embodiment 1, 2, or 3, or a tautomer thereof, or a pharmaceutically acceptable salt of said compound or said tautomer, wherein the compound is a compound of Formula VIIIa

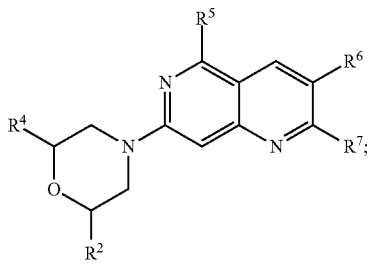

wherein
R² is H or methyl;
R⁴ is

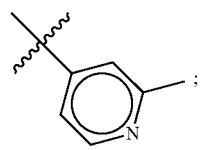

R⁵ is

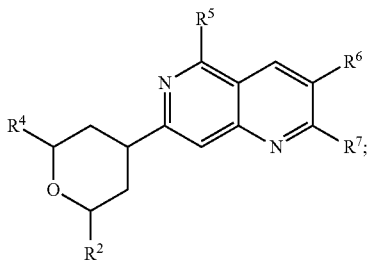

R⁶ is H or methyl; and
R⁷ is methyl.

Provided herein as Embodiment 156 is the compound according to Embodiment 1, 2, or 3, or a tautomer thereof, or a pharmaceutically acceptable salt of said compound or said tautomer, wherein the compound is a compound of Formula VIIIb VIIIb wherein
R² is H or methyl;
R⁴ is 5-membered heteroaryl or 6-membered heteroaryl; wherein the 5-membered heteroaryl or 6-membered heteroaryl group is optionally substituted with 1 to 3 substituents independently selected from $C_{1-6}$alkyl, $C_{1-6}$alkoxy, and $C_{3-6}$cycloalkyl;
R⁵ is $C_{1-6}$haloalkyl, $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-($C_{3-6}$cycloalkyl), wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH$_2$-($C_{3-6}$cycloalkyl) is further substituted with 1 to 4 substituents independently selected from halogen, $C_{1-3}$alkyl, $C_{1-3}$haloalkyl, and $C_{1-3}$alkoxy;

$R^6$ is H or methyl; and $R^7$ is methyl.

Provided herein as Embodiment 157 is the compound according to Embodiment 1, 2, or 3, or a tautomer thereof, or a pharmaceutically acceptable salt of said compound or said tautomer, wherein the compound is a compound of Formula IVb

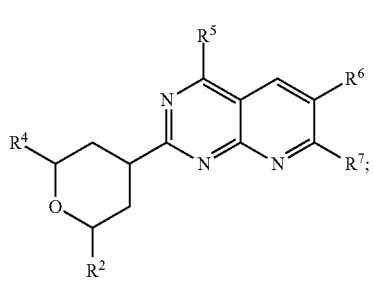

wherein $R^2$ is H or methyl;

$R^4$ is

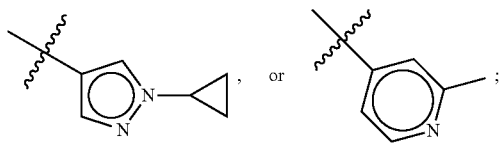

$R^5$ is $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-($C_{3-6}$cycloalkyl), wherein the $C_{3-6}$cycloalkyl, $C_{5-8}$spiroalkyl, $C_{5-8}$tricycloalkyl, cyclopent-1en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH$_2$-($C_{3-6}$cycloalkyl) is further substituted with 1 to 4 substituents independently selected from halogen, $C_{1-3}$alkyl, $C_{1-3}$haloalkyl, and $C_{1-3}$alkoxy;

$R^6$ is H or methyl; and $R^7$ is Me;

provided that when $R^2$ is H, $R^5$ is not

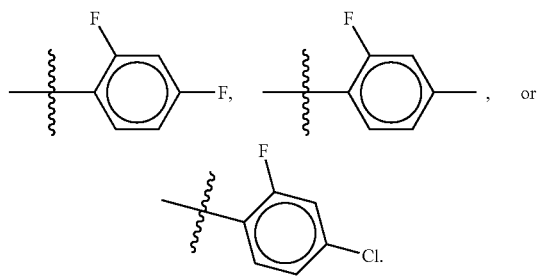

Provided herein as Embodiment 158 is the compound according to Embodiment 1, 2, or 3, or a tautomer thereof, or a pharmaceutically acceptable salt of said compound or said tautomer, wherein the compound is a compound of Formula IIIa

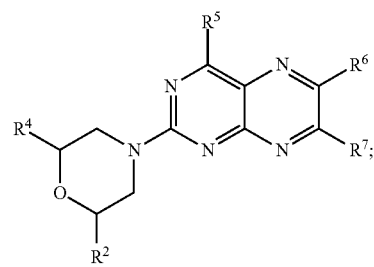

wherein $R^2$ is H;

$R^4$ is

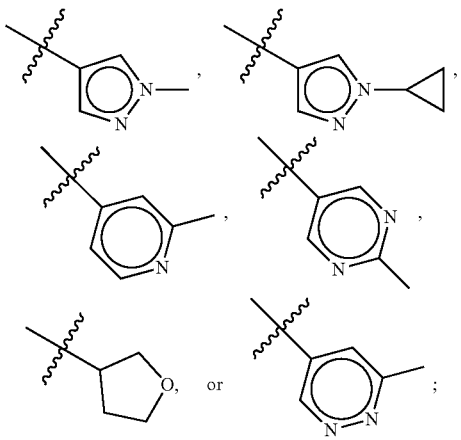

$R^5$ is $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-($C_{3-6}$cycloalkyl), wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH$_2$-(C$_{3-6}$cycloalkyl) is further substituted with 1 to 4 substituents independently selected from halogen, C$_{1-3}$alkyl, C$_{1-3}$haloalkyl, and C$_{1-3}$alkoxy;

R$^6$ is H or methyl; and

R$^7$ is methyl;

provided that R$^5$ is not

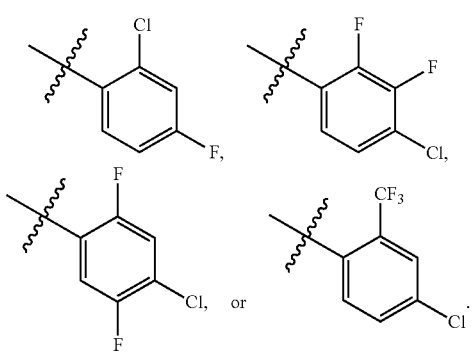

Provided herein as Embodiment 159 is the compound according to Embodiment 1, 2, or 3, or a tautomer thereof, or a pharmaceutically acceptable salt of said compound or said tautomer, wherein the compound is a compound of Formula IIIa

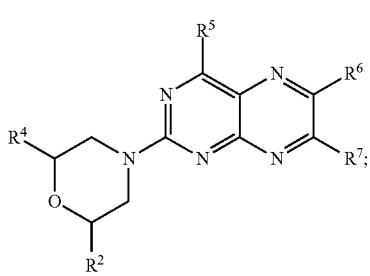

IIIa wherein

R$^2$ is H;

R$^4$ is 5-membered heteroaryl or 6-membered heteroaryl; wherein the 5-membered heteroaryl or 6-membered heteroaryl group is optionally substituted with 1 to 3 substituents independently selected from C$_{1-6}$alkyl, C$_{1-6}$alkoxy, and C$_{3-6}$cycloalkyl;

R$^5$ is —CH$_2$CH$_2$CF$_3$,

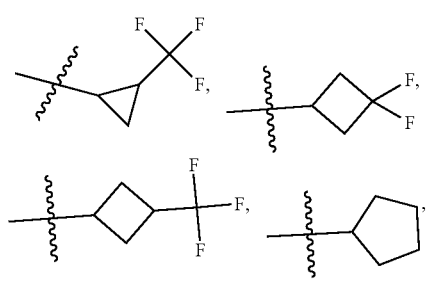

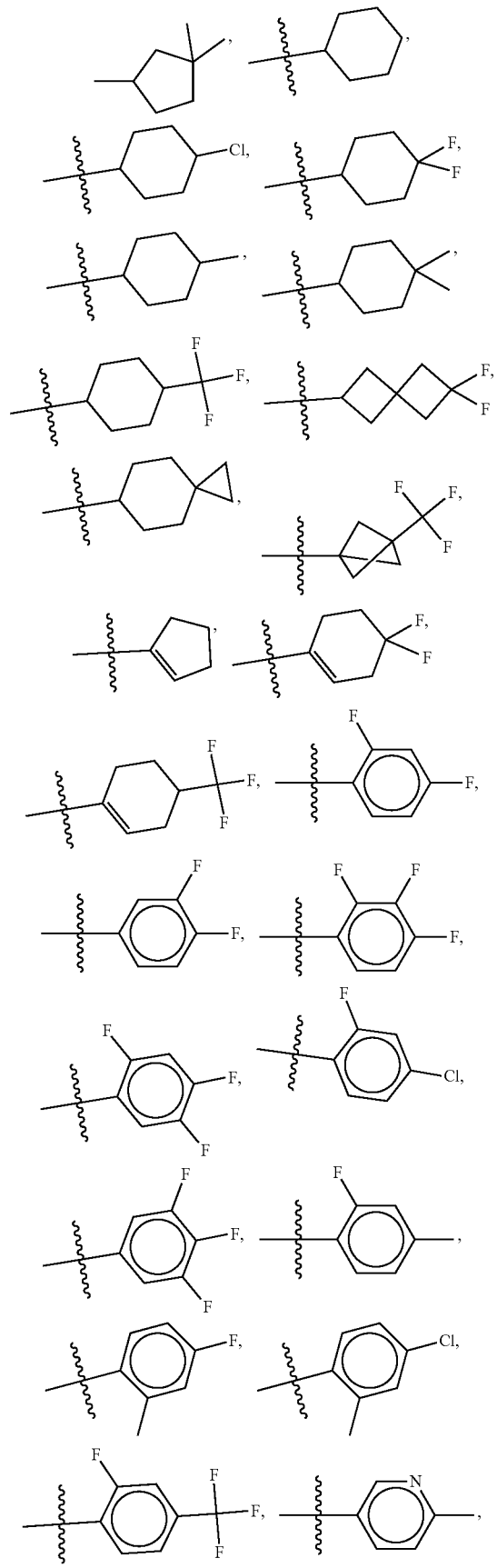

-continued
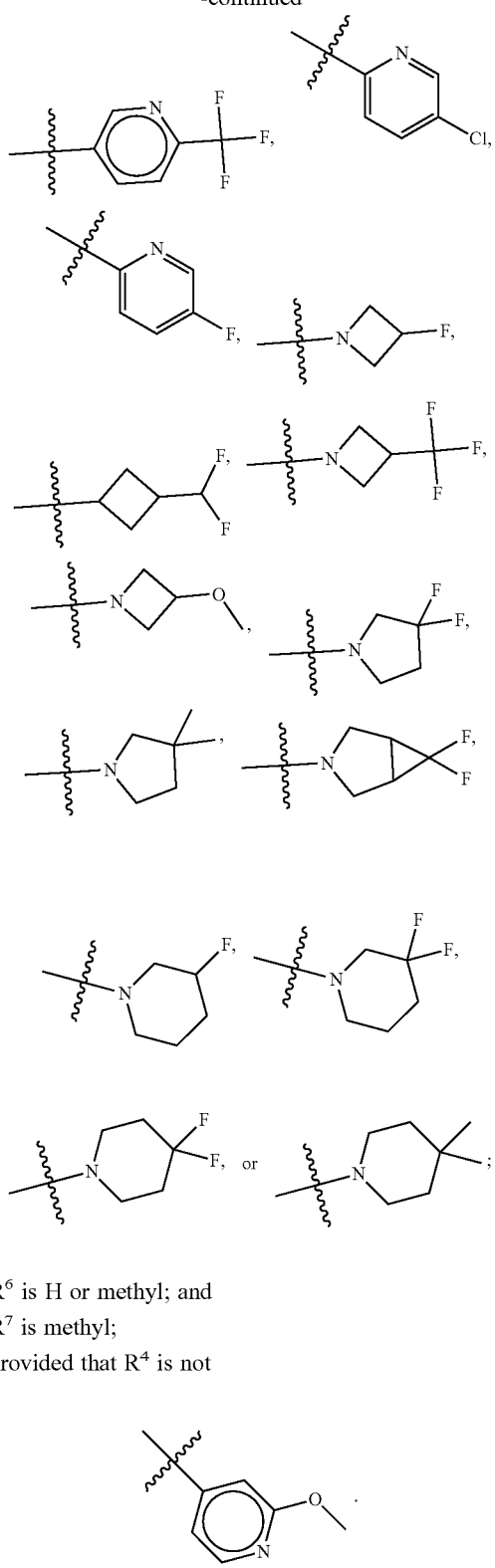
R[6] is H or methyl; and
R[7] is methyl;
provided that R[4] is not
Provided herein as Embodiment 160 is the compound according to Embodiment 1, 2, or 3, or a tautomer thereof, or a pharmaceutically acceptable salt of said compound or said tautomer, wherein the compound is a compound of Formula IIIa
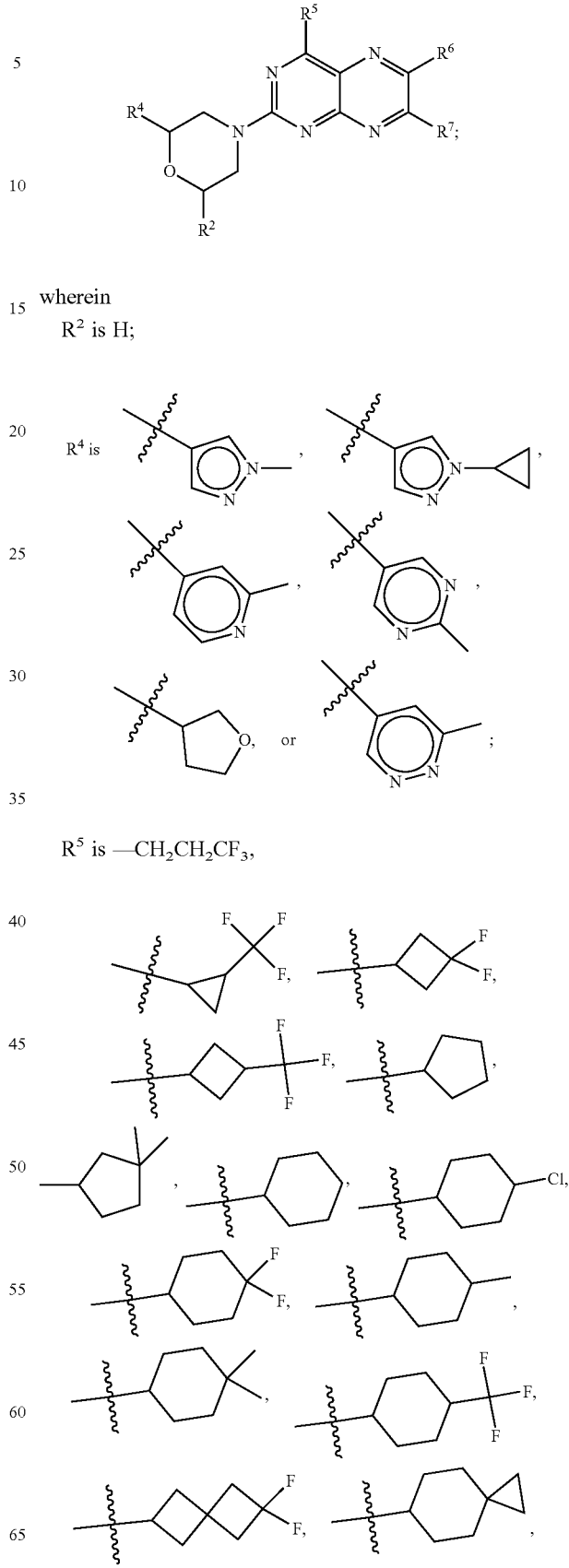
wherein
R[2] is H;
R[4] is
R[5] is —CH$_2$CH$_2$CF$_3$,

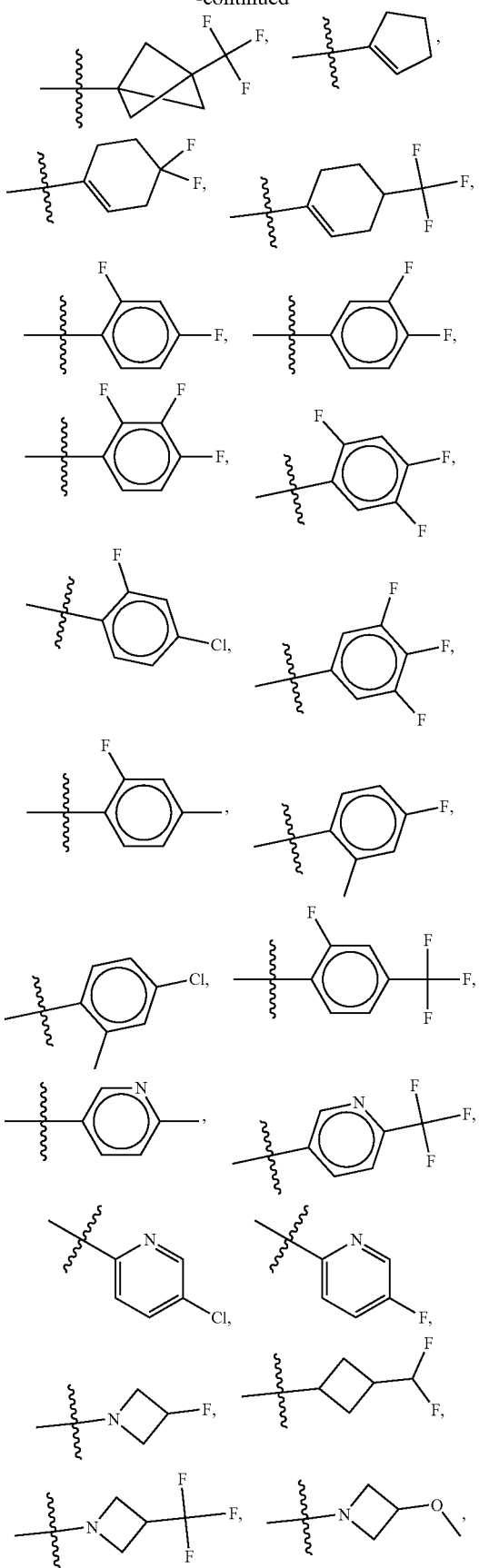
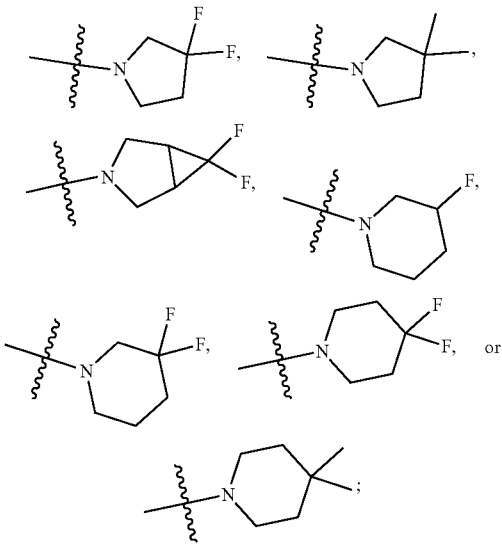
$R^6$ is H or methyl; and
$R^7$ is methyl.
Provided herein as Embodiment 161 is the compound according to Embodiment 1, 2, or 3, or a tautomer thereof, or a pharmaceutically acceptable salt of said compound or said tautomer, wherein the compound is a compound of Formula IIIb
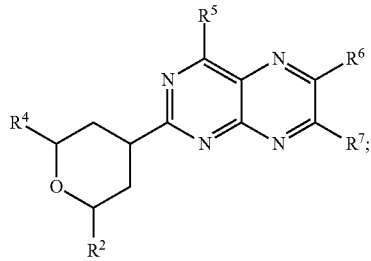
IIIb
wherein
$R^2$ is Me and $R^4$ is
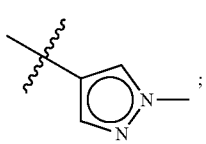
or
$R^2$ is H and $R^4$ is
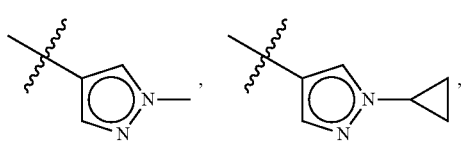

-continued

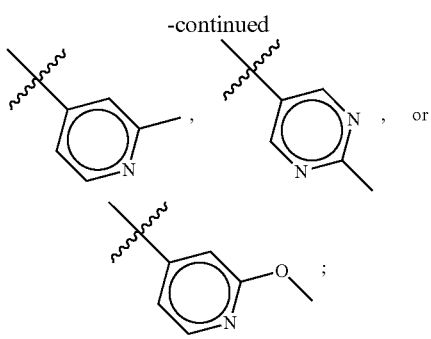

$R^5$ is $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-(C$_{3-6}$cycloalkyl),
  wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and
  wherein the aziridine-1-yl, pyrrolidine-1-yl, 3-azabicyclo[3.1.0]hexan-3-yl, piperidine-1-yl, and —OCH$_2$-(C$_{3-6}$cycloalkyl) is further substituted with 1 to 4 substituents independently selected from halogen, $C_{1-3}$alkyl, $C_{1-3}$haloalkyl, and $C_{1-3}$alkoxy;

$R^6$ is H or methyl; and $R^7$ is methyl;

provided that:

$R^5$ is not

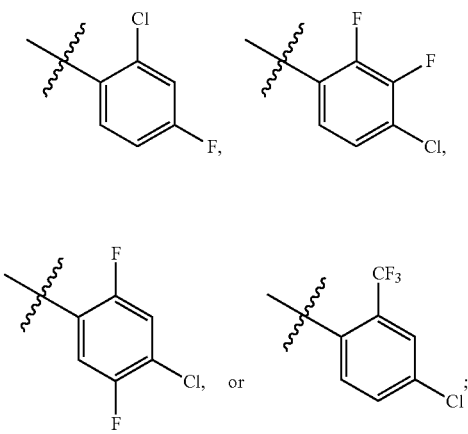 [SMILES: *c1ccc(F)cc1Cl ; *c1ccc(Cl)c(F)c1F ; *c1cc(F)c(Cl)cc1F ; *c1ccc(Cl)cc1C(F)(F)F]

when $R^4$ is

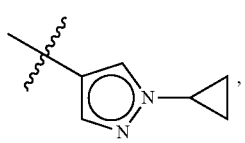

$R^5$ is not

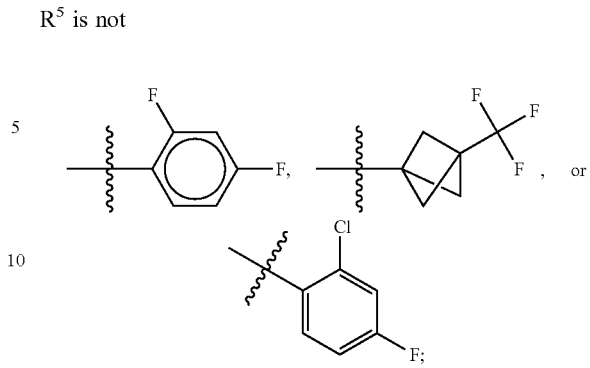

and
when $R^4$ is

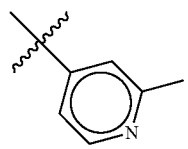

$R^5$ is not

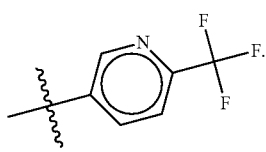

Provided herein as Embodiment 162 is the compound according to Embodiment 1, 2, or 3, or a tautomer thereof, or a pharmaceutically acceptable salt of said compound or said tautomer, wherein the compound is a compound of Formula IIIb

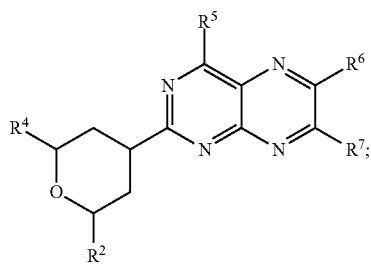

IIIb wherein
  $R^2$ is H or methyl;
  $R^4$ is 5-membered heteroaryl or 6-membered heteroaryl; wherein the 5-membered heteroaryl or 6-membered heteroaryl group is optionally substituted with 1 to 3 substituents independently selected from $C_{1-6}$alkyl, $C_{1-6}$alkoxy, and $C_{3-6}$cycloalkyl;

$R^5$ is

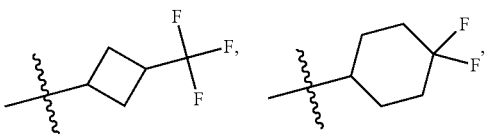

-continued

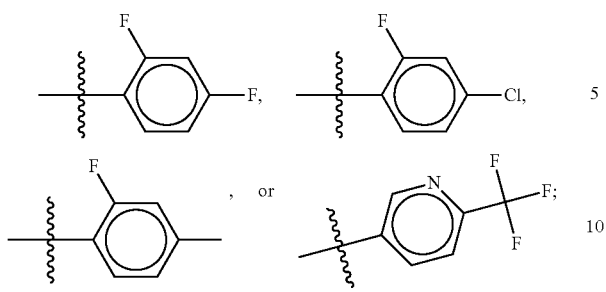

$R^6$ is H or methyl; and
$R^7$ is methyl;
provided that:
when $R^4$ is

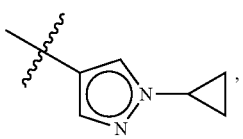

$R^5$ is not

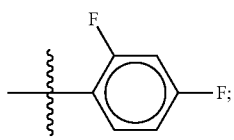

and
when $R^4$ is

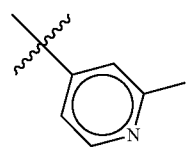

$R^5$ is not

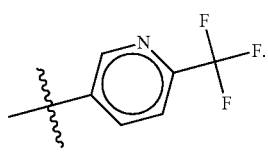

Provided herein as Embodiment 163 is the compound according to Embodiment 1, 2, or 3, or a tautomer thereof, or a pharmaceutically acceptable salt of said compound or said tautomer, wherein the compound is a compound of Formula IIIb

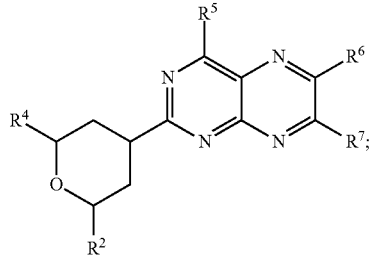

wherein
$R^2$ is Me and $R^4$ is

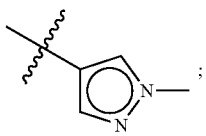

or
$R^2$ is H and $R^4$ is

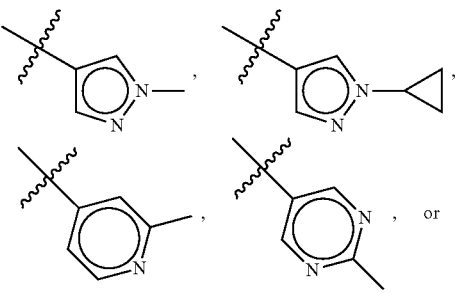

$R^5$ is

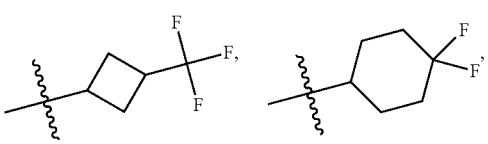

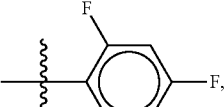 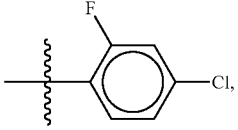

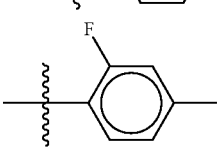 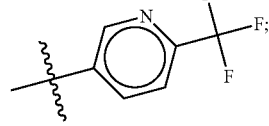

$R^6$ is H or methyl; and
$R^7$ is methyl;
provided that:
when $R^4$ is

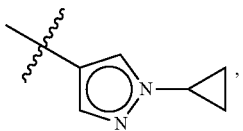

$R^5$ is not

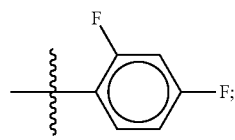

and
when $R^4$ is

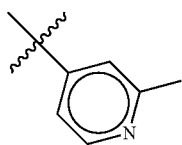

$R^5$ is not

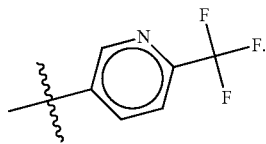

Provided herein as Embodiment 164 is the compound according to Embodiment 1, 2, or 3, or a tautomer thereof, or a pharmaceutically acceptable salt of said compound or said tautomer, wherein the compound is a compound of Formula IVa

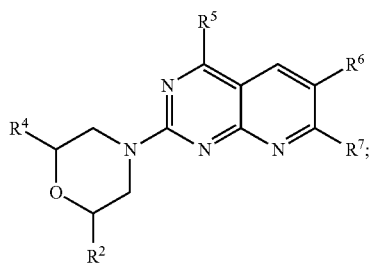

IVa wherein
$R^2$ is H or methyl;
$R^4$ is

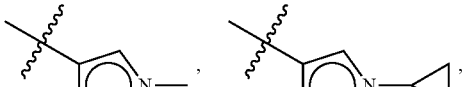

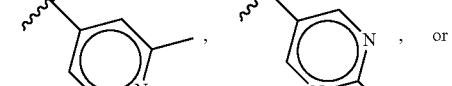

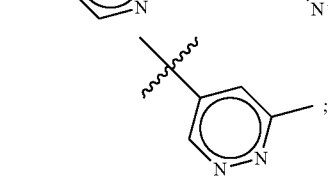

$R^5$ is $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-($C_{3-6}$cycloalkyl),
wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and
wherein the aziridine-1-yl, pyrrolidine-1-yl, 3-azabicyclo[3.1.0]hexan-3-yl, piperidine-1-yl, and —OCH$_2$-($C_{3-6}$cycloalkyl) is further substituted with 1 to 4 substituents independently selected from halogen, $C_{1-3}$alkyl, $C_{1-3}$haloalkyl, and $C_{1-3}$alkoxy;
$R^6$ is H or methyl; and
$R^7$ is Me, Cl or ethyl.

Provided herein as Embodiment 165 is the compound according to Embodiment 1, 2, or 3, or a tautomer thereof, or a pharmaceutically acceptable salt of said compound or said tautomer, wherein the compound is a compound of Formula IVa

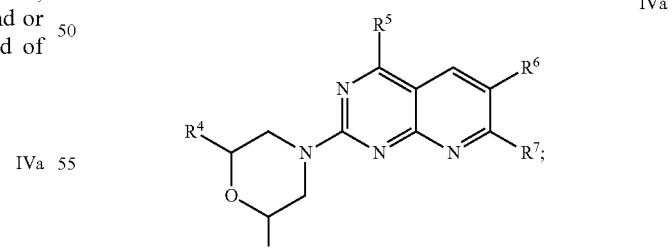

IVa wherein
$R^2$ is H or methyl;
$R^4$ is 5-membered heteroaryl or 6-membered heteroaryl;
wherein the 5-membered heteroaryl or 6-membered heteroaryl group is optionally substituted with 1 to 3 substituents independently selected from $C_{1-6}$alkyl, $C_{1-6}$alkoxy, and $C_{3-6}$cycloalkyl;

R⁵ is

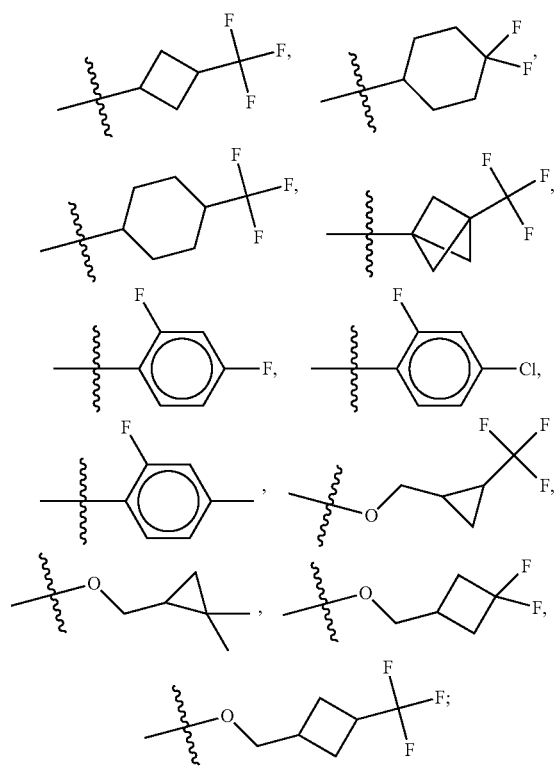

R⁶ is H or methyl; and
R⁷ is Me, Cl or ethyl.

Provided herein as Embodiment 166 is the compound according to Embodiment 1, 2, or 3, or a tautomer thereof, or a pharmaceutically acceptable salt of said compound or said tautomer, wherein the compound is a compound of Formula IVa

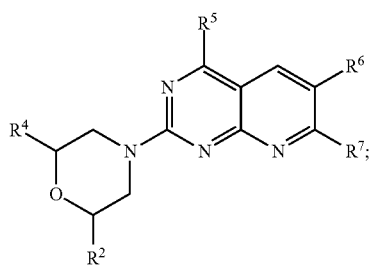

IVa wherein
R² is H or methyl;
R⁴ is

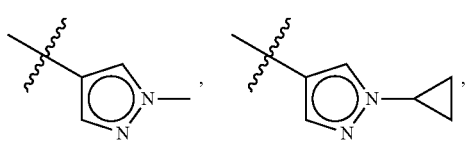

R⁵ is

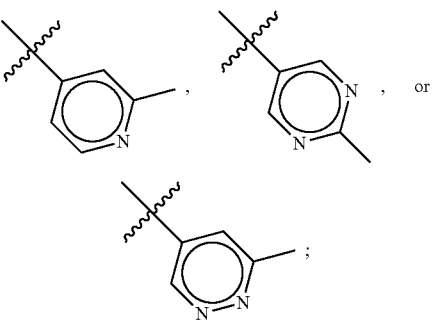

R⁵ is

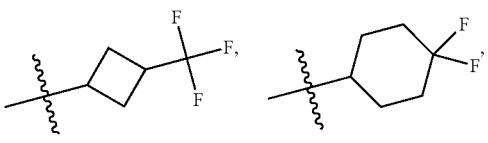

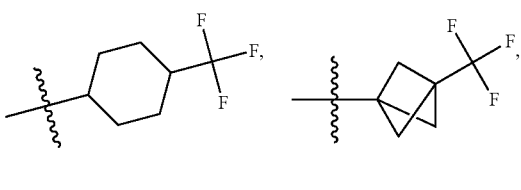

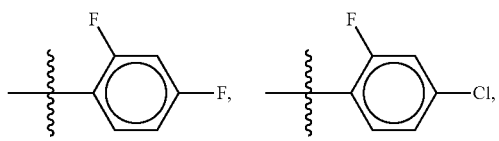

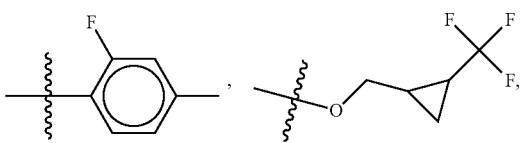

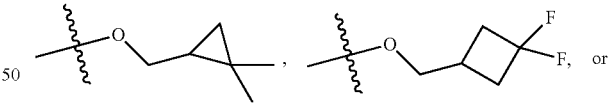

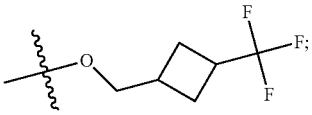

R⁶ is H or methyl; and
R⁷ is Me, Cl or ethyl.

Provided herein as Embodiment 167 is the compound according to Embodiment 1, 2, or 3, or a tautomer thereof, or a pharmaceutically acceptable salt of said compound or said tautomer, wherein the compound is a compound of Formula Va

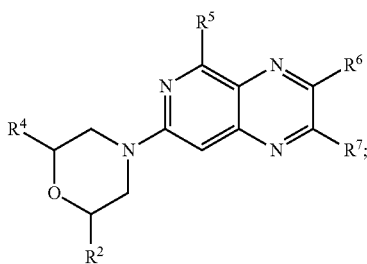

wherein
R² is H;
R⁴ is

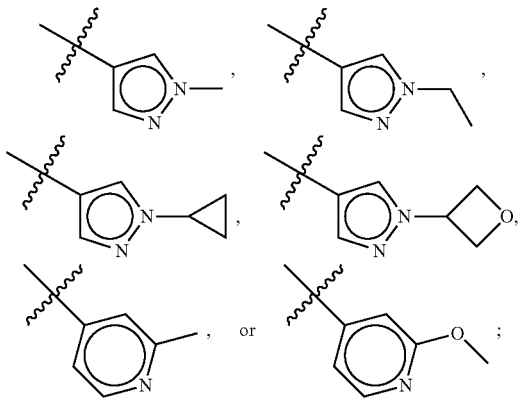

R⁵ is C₃₋₆cycloalkyl, C₅₋₈spiroalkyl, C₅₋₈tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-(C₃₋₆cycloalkyl),
  wherein the C₃₋₆cycloalkyl, C₅₋₈spiroalkyl, C₅₋₈tricycloalkyl, cyclopent-1-en-1-yl, cyclohex-1-en-1-yl, phenyl, and 6-membered heteroaryl is further optionally substituted with 1 to 4 substituents independently selected from halogen, C₁₋₃alkyl, and C₁₋₃haloalkyl, and
  wherein the aziridine-1-yl, pyrrolidine-1-yl, 3-azabicyclo[3.1.0]hexan-3-yl, piperidine-1-yl, and —OCH₂-(C₃₋₆cycloalkyl) is further substituted with 1 to 4 substituents independently selected from halogen, C₁₋₃alkyl, C₁₋₃haloalkyl, and C₁₋₃alkoxy;
R⁶ is H or methyl; and
R⁷ is methyl;
provided that R⁵ is not

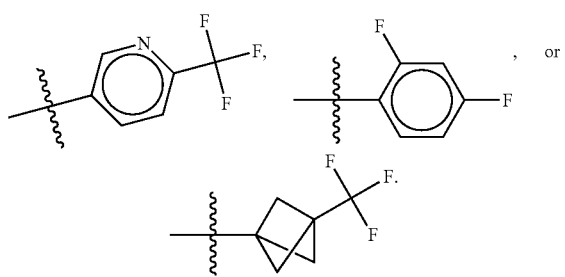

Provided herein as Embodiment 168 is the compound according to Embodiment 1, 2, or 3, or a tautomer thereof, or a pharmaceutically acceptable salt of said compound or said tautomer, wherein the compound is a compound of Formula Va

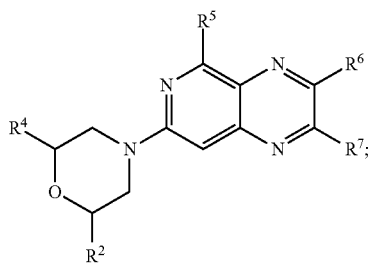

wherein
R² is H;
R⁴ is 5-membered heteroaryl or 6-membered heteroaryl; wherein the 5-membered heteroaryl or 6-membered heteroaryl group is optionally substituted with 1 to 3 substituents independently selected from C₁₋₆alkyl, C₁₋₆alkoxy, and C₃₋₆cycloalkyl;
R⁵ is

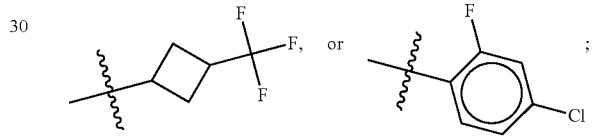

R⁶ is H or methyl; and
R⁷ is methyl.

Provided herein as Embodiment 169 is the compound according to Embodiment 1, 2, or 3, or a tautomer thereof, or a pharmaceutically acceptable salt of said compound or said tautomer, wherein the compound is a compound of Formula Va

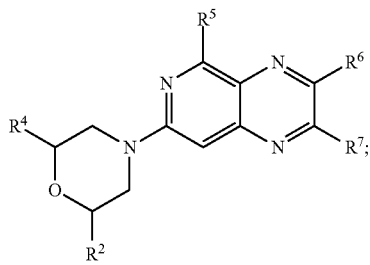

wherein
R² is H;
R⁴ is

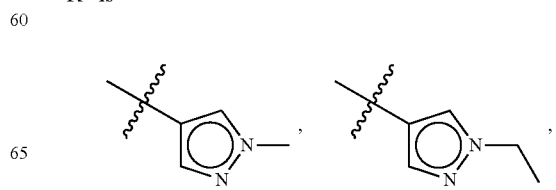

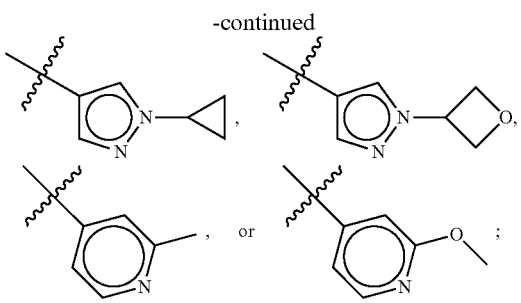

$R^5$ is

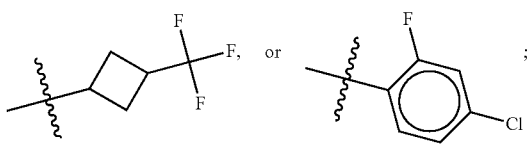

$R^6$ is H or methyl; and
$R^7$ is methyl.

Provided herein as Embodiment 170 is the compound according to Embodiment 1, 2, or 3, or a tautomer thereof, or a pharmaceutically acceptable salt of said compound or said tautomer, wherein the compound is a compound of Formula Vb

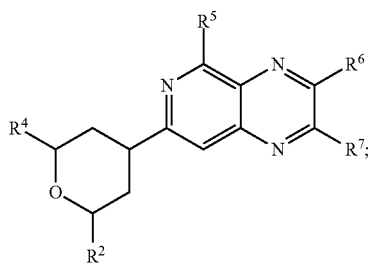

wherein
$R^2$ is H;
$R^4$ is

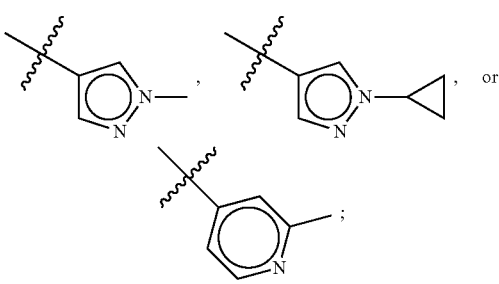

$R^5$ is $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-($C_{3-6}$cycloalkyl),
wherein the $C_{3-6}$cycloalkyl, $C_{5-8}$spiroalkyl, $C_{5-8}$tricycloalkyl, cyclopent-1-en-1-yl, cyclohex-1-en-1-yl, phenyl, and 6-membered heteroaryl is further optionally substituted with 1 to 4 substituents independently selected from halogen, $C_{1-3}$alkyl, and $C_{1-3}$haloalkyl, and wherein the aziridine-1-yl, pyrrolidine-1-yl, 3-azabicyclo[3.1.0]hexan-3-yl, piperidine-1-yl, and —OCH$_2$-($C_{3-6}$cycloalkyl) is further substituted with 1 to 4 substituents independently selected from halogen, $C_{1-3}$alkyl, $C_{1-3}$haloalkyl, and $C_{1-3}$alkoxy;

$R^6$ is H or methyl; and
$R^7$ is methyl;
provided that $R^5$ is not

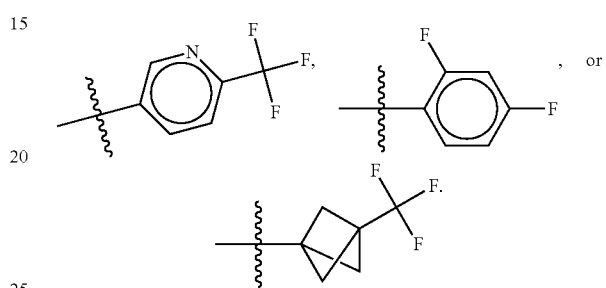

Provided herein as Embodiment 171 is the compound according to Embodiment 1, 2, or 3, or a tautomer thereof, or a pharmaceutically acceptable salt of said compound or said tautomer, wherein the compound is a compound of Formula Vb

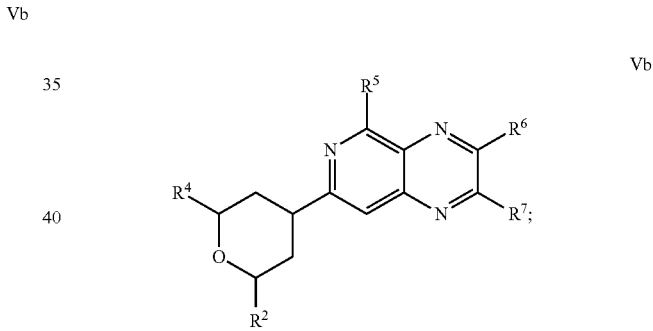

wherein
$R^2$ is H;
$R^4$ is 5-membered heteroaryl or 6-membered heteroaryl; wherein the 5-membered heteroaryl or 6-membered heteroaryl group is optionally substituted with 1 to 3 substituents independently selected from $C_{1-6}$alkyl, $C_{1-6}$alkoxy, and $C_{3-6}$cycloalkyl;
$R^5$ is

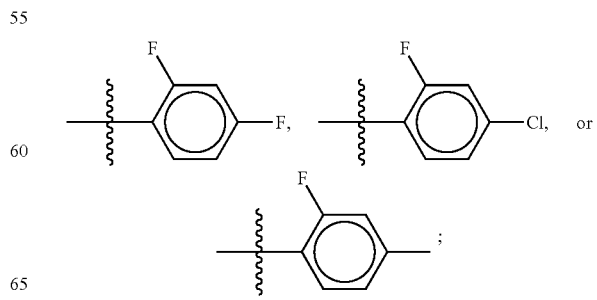

$R^6$ is H or methyl; and
$R^7$ is methyl;
provided that when $R^4$ is

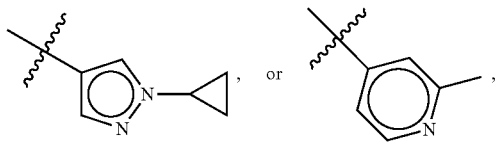, or $R^5$ is not

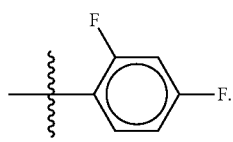.

Provided herein as Embodiment 172 is the compound according to Embodiment 1, 2, or 3, or a tautomer thereof, or a pharmaceutically acceptable salt of said compound or said tautomer, wherein the compound is a compound of Formula Vb

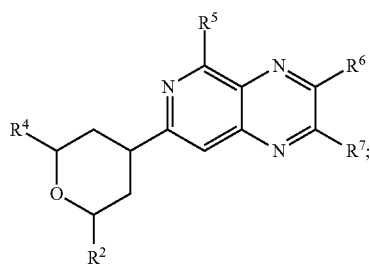

wherein
$R^2$ is H;
$R^4$ is

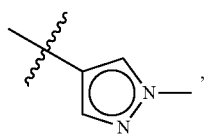

and $R^5$ is

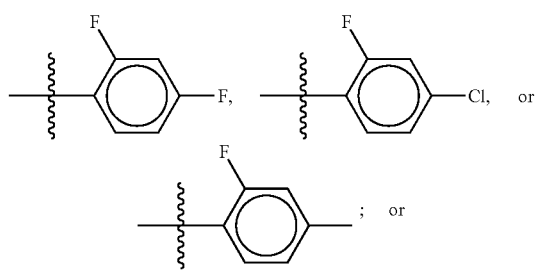; or $R^4$ is

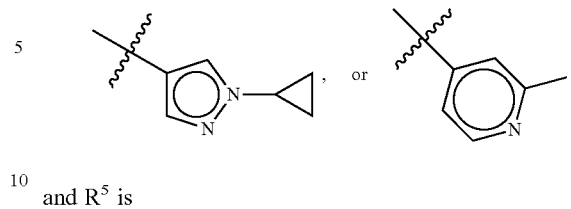

and $R^5$ is

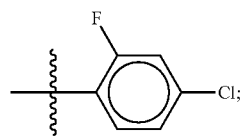;

$R^6$ is H or methyl; and
$R^7$ is methyl.

Provided herein as Embodiment 173 is the compound according to Embodiment 1, 2, or 3, or a tautomer thereof, or a pharmaceutically acceptable salt of said compound or said tautomer, wherein the compound is a compound of Formula VIIIa

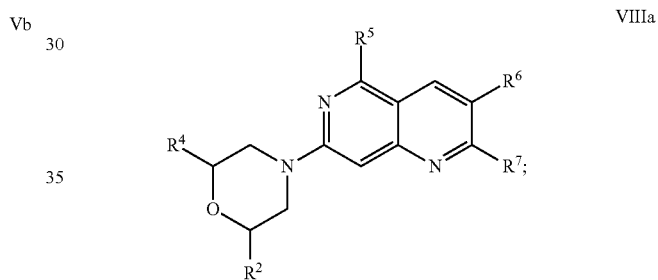

wherein
$R^2$ is H;
$R^4$ is

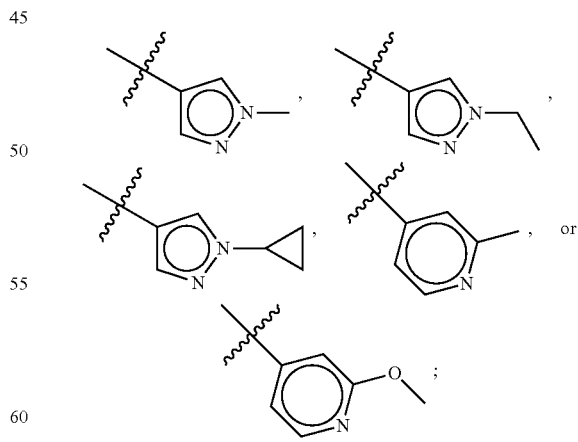

$R^5$ is $C_{3-6}$cycloalkyl, $C_{5-8}$spiroalkyl, $C_{5-8}$tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH$_2$-($C_{3-6}$cycloalkyl), wherein the C₃₋₆cycloalkyl, C₅₋₈spiroalkyl, C₅₋₈tricycloalkyl, cyclopent-1-en-1-yl, cyclohex-1-en-1-yl, phenyl, and 6-membered heteroaryl is further optionally substituted with 1 to 4 substituents independently selected from halogen, C₁₋₃alkyl, and C₁₋₃haloalkyl, and wherein the aziridine-1-yl, pyrrolidine-1-yl, 3-azabicyclo[3.1.0]hexan-3-yl, piperidine-1-yl, and —OCH₂-(C₃₋₆cycloalkyl) is further substituted with 1 to 4 substituents independently selected from halogen, C₁₋₃alkyl, C₁₋₃haloalkyl, and C₁₋₃alkoxy;

R⁶ is H or methyl; and
R⁷ is methyl;
provided that when R⁴ is

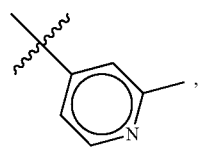

R⁵ is not

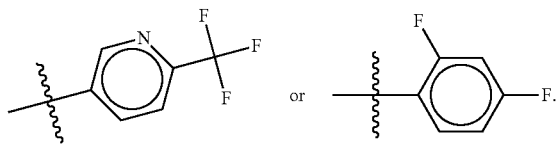

Provided herein as Embodiment 174 is the compound according to Embodiment 1, 2, or 3, or a tautomer thereof, or a pharmaceutically acceptable salt of said compound or said tautomer, wherein the compound is a compound of Formula VIIIa

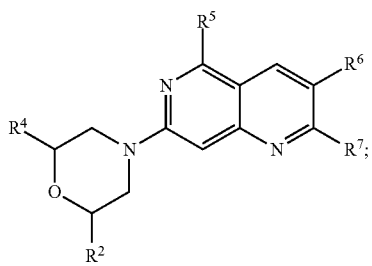

wherein
R² is H;
R⁴ is 5-membered heteroaryl or 6-membered heteroaryl; wherein the 5-membered heteroaryl or 6-membered heteroaryl group is optionally substituted with 1 to 3 substituents independently selected from C₁₋₆alkyl, C₁₋₆alkoxy, and C₃₋₆cycloalkyl;
R⁵ is

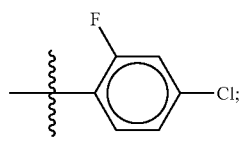

R⁶ is H or methyl; and
R⁷ is methyl.

Provided herein as Embodiment 175 is the compound according to Embodiment 1, 2, or 3, or a tautomer thereof, or a pharmaceutically acceptable salt of said compound or said tautomer, wherein the compound is a compound of Formula VIIIa

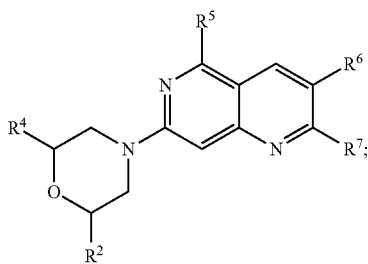

wherein
R² is H;
R⁴ is

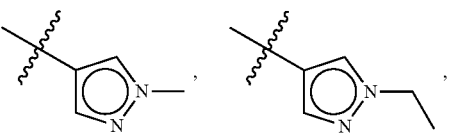

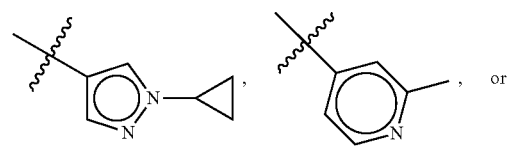

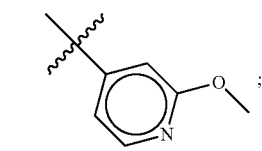

R⁵ is

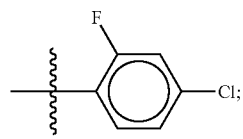

R⁶ is H or methyl; and
R⁷ is methyl.

Provided herein as Embodiment 176 is the compound according to Embodiment 1 or a tautomer thereof, or a pharmaceutically acceptable salt of said compound or said tautomer, wherein the compound is a compound of Formula XII

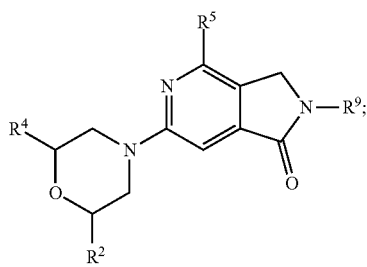

wherein
R² is H;
R⁴ is C₁₋₆alkyl, 5-membered heteroaryl or 6-membered heteroaryl; wherein the 5-membered heteroaryl or 6-membered heteroaryl group is optionally substituted with 1 to 3 substituents independently selected from C₁₋₆alkyl, C₁₋₆alkoxy, and C₃₋₆cycloalkyl;
R⁵ is C₃₋₆cycloalkyl, C₅₋₈spiroalkyl, C₅₋₈tricycloalkyl, cyclopent-1-en-1-yl, cyclohex-1-en-1-yl, phenyl, 6-membered heteroaryl, aziridine-1-yl, pyrrolidine-1-yl, 3-azabicyclo[3.1.0]hexan-3-yl, piperidine-1-yl, or —OCH₂-(C₃₋₆cycloalkyl),
wherein the C₃₋₆cycloalkyl, C₅₋₈spiroalkyl, C₅₋₈tricycloalkyl, cyclopent-1-en-1-yl, cyclohex-1-en-1-yl, phenyl, and 6-membered heteroaryl is further optionally substituted with 1 to 4 substituents independently selected from halogen, C₁₋₃alkyl, and C₁₋₃haloalkyl, and
wherein the aziridine-1-yl, pyrrolidine-1-yl, 3-azabicyclo[3.1.0]hexan-3-yl, piperidine-1-yl, and —OCH₂-(C₃₋₆cycloalkyl) is further substituted with 1 to 4 substituents independently selected from halogen, C₁₋₃alkyl, C₁₋₃haloalkyl, and C₁₋₃alkoxy; and
R⁹ is methyl, ethyl or isopropyl.

Provided herein as Embodiment 177 is the compound according to Embodiment 1 or a tautomer thereof, or a pharmaceutically acceptable salt of said compound or said tautomer, wherein the compound is a compound of Formula XII

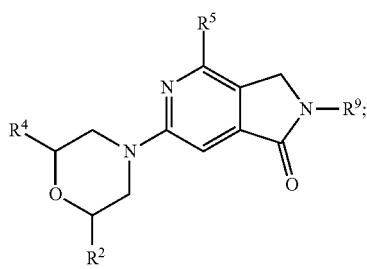

wherein
R² is H;
R⁴ is methyl,

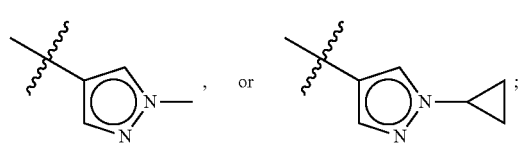

R⁵ is

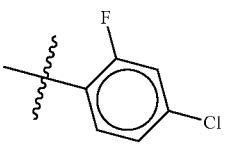 or 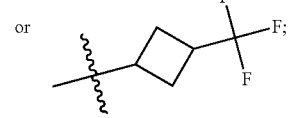

and
R⁹ is methyl, ethyl or isopropyl.

Exemplary compounds of the invention are set forth in Table A, below. In some embodiments, the compound is a compound set forth in Table A. Provided herein as Embodiment 178 is a compound depicted in Table A or a pharmaceutically acceptable salt thereof.

TABLE A

| Exemplary Compounds | |
|---|---|
| I-# | Structure |
| I-1 | ![structure] |
| I-2 | ![structure] |
| I-3 | ![structure] |

TABLE A-continued

Exemplary Compounds

| I-# | Structure |
|---|---|
| I-4 | 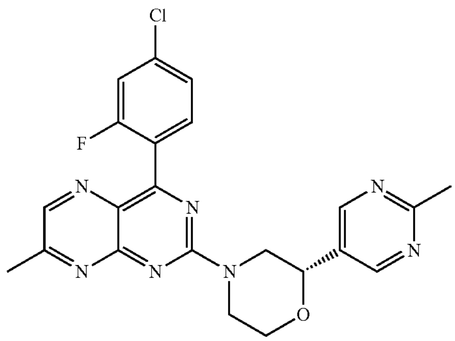 |
| I-5 | 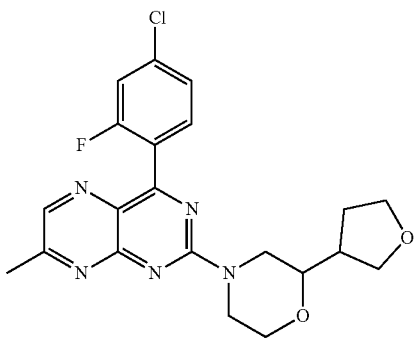 [SMILES: Cc1cnc2c(-c3ccc(Cl)cc3F)nc(N3CCOC(C4CCOC4)C3)nc2n1] |
| I-6 | 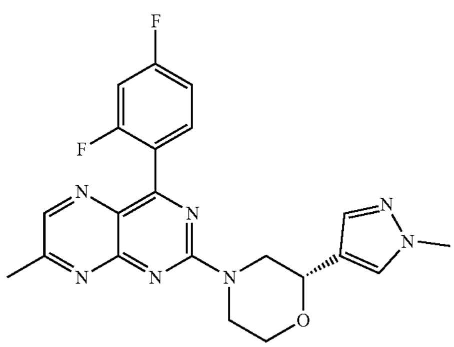 |
| I-7 | 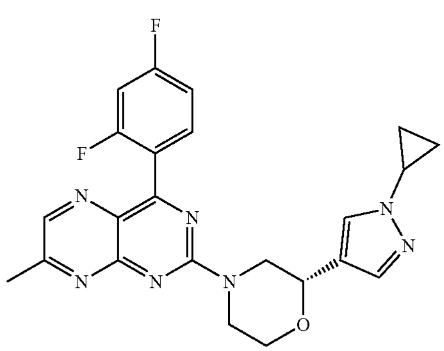 [SMILES: Cc1cnc2c(-c3ccc(F)cc3F)nc(N3CCO[C@@H](c4cnn(C5CC5)c4)C3)nc2n1] |
| I-8 | |
| I-9 | |
| I-10 | |
| I-11 | |

TABLE A-continued

Exemplary Compounds

| I-# | Structure |
|---|---|
| I-12 | 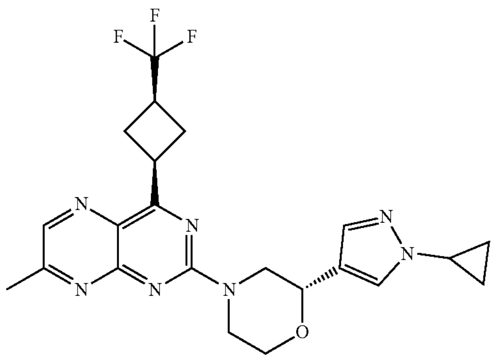 [SMILES: Cc1cnc2c(n1)nc(N1CCO[C@@H](c3cnn(C4CC4)c3)C1)nc2[C@H]1C[C@@H](C(F)(F)F)C1] |
| I-13 | 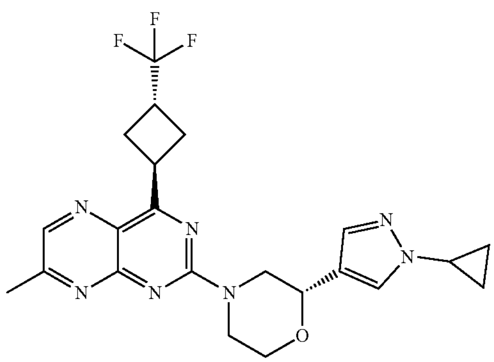 [SMILES: Cc1cnc2c(n1)nc(N1CCO[C@@H](c3cnn(C4CC4)c3)C1)nc2[C@H]1C[C@H](C(F)(F)F)C1] |
| I-14 | 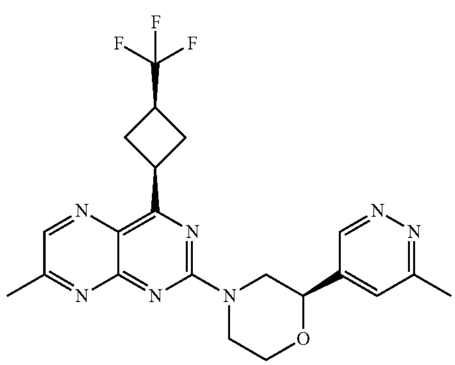 |
| I-15 | 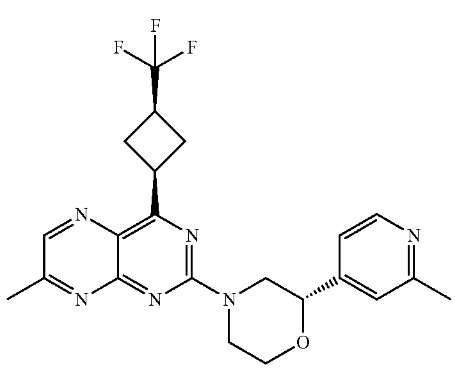 |
| I-16 | |
| I-17 | |
| I-18 | |
| I-19 | |

TABLE A-continued
Exemplary Compounds
| I-# | Structure |
|---|---|
| I-20 | 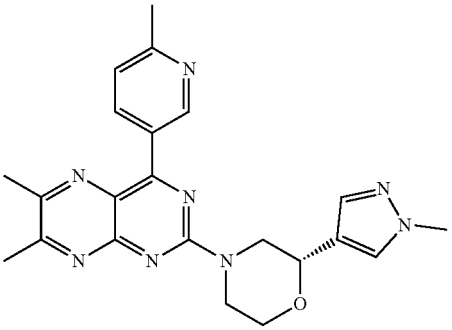 |
| I-21 | 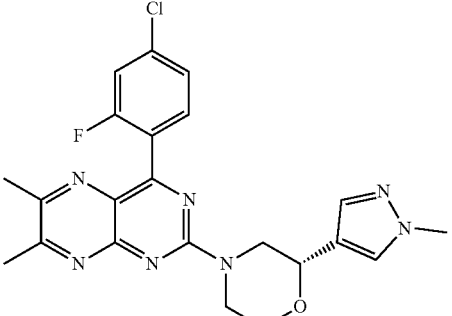 |
| I-22 | 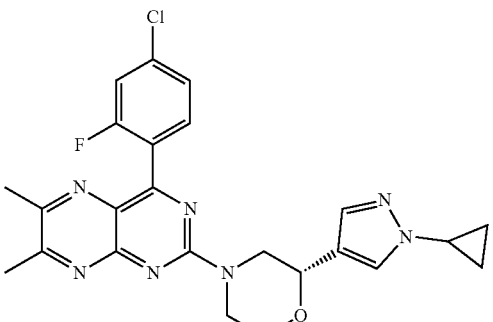 |
| I-23 | 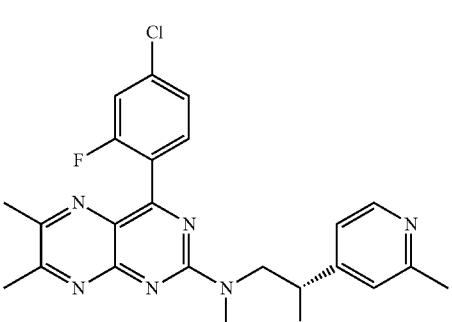 |
| I-24 | 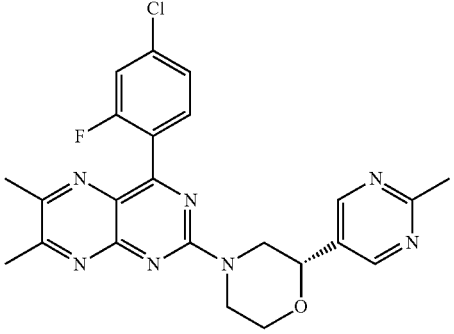 |
| I-25 | 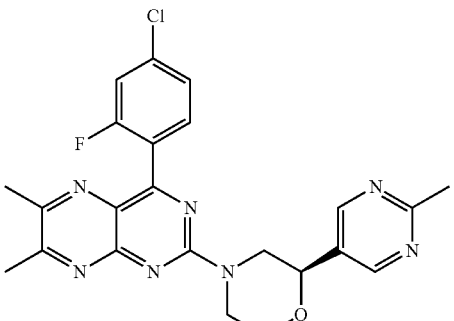 |
| I-26 | 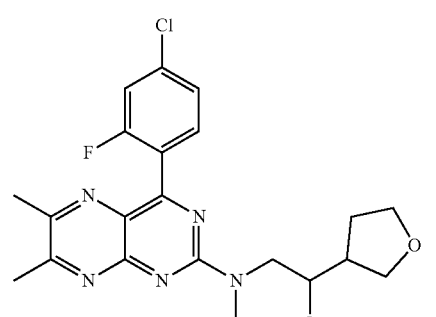 |
| I-27 | 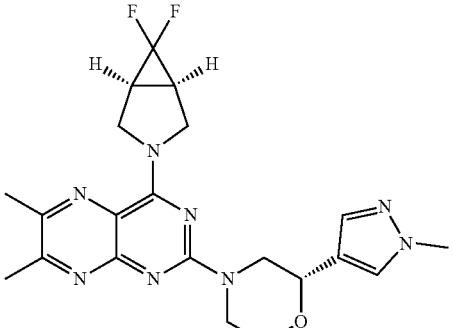 |

TABLE A-continued
Exemplary Compounds
| I-# | Structure |
|---|---|
| I-28 | 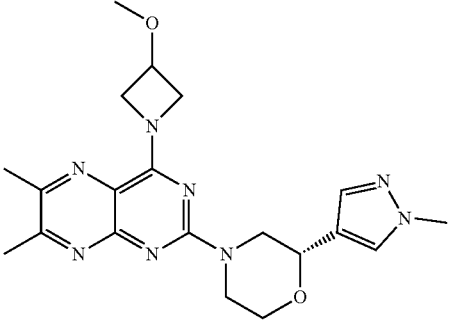 |
| I-29 | 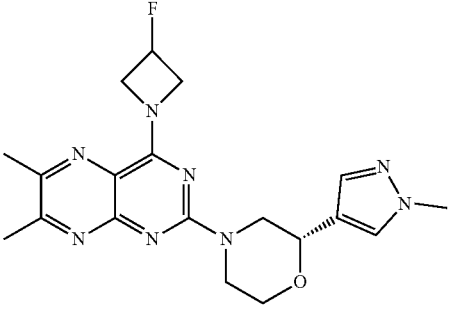 |
| I-30 | 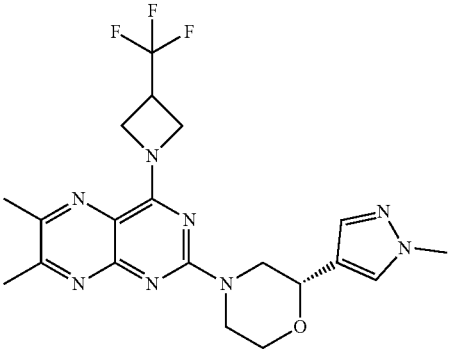 |
| I-31 | 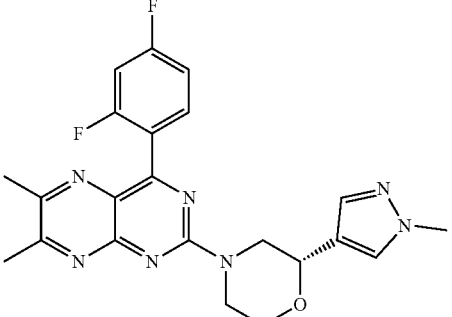 |
| I-32 | 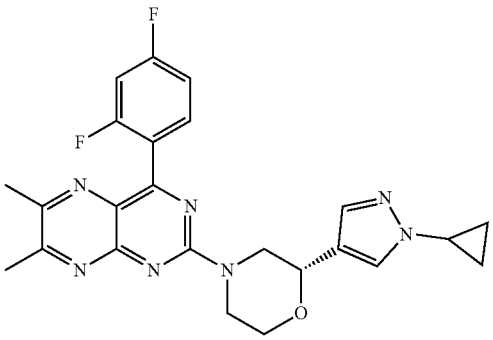 [SMILES: Cc1nc2nc(N3CCO[C@@H](c4cnn(C5CC5)c4)C3)nc(-c3ccc(Cl)cc3F)c2nc1C] |
| I-33 | 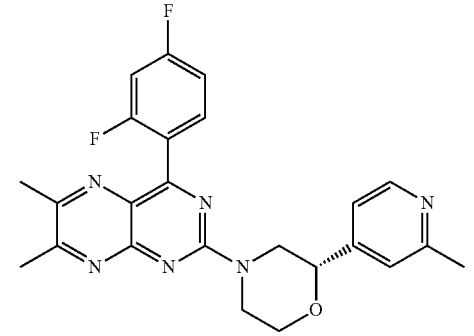 |
| I-34 | 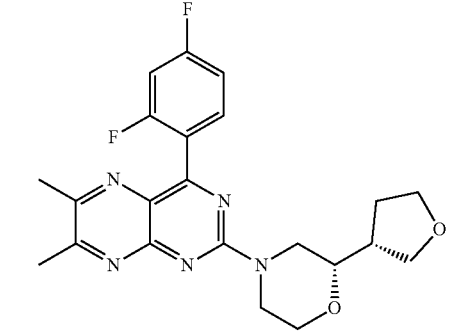 |
| I-35 | 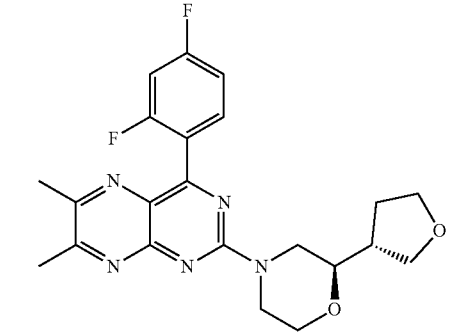 [SMILES: Cc1nc2nc(N3CCO[C@H]([C@@H]4CCOC4)C3)nc(-c3ccc(F)cc3F)c2nc1C] |

TABLE A-continued

Exemplary Compounds

| I-# | Structure |
|---|---|
| I-36 | 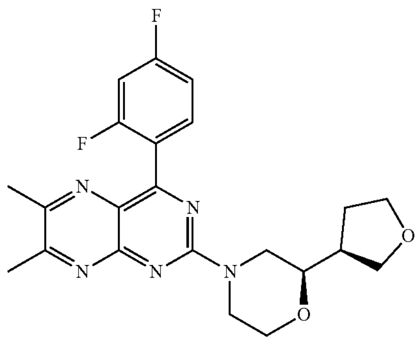 [SMILES: Cc1nc2nc(N3CCO[C@H]([C@H]4CCOC4)C3)nc(-c3ccc(F)cc3F)c2nc1C] |
| I-37 | 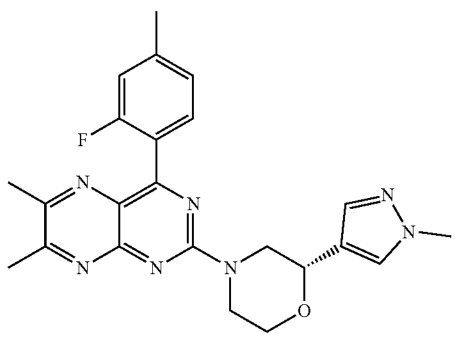 |
| I-38 | 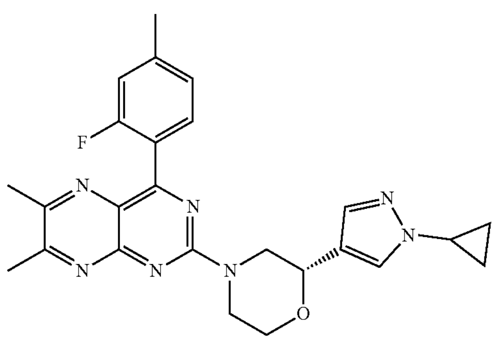 [SMILES: Cc1ccc(-c2nc(N3CCO[C@@H](c4cnn(C5CC5)c4)C3)nc3nc(C)c(C)nc23)c(F)c1] |
| I-39 | 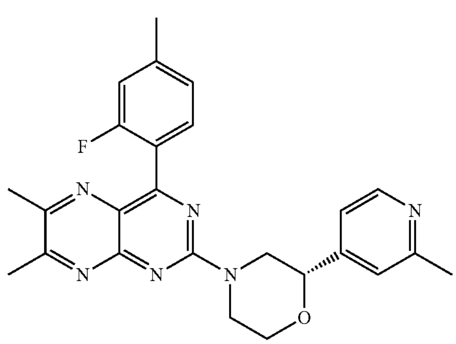 |
| I-40 | |
| I-41 | |
| I-42 | |
| I-43 | |

TABLE A-continued
Exemplary Compounds
| I-# | Structure |
|---|---|
| I-44 | 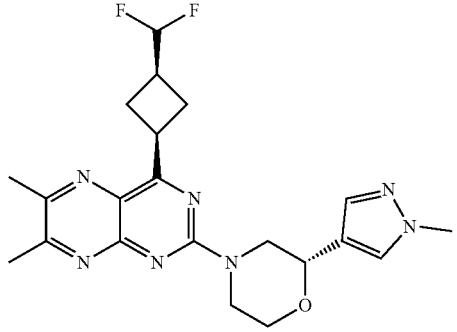 |
| I-45 | 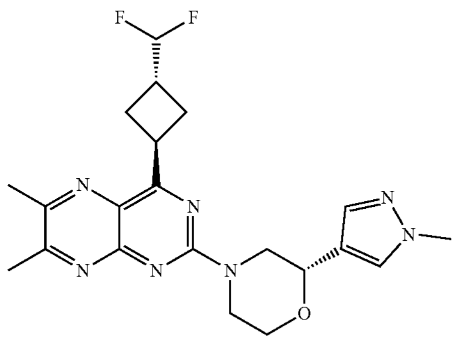 |
| I-46 | 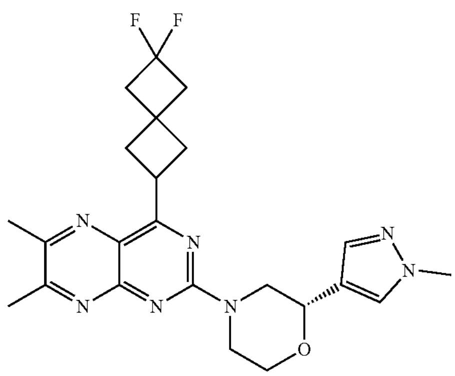 |
| I-47 | 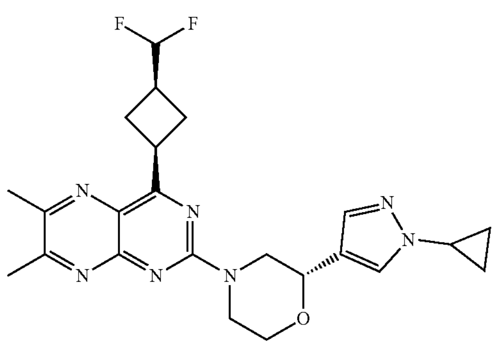 [SMILES: Cc1nc2nc(N3CCO[C@@H](c4cnn(C5CC5)c4)C3)nc([C@H]3C[C@@H](C(F)F)C3)c2nc1C] |
| I-48 |  |
| I-49 |  |
| I-50 |  |
| I-51 | 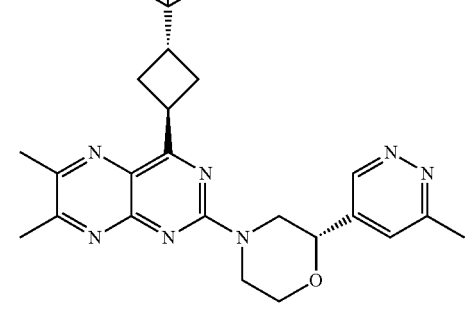 |

TABLE A-continued
Exemplary Compounds
| I-# | Structure |
|---|---|
| I-52 | 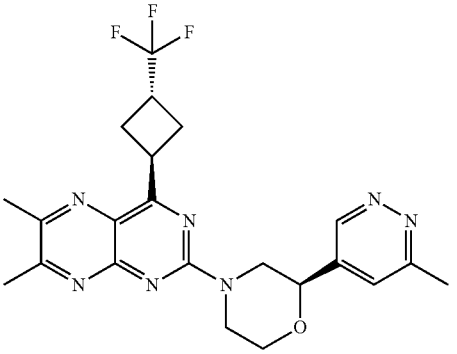 |
| I-53 | 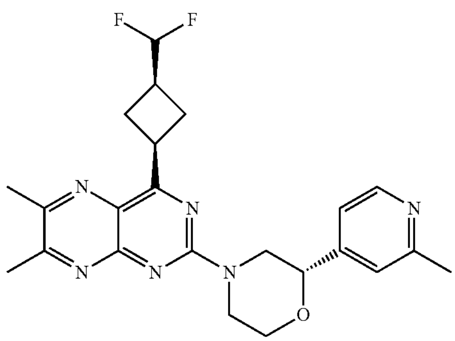 |
| I-54 | 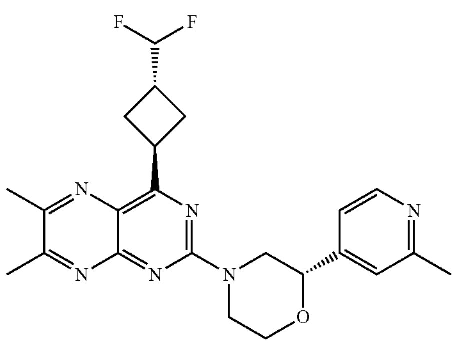 |
| I-55 | 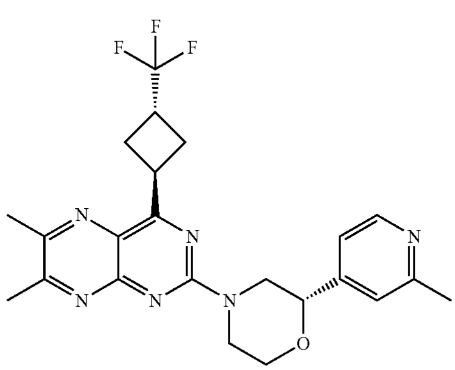 |
| I-56 | 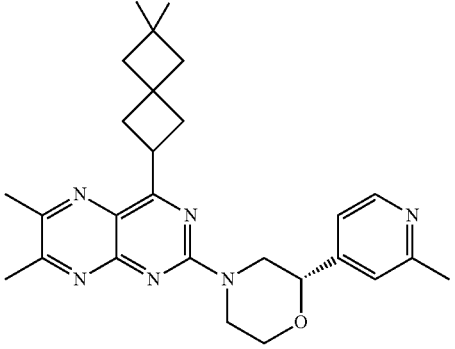 |
| I-57 |  |
| I-58 |  |
| I-59 |  |

TABLE A-continued

Exemplary Compounds

| I-# | Structure |
|---|---|
| I-60 | 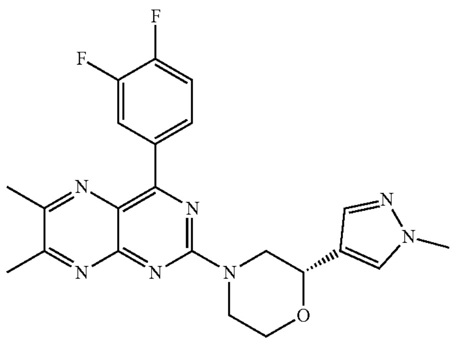 |
| I-61 | 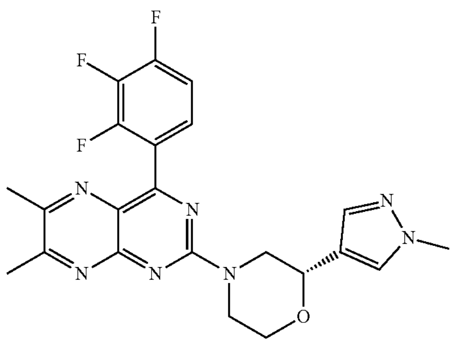 |
| I-62 | 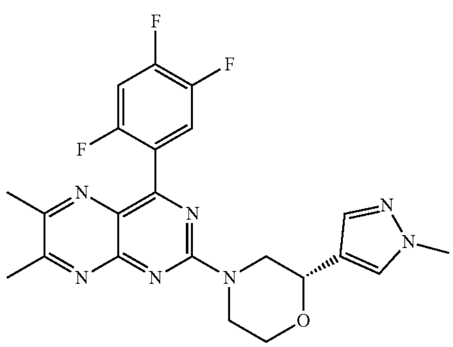 |
| I-63 | 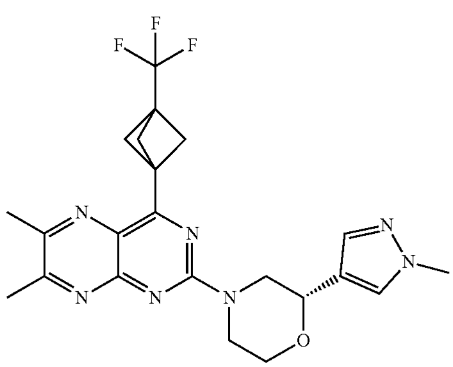 |
| I-64 | |
| I-65 | |
| I-66 | |
| I-67 | |

TABLE A-continued

Exemplary Compounds

| I-# | Structure |
|---|---|
| I-68 | 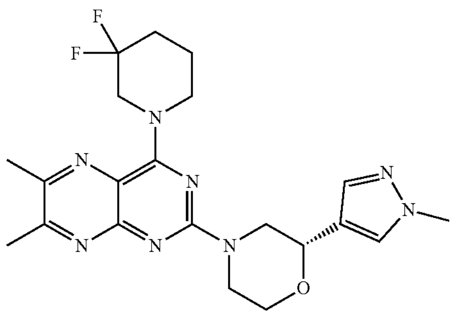 |
| I-69 | 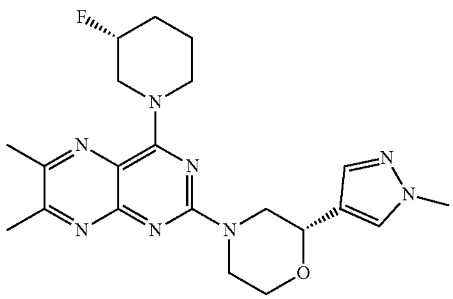 |
| I-70 | 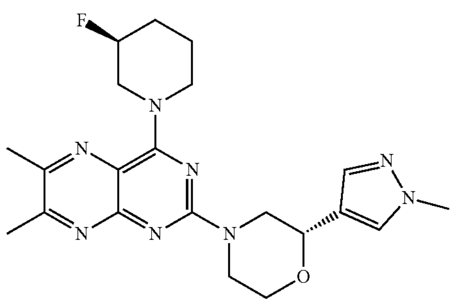 |
| I-71 | 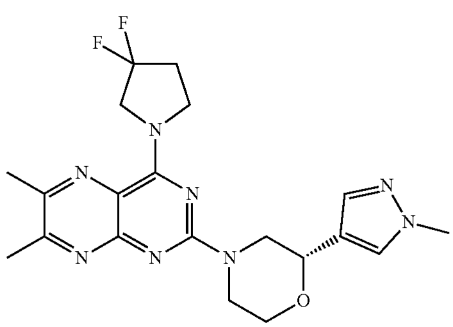 |
| I-72 | 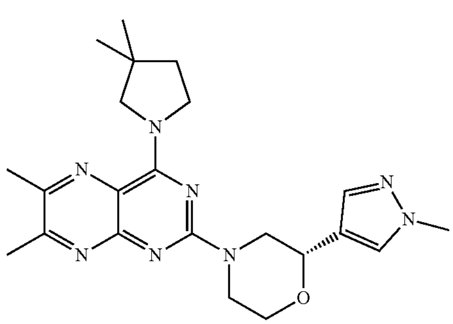 |
| I-73 | |
| I-74 | |
| I-75 | |
| I-76 | |

TABLE A-continued

Exemplary Compounds

| I-# | Structure |
|-----|-----------|
| I-77 | (structure) |
| I-78 | (structure) |
| I-79 | (structure) |
| I-80 | (structure) |
| I-81 | (structure) |
| I-82 | (structure) |
| I-83 | (structure) |
| I-84 | (structure) |

TABLE A-continued
Exemplary Compounds
| I-# | Structure |
|---|---|
| I-85 | 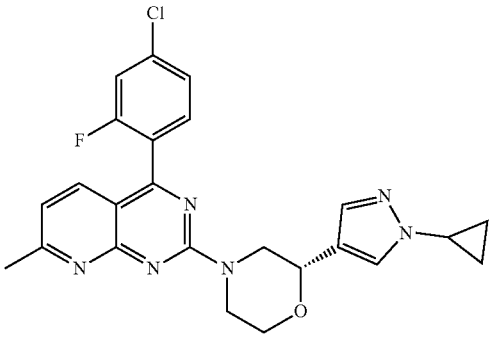 [SMILES: Cc1ccc2c(-c3ccc(Cl)cc3F)nc(N3CCO[C@@H](c4cnn(C5CC5)c4)C3)nc2n1] |
| I-86 | 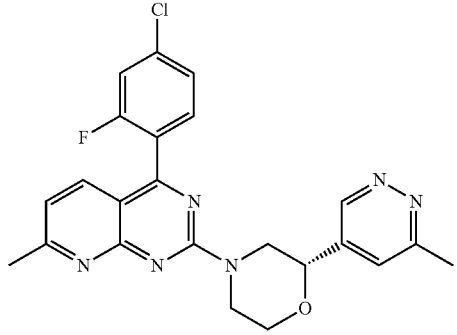 |
| I-87 | 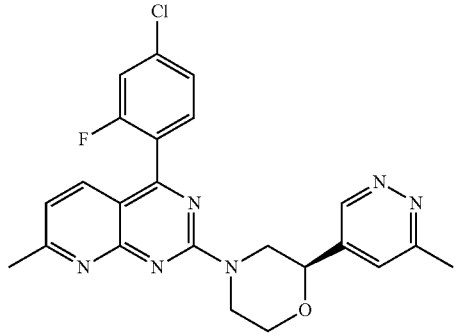 |
| I-88 | 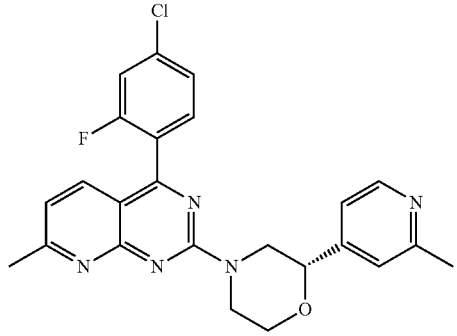 |
| I-89 | 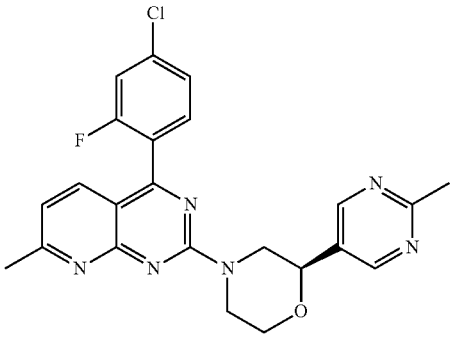 |
| I-90 | 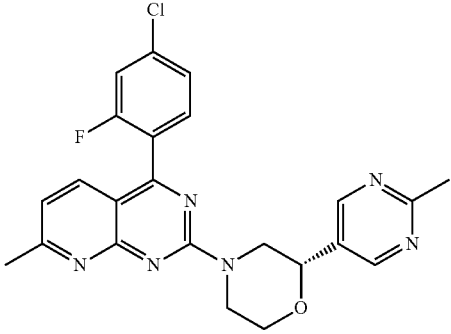 |
| I-91 | 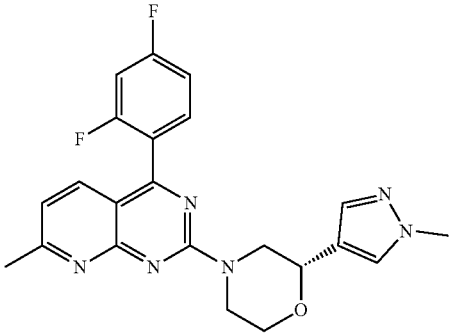 |
| I-92 | 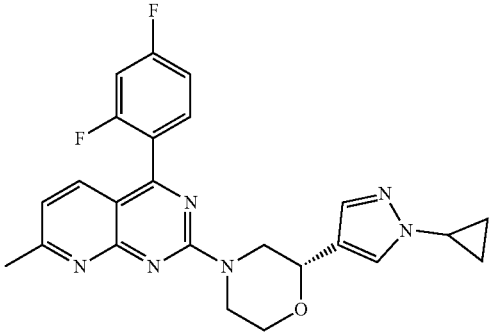 |

TABLE A-continued
Exemplary Compounds
| I-# | Structure |
|---|---|
| I-93 | 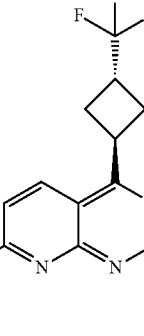 |
| I-94 | 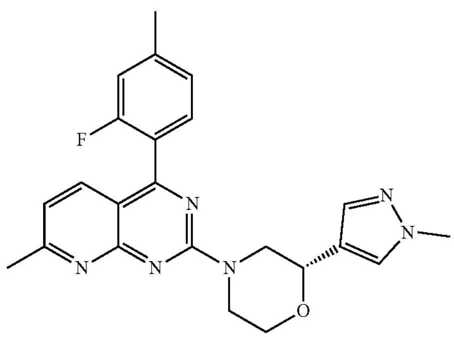 |
| I-95 | 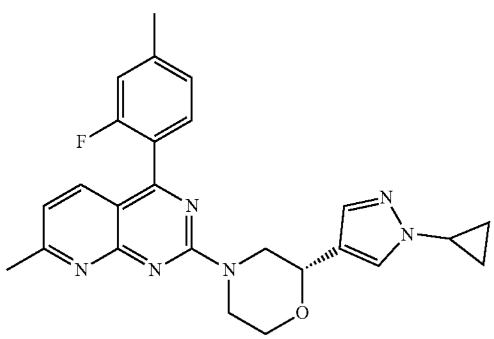 [SMILES: Cc1ccc(-c2nc(N3CCO[C@@H](c4cnn(C5CC5)c4)C3)nc3nc(C)ccc23)c(F)c1] |
| I-96 | 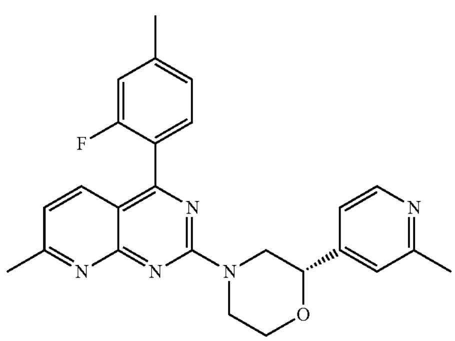 |
| I-97 |  |
| I-98 | |
| I-99 | |
| I-100 | |

TABLE A-continued
Exemplary Compounds
| I-# | Structure |
|---|---|
| I-101 | 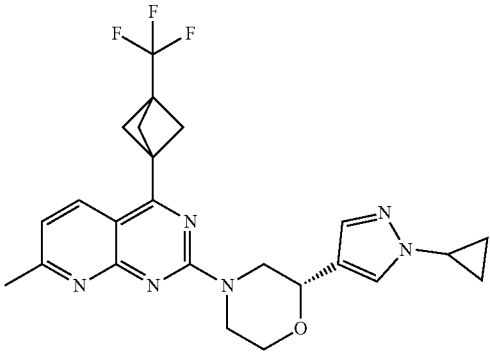 [SMILES: Cc1ccc2c(C34CC(C(F)(F)F)(C3)C4)nc(N3CCO[C@@H](c4cnn(C5CC5)c4)C3)nc2n1] |
| I-102 | 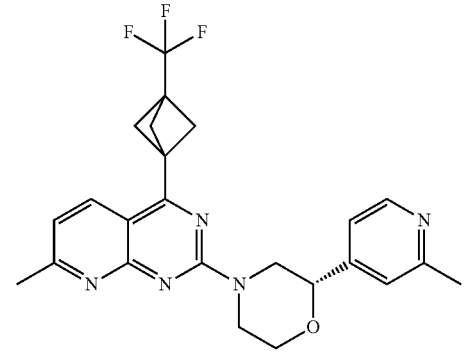 |
| I-103 | 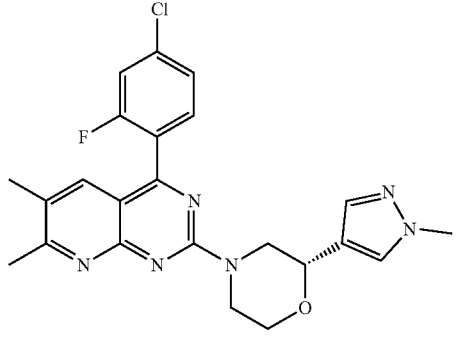 |
| I-104 | 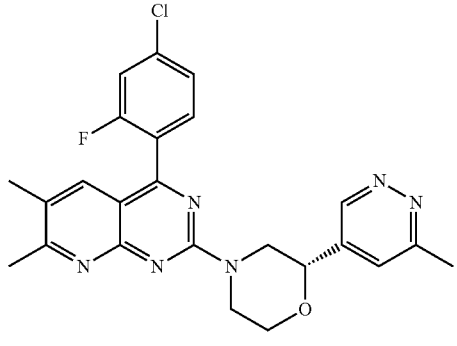 |
| I-105 | 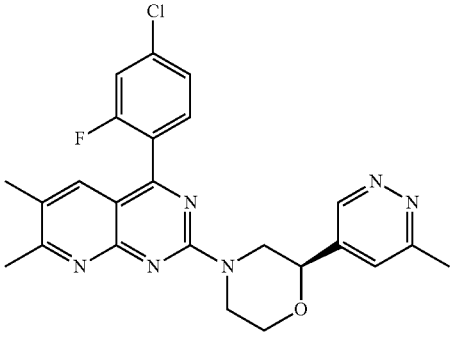 |
| I-106 | 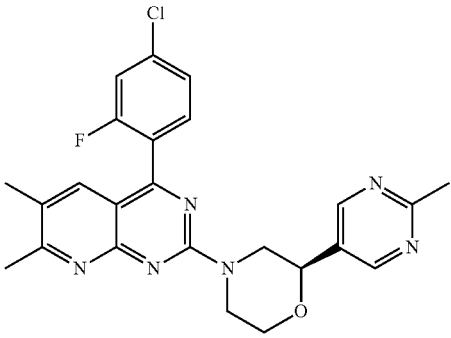 |
| I-107 | 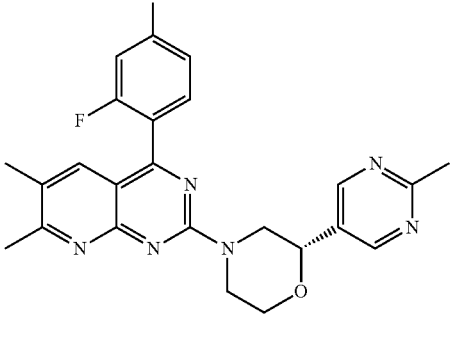 |
| I-108 | 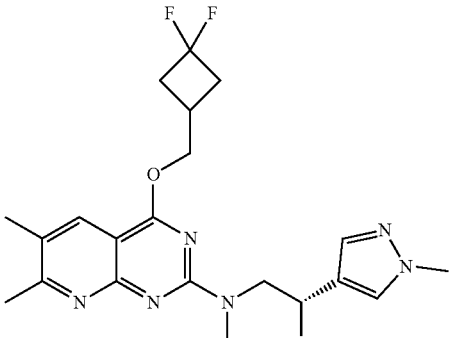 |

TABLE A-continued
Exemplary Compounds
| I-# | Structure |
|---|---|
| I-109 | 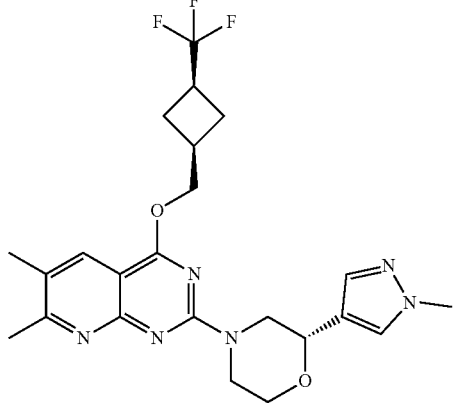 |
| I-110 | 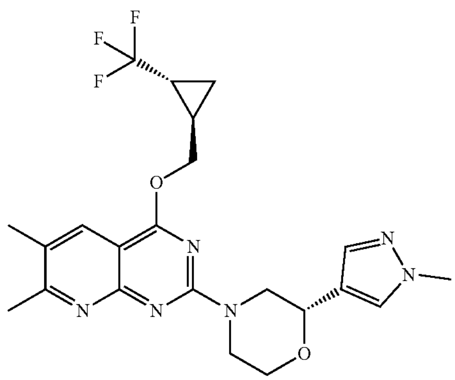 |
| I-111 | 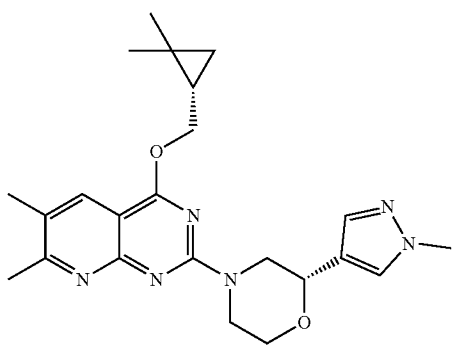 |
| I-112 | 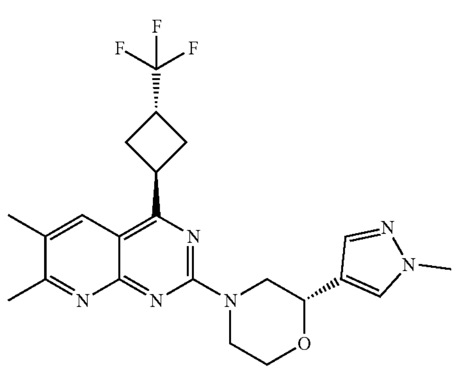 |
| I-113 | 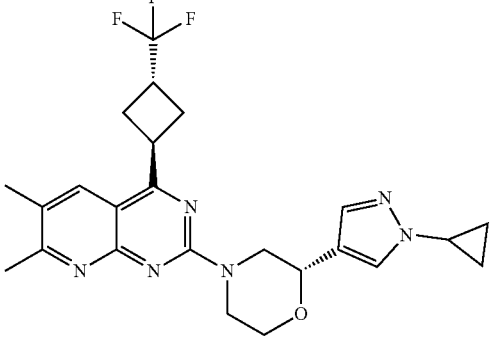 |
| I-114 | 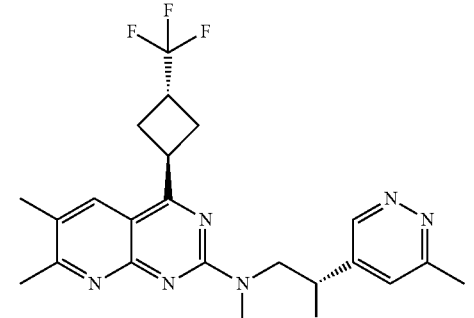 |
| I-115 | 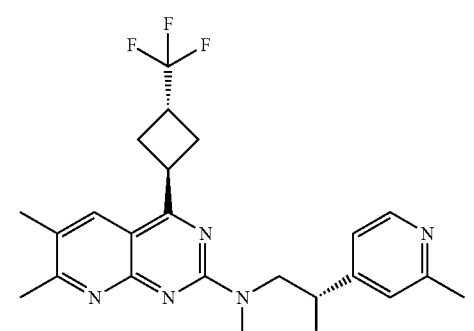 |
| I-116 | 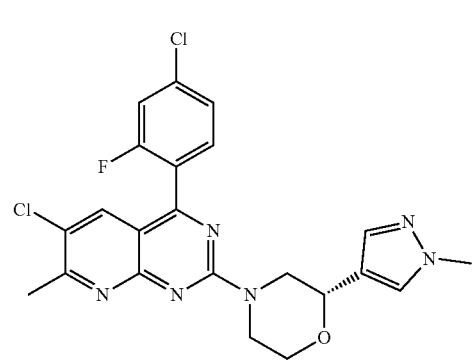 [SMILES: Cc1nc2nc(N3CCO[C@@H](c4cnn(C)c4)C3)nc(-c3ccc(Cl)cc3F)c2cc1Cl] |

TABLE A-continued
Exemplary Compounds
| I-# | Structure |
|---|---|
| I-117 | 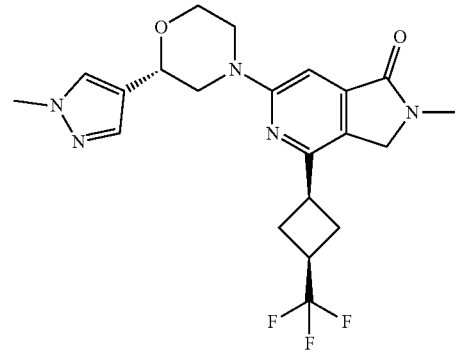 |
| I-118 | 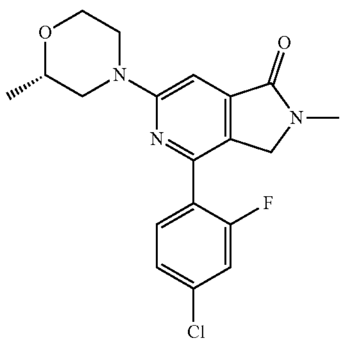 |
| I-119 | 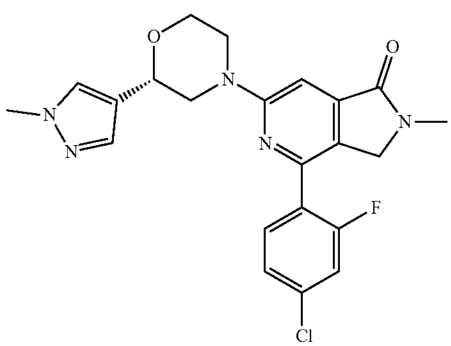 |
| I-120 | 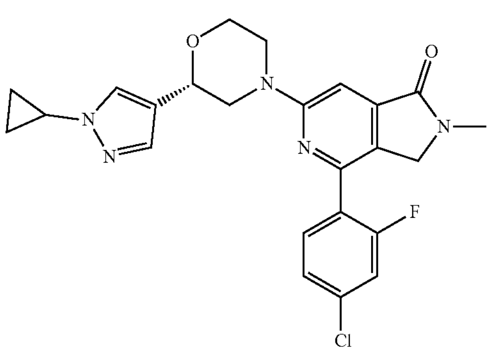 [SMILES: CN1Cc2c(cc(N3CCO[C@@H](c4cnn(C5CC5)c4)C3)nc2-c2ccc(Cl)cc2F)C1=O] |
| I-121 | 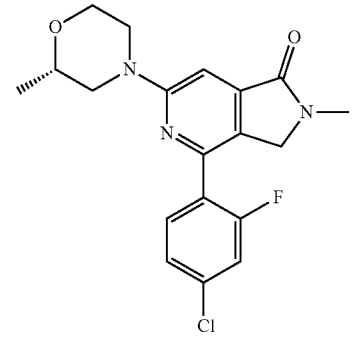 |
| I-122 | |
| I-123 | |
| I-124 | |

TABLE A-continued
Exemplary Compounds
| I-# | Structure |
|---|---|
| I-125 | 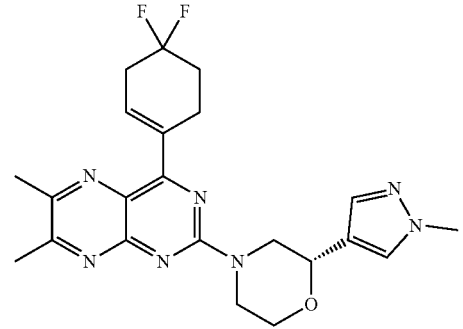 |
| I-126 | 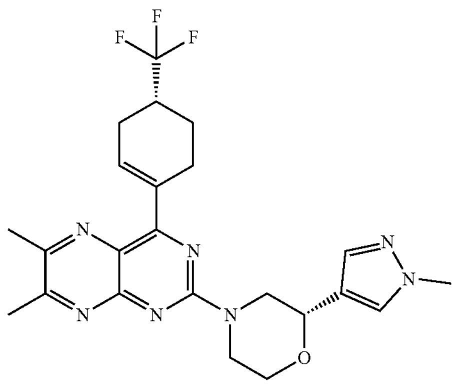 |
| I-127 | 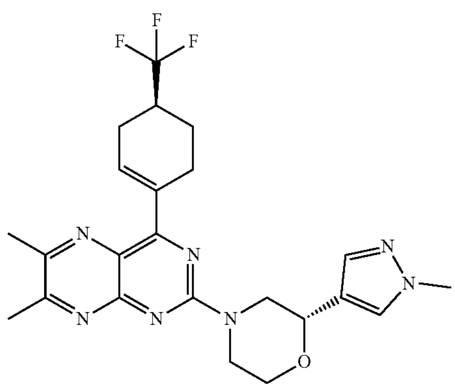 |
| I-128 | 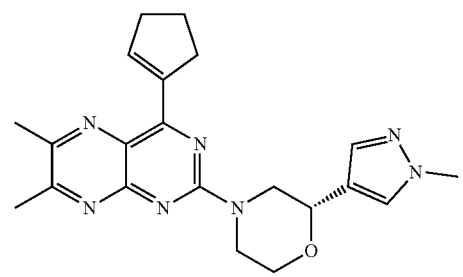 |
| I-129 | 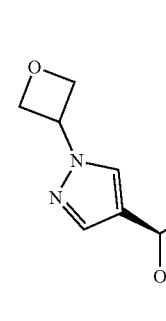 |
| I-130 | 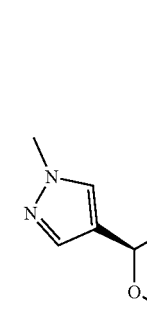 |
| I-131 | 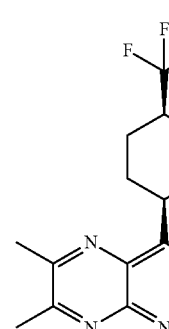 |
| I-132 | 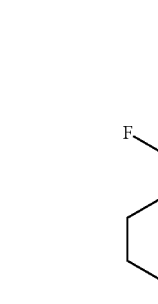 |

TABLE A-continued
Exemplary Compounds
| I-# | Structure |
|---|---|
| I-133 | 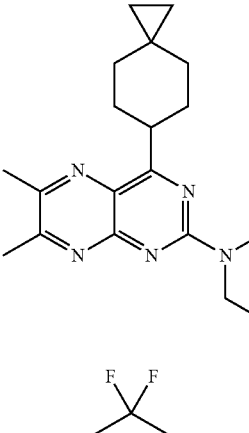 |
| I-134 | 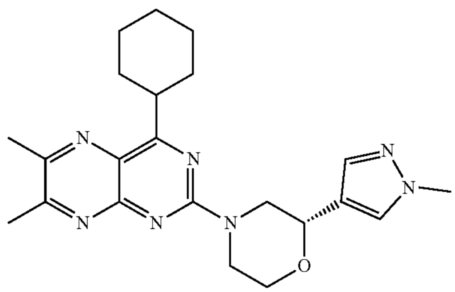 |
| I-135 | 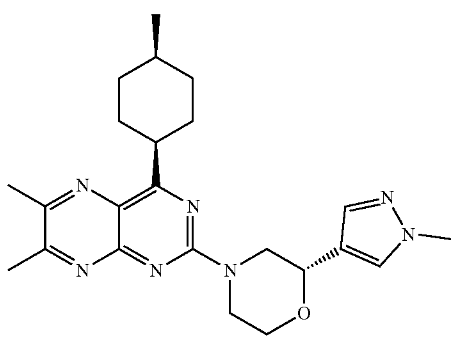 |
| I-136 | 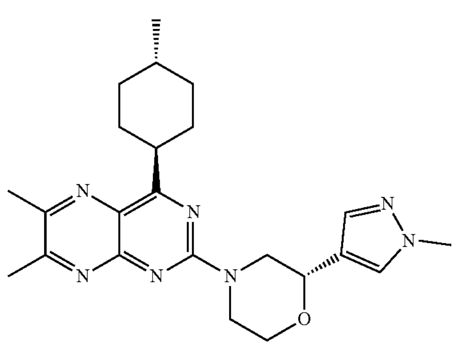 |
| I-137 | 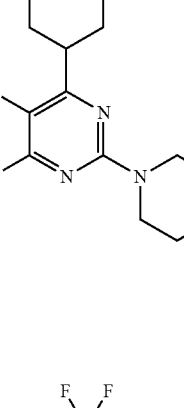 |
| I-138 | |
| I-139 | |
| I-140 | |

TABLE A-continued

Exemplary Compounds

| I-# | Structure |
|---|---|
| I-141 | 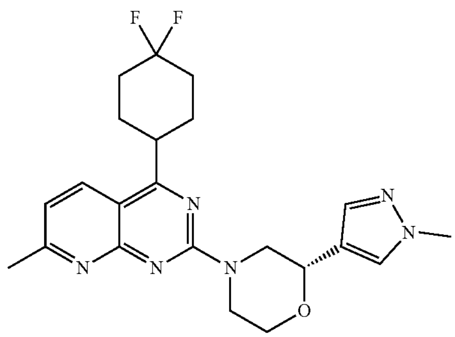 |
| I-142 | 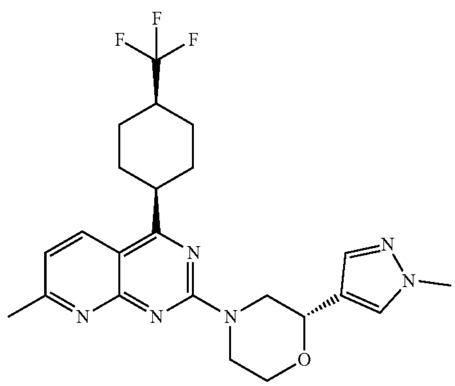 |
| I-143 | 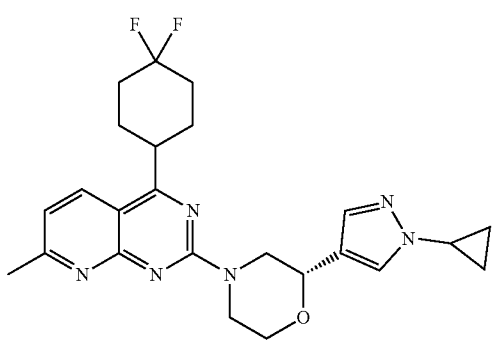 [SMILES: Cc1ccc2c(C3CCC(F)(F)CC3)nc(N3CCO[C@@H](c4cnn(C5CC5)c4)C3)nc2n1] |
| I-144 | 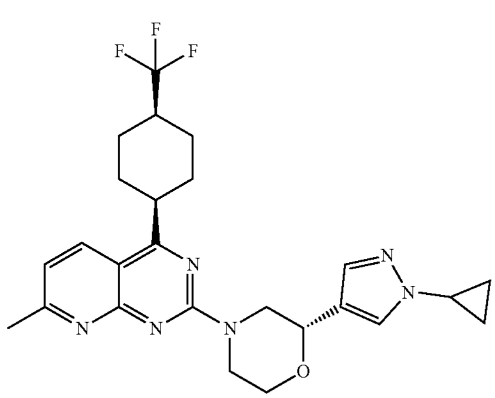 [SMILES: Cc1ccc2c(n1)nc(N1CCO[C@@H](c3cnn(C4CC4)c3)C1)nc2[C@H]1CC[C@@H](C(F)(F)F)CC1] |
| I-145 | |
| I-146 | |
| I-147 | |
| I-148 | |

TABLE A-continued
Exemplary Compounds
| I-# | Structure |
|---|---|
| I-149 | 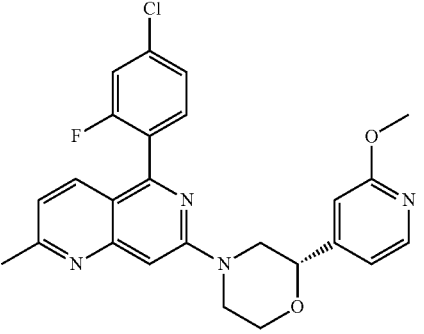 |
| I-150 | 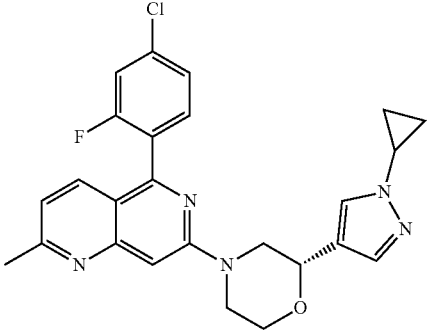 [SMILES: Cc1ccc2c(-c3ccc(Cl)cc3F)nc(N3CCO[C@@H](c4cnn(C5CC5)c4)C3)cc2n1] |
| I-151 | 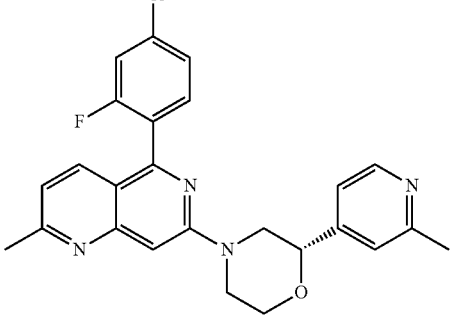 |
| I-152 | 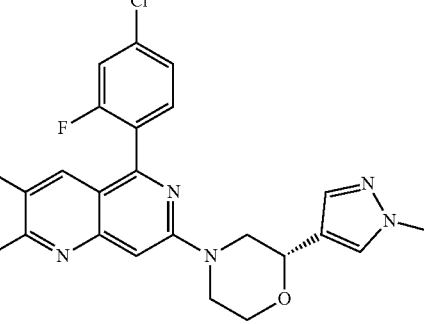 |
| I-153 | 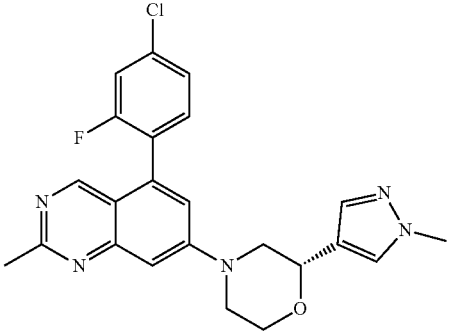 |
| I-154 | 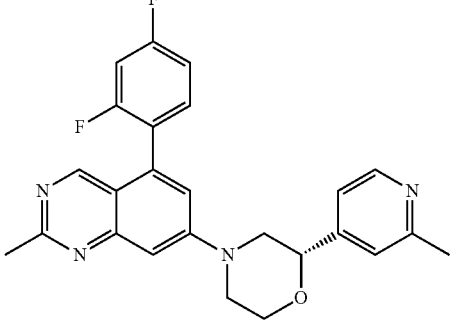 |
| I-155 | 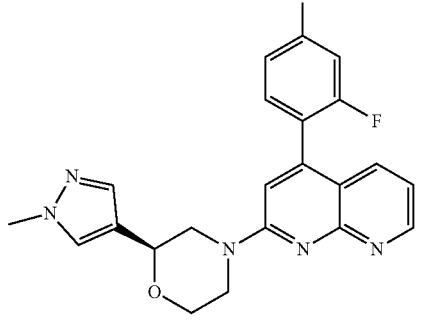 |
| I-156 | 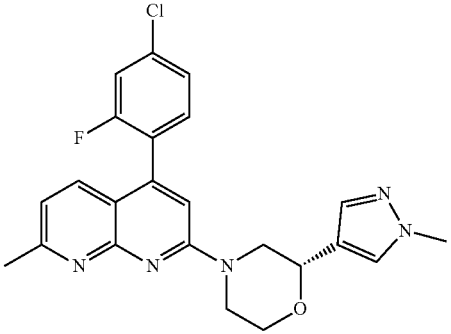 |

TABLE A-continued

Exemplary Compounds

| I-# | Structure |
|---|---|
| I-157 | (structure) |
| I-158 | (structure) |
| I-159 | (structure) |
| I-160 | (structure) |
| I-161 | (structure) |
| I-162 | (structure) |
| I-163 | (structure) |
| I-164 | (structure) |

TABLE A-continued
Exemplary Compounds
| I-# | Structure |
|---|---|
| I-165 | 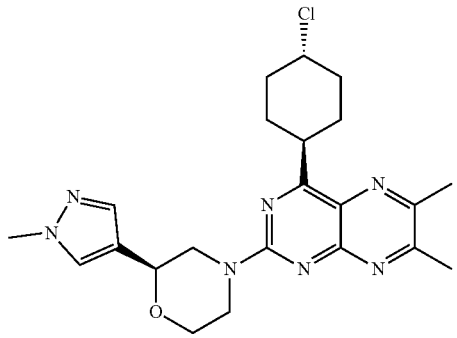 |
| I-166 | 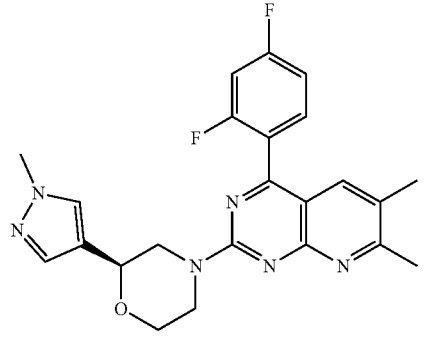 [SMILES: Cc1cc2c(-c3ccc(F)cc3F)nc(N3CCO[C@@H](c4cnn(C)c4)C3)nc2nc1C] |
| I-167 | 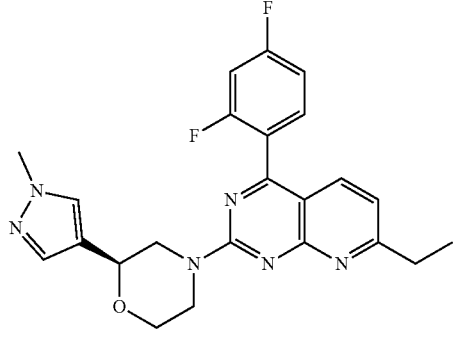 |
| I-168 | 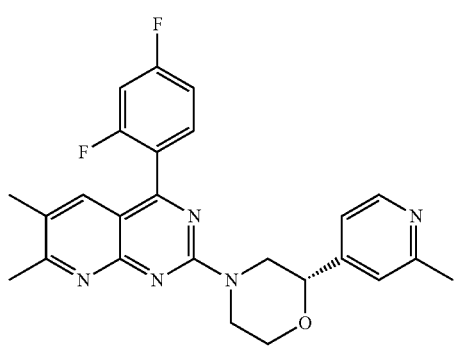 |
| I-169 | 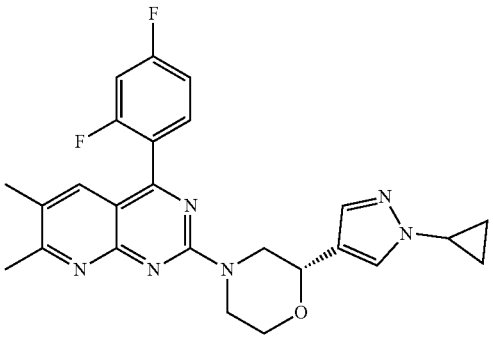 |
| I-170 | 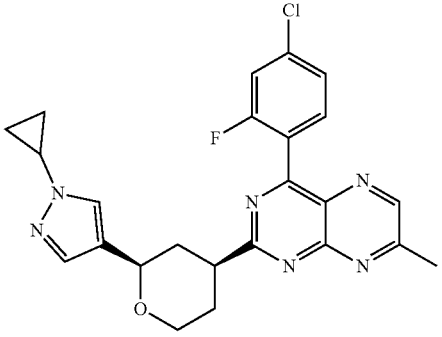 [SMILES: Cc1cnc2c(-c3ccc(Cl)cc3F)nc([C@H]3CCO[C@@H](c4cnn(C5CC5)c4)C3)nc2n1] |
| I-171 | 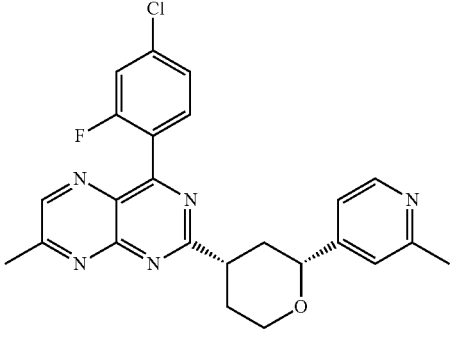 |
| I-172 | 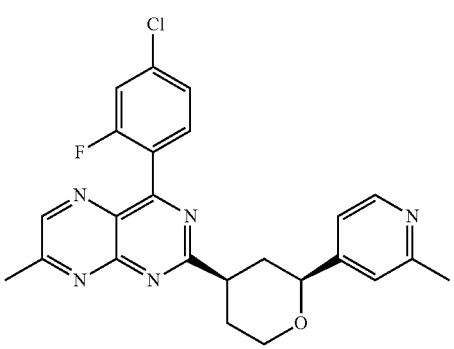 |

TABLE A-continued
Exemplary Compounds
| I-# | Structure |
|---|---|
| I-173 | 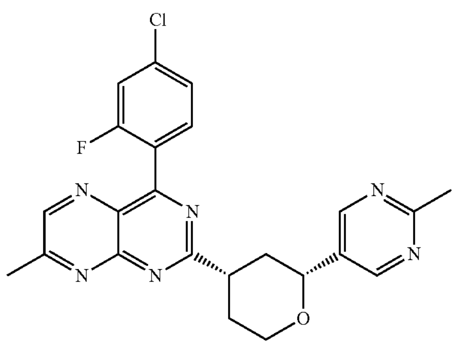 |
| I-174 | 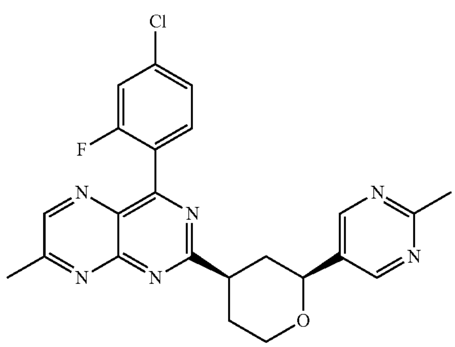 |
| I-175 | 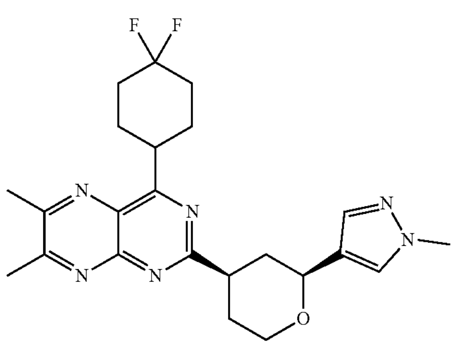 |
| I-176 | 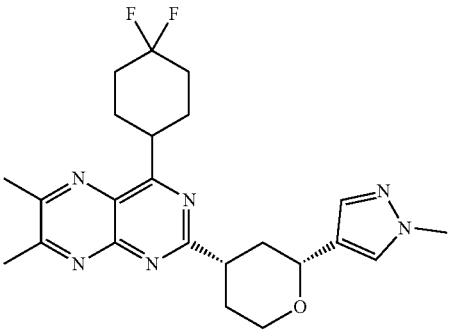 |
| I-177 |  |
| I-178 |  |
| I-179 |  |
| I-180 | 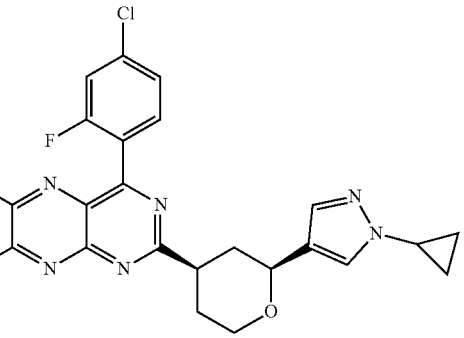 |

TABLE A-continued

Exemplary Compounds

| I-# | Structure |
|---|---|
| I-181 | 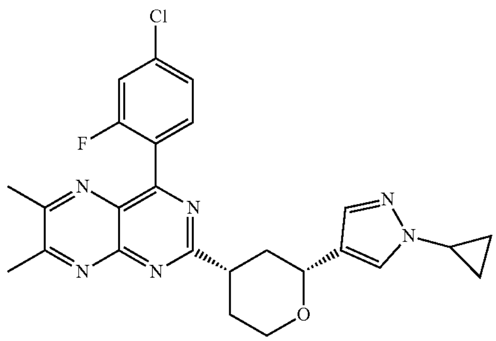 [SMILES: Cc1nc2nc([C@H]3CCO[C@@H](c4cnn(C5CC5)c4)C3)nc(-c3ccc(Cl)cc3F)c2nc1C] |
| I-182 | 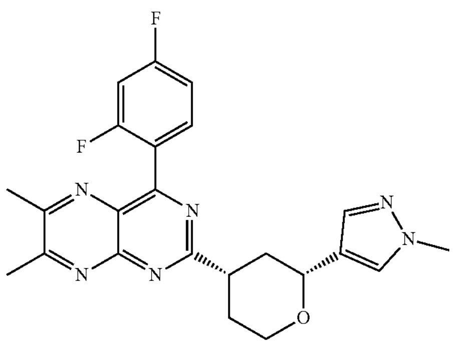 |
| I-183 | 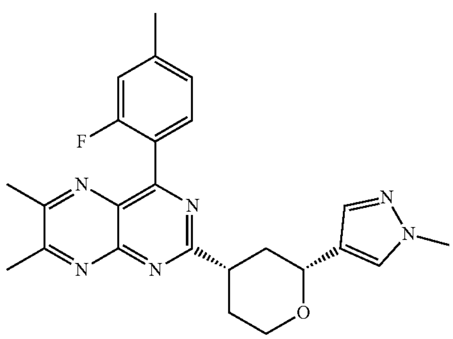 |
| I-184 | 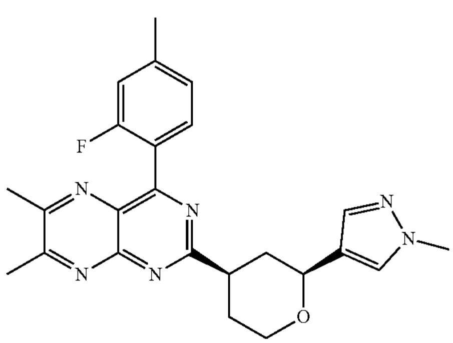 |
| I-185 | |
| I-186 | |
| I-187 | |
| I-188 | |

TABLE A-continued

Exemplary Compounds

| I-# | Structure |
|---|---|
| I-189 | 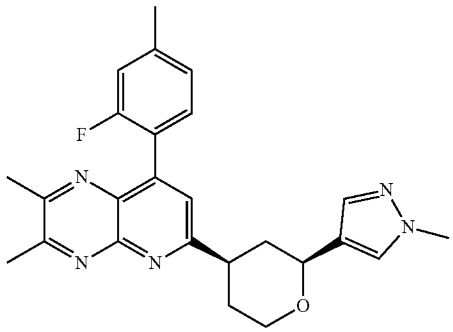 |
| I-190 | 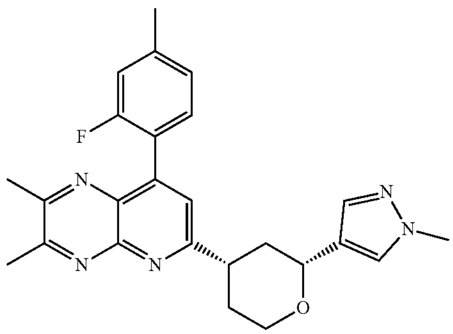 |
| I-191 | 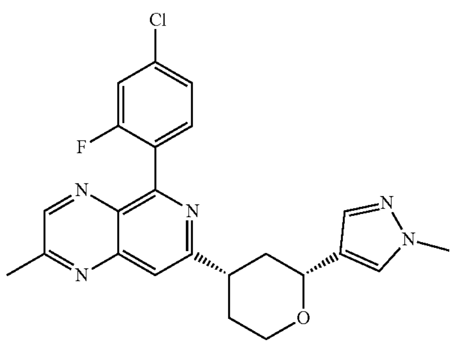 |
| I-192 | 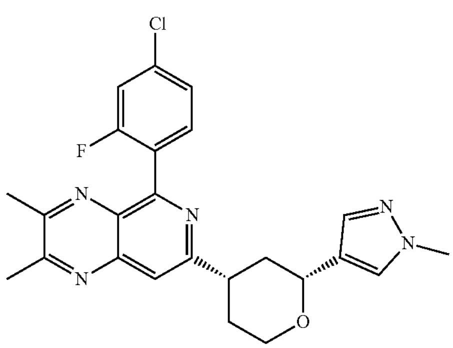 |
| I-193 | |
| I-194 | |
| I-195 | |
| I-196 | |

TABLE A-continued
Exemplary Compounds
| I-# | Structure |
|---|---|
| I-197 | 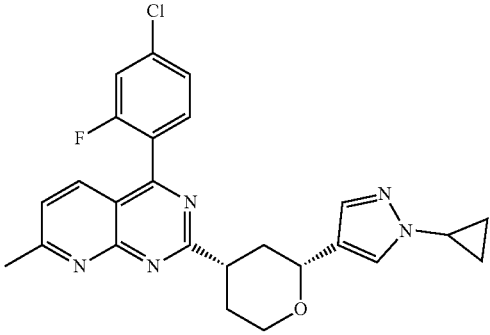 |
| I-198 | 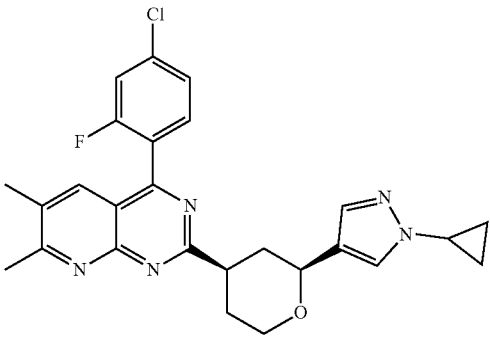 [SMILES: Cc1cc2c(-c3ccc(Cl)cc3F)nc([C@@H]3CCO[C@H](c4cnn(C5CC5)c4)C3)nc2nc1C] |
| I-199 | 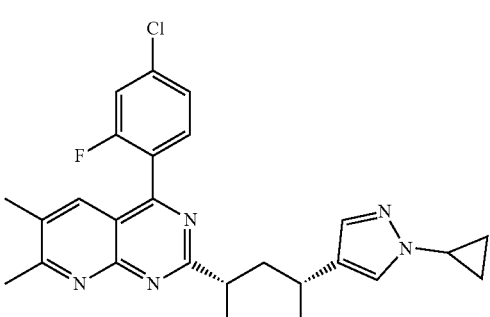 |
| I-200 | 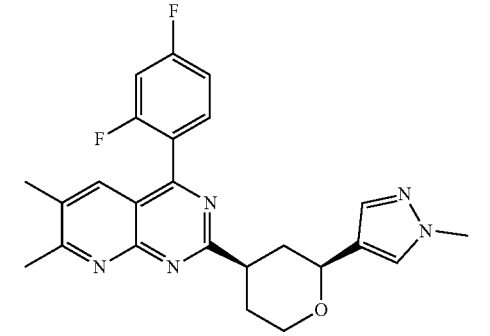 |
| I-201 | 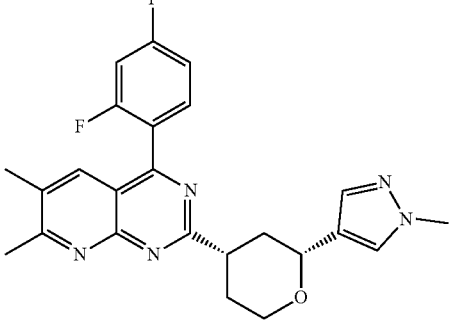 |
| I-202 | 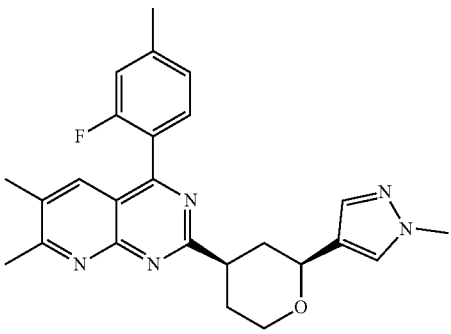 |
| I-203 | 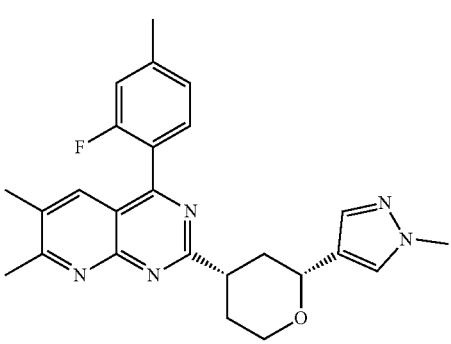 |
| I-204 | 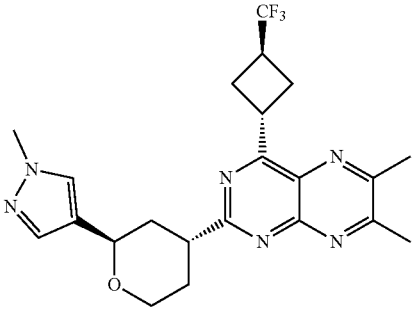 [SMILES: Cc1nc2nc([C@@H]3CCO[C@@H](c4cnn(C)c4)C3)nc([C@H]3C[C@H](C(F)(F)F)C3)c2nc1C] |

TABLE A-continued
Exemplary Compounds
| I-# | Structure |
|---|---|
| I-205 | 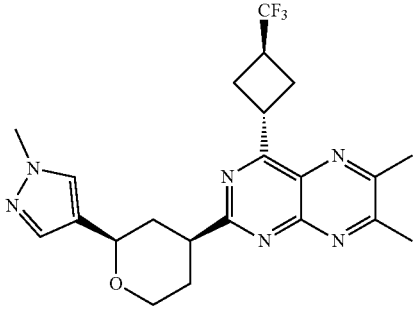 [SMILES: Cc1nc2nc([C@H]3CCO[C@@H](c4cnn(C)c4)C3)nc([C@H]3C[C@H](C(F)(F)F)C3)c2nc1C] |
| I-206 | 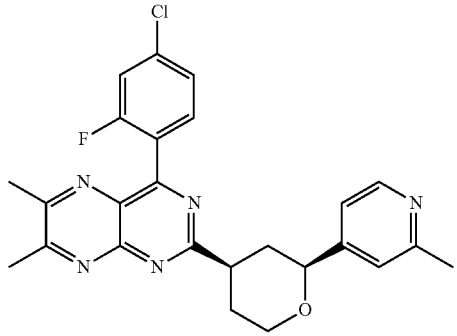 |
| I-207 | 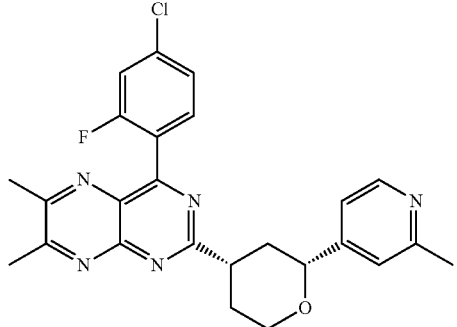 |
| I-208 | 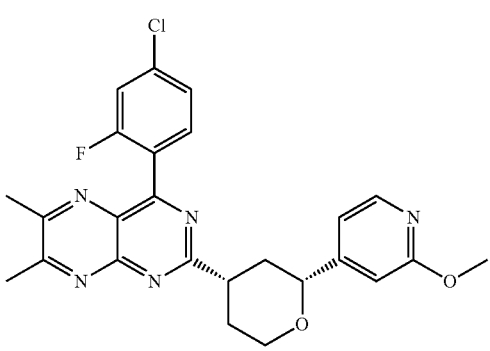 |
| I-209 | 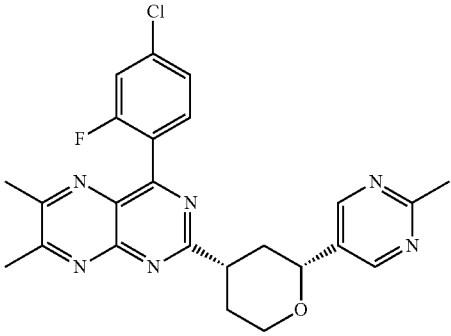 |
| I-210 | 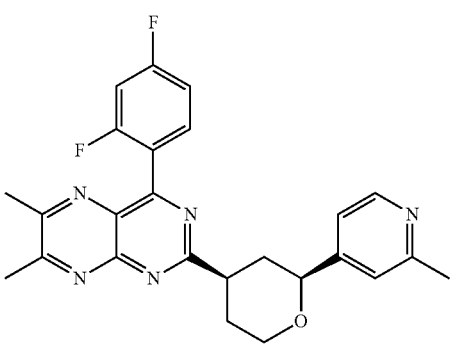 |
| I-211 | 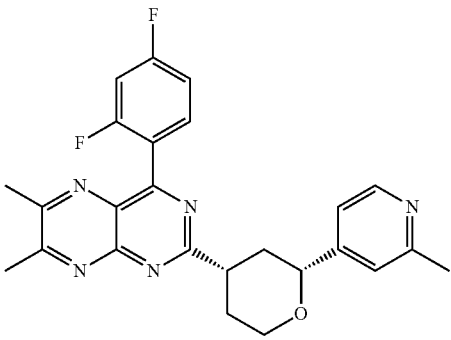 |
| I-212 | 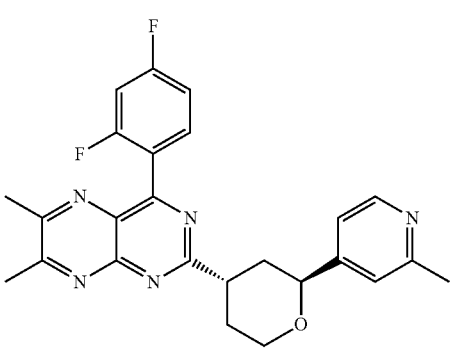 |

TABLE A-continued
Exemplary Compounds
| I-# | Structure |
|---|---|
| I-213 | 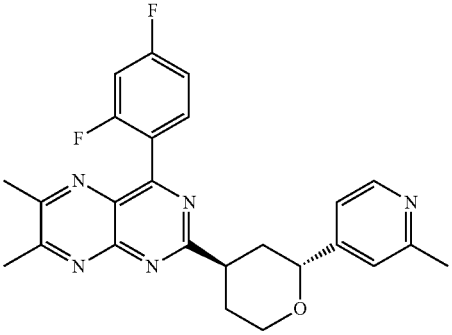 |
| I-214 | 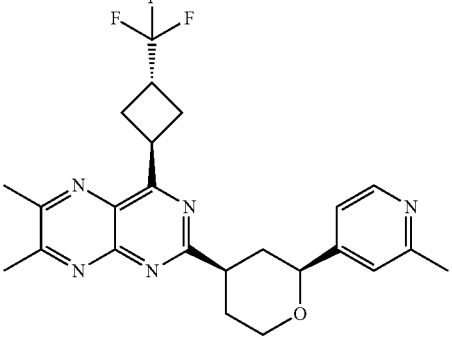 |
| I-215 | 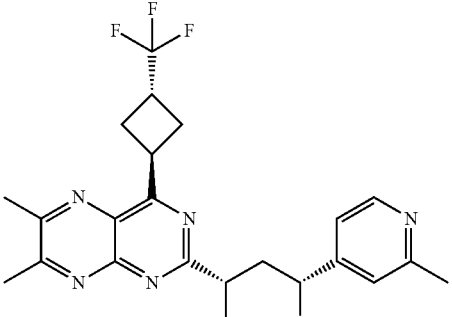 |
| I-216 | 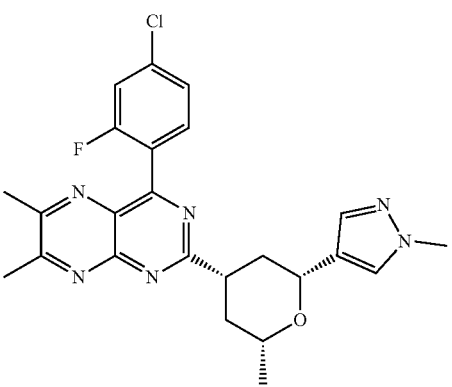 |
| I-217 | 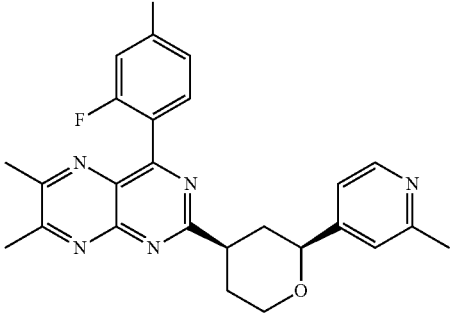 |
| I-218 | 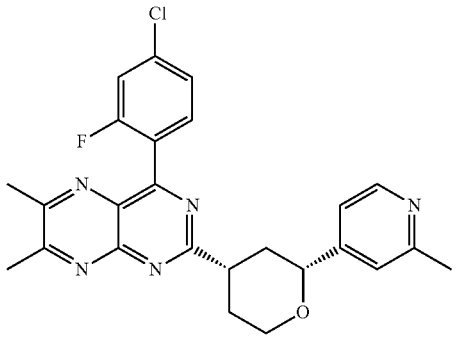 |
| I-219 | 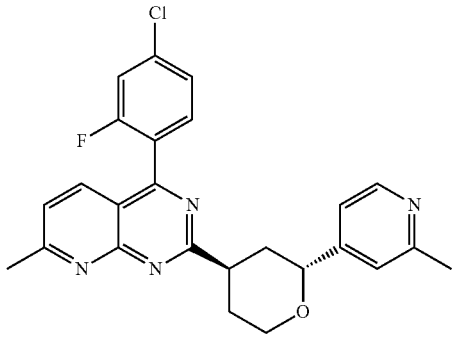 |
| I-220 | 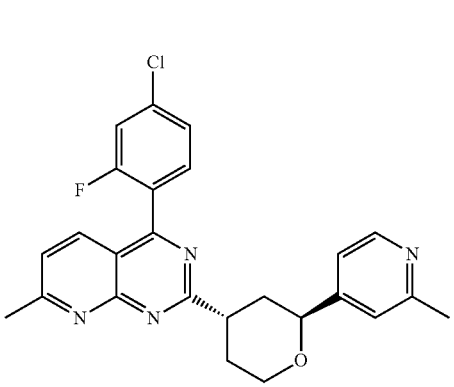 |

TABLE A-continued

Exemplary Compounds

| I-# | Structure |
|---|---|
| I-221 | 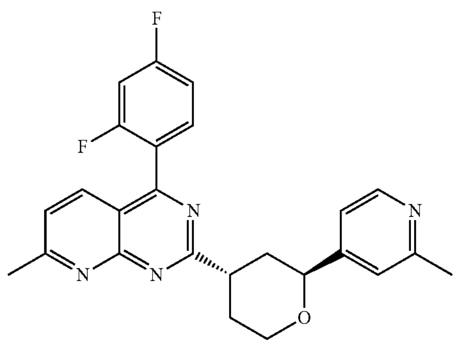 |
| I-222 | 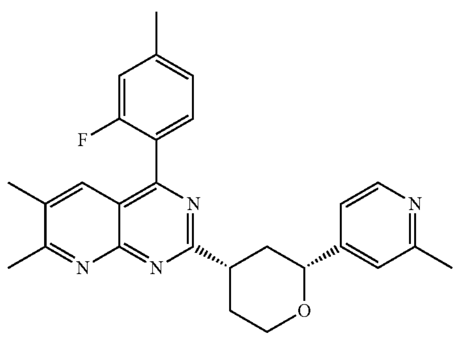 |
| I-223 | 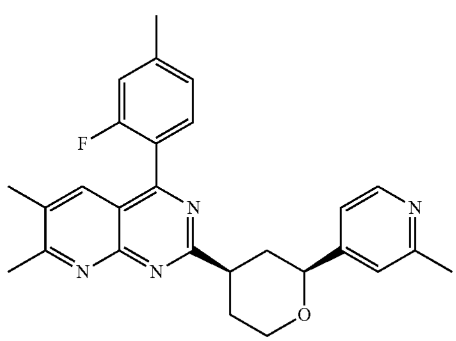 |
| I-224 | 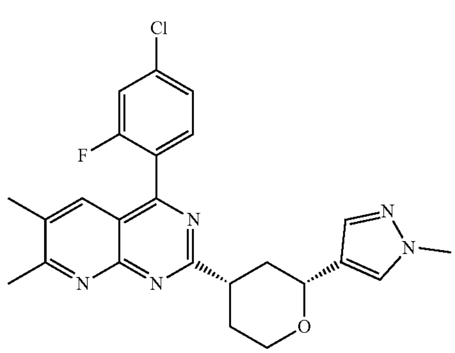 |
| I-225 | |
| I-226 | |
| I-227 | |
| I-228 | |

TABLE A-continued
Exemplary Compounds
| I-# | Structure |
|---|---|
| I-229 | 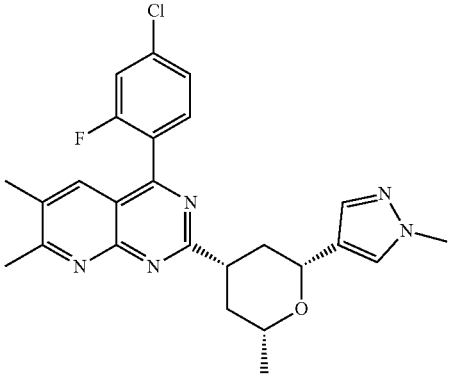 |
| I-230 | 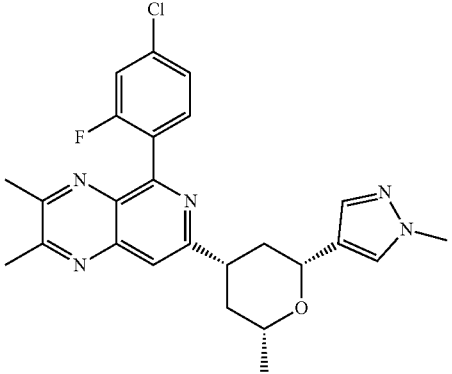 |
| I-231 | 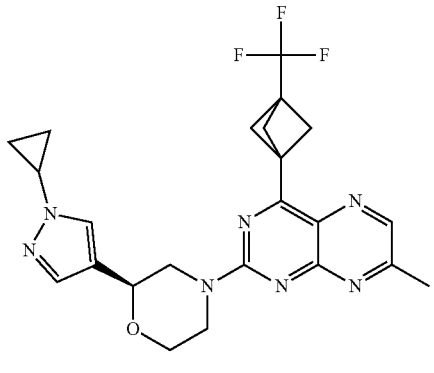 [SMILES: Cc1cnc2c(C34CC(C(F)(F)F)(C3)C4)nc(N3CCO[C@@H](c4cnn(C5CC5)c4)C3)nc2n1] |
| I-232 | 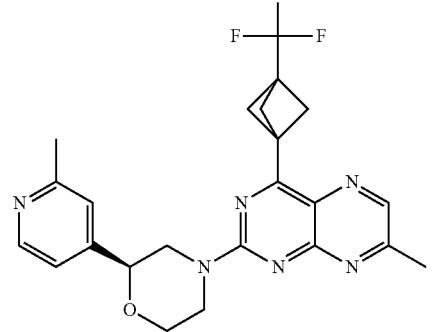 |
| I-233 | 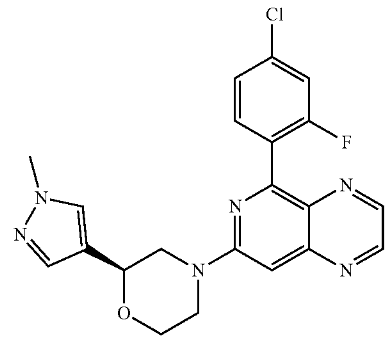 [SMILES: Cn1cc([C@H]2CN(c3cc4nccnc4c(-c4ccc(Cl)cc4F)n3)CCO2)cn1] |
| I-234 | 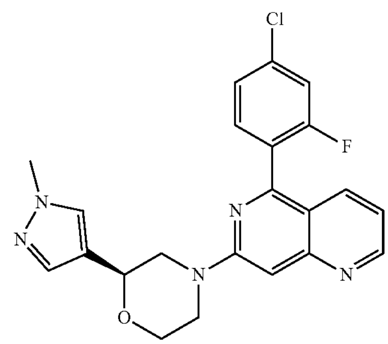 [SMILES: Cn1cc([C@H]2CN(c3cc4ncccc4c(-c4ccc(Cl)cc4F)n3)CCO2)cn1] |
| I-235 | 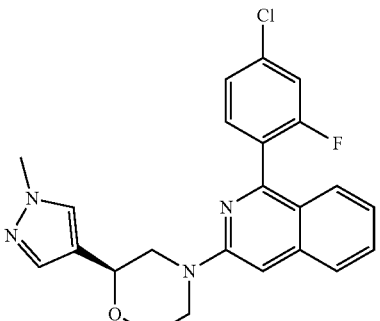 |
| I-236 | 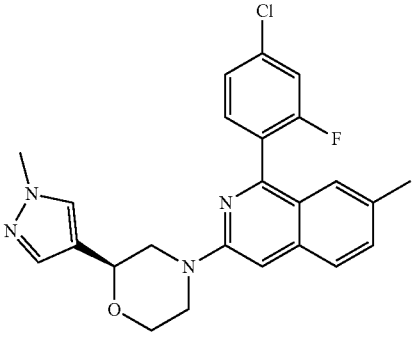 [SMILES: Cc1ccc2cc(N3CCO[C@@H](c4cnn(C)c4)C3)nc(-c3ccc(Cl)cc3F)c2c1] |

TABLE A-continued
Exemplary Compounds
| I-# | Structure |
|---|---|
| I-237 | 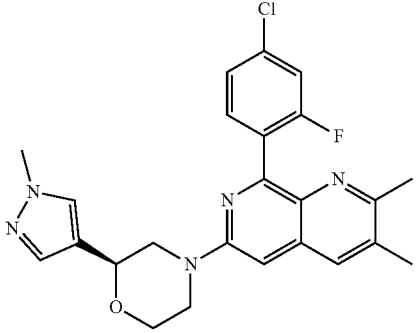 [SMILES: Cc1cc2cc(N3CCO[C@@H](c4cnn(C)c4)C3)nc(-c3ccc(Cl)cc3F)c2nc1C] |
| I-238 | 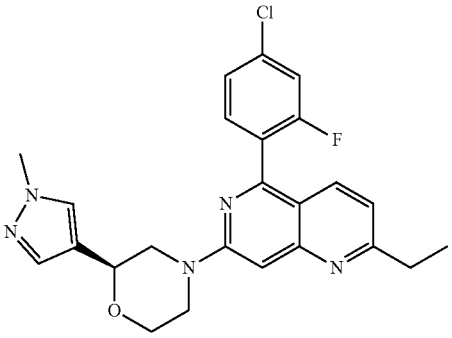 [SMILES: CCc1ccc2c(-c3ccc(Cl)cc3F)nc(N3CCO[C@@H](c4cnn(C)c4)C3)cc2n1] |
| I-239 | 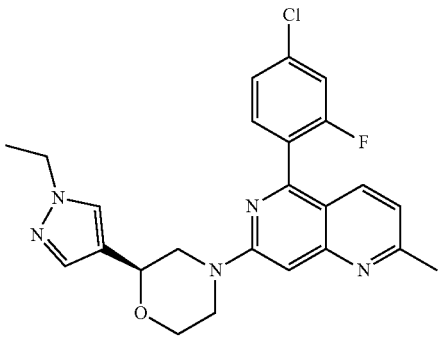 [SMILES: CCn1cc([C@H]2CN(c3cc4nc(C)ccc4c(-c4ccc(Cl)cc4F)n3)CCO2)cn1] |
| I-240 | 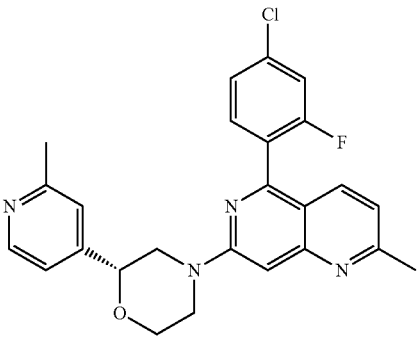 [SMILES: Cc1cc([C@@H]2CN(c3cc4nc(C)ccc4c(-c4ccc(Cl)cc4F)n3)CCO2)ccn1] |
| I-241 |  |
| I-242 |  |
| I-243 | 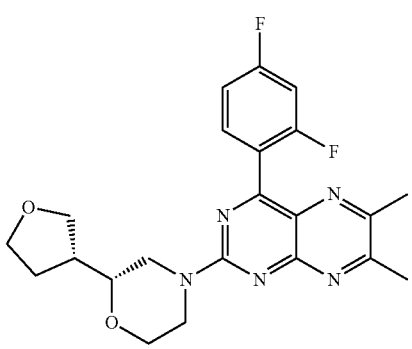 |
| I-244 |  |

TABLE A-continued

Exemplary Compounds

| I-# | Structure |
|---|---|
| I-245 | 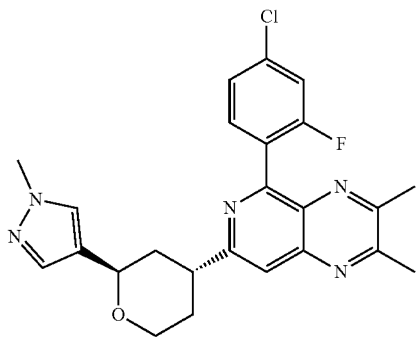 [SMILES: Cc1nc2cc([C@@H]3CCO[C@@H](c4cnn(C)c4)C3)nc(-c3ccc(Cl)cc3F)c2nc1C] |
| I-246 | 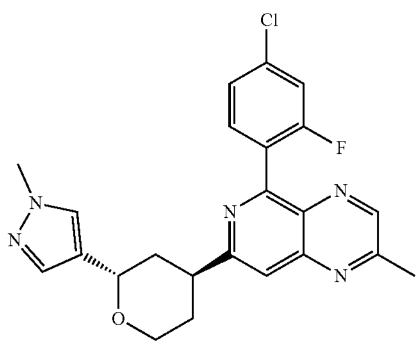 [SMILES: Cc1cnc2c(-c3ccc(Cl)cc3F)nc([C@H]3CCO[C@H](c4cnn(C)c4)C3)cc2n1] |
| I-247 | 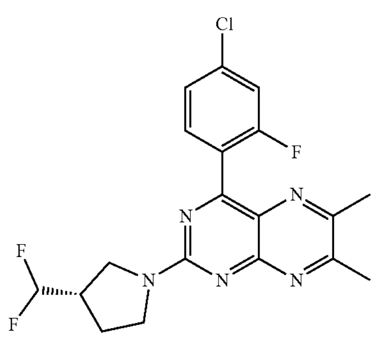 [SMILES: Cc1nc2nc(N3CC[C@H](C(F)F)C3)nc(-c3ccc(Cl)cc3F)c2nc1C] |
| I-248 | 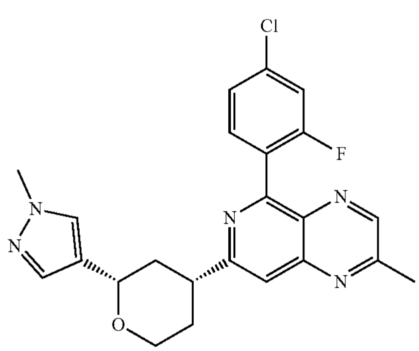 [SMILES: Cc1cnc2c(-c3ccc(Cl)cc3F)nc([C@@H]3CCO[C@H](c4cnn(C)c4)C3)cc2n1] |
| I-249 | |
| I-250 | |
| I-251 | |
| I-252 | |

TABLE A-continued

Exemplary Compounds

| I-# | Structure |
|---|---|
| I-253 | 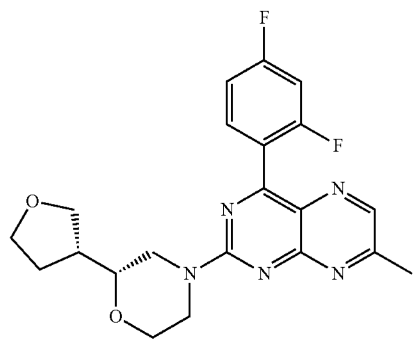 |
| I-254 | 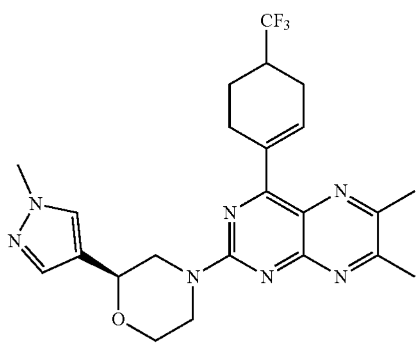 [SMILES: Cc1nc2nc(N3CCO[C@@H](c4cnn(C)c4)C3)nc(C3=CCC(C(F)(F)F)CC3)c2nc1C] |
| I-255 | 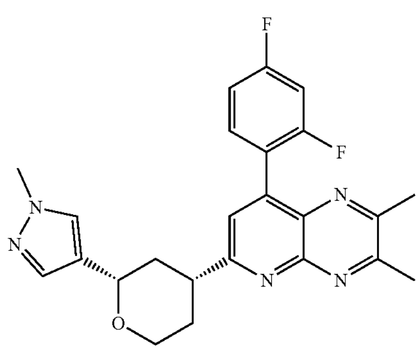 |
| I-256 | 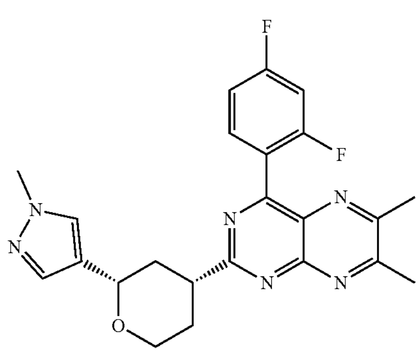 |
| I-257 | 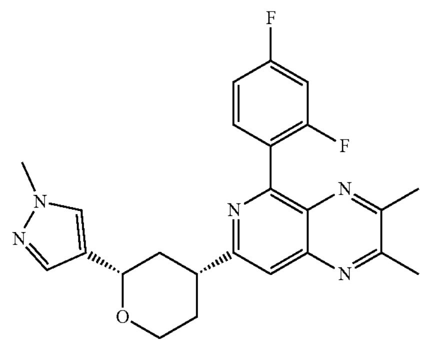 [SMILES: Cc1nc2cc([C@@H]3CCO[C@H](c4cnn(C)c4)C3)nc(-c3ccc(F)cc3F)c2nc1C] |
| I-258 | 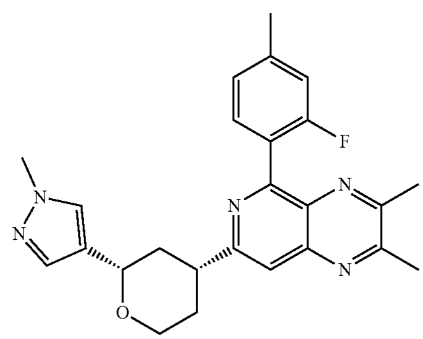 [SMILES: Cc1ccc(-c2nc([C@@H]3CCO[C@H](c4cnn(C)c4)C3)cc3nc(C)c(C)nc23)c(F)c1] |
| I-259 | 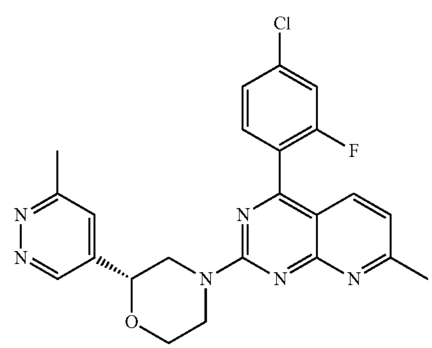 |
| I-260 | 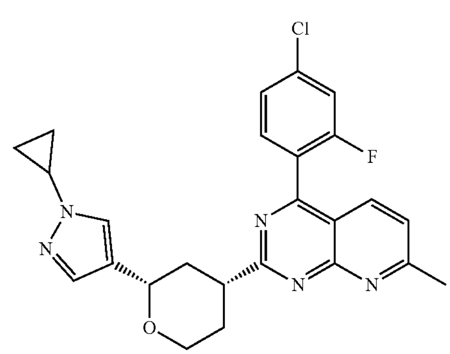 [SMILES: Cc1ccc2c(-c3ccc(Cl)cc3F)nc([C@@H]3CCO[C@H](c4cnn(C5CC5)c4)C3)nc2n1] |

TABLE A-continued
Exemplary Compounds
| I-# | Structure |
|---|---|
| I-261 | 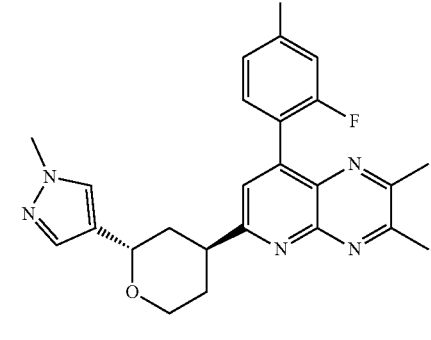 |
| I-262 | 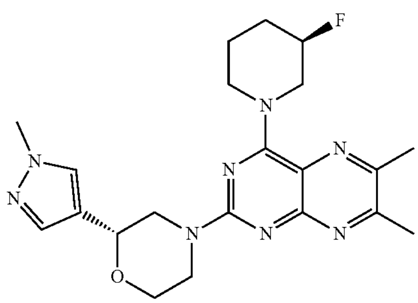 [SMILES: Cc1nc2nc(N3CCO[C@H](c4cnn(C)c4)C3)nc(N3CCC[C@@H](F)C3)c2nc1C] |
| I-263 | 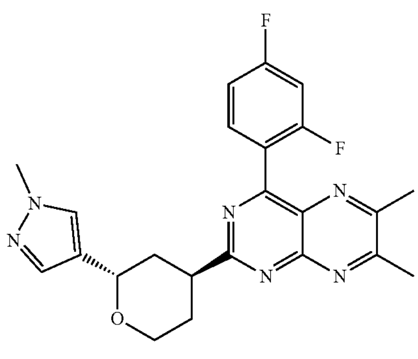 [SMILES: Cc1nc2nc([C@H]3CCO[C@H](c4cnn(C)c4)C3)nc(-c3ccc(F)cc3F)c2nc1C] |
| I-264 | 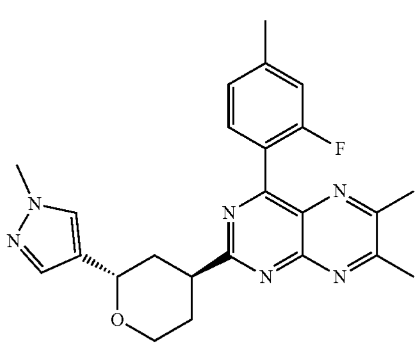 [SMILES: Cc1ccc(-c2nc([C@H]3CCO[C@H](c4cnn(C)c4)C3)nc3nc(C)c(C)nc23)c(F)c1] |
| I-265 | 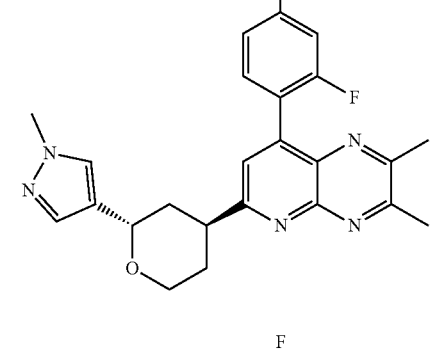 |
| I-266 | |
| I-267 | |
| I-268 | |

TABLE A-continued
Exemplary Compounds
| I-# | Structure |
|---|---|
| I-269 | 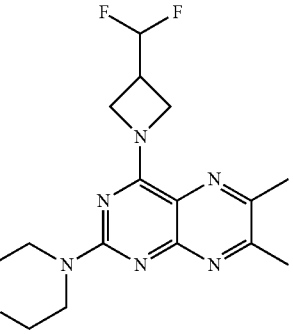 |
| I-270 | 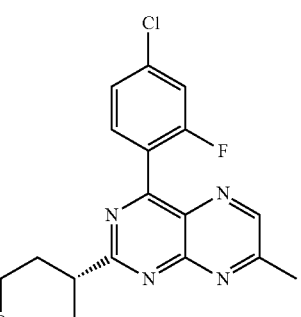 |
| I-271 | 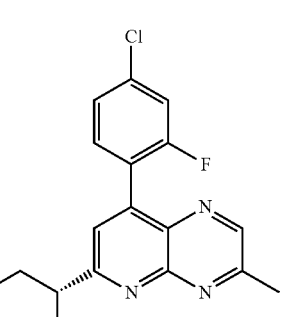 |
| I-272 | 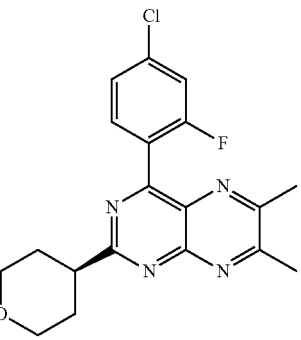 |
| I-273 | 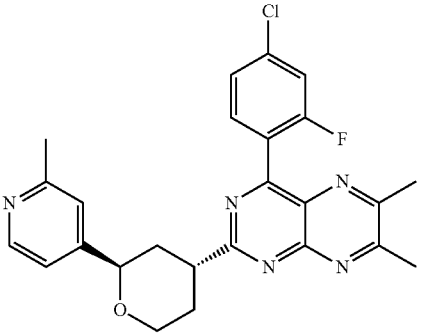 [SMILES: Cc1cc([C@H]2C[C@H](c3nc(-c4ccc(Cl)cc4F)c4nc(C)c(C)nc4n3)CCO2)ccn1] |
| I-274 | 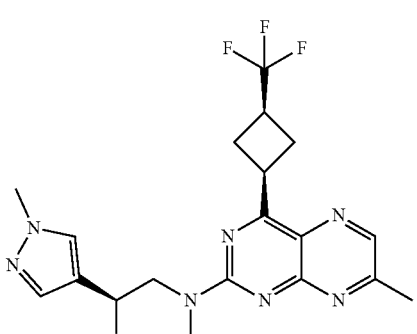 |
| I-275 | 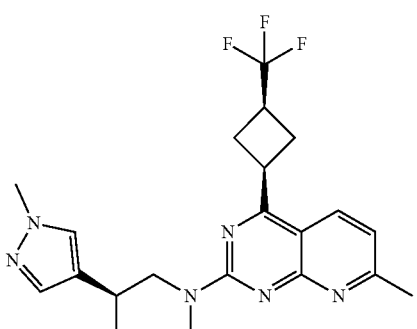 |
| I-276 | 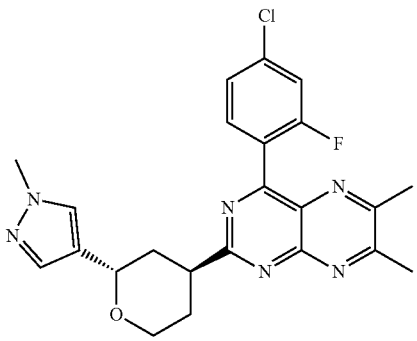 |

TABLE A-continued
Exemplary Compounds
| I-# | Structure |
|---|---|
| I-277 | 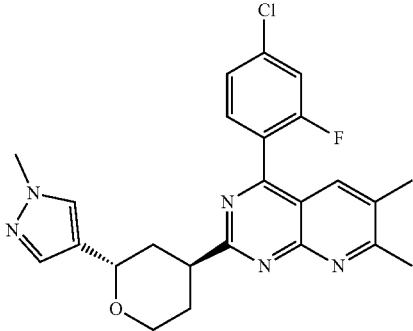 [SMILES: Cc1cc2c(-c3ccc(Cl)cc3F)nc([C@H]3CCO[C@H](c4cnn(C)c4)C3)nc2nc1C] |
| I-278 | 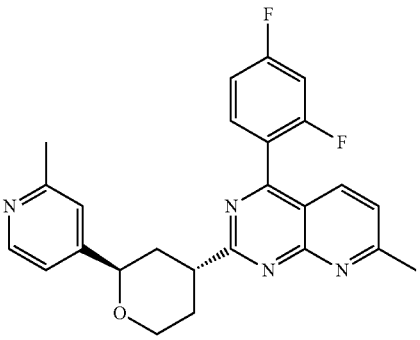 [SMILES: Cc1cc([C@H]2C[C@H](c3nc(-c4ccc(F)cc4F)c4ccc(C)nc4n3)CCO2)ccn1] |
| I-279 | 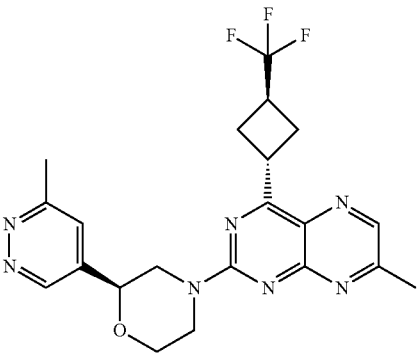 [SMILES: Cc1cc([C@H]2CN(c3nc4nc(C)cnc4c([C@H]4C[C@H](C(F)(F)F)C4)n3)CCO2)cnn1] |
| I-280 | 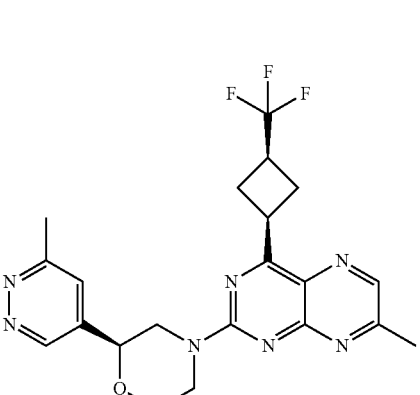 |
| I-281 | 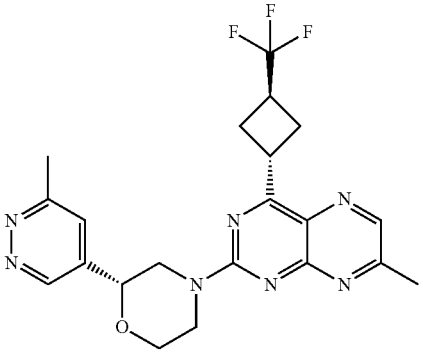 [SMILES: Cc1cc([C@@H]2CN(c3nc4nc(C)cnc4c([C@H]4C[C@H](C(F)(F)F)C4)n3)CCO2)cnn1] |
| I-282 | 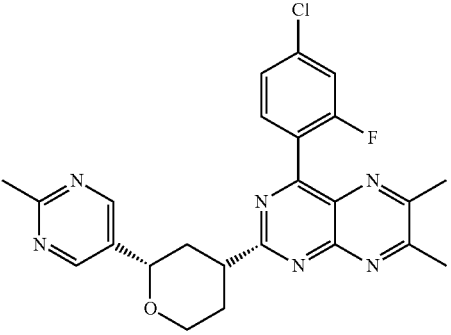 |
| I-283 | 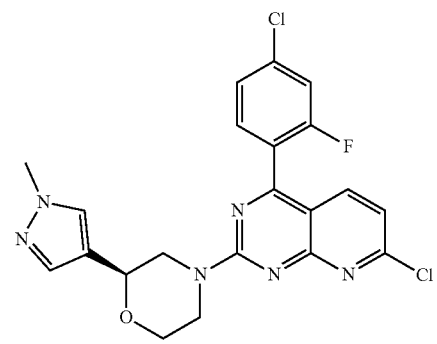 [SMILES: Cn1cc([C@H]2CN(c3nc(-c4ccc(Cl)cc4F)c4ccc(Cl)nc4n3)CCO2)cn1] |
| I-284 | 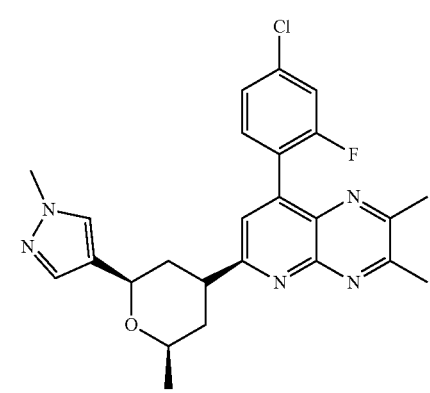 |

TABLE A-continued

Exemplary Compounds

| I-# | Structure |
|---|---|
| I-285 | 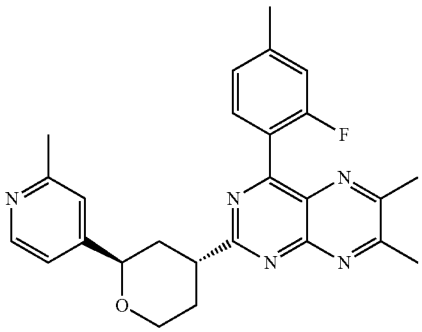 [SMILES: Cc1ccc(-c2nc([C@@H]3CCO[C@@H](c4ccnc(C)c4)C3)nc3nc(C)c(C)nc23)c(F)c1] |
| I-286 | 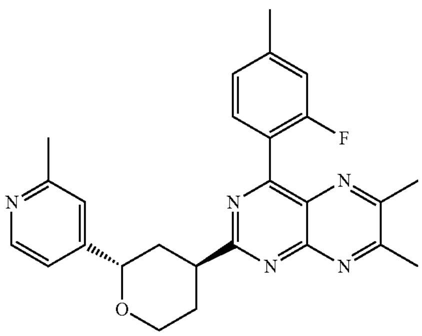 [SMILES: Cc1ccc(-c2nc([C@H]3CCO[C@H](c4ccnc(C)c4)C3)nc3nc(C)c(C)nc23)c(F)c1] |
| I-287 | 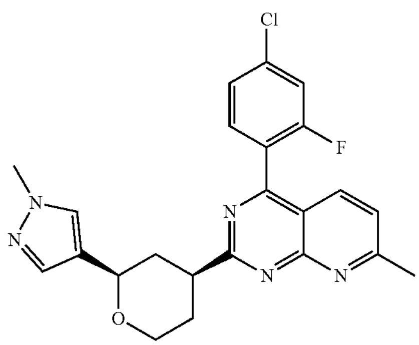 [SMILES: Cc1ccc2c(-c3ccc(F)cc3F)nc([C@H]3CCO[C@@H](c4cnn(C)c4)C3)nc2n1] |
| I-288 | 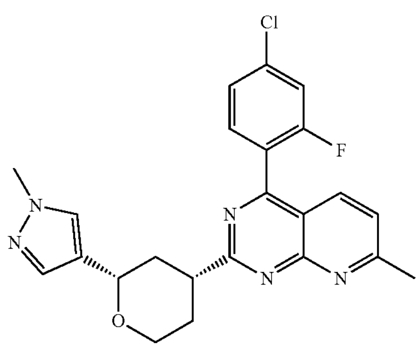 [SMILES: Cc1ccc2c(-c3ccc(F)cc3F)nc([C@@H]3CCO[C@H](c4cnn(C)c4)C3)nc2n1] |
| I-289 | |
| I-290 | |
| I-291 | |
| I-292 | |

TABLE A-continued
Exemplary Compounds
| I-# | Structure |
|---|---|
| I-293 | 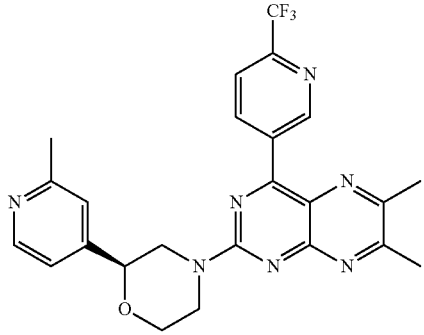 [SMILES: Cc1cc([C@H]2CN(c3nc(-c4ccc(C(F)(F)F)nc4)c4nc(C)c(C)nc4n3)CCO2)ccn1] |
| I-294 | 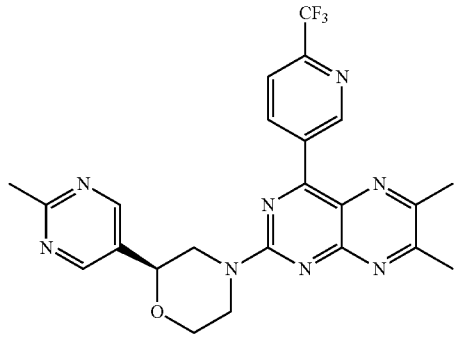 |
| I-295 | 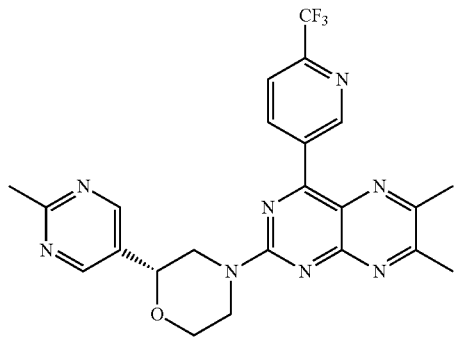 |
| I-296 | 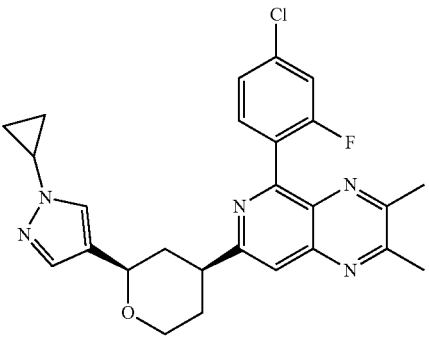 [SMILES: Cc1nc2cc([C@H]3CCO[C@@H](c4cnn(C5CC5)c4)C3)nc(-c3ccc(Cl)cc3F)c2nc1C] |
| I-297 | 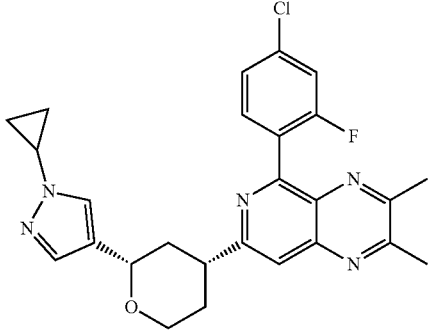 [SMILES: Cc1nc2cc([C@@H]3CCO[C@H](c4cnn(C5CC5)c4)C3)nc(-c3ccc(Cl)cc3F)c2nc1C] |
| I-298 | 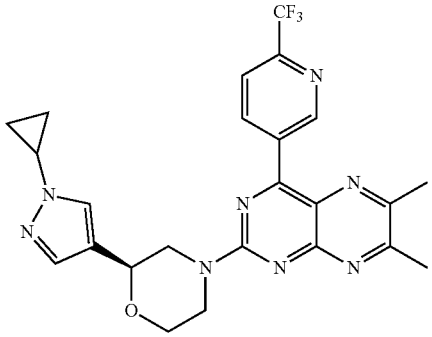 |
| I-299 | 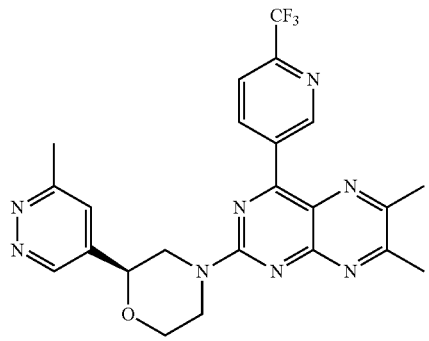 [SMILES: Cc1cc([C@H]2CN(c3nc(-c4ccc(C(F)(F)F)nc4)c4nc(C)c(C)nc4n3)CCO2)cnn1] |
| I-300 | 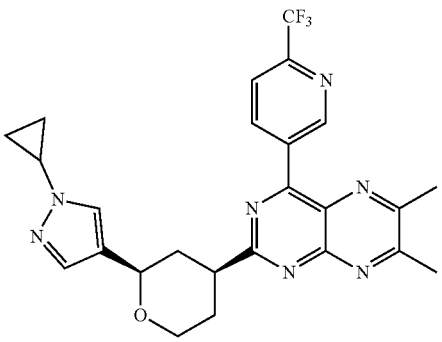 [SMILES: Cc1nc2nc([C@H]3CCO[C@@H](c4cnn(C5CC5)c4)C3)nc(-c3ccc(C(F)(F)F)nc3)c2nc1C] |

TABLE A-continued
Exemplary Compounds
| I-# | Structure |
|---|---|
| I-301 | 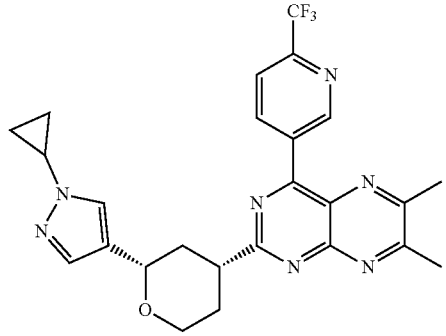 [SMILES: Cc1nc2nc([C@@H]3CCO[C@H](c4cnn(C5CC5)c4)C3)nc(-c3ccc(C(F)(F)F)nc3)c2nc1C] |
| I-302 | 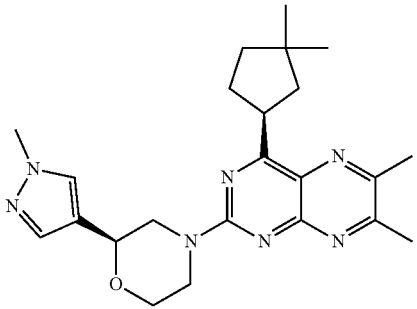 [SMILES: Cc1nc2nc(N3CCO[C@@H](c4cnn(C)c4)C3)nc([C@H]3CCC(C)(C)C3)c2nc1C] |
| I-303 | 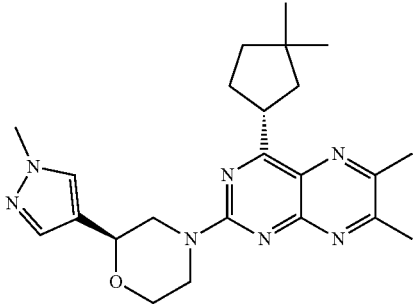 [SMILES: Cc1nc2nc(N3CCO[C@@H](c4cnn(C)c4)C3)nc([C@@H]3CCC(C)(C)C3)c2nc1C] |
| I-304 | 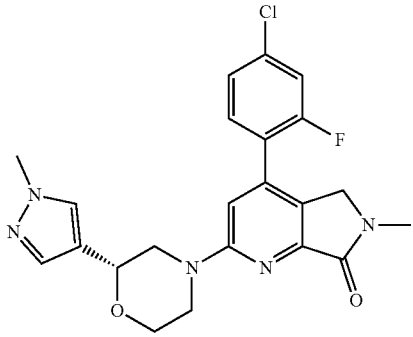 [SMILES: CN1Cc2c(-c3ccc(Cl)cc3F)cc(N3CCO[C@H](c4cnn(C)c4)C3)nc2C1=O] |
| I-305 | 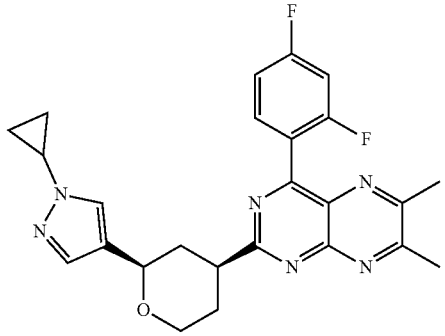 [SMILES: Cc1nc2nc([C@H]3CCO[C@@H](c4cnn(C5CC5)c4)C3)nc(-c3ccc(F)cc3F)c2nc1C] |
| I-306 | 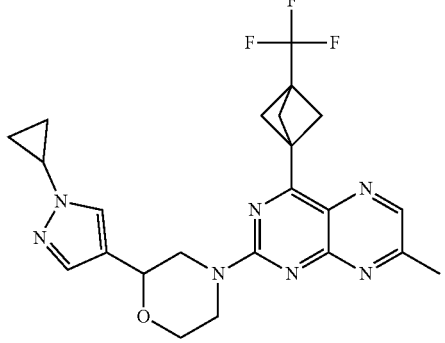 |
| I-307 | 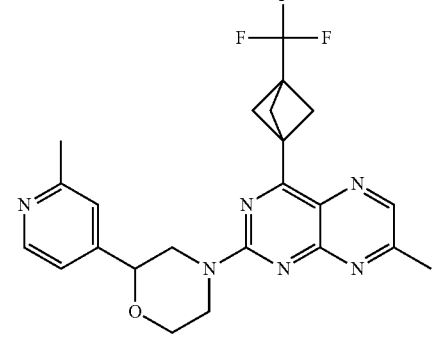 |
| I-308 | 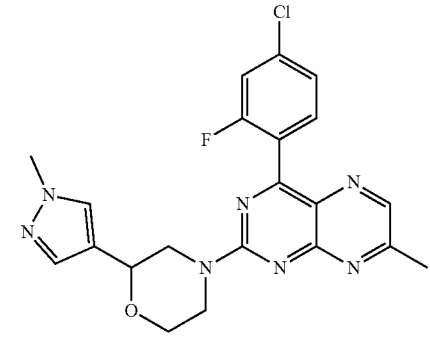 [SMILES: Cc1cnc2c(-c3ccc(Cl)cc3F)nc(N3CCOC(c4cnn(C)c4)C3)nc2n1] |

TABLE A-continued
Exemplary Compounds
| I-# | Structure |
|---|---|
| I-309 | 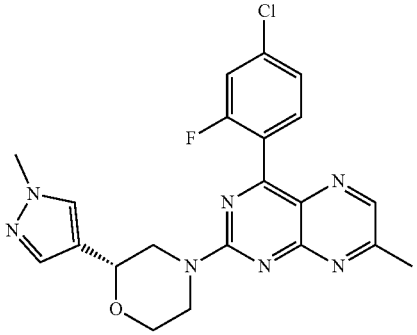 [SMILES: Cc1cnc2c(-c3ccc(Cl)cc3F)nc(N3CCO[C@H](c4cnn(C)c4)C3)nc2n1] |
| I-310 | 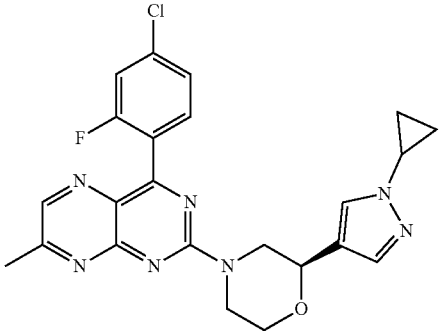 [SMILES: Cc1cnc2c(-c3ccc(Cl)cc3F)nc(N3CCO[C@H](c4cnn(C5CC5)c4)C3)nc2n1] |
| I-311 | 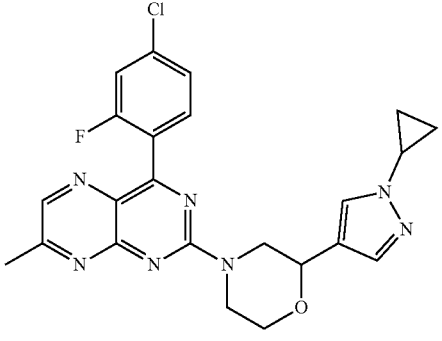 [SMILES: Cc1cnc2c(-c3ccc(Cl)cc3F)nc(N3CCOC(c4cnn(C5CC5)c4)C3)nc2n1] |
| I-312 | 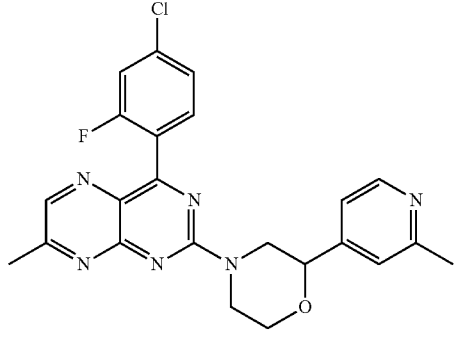 |
| I-313 | 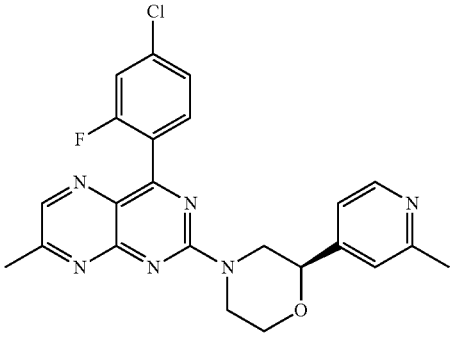 |
| I-314 | 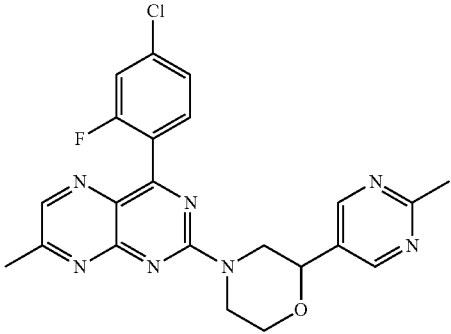 |
| I-315 | 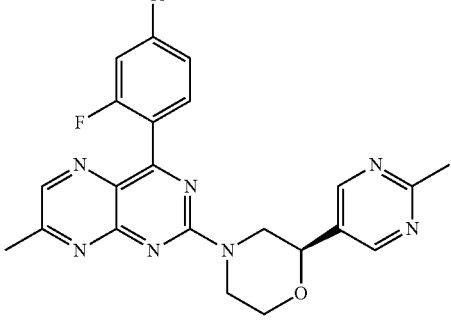 |
| I-316 | 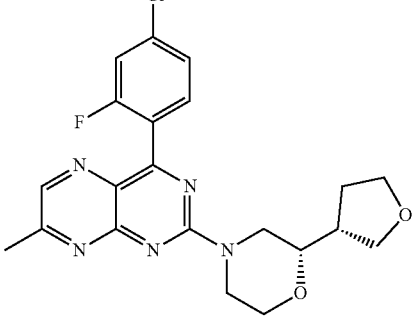 |

TABLE A-continued
Exemplary Compounds
| I-# | Structure |
|---|---|
| I-317 | 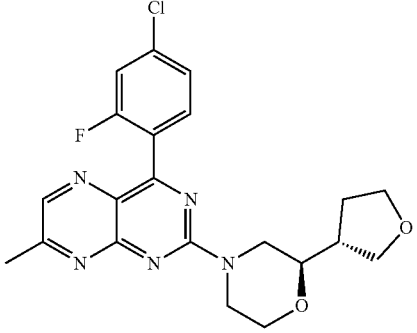 [SMILES: Cc1cnc2c(-c3ccc(Cl)cc3F)nc(N3CCO[C@H]([C@@H]4CCOC4)C3)nc2n1] |
| I-318 | 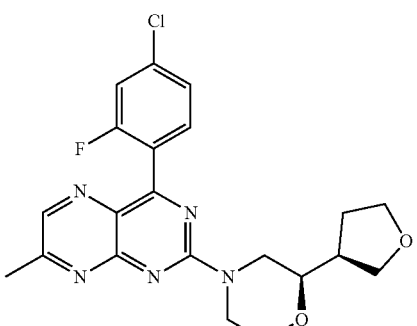 |
| I-319 | 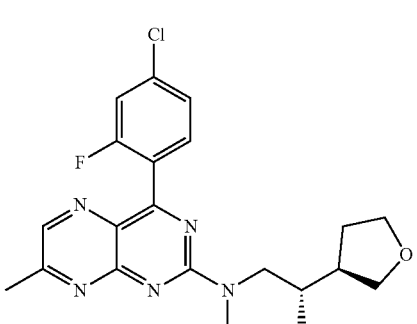 |
| I-320 | 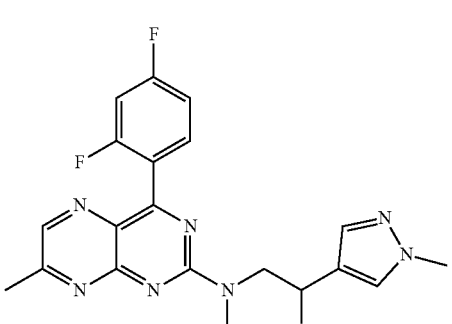 |
| I-321 | 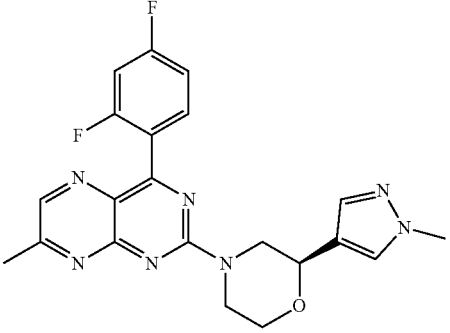 |
| I-322 | 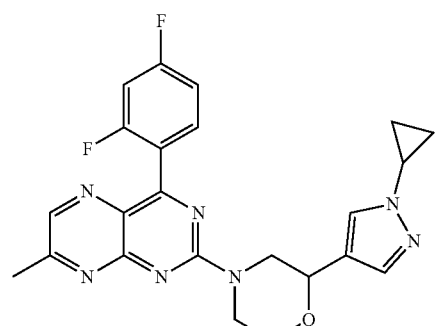 |
| I-323 | 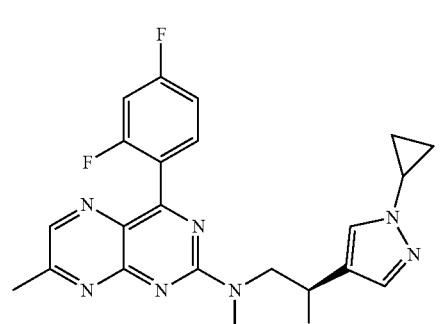 |
| I-324 | 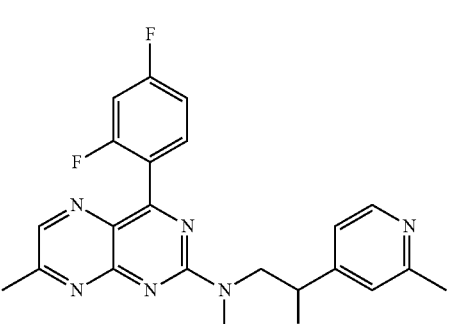 |

TABLE A-continued

Exemplary Compounds

| I-# | Structure |
|---|---|
| I-325 | (structure) |
| I-326 | (structure) |
| I-327 | (structure) |
| I-328 | (structure) |
| I-329 | (structure) |
| I-330 | (structure) |
| I-331 | (structure) |
| I-332 | (structure) |

TABLE A-continued

Exemplary Compounds

| I-# | Structure |
|---|---|
| I-333 | 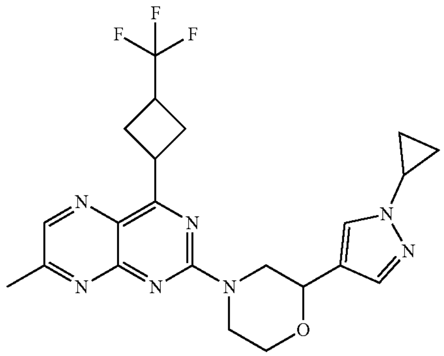 [SMILES: Cc1cnc2c(C3CC(C(F)(F)F)C3)nc(N3CCOC(c4cnn(C5CC5)c4)C3)nc2n1] |
| I-334 | 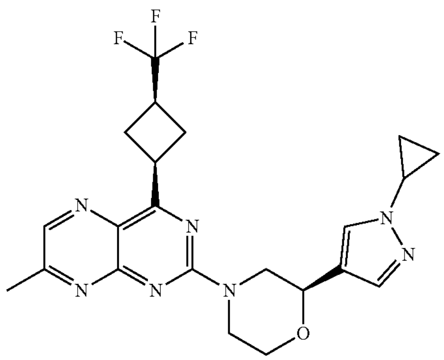 [SMILES: Cc1cnc2c(n1)nc(N1CCO[C@H](c3cnn(C4CC4)c3)C1)nc2[C@H]1C[C@@H](C(F)(F)F)C1] |
| I-335 | 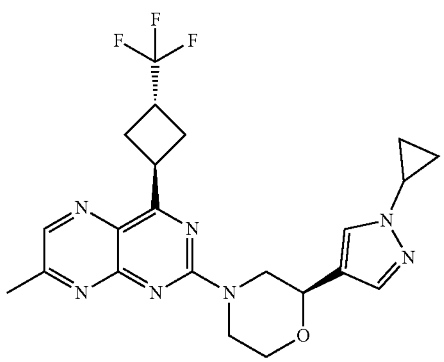 [SMILES: Cc1cnc2c(n1)nc(N1CCO[C@H](c3cnn(C4CC4)c3)C1)nc2[C@H]1C[C@H](C(F)(F)F)C1] |
| I-336 | 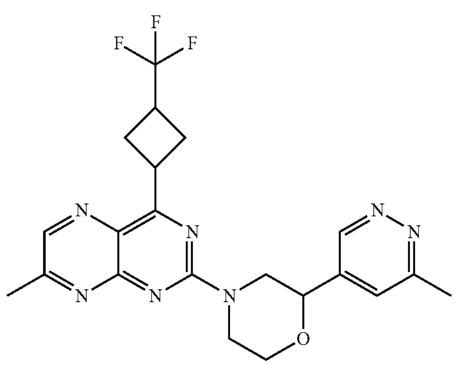 |
| I-337 | |
| I-338 | |
| I-339 | |
| I-340 | |

TABLE A-continued
Exemplary Compounds
| I-# | Structure |
|---|---|
| I-341 | 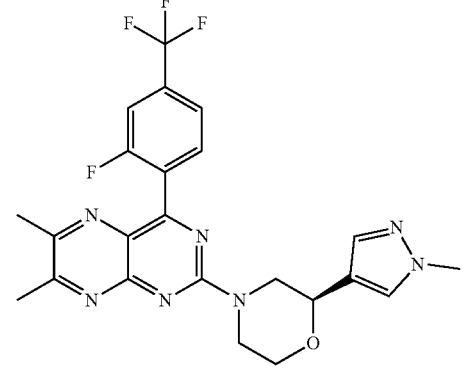 |
| I-342 | 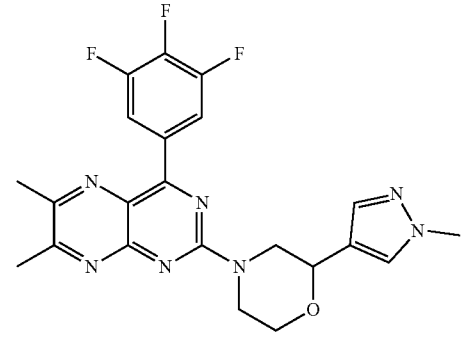 |
| I-343 | 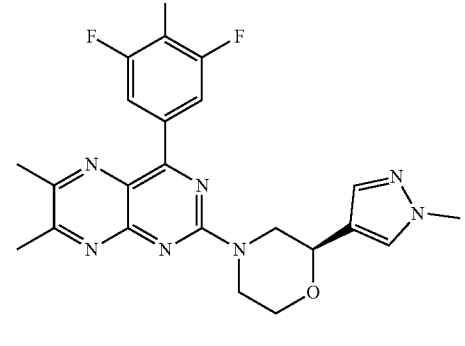 |
| I-344 | 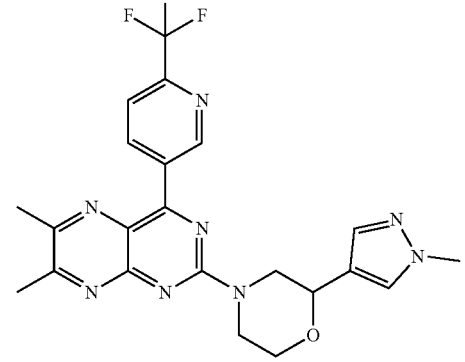 |
| I-345 | 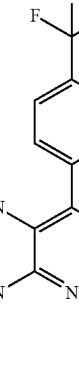 |
| I-346 | 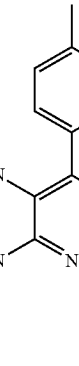 |
| I-347 | 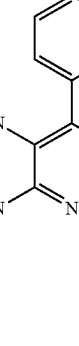 |
| I-348 | 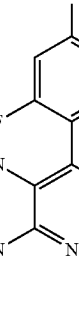 |

TABLE A-continued

Exemplary Compounds

| I-# | Structure |
|---|---|
| I-349 | 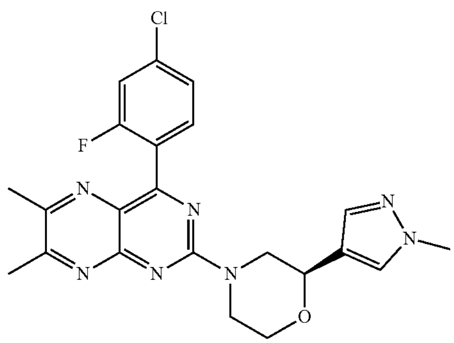 |
| I-350 | 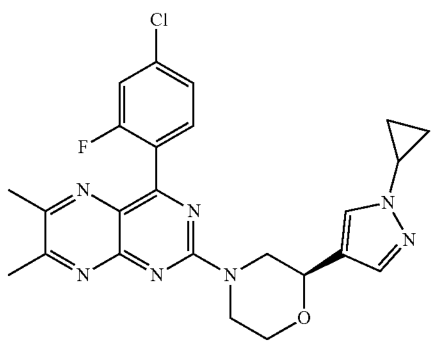 |
| I-351 | 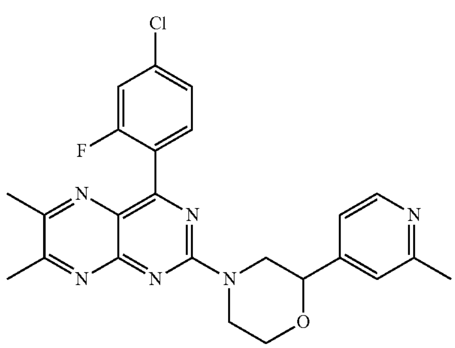 |
| I-352 | 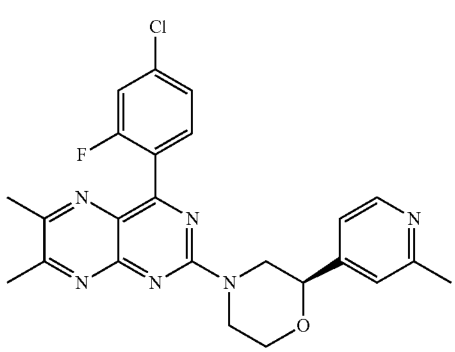 |
| I-353 | |
| I-354 | |
| I-355 | |
| I-356 | |

TABLE A-continued
Exemplary Compounds
| I-# | Structure |
|---|---|
| I-357 | 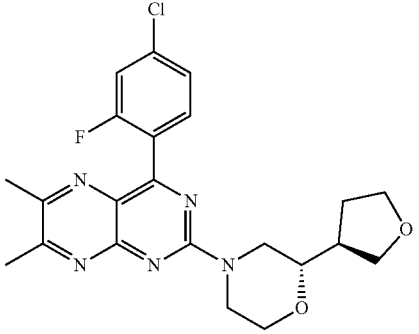 |
| I-358 | 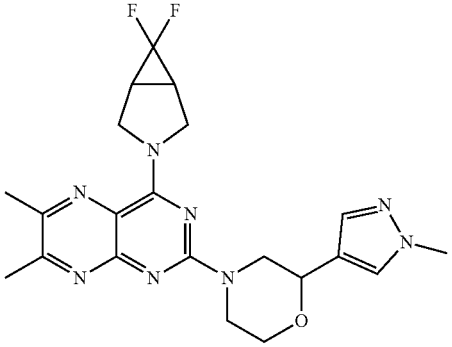 |
| I-359 | 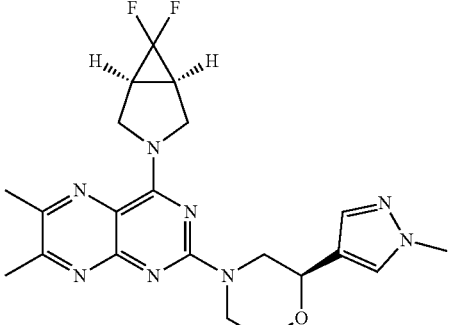 |
| I-360 | 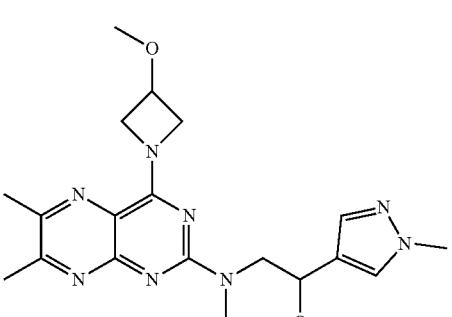 |
| I-361 | 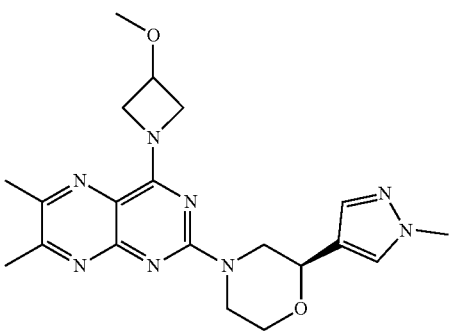 |
| I-362 | 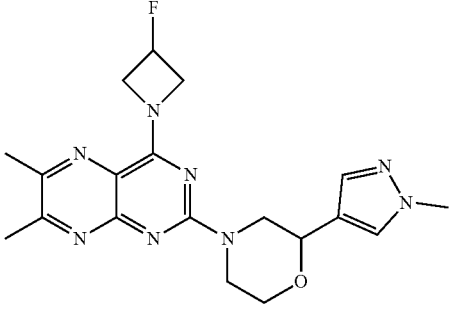 |
| I-363 | 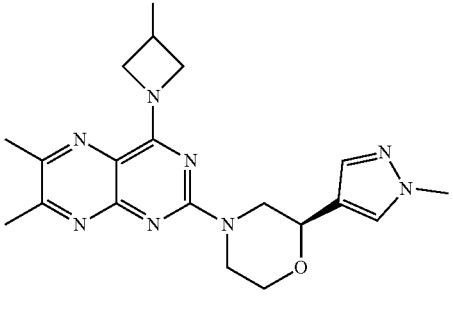 |
| I-364 | 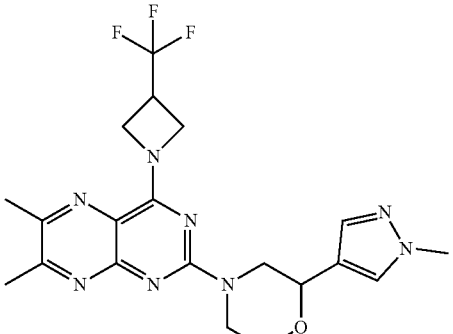 |

TABLE A-continued
Exemplary Compounds
| I-# | Structure |
|---|---|
| I-365 | 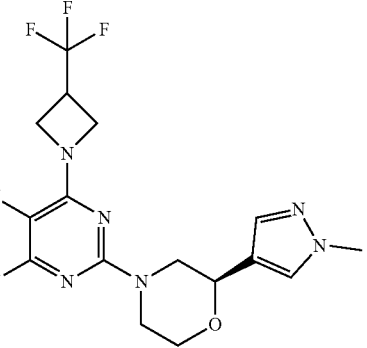 |
| I-366 | 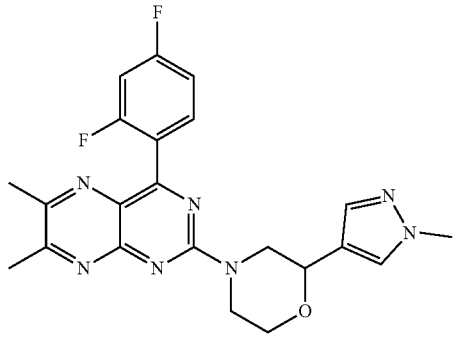 |
| I-367 | 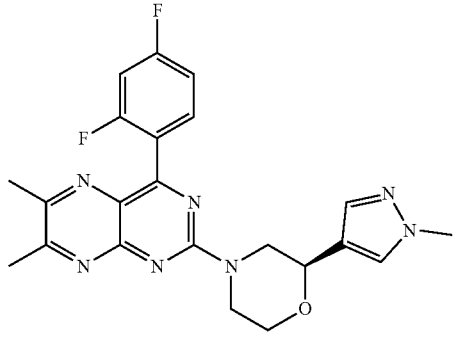 |
| I-368 | 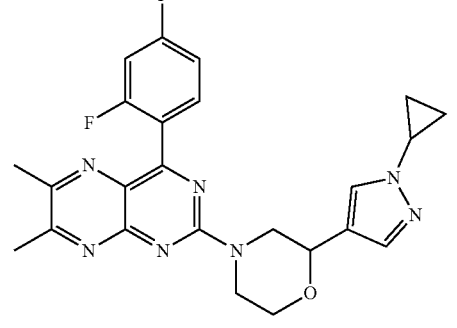 |
| I-369 | 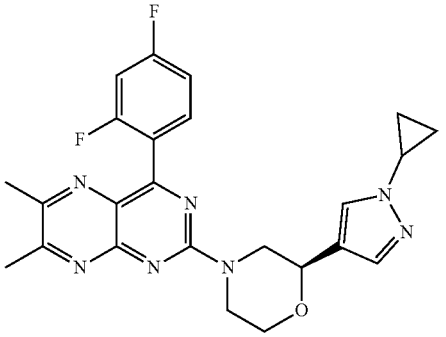 [SMILES: Cc1nc2nc(N3CCO[C@H](c4cnn(C5CC5)c4)C3)nc(-c3ccc(F)cc3F)c2nc1C] |
| I-370 | 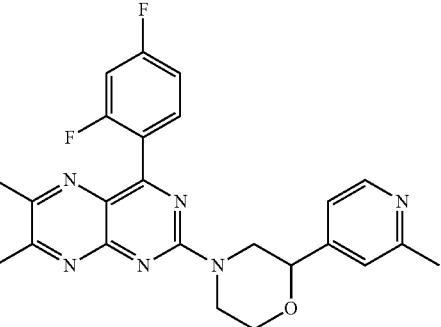 |
| I-371 | 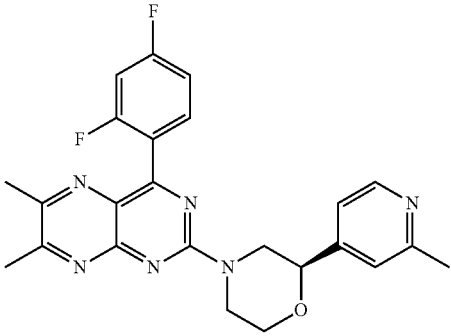 |
| I-372 | 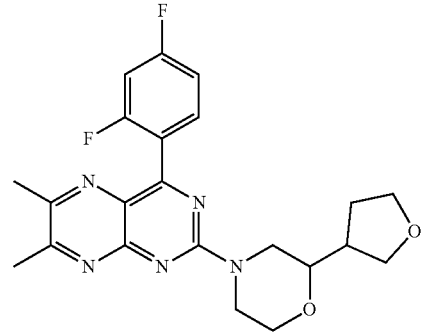 |

TABLE A-continued

Exemplary Compounds

| I-# | Structure |
|---|---|
| I-373 | 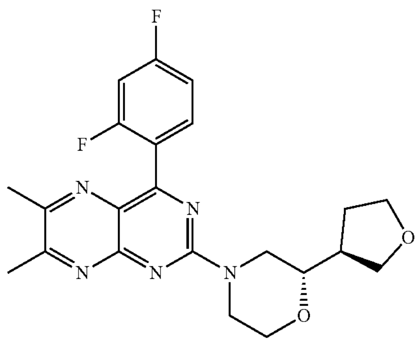 [SMILES: Cc1nc2nc(N3CCO[C@@H]([C@H]4CCOC4)C3)nc(-c3ccc(F)cc3F)c2nc1C] |
| I-374 | 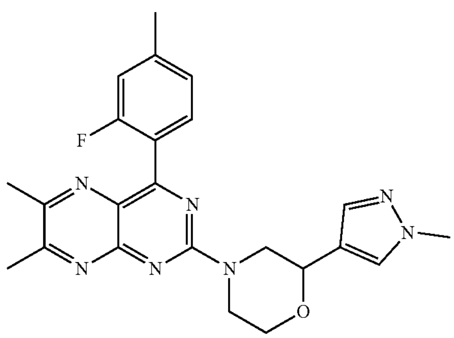 |
| I-375 | 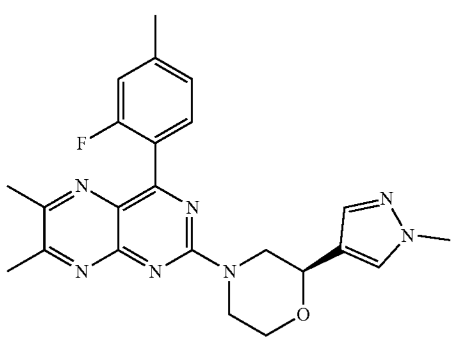 |
| I-376 | 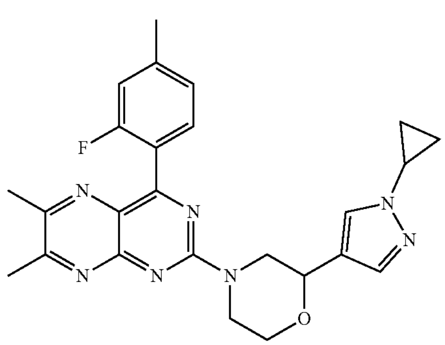 [SMILES: Cc1ccc(-c2nc(N3CCOC(c4cnn(C5CC5)c4)C3)nc3nc(C)c(C)nc23)c(F)c1] |
| I-377 | |
| I-378 | |
| I-379 | |
| I-380 | |

TABLE A-continued
Exemplary Compounds
| I-# | Structure |
|---|---|
| I-381 | 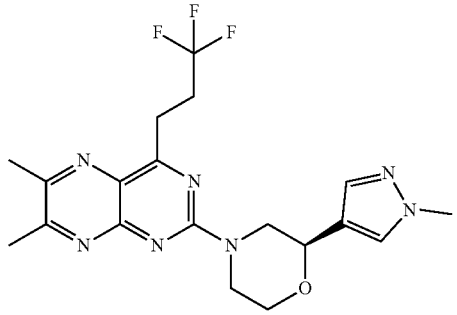 |
| I-382 | 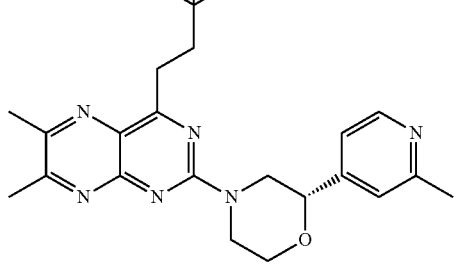 |
| I-383 | 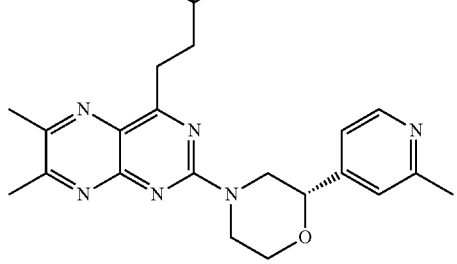 |
| I-384 | 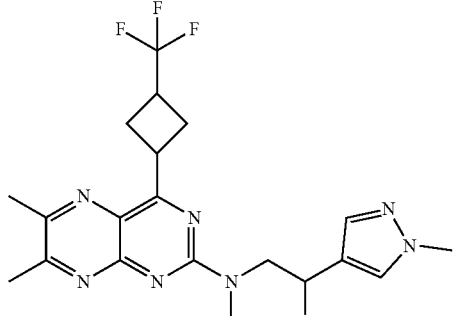 |
| I-385 | 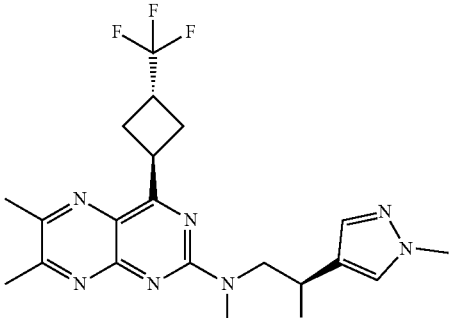 |
| I-386 | 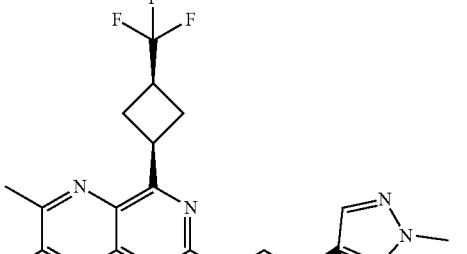 |
| I-387 | 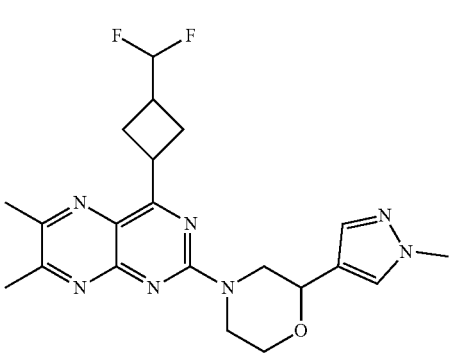 |
| I-388 | 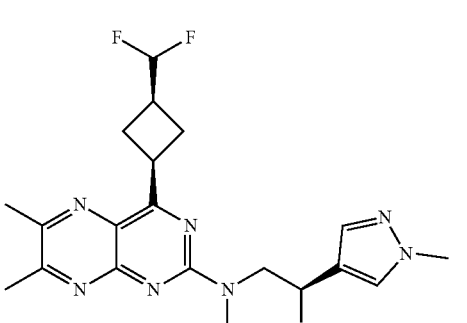 |

TABLE A-continued
Exemplary Compounds
| I-# | Structure |
|---|---|
| I-389 | 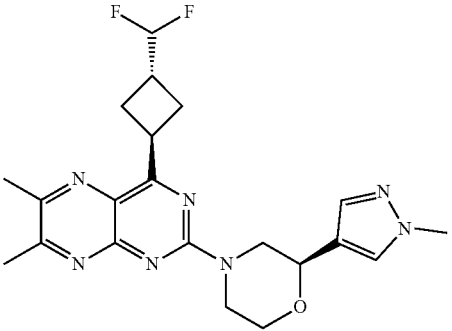 |
| I-390 | 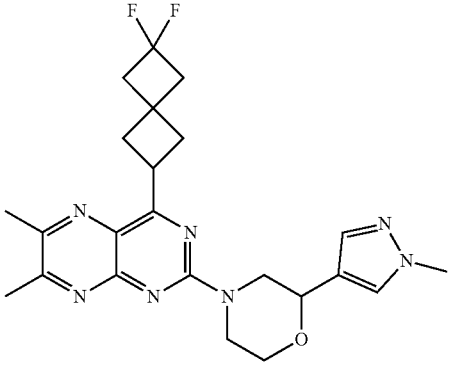 |
| I-391 | 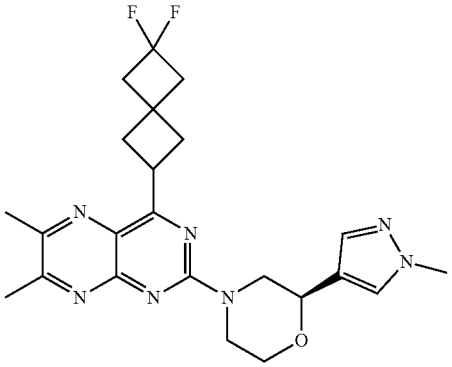 |
| I-392 | 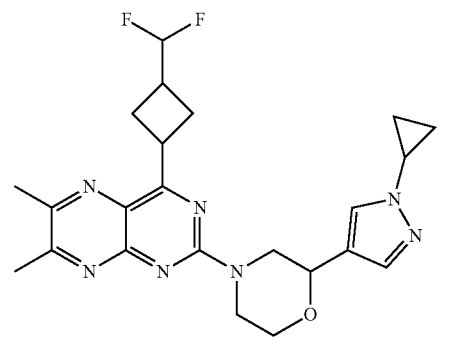 [SMILES: Cc1nc2nc(N3CCOC(c4cnn(C5CC5)c4)C3)nc(C3CC(C(F)F)C3)c2nc1C] |
| I-393 | 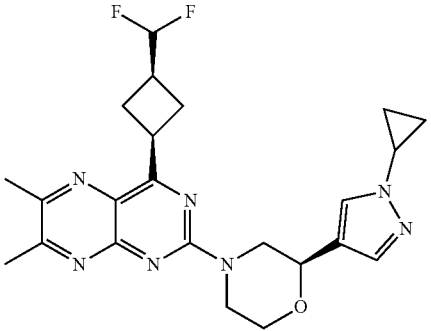 [SMILES: Cc1nc2nc(N3CCO[C@H](c4cnn(C5CC5)c4)C3)nc([C@H]3C[C@@H](C(F)F)C3)c2nc1C] |
| I-394 | 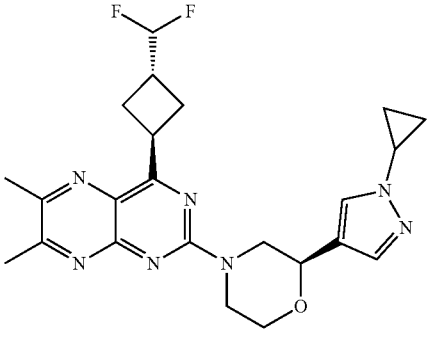 [SMILES: Cc1nc2nc(N3CCO[C@H](c4cnn(C5CC5)c4)C3)nc([C@H]3C[C@H](C(F)F)C3)c2nc1C] |
| I-395 | 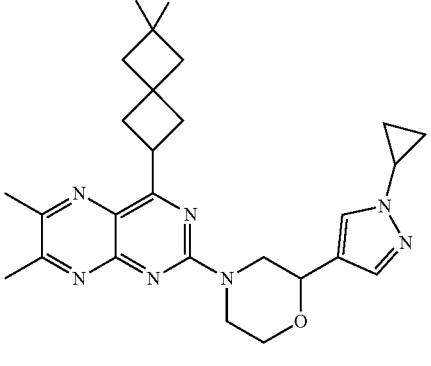 |
| I-396 | 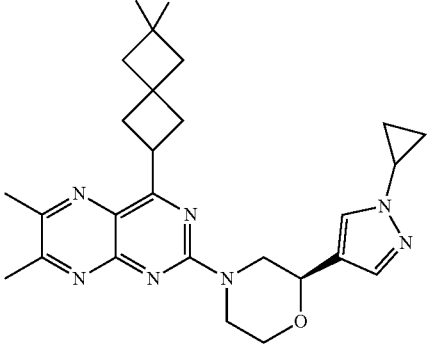 |

TABLE A-continued

Exemplary Compounds

| I-# | Structure |
|---|---|
| I-397 | (structure) |
| I-398 | (structure) |
| I-399 | (structure) |
| I-400 | (structure) |
| I-401 | (structure) |
| I-402 | (structure) |
| I-403 | (structure) |
| I-404 | (structure) |

TABLE A-continued
Exemplary Compounds
| I-# | Structure |
|---|---|
| I-405 | 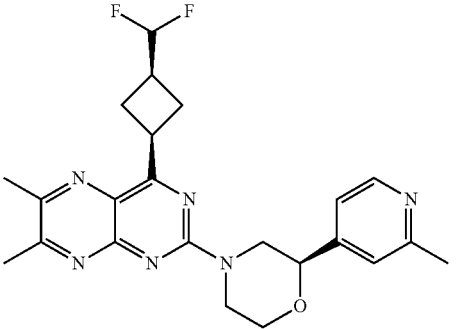 |
| I-406 | 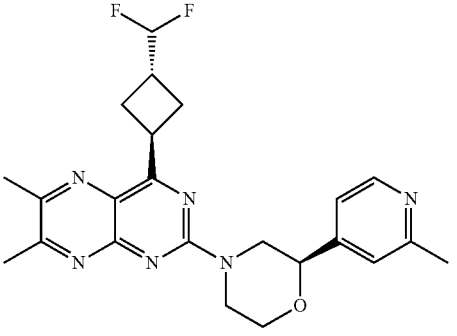 |
| I-407 | 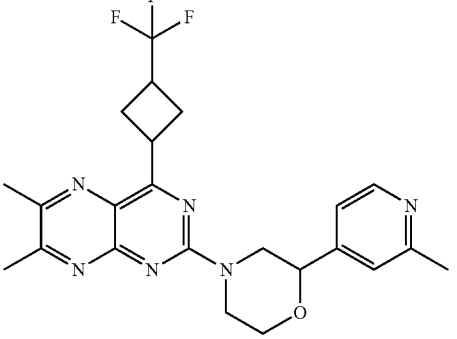 |
| I-408 | 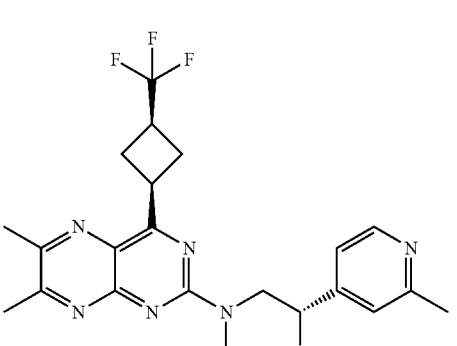 |
| I-409 | 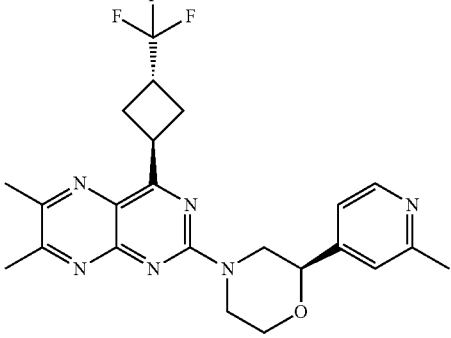 |
| I-410 | 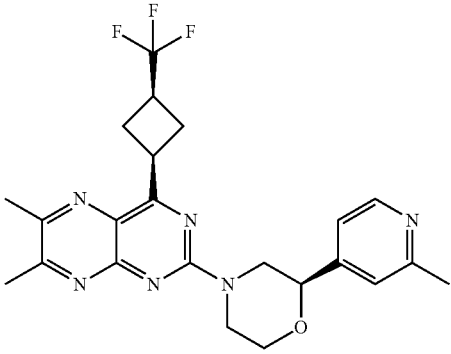 |
| I-411 | 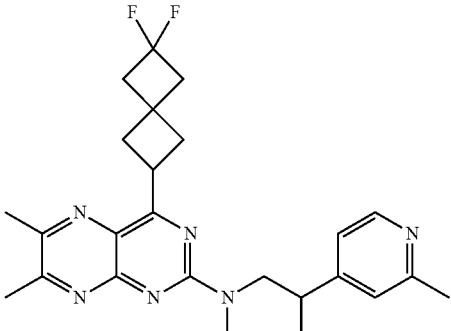 |
| I-412 | 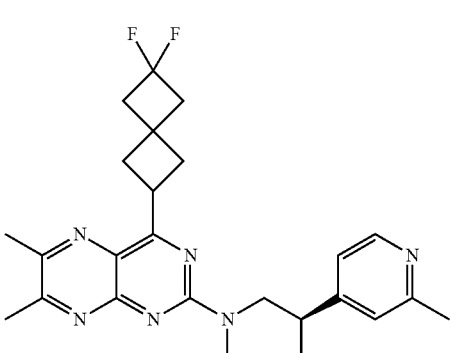 |

TABLE A-continued
Exemplary Compounds
| I-# | Structure |
|---|---|
| I-413 | 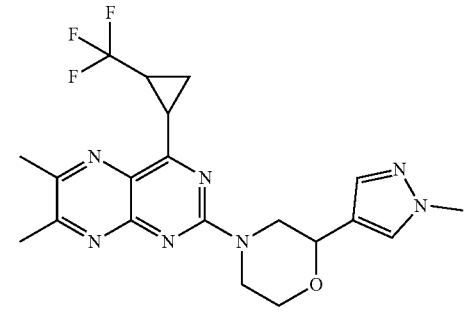 |
| I-414 | 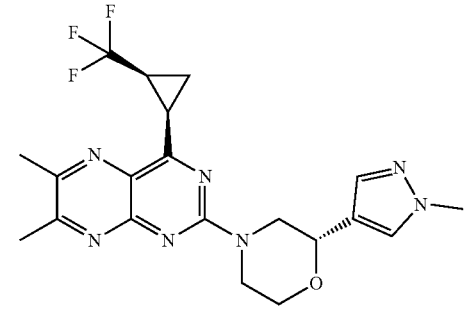 |
| I-415 | 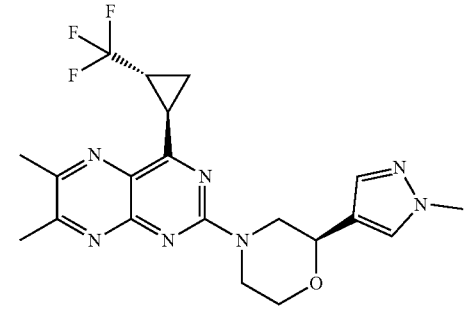 |
| I-416 | 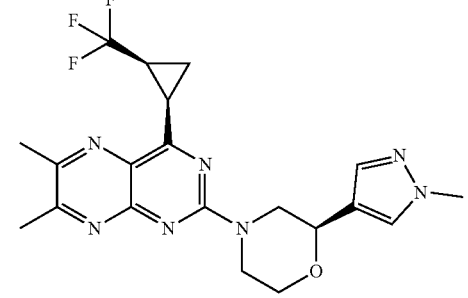 |
| I-417 | 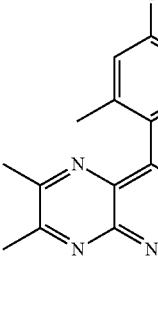 |
| I-418 | 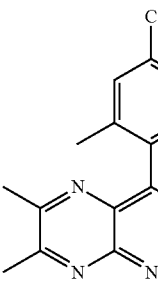 |
| I-419 | 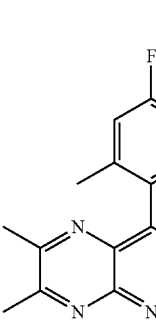 |
| I-420 |  |

TABLE A-continued
Exemplary Compounds
| I-# | Structure |
|---|---|
| I-421 | 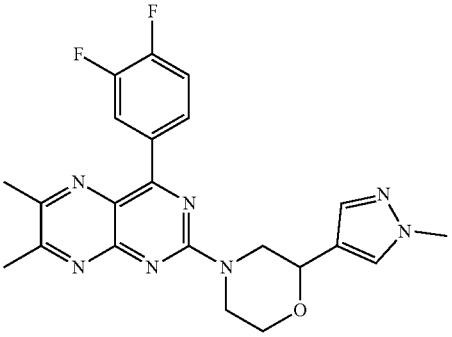 |
| I-422 | 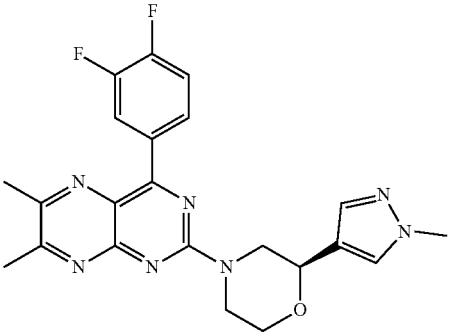 |
| I-423 | 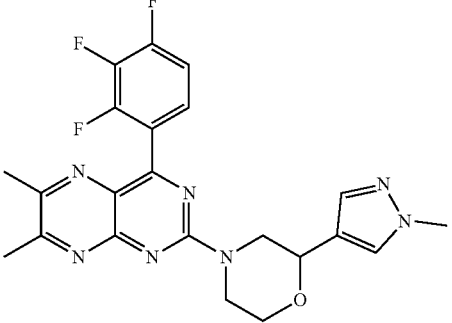 |
| I-424 | 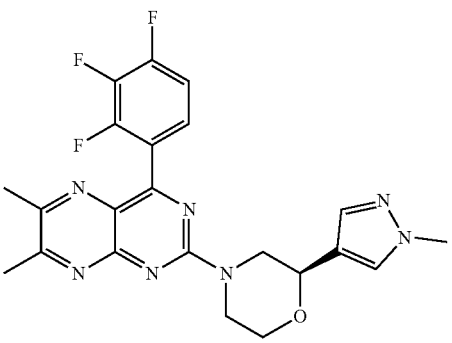 |
| I-425 | 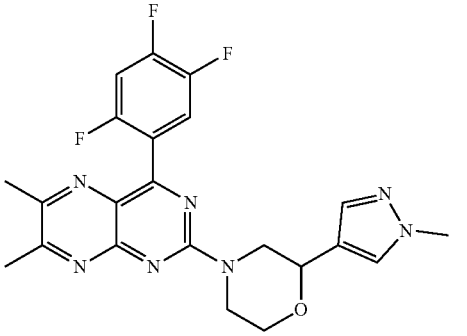 |
| I-426 | 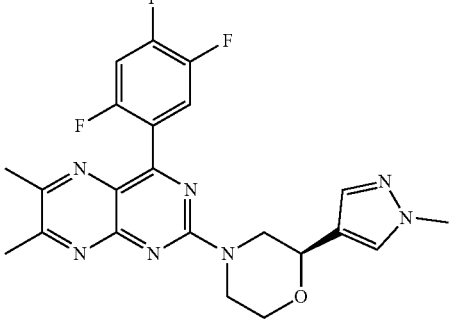 |
| I-427 | 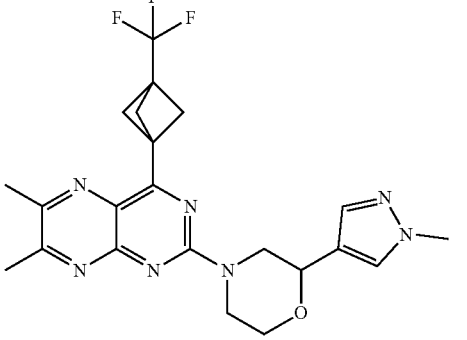 |
| I-428 | 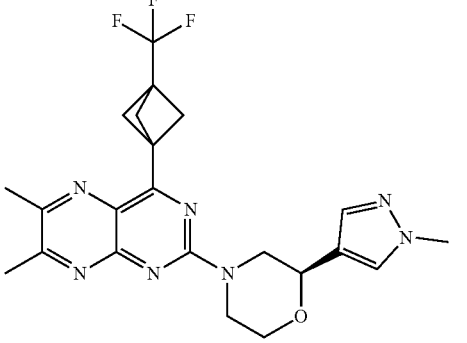 |

TABLE A-continued

Exemplary Compounds

| I-# | Structure |
|---|---|
| I-429 | 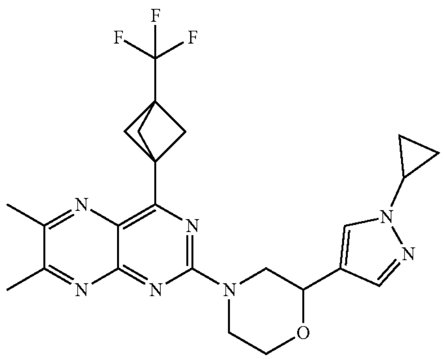 [SMILES: Cc1nc2nc(N3CCOC(c4cnn(C5CC5)c4)C3)nc(C34CC(C(F)(F)F)(C3)C4)c2nc1C] |
| I-430 | 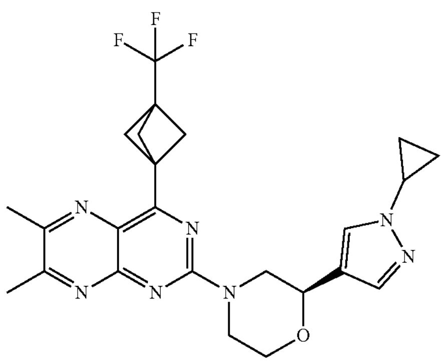 [SMILES: Cc1nc2nc(N3CCO[C@H](c4cnn(C5CC5)c4)C3)nc(C34CC(C(F)(F)F)(C3)C4)c2nc1C] |
| I-431 | 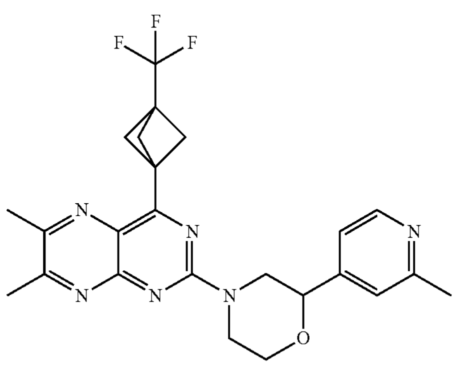 |
| I-432 | 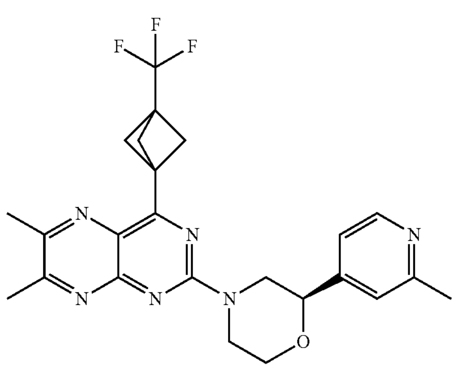 |
| I-433 | |
| I-434 | |
| I-435 | |
| I-436 | |

TABLE A-continued

Exemplary Compounds

| I-# | Structure |
|-----|-----------|
| I-437 | 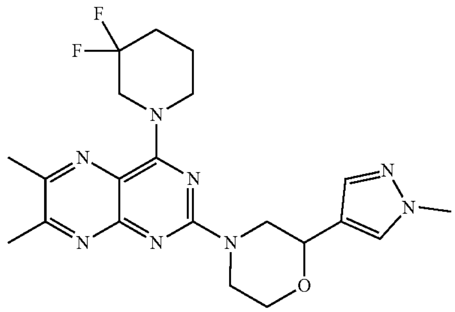 |
| I-438 | 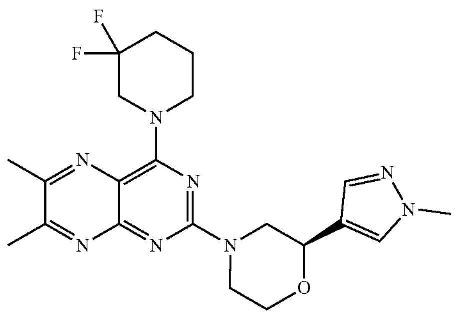 |
| I-439 | 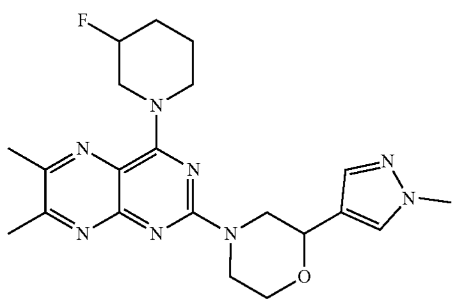 |
| I-440 | 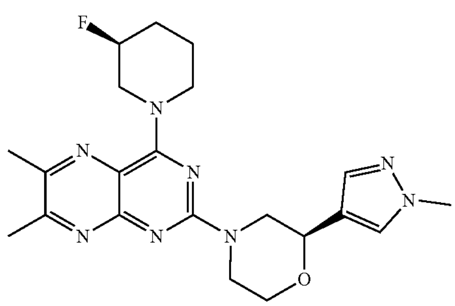 |
| I-441 | 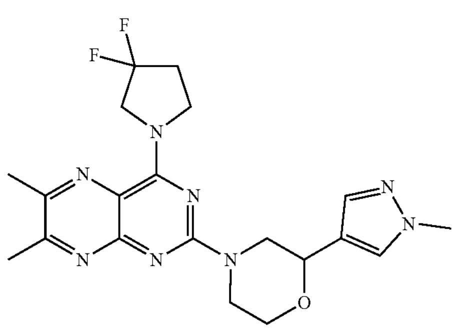 |
| I-442 | |
| I-443 | |
| I-444 | |
| I-445 | |

TABLE A-continued

Exemplary Compounds

| I-# | Structure |
| --- | --- |
| I-446 | 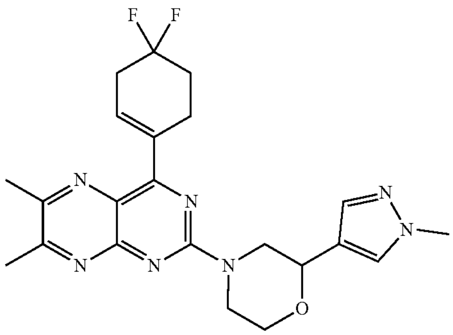 |
| I-447 | 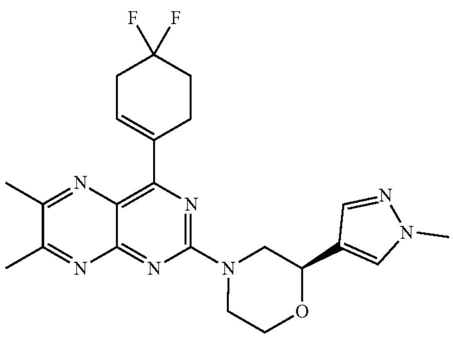 |
| I-448 | 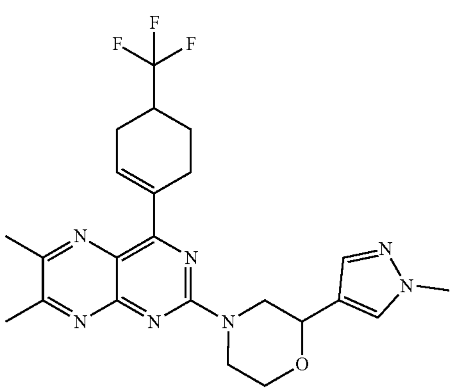 |
| I-449 | 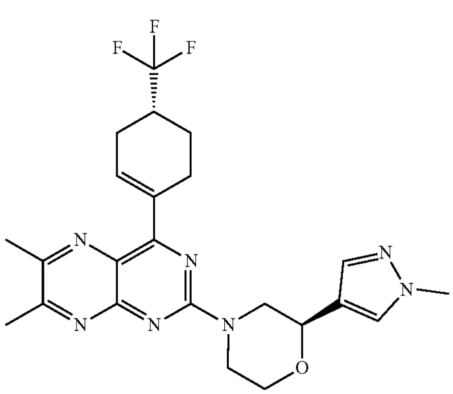 |
| I-450 | |
| I-451 | |
| I-452 | |
| I-453 | |

TABLE A-continued

Exemplary Compounds

| I-# | Structure |
|---|---|
| I-454 | 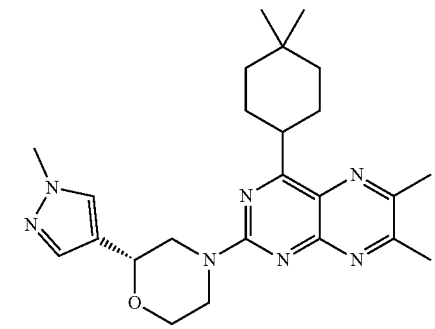 [SMILES: Cc1nc2nc(N3CCO[C@H](c4cnn(C)c4)C3)nc(C3CCC(C)(C)CC3)c2nc1C] |
| I-455 | 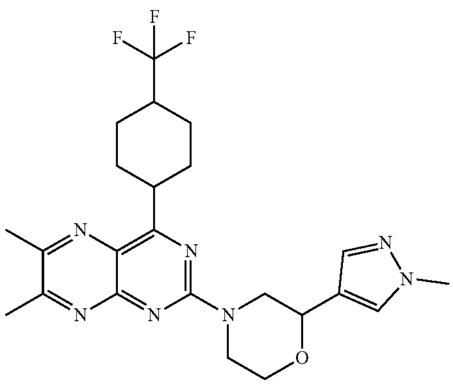 |
| I-456 | 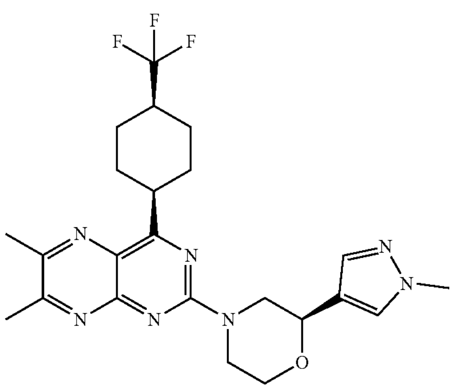 |
| I-457 | 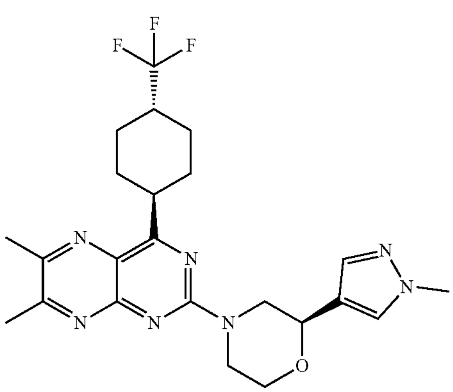 |
| I-458 | |
| I-459 | |
| I-460 | |
| I-461 | |

TABLE A-continued
Exemplary Compounds
| I-# | Structure |
|---|---|
| I-462 | 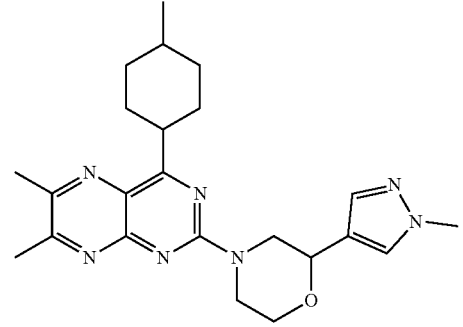 |
| I-463 | 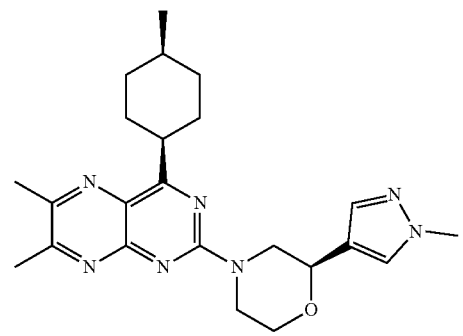 |
| I-464 | 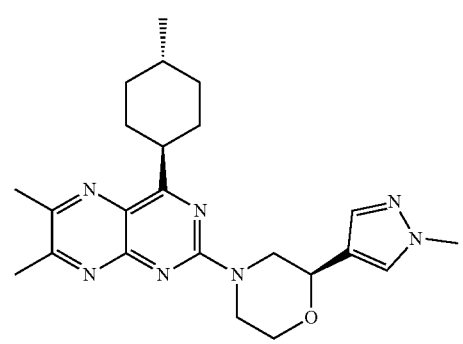 |
| I-465 | 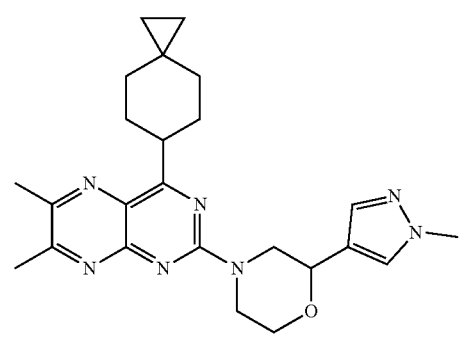 |
| I-466 | 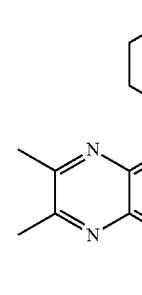 |
| I-467 | 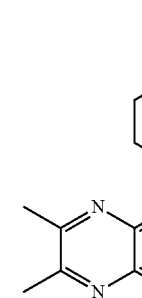 |
| I-468 | 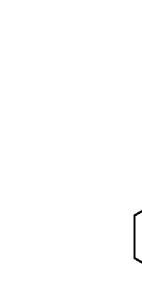 |
| I-469 | 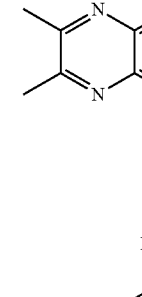 |

TABLE A-continued
Exemplary Compounds
| I-# | Structure |
|---|---|
| I-470 | 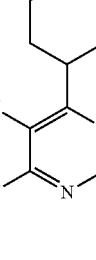 |
| I-471 | 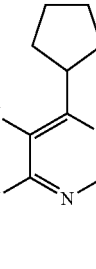 |
| I-472 | 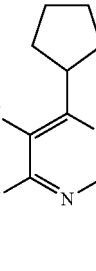 |
| I-473 | 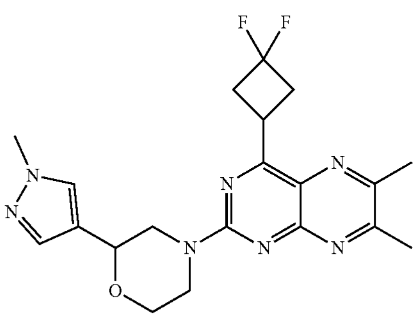 [SMILES: Cc1nc2nc(N3CCOC(c4cnn(C)c4)C3)nc(C3CC(F)(F)C3)c2nc1C] |
| I-474 | 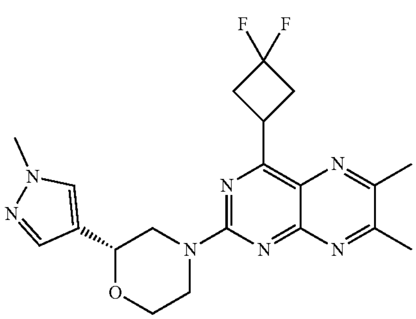 [SMILES: Cc1nc2nc(N3CCO[C@H](c4cnn(C)c4)C3)nc(C3CC(F)(F)C3)c2nc1C] |
| I-475 |  |
| I-476 |  |
| I-477 | 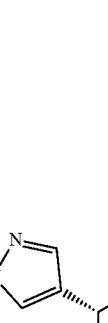 |
| I-478 |  |

TABLE A-continued
Exemplary Compounds
| I-# | Structure |
|---|---|
| I-479 | 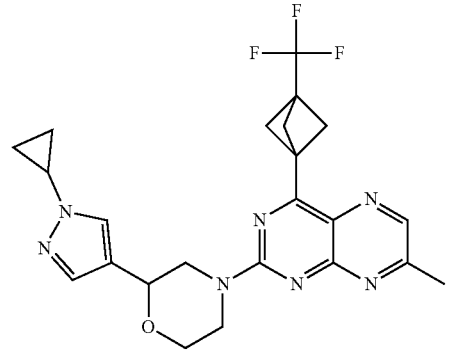 [SMILES: Cc1cnc2c(C34CC(C(F)(F)F)(C3)C4)nc(N3CCOC(c4cnn(C5CC5)c4)C3)nc2n1] |
| I-480 | 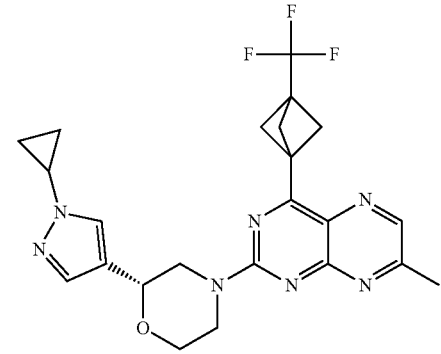 [SMILES: Cc1cnc2c(C34CC(C(F)(F)F)(C3)C4)nc(N3CCO[C@H](c4cnn(C5CC5)c4)C3)nc2n1] |
| I-481 | 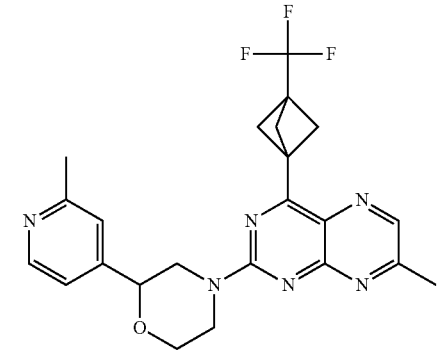 [SMILES: Cc1cc(C2CN(c3nc(C45CC(C(F)(F)F)(C4)C5)c4ncc(C)nc4n3)CCO2)ccn1] |
| I-482 | 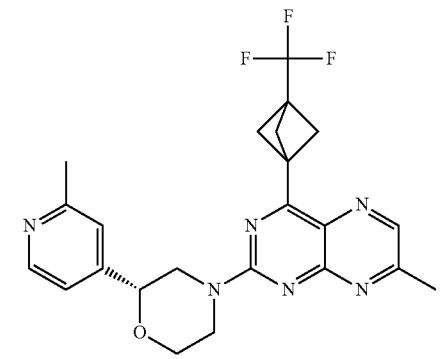 [SMILES: Cc1cc([C@@H]2CN(c3nc(C45CC(C(F)(F)F)(C4)C5)c4ncc(C)nc4n3)CCO2)ccn1] |
| I-483 | 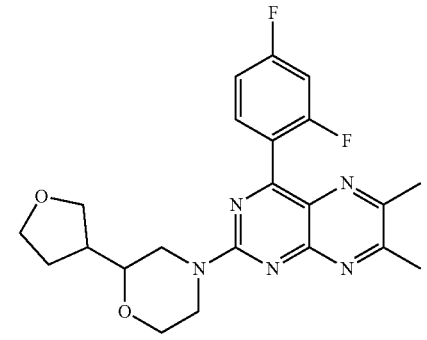 [SMILES: Cc1nc2nc(N3CCOC(C4CCOC4)C3)nc(-c3ccc(F)cc3F)c2nc1C] |
| I-484 | 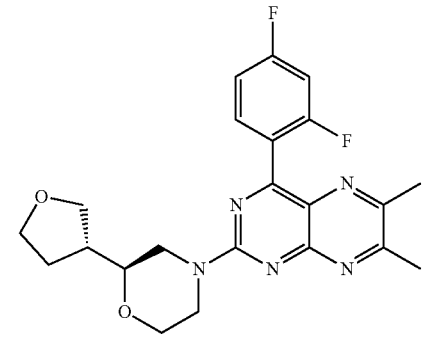 [SMILES: Cc1nc2nc(N3CCO[C@@H]([C@@H]4CCOC4)C3)nc(-c3ccc(F)cc3F)c2nc1C] |
| I-485 | 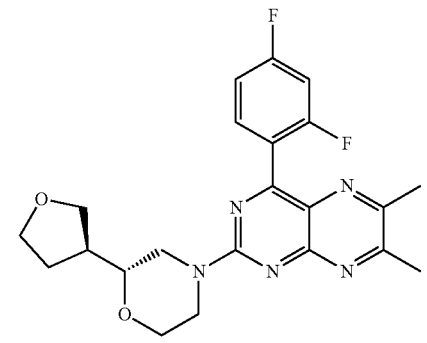 [SMILES: Cc1nc2nc(N3CCO[C@H]([C@H]4CCOC4)C3)nc(-c3ccc(F)cc3F)c2nc1C] |
| I-486 | 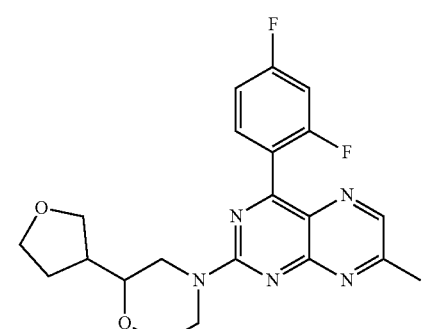 |

TABLE A-continued
Exemplary Compounds
| I-# | Structure |
|---|---|
| I-487 | 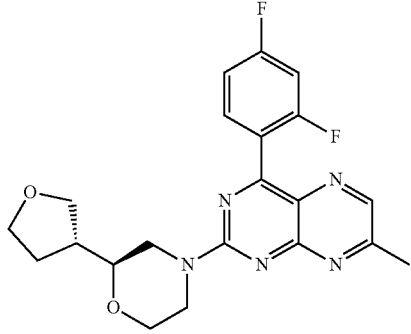 [SMILES: Cc1cnc2c(-c3ccc(F)cc3F)nc(N3CCO[C@@H]([C@@H]4CCOC4)C3)nc2n1] |
| I-488 | 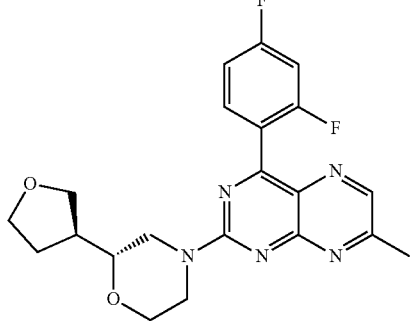 |
| I-489 | 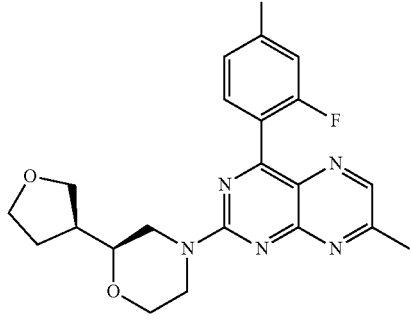 |
| I-490 | 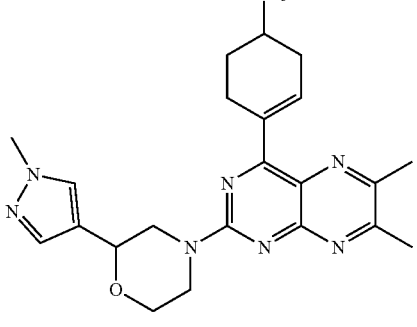 |
| I-491 | 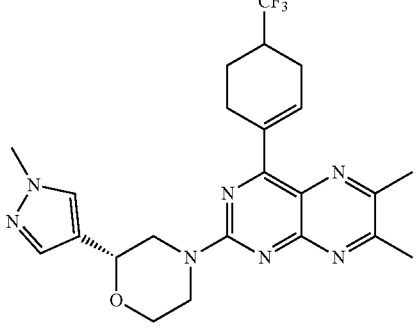 |
| I-492 | 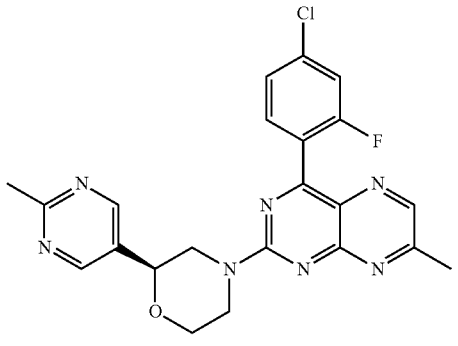 |
| I-493 | 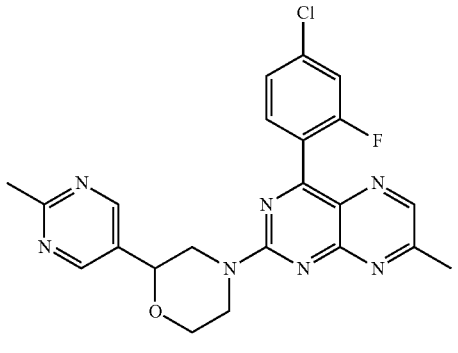 |
| I-494 | 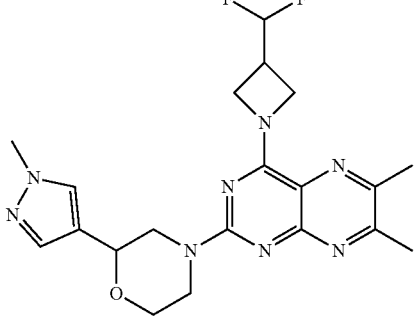 |

TABLE A-continued
Exemplary Compounds
| I-# | Structure |
|---|---|
| I-495 | 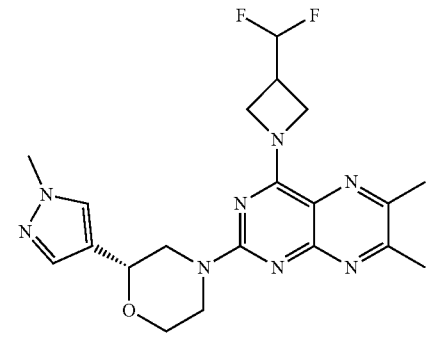 [SMILES: Cc1nc2nc(N3CCO[C@H](c4cnn(C)c4)C3)nc(N3CC(C(F)F)C3)c2nc1C] |
| I-496 | 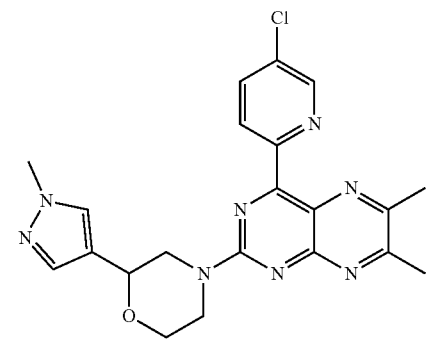 [SMILES: Cc1nc2nc(N3CCOC(c4cnn(C)c4)C3)nc(-c3ccc(Cl)cn3)c2nc1C] |
| I-497 | 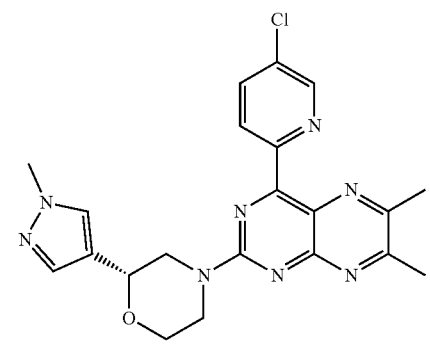 [SMILES: Cc1nc2nc(N3CCO[C@H](c4cnn(C)c4)C3)nc(-c3ccc(Cl)cn3)c2nc1C] |
| I-498 | 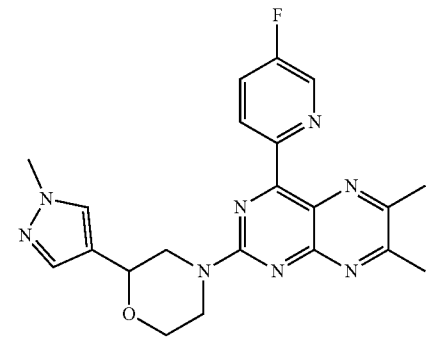 |
| I-499 | 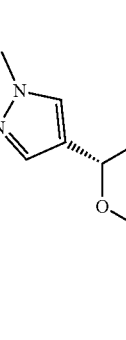 |
| I-500 | 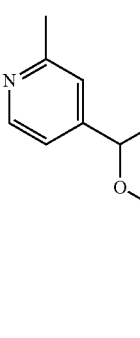 |
| I-501 | 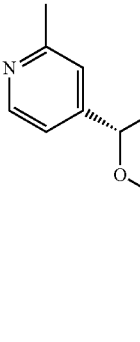 |
| I-502 | 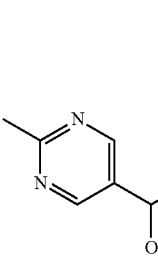 |

TABLE A-continued
Exemplary Compounds
| I-# | Structure |
|---|---|
| I-503 | 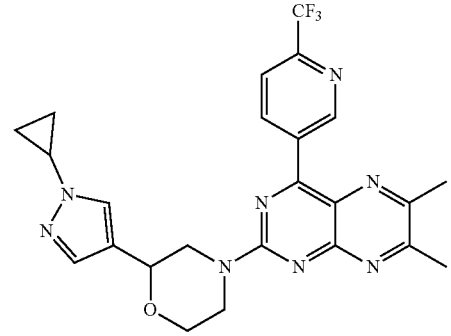 [SMILES: Cc1nc2nc(N3CCOC(c4cnn(C5CC5)c4)C3)nc(-c3ccc(C(F)(F)F)nc3)c2nc1C] |
| I-504 | 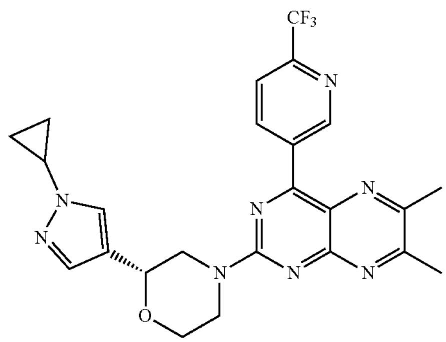 [SMILES: Cc1nc2nc(N3CCO[C@H](c4cnn(C5CC5)c4)C3)nc(-c3ccc(C(F)(F)F)nc3)c2nc1C] |
| I-505 | 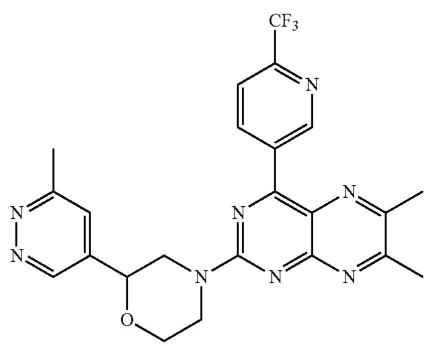 [SMILES: Cc1cc(C2CN(c3nc(-c4ccc(C(F)(F)F)nc4)c4nc(C)c(C)nc4n3)CCO2)cnn1] |
| I-506 | 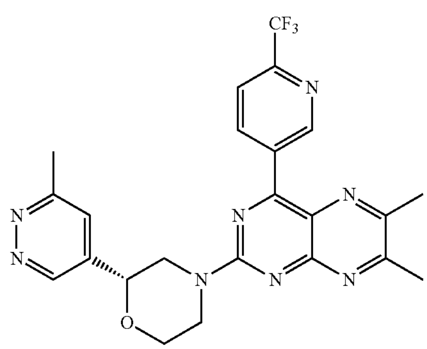 [SMILES: Cc1cc([C@@H]2CN(c3nc(-c4ccc(C(F)(F)F)nc4)c4nc(C)c(C)nc4n3)CCO2)cnn1] |
TABLE A-continued
Exemplary Compounds
| I-# | Structure |
|---|---|
| I-507 | 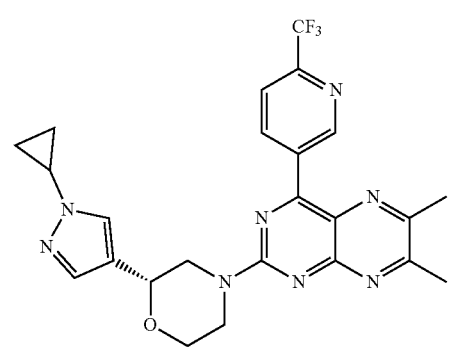 |
| I-508 | 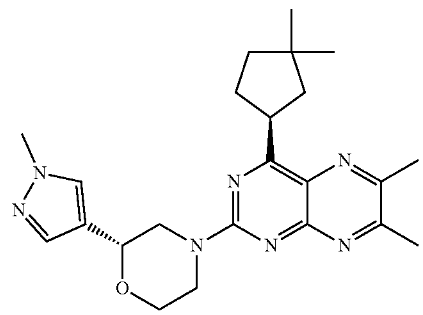 [SMILES: Cc1nc2nc(N3CCO[C@H](c4cnn(C)c4)C3)nc([C@H]3CCC(C)(C)C3)c2nc1C] |
| I-509 | 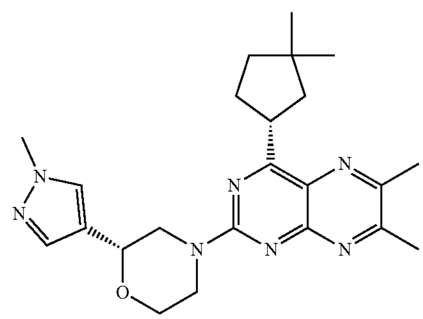 [SMILES: Cc1nc2nc(N3CCO[C@H](c4cnn(C)c4)C3)nc([C@@H]3CCC(C)(C)C3)c2nc1C] |
| I-510 | 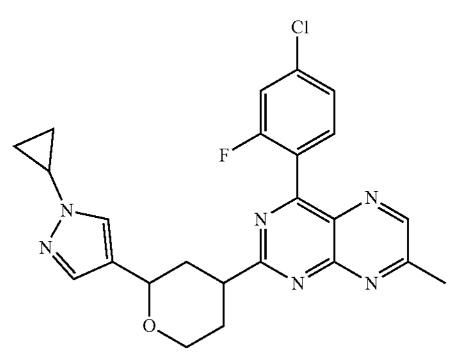 [SMILES: Cc1cnc2c(-c3ccc(Cl)cc3F)nc(C3CCOC(c4cnn(C5CC5)c4)C3)nc2n1] |

TABLE A-continued
Exemplary Compounds
| I-# | Structure |
|---|---|
| I-511 | 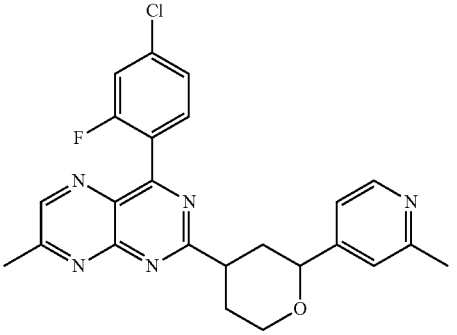 |
| I-512 | 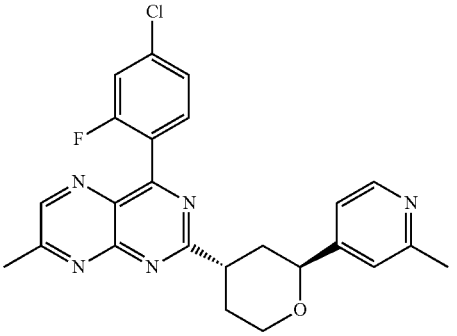 |
| I-513 | 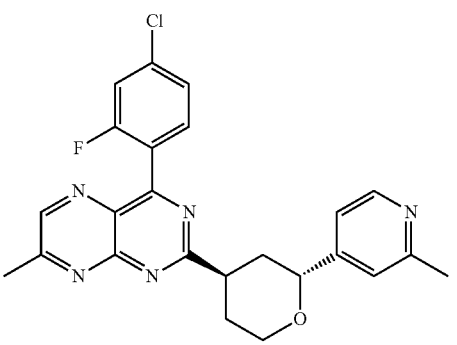 |
| I-514 | 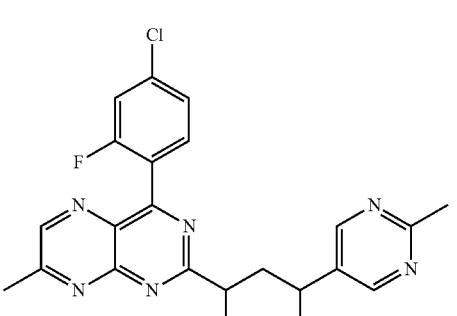 |
| I-515 | 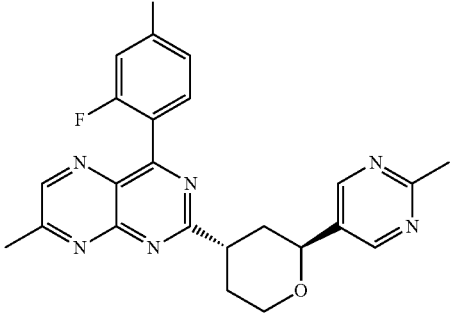 |
| I-516 | 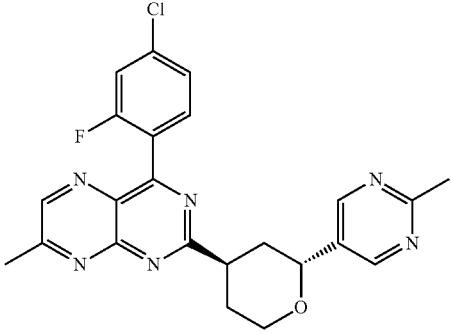 |
| I-517 | 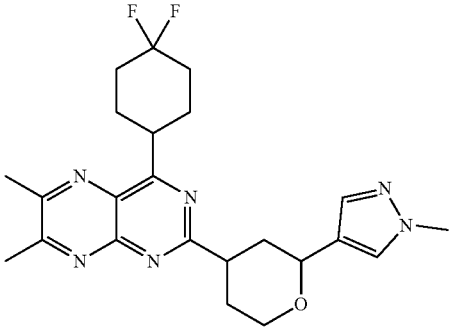 |
| I-518 | 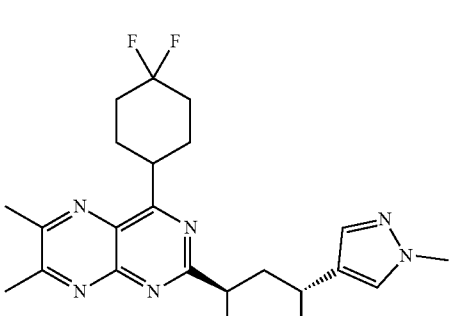 |

TABLE A-continued
Exemplary Compounds
| I-# | Structure |
|---|---|
| I-519 | 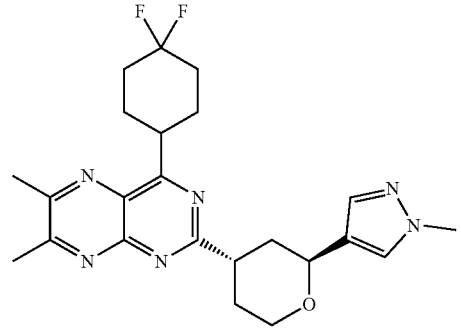 |
| I-520 | 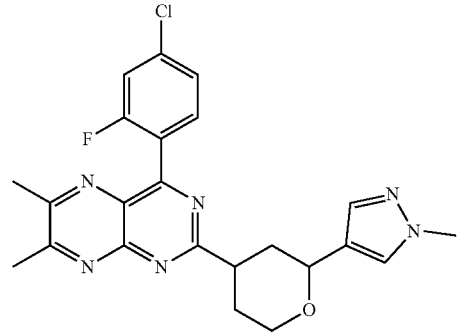 |
| I-521 | 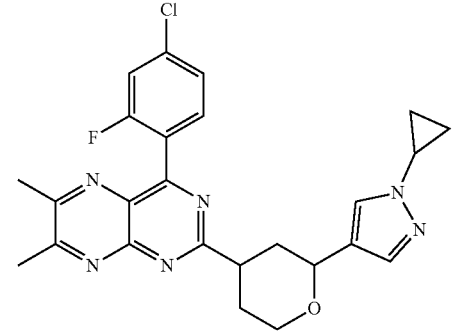 [SMILES: Cc1nc2nc(C3CCOC(c4cnn(C5CC5)c4)C3)nc(-c3ccc(Cl)cc3F)c2nc1C] |
| I-522 | 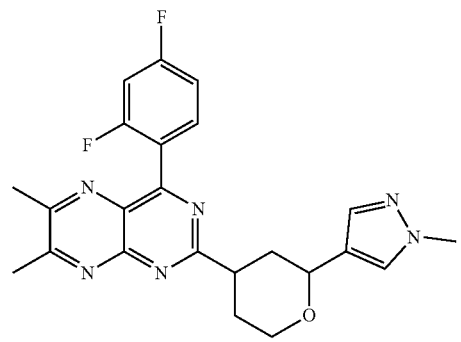 |
| I-523 |  |
| I-524 |  |
| I-525 | 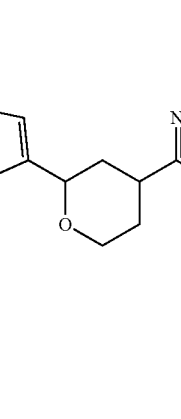 |
| I-526 | 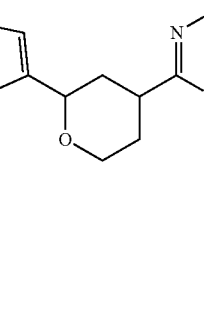 |

TABLE A-continued
Exemplary Compounds
| I-# | Structure |
|---|---|
| I-527 | 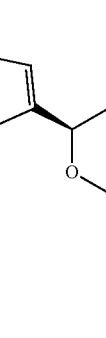 |
| I-528 | 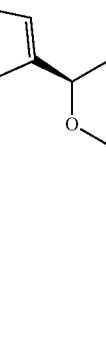 |
| I-529 | 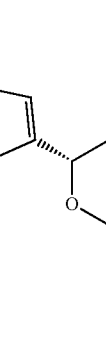 |
| I-530 | 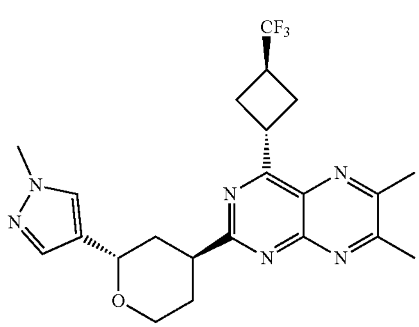 [SMILES: Cc1nc2nc([C@H]3CCO[C@H](c4cnn(C)c4)C3)nc([C@H]3C[C@H](C(F)(F)F)C3)c2nc1C] |
| I-531 | 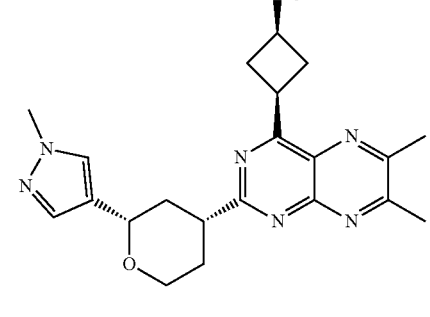 |
| I-532 | 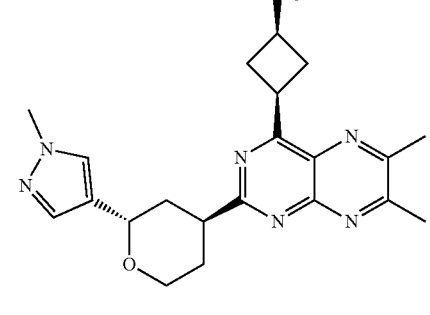 |
| I-533 | 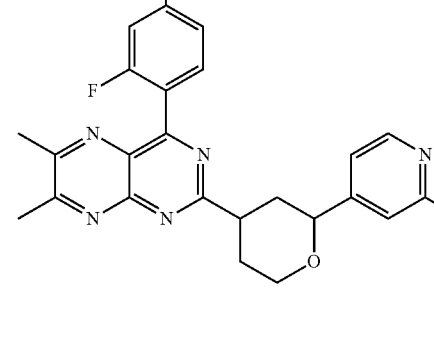 |
| I-534 | 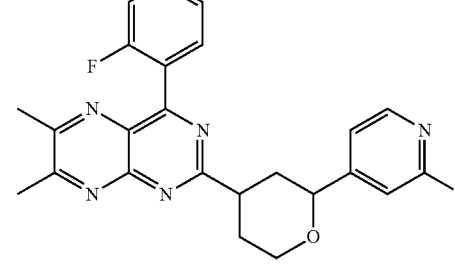 |

TABLE A-continued
Exemplary Compounds
| I-# | Structure |
|---|---|
| I-535 | 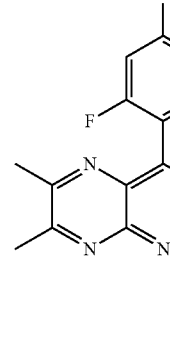 |
| I-536 | 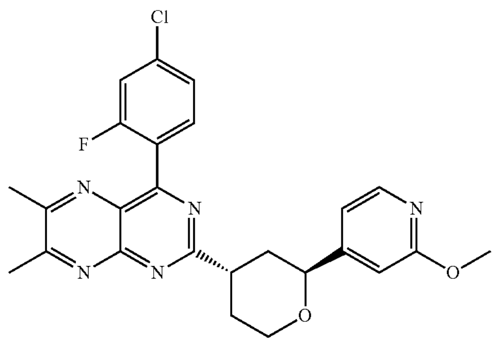 |
| I-537 | 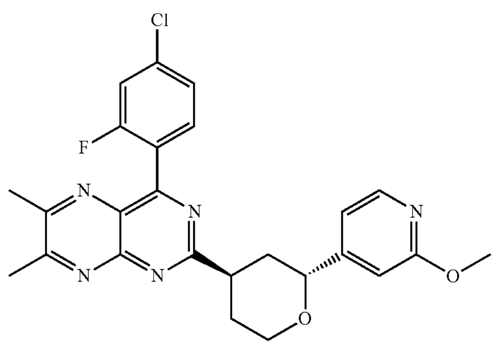 |
| I-538 | 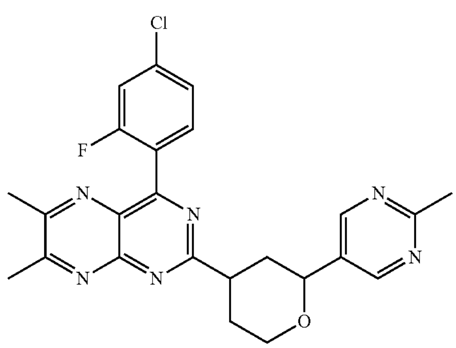 |
| I-539 | 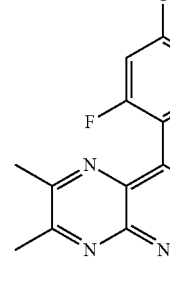 |
| I-540 | |
| I-541 | |
| I-542 | |

TABLE A-continued
Exemplary Compounds
| I-# | Structure |
|---|---|
| I-543 | 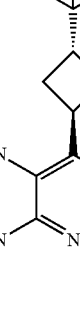 |
| I-544 | 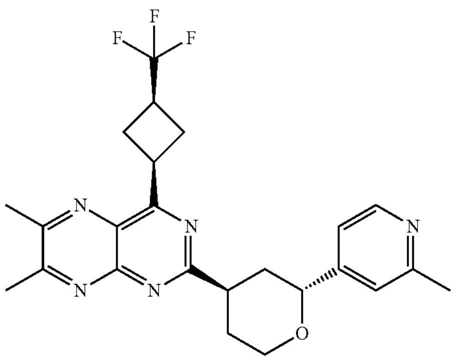 |
| I-545 | 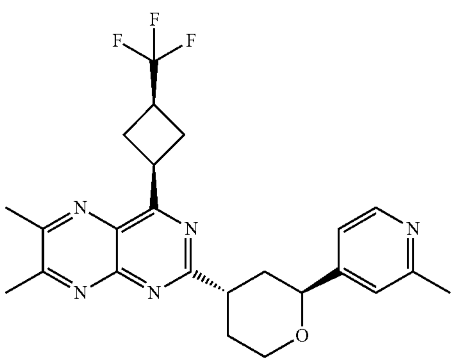 |
| I-546 | 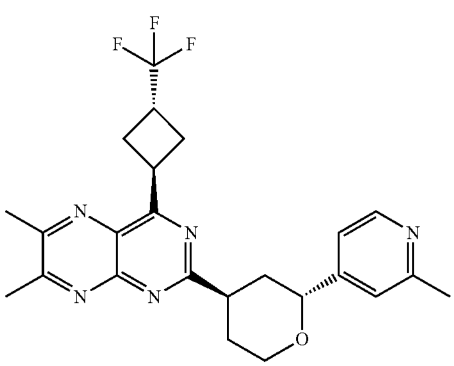 |
| I-547 | 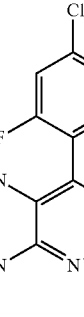 |
| I-548 | |
| I-549 | |
| I-550 | |

TABLE A-continued
Exemplary Compounds
| I-# | Structure |
|---|---|
| I-551 | 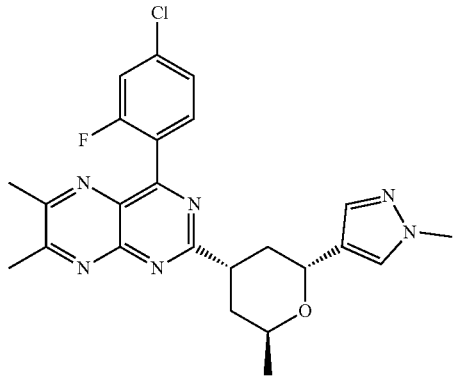 |
| I-552 | 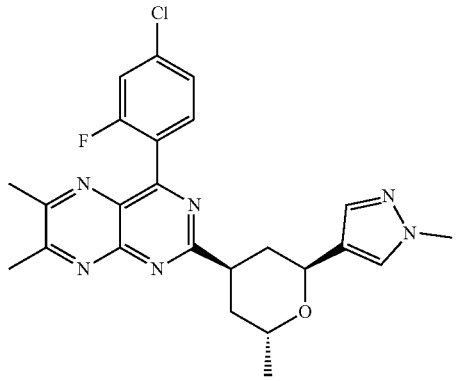 |
| I-553 | 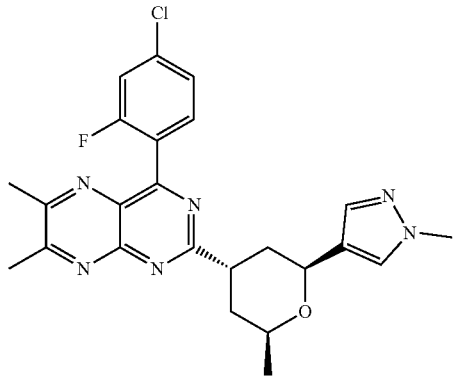 |
| I-554 | 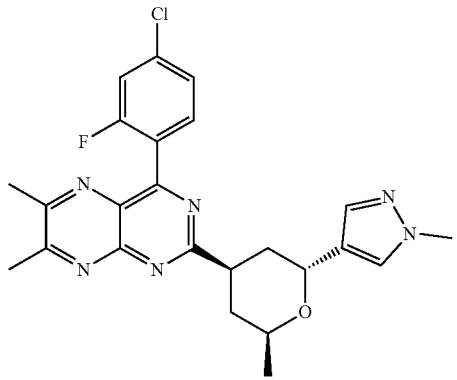 |
| I-555 | 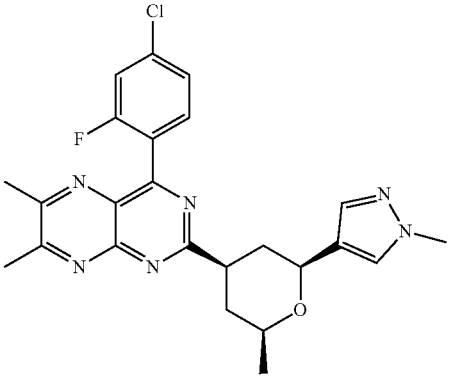 |
| I-556 | 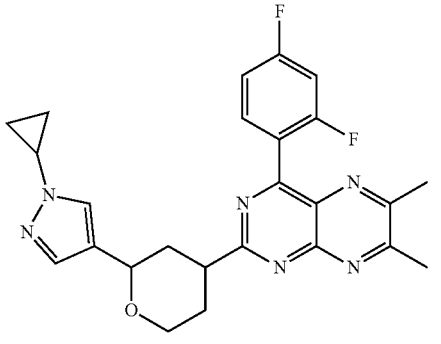 [SMILES: Cc1nc2nc(C3CCOC(c4cnn(C5CC5)c4)C3)nc(-c3ccc(F)cc3F)c2nc1C] |
| I-557 | 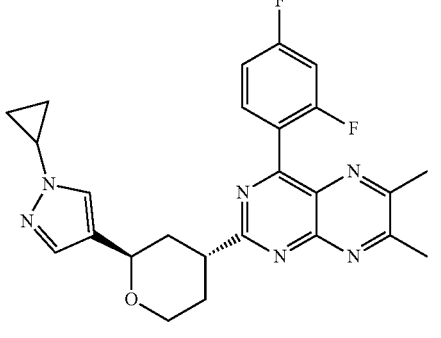 |
| I-558 | 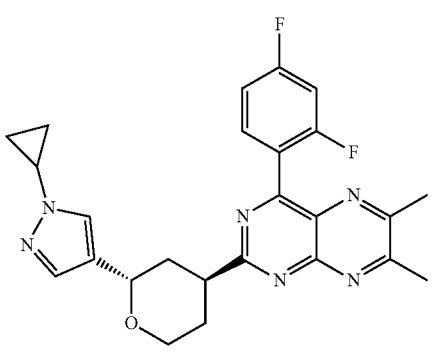 [SMILES: Cc1nc2nc([C@H]3CCO[C@H](c4cnn(C5CC5)c4)C3)nc(-c3ccc(F)cc3F)c2nc1C] |

TABLE A-continued
Exemplary Compounds
| I-# | Structure |
|---|---|
| I-559 | 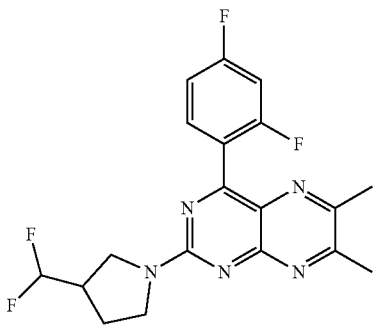 [SMILES: Cc1nc2nc(N3CCC(C(F)F)C3)nc(-c3ccc(F)cc3F)c2nc1C] |
| I-560 | 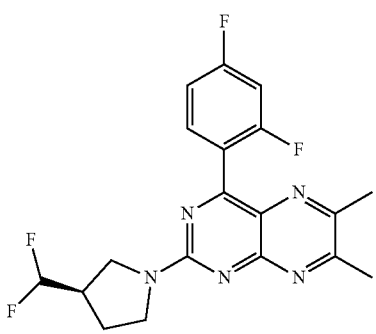 [SMILES: Cc1nc2nc(N3CC[C@@H](C(F)F)C3)nc(-c3ccc(F)cc3F)c2nc1C] |
| I-561 | 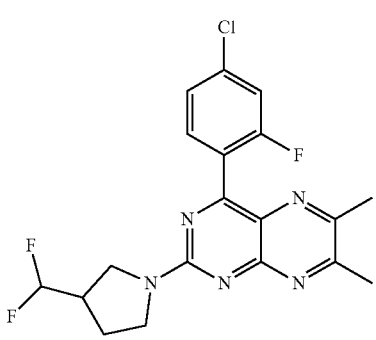 [SMILES: Cc1nc2nc(N3CCC(C(F)F)C3)nc(-c3ccc(Cl)cc3F)c2nc1C] |
| I-562 | 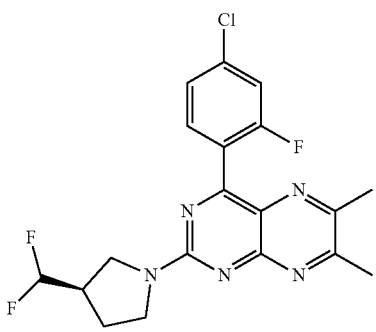 [SMILES: Cc1nc2nc(N3CC[C@@H](C(F)F)C3)nc(-c3ccc(Cl)cc3F)c2nc1C] |
| I-563 | 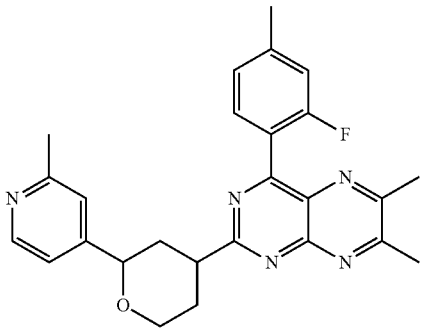 [SMILES: Cc1ccc(-c2nc(C3CCOC(c4ccnc(C)c4)C3)nc3nc(C)c(C)nc23)c(F)c1] |
| I-564 | 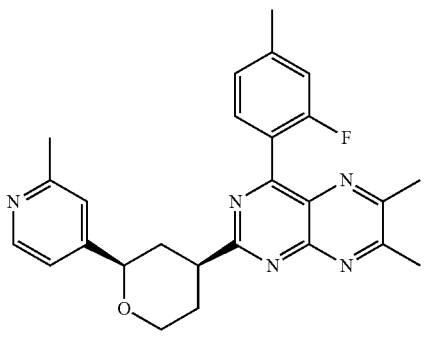 [SMILES: Cc1ccc(-c2nc([C@H]3CCO[C@@H](c4ccnc(C)c4)C3)nc3nc(C)c(C)nc23)c(F)c1] |
| I-565 | 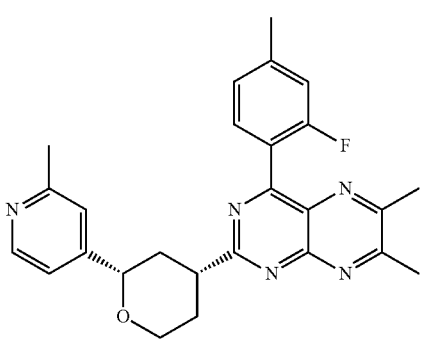 [SMILES: Cc1ccc(-c2nc([C@@H]3CCO[C@H](c4ccnc(C)c4)C3)nc3nc(C)c(C)nc23)c(F)c1] |
| I-566 | 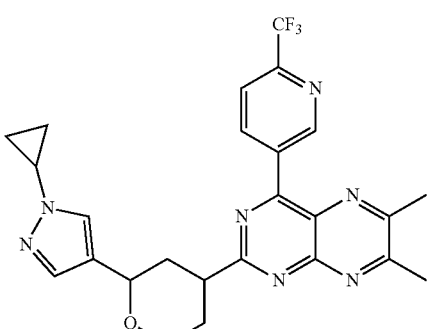 |

TABLE A-continued
Exemplary Compounds
| I-# | Structure |
|---|---|
| I-567 | 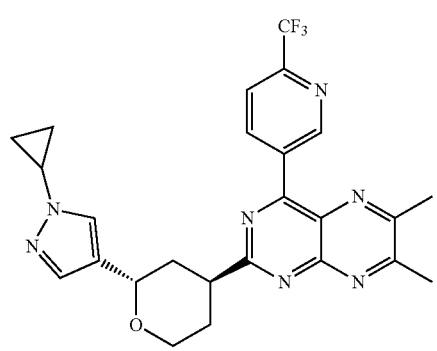 [SMILES: Cc1nc2nc([C@H]3CCO[C@H](c4cnn(C5CC5)c4)C3)nc(-c3ccc(C(F)(F)F)nc3)c2nc1C] |
| I-568 | 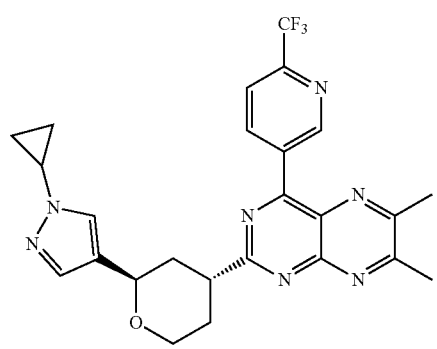 [SMILES: Cc1nc2nc([C@@H]3CCO[C@@H](c4cnn(C5CC5)c4)C3)nc(-c3ccc(C(F)(F)F)nc3)c2nc1C] |
| I-569 | 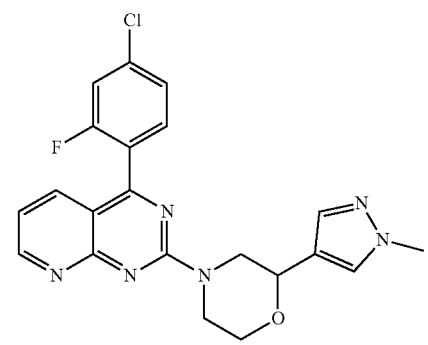 [SMILES: Cn1cc(C2CN(c3nc(-c4ccc(Cl)cc4F)c4cccnc4n3)CCO2)cn1] |
| I-570 | 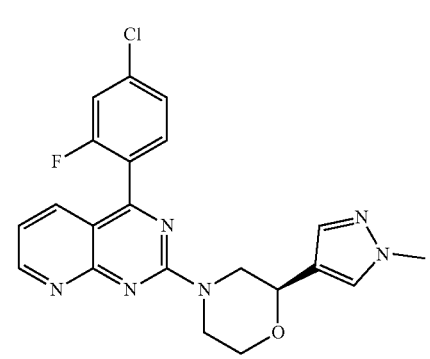 [SMILES: Cn1cc([C@@H]2CN(c3nc(-c4ccc(Cl)cc4F)c4cccnc4n3)CCO2)cn1] |
| I-571 | 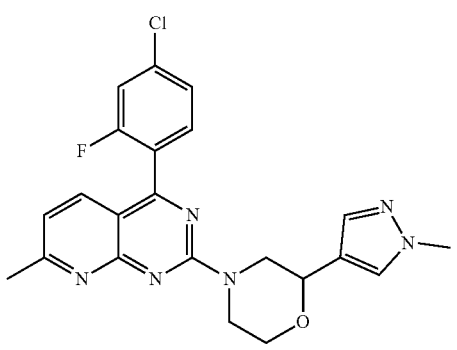 |
| I-572 | 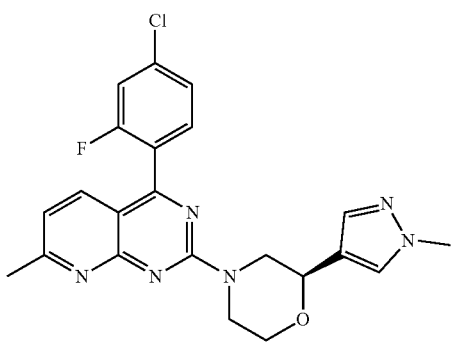 |
| I-573 | 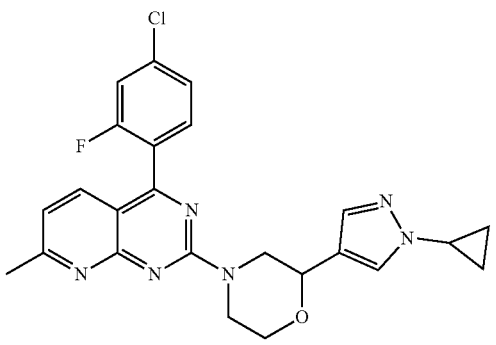 |
| I-574 | 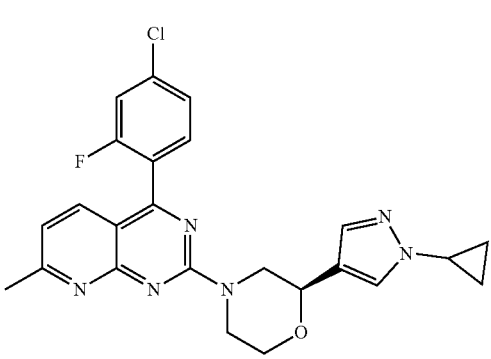 |

TABLE A-continued
Exemplary Compounds
| I-# | Structure |
|---|---|
| I-575 | 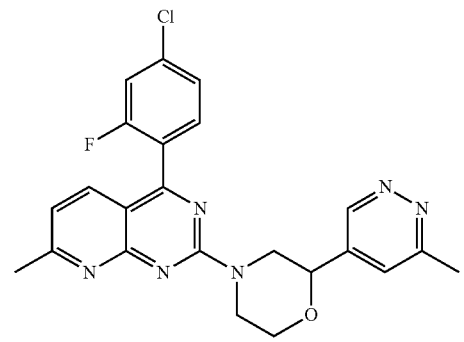 |
| I-576 | 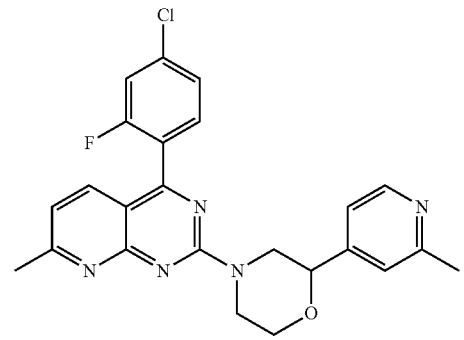 |
| I-577 | 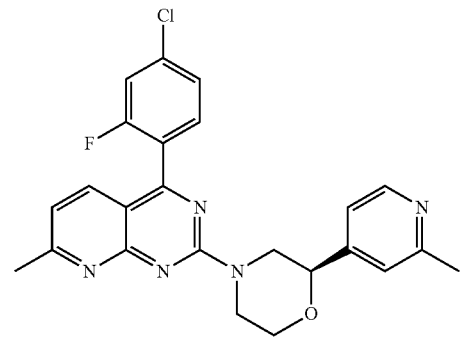 |
| I-578 | 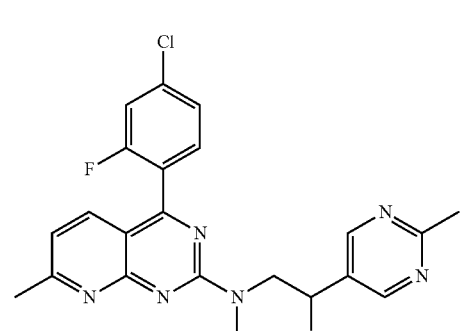 |
| I-579 | 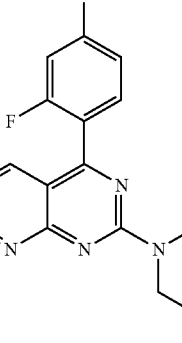 |
| I-580 | 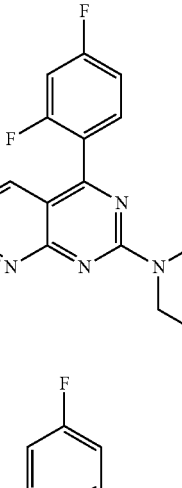 |
| I-581 | 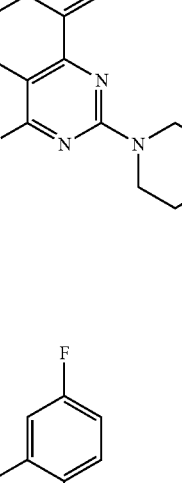 |
| I-582 | 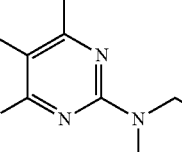 |

TABLE A-continued
Exemplary Compounds
| I-# | Structure |
|---|---|
| I-583 | 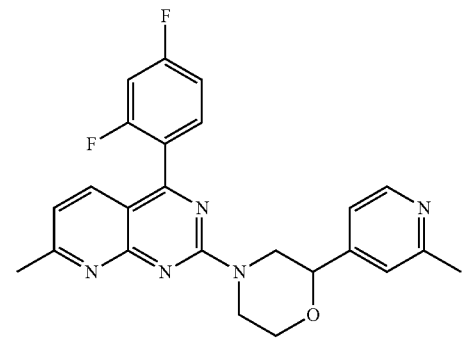 |
| I-584 | 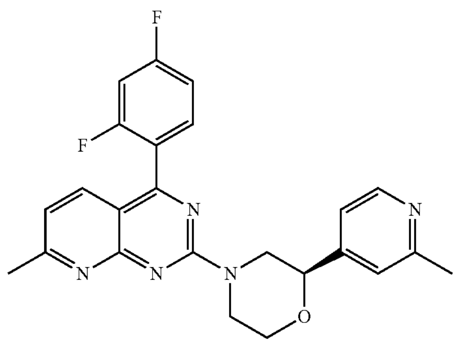 |
| I-585 | 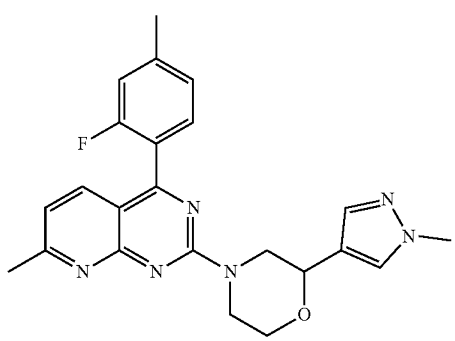 |
| I-586 | 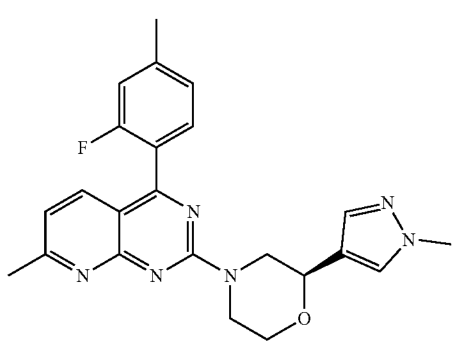 |
| I-587 | 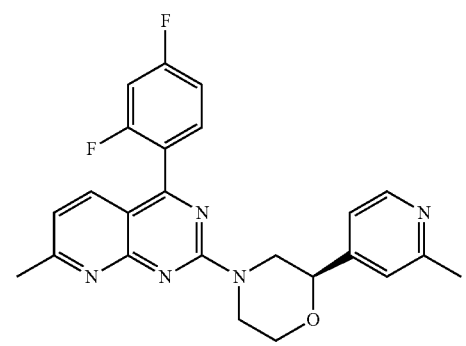 |
| I-588 | |
| I-589 | |
| I-590 | |

TABLE A-continued
Exemplary Compounds
| I-# | Structure |
|---|---|
| I-591 | 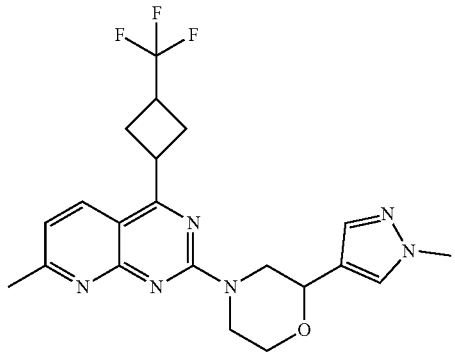 |
| I-592 | 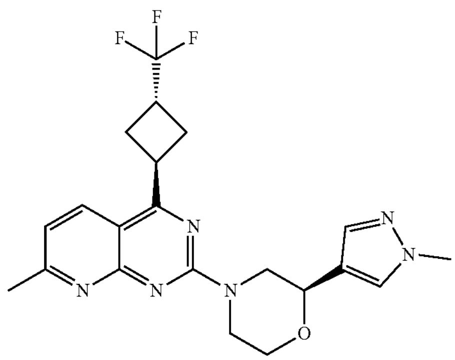 |
| I-593 | 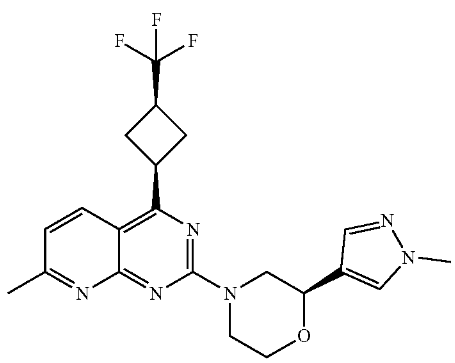 |
| I-594 | 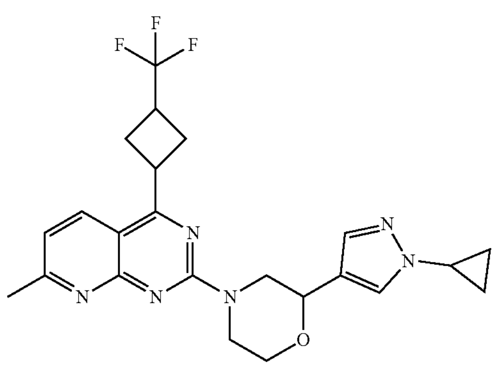 [SMILES: Cc1ccc2c(C3CC(C(F)(F)F)C3)nc(N3CCOC(c4cnn(C5CC5)c4)C3)nc2n1] |
TABLE A-continued
Exemplary Compounds
| I-# | Structure |
|---|---|
| I-595 | 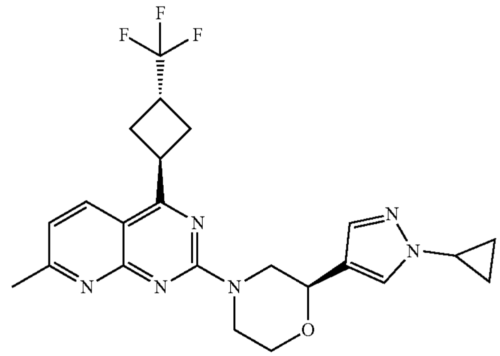 [SMILES: Cc1ccc2c(n1)nc(N1CCO[C@H](c3cnn(C4CC4)c3)C1)nc2[C@H]1C[C@H](C(F)(F)F)C1] |
| I-596 | 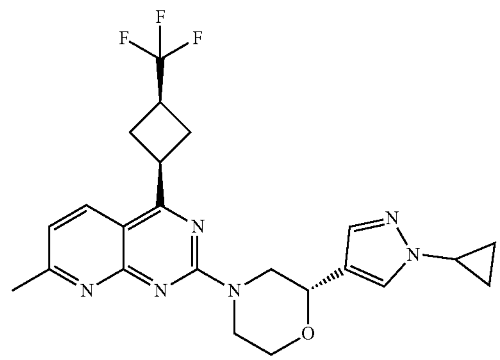 [SMILES: Cc1ccc2c(n1)nc(N1CCO[C@@H](c3cnn(C4CC4)c3)C1)nc2[C@H]1C[C@@H](C(F)(F)F)C1] |
| I-597 | 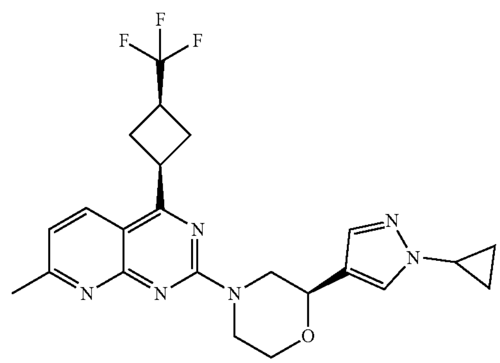 [SMILES: Cc1ccc2c(n1)nc(N1CCO[C@H](c3cnn(C4CC4)c3)C1)nc2[C@H]1C[C@@H](C(F)(F)F)C1] |
| I-598 | 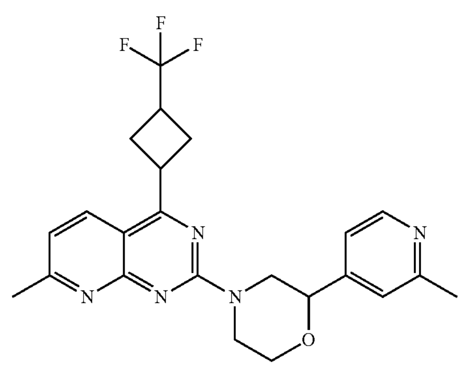 |

TABLE A-continued
Exemplary Compounds
| I-# | Structure |
|---|---|
| I-599 | 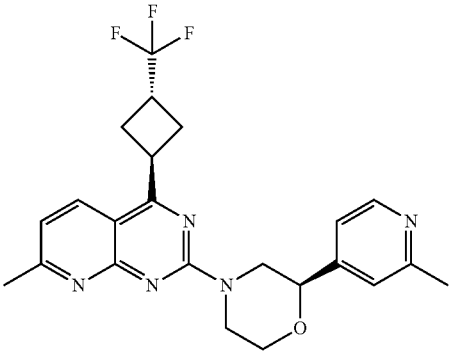 |
| I-600 | 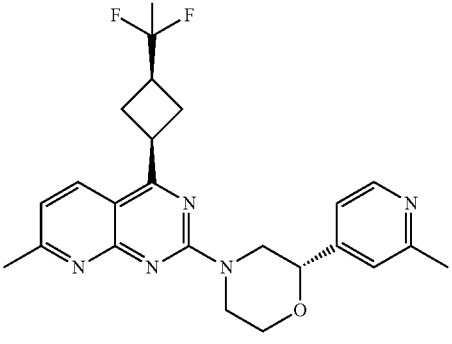 |
| I-601 | 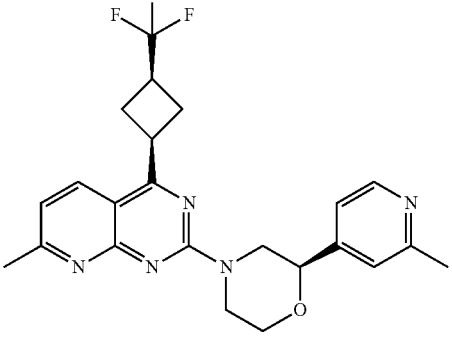 |
| I-602 | 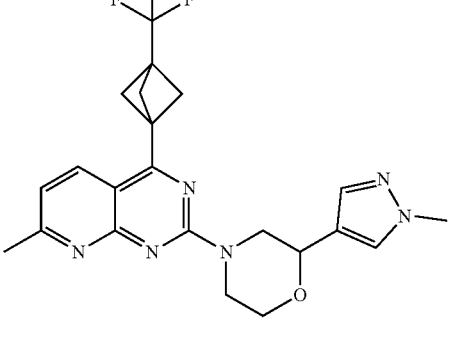 |
| I-603 | 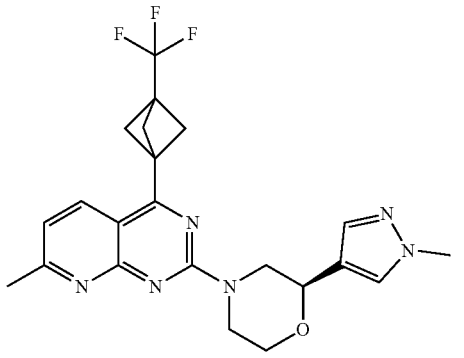 |
| I-604 | 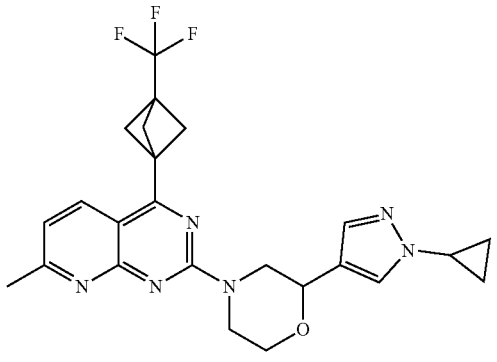 [SMILES: Cc1ccc2c(C34CC(C(F)(F)F)(C3)C4)nc(N3CCOC(c4cnn(C5CC5)c4)C3)nc2n1] |
| I-605 | 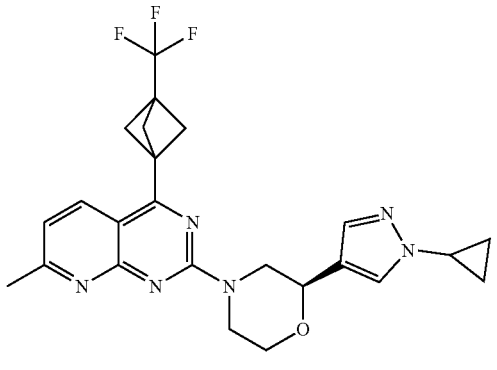 [SMILES: Cc1ccc2c(C34CC(C(F)(F)F)(C3)C4)nc(N3CCO[C@H](c4cnn(C5CC5)c4)C3)nc2n1] |
| I-606 | 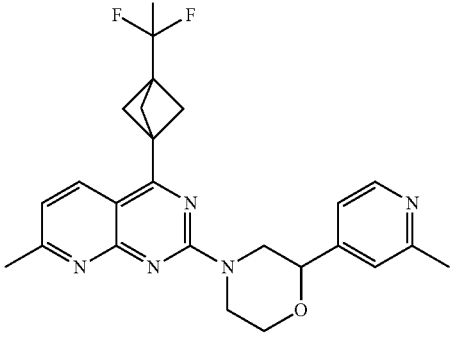 |

TABLE A-continued
Exemplary Compounds
| I-# | Structure |
|---|---|
| I-607 | 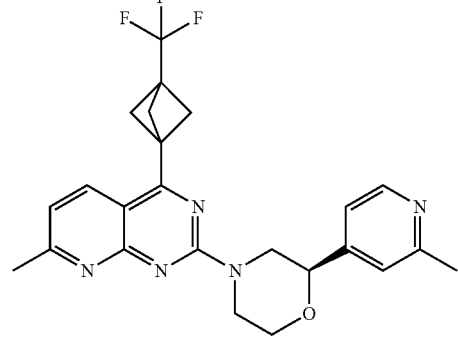 |
| I-608 | 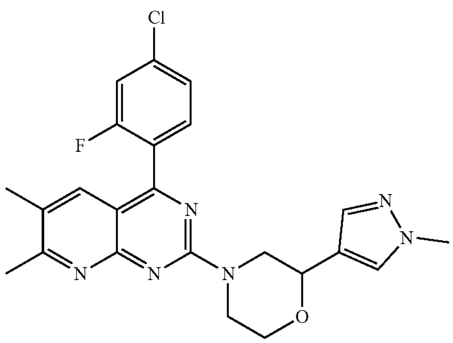 |
| I-609 | 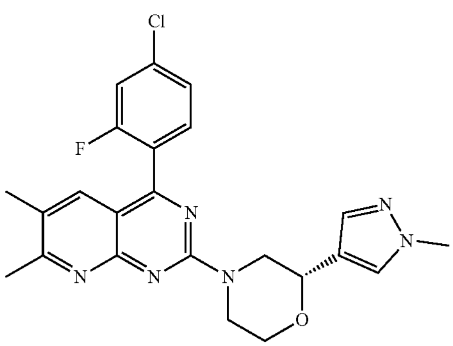 |
| I-610 | 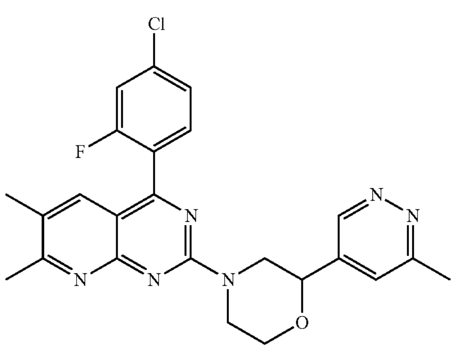 |
| I-611 | 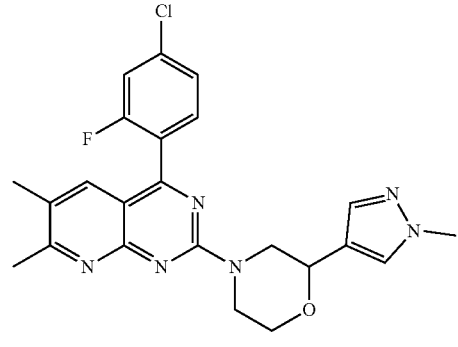 |
| I-612 | |
| I-613 | |
| I-614 | |

TABLE A-continued

Exemplary Compounds

| I-# | Structure |
|---|---|
| I-615 | |
| I-616 | |
| I-617 | |
| I-618 | 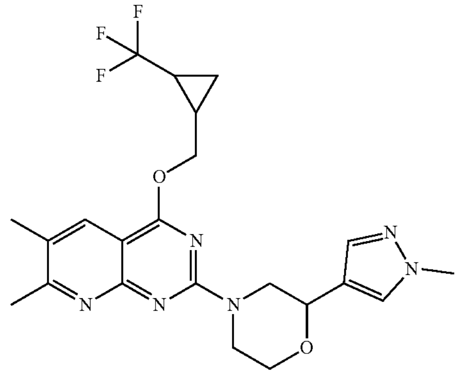 |
| I-619 | 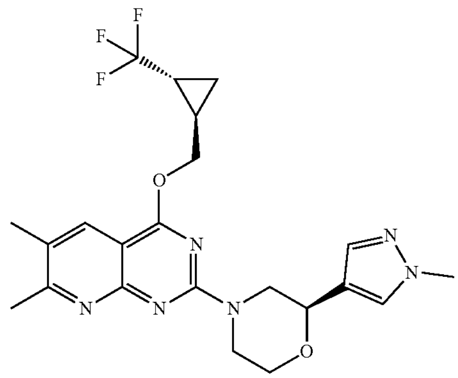 |
| I-620 | 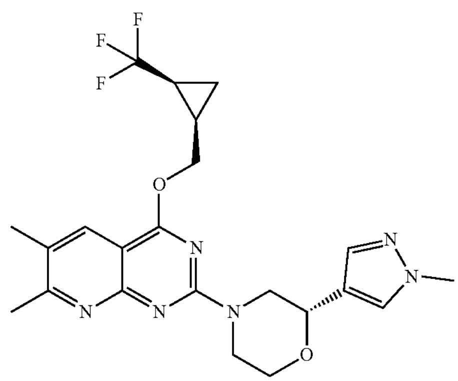 |
| I-621 | 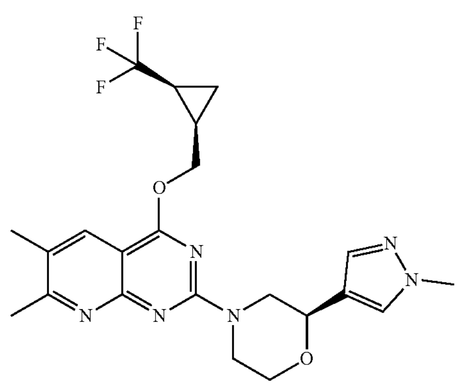 |

TABLE A-continued

Exemplary Compounds

| I-# | Structure |
|---|---|
| I-622 | 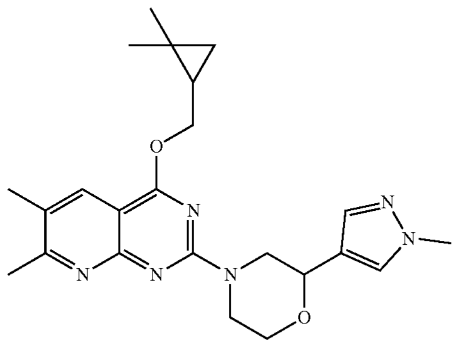 |
| I-623 | 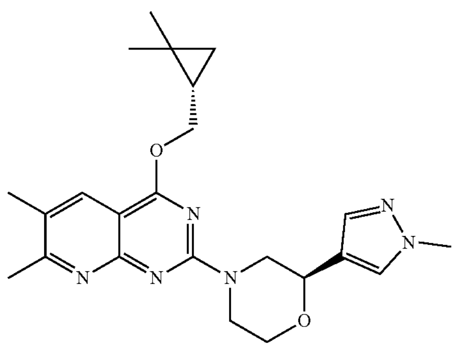 |
| I-624 | 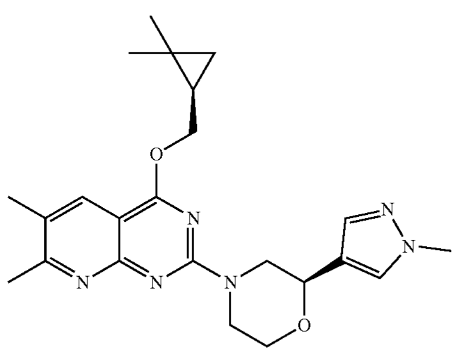 |
| I-625 | 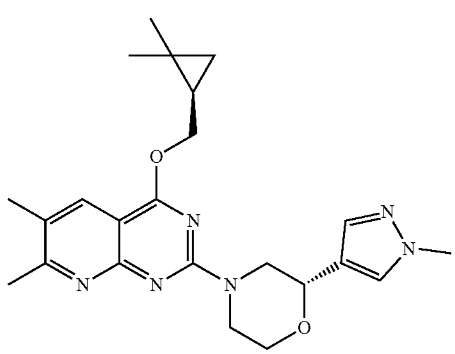 |
| I-626 | |
| I-627 | |
| I-628 | |
| I-629 | |

TABLE A-continued

Exemplary Compounds

| I-# | Structure |
|---|---|
| I-630 | 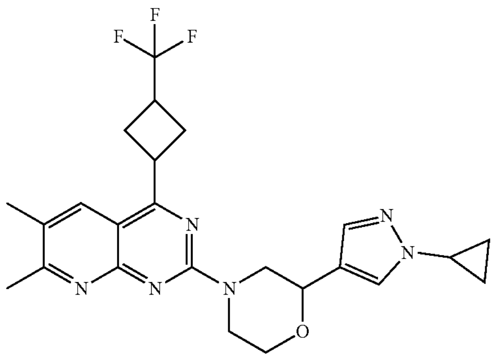 [SMILES: Cc1cc2c(C3CC(C(F)(F)F)C3)nc(N3CCOC(c4cnn(C5CC5)c4)C3)nc2nc1C] |
| I-631 | 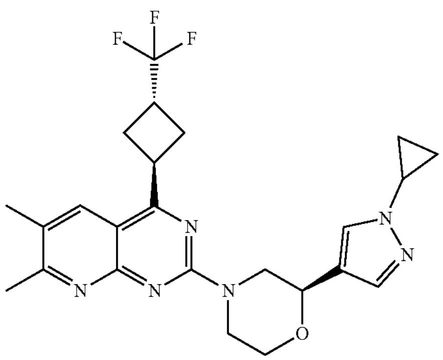 [SMILES: Cc1cc2c(nc(N3CCO[C@H](c4cnn(C5CC5)c4)C3)nc2[C@H]2C[C@H](C(F)(F)F)C2)nc1C] |
| I-632 | 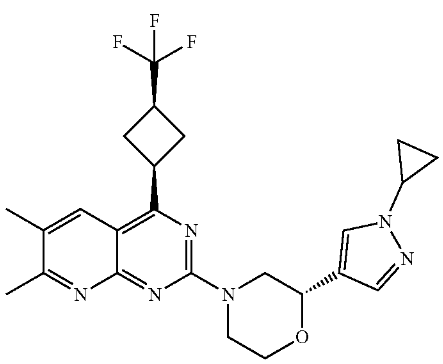 [SMILES: Cc1cc2c(nc(N3CCO[C@@H](c4cnn(C5CC5)c4)C3)nc2[C@H]2C[C@@H](C(F)(F)F)C2)nc1C] |
| I-633 | 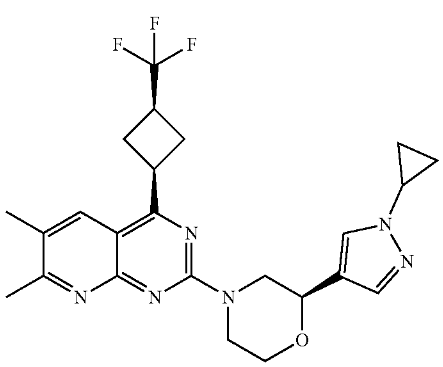 [SMILES: Cc1cc2c(nc(N3CCO[C@H](c4cnn(C5CC5)c4)C3)nc2[C@H]2C[C@@H](C(F)(F)F)C2)nc1C] |
| I-634 | |
| I-635 | |
| I-636 | |
| I-637 | |

TABLE A-continued
Exemplary Compounds
| I-# | Structure |
|---|---|
| I-638 | 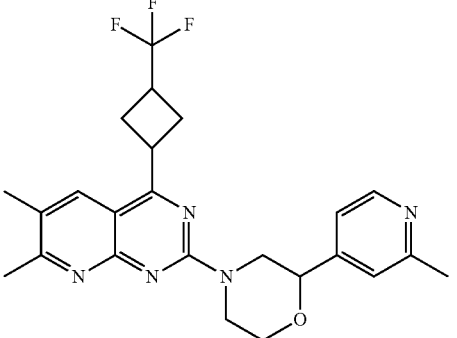 |
| I-639 | |
| I-640 | |
| I-641 | |
| I-# | Structure |
|---|---|
| I-642 | 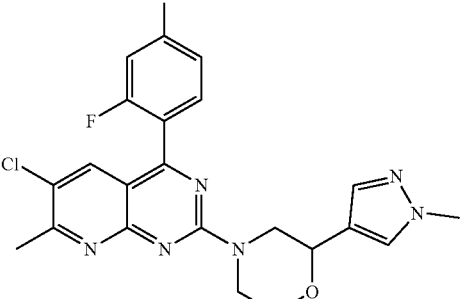 |
| I-643 | |
| I-644 | |
| I-645 | |

TABLE A-continued
Exemplary Compounds
| I-# | Structure |
|---|---|
| I-646 | 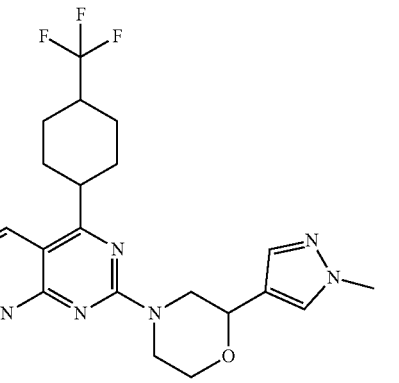 |
| I-647 | 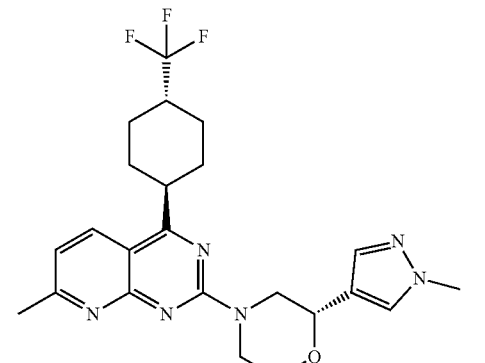 |
| I-648 | 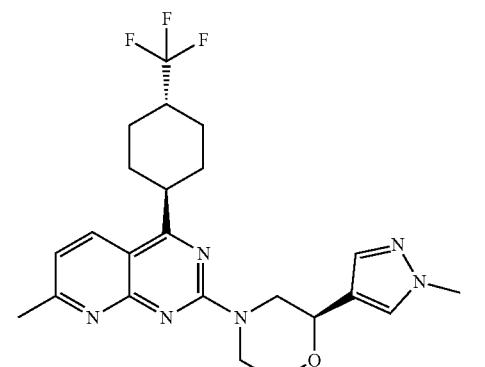 |
| I-649 | 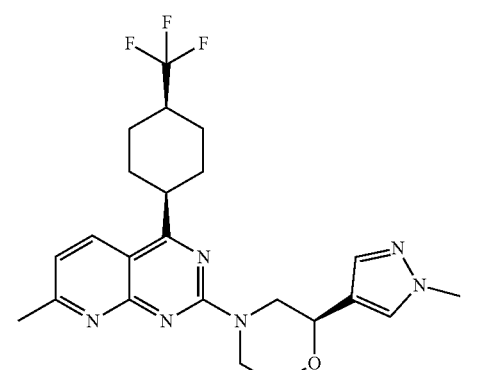 |
| I-650 | 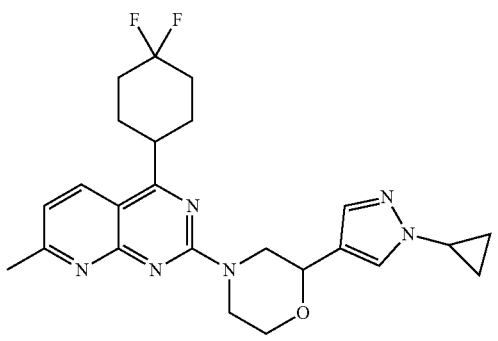 [SMILES: Cc1ccc2c(C3CCC(F)(F)CC3)nc(N3CCOC(c4cnn(C5CC5)c4)C3)nc2n1] |
| I-651 | 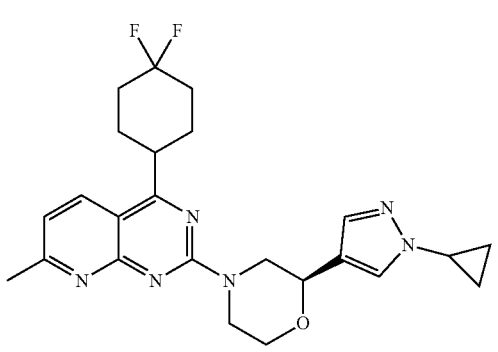 [SMILES: Cc1ccc2c(C3CCC(F)(F)CC3)nc(N3CCO[C@H](c4cnn(C5CC5)c4)C3)nc2n1] |
| I-652 | 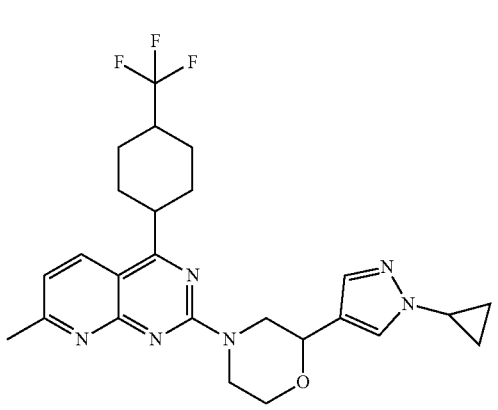 [SMILES: Cc1ccc2c(C3CCC(C(F)(F)F)CC3)nc(N3CCOC(c4cnn(C5CC5)c4)C3)nc2n1] |
| I-653 | 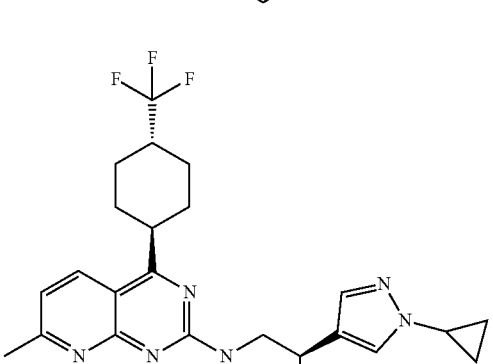 |

TABLE A-continued
Exemplary Compounds
| I-# | Structure |
|---|---|
| I-654 | 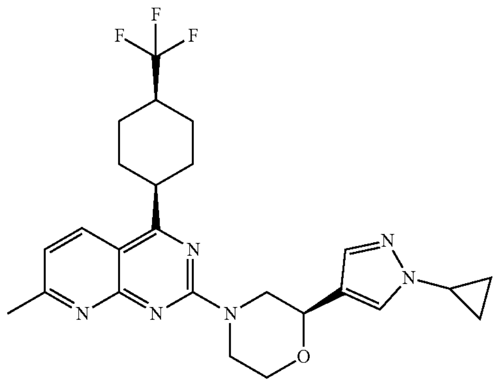 [SMILES: Cc1ccc2c(n1)nc(N1CCO[C@H](c3cnn(C4CC4)c3)C1)nc2[C@H]1CC[C@@H](C(F)(F)F)CC1] |
| I-655 | 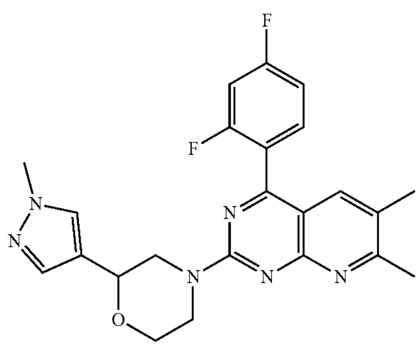 [SMILES: Cc1cc2c(-c3ccc(F)cc3F)nc(N3CCOC(c4cnn(C)c4)C3)nc2nc1C] |
| I-656 | 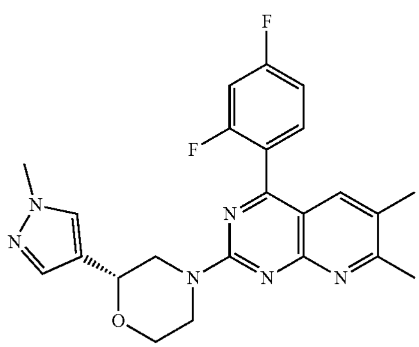 [SMILES: Cc1cc2c(-c3ccc(F)cc3F)nc(N3CCO[C@H](c4cnn(C)c4)C3)nc2nc1C] |
| I-657 | 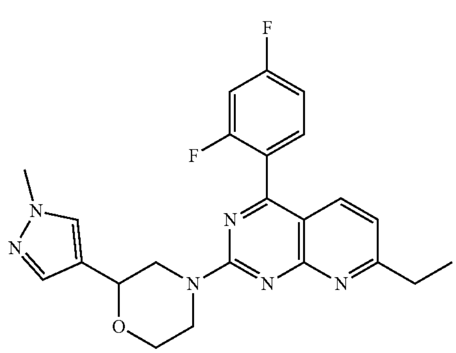 [SMILES: CCc1ccc2c(-c3ccc(F)cc3F)nc(N3CCOC(c4cnn(C)c4)C3)nc2n1] |
| I-658 |  |
| I-659 | |
| I-660 | |
| I-661 | |

TABLE A-continued

Exemplary Compounds

| I-# | Structure |
|---|---|
| I-662 | 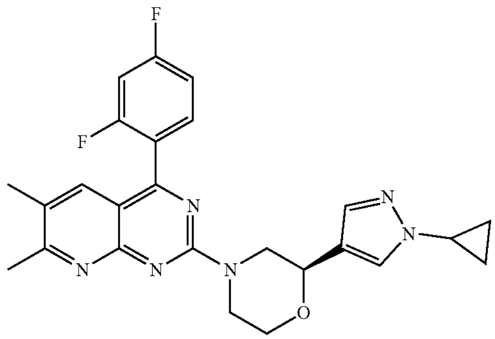 [SMILES: Cc1cc2c(-c3ccc(F)cc3F)nc(N3CCO[C@H](c4cnn(C5CC5)c4)C3)nc2nc1C] |
| I-663 | 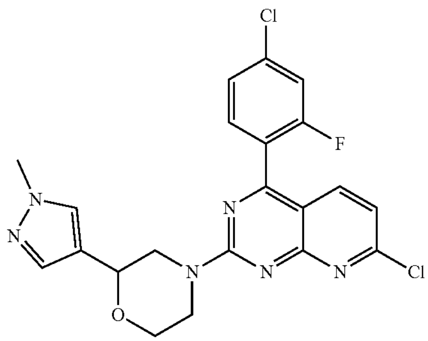 [SMILES: Cn1cc(C2CN(c3nc(-c4ccc(Cl)cc4F)c4ccc(Cl)nc4n3)CCO2)cn1] |
| I-664 | 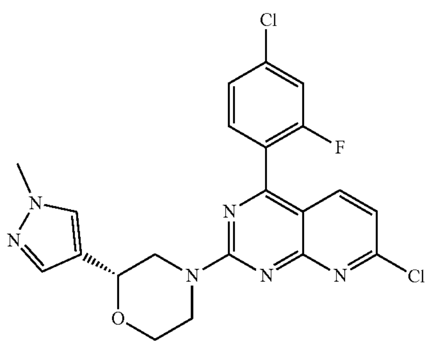 [SMILES: Cn1cc([C@@H]2CN(c3nc(-c4ccc(Cl)cc4F)c4ccc(Cl)nc4n3)CCO2)cn1] |
| I-665 | 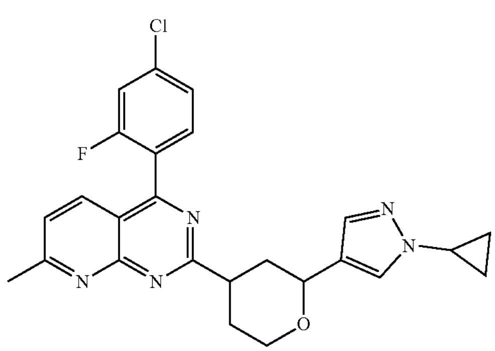 |
| I-666 | |
| I-667 | |
| I-668 | |
| I-669 | |

TABLE A-continued
Exemplary Compounds
| I-# | Structure |
|---|---|
| I-670 | 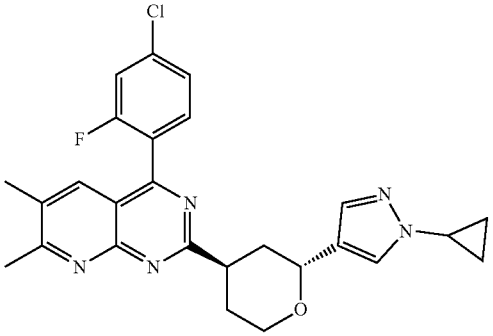 [SMILES: Cc1cc2c(-c3ccc(Cl)cc3F)nc([C@@H]3CCO[C@@H](c4cnn(C5CC5)c4)C3)nc2nc1C] |
| I-671 | 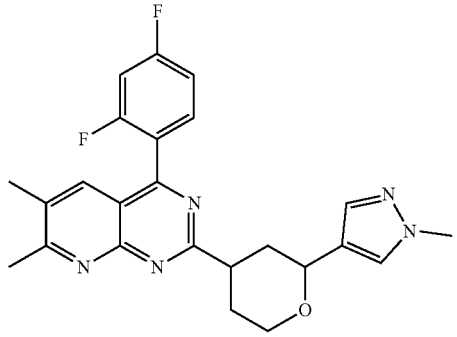 |
| I-672 | 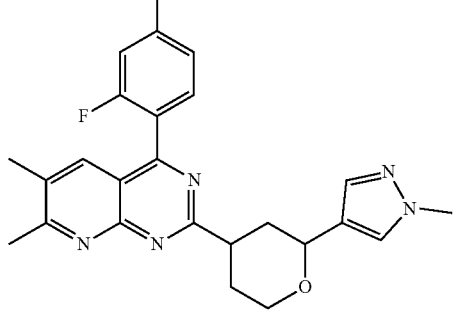 |
| I-673 | 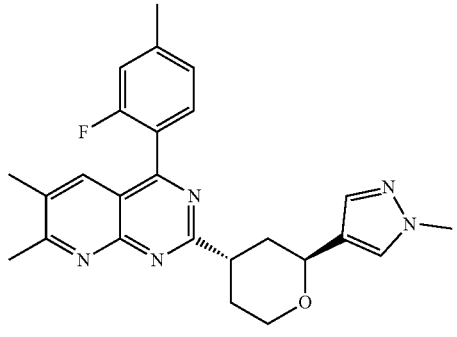 |
| I-674 | 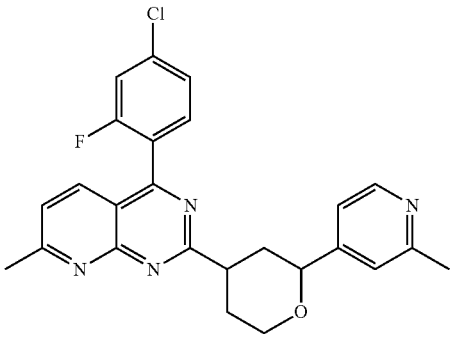 |
| I-675 | 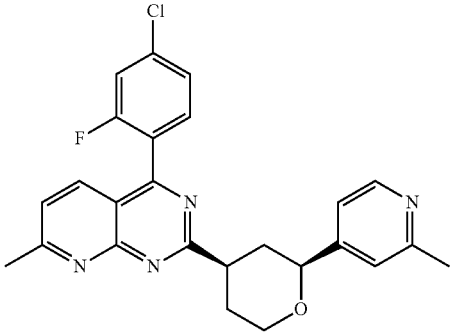 |
| I-676 | 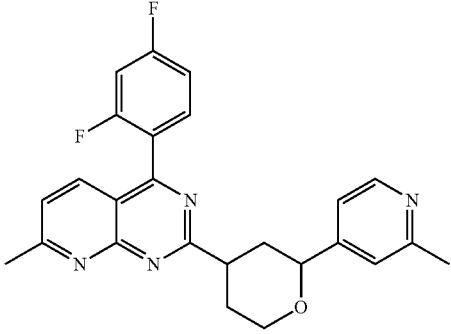 |
| I-677 | 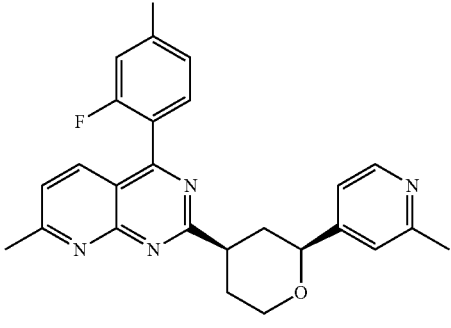 |

TABLE A-continued

Exemplary Compounds

| I-# | Structure |
|---|---|
| I-678 | 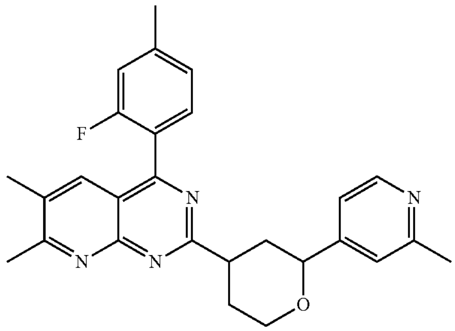 |
| I-679 | 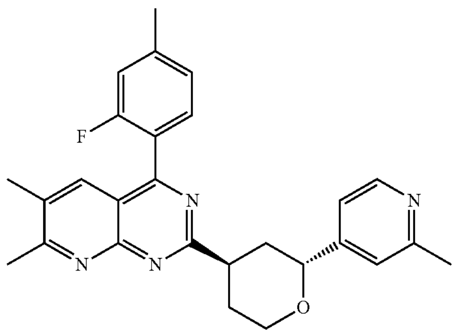 |
| I-680 | 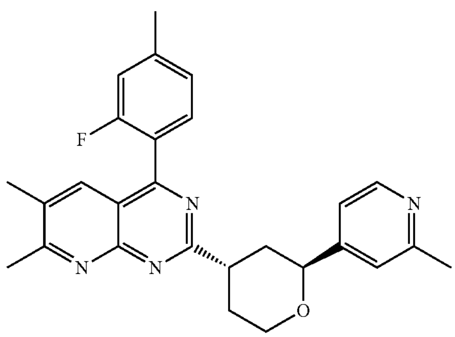 |
| I-681 | 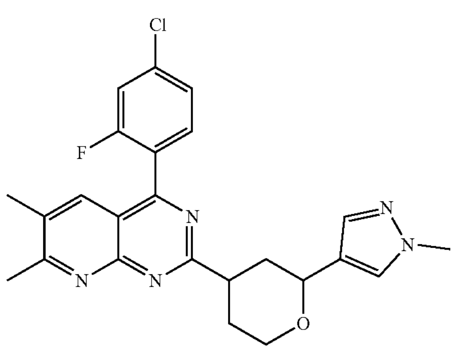 |
| I-682 | |
| I-683 | |
| I-684 | |
| I-685 | |

TABLE A-continued

Exemplary Compounds

| I-# | Structure |
|---|---|
| I-686 | 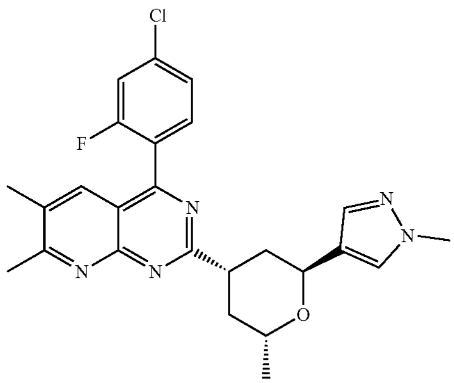 |
| I-687 | 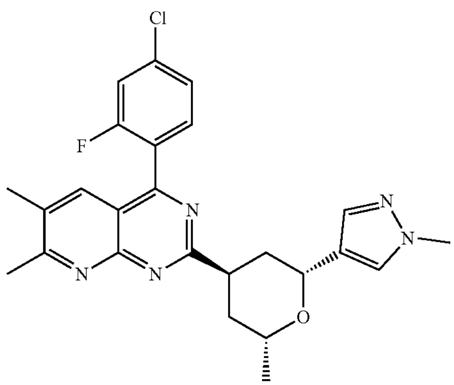 |
| I-688 | 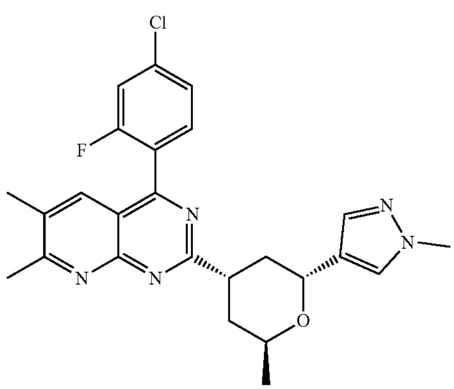 |
| I-689 | 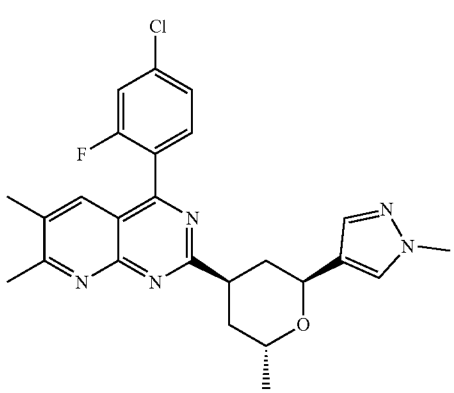 |
| I-690 | |
| I-691 | |
| I-692 | |
| I-693 | |

TABLE A-continued
Exemplary Compounds
| I-# | Structure |
|---|---|
| I-694 | 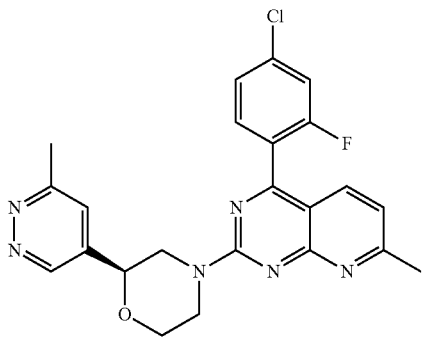 |
| I-695 | 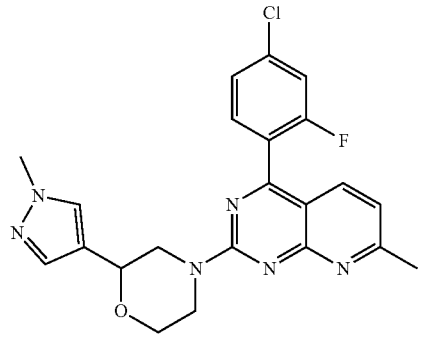 [SMILES: Cc1ccc2c(-c3ccc(Cl)cc3F)nc(N3CCOC(c4cnn(C)c4)C3)nc2n1] |
| I-696 | 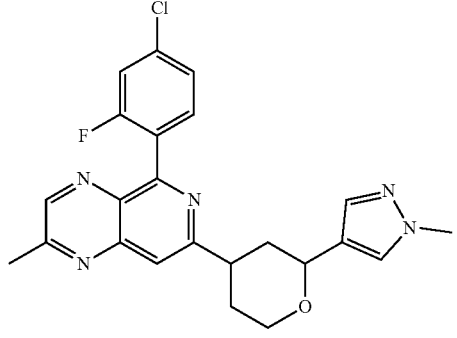 |
| I-697 | 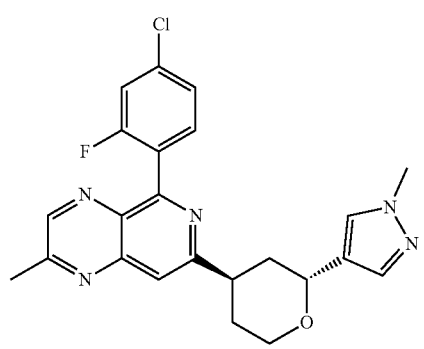 [SMILES: Cc1cnc2c(-c3ccc(Cl)cc3F)nc([C@@H]3CCO[C@@H](c4cnn(C)c4)C3)cc2n1] |
| I-698 | 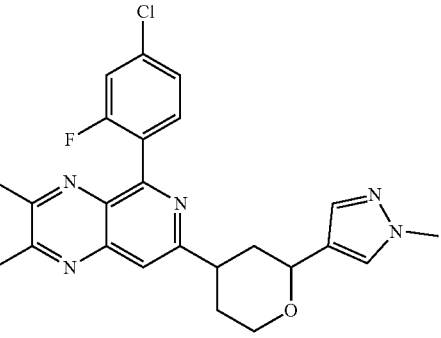 |
| I-699 | 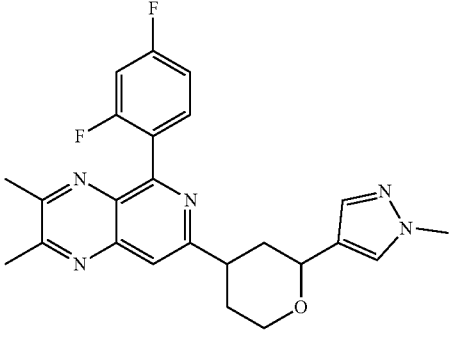 |
| I-700 | 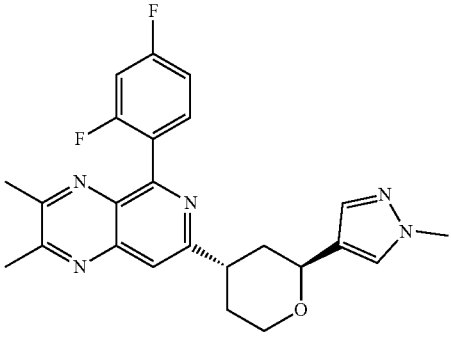 |
| I-701 | 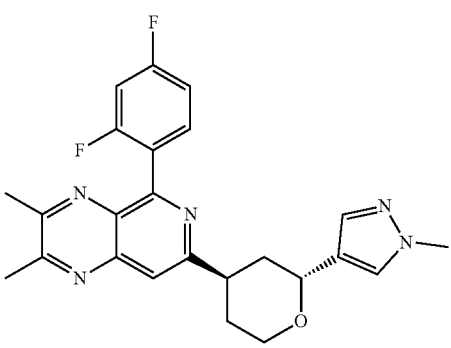 |

TABLE A-continued
Exemplary Compounds
| I-# | Structure |
|---|---|
| I-702 | 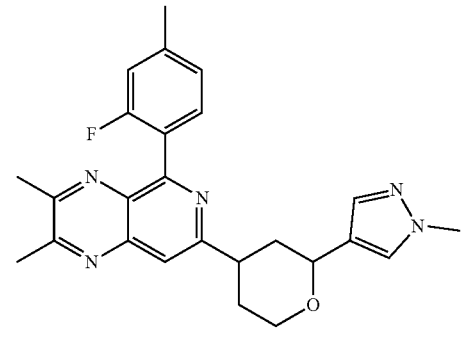 |
| I-703 | 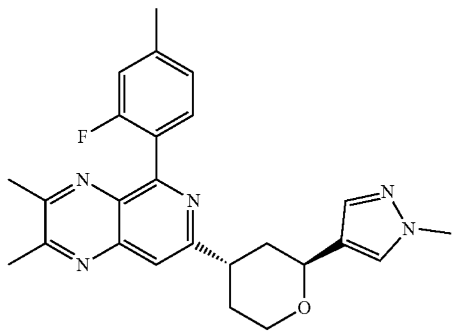 |
| I-704 | 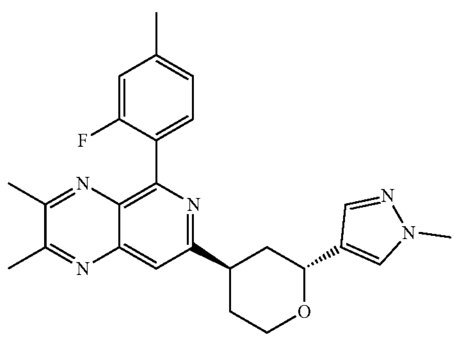 |
| I-705 | 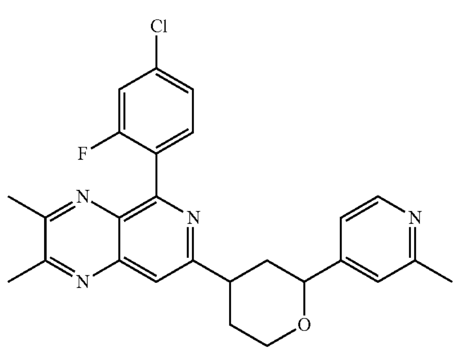 |
| I-706 | 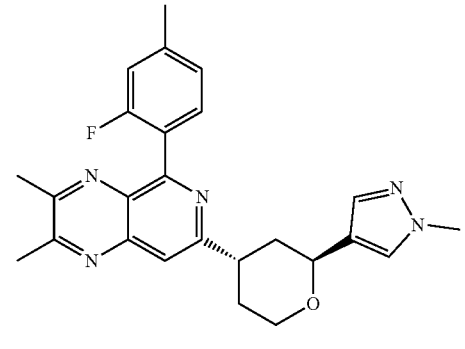 |
| I-707 | |
| I-708 | |
| I-709 | |

TABLE A-continued

Exemplary Compounds

| I-# | Structure |
|---|---|
| I-710 | 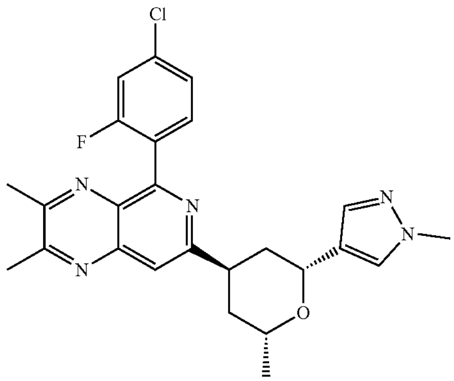 |
| I-711 | 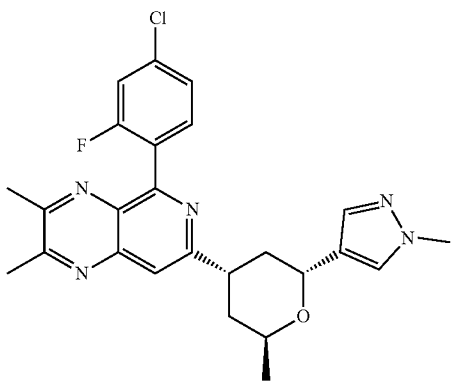 |
| I-712 | 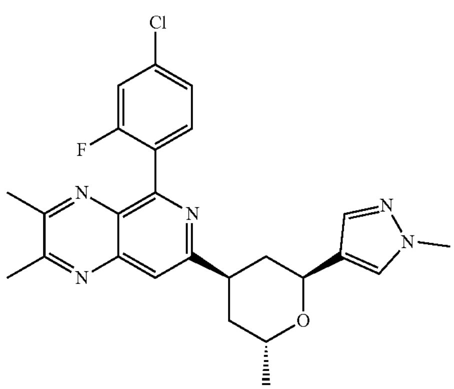 |
| I-713 | 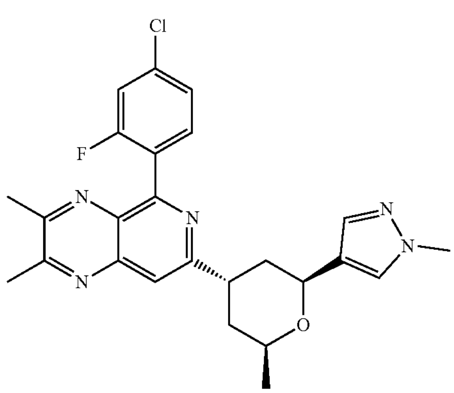 |
| I-714 | |
| I-715 | |
| I-716 | |
| I-717 | |

TABLE A-continued

Exemplary Compounds

| I-# | Structure |
|---|---|
| I-718 | 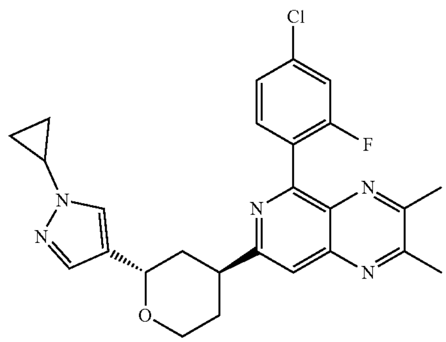 [SMILES: Cc1nc2cc([C@H]3CCO[C@H](c4cnn(C5CC5)c4)C3)nc(-c3ccc(Cl)cc3F)c2nc1C] |
| I-719 | 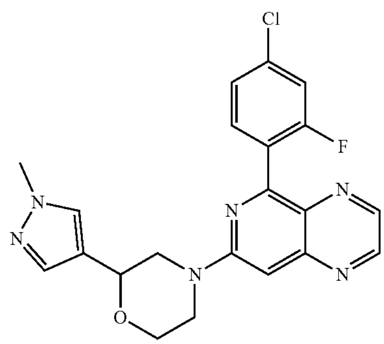 [SMILES: Cn1cc(C2CN(c3cc4nccnc4c(-c4ccc(Cl)cc4F)n3)CCO2)cn1] |
| I-720 | 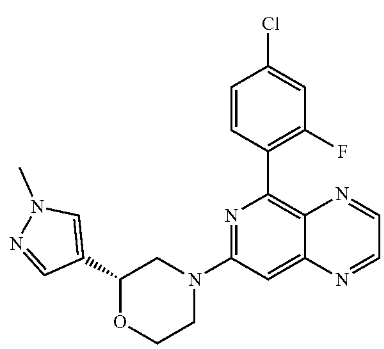 [SMILES: Cn1cc([C@@H]2CN(c3cc4nccnc4c(-c4ccc(Cl)cc4F)n3)CCO2)cn1] |
| I-721 | 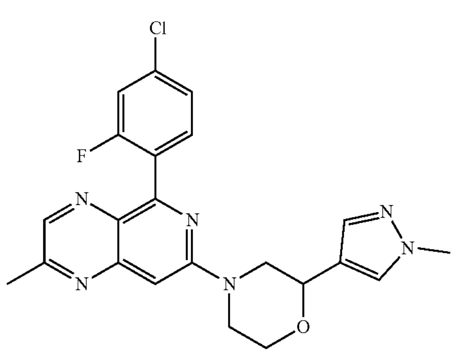 |
| I-722 | |
| I-723 | |
| I-724 | |
| I-725 | |

TABLE A-continued
Exemplary Compounds
| I-# | Structure |
|---|---|
| I-726 | 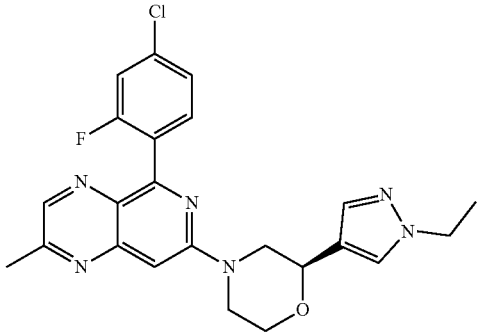 [SMILES: CCn1cc([C@@H]2CN(c3cc4nc(C)cnc4c(-c4ccc(Cl)cc4F)n3)CCO2)cn1] |
| I-727 | 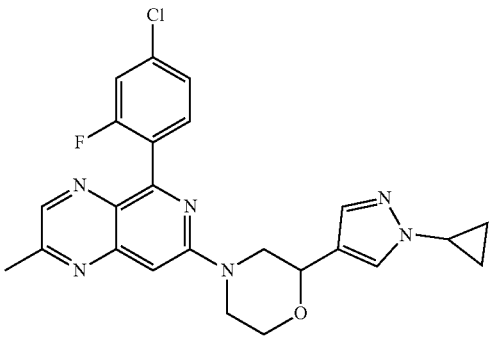 |
| I-728 | 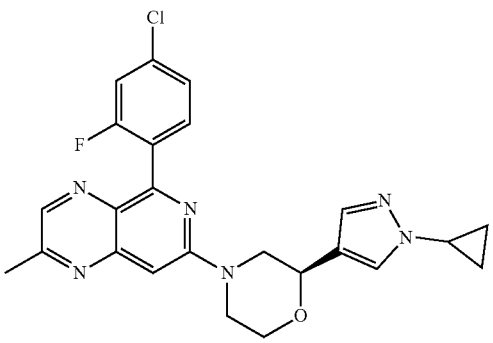 [SMILES: Cc1cnc2c(-c3ccc(Cl)cc3F)nc(N3CCO[C@H](c4cnn(C5CC5)c4)C3)cc2n1] |
| I-729 | 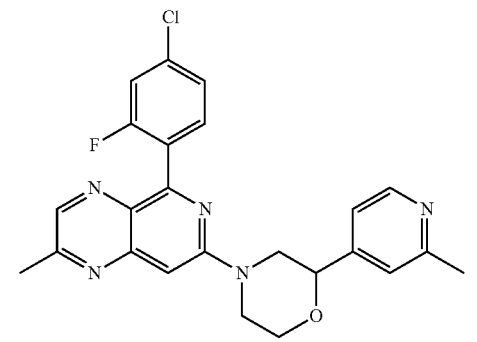 |
| I-730 | 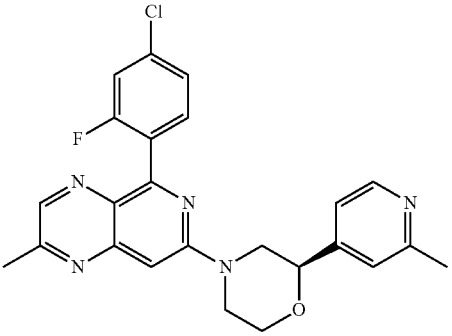 |
| I-731 | 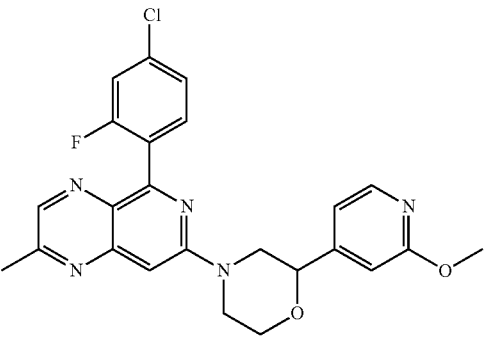 |
| I-732 | 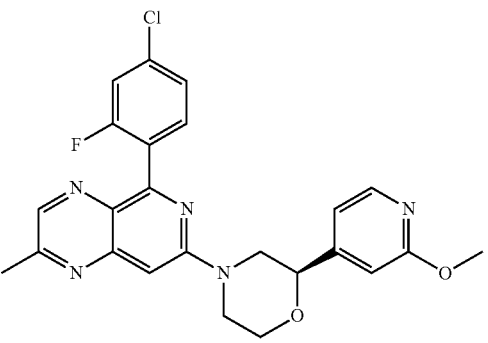 |
| I-733 | 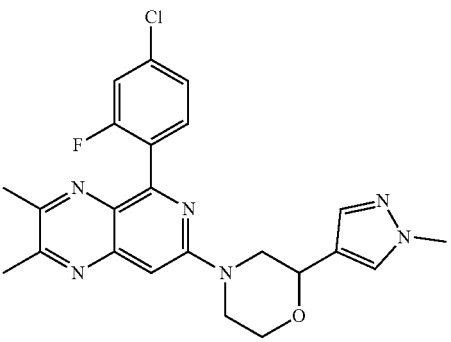 |

TABLE A-continued
Exemplary Compounds
| I-# | Structure |
|---|---|
| I-734 | 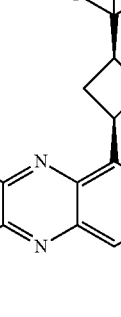 |
| I-735 | 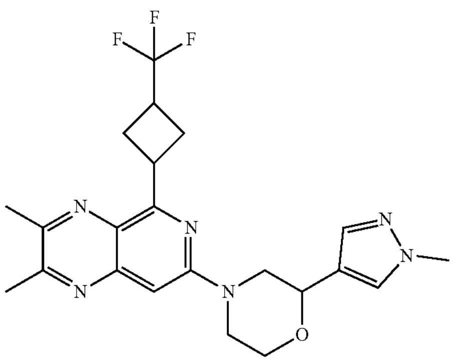 |
| I-736 | 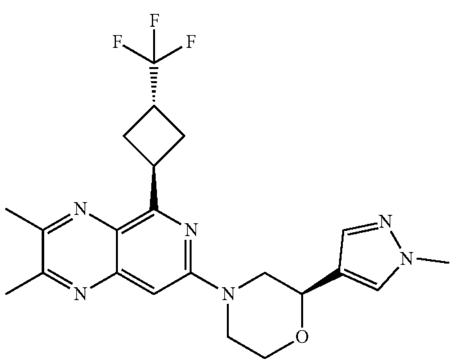 |
| I-737 | 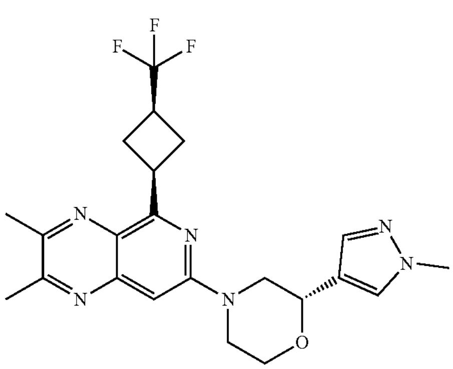 |
| I-738 | 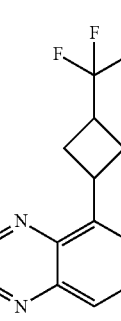 |
| I-739 | |
| I-740 | |
| I-741 | |

TABLE A-continued
Exemplary Compounds
| I-# | Structure |
|---|---|
| I-742 | 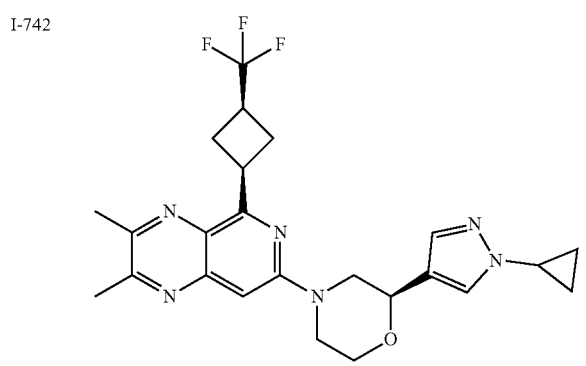 |
| I-743 | 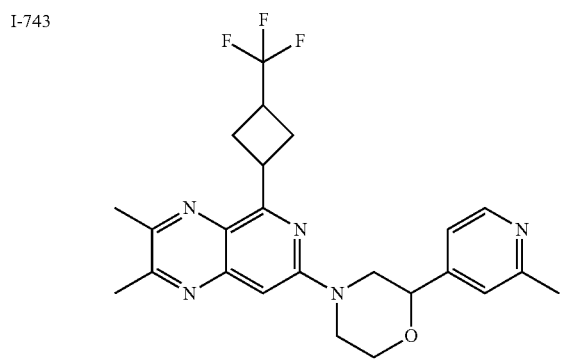 |
| I-744 | 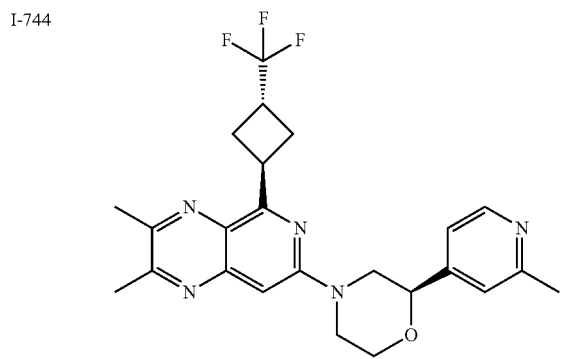 |
| I-745 | 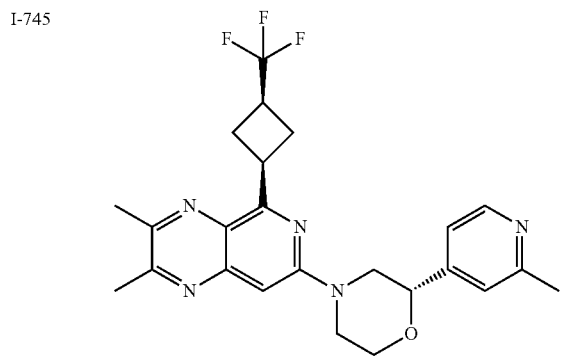 |
| I-746 | 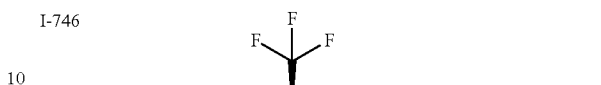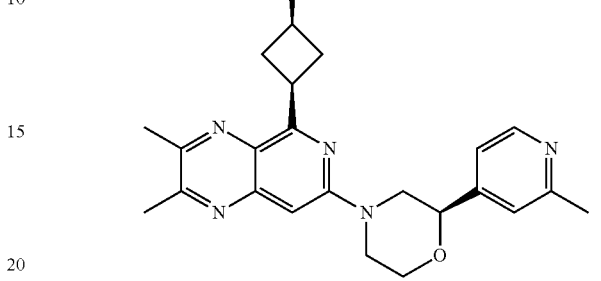 |
| I-747 | 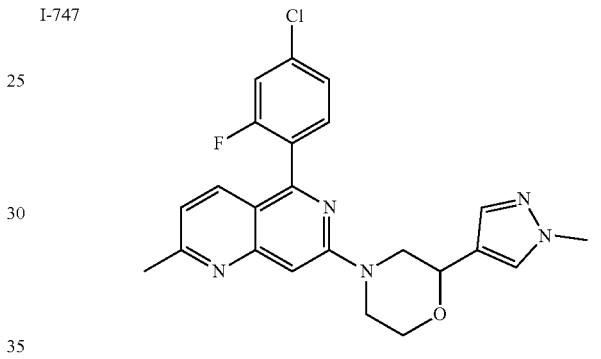 |
| I-748 | 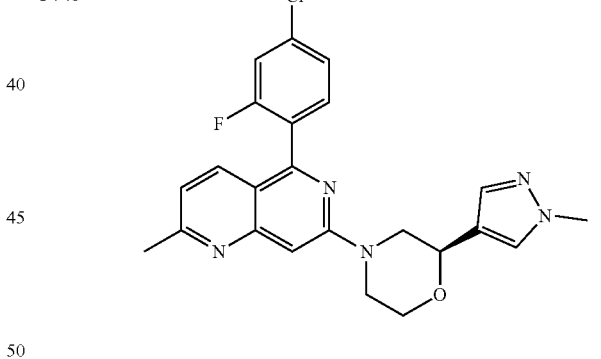 |
| I-749 | |

TABLE A-continued
Exemplary Compounds
| I-# | Structure |
|---|---|
| I-750 | 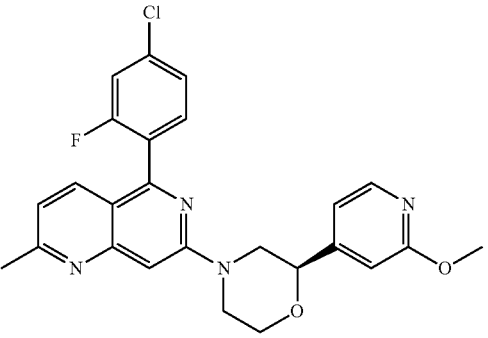 |
| I-751 | 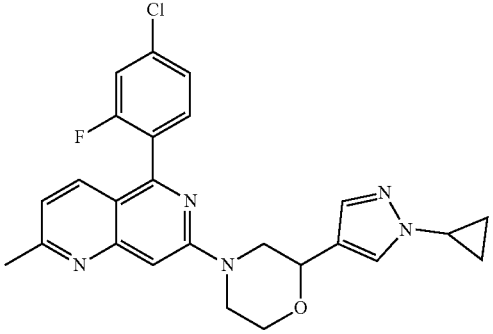 [SMILES: Cc1ccc2c(-c3ccc(Cl)cc3F)nc(N3CCOC(c4cnn(C5CC5)c4)C3)cc2n1] |
| I-752 | 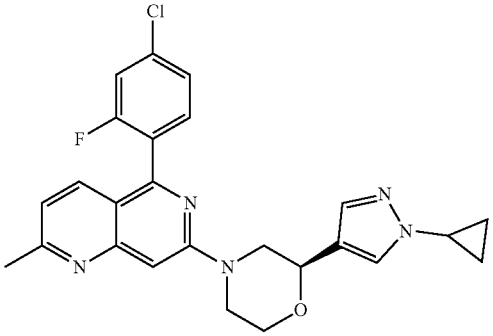 [SMILES: Cc1ccc2c(-c3ccc(Cl)cc3F)nc(N3CCO[C@H](c4cnn(C5CC5)c4)C3)cc2n1] |
| I-753 | 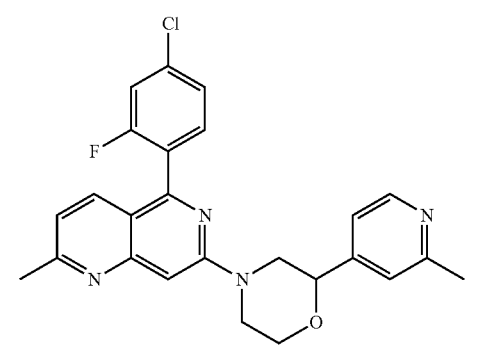 |
| I-754 | 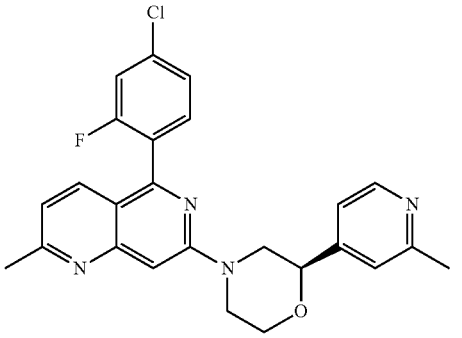 |
| I-755 | 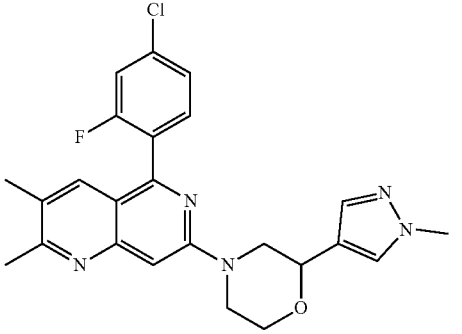 |
| I-756 | 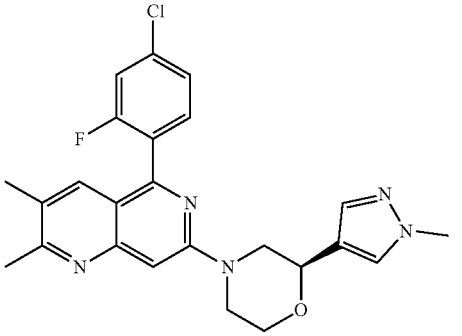 |
| I-757 | 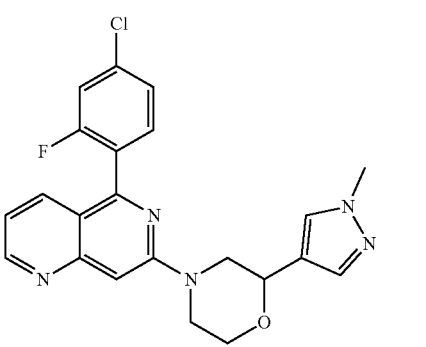 [SMILES: Cn1cc(C2CN(c3cc4ncccc4c(-c4ccc(Cl)cc4F)n3)CCO2)cn1] |

TABLE A-continued
Exemplary Compounds
| I-# | Structure |
|---|---|
| I-758 | 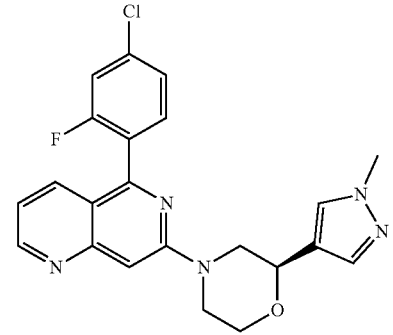 [SMILES: Cn1cc([C@@H]2CN(c3cc4ncccc4c(-c4ccc(Cl)cc4F)n3)CCO2)cn1] |
| I-759 | 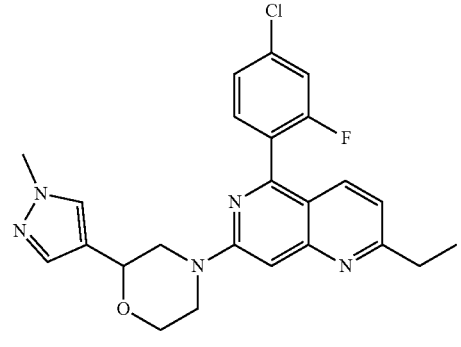 [SMILES: CCc1ccc2c(-c3ccc(Cl)cc3F)nc(N3CCOC(c4cnn(C)c4)C3)cc2n1] |
| I-760 | 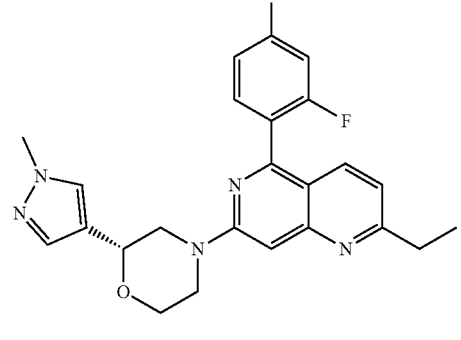 |
| I-761 | 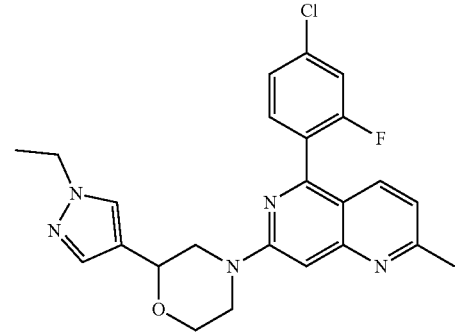 [SMILES: CCn1cc(C2CN(c3cc4nc(C)ccc4c(-c4ccc(Cl)cc4F)n3)CCO2)cn1] |
| I-762 | 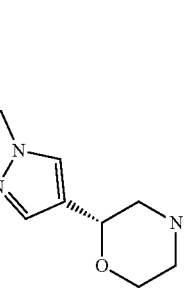 |
| I-763 | 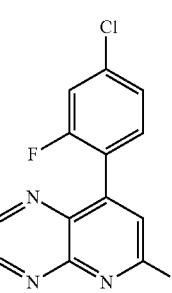 |
| I-764 | 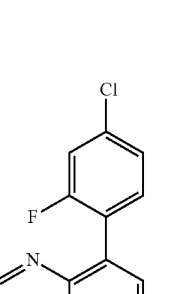 |
| I-765 |  |

TABLE A-continued

Exemplary Compounds

| I-# | Structure |
|---|---|
| I-766 | 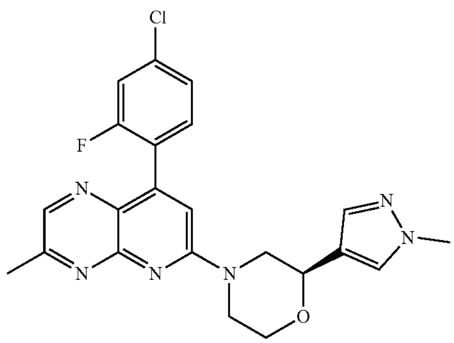 |
| I-767 | 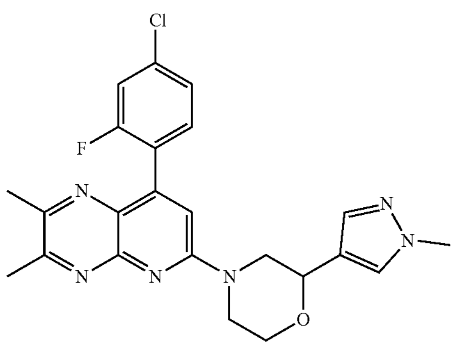 |
| I-768 | 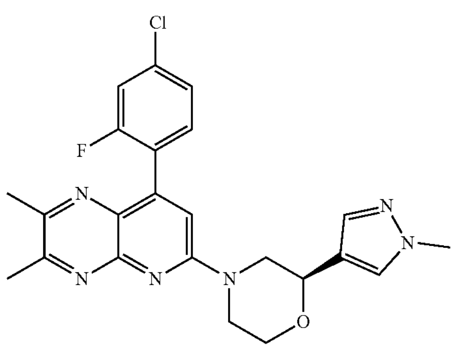 |
| I-769 | 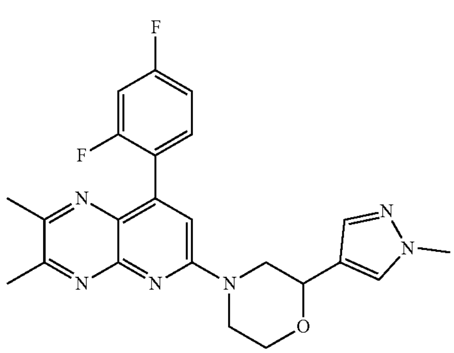 |
| I-770 | |
| I-771 | |
| I-772 | |
| I-773 | |

TABLE A-continued

Exemplary Compounds

| I-# | Structure |
|---|---|
| I-774 | 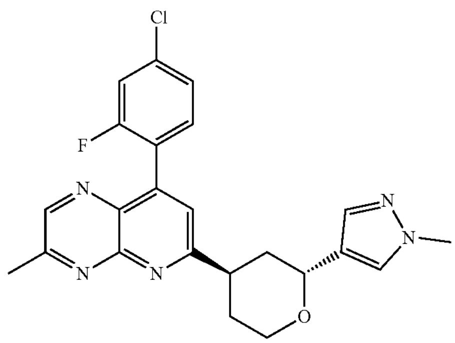 |
| I-775 | 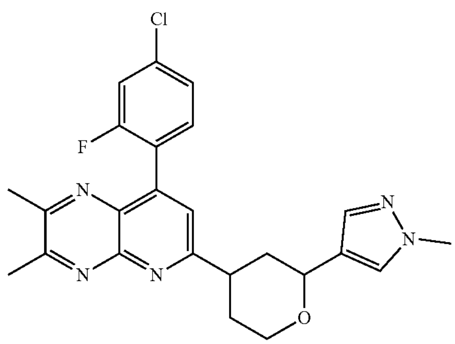 |
| I-776 | 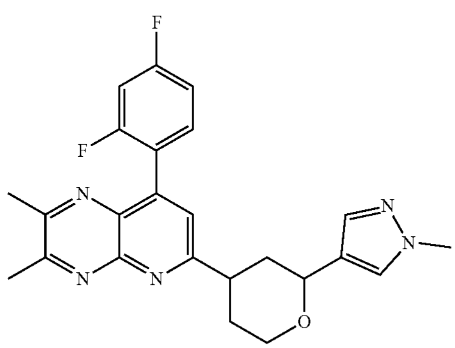 |
| I-777 | 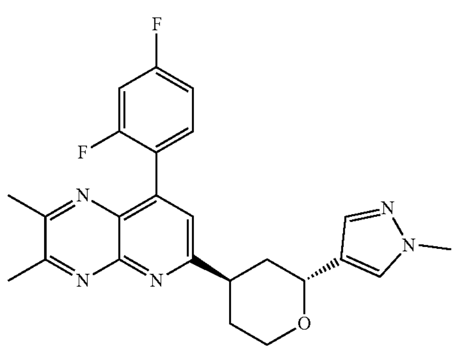 |
| I-778 | |
| I-779 | |
| I-780 | |
| I-781 | |

TABLE A-continued
Exemplary Compounds
| I-# | Structure |
|---|---|
| I-782 | 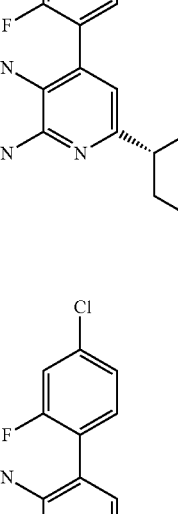 |
| I-783 | 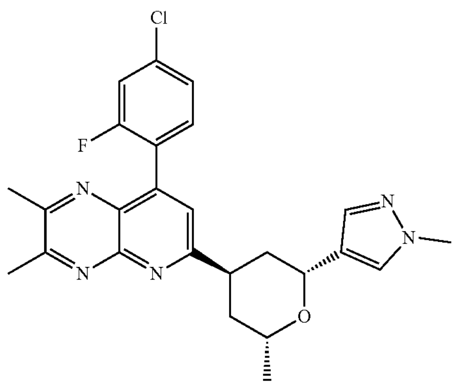 |
| I-784 | 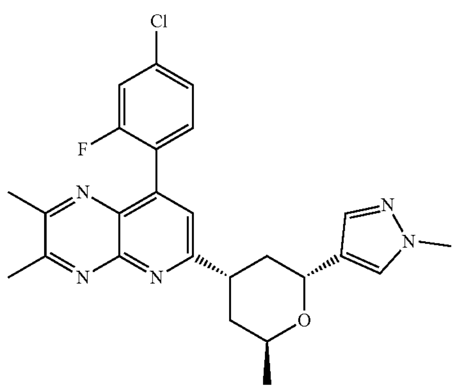 |
| I-785 | 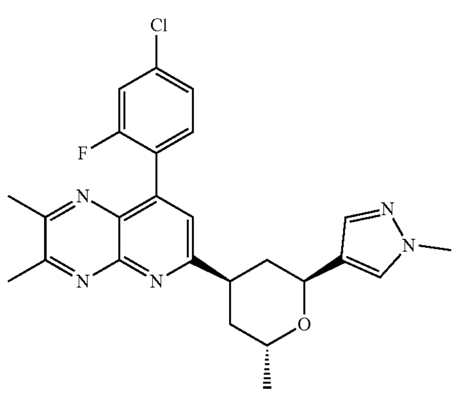 |
| I-786 | 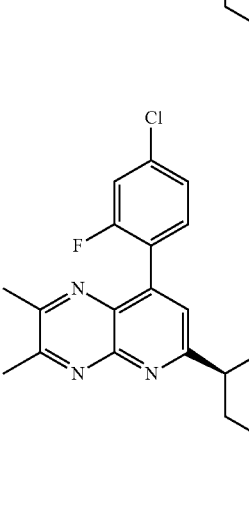 |
| I-787 | |
| I-788 | |
| I-789 | 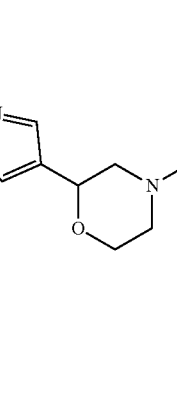 |

TABLE A-continued
Exemplary Compounds
| I-# | Structure |
|---|---|
| I-790 | 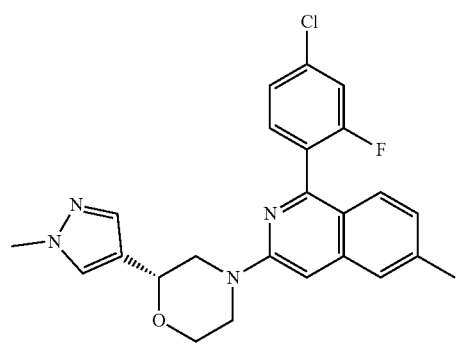 |
| I-791 | 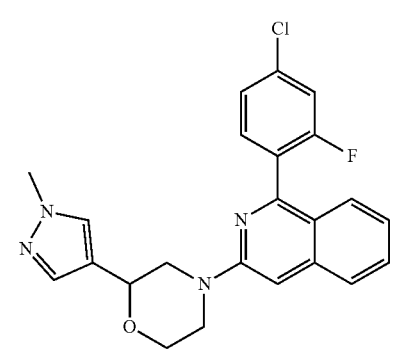 [SMILES: Cn1cc(C2CN(c3cc4ccccc4c(-c4ccc(Cl)cc4F)n3)CCO2)cn1] |
| I-792 | 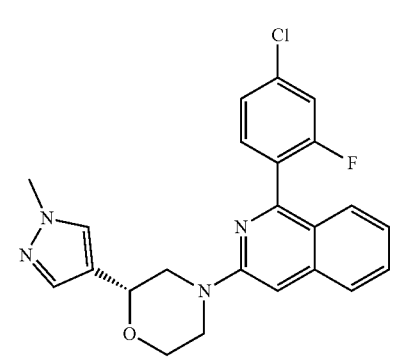 [SMILES: Cn1cc([C@@H]2CN(c3cc4ccccc4c(-c4ccc(Cl)cc4F)n3)CCO2)cn1] |
| I-793 | 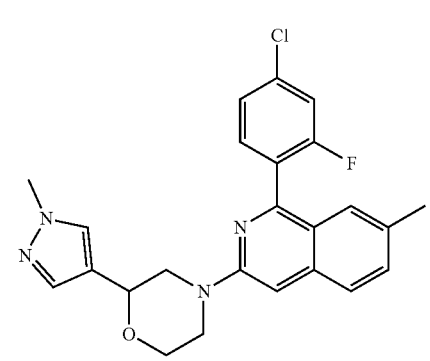 [SMILES: Cc1ccc2cc(N3CCOC(c4cnn(C)c4)C3)nc(-c3ccc(Cl)cc3F)c2c1] |
| I-794 | 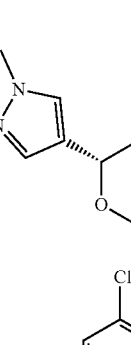 |
| I-795 | 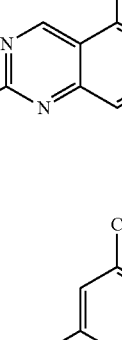 |
| I-796 |  |
| I-797 |  |

TABLE A-continued
Exemplary Compounds
| I-# | Structure |
|---|---|
| I-798 | 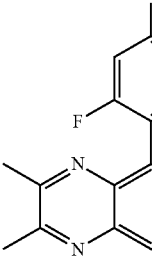 |
| I-799 | 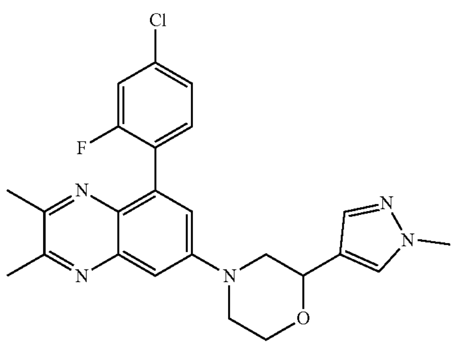 |
| I-800 | 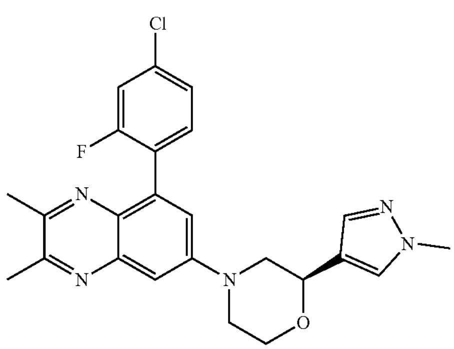 |
| I-801 | 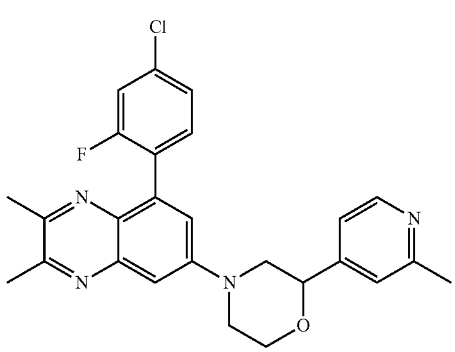 |
| I-802 | 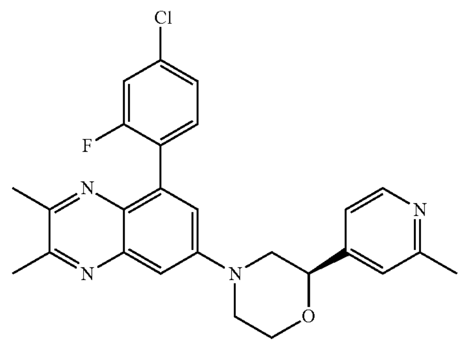 |
| I-803 | 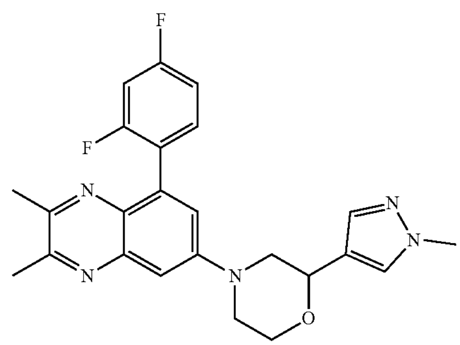 |
| I-804 | 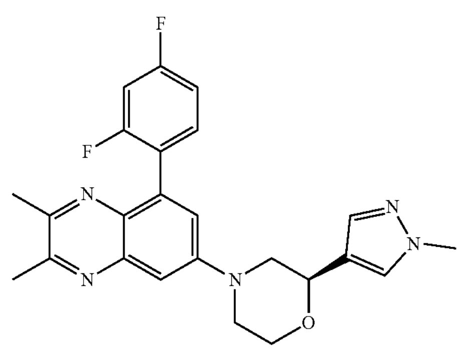 |
| I-805 | 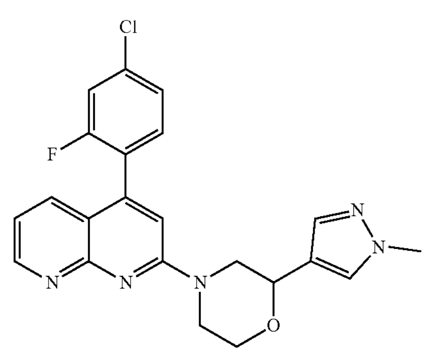 [SMILES: Cn1cc(C2CN(c3cc(-c4ccc(Cl)cc4F)c4cccnc4n3)CCO2)cn1] |

TABLE A-continued
Exemplary Compounds
| I-# | Structure |
|---|---|
| I-806 | 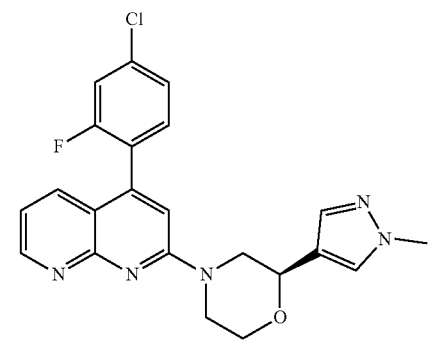 [SMILES: Cn1cc([C@@H]2CN(c3cc(-c4ccc(Cl)cc4F)c4cccnc4n3)CCO2)cn1] |
| I-807 | 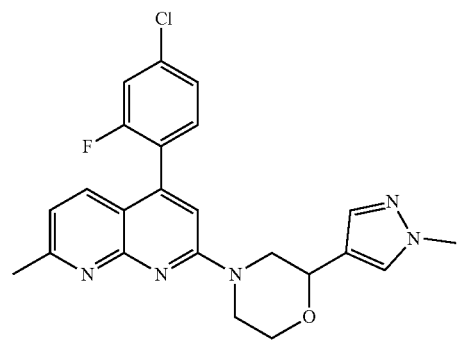 |
| I-808 | 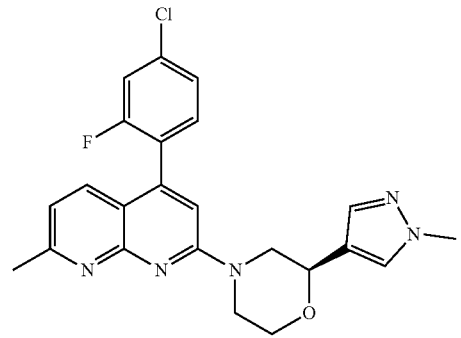 |
| I-809 | 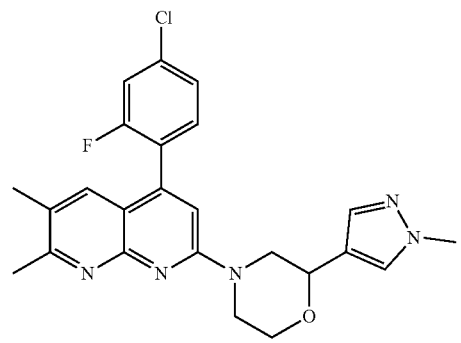 |
| I-810 | 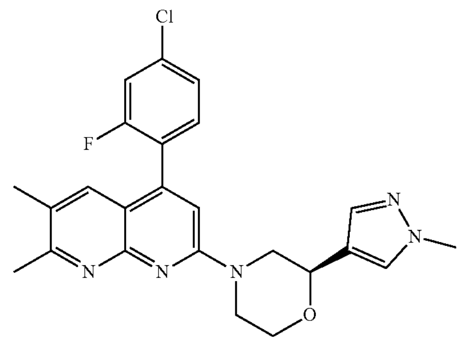 |
| I-811 | 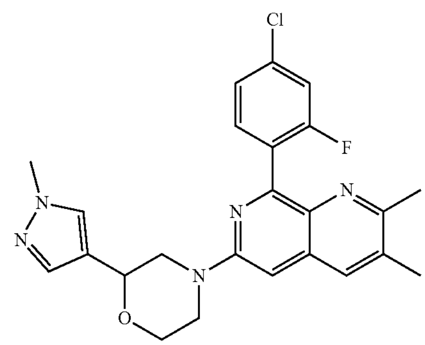 [SMILES: Cc1cc2cc(N3CCOC(c4cnn(C)c4)C3)nc(-c3ccc(Cl)cc3F)c2nc1C] |
| I-812 | 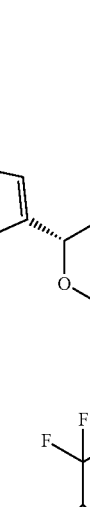 |
| I-813 | 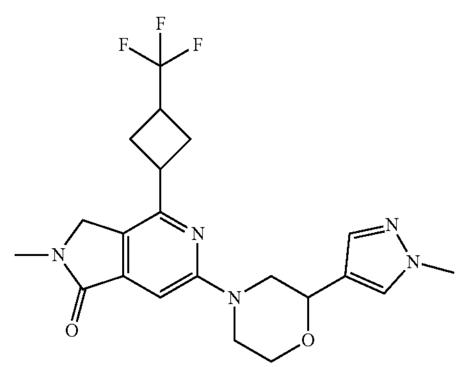 |

TABLE A-continued
Exemplary Compounds
| I-# | Structure |
|---|---|
| I-814 | 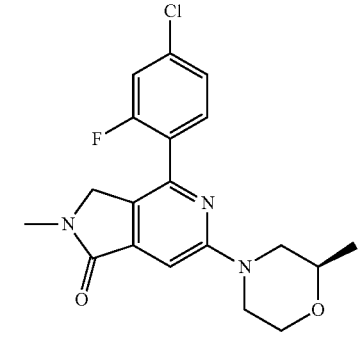 |
| I-815 | 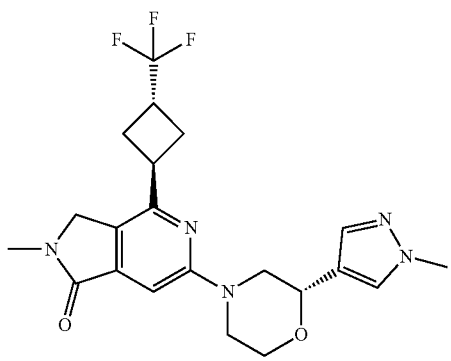 |
| I-816 | 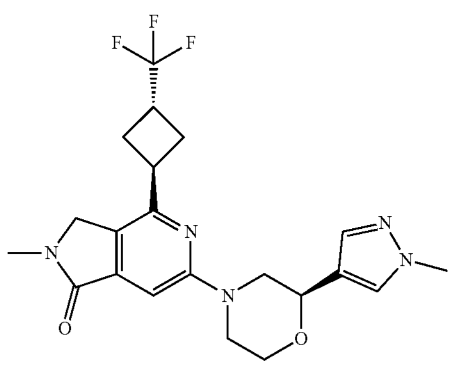 |
| I-817 | 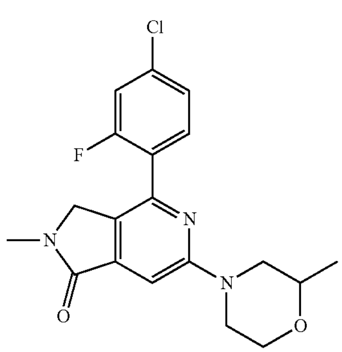 |
| I-818 | 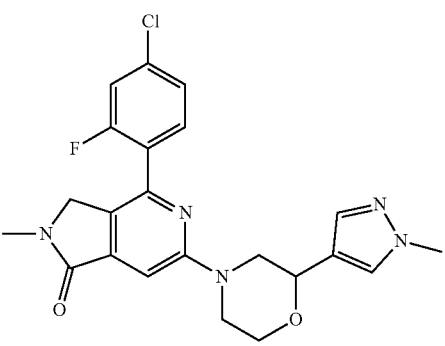 |
| I-819 | |
| I-820 | |
| I-821 | |

TABLE A-continued
Exemplary Compounds
| I-# | Structure |
|---|---|
| I-822 | 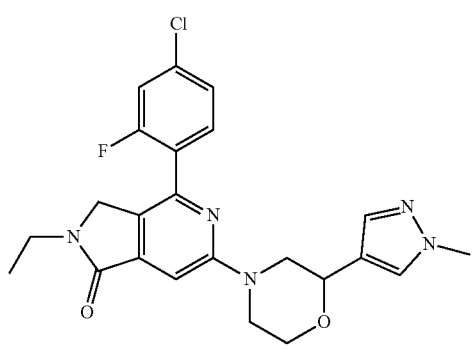 [SMILES: CCN1Cc2c(cc(N3CCOC(c4cnn(C)c4)C3)nc2-c2ccc(Cl)cc2F)C1=O] |
| I-823 | 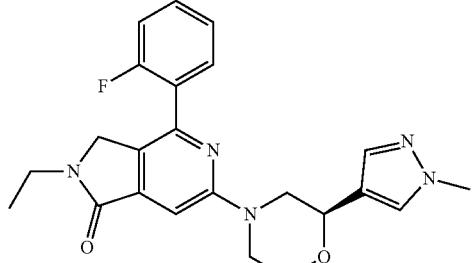 |
| I-824 | 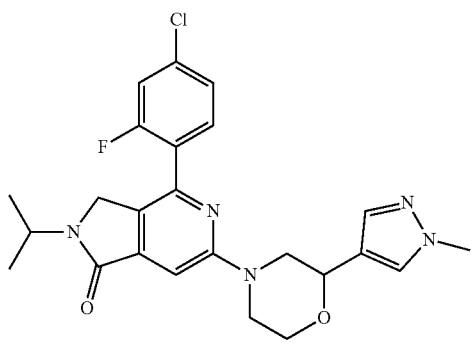 [SMILES: CC(C)N1Cc2c(cc(N3CCOC(c4cnn(C)c4)C3)nc2-c2ccc(Cl)cc2F)C1=O] |
| I-825 | 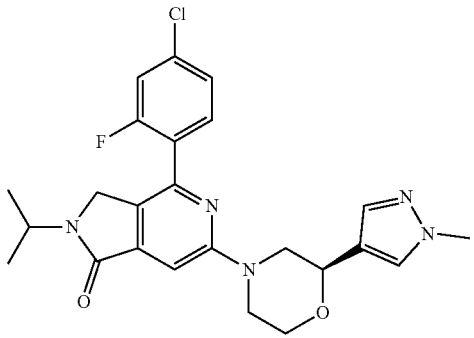 [SMILES: CC(C)N1Cc2c(cc(N3CCO[C@H](c4cnn(C)c4)C3)nc2-c2ccc(Cl)cc2F)C1=O] |
| I-826 | 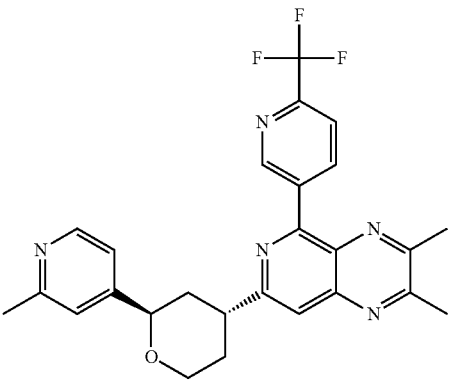 |
| I-827 | 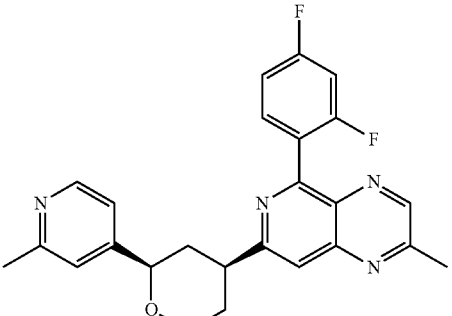 |
| I-828 | 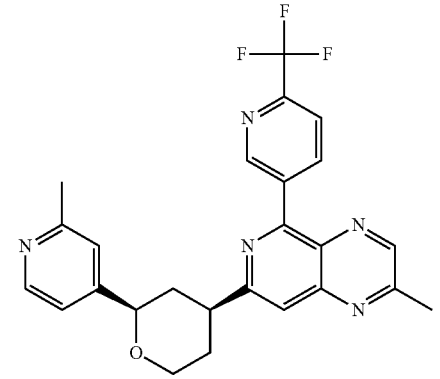 [SMILES: Cc1cc([C@H]2C[C@@H](c3cc4nc(C)cnc4c(-c4ccc(C(F)(F)F)nc4)n3)CCO2)ccn1] |
| I-829 | 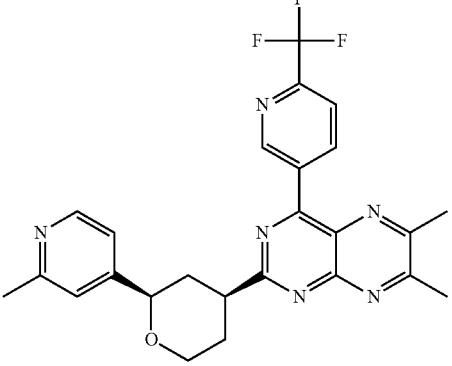 |

TABLE A-continued

Exemplary Compounds

| I-# | Structure |
|---|---|
| I-830 | 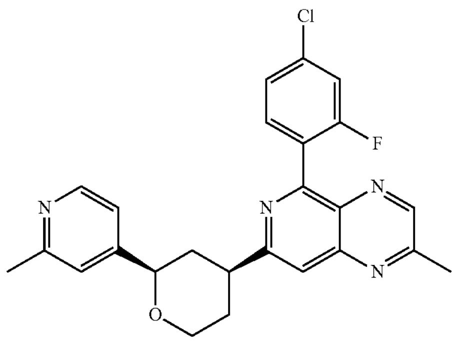 |
| I-831 | 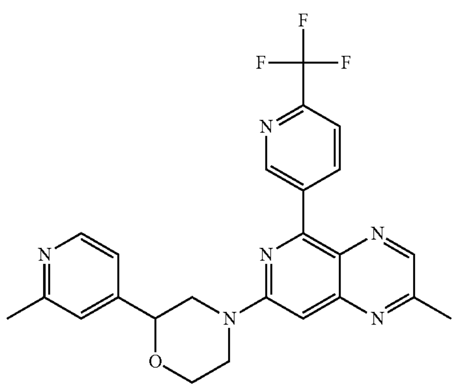 |
| I-832 | 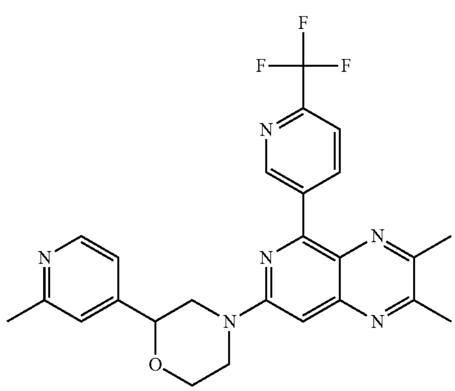 |
| I-833 | 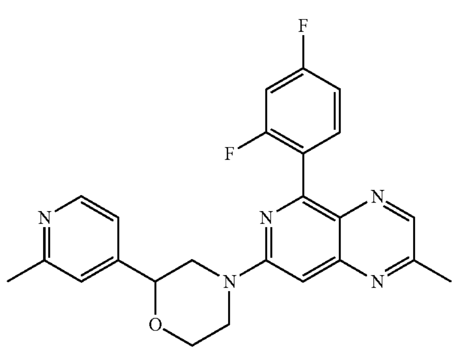 |
| I-834 | |
| I-835 | |
| I-836 | |
| I-837 | |

TABLE A-continued
Exemplary Compounds
| I-# | Structure |
|---|---|
| I-838 | 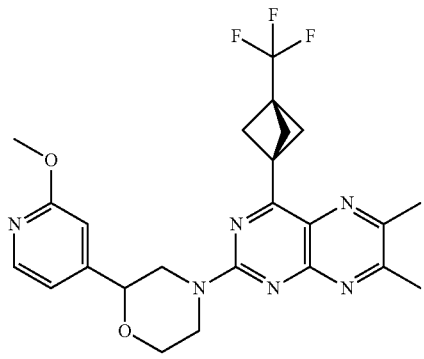 [SMILES: COc1cc(C2CN(c3nc4nc(C)c(C)nc4c([C@]45C[C@](C(F)(F)F)(C4)C5)n3)CCO2)ccn1] |
| I-839 | 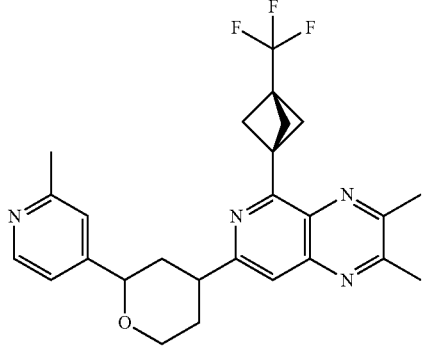 [SMILES: Cc1cc(C2CC(c3cc4nc(C)c(C)nc4c([C@]45C[C@](C(F)(F)F)(C4)C5)n3)CCO2)ccn1] |
| I-840 | 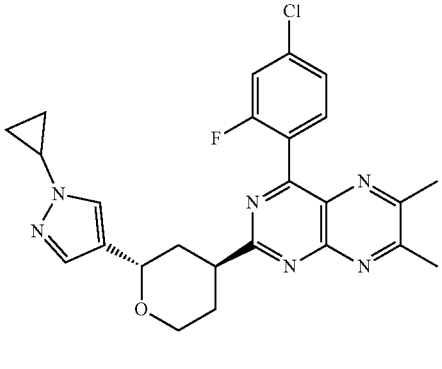 [SMILES: Cc1nc2nc([C@H]3CCO[C@H](c4cnn(C5CC5)c4)C3)nc(-c3ccc(Cl)cc3F)c2nc1C] |
| I-841 | 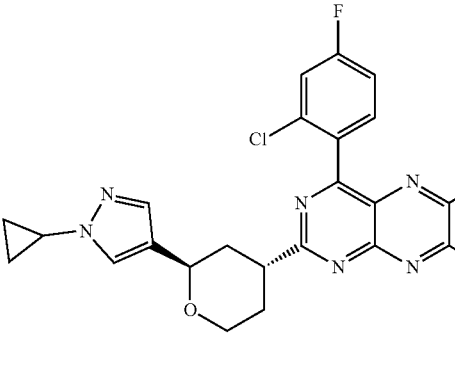 |
| I-842 | 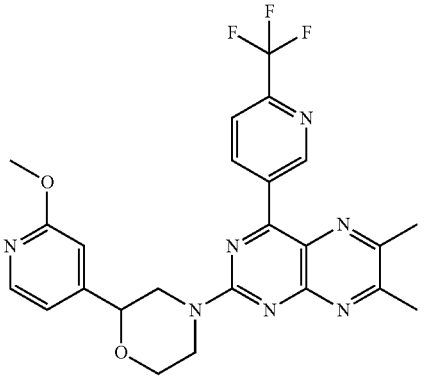 [SMILES: COc1cc(C2CN(c3nc(-c4ccc(C(F)(F)F)nc4)c4nc(C)c(C)nc4n3)CCO2)ccn1] |
| I-843 | 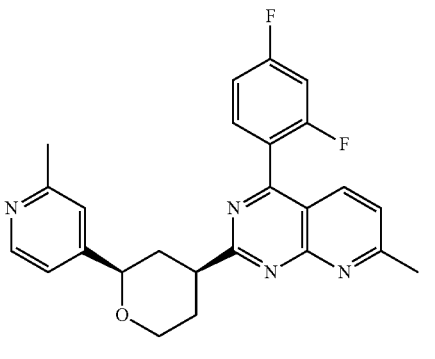 [SMILES: Cc1cc([C@H]2C[C@@H](c3nc(-c4ccc(F)cc4F)c4ccc(C)nc4n3)CCO2)ccn1] |
| I-844 | 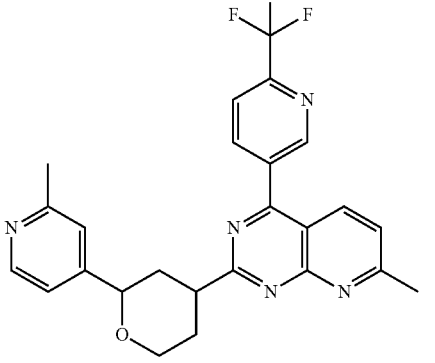 |
| I-845 | 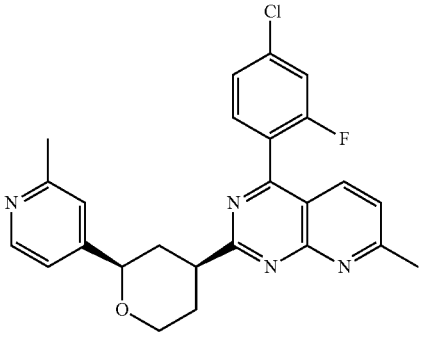 |

TABLE A-continued
Exemplary Compounds
| I-# | Structure |
|---|---|
| I-846 | 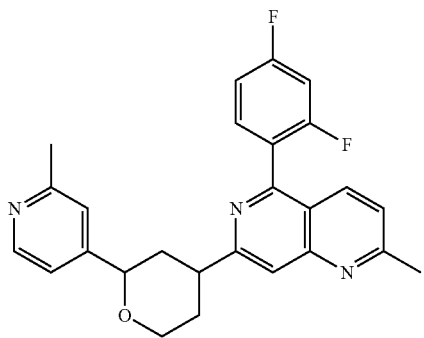 [SMILES: Cc1cc(C2CC(c3cc4nc(C)ccc4c(-c4ccc(F)cc4F)n3)CCO2)ccn1] |
| I-847 | 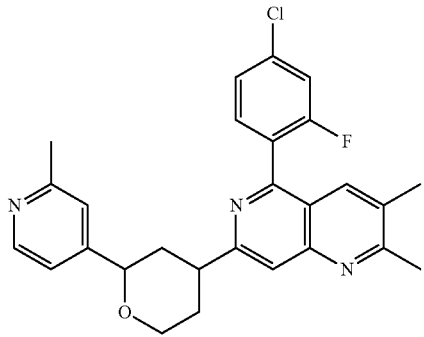 [SMILES: Cc1cc(C2CC(c3cc4nc(C)c(C)cc4c(-c4ccc(Cl)cc4F)n3)CCO2)ccn1] |
| I-848 | 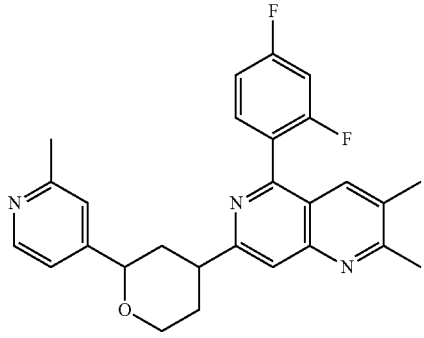 [SMILES: Cc1cc(C2CC(c3cc4nc(C)c(C)cc4c(-c4ccc(F)cc4F)n3)CCO2)ccn1] |
| I-849 | 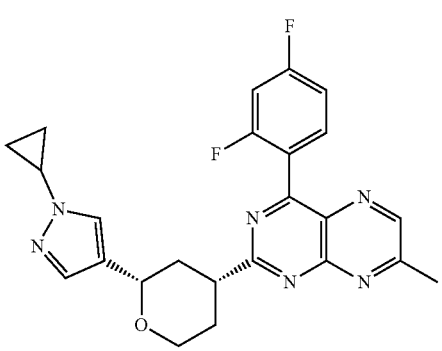 [SMILES: Cc1cnc2c(-c3ccc(F)cc3F)nc([C@@H]3CCO[C@H](c4cnn(C5CC5)c4)C3)nc2n1] |
| I-850 | 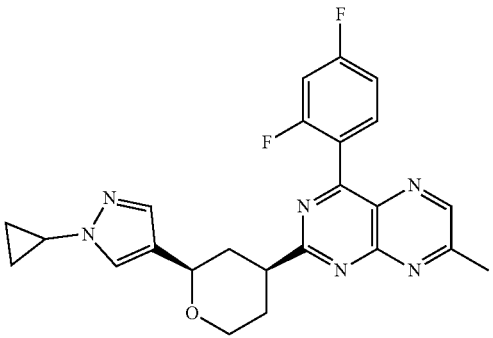 [SMILES: Cc1cnc2c(-c3ccc(F)cc3F)nc([C@H]3CCO[C@@H](c4cnn(C5CC5)c4)C3)nc2n1] |
| I-851 | 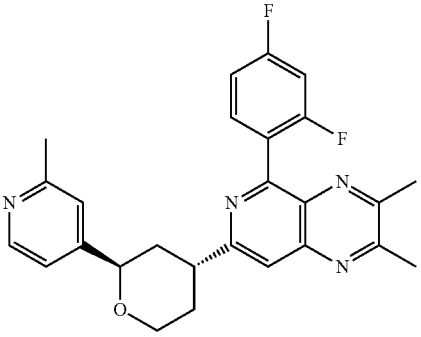 |
| I-852 | 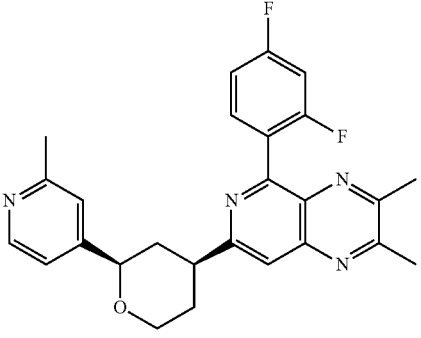 |
| I-853 | 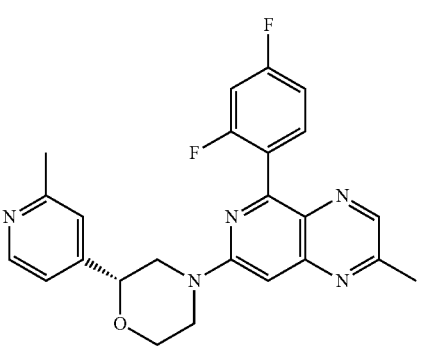 [SMILES: Cc1cc([C@@H]2CN(c3cc4nc(C)cnc4c(-c4ccc(F)cc4F)n3)CCO2)ccn1] |

TABLE A-continued
Exemplary Compounds
| I-# | Structure |
|---|---|
| I-854 | 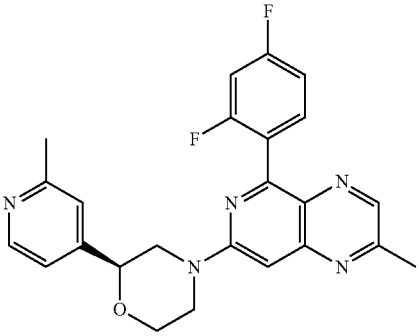 [SMILES: Cc1cc([C@H]2CN(c3cc4nc(C)cnc4c(-c4ccc(F)cc4F)n3)CCO2)ccn1] |
| I-855 | 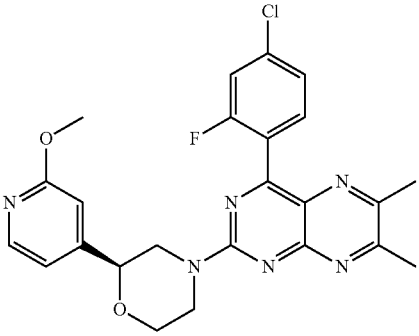 [SMILES: COc1cc([C@H]2CN(c3nc(-c4ccc(Cl)cc4F)c4nc(C)c(C)nc4n3)CCO2)ccn1] |
| I-856 | 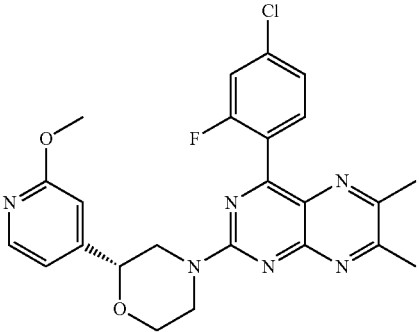 [SMILES: COc1cc([C@@H]2CN(c3nc(-c4ccc(Cl)cc4F)c4nc(C)c(C)nc4n3)CCO2)ccn1] |
| I-857 | 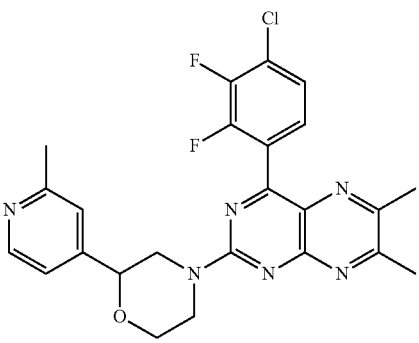 |
| I-858 | 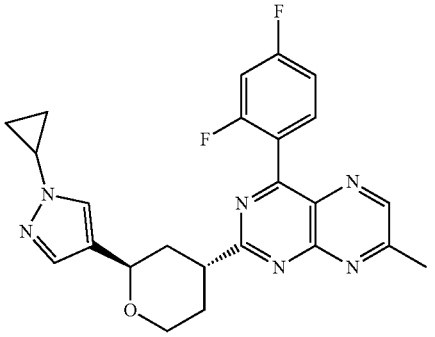 [SMILES: Cc1cnc2c(-c3ccc(F)cc3F)nc([C@@H]3CCO[C@@H](c4cnn(C5CC5)c4)C3)nc2n1] |
| I-859 | 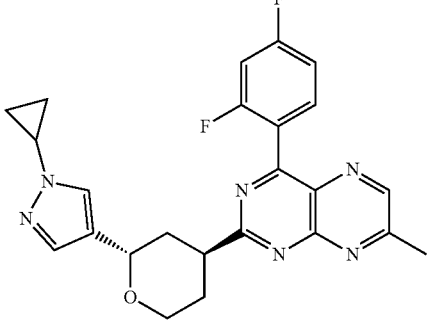 |
| I-860 | 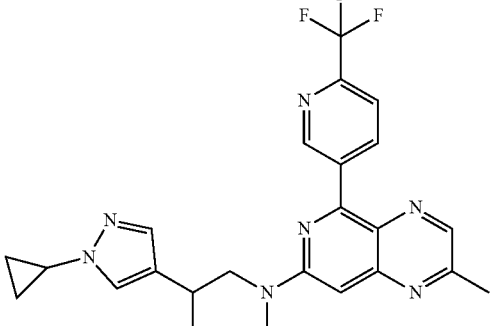 |
| I-861 | 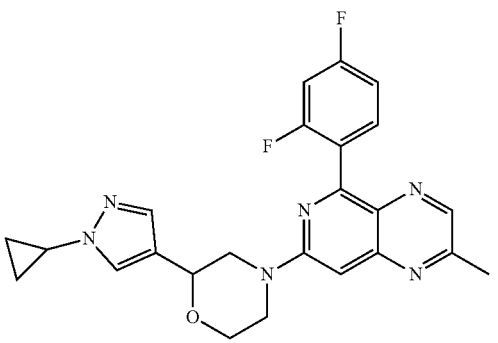 [SMILES: Cc1cnc2c(-c3ccc(F)cc3F)nc(N3CCOC(c4cnn(C5CC5)c4)C3)cc2n1] |

TABLE A-continued
Exemplary Compounds
| I-# | Structure |
|---|---|
| I-862 | 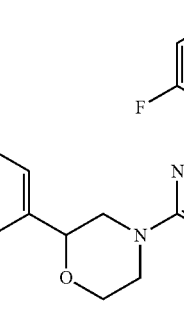 |
| I-863 | 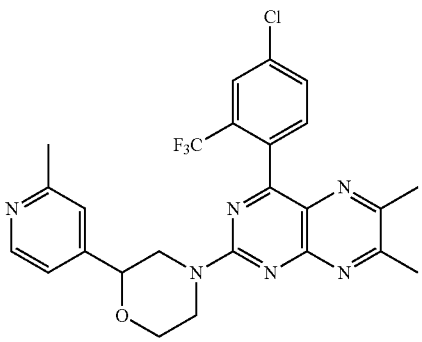 [SMILES: Cc1cc(C2CN(c3nc(-c4ccc(Cl)cc4C(F)(F)F)c4nc(C)c(C)nc4n3)CCO2)ccn1] |
| I-864 | 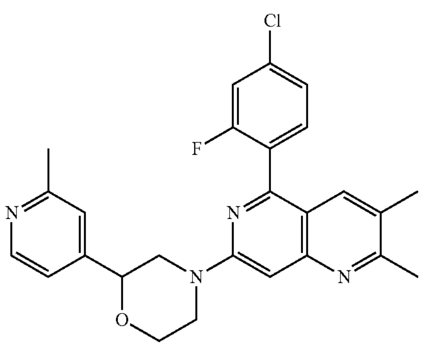 |
| I-865 | 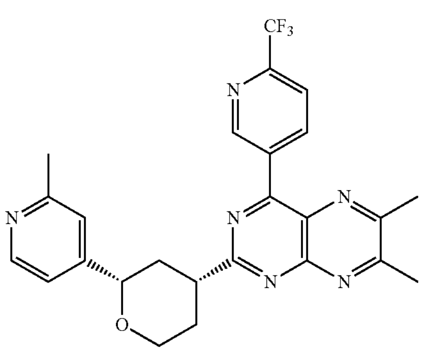 [SMILES: Cc1cc([C@@H]2C[C@H](c3nc(-c4ccc(C(F)(F)F)nc4)c4nc(C)c(C)nc4n3)CCO2)ccn1] |
TABLE A-continued
Exemplary Compounds
| I-# | Structure |
|---|---|
| I-866 | 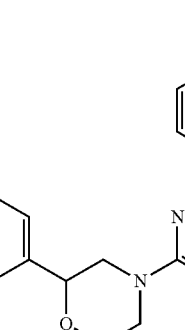 |
| I-867 | 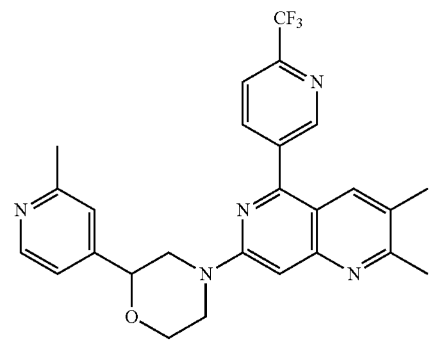 [SMILES: Cc1cc(C2CN(c3cc4nc(C)c(C)cc4c(-c4ccc(C(F)(F)F)nc4)n3)CCO2)ccn1] |
| I-868 | 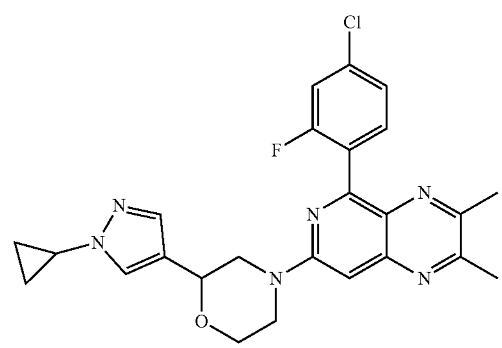 [SMILES: Cc1nc2cc(N3CCOC(c4cnn(C5CC5)c4)C3)nc(-c3ccc(Cl)cc3F)c2nc1C] |
| I-869 | 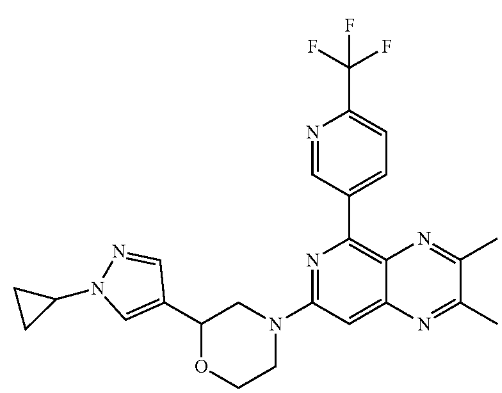 [SMILES: Cc1nc2cc(N3CCOC(c4cnn(C5CC5)c4)C3)nc(-c3ccc(C(F)(F)F)nc3)c2nc1C] |

TABLE A-continued
Exemplary Compounds
| I-# | Structure |
|---|---|
| I-870 | 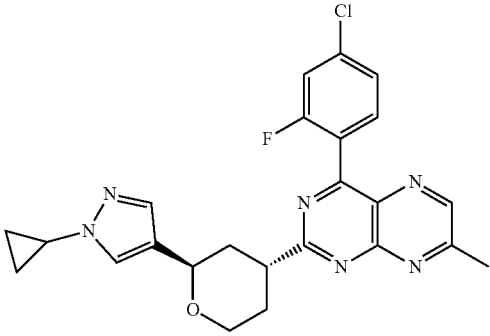 [SMILES: Cc1cnc2c(-c3ccc(Cl)cc3F)nc([C@@H]3CCO[C@@H](c4cnn(C5CC5)c4)C3)nc2n1] |
| I-871 | 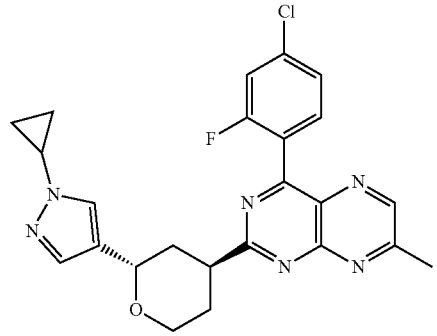 |
| I-872 | 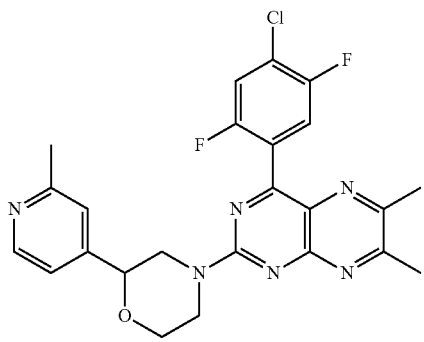 |
| I-873 | 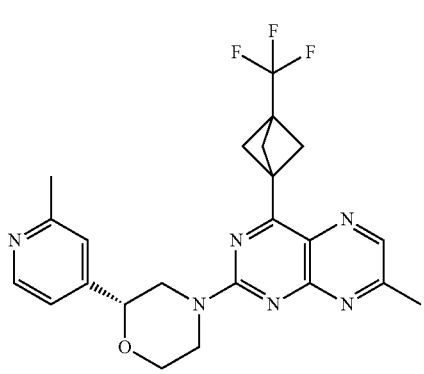 [SMILES: Cc1cc([C@@H]2CN(c3nc(C45CC(C(F)(F)F)(C4)C5)c4ncc(C)nc4n3)CCO2)ccn1] |
| I-874 | 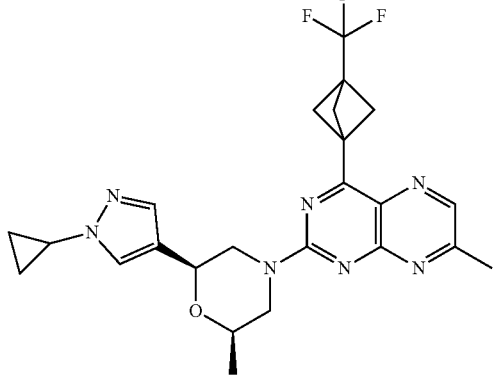 |
| I-875 | 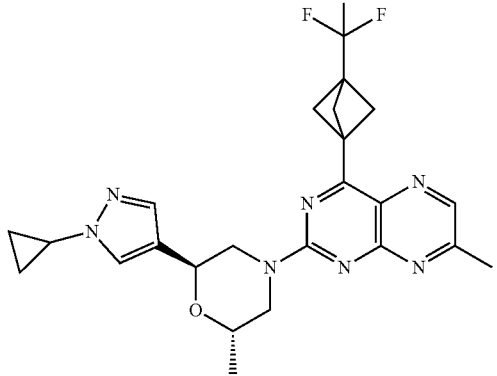 |
| I-876 | 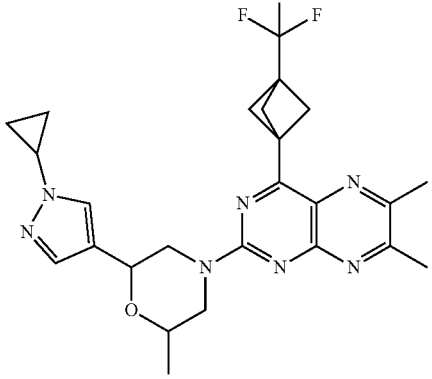 |
| I-877 | 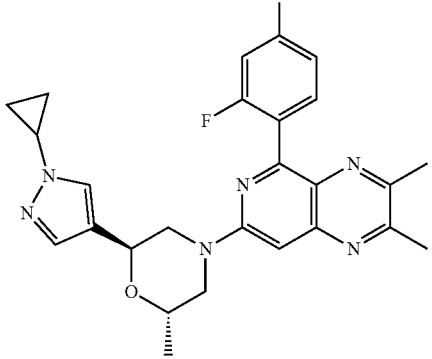 |

TABLE A-continued
Exemplary Compounds
| I-# | Structure |
|---|---|
| I-878 | 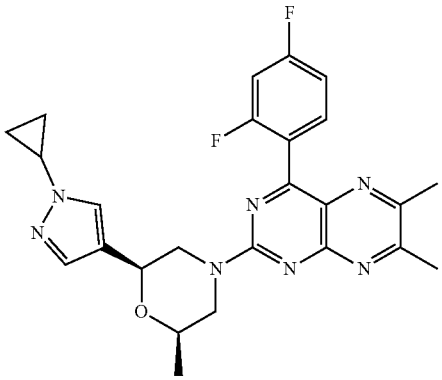 [SMILES: Cc1nc2nc(N3C[C@@H](C)O[C@@H](c4cnn(C5CC5)c4)C3)nc(-c3ccc(F)cc3F)c2nc1C] |
| I-879 | 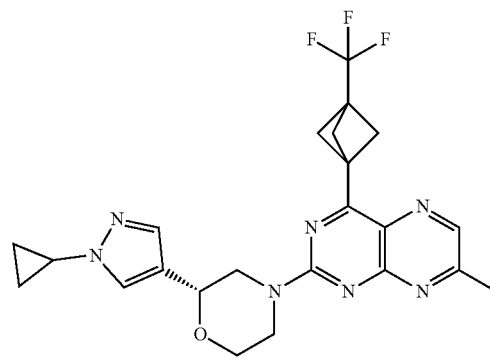 |
| I-880 | 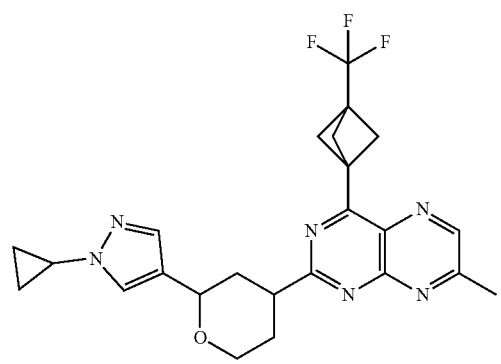 [SMILES: Cc1cnc2c(C34CC(C(F)(F)F)(C3)C4)nc(C3CCOC(c4cnn(C5CC5)c4)C3)nc2n1] |
| I-881 | 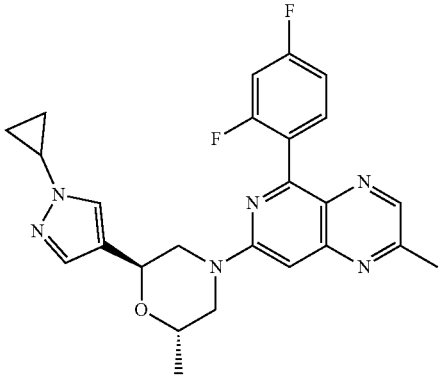 [SMILES: Cc1cnc2c(-c3ccc(F)cc3F)nc(N3C[C@H](C)O[C@@H](c4cnn(C5CC5)c4)C3)cc2n1] |
| I-882 | 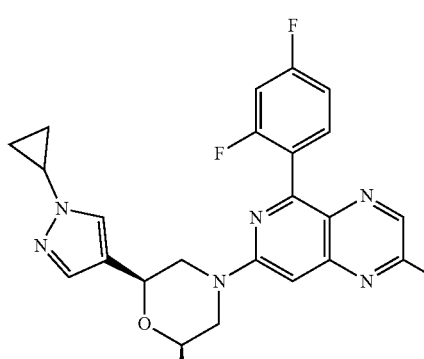 |
| I-883 | 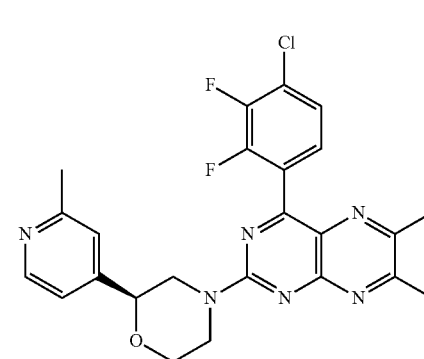 |
| I-884 | 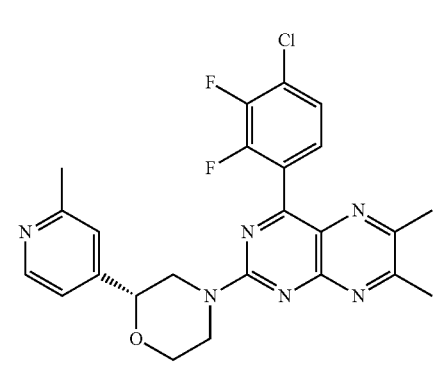 [SMILES: Cc1cc([C@@H]2CN(c3nc(-c4ccc(Cl)c(F)c4F)c4nc(C)c(C)nc4n3)CCO2)ccn1] |
| I-885 | 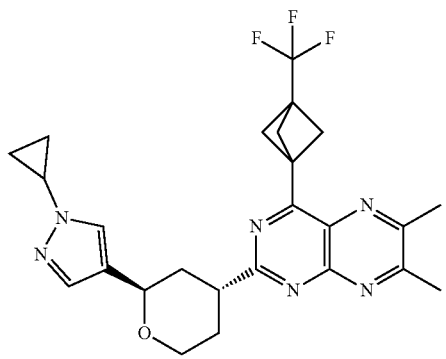 [SMILES: Cc1nc2nc([C@@H]3CCO[C@@H](c4cnn(C5CC5)c4)C3)nc(C34CC(C(F)(F)F)(C3)C4)c2nc1C] |

TABLE A-continued

Exemplary Compounds

| I-# | Structure |
|---|---|
| I-886 | 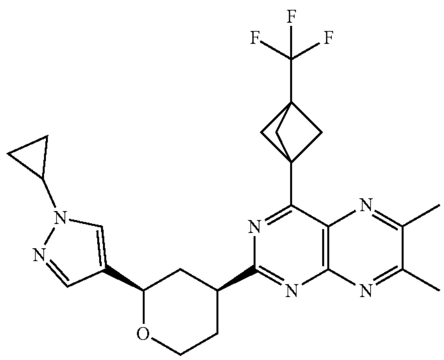 [SMILES: Cc1nc2nc([C@H]3CCO[C@@H](c4cnn(C5CC5)c4)C3)nc(C34CC(C(F)(F)F)(C3)C4)c2nc1C] |
| I-887 | 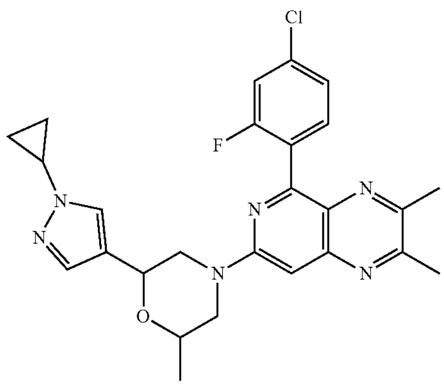 |
| I-888 | 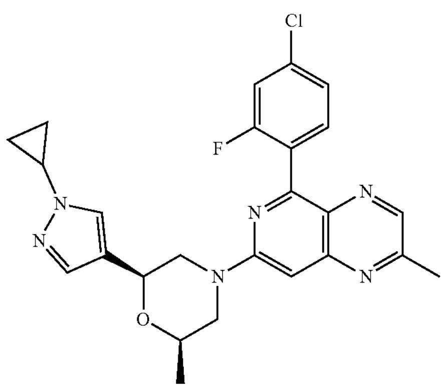 |
| I-889 | 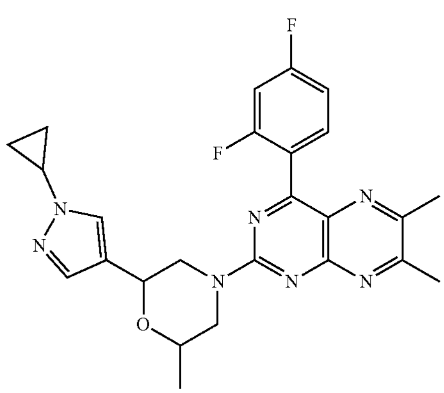 [SMILES: Cc1nc2nc(N3CC(C)OC(c4cnn(C5CC5)c4)C3)nc(-c3ccc(F)cc3F)c2nc1C] |
| I-890 | 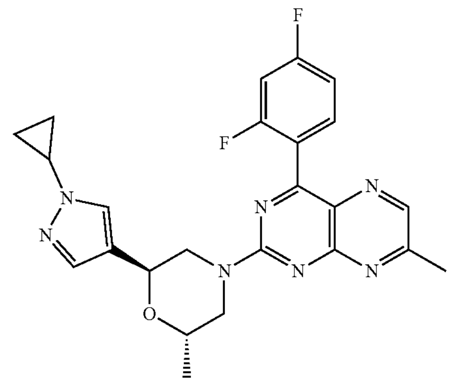 [SMILES: Cc1cnc2c(-c3ccc(F)cc3F)nc(N3C[C@H](C)O[C@@H](c4cnn(C5CC5)c4)C3)nc2n1] |
| I-891 | 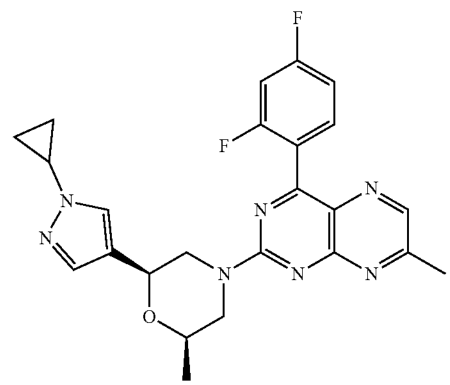 [SMILES: Cc1cnc2c(-c3ccc(F)cc3F)nc(N3C[C@@H](C)O[C@@H](c4cnn(C5CC5)c4)C3)nc2n1] |
| I-892 | 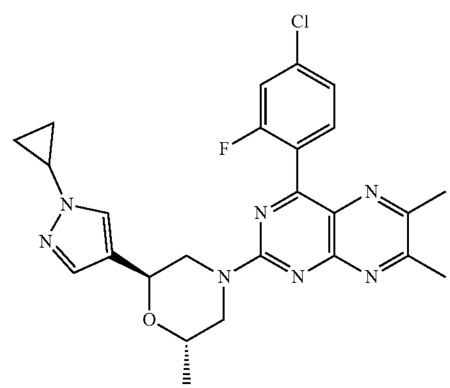 [SMILES: Cc1nc2nc(N3C[C@H](C)O[C@@H](c4cnn(C5CC5)c4)C3)nc(-c3ccc(Cl)cc3F)c2nc1C] |
| I-893 | 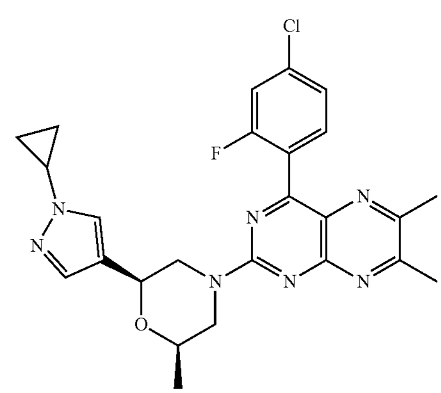 [SMILES: Cc1nc2nc(N3C[C@@H](C)O[C@@H](c4cnn(C5CC5)c4)C3)nc(-c3ccc(Cl)cc3F)c2nc1C] |

TABLE A-continued
Exemplary Compounds
| I-# | Structure |
|---|---|
| I-894 | 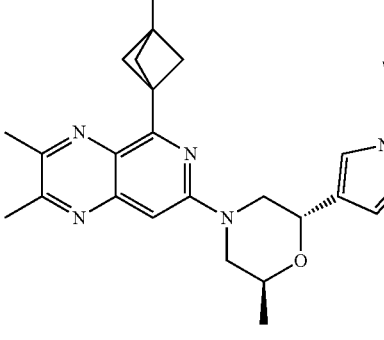 |
| I-895 | 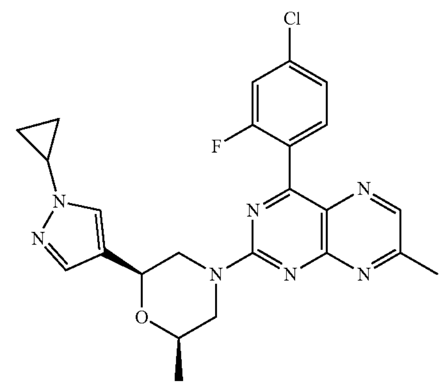 [SMILES: Cc1cnc2c(-c3ccc(Cl)cc3F)nc(N3C[C@@H](C)O[C@@H](c4cnn(C5CC5)c4)C3)nc2n1] |
| I-896 | 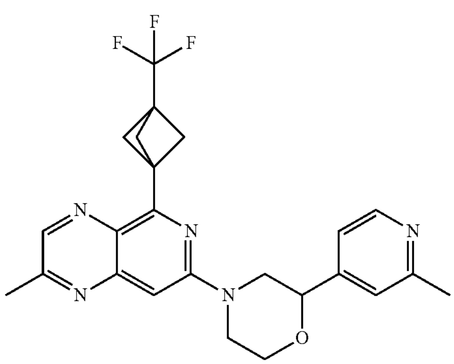 |
| I-897 | 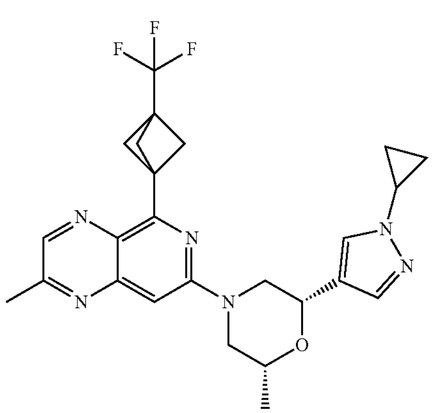 [SMILES: Cc1cnc2c(C34CC(C(F)(F)F)(C3)C4)nc(N3C[C@@H](C)O[C@@H](c4cnn(C5CC5)c4)C3)cc2n1] |
| I-898 | 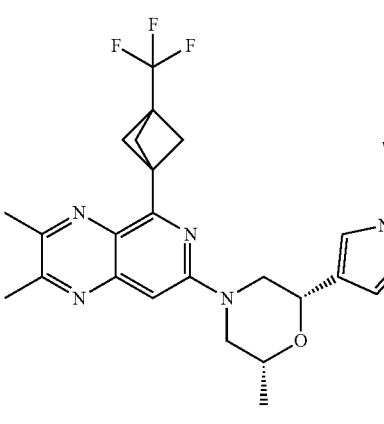 |
| I-899 | |
| I-900 | |
| I-901 | |

TABLE A-continued

Exemplary Compounds

| I-# | Structure |
|---|---|
| I-902 | 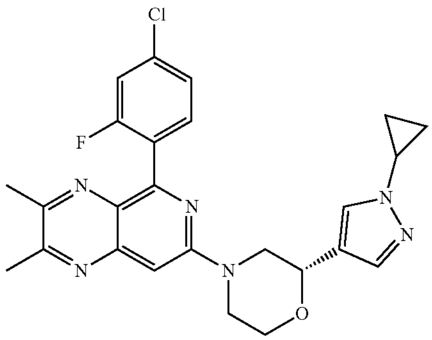 [SMILES: Cc1nc2cc(N3CCO[C@@H](c4cnn(C5CC5)c4)C3)nc(-c3ccc(Cl)cc3F)c2nc1C] |
| I-903 | 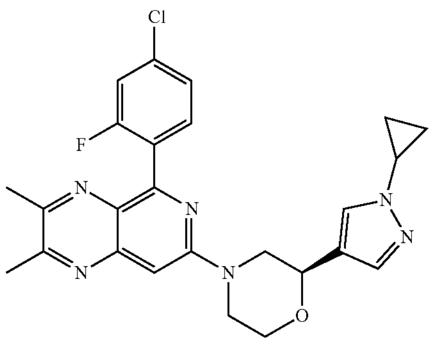 [SMILES: Cc1nc2cc(N3CCO[C@H](c4cnn(C5CC5)c4)C3)nc(-c3ccc(Cl)cc3F)c2nc1C] |
| I-904 | 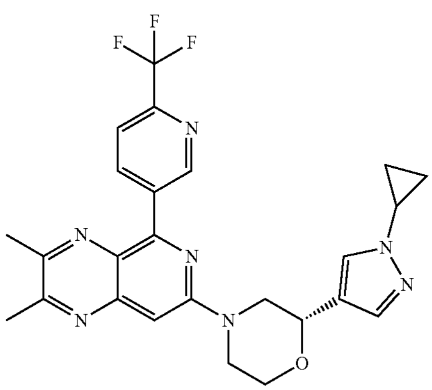 [SMILES: Cc1nc2cc(N3CCO[C@@H](c4cnn(C5CC5)c4)C3)nc(-c3ccc(C(F)(F)F)nc3)c2nc1C] |
| I-905 | 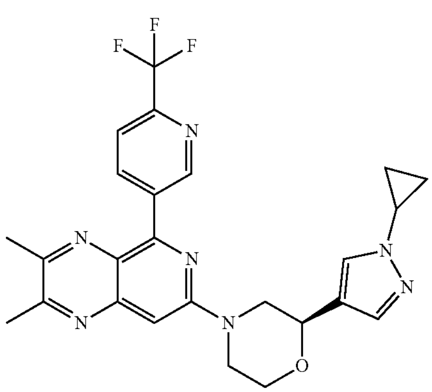 [SMILES: Cc1nc2cc(N3CCO[C@H](c4cnn(C5CC5)c4)C3)nc(-c3ccc(C(F)(F)F)nc3)c2nc1C] |
| I-906 | |
| I-907 | |
| I-908 | |
| I-909 | |

TABLE A-continued
Exemplary Compounds
| I-# | Structure |
|---|---|
| I-910 | 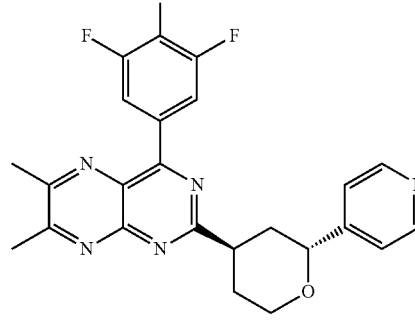 |
| I-911 | 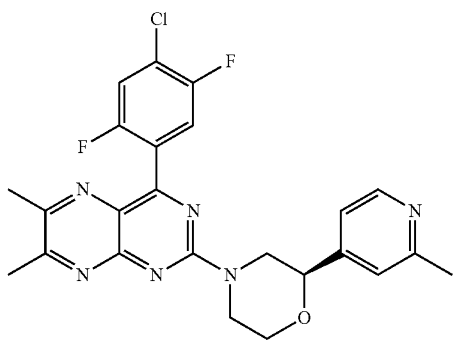 |
| I-912 | 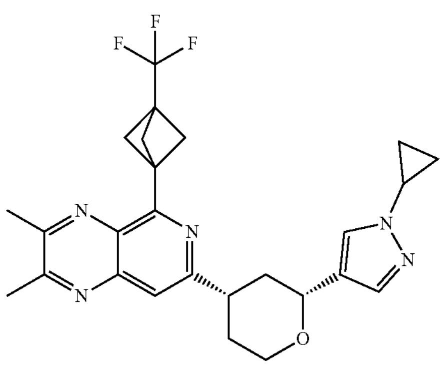 [SMILES: Cc1nc2cc([C@H]3CCO[C@@H](c4cnn(C5CC5)c4)C3)nc(C34CC(C(F)(F)F)(C3)C4)c2nc1C] |
| I-913 | 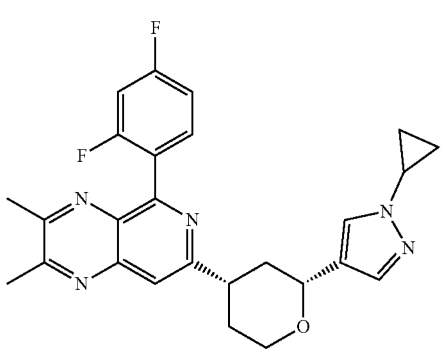 [SMILES: Cc1nc2cc([C@H]3CCO[C@@H](c4cnn(C5CC5)c4)C3)nc(-c3ccc(F)cc3F)c2nc1C] |
| I-914 | 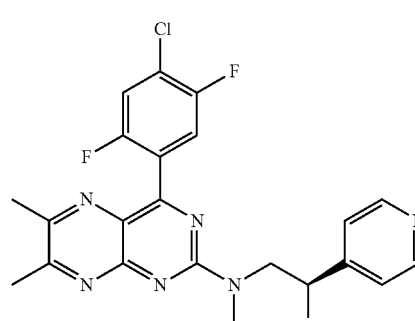 |
| I-915 | |
| I-916 | |
| I-917 | |

TABLE A-continued

Exemplary Compounds

| I-# | Structure |
|---|---|
| I-918 | 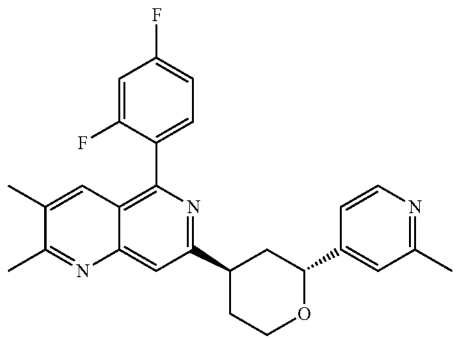 |
| I-919 | 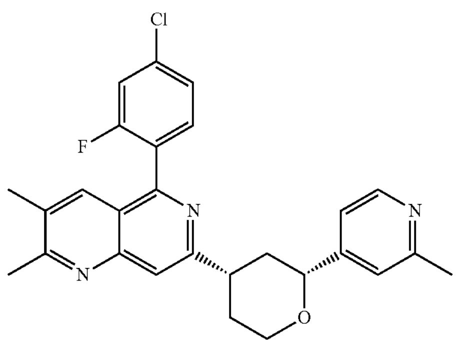 |
| I-920 | 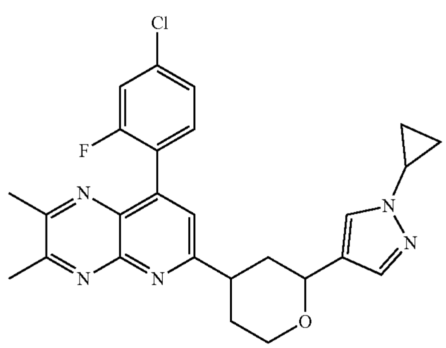 [SMILES: Cc1nc2nc(C3CCOC(c4cnn(C5CC5)c4)C3)cc(-c3ccc(Cl)cc3F)c2nc1C] |
| I-921 | 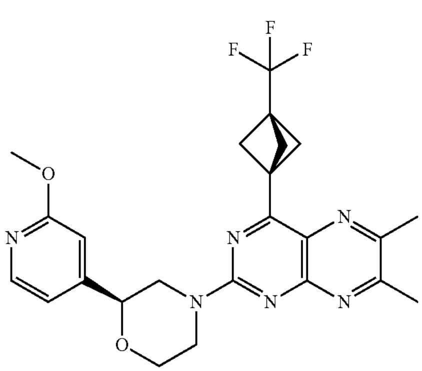 [SMILES: COc1cc([C@H]2CN(c3nc4nc(C)c(C)nc4c([C@]45C[C@](C(F)(F)F)(C4)C5)n3)CCO2)ccn1] |
| I-922 | |
| I-923 | |
| I-924 | |
| I-925 | |

TABLE A-continued
Exemplary Compounds
| I-# | Structure |
|---|---|
| I-926 | 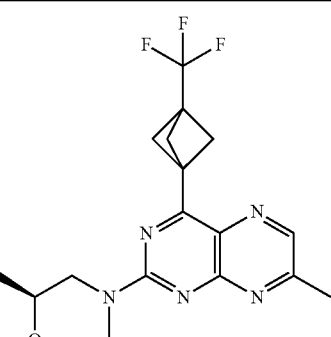 |
| I-927 | 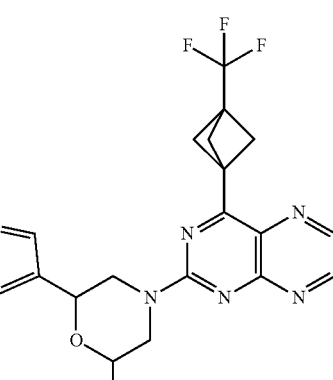 |
| I-928 | 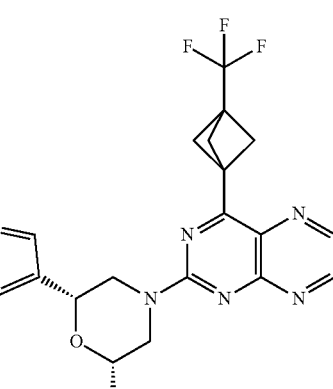 |
| I-929 | 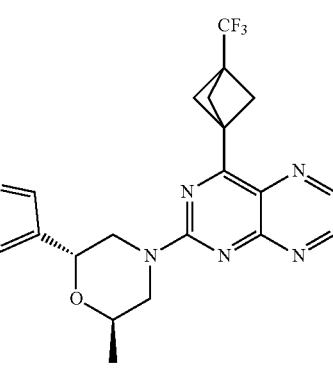 |
| I-930 | 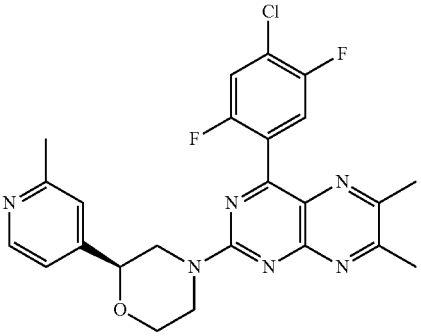 [SMILES: Cc1cc([C@H]2CN(c3nc(-c4cc(F)c(Cl)cc4F)c4nc(C)c(C)nc4n3)CCO2)ccn1] |
| I-931 | 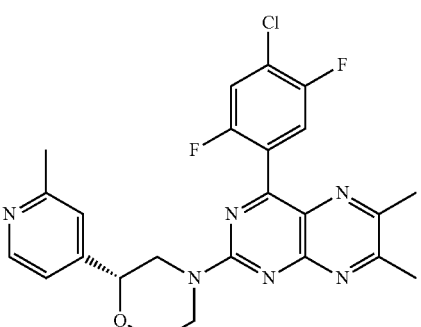 |
| I-932 | 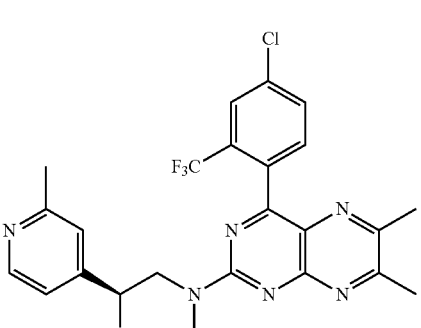 |
| I-933 | 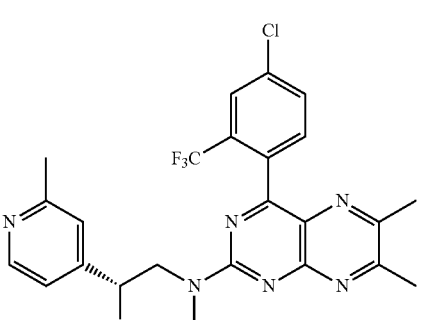 |

TABLE A-continued

Exemplary Compounds

| I-# | Structure |
|---|---|
| I-934 | |
| I-935 | |
| I-936 | |
| I-937 | 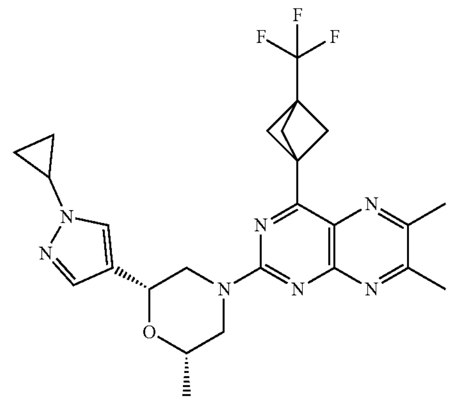 [SMILES: Cc1nc2nc(N3C[C@@H](c4cnn(C5CC5)c4)O[C@@H](C)C3)nc(C34CC(C(F)(F)F)(C3)C4)c2nc1C] |
| I-938 | 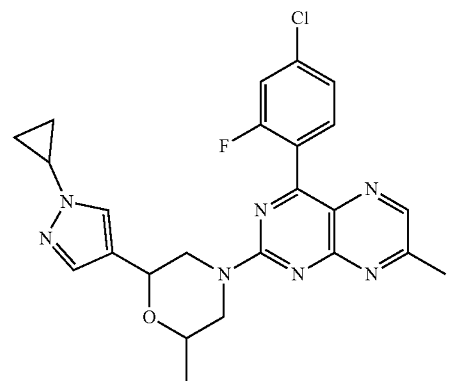 [SMILES: Cc1cnc2c(-c3ccc(Cl)cc3F)nc(N3CC(C)OC(c4cnn(C5CC5)c4)C3)nc2n1] |
| I-939 | 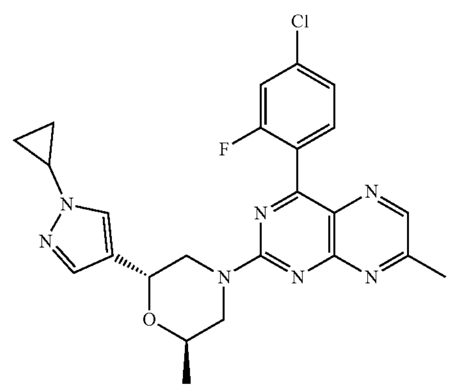 [SMILES: Cc1cnc2c(-c3ccc(Cl)cc3F)nc(N3C[C@@H](C)O[C@H](c4cnn(C5CC5)c4)C3)nc2n1] |
| I-940 | 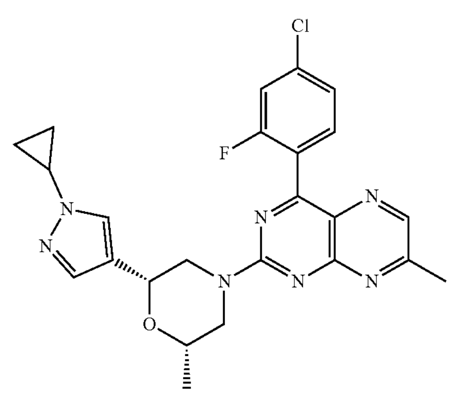 [SMILES: Cc1cnc2c(-c3ccc(Cl)cc3F)nc(N3C[C@@H](c4cnn(C5CC5)c4)O[C@@H](C)C3)nc2n1] |

TABLE A-continued
Exemplary Compounds
| I-# | Structure |
|---|---|
| I-941 | 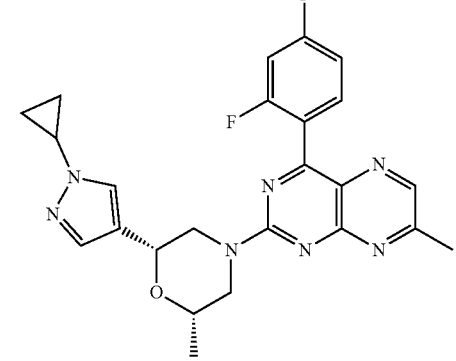 |
| I-942 | 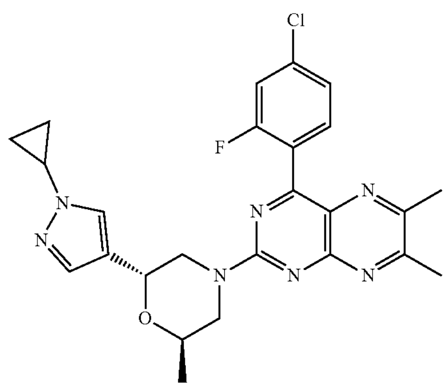 [SMILES: Cc1nc2nc(N3C[C@@H](C)O[C@H](c4cnn(C5CC5)c4)C3)nc(-c3ccc(Cl)cc3F)c2nc1C] |
| I-943 | 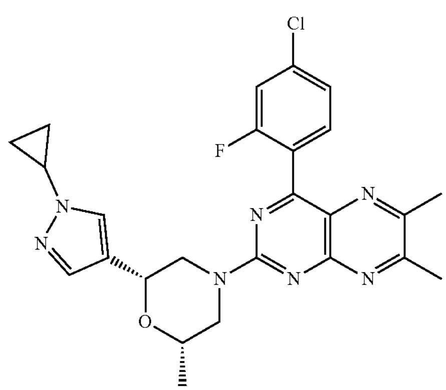 [SMILES: Cc1nc2nc(N3C[C@@H](c4cnn(C5CC5)c4)O[C@@H](C)C3)nc(-c3ccc(Cl)cc3F)c2nc1C] |
| I-944 | 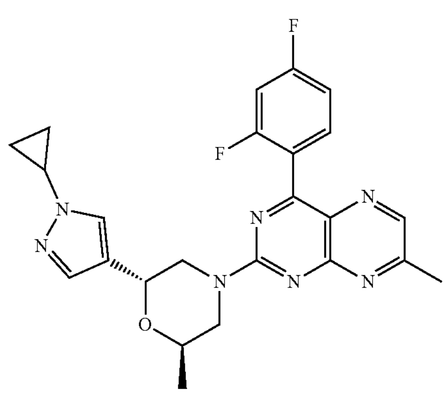 [SMILES: Cc1cnc2c(-c3ccc(F)cc3F)nc(N3C[C@@H](C)O[C@H](c4cnn(C5CC5)c4)C3)nc2n1] |
| I-945 | 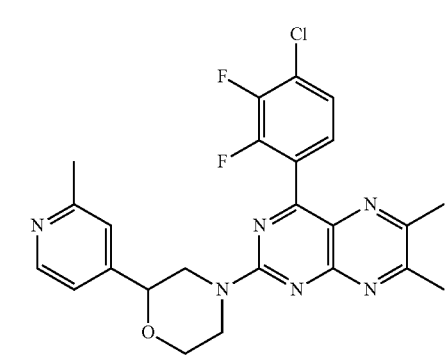 |
| I-946 | |
| I-947 | |
| I-948 | |

TABLE A-continued

Exemplary Compounds

| I-# | Structure |
|---|---|
| I-949 | (structure) |
| I-950 | (structure) |
| I-951 | (structure) |
| I-952 | (structure) |
| I-953 | (structure) |
| I-954 | (structure) |
| I-955 | (structure) |
| I-956 | (structure) |

TABLE A-continued
Exemplary Compounds
| I-# | Structure |
|---|---|
| I-957 | 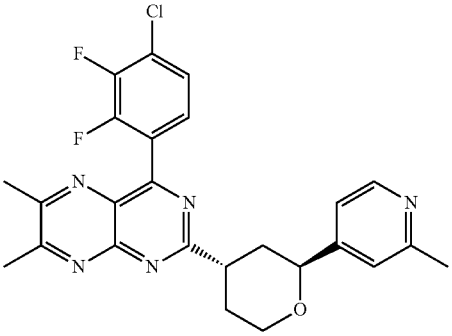 |
| I-958 | 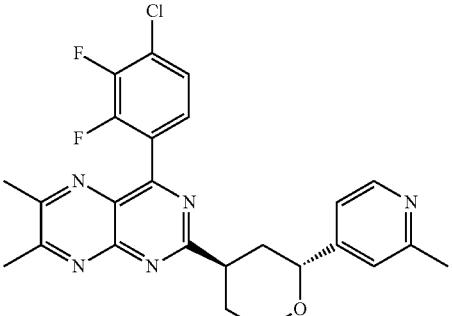 |
| I-959 | 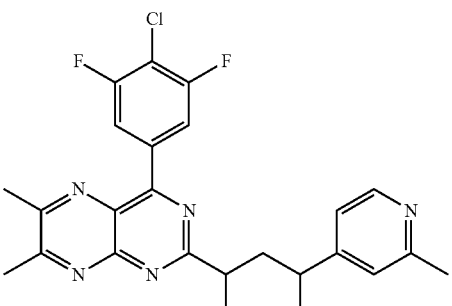 |
| I-960 | 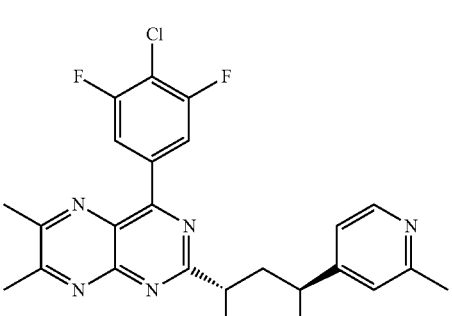 |
| I-961 | 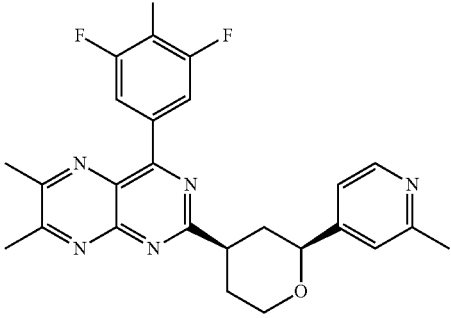 |
| I-962 | 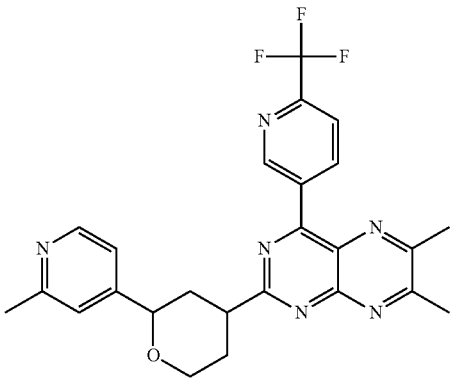 |
| I-963 | 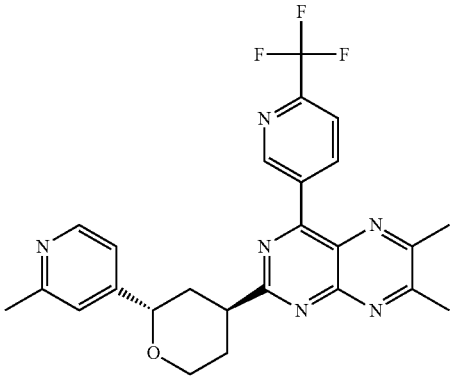 |
| I-964 | 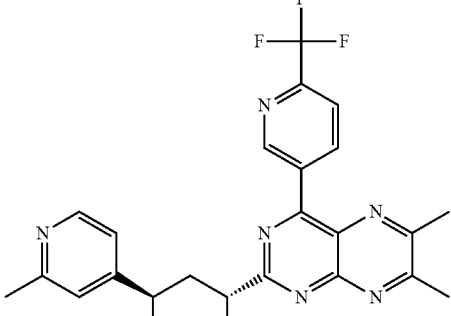 |

TABLE A-continued

Exemplary Compounds

| I-# | Structure |
|---|---|
| I-965 | 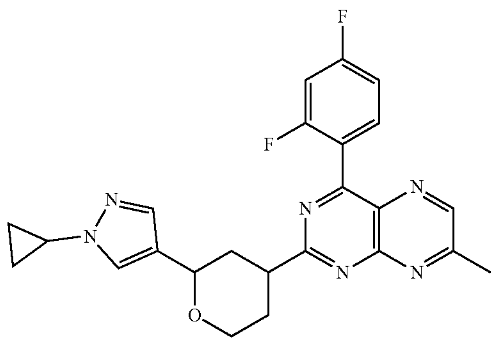 [SMILES: Cc1cnc2c(-c3ccc(F)cc3F)nc(C3CCOC(c4cnn(C5CC5)c4)C3)nc2n1] |
| I-966 | 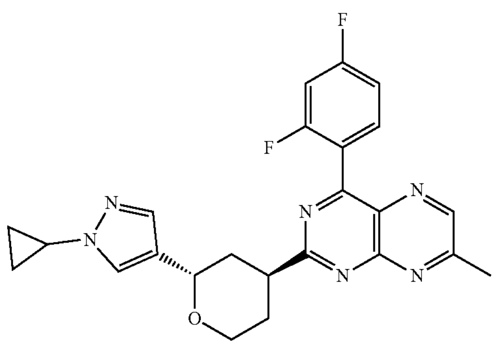 [SMILES: Cc1cnc2c(-c3ccc(F)cc3F)nc([C@H]3CCO[C@H](c4cnn(C5CC5)c4)C3)nc2n1] |
| I-967 | 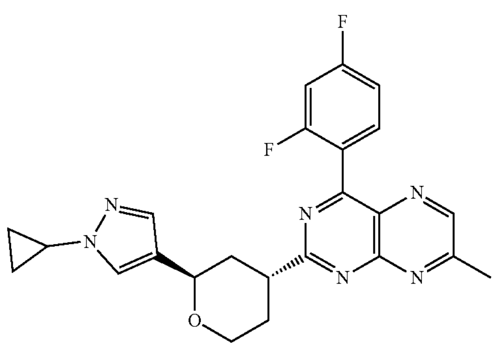 [SMILES: Cc1cnc2c(-c3ccc(F)cc3F)nc([C@@H]3CCO[C@@H](c4cnn(C5CC5)c4)C3)nc2n1] |
| I-968 | 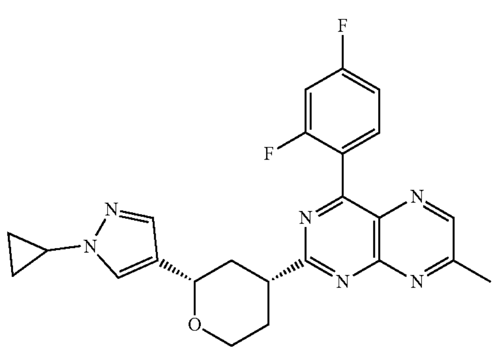 [SMILES: Cc1cnc2c(-c3ccc(F)cc3F)nc([C@@H]3CCO[C@H](c4cnn(C5CC5)c4)C3)nc2n1] |
| I-969 | |
| I-970 | |
| I-971 | |
| I-972 | |

TABLE A-continued
Exemplary Compounds
| I-# | Structure |
|---|---|
| I-973 | 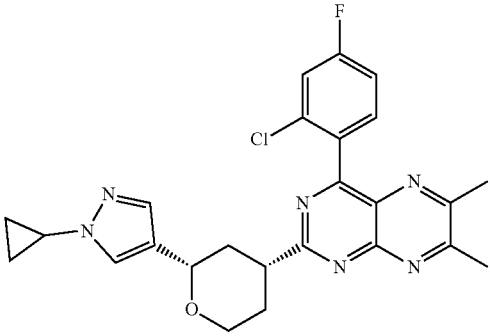 [SMILES: Cc1nc2nc([C@@H]3CCO[C@H](c4cnn(C5CC5)c4)C3)nc(-c3ccc(F)cc3Cl)c2nc1C] |
| I-974 | 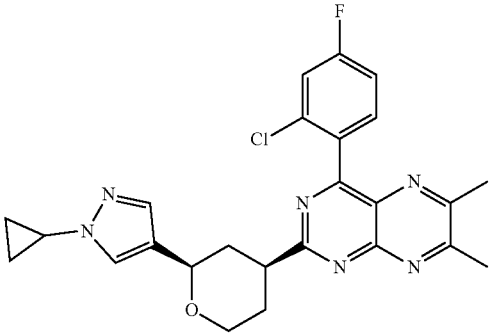 [SMILES: Cc1nc2nc([C@H]3CCO[C@@H](c4cnn(C5CC5)c4)C3)nc(-c3ccc(F)cc3Cl)c2nc1C] |
| I-975 | 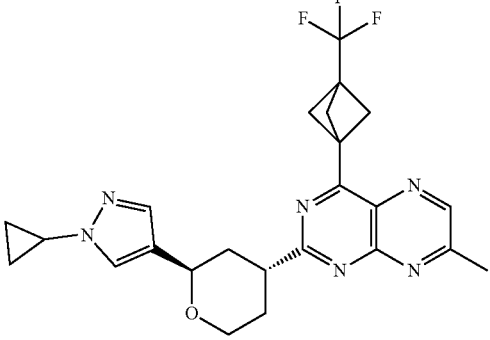 |
| I-976 | 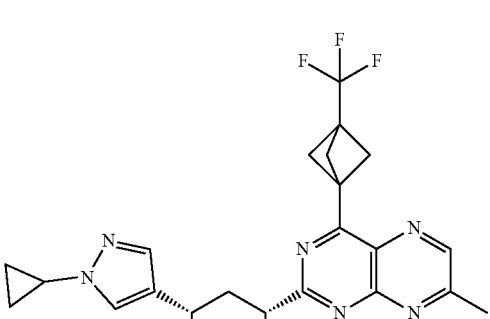 |
| I-977 | 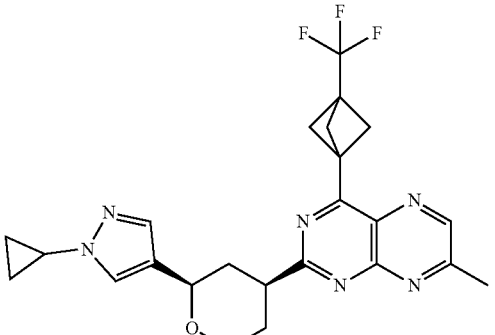 |
| I-978 | 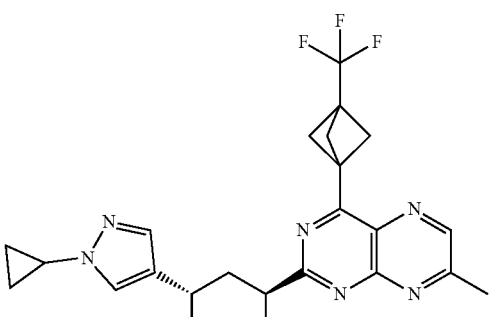 |
| I-979 | 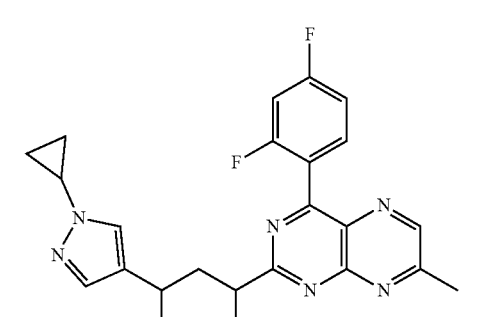 |
| I-980 | 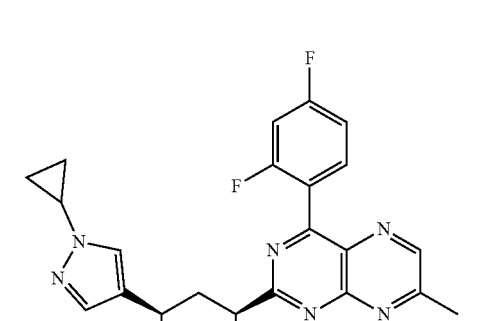 |

TABLE A-continued
Exemplary Compounds
| I-# | Structure |
|---|---|
| I-981 | 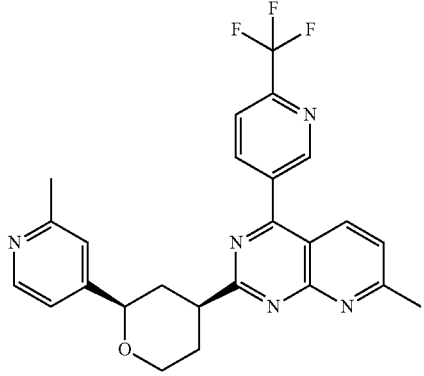 [SMILES: Cc1cc([C@H]2C[C@@H](c3nc(-c4ccc(C(F)(F)F)nc4)c4ccc(C)nc4n3)CCO2)ccn1] |
| I-982 | 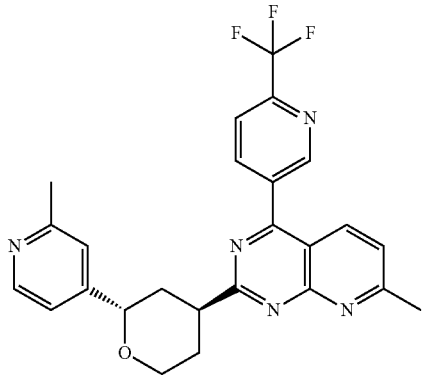 [SMILES: Cc1cc([C@@H]2C[C@@H](c3nc(-c4ccc(C(F)(F)F)nc4)c4ccc(C)nc4n3)CCO2)ccn1] |
| I-983 | 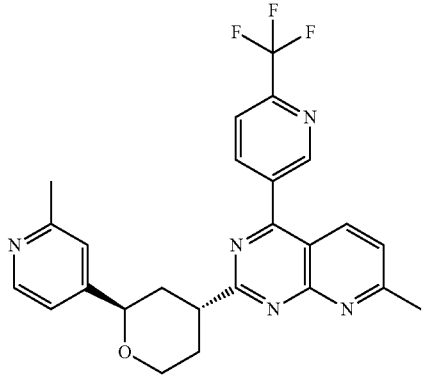 [SMILES: Cc1cc([C@H]2C[C@H](c3nc(-c4ccc(C(F)(F)F)nc4)c4ccc(C)nc4n3)CCO2)ccn1] |
| I-984 | 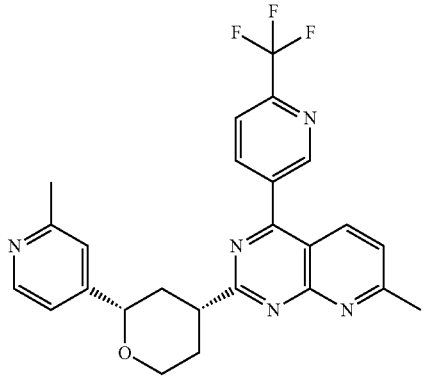 [SMILES: Cc1cc([C@@H]2C[C@H](c3nc(-c4ccc(C(F)(F)F)nc4)c4ccc(C)nc4n3)CCO2)ccn1] |
| I-985 | 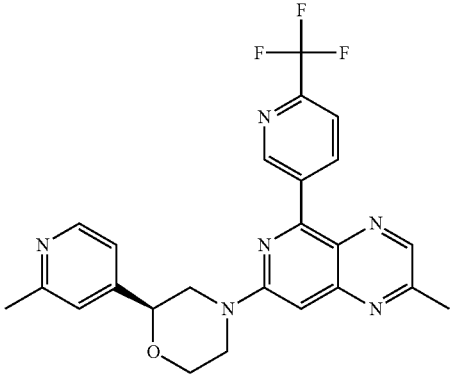 |
| I-986 | 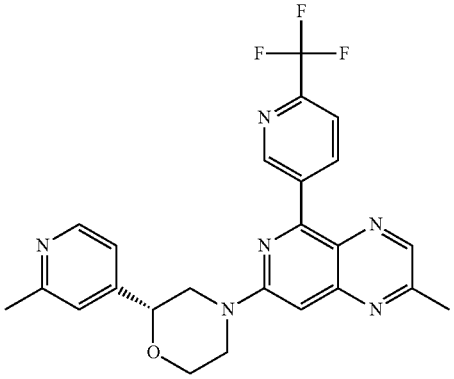 |
| I-987 | 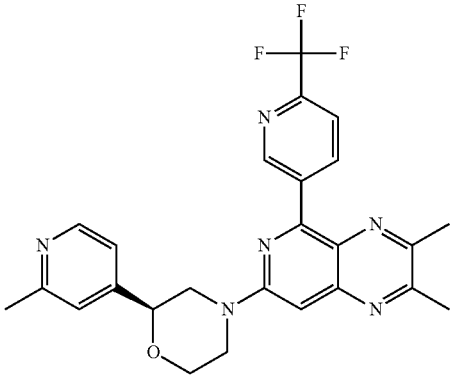 |
| I-988 | 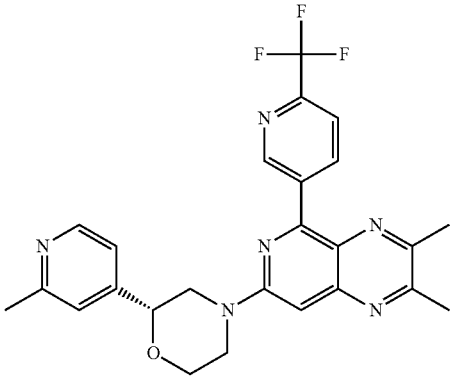 |

TABLE A-continued

Exemplary Compounds

| I-# | Structure |
|---|---|
| I-989 | 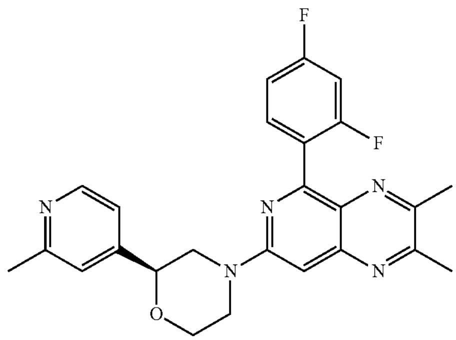 |
| I-990 | 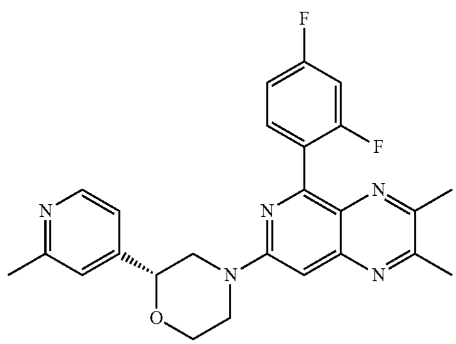 |
| I-991 | 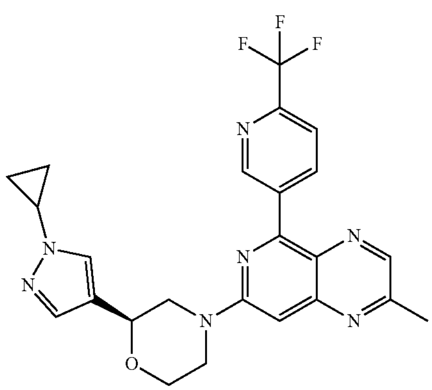 [SMILES: Cc1cnc2c(-c3ccc(C(F)(F)F)nc3)nc(N3CCO[C@@H](c4cnn(C5CC5)c4)C3)cc2n1] |
| I-992 | 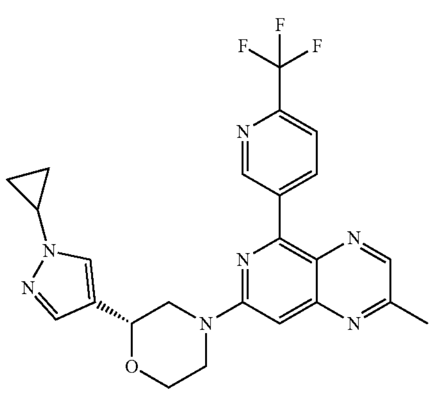 [SMILES: Cc1cnc2c(-c3ccc(C(F)(F)F)nc3)nc(N3CCO[C@H](c4cnn(C5CC5)c4)C3)cc2n1] |
| I-993 | |
| I-994 | |
| I-995 | |
| I-996 | |

TABLE A-continued

Exemplary Compounds

| I-# | Structure |
|---|---|
| I-997 | 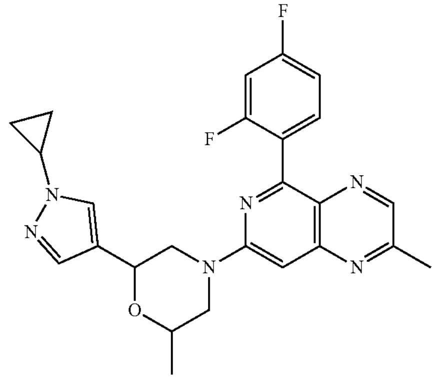 [SMILES: Cc1cnc2c(-c3ccc(F)cc3F)nc(N3CC(C)OC(c4cnn(C5CC5)c4)C3)cc2n1] |
| I-998 | 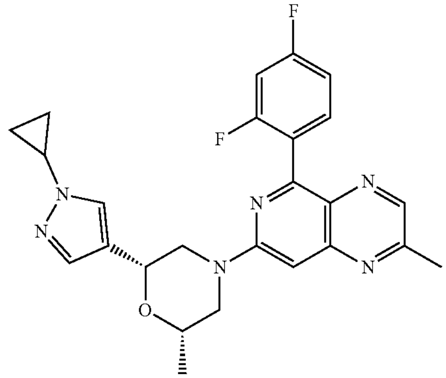 [SMILES: Cc1cnc2c(-c3ccc(F)cc3F)nc(N3C[C@@H](c4cnn(C5CC5)c4)O[C@@H](C)C3)cc2n1] |
| I-999 | 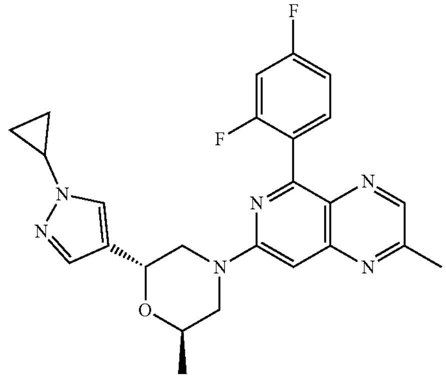 [SMILES: Cc1cnc2c(-c3ccc(F)cc3F)nc(N3C[C@@H](C)O[C@H](c4cnn(C5CC5)c4)C3)cc2n1] |
| I-1000 | 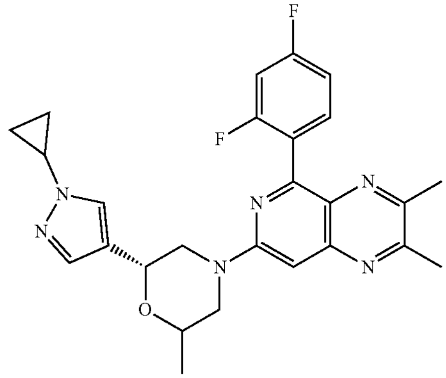 [SMILES: Cc1nc2cc(N3CC(C)O[C@H](c4cnn(C5CC5)c4)C3)nc(-c3ccc(F)cc3F)c2nc1C] |
| I-1001 | |
| I-1002 | |
| I-1003 | |
| I-1004 | |

TABLE A-continued

Exemplary Compounds

| I-# | Structure |
|---|---|
| I-1005 | 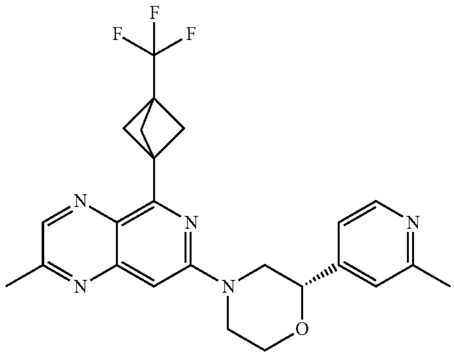 |
| I-1006 | 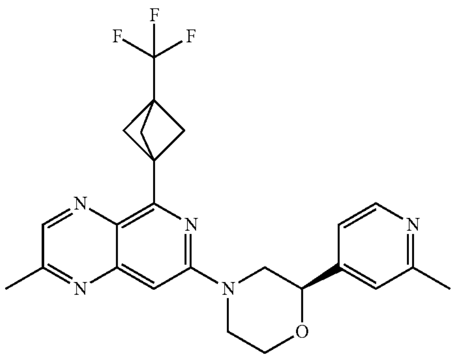 |
| I-1007 | 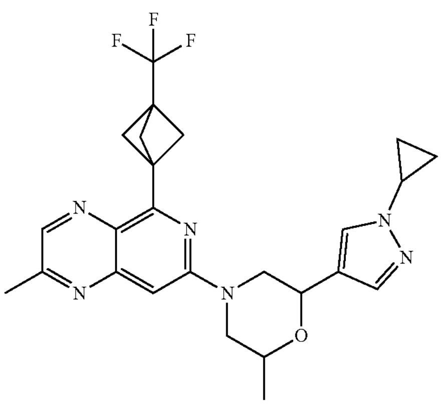 [SMILES: Cc1cnc2c(C34CC(C(F)(F)F)(C3)C4)nc(N3CC(C)OC(c4cnn(C5CC5)c4)C3)cc2n1] |
| I-1008 | 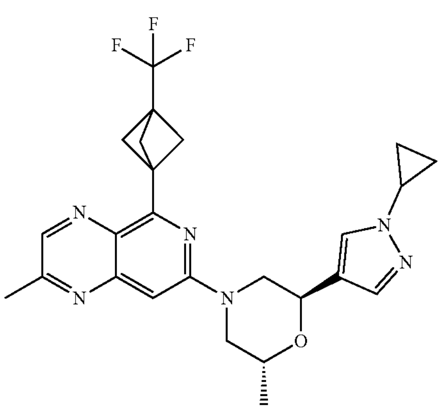 [SMILES: Cc1cnc2c(C34CC(C(F)(F)F)(C3)C4)nc(N3C[C@@H](C)O[C@H](c4cnn(C5CC5)c4)C3)cc2n1] |
| I-1009 | |
| I-1010 | |
| I-1011 | |

TABLE A-continued
Exemplary Compounds
| I-# | Structure |
|---|---|
| I-1012 | 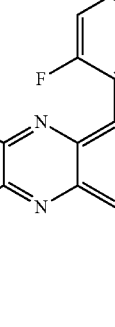 |
| I-1013 | 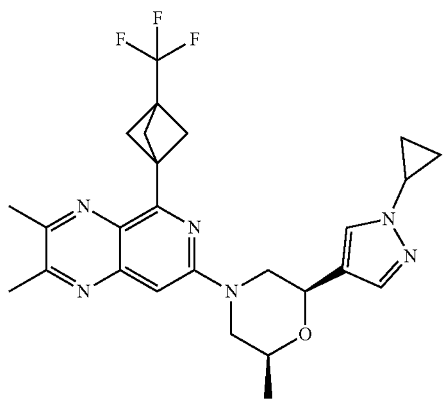 [SMILES: Cc1nc2cc(N3C[C@@H](c4cnn(C5CC5)c4)O[C@@H](C)C3)nc(C34CC(C(F)(F)F)(C3)C4)c2nc1C] |
| I-1014 | 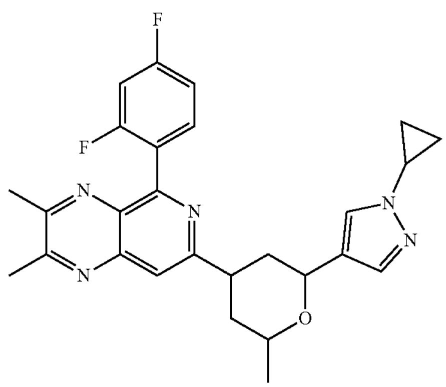 [SMILES: Cc1nc2cc(C3CC(C)OC(c4cnn(C5CC5)c4)C3)nc(-c3ccc(F)cc3F)c2nc1C] |
| I-1015 | 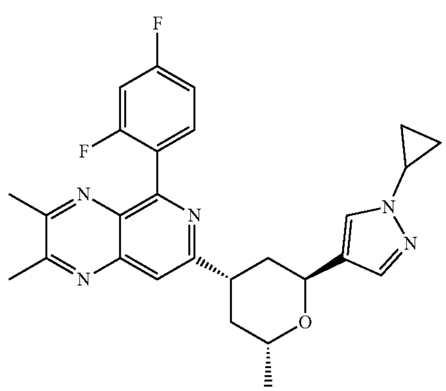 [SMILES: Cc1nc2cc([C@H]3C[C@@H](C)O[C@H](c4cnn(C5CC5)c4)C3)nc(-c3ccc(F)cc3F)c2nc1C] |
| I-1016 | 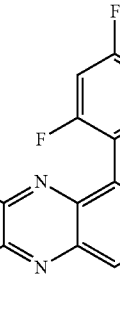 |
| I-1017 | |
| I-1018 | |
| I-1019 | |

TABLE A-continued

Exemplary Compounds

| I-# | Structure |
|---|---|
| I-1020 | 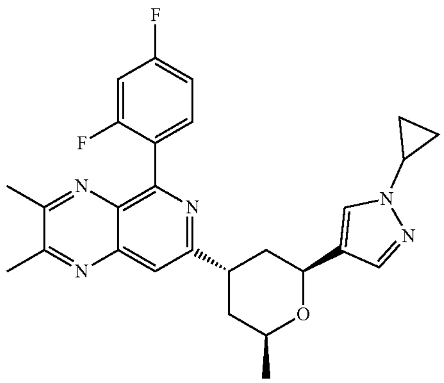 [SMILES: Cc1nc2cc([C@@H]3C[C@@H](c4cnn(C5CC5)c4)O[C@@H](C)C3)nc(-c3ccc(F)cc3F)c2nc1C] |
| I-1021 | 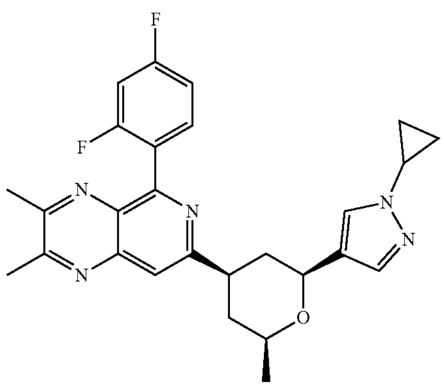 [SMILES: Cc1nc2cc([C@H]3C[C@@H](c4cnn(C5CC5)c4)O[C@@H](C)C3)nc(-c3ccc(F)cc3F)c2nc1C] |
| I-1022 | 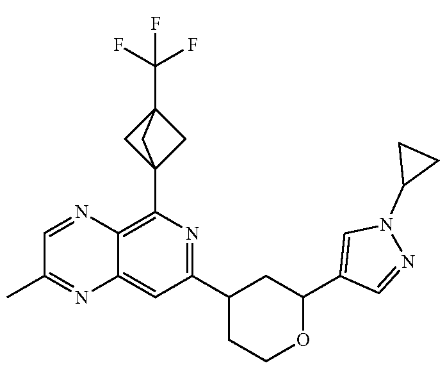 [SMILES: Cc1cnc2c(C34CC(C(F)(F)F)(C3)C4)nc(C3CCOC(c4cnn(C5CC5)c4)C3)cc2n1] |
| I-1023 | 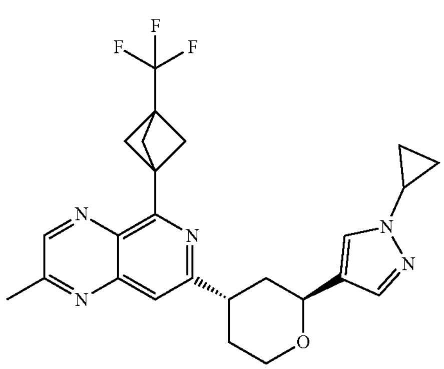 [SMILES: Cc1cnc2c(C34CC(C(F)(F)F)(C3)C4)nc([C@H]3CCO[C@H](c4cnn(C5CC5)c4)C3)cc2n1] |
| I-1024 | |
| I-1025 | |
| I-1026 | |
| I-1027 | |

TABLE A-continued
Exemplary Compounds
| I-# | Structure |
|---|---|
| I-1028 | 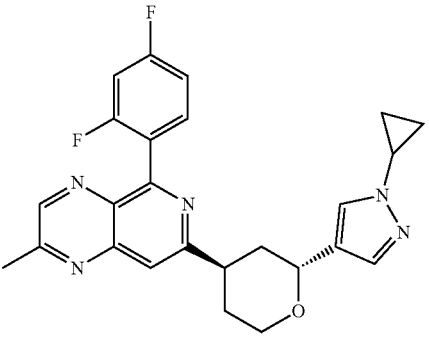 [SMILES: Cc1cnc2c(-c3ccc(F)cc3F)nc([C@@H]3CCO[C@@H](c4cnn(C5CC5)c4)C3)cc2n1] |
| I-1029 | 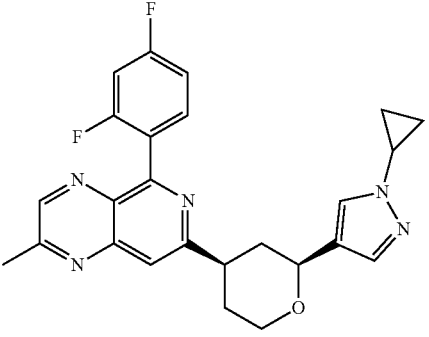 [SMILES: Cc1cnc2c(-c3ccc(F)cc3F)nc([C@@H]3CCO[C@H](c4cnn(C5CC5)c4)C3)cc2n1] |
| I-1030 | 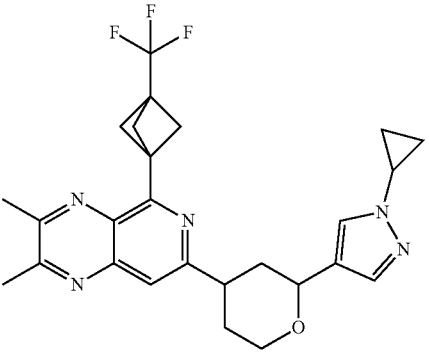 [SMILES: Cc1nc2cc(C3CCOC(c4cnn(C5CC5)c4)C3)nc(C34CC(C(F)(F)F)(C3)C4)c2nc1C] |
| I-1031 | 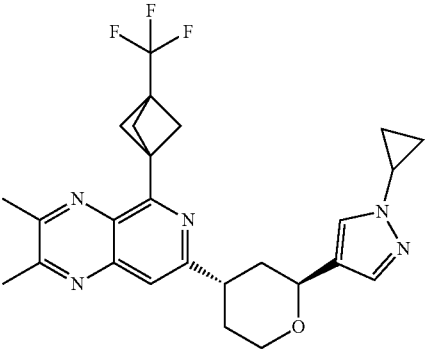 [SMILES: Cc1nc2cc([C@H]3CCO[C@H](c4cnn(C5CC5)c4)C3)nc(C34CC(C(F)(F)F)(C3)C4)c2nc1C] |
| I-1032 | 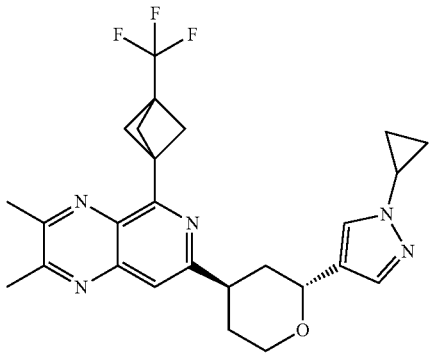 [SMILES: Cc1nc2cc([C@@H]3CCO[C@@H](c4cnn(C5CC5)c4)C3)nc(C34CC(C(F)(F)F)(C3)C4)c2nc1C] |
| I-1033 | 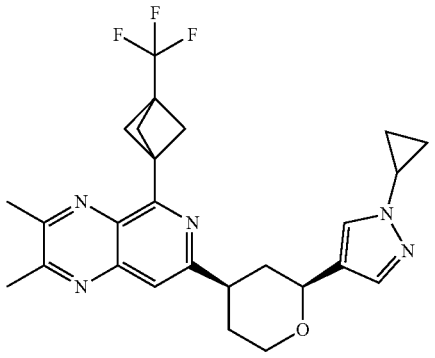 [SMILES: Cc1nc2cc([C@@H]3CCO[C@H](c4cnn(C5CC5)c4)C3)nc(C34CC(C(F)(F)F)(C3)C4)c2nc1C] |
| I-1034 | 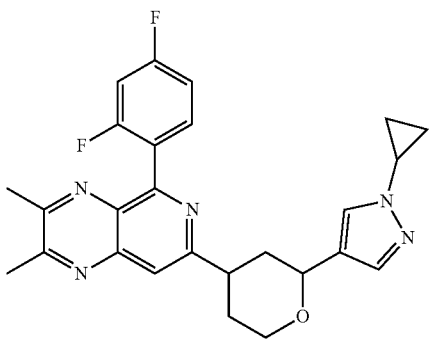 [SMILES: Cc1nc2cc(C3CCOC(c4cnn(C5CC5)c4)C3)nc(-c3ccc(F)cc3F)c2nc1C] |
| I-1035 | 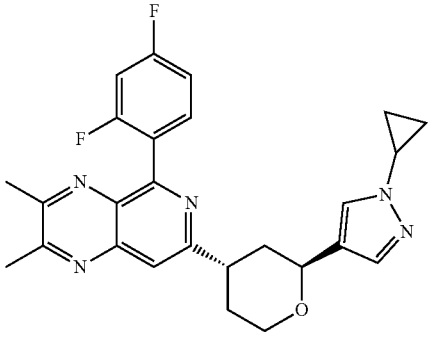 [SMILES: Cc1nc2cc([C@H]3CCO[C@H](c4cnn(C5CC5)c4)C3)nc(-c3ccc(F)cc3F)c2nc1C] |

TABLE A-continued
Exemplary Compounds
| I-# | Structure |
|---|---|
| I-1036 | 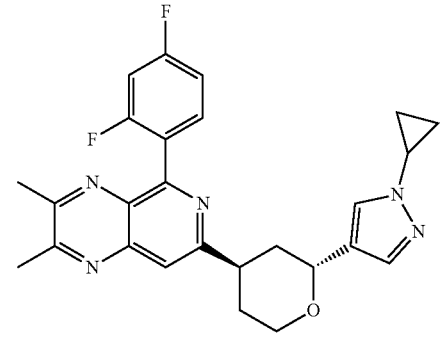 [SMILES: Cc1nc2cc([C@@H]3CCO[C@@H](c4cnn(C5CC5)c4)C3)nc(-c3ccc(F)cc3F)c2nc1C] |
| I-1037 | 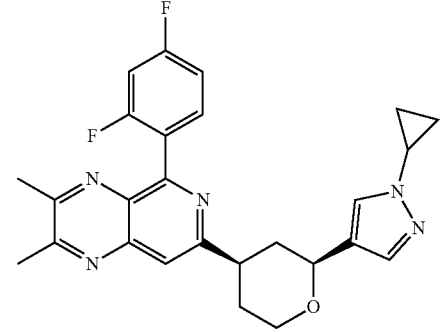 [SMILES: Cc1nc2cc([C@@H]3CCO[C@H](c4cnn(C5CC5)c4)C3)nc(-c3ccc(F)cc3F)c2nc1C] |
| I-1038 | 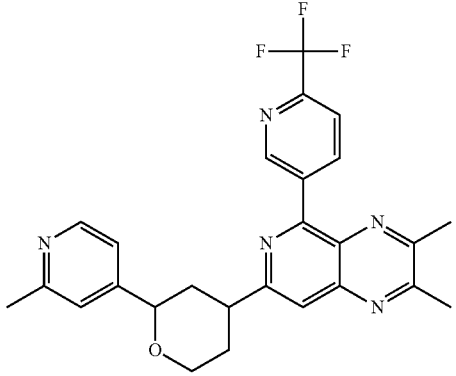 |
| I-1039 | 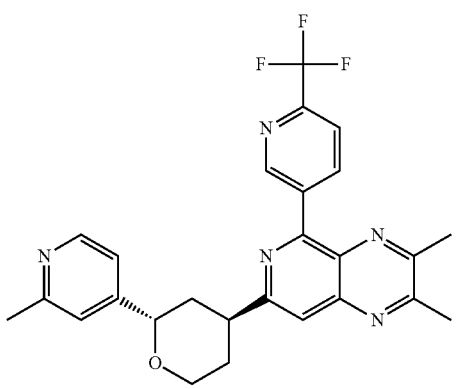 |
| I-1040 | 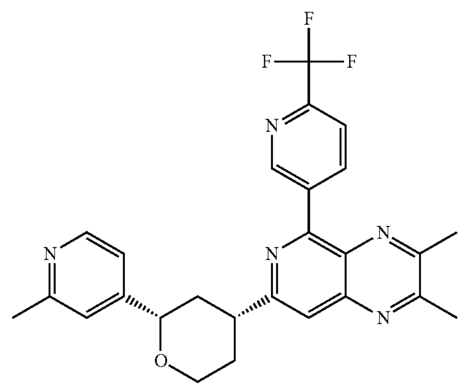 |
| I-1041 | 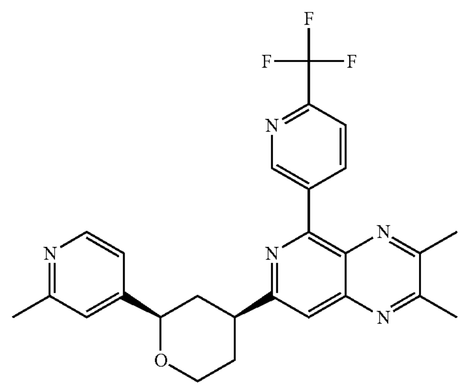 |
| I-1042 | 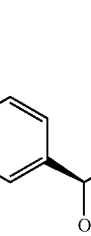 |
| I-1043 | 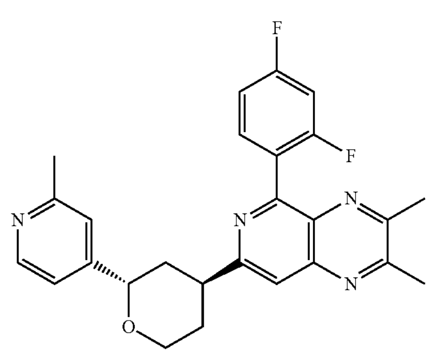 [SMILES: Cc1cc([C@@H]2C[C@@H](c3cc4nc(C)c(C)nc4c(-c4ccc(F)cc4F)n3)CCO2)ccn1] |

TABLE A-continued

Exemplary Compounds

| I-# | Structure |
|---|---|
| I-1044 | (structure) |
| I-1045 | (structure) |
| I-1046 | (structure) |
| I-1047 | (structure) |
| I-1048 | (structure) |
| I-1049 | (structure) |
| I-1050 | (structure) |
| I-1051 | (structure) |

TABLE A-continued

Exemplary Compounds

| I-# | Structure |
|---|---|
| I-1052 | 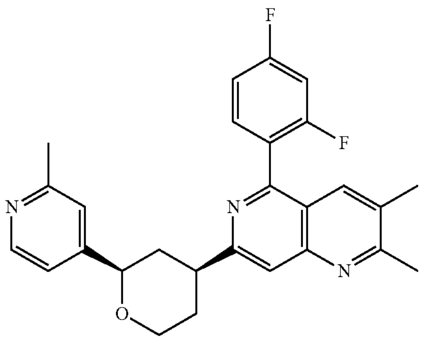 [SMILES: Cc1cc([C@H]2C[C@@H](c3cc4nc(C)c(C)cc4c(-c4ccc(F)cc4F)n3)CCO2)ccn1] |
| I-1053 | 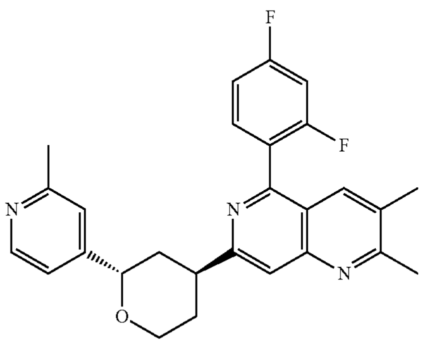 [SMILES: Cc1cc([C@@H]2C[C@@H](c3cc4nc(C)c(C)cc4c(-c4ccc(F)cc4F)n3)CCO2)ccn1] |
| I-1054 | 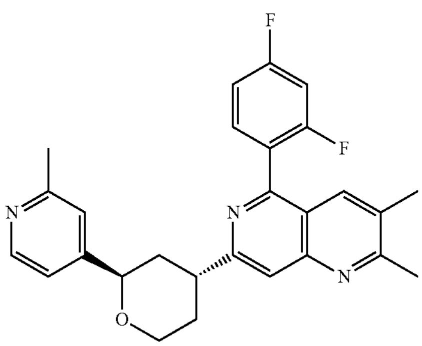 [SMILES: Cc1cc([C@H]2C[C@H](c3cc4nc(C)c(C)cc4c(-c4ccc(F)cc4F)n3)CCO2)ccn1] |
| I-1055 | 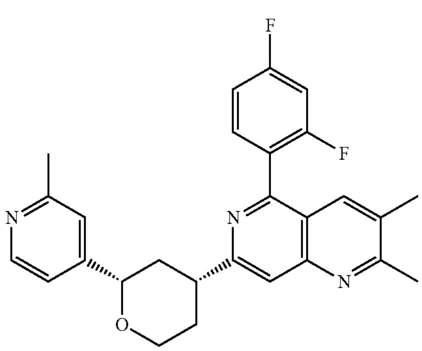 [SMILES: Cc1cc([C@@H]2C[C@H](c3cc4nc(C)c(C)cc4c(-c4ccc(F)cc4F)n3)CCO2)ccn1] |
| I-1056 | |
| I-1057 | |
| I-1058 | |
| I-1059 | |

TABLE A-continued

Exemplary Compounds

| I-# | Structure |
|---|---|
| I-1060 | 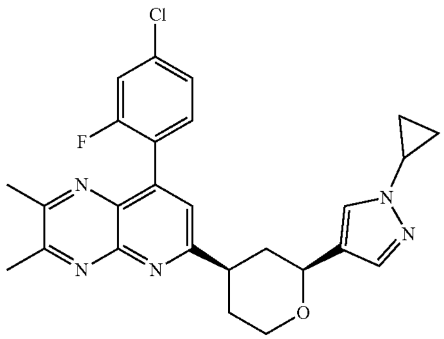 [SMILES: Cc1nc2nc([C@@H]3CCO[C@H](c4cnn(C5CC5)c4)C3)cc(-c3ccc(Cl)cc3F)c2nc1C] |
| I-1061 | 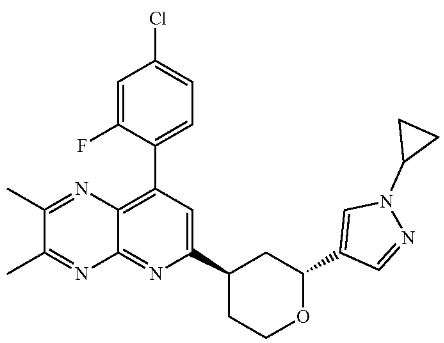 [SMILES: Cc1nc2nc([C@@H]3CCO[C@@H](c4cnn(C5CC5)c4)C3)cc(-c3ccc(Cl)cc3F)c2nc1C] |
| I-1062 | 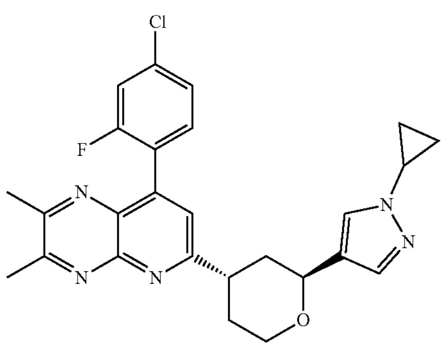 [SMILES: Cc1nc2nc([C@H]3CCO[C@H](c4cnn(C5CC5)c4)C3)cc(-c3ccc(Cl)cc3F)c2nc1C] |
| I-1063 | 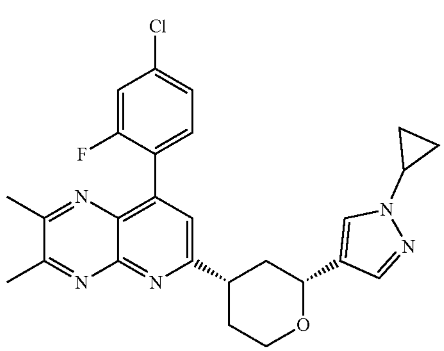 [SMILES: Cc1nc2nc([C@H]3CCO[C@@H](c4cnn(C5CC5)c4)C3)cc(-c3ccc(Cl)cc3F)c2nc1C] |
| I-1064 | |
| I-1065 | |
| I-1066 | |
| I-1067 | |

TABLE A-continued

Exemplary Compounds

| I-# | Structure |
|---|---|
| I-1068 | 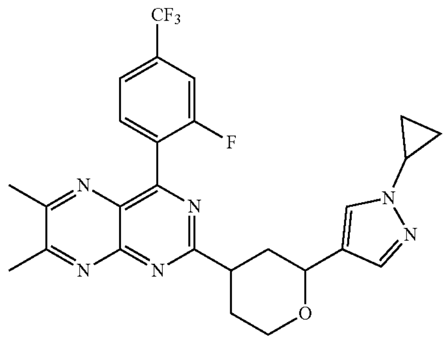 [SMILES: Cc1nc2nc(C3CCOC(c4cnn(C5CC5)c4)C3)nc(-c3ccc(C(F)(F)F)cc3F)c2nc1C] |
| I-1069 | 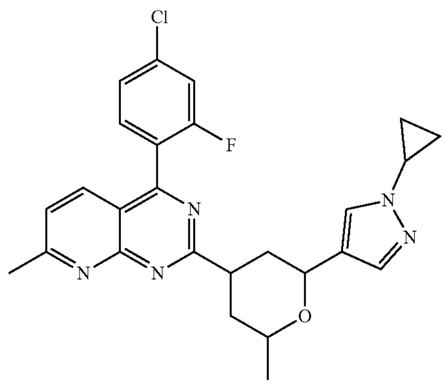 [SMILES: Cc1ccc2c(-c3ccc(Cl)cc3F)nc(C3CC(C)OC(c4cnn(C5CC5)c4)C3)nc2n1] |
| I-1070 | 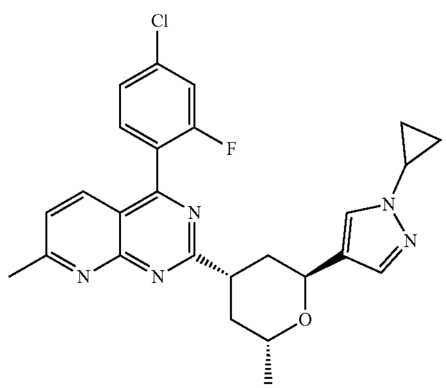 [SMILES: Cc1ccc2c(-c3ccc(Cl)cc3F)nc([C@H]3C[C@@H](C)O[C@H](c4cnn(C5CC5)c4)C3)nc2n1] |
| I-1071 | 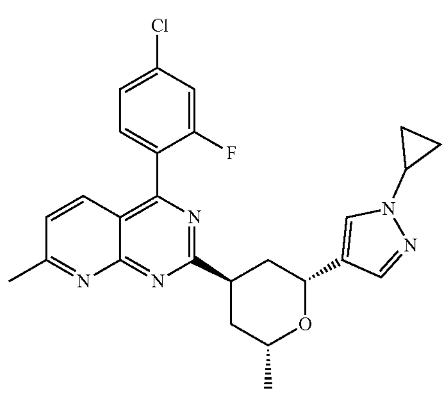 |
| I-1072 | |
| I-1073 | |
| I-1074 | |
| I-1075 | |

TABLE A-continued

Exemplary Compounds

| I-# | Structure |
|---|---|
| I-1076 | 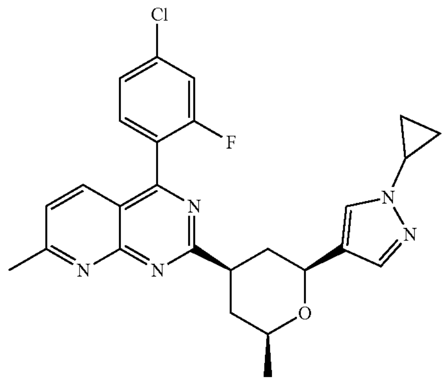 |
| I-1077 | 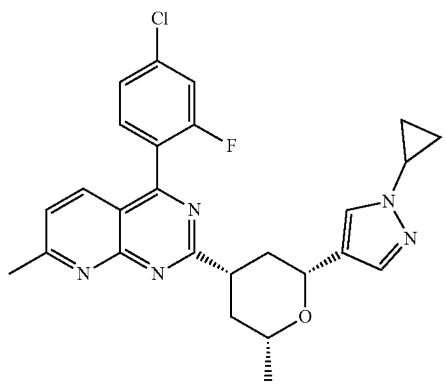 [SMILES: Cc1ccc2c(-c3ccc(Cl)cc3F)nc([C@H]3C[C@@H](C)O[C@@H](c4cnn(C5CC5)c4)C3)nc2n1] |
| I-1078 | 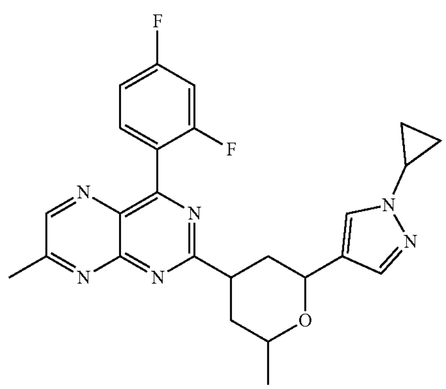 [SMILES: Cc1cnc2c(-c3ccc(F)cc3F)nc(C3CC(C)OC(c4cnn(C5CC5)c4)C3)nc2n1] |
| I-1079 | 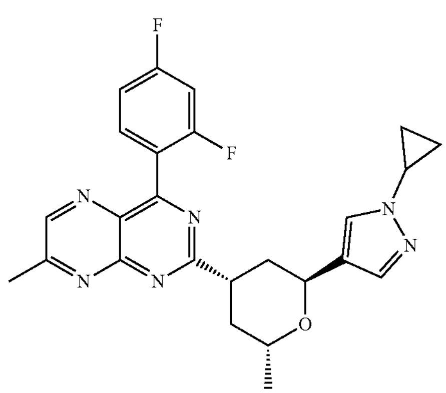 [SMILES: Cc1cnc2c(-c3ccc(F)cc3F)nc([C@H]3C[C@@H](C)O[C@H](c4cnn(C5CC5)c4)C3)nc2n1] |
| I-1080 | |
| I-1081 | |
| I-1082 | |
| I-1083 | |

TABLE A-continued

Exemplary Compounds

| I-# | Structure |
|---|---|
| I-1084 | 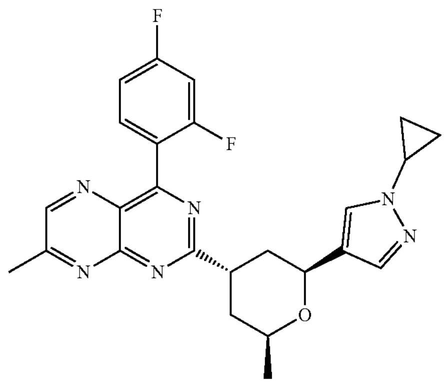 [SMILES: Cc1cnc2c(-c3ccc(F)cc3F)nc([C@@H]3C[C@@H](c4cnn(C5CC5)c4)O[C@@H](C)C3)nc2n1] |
| I-1085 | 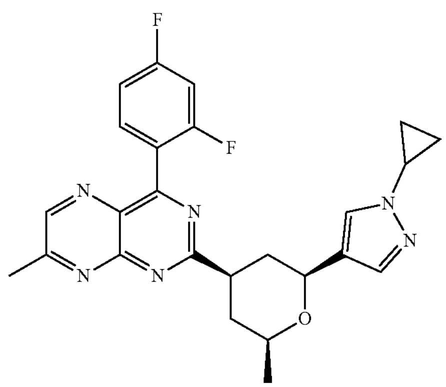 [SMILES: Cc1cnc2c(-c3ccc(F)cc3F)nc([C@H]3C[C@@H](c4cnn(C5CC5)c4)O[C@@H](C)C3)nc2n1] |
| I-1086 | 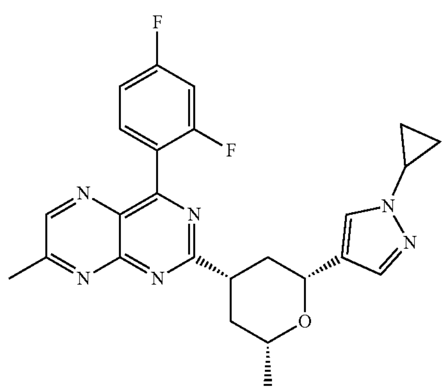 [SMILES: Cc1cnc2c(-c3ccc(F)cc3F)nc([C@H]3C[C@@H](C)O[C@@H](c4cnn(C5CC5)c4)C3)nc2n1] |
| I-1087 | 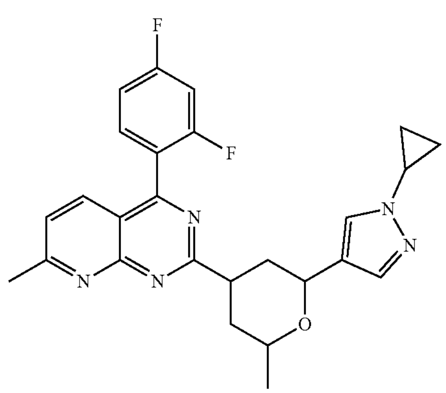 [SMILES: Cc1ccc2c(-c3ccc(F)cc3F)nc(C3CC(C)OC(c4cnn(C5CC5)c4)C3)nc2n1] |
| I-1088 | |
| I-1089 | |
| I-1090 | |
| I-1091 | |

TABLE A-continued

Exemplary Compounds

| I-# | Structure |
|---|---|
| I-1092 | 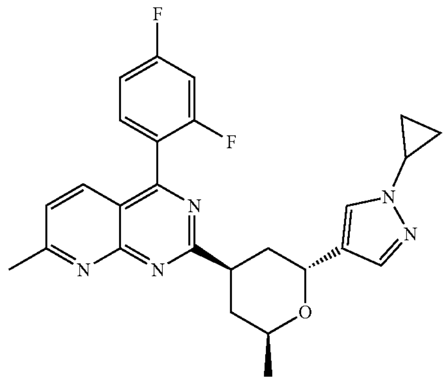 [SMILES: Cc1ccc2c(-c3ccc(F)cc3F)nc([C@@H]3C[C@H](C)O[C@@H](c4cnn(C5CC5)c4)C3)nc2n1] |
| I-1093 | 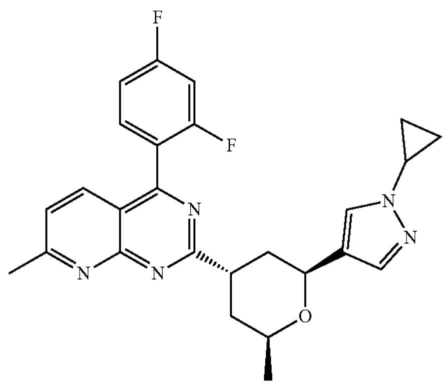 [SMILES: Cc1ccc2c(-c3ccc(F)cc3F)nc([C@@H]3C[C@@H](c4cnn(C5CC5)c4)O[C@@H](C)C3)nc2n1] |
| I-1094 | 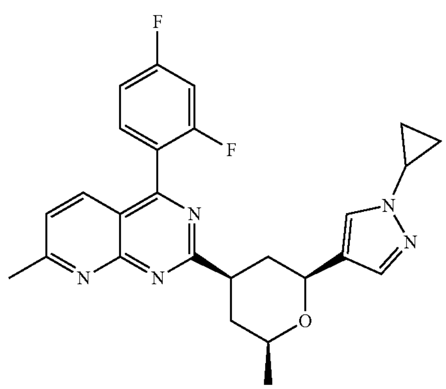 [SMILES: Cc1ccc2c(-c3ccc(F)cc3F)nc([C@H]3C[C@@H](c4cnn(C5CC5)c4)O[C@@H](C)C3)nc2n1] |
| I-1095 | 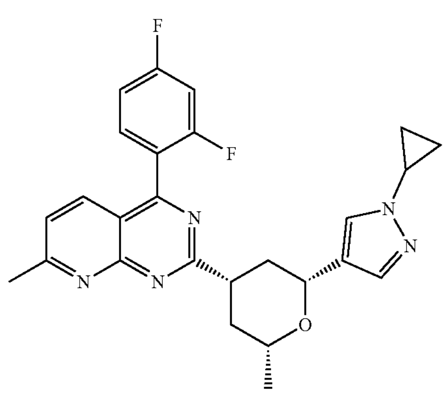 [SMILES: Cc1ccc2c(-c3ccc(F)cc3F)nc([C@H]3C[C@@H](C)O[C@@H](c4cnn(C5CC5)c4)C3)nc2n1] |
| I-1096 | |
| I-1097 | |
| I-1098 | |
| I-1099 | |

TABLE A-continued
Exemplary Compounds
| I-# | Structure |
|---|---|
| I-1100 | 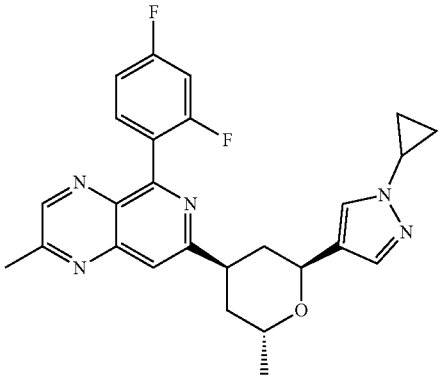 |
| I-1101 | 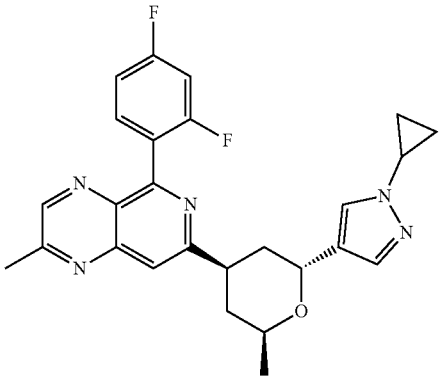 |
| I-1102 | 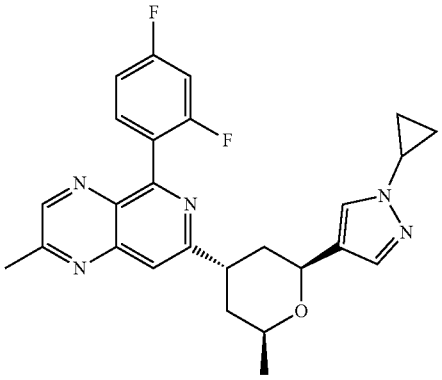 [SMILES: Cc1cnc2c(-c3ccc(F)cc3F)nc([C@@H]3C[C@@H](c4cnn(C5CC5)c4)O[C@@H](C)C3)cc2n1] |
| I-1103 | 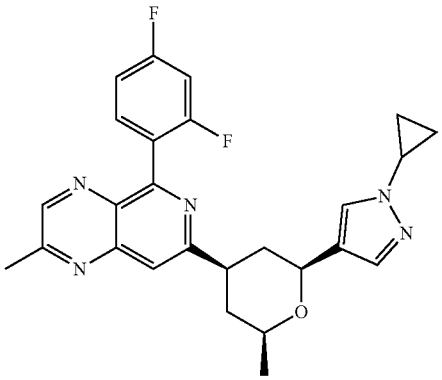 [SMILES: Cc1cnc2c(-c3ccc(F)cc3F)nc([C@H]3C[C@@H](c4cnn(C5CC5)c4)O[C@@H](C)C3)cc2n1] |
| I-1104 | 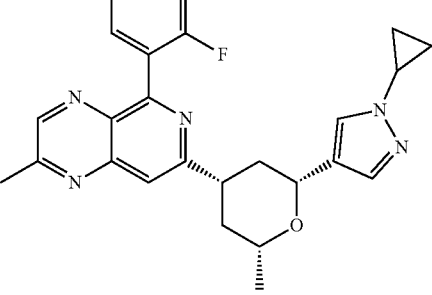 |
| I-1105 | 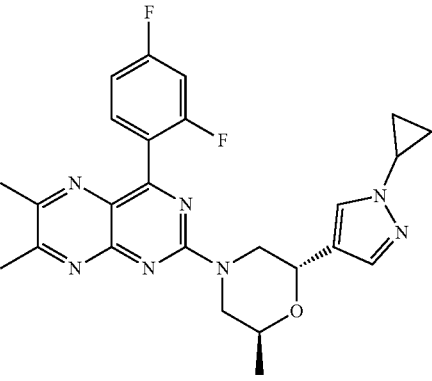 [SMILES: Cc1nc2nc(N3C[C@H](C)O[C@@H](c4cnn(C5CC5)c4)C3)nc(-c3ccc(F)cc3F)c2nc1C] |
| I-1106 | 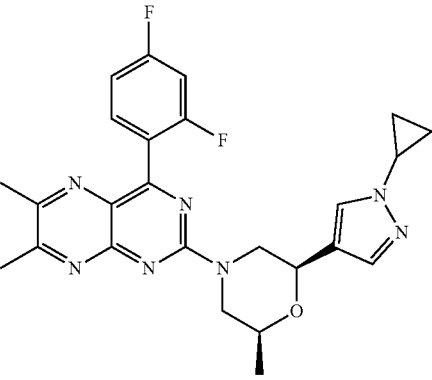 [SMILES: Cc1nc2nc(N3C[C@@H](c4cnn(C5CC5)c4)O[C@@H](C)C3)nc(-c3ccc(F)cc3F)c2nc1C] |
| I-1107 | 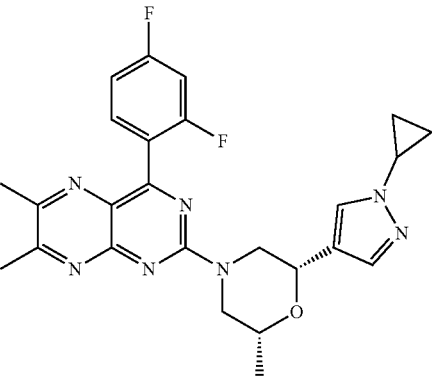 [SMILES: Cc1nc2nc(N3C[C@@H](C)O[C@@H](c4cnn(C5CC5)c4)C3)nc(-c3ccc(F)cc3F)c2nc1C] |

TABLE A-continued

Exemplary Compounds

| I-# | Structure |
|---|---|
| I-1108 | 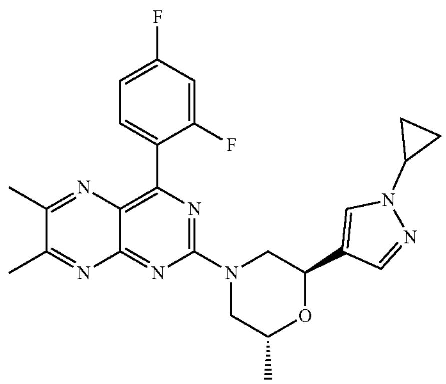 [SMILES: Cc1nc2nc(N3C[C@@H](C)O[C@H](c4cnn(C5CC5)c4)C3)nc(-c3ccc(F)cc3F)c2nc1C] |
| I-1109 | 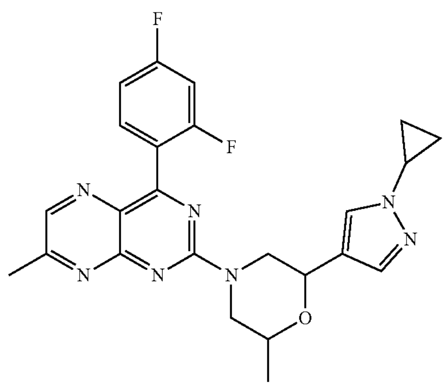 [SMILES: Cc1cnc2c(-c3ccc(F)cc3F)nc(N3CC(C)OC(c4cnn(C5CC5)c4)C3)nc2n1] |
| I-1110 | 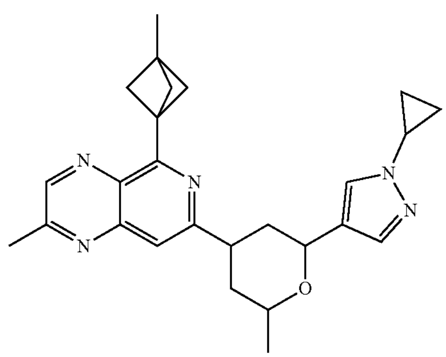 [SMILES: Cc1cnc2c(C34CC(C)(C3)C4)nc(C3CC(C)OC(c4cnn(C5CC5)c4)C3)cc2n1] |
| I-1111 | 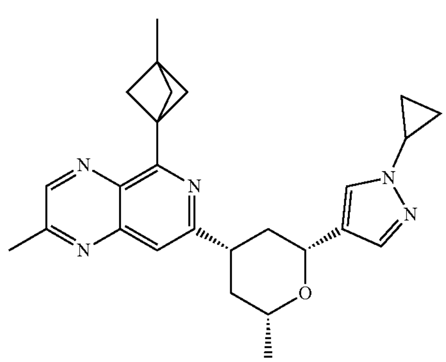 [SMILES: Cc1cnc2c(C34CC(C)(C3)C4)nc([C@H]3C[C@@H](C)O[C@@H](c4cnn(C5CC5)c4)C3)cc2n1] |
| I-1112 | |
| I-1113 | |
| I-1114 | |
| I-1115 | |

TABLE A-continued

Exemplary Compounds

| I-# | Structure |
| --- | --- |
| I-1116 | 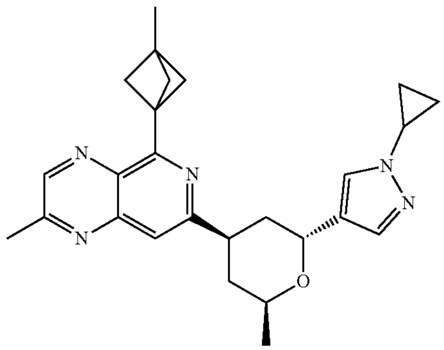 [SMILES: Cc1cnc2c(C34CC(C)(C3)C4)nc([C@@H]3C[C@H](C)O[C@@H](c4cnn(C5CC5)c4)C3)cc2n1] |
| I-1117 | 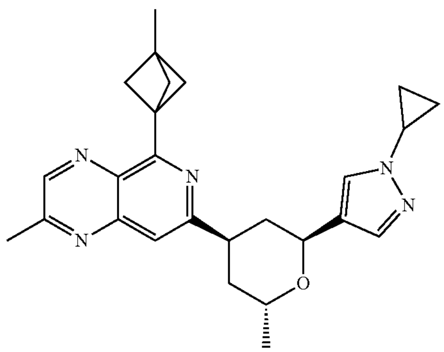 [SMILES: Cc1cnc2c(C34CC(C)(C3)C4)nc([C@@H]3C[C@@H](C)O[C@H](c4cnn(C5CC5)c4)C3)cc2n1] |
| I-1118 | 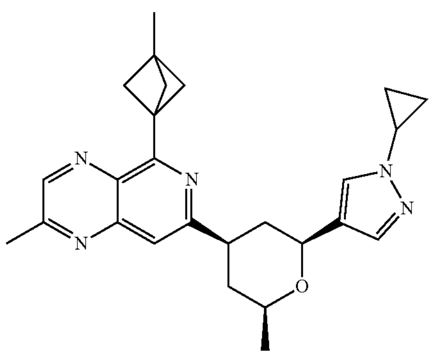 [SMILES: Cc1cnc2c(C34CC(C)(C3)C4)nc([C@H]3C[C@@H](c4cnn(C5CC5)c4)O[C@@H](C)C3)cc2n1] |
| I-1119 | 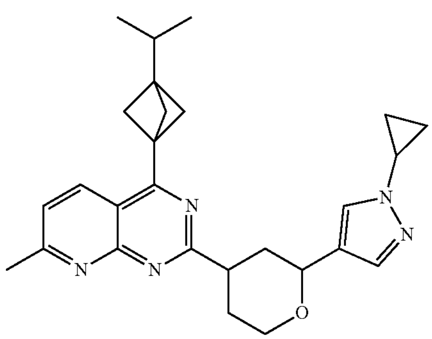 [SMILES: Cc1ccc2c(C34CC(C(C)C)(C3)C4)nc(C3CCOC(c4cnn(C5CC5)c4)C3)nc2n1] |
| I-1120 | |
| I-1121 | |
| I-1122 | |
| I-1123 | |

TABLE A-continued

Exemplary Compounds

| I-# | Structure |
|---|---|
| I-1124 | 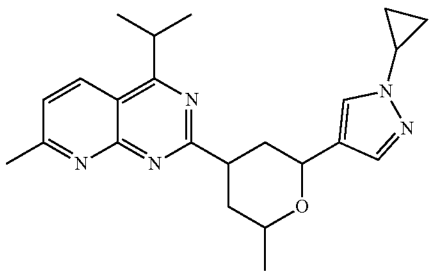 [SMILES: Cc1ccc2c(C(C)C)nc(C3CC(C)OC(c4cnn(C5CC5)c4)C3)nc2n1] |
| I-1125 | 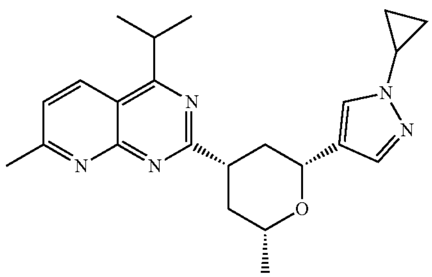 [SMILES: Cc1ccc2c(C(C)C)nc([C@H]3C[C@@H](C)O[C@@H](c4cnn(C5CC5)c4)C3)nc2n1] |
| I-1126 | 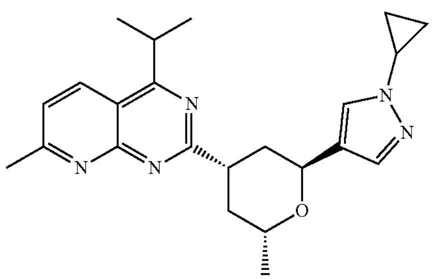 [SMILES: Cc1ccc2c(C(C)C)nc([C@H]3C[C@@H](C)O[C@H](c4cnn(C5CC5)c4)C3)nc2n1] |
| I-1127 | 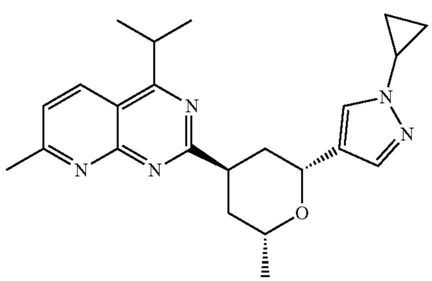 [SMILES: Cc1ccc2c(C(C)C)nc([C@@H]3C[C@@H](C)O[C@@H](c4cnn(C5CC5)c4)C3)nc2n1] |
| I-1128 | 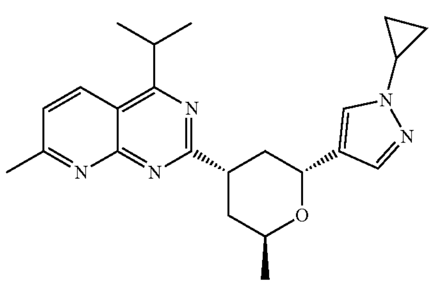 [SMILES: Cc1ccc2c(C(C)C)nc([C@H]3C[C@H](C)O[C@@H](c4cnn(C5CC5)c4)C3)nc2n1] |
| I-1129 | 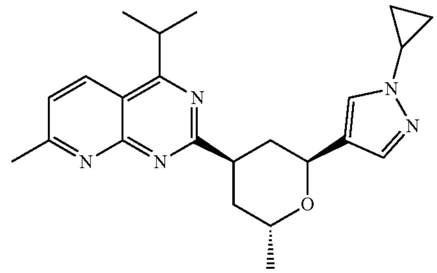 [SMILES: Cc1ccc2c(C(C)C)nc([C@@H]3C[C@@H](C)O[C@H](c4cnn(C5CC5)c4)C3)nc2n1] |
| I-1130 | 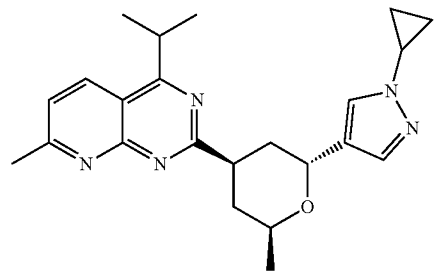 [SMILES: Cc1ccc2c(C(C)C)nc([C@@H]3C[C@H](C)O[C@@H](c4cnn(C5CC5)c4)C3)nc2n1] |
| I-1131 | 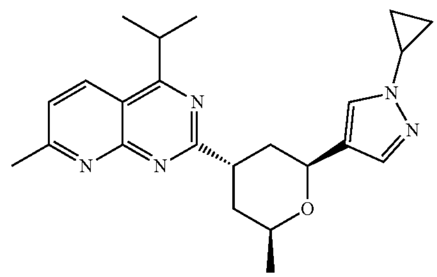 [SMILES: Cc1ccc2c(C(C)C)nc([C@@H]3C[C@@H](c4cnn(C5CC5)c4)O[C@@H](C)C3)nc2n1] |
| I-1132 | 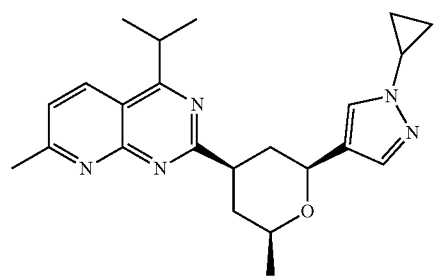 [SMILES: Cc1ccc2c(C(C)C)nc([C@H]3C[C@@H](c4cnn(C5CC5)c4)O[C@@H](C)C3)nc2n1] |

In some embodiments, the present invention provides a compound as depicted in Table A or a pharmaceutically acceptable salt thereof.

The foregoing merely summarizes certain aspects of this disclosure and is not intended, nor should it be construed, as limiting the disclosure in any way.

FORMULATION AND ROUTE OF ADMINISTRATION

While it may be possible to administer a compound disclosed herein alone in the uses described, the compound administered normally will be present as an active ingredient in a pharmaceutical composition. Thus, in one embodiment, provided herein is a pharmaceutical composition comprising a compound disclosed herein in combination with one or more pharmaceutically acceptable excipients, such as diluents, carriers, adjuvants and the like, and, if desired, other active ingredients. See, e.g., Remington: The Science and Practice of Pharmacy, Volume I and Volume II, twenty-second edition, edited by Loyd V. Allen Jr., Philadelphia, PA, Pharmaceutical Press, 2012; Pharmaceutical Dosage Forms (Vol. 1-3), Liberman et al., Eds., Marcel Dekker, New York, NY, 1992; Handbook of Pharmaceutical Excipients (3rd Ed.), edited by Arthur H. Kibbe, American Pharmaceutical Association, Washington, 2000; Pharmaceutical Formulation: The Science and Technology of Dosage Forms (Drug Discovery), first edition, edited by GD Tovey, Royal Society of Chemistry, 2018. In one embodiment, a pharmaceutical composition comprises a therapeutically effective amount of a compound disclosed herein.

The compound(s) disclosed herein may be administered by any suitable route in the form of a pharmaceutical composition adapted to such a route and in a dose effective for the treatment intended. The compounds and compositions presented herein may, for example, be administered orally, mucosally, topically, transdermally, rectally, pulmonarily, parentally, intranasally, intravascularly, intravenously, intraarterial, intraperitoneally, intrathecally, subcutaneously, sublingually, intramuscularly, intrasternally, vaginally or by infusion techniques, in dosage unit formulations containing conventional pharmaceutically acceptable excipients.

The pharmaceutical composition may be in the form of, for example, a tablet, chewable tablet, minitablet, caplet, pill, bead, hard capsule, soft capsule, gelatin capsule, granule, powder, lozenge, patch, cream, gel, sachet, microneedle array, syrup, flavored syrup, juice, drop, injectable solution, emulsion, microemulsion, ointment, aerosol, aqueous suspension, or oily suspension. The pharmaceutical composition is typically made in the form of a dosage unit containing a particular amount of the active ingredient.

Provided herein as Embodiment 179 is a pharmaceutical composition comprising the compound according to any one of Embodiments 1-178, or a tautomer thereof, or a pharmaceutically acceptable salt of said compound or said tautomer, and a pharmaceutically acceptable excipient.

Provided herein as Embodiment 180 is a compound according to any one of Embodiments 1-178, or a tautomer thereof, or a pharmaceutically acceptable salt of said compound or said tautomer, or the pharmaceutical composition according to Embodiment 179 for use as a medicament.

Pharmaceutically Acceptable Compositions

According to some embodiments, the present disclosure provides a composition comprising a compound of this disclosure or a pharmaceutically acceptable derivative thereof and a pharmaceutically acceptable carrier, adjuvant, or vehicle. The amount of compound in compositions of this disclosure is such that it is effective to measurably activate a TREM2 protein, or a mutant thereof, in a biological sample or in a patient. In certain embodiments, the amount of compound in compositions of this disclosure is such that it is effective to measurably activate a TREM2 protein, or a mutant thereof, in a biological sample or in a patient. In certain embodiments, a composition of this disclosure is formulated for administration to a patient in need of such composition. In some embodiments, a composition of this disclosure is formulated for oral administration to a patient.

Compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of compounds of the present disclosure that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

METHODS OF USE

As discussed herein (see, section entitled "Definitions"), the compounds described herein are to be understood to include all stereoisomers, tautomers, or pharmaceutically acceptable salts of any of the foregoing or solvates of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals and farm animals, including mammals, rodents, and the like. For example, animals including horses, dogs, and cats may be treated with compounds provided herein.

Without wishing to be bound by any particular theory, the following is noted: TREM2 has been implicated in several myeloid cell processes, including phagocytosis, proliferation, survival, and regulation of inflammatory cytokine production. Ulrich and Holtzman 2016. In the last few years, TREM2 has been linked to several diseases. For instance, mutations in both TREM2 and DAP12 have been linked to the autosomal recessive disorder Nasu-Hakola Disease, which is characterized by bone cysts, muscle wasting and demyelination phenotypes. Guerreiro et al. 2013. More recently, variants in the TREM2 gene have been linked to increased risk for Alzheimer's disease (AD) and other forms of dementia including frontotemporal dementia. Jonsson et al. 2013, Guerreiro, Lohmann et al. 2013, and Jay, Miller et al. 2015. In particular, the R47H variant has been identified in genome-wide studies as being associated with increased risk for late-onset AD with an overall adjusted odds ratio (for populations of all ages) of 2.3, second only to the strong genetic association of ApoE to Alzheimer's. The R47H mutation resides on the extracellular Ig V-set domain of the TREM2 protein and has been shown to impact lipid binding and uptake of apoptotic cells and Abeta (Wang et al. 2015; Yeh et al. 2016), suggestive of a loss-of-function linked to disease. Further, postmortem comparison of AD patients' brains with and without the R47H mutation are supportive of a novel loss-of-microglial barrier function for the carriers of the mutation, with the R47H carrier microglia putatively demonstrating a reduced ability to compact plaques and limit their spread. Yuan et al. 2016. Impairment in microgliosis has been reported in animal models of prion disease, multiple sclerosis, and stroke, suggesting that TREM2 may play an important role in supporting microgliosis in response to pathology or damage in the central nervous system. Ulrich and Holtzman 2016. In addition, knockdown of TREM2 has been shown to aggravate a-syn-induced inflammatory responses in vitro and exacerbate dopaminergic neuron loss in response to AAV-SYN in vivo (a model of Parkinson's disease), suggesting that impaired microglial TREM2 signaling exacerbates neurodegeneration by modulating microglial activation states. Guo et. al. 2019. A variety of animal models also suggest that Toll-Like Receptor (TLR) signaling is important in the pathogenesis of Rheumatoid Arthritis (RA) via persistent expression of pro-inflammatory cytokines by macrophages. Signaling through TREM2/DAP12 inhibits TLR responses by reducing MAPK (Erk1/2) activation, suggesting that TREM2 activation may act as a negative regulator of TLR driven RA pathogenesis. Huang and Pope 2009.

In view of the data indicating that deficits in TREM2 activity affect macrophage and microglia function, the compounds disclosed herein are of particular use in disorders, such as those described above and in the embodiments that follow and in neurodegenerative disorders more generally.

Provided herein as Embodiment 181 is a compound according to any one of Embodiments 1-178, or a tautomer thereof, or a pharmaceutically acceptable salt of said compound or said tautomer, or the pharmaceutical composition according to Embodiment 179 for use in treating or preventing a condition associated with a loss of function of human TREM2.

Provided herein as Embodiment 182 is a compound according to any one of Embodiments 1-178, or a tautomer thereof, or a pharmaceutically acceptable salt of said compound or said tautomer, or the pharmaceutical composition according to Embodiment 179 for use in treating or preventing Parkinson's disease, rheumatoid arthritis, Alzheimer's disease, Nasu-Hakola disease, frontotemporal dementia, multiple sclerosis, prion disease, or stroke.

Provided herein as Embodiment 183 is a use of the compound according to any one of Embodiments 1-178, or a tautomer thereof, or a pharmaceutically acceptable salt of said compound or said tautomer, or the pharmaceutical composition according to Embodiment 179 in the preparation of a medicament for treating or preventing a condition associated with a loss of function of human TREM2.

Provided herein as Embodiment 184 is a use of the compound according to any one of Embodiments 1-178, or a tautomer thereof, or a pharmaceutically acceptable salt of said compound or said tautomer, or the pharmaceutical composition according to Embodiment 179 in the preparation of a medicament for treating or preventing Parkinson's disease, rheumatoid arthritis, Alzheimer's disease, Nasu-Hakola disease, frontotemporal dementia, multiple sclerosis, prion disease, or stroke.

Provided herein as Embodiment 185 is a method of treating or preventing a condition associated with a loss of function of human TREM2 in a subject in need thereof, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179.

Provided herein as Embodiment 186 is a method of treating or preventing Parkinson's disease, rheumatoid arthritis, Alzheimer's disease, Nasu-Hakola disease, frontotemporal dementia, multiple sclerosis, prion disease, or stroke in a subject in need thereof, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179.

In some embodiments, the condition associated with a loss of function of human TREM2 is Parkinson's disease. In some embodiments, the condition associated with a loss of function of human TREM2 is rheumatoid arthritis. In some embodiments, the condition associated with a loss of function of human TREM2 is Alzheimer's disease. In some embodiments, the condition associated with a loss of function of human TREM2 is Nasu-Hakola disease. In some embodiments, the condition associated with a loss of function of human TREM2 is frontotemporal dementia. In some embodiments, the condition associated with a loss of function of human TREM2 is multiple sclerosis. In some embodiments, the condition associated with a loss of function of human TREM2 is prion disease. In some embodiments, the condition associated with a loss of function of human TREM2 is stroke.

CSF1R

CSF1R is a cell-surface receptor primarily for the cytokine colony stimulating factor 1 (CSF-1), also known until recently as macrophage colony-stimulating factor (M-CSF), which regulates the survival, proliferation, differentiation and function of mononuclear phagocytic cells, including microglia of the central nervous system. CSF1R is composed of a highly glycosylated extracellular ligand-binding domain, a trans-membrane domain and an intracellular tyrosine-kinase domain. Binding of CSF-1 to CSF1R results in the formation of receptor homodimers and subsequent autophosphorylation of several tyrosine residues in the cytoplasmic domain, notably Syk. In the brain, CSF1R is predominantly expressed in microglial cells. It has been found that microglia in CSF1R +/− patients are depleted and show increased apoptosis (Oosterhof et al., 2018).

The present invention relates to the unexpected discovery that administration of a TREM2 agonist can rescue the loss of microglia in cells having mutations in CSF1R. It has been previously shown that TREM2 agonist antibody 4D9 increases ATP luminescence (a measure of cell number and activity) in a dose dependent manner when the levels of M-CSF in media are reduced to 5 ng/mL (Schlepckow et al, EMBO Mol Med., 2020) and that TREM2 agonist AL002c increases ATP luminescence when M-CSF is completely removed from the media (Wang et al, J. Exp. Med.; 2020, 217(9): e20200785). This finding suggests that TREM2 agonism can compensate for deficiency in CSF1R signaling caused by a decrease in the concentration of its ligand. In a 5xFAD murine Alzheimer's disease model of amyloid pathology, doses of a CSF1R inhibitor that almost completely eliminate microglia in the brains of wild-type animals show surviving microglia clustered around the amyloid plaques (Spangenberg et al, Nature Communications 2019). Plaque amyloid has been demonstrated in the past to be a ligand for TREM2, and it has been shown that microglial engagement with amyloid is dependent on TREM2 (Condello et al, Nat Comm., 2015). The present invention relates to the unexpected discovery that it is activation of TREM2 that rescued the microglia in the presence of the CSF1R inhibitor, and that this effect is also observed in patients suffering from loss of microglia due to CSF1R mutation. This discovery has not been previously taught or suggested in the available art.

To date, no prior study has shown that TREM2 agonism can rescue the loss of microglia in cells where mutations in the CSF1R kinase domain reduce CSF1R activity, rather than the presence of a CSF1R inhibitor or a deficiency in CSF1R ligand. Furthermore, no prior study has taught or suggested that reversal of the loss of microglia due to a CSF1R mutation through TREM2 agonism can be used to treat a disease or disorder caused by and/or associated with a CSF1R mutation.

Adult-onset leukoencephalopathy with axonal spheroids and pigmented glia (ALSP), previously recognized as hereditary diffuse leukoencephalopathy with axonal spheroids (HDLS) or pigmentary orthochromatic leukodystrophy (POLD), is an autosomal-dominant central nervous system disease that manifests in the form of variable behavioral, cognitive and motor function changes in patients suffering from the disease. ALSP is characterized by patchy cerebral white matter abnormalities visible by magnetic resonance imaging. However, the clinical symptoms and MRI changes are not specific to ALSP and are common for other neurological conditions, including Nasu-Hakola disease (NHD) and AD, making diagnosis and treatment of ALSP very difficult.

Recent studies have discovered that ALSP is a Mendelian disorder in which patients carry a heterozygous loss of function mutation in the kinase domain of CSF1R, suggesting a reduced level of signaling on the macrophage colony-stimulating factor (M-CSF)/CSF1R axis (Rademakers et al, Nat Genet 2012; Konno et al, Neurology 2018). In one aspect, the present invention relates to the surprising discovery that activation of the TREM2 pathway can rescue the loss of microglia in CSF1R +/− ALSP patients, preventing microglia apoptosis, thereby treating the ALSP condition.

Provided herein as Embodiment 187 is a compound according to any one of Embodiments 1-178, or a tautomer thereof, or a pharmaceutically acceptable salt of said compound or said tautomer, or the pharmaceutical composition according to Embodiment 179 for use in treating or preventing a condition associated with dysfunction of Colony stimulating factor 1 receptor (CSF1R, also known as macrophage colony-stimulating factor receptor/M-CSFR, or cluster of differentiation 115/CD115).

Provided herein as Embodiment 188 is a compound according to any one of Embodiments 1-178, or a tautomer thereof, or a pharmaceutically acceptable salt of said compound or said tautomer, or the pharmaceutical composition according to Embodiment 179 for use in treating or preventing adult-onset leukoencephalopathy with axonal spheroids and pigmented glia (ALSP), hereditary diffuse leukoencephalopathy with axonal spheroids (HDLS), pigmentary orthochromatic leukodystrophy (POLD), pediatric-onset leukoencephalopathy, congenital absence of microglia, or brain abnormalities neurodegeneration and dysosteosclerosis (BANDDOS).

Provided herein as Embodiment 189 is a use of the compound according to any one of Embodiments 1-178, or a tautomer thereof, or a pharmaceutically acceptable salt of said compound or said tautomer, or the pharmaceutical composition according to Embodiment 179 in the preparation of a medicament for treating or preventing a condition associated with dysfunction of CSF1R.

Provided herein as Embodiment 190 is a use of the compound according to any one of Embodiments 1-178, or a tautomer thereof, or a pharmaceutically acceptable salt of said compound of said tautomer, or the pharmaceutical composition according to Embodiment 179 in the preparation of a medicament for treating or preventing adult-onset leukoencephalopathy with axonal spheroids and pigmented glia (ALSP), hereditary diffuse leukoencephalopathy with axonal spheroids (HDLS), pigmentary orthochromatic leukodystrophy (POLD), pediatric-onset leukoencephalopathy, congenital absence of microglia, or brain abnormalities neurodegeneration and dysosteosclerosis (BANDDOS).

Provided herein as Embodiment 191 is a method of treating or preventing a disease or disorder associated with dysfunction of CSF1R in a subject in need thereof, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179. In some embodiments, the subject is selected for treatment based on a diagnosis that includes the presence of a mutation in a CSF1R gene affecting the function of CSF1R. In some embodiments, the mutation in the CSF1R gene is a mutation that causes a decrease in CSF1R activity or a cessation of CSF1R activity. In some embodiments, the disease or disorder is caused by a heterozygous CSF1R mutation. In some embodiments, the disease or disorder is caused by a homozygous CSF1R mutation. In some embodiments, the disease or disorder is caused by a splice mutation in the csf1r gene. In some embodiments, the disease or disorder is caused by a missense mutation in the csf1r gene. In some embodiments, the disease or disorder is caused by a mutation in the catalytic kinase domain of CSF1R. In some embodiments, the disease or disorder is caused by a mutation in an immunoglobulin domain of CSF1R. In some embodiments, the disease or disorder is caused by a mutation in the ectodomain of CSF1R. In some embodiments, the disease or disorder is a disease or disorder resulting from a change (e.g. increase, decrease or cessation) in the activity of CSF1R. In some embodiments, the disease or disorder is a disease or disorder resulting from a decrease or cessation in the activity of CSF1R. CSF1R related activities that are changed in the disease or disorder include, but are not limited to: decrease or loss of microglia function; increased microglia apoptosis; decrease in Src signaling; decrease in Syk signaling; decreased microglial proliferation; decreased microglial response to cellular debris; decreased phagocytosis; and decreased release of cytokines in response to stimuli. In some embodiments, the disease or disorder is caused by a loss-of-function mutation in CSF1R. In some embodiments, the loss-of-function mutation results in a complete cessation of CSF1R function. In some embodiments, the loss-of-function mutation results in a partial loss of CSF1R function, or a decrease in CSF1R activity.

Provided herein as Embodiment 192 is a method of treating or preventing adult-onset leukoencephalopathy with axonal spheroids and pigmented glia (ALSP), hereditary diffuse leukoencephalopathy with axonal spheroids (HDLS), pigmentary orthochromatic leukodystrophy (POLD), pediatric-onset leukoencephalopathy, congenital absence of microglia, or brain abnormalities neurodegeneration and dysosteosclerosis (BANDDOS) in a subject in need thereof, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179. In some embodiments, the method treats or prevents ALSP, which is an encompassing and superseding name for both HDLS and POLD. In some embodiments, the disease or disorder is a homozygous mutation in CSF1R. In some embodiments, the method treats or prevents pediatric-onset leukoencephalopathy. In some embodiments, the method treats or prevents congenital absence of microglia. In some embodiments, the method treats or prevents brain abnormalities neurodegeneration and dysosteosclerosis (BANDDOS).

Provided herein as Embodiment 193 is a method of treating or preventing Nasu-Hakola disease, Alzheimer's disease, frontotemporal dementia, multiple sclerosis, Guillain-Bane syndrome, amyotrophic lateral sclerosis (ALS), Parkinson's disease, traumatic brain injury, spinal cord injury, systemic lupus erythematosus, rheumatoid arthritis, prion disease, stroke, osteoporosis, osteopetrosis, osteosclerosis, skeletal dysplasia, dysosteoplasia, Pyle disease, cerebral autosomal dominant arteriopathy with subcortical infarcts and leukoencephalopathy, cerebral autosomal recessive arteriopathy with subcortical infarcts and leukoencephalopathy, cerebroretinal vasculopathy, or metachromatic leukodystrophy wherein any of the aforementioned diseases or disorders are present in a patient exhibiting CSF1R dysfunction, or having a mutation in a gene affecting the function of CSF1R, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179.

ABCD1

The ABCD1 gene provides instructions for producing the adrenoleukodystrophy protein (ALDP). ABCD1 (ALDP) maps to Xq28. ABCD1 is a member of the ATP-binding cassette (ABC) transporter superfamily. The superfamily contains membrane proteins that translocate a wide variety of substrates across extra- and intracellular membranes, including metabolic products, lipids and sterols, and drugs.

ALDP is located in the membranes of cell structures called peroxisomes. Peroxisomes are small sacs within cells that process many types of molecules. ALDP brings a group of fats called very long-chain fatty acids (VLCFAs) into peroxisomes, where they are broken down. As ABCD1 is highly expressed in microglia, it is possible that microglial dysfunction and their close interaction with other cell types actively participates in neurodegenerative processes (Gong et al., Annals of Neurology. 2017; 82(5):813-827.). It has been shown that severe microglia loss and damage is an early feature in patients with cerebral form of x-linked ALD (cALD) carrying ABCD1 mutations (Bergner et al., Glia. 2019; 67:1196-1209). It has also been shown that ABCD1-deficiency leads to an impaired plasticity of myeloid lineage cells that is reflected in incomplete establishment of anti-inflammatory responses, thus possibly contributing to the devastating rapidly progressive demyelination in cerebral adrenoleukodystrophy (Weinhor et al., BRAIN 2018:141; 2329-2342). These findings emphasize microglia/monocytes/macrophages as crucial therapeutic targets for preventing or stopping myelin destruction in patients with X-linked adrenoleukodystrophy.

The present invention relates to the unexpected discovery that administration of a TREM2 agonist can rescue the loss of microglia in cells having mutations in the ABCD1 gene. It has been previously shown that TREM2 agonist antibody 4D9 increases ATP luminescence (a measure of cell number and activity) in a dose dependent manner when the levels of M-CSF in media are reduced to 5 ng/mL (Schlepckow et al, EMBO Mol Med., 2020) and that TREM2 agonist AL002c increases ATP luminescence when M-CSF is completely removed from the media (Wang et al, J. Exp. Med.; 2020, 217(9):e20200785). This finding suggests that TREM2 agonism can compensate for deficiency in ABCD1 function leading to sustained activation, proliferation, chemotaxis of microglia, maintenance of anti-inflammatory environment and reduced astrocytosis caused by a decrease in ABCD1 and accumulation of VLCFAs. The present invention relates to the unexpected discovery that activation of TREM2 can rescue the microglia in the presence of the ABCD1 mutation and an increase in VLCFA, and that this effect may be also observed in patients suffering from loss of microglia due to ABCD1 mutation. This discovery has not been previously taught or suggested in the available art.

To date, no prior study has shown that TREM2 agonism can rescue the loss of microglia in cells where mutations in the ABCD1 and a VLCFA increase is present. No prior study has taught or suggested that reversal of the loss of microglia due to an ABCD1 mutation through TREM2 agonism can be used to treat a disease or disorder caused by and/or associated with an ABCD1 mutation.

Provided herein as Embodiment 194 is a compound according to any one of Embodiments 1-178, or a tautomer thereof, or a pharmaceutically acceptable salt of said compound or said tautomer, or the pharmaceutical composition according to Embodiment 179 for use in treating or preventing a condition associated with dysfunction of ATP-binding cassette transporter 1 (ABCD1).

Provided herein as Embodiment 195 is a compound according to any one of Embodiments 1-178, or a tautomer thereof, or a pharmaceutically acceptable salt of said compound or said tautomer, or the pharmaceutical composition according to Embodiment 179 for use in treating or preventing X-linked adrenoleukodystrophy (x-ALD), Globoid cell leukodystrophy (also known as Krabbe disease), Metachromatic leukodystrophy (MLD), Cerebral autosomal dominant arteriopathy with subcortical infarcts and leukoencephalopathy (CADASIL), Vanishing white matter disease (VWM), Alexander disease, fragile X-associated tremor ataxia syndrome (FXTAS), adult-onset autosomal dominant leukodystrophy (ADLD), and X-linked Charcot-Marie-Tooth disease (CMTX).

Provided herein as Embodiment 196 is a use of the compound according to any one of Embodiments 1-178, or a tautomer thereof, or a pharmaceutically acceptable salt of said compound or said tautomer, or the pharmaceutical composition according to Embodiment 179 in the preparation of a medicament for treating or preventing a condition associated with dysfunction of ABCD1.

Provided herein as Embodiment 197 is a use of the compound according to any one of Embodiments 1-178, or a tautomer thereof, or a pharmaceutically acceptable salt of said compound or said tautomer, or the pharmaceutical composition according to Embodiment 179 in the preparation of a medicament for treating or preventing X-linked adrenoleukodystrophy (x-ALD), Globoid cell leukodystrophy (also known as Krabbe disease), Metachromatic leukodystrophy (MLD), Cerebral autosomal dominant arteriopathy with subcortical infarcts and leukoencephalopathy (CADASIL), Vanishing white matter disease (VWM), Alexander disease, fragile X-associated tremor ataxia syndrome (FXTAS), adult-onset autosomal dominant leukodystrophy (ADLD), and X-linked Charcot-Marie-Tooth disease (CMTX).

Provided herein as Embodiment 198 is a method of treating or preventing a disease or disorder associated with dysfunction of ABCD1 in a subject in need thereof, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179. In some embodiments, the patient is selected for treatment based on a diagnosis that includes the presence of a mutation in an ABCD1 gene affecting the function of ABCD1. In some embodiments, the mutation in the ABCD1 gene is a mutation that causes a decrease in ABCD1 activity or a cessation of ABCD1 activity. In some embodiments, the disease or disorder is caused by a heterozygous ABCD1 mutation. In some embodiments, the disease or disorder is caused by a homozygous ABCD1 mutation. In some embodiments, the disease or disorder is caused by a splice mutation in the ABCD1 gene. In some embodiments, the disease or disorder is caused by a missense mutation in the ABCD1 gene. In some embodiments, the disease or disorder is a disease or disorder resulting from a change (e.g. increase, decrease or cessation) in the activity of ABCD1. In some embodiments, the disease or disorder is a disease or disorder resulting from a decrease or cessation in the activity of ABCD1. ABCD1 related activities that are changed in the disease or disorder include, but are not limited to peroxisomal import of fatty acids and/or fatty acyl-CoAs and production of adrenoleukodystrophy protein (ALDP). In some embodiments, the disease or disorder is caused by a loss-of-function mutation in ABCD1. In some embodiments, the loss-of-function mutation results in a complete cessation of ABCD1 function. In some embodiments, the loss-of-function mutation results in a partial loss of ABCD1 function, or a decrease in ABCD1 activity. In some embodiments, the disease or disorder is caused by a homozygous mutation in ABCD1. In some embodiments, the disease or disorder is a neurodegenerative disorder. In some embodiments, the disease or disorder is a neurodegenerative disorder caused by and/or associated with an ABCD1 dysfunction. In some embodiments, the disease or disorder is an immunological disorder. In some embodiments, the disease or disorder is an immunological disorder caused by and/or associated with an ABCD1 dysfunction.

Provided herein as Embodiment 199 is a method of treating or preventing X-linked adrenoleukodystrophy (x-ALD), Globoid cell leukodystrophy (also known as Krabbe disease), Metachromatic leukodystrophy (MLD), Cerebral autosomal dominant arteriopathy with subcortical infarcts and leukoencephalopathy (CADASIL), Vanishing white matter disease (VWM), Alexander disease, fragile X-associated tremor ataxia syndrome (FXTAS), adult-onset autosomal dominant leukodystrophy (ADLD), and X-linked Charcot-Marie-Tooth disease (CMTX) in a subject in need thereof, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179. In some embodiments, any of the aforementioned diseases are present in a patient exhibiting ABCD1 dysfunction or having a mutation in a gene affecting the function of ABCD1. In some embodiments, the method treats or prevents X-linked adrenoleukodystrophy (x-ALD). In some embodiments, the x-ALD is a cerebral form of x-linked ALD (cALD). In some embodiments, the method treats or prevents Addison disease wherein the patient has been found to have a mutation in one or more ABCD1 genes affecting ABCD1 function. In some embodiments, the method treats or prevents Addison disease, wherein the patient has a loss-of-function mutation in ABCD1.

Provided herein as Embodiment 200 is a method of treating or preventing Nasu-Hakola disease, Alzheimer's disease, frontotemporal dementia, multiple sclerosis, Guillain-Barre syndrome, amyotrophic lateral sclerosis (ALS), or Parkinson's disease, wherein any of the aforementioned diseases or disorders are present in a patient exhibiting ABCD1 dysfunction, or having a mutation in a gene affecting the function of ABCD1, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179.

Autism Spectrum Disorders

It has been found that TREM2 deficient mice exhibit symptoms reminiscent of autism spectrum disorders (ASDs) (Filipello et al., Immunity, 2018, 48, 979-991). It has also been found that microglia depletion of the autophagy Aatg7 gene results in defective synaptic pruning and results in increased dendritic spine density, and abnormal social interaction and repetitive behaviors indicative of ASDs (Kim, et al., Molecular Psychiatry, 2017, 22, 1576-1584.). Further studies have shown that increased dendritic spin density detected in post-mortem ASD brains, likely caused by defective synaptic pruning, results in circuit hypoconnectivity and behavioral defects and are a potential origin of a number of neurodevelopmental diseases (Tang, et al., Neuron, 2014, 83, 1131-1143). Without intending to be limited to any particular theory, these findings suggest that TREM2 activation can reverse microglia depletion, and therefore correct the defective synaptic pruning that is central to neurodevelopmental diseases such as ASDs. The present invention relates to the unexpected discovery that activation of TREM2, using a compound of the present invention, can rescue microglia in subjects suffering from an ASD. This discovery has not been previously taught or suggested in the available art.

Provided herein as Embodiment 201 is a compound according to any one of Embodiments 1-178, or a tautomer thereof, or a pharmaceutically acceptable salt of said compound or said tautomer, or the pharmaceutical composition according to Embodiment 179 for use in treating autism or autism spectrum disorders.

Provided herein as Embodiment 202 is a use of the compound according to any one of Embodiments 1-178, or a tautomer thereof, or a pharmaceutically acceptable salt of said compound or said tautomer, or the pharmaceutical composition according to Embodiment 179 in the preparation of a medicament for treating autism or autism spectrum disorders.

Provided herein as Embodiment 203 is a method of treating autism or autism spectrum disorders in a subject in need thereof, the method comprising administering to the subject a therapeutically effective amount of the compound according to any one of Embodiments 1-178, or a tautomer thereof, or a pharmaceutically acceptable salt of said compound or said tautomer, or the pharmaceutical composition according to Embodiment 179. In some embodiments, the method treats autism. In some embodiments, the method treats Asperger syndrome.

In some embodiments, the disclosure provides a method of increasing the activity of TREM2, the method comprising contacting a compound of the present disclosure, or a pharmaceutically acceptable salt thereof with the TREM2. In some embodiments, the contacting takes place in vitro. In some embodiments, the contacting takes place in vivo. In some embodiments, the TREM2 is human TREM2.

Combination Therapies

Depending upon the particular condition, or disease, to be treated, additional therapeutic agents, which are normally administered to treat that condition, may be administered in combination with compounds and compositions of this disclosure. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this disclosure may also be combined with include, without limitation: treatments for Parkinson's disease, rheumatoid arthritis, Alzheimer's disease, Nasu-Hakola disease, frontotemporal dementia, multiple sclerosis, prion disease, or stroke.

As used herein, the term "combination," "combined," and related terms refers to the simultaneous or sequential administration of therapeutic agents in accordance with this disclosure. For example, a combination of the present disclosure may be administered with another therapeutic agent simultaneously or sequentially in separate unit dosage forms or together in a single unit dosage form.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the present disclosure, as part of a multiple dosage regimen. Alternatively, one or more other therapeutic agents may be part of a single dosage form, mixed together with a compound of this disclosure in a single composition. If administered as a multiple dosage regime, one or more other therapeutic agent and a compound or composition of the present disclosure may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the present disclosure are administered as a multiple dosage regimen within greater than 24 hours a parts.

In one embodiment, the present disclosure provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

DEFINITIONS

The following definitions are provided to assist in understanding the scope of this disclosure.

Unless otherwise indicated, all numbers expressing quantities of ingredients, reaction conditions, and so forth used in the specification or claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

As used herein, the following definitions shall apply unless otherwise indicated. For purposes of this disclosure, the chemical elements are identified in accordance with the Periodic Table of the Elements, CAS version, Handbook of Chemistry and Physics, $101^{st}$ Ed. Additionally, general principles of organic chemistry are described in "Organic Chemistry", Thomas Sorrell, University Science Books, Sausalito: 2005, and "March's Advanced Organic Chemistry: Reactions Mechanisms and Structure", $8^{th}$ Ed., Ed.: Smith, M.B., John Wiley & Sons, New York: 2019, the entire contents of which are hereby incorporated by reference.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, and atropoisomers. Accordingly, the scope of the instant disclosure is to be understood to encompass all possible stereoisomers of the illustrated compounds, including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers, or mixture of any of the foregoing) of any chemical structures disclosed herein (in whole or in part), unless the stereochemistry is specifically identified.

If the stereochemistry of a structure or a portion of a structure is not indicated with, for example, bold or dashed lines, the structure or portion of the structure is to be interpreted as encompassing all stereoisomers of it. If the stereochemistry of a structure or a portion of a structure is indicated with, for example, bold or dashed lines, the structure or portion of the structure is to be interpreted as encompassing only the stereoisomer indicated. For example, (1R)-1-methyl-2-(trifluoromethyl)cyclohexane is meant to encompass (1R,2R)-1-methyl-2-(trifluoromethyl)cyclohexane and (1R,2S)-1-methyl-2-(trifluoromethyl)cyclohexane. A bond drawn with a wavy line indicates that both stereoisomers are encompassed. This is not to be confused with a wavy line drawn perpendicular to a bond which indicates the point of attachment of a group to the rest of the molecule.

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of the other enantiomer and diastereomers of the compound. A typical stereoisomerically pure compound comprises greater than about 80% by weight of one stereoisomer of the compound and equal or less than about 20% by weight of other stereoisomers of the compound, greater than about 90% by weight of one stereoisomer of the compound and equal or less than about 10% by weight of the other stereoisomers of the compound, greater than about 95% by weight of one stereoisomer of the compound and equal or less than about 5% by weight of the other stereoisomers of the compound, or greater than about 97% by weight of one stereoisomer of the compound and equal or less than about 3% by weight of the other stereoisomers of the compound.

This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., Tetrahedron 33:2725; Eliel, Stereochemistry of Carbon Compounds (McGraw-Hill, NY, 1962); and Wilen, Tables of Resolving Agents and Optical Resolutions, page 268 (Eliel, Ed., Univ. of Notre Dame Press, Notre Dame, IN, 1972).

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example, the following is illustrative of tautomers of the compounds of Formula I, wherein Ring A together with the 6-membered ring system to which it is fused forms a bicyclic ring system of formula

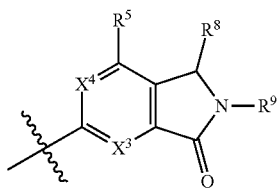

and wherein $R^9$ is H:

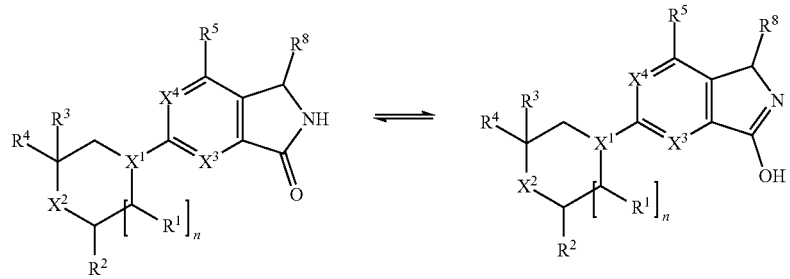

Accordingly, the scope of the instant disclosure is to be understood to encompass all tautomeric forms of the compounds disclosed herein.

Isotopically-Labelled Compounds

Further, the scope of the present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula I, for example, those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with isotopes such as deuterium ($^2$H or D) may afford certain therapeutic advantages resulting from greater metabolic stability, for example, increased in vivo half-life or reduced dosage requirements, and hence may be advantageous in some circumstances. Substitution with positron emitting isotopes, such as $^{11}$C, $^{18}$F, $^{15}$O and $^{13}$N, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Schemes and Examples using an appropriate isotopically-labelled reagent in place of the non-labelled reagent previously employed.

Solvates

As discussed above, the compounds disclosed herein and the stereoisomers, tautomers, and isotopically-labelled forms thereof or a pharmaceutically acceptable salt of any of the foregoing may exist in solvated or unsolvated forms.

The term "solvate" as used herein refers to a molecular complex comprising a compound or a pharmaceutically acceptable salt thereof as described herein and a stoichiometric or non-stoichiometric amount of one or more pharmaceutically acceptable solvent molecules. If the solvent is water, the solvate is referred to as a "hydrate."

Accordingly, the scope of the instant disclosure is to be understood to encompass all solvents of the compounds disclosed herein and the stereoisomers, tautomers and isotopically-labelled forms thereof or a pharmaceutically acceptable salt of any of the foregoing.

Miscellaneous Definitions

This section will define additional terms used to describe the scope of the compounds, compositions and uses disclosed herein.

The terms "$C_{1-3}$alkyl," "$C_{1-5}$alkyl," and "$C_{1-6}$alkyl" as used herein refer to a straight or branched chain hydrocarbon containing from 1 to 3, 1 to 5, and 1 to 6 carbon atoms, respectively. Representative examples of $C_{1-3}$alkyl, $C_{1-5}$alky, or $C_{1-6}$alkyl include, but are not limited to, methyl, ethyl, n-propyl, iso-propyl, n-butyl, sec-butyl, iso-butyl, tert-butyl, pentyl and hexyl.

The term "$C_{2-4}$alkenyl" as used herein refers to a saturated hydrocarbon containing 2 to 4 carbon atoms having at least one carbon-carbon double bond. Alkenyl groups include both straight and branched moieties. Representative examples of $C_{2-4}$alkenyl include, but are not limited to, 1-propenyl, 2-propenyl, 2-methyl-2-propenyl, and butenyl.

The term "$C_{3-6}$cycloalkyl" as used herein refers to a saturated carbocyclic molecule wherein the cyclic framework has 3 to 6 carbon atoms. Representative examples of $C_{3-5}$cycloalkyl include, but are not limited to, cyclopropyl, cyclobutyl, cyclopentyl, and cyclohexyl.

The terms "di$C_{1-3}$alkylamino" as used herein refer to —NR*R**, wherein R* and R** independently represent a $C_{1-3}$alkyl as defined herein. Representative examples of di$C_{1-3}$alkylamino include, but are not limited to, —N(CH$_3$)$_2$, —N(CH$_2$CH$_3$)$_2$, —N(CH$_3$)(CH$_2$CH$_3$), —N(CH$_2$CH$_2$CH$_3$)$_2$, and —N(CH(CH$_3$)$_2$)$_2$.

The term "$C_{1-3}$alkoxy" and "$C_{1-6}$alkoxy" as used herein refer to —OR$^{\#}$, wherein R$^{\#}$ represents a $C_{1-3}$alkyl and $C_{1-6}$alkyl group, respectively, as defined herein. Representative examples of $C_{1-3}$alkoxy or $C_{1-6}$alkoxy include, but are not limited to, methoxy, ethoxy, propoxy, iso-propoxy, and butoxy.

The term "halogen" as used herein refers to —F, —Cl, —Br, or —I.

The term "halo" as used herein as a prefix to another term for a chemical group refers to a modification of the chemical group, wherein one or more hydrogen atoms are substituted with a halogen as defined herein. The halogen is independently selected at each occurrence. For example, the term "$C_{1-6}$haloalkyl" refers to a $C_{1-6}$alkyl as defined herein, wherein one or more hydrogen atoms are substituted with a halogen. Representative examples of $C_{1-6}$haloalkyl include, but are not limited to, —CH$_2$F, —CHF$_2$, —CF$_3$, —CHFCl, —CH$_2$CF$_3$, —CFHCF$_3$, —CF$_2$CF$_3$, —CH(CF$_3$)$_2$, —CF(CHF$_2$)$_2$, and —CH(CH$_2$F)(CF$_3$). Further, the term "$C_{1-6}$haloalkoxy" for example refers to a $C_{1-6}$alkoxy as defined herein, wherein one or more hydrogen atoms are substituted with a halogen. Representative examples of $C_{1-6}$haloalkoxy include, but are not limited to, —OCH$_2$F, —OCHF$_2$, —OCF$_3$, —OCHFCl, —OCH$_2$CF$_3$, —OCFHCF$_3$, —OCF$_2$CF$_3$, —OCH(CF$_3$)$_2$, —OCF(CHF$_2$)$_2$, and —OCH(CH$_2$F)(CF$_3$).

The term "5-membered heteroaryl" or "6-membered heteroaryl" as used herein refers to a 5 or 6-membered carbon ring with two or three double bonds containing one ring heteroatom selected from N, S, and O and optionally one or two further ring N atoms instead of the one or more ring carbon atom(s). Representative examples of a 5-membered heteroaryl include, but are not limited to, furyl, imidazolyl, pyrazolyl, isoxazolyl, isothiazolyl, oxadiazolyl, and oxazolyl. Representative examples of a 6-membered heteroaryl include, but are not limited to, pyridyl, pyrimidyl, pyrazyl, and pyridazyl.

The term "$C_{3-6}$heterocycloalkyl" as used herein refers to a saturated carbocyclic molecule wherein the cyclic framework has 3 to 6 carbons and wherein one carbon atom is substituted with a heteroatom selected from N, O, and S. If the $C_{3-6}$heterocycloalkyl group is a $C_6$heterocycloalkyl, one or two carbon atoms are substituted with a heteroatom independently selected from N, O, and S. Representative examples of $C_{3-6}$heterocycloalkyl include, but are not limited to, aziridinyl, azetidinyl, oxetanyl, pyrrolidinyl, piperazinyl, morpholinyl, and thiomorpholinyl.

The term "$C_{5-8}$spiroalkyl" as used herein refers a bicyclic ring system, wherein the two rings are connected through a single common carbon atom. Representative examples of $C_{5-8}$spiroalkyl include, but are not limited to, spiro[2.2]pentanyl, spiro[3.2]hexanyl, spiro[3.3]heptanyl, spiro[3.4]octanyl, and spiro[2.5]octanyl.

The term "$C_{5-8}$tricycloalkyl" as used herein refers a tricyclic ring system, wherein all three cycloalkyl rings share the same two ring atoms. Representative examples of $C_{5-8}$tricycloalkyl include, but are not limited to, tricyclo[1.1.1.0$^{1,3}$]pentanyl,

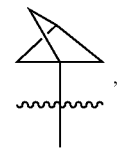 [SMILES: *C12CC(C1)C2]

tricyclo[2.1.1.0$^{1,4}$]hexanyl, tricyclo[3.1.1.0$^{1,5}$]hexanyl, and tricyclo[3.2.1.0$^{1,5}$]octanyl.

The term "aryl" used alone or as part of a larger moiety as in "aralkyl," "aralkoxy," or "aryloxyalkyl," refers to monocyclic or bicyclic ring systems having a total of 4 to 14 ring members, wherein at least one ring in the system is aromatic and wherein each ring in the system contains three to seven ring members. The term "aryl" may be used interchangeably with the term "aryl ring". In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" in the context of "heteroaryl" particularly includes, but is not limited to, nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. A heteroaryl ring may include one or more oxo (═O) or thioxo (═S) substituent. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As described herein, compounds of the present disclosure may contain "substituted" moieties. In general, the term "substituted" means that one or more hydrogens of the designated moiety are replaced with a suitable substituent. Unless otherwise indicated, an "optionally substituted" group may have a suitable substituent at one or more substitutable position of the group, and when more than one position in any given structure is substituted with more than one substituent selected from a specified group, the substituent may be either the same or different at every position. Combinations of substituents envisioned by the present disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., J. Pharm. Sci. 66(1):1-19 (1977). See also Stahl et al., Pharmaceutical Salts: Properties, Selection, and Use, 2$^{nd}$ Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "therapeutically effective amount" as used herein refers to that amount of a compound disclosed herein that will elicit the biological or medical response of a tissue, a system, or subject that is being sought by a researcher, veterinarian, medical doctor or other clinician.

The present disclosure includes Examples A3 and A4, wherein a compound of the present invention is tested for TREM2 target engagement in comparison to an anti-TREM2 antibody. Exemplary anti-TREM2 antibodies include those disclosed in PCT Application Publication WO2018/195506A1, which is incorporated by reference herein in its entirety. In some embodiments, anti-TREM2 antibodies comprise a heavy chain (HC) comprising a variable region (VH) having three complementarity determining regions (CDRs) referred to herein as VH-CDR1, VH-CDR2, and VH-CDR3, and a light chain (LC) comprising a variable region (VL) having three complementarity determining regions referred to herein as VL-CDR1, VL-CDR2, and VL-CDR3. In some embodiments, the amino acid sequences of the CDRs of an anti-TREM2 antibody comprise a VH-CDR1 having the amino acid sequence SYWIG (SEQ ID NO:1), a VH-CDR2 having the amino acid sequence IIYPG-DADARYSPSFQG (SEQ ID NO:2), a VH-CDR3 having the amino acid sequence RRQGIFGDALDF (SEQ ID NO:3), a VL-CDR1 having the amino acid sequence RASQSVSSNLA (SEQ ID NO:4), a VL-CDR2 having the amino acid sequence GASTRAT (SEQ ID NO:5), and a VL-CDR3 having the amino acid sequence LQDNNFPPT (SEQ ID NO:6). In some embodiments, an anti-TREM2 antibody comprises a VH chain corresponding in sequence to SEQ ID NO:7; and a VL chain corresponding in sequence to SEQ ID NO:8. In some embodiments, an anti-TREM2 antibody is Antibody Ab-1, comprising a heavy chain amino acid sequence according to SEQ ID NO:9, and a light chain amino acid sequence according to SEQ ID NO:10.

TABLE B

Anti-TREM2 Antibody Sequences

| Sequence Description | Amino Acid Sequence |
|---|---|
| VH Chain SEQ ID NO: 7 | EVQLVQSGAEVKKPGESLKISCKGSGYSFTSYWIG WVRQMPGKGLEWMGIIYPGDADARYSPSFQGQVTI SADKSISTAYLQWSSLKASDTAMYFCARRRQGIFG DALDFWGQGTLVTVSS |
| VL Chain SEQ ID NO: 8 | EIVMTQSPATLSVSPGERATLSCRASQSVSSNLAW FQQKPGQAPRLLIYGASTRATGIPARFSGSGSGTE FTLTISSLQPEDFAVYYCLQDNNFPPTFGQGTKVD IK |
| Ab-1 HC SEQ ID NO: 9 | EVQLVQSGAEVKKPGESLKISCKGSGYSFTSYWIG WVRQMPGKGLEWMGIIYPGDADARYSPSFQGQVTI SADKSISTAYLQWSSLKASDTAMYFCARRRQGIFG DALDFWGQGTLVTVSSAKTTPPSVYPLAPGSAAQT NSMVTLGCLVKGYFPEPVTVTWNSGSLSSGVHTFP AVLQSDLYTLSSSVTVPSSTWPSETVTCNVAHPAS STKVDKKIVPRDCGCKPCICTVPEVSSVFIFPPKP KDVLTITLTPKVTCVVVDISKDDPEVQFSWFVDDV EVHTAQTQPREEQFGSTFRSVSELPIMHQDWLNGK EFKCRVNSAAFPAPIEKTISKTKGRPKAPQVYTIP PPKEQMAKDKVSLTCMITDFFPEDITVEWQWNGQP AENYKNTQPIMDTDGSYFVYSKLNVQKSNWEAGNT FTCSVLHEGLHNHHTEKSLSHSPGK |
| Ab-1 LC SEQ ID NO: 10 | EIVMTQSPATLSVSPGERATLSCRASQSVSSNLAW FQQKPGQAPRLLIYGASTRATGIPARFSGSGSGTE FTLTISSLQPEDFAVYYCLQDNNFPPTFGQGTKVD IKRADAAPTVSIFPPSSEQLTSGGASVVCFLNNFY PKDINVKWKIDGSERQNGVLNSWTDQDSKDSTYSM SSTLTLTKDEYERHNSYTCEATHKTSTSPIVKSFN RNEC |

GENERAL SYNTHETIC PROCEDURES

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following schemes. Any variables used in the following scheme are the variables as defined for Formula I, unless otherwise noted. All starting materials are either commercially available, for example, from Merck Sigma-Aldrich Inc. and Enamine Ltd. or known in the art and may be synthesized by employing known procedures using ordinary skill. Starting material may also be synthesized via the procedures disclosed herein. Suitable reaction conditions, such as, solvent, reaction temperature, and reagents, for the Schemes discussed in this section, may be found in the examples provided herein. As used below, Z is a leaving group, which can include but is not limited to, halogens (e.g. fluoride, chloride, bromide, iodide), sulfonates (e.g. mesylate, tosylate, benzenesulfonate, brosylate, nosylate, triflate), diazonium, and the like. As used below, in certain embodiments Y is an organometal coupling reagent group, which can include but are not limited to, boronic acids and esters, organotin and organozinc reagents.

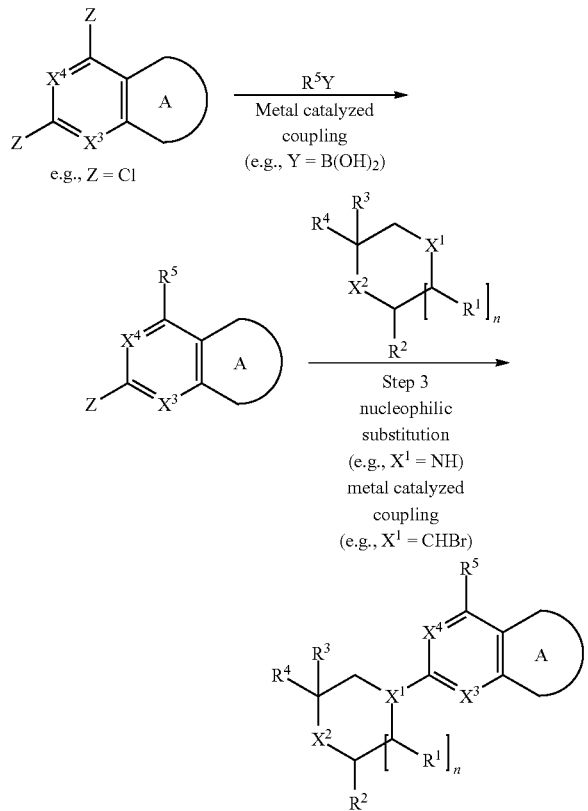

Scheme 1

As can be appreciated by the skilled artisan, the above synthetic scheme and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Purification methods for the compounds described herein are known in the art and include, for example, crystallization, chromatography (for example, liquid and gas phase), extraction, distillation, trituration, and reverse phase HPLC.

The disclosure further encompasses "intermediate" compounds, including structures produced from the synthetic procedures described, whether isolated or generated in-situ and not isolated, prior to obtaining the finally desired compound. These intermediates are included in the scope of this disclosure. Exemplary embodiments of such intermediate compounds are set forth in the Examples below.

EXAMPLES

This section provides specific examples of compounds of Formula I and methods of making the same.

| List of Abbreviations | |
|---|---|
| aq or aq. | aqueous |
| DCM | dichloromethane |
| DMAP | 4-dimethylaminopyridine |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | equivalent |
| ESI or ES | electrospray ionization |
| Et | ethyl |
| EtOAc or EA | ethyl acetate |
| g | gram(s) |
| h or hr | hour(s) |
| HPLC | high pressure liquid chromatography |
| iPr | isopropyl |
| iPr$_2$NEt or DIPEA | N-ethyl diisopropylamine (Hunig's base) |
| LC MS, LCMS, LC-MS or LC/MS | liquid chromatography mass spectroscopy |
| m/z | mass divided by charge |
| Me | methyl |
| CH$_3$CN | acetonitrile |
| MeOH | methanol |
| mg | milligrams |
| min | minutes |
| mL | milliliters |
| MS | mass spectra |
| n-BuLi | n-butyllithium |
| NMR | nuclear magnetic resonance |
| PE | Petroleum ether |
| Ph | phenyl |
| RT or rt or r.t. | room temperature |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate |
| sat. | saturated |
| SFC | supercritical fluid chromatography |
| TEA or Et$_3$N | triethylamine |
| THF | tetrahydrofuran |
| X antphos Pd G3 | [(4,5-Bis(diphenylphosphino)-9,9-dimethylxanthene)-2-(2'-amino-1,1'-biphenyl)]palladium(II) methanesulfonate |
| PE | Petroleum ether |

General Analytical and Purification Methods

Provided in this section are descriptions of the general analytical and purification methods used to prepare the specific compounds provided herein.

Chromatography:

Unless otherwise indicated, crude product-containing residues were purified by passing the crude material or concentrate through either a Biotage brand silica gel column pre-packed with flash silica (SiO$_2$) or reverse phase flash silica (C18) and eluting the product off the column with a solvent gradient as indicated. For example, a description of silica gel (0-40% EtOAc/hexane) means the product was obtained by elution from the column packed with silica using a solvent gradient of 0% to 40% EtOAc in hexanes. In some experiments, flash chromatography was performed on Teledyne Isco instruments using pre-packaged disposable $SiO_2$ stationary phase columns with eluent flow rate range of 15 to 200 mL/min, UV detection (254 and 220 nm).

Preparative HPLC Method:

Where so indicated, the compounds described herein were purified via reverse phase HPLC using Waters Fractionlynx semi-preparative HPLC-MS system utilizing one of the following two HPLC columns: (a) Phenominex Gemini column (5 micron, C18, 150×30 mm) or (b) Waters X-select CSH column (5 micron, C18, 100×30 mm).

A typical run through the instrument included: eluting at 45 mL/min with a linear gradient of 10% (v/v) to 100% MeCN (0.1% v/v formic acid) in water (0.1% formic acid) over 10 minutes; conditions can be varied to achieve optimal separations.

Preparative Chiral Supercritical Fluid Chromatography (SFC) Method:

Where so indicated, the compounds described herein were purified via chiral SFC using one of the two following chiral SFC columns: (a) Chiralpak IG 2×25 cm, 5 µm or (b) Chiralpak AD-H 2×15 cm, 5 µm.

A typical run through the instrument included: eluting with flowrates (F) of between 30 and 120 mL/min using solvent mixtures of between 30 and 80% EtOH in supercritical $CO_2$; conditions can be varied to achieve optimal separations.

Alternatively, some CP Analytical-SFC experiments were run on SFC Method Station (Thar, Waters) with the following conditions: Column temperature: 40° C., Mobile phase: $CO_2$/Methanol (0.2% Methanol Ammonia)=Flow: 4.0 ml/min, Back Pressure: 120 Bar, Detection wavelength: 214 nm.

In other runs, some CP Preparative-SFC experiments were run on SFC-80 (Thar, Waters) with the following conditions: Column temperature: 35° C., Mobile phase (example): $CO_2$/Methanol (0.2% Methanol Ammonia)=Flow rate: 80 g/min, Back pressure: 100 bar, Detection wavelength: 214 nm. Preparative CP Method: Acidic reversed phase MPLC: Instrument type: Reveleris™ prep MPLC; Column: Phenomenex LUNA C18(3)(150×25 mm, 10 µ); Flow: 40 mL/min; Column temp: room temperature; Eluent A: 0.1% (v/v) Formic acid in water, Eluent B: 0.1% (v/v) Formic acid in acetonitrile; using the indicated gradient and wavelength.

Proton NMR Spectra:

Unless otherwise indicated, all $^1$H NMR spectra were collected on a Bruker NMR Instrument at 300, 400 or 500 Mhz or a Varian NMR Instrument at 400 Mhz. Where so characterized, all observed protons are reported as parts-per-million (ppm) downfield from tetramethylsilane (TMS) using the internal solvent peak as reference. All NMR were collected at about 25° C.

Mass Spectra (MS)

Unless otherwise indicated, all mass spectral data for starting materials, intermediates and/or exemplary compounds are reported as mass/charge (m/z), having an $[M+H]^+$ molecular ion. The molecular ion reported was obtained by electrospray detection method (commonly referred to as an ESI MS) utilizing a Waters Acquity UPLC/MS system or a Gemini-NX UPLC/MS system. Compounds having a isotopic atom, such as bromine and the like, are generally reported according to the detected isotopic pattern, as appreciated by those skilled in the art.

Compound Names

The compounds disclosed and described herein have been named using the IUPAC naming function provided with Biovia Pipeline Pilot or ChemDraw Professional 17.0.

Specific Examples

Provided in this section are the procedures to synthesize specific examples of the compounds provided herein. All starting materials are either commercially available from Sigma-Aldrich Inc., unless otherwise noted, or known in the art and may be synthesized by employing known procedures using ordinary skill.

Synthesis of Examples

Method 1

Example 1: 4-(4-chloro-2-fluorophenyl)-7-methyl-2-((2S)-2-(1-methyl-1H-pyrazol-4-yl)-4-morpholinyl)pteridine

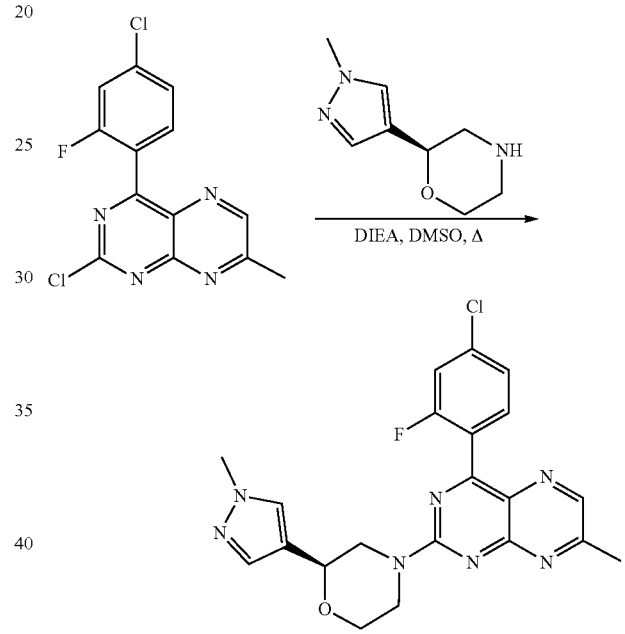

Example 1

To a solution of 2-chloro-4-(4-chloro-2-fluorophenyl)-7-methylpteridine (Intermediate 13) (0.0754 g, 0.244 mmol) and N-ethyl-N-isopropylpropan-2-amine (0.063 g, 0.085 mL, 0.488 mmol) in DMSO (0.813 mL) was added (S)-2-(1-methyl-1H-pyrazol-4-yl)morpholine (Enamine, Monmouth Jct., NJ, USA) (0.049 g, 0.293 mmol). The reaction mixture was stirred at 100° C. for 2 h. After cooling, the mixture was partitioned between DCM and $H_2O$. The organic phase was separated and concentrated under vacuum and the crude was purified by silica gel chromatography eluting with a gradient of 0-10% MeOH(+1%$NH_3$) in DCM to afford 4-(4-chloro-2-fluorophenyl)-7-methyl-2-((2S)-2-(1-methyl-1H-pyrazol-4-yl)-4-morpholinyl)pteridine (0.0694 g, 0.158 mmol, 64.7% yield). $^1$H NMR (500 MHz, DMSO-d6) δ ppm 8.53 (s, 1H), 7.74 (br d, J=8.2 Hz, 2H), 7.64 (dd, J=9.8, 1.8 Hz, 1H), 7.41-7.54 (m, 2H), 4.77 (br d, J=12.6 Hz, 1H), 4.64 (br d, J=13.6 Hz, 1H), 4.54 (br d, J=8.3 Hz, 1H), 3.95-4.11 (m, 1H), 3.82 (s, 3H), 3.62-3.73 (m, 1H), 3.20-3.29 (m, 2H), 2.66 (s, 3H). m/z (ESI, +ive ion):440.0 $(M+H)^+$.

TABLE 1

Compounds 2 to 128 were prepared following the procedure described in Method 1, as follows:

| Ex # | Structure | IUPAC Name | Starting Material 1 | Starting Material 2 |
|---|---|---|---|---|
| 2 | 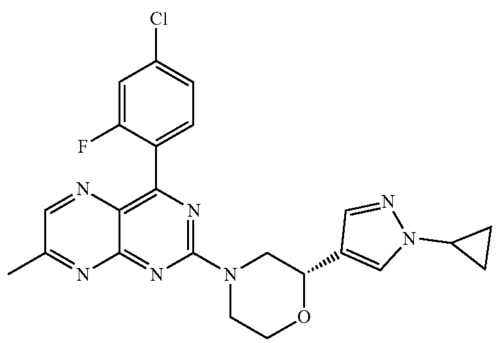 [SMILES: Cc1cnc2c(-c3ccc(Cl)cc3F)nc(N3CCO[C@@H](c4cnn(C5CC5)c4)C3)nc2n1] | 4-(4-chloro-2-fluorophenyl)-2-((2S)-2-(1-cyclopropyl-1H-pyrazol-4-yl)-4-morpholinyl)-7-methylpteridine | (S)-2-(1-cyclopropyl-1H-pyrazol-4-yl)morpholine (Azepine Ltd. Hampshire, UK) | 2-chloro-4-(4-chloro-2-fluorophenyl)-7-methylpteridine (Intermediate 13) |
| 3 | 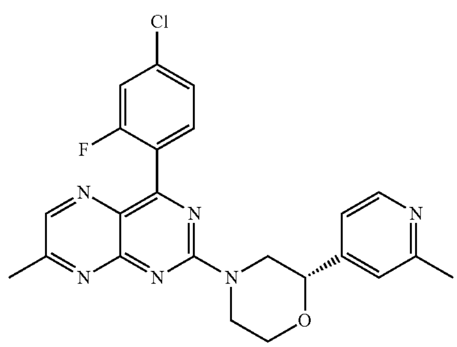 | 4-(4-chloro-2-fluorophenyl)-7-methyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(4-chloro-2-fluorophenyl)-7-methylpteridine (Intermediate 13) |
| 4 | 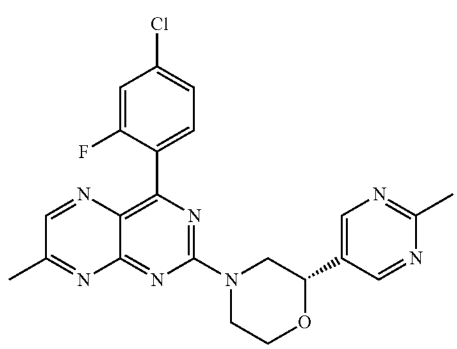 | 4-(4-chloro-2-fluorophenyl)-7-methyl-2-((2S)-2-(2-methyl-5-pyrimidinyl)-4-morpholinyl)pteridine | (S)-2-(2-methylpyrimidin-5-yl)morpholine (Azepine Ltd. Hampshire, UK) | 2-chloro-4-(4-chloro-2-fluorophenyl)-7-methylpteridine (Intermediate 13) |
| 5 | 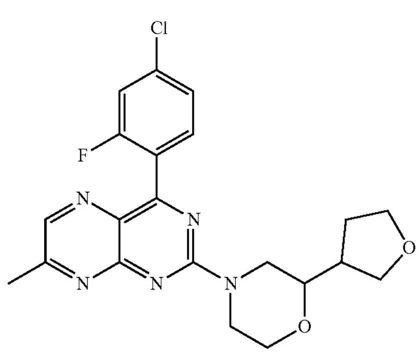 | 4-(4-chloro-2-fluorophenyl)-7-methyl-2-(2-(tetrahydro-3-furanyl)-4-morpholinyl)pteridine | 2-(tetrahydrofuran-3-yl)morpholine (Enamine, Monmouth Jct., NJ, USA) | 2-chloro-4-(4-chloro-2-fluorophenyl)-7-methylpteridine (Intermediate 13) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 6 | 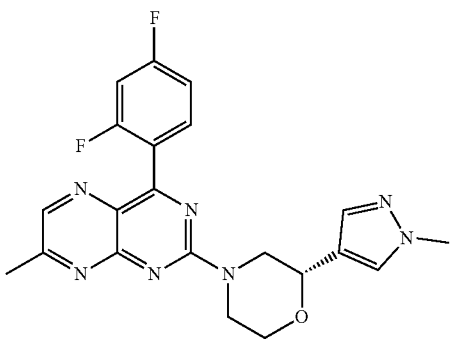 | 4-(2,4-difluorophenyl)-7-methyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(2,4-difluorophenyl)-7-methylpteridine (Intermediate 14) |
| 7 | 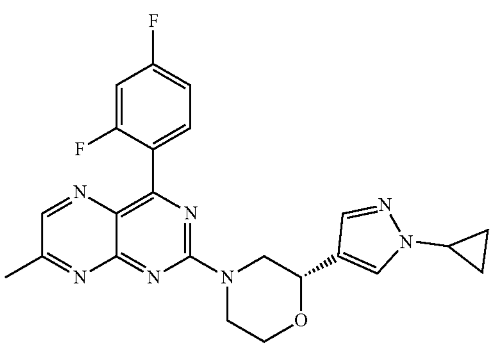 | 2-((2S)-2-(1-cyclopropyl-1H-pyrazol-4-yl)-4-morpholinyl)-4-(2,4-difluorophenyl)-7-methylpteridine | (S)-2-(1-cyclopropyl-1H-pyrazol-4-yl)morpholine (Azepine Ltd. Hampshire, UK) | 2-chloro-4-(2,4-difluorophenyl)-7-methylpteridine (Intermediate 14) |
| 8 | 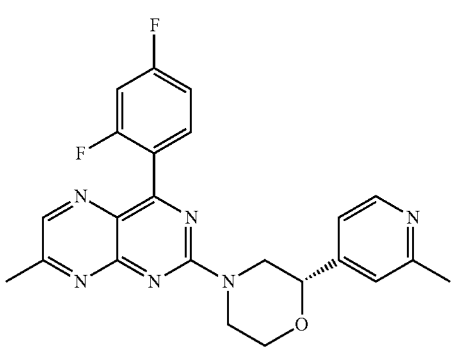 | 4-(2,4-difluorophenyl)-7-methyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(2,4-difluorophenyl)-7-methylpteridine (Intermediate 14) |
| 9 | 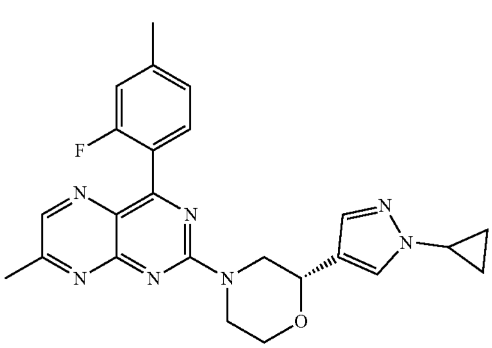 [SMILES: Cc1ccc(-c2nc(N3CCO[C@@H](c4cnn(C5CC5)c4)C3)nc3nc(C)cnc23)c(F)c1] | 2-((2S)-2-(1-cyclopropyl-1H-pyrazol-4-yl)-4-morpholinyl)-4-(2-fluoro-4-methylphenyl)-7-methylpteridine | (S)-2-(1-cyclopropyl-1H-pyrazol-4-yl)morpholine (Azepine Ltd. Hampshire, UK) | 2-chloro-4-(2,4-difluorophenyl)-7-methylpteridine (Intermediate 14) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 10 | 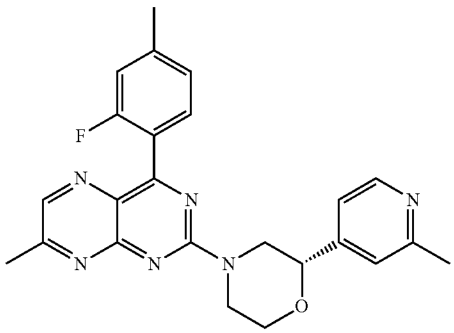 | 4-(2-fluoro-4-methylphenyl)-7-methyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(2-fluoro-4-methylphenyl)-7-methylpteridine (Intermediate 15) |
| 11 | 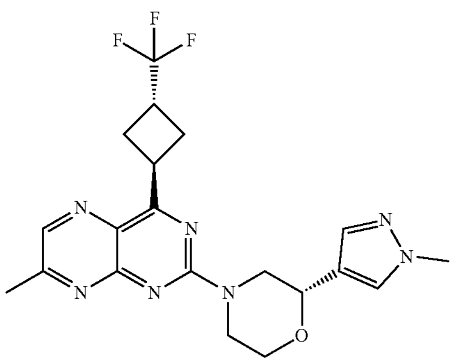 | 7-methyl-2-((2S)-2-(1-methyl-1H-pyrazol-4-yl)-4-morpholinyl)-4-(trans-3-(trifluoromethyl)cyclobutyl)pteridine | (S)-2-(1-methyl-1H-pyrazol-4-yl)morpholine (Enamine, Monmouth Jct., NJ, USA) | 2-chloro-7-methyl-4-(trans-3-(trifluoromethyl)cyclobutyl)pteridine (Intermediate 61) |
| 12 | 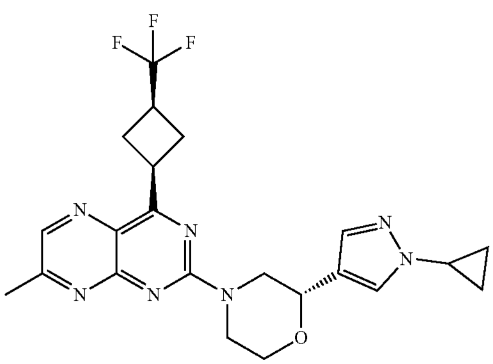 [SMILES: Cc1cnc2c(n1)nc(N1CCO[C@@H](c3cnn(C4CC4)c3)C1)nc2[C@H]1C[C@@H](C(F)(F)F)C1] | 2-((2S)-2-(1-cyclopropyl-1H-pyrazol-4-yl)-4-morpholinyl)-7-methyl-4-(cis-3-(trifluoromethyl)cyclobutyl)pteridine | (S)-2-(1-cyclopropyl-1H-pyrazol-4-yl)morpholine (Azepine Ltd. Hampshire, UK) | 2-chloro-7-methyl-4-(cis-3-(trifluoromethyl)cyclobutyl)pteridine (Intermediate 62) |
| 13 | 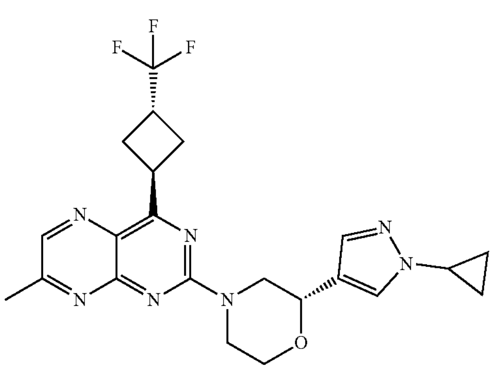 [SMILES: Cc1cnc2c(n1)nc(N1CCO[C@@H](c3cnn(C4CC4)c3)C1)nc2[C@H]1C[C@H](C(F)(F)F)C1] | 2-((2S)-2-(1-cyclopropyl-1H-pyrazol-4-yl)-4-morpholinyl)-7-methyl-4-(trans-3-(trifluoromethyl)cyclobutyl)pteridine | (S)-2-(1-cyclopropyl-1H-pyrazol-4-yl)morpholine (Azepine Ltd. Hampshire, UK) | 2-chloro-7-methyl-4-(trans-3-(trifluoromethyl)cyclobutyl)pteridine (Intermediate 61) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 14 | | 7-methyl-2-((2R)-2-(6-methyl-4-pyridazinyl)-4-morpholinyl)-4-(cis-3-(trifluoromethyl)cyclobutyl)pteridine. Absolute stereochemistry arbitrarily assigned. | 2-(6-methylpyridazin-4-yl)morpholine (Azepine Ltd. Hampshire, UK) | 2-chloro-7-methyl-4-(cis-3-(trifluoromethyl)cyclobutyl)pteridine (Intermediate 62) |
| 15 | | 7-methyl-2-((2S)-2-(2-methyl-4-pyridinyl)-4-morpholinyl)-4-(cis-3-(trifluoromethyl)cyclobutyl)pteridine | (S)-2-(2-methylpyridin-4-yl)morpholine (Intermed Ltd. Kiev, Ukraine) | 2-chloro-7-methyl-4-(cis-3-(trifluoromethyl)cyclobutyl)pteridine (Intermediate 62) |
| 16 | | 7-methyl-2-((2S)-2-(2-methyl-4-pyridinyl)-4-morpholinyl)-4-(trans-3-(trifluoromethyl)cyclobutyl)pteridine | (S)-2-(2-methylpyridin-4-yl)morpholine (Intermed Ltd. Kiev, Ukraine) | 2-chloro-7-methyl-4-(trans-3-(trifluoromethyl)cyclobutyl)pteridine (Intermediate 61) |
| 17 | | 4-(2-fluoro-4-(trifluoromethyl)phenyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(2-fluoro-4-(trifluoromethyl)phenyl)-6,7-dimethylpteridine (Intermediate 18) | ated
TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 18 | 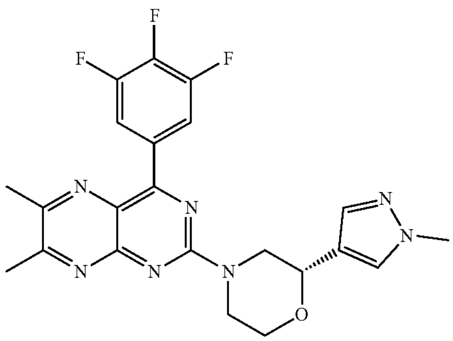 | 6,7-dimethyl-2-((2S)-2-(1-methyl-1H-pyrazol-4-yl)-4-morpholinyl)-4-(3,4,5-trifluorophenyl)pteridine | (S)-2-(1-methyl-1H-pyrazol-4-yl)morpholine (Enamine, Monmouth Jct., NJ, USA) | 2-chloro-6,7-dimethyl-4-(3,4,5-trifluorophenyl)pteridine (Intermediate 20) |
| 19 | 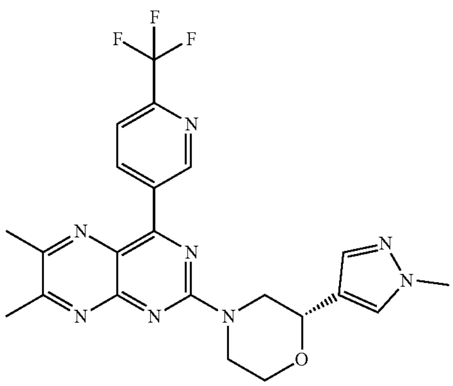 | 6,7-dimethyl-2-((2S)-2-(1-methyl-1H-pyrazol-4-yl)-4-morpholinyl)-4-(6-(trifluoromethyl)-3-pyridinyl)pteridine | (S)-2-(1-methyl-1H-pyrazol-4-yl)morpholine (Enamine, Monmouth Jct., NJ, USA) | 2-chloro-6,7-dimethyl-4-(6-(trifluoromethyl)pyridin-3-yl)pteridine (Intermediate 21) |
| 20 | 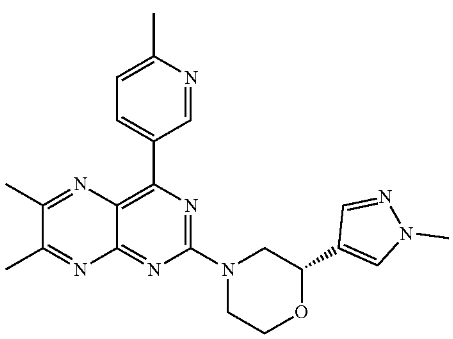 | 6,7-dimethyl-2-((2S)-2-(1-methyl-1H-pyrazol-4-yl)-4-morpholinyl)-4-(6-methyl-3-pyridinyl)pteridine | (S)-2-(1-methyl-1H-pyrazol-4-yl)morpholine (Enamine, Monmouth Jct., NJ, USA) | 2-chloro-6,7-dimethyl-4-(6-methylpyridin-3-yl)pteridine (Intermediate 22) |
| 21 | 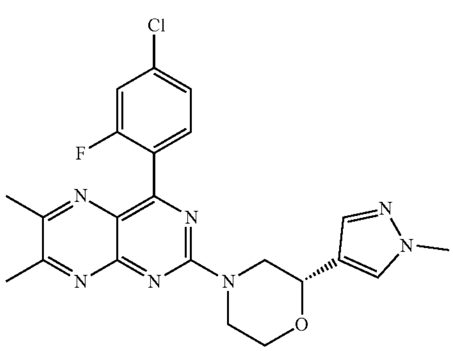 | 4-(4-chloro-2-fluorophenyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(4-chloro-2-fluorophenyl)-6,7-dimethylpteridine (Intermediate 16) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 22 | 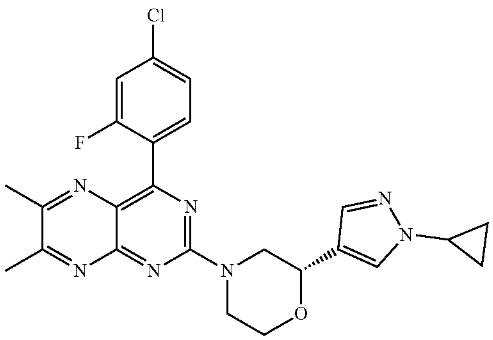 | 4-(4-chloro-2-fluorophenyl)-2-((2S)-2-(1-cyclopropyl-1H-pyrazol-4-yl)-4-morpholinyl)-6,7-dimethylpteridine | (S)-2-(1-cyclopropyl-1H-pyrazol-4-yl)morpholine (Azepine Ltd. Hampshire, UK) | 2-chloro-4-(4-chloro-2-fluorophenyl)-6,7-dimethylpteridine (Intermediate 16) |
| 23 | 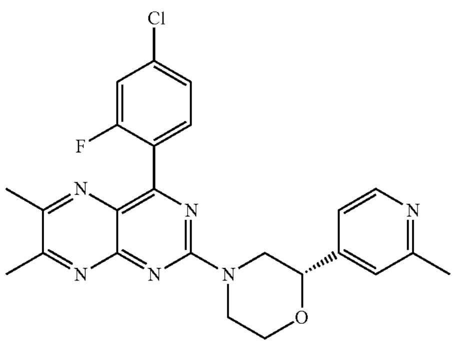 | 4-(4-chloro-2-fluorophenyl)-6,7-dimethyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(4-chloro-2-fluorophenyl)-6,7-dimethylpteridine (Intermediate 16) |
| 24 | 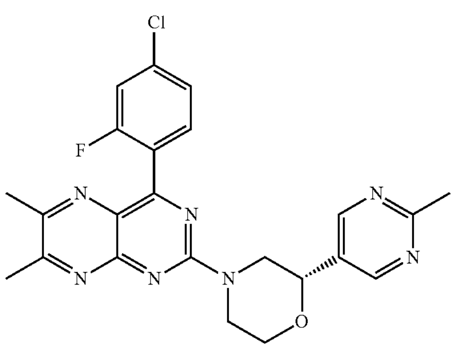 | 4-(4-chloro-2-fluorophenyl)-6,7-dimethyl-2-((2R)-2-(2-methyl-5-pyrimidinyl)-4-morpholinyl)pteridine. Purified by chiral SFC chromatography. Absolute stereochemistry arbitrarily assigned. | 2-(2-methylpyrimidin-5-yl)morpholine (Azepine Ltd. Hampshire, UK) | 2-chloro-4-(4-chloro-2-fluorophenyl)-6,7-dimethylpteridine (Intermediate 16) |
| 25 | 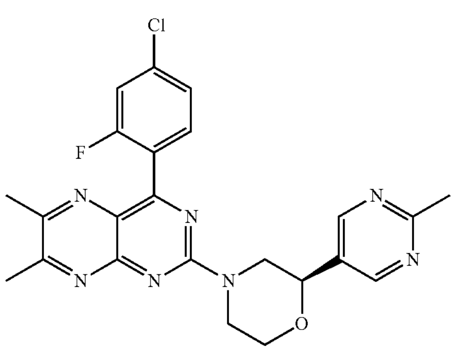 | 4-(4-chloro-2-fluorophenyl)-6,7-dimethyl-2-((2S)-2-(2-methyl-5-pyrimidinyl)-4-morpholinyl)pteridine Purified by chiral SFC chromatography. Absolute stereochemistry arbitrarily assigned. | 2-(2-methylpyrimidin-5-yl)morpholine (Azepine Ltd. Hampshire, UK) | 2-chloro-4-(4-chloro-2-fluorophenyl)-6,7-dimethylpteridine (Intermediate 16) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 26 | 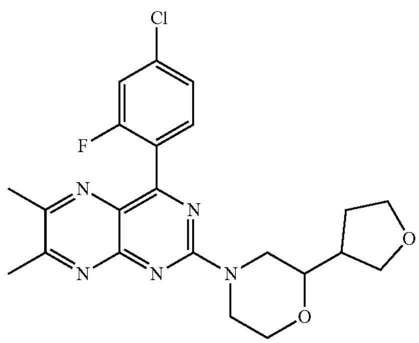 | 4-(4-chloro-2-fluorophenyl)-6,7-dimethyl-2-(2-(tetrahydro-3-furanyl)-4-morpholinyl)pteridine | 2-(tetrahydrofuran-3-yl)morpholine (Enamine, Monmouth Jct., NJ, USA) | 2-chloro-4-(4-chloro-2-fluorophenyl)-6,7-dimethylpteridine (Intermediate 16) |
| 27 | 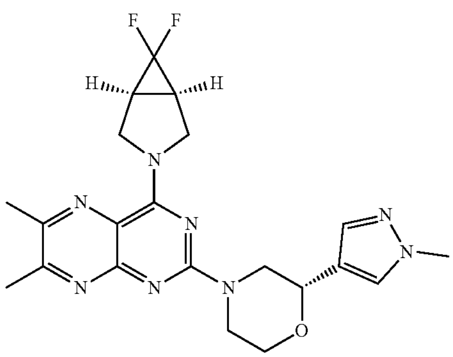 | 4-((1R,5S)-6,6-difluoro-3-azabicyclo[3.1.0]hexan-3-yl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-((1R,5S)-6,6-difluoro-3-azabicyclo[3.1.0]hexan-3-yl)-6,7-dimethylpteridine (Intermediate 86) |
| 28 | 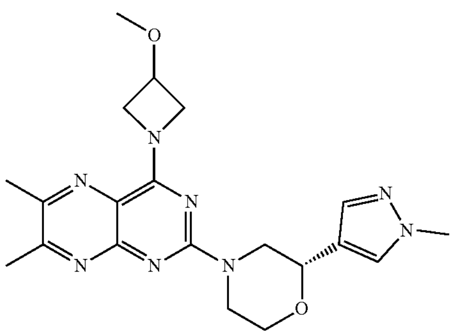 | 4-(3-methoxy-1-azetidinyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(3-methoxyazetidin-1-yl)-6,7-dimethylpteridine (Intermediate 83) |
| 29 | 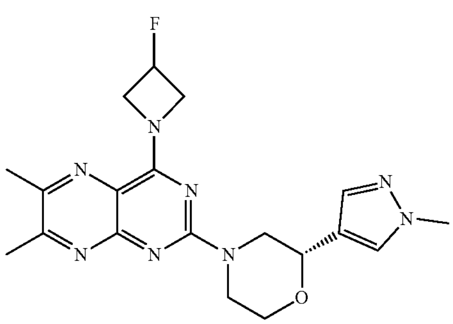 | 4-(3-fluoro-1-azetidinyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(3-fluoroazetidin-1-yl)-6,7-dimethylpteridine (Intermediate 84) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 30 | 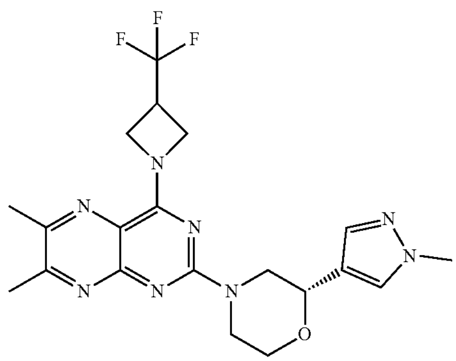 | 6,7-dimethyl-2-((2S)-2-(1-methyl-1H-pyrazol-4-yl)-4-morpholinyl)-4-(3-(trifluoromethyl)-1-azetidinyl)pteridine | (S)-2-(1-methyl-1H-pyrazol-4-yl)morpholine (Enamine, Monmouth Jct., NJ, USA) | 2-chloro-6,7-dimethyl-4-(3-(trifluoromethyl)azetidin-1-yl)pteridine (Intermediate 85) |
| 31 | 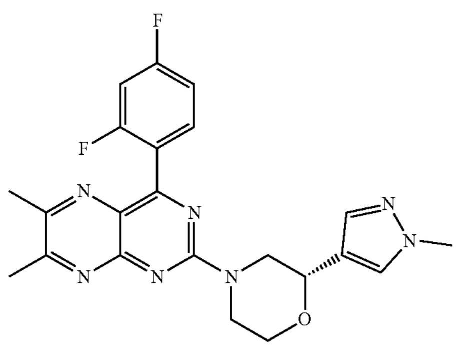 | 4-(2,4-difluorophenyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(2,4-difluorophenyl)-6,7-dimethylpteridine (Intermediate 17) |
| 32 | 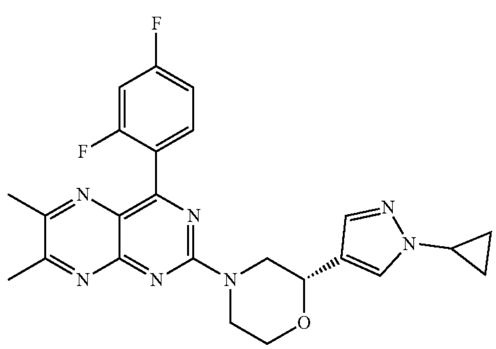 [SMILES: Cc1nc2nc(N3CCO[C@@H](c4cnn(C5CC5)c4)C3)nc(-c3ccc(F)cc3F)c2nc1C] | 2-((2S)-2-(1-cyclopropyl-1H-pyrazol-4-yl)-4-morpholinyl)-4-(2,4-difluorophenyl)-6,7-dimethylpteridine | (S)-2-(1-cyclopropyl-1H-pyrazol-4-yl)morpholine (Azepine Ltd. Hampshire, UK) | 2-chloro-4-(2,4-difluorophenyl)-6,7-dimethylpteridine (Intermediate 17) |
| 33 | 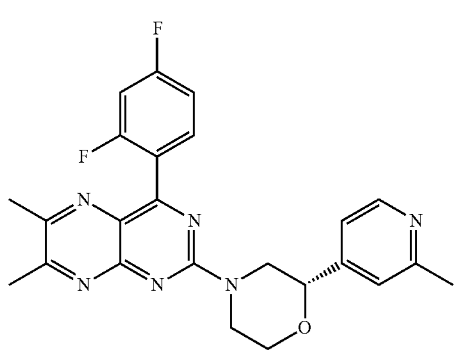 | 4-(2,4-difluorophenyl)-6,7-dimethyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(2,4-difluorophenyl)-6,7-dimethylpteridine (Intermediate 17) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 34 | 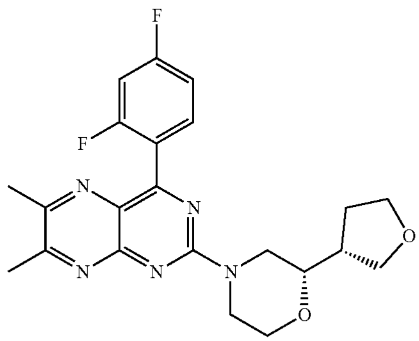 [SMILES: Cc1nc2nc(N3CCO[C@@H]([C@@H]4CCOC4)C3)nc(-c3ccc(F)cc3F)c2nc1C] | 4-(2,4-difluorophenyl)-6,7-dimethyl-2-((2S)-2-((3R)-tetrahydro-3-furanyl)-4-morpholinyl)pteridine Purified by chiral SFC Chromatography. Relative stereochemistry assigned by NMR. Absolute stereochemistry arbitrarily assigned. | 2-(tetrahydrofuran-3-yl)morpholine (Enamine, Monmouth Jct., NJ, USA) | 2-chloro-4-(2,4-difluorophenyl)-6,7-dimethylpteridine (Intermediate 17) |
| 35 | 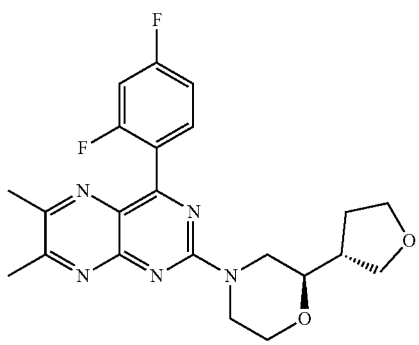 | 4-(2,4-difluorophenyl)-6,7-dimethyl-2-((2R)-2-((3R)-tetrahydro-3-furanyl)-4-morpholinyl)pteridine Purified by chiral SFC Chromatography. Relative stereochemistry assigned by NMR. Absolute stereochemistry arbitrarily assigned. | 2-(tetrahydrofuran-3-yl)morpholine (Enamine, Monmouth Jct., NJ, USA) | 2-chloro-4-(2,4-difluorophenyl)-6,7-dimethylpteridine (Intermediate 17) |
| 36 | 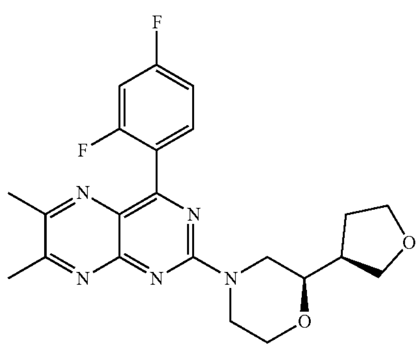 | 4-(2,4-difluorophenyl)-6,7-dimethyl-2-((2R)-2-((3S)-tetrahydro-3-furanyl)-4-morpholinyl)pteridine Purified by chiral SFC Chromatography. Relative stereochemistry assigned by NMR. Absolute stereochemistry arbitrarily assigned. | 2-(tetrahydrofuran-3-yl)morpholine (Enamine, Monmouth Jct., NJ, USA) | 2-chloro-4-(2,4-difluorophenyl)-6,7-dimethylpteridine (Intermediate 17) |
| 37 | 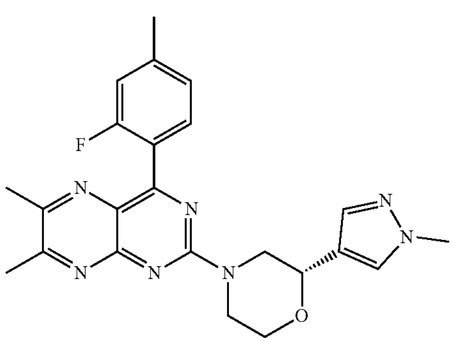 | 4-(2-fluoro-4-methylphenyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(2-fluoro-4-methylphenyl)-6,7-dimethylpteridine (Intermediate 19) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 38 | 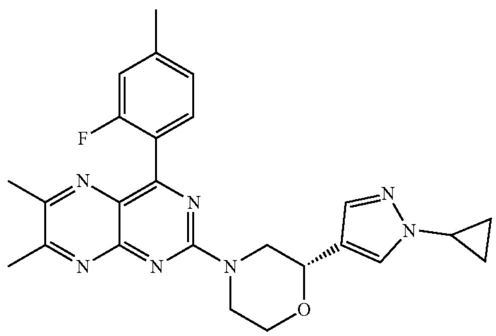 [SMILES: Cc1ccc(-c2nc(N3CCO[C@@H](c4cnn(C5CC5)c4)C3)nc3nc(C)c(C)nc23)c(F)c1] | 2-((2S)-2-(1-cyclopropyl-1H-pyrazol-4-yl)-4-morpholinyl)-4-(2-fluoro-4-methylphenyl)-6,7-dimethylpteridine | (S)-2-(1-cyclopropyl-1H-pyrazol-4-yl)morpholine (Azepine Ltd. Hampshire, UK) | 2-chloro-4-(2-fluoro-4-methylphenyl)-6,7-dimethylpteridine (Intermediate 19) |
| 39 | 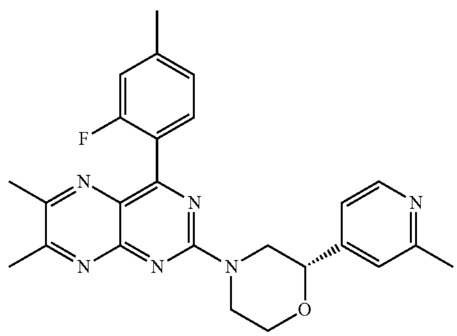 | 4-(2-fluoro-4-methylphenyl)-6,7-dimethyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(2-fluoro-4-methylphenyl)-6,7 dimethylpteridine (Intermediate 19) |
| 40 | 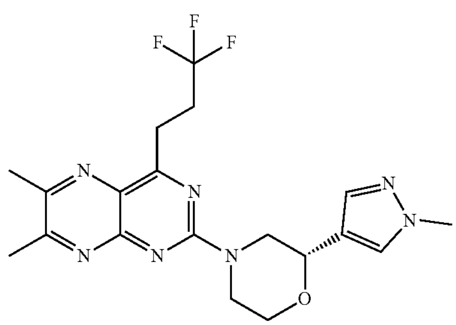 | 6,7-dimethyl-2-((2S)-2-(1-methyl-1H-pyrazol-4-yl)-4-morpholinyl)-4-(3,3,3-trifluoropropyl)pteridine | (S)-2-(1-methyl-1H-pyrazol-4-yl)morpholine (Enamine, Monmouth Jct., NJ, USA) | 2-chloro-6,7-dimethyl-4-(3,3,3-trifluoropropyl)pteridine (Intermediate (70) |
| 41 | 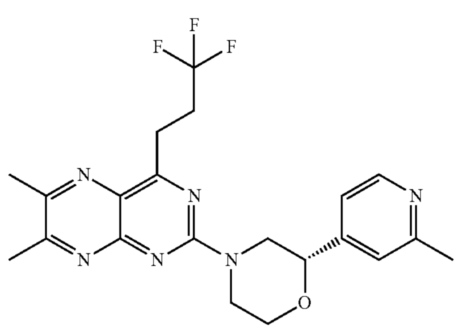 | 6,7-dimethyl-2-((2S)-2-(2-methyl-4-pyridinyl)-4-morpholinyl)-4-(3,3,3-trifluoropropyl)pteridine | (S)-2-(2-methylpyridin-4-yl)morpholine (Intermed Ltd. Kiev, Ukraine) | 2-chloro-6,7-dimethyl-4-(3,3,3-trifluoropropyl)pteridine (Intermediate (70) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 42 | 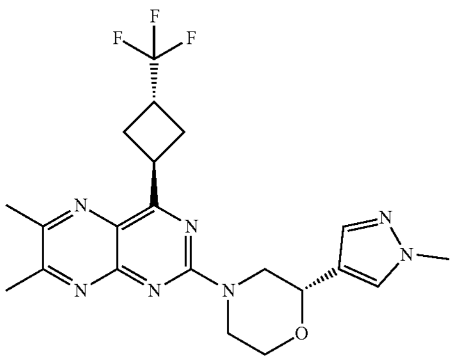 | 6,7-dimethyl-2-((2S)-2-(1-methyl-1H-pyrazol-4-yl)-4-morpholinyl)-4-(trans-3-(trifluoromethyl)cyclobutyl)pteridine | (S)-2-(1-methyl-1H-pyrazol-4-yl)morpholine (Enamine, Monmouth Jct., NJ, USA) | 2-chloro-6,7-dimethyl-4-((trans)-3-(trifluoromethyl)cyclobutyl)pteridine (Intermediate 59) |
| 43 | 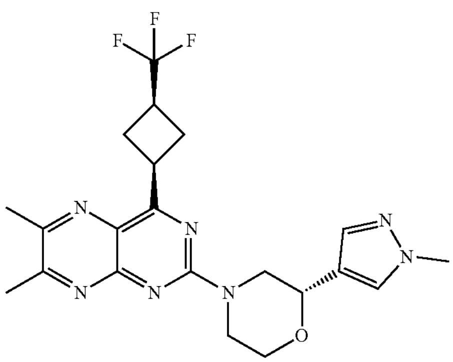 | 6,7-dimethyl-2-((2S)-2-(1-methyl-1H-pyrazol-4-yl)-4-morpholinyl)-4-(cis-3-(trifluoromethyl)cyclobutyl)pteridine | (S)-2-(1-methyl-1H-pyrazol-4-yl)morpholine (Enamine, Monmouth Jct., NJ, USA) | 2-chloro-6,7-dimethyl-4-(cis-3-(trifluoromethyl)cyclobutyl)pteridine (Intermediate 60) |
| 44 | 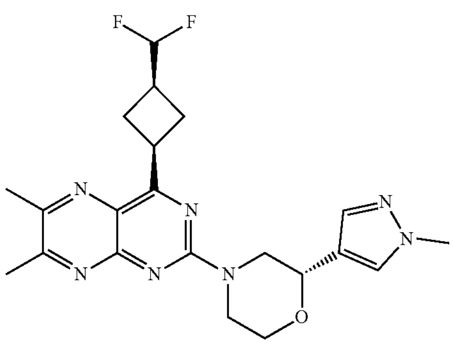 | 4-(cis-3-(difluoromethyl)cyclobutyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(3-(difluoromethyl)cyclobutyl)-6,7-dimethylpteridine (Intermediate 67) |
| 45 | 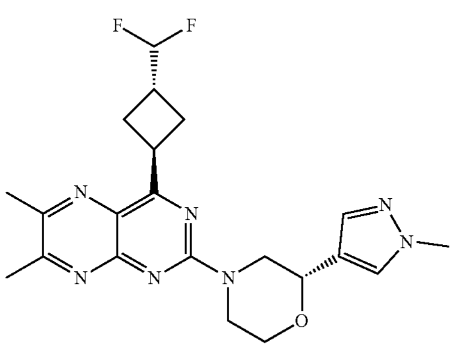 | 4-(trans-3-(difluoromethyl)cyclobutyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(3-(difluoromethyl)cyclobutyl)-6,7-dimethylpteridine (Intermediate 67) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 46 | 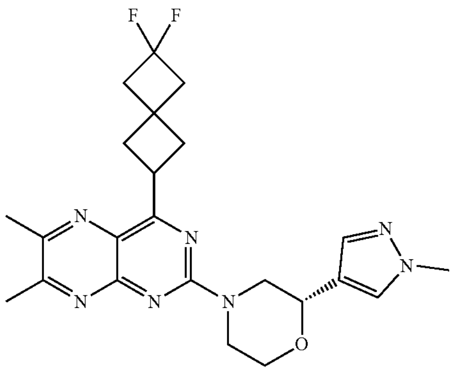 | 4-(6,6-difluorospiro[3.3]heptan-2-yl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(6,6-difluorospiro[3.3]heptan-2-yl)-6,7-dimethylpteridine (Intermediate (69) |
| 47 | 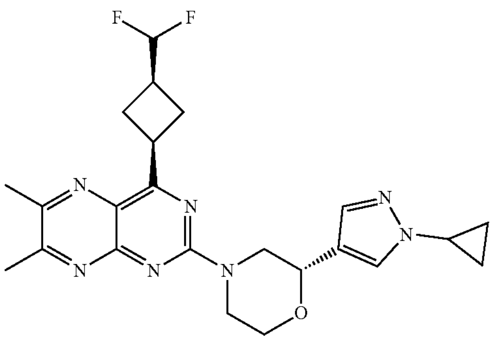 [SMILES: Cc1nc2nc(N3CCO[C@@H](c4cnn(C5CC5)c4)C3)nc([C@H]3C[C@@H](C(F)F)C3)c2nc1C] | 2-((2S)-2-(1-cyclopropyl-1H-pyrazol-4-yl)-4-morpholinyl)-4-(cis-3-(difluoromethyl)cyclobutyl)-6,7-dimethylpteridine | (S)-2-(1-cyclopropyl-1H-pyrazol-4-yl)morpholine (Azepine Ltd. Hampshire, UK) | 2-chloro-4-(3-(difluoromethyl)cyclobutyl)-6,7-dimethylpteridine (Intermediate 67) |
| 48 | 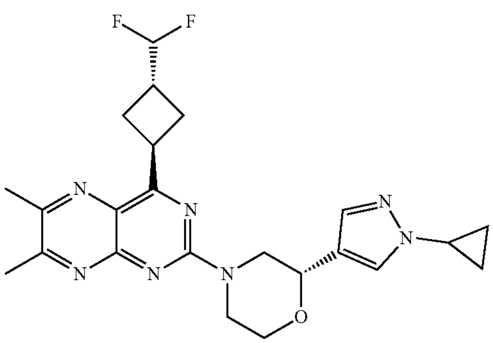 [SMILES: Cc1nc2nc(N3CCO[C@@H](c4cnn(C5CC5)c4)C3)nc([C@H]3C[C@H](C(F)F)C3)c2nc1C] | 2-((2S)-2-(1-cyclopropyl-1H-pyrazol-4-yl)-4-morpholinyl)-4-(trans-3-(difluoromethyl)cyclobutyl)-6,7-dimethylpteridine | (S)-2-(1-cyclopropyl-1H-pyrazol-4-yl)morpholine (Azepine Ltd. Hampshire, UK) | 2-chloro-4-(3-(difluoromethyl)cyclobutyl)-6,7-dimethylpteridine (Intermediate 67) |
| 49 | 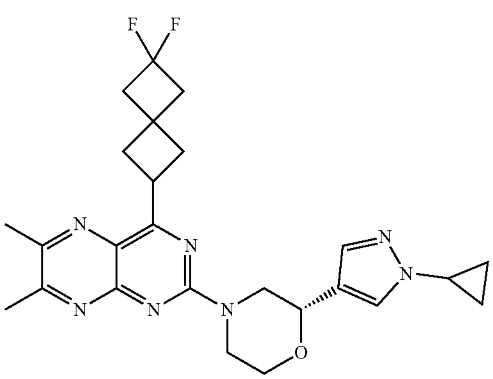 [SMILES: Cc1nc2nc(N3CCO[C@@H](c4cnn(C5CC5)c4)C3)nc(C3CC4(C3)CC(F)(F)C4)c2nc1C] | 2-((2S)-2-(1-cyclopropyl-1H-pyrazol-4-yl)-4-morpholinyl)-4-(6,6-difluorospiro[3.3]heptan-2-yl)-6,7-dimethylpteridine | (S)-2-(1-cyclopropyl-1H-pyrazol-4-yl)morpholine (Azepine Ltd. Hampshire, UK) | 2-chloro-4-(6,6-difluorospiro[3.3]heptan-2-yl)-6,7-dimethylpteridine (Intermediate (69) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 50 | 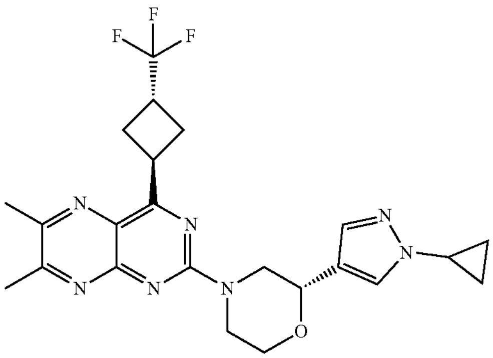 [SMILES: Cc1nc2nc(N3CCO[C@@H](c4cnn(C5CC5)c4)C3)nc([C@H]3C[C@H](C(F)(F)F)C3)c2nc1C] | 2-((2S)-2-(1-cyclopropyl-1H-pyrazol-4-yl)-4-morpholinyl)-6,7-dimethyl-4-(trans-3-(trifluoromethyl)cyclobutyl)pteridine | (S)-2-(1-cyclopropyl-1H-pyrazol-4-yl)morpholine (Azepine Ltd. Hampshire, UK) | 2-chloro-6,7-dimethyl-4-((trans)-3-(trifluoromethyl)cyclobutyl)pteridine (Intermediate 59) |
| 51 | 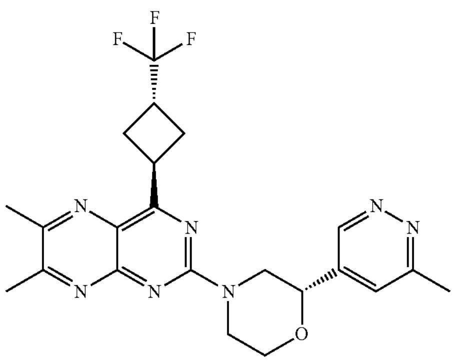 | 6,7-dimethyl-2-((2S)-2-(6-methyl-4-pyridazinyl)-4-morpholinyl)-4-(trans-3-(trifluoromethyl)cyclobutyl)pteridine | 2-(6-methylpyridazin-4-yl)morpholine (Azepine Ltd. Hampshire, UK) | 2-chloro-6,7-dimethyl-4-((trans)-3-(trifluoromethyl)cyclobutyl)pteridine (Intermediate 59) |
| 52 | 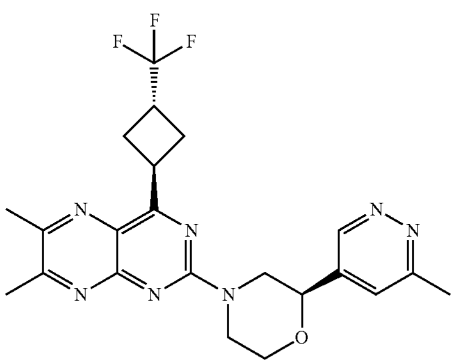 | 6,7-dimethyl-2-((2R)-2-(6-methyl-4-pyridazinyl)-4-morpholinyl)-4-(trans-3-(trifluoromethyl)cyclobutyl)pteridine | 2-(6-methylpyridazin-4-yl)morpholine (Azepine Ltd. Hampshire, UK) | 2-chloro-6,7-dimethyl-4-((trans)-3-(trifluoromethyl)cyclobutyl)pteridine (Intermediate 59) |
| 53 | 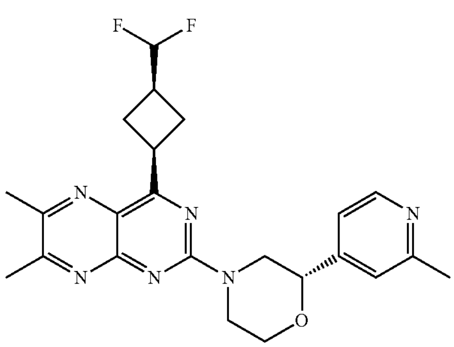 | 4-(cis-3-(difluoromethyl)cyclobutyl)-6,7-dimethyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(3-(difluoromethyl)cyclobutyl)-6,7-dimethylpteridine (Intermediate 67) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 54 | 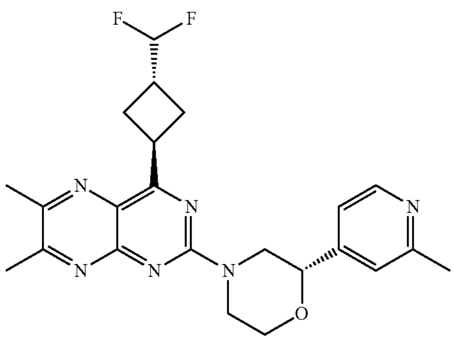 | 4-(trans-3-(difluoromethyl)cyclobutyl)-6,7-dimethyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(3-(difluoromethyl)cyclobutyl)-6,7-dimethylpteridine (Intermediate 67) |
| 55 | 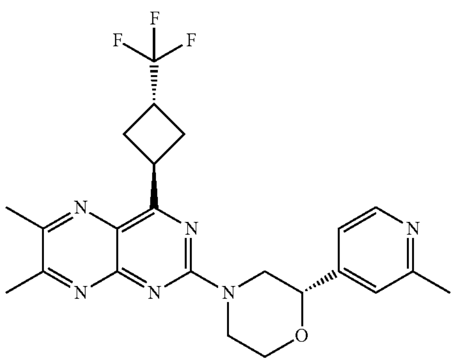 | 6,7-dimethyl-2-((2S)-2-(2-methyl-4-pyridinyl)-4-morpholinyl)-4-(trans-3-(trifluoromethyl)cyclobutyl)pteridine | (S)-2-(2-methylpyridin-4-yl)morpholine (Intermed Ltd. Kiev, Ukraine) | 2-chloro-6,7-dimethyl-4-((trans)-3-(trifluoromethyl)cyclobutyl)pteridine (Intermediate 59) |
| 56 | 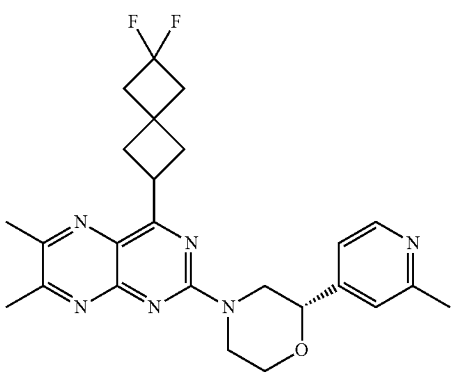 | 4-(6,6-difluorospiro[3.3]heptan-2-yl)-6,7-dimethyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(3-(difluoromethyl)cyclobutyl)-6,7-dimethylpteridine (Intermediate 67) |
| 57 | 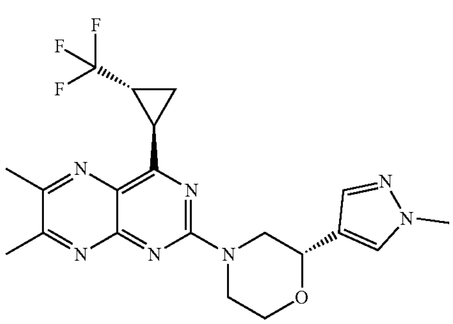 | 6,7-dimethyl-2-((2S)-2-(1-methyl-1H-pyrazol-4-yl)-4-morpholinyl)-4-((1R,2R)-2-(trifluoromethyl)cyclopropyl)pteridine | (S)-2-(1-methyl-1H-pyrazol-4-yl)morpholine (Enamine, Monmouth Jct., NJ, USA) | 2-chloro-6,7-dimethyl-4-((1S,2S)-2-(trifluoromethyl)cyclopropyl)pteridine (Intermediate 58) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 58 | 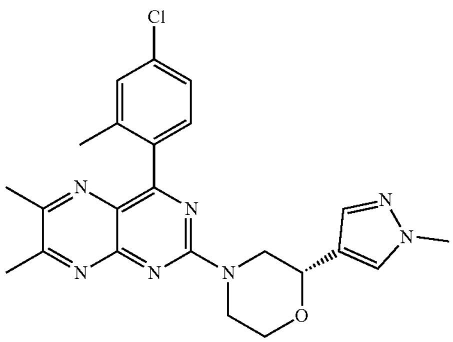 | 4-(4-chloro-2-methylphenyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(4-chloro-2-methylphenyl)-6,7-dimethylpteridine (Intermediate 23) |
| 59 | 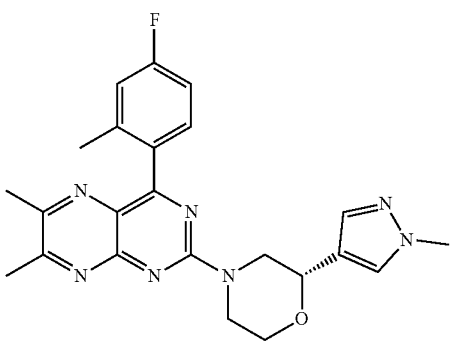 | 4-(4-fluoro-2-methylphenyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(4-fluoro-2-methylphenyl)-6,7-dimethylpteridine (Intermediate 24) |
| 60 | 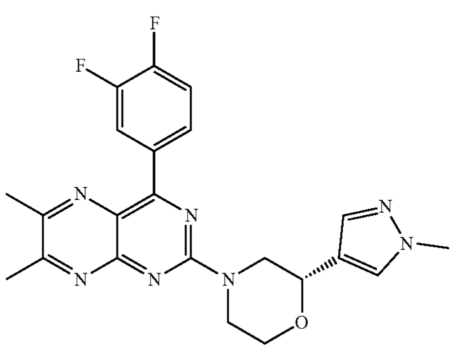 | 4-(3,4-difluorophenyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(3,4-difluorophenyl)-6,7-dimethylpteridine (Intermediate 25) |
| 61 | 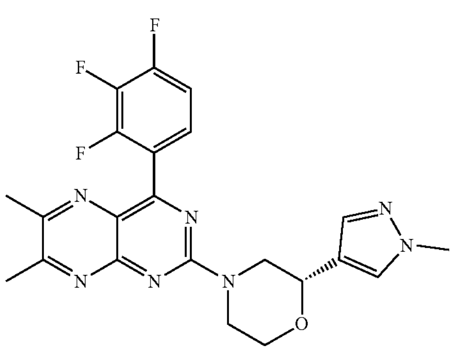 | 6,7-dimethyl-2-((2S)-2-(1-methyl-1H-pyrazol-4-yl)-4-morpholinyl)-4-(2,3,4-trifluorophenyl)pteridine | (S)-2-(1-methyl-1H-pyrazol-4-yl)morpholine (Enamine, Monmouth Jct., NJ, USA) | 2-chloro-6,7-dimethyl-4-(2,3,4-trifluorophenyl)pteridine (Intermediate 26) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 62 | 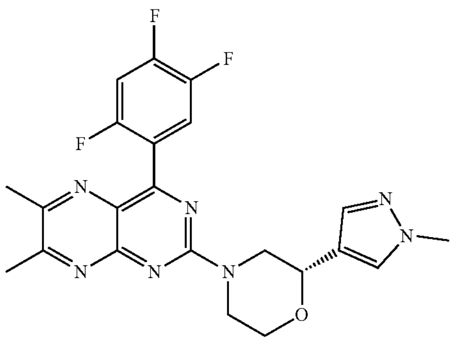 | 6,7-dimethyl-2-((2S)-2-(1-methyl-1H-pyrazol-4-yl)-4-morpholinyl)-4-(2,4,5-trifluorophenyl)pteridine | (S)-2-(1-methyl-1H-pyrazol-4-yl)morpholine (Enamine, Monmouth Jct., NJ, USA) | 2-chloro-6,7-dimethyl-4-(2,4,5-trifluorophenyl)pteridine (Intermediate 27) |
| 63 | 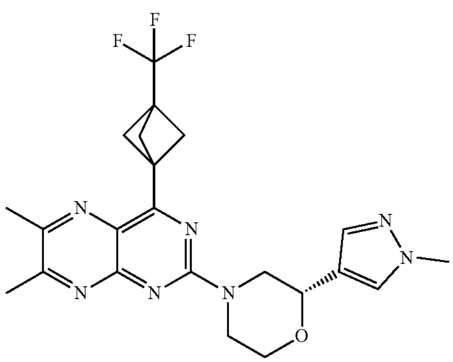 | 6,7-dimethyl-2-((2S)-2-(1-methyl-1H-pyrazol-4-yl)-4-morpholinyl)-4-(3-(trifluoromethyl)bicyclo[1.1.1]pentan-1-yl)pteridine | (S)-2-(1-methyl-1H-pyrazol-4-yl)morpholine (Enamine, Monmouth Jct., NJ, USA) | 2-chloro-6,7-dimethyl-4-(3-(trifluoromethyl)bicyclo[1.1.1]pentan-1-yl)pteridine (Intermediate 71) |
| 64 | 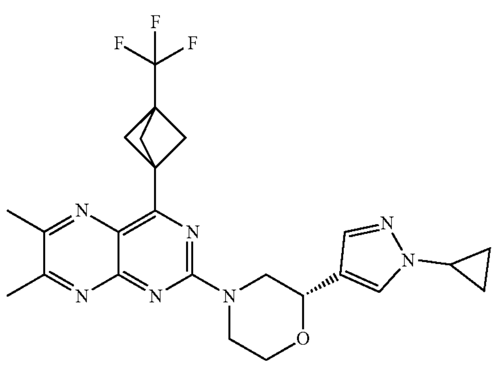 [SMILES: Cc1nc2nc(N3CCO[C@@H](c4cnn(C5CC5)c4)C3)nc(C34CC(C(F)(F)F)(C3)C4)c2nc1C] | 2-((2S)-2-(1-cyclopropyl-1H-pyrazol-4-yl)-4-morpholinyl)-6,7-dimethyl-4-(3-(trifluoromethyl)bicyclo[1.1.1]pentan-1-yl)pteridine | (S)-2-(1-cyclopropyl-1H-pyrazol-4-yl)morpholine (Azepine Ltd. Hampshire, UK) | 2-chloro-6,7-dimethyl-4-(3-(trifluoromethyl)bicyclo[1.1.1]pentan-1-yl)pteridine (Intermediate 71) |
| 65 | 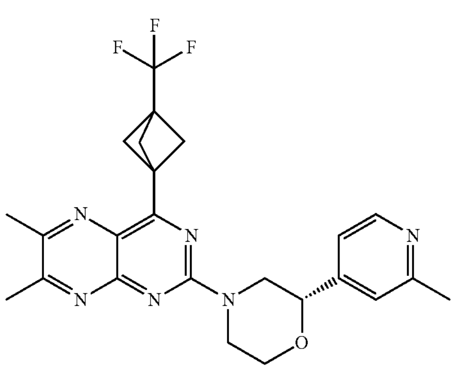 | 6,7-dimethyl-2-((2S)-2-(2-methyl-4-pyridinyl)-4-morpholinyl)-4-(3-(trifluoromethyl)bicyclo[1.1.1]pentan-1-yl)pteridine | (S)-2-(2-methylpyridin-4-yl)morpholine (Intermed Ltd. Kiev, Ukraine) | 2-chloro-6,7-dimethyl-4-(3-(trifluoromethyl)bicyclo[1.1.1]pentan-1-yl)pteridine (Intermediate 71) |

TABLE 1-continued

Compounds 2 to 128 were prepared following the procedure described in Method 1, as follows:

| Ex # | Structure | IUPAC Name | Starting Material 1 | Starting Material 2 |
| --- | --- | --- | --- | --- |
| 66 | 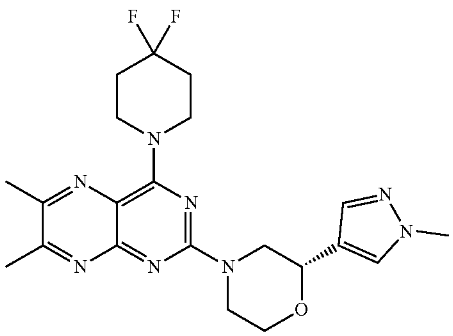 | 4-(4,4-difluoro-1-piperidinyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(4,4-difluoropiperidin-1-yl)-6,7-dimethylpteridine (Intermediate 87) |
| 67 | 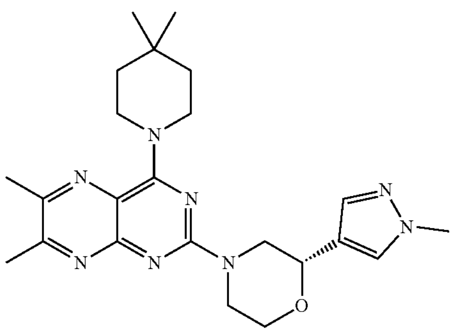 | 4-(4,4-dimethyl-1-piperidinyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(4,4-dimethylpiperidin-1-yl)-6,7-dimethylpteridine (Intermediate 88) |
| 68 | 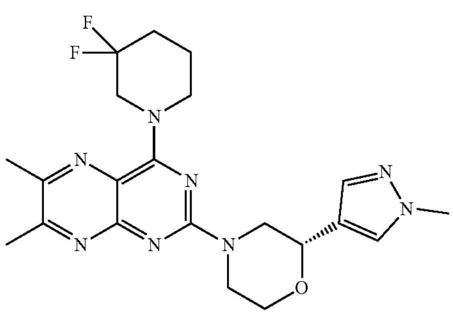 | 4-(3,3-difluoro-1-piperidinyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(3,3-difluoropiperidin-1-yl)-6,7-dimethylpteridine (Intermediate 89) |
| 69 | 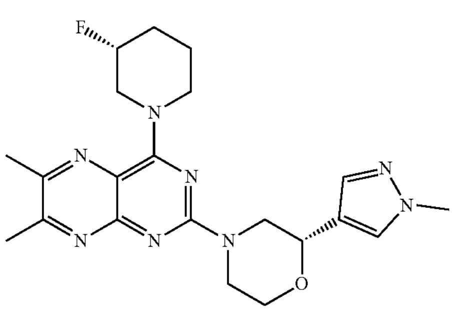 | 4-((3R)-3-fluoro-1-piperidinyl)-6,7-dimethyl-2-((2S)-2-(1-methyl-1H-pyrazol-4-yl)-4-morpholinyl)pteridine Purified by chiral SFC Chromatography. Absolute stereochemistry arbitrarily assigned. | (S)-2-(1-methyl-1H-pyrazol-4-yl)morpholine (Enamine, Monmouth Jct., NJ, USA) | 2-chloro-4-(3-fluoropiperidin-1-yl)-6,7-dimethylpteridine (Intermediate 90) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 70 | 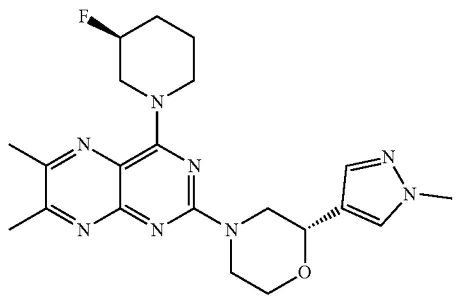 | 4-((3S)-3-fluoro-1-piperidinyl)-6,7-dimethyl-2-((2S)-2-(1-methyl-1H-pyrazol-4-yl)-4-morpholinyl)pteridine Purified by chiral SFC Chromatography. Absolute stereochemistry arbitrarily assigned. | (S)-2-(1-methyl-1H-pyrazol-4-yl)morpholine (Enamine, Monmouth Jct., NJ, USA) | 2-chloro-4-(3-fluoropiperidin-1-yl)-6,7-dimethylpteridine-(Intermediate 90) |
| 71 | 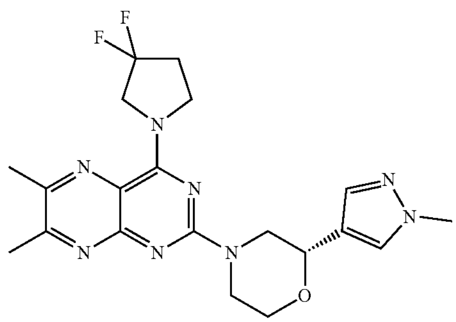 | 4-(3,3-difluoro-1-pyrrolidinyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(3,3-difluoropyrrolidin-1-yl)-6,7-dimethylpteridine (Intermediate 91) |
| 72 | 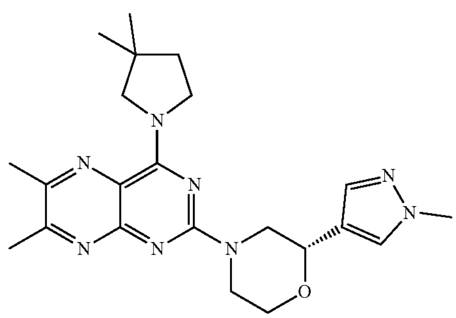 | 4-(3,3-dimethyl-1-pyrrolidinyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(3,3-dimethylpyrrolidin-1-yl)-6,7-dimethylpteridine (Intermediate 92) |
| 73 | 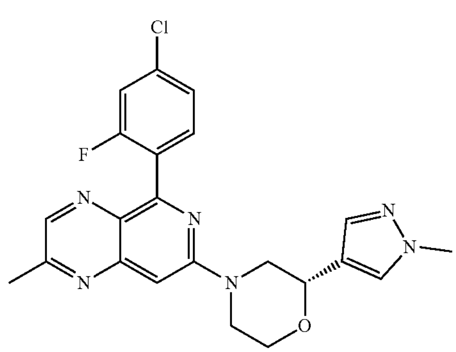 | 5-(4-chloro-2-fluorophenyl)-2-methyl-7-((2S)-2-(1-methyl-1H-pyrazol-4-yl)-4-morpholinyl)pyrido[3,4-b]pyrazine | (S)-2-(1-methyl-1H-pyrazol-4-yl)morpholine (Enamine, Monmouth Jct., NJ, USA) | 7-chloro-5-(4-chloro-2-fluorophenyl)-2-methylpyrido[3,4-b]pyrazine (Intermediate 32) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 74 | 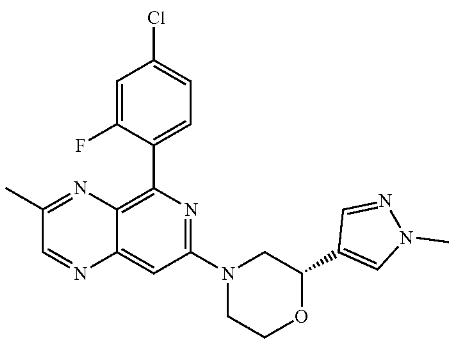 | 5-(4-chloro-2-fluorophenyl)-3-methyl-7-((2S)-2-(1-methyl-1H-pyrazol-4-yl)-4-morpholinyl)pyrido[3,4-b]pyrazine | (S)-2-(1-methyl-1H-pyrazol-4-yl)morpholine (Enamine, Monmouth Jct., NJ, USA) | 7-chloro-5-(4-chloro-2-fluorophenyl)-3-methylpyrido[3,4-b]pyrazine (Intermediate 33) |
| 75 | 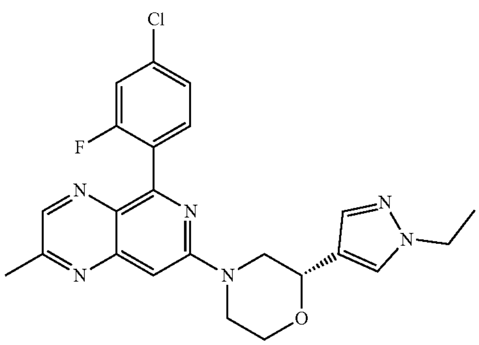 | 5-(4-chloro-2-fluorophenyl)-7-((2S)-2-(1-ethyl-1H-pyrazol-4-yl)-4-morpholinyl)-2-methylpyrido[3,4-b]pyrazine | (S)-2-(1-ethyl-1H-pyrazol-4-yl)morpholine (Intermed, Inc. Kiev, Ukraine) | 7-chloro-5-(4-chloro-2-fluorophenyl)-2-methylpyrido[3,4-b]pyrazine (Intermediate 32) |
| 76 | 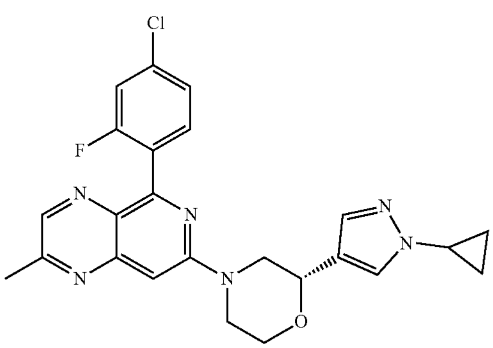 [SMILES: Cc1cnc2c(-c3ccc(Cl)cc3F)nc(N3CCO[C@@H](c4cnn(C5CC5)c4)C3)cc2n1] | 5-(4-chloro-2-fluorophenyl)-7-((2S)-2-(1-cyclopropyl-1H-pyrazol-4-yl)-4-morpholinyl)-2-methylpyrido[3,4-b]pyrazine | (S)-2-(1-cyclopropyl-1H-pyrazol-4-yl)morpholine (Azepine Ltd. Hampshire, UK) | 7-chloro-5-(4-chloro-2-fluorophenyl)-2-methylpyrido[3,4-b]pyrazine (Intermediate 32) |
| 77 | 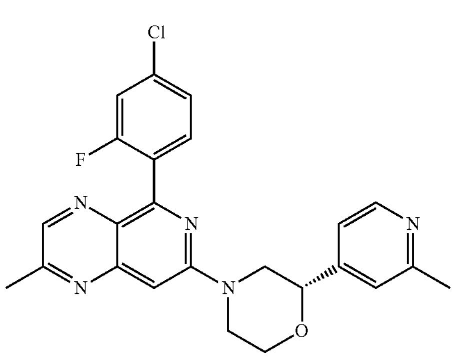 | 5-(4-chloro-2-fluorophenyl)-2-methyl-7-((2S)-2-(2-methyl-4-pyridinyl)-4-morpholinyl)pyrido[3,4-b]pyrazine | (S)-2-(2-methylpyridin-4-yl)morpholine (Intermed Ltd. Kiev, Ukraine) | 7-chloro-5-(4-chloro-2-fluorophenyl)-2-methylpyrido[3,4-b]pyrazine (Intermediate 32) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 78 | 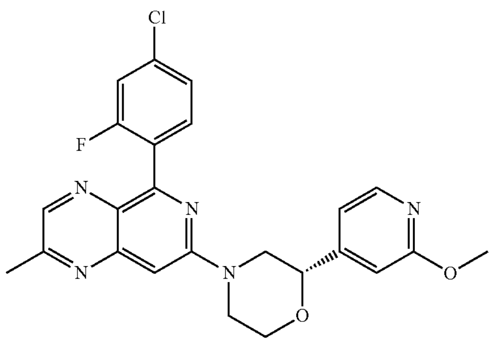 | 5-(4-chloro-2-fluorophenyl)-7-((2S)-2-(2-methoxy-4-pyridinyl)-4-morpholinyl)-2-methylpyrido[3,4-b]pyrazine | (S)-2-(2-methoxypyridin-4-yl)morpholine (Intermed Ltd. Kiev, Ukraine) | 7-chloro-5-(4-chloro-2-fluorophenyl)-2-methylpyrido[3,4-b]pyrazine (Intermediate 32) |
| 79 | 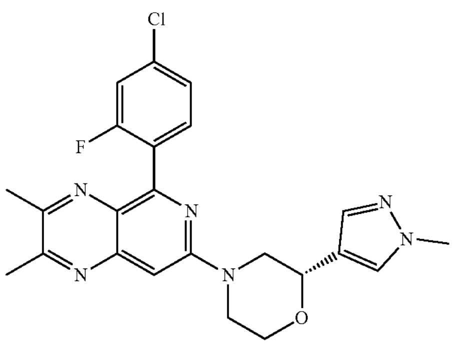 | 5-(4-chloro-2-fluorophenyl)-2,3-dimethyl-7-((2S)-2-(1-methyl-1H-pyrazol-4-yl)-4-morpholinyl)pyrido[3,4-b]pyrazine | (S)-2-(1-methyl-1H-pyrazol-4-yl)morpholine (Enamine, Monmouth Jct., NJ, USA) | 7-chloro-5-(4-chloro-2-fluorophenyl)-2,3-dimethylpyrido[3,4-b]pyrazine (Intermediate 33) |
| 80 | 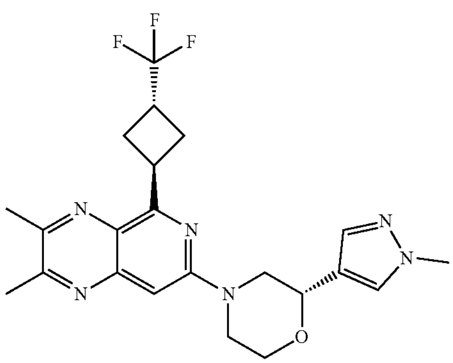 | 2,3-dimethyl-7-((2S)-2-(1-methyl-1H-pyrazol-4-yl)-4-morpholinyl)-5-(trans-3-(trifluoromethyl)cyclobutyl)pyrido[3,4-b]pyrazine | (S)-2-(1-methyl-1H-pyrazol-4-yl)morpholine (Enamine, Monmouth Jct., NJ, USA) | 7-chloro-2,3-dimethyl-5-(trans-3-(trifluoromethyl)cyclobutyl)pyrido[3,4-b]pyrazine (Intermediate 63) |
| 81 | 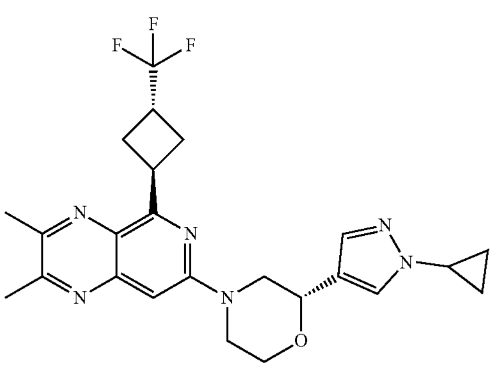 [SMILES: Cc1nc2cc(N3CCO[C@@H](c4cnn(C5CC5)c4)C3)nc([C@H]3C[C@H](C(F)(F)F)C3)c2nc1C] | 7-((2S)-2-(1-cyclopropyl-1H-pyrazol-4-yl)-4-morpholinyl)-2,3-dimethyl-5-(trans-3-(trifluoromethyl)cyclobutyl)pyrido[3,4-b]pyrazine | (S)-2-(1-cyclopropyl-1H-pyrazol-4-yl)morpholine (Azepine Ltd. Hampshire, UK) | 7-chloro-2,3-dimethyl-5-(trans-3-(trifluoromethyl)cyclobutyl)pyrido[3,4-b]pyrazine (Intermediate 63) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 82 | 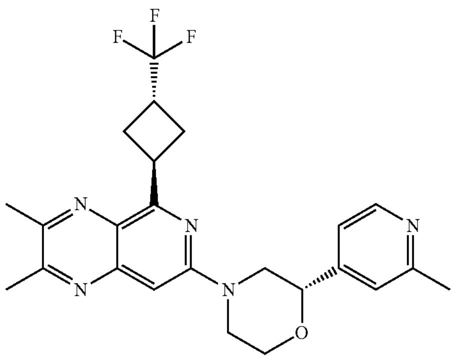 | 2,3-dimethyl-7-((2S)-2-(2-methyl-4-pyridinyl)-4-morpholinyl)-5-(trans-3-(trifluoromethyl)cyclo-butyl)pyrido[3,4-b]pyrazine | (S)-2-(2-methylpyridin-4-yl)morpholine (Intermed Ltd. Kiev, Ukraine) | 7-chloro-2,3-dimethyl-5-(trans-3-(trifluoromethyl)cyclobutyl)pyrido[3,4-b]pyrazine (Intermediate 63) |
| 83 | 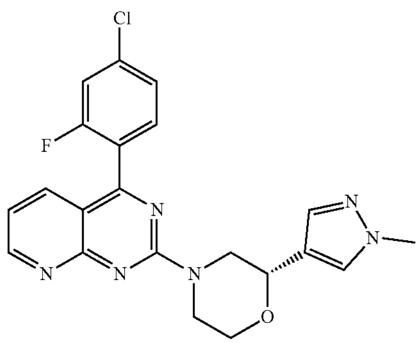 [SMILES: Cn1cc([C@H]2CN(c3nc(-c4ccc(Cl)cc4F)c4cccnc4n3)CCO2)cn1] | 4-(4-chloro-2-fluorophenyl)-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | 2-chloro-4-(4-chloro-2-fluorophenyl)pyrido[2,3-d]pyrimidine (Intermediate 36) |
| 84 | 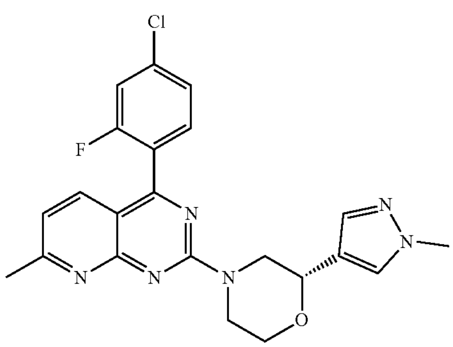 | 4-(4-chloro-2-fluorophenyl)-7-methyl-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | 2-chloro-4-(4-chloro-2-fluorophenyl)-7-methylpyrido[2,3-d]pyrimidine (Intermediate 37) |
| 85 | 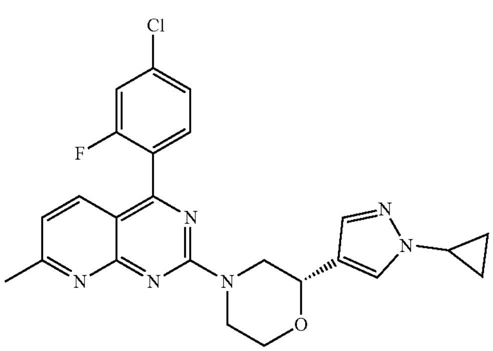 | 4-(4-chloro-2-fluorophenyl)-2-((2S)-2-(1-cyclopropyl-1H-pyrazol-4-yl)-4-morpholinyl)-7-methylpyrido[2,3-d]pyrimidine | (S)-2-(1-cyclopropyl-1H-pyrazol-4-yl)morpholine (Azepine Ltd. Hampshire, UK) | 2-chloro-4-(4-chloro-2-fluorophenyl)-7-methylpyrido[2,3-d]pyrimidine (Intermediate 37) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 86 | 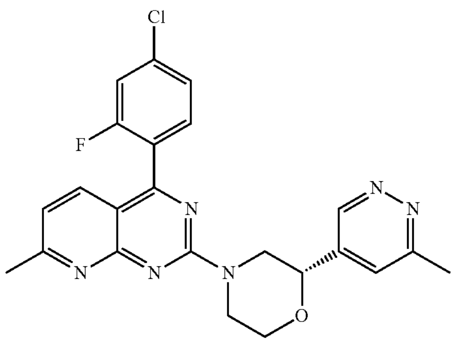 | 4-(4-chloro-2-fluorophenyl)-7-methyl-2-((2S)-2-(6-methyl-4-pyridazinyl)-4-morpholinyl)pyrido[2,3-d]pyrimidine. Absolute stereochemistry arbitrarily assigned. | 2-(6-methylpyridazin-4-yl)morpholine (Azepine Ltd. Hampshire, UK) | 2-chloro-4-(4-chloro-2-fluorophenyl)-7-methylpyrido[2,3-d]pyrimidine (Intermediate 37) |
| 87 | 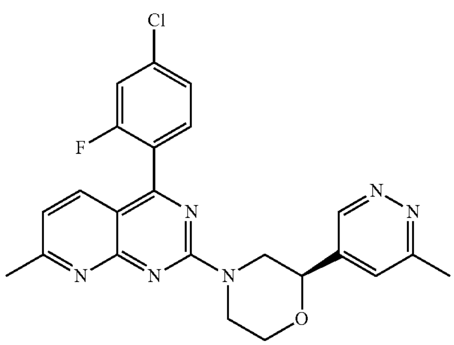 | 4-(4-chloro-2-fluorophenyl)-7-methyl-2-((2R)-2-(6-methyl-4-pyridazinyl)-4-morpholinyl)pyrido[2,3-d]pyrimidine. Absolute stereochemistry arbitrarily assigned. | 2-(6-methylpyridazin-4-yl)morpholine (Azepine Ltd. Hampshire, UK) | 2-chloro-4-(4-chloro-2-fluorophenyl)-7-methylpyrido[2,3-d]pyrimidine (Intermediate 37) |
| 88 | 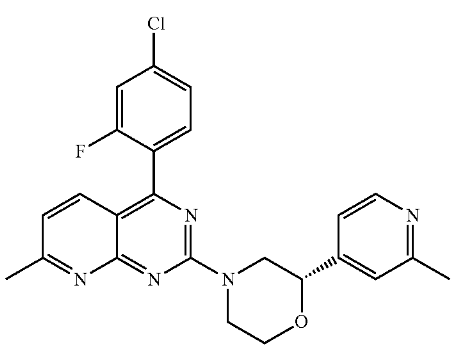 | 4-(4-chloro-2-fluorophenyl)-7-methyl-2-((2S)-2-(2-methyl-4-pyridinyl)-4-morpholinyl)pyrido[2,3-d]pyrimidine | (S)-2-(2-methylpyridin-4-yl)morpholine (Intermed Ltd. Kiev, Ukraine) | 2-chloro-4-(4-chloro-2-fluorophenyl)-7-methylpyrido[2,3-d]pyrimidine (Intermediate 37) |
| 89 | 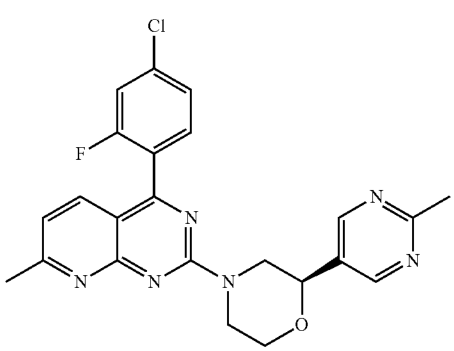 | 4-(4-chloro-2-fluorophenyl)-7-methyl-2-((2R)-2-(2-methyl-5-pyrimidinyl)-4-morpholinyl)pyrido[2,3-d]pyrimidine. Absolute stereochemistry arbitrarily assigned. | 2-(2-methylpyrimidin-5-yl)morpholine (Azepine Ltd. Hampshire, UK) | 2-chloro-4-(4-chloro-2-fluorophenyl)-7-methylpyrido[2,3-d]pyrimidine (Intermediate 37) |

TABLE 1-continued

Compounds 2 to 128 were prepared following the procedure described in Method 1, as follows:

| Ex # | Structure | IUPAC Name | Starting Material 1 | Starting Material 2 |
| --- | --- | --- | --- | --- |
| 90 | 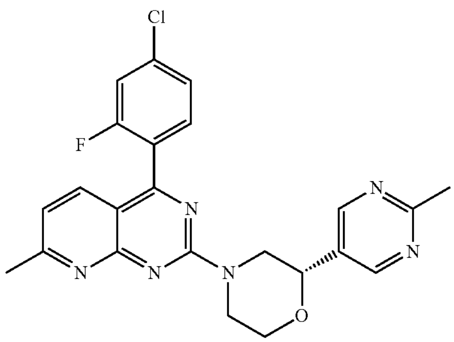 | 4-(4-chloro-2-fluorophenyl)-7-methyl-2-((2S)-2-(2-methyl-5-pyrimidinyl)-4-morpholinyl)pyrido[2,3-d]pyrimidine. Absolute stereochemistry arbitrarily assigned. | 2-(2-methylpyrimidin-5-yl)morpholine (Azepine Ltd. Hampshire, UK) | 2-chloro-4-(4-chloro-2-fluorophenyl)-7-methylpyrido[2,3-d]pyrimidine (Intermediate 37) |
| 91 | 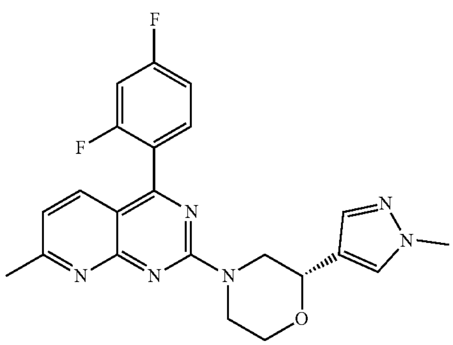 | 4-(2,4-difluorophenyl)-7-methyl-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | 2-chloro-4-(2,4-difluorophenyl)-7-methylpyrido[2,3-d]pyrimidine (Intermediate 38) |
| 92 | 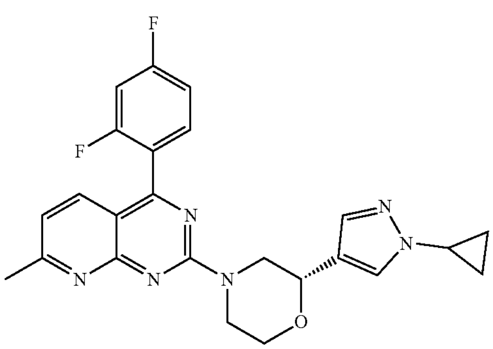 | 2-((2S)-2-(1-cyclopropyl-1H-pyrazol-4-yl)-4-morpholinyl)-4-(2,4-difluorophenyl)-7-methylpyrido[2,3-d]pyrimidine | (S)-2-(1-cyclopropyl-1H-pyrazol-4-yl)morpholine (Azepine Ltd. Hampshire, UK) | 2-chloro-4-(2,4-difluorophenyl)-7-methylpyrido[2,3-d]pyrimidine (Intermediate 38) |
| 93 | 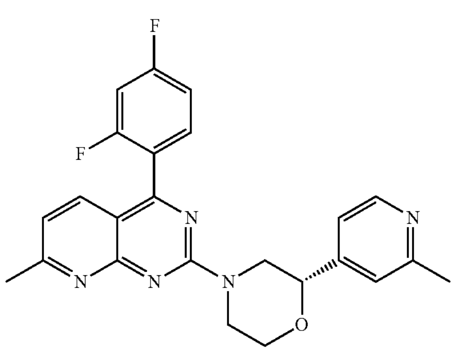 | 4-(2,4-difluorophenyl)-7-methyl-2-((2S)-2-(2-methyl-4-pyridinyl)-4-morpholinyl)pyrido[2,3-d]pyrimidine | (S)-2-(2-methylpyridin-4-yl)morpholine (Intermed Ltd. Kiev, Ukraine) | 2-chloro-4-(2,4-difluorophenyl)-7-methylpyrido[2,3-d]pyrimidine (Intermediate 38) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 94 | 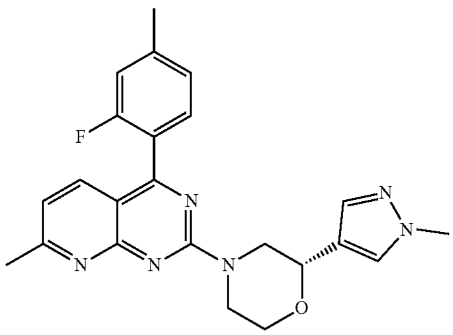 | 4-(2-fluoro-4-methylphenyl)-7-methyl-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | 2-chloro-4-(2-fluoro-4-methylphenyl)-7-methylpyrido[2,3-d]pyrimidine (Intermediate 39) |
| 95 | 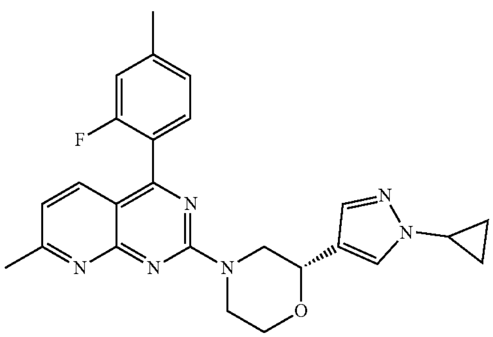 [SMILES: Cc1ccc(-c2nc(N3CCO[C@@H](c4cnn(C5CC5)c4)C3)nc3nc(C)ccc23)c(F)c1] | 2-((2S)-2-(1-cyclopropyl-1H-pyrazol-4-yl)-4-morpholinyl)-4-(2-fluoro-4-methylphenyl)-7-methylpyrido[2,3-d]pyrimidine | (S)-2-(1-cyclopropyl-1H-pyrazol-4-yl)morpholine (Azepine Ltd. Hampshire, UK) | 2-chloro-4-(2-fluoro-4-methylphenyl)-7-methylpyrido[2,3-d]pyrimidine (Intermediate 39) |
| 96 | 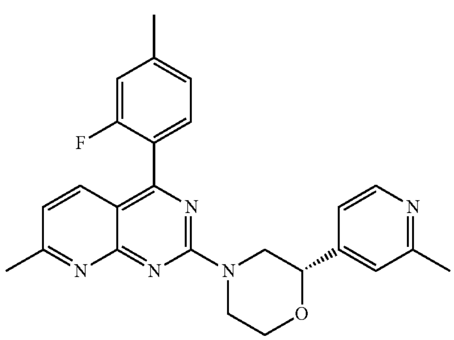 | 4-(2-fluoro-4-methylphenyl)-7-methyl-2-((2S)-2-(2-methyl-4-pyridinyl)-4-morpholinyl)pyrido[2,3-d]pyrimidine | (S)-2-(2-methylpyridin-4-yl)morpholine (Intermed Ltd. Kiev, Ukraine) | 2-chloro-4-(2-fluoro-4-methylphenyl)-7-methylpyrido[2,3-d]pyrimidine (Intermediate 39) |
| 97 | 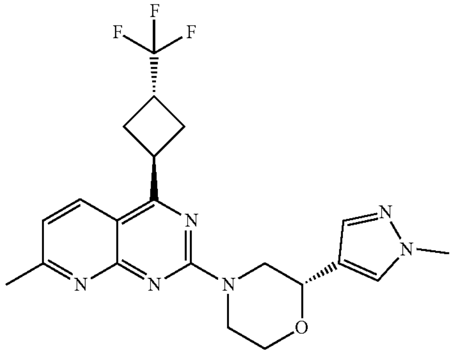 | 7-methyl-2-((2S)-2-(1-methyl-1H-pyrazol-4-yl)-4-morpholinyl)-4-(trans-3-(trifluoromethyl)cyclobutyl)pyrido[2,3-d]pyrimidine | (S)-2-(1-methyl-1H-pyrazol-4-yl)morpholine (Enamine, Monmouth Jct., NJ, USA) | 2-chloro-7-methyl-4-(trans-3-(trifluoromethyl)cyclobutyl)pyrido[2,3-d]pyrimidine (Intermediate 64) |

TABLE 1-continued

Compounds 2 to 128 were prepared following the procedure described in Method 1, as follows:

| Ex # | Structure | IUPAC Name | Starting Material 1 | Starting Material 2 |
| --- | --- | --- | --- | --- |
| 98 | 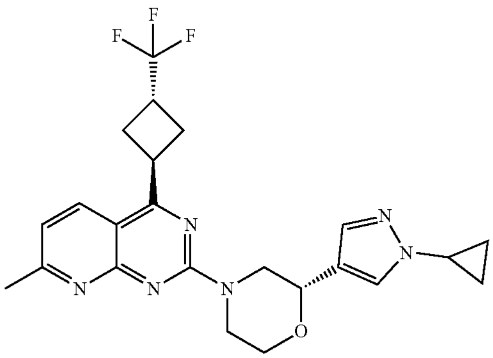 [SMILES: Cc1ccc2c(n1)nc(N1CCO[C@@H](c3cnn(C4CC4)c3)C1)nc2[C@H]1C[C@H](C(F)(F)F)C1] | 2-((2S)-2-(1-cyclopropyl-1H-pyrazol-4-yl)-4-morpholinyl)-7-methyl-4-(trans-3-(trifluoromethyl)cyclobutyl)pyrido[2,3-d]pyrimidine | (S)-2-(1-cyclopropyl-1H-pyrazol-4-yl)morpholine (Azepine Ltd. Hampshire, UK) | 2-chloro-7-methyl-4-(trans-3-(trifluoromethyl)cyclobutyl)pyrido[2,3-d]pyrimidine (Intermediate 64) |
| 99 | 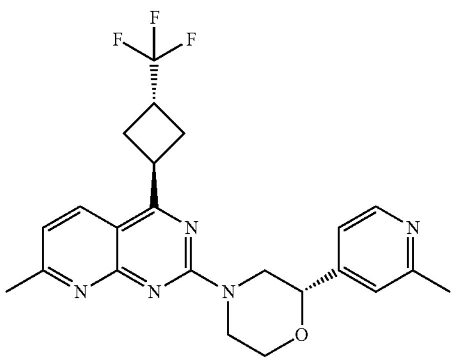 | 7-methyl-2-((2S)-2-(2-methyl-4-pyridinyl)-4-morpholinyl)-4-(trans-3-(trifluoromethyl)cyclobutyl)pyrido[2,3-d]pyrimidine | (S)-2-(2-methylpyridin-4-yl)morpholine (Intermed Ltd. Kiev, Ukraine) | 2-chloro-7-methyl-4-(trans-3-(trifluoromethyl)cyclobutyl)pyrido[2,3-d]pyrimidine (Intermediate 64) |
| 100 | 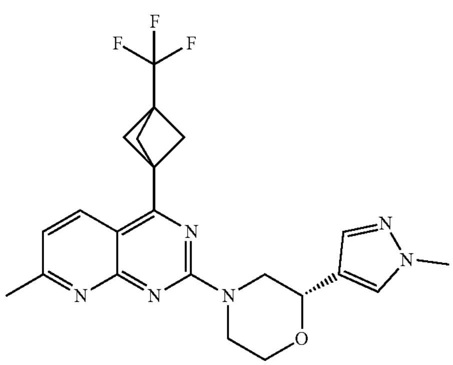 | 7-methyl-2-((2S)-2-(1-methyl-1H-pyrazol-4-yl)-4-morpholinyl)-4-(3-(trifluoromethyl)bicyclo[1.1.1]pentan-1-yl)pyrido[2,3-d]pyrimidine | (S)-2-(1-methyl-1H-pyrazol-4-yl)morpholine (Enamine, Monmouth Jct., NJ, USA) | 2-chloro-7-methyl-4-(3-(trifluoromethyl)bicyclo[1.1.1]pentan-1-yl)pyrido[2,3-d]pyrimidine (Intermediate 72) |
| 101 | 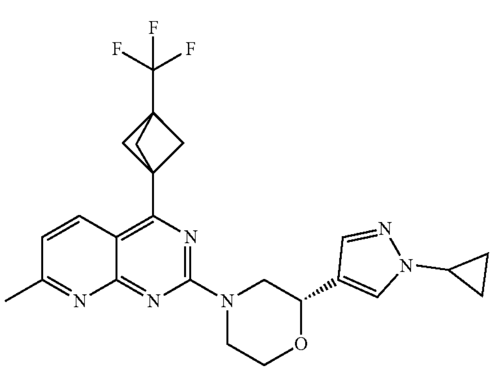 [SMILES: Cc1ccc2c(C34CC(C(F)(F)F)(C3)C4)nc(N3CCO[C@@H](c4cnn(C5CC5)c4)C3)nc2n1] | 2-((2S)-2-(1-cyclopropyl-1H-pyrazol-4-yl)-4-morpholinyl)-7-methyl-4-(3-(trifluoromethyl)bicyclo[1.1.1]pentan-1-yl)pyrido[2,3-d]pyrimidine | (S)-2-(1-cyclopropyl-1H-pyrazol-4-yl)morpholine (Azepine Ltd. Hampshire, UK) | 2-chloro-7-methyl-4-(3-(trifluoromethyl)bicyclo[1.1.1]pentan-1-yl)pyrido[2,3-d]pyrimidine (Intermediate 72) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 102 | 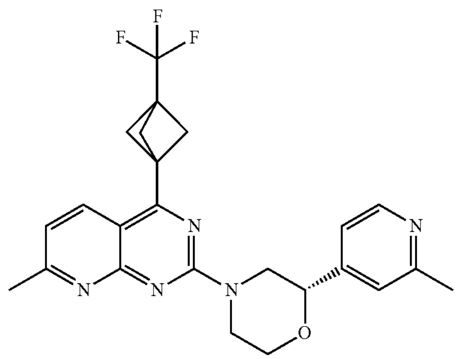 | 7-methyl-2-((2S)-2-(2-methyl-4-pyridinyl)-4-morpholinyl)-4-(3-(trifluoromethyl)bicyclo[1.1.1]pentan-1-yl)pyrido[2,3-d]pyrimidine | (S)-2-(2-methylpyridin-4-yl)morpholine (Intermed Ltd. Kiev, Ukraine) | 2-chloro-7-methyl-4-(3-(trifluoromethyl)bicyclo[1.1.1]pentan-1-yl)pyrido[2,3-d]pyrimidine (Intermediate 72) |
| 103 | 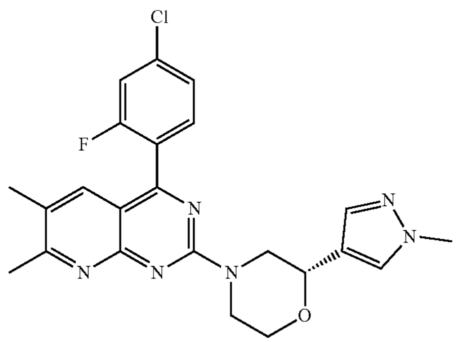 | 4-(4-chloro-2-fluorophenyl)-6,7-dimethyl-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | 2-chloro-4-(4-chloro-2-fluorophenyl)-6,7-dimethylpyrido[2,3-d]pyrimidine (Intermediate 40) |
| 104 | 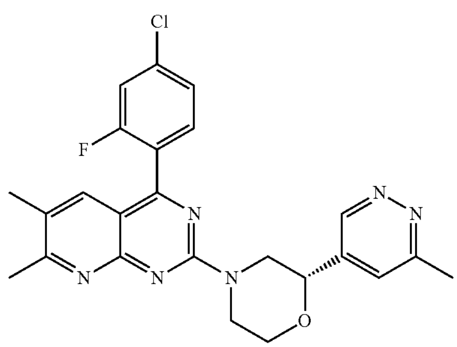 | 4-(4-chloro-2-fluorophenyl)-6,7-dimethyl-2-((2S)-2-(6-methyl-4-pyridazinyl)-4-morpholinyl)pyrido[2,3-d]pyrimidine. Absolute stereochemistry arbitrarily assigned. | 2-(6-methylpyridazin-4-yl)morpholine (Azepine Ltd. Hampshire, UK) | 2-chloro-4-(4-chloro-2-fluorophenyl)-6,7-dimethylpyrido[2,3-d]pyrimidine (Intermediate 40) |
| 105 | 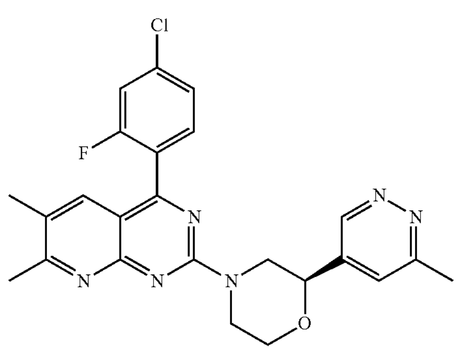 | 4-(4-chloro-2-fluorophenyl)-6,7-dimethyl-2-((2R)-2-(6-methyl-4-pyridazinyl)-4-morpholinyl)pyrido[2,3-d]pyrimidine. Absolute stereochemistry arbitrarily assigned. | 2-(6-methylpyridazin-4-yl)morpholine (Azepine Ltd. Hampshire, UK) | 2-chloro-4-(4-chloro-2-fluorophenyl)-6,7-dimethylpyrido[2,3-d]pyrimidine (Intermediate 40) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 106 | 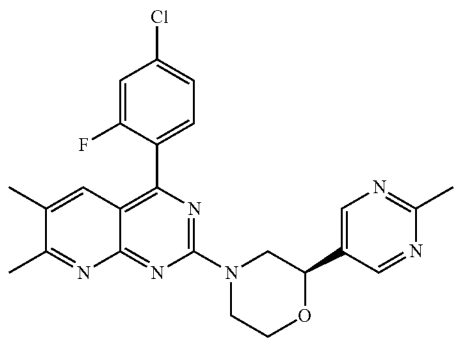 | 4-(4-chloro-2-fluorophenyl)-6,7-dimethyl-2-((2R)-2-(2-methyl-5-pyrimidinyl)-4-morpholinyl)pyrido[2,3-d]pyrimidine. Absolute stereochemistry arbitrarily assigned. | 2-(2-methylpyrimidin-5-yl)morpholine (Azepine Ltd. Hampshire, UK) | 2-chloro-4-(4-chloro-2-fluorophenyl)-6,7-dimethylpyrido[2,3-d]pyrimidine (Intermediate 40) |
| 107 | 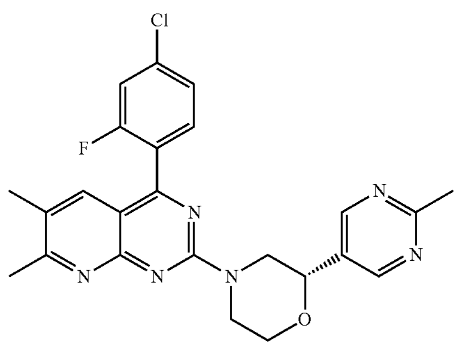 | 4-(4-chloro-2-fluorophenyl)-6,7-dimethyl-2-((2S)-2-(2-methyl-5-pyrimidinyl)-4-morpholinyl)pyrido[2,3-d]pyrimidine. Absolute stereochemistry arbitrarily assigned. | 2-(2-methylpyrimidin-5-yl)morpholine (Azepine Ltd. Hampshire, UK) | 2-chloro-4-(4-chloro-2-fluorophenyl)-6,7-dimethylpyrido[2,3-d]pyrimidine (Intermediate 40) |
| 108 | 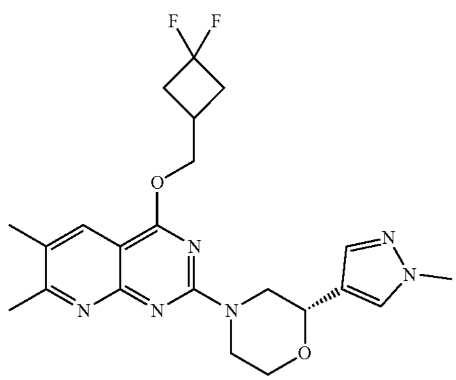 | 4-((3,3-difluorocyclobutyl)methoxy)-6,7-dimethyl-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | 2-chloro-4-((3,3-difluorocyclobutyl)methoxy)-6,7-dimethylpyrido[2,3-d]pyrimidine (Intermediate 93) |
| 109 | 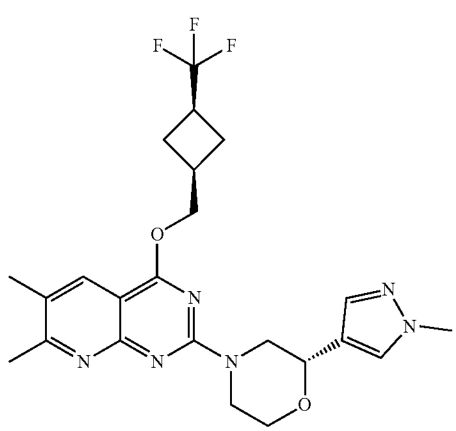 | 6,7-dimethyl-2-((2S)-2-(1-methyl-1H-pyrazol-4-yl)-4-morpholinyl)-4-((cis-3-(trifluoromethyl)cyclobutyl)methoxy)pyrido[2,3-d]pyrimidine | (S)-2-(1-methyl-1H-pyrazol-4-yl)morpholine (Enamine, Monmouth Jct., NJ, USA) | 2-chloro-6,7-dimethyl-4-(((cis)-3-(trifluoromethyl)cyclobutyl)methoxy)pyrido[2,3-d]pyrimidine (Intermediate 94) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 110 | 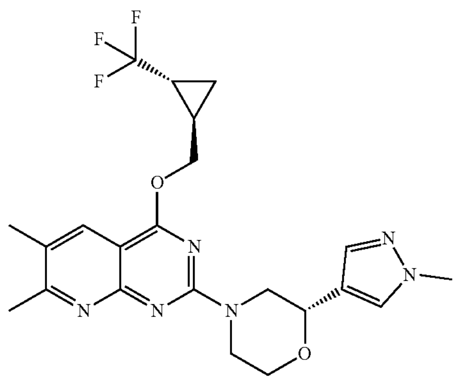 | 6,7-dimethyl-2-((2S)-2-(1-methyl-1H-pyrazol-4-yl)-4-morpholinyl)-4-(((1R,2R)-2-(trifluoromethyl)cyclopropyl)methoxy)pyrido[2,3-d]pyrimidine | (S)-2-(1-methyl-1H-pyrazol-4-yl)morpholine (Enamine, Monmouth Jct., NJ, USA) | 2-chloro-6,7-dimethyl-4-(((1R,2R)-2-(trifluoromethyl)cyclopropyl)methoxy)pyrido[2,3-d]pyrimidine (Intermediate 95) |
| 111 | 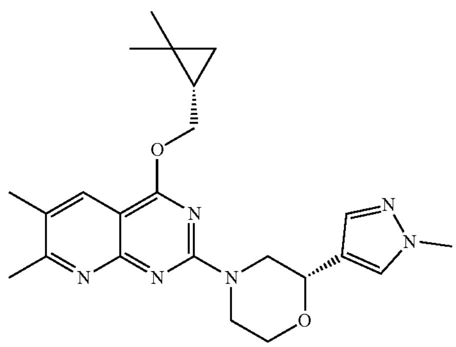 | 4-(((1S)-2,2-dimethylcyclopropyl)methoxy)-6,7-dimethyl-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | (S)-2-chloro-4-((2,2-dimethylcyclopropyl)methoxy)-6,7-dimethylpyrido[2,3-d]pyrimidine (Intermediate 96) |
| 112 | 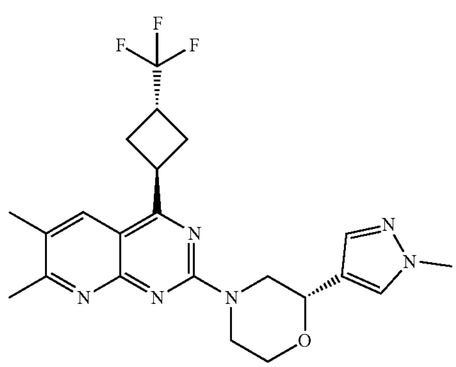 | 6,7-dimethyl-2-((2S)-2-(1-methyl-1H-pyrazol-4-yl)-4-morpholinyl)-4-(trans-3-(trifluoromethyl)cyclobutyl)pyrido[2,3-d]pyrimidine | (S)-2-(1-methyl-1H-pyrazol-4-yl)morpholine (Enamine, Monmouth Jct., NJ, USA) | 2-chloro-6,7-dimethyl-4-(trans-3-(trifluoromethyl)cyclobutyl)pyrido[2,3-d]pyrimidine (Intermediate 65) |
| 113 | 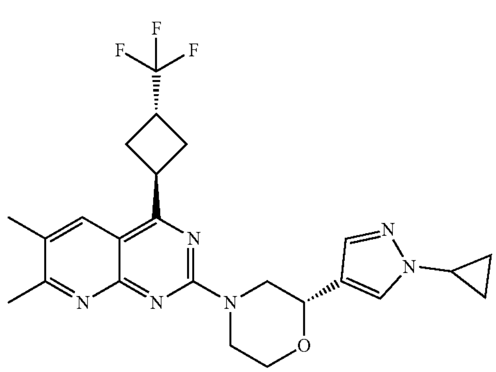 [SMILES: Cc1cc2c(nc(N3CCO[C@@H](c4cnn(C5CC5)c4)C3)nc2[C@H]2C[C@H](C(F)(F)F)C2)nc1C] | 2-((2S)-2-(1-cyclopropyl-1H-pyrazol-4-yl)-4-morpholinyl)-6,7-dimethyl-4-(trans-3-(trifluoromethyl)cyclobutyl)pyrido[2,3-d]pyrimidine | (S)-2-(1-cyclopropyl-1H-pyrazol-4-yl)morpholine (Azepine Ltd. Hampshire, UK) | 2-chloro-6,7-dimethyl-4-(trans-3-(trifluoromethyl)cyclobutyl)pyrido[2,3-d]pyrimidine (Intermediate 65) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 114 | 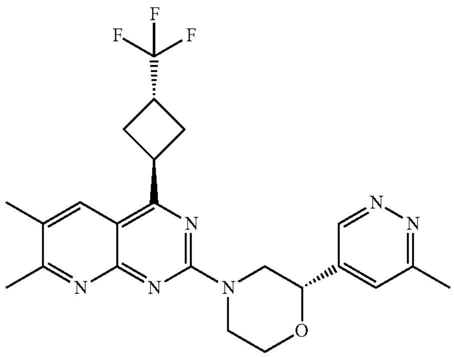 | 6,7-dimethyl-2-((2S)-2-(6-methyl-4-pyridazinyl)-4-morpholinyl)-4-(trans-3-(trifluoromethyl)cyclobutyl)pyrido[2,3-d]pyrimidine. Absolute stereochemistry arbitrarily assigned. | 2-(6-methylpyridazin-4-yl)morpholine (Azepine Ltd. Hampshire, UK) | 2-chloro-6,7-dimethyl-4-(trans-3-(trifluoromethyl)cyclobutyl)pyrido[2,3-d]pyrimidine (Intermediate 65) |
| 115 | 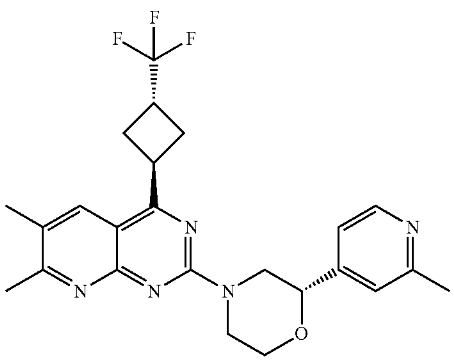 | 6,7-dimethyl-2-((2S)-2-(2-methyl-4-pyridinyl)-4-morpholinyl)-4-(trans-3-(trifluoromethyl)cyclobutyl)pyrido[2,3-d]pyrimidine | (S)-2-(2-methylpyridin-4-yl)morpholine (Intermed Ltd. Kiev, Ukraine) | 2-chloro-6,7-dimethyl-4-(trans-3-(trifluoromethyl)cyclobutyl)pyrido[2,3-d]pyrimidine (Intermediate 65) |
| 116 | 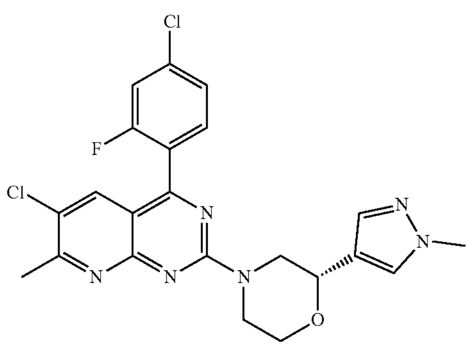 | 6-chloro-4-(4-chloro-2-fluorophenyl)-7-methyl-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | 2,6-dichloro-4-(4-chloro-2-fluorophenyl)-7-methylpyrido[2,3-d]pyrimidine (Intermediate 43) |
| 117 | 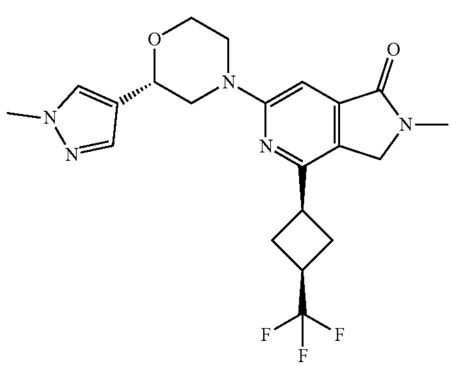 | 2-methyl-6-((2S)-2-(1-methyl-1H-pyrazol-4-yl)-4-morpholinyl)-4-(cis-3-(trifluoromethyl)cyclobutyl)-2,3-dihydro-1H-pyrrolo[3,4-c]pyridin-1-one | (S)-2-(1-methyl-1H-pyrazol-4-yl)morpholine (Enamine, Monmouth Jct., NJ, USA) | 6-chloro-2-methyl-4-(3-(trifluoromethyl)cyclobutyl)-2,3-dihydro-1H-pyrrolo[3,4-c]pyridin-1-one (Intermediate 66) |

TABLE 1-continued

Compounds 2 to 128 were prepared following the procedure described in Method 1, as follows:

| Ex # | Structure | IUPAC Name | Starting Material 1 | Starting Material 2 |
|------|-----------|------------|---------------------|---------------------|
| 118 | 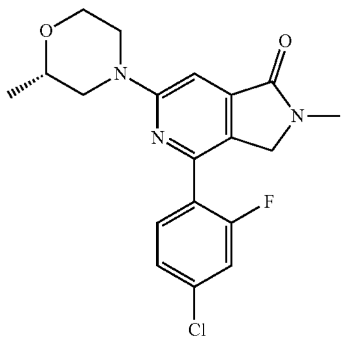 | 4-(4-chloro-2-fluorophenyl)-2-methyl-6-((2S)-2-methyl-4-morpholinyl)-2,3-dihydro-1H-pyrrolo[3,4-c]pyridin-1-one | (S)-2-methylmorpholine (Enamine, Monmouth Jct., NJ, USA) | 6-chloro-4-(4-chloro-2-fluorophenyl)-2-methyl-2,3-dihydro-1H-pyrrolo[3,4-c]pyridin-1-one (Intermediate 10) |
| 119 | 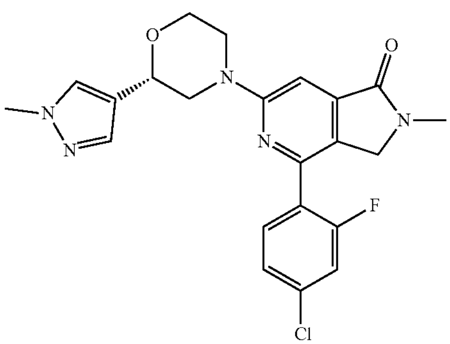 | 4-(4-chloro-2-fluorophenyl)-2-methyl-6-((2S)-2-(1-methyl-1H-pyrazol-4-yl)-4-morpholinyl)-2,3-dihydro-1H-pyrrolo[3,4-c]pyridin-1-one | (S)-2-(1-methyl-1H-pyrazol-4-yl)morpholine (Enamine, Monmouth Jct., NJ, USA) | 6-chloro-4-(4-chloro-2-fluorophenyl)-2-methyl-2,3-dihydro-1H-pyrrolo[3,4-c]pyridin-1-one (Intermediate 10) |
| 120 | 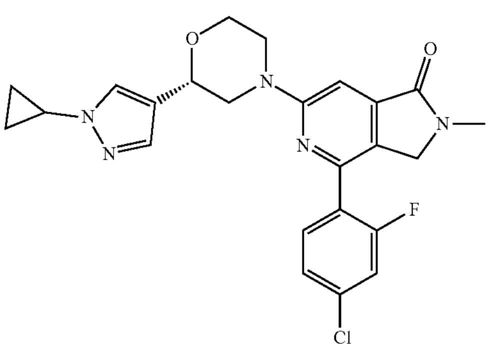 [SMILES: CN1Cc2c(cc(N3CCO[C@@H](c4cnn(C5CC5)c4)C3)nc2-c2ccc(Cl)cc2F)C1=O] | 4-(4-chloro-2-fluorophenyl)-6-((2S)-2-(1-cyclopropyl-1H-pyrazol-4-yl)-4-morpholinyl)-2-methyl-2,3-dihydro-1H-pyrrolo[3,4-c]pyridin-1-one | (S)-2-(1-cyclopropyl-1H-pyrazol-4-yl)morpholine (Azepine Ltd. Hampshire, UK) | 6-chloro-4-(4-chloro-2-fluorophenyl)-2-methyl-2,3-dihydro-1H-pyrrolo[3,4-c]pyridin-1-one (Intermediate 10) |
| 121 | 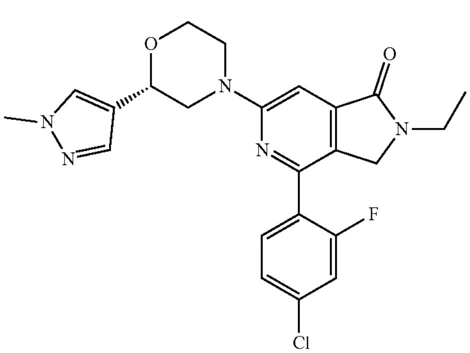 | 4-(4-chloro-2-fluorophenyl)-2-ethyl-6-((2S)-2-(1-methyl-1H-pyrazol-4-yl)-4-morpholinyl)-2,3-dihydro-1H-pyrrolo[3,4-c]pyridin-1-one | (S)-2-(1-methyl-1H-pyrazol-4-yl)morpholine (Enamine, Monmouth Jct., NJ, USA) | 6-chloro-4-(4-chloro-2-fluorophenyl)-2-ethyl-2,3-dihydro-1H-pyrrolo[3,4-c]pyridin-1-one (Intermediate 46) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 122 | 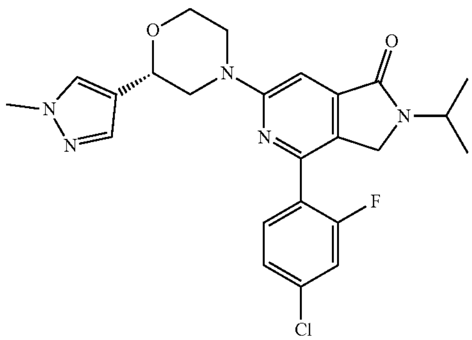 [SMILES: CC(C)N1Cc2c(cc(N3CCO[C@@H](c4cnn(C)c4)C3)nc2-c2ccc(Cl)cc2F)C1=O] | 4-(4-chloro-2-fluorophenyl)-6-((2S)-2-(1-methyl-1H-pyrazol-4-yl)-4-morpholinyl)-2-(2-propanyl)-2,3-dihydro-1H-pyrrolo[3,4-c]pyridin-1-one | (S)-2-(1-methyl-1H-pyrazol-4-yl)morpholine (Enamine, Monmouth Jct., NJ, USA) | 6-chloro-4-(4-chloro-2-fluorophenyl)-2-isopropyl-2,3-dihydro-1H-pyrrolo[3,4-c]pyridin-1-one (Intermediate 47) |
| 123 | 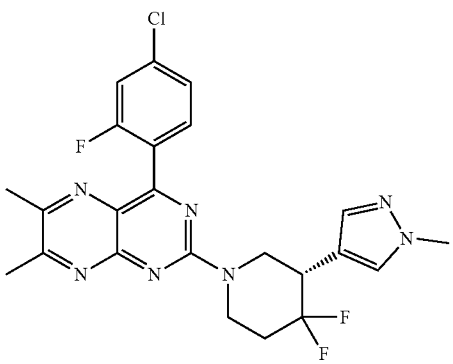 | 4-(4-chloro-2-fluorophenyl)-2-((3S)-4,4-difluoro-3-(1-methyl-1H-pyrazol-4-yl)-1-piperidinyl)-6,7-dimethylpteridine Purified by chiral SFC Chromatography. Absolute stereochemistry arbitrarily assigned. | 4,4-difluoro-3-(1-methyl-1H-pyrazol-4-yl)piperidine (Intermediate 73) | 2-chloro-4-(4-chloro-2-fluorophenyl)-6,7-dimethylpteridine (Intermediate 16) |
| 124 | 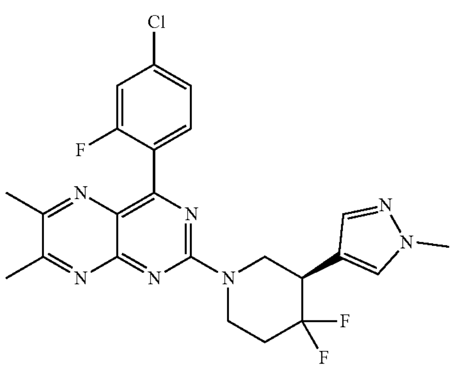 | 4-(4-chloro-2-fluorophenyl)-2-((3R)-4,4-difluoro-3-(1-methyl-1H-pyrazol-4-yl)-1-piperidinyl)-6,7-dimethylpteridine Purified by chiral SFC Chromatography. Absolute stereochemistry arbitrarily assigned. | 4,4-difluoro-3-(1-methyl-1H-pyrazol-4-yl)piperidine (Intermediate 73) | 2-chloro-4-(4-chloro-2-fluorophenyl)-6,7-dimethylpteridine (Intermediate 16) |
| 125 | 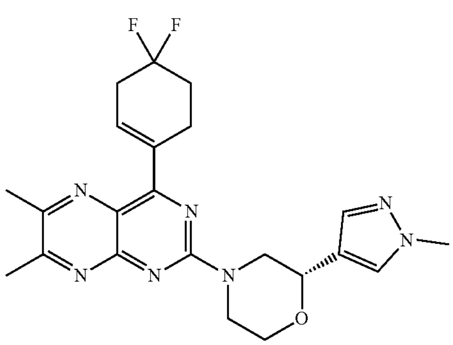 | 4-(4,4-difluoro-1-cyclohexen-1-yl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(4,4-difluorocyclohex-1-en-1-yl)-6,7-dimethylpteridine (Intermediate 49) |

TABLE 1-continued

Compounds 2 to 128 were prepared following the procedure described in Method 1, as follows:

| Ex # | Structure | IUPAC Name | Starting Material 1 | Starting Material 2 |
|---|---|---|---|---|
| 126 | 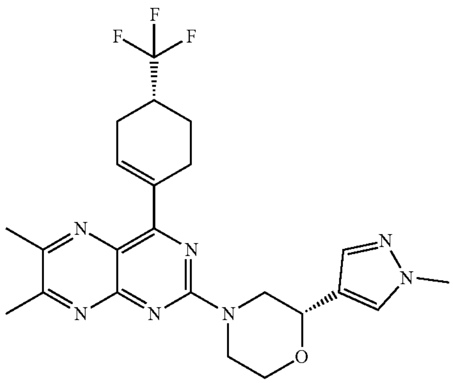 | 6,7-dimethyl-2-((2S)-2-(1-methyl-1H-pyrazol-4-yl)-4-morpholinyl)-4-((4R)-4-(trifluoromethyl)-1-cyclohexen-1-yl)pteridine Purified by chiral SFC Chromatography. Absolute stereochemistry arbitrarily assigned. | (S)-2-(1-methyl-1H-pyrazol-4-yl)morpholine (Enamine, Monmouth Jct., NJ, USA) | 2-chloro-6,7-dimethyl-4-(4-(trifluoromethyl)cyclohex-1-en-1-yl)pteridine (Intermediate 48) |
| 127 | 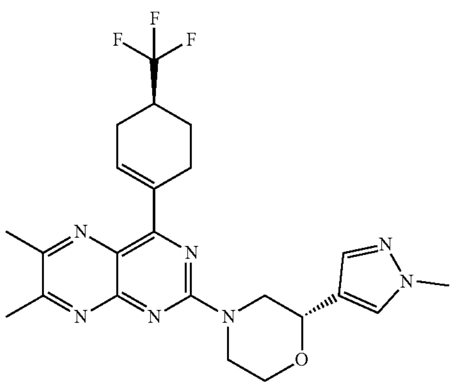 | 6,7-dimethyl-2-((2S)-2-(1-methyl-1H-pyrazol-4-yl)-4-morpholinyl)-4-((4S)-4-(trifluoromethyl)-1-cyclohexen-1-yl)pteridine Purified by chiral SFC Chromatography. Absolute stereochemistry arbitrarily assigned. | (S)-2-(1-methyl-1H-pyrazol-4-yl)morpholine (Enamine, Monmouth Jct., NJ, USA) | 2-chloro-6,7-dimethyl-4-(4-(trifluoromethyl)cyclohex-1-en-1-yl)pteridine (Intermediate 48) |
| 128 | 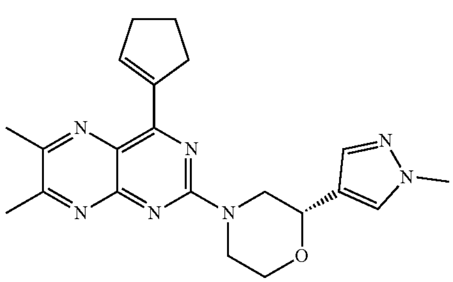 | 4-(1-cyclopenten-1-yl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(cyclopent-1-en-1-yl)-6,7-dimethylpteridine (Intermediate 51) |

Method 2

Example 129: 5-(4-chloro-2-fluorophenyl)-2-methyl-7-((2S)-2-(1-(3-oxetanyl)-1H-pyrazol-4-yl)-4-morpholinyl)pyrido[3,4-b]pyrazine

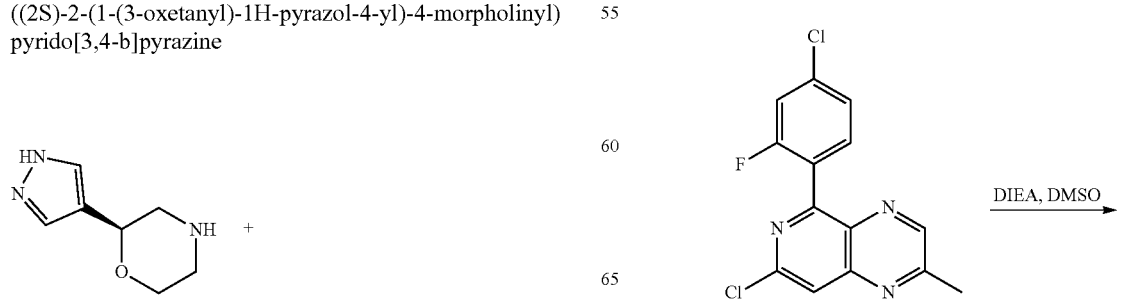

-continued

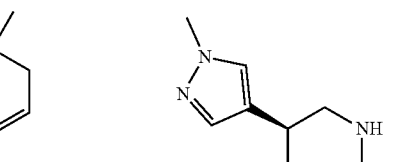

Example 129

To a 10 mL vial were added 7-chloro-5-(4-chloro-2-fluorophenyl)-2-methylpyrido[3,4-b]pyrazine (Intermediate 32) (0.154 g, 0.5 mmol), (S)-2-(1H-pyrazol-4-yl)morpholine (Enamine, Inc.) (0.128 g, 0.600 mmol), and diisopropylethylamine (0.323 g, 0.437 mL, 2.500 mmol), and DMSO (1.5 mL) The reaction mixture was stirred at 100° C. for 5 h, cooled to rt then partitioned between EtOAc and H₂O. The organic phase was dried over Na₂SO₄ and concentrated under vacuum. The crude intermediate (0.106 g, 0.25 mmol) was dissolved in N, N-dimethylformamide (1 mL), 3-iodooxetane (92 mg, 0.5 mmol) and Cs₂CO₃ (163 mg, 0.50 mmol) were added and the reaction was stirred at 60° C. for 12 h. The mixture was cooled to rt then partitioned between EtOAc and H₂O. The organic phase was dried over Na₂SO₄, concentrated under vacuum and the crude product was purified by reverse phase HPLC to provide 5-(4-chloro-2-fluorophenyl)-2-methyl-7-((2S)-2-(1-(3-oxetanyl)-1H-pyrazol-4-yl)-4-morpholinyl)pyrido[3,4-b]pyrazine. $^1$H NMR (600 MHz, DMSO-d6) δ ppm 8.49-8.55 (m, 1H), 7.98 (s, 1H), 7.62-7.68 (m, 2H), 7.53-7.58 (m, 1H), 7.42-7.47 (m, 1H), 7.19-7.24 (m, 1H), 5.51-5.61 (m, 1H), 4.87-4.94 (m, 4H), 4.58-4.65 (m, 1H), 4.42-4.48 m, 1H), 4.24-4.29 (m, 1H), 4.01-4.09 (m, 1H), 3.73-3.80 (m, 1H), 3.09-3.14 (m, 1H), 3.02-3.07 (m, 1H), 2.63-2.68 (m, 3H). m/z (ESI, +ive ion):481.0 (M+H)⁺.

Method 3

Example 130: 4-(4,4-dimethylcyclohexyl)-6,7-dimethyl-2-((2S)-2-(1-methyl-1H-pyrazol-4-yl)-4-morpholinyl)pteridine

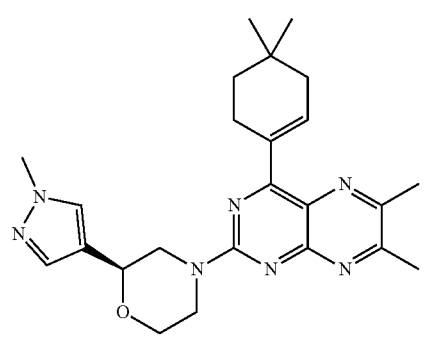

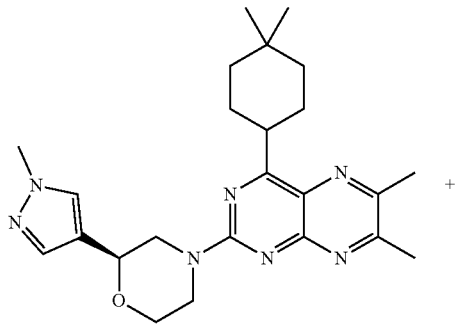

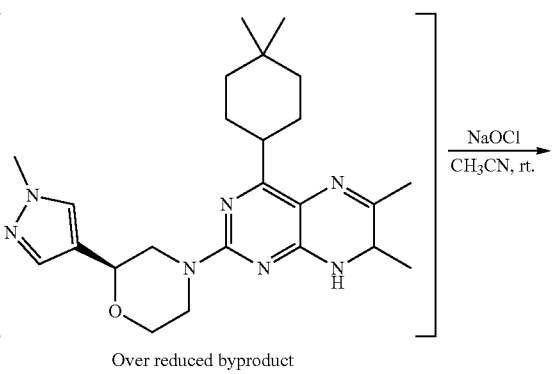

Over reduced byproduct

-continued

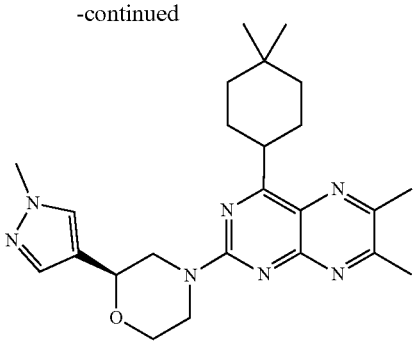

Example 130

Step 1: (S)-4-(4-(4,4-dimethylcyclohex-1-en-1-yl)-6,7-dimethylpteridin-2-yl)-2-(1-methyl-1H-pyrazol-4-yl)morpholine. To a 50-mL round bottomed flask was added 2-chloro-4-(4,4-dimethylcyclohex-1-en-1-yl)-6,7-dimethylpteridine (Intermediate 54, 270 mg, 0.892 mmol) and DIEA (0.3 mL, 1.76 mmol) in DMSO (8 mL). (S)-2-(1-methyl-1H-pyrazol-4-yl)morpholine (164 mg, 0.98 mmol) was then added and the reaction mass continued stirred at 10020 C. for 2 h. The reaction mixture was quenched with $H_2O$ (15 mL), extracted with DCM (2×20 mL). The combined organic layers were washed with brine (20 mL), dried over $Na_2SO_4$, and concentrated under reduced pressure. The crude material was purified by reverse-phase preparative HPLC using a Reveleris C18 column, $CH_3CN/H_2O$, gradient 0% to 55% over 30 min to provide (S)-4-(4-(4,4-dimethylcyclohex-1-en-1-yl)-6,7-dimethylpteridin-2-yl)-2-(1-methyl-1H-pyrazol-4-yl)morpholine (300 mg, 0.692 mmol, 65.5% yield) as a yellow solid. $^1$H NMR(400 MHz, DMSO-d6): δ ppm 7.77 (s, 1H), 7.47 (d, J=0.8 Hz, 1H), 7.40 (s, 1H), 4.72 (d, J=12.9 Hz, 1H), 4.61 (d, J=13.3 Hz, 1H), 4.51 (dd, J=10.4, 2.7 Hz, 1H), 4.01 (d, J=10.5 Hz, 1H), 3.84 (s, 3H), 3.66 (td, J=11.5, 2.7 Hz, 1H), 3.19 (q, J=14.7, 13.6 Hz, 2H), 2.59 (d, J=11.4 Hz, 8H), 2.14 (dt, J=4.7, 2.4 Hz, 2H), 1.51 (t, J=6.5 Hz, 2H), 0.98 (s, 6H).

Step 2: 4-(4,4-dimethylcyclohexyl)-6,7-dimethyl-2-((2S)-2-(1-methyl-1H-pyrazol-4-yl)-4-morpholinyl)pteridine and (2S)-4-(4-(4,4-dimethylcyclohexyl)-6,7-dimethyl-7,8-dihydropteridin-2-yl)-2-(1-methyl-1H-pyrazol-4-yl)morpholine. To a 100-mL round-bottomed flask was added (S)-4-(4-(4,4-dimethylcyclohex-1-en-1-yl)-6,7-dimethylpteridin-2-yl)-2-(1-methyl-1H-pyrazol-4-yl)morpholine (0.27 g, 0.623 mmol) in EtOH (20 mL) followed by 10% Pd/C (0.265 g, 2.491 mmol) and the reaction mixture was stirred under hydrogen gas atmosphere (balloon pressure) at RT for 5 h. The mixture was filtered through celite bed and concentrated under reduced pressure to give a ~1:1 mixture of desired product and over reduced byproduct ((2S)-4-(4-(4,4-dimethylcyclohexyl)-6,7-dimethyl-7,8-dihydropteridin-2-yl)-2-(1-methyl-1H-pyrazol-4-yl)morpholine), which was used in the next step without purification.

Step 3: 4-(4,4-dimethylcyclohexyl)-6,7-dimethyl-2-((2S)-2-(1-methyl-1H-pyrazol-4-yl)-4-morpholinyl)pteridine. To a 50-mL round-bottomed flask was added a ~1:1 mixture of 4-(4,4-dimethylcyclohexyl)-6,7-dimethyl-2-((2S)-2-(1-methyl-1H-pyrazol-4-yl)-4-morpholinyl)pteridine and (2S)-4-(4-(4,4-dimethylcyclohexyl)-6,7-dimethyl-7,8-dihydropteridin-2-yl)-2-(1-methyl-1H-pyrazol-4-yl)morpholine (0.23 g, 0.526 mmol) in $CH_3CN$ (20 mL). Sodium hypochlorite (2.19 mL, 26.3 mmol) was added and the reaction mixture was stirred at RT for 5 min. The reaction mixture was diluted with $H_2O$ (30 mL), extracted with EtOAc (2×30 mL) and the organic extracts were dried over $Na_2SO_4$. The combined organics were concentrated and the crude material was purified by reverse-phase preparative HPLC to provide 4-(4,4-dimethylcyclohexyl)-6,7-dimethyl-2-((2S)-2-(1-methyl-1H-pyrazol-4-yl)-4-morpholinyl)pteridine (0.103 g, 0.236 mmol, 45.0% yield) as a yellow solid. $^1$H NMR (400 MHz, Chloroform-d) δ ppm 7.57 (s, 1H), 7.46 (s, 1H), 5.02 (d, J=13.5 Hz, 1H), 4.85 (d,J=13.6 Hz, 1H), 4.62 (dd, J=10.1, 2.8 Hz, 1H), 4.11 (d, J=11.4 Hz, 1H), 3.93 (s, 3H), 3.76-3.89 (m, 2H), 3.35 (dd, J=28.4, 16.1 Hz, 2H), 2.68 (d, J=15.3 Hz, 6H), 1.91 (q, J=12.8, 11.3 Hz, 2H), 1.76 (dd, J=13.8, 3.6 Hz, 2H), 1.48 (td, J=13.2, 3.9 Hz, 4H), 1.03 (d, J=6.2 Hz, 6H). m/z (ESI, +ive ion):436.3 $(M+H)^+$.

TABLE 2

Compounds 131 to 145 were prepared following the procedure described in Method 3, as follows:

| Ex # | Structure | Name | Starting Material 1 | Starting Material 2 |
|---|---|---|---|---|
| 131 | 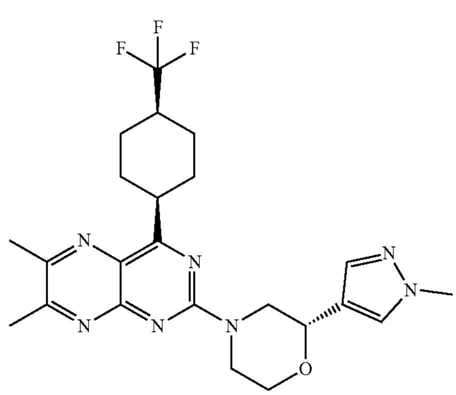 | 6,7-dimethyl-2-((2S)-2-(1-methyl-1H-pyrazol-4-yl)-4-morpholinyl)-4-(cis-4-(trifluoromethyl)cyclohexyl)pteridine | (S)-2-(1-methyl-1H-pyrazol-4-yl)morpholine (Enamine, Monmouth Jct., NJ, USA) | 2-chloro-6,7-dimethyl-4-(4-(trifluoromethyl)cyclohex-1-en-1-yl)pteridine (Intermediate 48) |

TABLE 2-continued

Compounds 131 to 145 were prepared following the procedure described in Method 3, as follows:

| Ex # | Structure | Name | Starting Material 1 | Starting Material 2 |
|---|---|---|---|---|
| 132 | 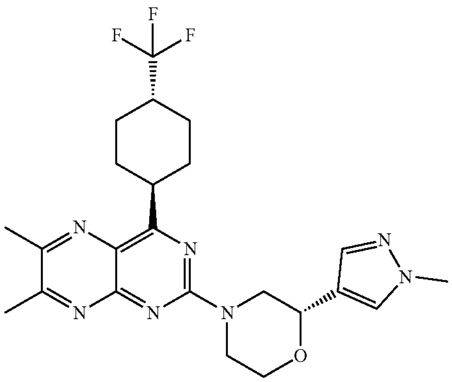 | 6,7-dimethyl-2-((2S)-2-(1-methyl-1H-pyrazol-4-yl)-4-morpholinyl)-4-(trans-4-(trifluoromethyl)cyclohexyl)pteridine | (S)-2-(1-methyl-1H-pyrazol-4-yl)morpholine (Enamine, Monmouth Jct., NJ, USA) | 2-chloro-6,7-dimethyl-4-(4-(trifluoromethyl)cyclohex-1-en-1-yl)pteridine (Intermediate 48) |
| 133 | 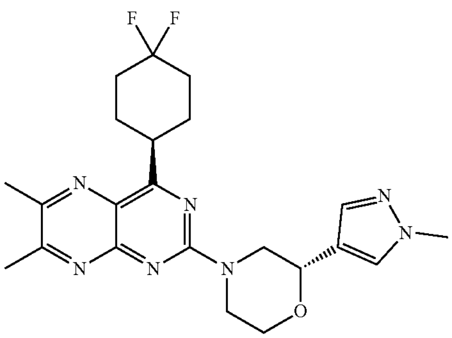 | 4-(4,4-difluorocyclohexyl)-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(4,4-difluorocyclohex-1-en-1-yl)-6,7-dimethylpteridine (Intermediate 49) |
| 134 | 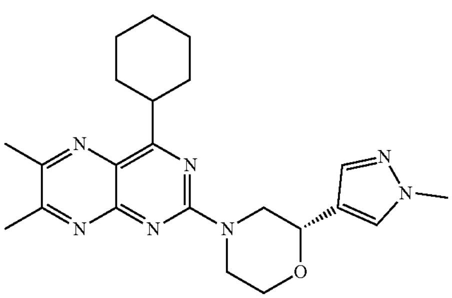 | 4-cyclohexyl-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(cyclohex-1-en-1-yl)-6,7-dimethylpteridine (Intermediate 52) |
| 135 | 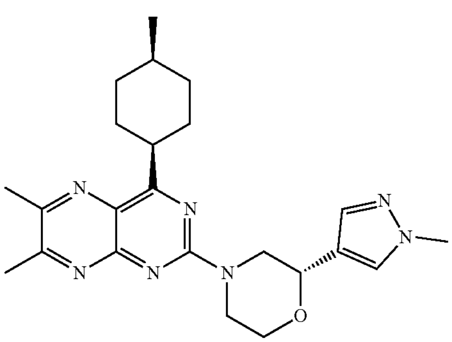 | 6,7-dimethyl-4-(cis-4-methylcyclohexyl)-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-6,7-dimethyl-4-(4-methylcyclohex-1-en-1-yl)pteridine (Intermediate 53) |

TABLE 2-continued

Compounds 131 to 145 were prepared following the procedure described in Method 3, as follows:

| Ex # | Structure | Name | Starting Material 1 | Starting Material 2 |
|---|---|---|---|---|
| 136 | 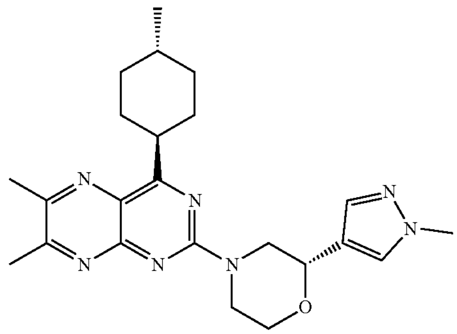 | 6,7-dimethyl-4-(trans-4-methylcyclohexyl)-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-6,7-dimethyl-4-(4-methylcyclohex-1-en-1-yl)pteridine (Intermediate 53) |
| 137 | 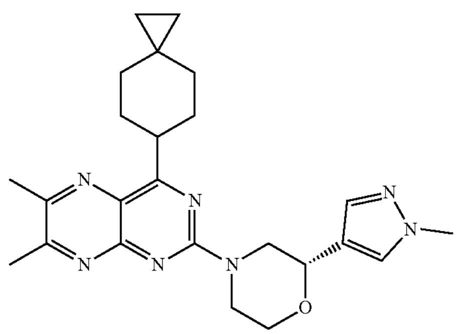 | 6,7-dimethyl-2-((2S)-2-(1-methyl-1H-pyrazol-4-yl)-4-morpholinyl)-4-(spiro[2.5]octan-6-yl)pteridine | (S)-2-(1-methyl-1H-pyrazol-4-yl)morpholine (Enamine, Monmouth Jct., NJ, USA) | 2-chloro-6,7-dimethyl-4-(spiro[2.5]oct-5-en-6-yl)pteridine (Intermediate 55) |
| 138 | 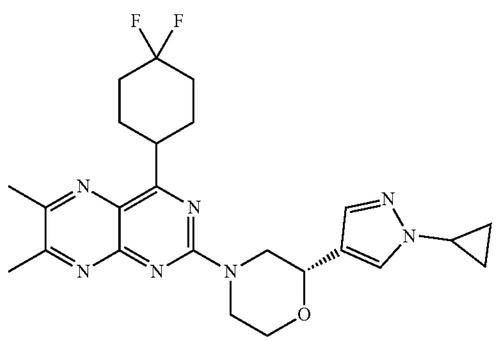 [SMILES: Cc1nc2nc(N3CCO[C@@H](c4cnn(C5CC5)c4)C3)nc(C3CCC(F)(F)CC3)c2nc1C] | 2-((2S)-2-(1-cyclopropyl-1H-pyrazol-4-yl)-4-morpholinyl)-4-(4,4-difluorocyclohexyl)-6,7-dimethylpteridine | (S)-2-(1-cyclopropyl-1H-pyrazol-4-yl)morpholine (Azepine Ltd. Hampshire, UK) | 2-chloro-4-(4,4-difluorocyclohex-1-en-1-yl)-6,7-dimethylpteridine (Intermediate 49) |
| 139 | 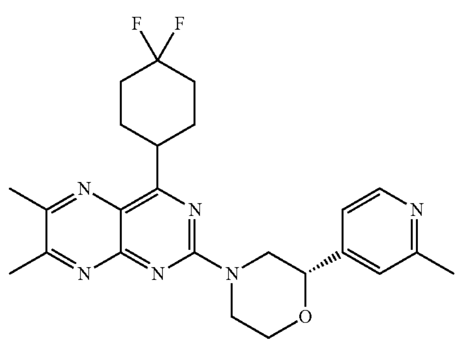 | 4-(4,4-difluorocyclohexyl)-6,7-dimethyl-2-((2S)-2-(2-methyl-4-pyridinyl)-4-morpholinyl)pteridine | (S)-2-(2-methylpyridin-4-yl)morpholine (Intermed Ltd. Kiev, Ukraine) | 2-chloro-4-(4,4-difluorocyclohex-1-en-1-yl)-6,7-dimethylpteridine (Intermediate 49) |

TABLE 2-continued

Compounds 131 to 145 were prepared following the procedure described in Method 3, as follows:

| Ex # | Structure | Name | Starting Material 1 | Starting Material 2 |
| --- | --- | --- | --- | --- |
| 140 | 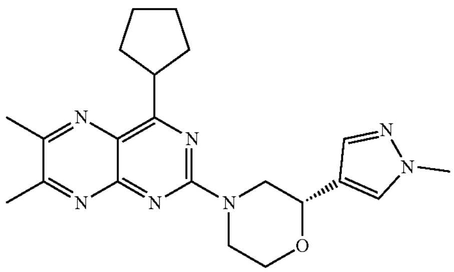 | 4-cyclopentyl-6,7-dimethyl-2-((2S)-2-(1-methyl-1H-pyrazol-4-yl)-4-morpholinyl)pteridine | (S)-2-(1-methyl-1H-pyrazol-4-yl)morpholine (Enamine, Monmouth Jct., NJ, USA) | 2-chloro-4-(cyclopent-1-en-1-yl)-6,7-dimethylpteridine (Intermediate 51) |
| 141 | 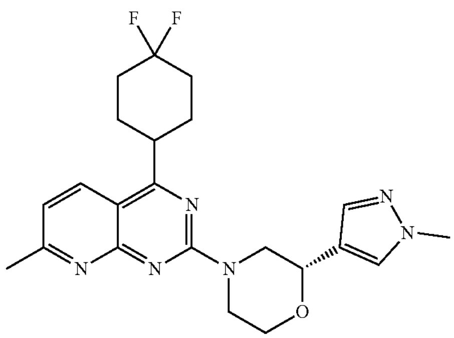 | 4-(4,4-difluorocyclohexyl)-7-methyl-2-((2S)-2-(1-methyl-1H-pyrazol-4-yl)-4-morpholinyl)pyrido[2,3-d]pyrimidine | (S)-2-(1-methyl-1H-pyrazol-4-yl)morpholine (Enamine, Monmouth Jct., NJ, USA) | 2-chloro-4-(4,4-difluorocyclohex-1-en-1-yl)-7-methylpyrido[2,3-d]pyrimidine (Intermediate 57) |
| 142 | 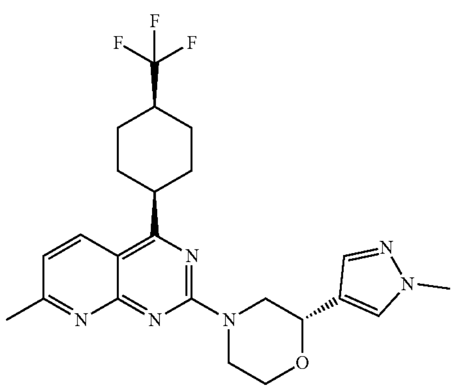 | 7-methyl-2-((2S)-2-(1-methyl-1H-pyrazol-4-yl)-4-morpholinyl)-4-(cis-4-(trifluoromethyl)cyclohexyl)pyrido[2,3-d]pyrimidine | (S)-2-(1-methyl-1H-pyrazol-4-yl)morpholine (Enamine, Monmouth Jct., NJ, USA) | 2-chloro-7-methyl-4-(4-(trifluoromethyl)cyclohex-1-en-1-yl)pyrido[2,3-d]pyrimidine (Intermediate 56) |
| 143 | 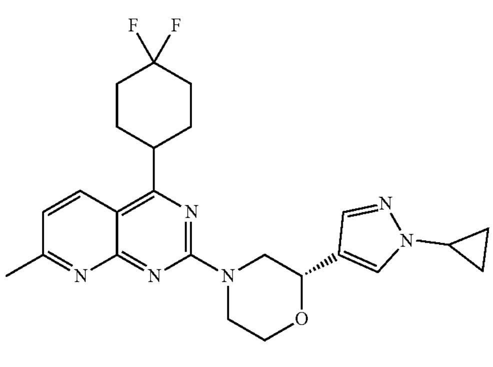 [SMILES: Cc1ccc2c(C3CCC(F)(F)CC3)nc(N3CCO[C@@H](c4cnn(C5CC5)c4)C3)nc2n1] | 2-((2S)-2-(1-cyclopropyl-1H-pyrazol-4-yl)-4-morpholinyl)-4-(4,4-difluorocyclohexyl)-7-methylpyrido[2,3-d]pyrimidine | (S)-2-(1-cyclopropyl-1H-pyrazol-4-yl)morpholine (Azepine Ltd. Hampshire, UK) | 2-chloro-4-(4,4-difluorocyclohex-1-en-1-yl)-7-methylpyrido[2,3-d]pyrimidine (Intermediate 57) |

TABLE 2-continued

Compounds 131 to 145 were prepared following the procedure described in Method 3, as follows:

| Ex # | Structure | Name | Starting Material 1 | Starting Material 2 |
|---|---|---|---|---|
| 144 | 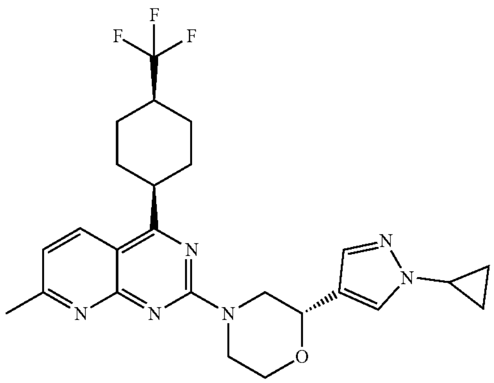 [SMILES: Cc1ccc2c(n1)nc(N1CCO[C@@H](c3cnn(C4CC4)c3)C1)nc2[C@H]1CC[C@@H](C(F)(F)F)CC1] | 2-((2S)-2-(1-cyclopropyl-1H-pyrazol-4-yl)-4-morpholinyl)-7-methyl-4-(cis-4-(trifluoromethyl)cyclohexyl)pyrido[2,3-d]pyrimidine | (S)-2-(1-cyclopropyl-1H-pyrazol-4-yl)morpholine (Azepine Ltd. Hampshire, UK) | 2-chloro-7-methyl-4-(4-(trifluoromethyl)cyclohex-1-en-1-yl)pyrido[2,3-d]pyrimidine (Intermediate 56) |
| 145 | 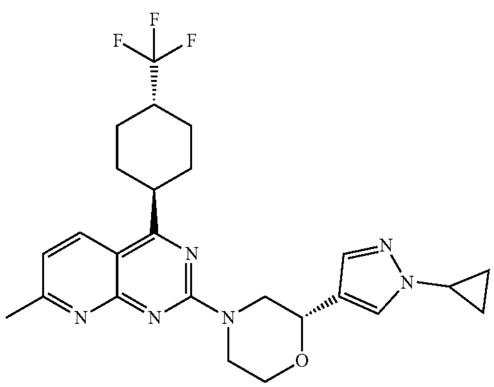 [SMILES: Cc1ccc2c(n1)nc(N1CCO[C@@H](c3cnn(C4CC4)c3)C1)nc2[C@H]1CC[C@H](C(F)(F)F)CC1] | 2-((2S)-2-(1-cyclopropyl-1H-pyrazol-4-yl)-4-morpholinyl)-7-methyl-4-(trans-4-(trifluoromethyl)cyclohexyl)pyrido[2,3-d]pyrimidine | (S)-2-(1-cyclopropyl-1H-pyrazol-4-yl)morpholine (Azepine Ltd. Hampshire, UK) | 2-chloro-7-methyl-4-(4-(trifluoromethyl)cyclohex-1-en-1-yl)pyrido[2,3-d]pyrimidine (Intermediate 56) |

Method 4

Example 146: 4-(3,3-difluorocyclobutyl)-6,7-dimethyl-2-((2S)-2-(1-methyl-1H-pyrazol-4-yl)-4-morpholinyl)pteridine.

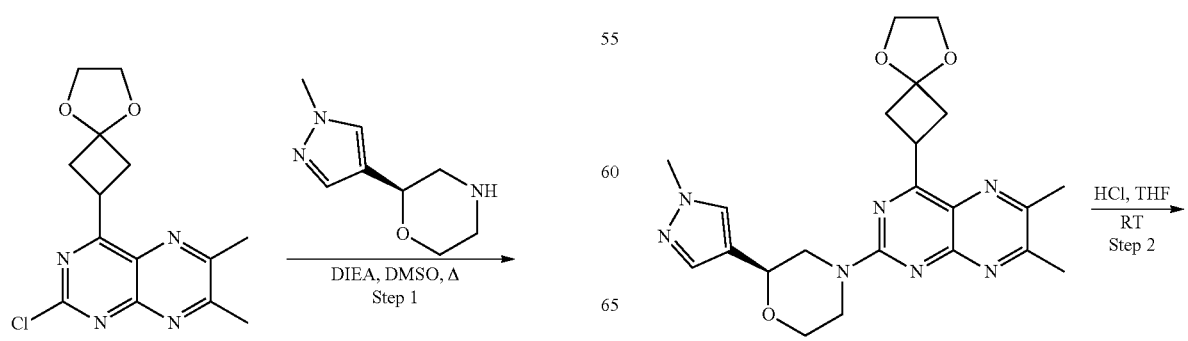

-continued

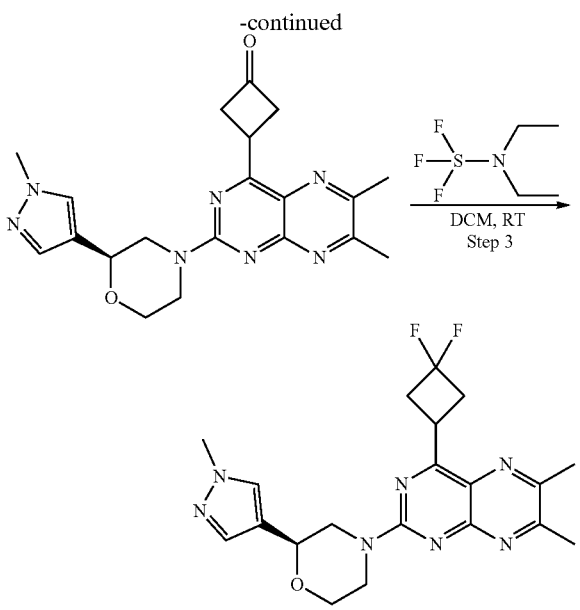

Example 146

Step 1: S)-4-(6,7-dimethyl-4-(5,8-dioxaspiro[3.4]octan-2-yl)pteridin-2-yl)-2-(1-methyl-1H-pyrazol-4-yl)morpholine. To a 20 mL vial were added crude 2-chloro-6,7-dimethyl-4-(5,8-dioxaspiro[3.4]octan-2-yl)pteridine (Intermediate 68, 1.07 g, 3.5 mmol), (S)-2-(1-methyl-1H-pyrazol-4-yl)morpholine (Enamine, Monmouth Jct., NJ, USA) (0.736 g, 4.40 mmol) and DIPEA (1.706 g, 2.306 mL, 13.20 mmol, Sigma) in 5 mL DMF. The mixture was heated at 90° C. for 12 h. The mixture was diluted with EtOAc (200 mL) and washed 2× with brine. The organic layer was dried over MgSO₄ and concentrated. The residue was purified by silica gel chromatography (0%-100% EtOAc/EtOH=3/1 blend in 10% DCM in heptane) to afford (S)-4-(6,7-dimethyl-4-(5,8-dioxaspiro[3.4]octan-2-yl)pteridin-2-yl)-2-(1-methyl-1H-pyrazol-4-yl)morpholine (298 mg, 0.681 mmol, 15.48% yield) as a red solid. $^1$H NMR (Chloroform-d, 500 MHz) δ 7.58 (s, 1H), 7.47 (s, 1H), 5.0-5.1 (m, 1H), 4.8-4.9 (m, 1H), 4.62 (dd, 1H, J=2.8, 10.2 Hz), 4.4-4.5 (m, 1H), 4.1-4.1 (m, 1H), 4.0-4.1 (m, 2H), 3.9-4.0 (m, 2H), 3.9-3.9 (m, 3H), 3.9-3.9 (m, 3H), 3.8-3.8 (m, 1H), 3.3-3.4 (m, 1H), 3.2-3.3 (m, 1H), 2.8-2.9 (m, 2H), 2.7-2.8 (m, 3H), 2.7-2.7 (m, 3H), 2.6-2.7 (m, 3H)

Step 2: (S)-3-(6,7-dimethyl-2-(2-(1-methyl-1H-pyrazol-4-yl)morpholino)pteridin-4-yl)cyclobutan-1-one. To a 40 mL vial was added (S)-4-(6,7-dimethyl-4-(5,8-dioxaspiro[3.4]octan-2-yl)pteridin-2-yl)-2-(1-methyl-1H-pyrazol-4-yl)morpholine (285 mg, 0.651 mmol, 126290-50) and THF (3257 µL). 1.5 mL 2N HCl was then added. The red suspension was stirred at 65° C. for 5 h. The reaction was quenched with NaHCO₃ (sat. 4 mL) and concentrated under vacuum. The aqueous layer was extracted with DCM (20 mL×3) and separated by phase separator. The solvent was concentrated under vacuum, and the black residue (S)-3-(6,7-dimethyl-2-(2-(1-methyl-1H-pyrazol-4-yl)morpholino)pteridin-4-yl)cyclobutan-1-one (251 mg, 0.638 mmol, 98% yield) was used directly in the next step without further purification.

Step 3: 4-(3,3-difluorocyclobutyl)-6,7-dimethyl-2-((2S)-2-(1-methyl-1H-pyrazol-4-yl)-4-morpholinyl)pteridine. To a 40 mL vial containing (S)-3-(6,7-dimethyl-2-(2-(1-methyl-1H-pyrazol-4-yl)morpholino)pteridin-4-yl)cyclobutan-1-one (135 mg, 0.343 mmol) was added diethylaminosulfur trifluoride, 1.0 M solution in DCM (7205 µL, 7.21 mmol) under N₂. The mixture was stirred at room temperature overnight. The reaction was cooled to 0° C., quenched with NaHCO₃ and the aqueous phase was extracted with DCM (20 mL×3). The DCM extracts were combined, concentrated and purified via silica gel column (RediSep 4 g, 2%-100% EA/EtOH=3/1 in 10% DCM in Heptane) to afford 4-(3,3-difluorocyclobutyl)-6,7-dimethyl-2-((2S)-2-(1-methyl-1H-pyrazol-4-yl)-4-morpholinyl)pteridine (22.3 mg, 0.054 mmol, 15.6% yield) as a light red solid. $^1$H NMR (Chloroform-d, 500 MHz) δ 7.5-7.6 (m, 1H), 7.45 (s, 1H), 5.03 (br d, 1H, J=12.8 Hz), 4.8-4.9 (m, 1H), 4.61 (dd, 1H, J=2.8, 10.2 Hz), 4.4-4.6 (m, 1H), 4.13 (br d, 1H, J=10.4 Hz), 3.93 (s, 3H), 3.81 (dt, 1H, J=2.9, 11.5 Hz), 3.38 (ddd, 1H, J=3.5, 11.3, 13.5 Hz), 3.2-3.3 (m, 1H), 3.0-3.1 (m, 4H), 2.71 (s, 3H), 2.65 (s, 3H). m/z (ESI, +ive ion):416.0 (M+H)⁺.

Method 5

Example 147: 1-(4-chloro-2-fluorophenyl)-6-methyl-3-((2S)-2-(1-methyl-1H-pyrazol-4-yl)-4-morpholinyl)isoquinoline.

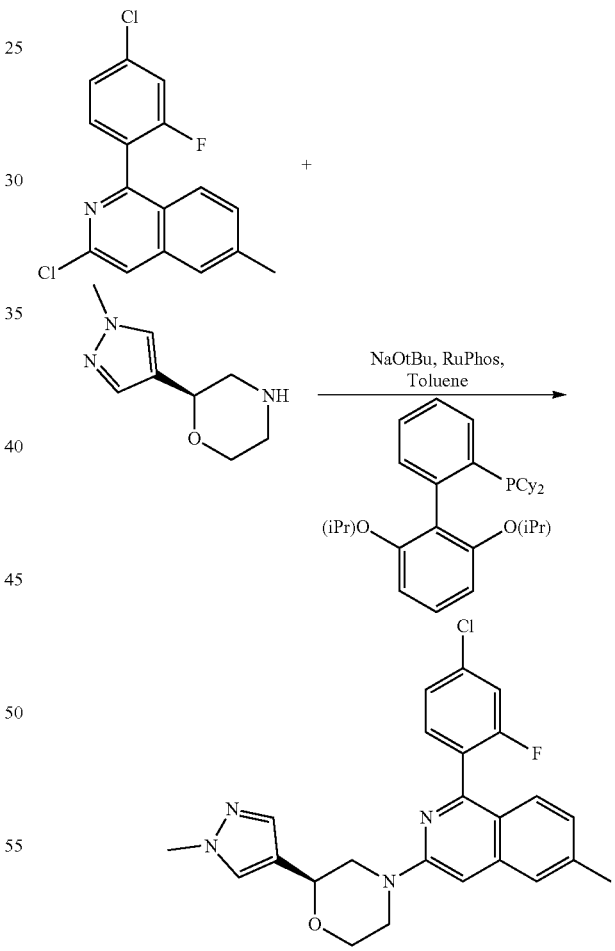

Example 147

To a 10 mL vial were added 3-chloro-1-(4-chloro-2-fluorophenyl)-6-methylisoquinoline (Intermediate 11) (77 mg, 0.250 mmol), (2-dicyclohexylphosphino-2',6'-diisopropoxy-1,1'-biphenyl)[2-(2'-amino-1,1'-biphenyl)]palladium(ii) methanesulfonate (20.91 mg, 0.025 mmol, Combi-Blocks Inc.), 2-dicyclohexylphosphino-2,6-di-i-propoxy-1, 1-biphenyl (11.67 mg, 0.025 mmol), 2-(1-methyl-1h-pyrazol-4-yl)morpholine (41.8 mg, 0.042 mL, 0.250 mmol, Enamine), and sodium tert-butoxide (72.1 mg, 0.750 mmol). Toluene (2 mL) was added, and the reaction was stirred at 100° C. for 1 h. The reaction mixture was quenched with H₂O and extracted with EtOAc. The combined organics were dried, concentrated, and purified via reverse phase chromatography to yield 1-(4-chloro-2-fluorophenyl)-6-methyl-3-((2S)-2-(1-methyl-1H-pyrazol-4-yl)-4-morpholinyl)isoquinoline. $^1$H NMR (500 MHz, Chloroform-d) δ ppm 7.55-7.58 (m, 1H), 7.48-7.53 (m, 2H), 7.44-7.48 (m, 2H), 7.29-7.33 (m, 1H), 7.28-7.29 (m, 1H), 7.25-7.28 (m, 1H), 7.07-7.11 (m, 1H), 6.78-6.83 (m, 1H), 4.70-4.75 (m, 1H), 4.30-4.35 (m, 1H), 4.12-4.17 (m, 1H), 4.05-4.12 (m, 1H), 3.93-3.98 (m, 1H), 3.90-3.93 (m, 3H), 3.09-3.17 (m, 1H), 3.00-3.07 (m, 1H), 2.47-2.51 (m, 3H). m/z (ESI, +ive ion):437.0 (M+H)⁺.

TABLE 3

Compounds 148 to 154 were prepared following the procedure described in Method 5, as follows:

| Ex # | Structure | Name | Starting Material 1 | Starting Material 2 |
|---|---|---|---|---|
| 148 | 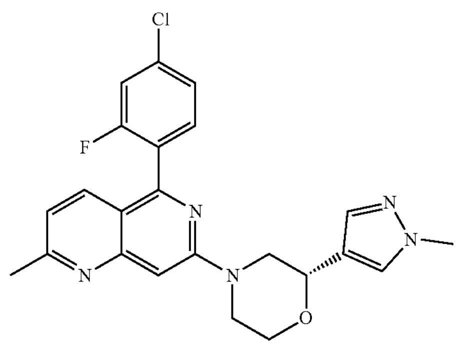 | 5-(4-chloro-2-fluorophenyl)-2-methyl-7-((2S)-2-(1-methyl-1H-pyrazol-4-yl)-4-morpholinyl)-1,6-naphthyridine | (S)-2-(1-methyl-1H-pyrazol-4-yl)morpholine (Enamine, Monmouth Jct., NJ, USA) | 7-chloro-5-(4-chloro-2-fluorophenyl)-2-methyl-1,6-naphthyridine (Intermediate 9) |
| 149 | 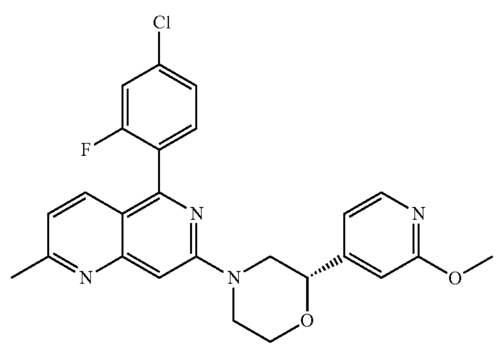 | 5-(4-chloro-2-fluorophenyl)-7-((2S)-2-(2-methoxy-4-pyridinyl)-4-morpholinyl)-2-methyl-1,6-naphthyridine | (S)-2-(2-methoxypyridin-4-yl)morpholine (Intermed Ltd. Kiev, Ukraine) | 7-chloro-5-(4-chloro-2-fluorophenyl)-2-methyl-1,6-naphthyridine (Intermediate 9) |
| 150 | 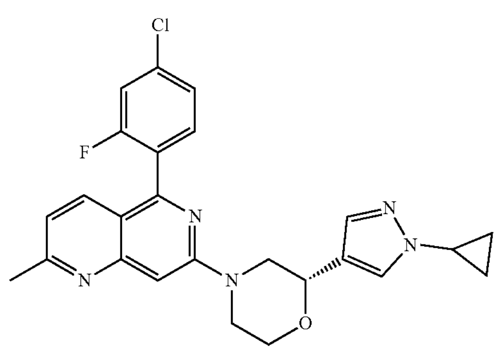 | 5-(4-chloro-2-fluorophenyl)-7-((2S)-2-(1-cyclopropyl-1H-pyrazol-4-yl)-4-morpholinyl)-2-methyl-1,6-naphthyridine | (S)-2-(1-cyclopropyl-1H-pyrazol-4-yl)morpholine (Azepine Ltd. Hampshire, UK) | 7-chloro-5-(4-chloro-2-fluorophenyl)-2-methyl-1,6-naphthyridine (Intermediate 9) |

TABLE 3-continued

Compounds 148 to 154 were prepared following the procedure described in Method 5, as follows:

| Ex # | Structure | Name | Starting Material 1 | Starting Material 2 |
| --- | --- | --- | --- | --- |
| 151 | 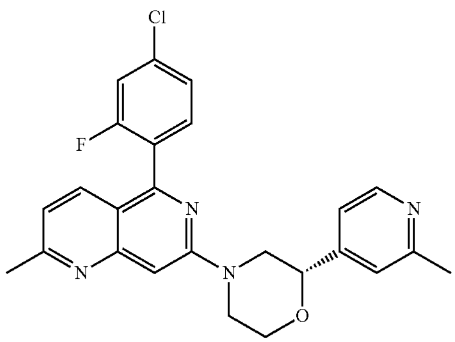 | 5-(4-chloro-2-fluorophenyl)-2-methyl-7-((2S)-2-(2-methyl-4-pyridinyl)-4-morpholinyl)-1,6-naphthyridine | (S)-2-(2-methylpyridin-4-yl)morpholine (Intermed Ltd. Kiev, Ukraine) | 7-chloro-5-(4-chloro-2-fluorophenyl)-2-methyl-1,6-naphthyridine (Intermediate 9) |
| 152 | 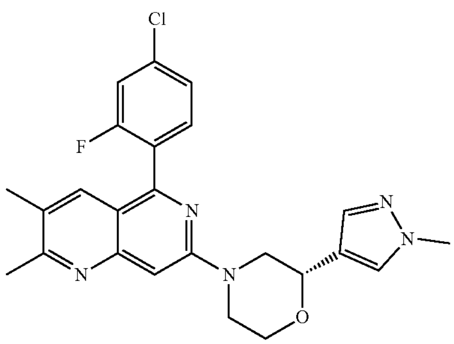 | 5-(4-chloro-2-fluorophenyl)-2,3-dimethyl-7-((2S)-2-(1-methyl-1H-pyrazol-4-yl)-4-morpholinyl)-1,6-naphthyridine | (S)-2-(1-methyl-1H-pyrazol-4-yl)morpholine (Enamine, Monmouth Jct., NJ, USA) | 7-chloro-5-(4-chloro-2-fluorophenyl)-2,3-dimethyl-1,6-naphthyridine (Intermediate 12) |
| 153 | 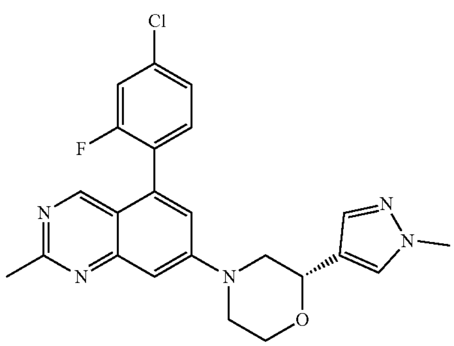 | 5-(4-chloro-2-fluorophenyl)-2-methyl-7-((2S)-2-(1-methyl-1H-pyrazol-4-yl)-4-morpholinyl)quinazoline | (S)-2-(1-methyl-1H-pyrazol-4-yl)morpholine (Enamine, Monmouth Jct., NJ, USA) | 7-chloro-5-(4-chloro-2-fluorophenyl)-2-methylquinazoline (Intermediate 44) |
| 154 | 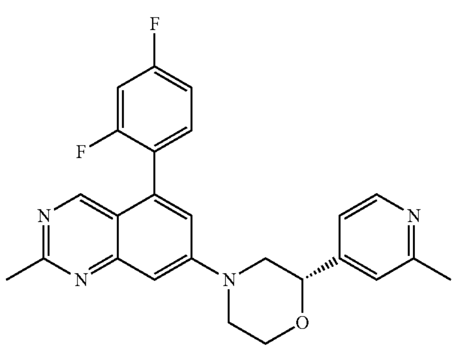 | 5-(2,4-difluorophenyl)-2-methyl-7-((2S)-2-(2-methyl-4-pyridinyl)-4-morpholinyl)quinazoline | (S)-2-(2-methylpyridin-4-yl)morpholine (Intermed Ltd. Kiev, Ukraine) | 7-chloro-5-(2,4-difluorophenyl)-2-methylquinazoline (Intermediate 45) |

Method 6
Example 155: 4-(4-chloro-2-fluorophenyl)-2-((2S)-2-(1-methyl-1H-pyrazol-4-yl)-4-morpholinyl)-1,8-naphthyridine.

Example 155

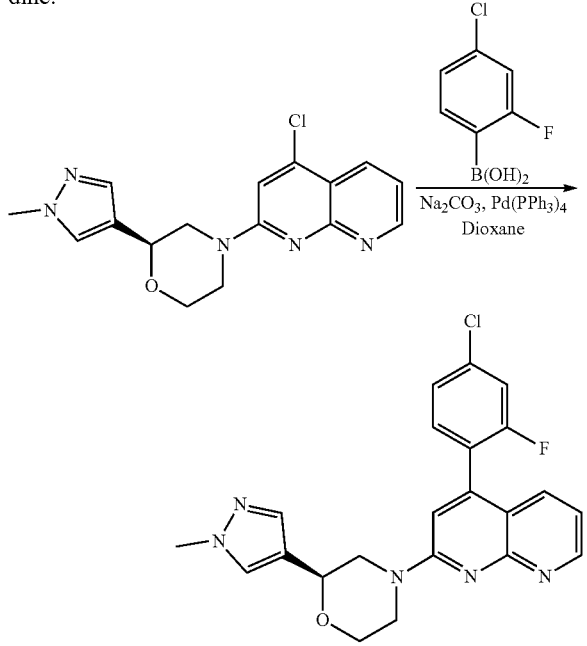

In a vial containing (S)-4-(4-chloro-1,8-naphthyridin-2-yl)-2-(1-methyl-1H-pyrazol-4-yl)morpholine (Intermediate 99) (0.1 g, 0.303 mmol), sodium carbonate (0.096 g, 0.910 mmol, JT Baker), (4-chloro-2-fluorophenyl)boronic acid (0.058 g, 0.334 mmol, combi-blocks), tetrakis palladium triphenylphosphine (0.018 g, 0.015 mmol) was added 1,4-dioxane (0.809 mL) and H$_2$O (0.202 mL). The vial was flushed under N$_2$ and the reaction mixture was stirred at 75 deg for 6 h. After cooling, the reaction mixture was worked up in DCM/H$_2$O and the organic phase was separated (phase separator) and concentrated under vacuo. The crude was purified by column chromatography eluting with a gradient of 0-10% MeOH(+1% NH$_3$) in DCM to afford 4-(4-chloro-2-fluorophenyl)-2-((2S)-2-(1-methyl-1H-pyrazol-4-yl)-4-morpholinyl)-1,8-naphthyridine (0.0134 g, 0.032 mmol, 10.43% yield). $^1$H NMR (500 MHz, DMSO-d6) δ ppm 8.76-8.80 (m, 1H), 7.74-7.77 (m, 1H), 7.67-7.73 (m, 2H), 7.55-7.59 (m, 1H), 7.47-7.53 (m, 2H), 7.41-7.44 (m, 1H), 7.21-7.24 (m, 1H), 4.60-4.67 (m, 1H), 4.47-4.56 (m, 2H), 4.01-4.07 (m, 1H), 3.81-3.83 (m, 3H), 3.68-3.75 (m, 1H), 3.14-3.20 (m, 1H), 3.06-3.12 (m, 1H). m/z (ESI, +ive ion):424.0 (M+H)$^+$.

TABLE 4

Compounds 156 to 164 were prepared following the procedure described in Method 6, as follows:

| Ex # | Structure | Name | Starting Material 1 | Starting Material 2 |
|---|---|---|---|---|
| 156 | 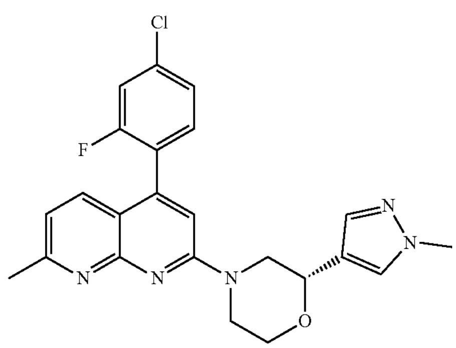 | 4-(4-chloro-2-fluorophenyl)-7-methyl-2-((2S)-2-(1-methyl-1H-pyrazol-4-yl)-4-morpholinyl)-1,8-naphthyridine | (4-chloro-2-fluorophenyl)boronic acid | (S)-4-(4-chloro-7-methyl-1,8-naphthyridin-2-yl)-2-(1-methyl-1H-pyrazol-4-yl)morpholine (Intermediate 98) |
| 157 | 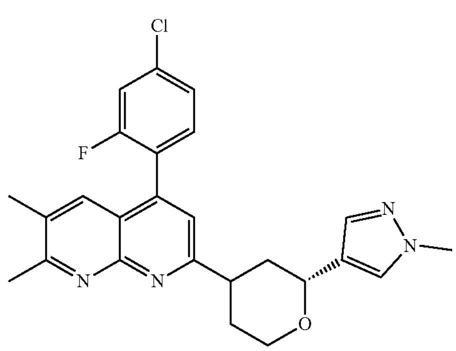 | 5-(4-chloro-2-fluorophenyl)-2,3-dimethyl-7-((2S)-2-(1-methyl-1H-pyrazol-4-yl)-4-morpholinyl)-1,8-naphthyridine | (4-chloro-2-fluorophenyl)boronic acid | (S)-4-(4-chloro-6,7-dimethyl-1,8-naphthyridin-2-yl)-2-(1-methyl-1H-pyrazol-4-yl)morpholine (Intermediate 97) |

TABLE 4-continued

Compounds 156 to 164 were prepared following the procedure described in Method 6, as follows:

| Ex # | Structure | Name | Starting Material 1 | Starting Material 2 |
|---|---|---|---|---|
| 158 | 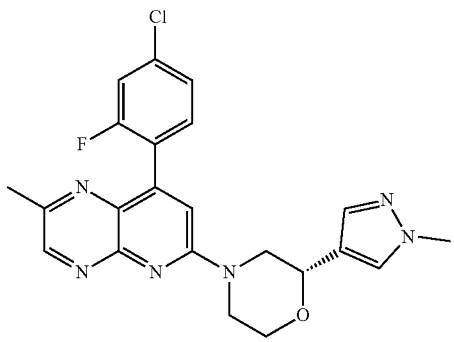 | 8-(4-chloro-2-fluorophenyl)-2-methyl-6-((2S)-2-(1-methyl-1H-pyrazol-4-yl)-4-morpholinyl)pyrido[2,3-b]pyrazine | (4-chloro-2-fluorophenyl) boronic acid | (S)-4-(8-chloro-2-methylpyrido[2,3-b]pyrazin-6-yl)-2-(1-methyl-1H-pyrazol-4-yl)morpholine (Intermediate 100) |
| 159 | 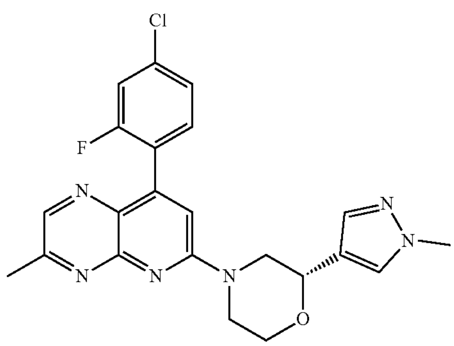 | 8-(4-chloro-2-fluorophenyl)-3-methyl-6-((2S)-2-(1-methyl-1H-pyrazol-4-yl)-4-morpholinyl)pyrido[2,3-b]pyrazine | (4-chloro-2-fluorophenyl) boronic acid | (S)-4-(8-chloro-3-methylpyrido[2,3-b]pyrazin-6-yl)-2-(1-methyl-1H-pyrazol-4-yl)morpholine (Intermediate 101) |
| 160 | 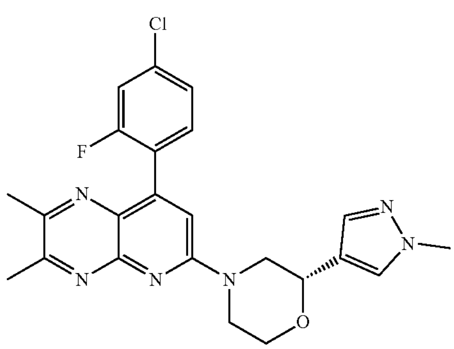 | 8-(4-chloro-2-fluorophenyl)-2,3-dimethyl-6-((2S)-2-(1-methyl-1H-pyrazol-4-yl)-4-morpholinyl)pyrido[2,3-b]pyrazine | (4-chloro-2-fluorophenyl) boronic acid | (S)-4-(8-chloro-2,3-dimethylpyrido[2,3-b]pyrazin-6-yl)-2-(1-methyl-1H-pyrazol-4-yl)morpholine (Intermediate 102) |
| 161 | 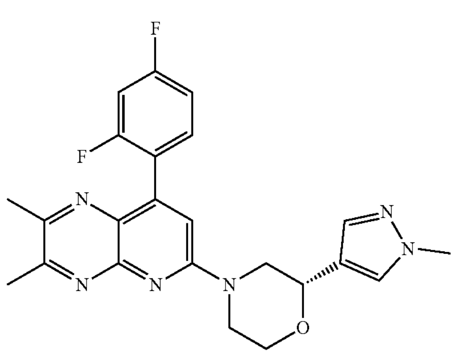 | 8-(2,4-difluorophenyl)-2,3-dimethyl-6-((2S)-2-(1-methyl-1H-pyrazol-4-yl)-4-morpholinyl)pyrido[2,3-b]pyrazine | (4-chloro-2-fluorophenyl) boronic acid | (S)-4-(8-chloro-2,3-dimethylpyrido[2,3-b]pyrazin-6-yl)-2-(1-methyl-1H-pyrazol-4-yl)morpholine (Intermediate 102) |

TABLE 4-continued

Compounds 156 to 164 were prepared following the procedure described in Method 6, as follows:

| Ex # | Structure | Name | Starting Material 1 | Starting Material 2 |
|---|---|---|---|---|
| 162 | (structure) | 5-(4-chloro-2-fluorophenyl)-2,3-dimethyl-7-((2S)-2-(1-methyl-1H-pyrazol-4-yl)-4-morpholinyl)quinoxaline | (4-chloro-2-fluorophenyl)boronic acid | (S)-4-(8-chloro-2,3-dimethylquinoxalin-6-yl)-2-(1-methyl-1H-pyrazol-4-yl)morpholine (Intermediate 104) |
| 163 | (structure) | 5-(4-chloro-2-fluorophenyl)-2,3-dimethyl-7-((2S)-2-(2-methyl-4-pyridinyl)-4-morpholinyl)quinoxaline | (4-chloro-2-fluorophenyl)boronic acid | (S)-4-(8-chloro-2,3-dimethylquinoxalin-6-yl)-2-(2-methylpyridin-4-yl)morpholine (Intermediate 103) |
| 164 | (structure) | 5-(2,4-difluorophenyl)-2,3-dimethyl-7-((2S)-2-(1-methyl-1H-pyrazol-4-yl)-4-morpholinyl)quinoxaline | (2,4-difluorophenyl)boronic acid | (S)-4-(8-chloro-2,3-dimethylquinoxalin-6-yl)-2-(1-methyl-1H-pyrazol-4-yl)morpholine (Intermediate 104) |

Method 7
Example 165: 4-(trans-4-chlorocyclohexyl)-6,7-dimethyl-2-((2S)-2-(1-methyl-1H-pyrazol-4-yl)-4-morpholinyl)pteridine

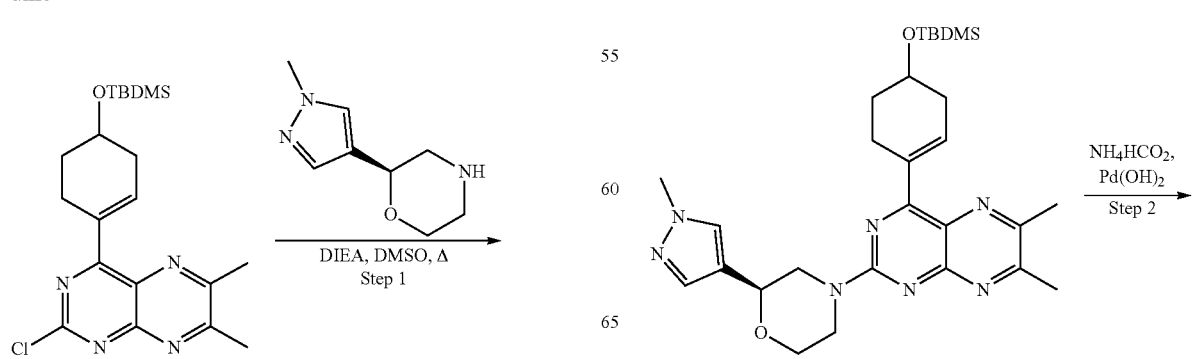

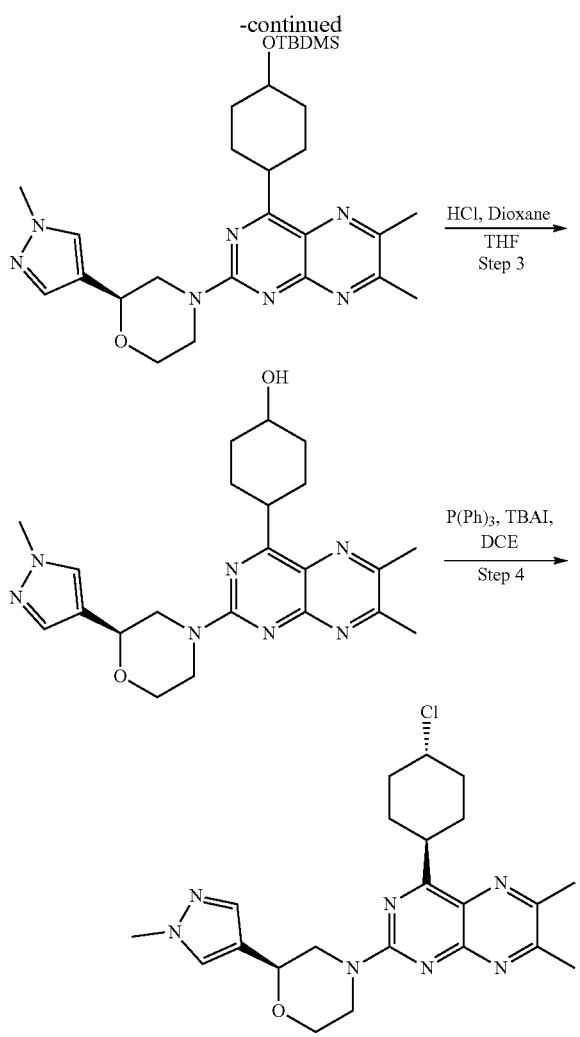

Example 165

Step 1: (2S)-4-(4-(4-((tert-butyldimethylsilyl)oxy)cyclohex-1-en-1-yl)-6,7-dimethylpteridin-2-yl)-2-(1-methyl-1H-pyrazol-4-yl)morpholine. To a 50-mL round-bottomed flask was added 4-(4-((tert-butyldimethylsilyl)oxy)cyclohex-1-en-1-yl)-2-chloro-6,7-dimethylpteridine (Intermediate 50) (0.35 g, 0.864 mmol) and (S)-2-(1-methyl-1H-pyrazol-4-yl)morpholine (Enamine, Monmouth Jct., NJ, USA) (0.159 g, 0.951 mmol) in DMSO(20 mL), and N-ethyl-N-isopropylpropan-2-amine (0.223 g, 1.728 mmol). The reaction was stirred at 100° C. for 2 h (monitored by TLC) then diluted with H$_2$O (30 mL) and extracted with DCM (3×50 mL). The combined organic layers were washed with brine, dried over anhydrous Na$_2$SO$_4$ and concentrated to give a yellow oil. The crude material was purified by silica gel chromatography (1% to 3% MeOH in DCM) to provide (2S)-4-(4-(4-((tert-butyldimethylsilyl)oxy)cyclohex-1-en-1-yl)-6,7-dimethylpteridin-2-yl)-2-(1-methyl-1H-pyrazol-4-yl)morpholine (0.3 g, 0.560 mmol, 64.8% yield) as a yellow oil.

Step 2: (S)-4-(4-(4-((tert-butyldimethylsilyl)oxy)cyclohexyl)-6,7-dimethylpteridin-2-yl)-2-(1-methyl-1H-pyrazol-4-yl)morpholine. To a 10-mL round-bottomed flask was added (2S)-4-(4-(4-((tert-butyldimethylsilyl)oxy)cyclohex-1-en-1-yl)-6,7-dimethylpteridin-2-yl)-2-(1-methyl-1H-pyrazol-4-yl)morpholine (0.05 g, 0.093 mmol) in 1-butanol (1.5 mL). The reaction mass was flushed under N$_2$ for 15 min. then to this was added palladium(II) hydroxide (0.013 g, 0.093 mmol) and the reaction was stirred at 80° C. for 4 h. The reaction mixture was filtered through celite and the filtrate diluted with H$_2$O (3 mL) and extracted with DCM (2×5 mL). The combined organic layers were dried over Na$_2$SO$_4$ and concentrated under reduced pressure to obtain (S)-4-(4-(4-((tert-butyldimethylsilyl)oxy)cyclohexyl)-6,7-dimethylpteridin-2-yl)-2-(1-methyl-1H-pyrazol-4-yl)morpholine (0.030 g, 0.056 mmol, 59.8% yield) as a light yellow material that was used in the next step without further purification.

Step 3: (S)-4-(6,7-dimethyl-2-(2-(1-methyl-1H-pyrazol-4-yl)morpholino)pteridin-4-yl)cyclohexan-1-ol. To a 50-mL round-bottomed flask was added (S)-4-(4-(4-((tert-butyldimethylsilyl)-oxy)cyclohexyl)-6,7-dimethylpteridin-2-yl)-2-(1-methyl-1H-pyrazol-4-yl)morpholine (0.28 g, 0.521 mmol) in THF (5 mL). The reaction mixture was cool to 0° C. and a solution of HCl in dioxane (1.302 mL, 5.21 mmol) was added drop-wise. The reaction was allowed to warm to RT and stirred for 1.5 h (monitored by LCMS). After completion of the reaction, H$_2$O (10 mL) was added and extracted with DCM (15 mL×2). The combined organic layers were dried over a generous amount of Na$_2$SO$_4$, filtered and concentrated under reduced pressure to obtain crude compound. The crude material was absorbed onto a plug of silica gel and purified by chromatography through a Redi-Sep pre-packed silica gel column (4 g), eluting with 100% EtOAc, to provide (S)-4-(6,7-dimethyl-2-(2-(1-methyl-1H-pyrazol-4-yl)morpholino)pteridin-4-yl)cyclohexan-1-ol (0.15 g, 0.354 mmol, 68.0% yield) as a yellow oil that was used in the next step without further purification.

Step 4: 4-(trans-4-chlorocyclohexyl)-6,7-dimethyl-2-((2S)-2-(1-methyl-1H-pyrazol-4-yl)-4-morpholinyl)pteridine. To a 100-mL round-bottomed flask was added (S)-4-(6,7-dimethyl-2-(2-(1-methyl-1H-pyrazol-4-yl)morpholino)pteridin-4-yl)cyclohexan-1-ol (0.150 g, 0.354 mmol) and perchloroethane (1.677 g, 7.08 mmol) followed by addition of tetrabutylammonium iodide (0.654 g, 1.771 mmol) and triphenylphosphine (0.464 g, 1.771 mmol) in 1,2-dichloroethane (20 mL). The reaction was stirred at 60° C. for 5 h (monitored by LCMS). After completion, the reaction mixture was allowed to cool to room temperature, poured into H$_2$O and extracted with DCM (2×30 mL). The organic extract was washed with sat. NaCl (50×mL) and dried over Na$_2$SO$_4$. The solution was concentrated to give the crude material as a yellow oil. The crude material was purified by silica gel chromatography (40% of EtOAc in Petroleum ether) to provide crude product which was further purified by preparative HPLC to provide 4-(trans-4-chlorocyclohexyl)-6,7-dimethyl-2-((2S)-2-(1-methyl-1H-pyrazol-4-yl)-4-morpholinyl)pteridine (0.017 g, 0.038 mmol, 10.86% yield) (7:2 mixture of isomers) as light yellow colored solid. $^1$H NMR (400 MHz, DMSO-d6) δ ppm 7.76 (s, 1H), 7.47 (d, J=3.3 Hz, 1H), 5.79 (s, 2H), 4.59-4.80 (m, 2H), 4.51 (dt, J=10.2, 2.4 Hz, 2H), 3.19-3.24 (s, 3H), 3.91-4.10 (m, 2H), 3.78 (s, 2H), 2.54-2.73 (m, 6H), 2.15-2.7 (m, 1H), 2.17-2.38 (m, 3H), 1.71-1.98 (m, 3H). m/z (ESI, +ive ion):442.3 (M+H)$^+$.

Method 8

Example 166: 4-(2,4-difluorophenyl)-6,7-dimethyl-2-((2S)-2-(1-methyl-1H-pyrazol-4-yl)-4-morpholinyl)pyrido[2,3-d]pyrimidine and Example 167: 4-(2,4-difluorophenyl)-7-ethyl-2-((2S)-2-(1-methyl-1H-pyrazol-4-yl)-4-morpholinyl)pyrido[2,3-d]pyrimidine

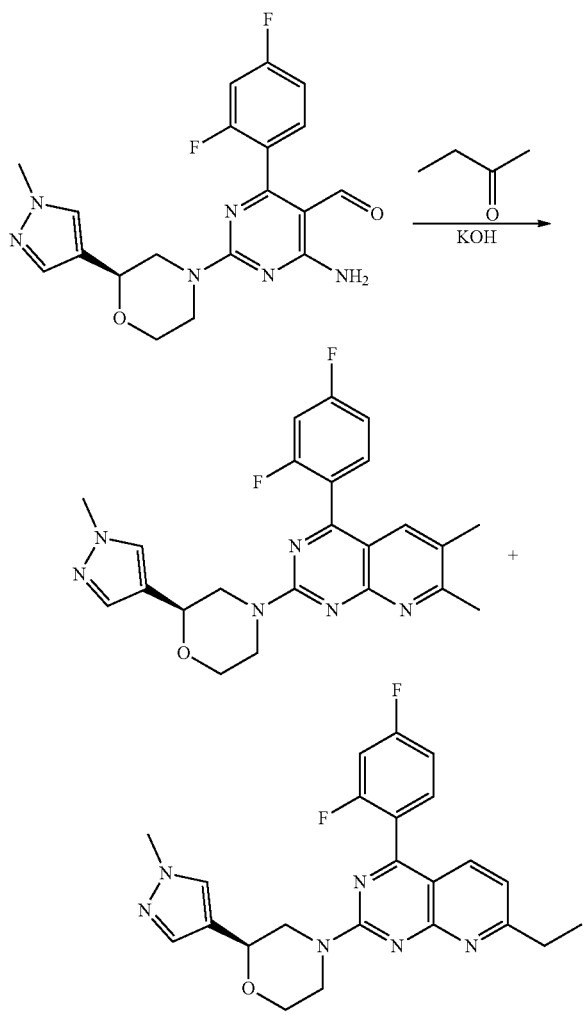

Example 166

Example 167

To a 5 mL vial were added (S)-4-amino-6-(2,4-difluorophenyl)-2-(2-(1-methyl-1H-pyrazol-4-yl)morpholino)pyrimidine-5-carbaldehyde (Intermediate 105) (2, 0.164 g, 0.410 mmol, 125891-11-1), methyl ethyl ketone (0.410 mL) and ground KOH (0.023 g, 0.410 mmol). The reaction mixture was stirred overnight at RT. H₂O was added and the aqueous phase was neutralized with HCl (1N) and extracted with DCM (phase separator). The solvent was concentrated under vacuum and the crude product purified by silica gel chromatography (0-10% MeOH (+1% NH₃) in DCM) to afford:

4-(2,4-difluorophenyl)-6,7-dimethyl-2-((2S)-2-(1-methyl-1H-pyrazol-4-yl)-4-morpholinyl)pyrido[2,3-d]pyrimidine (0.0502 g, 0.115 mmol, 28.0% yield). ¹H NMR (500 MHz, DMSO-d6) δ ppm 7.75 (s, 1H), 7.71 (dt, J=6.62, 8.37 Hz, 1H), 7.59 (br dd, J=0.78, 3.11 Hz, 1H), 7.50 (ddd, J=2.59, 9.47, 10.25 Hz, 1H), 7.46 (s, 1H), 7.32 (dt, J=2.08, 8.43 Hz, 1H), 4.67-4.83 (m, 1H), 4.60 (br d, J=13.49 Hz, 1H), 4.52 (br dd, J=2.47, 10.51 Hz, 1H), 3.93-4.08 (m, 1H), 3.82 (s, 3H), 3.59-3.73 (m, 1H), 3.11-3.25 (m, 2H), 2.57 (s, 3H), 2.30 (s, 3H). m/z (ESI, +ive ion):437.0 (M+H)⁺.

4-(2,4-difluorophenyl)-7-ethyl-2-((2S)-2-(1-methyl-1H-pyrazol-4-yl)-4-morpholinyl)pyrido[2,3-d]pyrimidine (0.0447 g, 0.102 mmol, 24.9% yield). ¹H NMR (500 MHz, DMSO-d6) δ ppm 7.81 (dd, J=8.3, 3.2 Hz, 1H), 7.69-7.78 (m, 2H), 7.48-7.54 (m, 1H), 7.46 (s, 1H), 7.32 (td, J=8.4, 2.5 Hz, 1H), 7.19 (d, J=8.4 Hz, 1H), 4.70-4.84 (m, 1H), 4.64 (br d, J=13.9 Hz, 1H), 4.52 (dd, J=10.3, 2.3 Hz, 1H), 4.01 (br d, J=13.0 Hz, 1H), 3.82 (s, 3H), 3.60-3.72 (m, 1H), 3.13-3.27 (m, 2H), 2.88 (q, J=7.6 Hz, 2H), 1.29 (t, J=7.5 Hz, 3H). m/z (ESI, +ive ion):437.2 (M+H)⁺.

TABLE 5

Compounds 168 to 169 were prepared following the procedure described in Method 8, as follows:

| Ex # | Structure | Name | Starting Material |
|---|---|---|---|
| 168 | ![structure] | 4-(2,4-difluorophenyl)-6,7-dimethyl-2-((2S)-2-(2-methyl-4-pyridinyl)-4-morpholinyl)pyrido[2,3-d]pyrimidine | (S)-4-amino-6-(2,4-difluorophenyl)-2-(2-(2-methylpyridin-4-yl)morpholino)pyrimidine-5-carbaldehyde (Intermediate 106) |

TABLE 5-continued

Compounds 168 to 169 were prepared following the procedure described in Method 8, as follows:

| Ex # | Structure | Name | Starting Material |
|---|---|---|---|
| 169 | 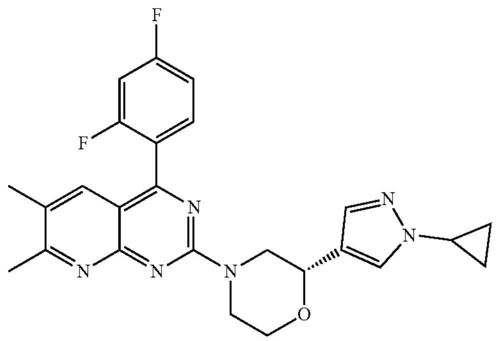 | 2-((2S)-2-(1-cyclopropyl-1H-pyrazol-4-yl)-4-morpholinyl)-4-(2,4-difluorophenyl)-6,7-dimethylpyrido[2,3-d]pyrimidine | (S)-4-amino-2-(2-(1-cyclopropyl-1H-pyrazol-4-yl)morpholino)-6-(2,4-difluorophenyl)pyrimidine-5-carbaldehyde (Intermediate 107) |

Method 9

Example 170: 4-(4-chloro-2-fluorophenyl)-2-((2R,4S)-2-(1-cyclopropyl-1H-pyrazol-4-yl)tetrahydro-2H-pyran-4-yl)-7-methylpteridine

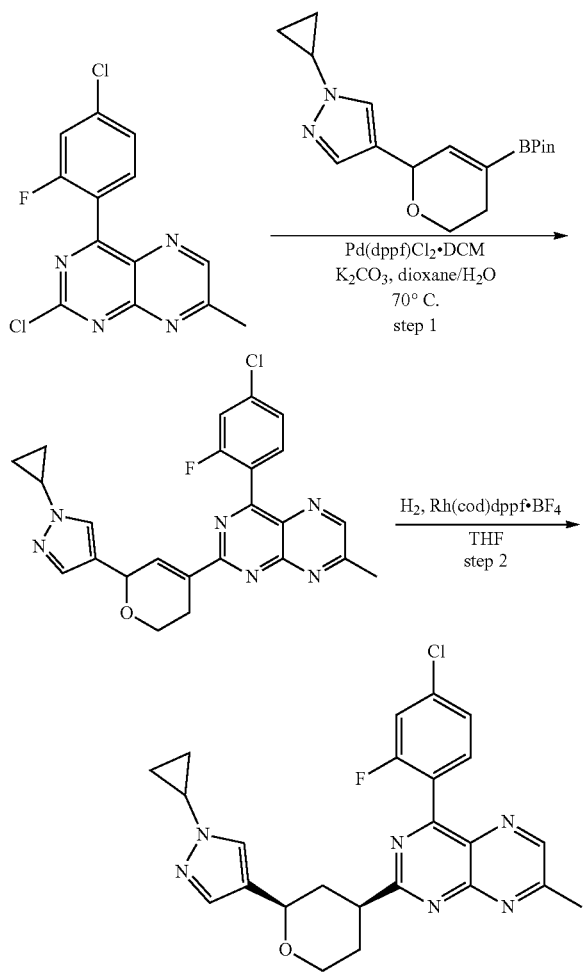

Example 170

Step 1: 4-(4-chloro-2-fluorophenyl)-2-(6-(1-cyclopropyl-1H-pyrazol-4-yl)-3,6-dihydro-2H-pyran-4-yl)-7-methylpteridine. To a 50 mL round-bottomed flask was added 2-chloro-4-(4-chloro-2-fluorophenyl)-7-methylpteridine (Intermediate 13) (600 mg, 1.857 mmol) and 1-cyclopropyl-4-(4-(4,4,5,5-tetramethyl-1,3,2-dioxaborolan-2-yl)-5,6-dihydro-2H-pyran-2-yl)-1H-pyrazole (Intermediate 80) (881 mg, 2.79 mmol) in dioxane; H$_2$O (9 mL, 5:1 v/v) followed by addition of potassium carbonate (513 mg, 3.71 mmol). The reaction was flushed under N$_2$ for 10 min. and PdCl$_2$(dppf)-DCM adduct (227 mg, 0.279 mmol) was added and the reaction stirred at 70° C. for 3 h. The reaction was filtered through celite, the pad washed with ethyl acetate (40 mL) and the filtrate was concentrated under reduced pressure to obtain crude product. Silica gel chromatography (70% EtOAc in Hexane) followed by trituration with 2 mL DCM in 50 mL Hexane provided 4-(4-chloro-2-fluorophenyl)-2-(6-(1-cyclopropyl-1H-pyrazol-4-yl)-3,6-dihydro-2H-pyran-4-yl)-7-methylpteridine (350 mg, 0.734 mmol, 39.5% yield) as off white solid. $^1$H NMR (400 MHz, DMSO-d6) δ 7.81 (s, 2H), 7.79 (s, 1H), 7.42 (s, 3H), 3.99 (s, 1H), 2.81 (d, J=4.6 Hz, 3H), 2.69 (d, J=4.6 Hz, 3H) 1.01 (s, 3H), 0.92 (t, J =1.0 Hz, 6H). m/z (ESI, +ive ion):477.1 (M+H)$^+$.

Step 2: 4-(4-chloro-2-fluorophenyl)-2-((2R,4S)-2-(1-cyclopropyl-1H-pyrazol-4-yl)tetrahydro-2H-pyran-4-yl)-7-methylpteridine. To a round bottomed flask (25 mL) was added 4-(4-chloro-2-fluorophenyl)-2-(6-(1-cyclopropyl-1H-pyrazol-4-yl)-3,6-dihydro-2H-pyran-4-yl)-7-methylpteridine (20 mg, 0.043 mmol) and 1,1'-bis(di-i-propylphosphino)ferrocene(1,5-cyclooctadiene)rhodium(I) tetrafluoroborate (20 mg, 0.043 mmol) in THF (10 mL). The reaction mixture was stirred at 14 psi pressure and monitored by TLC (EtOAc/Pet Ether mixtures). Upon reaction completion the mixture was filtered through celite and washed with ethyl acetate (10 ml). The filtrate was concentrated under reduced pressure to obtain crude material which was purified by silica gel chromatography, and eluted with 80% EtOAc in hexane, to provide a mixture of cis and trans isomers 4-(4-chloro-2-fluorophenyl)-2-(2-(1-cyclopropyl-1H-pyrazol-4-yl)tetrahydro-2H-pyran-4-yl)-7-methylpteridine (10 mg, 0.022 mmol, 49.8% yield) as brown gum. The racemic mixture was purified by chiral SFC (Chiralpak AD-H 2×15 cm, 5 um column, 30% EtOH, F=120 mL/min) to provide the title compound (first eluting peak) 4-(4-chloro-2-fluorophenyl)-2-((2R,4S)-2-(1-cyclopropyl-1H-pyrazol-4-yl)tetrahydro-2H-pyran-4-yl)-7-methylpteridine (6 mg, 0.013 mmol, 14% yield; absolute stereochemistry was arbitrarily assigned; relative stereochemistry (cis/trans) determined by NMR), as well as other (impure) isomers. $^1$H NMR (400 MHz, DMSO-d6) δ 9.00 (s, 1H), 7.78-7.84 (m, 1H), 7.74 (s, 1H), 7.70 (d, J=9.9 Hz, 1H), 7.55 (d, J=8.3 Hz, 1H), 7.40 (s, 1H), 4.53 (d, J=9.9 Hz, 1H), 4.16-4.08 (m, 1H), 3.74-3.62 (m, 2H), 3.56-3.45 (m, 1H), 2.82 (s, 3H), 2.31 (d, J=13.2 Hz, 1H), 2.08 (d, J=13.1 Hz, 1H), 1.87-1.99 (m, 2H), 1.06-0.96 (m, 2H), 0.94-0.83 (m, 2H). m/z (ESI, +ive ion):465.2 (M+H)$^+$.

TABLE 6

Compounds 171 to 203 were prepared following the procedure described in Method 9, as follows:

| Ex # | Structure | Name | Starting Material 1 | Starting Material 2 |
|---|---|---|---|---|
| 171 | 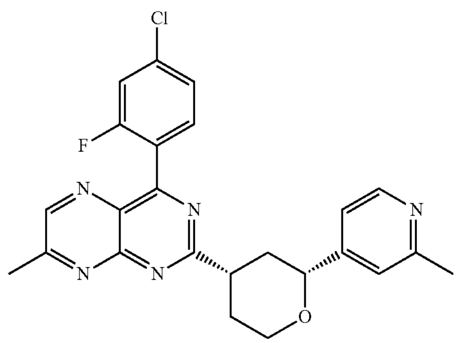 | 4-(4-chloro-2-fluorophenyl)-7-methyl-2-((2R,4S)-2-(2-methyl-4-pyridinyl)tetrahydro-2H-pyran-4-yl)pteridine. Absolute stereochemistry arbitrarily assigned. Relative stereochemistry (cis/trans) determined by NMR. | 2-methyl-4-(4-(4,4,5,5-tetramethyl-1,3,2-dioxaborolan-2-yl)-5,6-dihydro-2H-pyran-2-yl)pyridine (Intermediate 81) | 2-chloro-4-(4-chloro-2-fluorophenyl)-7-methylpteridine (Intermediate 13) |
| 172 | 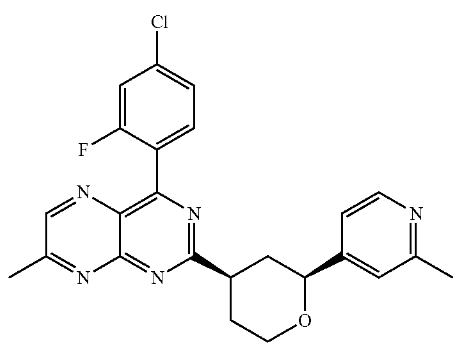 | 4-(4-chloro-2-fluorophenyl)-7-methyl-2-((2S,4R)-2-(2-methyl-4-pyridinyl)tetrahydro-2H-pyran-4-yl)pteridine. Absolute stereochemistry arbitrarily assigned. Relative stereochemistry (cis/trans) determined by NMR. | 2-methyl-4-(4-(4,4,5,5-tetramethyl-1,3,2-dioxaborolan-2-yl)-5,6-dihydro-2H-pyran-2-yl)pyridine (Intermediate 81) | 2-chloro-4-(4-chloro-2-fluorophenyl)-7-methylpteridine (Intermediate 13) |
| 173 | 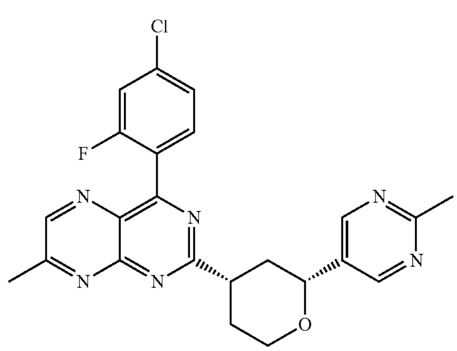 | 4-(4-chloro-2-fluorophenyl)-7-methyl-2-((2R,4S)-2-(2-methyl-5-pyrimidinyl)tetrahydro-2H-pyran-4-yl)pteridine. Absolute stereochemistry arbitrarily assigned. Relative stereochemistry (cis/trans) determined by NMR. | 2-methyl-5-(4-(4,4,5,5-tetramethyl-1,3,2-dioxaborolan-2-yl)-5,6-dihydro-2H-pyran-2-yl)pyrimidine (Intermediate 82) | 2-chloro-4-(4-chloro-2-fluorophenyl)-7-methylpteridine (Intermediate 13) |

TABLE 6-continued

Compounds 171 to 203 were prepared following the procedure described in Method 9, as follows:

| Ex # | Structure | Name | Starting Material 1 | Starting Material 2 |
|---|---|---|---|---|
| 174 | 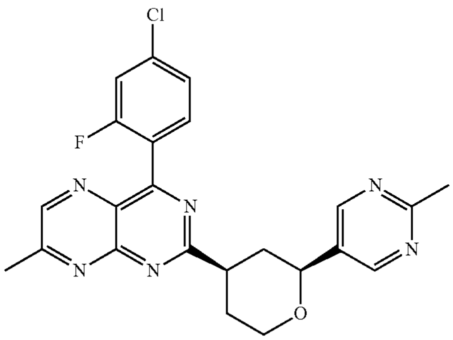 | 4-(4-chloro-2-fluorophenyl)-7-methyl-2-((2S,4R)-2-(2-methyl-5-pyrimidinyl)tetrahydro-2H-pyran-4-yl)pteridine. Absolute stereochemistry arbitrarily assigned. Relative stereochemistry (cis/trans) determined by NMR. | 2-methyl-5-(4-(4,4,5,5-tetramethyl-1,3,2-dioxaborolan-2-yl)-5,6-dihydro-2H-pyran-2-yl)pyrimidine (Intermediate 82) | 2-chloro-4-(4-chloro-2-fluorophenyl)-7-methylpteridine (Intermediate 13) |
| 175 | 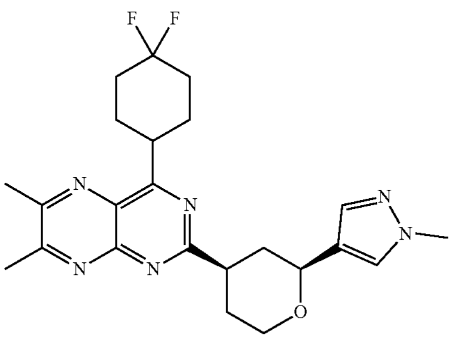 | 4-(4,4-difluorocyclohexyl)-6,7-dimethyl-2-((2S,4R)-2-(1-methyl-1H-pyrazol-4-yl)tetrahydro-2H-pyran-4-yl)pteridine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(4,4-difluorocyclohex-1-en-1-yl)-6,7-dimethylpteridine (Intermediate 49) |
| 176 | 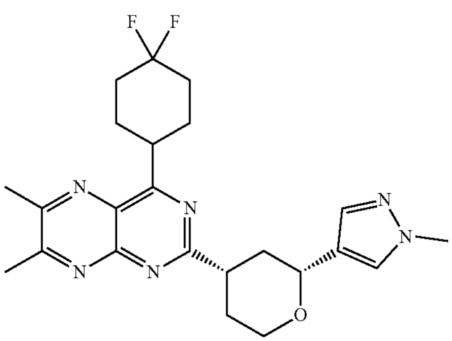 | 4-(4,4-difluorocyclohexyl)-6,7-dimethyl-2-((2R,4S)-2-(1-methyl-1H-pyrazol-4-yl)tetrahydro-2H-pyran-4-yl)pteridine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(4,4-difluorocyclohex-1-en-1-yl)-6,7-dimethylpteridine (Intermediate 49) |
| 177 | 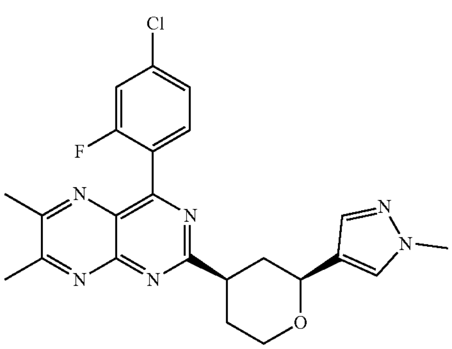 | 4-(4-chloro-2-fluorophenyl)-6,7-dimethyl-2-((2S,4R)-2-(1-methyl-1H-pyrazol-4-yl)tetrahydro-2H-pyran-4-yl)pteridine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(4-chloro-2-fluorophenyl)-6,7-dimethylpteridine (Intermediate 16) |

TABLE 6-continued

Compounds 171 to 203 were prepared following the procedure described in Method 9, as follows:

| Ex # | Structure | Name | Starting Material 1 | Starting Material 2 |
|---|---|---|---|---|
| 178 | 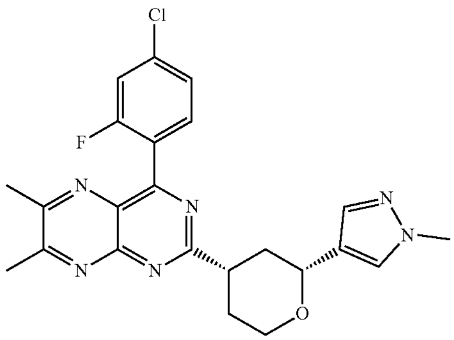 | 4-(4-chloro-2-fluorophenyl)-6,7-dimethyl-2-((2R,4S)-2-(1-methyl-1H-pyrazol-4-yl)tetrahydro-2H-pyran-4-yl)pteridine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(4-chloro-2-fluorophenyl)-6,7-dimethylpteridine (Intermediate 16) |
| 179 | 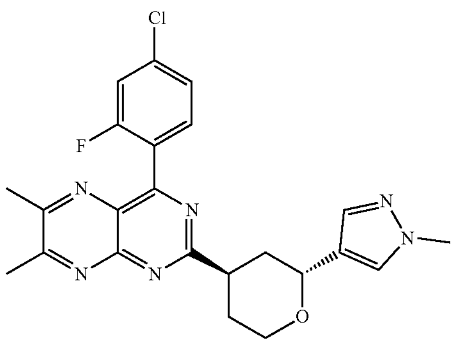 | 4-(4-chloro-2-fluorophenyl)-6,7-dimethyl-2-((2R,4R)-2-(1-methyl-1H-pyrazol-4-yl)tetrahydro-2H-pyran-4-yl)pteridine | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(4-chloro-2-fluorophenyl)-6,7-dimethylpteridine (Intermediate 16) |
| 180 | 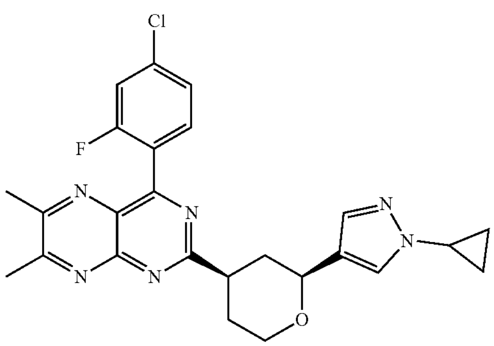 [SMILES: Cc1nc2nc([C@@H]3CCO[C@H](c4cnn(C5CC5)c4)C3)nc(-c3ccc(Cl)cc3F)c2nc1C] | 4-(4-chloro-2-fluorophenyl)-2-((2S,4R)-2-(1-cyclopropyl-1H-pyrazol-4-yl)tetrahydro-2H-pyran-4-yl)-6,7-dimethylpteridine. Absolute stereochemistry arbitrarily assigned. Relative stereochemistry (cis/trans) determined by NMR. | 1-cyclopropyl-4-(4-(4,4,5,5-tetramethyl-1,3,2-dioxaborolan-2-yl)-5,6-dihydro-2H-pyran-2-yl)-1H-pyrazole (Intermediate 80) | 2-chloro-4-(4-chloro-2-fluorophenyl)-6,7-dimethylpteridine (Intermediate 16) |
| 181 | 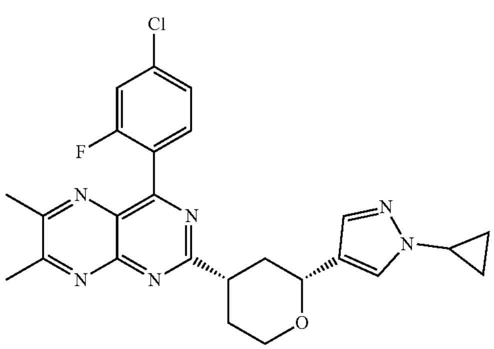 | 4-(4-chloro-2-fluorophenyl)-2-((2R,4S)-2-(1-cyclopropyl-1H-pyrazol-4-yl)tetrahydro-2H-pyran-4-yl)-6,7-dimethylpteridine. Absolute stereochemistry arbitrarily assigned. Relative stereochemistry (cis/trans) determined by NMR. | 1-cyclopropyl-4-(4-(4,4,5,5-tetramethyl-1,3,2-dioxaborolan-2-yl)-5,6-dihydro-2H-pyran-2-yl)-1H-pyrazole (Intermediate 80) | 2-chloro-4-(4-chloro-2-fluorophenyl)-6,7-dimethylpteridine (Intermediate 16) |

TABLE 6-continued

Compounds 171 to 203 were prepared following the procedure described in Method 9, as follows:

| Ex # | Structure | Name | Starting Material 1 | Starting Material 2 |
|---|---|---|---|---|
| 182 | 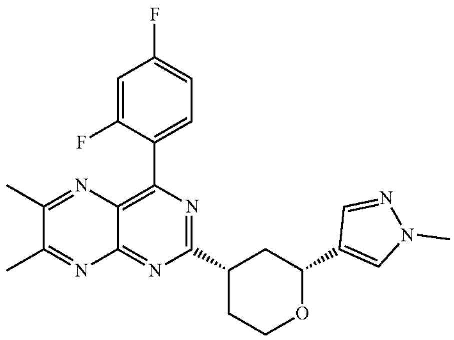 | 4-(2,4-difluorophenyl)-6,7-dimethyl-2-((2R,4S)-2-(1-methyl-1H-pyrazol-4-yl)tetrahydro-2H-pyran-4-yl)pteridine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(2,4-difluorophenyl)-6,7-dimethylpteridine (Intermediate 17) |
| 183 | 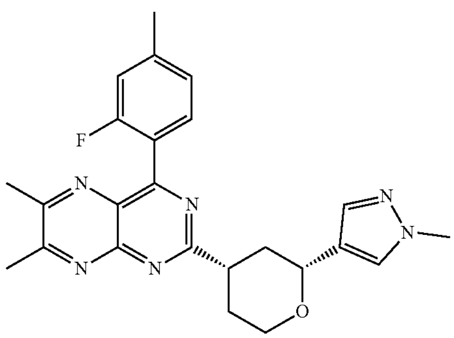 | 4-(2-fluoro-4-methylphenyl)-6,7-dimethyl-2-((2R,4S)-2-(1-methyl-1H-pyrazol-4-yl)tetrahydro-2H-pyran-4-yl)pteridine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(2-fluoro-4-methylphenyl)-6,7-dimethylpteridine (Intermediate 19) |
| 184 | 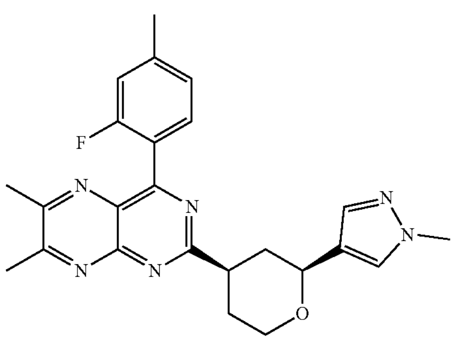 | 4-(2-fluoro-4-methylphenyl)-6,7-dimethyl-2-((2S,4R)-2-(1-methyl-1H-pyrazol-4-yl)tetrahydro-2H-pyran-4-yl)pteridine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(2-fluoro-4-methylphenyl)-6,7-dimethylpteridine (Intermediate 19) |
| 185 | 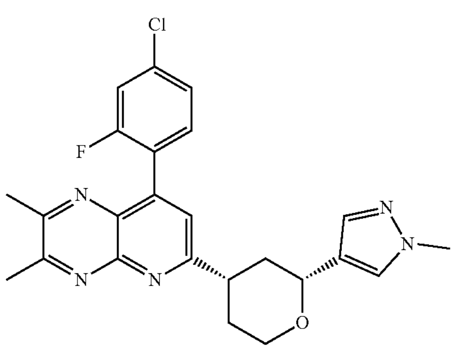 | 8-(4-chloro-2-fluorophenyl)-3-methyl-6-((2R,4S)-2-(1-methyl-1H-pyrazol-4-yl)tetrahydro-2H-pyran-4-yl)pyrido[2,3-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 6-chloro-8-(4-chloro-2-fluorophenyl)-3-methylpyrido[2,3-b]pyrazine (Intermediate 28) |

TABLE 6-continued

Compounds 171 to 203 were prepared following the procedure described in Method 9, as follows:

| Ex # | Structure | Name | Starting Material 1 | Starting Material 2 |
|---|---|---|---|---|
| 186 | 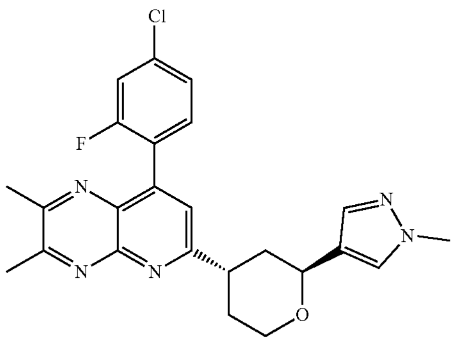 | 8-(4-chloro-2-fluorophenyl)-2,3-dimethyl-6-((2S,4S)-2-(1-methyl-1H-pyrazol-4-yl)tetrahydro-2H-pyran-4-yl)pyrido[2,3-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 6-chloro-8-(4-chloro-2-fluorophenyl)-2,3-dimethylpyrido[2,3-b]pyrazine (Intermediate 29) |
| 187 | 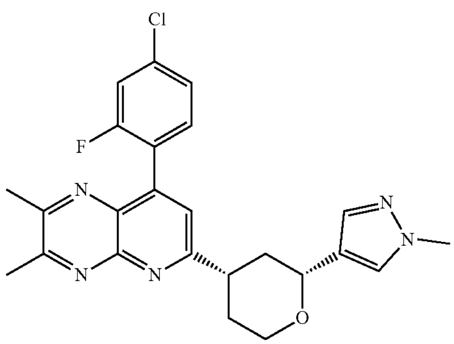 | 8-(4-chloro-2-fluorophenyl)-2,3-dimethyl-6-((2R,4S)-2-(1-methyl-1H-pyrazol-4-yl)tetrahydro-2H-pyran-4-yl)pyrido[2,3-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 6-chloro-8-(4-chloro-2-fluorophenyl)-2,3-dimethylpyrido[2,3-b]pyrazine (Intermediate 29) |
| 188 | 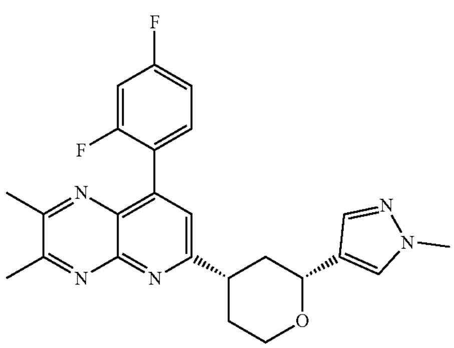 | 8-(2,4-difluorophenyl)-2,3-dimethyl-6-((2R,4S)-2-(1-methyl-1H-pyrazol-4-yl)tetrahydro-2H-pyran-4-yl)pyrido[2,3-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 6-chloro-8-(2,4-difluorophenyl)-2,3-dimethylpyrido[2,3-b]pyrazine (Intermediate 30) |
| 189 | 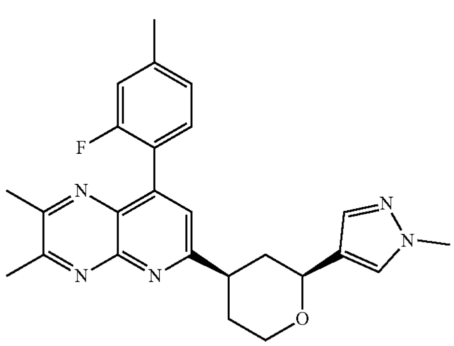 | 8-(2-fluoro-4-methylphenyl)-2,3-dimethyl-6-((2S,4R)-2-(1-methyl-1H-pyrazol-4-yl)tetrahydro-2H-pyran-4-yl)pyrido[2,3-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 6-chloro-8-(2-fluoro-4-methylphenyl)-2,3-dimethylpyrido[2,3-b]pyrazine (Intermediate 31) |

TABLE 6-continued

Compounds 171 to 203 were prepared following the procedure described in Method 9, as follows:

| Ex # | Structure | Name | Starting Material 1 | Starting Material 2 |
|---|---|---|---|---|
| 190 | 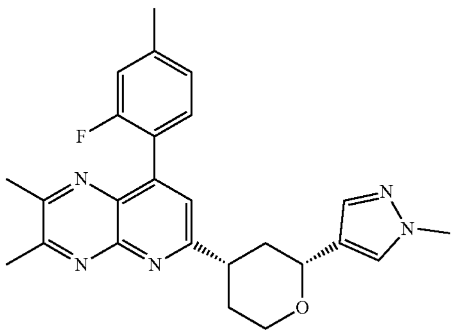 | 8-(2-fluoro-4-methylphenyl)-2,3-dimethyl-6-((2R,4S)-2-(1-methyl-1H-pyrazol-4-yl)tetrahydro-2H-pyran-4-yl)pyrido[2,3-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 6-chloro-8-(2-fluoro-4-methylphenyl)-2,3-dimethylpyrido[2,3-b]pyrazine (Intermediate 31) |
| 191 | 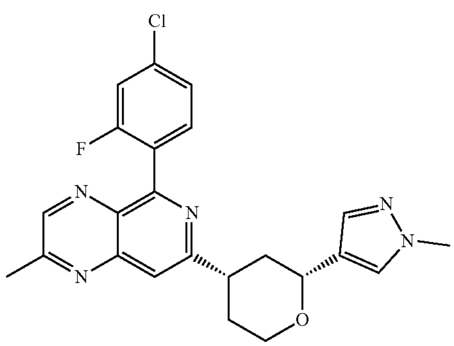 | 5-(4-chloro-2-fluorophenyl)-2-methyl-7-((2R,4S)-2-(1-methyl-1H-pyrazol-4-yl)tetrahydro-2H-pyran-4-yl)pyrido[3,4-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 7-chloro-5-(4-chloro-2-fluorophenyl)-2-methylpyrido[3,4-b]pyrazine (Intermediate 32) |
| 192 | 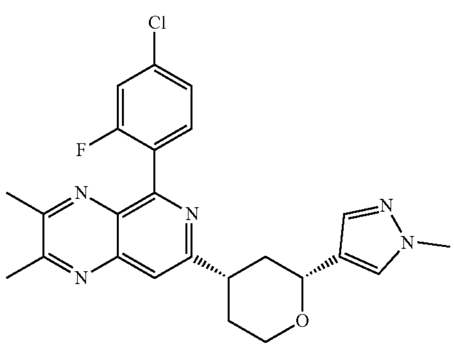 | 5-(4-chloro-2-fluorophenyl)-2,3-dimethyl-7-((2R,4S)-2-(1-methyl-1H-pyrazol-4-yl)tetrahydro-2H-pyran-4-yl)pyrido[3,4-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 7-chloro-5-(4-chloro-2-fluorophenyl)-2,3-dimethylpyrido[3,4-b]pyrazine (Intermediate 33) |
| 193 | 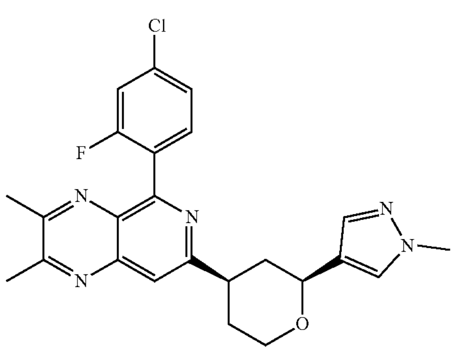 | 5-(4-chloro-2-fluorophenyl)-2,3-dimethyl-7-((2S,4R)-2-(1-methyl-1H-pyrazol-4-yl)tetrahydro-2H-pyran-4-yl)pyrido[3,4-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 7-chloro-5-(4-chloro-2-fluorophenyl)-2,3-dimethylpyrido[3,4-b]pyrazine (Intermediate 33) |

TABLE 6-continued

Compounds 171 to 203 were prepared following the procedure described in Method 9, as follows:

| Ex # | Structure | Name | Starting Material 1 | Starting Material 2 |
|---|---|---|---|---|
| 194 | 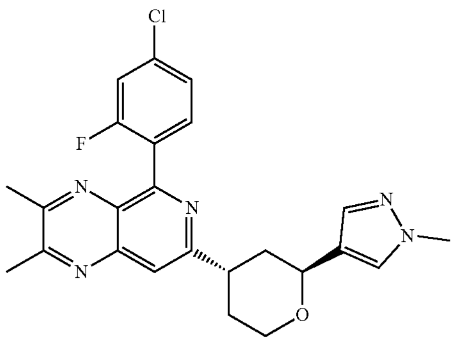 | 5-(4-chloro-2-fluorophenyl)-2,3-dimethyl-7-((2S,4S)-2-(1-methyl-1H-pyrazol-4-yl)tetrahydro-2H-pyran-4-yl)pyrido[3,4-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 7-chloro-5-(4-chloro-2-fluorophenyl)-2,3-dimethylpyrido[3,4-b]pyrazine (Intermediate 33) |
| 195 | 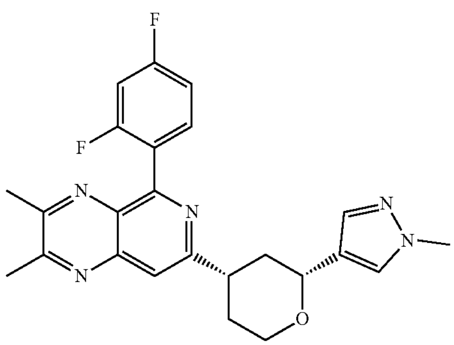 | 5-(2,4-difluorophenyl)-2,3-dimethyl-7-((2R,4S)-2-(1-methyl-1H-pyrazol-4-yl)tetrahydro-2H-pyran-4-yl)pyrido[3,4-b]pyrazine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 7-chloro-5-(2,4-difluorophenyl)-2,3-dimethylpyrido[3,4-b]pyrazine (Intermediate 34) |
| 196 | 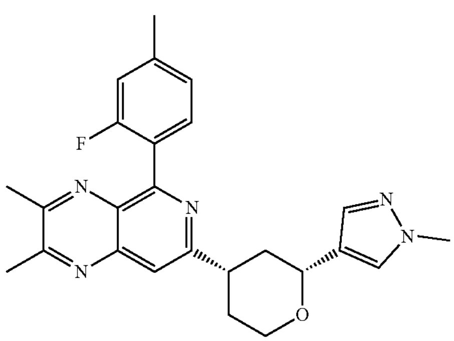 | 5-(2-fluoro-4-methylphenyl)-2,3-dimethyl-7-((2R,4S)-2-(1-methyl-1H-pyrazol-4-yl)tetrahydro-2H-pyran-4-yl)pyrido[3,4-b]pyrazine. Absolute stereochemistry arbitrarily assigned. Relative stereochemistry (cis/trans) determined by NMR | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 7-chloro-5-(2-fluoro-4-methylphenyl)-2,3-dimethylpyrido[3,4-b]pyrazine (Intermediate 35) |
| 197 | 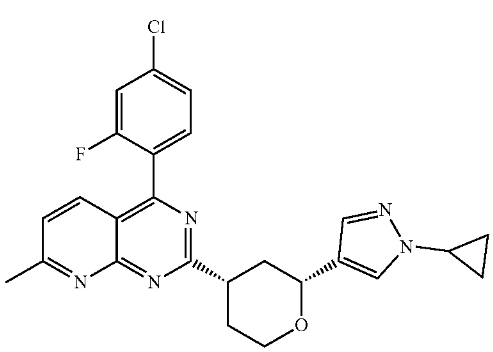 | 4-(4-chloro-2-fluorophenyl)-2-((2R,4S)-2-(1-cyclopropyl-1H-pyrazol-4-yl)tetrahydro-2H-pyran-4-yl)-7-methylpyrido[2,3-d]pyrimidine. Absolute stereochemistry arbitrarily assigned. Relative stereochemistry (cis/trans) determined by NMR. | 1-cyclopropyl-4-(4-(4,4,5,5-tetramethyl-1,3,2-dioxaborolan-2-yl)-5,6-dihydro-2H-pyran-2-yl)-1H-pyrazole (Intermediate 80) | 2-chloro-4-(4-chloro-2-fluorophenyl)-7-methylpyrido[2,3-d]pyrimidine (Intermediate 37) |

TABLE 6-continued

Compounds 171 to 203 were prepared following the procedure described in Method 9, as follows:

| Ex # | Structure | Name | Starting Material 1 | Starting Material 2 |
|---|---|---|---|---|
| 198 | 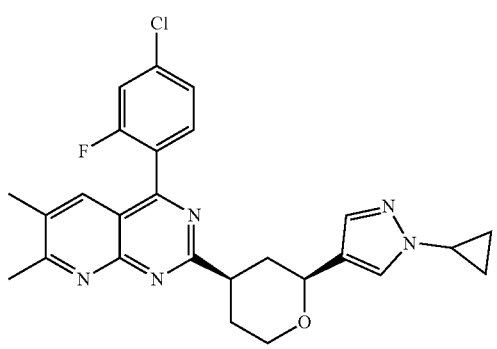 [SMILES: Cc1cc2c(-c3ccc(Cl)cc3F)nc([C@@H]3CCO[C@H](c4cnn(C5CC5)c4)C3)nc2nc1C] | 4-(4-chloro-2-fluorophenyl)-2-((2S,4R)-2-(1-cyclopropyl-1H-pyrazol-4-yl)tetrahydro-2H-pyran-4-yl)-6,7-dimethylpyrido[2,3-d]pyrimidine. Absolute stereochemistry arbitrarily assigned. Relative stereochemistry (cis/trans) determined by NMR. | 1-cyclopropyl-4-(4-(4,4,5,5-tetramethyl-1,3,2-dioxaborolan-2-yl)-5,6-dihydro-2H-pyran-2-yl)-1H-pyrazole (Intermediate 80) | 2-chloro-4-(4-chloro-2-fluorophenyl)-6,7-dimethylpyrido[2,3-d]pyrimidine (Intermediate 40) |
| 199 | 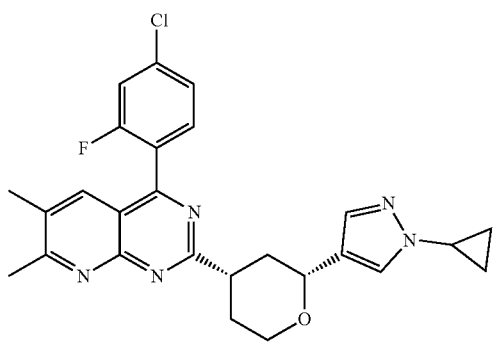 [SMILES: Cc1cc2c(-c3ccc(Cl)cc3F)nc([C@H]3CCO[C@@H](c4cnn(C5CC5)c4)C3)nc2nc1C] | 4-(4-chloro-2-fluorophenyl)-2-((2R,4S)-2-(1-cyclopropyl-1H-pyrazol-4-yl)tetrahydro-2H-pyran-4-yl)-6,7-dimethylpyrido[2,3-d]pyrimidine. Absolute stereochemistry arbitrarily assigned. Relative stereochemistry (cis/trans) determined by NMR. | 1-cyclopropyl-4-(4-(4,4,5,5-tetramethyl-1,3,2-dioxaborolan-2-yl)-5,6-dihydro-2H-pyran-2-yl)-1H-pyrazole (Intermediate 80) | 2-chloro-4-(4-chloro-2-fluorophenyl)-6,7-dimethylpyrido[2,3-d]pyrimidine (Intermediate 40) |
| 200 | 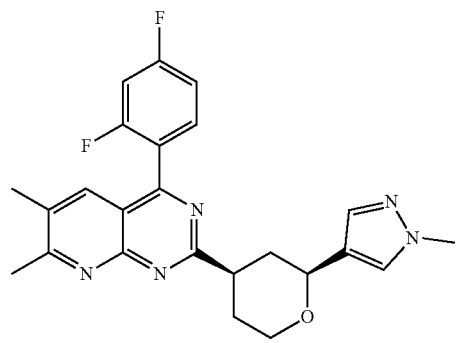 | 4-(2,4-difluorophenyl)-6,7-dimethyl-2-((2S,4R)-2-(1-methyl-1H-pyrazol-4-yl)tetrahydro-2H-pyran-4-yl)pyrido[2,3-d]pyrimidine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(2,4-difluorophenyl)-6,7-dimethylpyrido[2,3-d]pyrimidine (Intermediate 41) |
| 201 | 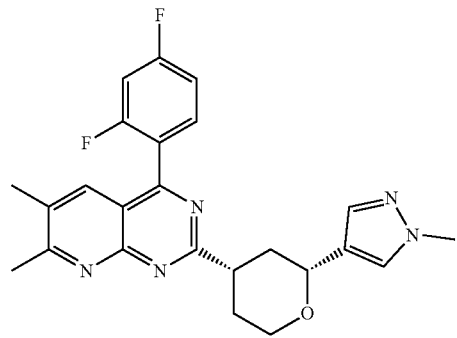 | 4-(2,4-difluorophenyl)-6,7-dimethyl-2-((2R,4S)-2-(1-methyl-1H-pyrazol-4-yl)tetrahydro-2H-pyran-4-yl)pyrido[2,3-d]pyrimidine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(2,4-difluorophenyl)-6,7-dimethylpyrido[2,3-d]pyrimidine (Intermediate 41) |

TABLE 6-continued

Compounds 171 to 203 were prepared following the procedure described in Method 9, as follows:

| Ex # | Structure | Name | Starting Material 1 | Starting Material 2 |
|---|---|---|---|---|
| 202 | 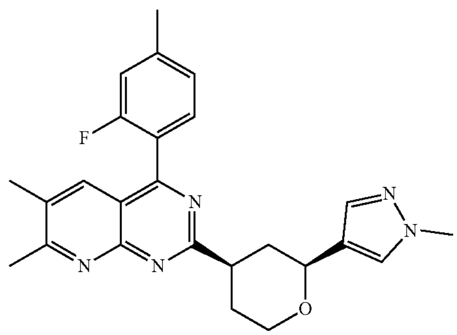 | 4-(2-fluoro-4-methylphenyl)-6,7-dimethyl-2-((2S,4R)-2-(1-methyl-1H-pyrazol-4-yl)tetrahydro-2H-pyran-4-yl)pyrido[2,3-d]pyrimidine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(2-fluoro-4-methylphenyl)-6,7-dimethylpyrido[2,3-d]pyrimidine (Intermediate 42) |
| 203 | 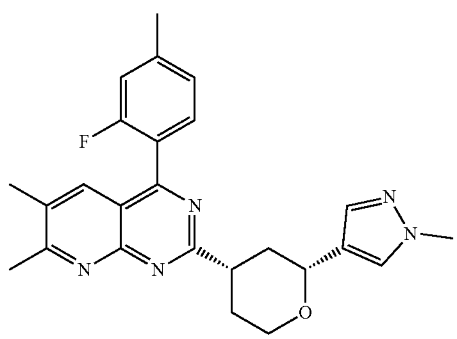 | 4-(2-fluoro-4-methylphenyl)-6,7-dimethyl-2-((2R,4S)-2-(1-methyl-1H-pyrazol-4-yl)tetrahydro-2H-pyran-4-yl)pyrido[2,3-d]pyrimidine. Absolute stereochemistry arbitrarily assigned. Relative stereochemistry (cis/trans) determined by NMR. | 1-methyl-4-(4-(4,4,5,5-tetramethyl-1,3,2-dioxaborolan-2-yl)-5,6-dihydro-2H-pyran-2-yl)-1H-pyrazole (Intermediate 79) | 2-chloro-4-(2-fluoro-4-methylphenyl)-6,7-dimethylpyrido[2,3-d]pyrimidine (Intermediate 42) |

Method 10

Example 204: 6,7-dimethyl-2-((2R,4R)-2-(1-methyl-1H-pyrazol-4-yl)tetrahydro-2H-pyran-4-yl)-4-(trans-3-(trifluoromethyl)cyclobutyl)pteridine; and Example 205: 6,7-dimethyl-2-((2R,4S)-2-(1-methyl-1H-pyrazol-4-yl)tetrahydro-2H-pyran-4-yl)-4-(trans-3-(trifluoromethyl)cyclobutyl)pteridine

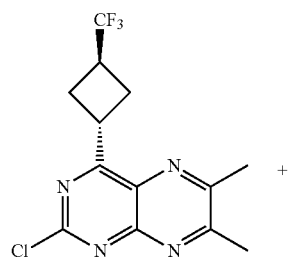

+

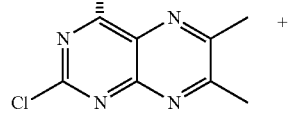

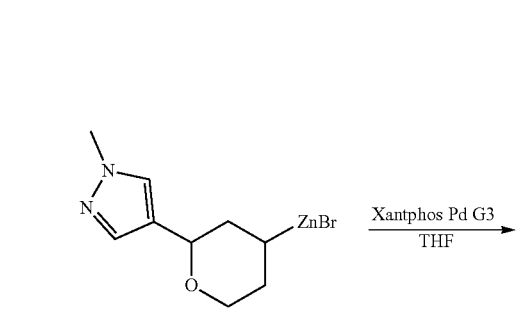

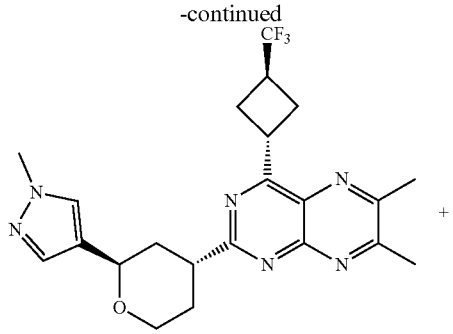

Example 204

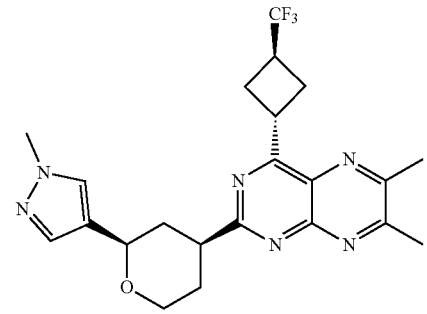

Example 205

Example 204
Example 205

To a 10 mL vial was added xantphos Pd G3 (1.46 mg, 0.023 mmol) and 2-chloro-6,7-dimethyl-4-(trans-3-(trifluoromethyl)cyclobutyl)pteridine (Intermediate 59) (89.6 mg, 0.283 mmol). The vial was evacuated and filled with N₂ 3 times. 0.2 mL THF was added followed by (2-(1-methyl-1H-pyrazol-4-yl)tetrahydro-2H-pyran-4-yl)zinc(II) bromide (Intermediate 74, 1476 µL, 0.339 mmol). The mixture was stirred at 50° C. for 5 h, and the suspension became a brown solution. The mixture was concentrated, DCM was added, and the mixture quenched with H₂O and 2N HCl. The aqueous layer was extracted with DCM, and the combined organics were concentrated. Silica gel chromatography (2%-60% EtOAc/EtOH 3/1 blend in 10% DCM in Heptane) afforded 6,7-dimethyl-2-(2-(1-methyl-1H-pyrazol-4-yl)tetrahydro-2H-pyran-4-yl)-4-(trans-3-(trifluoromethyl)cyclobutyl)pteridine (28 mg, 0.063 mmol, 22.17% yield) as a mixture of diastereomers. The mixture was purified by SFC (Chiralpak IG 2×25 cm, 5 µm column; 30% EtOH, F=80 mL/min) to provide 2 of 4 possible diastereomers:

Peak 1: 6,7-dimethyl-2-((2R,4R)-2-(1-methyl-1H-pyrazol-4-yl)tetrahydro-2H-pyran-4-yl)-4-(trans-3-(trifluoromethyl)cyclobutyl)pteridine (3.45 mg, ee>99%). ¹H NMR (Chloroform-d, 400 MHz) δ 7.5-7.6 (m, 1H), 7.42 (s, 1H), 4.9-5.0 (m, 2H), 3.9-4.0 (m, 5H), 3.69 (quin, 1H, J=5.5 Hz), 3.1-3.3 (m, 1H), 2.6-2.8 (m, 11H), 2.4-2.6 (m, 1H), 2.3-2.4 (m, 1H), 2.1-2.3 (m, 1H). m/z (ESI, +ive ion):447.0 (M+H)⁺. Absolute stereochemistry arbitrarily assigned. Relative stereochemistry determined by NMR.

Peak 2: 6,7-dimethyl-2-((2R,4S)-2-(1-methyl-1H-pyrazol-4-yl)tetrahydro-2H-pyran-4-yl)-4-(trans-3-(trifluoromethyl)cyclobutyl)pteridine (9.83 mg, ee>99%) ¹H NMR (Chloroform-d, 400 MHz) δ 7.54 (s, 1H), 7.44 (s, 1H), 4.91 (quin, 1H, J=8.1 Hz), 4.60 (dd, 1H, J=1.8, 11.4 Hz), 4.3-4.3 (m, 1H), 3.8-3.9 (m, 4H), 3.4-3.6 (m, 1H), 3.1-3.3 (m, 1H), 2.82 (s, 3H), 2.6-2.8 (m, 7H), 2.45 (br d, 1H, J=13.4 Hz), 2.1-2.3 (m, 3H). m/z (ESI, +ive ion):447.0 (M+H)⁺. Absolute stereochemistry arbitrarily assigned. Relative stereochemistry determined by NMR.

TABLE 7

| | | Compounds 206 to 230 were prepared following the procedure described in Method 10, as follows: | | |
|---|---|---|---|---|
| Ex # | Structure | Name | Starting Material 1 | Starting Material 2 |
| 206 | [structure] | 4-(4-chloro-2-fluorophenyl)-6,7-dimethyl-2-((2S,4R)-2-(2-methyl-4-pyridinyl)tetrahydro-2H-pyran-4-yl)pteridine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(4-chloro-2-fluorophenyl)-6,7-dimethylpteridine (Intermediate 16) |
| 207 | [structure] | 4-(4-chloro-2-fluorophenyl)-6,7-dimethyl-2-((2R,4S)-2-(2-methyl-4-pyridinyl)tetrahydro-2H-pyran-4-yl)pteridine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(4-chloro-2-fluorophenyl)-6,7-dimethylpteridine (Intermediate 16) |

TABLE 7-continued

Compounds 206 to 230 were prepared following the procedure described in Method 10, as follows:

| Ex # | Structure | Name | Starting Material 1 | Starting Material 2 |
|---|---|---|---|---|
| 208 | 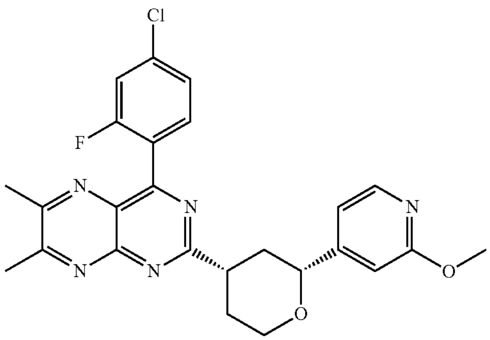 | 4-(4-chloro-2-fluorophenyl)-2-((2R,4S)-2-(2-methoxy-4-pyridinyl)tetrahydro-2H-pyran-4-yl)-6,7-dimethylpteridine. Absolute stereochemistry arbitrarily assigned. Relative stereochemistry determined by NMR. | (2-(2-methoxypyridin-4-yl)tetrahydro-2H-pyran-4-yl)zinc(II) bromide (Intermediate 76) | 2-chloro-4-(4-chloro-2-fluorophenyl)-6,7-dimethylpteridine (Intermediate 16) |
| 209 | 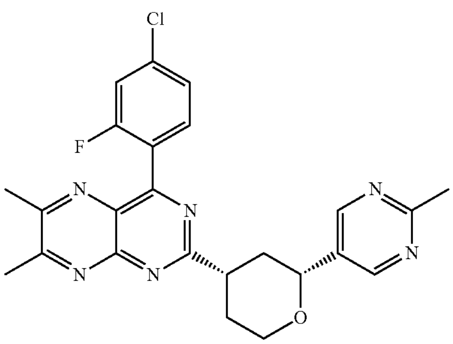 | 4-(4-chloro-2-fluorophenyl)-6,7-dimethyl-2-((2R,4S)-2-(2-methyl-5-pyrimidinyl)tetrahydro-2H-pyran-4-yl)pteridine. Absolute stereochemistry arbitrarily assigned. Relative stereochemistry determined by NMR. | (2-(2-methylpyrimidin-5-yl)tetrahydro-2H-pyran-4-yl)zinc(II) bromide (Intermediate 77) | 2-chloro-4-(4-chloro-2-fluorophenyl)-6,7-dimethylpteridine (Intermediate 16) |
| 210 | 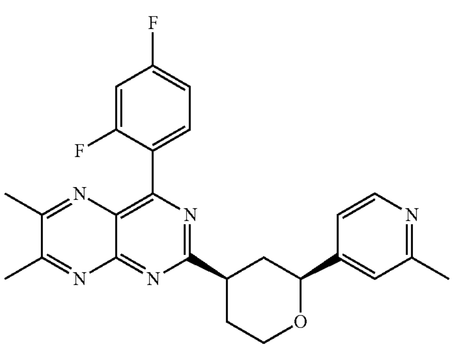 | 4-(2,4-difluorophenyl)-6,7-dimethyl-2-((2S,4R)-2-(2-methyl-4-pyridinyl)tetrahydro-2H-pyran-4-yl)pteridine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2,4-difluorophenyl)-6,7-dimethylpteridine (Intermediate 17) |
| 211 | 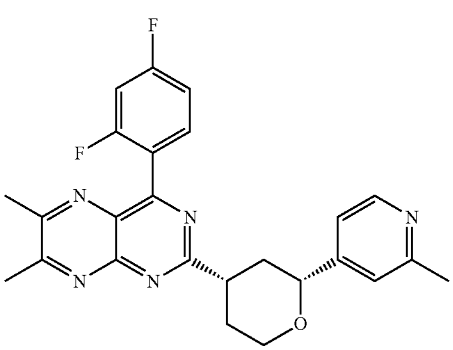 | 4-(2,4-difluorophenyl)-6,7-dimethyl-2-((2R,4S)-2-(2-methyl-4-pyridinyl)tetrahydro-2H-pyran-4-yl)pteridine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2,4-difluorophenyl)-6,7-dimethylpteridine (Intermediate 17) |

TABLE 7-continued

Compounds 206 to 230 were prepared following the procedure described in Method 10, as follows:

| Ex # | Structure | Name | Starting Material 1 | Starting Material 2 |
|---|---|---|---|---|
| 212 | 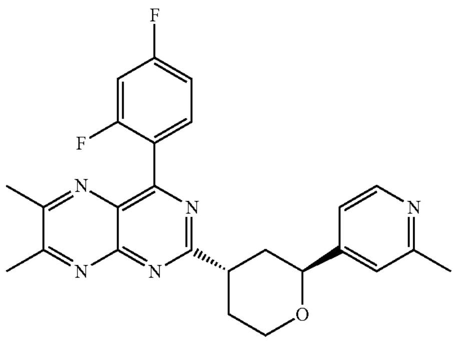 | 4-(2,4-difluorophenyl)-6,7-dimethyl-2-((2S,4S)-2-(2-methyl-4-pyridinyl)tetrahydro-2H-pyran-4-yl)pteridine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2,4-difluorophenyl)-6,7-dimethylpteridine (Intermediate 17) |
| 213 | 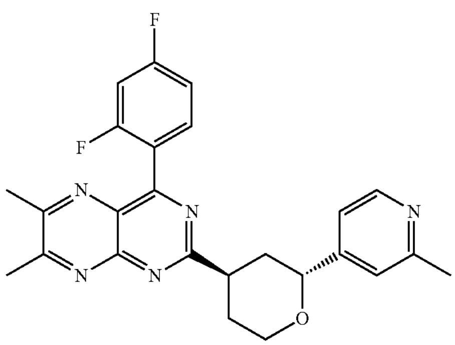 | 4-(2,4-difluorophenyl)-6,7-dimethyl-2-((2R,4R)-2-(2-methyl-4-pyridinyl)tetrahydro-2H-pyran-4-yl)pteridine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2,4-difluorophenyl)-6,7-dimethylpteridine (Intermediate 17) |
| 214 | 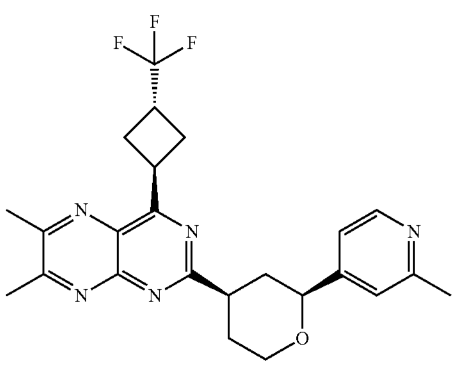 | 6,7-dimethyl-2-((2S,4R)-2-(2-methyl-4-pyridinyl)tetrahydro-2H-pyran-4-yl)-4-(trans-3-(trifluoromethyl)cyclobutyl) pteridine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-6,7-dimethyl-4-((trans)-3-(trifluoromethyl)cyclobutyl) pteridine (Intermediate 59) |
| 215 | 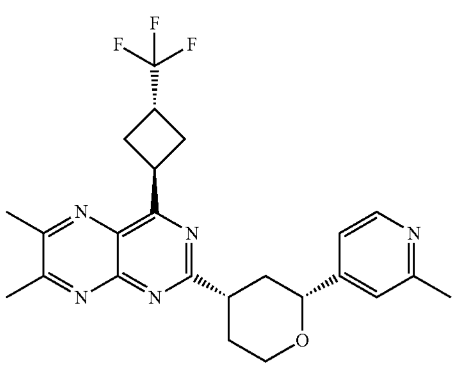 | 6,7-dimethyl-2-((2R,4S)-2-(2-methyl-4-pyridinyl)tetrahydro-2H-pyran-4-yl)-4-(trans-3-(trifluoromethyl)cyclobutyl) pteridine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-6,7-dimethyl-4-((trans)-3-(trifluoromethyl)cyclobutyl) pteridine (Intermediate 59) |

TABLE 7-continued

Compounds 206 to 230 were prepared following the procedure described in Method 10, as follows:

| Ex # | Structure | Name | Starting Material 1 | Starting Material 2 |
|---|---|---|---|---|
| 216 | 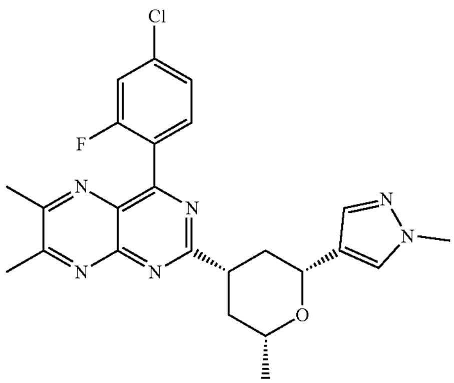 | 4-(4-chloro-2-fluorophenyl)-6,7-dimethyl-2-((2R,4S,6R)-2-methyl-6-(1-methyl-1H-pyrazol-4-yl)tetrahydro-2H-pyran-4-yl)pteridine. Absolute stereochemistry arbitrarily assigned. Relative stereochemistry determined by NMR. | (2-methyl-6-(1-methyl-1H-pyrazol-4-yl)tetrahydro-2H-pyran-4-yl)zinc(II) bromide (Intermediate 78) | 2-chloro-4-(4-chloro-2-fluorophenyl)-6,7-dimethylpteridine (Intermediate 16) |
| 217 | 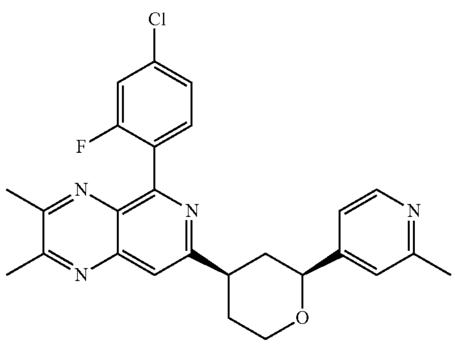 | 5-(4-chloro-2-fluorophenyl)-2,3-dimethyl-7-((2S,4R)-2-(2-methyl-4-pyridinyl)tetrahydro-2H-pyran-4-yl)pyrido[3,4-b]pyrazine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 7-chloro-5-(4-chloro-2-fluorophenyl)-2,3-dimethylpyrido[3,4-b]pyrazine (Intermediate 33) |
| 218 | 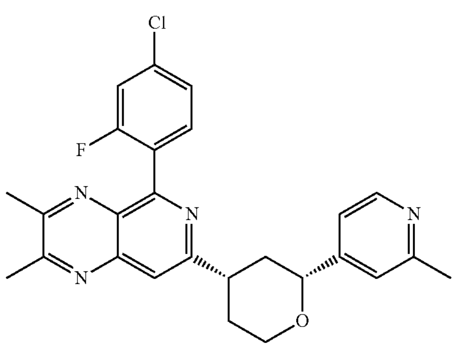 | 5-(4-chloro-2-fluorophenyl)-2,3-dimethyl-7-((2R,4S)-2-(2-methyl-4-pyridinyl)tetrahydro-2H-pyran-4-yl)pyrido[3,4-b]pyrazine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 7-chloro-5-(4-chloro-2-fluorophenyl)-2,3-dimethylpyrido[3,4-b]pyrazine (Intermediate 33) |
| 219 | 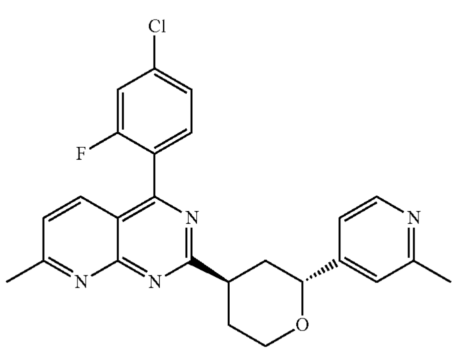 | 4-(4-chloro-2-fluorophenyl)-7-methyl-2-((2R,4R)-2-(2-methyl-4-pyridinyl)tetrahydro-2H-pyran-4-yl)pyrido[2,3-d]pyrimidine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(4-chloro-2-fluorophenyl)-7-methylpyrido[2,3-d]pyrimidine (Intermediate 37) |

TABLE 7-continued

Compounds 206 to 230 were prepared following the procedure described in Method 10, as follows:

| Ex # | Structure | Name | Starting Material 1 | Starting Material 2 |
|---|---|---|---|---|
| 220 | 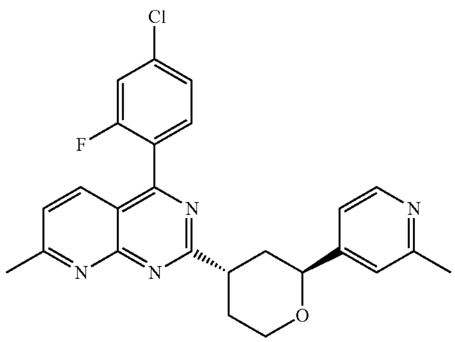 | 4-(4-chloro-2-fluorophenyl)-7-methyl-2-((2S,4S)-2-(2-methyl-4-pyridinyl)tetrahydro-2H-pyran-4-yl)pyrido[2,3-d]pyrimidine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(4-chloro-2-fluorophenyl)-7-methylpyrido[2,3-d]pyrimidine (Intermediate 37) |
| 221 | 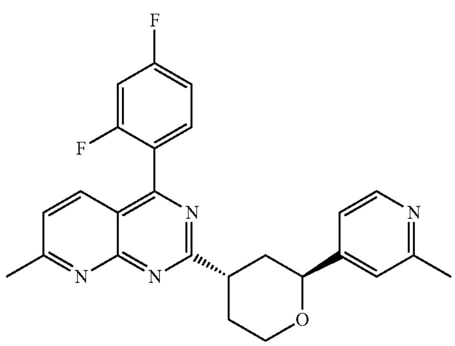 | 4-(2,4-difluorophenyl)-7-methyl-2-((2S,4S)-2-(2-methyl-4-pyridinyl)tetrahydro-2H-pyran-4-yl)pyrido[2,3-d]pyrimidine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2,4-difluorophenyl)-7-methylpyrido[2,3-d]pyrimidine (Intermediate 38) |
| 222 | 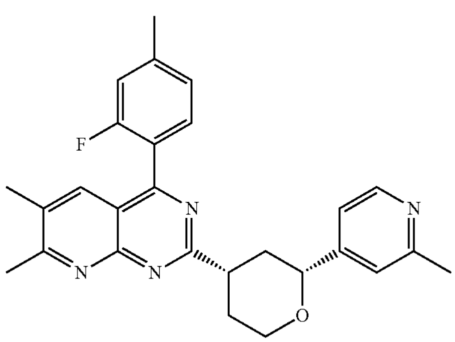 | 4-(2-fluoro-4-methylphenyl)-6,7-dimethyl-2-((2R,4S)-2-(2-methyl-4-pyridinyl)tetrahydro-2H-pyran-4-yl)pyrido[2,3-d]pyrimidine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2-fluoro-4-methylphenyl)-6,7-dimethylpyrido[2,3-d]pyrimidine (Intermediate 42) |
| 223 | 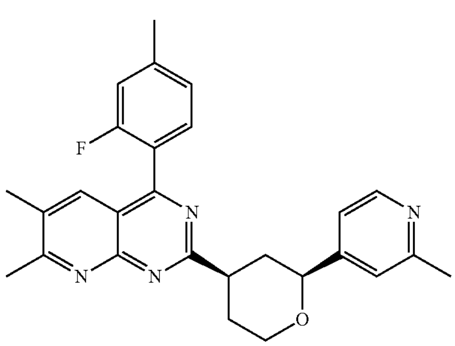 | 4-(2-fluoro-4-methylphenyl)-6,7-dimethyl-2-((2S,4R)-2-(2-methyl-4-pyridinyl)tetrahydro-2H-pyran-4-yl)pyrido[2,3-d]pyrimidine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2-fluoro-4-methylphenyl)-6,7-dimethylpyrido[2,3-d]pyrimidine (Intermediate 42) |

TABLE 7-continued

Compounds 206 to 230 were prepared following the procedure described in Method 10, as follows:

| Ex # | Structure | Name | Starting Material 1 | Starting Material 2 |
|---|---|---|---|---|
| 224 | 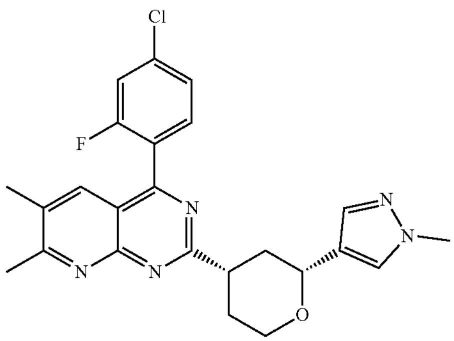 | 4-(4-chloro-2-fluorophenyl)-6,7-dimethyl-2-((2R,4S)-2-(1-methyl-1H-pyrazol-4-yl)tetrahydro-2H-pyran-4-yl)pyrido[2,3-d]pyrimidine. Absolute stereochemistry arbitrarily assigned. Relative stereochemistry determined by NMR. | 2-(1-methyl-1H-pyrazol-4-yl)tetrahydro-2H-pyran-4-yl)zinc(II) bromide | 2-chloro-4-(4-chloro-2-fluorophenyl)-6,7-dimethylpyrido[2,3-d]pyrimidine (Intermediate 40) |
| 225 | 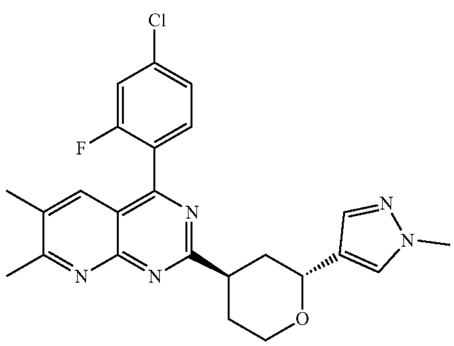 | 4-(4-chloro-2-fluorophenyl)-6,7-dimethyl-2-((2R,4R)-2-(1-methyl-1H-pyrazol-4-yl)tetrahydro-2H-pyran-4-yl)pyrido[2,3-d]pyrimidine. Absolute stereochemistry arbitrarily assigned. Relative stereochemistry determined by NMR. | 2-(1-methyl-1H-pyrazol-4-yl)tetrahydro-2H-pyran-4-yl)zinc(II) bromide | 2-chloro-4-(4-chloro-2-fluorophenyl)-6,7-dimethylpyrido[2,3-d]pyrimidine (Intermediate 40) |
| 226 | 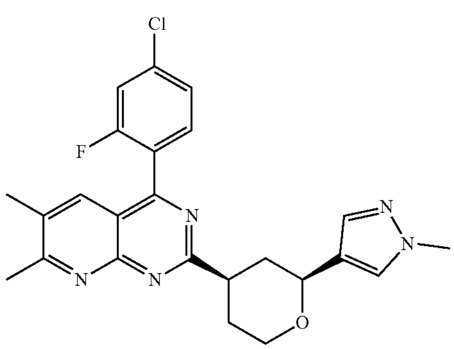 | 4-(4-chloro-2-fluorophenyl)-6,7-dimethyl-2-((2S,4R)-2-(1-methyl-1H-pyrazol-4-yl)tetrahydro-2H-pyran-4-yl)pyrido[2,3-d]pyrimidine. Absolute stereochemistry arbitrarily assigned. Relative stereochemistry determined by NMR. | 2-(1-methyl-1H-pyrazol-4-yl)tetrahydro-2H-pyran-4-yl)zinc(II) bromide | 2-chloro-4-(4-chloro-2-fluorophenyl)-6,7-dimethylpyrido[2,3-d]pyrimidine (Intermediate 40) |
| 227 | 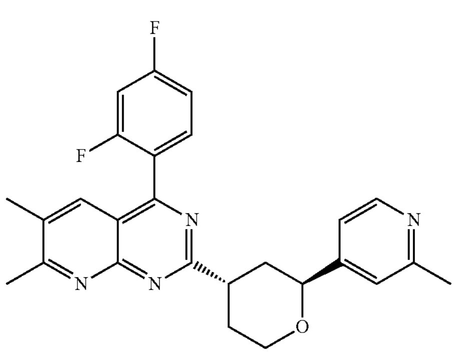 | 4-(2,4-difluorophenyl)-6,7-dimethyl-2-((2S,4S)-2-(2-methyl-4-pyridinyl)tetrahydro-2H-pyran-4-yl)pyrido[2,3-d]pyrimidine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2,4-difluorophenyl)-6,7-dimethylpyrido[2,3-d]pyrimidine (Intermediate 41) |

TABLE 7-continued

Compounds 206 to 230 were prepared following the procedure described in Method 10, as follows:

| Ex # | Structure | Name | Starting Material 1 | Starting Material 2 |
|---|---|---|---|---|
| 228 | 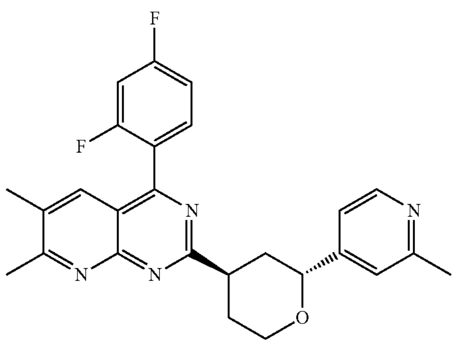 | 4-(2,4-difluorophenyl)-6,7-dimethyl-2-((2R,4R)-2-(2-methyl-4-pyridinyl)tetrahydro-2H-pyran-4-yl)pyrido[2,3-d]pyrimidine. Absolute stereochemistry arbitrarily assigned. Relative stereochemistry determined by NMR. | (2-(2-methylpyridin-4-yl)tetrahydro-2H-pyran-4-yl)zinc(II) bromide (Intermediate 75) | 2-chloro-4-(2,4-difluorophenyl)-6,7-dimethylpyrido[2,3-d]pyrimidine (Intermediate 41) |
| 229 | 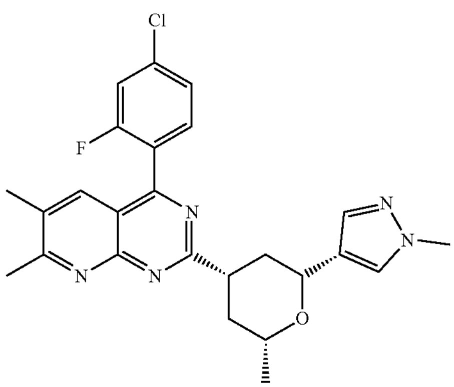 | 4-(4-chloro-2-fluorophenyl)-6,7-dimethyl-2-((2R,4S,6R)-2-methyl-6-(1-methyl-1H-pyrazol-4-yl)tetrahydro-2H-pyran-4-yl)pyrido[2,3-d]pyrimidine. Absolute stereochemistry arbitrarily assigned. Relative stereochemistry determined by NMR. | (2-methyl-6-(1-methyl-1H-pyrazol-4-yl)tetrahydro-2H-pyran-4-yl)zinc(II) bromide (Intermediate 78) | 2-chloro-4-(4-chloro-2-fluorophenyl)-6,7-dimethylpyrido[2,3-d]pyrimidine (Intermediate 40) |
| 230 | 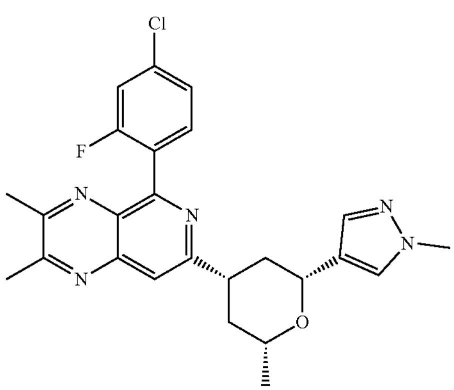 | 5-(4-chloro-2-fluorophenyl)-2,3-dimethyl-7-((2R,4S,6R)-2-methyl-6-(1-methyl-1H-pyrazol-4-yl)tetrahydro-2H-pyran-4-yl)pyrido[3,4-b]pyrazine. Absolute stereochemistry arbitrarily assigned. Relative stereochemistry determined by NMR. | (2-methyl-6-(1-methyl-1H-pyrazol-4-yl)tetrahydro-2H-pyran-4-yl)zinc(II) bromide (Intermediate 78) | 7-chloro-5-(4-chloro-2-fluorophenyl)-2,3-dimethylpyrido[3,4-b]pyrazine (Intermediate 33) |

Example 231: (S)-2-(1-cyclopropyl-1H-pyrazol-4-yl)-4-(7-methyl-4-(3-(trifluoromethyl)bicyclo[1.1.1]pentan-1-yl)pteridin-2-yl)morpholine Example 232: (S)-4-(7-methyl-4-(3-(trifluoromethyl)bicyclo[1.1.1]pentan-1-yl)pteridin-2-yl)-2-(2-methylpyridin-4-yl)morpholine

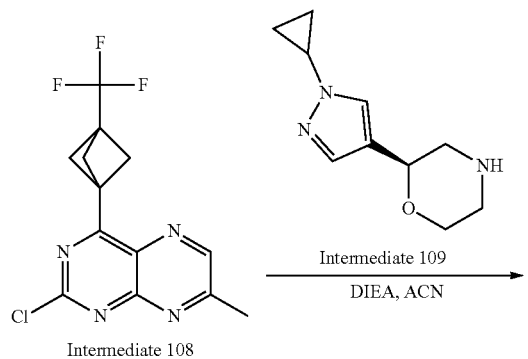

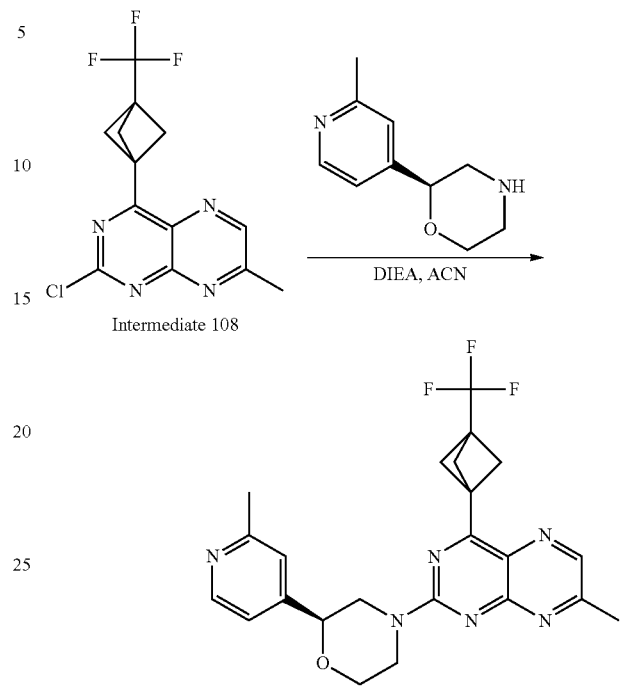

Example 231

Into a 1 dram vial was weighed 2-chloro-7-methyl-4-(3-trifluoromethyl) bicyclo[1.1.1]pentan-1-yl)pteridine (43.4 mg, 0.138 mmol, Intermediate 108) and (S)-2-(1-cyclopropyl-1H-pyrazol-4-yl)morpholine (32.0 mg, 0.165 mmol, Intermediate 109). The vial was fitted with a stirring bar and acetonitrile (690 µL) was added followed by N,N-diisopropylethylamine (53.5 mg, 72.3 µL, 0.414 mmol, Sigma-Aldrich Corporation). The mixture was left to stir at 24° C. and was monitored over time by LCMS. After sufficient conversion was observed, the reaction was terminated and the crude product was isolated and purified as described in Method 1 to afford (S)-2-(1-cyclopropyl-1H-pyrazol-4-yl)-4-(7-methyl-4-(3-(trifluoromethyl)bicyclo[1.1.1]pentan-1-yl)pteridin-2-yl)morpholine (22.5 mg, 0.0478 mmol, 35% yield) $^1$H NMR (600 MHz, DMSO-d6) δ ppm 8.53-8.56 (m, 1H), 7.84 (s, 1H), 7.47 (s, 1H), 4.76 (br d, J=12.53 Hz, 1H), 4.62 (br s, 1H), 4.49 (dd, J=10.35, 2.72 Hz, 1H), 3.98-4.05 (m, 1H), 3.68-3.73 (m, 1H), 3.60-3.68 (m, 1H), 3.14-3.25 (m, 1H), 2.63 (s, 3H), 2.57 (s, 6H), 1.19-1.32 (m, 1H), 0.93-1.05 (m, 5H). m/z (ESI, +ive ion):472.0 (M+H)$^+$.

Example 232

Into a 1 dram vial was weighed 2-chloro-7-methyl-4-(3-trifluoromethyl) bicyclo[1.1.1]pentan-1-yl)pteridine (43.4 mg, 0.138 mmol, Intermediate 108) and (S)-2-(2-methylpyridin-4-yl)morpholine (29.5 mg, 0.165 mmol, Syngene). The vial was fitted with a stirring bar and acetonitrile (690 µL) was added followed by N,N-diisopropylethylamine (53.5 mg, 72.3 µL, 0.414 mmol, Sigma-Aldrich Corporation). The mixture was left to stir at 24° C. and was monitored over time by LCMS. After sufficient conversion was observed, the reaction was terminated and the crude product was isolated and purified as described in Method 1 to afford (S)-4-(7-methyl-4-(3-(trifluoromethyl)bicyclo[1.1.1]pentan-1-yl)pteridin-2-yl)-2-(2-methylpyridin-4-yl)morpholine (11.7 mg, 0.0256 mmol, 18.5% yield). $^1$H NMR (600 MHz, DMSO-d6) δ ppm 8.56 (s, 1H), 8.43-8.51 (m, 1H), 7.35 (s, 1H), 7.25-7.32 (m, 1H), 4.87 (br d, J=11.63 Hz, 1H), 4.61 (br dd, =10.44, 2.45 Hz, 1H), 4.15 (br dd, J=11.90, 2.27 Hz, 1H), 3.68-3.77 (m, 1H), 2.98-3.10 (m, 1H), 2.64 (s, 3H), 2.58 (s, 5H), 2.52-2.53 (m, 1H), 2.43-2.49 (m, 1H), 0.97-1.07 (m, 1H). m/z (ESI, +ive ion):457.0 (M+H)$^+$.

Method 37

Example 309: 6,7-dimethyl-2-((2R,4S)-2-(2-methylpyridin-4-yl)tetrahydro-2H-pyran-4-yl)-4-(6-(trifluoromethyl)pyridin-3-yl)pteridine

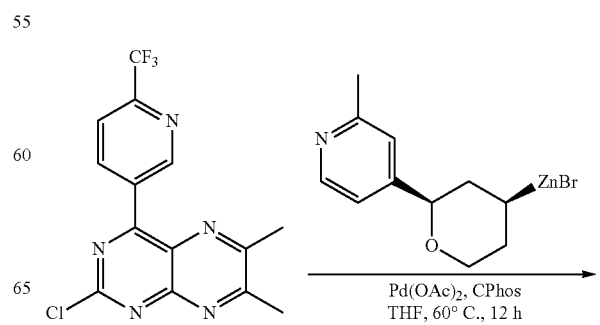

531

-continued

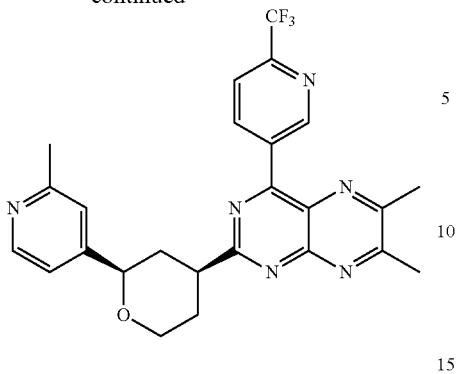

A flame-dried microwave vial under argon was charged with 2-chloro-6,7-dimethyl-4-(6-(trifluoromethyl)pyridin-3-yl)pteridine (105 mg, 308 μmol), CPhos (25.8 mg, 59.0 μmol) and THF (2.70 mL). The reaction mixture was degassed for 5 min with argon then ((2S,4S)-2-(2-methylpyridin-4-yl)tetrahydro-2H-pyran-4-yl)zinc(II) bromide (1.54 mL, 384 μmol) was added dropwise. The reaction vial was sealed and immersed in a pre-heated oil bath at 60° C. The reaction was stirred overnight at 60° C. When the conversion was judged complete by LCMS, the reaction mixture was cooled down to r.t., diluted with EtOAc (5 mL) and passed through a silica pad (1 cm). The silica was rinsed with EtOAc (10 mL) followed by 10% MeOH in $CH_2Cl_2$. The volatiles were removed in vacuo and the crude material was purified by flash chromatography (Isco RediSep® column 24 g, using a gradient from 50% EtOAc in $CH_2Cl_2$ to 100% EtOAc followed by 5 CV at 10% MeOH in $CH_2Cl_2$). The selected fractions were evaporated to yield the desired 6,7-dimethyl-2-((2R,4S)-2-(2-methylpyridin-4-yl)tetrahydro-2H-pyran-4-yl)-4-(6-(trifluoromethyl)pyridin-3-yl)pteridine (57.2 mg, 39%). LCMS:m/z (ESI) [M+H]$^+$ 481.20, $t_R$=1.302 min. $^1$H NMR Major dia. (DMSO-d$_6$, 400 MHz): $\delta_H$ 1.77 (1H, q, J=12.2 Hz), 2.06-1.93 (1H, m), 2.16 (1H, d, J=13.1 Hz), 2.44 (3H, s), 2.73 (3H, s), 2.78 (3H, s), 3.59 (1H, t, J=11.6 Hz), 3.80 (1H, t, J=11.8 Hz), 4.25 (1H, dd, J=11.3, 4.2 Hz), 4.62 (1H, d, J=11.2 Hz), 7.19 (1H, d, J=5.3 Hz), 7.27 (1H, s), 8.15 (1H, d, J=8.3 Hz), 8.37 (1H, d, J=5.3 Hz), 8.90 (1H, d, J=8.2 Hz), 9.59 (1H, s).

Method 38

Example 394: 4-(4-chloro-2,3-difluorophenyl)-7-methyl-2-((2R,4S)-2-(2-methylpyridin-4-yl)tetrahydro-2H-pyran-4-yl)pteridine

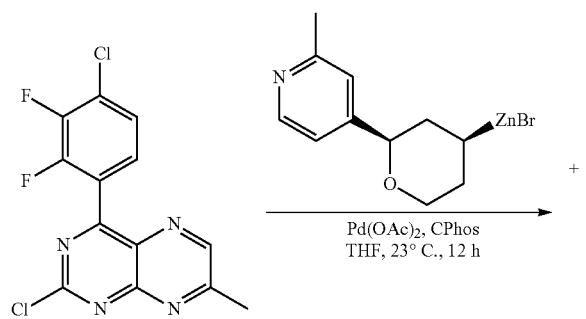

532

-continued

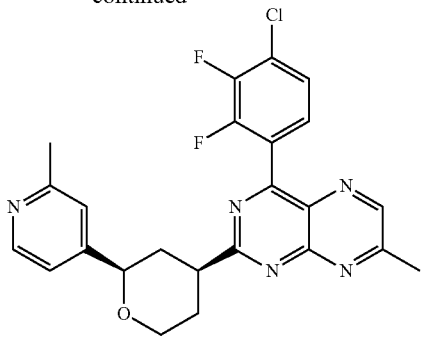

mixture of cis enantiomers

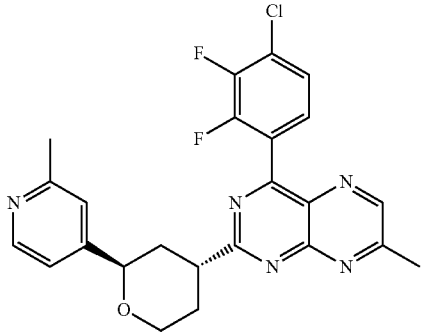

mixture of trans enantiomers

In a flame-dried 50 mL microwave vial, 2-chloro-4-(4-chloro-2,3-difluoro-phenyl)-7-methyl-pteridine (100 mg, 0.306 mmol), palladium acetate (6.9 mg, 0.0306 mmol), C-Phos (0.200 eq, 27 mg, 0.0611 mmol) and THF (3.5 mL) were added. The reaction mixture was degassed for 5 min under $N_2$ and bromo-[2-(2-methyl-4-pyridyl)tetrahydropyran-4-yl]zinc bromide solution (0.17 M in THF) (1.8 mL, 0.3057 mmol) was added dropwise over 30 min. The mixture was stirred at 22° C. for 2 h. The reaction was quenched by addition of sat. $NaHCO_3$ (20 mL) and the reaction mixture was extracted with DCM (50 mL). The aqueous layer was extracted with DCM (2×50 mL). The combined organic layer was dried over $Na_2SO_4$ and the solvent was removed in vacuo. The crude material was purified by flash chromatography (Isco RediSep® column 40 g) using EtOAc and hexanes (0-100%) then using MeOH and DCM (0-10%) to obtain a solid (100 mg) which was further purified by prep HPLC (Gemini® 5 μm NX-C18 110 Å, 100×30 mm column) using MeOH and aqueous 10 mM ammonium formate to obtain 4-(4-chloro-2,3-difluoro-phenyl)-7-methyl-2-[rac-(2R,4S)-2-(2-methyl-4-pyridyl)tetrahydropyran-4-yl]pteridine as a mixture of cis distereomers (32.3 mg, 22%) and 4-(4-chloro-2,3-difluoro-phenyl)-7-methyl-2-[rac-(2R,4R)-2-(2-methyl-4-pyridy)tetrahydropyran-4-yl]pteridine as a mixture of trans distereomers (2.8 mg, 2%). Cis isomers: ESI-MS (m/z+): 468.20 [M+H]$^+$, LC-RT: 1.307 min. $^1$H NMR (400 MHz, CD$_2$Cl$_2$) δ 8.81 (s, 1H), 8.41 (s, 1H), 7.50-7.45 (m, 1H), 7.43-7.37 (m, 1H), 7.23 (s, 1H), 7.13 (d, J=4.6 Hz, 1H), 4.55 (d, J=11.5 Hz, 1H), 4.34 (dd, J=10.6, 3.8 Hz, 1H), 3.84 (td, J=11.7, 3.2 Hz, 1H), 3.66-3.57 (m, 1H), 2.86 (s, 3H), 2.51 (s, 3H), 2.47-2.40 (m, 1H), 2.25-2.13 (m, 2H), 2.01-1.90 (m, 1H). $^{19}$F NMR (376 MHz, CD$_2$Cl$_2$) δ ppm -133.01 (s), -138.66 (s). Trans isomers: $^1$H NMR (400 MHz, CD$_2$Cl$_2$) δ ppm 8.85 (s, 1H), 8.42 (d, J=5.5 Hz, 1H), 7.56-7.51 (m, 1H), 7.46-7.38 (m, 1H), 7.21 (s, 1H), 7.12 (d, J=4.7 Hz, 1H), 4.78 (dd, J=9.6, 2.4 Hz, 1H), 4.04-3.97 (m, 1H), 3.90 (td, J=11.3, 2.5 Hz, 1H), 3.76-3.71 (m, 1H), 2.89 (s, 3H), 2.52 (s, 3H), 2.52 (s, 2H), 2.30-2.24 (m, 1H), 2.22-2.16 (m, 1H).

Method 39

Examples 392: 7-((2R,4S)-2-(1-cyclopropyl-1H-pyrazol-4-yl)tetrahydro-2H-pyran-4-yl)-2,3-dimethyl-5-(3-(trifluoromethyl)bicyclo[1.1.1]pentan-1-yl)pyrido[3,4-b]pyrazine

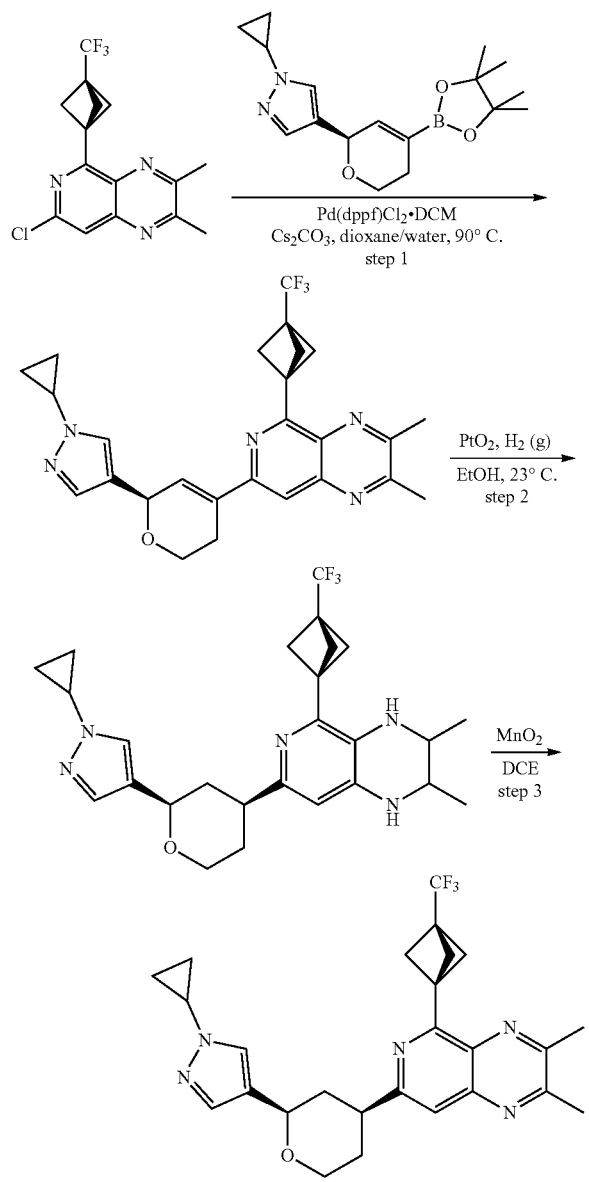

Step 1: To a solution of 7-chloro-2,3-dimethyl-5-[3-(trifluoromethyl)-1-bicyclo[1.1.1]pentanyl]pyrido[3,4-b]pyrazine (490 mg, 1.50 mmol, Intermediate 114) and 1-cyclopropyl-4-[(6R)-4-(4,4,5,5-tetramethyl-1,3,2-dioxaborolan-2-yl)-3,6-dihydro-2H-pyran-6-yl]pyrazole (520 mg, 1.64 mmol) in 1,4-dioxane (10 mL) was added cesium carbonate (1461 mg, 4.49 mmol), water (1 mL) and Pd(dppf)Cl₂ (109 mg, 0.150 mmol). The mixture was then stirred at 90° C. overnight. After completion, the mixture was cooled to rt, and diluted with EtOAc. The organic layer was then washed with water then brine and dried over MgSO₄, filtered through a plug of silica, and concentrated in vacuo. The residue was then purified by flash chromatography using a DCM/EtOAc gradient (20%-100%) to afford the desired material (560 mg, 75%) as a light-yellow foam. ¹H NMR (400 MHz, Chloroform-d): δ ppm 7.69 (1H, s), 7.53 (1H, s), 7.50 (1H, s), 7.18 (1H, s), 5.42 (1H, d, J=2.9 Hz), 4.09-4.16 (1H, m), 3.93 (1H, m), 3.54-3.60 (1H, m), 2.74 (4H, s), 2.73 (3H, s), 2.67 (1H, m), 2.62 (6H, s), 1.10-1.13 (2H, m), 0.97-1.03 (2H, m).

Step 2: To a flask under argon atmosphere containing 2,3-dimethyl-7-[(6R)-6-(1-cyclopropylpyrazol-4-yl)-3,6-dihydro-2H-pyran-4-yl]-5-[3-(trifluoromethyl)-1-bicyclo[1.1.1]pentanyl]pyrido[3,4-b]pyrazine (1.00 eq, 254 mg, 0.528 mmol) in ethanol (8 mL) was added PtO₂ (0.710 eq, 85 mg, 0.374 mmol). The system was purged with hydrogen and stirred overnight under 1 atm of H₂. When the reaction was judged complete by LCMS and ¹H NMR, the mixture was diluted with EtOAc and filtered through celite and evaporated. The crude material was used in the next step without further purification.

Step 3: To a flask under argon atmosphere containing 2,3-dimethyl-7-[(2R,4S)-2-(1-cyclopropylpyrazol-4-yl)tetrahydropyran-4-yl]-5-[3-(trifluoromethyl)-1-bicyclo[1.1.1]pentanyl]-1,2,3,4-tetrahydropyrido[3,4-b]pyrazine (1.00 eq, 254 mg, 0.521 mmol) in DCE (5 mL) was added MnO₂ (20.1 eq, 900 mg, 10.5 mmol). The reaction was then stirred overnight at 50° C. After completion, the mixture was cooled down to r.t., diluted with EtOAc and filtered through a plug of silica and the solvent was evaporated in vacuo. The residue was purified by column chromatography using a 35%-100% DCM/EtOAc gradient to afford the desired material as a 11:1 diastereomeric mixture. Further purification by reverse phase chromatography using a Gemini® 5 um NX-C18 110 Å, 100×30 mm column and a 55%-75% methanol/water (10 mm ammonium formate) gradient gave the desired material (113 mg, 45%) as a white solid after lyophilization. ¹H NMR (400 MHz, Chloroform-d): δ ppm 7.54 (1H, s), 7.48 (2H, s), 4.55 (1H, d, J=11.2 Hz), 4.25 (1H, d, J=11.4 Hz), 3.84-3.78 (1H, m), 3.59-3.53 (1H, m), 3.22 (1H, m), 2.74 (3H, s), 2.73 (3H, s), 2.61 (6H, s), 2.30 (1H, d, J=13.1 Hz), 2.02-1.95 (3H, m), 1.10 (2H, m), 1.04-0.97 (2H, m). LCMS: m/z (ESI) [M+H]⁺ 484.2

Method 40

Examples 346: 4-(5-(2,4-Difluorophenyl)-2,3-dimethyl-1,6-naphthyridin-7-yl)-2-(2-methylpyridin-4-yl)morpholine

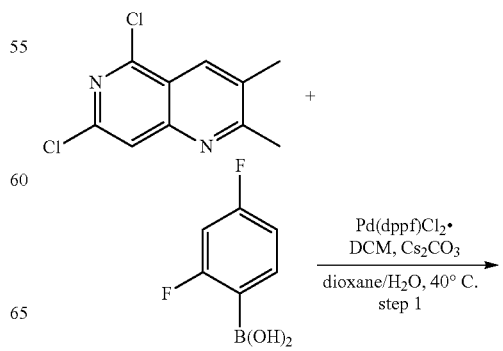

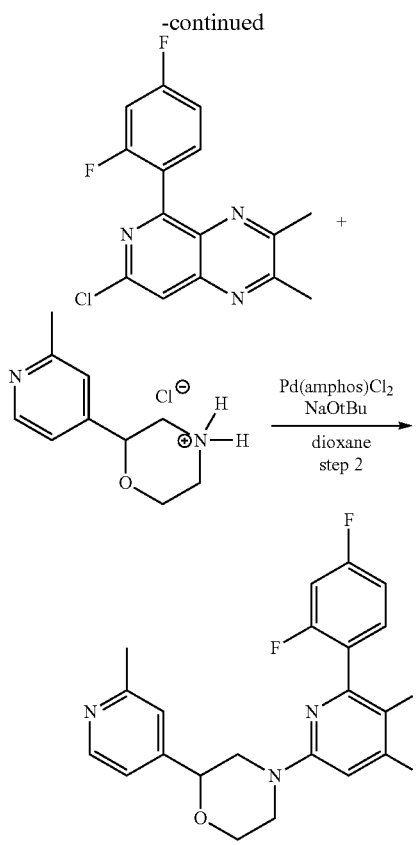

Step 1: A 50 mL microwave vial was charged with (2,4-difluorophenyl)boronic acid (556 mg, 3.52 mmol), 5,7-dichloro-2,3-dimethyl-1,6-naphthyridine (800 mg, 3.52 mmol), cesium carbonate (3.44 g, 10.6 mmol), 1,4-dioxane (16 mL) and water (4.8 mL). The reaction mixture was degassed with nitrogen for 10 min. Pd(dppf)Cl$_2$·CH$_2$Cl$_2$ (144 mg, 0.176 mmol) was added, and the mixture was heated at 40° C. for 1 h. The mixture was cooled to r.t., and diluted with DCM (50 mL) and water (10 mL). The aqueous layer was extracted with DCM (2×25 mL). The combined organic layers were washed with brine (10 mL), dried (Na$_2$SO$_4$) and concentrated under reduced pressure. The residue was purified by silica gel chromatography (80 g SilicaSep cartridge) using EtOAc and hexanes (30-40%) to obtain 7-chloro-5-(2,4-difluorophenyl)-2,3-dimethyl-1,6-naphthyridine (660 mg, 2.17 mmol, 62%) as a solid. ESI-MS (m/z+): 305.1 [M+H]$^+$, LC-RT: 2.09 min. $^1$H NMR (400 MHz, CDCl$_3$) δ ppm 7.92 (s, 1H), 7.70 (d, J=2.7 Hz, 1H), 7.62-7.53 (m, 1H), 7.13-7.05 (m, 1H), 7.04-6.95 (m, 1H), 2.73 (s, 3H), 2.43 (s, 3H). $^{19}$F NMR (376 MHz, CDCl$_3$) δ ppm −107.43 (s), −109.37 (s).

Step 2: A mixture of 7-chloro-5-(2,4-difluorophenyl)-2,3-dimethyl-1,6-naphthyridine (50 mg, 0.164 mmol), 2-(2-methyl-4-pyridyl)morpholin-4-ium chloride (36 mg, 0.169 mmol), sodium tert-butoxide (63 mg, 0.658 mmol), and Pd(amphos)Cl$_2$ (12 mg, 0.0164 mmol) in 10 mL microwave vial was subjected to three cycles of vacuum/nitrogen fill. 1,4-Dioxane (2.5 mL) was added, and the mixture was stirred at 80° C. for 5 h. The mixture was cooled to r.t., and diluted with EtOAc (50 mL) and water (20 mL). The layers were separated, and the aqueous layer was extracted with EtOAc (2×50 mL). The combined organic layers were washed with brine (10 mL), dried over Na$_2$SO$_4$, and concentrated in vacuo. The residue was purified by silica gel chromatography (SilicaSep® 24 g cartridge) using MeOH and dichloromethane (20-30%) to obtain an oil which was further purified by reverse phase chromatography on ACCQ prep HPLC (Gemini 150×30 mm C18 column) using acetonitrile and water (80-90%) to obtain 4-[5-(2,4-difluorophenyl)-2,3-dimethyl-1,6-naphthyridin-7-yl]-2-(2-methyl-4-pyridyl)morpholine (19 mg, 0.0410 mmol, 25%) as a yellow solid. ESI-MS (m/z+): 447.20 [M+H]+, LC-RT: 2.313 min. $^1$H NMR (400 MHz, CD2Cl2) δ ppm 8.45 (d, J=5.2 Hz, 1H), 7.57-7.49 (m, 2H), 7.25 (s, 1H), 7.18 (d, J=5.1 Hz, 1H), 7.12-6.98 (m, 3H), 4.64 (dd, J=10.4, 2.5 Hz, 1H), 4.46 (d, J=12.4 Hz, 1H), 4.25-4.16 (m, 2H), 3.95-3.86 (m, 1H), 3.19-3.09 (m, 1H), 2.85 (dd, J=12.7, 10.6 Hz, 1H), 2.62 (s, 3H), 2.54 (s, 3H), 2.32 (s, 3H). $^{19}$F NMR (376 MHz, CD$_2$Cl$_2$) δ ppm −109.71 (s), −110.69 (s).

Method 41

Examples 389 and 390: 4-(4-chloro-3,5-difluoro-phenyl)-6,7-dimethyl-2-[(2R,4S)-2-(2-methyl-4-pyridyl)tetrahydropyran-4-yl]pteridine and 4-(4-chloro-3,5-difluoro-phenyl)-6,7-dimethyl-2-[(2R,4R)-2-(2-methyl-4-pyridyl)tetrahydropyran-4-yl]pteridine

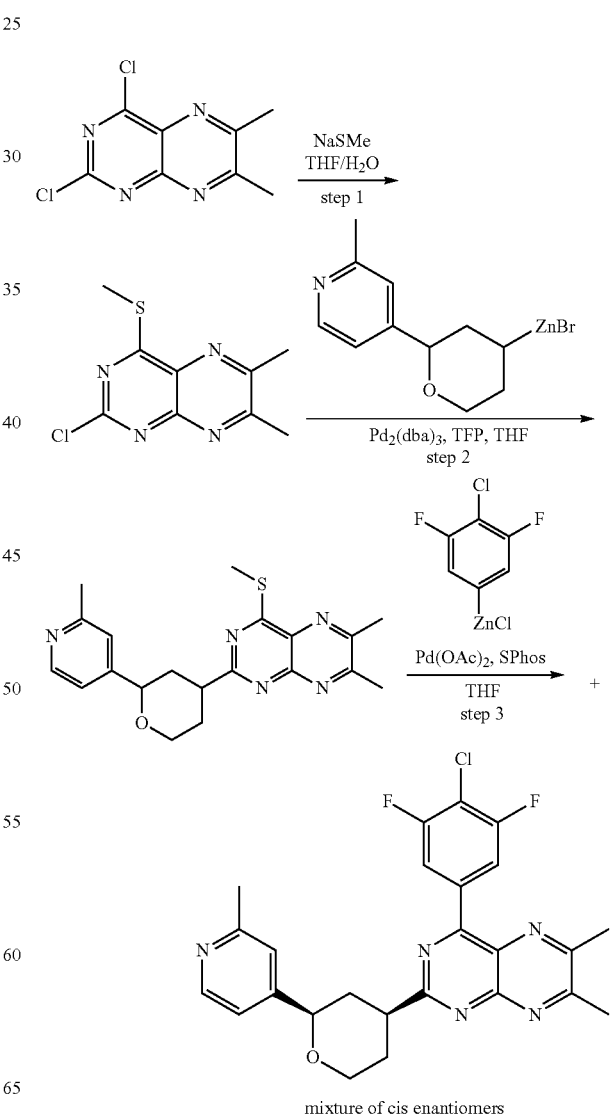

mixture of cis enantiomers

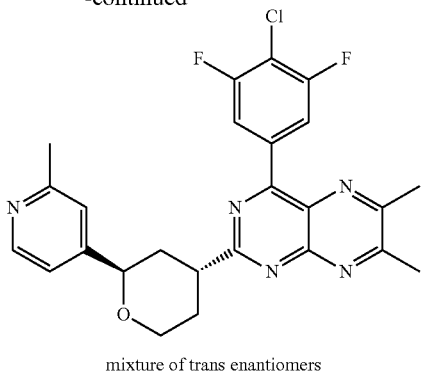

mixture of trans enantiomers

Step 1: A 100 mL round-bottom flask was charged with 2,4-dichloro-6,7-dimethyl-pteridine (3.00 g, 13.1 mmol) and THF (40 mL). The solution was cooled to −10° C. and a suspension of NaSMe (1.01 g, 14.4 mmol) in water (5 mL) was added dropwise. The reaction mixture was warmed to r.t. and stirred for 17 h. The mixture was diluted with DCM (50 mL) and water (10 mL). The aqueous layer was extracted with DCM (2×10 mL). Combined organic layers were dried over Na$_2$SO$_4$ and concentrated in vacuo. The crude residue was purified by silica gel chromatography (80 g SilicaSep column) using EtOAc and hexanes (50-60%) to obtain 2-chloro-6,7-dimethyl-4-methylsulfanyl-pteridine (1.92 g, 7.98 mmol, 61%) as a pale yellow solid. ESI-MS (m/z+): 241.0 [M+H]$^+$, LC-RT: 2.907 min. $^1$H NMR (400 MHz, CDCl$_3$) δ ppm 2.79 (s, 3H), 2.76 (s, 3H), 2.70 (s, 3H).

Step 2: A 50 mL microwave vial was charged with a solution of 2-chloro-6,7-dimethyl-4-methylsulfanyl-pteridine (600 mg, 2.49 mmol), Pd$_2$(dba)$_3$ (36 mg, 0.0626 mmol) and tri(2-furyl)phosphine (30 mg, 0.129 mmol) in THF (12 mL) and subjected to three cycles of vacuum/nitrogen fill. Bromo-[2-(2-methyl-4-pyridyl)tetrahydropyran-4-yl]zinc bromide solution (0.16 M in THF, 23 ml, 3.74 mmol) was then added dropwise at 25° C. and the mixture was stirred for 44 h. The mixture was diluted with DCM (100 mL) and sat. NaHCO$_3$ (20 mL). The aqueous layer was extracted with DCM (2×50 mL). The combined organic layer was washed with brine, dried over Na$_2$SO$_4$, and concentrated in vacuo. The residue was purified by silica gel chromatography (SilicaSep 40 g cartridge) using EtOAc and hexanes (0-100%) then MeOH and DCM (5-15%) to obtain an oil which was further purified by reverse phase chromatography (30 g C-18 cartridge) using acetonitrile and 0.1% aqueous formic acid to obtain 6,7-dimethyl-2-[2-(2-methyl-4-pyridyl)tetrahydropyran-4-yl]-4-methylsulfanyl-pteridine (255 mg, 0.655 mmol, 26%) as a solid. ESI-MS (m/z+): 382.10 [M+H]$^+$, LC-RT: 2.136 min. $^1$H NMR (400 MHz, CD$_2$Cl$_2$) δ ppm 8.41 (d, J=4.9 Hz, 1H), 7.23 (s, 1H), 7.14 (d, J=4.8 Hz, 1H), 4.56-4.49 (m, 1H), 4.37-4.28 (m, 1H), 3.85-3.77 (m, 1H), 3.48-3.38 (m, 1H), 2.74 (s, 3H), 2.72 (s, 3H), 2.66 (s, 3H), 2.52 (s, 3H), 2.43-2.36 (m, 1H), 2.17-2.09 (m, 2H), 1.95-1.84 (m, 1H).

Step 3: In a flame-dried 50 mL microwave vial 6,7-dimethyl-2-[2-(2-methyl-4-pyridyl)tetrahydropyran-4-yl]-4-methylsulfanyl-pteridine (122 mg, 0.320 mmol), Pd(OAc)$_2$ (1.8 mg, 0.0080 mmol), SPhos (6.6 mg, 0.016 mmol) and THF (1 mL) were added. The reaction mixture was degassed for 5 min under N$_2$ and chloro-(4-chloro-2,3-difluoro-phenyl)zinc chloride solution (0.089 M in THF) (5.3 mL, 0.4797 mmol) was added dropwise at 25° C. over 30 min. The mixture was stirred at 25° C. for 2 h. The reaction was quenched by addition of sat. NaHCO$_3$ (20 mL) and the reaction mixture was extracted with DCM (50 mL). The aqueous layer was extracted with (2×50 mL). The combined organic layer was dried over Na$_2$SO$_4$ and the solvent was removed in vacuo. The crude material was purified by flash chromatography (Isco RediSep® column 40 g) using EtOAc and hexanes (0-100%) then with MeOH and DCM (10-20%) to obtain a solid (34 mg), which was further purified by prep HPLC (Gemini® 5 μm NX-C18 110 Å, 100×30 mm) using MeOH and aqueous ammonium bicarbonate to obtain a mixture of cis isomers 4-(4-chloro-3,5-difluoro-phenyl)-6,7-dimethyl-2-[rac-(2R,4S)-2-(2-methyl-4-pyridyl)tetrahydropyran-4-yl]pteridine (14 mg, 0.0277 mmol, 9%) as one peak and a mixture of trans isomers 4-(4-chloro-3,5-difluoro-phenyl)-6,7-dimethyl-2-[rac-(2R,4R)-2-(2-methyl-4-ridyl)tetrahydropyran-4-yl]pteridine (4.5 mg, 0.00907 mmol, 3%) as another peak. Cis isomers: ESI-MS (m/z+): 482.2 [M+H]$^+$, LC-RT: 1.598 min. $^1$H NMR (400 MHz, CD$_2$Cl$_2$) δ ppm 8.41 (s, 2H), 8.39 (s, 1H), 7.23 (s, 1H), 7.14 (d, J=4.0 Hz, 1H), 4.56 (dd, J=11.3, 1.1 Hz, 1H), 4.39-4.32 (m, 1H), 3.90-3.79 (m, 1H), 3.64-3.51 (m, 1H), 2.81 (s, 3H), 2.79 (s, 3H), 2.52 (s, 3H), 2.48-2.40 (m, 1H), 2.24-2.13 (m, 2H), 2.01-1.88 (m, 1H). $^{19}$F NMR (376 MHz, CD$_2$Cl$_2$) δ ppm-113.77 (s),-113.80 (s). trans isomers: ESI-MS (m/z+): 482.2 [M+H]$^+$, LC-RT: 1.560 min. $^1$H NMR (400 MHz, CD$_2$Cl$_2$) δ ppm 8.42 (d, J=5.0 Hz, 1H), 8.35 (d, J=8.2 Hz, 2H), 7.23 (s, 1H), 7.14 (d, J=4.9 Hz, 1H), 4.69-4.57 (m, 2H), 4.40-4.33 (m, 1H), 3.99-3.89 (m, 1H), 2.83 (s, 3H), 2.82 (s, 3H), 2.52 (s, 3H), 2.34-2.24 (m, 1H), 2.23-2.16 (m, 1H), 2.12-2.01 (m, 1H), 2.01-1.93 (m, 1H). $^{19}$F NMR (376 MHz, CD$_2$Cl$_2$) δ ppm −113.54 (s), −113.56 (s).

Method 42

Examples 341: 2-(1-cyclopropylpyrazol-4-yl)-4-[5-(2,4-difluorophenyl)-2-methyl-pyrido[3,4-b]pyrazin-7-yl]morpholine

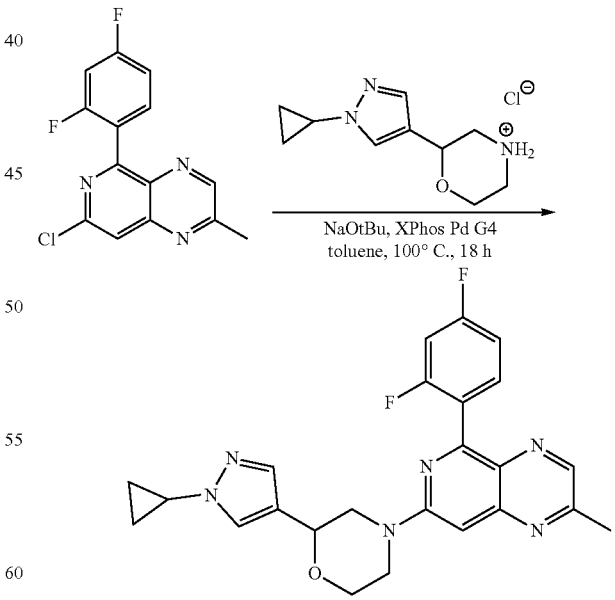

To a mixture of 7-chloro-5-(2,4-difluorophenyl)-2-methyl-pyrido[3,4-b]pyrazine (90 mg, 0.309 mmol), 2-(1-cyclopropylpyrazol-4-yl)morpholin-4-ium chloride (85 mg, 0.370 mmol), and sodium tert-butoxide (26 mg, 0.269 mmol) in toluene (2.5 mL) was added XPhos Pd G4 (19 mg, 0.022 mmol). The mixture was heated to 100° C. and stirred overnight. The reaction was cooled to r.t., and water was added. The solid was filtered over celite and rinsed with EtOAc. The product was extracted from the filtrate with EtOAc, and the combined organic layers were washed with brine, dried over $Na_2SO_4$, filtered, and concentrated in vacuo. The crude material was purified by silica gel chromatography eluting with 20-100% EtOAc in hexanes to provide the title compound 2-(1-cyclopropylpyrazol-4-yl)-4-[5-(2,4-difluorophenyl)-2-methyl-pyrido[3,4-b]pyrazin-7-yl]morpholine (65 mg, 0.138 mmol, 45% yield) as an orange solid. $^1$H NMR (400 MHz, DMSO-$d_6$) δ ppm 8.51 (s, 1H), 7.85 (s, 1H), 7.66 (td, J=8.4, 6.6 Hz, 1H), 7.48 (s, 1H), 7.36 (td, J=9.8, 2.5 Hz, 1H), 7.23 (td, J=8.6, 2.6 Hz, 1H), 7.18 (s, 1H), 4.56 (dd, J=10.4, 2.7 Hz, 1H), 4.41 (d, J=13.2 Hz, 1H), 4.29-4.19 (m, 1H), 4.09-3.86 (m, 1H), 3.89-3.52 (m, 2H), 3.21-2.84 (m, 2H), 2.64 (s, 3H), 1.11-0.98 (m, 2H), 0.98-0.89 (m, 2H). LC/MS (ESI$^+$) m/z=449.2 [M+H]$^+$ Method 44

Example 402: 8-(4-chloro-2-fluorophenyl)-6-(2-(1-cyclopropyl-1H-pyrazol-4-yl)tetrahydro-2H-pyran-4-yl)-2,3-dimethylpyrido[2,3-b]pyrazine

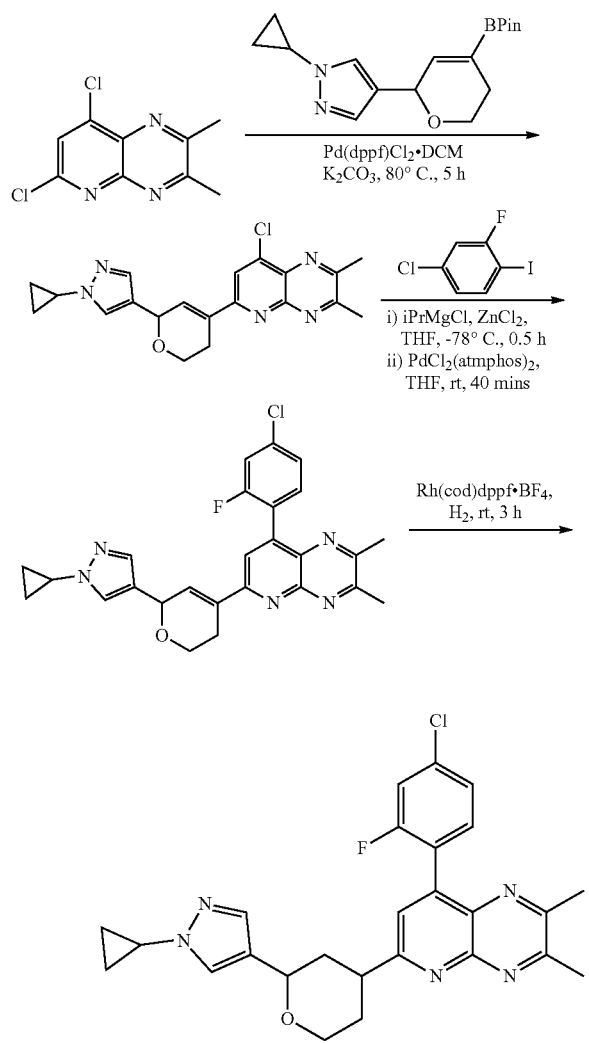

Step 1: To a solution of 6,8-dichloro-2,3-dimethylpyrido[2,3-b]pyrazine (1 g, 4.4 mmol) in dioxane (20 mL) and $H_2O$ (4 mL) was added 1-cyclopropyl-4-(4-(4,4,5,5-tetramethyl-1,3,2-dioxaborolan-2-yl)-5,6-dihydro-2H-pyran-2-yl)-1H-pyrazole (1.4 g, 4.4 mmol) and $K_2CO_3$ (1.8 g, 13 mmol) and the reaction mixture was purged with nitrogen. Then Pd(dppf)Cl$_2$·DCM (0.29 g, 0.36 mmol) was added and the reaction mixture was heated at 80° C. for 5 h. The reaction mixture was then cooled to RT and monitored by LCMS. After completion, the aqueous layer was extracted with ethyl acetate (3×200 ml) and the combined organic layers were dried over anhydrous sodium sulphate and concentrated under reduced pressure to get the crude residue. The residue was purified via column chromatography on silica gel (PE:EA=1:1) to afford 8-chloro-6-(6-(1-cyclopropyl-1H-pyrazol-4-yl)-3,6-dihydro-2H-pyran-4-yl)-2,3-dimethylpyrido[2,3-b]pyrazine (1.3 g, 76%) as a purple solid. LCMS: (M+H)$^+$=382.0;

Step 2: To a 250 mL round-bottomed flask was added 4-chloro-2-fluoro-1-iodobenzene (2.2 g, 8.6 mmol) in THF (40 mL). The mixture was cooled to -40° C. and iPrMgCl (4.7 mL, 9.5 mmol) (2 M solution in THF) was added dropwise and stirred for 30 min at -40° C., then the reaction mixture was cooled to -78° C. $ZnCl_2$ (4.3 mL, 8.6 mmol) (2 M solution in THF) was then added dropwise and the reaction mixture was allowed to warm to RT and 40 mL of THF was added and stirred for 10 min to give (4-chloro-2-fluorophenyl)zinc(II) iodide, which was used in the next reaction directly.

Into a 250-mL 3-necked round-bottom flask purged and maintained with $N_2$, was placed 8-chloro-6-(6-(1-cyclopropyl-1H-pyrazol-4-yl)-3,6-dihydro-2H-pyran-4-yl)-2,3-dimethylpyrido[2,3-b]pyrazine (1.1 g, 2.9 mmol) and PdCl$_2$ (Atmphos)$_2$ (0.1 g, 0.14 mmol) in THF (10 mL). The reaction mixture was stirred and (4-chloro-2-fluorophenyl)zinc(II) iodide (2.2 g, 8.6 mmol) was added. The reaction mixture was stirred at room temp for 40 min and monitored by LCMS. After completion, the reaction mixture was quenched with $H_2O$ (200 ml). The aqueous layer was extracted with EA (3×200 ml) and the combined organic layers were dried over anhydrous sodium sulphate, and then concentrated under reduced pressure to get the crude residue. The residue was purified via column chromatography on silica gel (PE:EA=1:1) to afford 8-(4-chloro-2-fluorophenyl)-6-(6-(1-cyclopropyl-1H-pyrazol-4-yl)-3,6-dihydro-2H-pyran-4-yl)-2,3-dimethylpyrido[2,3-b]pyrazine (900 mg, 64%) as a white solid. LCMS: (M+H)$^+$=476.0.

Step 3: To a solution of 8-(4-chloro-2-fluorophenyl)-6-(6-(1-cyclopropyl-1H-pyrazol-4-yl)-3,6-dihydro-2H-pyran-4-yl)-2,3-dimethylpyrido[2,3- b]pyrazine (400 mg, 0.84 mmol) in THF (8 mL) was added Rh(cod)dppf.BF$_4$ (122 mg, 0.17 mmol) and the reaction mixture was purged with hydrogen for 3 h at room temp. The reaction was monitored by LCMS. After completion the reaction mixture was evaporated under reduced pressure to get the crude residue. The residue was purified by silica gel chromatography (PE:EA=1:2) to afford 8-(4-chloro-2-fluorophenyl)-6-(2-(1-cyclopropyl-1H-pyrazol-4-yl)tetrahydro-2H-pyran-4-yl)-2,3-dimethylpyrido[2,3-b]pyrazine (123 mg, 31%) as a white solid. LCMS:(M+H)$^+$=478.0.

TABLE 8

Analytical Data for Examples 1-232

| Ex # | NMR | M + H |
|---|---|---|
| 1 | $^1$H NMR (500 MHz, DMSO-d6) δ ppm 8.53 (s, 1 H), 7.74 (br d, J = 8.2 Hz, 2 H), 7.64 (dd, J = 9.8, 1.8 Hz, 1 H), 7.41-7.54 (m, 2 H), 4.77 (br d, J = 12.6 Hz, 1 H), 4.64 (br d, J = 13.6 Hz, 1 H), 4.54 (br d, J = 8.3 Hz, 1 H), 3.95-4.11 (m, 1 H), 3.82 (s, 3 H), 3.62-3.73 (m, 1 H), 3.20-3.29 (m, 2 H), 2.66 (s, 3 H) | 440.0 |
| 2 | $^1$H NMR (500 MHz, DMSO-d6) δ ppm 8.53 (s, 1H), 7.84 (br s, 1H), 7.73 (br t, J = 7.91 Hz, 1H), 7.63 (dd, J = 1.82, 9.60 Hz, 1H), 7.41-7.53 (m, 2H), 4.77 (br d, J = 11.94 Hz, 1H), 4.65 (br d, J = 13.49 Hz, 1H), 4.41-4.60 (m, 1H), 3.90-4.12 (m, 1H), 3.57-3.78 (m, 2H), 3.16-3.35 (m, 2H), 2.65 (s, 3H), 0.98-1.07 (m, 2H), 0.90-0.97 (m, 2H) | 466.0 |
| 3 | $^1$H NMR (500 MHz, DMSO-d6) δ ppm 8.55 (s, 1H), 8.46 (br d, J = 4.67 Hz, 1H), 7.75 (br t, J = 7.91 Hz, 1H), 7.64 (br dd, J = 2.08, 9.86 Hz, 1H), 7.50 (br dd, J = 1.95, 8.17 Hz, 1H), 7.33 (br s, 1H), 7.21-7.30 (m, 1H), 4.81-4.95 (m, 1H), 4.73 (br d, J = 13.49 Hz, 1H), 4.64 (br dd, J = 1.82, 10.12 Hz, 1H), 4.09-4.23 (m, 1H), 3.77 (dt, J = 1.69, 11.74 Hz, 1H), 3.30-3.34 (m, 1H), 3.01-3.14 (m, 1H), 2.67 (s, 3H) (one Me singlet not observed due to overlap with solvent peak) | 451.0 |
| 4 | $^1$H NMR (400 MHz, DMSO-d$_6$) δ 8.80 (s, 2 H), 8.56 (s, 1 H), 7.77 (t, J = 7.9 Hz, 1 H), 7.66 (dd, J = 9.8, 2.1 Hz, 1 H), 7.51 (d, J = 8.2 Hz, 1 H), 4.85 (d, J = 13.2 Hz, 1 H), 4.73 (d, J = 11.7 Hz, 2 H), 4.15 (d, J = 11.3 Hz, 1 H), 3.77 (t, J = 11.4 Hz, 1 H), 3.25-3.45 (m, 2 H), 2.67 (s, 3 H), 2.64 (s, 3 H) | 452.1 |
| 5 | $^1$H NMR (500 MHz, DMSO-d6) δ ppm 8.51-8.53 (m, 1 H), 7.71-7.76 (m, 1 H), 7.62-7.66 (m, 1 H), 7.49-7.53 (m, 1 H), 4.59-4.78 (m, 2 H), 3.94-4.04 (m, 1 H), 3.71-3.85 (m, 2 H), 3.54-3.68 (m, 3 H), 3.41-3.53 (m, 1 H), 3.16-3.24 (m, 1 H), 2.90-3.01 (m, 1 H), 2.65-2.67 (m, 3 H), 2.29-2.37 (m, 1 H), 1.89-2.05 (m, 1 H), 1.56-1.75 (m, 1 H) | 430.0 |
| 6 | $^1$H NMR (500 MHz, DMSO-d6) δ ppm 8.47-8.59 (m, 1 H), 7.73-7.81 (m, 2 H), 7.38-7.52 (m, 2 H), 7.23-7.32 (m, 1 H), 4.72-4.84 (m, 1 H), 4.61-4.68 (m, 1 H), 4.50-4.57 (m, 1 H), 3.96-4.06 (m, 1 H), 3.78-3.87 (m, 3 H), 3.62-3.72 (m, 1 H), 3.19-3.30 (m, 2 H), 2.61-2.70 (m, 3 H) | 424.2 |
| 7 | $^1$H NMR (500 MHz, DMSO-d6) δ ppm 8.50-8.56 (m, 1 H), 7.85 (br s, 1 H), 7.74-7.81 (m, 1 H), 7.40-7.49 (m, 2 H), 7.24-7.32 (m, 1 H), 4.73-4.83 (m, 1 H), 4.62-4.68 (m, 1 H), 4.47-4.56 (m, 1 H), 3.99-4.08 (m, 1 H), 3.62-3.73 (m, 2 H), 3.21-3.29 (m, 2 H), 2.64-2.66 (m, 3 H), 1.00-1.05 (m, 2 H), 0.91-0.96 (m, 2 H) | 450.0 |
| 8 | $^1$H NMR (500 MHz, DMSO-d6) δ ppm 8.53-8.58 (m, 1 H), 8.42-8.49 (m, 1 H), 7.76-7.83 (m, 1 H), 7.45 (td, J = 9.9, 2.6 Hz, 1 H), 7.23-7.36 (m, 3 H), 4.82-4.93 (m, 1 H), 4.70-4.77 (m, 1 H), 4.61-4.67 (m, 1H), 4.12-4.23 (m, 1 H), 3.73-3.82 (m, 1 H), 3.26-3.30 (m, 1 H), 3.01-3.15 (m, 1 H), 2.66-2.67 (m, 3 H), 2.49-2.49 (m, 3 H) | 435.2 |
| 9 | $^1$H NMR (500 MHz, DMSO-d6) δ ppm 8.49-8.55 (m, 1 H), 7.78-7.90 (m, 1 H), 7.52-7.60 (m, 1 H), 7.43-7.51 (m, 1 H), 7.14-7.24 (m, 2 H), 4.71-4.83 (m, 1 H), 4.63-4.69 (m, 1 H), 4.49-4.56 (m, 1 H), 3.97-4.08 (m, 1 H), 3.61-3.75 (m, 2 H), 3.19-3.28 (m, 2 H), 2.64-2.66 (m, 3 H), 2.38-2.43 (m, 3 H), 1.00-1.06 (m, 2 H), 0.90-0.97 (m, 2 H) | 446.2 |
| 10 | $^1$H NMR (500 MHz, DMSO-d6) δ ppm 8.51-8.57 (m, 1 H), 8.42-8.48 (m, 1 H), 7.55-7.62 (m, 1 H), 7.30-7.36 (m, 1 H), 7.23-7.28 (m, 1 H), 7.15-7.23 (m, 2 H), 4.82-4.92 (m, 1 H), 4.69-4.77 (m, 1 H), 4.59 (s, 1 H), 4.11-4.21 (m, 1 H), 3.72-3.81 (m, 1 H), 3.25-3.30 (m, 1 H), 3.02-3.13 (m, 1 H), 2.64-2.68 (m, 3 H), 2.48-2.49 (m, 3 H), 2.42-2.44 (m, 3 H) | 431.2 |
| 11 | $^1$H NMR (600 MHz, DMSO-d6) δ ppm 8.43-8.55 (m, 1 H), 7.70-7.85 (m, 1 H), 7.45-7.52 (m, 1 H), 4.49-4.98 (m, 5 H), 3.98-4.12 (m, 1 H), 3.97-4.15 (m, 1 H), 4.04 (br d, J = 11.4 Hz, 1 H), 3.62-3.74 (m, 1 H), 3.54-3.79 (m, 1 H), 3.2-3.3 (m, 2 H), 2.65-2.76 (m, 2 H), 2.59-2.65 (m, 3 H), 2.52-2.59 (m, 2 H) | 434.0 |
| 12 | $^1$H NMR (600 MHz, DMSO-d6) δ ppm 8.49-8.53 (m, 1H), 7.82 (br s, 1 H), 7.45 (br s, 1 H), 4.80 (br s, 1 H), 4.53-4.63 (m, 1 H), 4.52 (dd, J = 10.26, 2.45 Hz, 1 H), 4.03 (br d, J = 10.90 Hz, 1 H), 3.69-3.73 (m, 1 H), 3.64-3.69 (m, 1 H), 2.62 (s, 3 H), 2.52-2.59 (m, 3 H), 0.99-1.05 (m, 2 H), 0.93-0.99 (m, 2 H) | 460.0 |
| 13 | $^1$H NMR (600 MHz, DMSO-d6) δ ppm 0.93-0.98 (m, 2 H) 0.99-1.06 (m, 2 H) 2.51-2.58 (m, 2 H) 2.59-2.65 (m, 3 H) 2.66-2.77 (m, 2 H) 3.14-3.25 (m, 1 H) 3.64-3.74 (m, 2 H) 4.03 (br d, J = 11.63 Hz, 1 H) 4.52 (dd, J = 10.26, 2.63 Hz, 1 H) 4.63 (dt, J = 16.53, 8.45 Hz, 1 H) 4.82 (br s, 1 H) 7.48 (s, 1H) 7.85 (s, 1 H) 8.50 (s, 1H) | 460.0 |
| 14 | $^1$H NMR (600 MHz, DMSO-d6) δ ppm 9.15 (br s, 1H), 8.54 (s, 1H), 7.61 (br s, 1H), 4.77-5.19 (m, 2H), 4.74 (dd, J = 2.36, 10.17 Hz, 1H), 4.59 (quin, J = 8.72 Hz, 1H), 4.19 (br d, J = 11.08 Hz, 1H), 3.78 (dt, J = 2.63, 11.67 Hz, 1H), 3.31-3.46 (m, 2H), 3.22-3.29 (m, 1H), 2.66 (s, 3H), 2.64 (s, 3H), 2.52-2.62 (m, 4H) | 446.2 |

TABLE 8-continued

Analytical Data for Examples 1-232

| Ex # | NMR | M + H |
|---|---|---|
| 15 | $^1$H NMR (600 MHz, DMSO-d6) δ ppm δ ppm 2.48-2.52 (m, 4 H) 2.54-2.61 (m, 4 H) 2.63 (s, 4 H) 3.75 (td, J = 11.72, 2.72 Hz, 1 H) 4.17 (br d, J = 9.99 Hz, 1 H) 4.56-4.66 (m, 3 H) 4.89 (br s, 1 H) 7.20-7.29 (m, 1 H) 7.29-7.35 (m, 1 H) 8.47 (d, J = 5.09 Hz, 1 H) 8.53 (s, 1 H) | 445.0 |
| 16 | $^1$H NMR (600 MHz, DMSO-d6) δ ppm 2.51-2.59 (m, 2 H) 2.61-2.65 (m, 3 H) 2.73 (br d, J = 10.72 Hz, 2 H) 3.05 (br s, 1 H) 3.72-3.81 (m, 1 H) 4.17 (br d, J = 11.44 Hz, 1 H) 4.60-4.67 (m, 2 H) 4.92 (br s, 1 H) 7.27 (br d, J = 5.09 Hz, 1 H) 7.34 (s, 1 H) 8.47 (d, J = 5.09 Hz, 1 H) 8.50-8.55 (m, 1 H) | 445.0 |
| 17 | $^1$H NMR (400 MHz, Chloroform-d) δ ppm 7.83 (t, J = 7.3 Hz, 1 H), 7.55-7.63 (m, 2 H), 7.52 (d, J = 9.4 Hz, 1 H), 7.46 (s, 1 H), 5.03 (s, 1 H), 4.85 (d, J = 13.8 Hz, 1 H), 4.62 (dd, J = 9.9, 2.7 Hz, 1 H), 4.12 (d, J = 11.6 Hz, 1 H), 3.92 (s, 3 H), 3.83 (td, J = 11.5, 2.7 Hz, 1 H), 3.40 (t, J = 12.2 Hz, 1 H), 3.31 (dd, J = 13.4, 10.3 Hz, 1 H), 2.75 (s, 3 H), 2.61 (s, 3 H) | 488.1 |
| 18 | $^1$H NMR (400 MHz, Chloroform-d) δ ppm 8.28 (t, J = 8.1 Hz, 2 H), 7.59 (s, 1 H), 7.47 (s, 1 H), 5.04 (s, 1 H), 4.88 (d, J = 13.5 Hz, 1 H), 4.62 (dd, J = 10.3, 2.8 Hz, 1 H), 4.15 (d, J = 11.9 Hz, 1 H), 3.93 (s, 3 H), 3.83 (td, J = 11.5, 2.8 Hz, 1 H), 3.26-3.47 (m, 2 H), 2.75 (s, 3 H), 2.71 (s, 3 H) | 456.2 |
| 19 | $^1$H NMR (400 MHz, Chloroform-d) δ ppm 9.73 (1H, d, J = 1.8 Hz), 8.89 (1H, dd, J = 7.8, 2.1 Hz), 7.88 (1H, dd, J = 8.2, 0.9 Hz), 7.59 (1H, s), 7.47 (1H, s), 5.07 (1H, s), 4.90 (1H, d, J = 13.5 Hz), 4.63 (1H, dd, J = 10.4, 2.8 Hz), 4.12-4.18 (1H, m), 3.94 (3H, s), 3.84 (1H, td, J = 11.5, 2.8 Hz), 3.37-3.48 (1H, m), 3.32 (1H, dd, J = 13.4, 10.3 Hz), 2.77 (3H, s), 2.69 (3H, s) | 471.1 |
| 20 | $^1$H NMR (400 MHz, Chloroform-d) δ ppm 9.34 (d, J = 2.0 Hz, 1H), 8.54 (dd, J = 7.9, 2.3 Hz, 1H), 7.78 (s, 1H), 7.41-7.54 (m, 2H), 4.81 (d, J = 11.5 Hz, 1H), 4.55 (dd, J = 10.3, 2.7 Hz, 1H), 4.00-4.07 (m, 1H), 3.84 (s, 3H), 3.70 (td, J = 11.6, 2.8 Hz, 1H), 3.20 (d, J = 12.1 Hz, 3H), 2.66 (s, 3H), 2.60 (d, J = 9.0 Hz, 6H) | 417.1 |
| 21 | $^1$H NMR (500 MHz, DMSO-d6) δ ppm 7.70-7.81 (m, 2 H), 7.64 (dd, J = 9.7, 1.9 Hz, 1 H), 7.42-7.54 (m, 2 H), 4.73 (br d, J = 13.0 Hz, 1 H), 4.61 (br d, J = 13.8 Hz, 1 H), 4.53 (dd, J = 10.3, 2.5 Hz, 1 H), 4.02 (br d, J = 11.2 Hz, 1 H), 3.82 (s, 3 H), 3.68 (td, J = 11.5, 2.6 Hz, 1 H), 3.16-3.27 (m, 2 H), 2.65 (s, 3 H), 2.51 (s, 3 H) | 454.0 |
| 22 | $^1$H NMR (500 MHz, DMSO-d6) δ ppm 7.83 (s, 1H), 7.72 (br t, J = 7.91 Hz, 1H), 7.63 (dd, J = 1.95, 9.73 Hz, 1H), 7.48 (dd, J = 1.82, 8.30 Hz, 1H), 7.46 (s, 1H), 4.73 (br d, J = 12.46 Hz, 1H), 4.61 (br d, J = 13.49 Hz, 1H), 4.52 (dd, J = 2.34, 10.38 Hz, 1H), 3.91-4.08 (m, 1H), 3.59-3.75 (m, 2H), 3.16-3.28 (m, 2H), 2.65 (s, 3H), 2.52 (s, 3H), 0.98-1.06 (m, 2H), 0.89-0.98 (m, 2H) | 480.2 |
| 23 | $^1$H NMR (500 MHz, DMSO-d6) δ ppm 8.45 (d, J = 5.1 Hz, 1 H), 7.74 (t, J = 7.9 Hz, 1 H), 7.65 (dd, J = 9.7, 1.9 Hz, 1 H), 7.50 (dd, J = 8.3, 1.8 Hz, 1 H), 7.33 (s, 1 H), 7.25 (br d, J = 4.0 Hz, 1 H), 4.83 (br d, J = 12.8 Hz, 1 H), 4.69 (br d, J = 13.6 Hz, 1 H), 4.63 (dd, J = 10.5, 2.3 Hz, 1 H), 4.09-4.22 (m, 1 H), 3.76 (td, J = 11.8, 2.7 Hz, 1 H), 3.30 (s, 3 H), 3.22-3.30 (m, 1 H), 2.96-3.07 (m, 1 H), 2.66 (s, 3 H), 2.52 (s, 3 H) | 465.0 |
| 24 | $^1$H NMR (400 MHz, DMSO-d6) δ ppm 8.80 (s, 2 H), 7.75 (t, J = 8.0 Hz, 1 H), 7.66 (dd, J = 9.8, 2.0 Hz, 1 H), 7.47-7.54 (m, 1 H), 4.81 (d, J = 13.4 Hz, 1 H), 4.70 (t, J = 10.2 Hz, 2 H), 4.15 (d, J = 11.5 Hz, 1 H), 3.76 (t, J = 11.2 Hz, 1 H), 3.18-3.27 (m, 1 H), 2.66 (d, J = 6.3 Hz, 4 H), 2.55 (s, 6 H) | 466.1 |
| 25 | $^1$H NMR (400 MHz, DMSO-d6) δ ppm 8.80 (s, 2 H), 7.75 (t, J = 8.0 Hz, 1 H), 7.66 (dd, J = 9.8, 2.0 Hz, 1 H), 7.47-7.54 (m, 1 H), 4.81 (d, J = 13.4 Hz, 1 H), 4.70 (t, J = 10.2 Hz, 2 H), 4.15 (d, J = 11.5 Hz, 1 H), 3.76 (t, J = 11.2 Hz, 1 H), 3.18-3.27 (m, 1 H), 2.66 (d, J = 6.3 Hz, 4 H), 2.55 (s, 6 H) | 466.1 |
| 26 | $^1$H NMR (500 MHz, DMSO-d6) δ ppm 7.72 (t, J = 7.9 Hz, 2 H), 7.64 (dd, J = 9.7, 1.9 Hz, 2 H), 7.49 (dd, J = 8.3, 1.9 Hz, 2 H), 4.70 (br d, J = 13.1 Hz, 1 H), 4.57 (br d, J = 13.2 Hz, 3 H), 3.98 (br t, J = 12.3 Hz, 2 H), 3.69-3.85 (m, 4 H), 3.50-3.68 (m, 5 H), 3.43-3.49 (m, 1 H), 3.32-3.42 (m, 2 H), 3.09-3.21 (m, 2 H), 2.86-2.96 (m, 2 H), 2.65 (s, 6 H), 2.51 (br s, 6 H), 2.32-2.38 (m, 2 H), 1.90-2.07 (m, 2 H), 1.82 (dq, J = 12.3, 7.6 Hz, 1 H), 1.55-1.67 (m, 1 H) (note: this is a racemic 1:1 mixture of diastereomers) | 444.0 |
| 27 | $^1$H NMR (600 MHz, DMSO-d6) δ ppm 7.60-7.82 (m, 1 H), 7.28-7.53 (m, 1 H), 4.74-4.86 (m, 1 H), 4.79 (br d, J = 12.7 Hz, 1 H), 4.64 (br d, J = 12.7 Hz, 1 H), 4.59-4.69 (m, 1 H), 4.52 (br d, J = 13.1 Hz, 1 H), 4.41-4.47 (m, 1 H), 4.43 (br d, J = 9.8 Hz, 1 H), 4.28-4.40 (m, 1 H), 4.10-4.20 (m, 1 H), 3.91-4.01 (m, 2 H), 3.76-3.86 (m, 3 H), 3.53-3.64 (m, 1 H), 3.14-3.20 (m, 2 H), 2.96-3.14 (m, 2 H), 2.75-2.84 (m, 1 H), 2.57-2.69 (m, 1 H), 2.45-2.53 (m, 4 H) | 443.0 |
| 28 | $^1$H NMR (600 MHz, DMSO-d6) δ ppm 2.38-2.49 (m, 2 H) 2.52-2.63 (m, 1 H) 3.02 (br dd, J = 13.17, 10.45 Hz, 1 H) 3.05-3.11 (m, 1 H) 3.15-3.25 (m, 1 H) 3.58 (td, J = 11.49, 2.63 Hz, 1 H) 3.77- | 411.0 |

TABLE 8-continued

Analytical Data for Examples 1-232

| Ex # | NMR | M + H |
|---|---|---|
| | 3.86(m, 4 H) 3.95 (dt, J = 9.85, 1.70 Hz, 1 H) 4.34-4.39 (m, 2 H) 4.41-4.48 (m, 2 H) 4.53 (br d, J = 13.44 Hz, 1 H) 4.66 (br d, J = 13.26 Hz, 1 H) 4.89 (br s, 1 H) 7.41-7.48 (m, 1 H) 7.70-7.76 (m, 1 H) | |
| 29 | $^1$H NMR (600 MHz, DMSO-d6) δ ppm 3.44 (br dd, J = 6.90, 5.09 Hz, 1 H), 3.15-3.28 (m, 10 H) 2.61 (br s, 2 H), 2.35-2.48 (m, 3 H), 1.50 (s, 1 H), 1.35 (s, 1 H), 1.23 (br s, 1 H), 1.03-1.18 (m, 3 H), 0.85 (s, 1 H) | 399.0 |
| 30 | $^1$H NMR (600 MHz, DMSO-d6) δ ppm 7.72 (s, 1 H), 7.44 (s, 1 H), 4.93 (br s, 1 H), 4.67 (br d, J = 13.26 Hz, 2 H) 4.54 (br d, J = 13.08 Hz, 1 H), 4.43 (br dd, J = 10.08, 2.27 Hz, 2 H), 4.19 (br s, 1 H), 3.95 (br d, J = 11.44 Hz, 1 H), 3.82 (s, 3 H), 3.79 (br dd, J = 9.26, 4.90 Hz, 1 H), 3.59 (td, J = 11.44, 2.72 Hz, 1 H), 3.25-3.14 (m, 1 H), 3.12-3.06 (m, 1 H), 3.03 (dd, J = 13.26, 10.35 Hz, 1 H), 2.53-2.51 (m, 2 H) | 449.0 |
| 31 | $^1$H NMR (500 MHz, DMSO-d6) δ ppm 7.73-7.80 (m, 2 H), 7.47 (s, 1 H), 7.44 (td, J = 9.9, 2.5 Hz, 1 H), 7.28 (td, J = 8.4, 2.6 Hz, 1 H), 4.75 (br d, J = 13.2 Hz, 1 H), 4.62 (br d, J = 13.6 Hz, 1 H), 4.54 (dd, J = 10.4, 2.6 Hz, 1 H), 4.02 (br d, J = 10.9 Hz, 1 H), 3.83 (s, 3 H), 3.69 (td, J = 11.6, 2.7 Hz, 1 H), 3.17-3.27 (m, 2 H), 2.66 (s, 3 H), 2.53 (s, 3 H) | 438.2 |
| 32 | $^1$H NMR (500 MHz, DMSO-d6) δ ppm 7.84 (s, 1 H), 7.71-7.81 (m, 1 H), 7.46 (s, 1 H), 7.39-7.46 (m, 1 H), 7.27 (td, J = 8.4, 2.1 Hz, 1 H), 4.74 (br d, J = 13.2 Hz, 1 H), 4.62 (br d, J = 13.1 Hz, 1 H), 4.51 (dd, J = 10.4, 2.3 Hz, 1 H), 3.96-4.05 (m, 1 H), 3.58-3.78 (m, 2 H), 3.17-3.28 (m, 2 H), 2.65 (s, 3 H), 2.52 (s, 3 H), 0.99-1.08 (m, 2 H), 0.90-0.97 (m, 2 H) | 464.2 |
| 33 | $^1$H NMR (500 MHz, DMSO-d6) δ ppm 2.52 (s, 3H), 2.64-2.66 (m, 3H), 3.03 (br t, J = 11.68 Hz, 1H), 3.23-3.27 (m, 1H), 3.76 (td, J = 11.68, 2.72 Hz, 1H), 4.15 (br d, J = 9.34 Hz, 1H), 4.63 (dd, J = 10.25, 2.47 Hz, 1H), 4.70 (br d, J = 13.10 Hz, 1H), 4.84 (br d, J = 13.23 Hz, 1H), 7.23-7.34 (m, 3H), 7.44 (td, J = 9.86, 2.47 Hz, 1H), 7.78 (td, J = 8.34, 6.68 Hz, 1H), 8.46 (d, J = 4.93 Hz, 1H) | 449.2 |
| 34 | $^1$H NMR (600 MHz, DMSO-d6) δ ppm 7.73-7.82 (m, 1 H), 7.44 (td, J = 9.9, 2.3 Hz, 1 H), 7.29 (td, J = 8.4, 2.2 Hz, 1 H), 4.71 (br d, J = 13.0 Hz, 1 H), 4.59 (br d, J = 13.3 Hz, 1 H), 3.92-4.02 (m, 1 H), 3.81 (br t, J = 8.1 Hz, 1 H), 3.72-3.79 (m, 1 H), 3.64 (q, J = 7.7 Hz, 1 H), 3.49-3.62 (m, 2 H), 3.34-3.43 (m, 1 H), 3.09-3.21 (m, 1 H), 2.91 (br dd, J = 12.8, 10.8 Hz, 1 H), 2.66 (s, 3 H), 2.52 (s, 3 H), 2.31-2.38 (m, 1 H), 1.93-2.09 (m, 1 H), 1.56-1.71 (m, 1 H) | 428.0 |
| 35 | $^1$H NMR (600 MHz, DMSO-d6) δ ppm 7.73-7.81 (m, 1 H), 7.44 (td, J = 9.8, 2.4 Hz, 1 H), 7.29 (td, J = 8.5, 2.1 Hz, 1 H), 4.58 (br d, J = 13.3 Hz, 2 H), 4.01 (br d, J = 10.6 Hz, 1 H), 3.81 (br t, J = 5.8 Hz, 1 H), 3.70-3.78 (m, 1 H), 3.62-3.69 (m, 1 H), 3.57 (td, J = 11.5, 2.2 Hz, 1 H), 3.48 (br t, J = 7.2 Hz, 1 H), 3.35-3.44 (m, 1 H), 3.14-3.23 (m, 1 H), 2.94 (br dd, J = 13.0, 10.6 Hz, 1 H), 2.65 (s, 3 H), 2.52 (s, 3 H), 2.33-2.42 (m, 1 H), 1.90-2.04 (m, 1 H), 1.78-1.88 (m, 1 H) | 428.0 |
| 36 | $^1$H NMR (600 MHz, DMSO-d6) δ ppm 7.73-7.80 (m, 1 H), 7.44 (td, J = 9.8, 2.2 Hz, 1 H), 7.29 (td, J = 8.5, 2.2 Hz, 1 H), 4.71 (br d, J = 13.3 Hz, 1 H), 4.59 (br d, J = 13.3 Hz, 1 H), 3.98 (br d, J = 9.8 Hz, 1 H), 3.81 (t, J = 8.1 Hz, 1 H), 3.71-3.79 (m, 1 H), 3.64 (q, J = 7.7 Hz, 1 H), 3.51-3.61 (m, 2 H), 3.35-3.39 (m, 1 H), 3.12-3.20 (m, 1 H), 2.91 (dd, J = 12.9, 10.7 Hz, 1 H), 2.65 (s, 3 H), 2.52 (s, 3 H), 2.30-2.38 (m, 1 H), 1.95-2.06 (m, 1 H), 1.58-1.67 (m, 1 H) | 428.0 |
| 37 | $^1$H NMR (500 MHz, DMSO-d6) δ ppm 7.75 (s, 1 H), 7.56 (t, J = 7.7 Hz, 1 H), 7.46 (s, 1 H), 7.15-7.24 (m, 2 H), 4.74 (br d, J = 13.2 Hz, 1 H), 4.61 (br d, J = 13.5 Hz, 1 H), 4.53 (dd, J = 10.3, 2.5 Hz, 1 H), 4.01 (br d, J = 11.5 Hz, 1 H), 3.82 (s, 3 H), 3.68 (td, J = 11.5, 2.7 Hz, 1 H), 3.15-3.28 (m, 2 H), 2.64 (s, 3 H), 2.51 (br s, 3 H), 2.42 (s, 3 H) | 434.2 |
| 38 | $^1$H NMR (500 MHz, DMSO-d6) δ ppm 7.84 (s, 1 H), 7.55 (t, J = 7.7 Hz, 1 H), 7.46 (s, 1 H), 7.15-7.22 (m, 2 H), 4.70-4.78 (m, 1 H), 4.62 (br d, J = 13.0 Hz, 1 H), 4.51 (dd, J = 10.4, 2.5 Hz, 1 H), 3.93-4.05 (m, 1 H), 3.60-3.75 (m, 2 H), 3.17-3.27 (m, 2 H), 2.64 (s, 3 H), 2.51 (br s, 3 H), 2.42 (s, 3 H), 0.99-1.07 (m, 2 H), 0.90-0.97 (m, 2 H) | 460.2 |
| 39 | $^1$H NMR (500 MHz, DMSO-d6) δ ppm 8.45 (d, J = 4.9 Hz, 1 H), 7.57 (t, J = 7.7 Hz, 1 H), 7.33 (s, 1 H), 7.25 (br d, J = 3.6 Hz, 1 H), 7.16-7.23 (m, 2 H), 4.84 (br d, J = 13.0 Hz, 1 H), 4.70 (br d, J = 13.2 Hz, 1 H), 4.63 (dd, J = 10.3, 2.5 Hz, 1 H), 4.10-4.19 (m, 1 H), 3.76 (td, J = 11.6, 2.7 Hz, 1H), 3.23-3.29 (m, 1 H), 2.98-3.06 (m, 1 H), 2.65 (s, 3 H), 2.52 (s, 3 H), 2.43 (s, 3 H) | 445.2 |
| 40 | $^1$H NMR (Chloroform-d, 500 MHz) δ 7.57 (s, 1H), 7.46 (s, 1H), 5.00 (br d, 1H, J = 11.7 Hz), 4.83 (br d, 1H, J = 13.8 Hz), 4.59 (dd, 1H, J = 2.7, 10.3 Hz), 4.1-4.2 (m, 1H), 3.93 (s, 3H), 3.6-3.7 (m, 2H), 3.2-3.4 (m, 2H), 2.6-2.8 (m, 8H) | 422.2 |
| 41 | $^1$H NMR (400 MHz, Chloroform-d) δ ppm 8.53 (d, J = 5.18 Hz, 1 H), 7.29-7.34 (m, 1 H), 7.24 (d, J = 5.30 Hz, 1 H), 5.10 (br d, J = 13.06 Hz, 1 H), 4.93 (br d, J = 13.58 Hz, 1 H), 4.56 (dd, J = 10.52, 2.64 Hz, 1 H), 4.22 (dd, J = 11.66, 2.54 Hz, 1 H), 3.83 (td, J = 11.77, 2.80 Hz, 1 | 433.2 |

TABLE 8-continued

Analytical Data for Examples 1-232

| Ex # | NMR | M + H |
|---|---|---|
| | H), 3.58-3.67 (m, 2 H), 3.30 (ddd, J = 13.55, 11.90, 3.58 Hz, 1 H), 2.95-3.10 (m, 1 H), 2.56-2.83 (m, 11 H) | |
| 42 | $^1$H NMR (Chloroform-d, 500 MHz) δ 7.58 (s, 1H), 7.46 (s, 1H), 5.06 (br d, 1H, J = 13.2 Hz), 4.89 (br d, 1H, J = 13.8 Hz), 4.7-4.8 (m, 1H), 4.62 (dd, 1H, J = 2.7, 10.3 Hz), 4.13 (br d, 1H, J = 11.0 Hz), 3.93 (s, 3H), 3.83 (dt, 1H, J = 2.7, 11.5 Hz), 3.3-3.5 (m, 1H), 3.2-3.3 (m, 1H), 3.0-3.2 (m, 1H), 2.6-2.7 (m, 10H) | 448.0 |
| 43 | $^1$H NMR (Chloroform-d, 500 MHz) δ 7.57 (s, 1H), 7.45 (s, 1H), 5.07 (br d, 1H, J = 13.5 Hz), 4.88 (br d, 1H, J = 12.2 Hz), 4.5-4.7 (m, 2H), 4.13 (br d, 1H, J = 10.6 Hz), 3.93 (s, 3H), 3.82 (dt, 1H, J = 2.8, 11.5 Hz), 3.3-3.4 (m, 1H), 3.2-3.3 (m, 1H), 3.11 (qd, 1H, J = 9.0, 17.7 Hz), 2.6-2.7 (m, 10H) | 448.0 |
| 44 | $^1$H NMR (600 MHz, DMSO-d6) δ ppm 7.68-7.83 (m, 1 H), 7.28-7.54 (m, 1 H), 5.81-6.27 (m, 1 H), 5.77-6.21 (m, 1 H), 4.61-4.86 (m, 2 H), 4.46-4.56 (m, 2 H), 3.99-4.07 (m, 1 H), 4.02 (br d, J = 11.4 Hz, 1H), 3.67 (td, J = 11.5, 2.6 Hz, 1 H), 3.57-3.63 (m, 1 H), 2.83-2.98 (m, 1 H), 2.55-2.63 (m, 6 H), 2.39-2.44 (m, 1 H), 2.42 (br t, J = 8.9 Hz, 3 H) | 430.0 |
| 45 | $^1$H NMR (600 MHz, DMSO-d6) δ ppm 7.68-7.87 (m, 1 H), 7.28-7.56 (m, 1 H), 6.11-6.56 (m, 1 H), 6.05-6.64 (m, 1 H), 4.46-4.87 (m, 4H), 4.03 (br d, J = 11.6 Hz, 1 H), 3.95-4.08 (m, 1 H), 3.79-3.88 (m, 3 H), 3.61-3.62 (m, 1 H), 3.57-3.74 (m, 1 H), 2.71-2.86 (m, 1 H), 2.56-2.63 (m, 6 H), 2.40-2.47 (m, 2 H), 0.91-1.37 (m, 2 H) | 430.0 |
| 46 | $^1$H NMR (600 MHz, DMSO-d6) δ ppm 7.74 (s, 1 H), 7.46 (s, 1 H), 4.70-4.84 (m, 1 H), 4.65 (br s, 1 H), 4.44-4.59 (m, 2 H), 4.01 (br d, J = 11.26 Hz, 1 H), 3.82 (s, 3 H), 3.60-3.71 (m, 1 H), 3.16-3.27 (m, 2 H), 2.78 (br t, J = 12.35 Hz, 2 H), 2.51-2.61 (m, 11 H) | 456.0 |
| 47 | $^1$H NMR (600 MHz, DMSO-d6) δ ppm 0.92-0.99 (m, 2 H) 0.99-1.04 (m, 2 H) 2.38-2.45 (m, 4 H) 2.58 (s, 3 H) 2.59-2.63 (m, 3 H) 2.91 (ttd, J = 13.89, 13.89, 9.37, 9.37, 4.72 Hz, 1 H) 3.20-3.25 (m, 1 H) 3.63-3.69 (m, 1 H) 3.69-3.73 (m, 1 H) 4.02 (br d, J = 11.63 Hz, 1 H) 4.46-4.54 (m, 2 H) 4.69 (br s, 1 H) 4.78 (br s, 1 H) 5.95 (br s, 1 H) 6.00-6.15 (m, 1 H) 7.46 (s, 1 H) 7.82 (s, 1 H) | 456.0 |
| 48 | $^1$H NMR (600 MHz, DMSO-d6) δ ppm 7.80-7.98 (m, 1 H), 7.40-7.62 (m, 1 H), 6.20-6.57 (m, 1 H), 4.54-4.92 (m, 4 H), 4.06-4.13 (m, 1 H), 3.68-3.83 (m, 2 H), 3.35-3.23 (m, 2H), 2.79-2.92 (m, 1 H), 2.58-2.70 (m, 8 H), 2.55-2.58 (m, 2 H), 0.95-1.15 (m, 4 H) | 456.0 |
| 49 | $^1$H NMR (600 MHz, DMSO-d6) δ ppm 7.80-7.86 (m, 1 H), 7.46 (s, 1 H), 4.72-4.87 (m, 1 H), 4.67 (br s, 1 H), 4.46-4.63 (m, 2 H), 3.97-4.06 (m, 1 H), 3.61-3.74 (m, 2 H), 3.30-3.33 (m, 1 H), 3.20-3.27 (m, 1 H), 3.17 (br d, J = 5.27 Hz, 1 H), 2.79 (br t, J = 12.53 Hz, 2 H), 2.51-2.61 (m, 10 H), 0.90-1.06 (m, 4 H) | 482.0 |
| 50 | $^1$H NMR (600 MHz, DMSO-d6) δ ppm 7.84 (s, 1 H), 7.47 (s, 1 H), 4.79 (br s, 1 H), 4.56-4.68 (m, 2 H), 4.51 (dd, J = 10.35, 2.54 Hz, 1 H), 3.98-4.06 (m, 1 H), 3.64-3.73 (m, 2 H), 3.18-3.29 (m, 2 H), 2.65-2.77 (m, 2 H), 2.51-2.64 (m, 9 H), 0.91-1.07 (m, 4 H) | 474.0 |
| 51 | $^1$H NMR (Chloroform-d, 500 MHz) δ 9.45 (br s, 1H), 8.06 (br s, 1H), 5.30 (br d, 1H, J = 12.8 Hz), 5.01 (br d, 1H, J = 13.5 Hz), 4.7-4.9 (m, 2H), 4.2-4.4 (m, 1H), 3.91 (dt, 1H, J = 2.7, 11.7 Hz), 3.44 (br t, 1H, J = 11.0 Hz), 3.1-3.2 (m, 2H), 2.9-3.0 (m, 3H), 2.7-2.8 (m, 10H) | 460.0 |
| 52 | $^1$H NMR (500 MHz, Chloroform-d) δ ppm 9.46 (br s, 1 H), 8.07 (br s, 1 H), 5.30 (br d, J = 12.85 Hz, 1 H), 5.01 (br d, J = 13.36 Hz, 1 H), 4.72-4.91 (m, 2 H), 4.31 (br dd, J = 11.74, 2.01 Hz, 1 H), 3.91 (td, J = 11.68, 2.72 Hz, 1 H), 3.44 (br t, J = 11.22 Hz, 1 H), 3.05-3.18 (m, 2 H), 2.88-2.95 (m, 3 H), 2.64-2.83 (m, 10 H) | 460.0 |
| 53 | $^1$H NMR (600 MHz, DMSO-d6) δ ppm 8.47-8.58 (m, 1 H), 7.18-7.41 (m, 2 H), 5.97-6.31 (m, 1 H), 5.85-6.45 (m, 1 H), 4.52-5.05 (m, 5 H), 4.00-4.30 (m, 2 H), 3.73-3.92 (m, 1 H), 3.70-3.87 (m, 1 H), 3.5-3.3 (m, 3H) 2.91-3.02 (m, 1 H), 2.62-2.70 (m, 6 H), 2.54-2.58 (m, 3 H) | 441.0 |
| 54 | $^1$H NMR (600 MHz, DMSO-d6) δ ppm 8.44-8.61 (m, 1 H), 8.51 (d, J = 5.1 Hz, 1 H), 7.37-7.39 (m, 1 H), 7.38 (s, 1 H), 7.28-7.33 (m, 1 H), 7.31 (br d, J = 4.9 Hz, 1 H), 6.22-6.53 (m, 1 H), 6.20-6.51 (m, 1 H), 4.59-5.02 (m, 4 H), 4.17-4.27 (m, 1 H), 4.21 (br d, J = 11.4 Hz, 1 H), 3.74-3.84 (m, 1 H), 3.45-3.25 (m, 3H), 3.02-3.14 (m, 1 H), 2.83-2.94 (m, 1 H), 2.65 (d, J = 20.0 Hz, 6 H), 2.55 (s, 3 H) | 441.0 |
| 55 | $^1$H NMR (600 MHz, DMSO-d6) δ ppm 8.67 (br d, J = 5.27 Hz, 1 H), 7.72 (br s, 1 H), 7.65 (br s, 1 H), 4.96 (br s, 1 H), 4.80 (br d, J = 10.17 Hz, 2 H), 4.59-4.70 (m, 1 H), 4.20 (br d, J = 11.08 Hz, 1 H), 3.76-3.84 (m, 1 H), 3.36-3.54 (m, 1 H), 3.23-3.34 (m, 2 H), 2.54-2.72 (m, 15 H) | 459.0 |
| 56 | $^1$H NMR (600 MHz, DMSO-d6) δ ppm 8.46 (d, J = 5.09 Hz, 1 H), 7.32 (s, 1 H), 7.25 (br d, J = 4.90 Hz, 1 H), 4.88 (br s, 1 H), 4.75 (br s, 1 H), 4.58-4.70 (m, 1 H), 4.49-4.57 (m, 1 H), 4.16 (br d, J = 11.26 Hz, 1 H), 3.71-3.79 (m, 1 H), 3.20-3.35 (m, 1 H), 3.00 (br s, 1 H), 2.79 (br t, J = 12.53 Hz, 2 H), 2.53-2.63 (m, 12 H), 2.47-2.51 (m, 2 H) | 467.0 |

TABLE 8-continued

Analytical Data for Examples 1-232

| Ex # | NMR | M + H |
|---|---|---|
| 57 | ¹H NMR (Chloroform-d, 500 MHz) δ 7.56 (s, 1H), 7.45 (s, 1H), 4.5-4.7 (m, 1H), 4.10 (td, 1H, J = 1.6, 11.6 Hz), 3.9-4.0 (m, 4H), 3.7-3.9 (m, 2H), 3.2-3.3 (m, 2H), 2.73 (s, 3H), 2.70 (s, 3H), 2.4-2.6 (m, 1H), 1.5-1.7 (m, 3H) | 434.0 |
| 58 | ¹H NMR (400 MHz, DMSO-d6) δ ppm 7.55 (s, 1 H), 7.42-7.48 (m, 2 H), 7.28-7.38 (m, 2 H), 5.03 (s, 1 H), 4.85 (d, J = 13.5 Hz, 1 H), 4.60 (dd, J = 10.6, 2.8 Hz, 1 H), 4.10 (ddd, J = 11.7, 3.7, 1.8 Hz, 1 H), 3.91 (s, 3 H), 3.81 (td, J = 11.6, 2.8 Hz, 1 H), 3.30-3.42 (m, 1 H), 3.26 (dd, J = 13.4, 10.4 Hz, 1 H), 2.72 (s, 3 H), 2.58 (s, 3 H), 2.27 (s, 3 H) | 450.0 |
| 59 | ¹H NMR (400 MHz, Chloroform-d) δ ppm 7.57 (1H, s), 7.51 (1H, dd, J = 8.4, 6.0 Hz), 7.45 (1H, s), 7.01-7.09 (2H, m), 5.05 (1H, s), 4.86 (1H, d, J = 13.3 Hz), 4.61 (1H, d, J = 10.0 Hz), 4.07-4.15 (1H, m), 3.92 (3H, s), 3.82 (1H, t, J = 11.2 Hz), 3.37 (1H, t, J = 12.1 Hz), 3.27 (1H, dd, J = 13.4, 10.3 Hz), 2.74 (3H, s), 2.60 (3H, s), 2.31 (3H, s) | 434.2 |
| 60 | ¹H NMR (400 MHz, DMSO-d6) δ ppm 8.37-8.50 (m, 1 H), 8.27 (s, 1 H), 7.78 (s, 1 H), 7.64 (dt, J = 10.6, 8.5 Hz, 1 H), 7.49 (d, J = 0.8 Hz, 1 H), 4.70-4.81 (m, 2 H), 4.54 (dd, J = 10.4, 2.7 Hz, 1 H), 4.10 (d, J = 9.94 Hz, 1 H), 3.84 (s, 3 H), 3.69 (td, J = 11.6, 2.8 Hz, 1 H), 3.17-3.25 (m, 2 H), 2.66 (s, 3 H), 2.61 (s, 3 H) | 438.2 |
| 61 | ¹H NMR (400 MHz, Chloroform-d) δ ppm 7.57 (s, 1 H), 7.47 (d, J = 10.9 Hz, 2 H), 7.08-7.19 (m, 1 H), 5.02 (s, 1 H), 4.85 (d, J = 13.6 Hz, 1 H), 4.62 (dd, J = 10.3, 2.8 Hz, 1 H), 4.08-4.17 (m, 1 H), 3.92 (s, 3 H), 3.82 (td, J = 11.5, 2.8 Hz, 1 H), 3.33-3.44 (m, 1 H), 3.30 (dd, J = 13.4, 10.3 Hz, 1 H), 2.74 (s, 3 H), 2.62 (s, 3 H) | 456.2 |
| 62 | ¹H NMR (400 MHz, Chloroform-d) δ ppm 7.58-7.64 (m, 1 H), 7.57 (s, 1 H), 7.46 (s, 1 H), 7.11 (td, J = 9.7, 6.4 Hz, 1 H), 5.02 (bs, 1 H), 4.85 (d, J = 13.5 Hz, 1 H), 4.62 (d, J = 10.2 Hz, 1 H), 4.12 (d, J = 11.6 Hz, 1 H), 3.92 (s, 3 H), 3.82 (td, J = 11.5, 2.8 Hz, 1 H), 3.20-3.39 (m, 2 H), 2.74 (s, 3 H), 2.62 (s, 3 H) | 456.2 |
| 63 | ¹H NMR (Chloroform-d, 500 MHz) δ 7.56 (s, 1H), 7.45 (s, 1H), 4.99 (br d, 1H, J = 13.2 Hz), 4.7-4.9 (m, 1H), 4.59 (dd, 1H, J = 2.8, 10.2 Hz), 4.1-4.1 (m, 1H), 3.93 (s, 3H), 3.79 (dt, 1H, J = 2.9, 11.5 Hz), 3.2-3.4 (m, 2H), 2.70 (s, 3H), 2.65 (s, 3H), 2.6-2.6 (m, 6H) | 460.0 |
| 64 | ¹H NMR (600 MHz, DMSO-d6) δ ppm 7.80-7.86 (m, 1 H), 7.46 (s, 1 H), 4.72 (br d, J = 12.72 Hz, 1 H), 4.61 (br s, 1 H), 4.48 (dd, J = 10.35, 2.54 Hz, 1 H), 3.96-4.04 (m, 1 H), 3.60-3.73 (m, 2 H), 3.12-3.28 (m, 2 H), 2.60 (d, J = 4.00 Hz, 6 H), 2.57 (s, 6 H), 0.90-1.07 (m, 4 H) | 486.0 |
| 65 | ¹H NMR (600 MHz, DMSO-d6) δ ppm 8.46 (d, J = 5.09 Hz, 1 H), 7.32 (s, 1 H), 7.24 (br d, J = 4.90 Hz, 1 H), 4.83 (br d, J = 12.72 Hz, 1 H), 4.70 (br s, 1 H), 4.59 (dd, J = 10.35, 2.36 Hz, 1 H), 4.14 (br dd, J = 11.54, 2.45 Hz, 1 H), 3.73 (td, J = 11.67, 2.63 Hz, 1 H), 3.20-3.27 (m, 1 H), 2.92-3.03 (m, 1 H), 2.56-2.65 (m, 11 H), 2.44-2.54 (m, 3 H) | 471.0 |
| 66 | ¹H NMR (400 MHz, Chloroform-d) δ ppm 7.57 (s, 1 H), 7.46 (s, 1 H), 5.00 (s, 1 H), 4.83 (d, J = 13.4 Hz, 1 H), 4.60 (dd, J = 10.2, 2.8 Hz, 1 H), 4.08 (dd, J = 26.1, 9.5 Hz, 2 H), 3.93 (s, 3 H), 3.80 (td, J = 11.4, 2.8 Hz, 1 H), 3.33 (dd, J = 29.6, 17.4 Hz, 2 H), 2.71 (s, 3 H), 2.67 (s, 3 H), 2.21-2.34 (m, 2 H), 1.92-2.12 (m, 6 H) | 444.1 |
| 67 | ¹H NMR (400 MHz, Chloroform-d) δ ppm 7.67 (s, 1 H), 7.53 (s, 1 H), 4.75 (d, J = 13.4 Hz, 1 H), 4.57 (ddd, J = 18.7, 11.9, 2.6 Hz, 2 H), 4.33 (s, 4 H), 4.02 (ddd, J = 11.4, 3.4, 1.9 Hz, 1 H), 3.90 (s, 3 H), 3.72 (td, J = 11.3, 2.8 Hz, 1 H), 3.10-3.26 (m, 2 H), 2.56 (d, J = 10.9 Hz, 6 H), 1.49-1.56 (m, 4 H), 1.06 (s, 6 H) | 437.3 |
| 68 | ¹H NMR (600 MHz, DMSO-d6) δ ppm 1.79-1.89 (m, 2 H) 2.08-2.18 (m, 2 H) 2.52 (s, 3 H) 2.53 (s, 3H) 3.07 (br t, J = 11.53 Hz, 1 H) 3.10-3.18 (m, 1 H) 3.61 (td, J = 11.49, 2.82 Hz, 1 H) 3.82 (s, 3 H) 3.93-4.00 (m, 1 H) 4.15 (br s, 2 H) 4.43-4.55 (m, 2 H) 4.61 (br d, J = 11.26 Hz, 1 H) 4.77 (br s, 2 H) 7.44 (s, 1 H) 7.72 (s, 1 H) | 445.0 |
| 69 | ¹H NMR (600 MHz, DMSO-d6) δ ppm 7.72 (s, 1 H) 7.44 (s, 1 H) 4.87 (br s, 1 H) 4.79 (br s, 1 H) 4.61 (br d, J = 11.08 Hz, 1 H) 4.49 (br d, J = 12.72 Hz, 2 H) 4.45 (br dd, J = 10.17, 2.54 Hz, 1 H) 4.13 (br d, J = 17.62 Hz, 1 H) 3.88-3.99 (m, 1 H) 3.82 (s, 3 H) 3.56-3.66 (m, 1 H) 3.17 (d, J = 5.09 Hz, 1 H) 3.08-3.14 (m, 1 H) 3.03-3.08 (m, 1 H) 2.51-2.54 (m, 3 H) 2.37-2.48 (m, 1 H) 1.97 (br d, J = 11.44 Hz, 1 H) 1.90 (br dd, J = 9.08, 5.81 Hz, 3 H) 1.58-1.66 (m, 1 H) 1.19-1.30 (m, 1 H) | 427.0 |
| 70 | ¹H NMR (600 MHz, DMSO-d6) δ ppm 7.72 (s, 1 H), 7.44 (s, 1 H), 4.76-4.91 (m, 1 H), 4.62 (br d, J = 11.63 Hz, 1 H), 4.41-4.56 (m, 4 H), 4.04-4.21 (m, 1 H), 3.91-4.00 (m, 1 H), 3.60 (td, J = 11.44, 2.72 Hz, 1 H), 3.24-3.34 (m, 4 H), 3.02-3.24 (m, 4 H), 2.51-2.54 (m, 3 H), 1.97 (br d, J = 10.54 Hz, 1 H), 1.85-1.93 (m, 3 H), 1.57-1.64 (m, 1 H) | 427.0 |
| 71 | ¹H NMR (400 MHz, Methanol-d4) δ ppm 7.69 (d, J = 3.5 Hz, 1 H), 7.55 (d, J = 3.3 Hz, 1 H), 4.82 (d, J = 13.8 Hz, 3 H), 4.55-4.70 (m, 4 H), 4.04 (d, J = 11.9 Hz, 2 H), 3.91 (d, J = 3.1 Hz, 3 H), 3.74 (td, J = 11.5, 3.0 Hz, 1 H), 3.14-3.29 (m, 3 H), 2.60 (d, J = 4.8 Hz, 6 H) | 431.1 |

TABLE 8-continued

Analytical Data for Examples 1-232

| Ex # | NMR | M + H |
|---|---|---|
| 72 | ¹H NMR (400 MHz, Methanol-d4) δ ppm 7.68 (s, 1 H), 7.53-7.55 (m, 1 H), 4.80 (t, J = 10.9 Hz, 1 H), 4.65 (d, J = 13.7 Hz, 1 H), 4.55 (dd, J = 10.2, 2.8 Hz, 1 H), 4.39 (t, J = 7.1 Hz, 1 H), 4.08 (s, 1 H), 4.00-4.05 (m, 1 H), 3.91 (s, 3 H), 3.84 (t, J = 7.2 Hz, 1 H), 3.73 (td, J = 11.4, 2.8 Hz, 1 H), 3.53 (s, 1 H), 3.11-3.26 (m, 2 H), 2.56 (d, J = 5.9 Hz, 6 H), 1.89 (t, J = 7.1 Hz, 1 H), 1.77 (t, J = 7.2 Hz, 1 H), 1.18 (d, J = 5.6 Hz, 6 H) | 423.3 |
| 73 | ¹H NMR (500 MHz, DMSO-d6) δ ppm 8.51-8.55 (m, 1 H), 7.73-7.77 (m, 1 H), 7.62-7.67 (m, 1 H), 7.54-7.58 (m, 1 H), 7.47-7.49 (m, 1 H), 7.42-7.46 (m, 1 H), 7.17-7.21 (m, 1 H), 4.56-4.62 (m, 1 H), 4.40-4.45 (m, 1 H), 4.22-4.27 (m, 1 H), 4.01-4.08 (m, 1 H), 3.81-3.85 (m, 3 H), 3.72-3.79 (m, 1 H), 3.07-3.14 (m, 1 H), 3.01-3.06 (m, 1 H), 2.64-2.67 (m, 3 H) | 439.0 |
| 74 | ¹H NMR (500 MHz, DMSO-d6) δ ppm 8.82-8.88 (m, 1 H), 7.74-7.77 (m, 1 H), 7.62-7.68 (m, 1 H), 7.53-7.59 (m, 1 H), 7.46-7.51 (m, 1 H), 7.42-7.46 (m, 1 H), 7.22-7.28 (m, 1 H), 4.56-4.62 (m, 1 H), 4.36-4.44 (m, 1 H), 4.19-4.26 (m, 1 H), 4.01-4.08 (m, 1 H), 3.80-3.86 (m, 3 H), 3.73-3.78 (m, 1 H), 3.05-3.12 (m, 1 H), 2.98-3.05 (m, 1 H), 2.53-2.57 (m, 3 H) | 439.0 |
| 75 | ¹H NMR (500 MHz, DMSO-d6) δ ppm 8.51-8.53 (m, 1 H), 7.78-7.81 (m, 1 H), 7.62-7.66 (m, 1 H), 7.54-7.58 (m, 1 H), 7.48-7.51 (m, 1 H), 7.42-7.47 (m, 1 H), 7.18-7.21 (m, 1 H), 4.55-4.62 (m, 1 H), 4.41-4.46 (m, 1 H), 4.23-4.30 (m, 1 H), 4.08-4.15 (m, 2 H), 4.01-4.06 (m, 1 H), 3.72-3.78 (m, 1 H), 3.07-3.14 (m, 1 H), 3.00-3.06 (m, 1 H), 2.64-2.67 (m, 3 H), 1.35-1.40 (m, 3 H) | 453.0 |
| 76 | ¹H NMR (600 MHz, DMSO-d6) δ ppm 8.49-8.54 (m, 1 H), 7.79-7.87 (m, 1 H), 7.61-7.66 (m, 1 H), 7.54-7.58 (m, 1 H), 7.47-7.49 (m, 1 H), 7.43-7.46 (m, 1 H), 7.17-7.24 (m, 1 H), 4.54-4.59 (m, 1 H), 4.38-4.46 (m, 1 H), 4.23-4.30 (m, 1 H), 4.01-4.06 (m, 1 H), 3.72-3.77 (m, 1 H), 3.65-3.71 (m, 1 H), 3.07-3.14 (m, 1 H), 3.01-3.06 (m, 1 H), 2.64-2.68 (m, 3 H), 1.00-1.05 (m, 2 H), 0.92-0.97 (m, 2 H) | 465.0 |
| 77 | ¹H NMR (500 MHz, DMSO-d6) δ ppm 8.52-8.54 (m, 1 H), 8.42-8.47 (m, 1 H), 7.63-7.68 (m, 1 H), 7.55-7.59 (m, 1 H), 7.44-7.47 (m, 1 H), 7.37-7.40 (m, 1 H), 7.28-7.31 (m, 1 H), 7.25-7.28 (m, 1 H), 4.65-4.70 (m, 1 H), 4.50-4.55 (m, 1 H), 4.34-4.39 (m, 1 H), 4.14-4.20 (m, 1 H), 3.79-3.85 (m, 1 H), 3.09-3.16 (m, 1 H), 2.86-2.92 (m, 1 H), 2.64-2.68 (m, 3 H), 2.49-2.50 (m, 3 H) | 450.0 |
| 78 | ¹H NMR (500 MHz, Chloroform-d) δ ppm 8.44-8.49 (m, 1 H), 8.17-8.21 (m, 1 H), 7.57-7.62 (m, 1 H), 7.30-7.33 (m, 1 H), 7.25-7.28 (m, 1 H), 6.98-7.00 (m, 1 H), 6.95-6.98 (m, 1 H), 6.85-6.90 (m, 1 H), 4.62-4.68 (m, 1 H), 4.52-4.60 (m, 1 H), 4.21-4.29 (m, 2 H), 3.96-3.99 (m, 3 H), 3.89-3.96 (m, 1 H), 3.18-3.29 (m, 1 H), 2.97 (dd, J = 13.0, 10.4 Hz, 1 H), 2.71-2.74 (m, 3 H) | 466.0 |
| 79 | ¹H NMR (500 MHz, DMSO-d6) δ ppm 7.73-7.76 (m, 1 H), 7.61-7.66 (m, 1 H), 7.54-7.58 (m, 1 H), 7.47-7.50 (m, 1 H), 7.41-7.45 (m, 1H), 7.17-7.20 (m, 1 H), 4.56-4.61 (m, 1 H), 4.37-4.42 (m, 1 H), 4.19-4.24 (m, 1 H), 4.01-4.07 (m, 1 H), 3.81-3.85 (m, 3 H), 3.73-3.78 (m, 1 H), 3.04-3.10 (m, 1 H), 2.96-3.02 (m, 1 H), 2.64-2.67 (m, 3 H), 2.52-2.54 (m, 3 H) | 453.0 |
| 80 | ¹H NMR (500 MHz, Chloroform-d) δ 7.58 (s, 1H), 7.47 (s, 1H), 6.85 (br s, 1H), 4.84 (quin, J = 8.17 Hz, 1H), 4.72 (dd, J = 2.85, 10.25 Hz, 1H), 4.45 (br d, J = 12.59 Hz, 1H), 4.26 (br d, J = 13.23 Hz, 1H), 4.15-4.20 (m, 1H), 3.90-3.96 (m, 4H), 3.22 (dt, J = 3.63, 12.13 Hz, 1H), 3.04-3.18 (m, 2H), 2.68-2.76 (m, 7H), 2.67 (s, 3H) | 447.2 |
| 81 | ¹H NMR (500 MHz, Chloroform-d) δ 7.56 (s, 1H), 7.56 (s, 1H), 6.81 (s, 1H), 4.84 (quin, J = 8.17 Hz, 1H), 4.71 (dd, J = 2.66, 10.32 Hz, 1H), 4.43 (br d, J = 12.59 Hz, 1H), 4.26 (br d, J = 12.72 Hz, 1H), 4.13-4.21 (m, 1H), 3.93 (dt, J = 2.85, 11.48 Hz, 1H), 3.62 (tt, J = 3.71, 7.31 Hz, 1H), 3.17-3.24 (m, 1H), 3.13 (dd, J = 10.38, 12.72 Hz, 2H), 2.70-2.74 (m, 2H), 2.68 (s, 3H), 2.66 (s, 3H), 1.28 (s, 2H), 1.13-1.18 (m, 2H), 1.02-1.07 (m, 2H) | 473.2 |
| 82 | ¹H NMR (500 MHz, Chloroform-d) δ 8.56 (d, J = 5.19 Hz, 1H), 7.33 (br s, 1H), 7.25 (br dd, J = 3.96, 5.13 Hz, 1H), 6.83 (s, 1H), 4.80-4.90 (m, 1H), 4.67-4.74 (m, 1H), 4.53 (br d, J = 12.20 Hz, 1H), 4.34 (br d, J = 13.36 Hz, 1H), 4.25-4.30 (m, 1H), 3.98 (dt, J = 2.79, 11.71 Hz, 1H), 3.22 (dt, J = 3.50, 12.26 Hz, 1H), 3.09-3.17 (m, 1H), 2.95 (dd, J = 10.51, 12.72 Hz, 1H), 2.63-2.76 (m, 13H) | 458.0 |
| 83 | ¹H NMR (500 MHz, DMSO-d6) δ ppm 8.94-8.98 (m, 1 H), 7.91-7.95 (m, 1 H), 7.69-7.77 (m, 3 H), 7.51-7.56 (m, 1 H), 7.44-7.48 (m, 1 H), 7.25-7.29 (m, 1 H), 4.73-4.81 (m, 1 H), 4.61-4.67 (m, 1 H), 4.54 (br dd, J = 10.4, 2.3 Hz, 1 H), 3.98-4.07 (m, 1 H), 3.77-3.84 (m, 3 H), 3.63-3.72 (m, 1 H), 3.18-3.27 (m, 2 H) | 425.0 |
| 84 | ¹H NMR (500 MHz, DMSO-d6) δ ppm 7.80 (dd, J = 3.11, 8.30 Hz, 1H), 7.75 (br s, 1H), 7.70 (dd, J = 1.56, 10.12 Hz, 1H), 7.69 (t, J = 7.79 Hz, 1H), 7.53 (dd, J = 1.82, 8.30 Hz, 1H), 7.46 (br s, 1H), 7.17 (d, J = 8.30 Hz, 1H), 4.66-4.84 (m, 1H), 4.57-4.66 (m, 1H), 4.52 (br dd, | 439.0 |

TABLE 8-continued

Analytical Data for Examples 1-232

| Ex # | NMR | M + H |
|---|---|---|
| | J = 2.08, 10.38 Hz, 1H), 3.94-4.08 (m, 1H), 3.82 (s, 3H), 3.60-3.72 (m, 1H), 3.14-3.27 (m, 2H), 2.60 (s, 3H) | |
| 85 | $^1$H NMR (400 MHz, Chloroform-d) δ ppm 7.76 (dd, J = 8.3, 3.8 Hz, 1 H), 7.50-7.58 (m, 3 H), 7.37 (d, J = 8.0 Hz, 1H), 7.34 (d, J = 8.0 Hz, 1H), 7.04 (d, J = 8.0 Hz, 1H), 5.12 (bs, 1H), 4.83-4.91 (m, 1 H), 4.58 (d, J = 10.4 Hz, 1 H), 4.10 (dd, J = 11.6, 1.7 Hz, 1 H), 3.81 (td, J = 11.5, 2.8 Hz, 1 H), 3.55-3.65 (m, 1 H), 3.22-3.44 (m, 2 H), 2.75 (s, 3 H), 0.99-1.20 (m, 4 H) | 465.1 |
| 86 | $^1$H NMR (500 MHz, DMSO-d6) δ ppm 9.17 (s, 1H), 7.83 (dd, J = 3.37, 8.30 Hz, 1H), 7.67-7.79 (m, 2H), 7.63 (s, 1H), 7.54 (dd, J = 2.08, 8.30 Hz, 1H), 7.20 (d, J = 8.30 Hz, 1H), 4.80-4.97 (m, 1H), 4.60-4.80 (m, 2H), 4.08-4.27 (m, 1H), 3.77 (dt, J = 2.60, 11.68 Hz, 1H), 3.24-3.29 (m, 1H), 3.11 (br dd, J = 10.38, 13.23 Hz, 1H), 2.66 (s, 3H), 2.62 (s, 3H) | 451.2 |
| 87 | $^1$H NMR (500 MHz, DMSO-d6) δ ppm 9.17 (s, 1H), 7.83 (dd, J = 3.37, 8.30 Hz, 1H), 7.67-7.78 (m, 2H), 7.63 (s, 1H), 7.54 (dd, J = 1.82, 8.30 Hz, 1H), 7.20 (d, J = 8.30 Hz, 1H), 4.81-4.96 (m, 1H), 4.61-4.79 (m, 2H), 4.09-4.22 (m, 1H), 3.77 (dt, J = 2.60, 11.55 Hz, 1H), 3.23-3.29 (m, 1H), 3.11 (br dd, J = 10.64, 12.72 Hz, 1H), 2.66 (s, 3H), 2.62 (s, 3H) | 451.2 |
| 88 | $^1$H NMR (400 MHz, DMSO-d6) δ ppm 8.78 (s, 1 H), 8.03-8.09 (m, 1 H), 7.91 (s, 1 H), 7.82 (s, 1 H), 7.71-7.78 (m, 2 H), 7.58 (dd, J = 8.3, 2.0 Hz, 1 H), 7.32 (d, J = 8.5 Hz, 1 H), 4.98 (d, J = 13.3 Hz, 1 H), 4.91 (d, J = 10.2 Hz, 1 H), 4.76 (d, J = 13.4 Hz, 1 H), 4.23 (d, J = 11.6 Hz, 1 H), 3.80-3.86 (m, 1 H), 3.33 (t, J = 12.4 Hz, 1 H), 3.11 (t, J = 11.8 Hz, 1 H), 2.70 (d, J = 10.8 Hz, 6 H) | 450.1 |
| 89 | $^1$H NMR (400 MHz, DMSO-d6) δ ppm 8.80 (s, 2H), 7.84 (dd, J = 8.3, 3.4 Hz, 1H), 7.68-7.76 (m, 2H), 7.54 (dd, J = 8.3, 2.1 Hz, 1H), 7.20 (d, J = 8.3 Hz, 1H), 4.83 (d, J = 13.4 Hz, 1H), 4.66-4.74 (m, 1H), 4.14 (d, J = 11.6 Hz, 1H), 3.69-3.80 (m, 1H), 3.17-3.32 (m, 3H), 2.63 (d, J = 10.3 Hz, 6H) | 451.1 |
| 90 | $^1$H NMR (400 MHz, DMSO-d6) δ ppm 8.80 (s, 2H), 7.84 (dd, J = 8.3, 3.4 Hz, 1H), 7.68-7.76 (m, 2H), 7.54 (dd, J = 8.3, 2.1 Hz, 1H), 7.20 (d, J = 8.3 Hz, 1H), 4.83 (d, J = 13.4 Hz, 1H), 4.66-4.74 (m, 1H), 4.14 (d, J = 11.6 Hz, 1H), 3.69-3.80 (m, 1H), 3.17-3.32 (m, 3H), 2.63 (d, J = 10.3 Hz, 6H) | 451.1 |
| 91 | $^1$H NMR (500 MHz, DMSO-d6) δ ppm 7.79 (dd, J = 3.37, 8.30 Hz, 1H), 7.67-7.77 (m, 2H), 7.50 (dt, J = 2.47, 9.93 Hz, 1H), 7.46 (s, 1H), 7.32 (dt, J = 2.47, 8.37 Hz, 1H), 7.17 (d, J = 8.30 Hz, 1H), 4.76 (br d, J = 13.49 Hz, 1H), 4.63 (br d, J = 13.49 Hz, 1H), 4.53 (br dd, J = 2.47, 10.25 Hz, 1H), 3.94-4.07 (m, 1H), 3.82 (s, 3H), 3.67 (dt, J = 2.34, 11.42 Hz, 1H), 3.12-3.27 (m, 2H), 2.61 (s, 3H) | 423.2 |
| 92 | $^1$H NMR (500 MHz, DMSO-d6) δ ppm 7.83 (s, 1H), 7.80 (dd, J = 3.37, 8.30 Hz, 1H), 7.67-7.76 (m, 1H), 7.50 (dt, J = 2.34, 9.86 Hz, 1H), 7.46 (s, 1H), 7.32 (dt, J = 2.34, 8.43 Hz, 1H), 7.17 (d, J = 8.30 Hz, 1H), 4.75 (br d, J = 12.72 Hz, 1H), 4.63 (br d, J = 13.49 Hz, 1H), 4.51 (br dd, J = 2.21, 10.25 Hz, 1H), 3.94-4.06 (m, 1H), 3.58-3.76 (m, 2H), 3.16-3.26 (m, 2H), 2.61 (s, 3H), 0.99-1.06 (m, 2H), 0.90-0.96 (m, 2H) | 449.2 |
| 93 | $^1$H NMR (500 MHz, DMSO-d6) δ ppm 8.46 (br d, J = 4.93 Hz, 1H), 7.81 (dd, J = 3.37, 8.30 Hz, 1H), 7.74 (dt, J = 6.62, 8.50 Hz, 1H), 7.51 (ddd, J = 2.47, 9.47, 10.38 Hz, 1H), 7.29-7.37 (m, 2H), 7.26 (br d, J = 4.15 Hz, 1H), 7.19 (d, J = 8.30 Hz, 1H), 4.86 (br d, J = 12.46 Hz, 1H), 4.71 (br d, J = 13.49 Hz, 1H), 4.62 (br dd, J = 2.60, 10.38 Hz, 1H), 4.08-4.19 (m, 1H), 3.75 (dt, J = 2.34, 11.68 Hz, 1H), 3.21-3.28 (m, 1H), 3.02 (br t, J = 11.68 Hz, 1H), 2.62 (s, 3H), (one Me singlet not observed because of overlap with solvent peak) | 434.2 |
| 94 | $^1$H NMR (600 MHz, DMSO-d6) δ ppm 77.70-7.81 (m, 2H), 7.52 (br t, J = 7.63, 1H), 7.46 (br s, 1H), 7.21-7.30 (m, 2H), 7.15 (d, J = 8.36, 1H), 4.76 (br d, J = 13.81, 1H), 4.53 (br d, J = 12.90, 1H), 4.52 (br d, J = 9.99, 1H), 4.01 (br d, J = 11.26, 1H), 3.82 (s, 3H), 3.63-3.75 (m, 1H), 3.15-3.24 (m, 2H), 2.60 (s, 3H), 2.43 (s, 3H) | 419.0 |
| 95 | $^1$H NMR (500 MHz, DMSO-d6) δ ppm 7.83 (s, 1H), 7.77 (dd, J = 3.37, 8.30 Hz, 1H), 7.52 (t, J = 7.79 Hz, 1H), 7.46 (s, 1H), 7.27 (d, J = 11.42 Hz, 1H), 7.24 (d, J = 7.79 Hz, 1H), 7.16 (d, J = 8.30 Hz, 1H), 4.76 (br d, J = 13.75 Hz, 1H), 4.64 (br d, J = 13.75 Hz, 1H), 4.51 (br dd, J = 2.47, 10.51 Hz, 1H), 4.00 (br d, J = 11.16 Hz, 1H), 3.60-3.73 (m, 2H), 3.13-3.26 (m, 2H), 2.60 (s, 3H), 2.44 (s, 3H), 0.97-1.08 (m, 2H), 0.90-0.97 (m, 2H) | 445.2 |
| 96 | $^1$H NMR (500 MHz, DMSO-d6) δ ppm 8.46 (br d, J = 4.93 Hz, 1H), 7.79 (dd, J = 3.63, 8.30 Hz, 1H), 7.53 (t, J = 7.79 Hz, 1H), 7.33 (br s, 1H), 7.22-7.32 (m, 3H), 7.18 (d, J = 8.30 Hz, 1H), 4.80-4.96 (m, 1H), 4.72 (br d, J = 13.75 Hz, 1H), 4.62 (dd, J = 2.08, 10.12 Hz, 1H), 4.07-4.21 (m, 1H), 3.75 (dt, J = 2.72, 11.74 Hz, 1H), 3.19-3.27 (m, 1H), 3.01 (br t, J = 11.68 Hz, 1H), 2.61 (s, 3H), 2.44 (s, 3H) (one Me singlet not observed, likely overlap with solvent peak) | 430.2 |

TABLE 8-continued

Analytical Data for Examples 1-232

| Ex # | NMR | M + H |
|---|---|---|
| 97 | ¹H NMR (500 MHz, Chloroform-d) δ ppm 7.88 (d, J = 8.30 Hz, 1H), 7.55 (s, 1H), 7.44 (s, 1H), 7.02 (d, J = 8.30 Hz, 1H), 5.07 (br s, 1H), 4.90 (br d, J = 13.62 Hz, 1H), 4.58 (dd, J = 2.72, 10.25 Hz, 1H), 4.21-4.32 (m, 1H), 4.10 (br d, J = 10.90 Hz, 1H), 3.90 (s, 3H), 3.79 (dt, J = 2.72, 11.55 Hz, 1H), 3.34 (ddd, J = 3.50, 11.42, 13.49 Hz, 1H), 3.25 (br t, J = 10.77 Hz, 1H), 2.94-3.11 (m, 1H), 2.72-2.83 (m, 2H), 2.68 (s, 3H), 2.58-2.66 (m, 2H) | 433.3 |
| 98 | ¹H NMR (500 MHz, Chloroform-d) δ ppm 7.91 (br d, J = 8.04 Hz, 1H), 7.55 (br d, J = 5.19 Hz, 2H), 7.04 (br d, J = 8.17 Hz, 1H), 4.98-5.19 (m, 1H), 4.92 (br d, J = 13.36 Hz, 1H), 4.58 (br d, J = 9.08 Hz, 1H), 4.28 (quin, J = 8.17 Hz, 1H), 4.08-4.19 (m, 1H), 3.81 (br t, J = 11.03 Hz, 1H), 3.60 (tt, J = 3.42, 6.96 Hz, 1H), 3.31-3.43 (m, 1H), 3.14-3.31 (m, 1H), 2.95-3.12 (m, 1H), 2.75-2.88 (m, 2H), 2.71 (br s, 3H), 2.58-2.70 (m, 2H), 1.09-1.16 (m, 2H), 0.98-1.06 (m, 2H) | 459.0 |
| 99 | ¹H NMR (500 MHz, Chloroform-d) δ ppm 8.52 (br d, J = 5.06 Hz, 1H), 7.91 (d, J = 8.17 Hz, 1H), 7.30 (s, 1H), 7.22 (br s, 1H), 7.06 (d, J = 8.17 Hz, 1H), 5.20 (br d, J = 8.43 Hz, 1H), 5.02 (br d, J = 13.36 Hz, 1H), 4.57 (br d, J = 10.12 Hz, 1H), 4.29 (quin, J = 8.08 Hz, 1H), 4.22 (br d, J = 11.42 Hz, 1H), 3.85 (br t, J = 10.77 Hz, 1H), 3.32 (dt, J = 2.60, 11.42 Hz, 1H), 2.95-3.16 (m, 2H), 2.73-2.86 (m, 2H), 2.71 (s, 3H), 2.64-2.70 (m, 2H), 2.61 (s, 3H) | 444.2 |
| 100 | ¹H NMR (600 MHz, DMSO-d6) δ ppm 8.47 (d, J = 8.17 Hz, 1 H), 7.74 (s, 1 H), 7.46 (s, 1 H), 7.15 (d, J = 8.36 Hz, 1 H), 4.76 (br d, J = 12.35 Hz, 1 H), 4.62 (br s, 1 H), 4.49 (dd, J = 10.26, 2.45 Hz, 1 H), 4.00 (br d, J = 11.63 Hz, 1 H), 3.64 (td, J = 11.44, 2.54 Hz, 1 H), 3.08-3.28 (m, 5 H), 2.56-2.61 (m, 8 H) | 445.2 |
| 101 | ¹H NMR (600 MHz, DMSO-d6) δ ppm 8.38 (d, J = 4.90 Hz, 1 H), 8.22-8.30 (m, 1 H), 7.16-7.29 (m, 1 H), 6.65-6.75 (m, 1 H), 4.84-4.92 (m, 1H), 4.27-4.37 (m, 1 H), 4.16-4.25 (m, 1 H), 3.85-4.03 (m, 1 H), 3.65-3.78 (m, 1 H), 3.55 (br d, J = 10.54 Hz, 1 H), 3.40-3.50 (m, 2 H), 3.13-3.31 (m, 3 H), 2.68-2.89 (m, 2 H), 2.19-2.32 (m, 1 H), 1.75-2.03 (m, 5 H), 1.33-1.43 (m, 2 H), 0.91-0.96 (m, 2 H) | 471.2 |
| 102 | ¹H NMR (600 MHz, DMSO-d6) δ ppm 8.44-8.52 (m, 2 H), 7.32 (s, 1 H), 7.25 (br d, J = 4.72 Hz, 1 H), 7.17 (d, J = 8.36 Hz, 1 H), 4.86 (br d, J = 12.90 Hz, 1 H), 4.71 (br s, 1 H), 4.55-4.61 (m, 1 H), 4.14 (br dd, J = 11.53, 2.27 Hz, 1 H), 3.72 (td, J = 11.67, 2.63 Hz, 1 H), 3.15-3.30 (m, 4 H), 2.97 (br s, 1 H), 2.56-2.63 (m, 9 H) | 456.2 |
| 103 | ¹H NMR (500 MHz, DMSO-d6) δ ppm 7.75 (s, 1 H), 7.63-7.72 (m, 2 H), 7.60 (d, J = 2.3 Hz, 1 H), 7.52 (dd, J = 8.2, 1.9 Hz, 1 H), 7.46 (s, 1 H), 4.73 (br d, J = 12.3 Hz, 1 H), 4.60 (br d, J = 13.4 Hz, 1 H), 4.52 (dd, J = 10.4, 2.6 Hz, 1 H), 4.00 (br d, J = 11.3 Hz, 1 H), 3.82 (s, 3 H), 3.67 (td, J = 11.5, 2.7 Hz, 1 H), 3.11-3.26 (m, 2 H), 2.57 (s, 3 H), 2.29 (s, 3 H) | 453.0 |
| 104 | ¹H NMR (500 MHz, DMSO-d6) δ ppm 9.17 (s, 1H), 7.65-7.75 (m, 2H), 7.62-7.64 (m, 2H), 7.54 (dd, J = 1.82, 8.30 Hz, 1H), 4.86 (br d, J = 13.23 Hz, 1H), 4.73 (dd, J = 2.60, 10.64 Hz, 1H), 4.68 (br d, J = 13.23 Hz, 1H), 4.10-4.21 (m, 1H), 3.77 (dt, J = 2.60, 11.68 Hz, 1H), 3.21-3.27 (m, 1H), 3.07 (dd, J = 10.64, 12.98 Hz, 1H), 2.66 (s, 3H), 2.59 (s, 3H), 2.31 (s, 3H) | 465.2 |
| 105 | ¹H NMR (500 MHz, DMSO-d6) δ ppm 9.16 (s, 1H), 7.66-7.73 (m, 2H), 7.62-7.64 (m, 2H), 7.53 (dd, J = 1.82, 8.30 Hz, 1H), 4.86 (br d, J = 12.72 Hz, 1H), 4.73 (dd, J = 2.47, 10.51 Hz, 1H), 4.68 (br d, J = 13.49 Hz, 1H), 4.08-4.22 (m, 1H), 3.77 (dt, J = 2.72, 11.61 Hz, 1H), 3.19-3.28 (m, 1H), 3.07 (dd, J = 10.64, 12.98 Hz, 1H), 2.66 (s, 3H), 2.59 (s, 3H), 2.31 (s, 3H) | 465.2 |
| 106 | ¹H NMR (400 MHz, DMSO-d6) δ ppm 8.79 (s, 2 H), 7.61-7.74 (m, 3 H), 7.53 (d, J = 8.0 Hz, 1 H), 4.80 (d, J = 13.2 Hz, 1 H), 4.69 (t, J = 11.4 Hz, 2 H), 4.14 (d, J = 11.7 Hz, 1 H), 3.75 (dd, J = 12.6, 9.8 Hz, 1 H), 3.17-3.28 (m, 2 H), 2.64 (s, 3 H), 2.59 (s, 3 H), 2.31 (s, 3 H) | 465.1 |
| 107 | ¹H NMR (400 MHz, DMSO-d6) δ ppm 8.79 (s, 2 H), 7.61-7.74 (m, 3 H), 7.53 (d, J = 8.0 Hz, 1 H), 4.80 (d, J = 13.2 Hz, 1 H), 4.69 (t, J = 11.4 Hz, 2 H), 4.14 (d, J = 11.7 Hz, 1 H), 3.75 (dd, J = 12.6, 9.8 Hz, 1 H), 3.17-3.28 (m, 2 H), 2.64 (s, 3 H), 2.59 (s, 3 H), 2.31 (s, 3 H) | 465.1 |
| 108 | ¹H NMR (600 MHz, DMSO-d6) δ ppm 7.93 (s, 1H), 7.73 (s, 1H), 7.46 (s, 1H), 4.67 (br d, J = 12.17 Hz, 1H), 4.51-4.59 (m, 3H), 4.47 (dd, J = 2.54, 10.35 Hz, 1H), 3.95-4.01 (m, 1H), 3.82 (s, 3H), 3.63 (dt, J = 2.63, 11.49 Hz, 1H), 3.07-3.20 (m, 2H), 2.65-2.82 (m, 3H), 2.53-2.64 (m, 2H), 2.51 (s, 3H), 2.31 (s, 3H) | 445.2 |
| 109 | 2.17:1 mixture of trans and cis cyclobutane isomers. Major isomer: ¹H NMR (600 MHz, DMSO-d6) δ ppm 7.96 (s, 1H), 7.74 (s, 1H), 7.46 (s, 1H), 4.68 (br d, J = 12.53 Hz, 1H), 4.45-4.60 (m, 1H), 4.53 (br d, J = 6.72 Hz, 2H) 4.45-4.47 (m, 1H), 3.93-4.01 (m, 1H), 3.82 (s, 3H), 3.59-3.66 (m, 1H), 3.21-3.28 (m, 1H), 3.07-3.20 (m, 2H), 2.78-2.91 (m, 1H), 2.51 (s, 3H), 2.32 (s, 3H), 2.16-2.30 (m, 3H), 2.04-2.11 (m, 1H) | 477.2 |

TABLE 8-continued

Analytical Data for Examples 1-232

| Ex # | NMR | M + H |
|---|---|---|
| | Minor isomer: ¹H NMR (600 MHz, DMSO-d6) δ ppm 7.92 (s, 1H), 7.73 (s, 1H), 7.45 (s, 1H), 4.68 (br d, J = 12.53 Hz, 1H), 4.45-4.60 (m, 1H), 4.45-4.47 (m, 1H), 4.44 (d, J = 5.45 Hz, 2H), 3.93-4.01 (m, 1H), 3.82 (s, 3H), 3.59-3.66 (m, 1H), 3.07-3.20 (m, 3H), 2.78-2.84 (m, 1H), 2.51 (s, 3H), 2.31 (s, 3H), 2.16-2.30 (m, 4H). | |
| 110 | ¹H NMR (600 MHz, DMSO-d6) δ ppm 7.93 (s, 1H), 7.73 (s, 1H), 7.45 (s, 1H), 4.67 (br d, J = 12.17 Hz, 1H), 4.55 (br d, J = 13.08 Hz, 1H), 4.43-4.52 (m, 1H), 4.33-4.43 (m, 1H), 3.92-4.03 (m, 1H), 3.82 (s, 3H), 3.62 (dt, J = 2.54, 11.44 Hz, 1H), 3.02-3.21 (m, 2H), 2.51 (s, 3H), 2.32 (s, 3H), 2.02-2.12 (m, 1H), 1.73-1.83 (m, 1H), 1.01-1.09 (m, 2H) | 463.2 |
| 111 | ¹H NMR (600 MHz, DMSO-d6) δ ppm 7.92 (s, 1H), 7.73 (s, 1H), 7.45 (s, 1H), 4.61-4.73 (m, 2H), 4.55 (br d, J = 13.26 Hz, 1H), 4.47 (dd, J = 2.45, 10.26 Hz, 1H), 4.27-4.38 (m, 1H), 3.98 (br d, J = 11.63 Hz, 1H), 3.82 (s, 3H), 3.62 (dt, J = 2.18, 11.44 Hz, 1H), 3.06-3.19 (m, 2H), 2.51 (s, 3H), 2.33 (s, 3H), 1.11-1.20 (m, 4H), 1.08 (d, J = 1.09 Hz, 3H), 0.58 (dd, J = 4.18, 8.54 Hz, 1H), 0.34-0.42 (m, 1H) | 423.3 |
| 112 | ¹H NMR (600 MHz, DMSO-d6) δ ppm 7.97 (s, 1 H), 7.75 (s, 1 H), 7.47 (s, 1 H), 4.80 (br d, J = 11.63 Hz, 1 H), 4.68 (br s, 1 H), 4.51 (dd, J = 10.35, 2.54 Hz, 1 H), 4.31-4.40 (m, 1 H), 3.98-4.06 (m, 1 H), 3.83 (s, 3 H), 3.67 (td, J = 11.49, 2.63 Hz, 1 H), 3.09-3.28 (m, 3 H), 2.65-2.77 (m, 2 H), 2.59-2.65 (m, 2 H), 2.51-2.54 (m, 3 H), 2.34 (s, 3 H) | 447.0 |
| 113 | ¹H NMR (600 MHz, DMSO-d6) δ ppm 7.97 (s, 1 H), 7.84 (s, 1 H), 7.47 (s, 1 H), 4.79 (br d, J = 12.35 Hz, 1 H), 4.69 (br s, 1 H), 4.50 (dd, J = 10.35, 2.54 Hz, 1 H), 4.35 (quin, J = 8.22 Hz, 1 H), 3.98-4.05 (m, 1 H), 3.62-3.74 (m, 2 H), 3.13-3.24 (m, 2 H), 2.65-2.76 (m, 2 H), 2.58-2.65 (m, 2H), 2.51-2.54 (m, 3 H), 2.34 (s, 3 H), 0.90-1.08 (m, 4 H) | 473.0 |
| 114 | ¹H NMR (600 MHz, DMSO-d6) δ ppm 9.16-9.20 (m, 1 H), 8.01 (s, 1 H), 7.64 (s, 1 H), 4.94 (br d, J = 11.81 Hz, 1 H), 4.77 (br s, 1 H), 4.72 (dd, J = 10.26, 2.63 Hz, 1 H), 4.29-4.43 (m, 1 H), 4.17 (br dd, J = 11.63, 2.00 Hz, 1 H), 3.77 (td, J = 11.63, 2.54 Hz, 1 H), 3.13-3.29 (m, 2 H), 3.07 (br s, 1 H), 2.68-2.77 (m, 2 H), 2.57-2.68 (m, 5 H), 2.51-2.55 (m, 3 H), 2.33-2.39 (m, 3 H) | 459.0 |
| 115 | ¹H NMR (600 MHz, DMSO-d6) δ ppm 8.46 (d, J = 4.90 Hz, 1 H), 7.99 (s, 1 H), 7.33 (s, 1 H), 7.26 (br d, J = 4.90 Hz, 1 H), 4.90 (br d, J = 11.63 Hz, 1 H), 4.78 (br s, 1 H), 4.60 (dd, J = 10.45, 2.45 Hz, 1 H), 4.29-4.41 (m, 1 H), 4.16 (br dd, J = 11.44, 2.36 Hz, 1 H), 3.75 (td, J = 11.63, 2.54 Hz, 1 H), 3.18-3.27 (m, 2 H), 2.87-3.06 (m, 1 H), 2.52-2.75 (m, 7 H), 2.50 (s, 3 H), 2.32-2.39 (m, 3 H) | 458.0 |
| 116 | ¹H NMR (600 MHz, DMSO-d6) δ ppm 7.91 (d, J = 2.91 Hz, 1 H), 7.74 (br s, 1 H), 7.67-7.73 (m, 2 H), 7.53 (br d, J = 7.99 Hz, 1 H), 7.45 (br s, 1 H), 4.75 (br s, 1 H), 4.62 (br d, J = 13.08 Hz, 1 H), 4.52 (br d, J = 9.81 Hz, 1 H), 3.85-4.03 (m, 1 H), 3.62-3.78 (m, 1 H), 3.19-3.31 (m, 4 H), 2.68 (s, 3 H) | 472.8 |
| 117 | ¹H NMR (500 MHz, Chloroform-d) δ ppm 7.56 (s, 1H), 7.45 (s, 1H), 6.94 (s, 1H), 4.66 (dd, J = 2.72, 10.25 Hz, 1H), 4.39-4.44 (m, 1H), 4.31 (s, 2H), 4.15-4.21 (m, 1H), 4.12 (ddd, J = 1.82, 3.44, 11.61 Hz, 1H), 3.93 (s, 3H), 3.86 (dt, J = 2.72, 11.48 Hz, 1H), 3.55 (quin, J = 8.66 Hz, 1H), 3.20 (s, 3H), 3.12-3.20 (m, 1H), 3.08 (dd, J = 10.25, 12.85 Hz, 1H), 2.95-3.04 (m, 1H), 2.64-2.74 (m, 2H), 2.41-2.52 (m, 2H) | 436.0 |
| 118 | ¹H NMR (400 MHz, DMSO-d6) δ ppm 7.70 (t, J = 8.2 Hz, 1 H), 7.62 (dd, J = 10.5, 2.1 Hz, 1 H), 7.45 (d, J = 8.4 Hz, 1 H), 7.13 (s, 1 H), 4.39 (s, 2 H), 4.14-4.28 (m, 2 H), 3.92 (d, J = 11.5 Hz, 1 H), 3.52-3.64 (m, 2 H), 3.06 (s, 3 H), 2.82-2.91 (m, 1 H), 2.54-2.61 (m, 1 H), 1.17 (d, J = 6.2 Hz, 3 H) | 376.1 |
| 119 | ¹H NMR (400 MHz, Chloroform-d) δ ppm 7.67 (t, J = 7.8 Hz, 1 H), 7.51 (s, 1 H), 7.40 (s, 1 H), 7.30-7.35 (m, 1 H), 7.26-7.30 (m, 1 H), 5.00 (d, J = 14.7 Hz, 2 H), 3.91 (s, 3 H), 3.62 (t, J = 12.2 Hz, 2 H), 3.19-3.34 (m, 1 H), 2.74 (s, 3 H), 2.62 (s, 3 H), 2.21-2.39 (m, 1 H), 2.09 (dt, J = 29.8, 12.8 Hz, 1 H) | 442.1 |
| 120 | ¹H NMR (600 MHz, DMSO-d6) δ ppm 7.8-7.9 (m, 1H), 7.7-7.7 (m, 1H), 7.6-7.6 (m, 1H), 7.4-7.5 (m, 1H), 7.43 (dd, 1H, J = 2.0, 8.4 Hz), 7.2-7.2 (m, 1H), 4.5-4.6 (m, 1H), 4.40 (s, 2H), 4.35 (br d, 1H, J = 12.7 Hz), 4.21 (br d, 1H, J = 12.2 Hz), 4.0-4.0 (m, 1H), 3.6-3.7 (m, 2H), 3 3.0-3.1 (s, 3H), 3.00 (dt, 1H, J = 2.9, 12.4 Hz), 2.9-3.0 (m, 1H), 0.9-1.0 (m, 4H) | 468.0 |
| 121 | ¹H NMR (400 MHz, DMSO-d6) δ ppm 7.74 (s, 1 H), 7.70 (d, J = 8.2 Hz, 1 H), 7.62 (dd, J = 10.5, 2.1 Hz, 1 H), 7.47 (s, 1 H), 7.44 (dd, J = 8.3, 2.1 Hz, 1 H), 7.20 (s, 1 H), 4.54 (d, J = 10.4 Hz, 1 H), 4.42 (s, 2 H), 4.35 (d, J = 12.8 Hz, 1 H), 4.20 (d, J = 12.8 Hz, 1 H), 4.00 (d, J = 7.6 Hz, 1 H), 3.81 (s, 3 H), 3.42-3.79 (m, 3 H), 2.87-3.06 (m, 2 H), 1.15 (t, J = 7.2 Hz, 3 H) | 456.1 |

TABLE 8-continued

Analytical Data for Examples 1-232

| Ex # | NMR | M + H |
|---|---|---|
| 122 | $^1$H NMR (400 MHz, DMSO-d6) δ ppm 7.70-7.76 (m, 2 H), 7.62 (d, J = 10.4 Hz, 1 H), 7.46 (s, 1 H), 7.42-7.45 (m, 1 H), 7.20 (s, 1 H), 4.54 (d, J = 10.4 Hz, 1 H), 4.40-4.47 (m, 1 H), 4.33-4.38 (m, 3 H), 4.19 (d, J = 12.8 Hz, 1 H), 3.96-4.06 (m, 1 H), 3.82 (s, 3 H), 3.67-3.75 (m, 1 H), 2.86-3.06 (m, 2 H), 1.21 (d, J = 6.7 Hz, 6 H) | 470.1 |
| 123 | $^1$H NMR (400 MHz, chloroform-d) δ ppm 7.67 (t, J = 7.8 Hz, 1 H), 7.51 (s, 1 H), 7.40 (s, 1 H), 7.30-7.35 (m, 1 H), 7.26-7.30 (m, 1 H), 5.00 (d, J = 14.7 Hz, 2 H), 3.91 (s, 3 H), 3.62 (t, J = 12.2 Hz, 2 H), 3.19-3.34 (m, 1 H), 2.74 (s, 3 H), 2.62 (s, 3 H), 2.21-2.39 (m, 1 H), 2.09 (dt, J = 29.8, 12.8 Hz, 1 H) | 488.1 |
| 124 | $^1$H NMR (400 MHz, chloroform-d) δ ppm 7.67 (t, J = 7.8 Hz, 1 H), 7.51 (s, 1 H), 7.40 (s, 1 H), 7.30-7.35 (m, 1 H), 7.26-7.30 (m, 1 H), 5.00 (d, J = 14.7 Hz, 2 H), 3.91 (s, 3 H), 3.62 (t, J = 12.2 Hz, 2 H), 3.19-3.34 (m, 1 H), 2.74 (s, 3 H), 2.62 (s, 3 H), 2.21-2.39 (m, 1 H), 2.09 (dt, J = 29.8, 12.8 Hz, 1 H) | 488.1 |
| 125 | $^1$H NMR (400 MHz, chloroform-d) δ ppm 7.57 (d, J = 0.8 Hz, 1 H), 7.46 (s, 1 H), 7.42 (s, 1 H), 4.99 (d, J = 12.8 Hz, 1 H), 4.82 (d, J = 13.5 Hz, 1 H), 4.60 (dd, J = 10.3, 2.8 Hz, 1 H), 4.11 (ddd, J = 11.6, 3.6, 1.8 Hz, 1 H), 3.93 (s, 3 H), 3.80 (td, J = 11.5, 2.8 Hz, 1 H), 3.22-3.40 (m, 2 H), 3.02 (s, 2 H), 2.86-2.98 (m, 2 H), 2.71 (s, 3 H), 2.25 (tt, J = 13.7, 6.7 Hz, 2H) | 442.2 |
| 126 | $^1$H NMR (600 MHz, DMSO-d6) δ ppm 7.75 (s, 1 H), 7.46 (s, 1 H), 7.43 (br s, 1 H), 4.72 (br d, J = 12.9 Hz, 1 H), 4.60 (br d, J = 12.4 Hz, 1 H), 4.50 (br dd, J = 10.2, 1.8 Hz, 1 H), 4.01 (br d, J = 10.5 Hz, 1 H), 3.83 (s, 3 H), 3.57-3.73 (m, 1 H), 3.12-3.25 (m, 2 H), 2.81 (br s, 1 H), 2.70 (br d, J = 15.4 Hz, 2 H), 2.61-2.64 (m, 1 H), 2.60 (s, 3 H), 2.58 (s, 3 H), 2.31-2.42 (m, 1 H), 2.11 (br d, J = 10.5 Hz, 1 H), 1.59 (qd, J = 12.0, 5.3 Hz, 1 H) | 474.8 |
| 127 | $^1$H NMR (600 MHz, DMSO-d6) δ ppm 7.75 (s, 1 H), 7.46 (s, 1 H), 7.42 (br s, 1 H), 4.72 (br d, J = 12.9 Hz, 1 H), 4.60 (br d, J = 11.6 Hz, 1 H), 4.50 (br dd, J = 10.3, 2.1 Hz, 1 H), 4.01 (br d, J = 10.5 Hz, 1 H), 3.83 (s, 3 H), 3.60-3.69 (m, 1 H), 3.13-3.25 (m, 2 H), 2.84 (br d, J = 16.9 Hz, 1 H), 2.65-2.76 (m, 2 H), 2.61-2.64 (m, 1 H), 2.60 (s, 3 H), 2.58 (s, 3 H), 2.31-2.43 (m, 1 H), 2.11 (br d, J = 10.4 Hz, 1 H), 1.60 (qd, J = 12.1, 5.2 Hz, 1 H) | 474.0 |
| 128 | $^1$H NMR (400 MHz, DMSO-d6) δ ppm 7.86 (td, J = 2.8, 1.4 Hz, 1 H), 7.76 (s, 1 H), 7.47 (d, J = 0.8 Hz, 1 H), 4.73 (d, J = 12.9 Hz, 1 H), 4.61 (d, J = 13.6 Hz, 1 H), 4.50 (dd, J = 10.4, 2.7 Hz, 1 H), 3.83 (s, 3 H), 3.65 (td, J = 11.5, 2.8 Hz, 1 H), 3.18 (dt, J = 23.0, 11.4 Hz, 2 H), 2.91 (s, 2 H), 2.53-2.73 (m, 9 H), 1.92 (p, J = 7.6 Hz, 2 H) | 392.2 |
| 129 | $^1$H NMR (600 MHz, DMSO-d6) δ ppm 8.49-8.55 (m, 1 H), 7.98 (s, 1 H), 7.62-7.68 (m, 2 H), 7.53-7.58 (m, 1 H), 7.42-7.47 (m, 1 H), 7.19-7.24 (m, 1 H), 5.51-5.61 (m, 1 H), 4.87-4.94 (m, 4 H), 4.58-4.65 (m, 1 H), 4.42-4.48 (m, 1 H), 4.24-4.29 (m, 1 H), 4.01-4.09 (m, 1 H), 3.73-3.80 (m, 1 H), 3.09-3.14 (m, 1 H), 3.02-3.07 (m, 1 H), 2.63-2.68 (m, 3 H) | 481.0 |
| 130 | $^1$H NMR (400 MHz, Chloroform-d) δ ppm 7.57 (s, 1H), 7.46 (s, 1H), 5.02 (d, J = 13.5 Hz, 1H), 4.85 (d, J = 13.6 Hz, 1H), 4.62 (dd, J = 10.1, 2.8 Hz, 1H), 4.11 (d, J = 11.4 Hz, 1H), 3.93 (s, 3H), 3.76-3.89 (m, 2H), 3.35 (dd, J = 28.4, 16.1 Hz, 2H), 2.68 (d, J = 15.3 Hz, 6H), 1.91 (q, J = 12.8, 11.3 Hz, 2H), 1.76 (dd, J = 13.8, 3.6 Hz, 2H), 1.48 (td, J = 13.2, 3.9 Hz, 4H), 1.03 (d, J = 6.2 Hz, 6H) | 436.3 |
| 131 | $^1$H NMR (400 MHz, DMSO-d6) δ ppm 7.76 (s, 1 H), 7.48 (d, J = 0.8 Hz, 1 H), 4.76 (d, J = 13.5 Hz, 1 H), 4.63 (d, J = 13.5 Hz, 1 H), 4.50 (dt, J = 10.3, 2.6 Hz, 2 H), 4.01 (ddd, J = 11.5, 3.6, 1.7 Hz, 1 H), 3.90 (ddd, J = 11.5, 3.6, 1.7 Hz, 2 H), 3.83 (td, J = 11.5, 2.5 Hz, 2 H), 3.2 (dt, J = 21.8, 12.2 Hz, 3 H), 2.60 (d, J = 10.9 Hz, 6 H), 2.02-1.96 (m, 4 H), 1.76-1.67 (q, J = 13.3 Hz, 2 H), 1.50-1.45 (qd, J = 12.1, 5.3 Hz, 2 H) | 476.3 |
| 132 | $^1$H NMR (400 MHz, DMSO-d6) δ ppm 7.72 (s, 1 H), 7.42 (d, J = 0.8 Hz, 1 H), 4.72 (d, J = 13.5 Hz, 1 H), 4.61 (d, J = 13.5 Hz, 1 H), 4.50 (dt, J = 10.3, 2.6 Hz, 1 H), 4.01 (ddd, J = 11.5, 3.6, 1.7 Hz, 1 H), 3.83 (s, 3 H), 3.66 (td, J = 11.5, 2.5 Hz, 1 H), 3.19 (dt, J = 21.8, 12.2 Hz, 3 H), 2.82 (s, 1 H), 2.70 (s, 2 H), 2.60 (d, J = 10.9 Hz, 6 H), 2.36-2.48 (m, 2 H), 2.12 (d, J = 13.3 Hz, 2 H), 1.60 (qd, J = 12.1, 5.3 Hz, 2 H) | 476.3 |
| 133 | $^1$H NMR (400 MHz, chloroform-d) δ ppm 7.57 (s, 1 H), 7.46 (s, 1 H), 5.00 (s, 1 H), 4.83 (d, J = 13.4 Hz, 1 H), 4.60 (dd, J = 10.2, 2.8 Hz, 1 H), 4.08 (dd, J = 26.1, 9.5 Hz, 2 H), 3.93 (s, 3 H), 3.80 (td, J = 11.4, 2.8 Hz, 1 H), 3.33 (dd, J = 29.6, 17.4 Hz, 2 H), 2.71 (s, 3 H), 2.67 (s, 3 H), 2.21-2.34 (m, 2 H), 1.92-2.12 (m, 6 H) | 444.1 |
| 134 | $^1$H NMR (400 MHz, chloroform-d) δ ppm 7.58 (s, 1H), 7.47 (s, 1H), 5.02 (d, J = 13.5 Hz, 1H), 4.85 (d, J = 13.6 Hz, 1H), 4.61 (dd, J = 10.2, 2.8 Hz, 1H), 4.10 (d, J = 11.5 Hz, 1H), 3.93 (s, 4H), 3.81 (td, J = 11.4, 2.8 Hz, 1H), 3.33 (dd, J = 28.6, 16.1 Hz, 2H), 2.68 (d, J = 13.4 Hz, 6H), 2.03 (s, 1H), 1.87 (dt, J = 28.9, 13.0 Hz, 4H), 1.65-1.73 (m, 2H), 1.53 (t, J = 12.7 Hz, 2H), 1.36 (t, J = 12.6 Hz, 1H) | 408.2 |

TABLE 8-continued

Analytical Data for Examples 1-232

| Ex # | NMR | M + H |
|---|---|---|
| 135 | ¹H NMR (400 MHz, chloroform-d) δ ppm 7.57 (d, J = 0.7 Hz, 1H), 7.46 (s, 1H), 5.03 (d, J = 13.6 Hz, 1H), 4.85 (d, J = 13.6 Hz, 1H), 4.62 (dd, J = 10.1, 2.8 Hz, 1H), 4.11 (d, J = 11.4 Hz, 1H), 4.01 (dq, J = 9.6, 5.5, 4.7 Hz, 1H), 3.93 (s, 3H), 3.82 (td, J = 11.4, 2.8 Hz, 1H), 3.35 (dd, J = 29.3, 16.7 Hz, 2H), 2.68 (d, J = 15.3 Hz, 6H), 1.90-2.05 (m, 3H), 1.70-1.81 (m, 4H), 1.60-1.63 (m, 2H), 1.06 (d, J = 7.0 Hz, 3H) | 422.3 |
| 136 | ¹H NMR (400 MHz, Chloroform-d) δ ppm 7.58 (s, 1H), 7.46 (s, 1H), 5.01 (d, J = 13.6 Hz, 1H), 4.84 (d, J = 13.5 Hz, 1H), 4.60 (dd, J = 10.2, 2.8 Hz, 1H), 4.06-4.15 (m, 1H), 3.77-3.96 (m, 5H), 3.33 (dd, J = 28.7, 15.4 Hz, 2H), 2.68 (d, J = 14.3 Hz, 6H), 1.81-1.99 (m, 4H), 1.69-1.78 (m, 2H), 1.52 (s, 1H), 1.23 (qd, J = 12.8, 3.4 Hz, 2H), 0.99 (d, J = 6.5 Hz, 3H) | 422.3 |
| 137 | ¹H NMR (400 MHz, chloroform-d) δ ppm 7.58 (s, 1H), 7.47 (s, 1H), 5.03 (d, J = 13.5 Hz, 1H), 4.86 (d, J = 13.7 Hz, 1H), 4.60-4.68 (m, 1H), 4.11 (d, J = 11.6 Hz, 1H), 3.93 (s, 4H), 3.82 (td, J = 11.4, 2.8 Hz, 1H), 3.35 (dd, J = 28.0, 15.9 Hz, 2H), 2.69 (d, J = 12.9 Hz, 6H), 2.05 (td, J = 12.9, 3.9 Hz, 2H), 1.88 (q, J = 12.6 Hz, 4H), 1.02 (d, J = 13.1 Hz, 2H), 0.28-0.44 (m, 4H) | 434.3 |
| 138 | ¹H NMR (400 MHz, DMSO-d6) δ ppm 7.85 (s, 1 H), 7.47 (s, 1 H), 4.67-4.74 (m, 1 H), 4.61 (s, 1 H), 4.50 (dd, J = 10.3, 2.7 Hz, 1 H), 4.01 (d, J = 11.1 Hz, 2 H), 3.71 (qd, J = 7.8, 3.4 Hz, 1 H), 3.64 (dd, J = 11.5, 2.8 Hz, 1 H), 3.20 (dd, J = 11.4, 3.2 Hz, 2 H), 2.63 (s, 3 H), 2.61 (s, 3 H), 2.13 (d, J = 14.9 Hz, 3 H), 1.99 (d, J = 12.5 Hz, 3 H), 1.90 (t, J = 11.4 Hz, 2 H), 1.00-1.08 (m, 2 H), 0.92-1.00 (m, 2 H) | 470.3 |
| 139 | ¹H NMR (400 MHz, DMSO-d6) δ ppm 8.54 (d, J = 5.2 Hz, 1 H), 7.32 (s, 1 H), 7.26 (s, 1 H), 5.11 (s, 1 H), 4.92 (d, J = 14.0 Hz, 1 H), 4.57 (dd, J = 10.5, 2.8 Hz, 1 H), 4.21 (d, J = 11.6 Hz, 1 H), 4.00-4.11 (m, 1 H), 3.83 (td, J = 11.7, 2.8 Hz, 1 H), 3.30 (t, J = 12.3 Hz, 1 H), 3.02 (s, 1 H), 2.72 (s, 3 H), 2.74-2.62 (m, 1 H), 2.67 (s, 3 H), 2.63 (s, 3 H), 2.27 (d, J = 15.3 Hz, 2 H), 2.05 (s, 5 H) | 455.1 |
| 140 | ¹H NMR (400 MHz, DMSO-d6) δ ppm 7.76 (s, 1 H), 7.47 (s, 1 H), 4.73 (d, J = 12.7 Hz, 1 H), 4.62 (s, 1 H), 4.51 (dd, J = 10.4, 2.7 Hz, 1 H), 4.29 (p, J = 7.9 Hz, 1 H), 4.01 (ddd, J = 11.4, 3.5, 1.7 Hz, 1 H), 3.83 (s, 3H), 3.66 (td, J = 11.5, 2.8 Hz, 1 H), 3.22 (ddd, J = 13.3, 11.4, 3.5 Hz, 1 H), 2.53-2.67 (m, 6 H), 2.46 (q, J = 1.8 Hz, 1 H), 2.04 (ddd, J = 13.4, 8.0, 4.4 Hz, 2 H), 1.78-1.90 (m, 6 H) | 394.3 |
| 141 | ¹H NMR (400 MHz, chloroform-d) δ ppm 8.11 (dd, J = 13.7, 8.3 Hz, 1 H), 7.57 (s, 1 H), 7.46 (s, 1 H), 7.06 (dd, J = 13.5, 8.3 Hz, 1 H), 5.05 (s, 1 H), 4.86 (d, J = 13.4 Hz, 1 H), 4.59 (dd, J = 10.2, 2.8 Hz, 1 H), 4.11 (d, J = 11.5 Hz, 1 H), 3.93 (d, J = 1.5 Hz, 3 H), 3.80 (td, J = 11.5, 2.8 Hz, 1 H), 3.34 (ddd, J = 48.1, 24.4, 11.5 Hz, 3 H), 2.87 (d, J = 11.3 Hz, 1 H), 2.73 (s, 3 H), 2.29 (dd, J = 20.2, 12.7 Hz, 2 H), 2.03 (tt, J = 43.6, 13.4 Hz, 5 H) | 429.1 |
| 142 | ¹H NMR (400 MHz, Chloroform-d) δ ppm 8.08 (d, J = 8.2 Hz, 1 H), 7.56 (s, 1 H), 7.44 (s, 1 H), 7.05 (d, J = 8.3 Hz, 1 H), 4.83 (s, 1 H), 4.57-4.62 (m, 1 H), 4.11 (d, J = 11.7 Hz, 1 H), 3.92 (d, J = 1.2 Hz, 3 H), 3.80 (t, J = 11.3 Hz, 2 H), 3.68 (d, J = 5.4 Hz, 1 H), 3.37 (d, J = 10.4 Hz, 2 H), 3.26 (s, 2 H), 2.71 (d, J = 1.2 Hz, 3 H), 2.28 (s, 1 H), 2.14 (m, 3 H), 1.87 (m, 3 H) | 461.2 |
| 143 | ¹H NMR (400 MHz, DMSO-d6) δ ppm 8.46 (d, J = 8.4 Hz, 1 H), 7.85 (s, 1 H), 7.47 (s, 1 H), 7.20 (d, J = 8.4 Hz, 1 H), 4.73 (d, J = 13.2 Hz, 1 H), 4.63 (bs, 1 H), 4.49 (d, J = 10.3 Hz, 1 H), 4.01 (d, J = 11.5 Hz, 1 H), 3.61-3.79 (m, 3 H), 3.14-3.26 (m, 2 H), 2.58 (s, 3 H), 2.10-2.21 (m, 4 H), 1.80-1.99 (m, 4 H), 1.01-1.06 (m, 2 H), 0.99-1.06 (m, 2 H) | 455.2 |
| 144 | ¹H NMR (400 MHz, Chloroform-d) δ ppm 8.10 (d, J = 8.4 Hz, 1 H), 7.57 (s, 1 H), 7.55 (s, 1 H), 7.07 (d, J = 8.4 Hz, 1 H), 5.02 (bs, 1 H), 4.87 (d, J = 13.5 Hz, 1 H), 4.57 (d, J = 10.4 Hz, 1 H), 4.10 (d, J = 11.7 Hz, 1 H), 3.79 (td, J = 11.5, 2.9 Hz, 1 H), 3.60-3.65 (m, 1H), 3.16-3.40 (m, 3 H), 2.71 (s, 3 H), 1.98-2.24 (m, 5 H), 1.82 (q, J = 13.0 Hz, 2 H), 1.65-1.80 (m, 2 H), 1.10-1.19 (m, 2 H), 1.01-1.07 (m, 2 H) | 487.1 |
| 145 | ¹H NMR (400 MHz, DMSO-d6) δ ppm 8.08 (d, J = 8.4 Hz, 1 H), 7.55 (s, 1 H), 7.52 (s, 1 H), 7.05 (d, J = 8.3 Hz, 1 H), 4.85 (bs, 1 H), 4.57 (d, J = 10.3 Hz, 1 H), 4.11 (d, J = 11.6 Hz, 1 H), 3.80 (td, J = 11.5, 2.8 Hz, 1 H), 3.68 (t, J = 5.0 Hz, 1 H), 3.52-3.63 (m, 1 H), 3.34 (t, J = 12.1 Hz, 1 H), 3.16-3.30 (m, 2 H), 2.71 (s, 3 H), 2.13-2.22 (m, 1 H), 2.01-2.11 (m, 4 H), 1.78-1.96 (m, 4 H), 1.10-1.19 (m, 2 H), 1.01-1.07 (m, 2 H) | 487.1 |
| 146 | ¹H NMR (Chloroform-d, 500 MHz) δ 7.5-7.6 (m, 1H), 7.45 (s, 1H), 5.03 (br d, 1H, J = 12.8 Hz), 4.8-4.9 (m, 1H), 4.61 (dd, 1H, J = 2.8, 10.2 Hz), 4.4-4.6 (m, 1H), 4.13 (br d, 1H, J = 10.4 Hz), 3.93 (s, 3H), 3.81 (dt, 1H, J = 2.9, 11.5 Hz), 3.38 (ddd, 1H, J = 3.5, 11.3, 13.5 Hz), 3.2-3.3 (m, 1H), 3.0-3.1 (m, 4H), 2.71 (s, 3H), 2.65 (s, 3H) | 416.0 |
| 147 | ¹H NMR (500 MHz, Chloroform-d) δ ppm 7.55-7.58 (m, 1 H), 7.48-7.53 (m, 2 H), 7.44-7.48 (m, 2 H), 7.29-7.33 (m, 1 H), 7.28-7.29 | 437.0 |

TABLE 8-continued

Analytical Data for Examples 1-232

| Ex # | NMR | M + H |
|---|---|---|
| | (m, 1 H), 7.25-7.28 (m, 1 H), 7.07-7.11 (m, 1 H), 6.78-6.83 (m, 1 H), 4.70-4.75 (m, 1 H), 4.30-4.35 (m, 1 H), 4.12-4.17 (m, 1 H), 4.05-4.12 (m, 1 H), 3.93-3.98 (m, 1 H), 3.90-3.93 (m, 3 H), 3.09-3.17 (m, 1 H), 3.00-3.07 (m, 1 H), 2.47-2.51 (m, 3 H) | |
| 148 | $^1$H NMR (500 MHz, DMSO-d6) δ ppm 7.73-7.79 (m, 2 H), 7.59-7.67 (m, 2 H), 7.47-7.51 (m, 2 H), 7.13-7.18 (m, 2 H), 4.55-4.61 (m, 1 H), 4.38 (br d, J = 12.2 Hz, 1 H), 4.14-4.22 (m, 1 H), 3.99-4.07 (m, 1 H), 3.79-3.84 (m, 3 H), 3.71-3.78 (m, 1 H), 3.01-3.08 (m, 1 H), 2.93-3.00 (m, 1 H), 2.59-2.65 (m, 3 H) | 438.0 |
| 149 | $^1$H NMR (600 MHz, DMSO-d6) δ ppm 8.15-8.18 (m, 1 H), 7.75-7.80 (m, 1 H), 7.60-7.67 (m, 2 H), 7.48-7.52 (m, 1 H), 7.19-7.23 (m, 1 H), 7.14-7.18 (m, 1 H), 7.08-7.12 (m, 1 H), 6.88-6.93 (m, 1 H), 4.64-4.70 (m, 1 H), 4.46-4.51 (m, 1 H), 4.25-4.31 (m, 1 H), 4.13-4.19 (m, 1 H), 3.86-3.88 (m, 3 H), 3.79-3.84 (m, 1 H), 3.04-3.11 (m, 1 H), 2.80-2.86 (m, 1 H), 2.60-2.63 (m, 3 H) | 465.0 |
| 150 | $^1$H NMR (600 MHz, DMSO-d6) δ ppm 7.83-7.88 (m, 1 H), 7.73-7.80 (m, 1 H), 7.58-7.67 (m, 2 H), 7.44-7.52 (m, 2 H), 7.13-7.21 (m, 2 H), 4.53-4.59 (m, 1 H), 4.32-4.40 (m, 1 H), 4.18-4.25 (m, 1 H), 3.98-4.08 (m, 1 H), 3.71-3.77 (m, 1 H), 3.66-3.71 (m, 1 H), 2.99-3.08 (m, 1 H), 2.94-2.99 (m, 1 H), 2.59-2.64 (m, 3 H), 0.99-1.05 (m, 2 H), 0.92-0.97 (m, 2 H) | 464.0 |
| 151 | $^1$H NMR (600 MHz, DMSO-d6) δ ppm 8.43-8.46 (m, 1 H), 7.77 (dd, J = 8.4, 2.9 Hz, 1 H), 7.61-7.68 (m, 2 H), 7.48 (s, 1 H), 7.36-7.40 (m, 1 H), 7.28-7.31 (m, 1 H), 7.21-7.24 (m, 1 H), 7.15-7.18 (m, 1 H), 4.65-4.68 (m, 1 H), 4.46-4.51 (m, 1 H), 4.27-4.33 (m, 1 H), 4.13-4.19 (m, 1 H), 3.78-3.85 (m, 1 H), 3.04-3.11 (m, 1 H), 2.79-2.87 (m, 1 H), 2.60-2.64 (m, 3 H), 2.47-2.50 (m, 3 H) | 449.0 |
| 152 | $^1$H NMR (600 MHz, DMSO-d6) δ ppm 7.73-7.77 (m, 1 H), 7.62-7.65 (m, 1 H), 7.57-7.61 (m, 1 H), 7.54-7.56 (m, 1 H), 7.46-7.49 (m, 2 H), 7.13-7.16 (m, 1 H), 4.55-4.60 (m, 1 H), 4.33-4.38 (m, 1 H), 4.13-4.18 (m, 1 H), 4.00-4.05 (m, 1 H), 3.81-3.83 (m, 3 H), 3.72-3.78 (m, 1 H), 2.99-3.05 (m, 1 H), 2.92-2.97 (m, 1 H), 2.58-2.61 (m, 3 H), 2.30-2.34 (m, 3 H) | 452.0 |
| 153 | $^1$H NMR (400 MHz, DMSO-d6) δ ppm 8.69 (d, J = 2.7 Hz, 1H), 7.76 (s, 1H), 7.66 (dd, J = 9.8, 2.0 Hz, 1H), 7.59 (t, J = 8.2 Hz, 1H), 7.46-7.55 (m, 3H), 7.21 (d, J = 2.4 Hz, 1H), 4.61 (dd, J = 10.4, 2.6 Hz, 1H), 4.15 (dd, J = 12.6, 2.7 Hz, 1H), 4.01-4.08 (m, 1H), 3.93 (d, J = 12.6 Hz, 1H), 3.82 (s, 4H), 3.04 (td, J = 12.1, 3.6 Hz, 1H), 2.95 (dd, J = 12.6, 10.5 Hz, 1H), 2.67 (s, 3H) | 438.1 |
| 154 | $^1$H NMR (400 MHz, DMSO-d6) δ ppm 8.68 (d, J = 2.7 Hz, 1H), 8.44 (d, J = 5.1 Hz, 1H), 7.62 (td, J = 8.6, 6.6 Hz, 1H), 7.56 (d, J = 2.5 Hz, 1H), 7.48 (td, J = 9.8, 2.6 Hz, 1H), 7.40 (s, 1H), 7.26-7.36 (m, 2H), 7.24 (d, J = 2.3 Hz, 1H), 4.69 (dd, J = 10.5, 2.7 Hz, 1H), 4.28 (d, J = 12.4 Hz, 1H), 4.13-4.22 (m, 1H), 4.00 (d, J = 12.7 Hz, 1H), 3.85 (td, J = 11.7, 2.7 Hz, 1H), 3.07 (td, J = 12.2, 3.6 Hz, 1H), 2.80 (dd, J = 12.5, 10.6 Hz, 1H), 2.67 (s, 3H), 2.49 (s, 3H) | 433.2 |
| 155 | $^1$H NMR (500 MHz, DMSO-d6) δ ppm 8.76-8.80 (m, 1 H), 7.74-7.77 (m, 1 H), 7.67-7.73 (m, 2 H), 7.55-7.59 (m, 1 H), 7.47-7.53 (m, 2 H), 7.41-7.44 (m, 1 H), 7.21-7.24 (m, 1 H), 4.60-4.67 (m, 1 H), 4.47-4.56 (m, 2 H), 4.01-4.07 (m, 1 H), 3.81-3.83 (m, 3 H), 3.68-3.75 (m, 1 H), 3.14-3.20 (m, 1 H), 3.06-3.12 (m, 1 H) | 424.0 |
| 156 | $^1$H NMR (600 MHz, DMSO-d6) δ ppm 7.75-7.76 (m, 1 H), 7.65-7.68 (m, 1 H), 7.58-7.60 (m, 1 H), 7.54-7.57 (m, 1 H), 7.48-7.51 (m, 2 H), 7.32-7.34 (m, 1 H), 7.11-7.14 (m, 1 H), 4.58-4.64 (m, 1 H), 4.54 (dd, J = 10.5, 2.5 Hz, 1 H), 4.45-4.50 (m, 1 H), 4.02-4.05 (m, 1 H), 3.82-3.84 (m, 3 H), 3.69-3.74 (m, 1 H), 3.12-3.17 (m, 1 H), 3.06-3.11 (m, 1 H), 2.57-2.59 (m, 3 H) | 438.0 |
| 157 | $^1$H NMR (600 MHz, DMSO-d6) δ ppm 7.74 (s, 1H), 7.65 (dd, J = 1.91, 9.63 Hz, 1H), 7.53 (t, J = 8.17 Hz, 1H), 7.49 (dd, J = 2.00, 8.27 Hz, 1H), 7.47 (s, 1H), 7.40 (br s, 1H), 7.28 (s, 1H), 4.49-4.60 (m, 2H), 4.42 (br d, J = 12.90 Hz, 1H), 3.98-4.05 (m, 1H), 3.82 (s, 3H), 3.70 (dt, J = 2.54, 11.44 Hz, 1H), 3.07-3.14 (m, 1H), 3.04 (dd, J = 10.31, 12.67 Hz, 1H), 2.54 (s, 3H), 2.27 (s, 3H) | 452.2 |
| 158 | $^1$H NMR (500 MHz, DMSO-d6) δ ppm 8.43-8.47 (m, 1 H), 7.74-7.76 (m, 1 H), 7.55-7.61 (m, 3 H), 7.47-7.50 (m, 1 H), 7.43-7.46 (m, 1 H), 4.61-4.67 (m, 1 H), 4.48-4.56 (m, 2 H), 4.01-4.06 (m, 1 H), 3.80-3.84 (m, 3 H), 3.67-3.73 (m, 1 H), 3.16-3.23 (m, 1 H), 3.10-3.16 (m, 1 H), 2.60-2.62 (m, 3 H) | 439.0 |
| 159 | $^1$H NMR (500 MHz, DMSO-d6) δ ppm 8.72 (s, 1 H), 7.75 (s, 1 H), 7.64 (s, 1 H), 7.54-7.61 (m, 2 H), 7.48 (s, 1 H), 7.45 (dd, J = 8.2, 1.9 Hz, 1 H), 4.61 (br d, J = 12.2 Hz, 1 H), 4.55 (dd, J = 10.4, 2.6 Hz, 1 H), 4.50 (br d, J = 13.8 Hz, 1 H), 3.97-4.11 (m, 1 H), 3.82 (s, 3 H), 3.71 (td, J = 11.6, 2.7 Hz, 1 H), 3.07-3.22 (m, 2 H), 2.51 (s, 3 H) | 439.0 |
| 160 | $^1$H NMR (500 MHz, DMSO-d6) δ ppm 7.75 (s, 1H), 7.58 (dd, J = 9.6, 2.08 Hz, 1H), 7.57 (t, J = 8.04 Hz, 1H), 7.52 (s, 1H), 7.48 (s, 1H), 7.44 (dd, J = 2.08, 8.30 Hz, 1H), 4.59 (br d, J = 13.23 Hz, 1H), 4.54 (dd, | 453.0 |

TABLE 8-continued

Analytical Data for Examples 1-232

| Ex # | NMR | M + H |
|---|---|---|
| | J = 2.59, 10.38 Hz, 1H), 4.47 (br d, J = 14.01 Hz, 1H), 3.99-4.08 (m, 1H), 3.82 (s, 3H), 3.70 (dt, J = 2.72, 11.61 Hz, 1H), 3.12-3.19 (m, 1H), 3.09 (br dd, J = 10.38, 12.98 Hz, 1H), 2.60 (s, 3H), 2.48 (s, 4H) | |
| 161 | $^1$H NMR (500 MHz, DMSO-d6) δ ppm 7.75 (s, 1 H), 7.54-7.62 (m, 2 H), 7.52 (s, 1 H), 7.48 (s, 1 H), 7.44 (dd, J = 8.2, 1.9 Hz, 1 H), 4.56-4.63 (m, 1 H), 4.54 (dd, J = 10.3, 2.7 Hz, 1 H), 4.40-4.51 (m, 1 H), 4.00-4.06 (m, 1 H), 3.82 (s, 3 H), 3.70 (td, J = 11.5, 2.6 Hz, 1 H), 3.05-3.19 (m, 2 H), 2.60 (s, 3 H), 2.48 (s, 3 H) | 437.2 |
| 162 | $^1$H NMR (400 MHz, Methanol-d4) δ ppm 7.71 (s, 1H), 7.58 (d, J = 2.3 Hz, 2H), 7.45-7.51 (m, 1H), 7.29-7.35 (m, 3H), 4.77 (dd, J = 10.2, 2.7 Hz, 1H), 4.14 (ddd, J = 11.5, 3.4, 1.8 Hz, 1H), 3.88-4.00 (m, 5H), 3.74-3.81 (m, 1H), 3.09 (td, J = 11.7, 3.5 Hz, 1H), 3.00 (dd, J = 12.2, 10.3 Hz, 1H), 2.70 (s, 3H), 2.59 (s, 3H) | 452.1 |
| 163 | $^1$H NMR (400 MHz, Methanol-d4) δ ppm 7.68 (s, 1 H), 7.61 (d, J = 2.2 Hz, 1 H), 7.55 (s, 1 H), 6.64 (s, 1 H), 6.45 (b s, 1 H), 4.63 (dd, J = 10.3, 2.7 Hz, 1 H), 4.50 (dd, J = 10.3, 2.7 Hz, 1 H), 4.39 (d, J = 13.0 Hz, 1 H), 4.22 (d, J = 13.0 Hz, 1 H), 3.95 (s, 3 H), 3.89 (s, 3 H), 3.80 (td, J = 11.6, 2.9 Hz, 1 H), 3.48 (s, 3 H), 3.05-3.22 (m, 2 H), 2.60 (s, 3 H) | 463.1 |
| 164 | $^1$H NMR (400 MHz, DMSO-d6) δ ppm 7.77 (s, 1H), 7.61 (d, J = 2.8 Hz, 1H), 7.49-7.57 (m, 2H), 7.31-7.38 (m, 2H), 7.17-7.23 (m, 1H), 4.63 (dd, J = 10.3, 2.6 Hz, 1H), 4.04 (t, J = 11.5 Hz, 2H), 3.82 (s, 5H), 2.90-2.99 (m, 1H), 2.85 (dd, J = 12.2, 10.4 Hz, 1H), 2.62 (s, 3H), 2.51 (s, 3H) | 436.1 |
| 165 | $^1$H NMR (400 MHz, DMSO-d6) δ ppm 7.76 (s, 1H), 7.47 (d, J = 3.3 Hz, 1H), 5.79 (s, 2H), 4.59-4.80 (m, 2H), 4.51 (dt, J = 10.2, 2.4 Hz, 2H), 3.19-3.24 (s, 3H), 3.91-4.10 (m, 2H), 3.78 (s, 2H), 2.54-2.73 (m, 6H), 2.15-2.7 (m, 1H), 2.17-2.38 (m, 3H), 1.71-1.98 (m, 3H) | 442.3 |
| 166 | $^1$H NMR (500 MHz, DMSO-d6) δ ppm 7.75 (s, 1H), 7.71 (dt, J = 6.62, 8.37 Hz, 1H), 7.59 (br dd, J = 0.78, 3.11 Hz, 1H), 7.50 (ddd, J = 2.59, 9.47, 10.25 Hz, 1H), 7.46 (s, 1H), 7.32 (dt, J = 2.08, 8.43 Hz, 1H), 4.67-4.83 (m, 1H), 4.60 (br d, J = 13.49 Hz, 1H), 4.52 (br dd, J = 2.47, 10.51 Hz, 1H), 3.93-4.08 (m, 1H), 3.82 (s, 3H), 3.59-3.73 (m, 1H), 3.11-3.25 (m, 2H), 2.57 (s, 3H), 2.30 (s, 3H) | 437.0 |
| 167 | $^1$H NMR (500 MHz, DMSO-d6) δ ppm 7.81 (dd, J = 8.3, 3.2 Hz, 1 H), 7.69-7.78 (m, 2 H), 7.48-7.54 (m, 1 H), 7.46 (s, 1 H), 7.32 (td, J = 8.4, 2.5 Hz, 1 H), 7.19 (d, J = 8.4 Hz, 1 H), 4.70-4.84 (m, 1 H), 4.64 (br d, J = 13.9 Hz, 1 H), 4.52 (dd, J = 10.3, 2.3 Hz, 1 H), 4.01 (br d, J = 13.0 Hz, 1 H), 3.82 (s, 3 H), 3.60-3.72 (m, 1 H), 3.13-3.27 (m, 2 H), 2.88 (q, J = 7.6 Hz, 2 H), 1.29 (t, J = 7.5 Hz, 3 H) | 437.2 |
| 168 | $^1$H NMR (500 MHz, DMSO-d6) δ ppm 8.45 (d, J = 5.19 Hz, 1H), 7.72 (td, J = 8.43, 6.62 Hz, 1H), 7.60 (d, J = 2.47 Hz, 1H), 7.51 (td, J = 9.86, 2.47 Hz, 1H), 7.37-7.29 (m, 2H), 7.25 (br d, J = 4.93 Hz, 1H), 4.83 (br d, J = 12.20 Hz, 1H), 4.71-4.59 (m, 2H), 4.14 (br d, J = 11.16 Hz, 1H), 3.78-3.71 (m, 1H), 3.26-3.19 (m, 1H), 2.98 (br t, J = 12.07 Hz, 1H), 2.58 (s, 3H), 2.45 (s, 3H), 2.30 (s, 3H) | 448.2 |
| 169 | $^1$H NMR (500 MHz, DMSO-d6) δ ppm 7.83 (s, 1H), 7.70 (dt, J = 6.62, 8.37 Hz, 1H), 7.59 (dd, J = 0.78, 3.63 Hz, 1H), 7.50 (dt, J = 2.34, 9.86 Hz, 1H), 7.46 (s, 1H), 7.32 (dt, J = 2.21, 8.37 Hz, 1H), 4.66-4.79 (m, 1H), 4.60 (br d, J = 13.75 Hz, 1H), 4.50 (dd, J = 2.47, 10.25 Hz, 1H), 3.93-4.05 (m, 1H), 3.59-3.74 (m, 2H), 3.10-3.25 (m, 2H), 2.57 (s, 3H), 2.29 (s, 3H), 0.97-1.06 (m, 2H), 0.88-0.97 (m, 2H) | 463.0 |
| 170 | $^1$H NMR (400 MHz, DMSO-d6) δ ppm 9.00 (s, 1 H), 7.78-7.84 (m, 1 H), 7.74 (s, 1 H), 7.70 (d, J = 9.9 Hz, 1 H), 7.55 (d, J = 8.3 Hz, 1 H), 7.40 (s, 1 H), 4.53 (d, J = 9.9 Hz, 1 H), 4.16-4.08 (m, 1 H), 3.74-3.62 (m, 2 H), 3.56-3.45 (m, 1 H), 2.82 (s, 3 H), 2.31 (d, J = 13.2 Hz, 1 H), 2.08 (d, J = 13.1 Hz, 1 H), 1.87-1.99 (m, 2 H), 1.06-0.96 (m, 2 H), 0.94-0.83 (m, 2 H) | 465.2 |
| 171 | $^1$H NMR (500 MHz, Chloroform-d) δ ppm 8.84 (s, 1 H), 8.47 (d, J = 5.2 Hz, 1 H), 7.70 (t, J = 7.8 Hz, 1 H), 7.38 (dd, J = 8.3, 1.7 Hz, 1 H), 7.32 (dd, J = 9.5, 1.8 Hz, 1 H), 7.25 (s, 1 H), 7.14 (br d, J = 4.8 Hz, 1 H), 4.51-4.66 (m, 1 H), 4.33-4.49 (m, 1 H), 3.79-3.91 (m, 1 H), 3.65 (ddd, J = 15.8, 11.9, 3.8 Hz, 1 H), 2.91 (s, 3 H), 2.57 (s, 3 H), 2.48 (br d, J = 13.2 Hz, 1 H), 2.22-2.32 (m, 2 H), 2.04-2.14 (m, 1 H) | 450.0 |
| 172 | $^1$H NMR (500 MHz, Chloroform-d) δ ppm 8.84 (s, 1 H), 8.48 (d, J = 5.2 Hz, 1 H), 7.67-7.74 (m, 1 H), 7.39 (dd, J = 8.2, 1.6 Hz, 1 H), 7.33 (dd, J = 9.5, 1.9 Hz, 1 H), 7.27-7.28 (m, 1 H), 7.18 (br d, J = 4.7 Hz, 1 H), 4.58 (dd, J = 11.4, 1.8 Hz, 1 H), 4.33-4.47 (m, 1 H), 3.83-3.89 (m, 1 H), 3.56-3.72 (m, 1 H), 2.91 (s, 3 H), 2.60 (s, 3 H), 2.49 (br dd, J = 13.3, 1.9 Hz, 1 H), 2.25-2.32 (m, 2 H), 2.03-2.17 (m, 1 H) | 450.6 |

TABLE 8-continued

Analytical Data for Examples 1-232

| Ex # | NMR | M + H |
|---|---|---|
| 173 | ¹H NMR (600 MHz, DMSO-d6) δ 8.98 (s, 1H), 8.71 (s, 1H), 7.77 (t, J = 7.90 Hz, 1H), 7.66 (dd, J = 1.73, 9.72 Hz, 1H), 7.52 (dd, J = 1.73, 8.27 Hz, 1H), 4.70 (br d, J = 11.44 Hz, 1H), 4.24 (br dd, J = 4.18, 10.90 Hz, 1H), 4.10 (q, J = 5.21 Hz, 2H), 3.75-3.85 (m, 1H), 3.59 (tdd, J = 3.95, 8.08, 11.99 Hz, 1H), 2.80 (s, 3H), 2.60 (s, 3H), 2.40 (br dd, J = 1.36, 12.99 Hz, 1H), 2.15 (br d, J = 13.44 Hz, 1H), 2.02 (dq, J = 4.54, 12.53 Hz, 1H), 1.89 (q, J = 11.99 Hz, 1H) | 451.2 |
| 174 | ¹H NMR (600 MHz, DMSO-d6) δ 8.98 (s, 1H), 8.70-8.71 (m, 1H), 7.78 (t, J = 7.99 Hz, 1H), 7.66 (dd, J = 1.73, 9.72 Hz, 1H), 7.52 (dd, J = 1.82, 8.17 Hz, 1H), 4.70 (br d, J = 11.26 Hz, 1H), 4.25 (br dd, J = 4.18, 10.90 Hz, 1H), 3.77-3.84 (m, 1H), 3.59 (tt, J = 3.63, 11.90 Hz, 1H), 2.80 (s, 3H), 2.60 (s, 3H), 2.41 (br d, J = 12.90 Hz, 1H), 2.15 (br d, J = 13.26 Hz, 1H), 2.02 (dq, J = 4.45, 12.62 Hz, 1H), 1.89 (q, J = 11.93 Hz, 1H), 1.12 (br t, J = 7.08 Hz, 1H) | 451.2 |
| 175 | ¹H NMR (400 MHz, Chloroform-d) δ ppm 7.54 (s, 1 H), 7.44 (s, 1 H), 4.59 (d, J = 11.4 Hz, 1 H), 4.28 (d, J = 11.2 Hz, 1 H), 4.18 (t, J = 11.7 Hz, 1 H), 3.90 (s, 3 H), 3.79-3.86 (m, 1 H), 3.41-3.52 (m, 1 H), 2.84 (s, 3 H), 2.80 (s, 3 H), 2.42 (d, J = 13.5 Hz, 1 H), 2.32 (d, J = 8.2 Hz, 2 H), 2.96-2.23 (m, 9 H) | 443.3 |
| 176 | ¹H NMR (400 MHz, Chloroform-d) δ ppm 7.54 (s, 1 H), 7.44 (s, 1 H), 4.59 (d, J = 11.4 Hz, 1 H), 4.28 (d, J = 11.2 Hz, 1 H), 4.18 (t, J = 11.7 Hz, 1 H), 3.92 (s, 3 H), 3.77-3.89 (m, 1 H), 3.41-3.52 (m, 1 H), 2.84 (s, 3 H), 2.80 (s, 3 H), 2.42 (d, J = 13.5 Hz, 1 H), 2.32 (d, J = 8.2 Hz, 2 H), 1.99-2.20 (m, 9 H) | 443.2 |
| 177 | ¹H NMR (600 MHz, DMSO-d6) δ ppm 1.83-2.02 (m, 2 H) 2.04-2.15 (m, 1 H) 2.26-2.36 (m, 1 H)2.64-2.72 (m, 3 H) 2.74-2.85 (m, 3 H) 3.44-3.56 (m, 1 H) 3.69-3.77 (m, 1 H) 3.77-3.82 (m, 3 H)4.02-4.18 (m, 1 H) 4.49-4.60 (m, 1 H) 7.34-7.42 (m, 1 H) 7.48-7.57 (m, 1 H) 7.64-7.71 (m, 2 H) 7.73-7.81 (m, 1 H) | 453.0 |
| 178 | ¹H NMR (600 MHz, DMSO-d6) δ ppm 1.88-1.98 (m, 2 H) 2.07 (br d, J = 13.26 Hz, 1 H) 2.31 (br d, J = 12.99 Hz, 1 H) 2.66 (s, 3 H) 2.78 (s, 3 H) 3.45-3.51 (m, 1 H) 3.66-3.76 (m, 1 H) 3.78 (s, 3 H) 4.08-4.13 (m, 1 H) 4.53 (dd, J = 11.40, 1.86 Hz, 1 H) 7.38 (s, 1 H) 7.52 (dd, J = 8.27, 2.00 Hz, 1 H) 7.65 (s, 1 H) 7.67 (dd, J = 9.81, 1.91 Hz, 1 H) 7.77 (t, J = 7.95 Hz, 1 H) | 453.0 |
| 179 | ¹H NMR (500 MHz, Chloroform-d) δ ppm 7.70-7.76 (m, 1 H), 7.52 (s, 1 H), 7.40 (s, 1 H), 7.37 (dd, J = 8.3, 1.6 Hz, 1 H), 7.32 (dd, J = 9.5, 1.9 Hz, 1 H), 4.93 (dd, J = 7.7, 3.6 Hz, 1 H), 3.93-4.02 (m, 2 H), 3.91 (s, 3 H), 3.69-3.79 (m, 1 H), 2.88 (s, 3 H), 2.77-2.82 (m, 1 H), 2.76 (s, 3 H), 2.43-2.54 (m, 1 H), 2.32-2.42 (m, 1 H), 2.14-2.26 (m, 1 H) | 453.0 |
| 180 | ¹H NMR (400 MHz, DMSO-d6) δ ppm 7.79 (d, J = 7.9 Hz, 1H), 7.75 (d, J = 7.2 Hz, 1H), 7.69 (dd, J = 9.8, 2.0 Hz, 1H), 7.54 (dd, J = 8.3, 2.0 Hz, 1H), 7.39 (s, 1H), 4.52 (dd, J = 11.4, 2.1 Hz, 1H), 4.11 (dd, J = 11.1, 4.2 Hz, 1H), 3.71-3.77 (m, 1H), 3.62-3.71 (m, 1H), 3.43-3.53 (m, 1H), 2.79 (s, 3H), 2.67 (s, 3H), 2.30 (s, 2H), 1.24 (s, 2H), 0.97-1.04 (m, 2H), 0.92 (td, J = 7.3, 5.1 Hz, 2H) | 479.1 |
| 181 | ¹H NMR (400 MHz, DMSO-d6) δ ppm 7.79 (d, J = 7.9 Hz, 1H), 7.75 (d, J = 7.2 Hz, 1H), 7.69 (dd, J = 9.8, 2.0 Hz, 1H), 7.54 (dd, J = 8.3, 2.0 Hz, 1H), 7.39 (s, 1H), 4.52 (dd, J = 11.4, 2.1 Hz, 1H), 4.11 (dd, J = 11.1, 4.2 Hz, 1H), 3.71-3.77 (m, 1H), 3.62-3.71 (m, 1H), 3.43-3.53 (m, 1H), 2.79 (s, 3H), 2.67 (s, 3H), 2.30 (s, 2H), 1.24 (s, 2H), 0.97-1.04 (m, 2H), 0.92 (td, J = 7.3, 5.1 Hz, 2H) | 479.1 |
| 182 | ¹H NMR (400 MHz, DMSO-d6) δ ppm 7.77-7.88 (m, 1 H), 7.66 (s, 1 H), 7.49 (td, J = 9.9, 2.5 Hz, 1 H), 7.39 (s, 1 H), 7.33 (td, J = 8.5, 2.5 Hz, 1 H), 4.49-4.57 (m, 1 H), 4.11 (dd, J = 11.0, 4.3 Hz, 1 H), 3.79 (s, 3 H), 3.71 (d, J = 12.0 Hz, 1 H), 3.48 (t, J = 12.0 Hz, 1 H), 2.78 (s, 3 H), 2.66 (s, 3 H), 2.30 (s, 1 H), 2.07 (d, J = 13.1 Hz, 1 H), 1.88-1.99 (m, 2 H) | 437.0 |
| 183 | ¹H NMR (400 MHz, DMSO-d6) δ ppm 7.67 (s, 1 H), 7.62 (q, J = 7.8 Hz, 1 H), 7.39 (d, J = 0.8 Hz, 1 H), 7.20-7.28 (m, 2 H), 4.53 (dd, J = 11.3, 2.1 Hz, 1 H), 4.11 (d, J = 12.6 Hz, 1 H), 3.79 (s, 3 H), 3.68-3.76 (m, 1 H), 3.42-3.54 (m, 1 H), 2.78 (s, 3 H), 2.66 (s, 3 H), 2.45 (s, 3 H), 2.25-2.33 (m, 1H), 2.07 (d, J = 13.5 Hz, 1 H), 1.87-1.99 (m, 2 H) | 433.0 |
| 184 | ¹H NMR (400 MHz, DMSO-d6) δ ppm 7.67 (s, 1 H), 7.62 (q, J = 7.8 Hz, 1 H), 7.39 (d, J = 0.8 Hz, 1 H), 7.20-7.28 (m, 2 H), 4.53 (dd, J = 11.3, 2.1 Hz, 1 H), 4.11 (d, J = 12.6 Hz, 1 H), 3.79 (s, 3 H), 3.68-3.76 (m, 1 H), 3.42-3.54 (m, 1 H), 2.78 (s, 3 H), 2.66 (s, 3 H), 2.45 (s, 3 H), 2.25-2.33 (m, 1H), 2.07 (d, J = 13.5 Hz, 1 H), 1.87-1.99 (m, 2 H) | 433.0 |
| 185 | ¹H NMR (500 MHz, Chloroform-d) δ ppm 8.78 (s, 1 H), 7.61 (s, 1 H), 7.47-7.53 (m, 2 H), 7.42 (s, 1 H), 7.29-7.35 (m, 2 H), 4.59 (dd, J = 11.3, 2.1 Hz, 1 H), 4.29 (ddd, J = 11.5, 4.5, 1.4 Hz, 1 H), 3.89 (s, 3 H), 3.82 (td, J = 11.9, 2.2 Hz, 1 H), 3.43 (tt, J = 12.1, 3.7 Hz, 1 H), 2.87 (s, 3 H), 2.35 (ddt, J = 13.2, 3.7, 2.0, 2.0 Hz, 1 H), 2.15-2.27 (m, 2 H), 2.04-2.12 (m, 1 H) | 438.2 |
| 186 | ¹H NMR (500 MHz, DMSO-d6) δ ppm 7.83 (s, 1 H), 7.72 (s, 1 H), 7.61-7.67 (m, 2 H), 7.48 (dd, J = 8.3, 1.9 Hz, 1 H), 7.42 (s, 1 H), 4.95 | 452.0 |

TABLE 8-continued

Analytical Data for Examples 1-232

| Ex # | NMR | M + H |
|---|---|---|
| | (t, J = 4.7 Hz, 1 H), 3.83 (s, 3 H), 3.71-3.81 (m, 2 H), 3.47-3.57 (m, 1 H), 2.74 (s, 3 H), 2.62 (s, 3 H), 2.38-2.44 (m, 1 H), 2.25 (dt, J = 13.6, 4.9 Hz, 1 H), 2.12 (ddt, J = 17.2, 7.9, 3.8, 3.8 Hz, 1 H), 1.94-2.03 (m, 1 H) | |
| 187 | $^1$H NMR (500 MHz, DMSO-d6) δ ppm 7.79 (s, 1 H), 7.67 (s, 1 H), 7.60-7.66 (m, 2 H), 7.48 (dd, J = 8.3, 1.8 Hz, 1 H), 7.40 (s, 1 H), 4.51 (dd, J = 11.2, 1.9 Hz, 1 H), 4.08-4.15 (m, 1 H), 3.80 (s, 3 H), 3.71 (td, J = 11.6, 2.8 Hz, 1 H), 3.40 (tt, J = 11.6, 4.0 Hz, 1 H), 2.73 (s, 3 H), 2.62 (s, 3 H), 2.23 (dt, J = 13.0, 1.7 Hz, 1 H), 1.87-2.02 (m, 3 H) | 452.2 |
| 188 | $^1$H NMR (400 MHz, DMSO-d6) δ ppm 7.78 (s, 1 H), 7.63-7.70 (m, 2 H), 7.45 (ddd, J = 10.3, 9.4, 2.6 Hz, 1 H), 7.40 (d, J = 0.8 Hz, 1 H), 7.25-7.31 (m, 1 H), 4.51 (dd, J = 11.3, 2.1 Hz, 1 H), 4.11 (ddd, J = 11.3, 4.3, 1.9 Hz, 1 H), 3.79 (s, 3 H), 3.71 (td, J = 11.4, 3.2 Hz, 1 H), 3.36-3.46 (m, 1 H), 2.73 (s, 3 H), 2.61 (s, 3 H), 2.22 (ddt, J = 13.0, 3.8, 1.9 Hz, 1 H), 1.94-2.01 (m, 3 H) | 436.0 |
| 189 | $^1$H NMR (400 MHz, DMSO-d6) δ ppm 7.73 (s, 1 H), 7.67 (s, 1 H), 7.46 (t, J = 7.7 Hz, 1 H), 7.40 (s, 1 H), 7.16-7.24 (m, 2 H), 4.50 (dd, J = 11.3, 2.1 Hz, 1 H), 4.11 (dt, J = 11.4, 2.8 Hz, 1 H), 3.79 (s, 3 H), 3.70 (td, J = 11.3, 3.4 Hz, 1 H), 3.36-3.46 (m, 1 H), 2.72 (s, 3 H), 2.60 (s, 3 H), 2.43 (s, 3 H), 2.21 (d, J = 13.1 Hz, 1 H), 1.88-2.02 (m, 3 H) | 432.1 |
| 190 | $^1$H NMR (400 MHz, DMSO-d6) δ ppm 7.73 (s, 1 H), 7.67 (s, 1 H), 7.46 (t, J = 7.7 Hz, 1 H), 7.40 (s, 1 H), 7.16-7.24 (m, 2 H), 4.50 (dd, J = 11.3, 2.1 Hz, 1 H), 4.11 (dt, J = 11.4, 2.8 Hz, 1 H), 3.79 (s, 3 H), 3.70 (td, J = 11.3, 3.4 Hz, 1 H), 3.36-3.46 (m, 1 H), 2.72 (s, 3 H), 2.60 (s, 3 H), 2.43 (s, 3 H), 2.21 (d, J = 13.1 Hz, 1 H), 1.88-2.02 (m, 3 H) | 432.1 |
| 191 | $^1$H NMR (500 MHz, DMSO-d6) δ ppm 8.89 (s, 1 H), 7.88 (s, 1 H), 7.69 (t, J = 8.0 Hz, 1 H), 7.66 (s, 1 H), 7.60 (dd, J = 9.7, 2.1 Hz, 1 H), 7.48 (dd, J = 8.3, 2.1 Hz, 1 H), 7.39 (s, 1 H), 4.52 (dd, J = 11.2, 1.9 Hz, 1 H), 4.04-4.16 (m, 1 H), 3.79 (s, 3 H), 3.72 (td, J = 11.6, 2.8 Hz, 1 H), 3.32-3.41 (m, 1 H), 2.77 (s, 3 H), 2.23 (dt, J = 13.0, 1.6 Hz, 1 H), 1.84-2.01 (m, 3 H) | 438.0 |
| 192 | $^1$H NMR (600 MHz, DMSO-d6) δ ppm 7.84 (s, 1 H), 7.63-7.69 (m, 2 H), 7.59 (dd, J = 9.7, 1.9 Hz, 1 H), 7.47 (dd, J = 8.2, 1.9 Hz, 1 H), 7.39 (s, 1 H), 4.51 (dd, J = 11.3, 1.5 Hz, 1 H), 4.06-4.13 (m, 1 H), 3.79 (s, 3 H), 3.71 (td, J = 11.7, 2.3 Hz, 1 H), 3.32-3.38 (m, 1 H), 2.74 (s, 3 H), 2.63 (s, 3 H), 2.21 (br dd, J = 12.9, 1.3 Hz, 1 H), 1.84-2.01 (m, 3 H) | 452.0 |
| 193 | $^1$H NMR (600 MHz, DMSO-d6) δ ppm 7.84 (s, 1 H), 7.63-7.70 (m, 2 H), 7.59 (dd, J = 9.5, 1.2 Hz, 1 H), 7.47 (dd, J = 8.4, 1.3 Hz, 1 H), 7.39 (s, 1 H), 4.51 (br d, J = 11.1 Hz, 1 H), 4.10 (br dd, J = 11.1, 3.5 Hz, 1 H), 3.79 (s, 3 H), 3.67-3.74 (m, 1 H), 3.32-3.37 (m, 1 H), 2.74 (s, 3 H), 2.63 (s, 3 H), 2.22 (br dd, J = 13.1, 0.7 Hz, 1 H), 1.83-2.00 (m, 3 H) | 452.0 |
| 194 | $^1$H NMR (600 MHz, DMSO-d6) δ ppm 7.92 (s, 1 H), 7.66-7.71 (m, 2 H), 7.60 (dd, J = 9.7, 1.9 Hz, 1 H), 7.48 (dd, J = 8.2, 1.8 Hz, 1 H), 7.40 (s, 1 H), 4.82-5.01 (m, 1 H), 3.83 (s, 3 H), 3.74 (t, J = 5.4 Hz, 2 H), 3.42-3.50 (m, 1 H), 2.74 (s, 3 H), 2.63 (s, 3 H), 2.38-2.44 (m, 1 H), 2.20-2.30 (m, 1 H), 2.02-2.14 (m, 1 H), 1.90-2.01 (m, 1 H) | 452.0 |
| 195 | $^1$H NMR (400 MHz, DMSO-d6) δ ppm 7.83 (s, 1H), 7.68-7.73 (m, 1H), 7.66 (s, 1H), 7.37-7.44 (m, 2H), 7.22-7.30 (m, 1H), 4.51 (dd, J = 11.2, 2.1 Hz, 1H), 4.10 (ddd, J = 11.4, 4.4, 1.8 Hz, 1H), 3.78 (s, 3H), 3.71 (td, J = 11.4, 3.0 Hz, 1H), 3.30 (s, 1H), 2.73 (s, 3H), 2.62 (s, 3H), 2.21 (ddt, J = 13.0, 4.0, 1.9 Hz, 1H), 1.86-1.97 (m, 3H) | 436.0 |
| 196 | $^1$H NMR (400 MHz, Chloroform-d) δ ppm 7.71 (s, 1H), 7.57 (t, J = 7.6 Hz, 1H), 7.52 (s, 1H), 7.41 (s, 1H), 7.15 (d, J = 7.9 Hz, 1H), 7.05 (d, J = 10.8 Hz, 1H), 4.60 (dd, J = 11.3, 2.1 Hz, 1H), 4.26-4.32 (m, 1H), 3.90 (s, 3H), 3.84 (td, J = 11.7, 2.7 Hz, 1H), 3.38 (ddt, J = 11.8, 7.5, 3.8 Hz, 1H), 2.78 (s, 3H), 2.70 (s, 3H), 2.48 (s, 3H), 2.39-2.46 (m, 1H), 1.98-2.13 (m, 3H) | 432.0 |
| 197 | $^1$H NMR (400 MHz, Chloroform-d) δ ppm 8.14 (dd, J = 8.5, 3.5 Hz, 1 H), 7.70-7.79 (m, 3 H), 7.55-7.63 (m, 2 H), 7.39 (s, 1 H), 4.51 (dd, J = 11.4, 2.1 Hz, 1 H), 4.05-4.16 (m, 1 H), 3.62-3.77 (m, 2 H), 3.45 (tt, J = 11.9, 3.8 Hz, 1 H), 2.76 (s, 3 H), 2.26-2.37 (m, 1 H), 2.06 (d, J = 13.1 Hz, 1 H), 1.85-2.02 (m, 2 H), 0.98-1.05 (m, 2 H), 0.88-0.97 (m, 2 H) | 464.1 |
| 198 | $^1$H NMR (400 MHz, DMSO-d6) δ ppm 7.93 (s, 1 H), 7.70-7.77 (m, 3 H), 7.57 (d, J = 8.3 Hz, 1 H), 7.39 (s, 1 H), 4.51 (d, J = 11.4 Hz, 1 H), 4.07-4.16 (m, 1 H), 3.62-3.77 (m, 2 H), 3.35-3.50 (m, 1 H), 2.71 (s, 3 H), 2.44 (s, 3 H), 2.29 (d, J = 13.0 Hz, 1 H), 2.01-2.12 (m, 1 H), 1.90-2.00 (m, 2 H), 0.98-1.05 (m, 2 H), 0.89-0.98 (m, 2 H) | 478.1 |
| 199 | $^1$H NMR (400 MHz, DMSO-d6) δ ppm 7.93 (s, 1 H), 7.70-7.78 (m, 3 H), 7.57 (d, J = 8.3 Hz, 1 H), 7.39 (s, 1 H), 4.50 (d, J = 11.4 Hz, 1 H), 4.06-4.18 (m, 1 H), 3.62-3.79 (m, 2 H), 3.35-3.50 (m, 1 H), 2.71 (s, 3 H), 2.44 (s, 3 H), 2.29 (d, J = 13.6 Hz, 1 H), 2.01-2.12 (m, 1 H), 1.90-1.98 (m, 2 H), 0.82-1.03 (m, 4 H) | 478.1 |

TABLE 8-continued

Analytical Data for Examples 1-232

| Ex # | NMR | M + H |
|---|---|---|
| 200 | ¹H NMR (400 MHz, Chloroform-d) δ ppm 7.78 (dd, J = 4.1, 1.1 Hz, 1 H), 7.65 (td, J = 8.3, 6.4 Hz, 1 H), 7.52 (d, J = 0.8 Hz, 1 H), 7.43 (s, 1 H), 7.15 (tdd, J = 8.5, 2.4, 0.9 Hz, 1 H), 7.06 (ddd, J = 10.0, 8.8, 2.4 Hz, 1H), 4.55-4.63 (m, 1 H), 4.28 (ddd, J = 11.5, 4.4, 1.9 Hz, 1 H), 3.78-3.91 (m, 4 H), 3.53 (ddt, J = 11.7, 7.7, 3.9 Hz, 1 H), 2.82 (s, 3 H), 2.41-2.50 (m, 4 H), 2.15-2.32 (m, 3 H) | 436.0 |
| 201 | H NMR (400 MHz, chloroform-d) δ ppm 7.78 (dd, J = 4.1, 1.1 Hz, 1 H), 7.65 (td, J = 8.3, 6.4 Hz, 1 H), 7.52 (d, J = 0.8 Hz, 1 H), 7.43 (s, 1 H), 7.15 (tdd, J = 8.5, 2.4, 0.9 Hz, 1 H), 7.06 (ddd, J = 10.0, 8.8, 2.4 Hz, 1 H), 4.55-4.63 (m, 1 H), 4.28 (ddd, J = 11.5, 4.4, 1.9 Hz, 1 H), 3.78-3.91 (m, 4 H), 3.53 (ddt, J = 11.7, 7.7, 3.9 Hz, 1 H), 2.82 (s, 3 H), 2.41-2.50 (m, 4 H), 2.15-2.32 (m, 3 H) | 436.0 |
| 202 | ¹H NMR (400 MHz, DMSO-d6) δ ppm 7.87 (s, 1 H), 7.66 (s, 1 H), 7.57 (t, J = 7.7 Hz, 1 H), 7.39 (s, 1 H), 7.23-7.32 (m, 2 H), 4.52 (d, J = 11.5 Hz, 1 H), 4.06-4.18 (m, 1 H), 3.79 (s, 3 H), 3.70-3.76 (m, 1 H), 3.32-3.39 (m, 1 H), 2.70 (s, 3 H), 2.46 (s, 3 H), 2.42 (s, 3 H), 2.25-2.33 (m, 1 H), 1.80-2.10 (m, 3 H) | 432.1 |
| 203 | ¹H NMR (400 MHz, DMSO-d6) δ ppm 7.86 (s, 1 H), 7.66 (s, 1 H), 7.57 (t, J = 7.7 Hz, 1 H), 7.39 (s, 1 H), 7.22-7.29 (m, 2 H), 4.52 (d, J = 11.5 Hz, 1 H), 4.05-4.18 (m, 1 H), 3.79 (s, 3 H), 3.68-3.76 (m, 1 H), 3.34-3.44 (m, 1 H), 2.70 (s, 3 H), 2.46 (s, 3 H), 2.42 (s, 3 H), 2.23-2.36 (m, 1 H), 2.01-2.11 (m, 1 H), 1.90-1.99 (m, 2 H) | 432.1 |
| 204 | ¹H NMR (400 MHz, Chloroform-d) δ ppm 7.52-7.57 (m, 1 H), 7.42 (s, 1 H), 4.88-4.98 (m, 1 H), 3.88-3.99 (m, 4 H), 3.69 (quin, J = 5.52 Hz, 1 H), 3.06-3.27 (m, 1 H), 2.72-2.84 (m, 9 H), 2.43-2.57 (m, 1 H), 2.30-2.43 (m, 1 H), 2.13-2.26 (m, 1 H), 1.86 (br s, 4 H) | 447.0 |
| 205 | ¹H NMR (Chloroform-d, 400 MHz) δ 7.54 (s, 1H), 7.44 (s, 1H), 4.91 (quin, 1H, J = 8.1 Hz), 4.60 (dd, 1H, J = 1.8, 11.4 Hz), 4.3-4.3 (m, 1H), 3.8-3.9 (m, 4H), 3.4-3.6 (m, 1H), 3.1-3.3 (m, 1H), 2.82 (s, 3H), 2.6-2.8 (m, 7H), 2.45 (br d, 1H, J = 13.4 Hz), 2.1-2.3 (m, 3H) | 447.0 |
| 206 | ¹H NMR (500 MHz, Chloroform-d) δ ppm 8.47 (d, J = 5.1 Hz, 1 H), 7.65-7.76 (m, 1 H), 7.37 (dd, J = 8.0, 1.9 Hz, 1 H), 7.31 (dd, J = 9.5, 1.9 Hz, 1 H), 7.26 (s, 1 H), 7.15 (d, J = 4.7 Hz, 1 H), 4.56 (dd, J = 11.4, 1.9 Hz, 1 H), 4.33-4.45 (m, 1 H), 3.78-3.92 (m, 1 H), 3.57-3.67 (m, 1 H), 2.86 (s, 3 H), 2.74 (s, 3 H), 2.58 (s, 3 H), 2.47 (br d, J = 13.2 Hz, 1 H), 2.20-2.30 (m, 2 H), 2.02-2.14 (m, 1 H) | 464.0 |
| 207 | ¹H NMR (500 MHz, Chloroform-d) δ ppm 8.47 (d, J = 5.1 Hz, 1 H), 7.70 (dd, J = 8.1, 7.5 Hz, 1 H), 7.37 (dd, J = 8.0, 1.8 Hz, 1 H), 7.31 (dd, J = 9.5, 1.9 Hz, 1 H), 7.26 (s, 1 H), 7.15 (d, J = 5.3 Hz, 1 H), 4.56 (dd, J = 11.5, 1.9 Hz, 1 H), 4.33-4.44 (m, 1 H), 3.81-3.89 (m, 1 H), 3.56-3.66 (m, 1 H), 2.86 (s, 3 H), 2.74 (s, 3 H), 2.58 (s, 3 H), 2.47 (br d, J = 13.6 Hz, 1 H), 2.21-2.29 (m, 2 H), 2.07 (dt, J = 13.2, 11.9 Hz, 1 H) | 464.2 |
| 208 | ¹H NMR (Chloroform-d, 500 MHz) δ 8.15 (d, 1H, J = 5.4 Hz), 7.70 (t, 1H, J = 7.6 Hz), 7.2-7.4 (m, 2H), 6.96 (dd, 1H, J = 1.2, 5.4 Hz), 6.8-6.9 (m, 1H), 4.55 (dd, 1H, J = 1.9, 11.5 Hz), 4.3-4.5 (m, 1H), 3.9-4.0 (m, 3H), 3.8-3.9 (m, 1H), 3.6-3.7 (m, 1H), 2.85 (s, 3H), 2.74 (s, 3H), 2.46 (br d, 1H, J = 13.4 Hz), 2.1-2.3 (m, 2H), 1.9-2.1 (m, 1H) | 480.2 |
| 209 | ¹H NMR (600 MHz, DMSO-d6) δ 1.84-1.92 (m, 1 H) 2.01 (qd, J = 12.62, 4.45 Hz, 1 H) 2.14 (br dd, J = 13.26, 1.82 Hz, 1 H) 2.37-2.49 (m, 1 H) 2.61 (s, 3 H) 2.66 (s, 3 H) 2.71-2.80 (m, 3 H) 3.57 (tt, J = 11.94, 3.77 Hz, 1 H) 3.80 (td, J = 11.99, 2.00 Hz, 1 H) 4.25 (br dd, J = 10.72, 4.00 Hz, 1 H) 4.66-4.74 (m, 1 H) 7.52 (d, J = 8.32 Hz, 1 H) 7.67 (d, J = 9.45 Hz, 1 H) 7.77 (t, J = 7.90 Hz, 1 H) 8.71 (s, 2 H) | 465.0 |
| 210 | ¹H NMR (500 MHz, Chloroform-d) δ ppm 8.46 (d, J = 5.1 Hz, 1 H), 7.75 (td, J = 8.1, 6.5 Hz, 1 H), 7.25 (s, 1 H), 7.14 (d, J = 4.8 Hz, 1 H), 7.07-7.12 (m, 1 H), 6.98-7.04 (m, 1 H), 4.55 (dd, J = 11.5, 1.9 Hz, 1 H), 4.38 (dt, J = 11.2, 3.2 Hz, 1 H), 3.79-3.93 (m, 1 H), 3.53-3.68 (m, 1 H), 2.85 (s, 3 H), 2.74 (s, 3 H), 2.57 (s, 3 H), 2.46 (br d, J = 13.4 Hz, 1 H), 2.21-2.30 (m, 2 H), 2.00-2.12 (m, 1 H) | 448.2 |
| 211 | ¹H NMR (500 MHz, Chloroform-d) δ ppm 8.46 (d, J = 5.2 Hz, 1 H), 7.76 (td, J = 8.1, 6.6 Hz, 1 H), 7.25 (s, 1 H), 7.14 (d, J = 4.9 Hz, 1 H), 7.10 (td, J = 8.1, 2.1 Hz, 1 H), 7.01 (td, J = 9.4, 2.5 Hz, 1 H), 4.55 (dd, J = 11.4, 1.9 Hz, 1 H), 4.39 (dt, J = 11.2, 3.2 Hz, 1 H), 3.79-3.90 (m, 1 H), 3.55-3.67 (m, 1 H), 2.85 (s, 3 H), 2.74 (s, 3 H), 2.57 (s, 3 H), 2.47 (br d, J = 13.4 Hz, 1 H), 2.20-2.28 (m, 2 H), 2.00-2.16 (m, 1 H) | 448.2 |
| 212 | ¹H NMR (400 MHz, DMSO-d6) δ ppm 8.41 (d, J = 5.2 Hz, 1 H), 7.87 (td, J = 8.4, 6.7 Hz, 1 H), 7.52 (ddd, J = 10.2, 9.4, 2.5 Hz, 1 H), 7.36 (td, J = 8.5, 2.5 Hz, 1 H), 7.22 (s, 1 H), 7.11-7.16 (m, 1 H), 4.72 (d, J = 8.6 Hz, 1 H), 3.90-3.98 (m, 1 H), 3.76-3.88 (m, 1 H), 3.63-3.73 (m, 1 H), 2.81 (s, 3 H), 2.69-2.75 (m, 4 H), 2.47 (s, 3 H), 2.42 (s, 1 H), 2.02-2.22 (m, 2H) | 448.2 |
| 213 | ¹H NMR (400 MHz, DMSO-d6) δ ppm 8.41 (d, J = 5.2 Hz, 1 H), 7.87 (td, J = 8.5, 6.7 Hz, 1 H), 7.52 (ddd, J = 10.5, 9.5, 2.5 Hz, 1 H), 7.31-7.42 (m, 1 H), 7.19-7.25 (m, 1 H), 7.13 (d, J = 5.3 Hz, 1 H), 4.72 (d, J = 9.2 Hz, 1 H), 3.91-4.02 (m, 1 H), 3.76-3.87 (m, 1 H), 3.68 (s, 1 H), 2.81 (s, 3 H), 2.63-2.76 (m, 4 H), 2.47 (s, 3 H), 1.99-2.23 (m, 3 H) | 448.2 |

TABLE 8-continued

Analytical Data for Examples 1-232

| Ex # | NMR | M + H |
|---|---|---|
| 214 | ¹H NMR (500 MHz, Chloroform-d) δ ppm 8.47 (d, J = 5.2 Hz, 1 H), 7.26 (s, 1 H), 7.15 (d, J = 4.8 Hz, 1 H), 4.91 (quin, J = 8.1 Hz, 1 H), 4.57 (dd, J = 11.4, 1.7 Hz, 1 H), 4.33-4.46 (m, 1 H), 3.80-3.92 (m, 1 H), 3.50-3.62 (m, 1 H), 3.10-3.26 (m, 1 H), 2.82 (s, 3 H), 2.77 (s, 7 H), 2.58 (s, 3 H), 2.46 (br d, J = 13.4 Hz, 1 H), 2.15-2.28 (m, 2 H), 1.99-2.09 (m, 1 H) | 458.0 |
| 215 | ¹H NMR (500 MHz, Chloroform-d) δ ppm 8.47 (d, J = 5.2 Hz, 1 H), 7.26 (s, 1 H), 7.15 (d, J = 4.9 Hz, 1 H), 4.91 (quin, J = 8.1 Hz, 1 H), 4.57 (dd, J = 11.4, 1.5 Hz, 1 H), 4.33-4.46 (m, 1 H), 3.80-3.94 (m, 1 H), 3.52-3.60 (m, 1 H), 3.10-3.25 (m, 1 H), 2.82 (s, 3 H), 2.70-2.79 (m, 7 H), 2.58 (s, 3 H), 2.46 (br d, J = 13.4 Hz, 1 H), 2.18-2.28 (m, 2 H), 1.98-2.09 (m, 1 H) | 458.0 |
| 216 | ¹H NMR (500 MHz, Chloroform-d) δ ppm 7.68-7.75 (m, 1 H), 7.53 (s, 1 H), 7.45 (s, 1 H), 7.37 (dd, J = 8.2, 1.8 Hz, 1 H), 7.31 (dd, J = 9.5, 1.9 Hz, 1 H), 4.65 (dd, J = 11.5, 2.0 Hz, 1 H), 3.89 (s, 3 H), 3.87 (td, J = 5.5, 1.9 Hz, 1 H), 3.59 (tt, J = 12.2, 3.6 Hz, 1 H), 2.86 (s, 3 H), 2.75 (s, 3 H), 2.40-2.46 (m, 1 H), 2.22-2.28 (m, 1 H), 2.08-2.20 (m, 1 H), 1.84-1.93 (m, 1 H), 1.35 (d, J = 6.1 Hz, 3 H) | 467.0 |
| 217 | ¹H NMR (600 MHz, DMSO-d6) δ ppm 8.39 (d, J = 5.0 Hz, 1 H), 7.85 (s, 1 H), 7.65 (t, J = 7.9 Hz, 1 H), 7.59 (dd, J = 9.6, 1.8 Hz, 1 H), 7.47 (dd, J = 8.2, 1.9 Hz, 1 H), 7.28 (s, 1 H), 7.20 (d, J = 4.6 Hz, 1 H), 4.53-4.62 (m, 1 H), 4.14-4.30 (m, 1 H), 3.79 (td, J = 11.7, 2.5 Hz, 1 H), 3.41-3.49 (m, 1 H), 2.74 (s, 3 H), 2.63 (s, 3 H), 2.46 (s, 3 H), 2.27-2.33 (m, 1 H), 1.91-2.05 (m, 2 H), 1.74 (q, J = 11.9 Hz, 1 H) | 463.0 |
| 218 | ¹H NMR (600 MHz, DMSO-d6) δ ppm 8.39 (d, J = 5.2 Hz, 1 H), 7.85 (s, 1 H), 7.65 (t, J = 7.9 Hz, 1 H), 7.59 (dd, J = 9.6, 1.9 Hz, 1 H), 7.47 (dd, J = 8.2, 2.0 Hz, 1 H), 7.28 (s, 1 H), 7.20 (d, J = 4.8 Hz, 1 H), 4.60 (br d, J = 9.8 Hz, 1 H), 4.25 (br dd, J = 11.3, 3.0 Hz, 1 H), 3.79 (td, J = 11.7, 2.5 Hz, 1 H), 3.43 (ddt, J = 11.6, 7.8, 3.9, 3.9 Hz, 1 H), 2.74 (s, 3 H), 2.63 (s, 3 H), 2.46 (s, 3 H), 2.29 (br d, J = 12.8 Hz, 1 H), 1.92-2.06 (m, 2 H), 1.74 (q, J = 12.0 Hz, 1 H) | 463.0 |
| 219 | ¹H NMR (400 MHz, DMSO-d6) δ ppm 8.41 (d, J = 5.1 Hz, 1 H), 8.19 (dd, J = 8.5, 3.5 Hz, 1 H), 7.75-7.84 (m, 2 H), 7.57-7.66 (m, 2 H), 7.22 (s, 1 H), 7.10-7.16 (m, 1 H), 4.73 (dd, J = 10.2, 2.7 Hz, 1 H), 3.90-3.98 (m, 1 H), 3.83 (dd, J = 12.4, 9.8 Hz, 1 H), 3.65 (t, J = 4.4 Hz, 1 H), 2.79 (s, 3 H), 2.65-2.76 (m, 2H), 2.47 (s, 3H), 2.01-2.21 (m, 2H) | 449.0 |
| 220 | ¹H NMR (400 MHz, DMSO-d6) δ ppm 8.41 (d, J = 5.1 Hz, 1 H), 8.19 (dd, J = 8.5, 3.5 Hz, 1 H), 7.74-7.85 (m, 2 H), 7.57-7.67 (m, 2 H), 7.22 (s, 1 H), 7.13 (d, J = 5.1 Hz, 1 H), 4.73 (d, J = 9.2 Hz, 1 H), 3.90-3.99 (m, 1 H), 3.77-3.88 (m, 1 H), 3.65 (d, J = 5.2 Hz, 1 H), 2.79 (s, 3H), 2.70 (d, J = 15.3 Hz, 2 H), 2.47 (s, 3 H), 1.99-2.21 (m, 2 H) | 449.0 |
| 221 | ¹H NMR (400 MHz, DMSO-d6) δ ppm 8.41 (d, J = 5.2 Hz, 1 H), 8.18 (dd, J = 8.4, 3.5 Hz, 1 H), 7.84 (td, J = 8.5, 6.5 Hz, 1 H), 7.64 (d, J = 8.5 Hz, 1 H), 7.55-7.62 (m, 1 H), 7.40 (td, J = 8.4, 2.5 Hz, 1 H), 7.22 (s, 1 H), 7.13 (d, J = 5.6 Hz, 1 H), 4.73 (dd, J = 10.2, 2.7 Hz, 1 H), 3.91-3.99 (m, 1 H), 3.79-3.90 (m, 1 H), 3.61-3.72 (m, 1 H), 2.79 (s, 3 H), 2.65-2.75 (m, 2 H), 2.47 (s, 3 H), 2.00-2.21 (m, 2 H) | 432.48 |
| 222 | ¹H NMR (400 MHz, DMSO-d6) δ ppm 8.46 (s, 1 H), 7.88 (d, J = 3.8 Hz, 1 H), 7.54 (t, J = 7.6 Hz, 1 H), 7.09-7.28 (m, 4 H), 4.83 (d, J = 9.4 Hz, 1 H), 3.95-4.07 (m, 2 H), 3.71 (q, J = 4.7 Hz, 1 H), 2.91 (d, J = 13.7 Hz, 1 H), 2.83 (s, 3 H), 2.61-2.71 (m, 1 H), 2.44-2.60 (m, 9 H), 2.13-2.33 (m, 2 H) | 443.2 |
| 223 | ¹H NMR (400 MHz, Chloroform-d) δ ppm 8.42-8.51 (m, 1 H), 7.88 (d, J = 3.8 Hz, 1 H), 7.54 (t, J = 7.6 Hz, 1 H), 7.20-7.28 (m, 2 H), 7.09-7.20 (m, 2 H), 4.83 (dd, J = 9.8, 2.9 Hz, 1 H), 3.95-4.07 (m, 2 H), 3.72 (t, J = 4.7 Hz, 1 H), 2.91 (d, J = 13.7 Hz, 1 H), 2.83 (s, 3 H), 2.61-2.70 (m, 1 H), 2.45-2.60 (m, 9 H), 2.22 (dddd, J = 18.6, 14.3, 9.6, 5.0 Hz, 2 H) | 443.2 |
| 224 | ¹H NMR (500 MHz, Chloroform-d) δ ppm 7.72-7.79 (m, 1 H), 7.60 (t, J = 7.9 Hz, 1 H), 7.52 (s, 1 H), 7.43 (s, 1 H), 7.41 (dd, J = 8.4, 1.9 Hz, 1 H), 7.35 (dd, J = 9.6, 1.9 Hz, 1 H), 4.58 (dd, J = 11.4, 1.9 Hz, 1 H), 4.28 (ddd, J = 11.5, 4.4, 1.6 Hz, 1 H), 3.89 (s, 3 H), 3.82 (td, J = 11.8, 2.6 Hz, 1 H), 3.53 (tt, J = 11.9, 3.8 Hz, 1 H), 2.82 (s, 3 H), 2.48 (d, J = 0.6 Hz, 3 H), 2.41-2.47 (m, 1 H), 2.14-2.30 (m, 3 H) | 452.0 |
| 225 | ¹H NMR (500 MHz, Chloroform-d) δ ppm 7.79 (d, J = 4.0 Hz, 1 H), 7.60 (t, J = 7.9 Hz, 1 H), 7.51 (s, 1 H), 7.38-7.43 (m, 2 H), 7.36 (dd, J = 9.5, 1.9 Hz, 1 H), 4.94 (dd, J = 7.3, 3.6 Hz, 1 H), 3.92-4.01 (m, 2 H), 3.91 (s, 3 H), 3.66-3.77 (m, 1 H), 2.83 (s, 3 H), 2.79 (ddd, J = 13.5, 6.7, 3.6 Hz, 1 H), 2.49 (d, J = 0.6 Hz, 4 H), 2.32-2.41 (m, 1 H), 2.13-2.23 (m, 1 H) | 452.0 |
| 226 | ¹H NMR (400 MHz, chloroform-d) δ ppm 7.77 (d, J = 3.9 Hz, 1 H), 7.60 (t, J = 7.9 Hz, 1 H), 7.52 (d, J = 0.8 Hz, 1 H), 7.39-7.44 (m, 2 H), 7.35 (dd, J = 9.5, 1.9 Hz, 1 H), 4.58 (dd, J = 11.5, 2.2 Hz, 1 H), 4.28 (ddd, J = 11.5, 4.4, 1.8 Hz, 1 H), 3.89 (s, 3 H), 3.82 (td, J = 11.7, 2.9 | 451.9 |

TABLE 8-continued

Analytical Data for Examples 1-232

| Ex # | NMR | M + H |
|---|---|---|
|  | Hz, 1 H), 3.47-3.58 (m, 1 H), 2.82 (s, 3 H), 2.42-2.51 (m, 4 H), 2.11-2.31 (m, 4 H) |  |
| 227 | $^1$H NMR (400 MHz, DMSO-d6) δ ppm 8.46 (d, J = 5.2 Hz, 1 H), 7.83 (dd, J = 3.9, 1.1 Hz, 1 H), 7.66 (td, J = 8.4, 6.3 Hz, 1 H), 7.25 (d, J = 7.6 Hz, 1 H), 7.14-7.20 (m, 2 H), 7.09 (ddd, J = 10.0, 8.7, 2.4 Hz, 1 H), 4.82 (dd, J = 9.7, 2.9 Hz, 1 H), 3.93-4.07 (m, 2 H), 3.71 (p, J = 4.6 Hz, 1 H), 2.78-2.97 (m, 4 H), 2.63 (dd, J = 13.2, 4.2 Hz, 1 H), 2.58 (s, 3 H), 2.51 (d, J = 1.0 Hz, 3 H), 2.16-2.31 (m, 2 H) | 447.1 |
| 228 | $^1$H NMR (400 MHz, chloroform-d) δ ppm 8.47 (d, J = 5.2 Hz, 1 H), 7.83 (dd, J = 3.9, 1.1 Hz, 1 H), 7.66 (td, J = 8.3, 6.3 Hz, 1 H), 7.26 (s, 1 H), 7.13-7.21 (m, 2 H), 7.09 (ddd, J = 10.0, 8.7, 2.4 Hz, 1 H), 4.82 (dd, J = 9.8, 2.9 Hz, 1 H), 3.93-4.09 (m, 2 H), 3.71 (p, J = 4.7 Hz, 1 H), 2.85-2.95 (m, 1 H), 2.84 (s, 3 H), 2.61-2.69 (m, 1 H), 2.58 (s, 3 H), 2.51 (d, J = 1.1 Hz, 3 H), 2.24 (dddd, J = 16.2, 13.8, 10.0, 5.1 Hz, 2 H) | 447.1 |
| 229 | $^1$H NMR (500 MHz, Chloroform-d) δ ppm 7.76 (d, J = 3.1 Hz, 1 H), 7.59 (t, J = 7.9 Hz, 1 H), 7.52 (s, 1 H), 7.44 (s, 1 H), 7.41 (dd, J = 8.2, 1.9 Hz, 1 H), 7.35 (dd, J = 9.5, 1.9 Hz, 1 H), 4.63 (dd, J = 11.4, 2.1 Hz, 1 H), 3.88 (s, 3 H), 3.85 (td, J = 5.5, 1.9 Hz, 1 H), 3.55 (tt, J = 12.2, 3.8 Hz, 1 H), 2.82 (s, 3 H), 2.48 (s, 3 H), 2.41 (ddt, J = 13.2, 3.7, 1.9, 1.9 Hz, 1 H), 2.23 (ddt, J = 13.2, 3.7, 1.9, 1.9 Hz, 1 H), 2.11-2.21 (m, 1 H), 1.85-1.99 (m, 1 H), 1.34 (d, J = 6.2 Hz, 3 H) | 466.0 |
| 230 | $^1$H NMR (400 MHz, Chloroform-d) δ ppm 7.74 (s, 1 H), 7.63 (t, J = 7.8 Hz, 1 H), 7.52 (s, 1 H), 7.42 (s, 1 H), 7.31-7.36 (m, 1 H), 7.24-7.27 (m, 1 H), 4.65 (dd, J = 11.3, 1.9 Hz, 1 H), 3.83-3.94 (m, 4 H), 3.35-3.52 (m, 1 H), 2.78 (s, 3 H), 2.70 (s, 3 H), 2.31-2.45 (m, 1 H), 2.10-2.25 (m, 1 H), 1.95 (q, J = 12.3 Hz, 1 H), 1.63-1.74 (m, 1 H), 1.35 (d, J = 6.1 Hz, 3H) | 466.0 |
| 231 | $^1$H NMR (600 MHz, DMSO-d6) δ ppm 8.53-8.56 (m, 1 H), 7.84 (s, 1 H), 7.47 (s, 1 H), 4.76 (br d, J = 12.53 Hz, 1 H), 4.62 (br s, 1 H), 4.49 (dd, J = 10.35, 2.72 Hz, 1 H), 3.98-4.05 (m, 1 H), 3.68-3.73 (m, 1 H), 3.60-3.68 (m, 1 H), 3.14-3.25 (m, 1 H), 2.63 (s, 3 H), 2.57 (s, 6 H), 1.19-1.32 (m, 1 H), 0.93-1.05 (m, 5 H) | 472.0 |
| 232 | $^1$H NMR (600 MHz, DMSO-d6) δ ppm 8.56 (s, 1 H), 8.43-8.51 (m, 1 H), 7.35 (s, 1 H), 7.25-7.32 (m, 1 H), 4.87 (br d, J = 11.63 Hz, 1 H), 4.61 (br dd, = 10.44, 2.45 Hz, 1 H), 4.15 (br dd, J = 11.90, 2.27 Hz, 1 H), 3.68-3.77 (m, 1 H), 2.98-3.10 (m, 1 H), 2.64 (s, 3 H), 2.58 (s, 5 H), 2.52-2.53 (m, 1 H), 2.43-2.49 (m, 1 H), 0.97-1.07 (m, 1 H) | 457.0 |

TABLE 8A

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 233 | 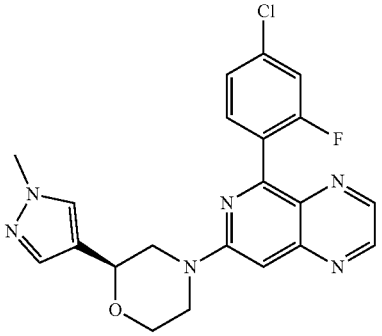 [SMILES: Cn1cc([C@H]2CN(c3cc4nccnc4c(-c4ccc(Cl)cc4F)n3)CCO2)cn1] | (S)-4-(5-(4-chloro-2-fluorophenyl)pyrido[3,4-b]pyrazin-7-yl)-2-(1-methyl-1H-pyrazol-4-yl)morpholine | 425.2 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 234 | 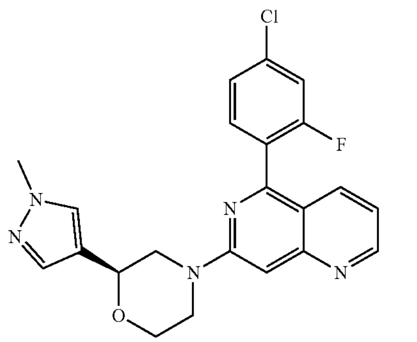 [SMILES: Cn1cc([C@H]2CN(c3cc4ncccc4c(-c4ccc(Cl)cc4F)n3)CCO2)cn1] | (S)-4-(5-(4-chloro-2-fluorophenyl)-1,6-naphthyridin-7-yl)-2-(1-methyl-1H-pyrazol-4-yl)morpholine | 424.0 |
| 235 | 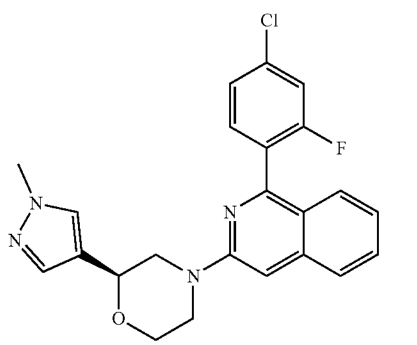 [SMILES: Cn1cc([C@H]2CN(c3cc4ccccc4c(-c4ccc(Cl)cc4F)n3)CCO2)cn1] | (S)-4-(1-(4-chloro-2-fluorophenyl)isoquinolin-3-yl)-2-(1-methyl-1H-pyrazol-4-yl)morpholine | 423.0 |
| 236 | 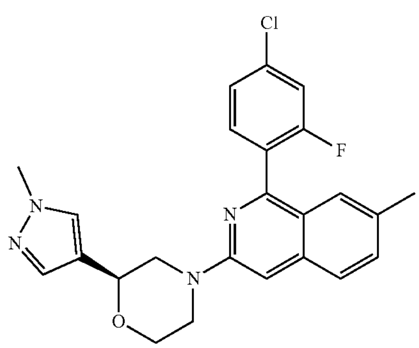 [SMILES: Cc1ccc2cc(N3CCO[C@@H](c4cnn(C)c4)C3)nc(-c3ccc(Cl)cc3F)c2c1] | (S)-4-(1-(4-chloro-2-fluorophenyl)-7-methylisoquinolin-3-yl)-2-(1-methyl-1H-pyrazol-4-yl)morpholine | 437.2 |
| 237 | 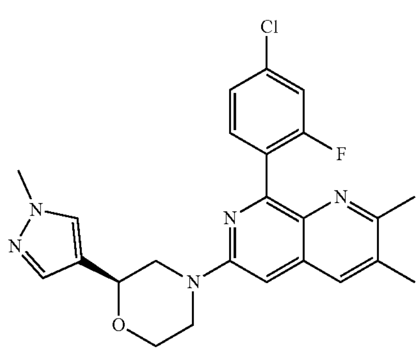 [SMILES: Cc1cc2cc(N3CCO[C@@H](c4cnn(C)c4)C3)nc(-c3ccc(Cl)cc3F)c2nc1C] | (S)-4-(8-(4-chloro-2-fluorophenyl)-2,3-dimethyl-1,7-naphthyridin-6-yl)-2-(1-methyl-1H-pyrazol-4-yl)morpholine | 452.0 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 238 | 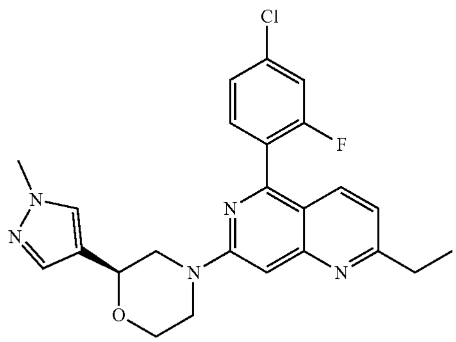 [SMILES: CCc1ccc2c(-c3ccc(Cl)cc3F)nc(N3CCO[C@@H](c4cnn(C)c4)C3)cc2n1] | (S)-4-(5-(4-chloro-2-fluorophenyl)-2-ethyl-1,6-naphthyridin-7-yl)-2-(1-methyl-1H-pyrazol-4-yl)morpholine | 452.0 |
| 239 | 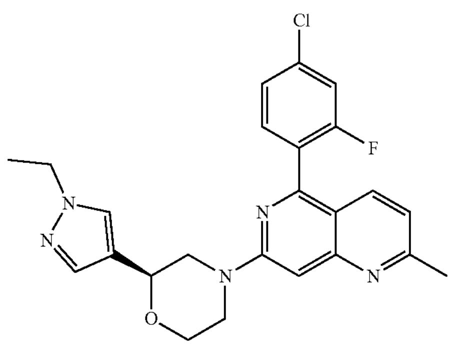 [SMILES: CCn1cc([C@H]2CN(c3cc4nc(C)ccc4c(-c4ccc(Cl)cc4F)n3)CCO2)cn1] | (S)-4-(5-(4-chloro-2-fluorophenyl)-2-methyl-1,6-naphthyridin-7-yl)-2-(1-ethyl-1H-pyrazol-4-yl)morpholine | 452.0 |
| 240 | 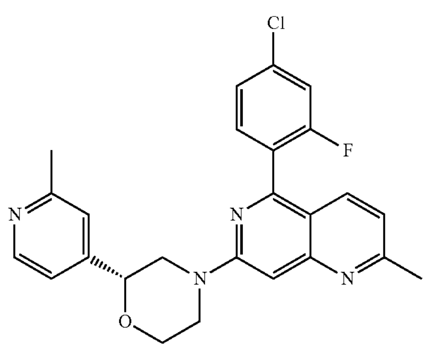 [SMILES: Cc1cc([C@@H]2CN(c3cc4nc(C)ccc4c(-c4ccc(Cl)cc4F)n3)CCO2)ccn1] | (R)-4-(5-(4-chloro-2-fluorophenyl)-2-methyl-1,6-naphthyridin-7-yl)-2-(2-methylpyridin-4-yl)morpholine | 449.0 |
| 241 | 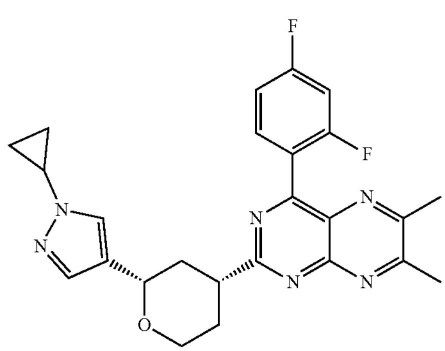 [SMILES: Cc1nc2nc([C@@H]3CCO[C@H](c4cnn(C5CC5)c4)C3)nc(-c3ccc(F)cc3F)c2nc1C] | 2-((2S,4R)-2-(1-cyclopropyl-1H-pyrazol-4-yl)tetrahydro-2H-pyran-4-yl)-4-(2,4-difluorophenyl)-6,7-dimethylpteridine | 463.2 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 242 | 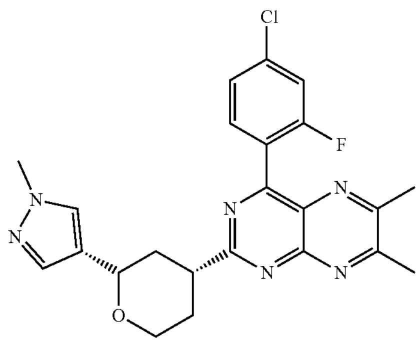 | 4-(4-chloro-2-fluorophenyl)-6,7-dimethyl-2-((2S,4R)-2-(1-methyl-1H-pyrazol-4-yl)tetrahydro-2H-pyran-4-yl)pteridine | 453.0 |
| 243 | 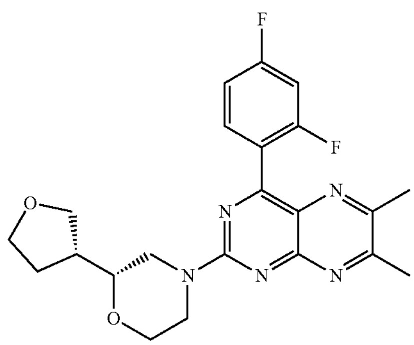 | (R)-4-(4-(2,4-difluorophenyl)-6,7-dimethylpteridin-2-yl)-2-((R)-tetrahydrofuran-3-yl)morpholine | 428.2 |
| 244 | 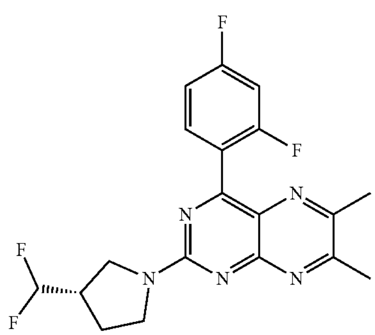 [SMILES: Cc1nc2nc(N3CC[C@H](C(F)F)C3)nc(-c3ccc(F)cc3F)c2nc1C] | (S)-2-(3-(difluoromethyl)pyrrolidin-1-yl)-4-(2,4-difluorophenyl)-6,7-dimethylpteridine | 392.0 |
| 245 | 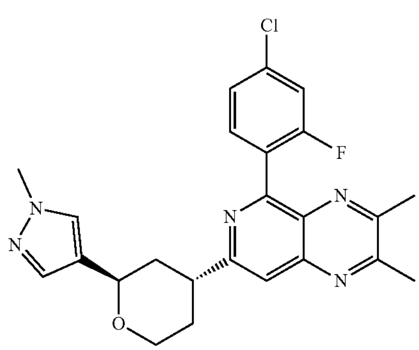 [SMILES: Cc1nc2cc([C@@H]3CCO[C@@H](c4cnn(C)c4)C3)nc(-c3ccc(Cl)cc3F)c2nc1C] | 5-(4-chloro-2-fluorophenyl)-2,3-dimethyl-7-((2R,4R)-2-(1-methyl-1H-pyrazol-4-yl)tetrahydro-2H-pyran-4-yl)pyrido[3,4-b]pyrazine | 452.0 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 246 | 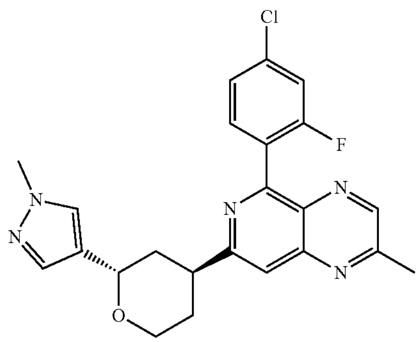 [SMILES: Cc1cnc2c(-c3ccc(Cl)cc3F)nc([C@H]3CCO[C@H](c4cnn(C)c4)C3)cc2n1] | 5-(4-chloro-2-fluorophenyl)-2-methyl-7-((2S,4S)-2-(1-methyl-1H-pyrazol-4-yl)tetrahydro-2H-pyran-4-yl)pyrido[3,4-b]pyrazine | 438.0 |
| 247 | 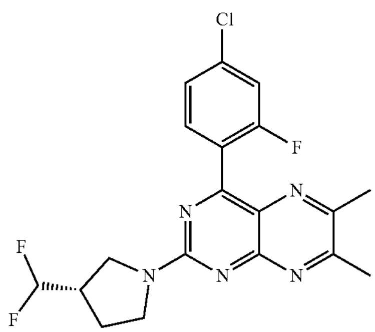 [SMILES: Cc1nc2nc(N3CC[C@H](C(F)F)C3)nc(-c3ccc(Cl)cc3F)c2nc1C] | (S)-4-(4-chloro-2-fluorophenyl)-2-(3-difluoromethyl)pyrrolidin-1-yl)-6,7-dimethylpteridine | 408.0 |
| 248 | 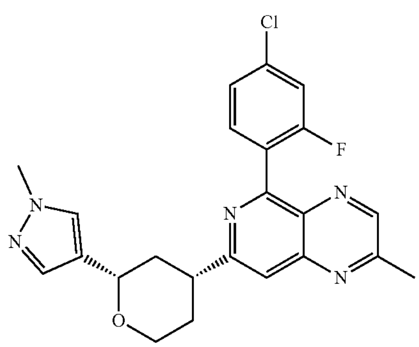 [SMILES: Cc1cnc2c(-c3ccc(Cl)cc3F)nc([C@@H]3CCO[C@H](c4cnn(C)c4)C3)cc2n1] | 5-(4-chloro-2-fluorophenyl)-2-methyl-7-((2S,4R)-2-(1-methyl-1H-pyrazol-4-yl)tetrahydro-2H-pyran-4-yl)pyrido[3,4-b]pyrazine | 438.0 |
| 249 | 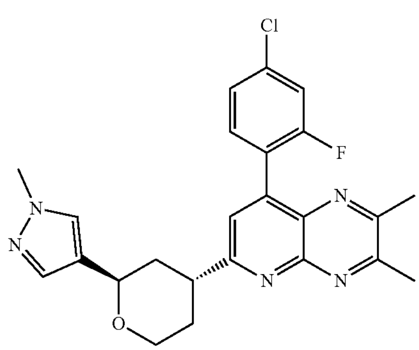 [SMILES: Cc1nc2nc([C@@H]3CCO[C@@H](c4cnn(C)c4)C3)cc(-c3ccc(Cl)cc3F)c2nc1C] | 8-(4-chloro-2-fluorophenyl)-2,3-dimethyl-6-((2R,4R)-2-(1-methyl-1H-pyrazol-4-yl)tetrahydro-2H-pyran-4-yl)pyrido[2,3-b]pyrazine | 452.2 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 250 | 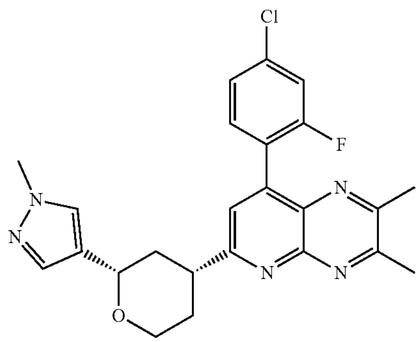 [SMILES: Cc1nc2nc([C@@H]3CCO[C@H](c4cnn(C)c4)C3)cc(-c3ccc(Cl)cc3F)c2nc1C] | 8-(4-chloro-2-fluorophenyl)-2,3-dimethyl-6-((2S,4R)-2-(1-methyl-1H-pyrazol-4-yl)tetrahydro-2H-pyran-4-yl)pyrido[2,3-b]pyrazine | 452.0 |
| 251 | 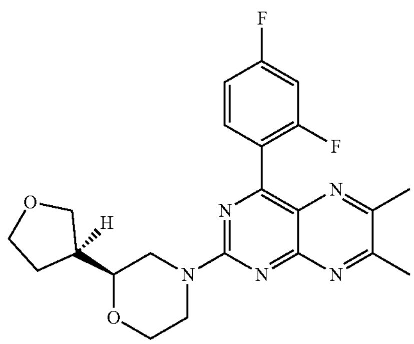 [SMILES: Cc1nc2nc(N3CCO[C@@H]([C@H]4CCOC4)C3)nc(-c3ccc(F)cc3F)c2nc1C] | (S)-4-(4-(2,4-difluorophenyl)-6,7-dimethylpteridin-2-yl)-2-((S)-tetrahydrofuran-3-yl)morpholine | 428.0 |
| 252 | 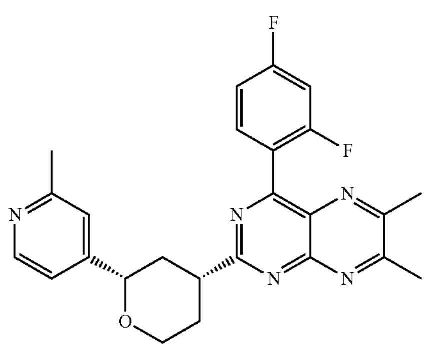 [SMILES: Cc1cc([C@@H]2C[C@H](c3nc(-c4ccc(F)cc4F)c4nc(C)c(C)nc4n3)CCO2)ccn1] | 4-(2,4-difluorophenyl)-6,7-dimethyl-2-((2S,4R)-2-(2-methylpyridin-4-yl)tetrahydro-2H-pyran-4-yl)pteridine | 448.2 |
| 253 | 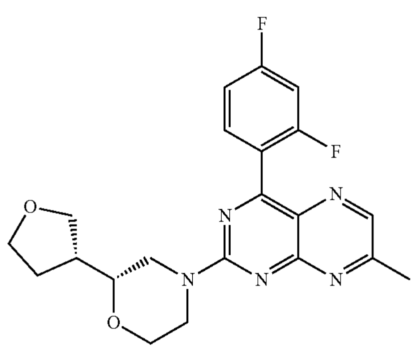 | (R)-4-(4-(2,4-difluorophenyl)-7-methylpteridin-2-yl)-2-((R)-tetrahydrofuran-3-yl)morpholine | 414.0 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
| --- | --- | --- | --- |
| 254 | 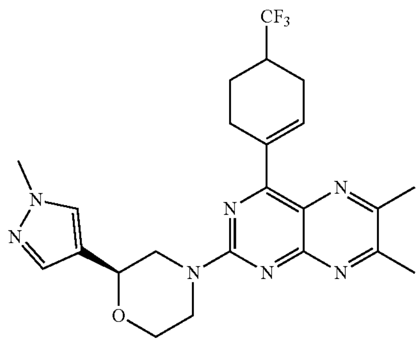 [SMILES: Cc1nc2nc(N3CCO[C@@H](c4cnn(C)c4)C3)nc(C3=CCC(C(F)(F)F)CC3)c2nc1C] | (2S)-4-(6,7-dimethyl-4-(4-(trifluoromethyl)cyclohex-1-en-1-yl)pteridin-2-yl)-2-(1-methyl-1H-pyrazol-4-yl)morpholine | 474.3 |
| 255 | 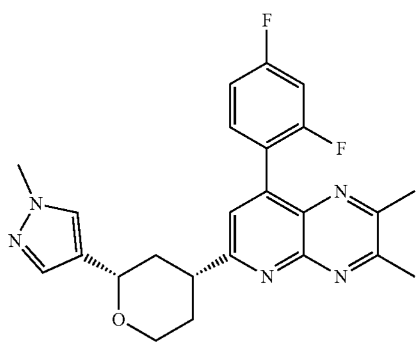 [SMILES: Cc1nc2nc([C@@H]3CCO[C@H](c4cnn(C)c4)C3)cc(-c3ccc(F)cc3F)c2nc1C] | 8-(2,4-difluorophenyl)-2,3-dimethyl-6-((2S,4R)-2-(1-methyl-1H-pyrazol-4-yl)tetrahydro-2H-pyran-4-yl)pyrido[2,3-b]pyrazine | 436.0 |
| 256 | 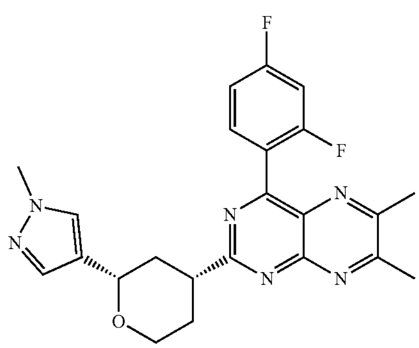 [SMILES: Cc1nc2nc([C@@H]3CCO[C@H](c4cnn(C)c4)C3)nc(-c3ccc(F)cc3F)c2nc1C] | 4-(2,4-difluorophenyl)-6,7-dimethyl-2-((2S,4R)-2-(1-methyl-1H-pyrazol-4-yl)tetrahydro-2H-pyran-4-yl)pteridine | 437.2 |
| 257 | 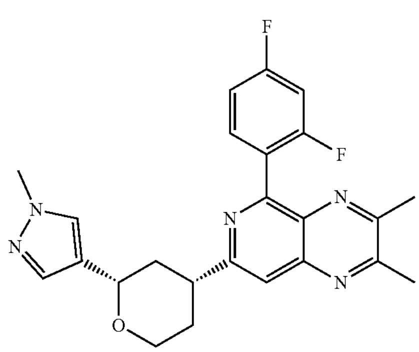 [SMILES: Cc1nc2cc([C@@H]3CCO[C@H](c4cnn(C)c4)C3)nc(-c3ccc(F)cc3F)c2nc1C] | 5-(2,4-difluorophenyl)-2,3-dimethyl-7-((2S,4R)-2-(1-methyl-1H-pyrazol-4-yl)tetrahydro-2H-pyran-4-yl)pyrido[3,4-b]pyrazine | 436.0 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 258 | 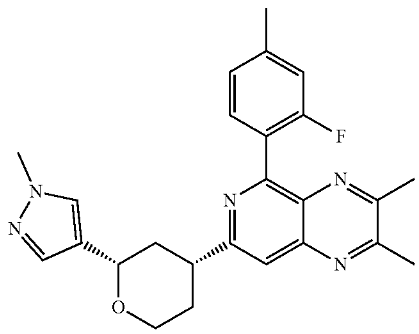 [SMILES: Cc1ccc(-c2nc([C@@H]3CCO[C@H](c4cnn(C)c4)C3)cc3nc(C)c(C)nc23)c(F)c1] | 5-(2-fluoro-4-methylphenyl)-2,3-dimethyl-7-((2S,4R)-2-(1-methyl-1H-pyrazol-4-yl)tetrahydro-2H-pyran-4-yl)pyrido[3,4-b]pyrazine | 432.0 |
| 259 | 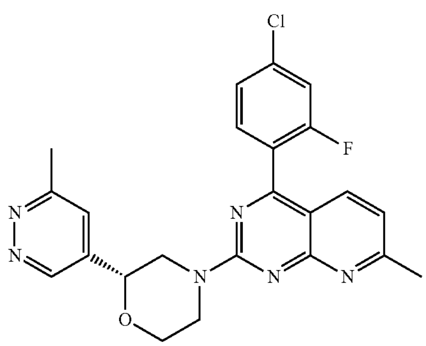 [SMILES: Cc1cc([C@@H]2CN(c3nc(-c4ccc(Cl)cc4F)c4ccc(C)nc4n3)CCO2)cnn1] | (R)-4-(4-(4-chloro-2-fluorophenyl)-7-methylpyrido[2,3-d]pyrimidin-2-yl)-2-(6-methylpyridazin-4-yl)morpholine | 451.2 |
| 260 | 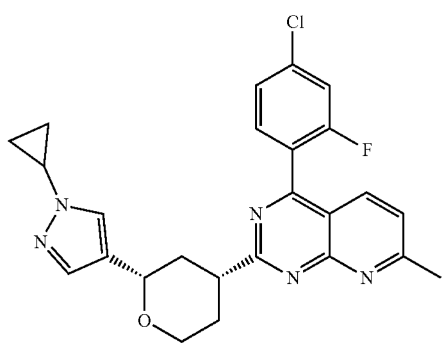 [SMILES: Cc1ccc2c(-c3ccc(Cl)cc3F)nc([C@@H]3CCO[C@H](c4cnn(C5CC5)c4)C3)nc2n1] | 4-(4-chloro-2-fluorophenyl)-2-((2S,4R)-2-(1-cyclopropyl-1H-pyrazol-4-yl)tetrahydro-2H-pyran-4-yl)-7-methylpyrido[2,3-d]pyrimidine | 464.2 |
| 261 | 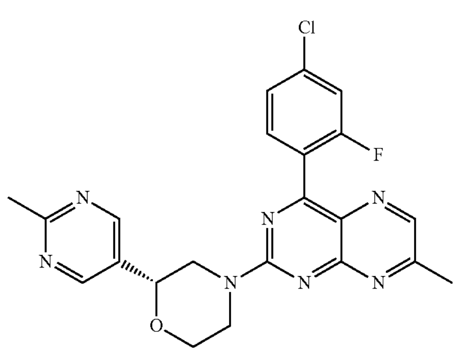 | (R)-4-(4-(4-chloro-2-fluorophenyl)-7-methylpteridin-2-yl)-2-(2-methylpyrimidin-5-yl)morpholine | 452.1 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 262 | 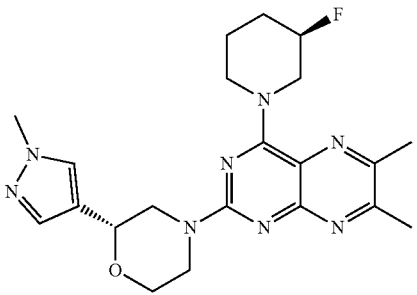 [SMILES: Cc1nc2nc(N3CCO[C@H](c4cnn(C)c4)C3)nc(N3CCC[C@@H](F)C3)c2nc1C] | (R)-4-(4-((R)-3-fluoropiperidin-1-yl)-6,7-dimethylpteridin-2-yl)-2-(1-methyl-1H-pyrazol-4-yl)morpholine | 427.0 |
| 263 | 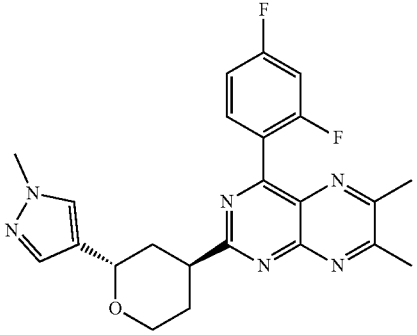 | 4-(2,4-difluorophenyl)-6,7-dimethyl-2-((2S,4S)-2-(1-methyl-1H-pyrazol-4-yl)tetrahydro-2H-pyran-4-yl)pteridine | 437.0 |
| 264 | 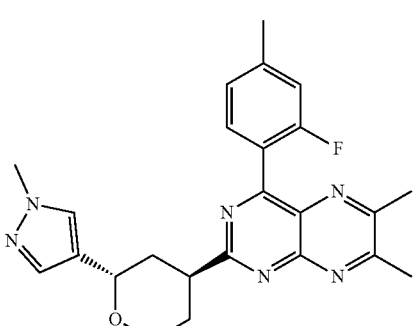 | 4-(2-fluoro-4-methylphenyl)-6,7-dimethyl-2-((2S,4S)-2-(1-methyl-1H-pyrazol-4-yl)tetrahydro-2H-pyran-4-yl)pteridine | 433.0 |
| 265 | 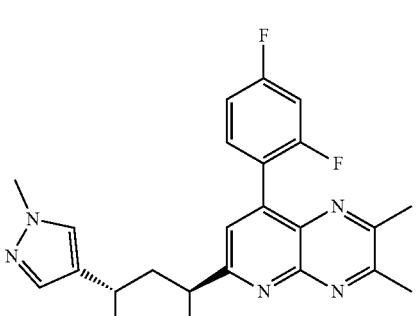 | 8-(2,4-difluorophenyl)-2,3-dimethyl-6-((2S,4S)-2-(1-methyl-1H-pyrazol-4-yl)tetrahydro-2H-pyran-4-yl)pyrido[2,3-b]pyrazine | 436.1 |

TABLE 8A-continued

Additional Compounds
The compound disclosed below in Table 8A were made by a method of the present
disclosure or a similar method. The appropriate reagents, starting materials and conditions
necessary for synthesizing the compounds of Table 8A would be apparent to a person of
ordinary skill in the art.

| Ex # | Structure | Name | M +H |
|---|---|---|---|
| 266 | 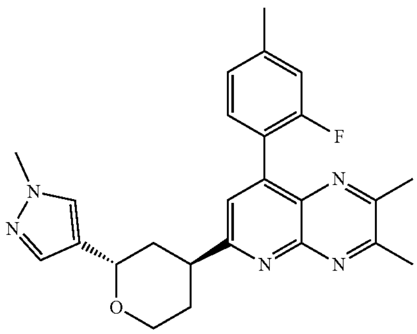 [SMILES: Cc1ccc(-c2cc([C@H]3CCO[C@H](c4cnn(C)c4)C3)nc3nc(C)c(C)nc23)c(F)c1] | 8-(2-fluoro-4-methylphenyl)-2,3-dimethyl-6-((2S,4S)-2-(1-methyl-1H-pyrazol-4-yl)tetrahydro-2H-pyran-4-yl)pyrido[2,3-b]pyrazine | 432.4 |
| 267 | 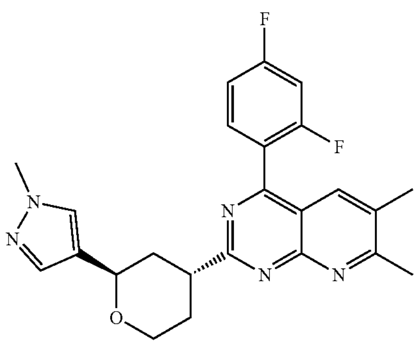 [SMILES: Cc1cc2c(-c3ccc(F)cc3F)nc([C@@H]3CCO[C@@H](c4cnn(C)c4)C3)nc2nc1C] | 4-(2,4-difluorophenyl)-6,7-dimethyl-2-((2R,4R)-2-(1-methyl-1H-pyrazol-4-yl)tetrahydro-2H-pyran-4-yl)pyrido[2,3-d]pyrimidine | 436.0 |
| 268 | 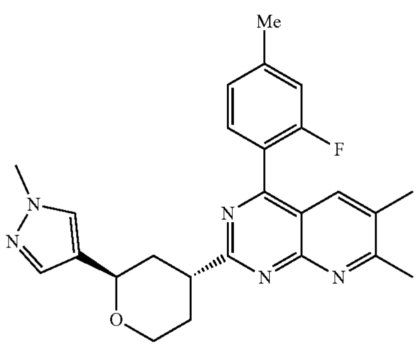 [SMILES: Cc1ccc(-c2nc([C@@H]3CCO[C@@H](c4cnn(C)c4)C3)nc3nc(C)c(C)cc23)c(F)c1] | 4-(2-fluoro-4-methylphenyl)-6,7-dimethyl-2-((2R,4R)-2-(1-methyl-1H-pyrazol-4-yl)tetrahydro-2H-pyran-4-yl)pyrido[2,3-d]pyrimidine | 432.1 |
| 269 | 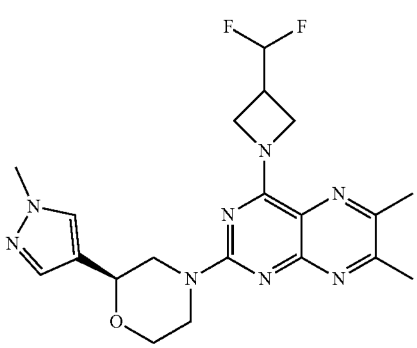 [SMILES: Cc1nc2nc(N3CCO[C@@H](c4cnn(C)c4)C3)nc(N3CC(C(F)F)C3)c2nc1C] | (S)-4-(4-(3-(difluoromethyl)azetidin-1-yl)-6,7-dimethylpteridin-2-yl)-2-(1-methyl-1H-pyrazol-4-yl)morpholine | 431.0 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 270 | 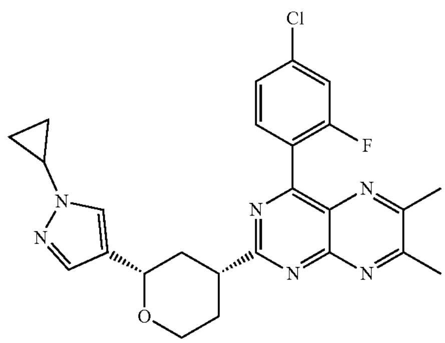 | 4-(4-chloro-2-fluorophenyl)-2-((2S,4R)-2-(1-cyclopropyl-1H-pyrazol-4-yl)tetrahydro-2H-pyran-4-yl)-7-methylpteridine | 465.1 |
| 271 | 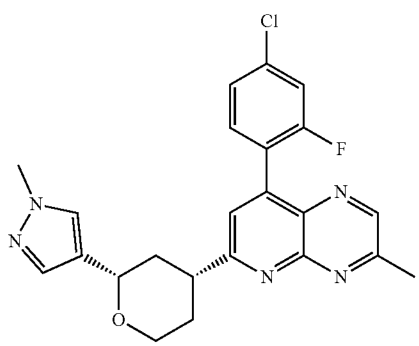 [SMILES: Cc1cnc2c(-c3ccc(Cl)cc3F)cc([C@@H]3CCO[C@H](c4cnn(C)c4)C3)nc2n1] | 8-(4-chloro-2-fluorophenyl)-3-methyl-6-((2S,4R)-2-(1-methyl-1H-pyrazol-4-yl)tetrahydro-2H-pyran-4-yl)pyrido[2,3-b]pyrazine | 438.2 |
| 272 | 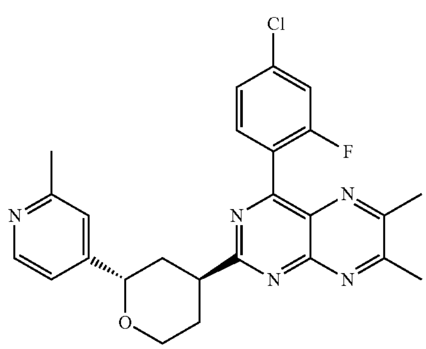 [SMILES: Cc1cc([C@@H]2C[C@@H](c3nc(-c4ccc(Cl)cc4F)c4nc(C)c(C)nc4n3)CCO2)ccn1] | 4-(4-chloro-2-fluorophenyl)-6,7-dimethyl-2-((2S,4S)-2-(2-methylpyridin-4-yl)tetrahydro-2H-pyran-4-yl)pteridine | 464.1 |
| 273 | 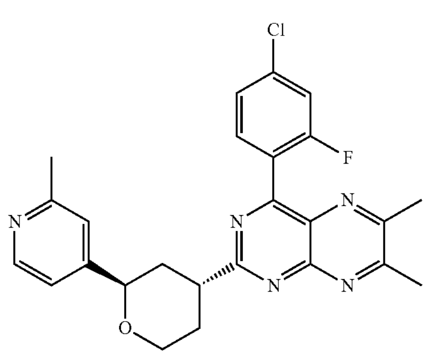 [SMILES: Cc1cc([C@H]2C[C@H](c3nc(-c4ccc(Cl)cc4F)c4nc(C)c(C)nc4n3)CCO2)ccn1] | 4-(4-chloro-2-fluorophenyl)-6,7-dimethyl-2-((2R,4R)-2-(2-methylpyridin-4-yl)tetrahydro-2H-pyran-4-yl)pteridine | 464.1 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 274 | 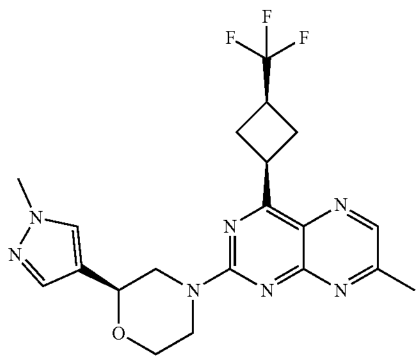 [SMILES: Cc1cnc2c(n1)nc(N1CCO[C@@H](c3cnn(C)c3)C1)nc2[C@H]1C[C@@H](C(F)(F)F)C1] | (S)-2-(1-methyl-1H-pyrazol-4-yl)-4-(7-methyl-4-((1s,3R)-3-(trifluoromethyl)cyclobutyl)pteridin-2-yl)morpholine | 434.0 |
| 275 | 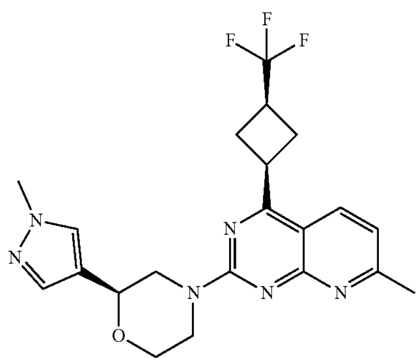 [SMILES: Cc1ccc2c(n1)nc(N1CCO[C@@H](c3cnn(C)c3)C1)nc2[C@H]1C[C@@H](C(F)(F)F)C1] | (S)-2-(1-methyl-1H-pyrazol-4-yl)-4-(7-methyl-4-((1s,3R)-3-(trifluoromethyl)cyclobutyl)pyrido[2,3-d]pyrimidin-2-yl)morpholine | 433.2 |
| 276 | 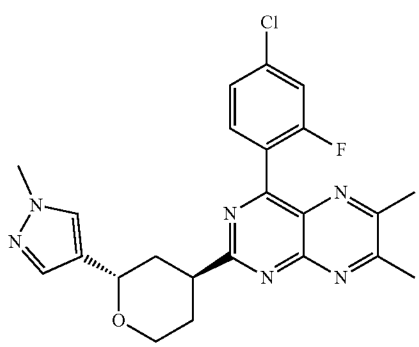 | 4-(4-chloro-2-fluorophenyl)-6,7-dimethyl-2-((2S,4R)-2-(1-methyl-1H-pyrazol-4-yl)tetrahydro-2H-pyran-4-yl)pteridine | 453.0 |
| 277 | 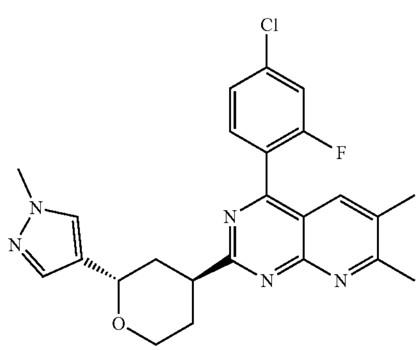 [SMILES: Cc1cc2c(-c3ccc(Cl)cc3F)nc([C@H]3CCO[C@H](c4cnn(C)c4)C3)nc2nc1C] | 4-(4-chloro-2-fluorophenyl)-6,7-dimethyl-2-((2S,4R)-2-(1-methyl-1H-pyrazol-4-yl)tetrahydro-2H-pyran-4-yl)pyrido[2,3-d]pyrimidine | 452.0 |

TABLE 8A-continued

Additional Compounds

The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 278 | 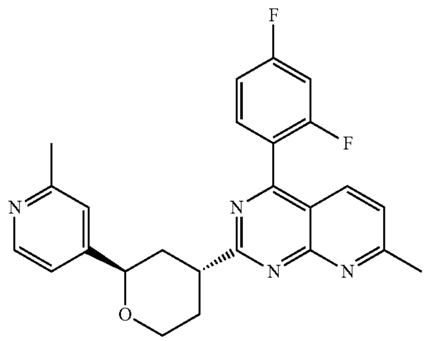 [SMILES: Cc1cc([C@H]2C[C@H](c3nc(-c4ccc(F)cc4F)c4ccc(C)nc4n3)CCO2)ccn1] | 4-(2,4-difluorophenyl)-7-methyl-2-((2R,4R)-2-(2-methylpyridin-4-yl)tetrahydro-2H-pyran-4-yl)pyrido[2,3-d]pyrimidine | 433.0 |
| 279 | 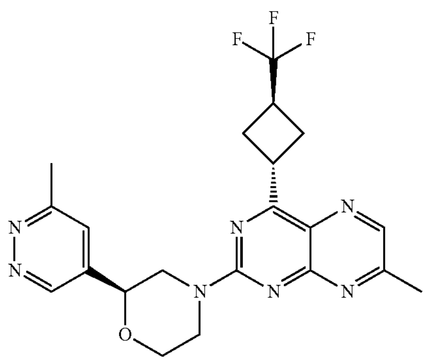 [SMILES: Cc1cc([C@H]2CN(c3nc4nc(C)cnc4c([C@H]4C[C@H](C(F)(F)F)C4)n3)CCO2)cnn1] | (S)-4-(7-methyl-4--((1r,3S)-3-(trifluoromethyl)cyclobutyl)pteridin-2-yl)-2-(6-methylpyridazin-4-yl)morpholine | 446.0 |
| 280 | 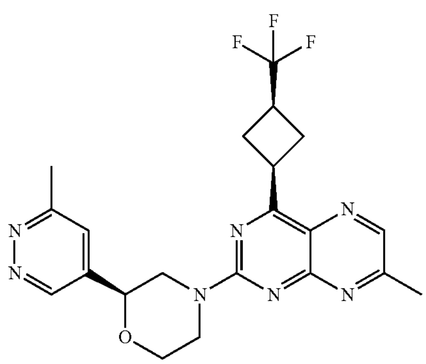 [SMILES: Cc1cc([C@H]2CN(c3nc4nc(C)cnc4c([C@H]4C[C@@H](C(F)(F)F)C4)n3)CCO2)cnn1] | (S)-4-(7-methyl-4-((1s,3R)-3-(trifluoromethyl)cyclobutyl)pteridin-2-yl)-2-(6-methylpyridazin-4-yl)morpholine | 446.0 |
| 281 | 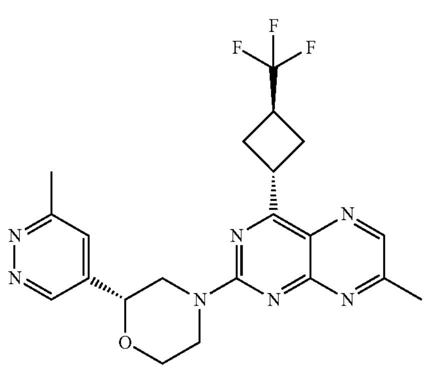 [SMILES: Cc1cc([C@@H]2CN(c3nc4nc(C)cnc4c([C@H]4C[C@H](C(F)(F)F)C4)n3)CCO2)cnn1] | (R)-4-(7-methyl-4-((1r,3S)-3-(trifluoromethyl)cyclobutyl)pteridin-2-yl)-2-(6-methylpyridazin-4-yl)morpholine | 446.0 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 282 | 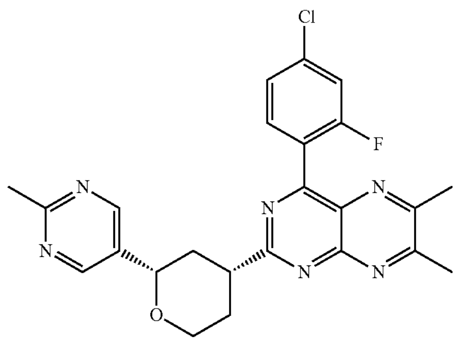 | 4-(4-chloro-2-fluorophenyl)-6,7-dimethyl-2-((2S,4R)-2-(2-methylpyrimidin-5-yl)tetrahydro-2H-pyran-4-yl)pteridine | 465.0 |
| 283 | 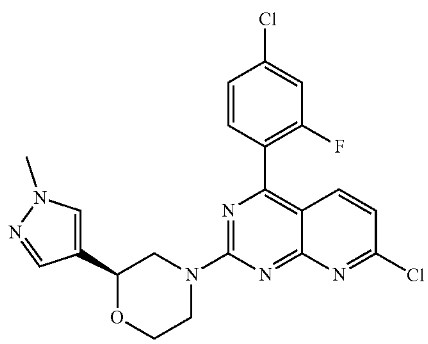 [SMILES: Cn1cc([C@H]2CN(c3nc(-c4ccc(Cl)cc4F)c4ccc(Cl)nc4n3)CCO2)cn1] | (S)-4-(7-chloro-4-(4-chloro-2-fluorophenyl)pyrido[2,3-d]pyrimidin-2-yl)-2-(1-methyl-1H-pyrazol-4-yl)morpholine | 461.1 |
| 284 | 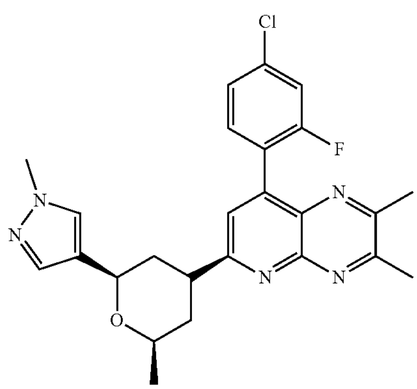 | 8-(4-chloro-2-fluorophenyl)-2,3-dimethyl-6-((2R,4R,6R)-2-methyl-6-(1-methyl-1H-pyrazol-4-yl)tetrahydro-2H-pyran-4-yl)pyrido[2,3-b]pyrazine | 466.0 |
| 285 | 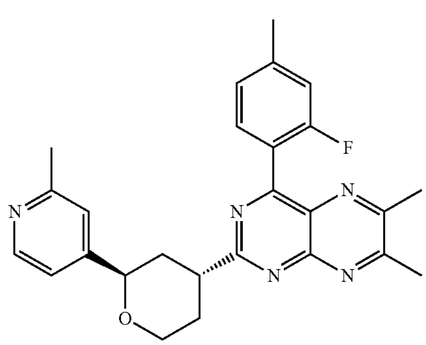 [SMILES: Cc1ccc(-c2nc([C@@H]3CCO[C@@H](c4ccnc(C)c4)C3)nc3nc(C)c(C)nc23)c(F)c1] | 4-(2-fluoro-4-methylphenyl)-6,7-dimethyl-2-((2R,4R)-2-(2-methylpyridin-4-yl)tetrahydro-2H-pyran-4-yl)pteridine | 444.3 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|------|-----------|------|------|
| 286 | 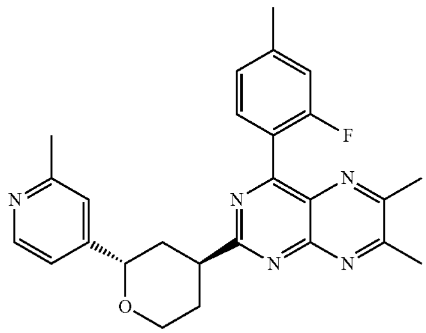 [SMILES: Cc1ccc(-c2nc([C@H]3CCO[C@H](c4ccnc(C)c4)C3)nc3nc(C)c(C)nc23)c(F)c1] | 4-(2-fluoro-4-methylphenyl)-6,7-dimethyl-2-((2S,4S)-2-(2-methylpyridin-4-yl)tetrahydro-2H-pyran-4-yl)pteridine | 444.2 |
| 287 | 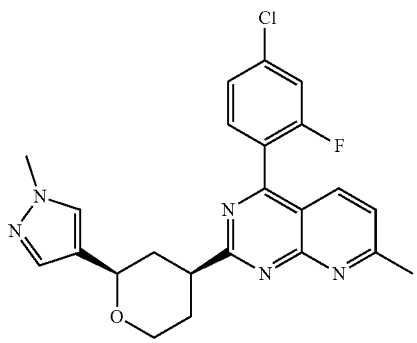 [SMILES: Cc1ccc2c(-c3ccc(Cl)cc3F)nc([C@H]3CCO[C@@H](c4cnn(C)c4)C3)nc2n1] | 4-(4-chloro-2-fluorophenyl)-7-methyl-2-((2R,4S)-2-(1-methyl-1H-pyrazol-4-yl)tetrahydro-2H-pyran-4-yl)pyrido[2,3-d]pyrimidine | 438.1 |
| 288 | 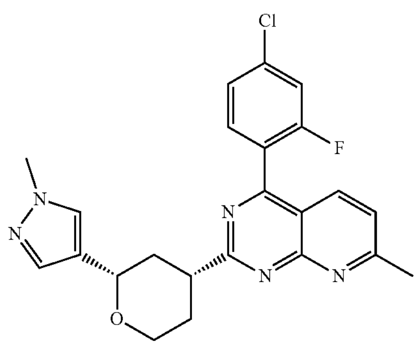 [SMILES: Cc1ccc2c(-c3ccc(Cl)cc3F)nc([C@@H]3CCO[C@H](c4cnn(C)c4)C3)nc2n1] | 4-(4-chloro -2-fluorophenyl)-7-methyl-2((2S,4R)-2-(1-methyl-1H-pyrazol-4-yl)tetrahydro-2H-pyran-4-yl)pyrido[2,3-d]pyrimidine | 438.1 |
| 289 | 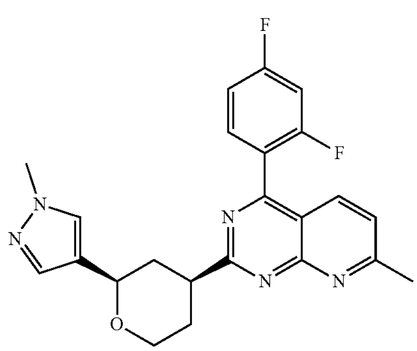 [SMILES: Cc1ccc2c(-c3ccc(F)cc3F)nc([C@H]3CCO[C@@H](c4cnn(C)c4)C3)nc2n1] | 4-(2,4-difluorophenyl)-7-methyl-2-((2R,4S)-2-(1-methyl-1H-pyrazol-4-yl)tetrahydro-2H-pyran-4-yl)pyrido[2,3-d]pyrimidine | 422.2 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 290 | 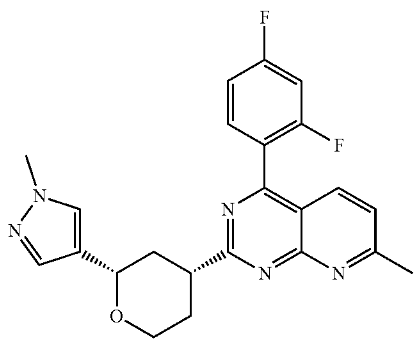 [SMILES: Cc1ccc2c(-c3ccc(F)cc3F)nc([C@@H]3CCO[C@H](c4cnn(C)c4)C3)nc2n1] | 4-(2,4-difluorophenyl)-7-methyl-2-((2S,4R)-2-(1-methyl-1H-pyrazol-4-yl)tetrahydro-2H-pyran-4-yl)pyrido[2,3-d]pyrimidine | 422.2 |
| 291 | 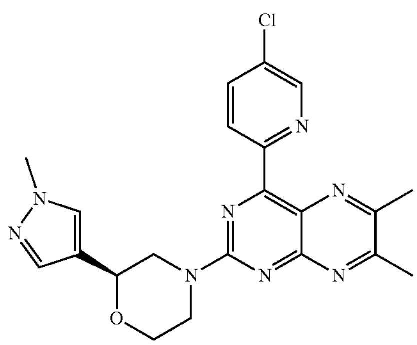 [SMILES: Cc1nc2nc(N3CCO[C@@H](c4cnn(C)c4)C3)nc(-c3ccc(Cl)cn3)c2nc1C] | (S)-4-(4-(5-chloropyridin-2-yl)-6,7-dimethylpteridin-2-yl)-2-(1-methyl-1H-pyrazol-4-yl)morpholine | 437.1 |
| 292 | 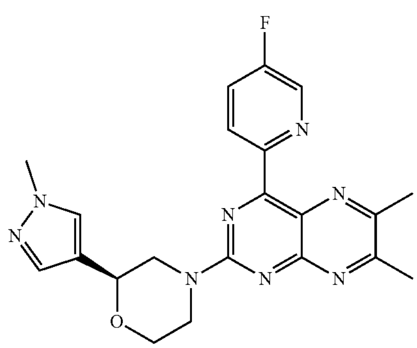 [SMILES: Cc1nc2nc(N3CCO[C@@H](c4cnn(C)c4)C3)nc(-c3ccc(F)cn3)c2nc1C] | (S)-4-(4-(5-fluoropyridin-2-yl)-6,7-dimethylpteridin-2-yl)-2-(1-methyl-1H-pyrazol-4-yl)morpholine | 421.2 |
| 293 | 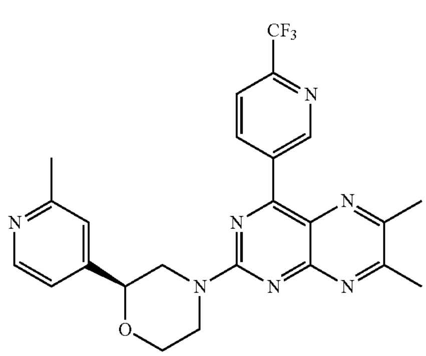 | (S)-4-(6,7-dimethyl-4-(6-(trifluoromethyl)pyridin-3-yl)pteridin-2-yl)-2-(2-methylpyridin-4-yl)morpholine | 482.0 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 294 | 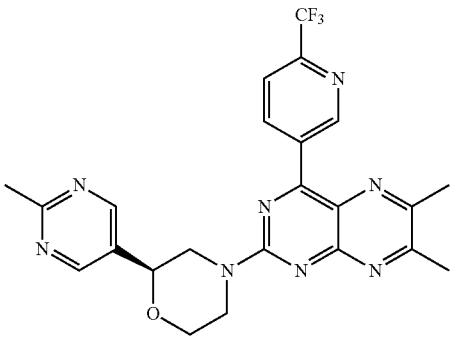 | (S)-4-(6,7-dimethyl-4-(6-(trifluoromethyl)pyridin-3-yl)pteridin-2-yl)-2-(2-methylpyrimidin-5-yl)morpholine | 483.1 |
| 295 | 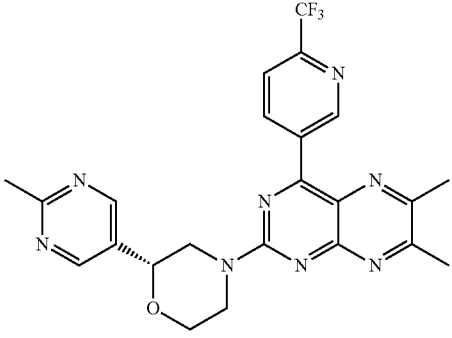 | (R)-4-(6,7-dimethyl-4-(6-(trifluoromethyl)pyridin-3-yl)pteridin-2-yl)-2-(2-methylpyrimidin-5-yl)morpholine | 483.1 |
| 296 | 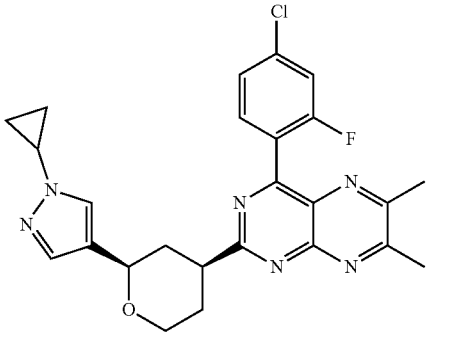 | 5-(4-chloro-2-fluorophenyl)-7-((2R,4S)-2-(1-cyclopropyl-1H-pyrazol-4-yl)tetrahydro-2H-pyran-4-yl)-2,3-dimethylpyrido[3,4-b]pyrazine | 478.2 |
| 297 | 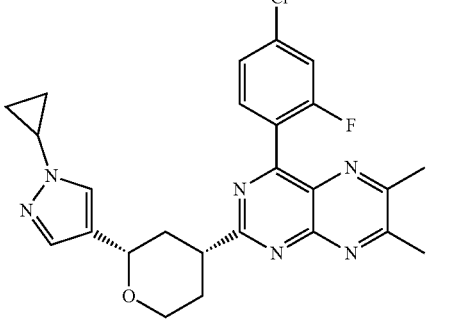 | 5-(4-chloro-2-fluorophenyl)-7-((2S,4R)-2-(1-cyclopropyl-1H-pyrazol-4-yl)tetrahydro-2H-pyran-4-yl)-2,3-dimethylpyrido[3,4-b]pyrazine | 478.1 |

TABLE 8A-continued

Additional Compounds
The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 298 | 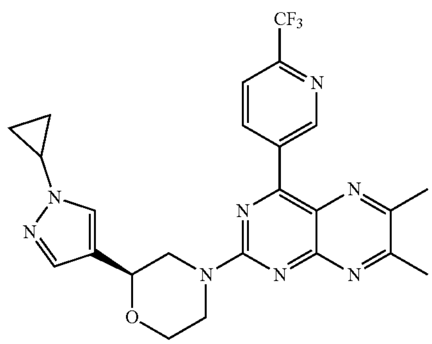 [SMILES: Cc1nc2nc(N3CCO[C@@H](c4cnn(C5CC5)c4)C3)nc(-c3ccc(C(F)(F)F)nc3)c2nc1C] | (S)-2-(1-cyclopropyl-1H-pyrazol-4-yl)-4-(6,7-dimethyl-4-(6-(trifluoromethyl)pyridin-3-yl)pteridin-2-yl)morpholine | 497.0 |
| 299 | 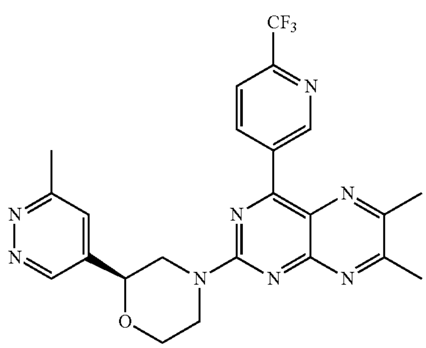 | (S)-4-(6,7-dimethyl-4-(6-(trifluoromethyl)pyridin-3-yl)pteridin-2-yl)-2-(6-methylpyridazin-4-yl)morpholine | 483.1 |
| 300 | 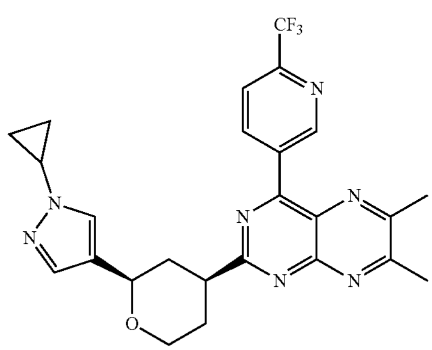 [SMILES: Cc1nc2nc([C@H]3CCO[C@@H](c4cnn(C5CC5)c4)C3)nc(-c3ccc(C(F)(F)F)nc3)c2nc1C] | 2-((2R,4S)-2-(1-cyclopropyl-1H-pyrazol-4-yl)tetrahydro-2H-pyran-4-yl)-6,7-dimethyl-4-(6-(trifluoromethyl)pyridin-3-yl)pteridine | 496.0 |
| 301 | 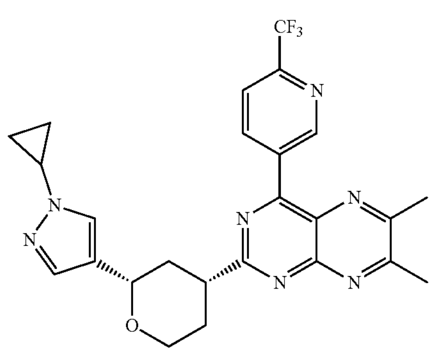 [SMILES: Cc1nc2nc([C@@H]3CCO[C@H](c4cnn(C5CC5)c4)C3)nc(-c3ccc(C(F)(F)F)nc3)c2nc1C] | 2-((2S,4R)-2-(1-cyclopropyl-1H-pyrazol-4-yl)tetrahydro-2H-pyran-4-yl)-6,7-dimethyl-4-(6-(trifluoromethyl)pyridin-3-yl)pteridine | 496.0 |

TABLE 8A-continued

Additional Compounds

The compound disclosed below in Table 8A were made by a method of the present disclosure or a similar method. The appropriate reagents, starting materials and conditions necessary for synthesizing the compounds of Table 8A would be apparent to a person of ordinary skill in the art.

| Ex # | Structure | Name | M +H |
|---|---|---|---|
| 302 | 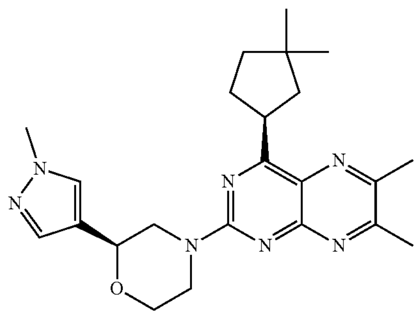 [SMILES: Cc1nc2nc(N3CCO[C@@H](c4cnn(C)c4)C3)nc([C@H]3CCC(C)(C)C3)c2nc1C] | (S)-4-(4-((S)-3,3-dimethylcyclopentyl)-6,7-dimethylpteridin-2-yl)-2-(1-methyl-1H-pyrazol-4-yl)morpholine | 422.2 |
| 303 | 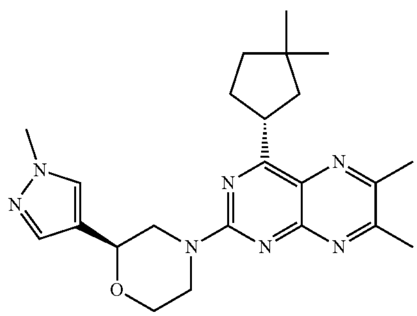 [SMILES: Cc1nc2nc(N3CCO[C@@H](c4cnn(C)c4)C3)nc([C@@H]3CCC(C)(C)C3)c2nc1C] | (S)-4-(4-((R)-3,3-dimethylcyclopentyl)-6,7-dimethylpteridin-2-yl)-2-(1-methyl-1H-pyrazol-4-yl)morpholine | 422.3 |
| 304 | 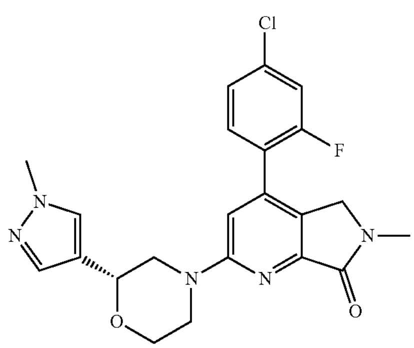 [SMILES: CN1Cc2c(-c3ccc(Cl)cc3F)cc(N3CCO[C@H](c4cnn(C)c4)C3)nc2C1=O] | (R)-4-(4-chloro-2-fluorophenyl)-6-methyl-2-(2-(1-methyl-1H-pyrazol-4-yl)morpholino)-5,6-dihydro-7H-pyrrolo[3,4-b]pyridin-7-one | 442.0 |
| 305 | 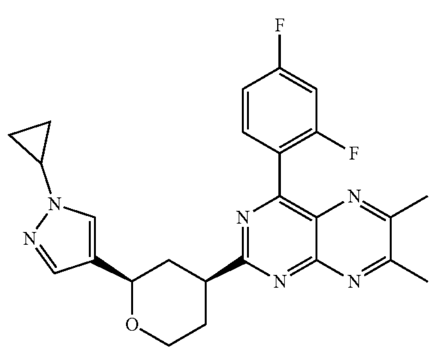 [SMILES: Cc1nc2nc([C@H]3CCO[C@@H](c4cnn(C5CC5)c4)C3)nc(-c3ccc(F)cc3F)c2nc1C] | 2-((2R,4S)-2-(1-cyclopropyl-1H-pyrazol-4-yl)tetrahydro-2H-pyran-4-yl)-4-(2,4-difluorophenyl)-6,7-dimethylpteridine | 463.2 |

TABLE 8B

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 306 | 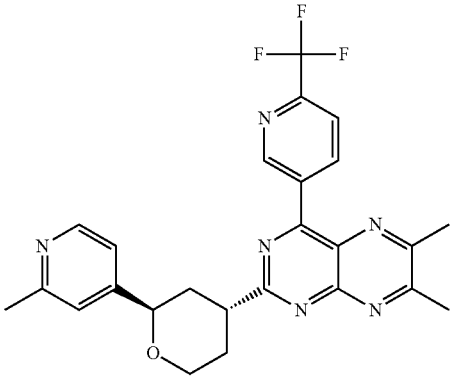 (+/−) | (2,3-dimethyl-7-(2-(2-methylpyridin-4-yl)tetrahydro-2H-pyran-4-yl)-6-(trifluoromethyl)pyridin-3-yl)pyrido[3,4-b]pyrazine | Method 37 |
| 307 | 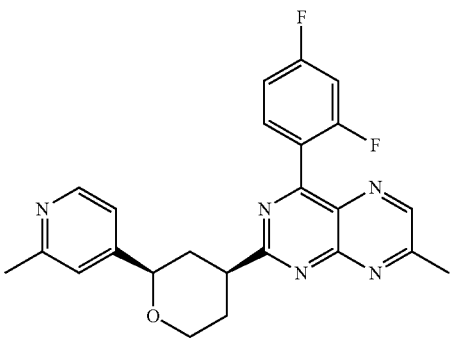 (+/−) | 5-(2,4-difluorophenyl)-2-methyl-7-(2-(2-methylpyridin-4-yl)tetrahydro-2H-pyran-4-yl)pyrido[3,4-b]pyrazine | Method 37 |
| 308 | 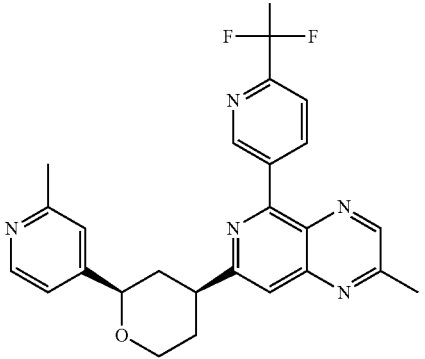 (+/−) | 2-methyl-7-(2-(2-methylpyridin-4-yl)tetrahydro-2H-pyran-4-yl)-5-(6-(trifluoromethyl)pyridin-3-yl)pyrido[3,4-b]pyrazine | Method 37 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 309 | 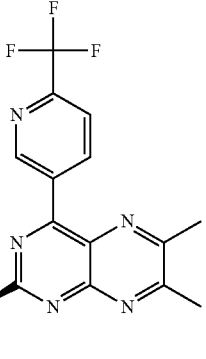 (+/−) | 6,7-dimethyl-2-(2-(2-methylpyridin-4-yl)tetrahydro-2H-pyran-4-yl)-4-(6-(trifluoromethyl)pyridin-3-yl)pteridine | Method 37 |
| 310 | 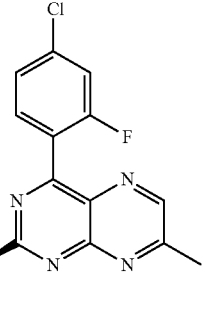 (+/−) | 5-(4-chloro-2-fluorophenyl)-2-methyl-7-(2-(2-methylpyridin-4-yl)tetrahydro-2H-pyran-4-yl)pyrido[3,4-b]pyrazine | Method 37 |
| 311 | 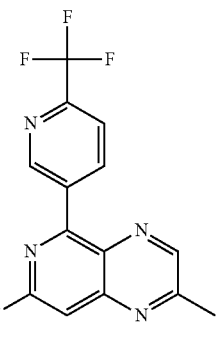 (rac) | 4-(2-methyl-5-(6-(trifluoromethyl)pyridin-3-yl)pyrido[3,4-b]pyrazin-7-yl)-2-(2-methylpyridin-4-yl)morpholine | Method 42 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 312 | 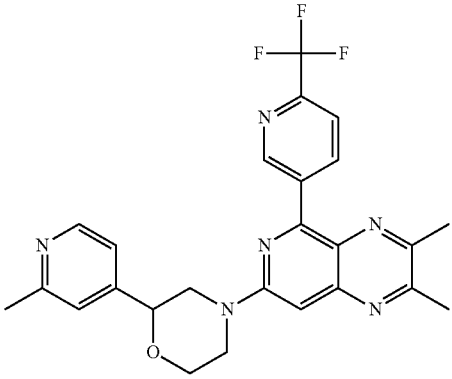 (rac) | 4-(2,3-dimethyl-5-(6-(trifluoromethyl)pyridin-3-yl)pyrido[3,4-b]pyrazin-7-yl)-2-(2-methylpyridin-4-yl)morpholine | Method 42 |
| 313 | 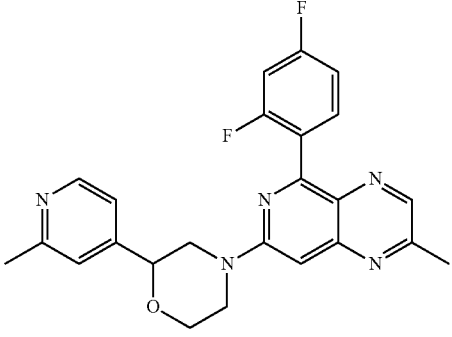 (rac) | 4-(5-(2,4-difluorophenyl)-2-methylpyrido[3,4-b]pyrazin-7-yl)-2-(2-methylpyridin-4-yl)morpholine | Method 42 |
| 314 | 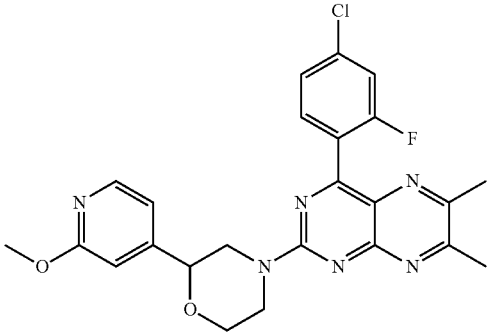 (rac) | 4-(4-(4-chloro-2-fluorophenyl)-6,7-dimethylpteridin-2-yl)-2-(2-methoxypyridin-4-yl)morpholine | Method 1 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 315 | 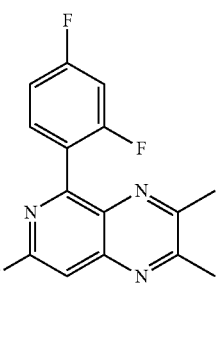 (rac) | 4-(5-(2,4-difluorophenyl)-2,3-dimethylpyrido[3,4-b]pyrazin-7-yl)-2-(2-methylpyridin-4-yl)morpholine | Method 42 |
| 316 | 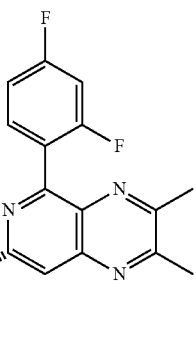 | 5-(2,4-difluorophenyl)-2,3-dimethyl-7-[(2S,4R)-2-(2-methyl-4-pyridyl)tetrahydropyran-4-yl]pyrido[3,4-b]pyrazine | Method 37 |
| 317 | 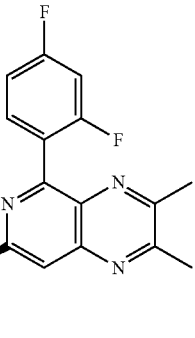 | 5-(2,4-difluorophenyl)-2,3-dimethyl-7-[(2R,4S)-2-(2-methyl-4-pyridyl)tetrahydropyran-4-yl]pyrido[3,4-b]pyrazine | Method 37 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|------|-----------|------|---------------------------|
| 318 | 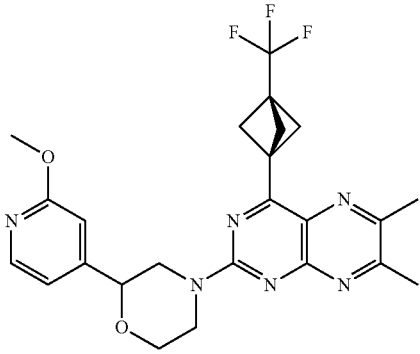 (rac) | 4-(6,7-dimethyl-4-(3-(trifluoromethyl)bicyclo[1.1.1]pentan-1-yl)pteridin-2-yl)-2-(2-methoxypyridin-4-yl)morpholine | Method 1 |
| 319 | 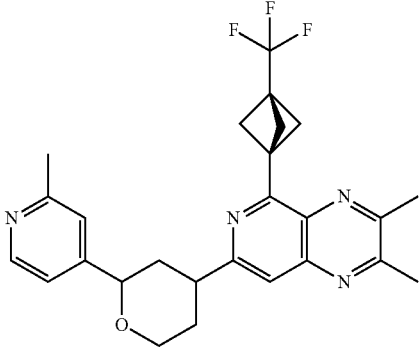 (rac) | 2,3-dimethyl-7-(2-(2-methylpyridin-4-yl)tetrahydro-2H-pyran-4-yl)-5-(3-(trifluoromethyl)bicyclo[1.1.1]pentan-1-yl)pyrido[3,4-b]pyrazine | Method 37 |
| 320 | 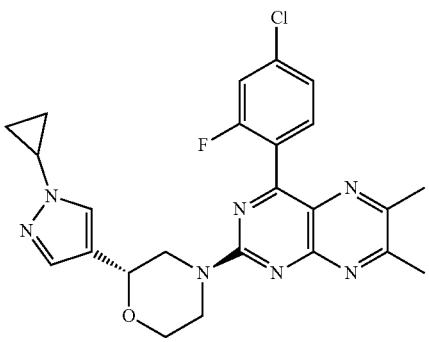 | 4-(4-chloro-2-fluorophenyl)-2-((2S,4S)-2-(1-cyclopropyl-1H-pyrazol-4-yl)tetrahydro-2H-pyran-4-yl)-6,7-dimethylpteridine | Method 9 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 321 | 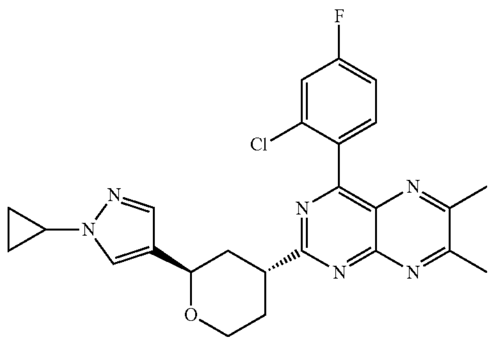 [SMILES: Cc1nc2nc([C@@H]3CCO[C@@H](c4cnn(C5CC5)c4)C3)nc(-c3ccc(F)cc3Cl)c2nc1C] | 4-(2-chloro-4-fluorophenyl)-2-((2R,4R)-2-(1-cyclopropyl-1H-pyrazol-4-yl)tetrahydro-2H-pyran-4-yl)-6,7-dimethylpteridine | Method 9 |
| 322 | (rac) | 4-(6,7-dimethyl-4-(6-(trifluoromethyl)pyridin-3-yl)pteridin-2-yl)-2-(2-methoxypyridin-4-yl)morpholine | Method 37 |
| 323 | (+/−) | 4-(2,4-difluorophenyl)-7-methyl-2-(2-(2-methylpyridin-4-yl)tetrahydro-2H-pyran-4-yl)pyrido[2,3-d]pyrimidine | Method 37 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 324 | 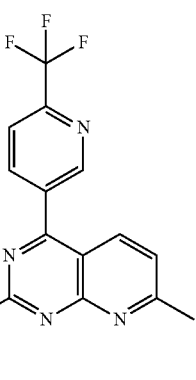 (rac) | 7-methyl-2-(2-(2-methylpyridin-4-yl)tetrahydro-2H-pyran-4-yl)-4-(6-(trifluoromethyl)pyridin-3-yl)pyrido[2,3-d]pyrimidine | Method 37 |
| 325 | 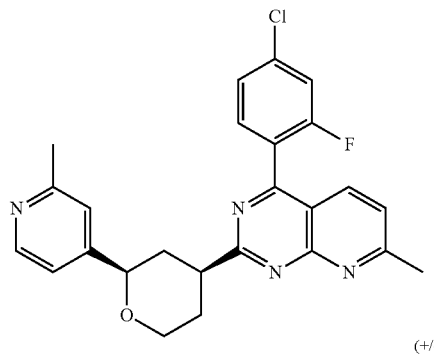 (+/−) | 4-(4-chloro-2-fluorophenyl)-7-methyl-2-(2-(2-methylpyridin-4-yl)tetrahydro-2H-pyran-4-yl)pyrido[2,3-d]pyrimidine | Method 37 |
| 326 | 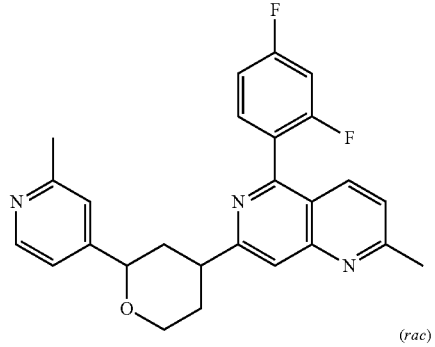 [SMILES: Cc1cc(C2CC(c3cc4nc(C)ccc4c(-c4ccc(F)cc4F)n3)CCO2)ccn1] (rac) | 5-(2,4-difluorophenyl)-2-methyl-7-(2-(2-methylpyridin-4-yl)tetrahydro-2H-pyran-4-yl)-1,6-naphthyridine | Method 37 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 327 | 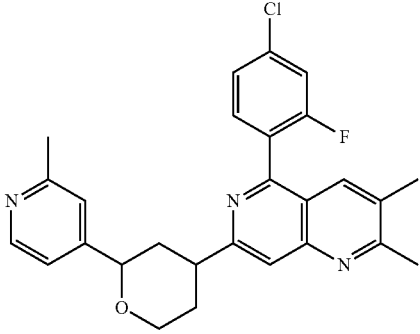 (rac) | 5-(4-chloro-2-fluorophenyl)-2,3-dimethyl-7-(2-(2-methylpyridin-4-yl)tetrahydro-2H-pyran-4-yl)-1,6-naphthyridine | Method 37 |
| 328 | 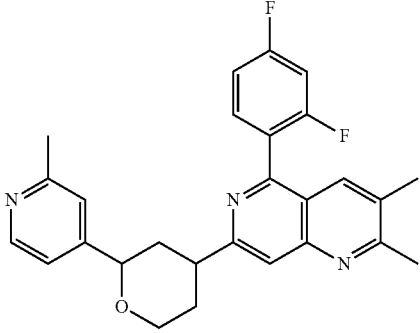 (rac) | 5-(2,4-difluorophenyl)-2,3-dimethyl-7-(2-(2-methylpyridin-4-yl)tetrahydro-2H-pyran-4-yl)-1,6-naphthyridine | Method 37 |
| 329 | 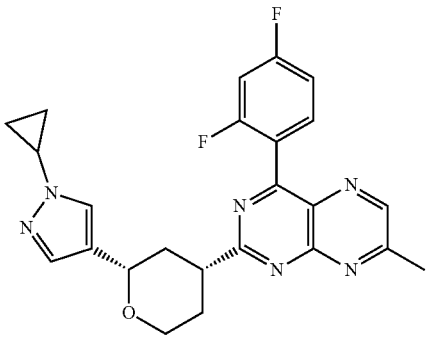 [SMILES: Cc1cnc2c(-c3ccc(F)cc3F)nc([C@@H]3CCO[C@H](c4cnn(C5CC5)c4)C3)nc2n1] | 2-[(2S,4R)-2-(1-cyclopropylpyrazol-4-yl)tetrahydropyran-4-yl]-4-(2,4-difluorophenyl)-7-methyl-pteridine | Method 9 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 330 | 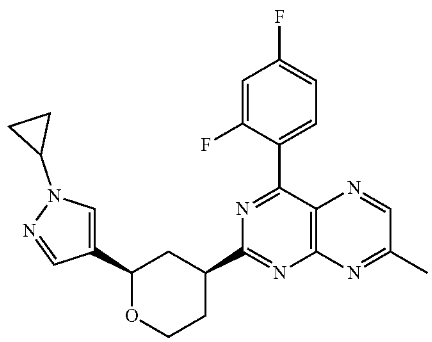 [SMILES: Cc1cnc2c(-c3ccc(F)cc3F)nc([C@H]3CCO[C@@H](c4cnn(C5CC5)c4)C3)nc2n1] | 2-[(2R,4S)-2-(1-cyclopropylpyrazol-4-yl)tetrahydropyran-4-yl]-4-(2,4-difluorophenyl)-7-methyl-pteridine | Method 9 |
| 331 | 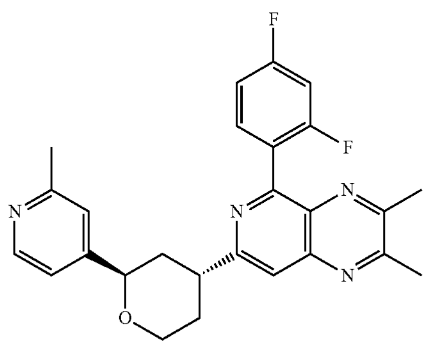 [SMILES: Cc1cc([C@H]2C[C@H](c3cc4nc(C)c(C)nc4c(-c4ccc(F)cc4F)n3)CCO2)ccn1] | 5-(2,4-difluorophenyl)-2,3-dimethyl-7-((2R,4R)-2-(2-methylpyridin-4-yl)tetrahydro-2H-pyran-4-yl)pyrido[3,4-b]pyrazine | Method 42 |
| 332 | 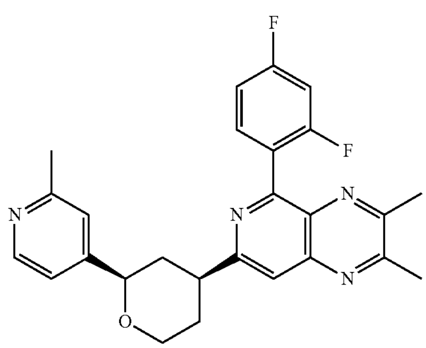 | 5-(2,4-difluorophenyl)-2,3-dimethyl-7-((2R,4S)-2-(2-methylpyridin-4-yl)tetrahydro-2H-pyran-4-yl)pyrido[3,4-b]pyrazine | Method 42 |
| 333 | 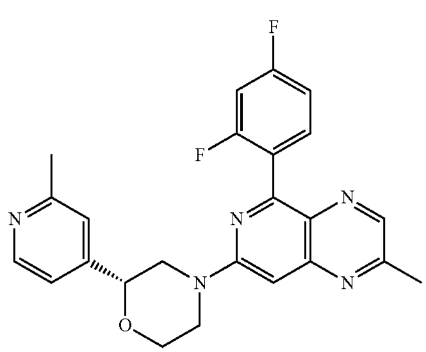 [SMILES: Cc1cc([C@@H]2CN(c3cc4nc(C)cnc4c(-c4ccc(F)cc4F)n3)CCO2)ccn1] | (R)-4-(5-(2,4-difluorophenyl)-2-methylpyrido[3,4-b]pyrazin-7-yl)-2-(2-methylpyridin-4-yl)morpholine | Method 42 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 334 | 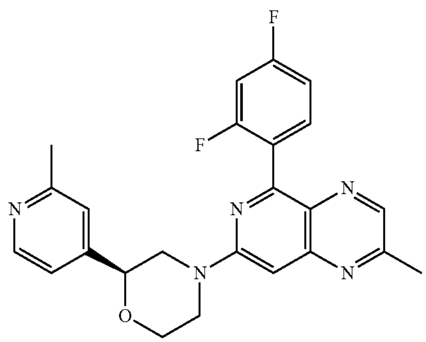 [SMILES: Cc1cc([C@H]2CN(c3cc4nc(C)cnc4c(-c4ccc(F)cc4F)n3)CCO2)ccn1] | (S)-4-(5-(2,4-difluorophenyl)-2-methylpyrido[3,4-b]pyrazin-7-yl)-2-(2-methylpyridin-4-yl)morpholine | Method 42 |
| 335 | 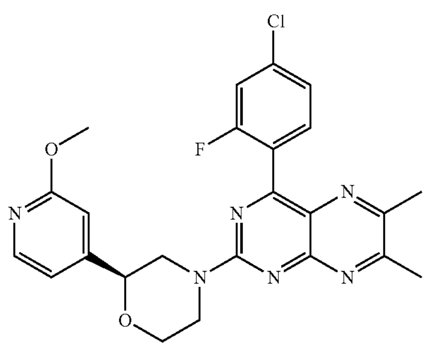 [SMILES: COc1cc([C@H]2CN(c3nc(-c4ccc(Cl)cc4F)c4nc(C)c(C)nc4n3)CCO2)ccn1] | (S)-4-(4-(4-chloro-2-fluorophenyl)-6,7-dimethylpteridin-2-yl)-2-(2-methoxypyridin-4-yl)morpholine | Method 1 |
| 336 | 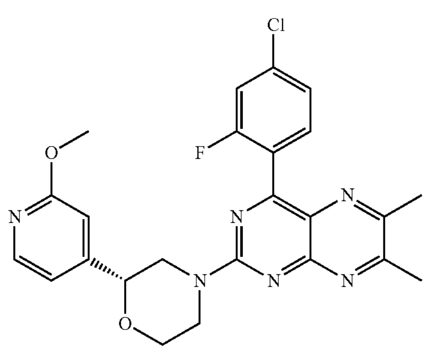 [SMILES: COc1cc([C@@H]2CN(c3nc(-c4ccc(Cl)cc4F)c4nc(C)c(C)nc4n3)CCO2)ccn1] | (R)-4-(4-(4-chloro-2-fluorophenyl)-6,7-dimethylpteridin-2-yl)-2-(2-methoxypyridin-4-yl)morpholine | Method 1 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 337 | 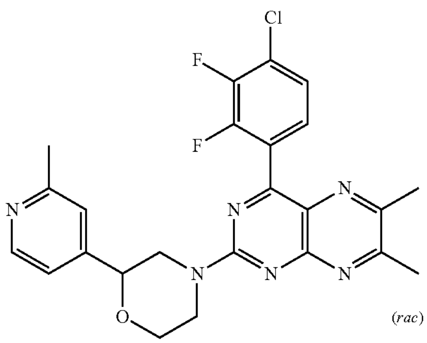 [SMILES: Cc1cc(C2CN(c3nc(-c4ccc(Cl)c(F)c4F)c4nc(C)c(C)nc4n3)CCO2)ccn1] | 4-(4-(4-chloro-2,3-difluorophenyl)-6,7-dimethylpteridin-2-yl)-2-(2-methylpyridin-4-yl)morpholine | Method 1 |
| 338 | 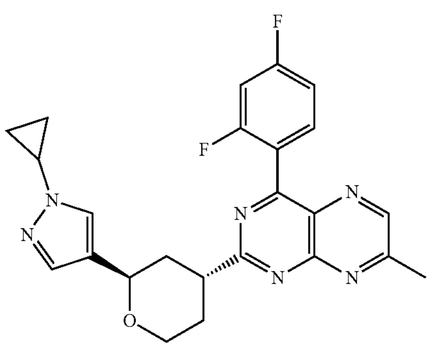 | 2-((2R,4R)-2-(1-cyclopropyl-1H-pyrazol-4-yl)tetrahydro-2H-pyran-4-yl)-4-(2,4-difluorophenyl)-7-methylpteridine | Method 9 |
| 339 | 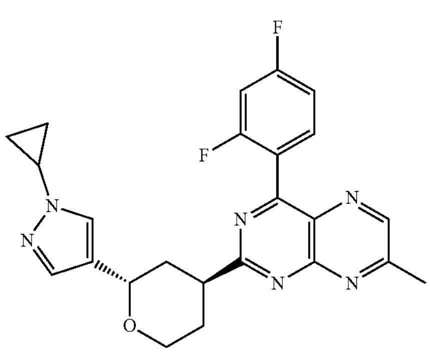 [SMILES: Cc1cnc2c(-c3ccc(F)cc3F)nc([C@H]3CCO[C@H](c4cnn(C5CC5)c4)C3)nc2n1] | 2-((2S,4S)-2-(1-cyclopropyl-1H-pyrazol-4-yl)tetrahydro-2H-pyran-4-yl)-4-(2,4-difluorophenyl)-7-methylpteridine | Method 9 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 340 | 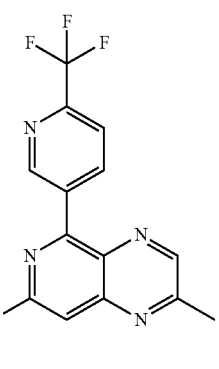 (rac) | 2-(1-cyclopropyl-1H-pyrazol-4-yl)-4-(2-methyl-5-(6-(trifluoromethyl)pyridin-3-yl)pyrido[3,4-b]pyrazin-7-yl)morpholine | Method 42 |
| 341 | 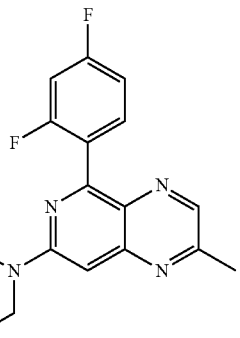 (rac) | 2-(1-cyclopropyl-1H-pyrazol-4-yl)-4-(5-(2,4-difluorophenyl)-2-methylpyrido[3,4-b]pyrazin-7-yl)morpholine | Method 42 |
| 342 | 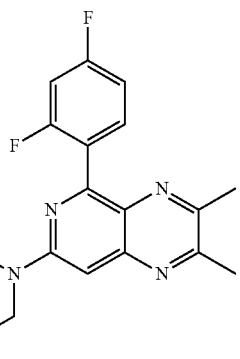 (rac) | 2-(1-cyclopropyl-1H-pyrazol-4-yl)-4-(5-(2,4-difluorophenyl)-2,3-dimethylpyrido[3,4-b]pyrazin-7-yl)morpholine | Method 42 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 343 | 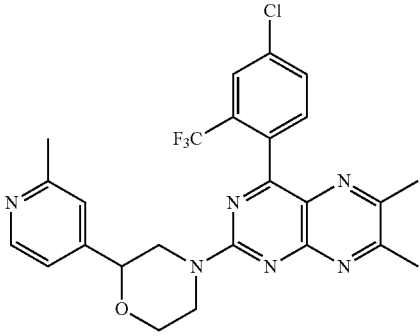 (rac) | 4-(4-(4-chloro-2-(trifluoromethyl)phenyl)-6,7-dimethylpteridin-2-yl)-2-(2-methylpyridin-4-yl)morpholine | Method 1 |
| 344 | 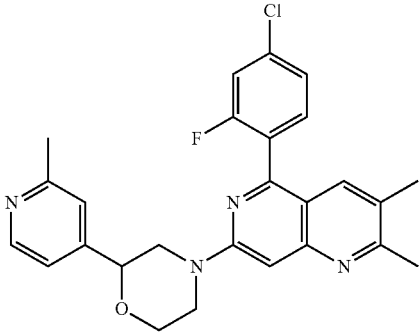 (rac) | 4-(5-(4-chloro-2-fluorophenyl)-2,3-dimethyl-1,6-naphthyridin-7-yl)-2-(2-methylpyridin-4-yl)morpholine | Method 40 |
| 345 | 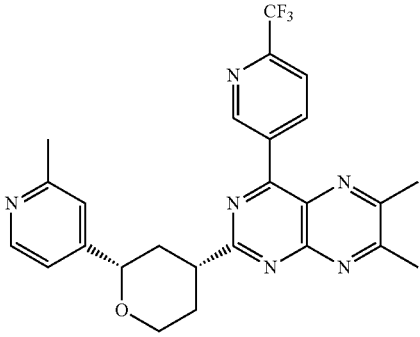 (+/−) | 6,7-dimethyl-2-(2-(2-methylpyridin-4-yl)tetrahydro-2H-pyran-4-yl)-4-(6-(trifluoromethyl)pyridin-3-yl)pteridine | Method 37 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 346 | 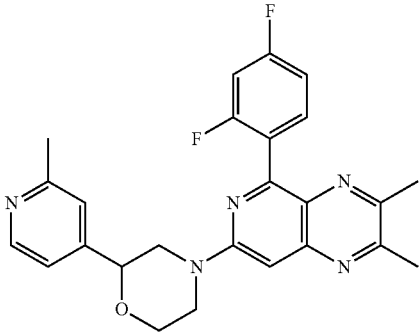 (rac) | 4-(5-(2,4-difluorophenyl)-2,3-dimethyl-1,6-naphthyridin-7-yl)-2-(2-methylpyridin-4-yl)morpholine | Method 40 |
| 347 | 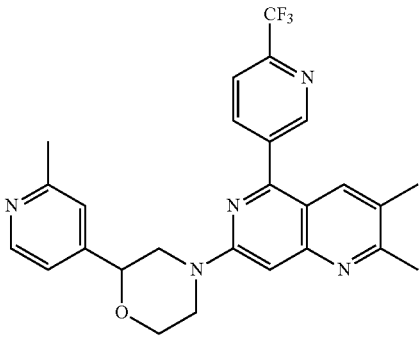 (rac) | 4-(2,3-dimethyl-5-(6-(trifluoromethyl)pyridin-3-yl)-1,6-naphthyridin-7-yl)-2-(2-methylpyridin-4-yl)morpholine | Method 40 |
| 348 | 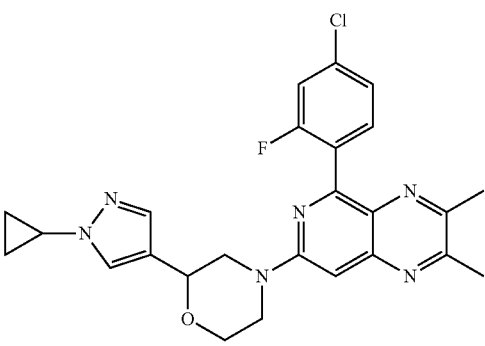 (rac) | 4-(5-(4-chloro-2-fluorophenyl)-2,3-dimethylpyrido[3,4-b]pyrazin-7-yl)-2-(1-cyclopropyl-1H-pyrazol-4-yl)morpholine | Method 42 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 349 | 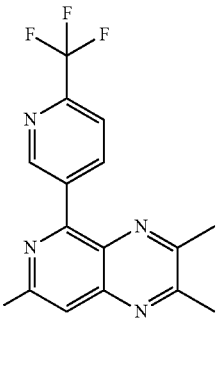 (rac) | 2-(1-cyclopropyl-1H-pyrazol-4-yl)-4-(2,3-dimethyl-5-(6-(trifluoromethyl)pyridin-3-yl)pyrido[3,4-b]pyrazin-7-yl)morpholine | Method 42 |
| 350 | 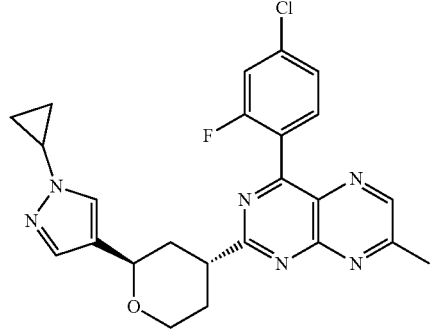 [SMILES: Cc1cnc2c(-c3ccc(Cl)cc3F)nc([C@@H]3CCO[C@@H](c4cnn(C5CC5)c4)C3)nc2n1] | 4-(4-chloro-2-fluorophenyl)-2-((2R,4R)-2-(1-cyclopropyl-1H-pyrazol-4-yl)tetrahydro-2H-pyran-4-yl)-7-methylpteridine | Method 9 |
| 351 | 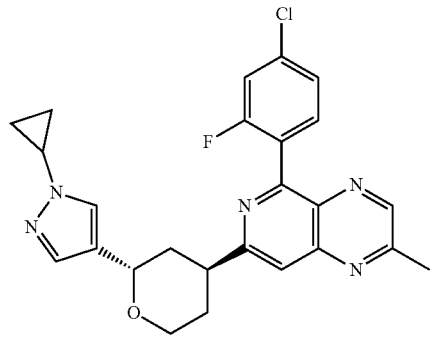 [SMILES: Cc1cnc2c(-c3ccc(Cl)cc3F)nc([C@H]3CCO[C@H](c4cnn(C5CC5)c4)C3)cc2n1] | 4-(4-chloro-2-fluorophenyl)-2-(2-(1-cyclopropyl-1H-pyrazol-4-yl)tetrahydro-2H-pyran-4-yl)-7-methylpteridine | Method 9 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|------|-----------|------|---------------------------|
| 352 | 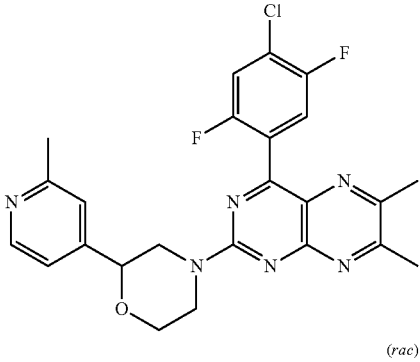 [SMILES: Cc1cc(C2CN(c3nc(-c4cc(F)c(Cl)cc4F)c4nc(C)c(C)nc4n3)CCO2)ccn1] (rac) | 4-(4-(4-chloro-2,5-difluorophenyl)-6,7-dimethylpteridin-2-yl)-2-(2-methylpyridin-4-yl)morpholine | Method 1 |
| 353 | 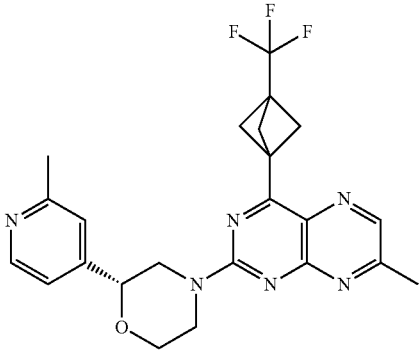 | (R)-4-(7-methyl-4-(3-(trifluoromethyl)bicyclo[1.1.1]pentan-1-yl)pteridin-2-yl)-2-(2-methylpyridin-4-yl)morpholine | Method 1 |
| 354 | 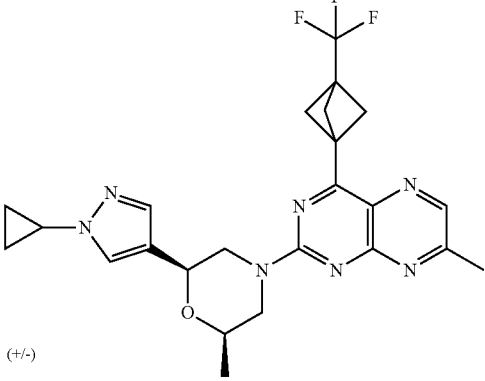 (+/−) | 2-(1-cyclopropyl-1H-pyrazol-4-yl)-6-methyl-4-(7-methyl-4-(3-(trifluoromethyl)bicyclo[1.1.1]pentan-1-yl)pteridin-2-yl)morpholine | Method 1 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 355 | 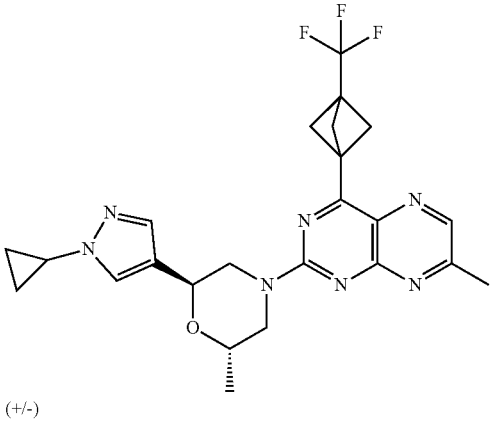 [SMILES: Cc1cnc2c(C34CC(C(F)(F)F)(C3)C4)nc(N3C[C@H](C)O[C@@H](c4cnn(C5CC5)c4)C3)nc2n1] (+/−) | 2-(1-cyclopropyl-1H-pyrazol-4-yl)-6-methyl-4-(7-methyl-4-(3-(trifluoromethyl)bicyclo[1.1.1]pentan-1-yl)pteridin-2-yl)morpholine | Method 1 |
| 356 | 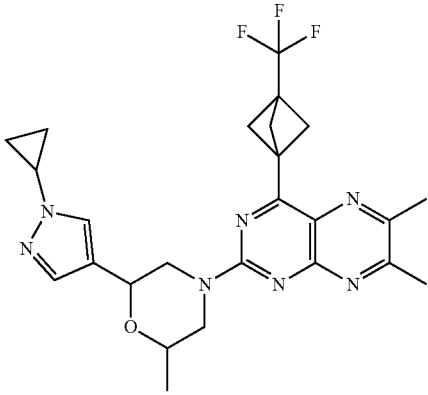 (rac) | 2-(1-cyclopropyl-1H-pyrazol-4-yl)-4-(6,7-dimethyl-4-(3-(trifluoromethyl)bicyclo[1.1.1]pentan-1-yl)pteridin-2-yl)-6-methylmorpholine | Method 1 |
| 357 | 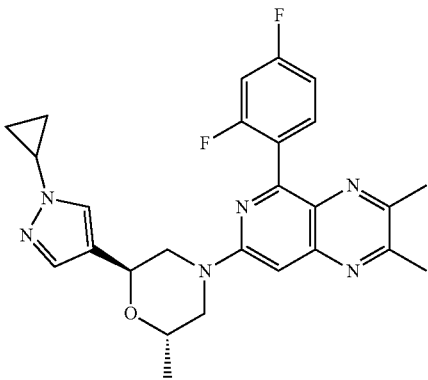 (+/−) | 2-(1-cyclopropyl-1H-pyrazol-4-yl)-4-(5-(2,4-difluorophenyl)-2,3-dimethylpyrido[3,4-b]pyrazin-7-yl)-6-methylmorpholine | Method 10 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 358 | 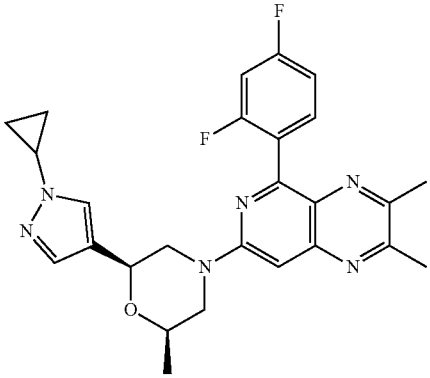 (+/−) | 2-(1-cyclopropyl-1H-pyrazol-4-yl)-4-(5-(2,4-difluorophenyl)-2,3-dimethylpyrido[3,4-b]pyrazin-7-yl)-6-methylmorpholine | Method 10 |
| 359 | 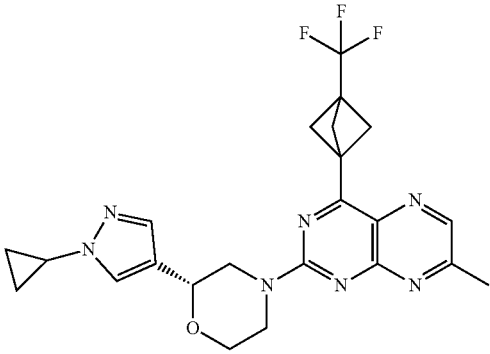 [SMILES: Cc1cnc2c(C34CC(C(F)(F)F)(C3)C4)nc(N3CCO[C@H](c4cnn(C5CC5)c4)C3)nc2n1] | (R)-2-(1-cyclopropyl-1H-pyrazol-4-yl)-4-(7-methyl-4-(3-(trifluoromethyl)bicyclo[1.1.1]pentan-1-yl)pteridin-2-yl)morpholine | Method 1 |
| 360 | 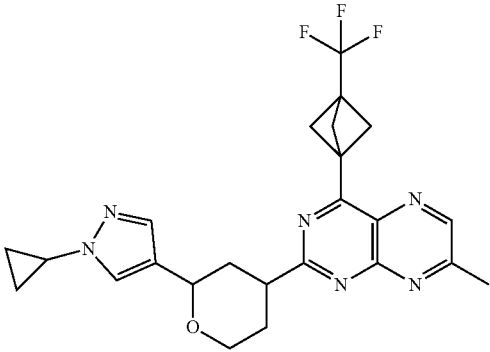 (rac) | 2-(2-(1-cyclopropyl-1H-pyrazol-4-yl)tetrahydro-2H-pyran-4-yl)-7-methyl-4-(3-(trifluoromethyl)bicyclo[1.1.1]pentan-1-yl)pteridine | Method 9 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 361 | (+/−) | 2-(1-cyclopropyl-1H-pyrazol-4-yl)-4-(5-(2,4-difluorophenyl)-2-methylpyrido[3,4-b]pyrazin-7-yl)-6-methylmorpholine | Method 10 |
| 362 | (+/−) | 2-(1-cyclopropyl-1H-pyrazol-4-yl)-4-(5-(2,4-difluorophenyl)-2-methylpyrido[3,4-b]pyrazin-7-yl)-6-methylmorpholine | Method 10 |
| 363 | 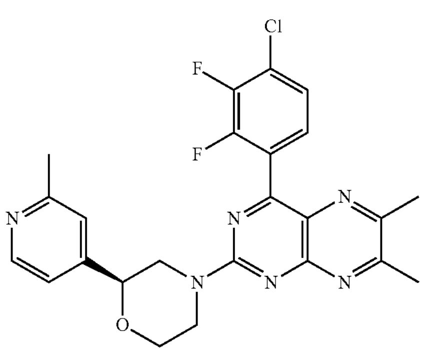 [SMILES: Cc1cc([C@H]2CN(c3nc(-c4ccc(Cl)c(F)c4F)c4nc(C)c(C)nc4n3)CCO2)ccn1] | (S)-4-(4-(4-chloro-2,3-difluorophenyl)-6,7-dimethylpteridin-2-yl)-2-(2-methylpyridin-4-yl)morpholine | Method 1 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 364 | 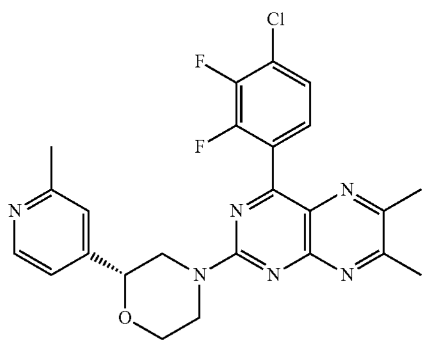 | (R)-4-(4-(4-chloro-2,3-difluorophenyl)-6,7-dimethylpteridin-2-yl)-2-(2-methylpyridin-4-yl)morpholine | Method 1 |
| 365 | 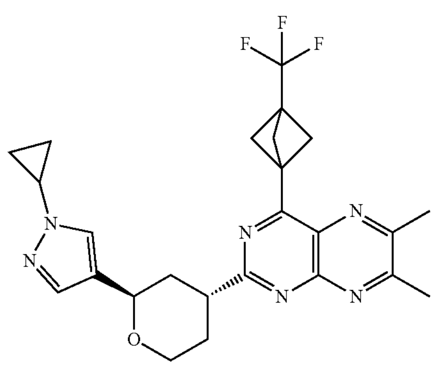 [SMILES: Cc1nc2nc([C@@H]3CCO[C@@H](c4cnn(C5CC5)c4)C3)nc(C34CC(C(F)(F)F)(C3)C4)c2nc1C] | 2-(2-(1-cyclopropyl-1H-pyrazol-4-yl)tetrahydro-2H-pyran-4-yl)-6,7-dimethyl-4-(3-(trifluoromethyl)bicyclo[1.1.1]pentan-1-yl)pteridine | Method 9 |
| 366 | 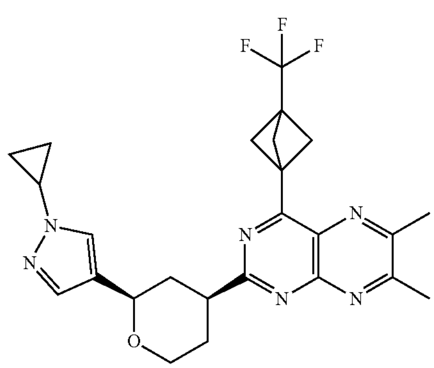 [SMILES: Cc1nc2nc([C@H]3CCO[C@@H](c4cnn(C5CC5)c4)C3)nc(C34CC(C(F)(F)F)(C3)C4)c2nc1C] | 2-(2-(1-cyclopropyl-1H-pyrazol-4-yl)tetrahydro-2H-pyran-4-yl)-6,7-dimethyl-4-(3-(trifluoromethyl)bicyclo[1.1.1]pentan-1-yl)pteridine | Method 9 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 367 | (rac) | 4-(5-(4-chloro-2-fluorophenyl)-2,3-dimethylpyrido[3,4-b]pyrazin-7-yl)-2-(1-cyclopropyl-1H-pyrazol-4-yl)-6-methylmorpholine | Method 10 |
| 368 | (+/−) | 4-(5-(4-chloro-2-fluorophenyl)-2-methylpyrido[3,4-b]pyrazin-7-yl)-2-(1-cyclopropyl-1H-pyrazol-4-yl)-6-methylmorpholine | Method 10 |
| 369 | (rac) | 2-(1-cyclopropyl-1H-pyrazol-4-yl)-4-(4-(2,4-difluorophenyl)-6,7-dimethylpteridin-2-yl)-6-methylmorpholine | Method 1 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 370 | (+/−) | 2-(1-cyclopropyl-1H-pyrazol-4-yl)-4-(4-(2,4-difluorophenyl)-7-methylpteridin-2-yl)-6-methylmorpholine | Method 1 |
| 371 | (+/−) | 2-(1-cyclopropyl-1H-pyrazol-4-yl)-4-(4-(2,4-difluorophenyl)-7-methylpteridin-2-yl)-6-methylmorpholine | Method 1 |
| 372 | (+/−) | 4-(4-(4-chloro-2-fluorophenyl)-6,7-dimethylpteridin-2-yl)-2-(1-cyclopropyl-1H-pyrazol-4-yl)-6-methylmorpholine | Method 1 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 373 | 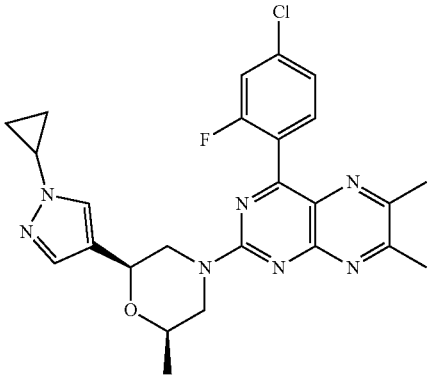 (+/−) | 4-(4-(4-chloro-2-fluorophenyl)-6,7-dimethylpteridin-2-yl)-2-(1-cyclopropyl-1H-pyrazol-4-yl)-6-methylmorpholine | Method 1 |
| 374 | 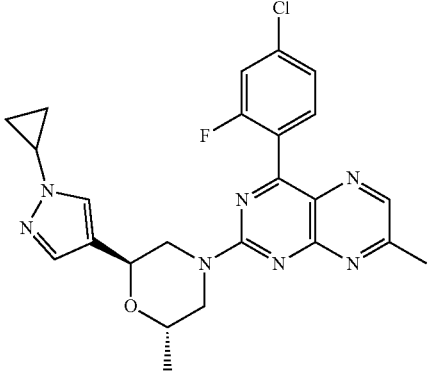 (+/−) | 4-(4-(4-chloro-2-fluorophenyl)-7-methylpteridin-2-yl)-2-(1-cyclopropyl-1H-pyrazol-4-yl)-6-methylmorpholine | Method 1 |
| 375 | 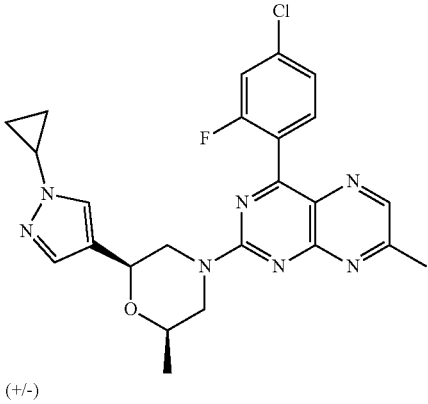 [SMILES: Cc1cnc2c(-c3ccc(Cl)cc3F)nc(N3C[C@@H](C)O[C@@H](c4cnn(C5CC5)c4)C3)nc2n1] (+/−) | 4-(4-(4-chloro-2-fluorophenyl)-7-methylpteridin-2-yl)-2-(1-cyclopropyl-1H-pyrazol-4-yl)-6-methylmorpholine | Method 1 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 376 | 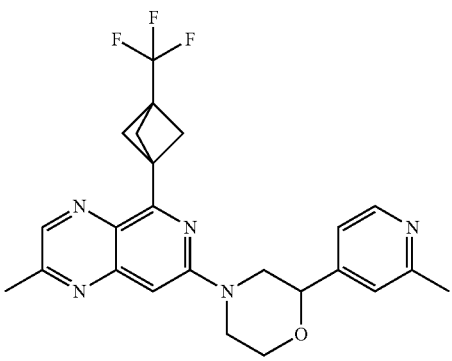 (rac) | 2-(2-methyl-4-pyridyl)-4-[2-methyl-5-[3-(trifluoromethyl)-1-bicyclo[1.1.1]pentanyl]pyrido[3,4-b]pyrazin-7-yl]morpholine | Method 5 |
| 377 | 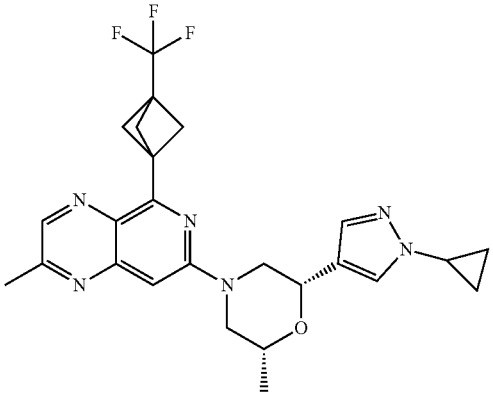 (+/−) | 2-(1-cyclopropylpyrazol-4-yl)-6-methyl-4-[2-methyl-5-[3-(trifluoromethyl)-1-bicyclo[1.1.1]pentanyl]pyrido[3,4-b]pyrazin-7-yl]morpholine | Method 10 |
| 378 | 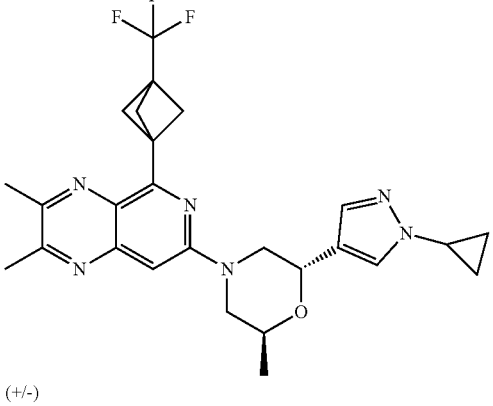 (+/−) | 2-(1-cyclopropylpyrazol-4-yl)-4-[2,3-dimethyl-5-[3-(trifluoromethyl)-1-bicyclo[1.1.1]pentanyl]pyrido[3,4-b]pyrazin-7-yl]-6-methyl-morpholine | Method 10 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 379 | 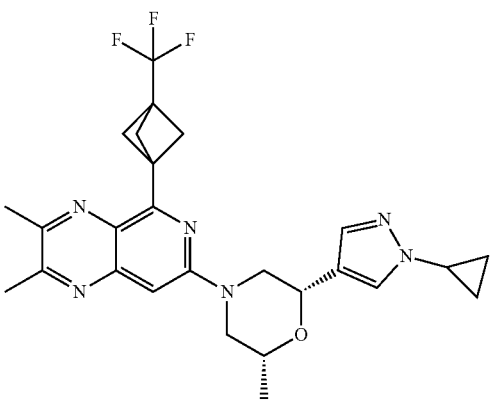 (+/−) | 2-(1-cyclopropylpyrazol-4-yl)-4-[2,3-dimethyl-5-[3-(trifluoromethyl)-1-bicyclo[1.1.1]pentanyl]pyrido[3,4-b]pyrazin-7-yl]-6-methyl-morpholine | Method 10 |
| 380 | 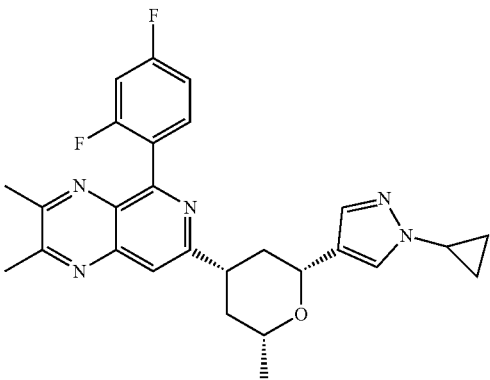 [SMILES: Cc1nc2cc([C@H]3C[C@@H](C)O[C@@H](c4cnn(C5CC5)c4)C3)nc(-c3ccc(F)cc3F)c2nc1C] | 7-[(2R,4S,6R)-2-(1-cyclopropylpyrazol-4-yl)-6-methyl-tetrahydropyran-4-yl]-5-(2,4-difluorophenyl)-2,3-dimethyl-pyrido[3,4-b]pyrazine | Method 37 |
| 381 | 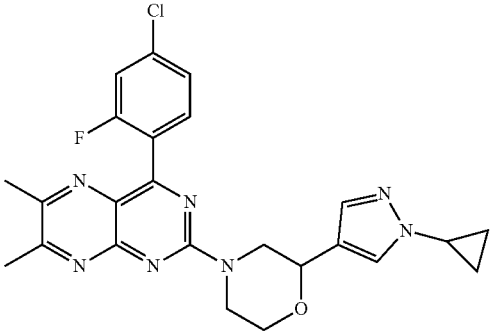 (rac) | 4-[4-(4-chloro-2-fluoro-phenyl)-6,7-dimethyl-pteridin-2-yl]-2-(1-cyclopropylpyrazol-4-yl)morpholine | Method 1 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 382 | 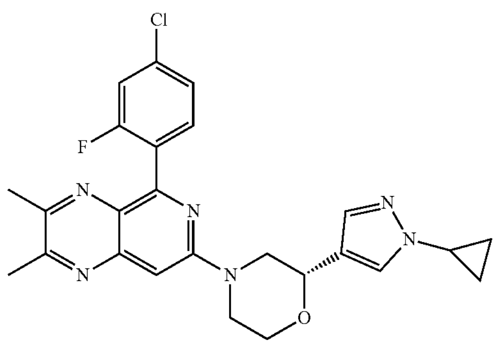 [SMILES: Cc1nc2cc(N3CCO[C@@H](c4cnn(C5CC5)c4)C3)nc(-c3ccc(Cl)cc3F)c2nc1C] | (2S)-4-[5-(4-chloro-2-fluoro-phenyl)-2,3-dimethyl-pyrido[3,4-b]pyrazin-7-yl]-2-(1-cyclopropylpyrazol-4-yl)morpholine | Method 42 |
| 383 | 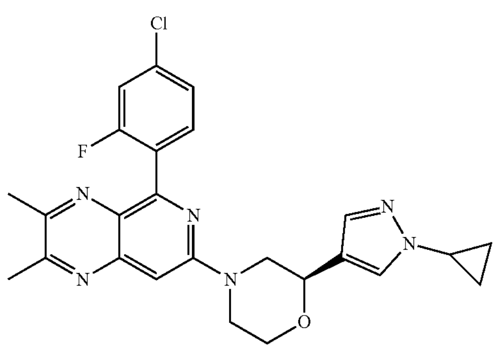 [SMILES: Cc1nc2cc(N3CCO[C@H](c4cnn(C5CC5)c4)C3)nc(-c3ccc(Cl)cc3F)c2nc1C] | (2R)-4-[5-(4-chloro-2-fluoro-phenyl)-2,3-dimethyl-pyrido[3,4-b]pyrazin-7-yl]-2-(1-cyclopropylpyrazol-4-yl)morpholine | Method 42 |
| 384 | 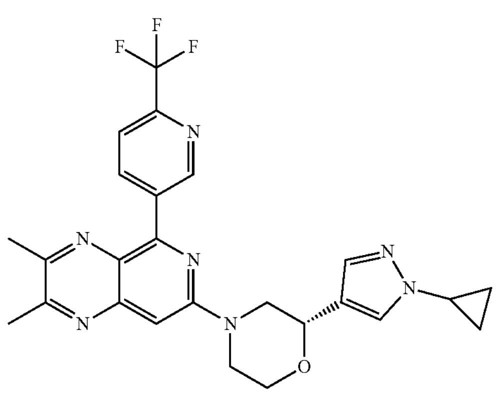 [SMILES: Cc1nc2cc(N3CCO[C@@H](c4cnn(C5CC5)c4)C3)nc(-c3ccc(C(F)(F)F)nc3)c2nc1C] | (2S)-2-(1-cyclopropylpyrazol-4-yl)-4-[2,3-dimethyl-5-[6-(trifluoromethyl)-3-pyridyl]pyrido[3,4-b]pyrazin-7-yl]morpholine | Method 42 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 385 | 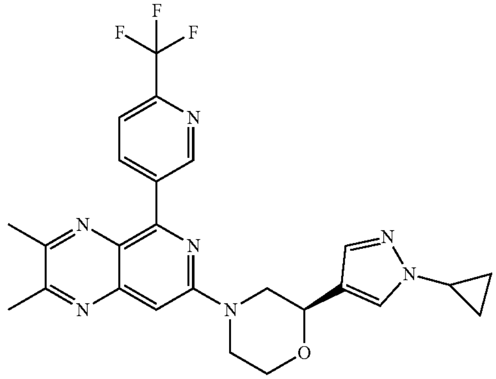 [SMILES: Cc1nc2cc(N3CCO[C@H](c4cnn(C5CC5)c4)C3)nc(-c3ccc(C(F)(F)F)nc3)c2nc1C] | (2R)-2-(1-cyclopropylpyrazol-4-yl)-4-[2,3-dimethyl-5-[6-(trifluoromethyl)-3-pyridyl]pyrido[3,4-b]pyrazin-7-yl]morpholine | Method 42 |
| 386 | (+/−) | 2-methyl-7-[2-(1-cyclopropylpyrazol-4-yl)tetrahydropyran-4-yl]-5-[3-(trifluoromethyl)-1-bicyclo[1.1.1]pentanyl]pyrido[3,4-b]pyrazine | Method 39 |
| 387 | 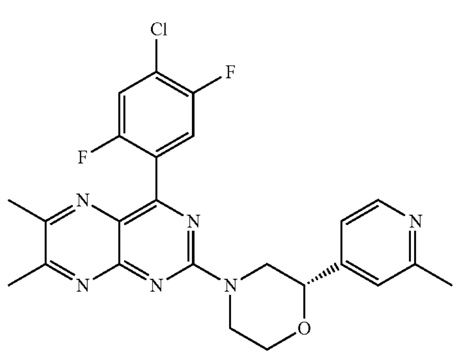 | (2S)-4-[4-(4-chloro-2,5-difluoro-phenyl)-6,7-dimethyl-pteridin-2-yl]-2-(2-methyl-4-pyridyl)morpholine | Method 1 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 388 | 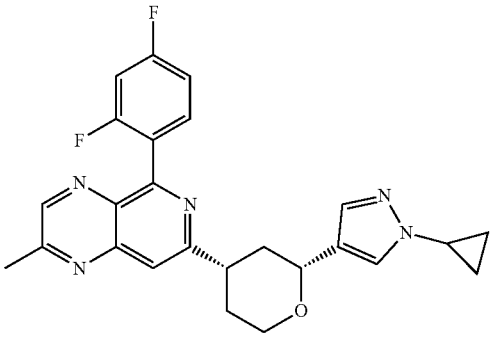 (+/−) | 5-(2,4-difluorophenyl)-2-methyl-7-[2-(1-cyclopropylpyrazol-4-yl)tetrahydropyran-4-yl]pyrido[3,4-b]pyrazine | Method 39 |
| 389 | 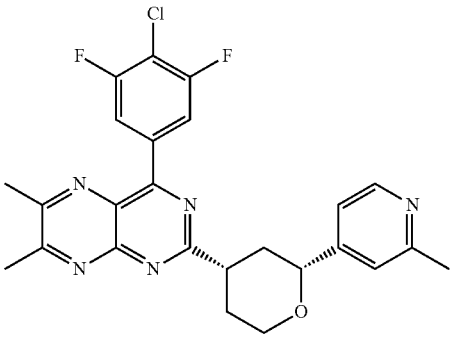 (+/−) | 4-(4-chloro-3,5-difluoro-phenyl)-6,7-dimethyl-2-[2-(2-methyl-4-pyridyl)tetrahydropyran-4-yl]pteridine | Method 41 |
| 390 | 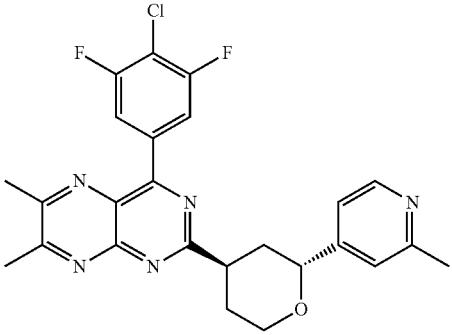 (+/−) | 4-(4-chloro-3,5-difluoro-phenyl)-6,7-dimethyl-2-[2-(2-methyl-4-pyridyl)tetrahydropyran-4-yl]pteridine | Method 41 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 391 | 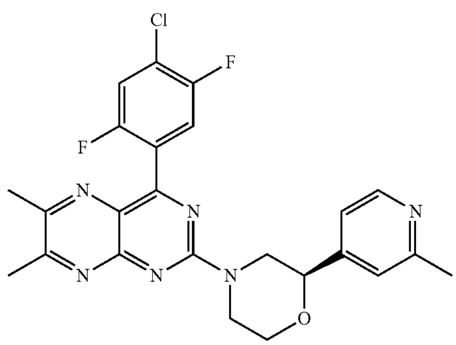 | (2R)-4-[4-(4-chloro-2,5-difluoro-phenyl)-6,7-dimethyl-pteridin-2-yl]-2-(2-methyl-4-pyridyl)morpholine | Method 1 |
| 392 | (+/−) | 2,3-dimethyl-7-[2-(1-cyclopropylpyrazol-4-yl)tetrahydropyran-4-yl]-5-[3-(trifluoromethyl)-1-bicyclo[1.1.1]pentanyl]pyrido[3,4-b]pyrazine | Method 39 |
| 393 | (+/−) | 7-[2-(1-cyclopropylpyrazol-4-yl)tetrahydropyran-4-yl]-5-(2,4-difluorophenyl)-2,3-dimethyl-pyrido[3,4-b]pyrazine | Method 39 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|------|-----------|------|---------------------------|
| 394 | 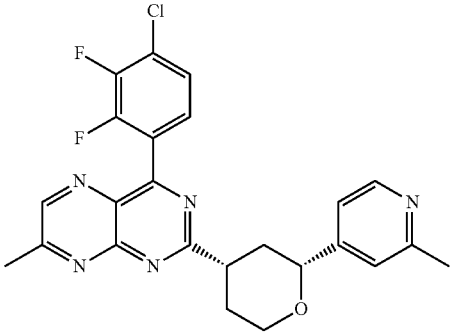 (+/−) | 4-(4-chloro-2,3-difluoro-phenyl)-7-methyl-2-[2-(2-methyl-4-pyridyl)tetrahydropyran-4-yl]pteridine | Method 38 |
| 395 | 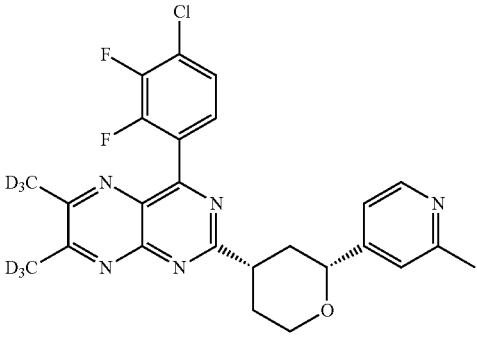 (+/−) | 4-(4-chloro-2,3-difluoro-phenyl)-2-[2-(2-methyl-4-pyridyl)tetrahydropyran-4-yl]-6,7-bis(trideuteriomethyl)pteridine | Method 38 |
| 396 | 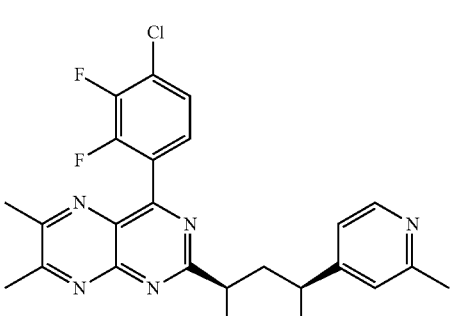 | 4-(4-chloro-2,3-difluorophenyl)-6,7-dimethyl-2-((2S,4R)-2-(2-methylpyridin-4-yl)tetrahydro-2H-pyran-4-yl)pteridine | Method 41 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 397 | 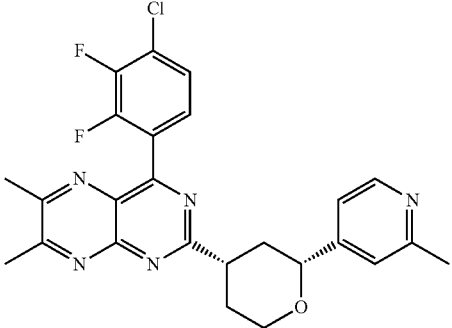 | 4-(4-chloro-2,3-difluorophenyl)-6,7-dimethyl-2-((2R,4S)-2-(2-methylpyridin-4-yl)tetrahydro-2H-pyran-4-yl)pteridine | Method 41 |
| 398 | 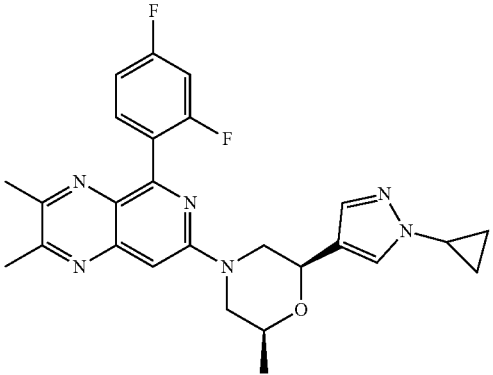 [SMILES: Cc1nc2cc(N3C[C@@H](c4cnn(C5CC5)c4)O[C@@H](C)C3)nc(-c3ccc(F)cc3F)c2nc1C] | (2R,6S)-2-(1-cyclopropyl-1H-pyrazol-4-yl)-4-(5-(2,4-difluorophenyl)-2,3-dimethylpyrido[3,4-b]pyrazin-7-yl)-6-methylmorpholine | Method 10 |
| 399 (+/−) | 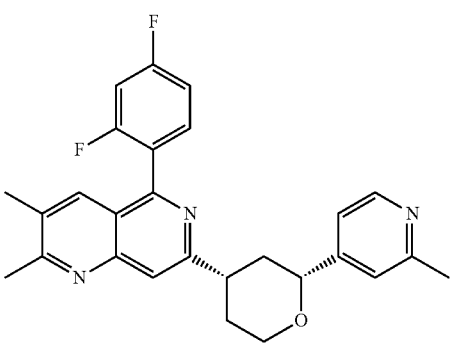 | 5-(2,4-difluorophenyl)-2,3-dimethyl-7-[2-(2-methyl-4-pyridyl)tetrahydropyran-4-yl]-1,6-naphthyridine | |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 400 | 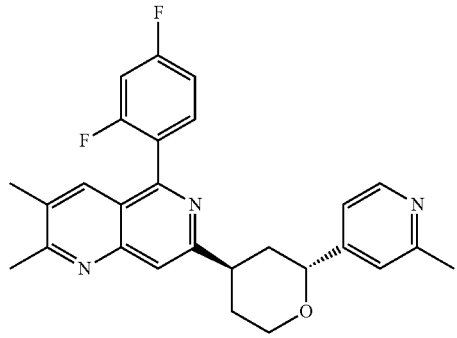 (+/−) | 5-(2,4-difluorophenyl)-2,3-dimethyl-7-[2-(2-methyl-4-pyridyl)tetrahydropyran-4-yl]-1,6-naphthyridine | |
| 401 | 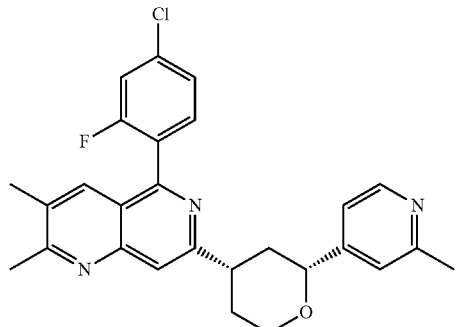 (+/−) | 5-(4-chloro-2-fluoro-phenyl)-2,3-dimethyl-7-[2-(2-methyl-4-pyridyl)tetrahydropyran-4-yl]-1,6-naphthyridine | |
| 402 | 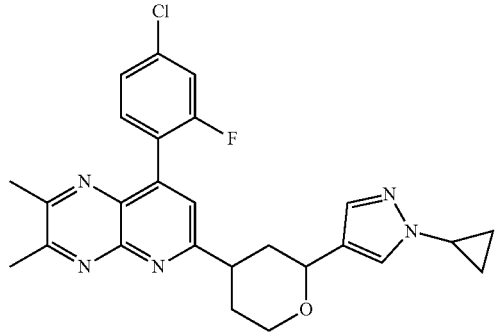 (rac) | 8-(4-chloro-2-fluorophenyl)-6-(2-(1-cyclopropyl-1H-pyrazol-4-yl)tetrahydro-2H-pyran-4-yl)-2,3-dimethylpyrido[2,3-b]pyrazine | Method 44 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 403 | 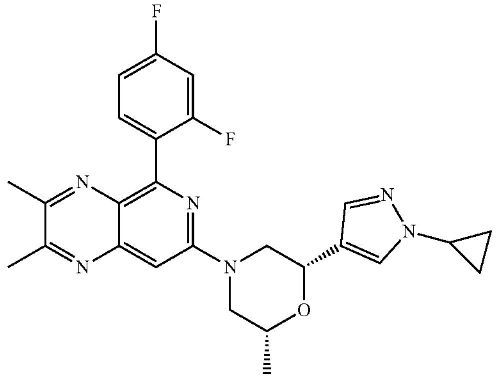 [SMILES: Cc1nc2cc(N3C[C@@H](C)O[C@@H](c4cnn(C5CC5)c4)C3)nc(-c3ccc(F)cc3F)c2nc1C] | (2S,6R)-2-(1-cyclopropyl-1H-pyrazol-4-yl)-4-(5-(2,4-difluorophenyl)-2,3-dimethylpyrido[3,4-b]pyrazin-7-yl)-6-methylmorpholine | Method 10 |
| 404 | 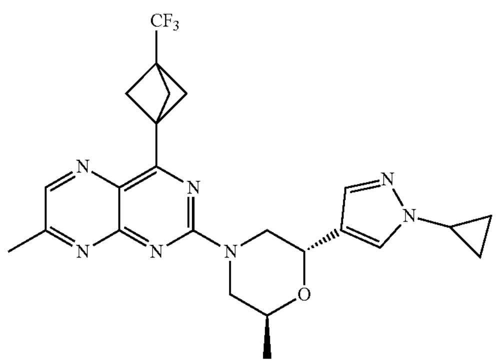 [SMILES: Cc1cnc2c(C34CC(C(F)(F)F)(C3)C4)nc(N3C[C@H](C)O[C@@H](c4cnn(C5CC5)c4)C3)nc2n1] | (2S,6S)-2-(1-cyclopropyl-1H-pyrazol-4-yl)-6-methyl-4-(7-methyl-4-(3-(trifluoromethyl)bicyclo[1.1.1]pentan-1-yl)pteridin-2-yl)morpholine | Method 1 |
| 405 | 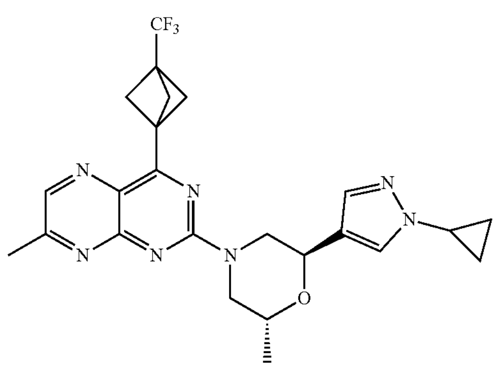 [SMILES: Cc1cnc2c(C34CC(C(F)(F)F)(C3)C4)nc(N3C[C@@H](C)O[C@H](c4cnn(C5CC5)c4)C3)nc2n1] | (2R,6R)-2-(1-cyclopropyl-1H-pyrazol-4-yl)-6-methyl-4-(7-methyl-4-(3-(trifluoromethyl)bicyclo[1.1.1]pentan-1-yl)pteridin-2-yl)morpholine | Method 1 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 406 | 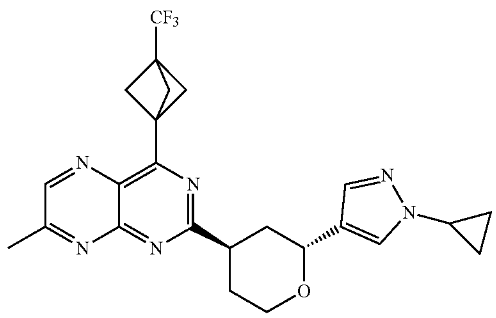 [SMILES: Cc1cnc2c(C34CC(C(F)(F)F)(C3)C4)nc([C@@H]3CCO[C@@H](c4cnn(C5CC5)c4)C3)nc2n1] | 2-((2R,4R)-2-(1-cyclopropyl-1H-pyrazol-4-yl)tetrahydro-2H-pyran-4-yl)-7-methyl-4-(3-(trifluoromethyl)bicyclo[1.1.1]pentan-1-yl)pteridine | Method 9 |
| 407 | 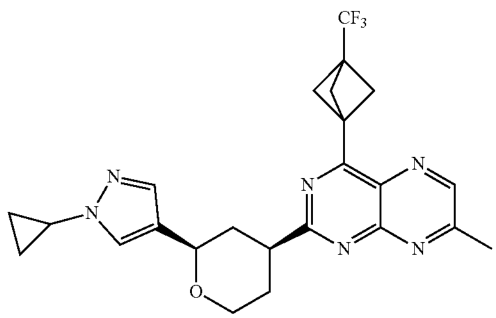 [SMILES: Cc1cnc2c(C34CC(C(F)(F)F)(C3)C4)nc([C@H]3CCO[C@@H](c4cnn(C5CC5)c4)C3)nc2n1] | 2-((2R,4S)-2-(1-cyclopropyl-1H-pyrazol-4-yl)tetrahydro-2H-pyran-4-yl)-7-methyl-4-(3-(trifluoromethyl)bicyclo[1.1.1]pentan-1-yl)pteridine | Method 9 |
| 408 | 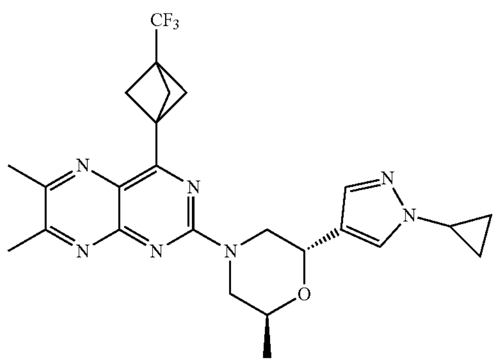 [SMILES: Cc1nc2nc(N3C[C@H](C)O[C@@H](c4cnn(C5CC5)c4)C3)nc(C34CC(C(F)(F)F)(C3)C4)c2nc1C] | (2S,6S)-2-(1-cyclopropyl-1H-pyrazol-4-yl)-4-(6,7-dimethyl-4-(3-(trifluoromethyl)bicyclo[1.1.1]pentan-1-yl)pteridin-2-yl)-6-methylmorpholine | Method 1 |
| 409 | 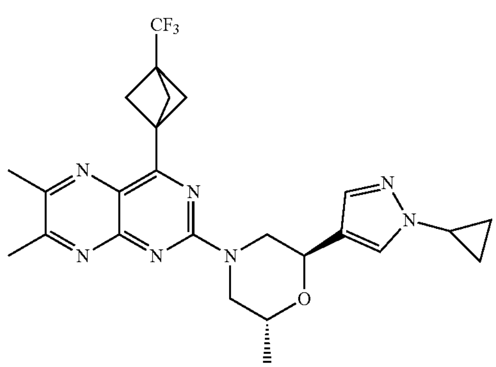 [SMILES: Cc1nc2nc(N3C[C@@H](C)O[C@H](c4cnn(C5CC5)c4)C3)nc(C34CC(C(F)(F)F)(C3)C4)c2nc1C] | (2R,6R)-2-(1-cyclopropyl-1H-pyrazol-4-yl)-4-(6,7-dimethyl-4-(3-(trifluoromethyl)bicyclo[1.1.1]pentan-1-yl)pteridin-2-yl)-6-methylmorpholine | Method 1 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 410 | 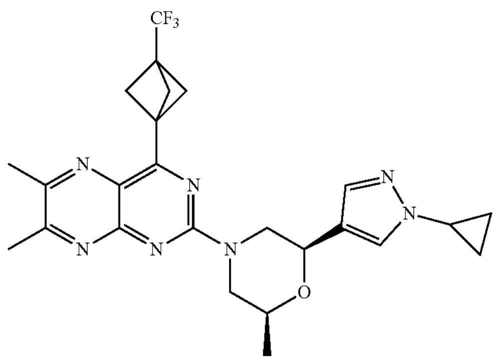 [SMILES: Cc1nc2nc(N3C[C@@H](c4cnn(C5CC5)c4)O[C@@H](C)C3)nc(C34CC(C(F)(F)F)(C3)C4)c2nc1C] | (2R,6S)-2-(1-cyclopropyl-1H-pyrazol-4-yl)-4-(6,7-dimethyl-4-(3-(trifluoromethyl)bicyclo[1.1.1]pentan-1-yl)pteridin-2-yl)-6-methylmorpholine | Method 1 |
| 411 | 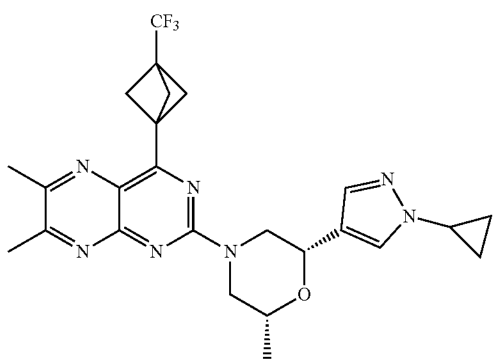 [SMILES: Cc1nc2nc(N3C[C@@H](C)O[C@@H](c4cnn(C5CC5)c4)C3)nc(C34CC(C(F)(F)F)(C3)C4)c2nc1C] | (2S,6R)-2-(1-cyclopropyl-1H-pyrazol-4-yl)-4-(6,7-dimethyl-4-(3-(trifluoromethyl)bicyclo[1.1.1]pentan-1-yl)pteridin-2-yl)-6-methylmorpholine | Method 1 |
| 412 | 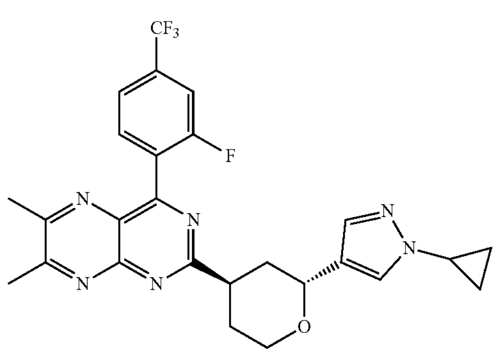 [SMILES: Cc1nc2nc([C@@H]3CCO[C@@H](c4cnn(C5CC5)c4)C3)nc(-c3ccc(C(F)(F)F)cc3F)c2nc1C] | 2-((2R,4R)-2-(1-cyclopropyl-1H-pyrazol-4-yl)tetrahydro-2H-pyran-4-yl)-4-(2-fluoro-4-(trifluoromethyl)phenyl)-6,7-dimethylpteridine | Method 9 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 413 | 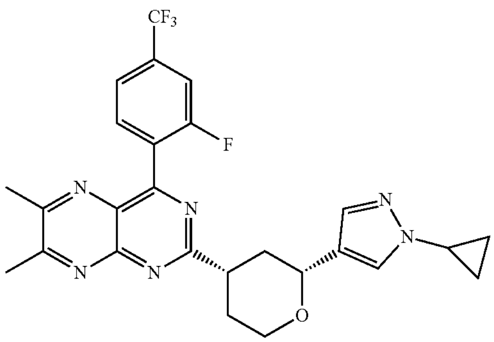 [SMILES: Cc1nc2nc([C@H]3CCO[C@@H](c4cnn(C5CC5)c4)C3)nc(-c3ccc(C(F)(F)F)cc3F)c2nc1C] | 2-((2R,4S)-2-(1-cyclopropyl-1H-pyrazol-4-yl)tetrahydro-2H-pyran-4-yl)-4-(2-fluoro-4-(trifluoromethyl)phenyl)-6,7-dimethylpteridine | Method 9 |
| 414 | 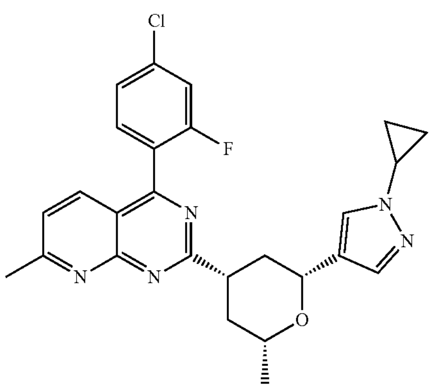 [SMILES: Cc1ccc2c(-c3ccc(Cl)cc3F)nc([C@H]3C[C@@H](C)O[C@@H](c4cnn(C5CC5)c4)C3)nc2n1] | 4-(4-chloro-2-fluorophenyl)-2-((2R,4S,6R)-2-(1-cyclopropyl-1H-pyrazol-4-yl)-6-methyltetrahydro-2H-pyran-4-yl)-7-methylpyrido[2,3-d]pyrimidine | |
| 415 | 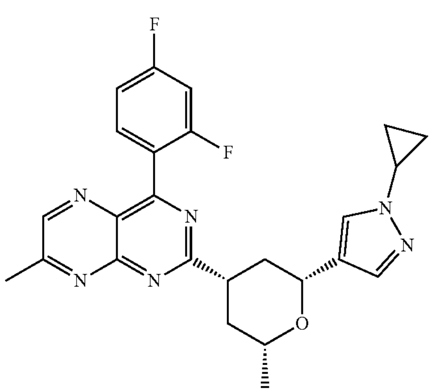 [SMILES: Cc1cnc2c(-c3ccc(F)cc3F)nc([C@H]3C[C@@H](C)O[C@@H](c4cnn(C5CC5)c4)C3)nc2n1] | 2-((2R,4S,6R)-2-(1-cyclopropyl-1H-pyrazol-4-yl)-6-methyltetrahydro-2H-pyran-4-yl)-4-(2,4-difluorophenyl)-7-methylpteridine | |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 416 | 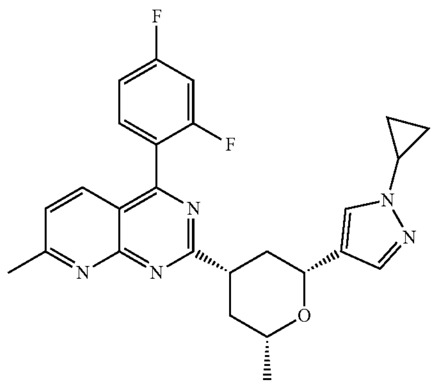 [SMILES: Cc1ccc2c(-c3ccc(F)cc3F)nc([C@H]3C[C@@H](C)O[C@@H](c4cnn(C5CC5)c4)C3)nc2n1] | 2-((2R,4S,6R)-2-(1-cyclopropyl-1H-pyrazol-4-yl)-6-methyltetrahydro-2H-pyran-4-yl)-4-(2,4-difluorophenyl)-7-methylpyrido[2,3-d]pyrimidine | |
| 417 | 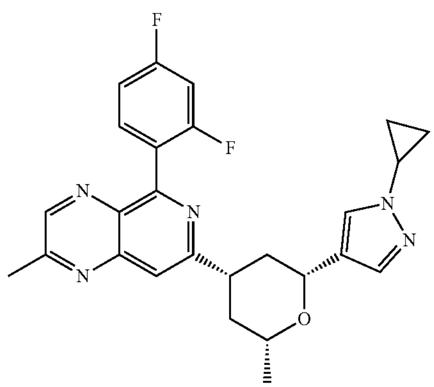 [SMILES: Cc1cnc2c(-c3ccc(F)cc3F)nc([C@H]3C[C@@H](C)O[C@@H](c4cnn(C5CC5)c4)C3)cc2n1] | 7-((2R,4S,6R)-2-(1-cyclopropyl-1H-pyrazol-4-yl)-6-methyltetrahydro-2H-pyran-4-yl)-5-(2,4-difluorophenyl)-2-methylpyrido[3,4-b]pyrazine | |
| 418 (+/−) | | 2-(1-cyclopropyl-1H-pyrazol-4-yl)-4-(4-(2,4-difluorophenyl)-6,7-dimethylpteridin-2-yl)-6-methylmorpholine | Method 1 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|------|-----------|------|---------------------------|
| 419 | 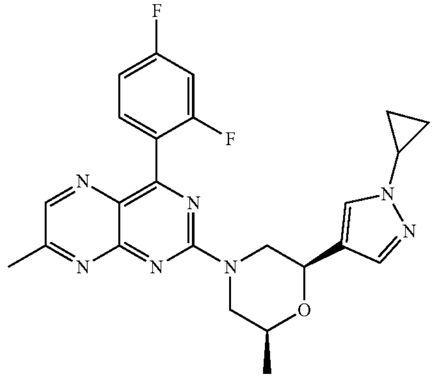 [SMILES: Cc1cnc2c(-c3ccc(F)cc3F)nc(N3C[C@@H](c4cnn(C5CC5)c4)O[C@@H](C)C3)nc2n1] | (2R,6S)-2-(1-cyclopropyl-1H-pyrazol-4-yl)-4-(4-(2,4-difluorophenyl)-7-methylpteridin-2-yl)-6-methylmorpholine | Method 1 |
| 420 | 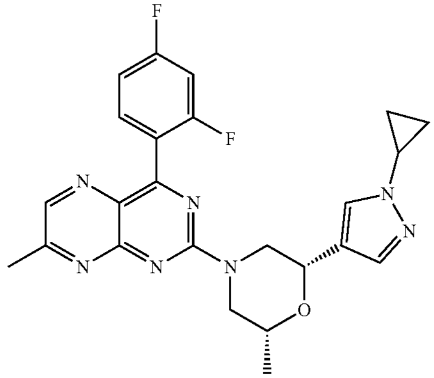 [SMILES: Cc1cnc2c(-c3ccc(F)cc3F)nc(N3C[C@@H](C)O[C@@H](c4cnn(C5CC5)c4)C3)nc2n1] | (2S,6R)-2-(1-cyclopropyl-1H-pyrazol-4-yl)-4-(4-(2,4-difluorophenyl)-7-methylpteridin-2-yl)-6-methylmorpholine | Method 1 |
| 421 | 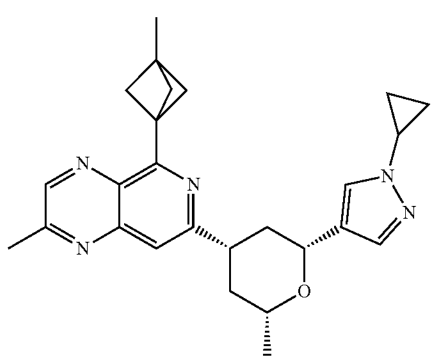 [SMILES: Cc1cnc2c(C34CC(C)(C3)C4)nc([C@H]3C[C@@H](C)O[C@@H](c4cnn(C5CC5)c4)C3)cc2n1] | 7-((2R,4S,6R)-2-(1-cyclopropyl-1H-pyrazol-4-yl)-6-methyltetrahydro-2H-pyran-4-yl)-2-methyl-5-(3-methylbicyclo[1.1.1]pentan-1-yl)pyrido[3,4-b]pyrazine | |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 422 | 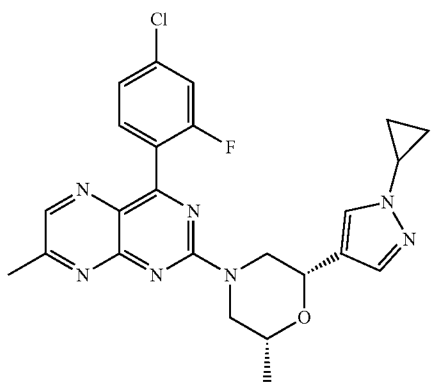 | (2S,6R)-4-(4-(4-chloro-2-fluorophenyl)-7-methylpteridin-2-yl)-2-(1-cyclopropyl-1H-pyrazol-4-yl)-6-methylmorpholine | Method 1 |
| 423 | 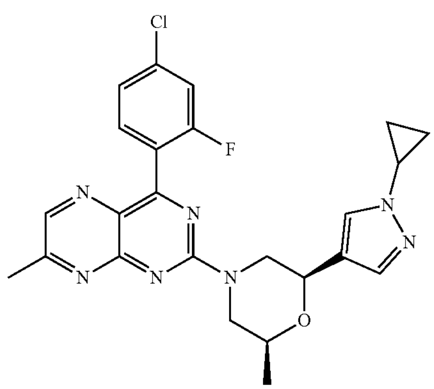 | (2R,6S)-4-(4-(4-chloro-2-fluorophenyl)-7-methylpteridin-2-yl)-2-(1-cyclopropyl-1H-pyrazol-4-yl)-6-methylmorpholine | Method 1 |
| 424 | 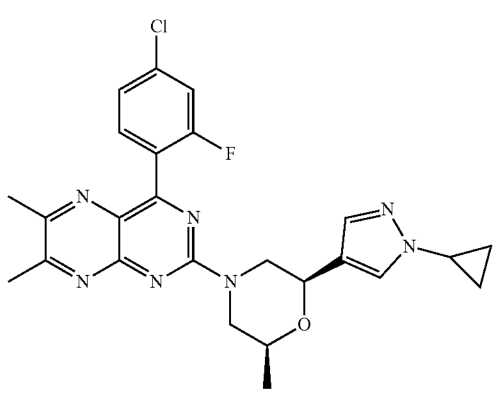 | (2R,6S)-4-(4-(4-chloro-2-fluorophenyl)-6,7-dimethylpteridin-2-yl)-2-(1-cyclopropyl-1H-pyrazol-4-yl)-6-methylmorpholine | Method 1 |

TABLE 8B-continued

Additional Compounds

The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 425 | 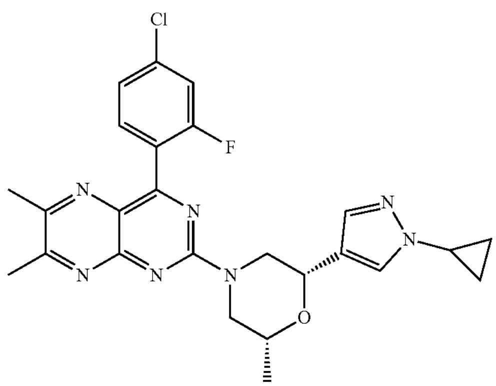 | (2S,6R)-4-(4-(4-chloro-2-fluorophenyl)-6,7-dimethylpteridin-2-yl)-2-(1-cyclopropyl-1H-pyrazol-4-yl)-6-methylmorpholine | Method 1 |
| 426 | 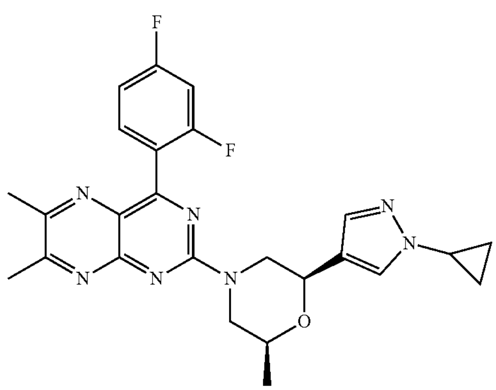 [SMILES: Cc1nc2nc(N3C[C@@H](c4cnn(C5CC5)c4)O[C@@H](C)C3)nc(-c3ccc(F)cc3F)c2nc1C] | (2R,6S)-2-(1-cyclopropyl-1H-pyrazol-4-yl)-4-(4-(2,4-difluorophenyl)-6,7-dimethylpteridin-2-yl)-6-methylmorpholine | Method 1 |
| 427 | 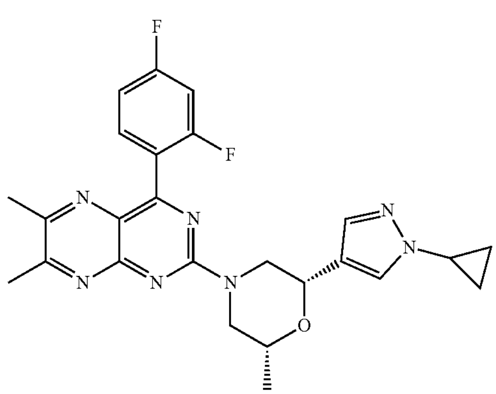 [SMILES: Cc1nc2nc(N3C[C@@H](C)O[C@@H](c4cnn(C5CC5)c4)C3)nc(-c3ccc(F)cc3F)c2nc1C] | (2S,6R)-2-(1-cyclopropyl-1H-pyrazol-4-yl)-4-(4-(2,4-difluorophenyl)-6,7-dimethylpteridin-2-yl)-6-methylmorpholine | Method 1 |

TABLE 8B-continued

Additional Compounds
The compounds disclosed below in Table 8B were made by a method of the present disclosure or a similar method. The appropriate reagents, starting materials and conditions necessary for synthesizing the compounds of Table 8B would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound. Compounds lacking either designation were isolated with the specific stereochemistry shown, such that the specific stereoisomer shown made up at least 90% of the isolated product.

| Ex # | Structure | Name | Method used to synthesize |
|---|---|---|---|
| 428 | 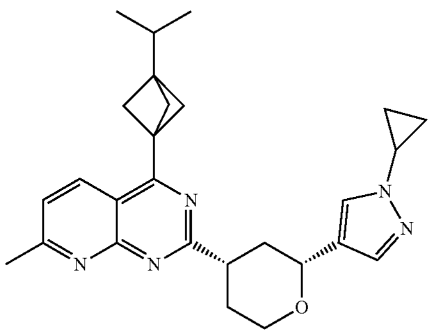 [SMILES: Cc1ccc2c(C34CC(C(C)C)(C3)C4)nc([C@H]3CCO[C@@H](c4cnn(C5CC5)c4)C3)nc2n1] | 2-((2R,4S)-2-(1-cyclopropyl-1H-pyrazol-4-yl)tetrahydro-2H-pyran-4-yl)-4-(3-isopropylbicyclo[1.1.1]pentan-1-yl)-7-methylpyrido[2,3-d]pyrimidine | |
| 429 | 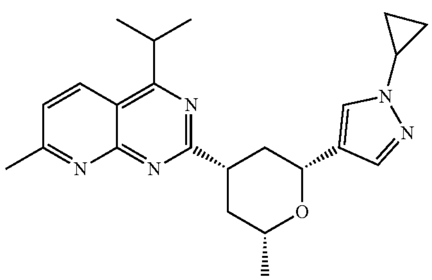 [SMILES: Cc1ccc2c(C(C)C)nc([C@H]3C[C@@H](C)O[C@@H](c4cnn(C5CC5)c4)C3)nc2n1] | 2-((2R,4S,6R)-2-(1-cyclopropyl-1H-pyrazol-4-yl)-6-methyltetrahydro-2H-pyran-4-yl)-4-isopropyl-7-methylpyrido[2,3-d]pyrimidine | |

TABLE 8C

Analytical data for compounds of Table 8B

| Ex # | NMR | M + H |
|---|---|---|
| 306 | ¹H NMR (400 MHz, DMSO-d6) δ ppm 8.87 (1H, s), 8.39 (1H, d, J = 5.2 Hz), 7.85 (1H, s), 7.66 (1H, q, J = 7.7 Hz), 7.37-7.32 (1H, m), 7.31-7.29 (1H, m), 7.26-7.20 (2H, m), 4.59 (1H, d, J = 11.1 Hz), 4.24-4.21 (1H, m), 3.80-3.73 (1H, m), 2.73 (3H, s), 2.45 (3H, s), 2.28 (1H, d, J = 13.6 Hz), 2.00-1.96 (2H, m), 1.72 (1H, q, J = 12.1 Hz). | 480.2 |
| 307 | ¹H NMR (400 MHz, DMSO-d6) δ ppm 9.43 (1H, s), 9.00 (1H, s), 8.75 (1H, d, J = 8.2 Hz), 8.42 (1H, d, J = 5.2 Hz), 8.14-8.10 (2H, m), 7.94 (1H, s), 7.34 (2H, s), 7.26 (2H, d, J = 5.1 Hz), 4.65 (1H, d, J = 11.1 Hz), 4.28 (1H, d, J = 11.3 Hz), 3.89-3.79 (2H, m), 3.53 (2H, br s), 3.34 (3H, s), 2.80 (3H, s), 2.49 (4H, s), 2.36 (2H, d, J = 12.8 Hz), 2.07-2.05 (2H, m), 1.82 (1H, q, J = 12.1 Hz). | 433.2 |
| 308 | ¹H NMR (400 MHz, DMSO-d6) δ ppm 9.59 (1H, s), 8.90 (1H, d, J = 8.2 Hz), 8.37 (1H, d, J = 5.3 Hz), 8.15 (1H, d, J = 8.3 Hz), 7.27 (1H, s), 7.19 (1H, d, J = 5.3 Hz), 4.62 (1H, d, J = 11.2 Hz), 4.25 (1H, dd, J = 11.3, 4.2 Hz), 3.80 (1H, t, J = 11.8 Hz), 3.59 (1H, t, J = 11.6 Hz), 2.78 (3H, s), 2.73 (3H, s), 2.44 (4H, s), 2.16 (2H, d, J = 13.1 Hz), 2.06-1.93 (1H, m), 1.77 (1H, q, J = 12.2 Hz). | 466.2 |
| 309 | ¹H NMR (400 MHz, DMSO-d6): δ 9.59 (s, 1 H), 8.90 (d, 1 H), 8.37 (d, 1 H), 8.15 (d, 1 H), 7.27 (s, 1 H), 7.19 (d, 1 H), 4.62 (d, 1 H), 4.25 (d, 1 H), 3.80 (t, 1 H), 3.59 (s, 1 H), 2.78 (s, 3 H), 2.73 (s, 3H), 2.39-2.44 (m, 4 H), 2.16 (d, 1 H), 1.99 (d, 1 H), 1.77 (q, 1 H). | 481.2 |
| 310 | ¹H NMR (400 MHz, Chloroform-d): δ H ppm 8.78 (1H, s), 8.74 (3H, s), 8.46 (4H, t, J = 5.5 Hz), 7.86 (1H, s), 7.74 (3H, s), 7.64 (1H, t, J = 7.9 Hz), 7.58 (3H, t, J = 7.8 Hz), 7.33 (5H, t, J = 8.4 Hz), 7.22 (5H, s), 7.11 (5H, d, J = 5.0 Hz), 4.91-4.88 (1H, m), 4.55 (4H, d, J = 11.2 Hz), 4.38 (4H, d, J = 11.5 Hz), 3.96 (2H, dd, J = 6.4, 4.3 Hz), 3.87-3.81 (3H, m), 3.55-3.52 (1H, m), 3.47-3.39 (3H, m), 2.80 (10H, s), 2.56-2.55 (14H, m), 2.33-2.24 (3H, m), 2.15-2.07 (7H, m), 1.84 (4H, q, J = 12.2 Hz). | 449.1 |
| 311 | ¹H NMR (400 MHz, Chloroform-d) δ ppm 9.60 (1H, s), 8.75 (1H, d, J = 8.2 Hz), 8.53 (1H, d, J = 5.1 Hz), 7.83 (1H, d, J = 8.1 Hz), 7.18 (1H, d, J = 5.1 Hz), 7.03 (1H, s), 4.65 (1H, d, J = 10.5 Hz), 4.52 (1H, d, J = 13.0 Hz), 4.28 (2H, t, J = 9.1 Hz), 3.94 (1H, dd, J = 12.7, 10.5 Hz), 3.23 (1H, dd, J = 13.3, 10.4 Hz), 2.95 (1H, dd, J = 12.7, 10.6 Hz), 2.71 (3H, s), 2.67 (3H, s), 2.60 (3H, s). Note: One aromatic proton is obscured by solvent signal. 19F NMR (376 MHz, Chloroform-d) δ ppm −67.9. | 446.8 |
| 312 | ¹H NMR (400 MHz, Chloroform-d) δ ppm 8.51 (d, J = 4.9 Hz, 1H), 8.46 (s, 1H), 7.66-7.58 (m, 1H), 7.18 (d, J = 5.5 Hz, 1H), 7.07-7.01 (m, 1H), 7.00-6.93 (m, 2H), 4.64 (d, J = 9.9 Hz, 1H), 4.53 (d, J = 12.6 Hz, 1H), 4.32-4.20 (m, 2H), 3.97-3.88 | 480.4 |

TABLE 8C-continued

Analytical data for compounds of Table 8B

| Ex # | NMR | M + H |
|---|---|---|
|  | (m, 1H), 3.23 (td, J = 12.7, 3.3 Hz, 1H), 3.00-2.89 (m, 1H), 2.71 (s, 3H), 2.59 (s, 3H). Note: One aromatic proton is obscured by solvent signal. 19F NMR (376 MHz, Chloroform-d) δ ppm −108.30 (s), −108.66 (s). |  |
| 313 | $^1$H NMR (400 MHz, CD2Cl2) δ ppm 8.41 (d, J = 5.1 Hz, 1H), 7.51-7.44 (m, 1H), 7.44-7.36 (m, 1H), 7.22 (s, 1H), 7.13 (d, J = 4.7 Hz, 1H), 4.54 (dd, J = 11.6, 1.2 Hz, 1H), 4.37-4.30 (m, 1H), 3.88-3.77 (m, 1H), 3.63-3.52 2.80 (s, 3H), 2.70 (s, 3H), 2.51 (s, 3H), 2.46-2.39 (m, 1H), 2.23-2.11 (m ,2H), 2.00-1.89 (m, 1H) | 434.8 |
| 314 | $^1$H NMR (400 MHz, DMSO-d6) δ ppm 8.18 (d, J = 5.3 Hz, 1H), 7.74 (t, J = 7.9 Hz, 1H), 7.65 (d, J = 9.7 Hz, 1H), 7.50 (d, J = 8.3 Hz, 1H), 7.06 (d, J = 5.3 Hz, 1H), 6.87 (s, 1H), 4.81 (d, J = 13.2 Hz, 1H), 4.66 (t, J = 12.5 Hz, 1H), 4.14 (d, J = 11.5 Hz, 1H), 3.86 (s, 3H), 3.83-3.64 (m, 1H), 3.30-3.22 (m, 1H), 3.04 (dd, J = 13.1, 10.5 Hz, 1H), 2.66 (s, 3H), 2.52 (s, 3H). | 481.2 |
| 315 | 1H NMR (400 MHz, DMSO-d6) δ ppm 8.44 (d, J = 5.1 Hz, 1H), 7.66 (q, J = 7.8 Hz, 1H), 7.44-7.32 (m, 2H), 7.30-7.19 (m, 3H), 4.78-4.57 (m, 1H), 4.58-4.39 (m, 1H), 4.32 (d, J = 12.9 Hz, 1H), 4.15 (d, J = 11.8 Hz, 1H), 3.81 (t, J = 11.5 Hz, 1H), 3.07 (dd, J = 13.4. 10.1 Hz, 1H), 2.94-2.73 (m, 1H), 2.64 (s, 3H), 2.52 (s, 3H), 2.49 (s, 3H). | 448.2 |
| 316 | $^1$H NMR (400 MHz, Chloroform-d) δ ppm 8.46 (3H, t, J = 5.2 Hz), 7.82 (1H, s), 7.72-7.68 (2H, m), 7.66-7.60 (3H, m), 7.22 (3H, s), 7.12 (3H, d, J = 5.1 Hz), 7.08-7.00 (3H, m), 6.99-6.93 (3H, m), 4.89 (1H, dd, J = 8.6, 3.1 Hz), 4.54 (2H, d, J = 11.2 Hz), 4.39-4.35 (2H, m), 3.96 (2H, dd, J = 6.6, 4.2 Hz), 3.83 (2H, td, J = 11.4, 3.2 Hz), 3.53 (1H, t, J = 5.2 Hz), 3.41 (2H, tt, J = 11.7, 4.0 Hz), 2.78 (3H, s), 2.75 (6H, s), 2.71 (3H, s), 2.67 (6H, s), 2.56 (10H, m), 2.39 (2H, d, J = 13.4 Hz), 2.29-2.23 (3H, m), 2.14-2.05 (4H, m), 1.86-1.77 (2H, m). | 448.2 |
| 317 | $^1$H NMR (400 MHz, Chloroform-d) δ ppm 8.46 (1H, d, J = 5.1 Hz), 7.69 (1H, s), 7.63 (1H, m), 7.26 (1H, s), 7.18 (1H, s), 7.05 (1H, m), 6.96 (1H, m), 4.56 (1H, d, J = 11.2 Hz), 4.38 (1H, d, J = 11.5 Hz), 3.84 (1H, m), 3.41 (1H, m), 2.75 (3H, s), 2.67 (3H, s), 2.60 (3H, s), 2.40 (1H, d, J = 13.3 Hz), 2.12 (2H, m), 1.80 (1H, m). | 448.2 |
| 318 | $^1$H NMR (400 MHz, DMSO-d6) δ ppm 11.51-11.55 (1H, m), 7.35-7.38 (1H, m), 6.34 (1H, s), 6.19-6.22 (1H, m), 4.59-4.81 (1H, m), 4.38-4.41 (1H, m), 4.07-4.11 (1H, m), 3.62-3.69 (1H m), 3.16-3.25 (1H, m), 2.92-3.01 (1H, m), 2.60-2.61 (3H, m), 2.59 (3H, s), 2.56 (6H, s). | 487.2 |
| 319 | $^1$H NMR (400 MHz, Chloroform-d): δppm 8.47 (1H, m), 7.53 (1H, s), 7.23 (1H, s), 7.13 (1H, m), 4.54 (1H, d, J = 11.3 Hz), 4.36 (1H, d, J = 11.4 Hz), 3.86-3.80 (1H, m), 3.29 (1H, m), 2.73 (3H, s), 2.72 (3H, s), 2.60 (6H, s), 2.57 (3H, s), 2.30 (1H, d, J = 13.5 Hz), 2.22-2.15 (1H, m), 2.05 (2H, m), 1.82-1.73 (1H, m). | 469.2 |
| 320 | $^1$H NMR (400 MHz, DMSO-d6) δ ppm 7.79 (d, J = 7.9 Hz, 1H), 7.75 (d, J = 7.2 Hz, 1H), 7.69 (dd, J = 9.8, 2.0 Hz, 1H), 7.54 (dd, J = 8.3, 2.0 Hz, 1H), 7.39 (s, 1H), 4.52 (dd, J = 11.4, 2.1 Hz, 1H), 4.11 (dd, J = 11.1, 4.2 Hz, 1H), 3.71-3.77 (m, 1H), 3.62-3.71 (m, 1H), 3.43-3.53 (m, 1H), 2.79 (s, 3H), 2.67 (s, 3H), 2.30 (s, 2H), 1.24 (s, 2H), 0.97-1.04 (m, 2H), 0.92 (td, J = 7.3, 5.1 Hz, 2H) | 479.0 |
| 321 | $^1$H NMR (400 MHz, DMSO-d6) δ ppm 7.79 (d, J = 7.9 Hz, 1H), 7.75 (d, J = 7.2 Hz, 1H), 7.69 (dd, J = 9.8, 2.0 Hz, 1H), 7.54 (dd, J = 8.3, 2.0 Hz, 1H), 7.39 (s, 1H), 4.52 (dd, J = 11.4, 2.1 Hz, 1H), 4.11 (dd, J = 11.1, 4.2 Hz, 1H), 3.71-3.77 (m, 1H), 3.62-3.71 (m, 1H), 3.43-3.53 (m, 1H), 2.79 (s, 3H), 2.67 (s, 3H), 2.30 (s, 2H), 1.24 (s, 2H), 0.97-1.04 (m, 2H), 0.97-1.04 (m, 2H), 0.92 (td, J = 7.3, 5.1 Hz, 2H) | 478.9 |
| 322 | $^1$H NMR (DMSO-d6, 400 MHz): δH 9.57 (1H, s), 8.87-8.90 (1H, m), 8.18 (1H, d, J = 5.1 Hz), 8.13 | 498.2 |
|  | (1H, d, J = 8.3 Hz), 7.07-7.08 (1H, m), 6.89 (1H, s), 4.82 (2H, bd, J = 64.4 Hz), 4.64 (1H, d, J = 10.1 Hz), 4.13-4.18 (1H, m), 3.85 (3H, s), 3.71-3.79 (1H, m), 3.00-3.12 (1H, m), 2.71-2.77 (1H, m), 2.65-2.67 (3H, s), 2.61-2.61 (3H, s). |  |
| 323 | $^1$H NMR (400 MHz, Chloroform-d) δ ppm 8.46 (1H, d, J = 5.3 Hz), 8.07 (1H, dd, J = 8.5, 3.8 Hz), 7.69-7.63 (1H, m), 7.46-7.43 (1H, m), 7.32-7.31 (2H, m), 7.17-7.10 (1H, m), 7.12-7.03 (1H, m), 4.85 (1H, dd, J = 9.7, 2.7 Hz), 4.04-3.97 (2H, m), 3.97-3.93 (1H, m), 3.74-3.69 (1H, m), 2.88 (3H, s), 2.62-2.57 (4H, m), 2.32-2.23 (1H, m), 2.22-2.14 (1H, m). | 434.2 |
| 324 | $^1$H NMR (400 MHz, Chloroform-d) δ ppm 8.48 (1H, d, J = 5.3 Hz), 8.22 (1H, m), 8.07 (1H, d, J = 8.2 Hz), 7.59 (1H, t, J = 7.9 Hz), 7.47-7.35 (4H, m), 4.86 (1H, d, J = 9.9 Hz), 4.01-3.94 (2H, m), 3.72 (1H, m), 2.92-2.88 (4H, m), 2.63 (4H, s), 2.25 (1H, m), 2.16 (1H, m). 19F NMR (376 MHz, Chloroform-d) δ F −110.9. | 467.2 |
| 325 | $^1$H NMR (400 MHz, Chloroform-d) δ ppm 8.46 (2H, m), 7.99 (1H, dd, J = 8.6, 3.3 Hz), 7.92 (1H, dd, J = 8.7, 3.5 Hz), 7.87 (1H, s), 7.73 (1H, s), 7.61-7.52 (2H, m), 7.37-7.34 (1H, m), 7.32-7.29 (3H, m), 7.23-7.17 (2H, m), 7.12-7.05 (2H, m), 7.03-6.97 (2H, m), 4.90-4.87 (1H, m), 4.56 (1H, dd, J = 11.2, 2.0 Hz), 4.40-4.36 (1H, m), 3.98-3.94 (2H, m), 2.86-3.79 (1H, m), 3.54-3.51 (1H, m), 3.42-3.35 (1H, m), 2.80 (3H, s), 2.77 (3H, s), 2.66-2.59 (7H, m), 2.45-2.37 (2H, m), 2.32-2.20 (2H, m), 2.15-2.03 (2H, m), 1.87-1.75 (1H, m). | 450.1 |
| 326 | $^1$H NMR (400 MHz, Chloroform-d) δ ppm 8.46-8.43 (2H, m), 7.84 (1H, s), 7.74-7.71 (3H, m), 7.67-7.65 (3H, m), 7.54-7.47 (2H, m), 7.45-7.33 (3H, m), 7.19-7.12 (3H, m), 4.88-4.85 (1H, m), 4.57-4.53 (1H, m), 4.39-4.34 (1H, m), 3.98-3.94 (1H, m), 3.85-3.78 (2H, m), 3.52-3.49 (1H, m), 3.41-3.36 (1H, m), 2.74 (6H, m), 2.68 (6H, s), 2.42 (6H, m), 2.33-2.16 (3H, m), 2.14-1.99 (4H, m), 1.85-1.74 (1H, m). | 432.2 |
| 327 | $^1$H NMR (400 MHz, Chloroform-d) δ ppm 8.46 (2H, m), 7.84 (1H, s), 7.74-7.73 (1H, m), 7.71 (1H, s), 7.67 (1H, m), 7.58-7.49 (2H, m), 7.22-7.16 (2H, m), 7.12-6.97 (6H, m), 4.90-4.86 (1H, m), 4.56-4.53 (1H, m), 4.39-4.34 (1H, m), 3.97-3.94 (2H, m), 3.85-3.78 (2H, m), 3.54-3.50 (1H, m), 3.42-3.34 (1H, m), 2.74 (3H, s), 2.71 (3H, s), 2.64-2.55 (6H, m), 2.45 (3H, s), 2.42 (3H, s), 2.39-2.35 (2H, m), 2.32-2.18 (2H, m), 2.14-2.03 (3H, m), 1.84-1.73 (1H, m). | 462.2 |
| 328 | $^1$H NMR (400 MHz, Chloroform-d) δ ppm 8.48-8.46 (1H, m), 7.82 (1H, s), 7.71-7.67 (1H, m), 7.33 (2H, m), 7.08-7.03 (1H, m), 7.02-6.96 (1H, m), 4.96-4.92 (1H, m), 3.98 (2H, m), 3.56-3.53 (1H, m), 2.78 (3H, s), 2.70 (3H, s), 2.66-2.60 (4H, m), 2.30-2.17 (3H, m). | 446.2 |
| 329 | $^1$H NMR (400 MHz, DMSO-d6) δ ppm 8.98 (d, J = 14.8 Hz, 1H), 7.83 (td, J = 8.4, 6.7 Hz, 1H), 7.74 (s, 1H), 7.53-7.43 (m, 1H), 7.39 (s, 1H), 7.33 (td, J = 8.3, 2.3 Hz, 1H), 4.57-4.47 (m, 1H), 4.11 (dd, J = 11.4, 3.2 Hz, 1H), 3.78-3.60 (m, 2H), 3.51 (s, 1H), 2.81 (s, 3H), 2.32 (d, J = 12.1 Hz, 1H), 2.08 (d, J = 12.8 Hz, 1H), 2.02-1.85 (m, 2H), 1.03-0.84 (m, 4H). | 449.1 |
| 330 | $^1$H NMR (400 MHz, DMSO-d6) δ ppm 9.00 (s, 1H), 7.83 (td, J = 8.4, 6.7 Hz, 1H), 7.74 (s, 1H), 7.49 (td, J = 10.1, 2.5 Hz, 1H), 7.39 (s, 1H), 7.33 (td, J = 8.4, 2.0 Hz, 1H), 4.58-4.46 (m, 1H), 4.11 (dd, J = 11.4, 3.2 Hz, 1H), 3.80-3.59 (m, 2H), 3.51 (ddd, J = 12.1, 8.3, 3.6 Hz, 1H), 2.81 (s, 3H), 2.32 (d, J = 11.9 Hz, 1H), 2.08 (d, J = 11.7 Hz, 1H), 1.99-1.88 (m, 2H), 1.04-0.97 (m, 2H), 0.94-0.87 (m, 2H). | 449.1 |
| 331 | $^1$H NMR (400 MHz, Chloroform-d) δ ppm 8.46 (1H, d, J = 5.1 Hz), 7.69 (1H, s), 7.63 (1H, m), 7.26 (1H, s), 7.18 (1H, s), 7.05 (1H, m), 6.96 (1H, m), 4.56 (1H, d, J = 11.2 Hz), 4.38 (1H, d, J = 11.5 | 448.2 |

TABLE 8C-continued

Analytical data for compounds of Table 8B

| Ex # | NMR | M + H |
|---|---|---|
|  | Hz), 3.84 (1H, m), 3.41 (1H, m), 2.75 (3H, s), 2.67 (3H, s), 2.60 (3H, s), 2.40 (1H, d, J = 13.3 Hz), 2.12 (2H, m), 1.80 (1H, m). |  |
| 332 | $^1$H NMR (400 MHz, Chloroform-d) δ ppm 8.53 (s, 1H), 8.44 (d, J = 5.1 Hz, 1H), 7.72-7.64 (m, 1H), 7.41-7.33 (m, 2H), 7.29 (d, J = 6.0 Hz, 1H), 7.26-7.20 (m, 2H), 4.66 (d, J = 8.9 Hz, 1H), 4.51 (d, J = 12.1 Hz, 1H), 4.36 (d, J = 12.4 Hz, 1H), 4.16 (d, J = 10.9 Hz, 1H), 3.81 (t, J = 11.5 Hz, 1H), 3.11 (t, J = 11.1 Hz, 1H), 2.92-2.82 (m, 1H), 2.65 (s, 3H). Note: One methyl signal is obscured by solvent peak. 19F NMR (376 MHz, DMSO-d6) δ ppm −108.64 (s), −109.12 (s). | 448.2 |
| 333 | $^1$H NMR (400 MHz, DMSO-d6) δ ppm 8.53 (s, 1H), 8.44 (d, J = 5.1 Hz, 1H), 7.72-7.63 (m, 1H), 7.42-7.34 (m, 2H), 7.29 (d, J = 4.2 Hz, 1H), 7.27-7.20 (m, 2H), 4.66 (d, J = 10.2 Hz, 1H), 4.51 (d, J = 13.0 Hz, 1H), 4.36 (d, J = 12.1 Hz, 1H), 4.16 (d, J = 8.5 Hz, 1H), 3.81 (t, J = 10.5 Hz, 1H), 3.11 (t, J = 10.6 Hz, 1H), 2.93-2.82 (m, 1H), 2.65 (s, 3H). Note: One methyl signal is obscured by solvent peak. 19F NMR (376 MHz, DMSO-d6) δ ppm −108.64 (s), −109.12 (s). | 434.2 |
| 334 | $^1$H NMR (400 MHz, DMSO-d6) δ ppm 8.18 (d, J = 5.2 Hz, 1H), 7.74 (t, J = 7.9 Hz, 1H), 7.65 (dd, J = 9.8, 2.1 Hz, 1H), 7.50 (dd, J = 8.2, 2.0 Hz, 1H), 7.05 (d, J = 5.3 Hz, 1H), 6.87 (s, 1H), 4.81 (d, J = 13.2 Hz, 1H), 4.65 (t, J = 12.5 Hz, 2H), 4.14 (d, J = 11.5 Hz, 1H), 3.86 (s, 3H), 3.75 (t, J = 11.5 Hz, 1H), 3.30-3.19 (m, 1H), 3.04 (dd, J = 13.2, 10.5 Hz, 1H), 2.65 (s, 3H), 2.52 (s, 3H). | 434.2 |
| 335 | $^1$H NMR (400 MHz, DMSO-d6) δ ppm 8.18 (d, J = 5.2 Hz, 1H), 7.74 (t, J = 7.9 Hz, 1H), 7.65 (dd, J = 9.8, 2.0 Hz, 1H), 7.54-7.43 (m, 1H), 7.06 (d, J = 5.3 Hz, 1H), 6.87 (s, 1H), 4.81 (d, J = 13.2 Hz, 1H), 4.65 (t, J = 12.5 Hz, 2H), 4.20-4.08 (m, 1H), 3.86 (s, 3H), 3.79-3.64 (m, 1H), 3.26 (d, J = 14.6 Hz, 1H), 3.04 (dd, J = 13.2, 10.5 Hz, 1H), 2.66 (s, 3H), 2.52 (s, 3H). | 481.1 |
| 336 | v NMR (400 MHz, Chloroform-d) δ ppm 7.71 (1H, s), 7.61 (1H, t, J = 7.8 Hz), 7.48-7.45 (2H, m), 7.31 (1H, d, J = 8.4 Hz), 7.23 (1H, m), 4.56 (1H, d, J = 11.2 Hz), 4.26 (1H, d, J = 11.5 Hz), 3.83-3.78 (1H, m), 3.57-3.53 (1H, m), 3.34 (1H, m), 2.76 (3H, s), 2.68-2.67 (3H, s), 2.38 (1H, d, J = 13.2 Hz), 2.08-1.93 (3H, m), 1.09 (2H, t, J = 3.9 Hz), 1.00-0.95 (2H, m). 19F NMR (376 MHz, Chloroform-d) δ F −109.5 | 481.1 |
| 337 | $^1$H NMR (400 MHz, Chloroform-d) δ ppm 7.71 (1H, s), 7.61 (1H, t, J = 7.8 Hz), 7.48-7.45 (2H, m), 7.31 (1H, d, J = 8.4 Hz), 7.23 (1H, m), 4.56 (1H, d, J = 11.2 Hz), 4.26 (1H, d, J = 11.5 Hz), 3.83-3.78 (1H, m), 3.57-3.53 (1H, m), 3.34 (1H, m), 2.76 (3H, s), 2.68-2.67 (3H, s), 2.38 (1H, d, J = 13.2 Hz), 2.08-1.93 (3H, m), 1.09 (2H, t, J = 3.9 Hz), 1.00-0.95 (2H, m). 19 F NMR (376 MHz, Chloroform-d) δ F −109.5 | 483.2 |
| 338 | $^1$H NMR (400 MHz, DMSO-d6) δ ppm 8.98 (d, J = 14.8 Hz, 1H), 7.83 (td, J = 8.4, 6.7 Hz, 1H), 7.74 (s, 1H), 7.53-7.43 (m, 1H), 7.39 (s, 1H), 7.33 (td, J = 8.3, 2.3 Hz, 1H), 4.57-4.47 (m, 1H), 4.11 (dd, J = 11.4, 3.2 Hz, 1H), 3.78-3.60 (m, 2H), 3.51 (s, 1H), 2.81 (s, 3H), 2.32 (d, J = 12.1 Hz, 1H), 2.08 (d, J = 12.8 Hz, 1H), 2.02-1.85 (m, 2H), 1.03-0.84 (m, 4H). | 449.1 |
| 339 | $^1$H NMR (400 MHz, DMSO-d6) δ ppm 9.00 (s, 1H), 7.83 (td, J = 8.4, 6.7 Hz, 1H), 7.74 (s, 1H), 7.49 (td, J = 10.1, 2.5 Hz, 1H), 7.39 (s, 1H), 7.33 (td, J = 8.4, 2.0 Hz, 1H), 4.58-4.46 (m, 1H), 4.11 (dd, J = 11.4, 3.2 Hz, 1H), 3.80-3.59 (m, 2H), 3.51 (ddd, J = 12.1, 8.3, 3.6 Hz, 1H), 2.81 (s, 3H), 2.32 (d, J = 11.9 Hz, 1H), 2.08 (d, J = 11.7 Hz, 1H), 1.99-1.88 (m, 2H), 1.04-0.97 (m, 2H), 0.94-0.87 (m, 2H). | 449.1 |
| 340 | $^1$H NMR (400 MHz, DMSO-d6) δ ppm 8.51 (s, 1H), 7.85 (s, 1H), 7.66 (td, J = 8.4, 6.6 Hz, 1H), 7.48 (s, 1H), 7.36 (td, J = 9.8, 2.5 Hz, 1H), 7.23 (td, J = 8.6, 2.6 Hz, 1H), 7.18 (s, 1H), 4.56 (dd, J = 10.4, 2.7 Hz, 1H), 4.41 (d, J = 13.2 Hz, 1H), 4.29-4.19 (m, 1H), 4.09-3.86 (m, 1H), 3.89-3.52 (m, 2H), 3.21-2.84 (m, 2H), 2.64 (s, 3H), 1.11-0.98 (m, 2H), 0.98-0.89 (m, 2H). | 483.2 |
| 341 | $^1$H NMR (400 MHz, DMSO-d6) δ ppm 7.84 (s, 1H), 7.65 (td, J = 8.4, 6.7 Hz, 1H), 7.47 (s, 1H), 7.36 (td, J = 9.8, 2.5 Hz, 1H), 7.22 (td, J = 9.5, 9.0, 3.1 Hz, 1H), 7.18 (s, 1H), 4.55 (dd, J = 10.5, 2.7 Hz, 1H), 4.37 (d, J = 12.6 Hz, 1H), 4.22 (d, J = 12.8 Hz, 1H), 4.02 (dd, J = 11.6, 3.2 Hz, 1H), 3.82-3.55 (m, 2H), 3.18-2.84 (m, 2H), 2.64 (s, 3H), 2.51 (s, 3H), 1.08-0.99 (m, 2H), 0.98-0.89 (m, 2H). | 449.2 |
| 342 | $^1$H NMR (400 MHz, CD$_2$Cl$_2$) δ ppm 8.45 (d, J = 4.7 Hz, 1H), 7.86 (s, 1H), 7.67 (d, J = 8.2 Hz, 1H), 7.52 (d, J = 8.2 Hz, 1H), 7.25 (m, 1H), 7.17 (s, 1H), 5.01 (d, J = 11.9 Hz, 1H), 4.83 (d, J = 13.0 Hz, 1H), 4.54 (d, J = 10.8 Hz, 1H), 4.17 (d, J = 9.9 Hz, 1H), 3.81 (t, J = 10.5 Hz, 1H), 3.28 (t, J = 12.4 Hz, 1H), 3.00 (d, J = 13.3, 10.7 Hz, 1H), 2.67 (s, 3H), 2.54 (s, 3H), 2.51 (s, 3H). 19F NMR (376 (MHz, CD$_2$Cl$_2$) δ ppm −57.89 (s). | 463.2 |
| 343 | $^1$H NMR (400 MHz, CD$_2$Cl$_2$) δ ppm 8.46 (d, J = 5.2 Hz, 1H), 7.64 (s, 1H), 7.50 (t, J = 7.9 Hz, 1H), 7.40-7.30 (m, 3H), 7.26 (s, 2H), 4.66 (dd, J = 10.3, 1.6 Hz, 1H), 4.53 (dd, J = 12.1, 1.7 Hz, 1H), 4.27-4.17 (m, 2H), 3.90 (td, J = 11.7, 2.9 Hz, 1H), 3.19 (t, J = 11.1 Hz, 1H), 2.93-2.84 (m, 1H), 2.70 (s, 3H), 2.60 (s, 3H), 2.34 (s, 3H). 19F NMR (376 MHz, CD$_2$Cl$_2$) δ ppm −112.30 (s). | 515.20 |
| 344 | $^1$H NMR (400 MHz, CD$_2$Cl$_2$) δ ppm 8.46 (d, J = 5.2 Hz, 1H), 7.64 (s, 1H), 7.50 (t, J = 7.9 Hz, 1H), 7.40-7.30 (m, 3H), 7.26 (s, 2H), 4.66 (dd, J = 10.3, 1.6 Hz, 1H), 4.53 (dd, J = 12.1, 1.7 Hz, 1H), 4.27-4.17 (m, 2H), 3.90 (td, J = 11.7, 2.9 Hz, 1H), 3.19 (t, J = 11.1 Hz, 1H), 2.93-2.84 (m, 1H), 2.70 (s, 3H), 2.70 (s, 3H), 2.60 (s, 3H), 2.34 (s, 3H). $^{19}$F NMR (376 MHz, CD$_2$Cl$_2$) δ ppm −112.30. | 463.2 |
| 345 | $^1$H NMR (400 MHz, Chloroform-d): δ ppm 9.84 (1H, s), 8.95 (1H, d, J = 8.3 Hz), 8.47-8.44 (1H, m), 7.91-7.87 (m, 1H), 7.26-7.24 (3H, m), 7.15-7.08 (1H, m), 4.58-4.52 (1H, m), 4.41-4.37 (1H, m), 3.89-3.83 (1H, m), 3.67-3.59 (1H, m) 2.87 (3H, s), 2.81 (3H, s), 2.56 (3H, s), 2.50-2.46 (1H, m), 2.29-2.21 (3H, m), 2.09-2.00 (1H, m). 19F NMR (376 MHz, Chloroform-d): δ ppm −68.1. | 481.2 |
| 346 | $^1$H NMR (400 MHz, CD$_2$Cl$_2$) δ ppm 9.03 (s, 1H), 8.46 (d, J = 5.1 Hz, 1H), 8.20 (d, J = 8.0 Hz, 1H), 7.87 (d, J = 8.0 Hz, 1H), 7.80 (s, 1H), 7.27 (s, 1H), 7.19 (d, J = 4.9 Hz, 1H), 7.10 (s, 1H), 4.65 (dd, J = 10.4, 2.5 Hz, 1H), 4.50 (d, J = 13.0 Hz, 1H), 4.29-4.17 (m, 2H), 3.96-3.87 (m, 1H), 3.22-3.11 (m, 1H), 2.87 (dd, J = 12.7, 10.6 Hz, 1H), 2.64 (s, 3H), 2.56 (s, 3H), 2.35 (s, 3H). 19F NMR (376 MHz, CD2Cl2) δ ppm −68.18 (s) | 447.2 |
| 347 | $^1$H NMR (400 MHz, CD$_2$Cl$_2$) δ ppm 9.03 (s, 1H), 8.46 (d, J = 5.1 Hz, 1H), 8.20 (d, J = 8.0 Hz, 1H), 7.87 (d, J = 8.0 Hz, 1H), 7.80 (s, 1H), 7.27 (s, 1H), 7.19 (d, J = 4.9 Hz, 1H), 7.10 (s, 1H), 4.65 (dd, J = 10.4, 2.5 Hz, 1H), 4.50 (d, J = 13.0 Hz, 1H), 4.29-4.17 (m, 2H), 3.96-3.87 (m, 1H), 3.22-3.11 (m, 1H), 2.87 (dd, J = 12.7, 10.6 Hz, 1H), 2.64 (s, 3H), 2.56 (s, 3H), 2.35 (s, 3H). $^{19}$F NMR (376 MHz, CD$_2$Cl$_2$) δ ppm −68.18. | 480.2 |
| 348 | $^1$H NMR (400 MHz, DMSO-d6) δ ppm 9.48 (d, J = 2.0 Hz, 1H), 8.78 (dd, J = 8.1, 2.1 Hz, 1H), 8.07 (d, J = 8.2 Hz, 1H), 7.86 (s, 1H), 7.50 (s, 1H), 7.25 (s, 1H), 4.58 (dd, J = 10.5, 2.7 Hz, 1H), 4.46 (d, J = 12.7 Hz, 1H), 4.32 (d, J = 12.8 Hz, 1H), 4.14-3.98 (m, 1H), 3.75 (dd, J = 10.7, 2.3 Hz, 1H), 3.69 (dq, J = 7.4, 3.8 Hz, 1H), 3.09 (dd, J = 12.5, 3.5 Hz, 1H), 3.02 (dd, J = 12.9, 10.5 Hz, 1H), 2.66 (s, 3H), 2.61 (s, 3H), 1.06-1.00 (m, 2H), 0.95 (td, J = 7.4, 5.1 Hz, 2H). | 479.1 |

TABLE 8C-continued

Analytical data for compounds of Table 8B

| Ex # | NMR | M + H |
|---|---|---|
| 349 | ¹H NMR (400 MHz, CD₂Cl₂) δ ppm 9.67-9.68 (1H, m), 8.87-8.90 (1H, m), 7.86-7.88 (1H, m), 7.28-7.31 (1H, m), 6.61-6.63 (1H, m), 6.33-6.35 (1H, m), 5.02-5.09 (1H, m), 4.86-4.91 (1H, m), 4.43-4.47 (1H, m), 4.17-4.21 (1H, m), 3.78-3.85 (1H, m), 3.32-3.36 (1H, m), 3.04-3.11 (1H, m), 2.71 (3H, s), 2.65 (3H, s). Note: The exchangeable proton was not observed. 19F NMR (CH2Cl2-d2), 376 MHz) δ ppm −68.4 | 496.2 |
| 350 | ¹H NMR (400 MHz, DMSO-d6) δ ppm 9.00 (s, 1 H), 7.78-7.84 (m, 1 H), 7.74 (s, 1 H), 7.70 (d, J = 9.9 Hz, 1 H), 7.55 (d, J = 8.3 Hz, 1 H), 7.40 (s, 1 H), 4.53 (d, J = 9.9 Hz, 1 H), 4.16-4.08 (m, 1 H), 3.74-3.62 (m, 2 H), 3.56-3.45 (m, 1 H), 2.82 (s, 3 H), 2.31 (d, J = 13.2 Hz, 1 H), 2.08 (d, J = 13.1 Hz, 1 H), 1.87-1.99 (m, 2 H), 1.06-0.96 (m, 2 H), 0.94-0.83 (m, 2 H) | 465.0 |
| 351 | ¹H NMR (400 MHz, DMSO-d6) δ ppm 9.00 (s, 1 H), 7.78-7.84 (m, 1 H), 7.74 (s, 1 H), 7.70 (d, J = 9.9 Hz, 1 H), 7.55 (d, J = 8.3 Hz, 1 H), 7.40 (s, 1 H), 4.53 (d, J = 9.9 Hz, 1 H), 4.16-4.08 (m, 1 H), 3.74-3.62 (m, 2 H), 3.56-3.45 (m, 1 H), 2.82 (s, 3 H), 2.31 (d, J = 13.2 Hz, 1 H), 2.08 (d, J = 13.1 Hz, 1 H), 1.87-1.99 (m, 2 H), 1.06-0.96 (m, 2 H), 0.94-0.83 (m, 2 H) | 465.0 |
| 352 | ¹H NMR (400 MHz, CD₂Cl₂) δ ppm 8.46 (d, J = 5.0 Hz, 1H), 7.49-7.42 (m, 1H), 7.39-7.34 (m, 1H), 7.27 (s, 1H), 7.19 (d, J = 4.4 Hz, 1H), 5.02 (d, J = 13.6 Hz, 1H), 4.85 (d, J = 13.3 Hz, 1H), 4.56 (dd, J = 10.6, 1.5 Hz, 1H), 4.18 (dd, J = 12.0, 2.5 Hz, 1H), 3.88-3.77 (m, 1H), 3.36-3.25 (m, 1H), 3.03 (dd, J = 13.3, 10.7 Hz, 1H), 2.69 (s, 3H), 2.57 (s, 3H), 2.55 (s, 3H). 19F NMR (376 MHz, CD₂Cl₂) δ ppm −133.16 (s), −139.03 (s). | 483.2 |
| 353 | ¹H NMR (600 MHz, DMSO-d6) δ ppm 8.56 (s, 1 H), 8.43-8.51 (m, 1 H), 7.35 (s, 1 H), 7.25-7.32 (m, 1 H), 4.87 (br d, J = 11.63 Hz, 1 H), 4.61 (br dd, = 10.44, 2.45 Hz, 1 H), 4.15 (br dd, J = 11.90, 2.27 Hz, 1 H), 3.68-3.77 (m, 1 H), 2.98-3.10 (m, 1 H), 2.64 (s, 3 H), 2.58 (s, 5 H), 2.52-2.53 (m, 1 H), 2.43-2.49 (m, 1 H), 0.97-1.07 (m, 1 H) | 457.0 |
| 354 | ¹H NMR (400 MHz, CDCl₃) δ ppm 8.38 (s, 1H), 7.66-7.36 (m, 2H), 5.06 (s, 1H), 4.70 (dt, J = 100.5, 50.4 Hz, 2H), 4.05-3.68 (m, 2H), 3.49 (dq, J = 7.3, 3.8 Hz, 1H), 3.27 (d, J = 87.1 Hz, 1H), 2.70 (s, 3H), 2.59 (d, J = 10.7 Hz, 6H), 1.24 (s, 3H), 1.02 (dd, J = 8.4, 4.9 Hz, 2H), 0.93 (t, J = 16.8 Hz, 2H). | 486.0 |
| 355 | ¹H NMR (400 MHz, CDCl₃) δ ppm 8.38 (s, 1H), 7.54 (d, J = 8.6 Hz, 2H), 5.06 (s, J = 44.1 Hz, 2H), 4.57 (dd, J = 10.9, 2.4 Hz, 1H), 3.80 (ddd, J = 10.6, 6.3, 2.5 Hz, 1H), 3.65-3.52 (m, 1H), 3.05 (s, 1H), 2.81 (dd, J = 13.2, 10.8 Hz, 1H), 2.71 (s, 3H), 2.58 (s, 6H), 1.33 (d, J = 4.2 Hz, 3H), 1.13 (s, 3H), 0.99 (dd, J = 27.6, 6.8 Hz, 2H). | 486.0 |
| 356 | ¹H NMR (400 MHz, CDCl₃) δ ppm 7.46 (s, 2H), 5.05 (t, J = 3.5 Hz, 1H), 4.86 (s, 1H), 4.60 (s, 1H), 3.90 (s, 2H), 3.49 (ddd, J = 11.1, 7.3, 3.8 Hz, 1H), 3.15 (s, 1H), 2.70 (d, J = 14.3 Hz, 3H), 2.63 (s, 3H), 2.60 (s, 6H), 1.26-1.22 (m, 1H), 1.05-0.99 (m, 2H), 0.95 (d, J = 14.3 Hz, 2H). | 500.0 |
| 357 | ¹H NMR (400 MHz, CDCl₃) δ ppm 7.65 (dd, J = 14.9, 8.2 Hz, 1H), 7.53 (d, J = 6.8 Hz, 2H), 7.05-6.88 (m, 3H), 4.69 (dd, J = 10.8, 2.6 Hz, 1H), 4.44 (d, J = 12.7 Hz, 1H), 4.27 (d, J = 12.7 Hz, 1H), 3.95-3.86 (m, 1H), 3.58 (ddd, J = 11.0, 7.3, 3.8 Hz, 1H), 2.99-2.92 (m, 1H), 2.79-2.65 (m, 4H), 2.60 (s, 3H), 1.34 (d, J = 6.2 Hz, 3H), 1.12 (dd, J = 7.0, 4.4 Hz, 2H), 1.00 (t, J = 5.9 Hz, 2H). | 477.0 |
| 358 | ¹H NMR (400 MHz, CDCl₃) δ ppm 7.65 (dd, J = 14.9, 8.2 Hz, 1H), 7.54 (s, 2H), 7.04-6.91 (m, 3H), 4.69 (dd, J = 10.8, 2.5 Hz, 1H), 4.45 (d, J = 12.8 Hz, 1H), 4.27 (d, J = 12.6 Hz, 1H), 3.96-3.88 (m, 1H), 3.60-3.55 (m, 1H), 3.01-2.93 (m, 1H), 2.78-2.68 (m, 4H), 2.60 (s, 3H), 1.34 (d, J = 6.2 Hz, 3H), 1.12 (dd, J = 7.1, 4.4 Hz, 2H), 1.00 (t, J = 6.1 Hz, 2H). | 477.0 |
| 359 | ¹H NMR (600 MHz, DMSO-d6) δ ppm 8.53-8.56 (m, 1 H), 7.84 (s, 1H), 7.47 (s 1 H), 4.76 (br d, J = 12.53 Hz, 1 H), 4.62 (br s, 1 H), 4.49 (dd, J = 10.35, 2.72 Hz, 1 H), 3.98-4.05 (m, 1 H), 3.68-3.73 (m, 1 H), 3.60-3.68 (m, 1 H), 3.14-3.25 (m, 1 H), 2.63 (s, 3 H), 2.57 (s, 6 H), 1.19-1.32 (m, 1 H), 0.93-1.05 (m, 5 H). | 472.0 |
| 360 | ¹H NMR (400 MHz, CDCl₃) δ ppm 8.75 (d, J = 7.1 Hz, 1H), 7.56 (d, J = 3.9 Hz, 1H), 7.47 (d, J = 15.4 Hz, 1H), 4.86-4.13 (m, 2H), 3.88-3.75 (m, 1H), 3.51 (t, J = 33.6 Hz, 2H), 2.81 (d, J = 5.2 Hz, 3H), 2.59 (s, 7H), 2.32 (d, J = 13.7 Hz, 1H), 2.08 (dd, J = 20.6, 8.9 Hz, 2H), 1.03 (d, J = 5.0 Hz, 4H). | 471.0 |
| 361 | ¹H NMR (400 MHz, CDCl₃) δ ppm 8.48 (s, 1H), 7.66-7.60 (m, 2H), 7.52 (s, 1H), 7.50 (d, J = 3.1 Hz, 2H), 7.00 (s, 1H), 5.08 (s, 1H), 4.51-4.47 (m, 1H), 4.01-3.99 (m, 1H), 3.73 (d, J = 9.2 Hz, 1H), 3.53 (d, J = 3.6 Hz, 2H), 3.25-3.17 (m, 2H), 2.87 (s, 3H), 1.28 (d, J = 6.3 Hz, 3H), 1.06 (d, J = 4.0 Hz, 1H), 0.98 (d, J = 5.3 Hz, 2H). | 463.0 |
| 362 | ¹H NMR (400 MHz, CDCl₃) δ ppm 8.48 (s, 1H), 7.66-7.60 (m, 2H), 7.52 (s, 1H), 7.50 (d, J = 3.1 Hz, 2H), 7.00 (s, 1H), 5.08 (s, 1H), 4.51-4.47 (m, 1H), 4.01-3.99 (m, 1H), 3.73 (d, J = 9.2 Hz, 1H), 3.53 (d, J = 3.6 Hz, 2H), 3.25-3.17 (m, 2H), 2.87 (s, 3H), 1.28 (d, J = 6.3 Hz, 3H), 1.06 (d, J = 4.0 Hz, 1H), 0.98 (d, J = 5.3 Hz, 2H). | 462.9 |
| 363 | ¹H NMR (400 MHz, CD₂Cl₂) δ ppm 8.47 (d, J = 4.9 Hz, 1H), 7.49-7.41 (m, 1H), 7.39-7.33 (m, 1H), 7.27 (s, 1H), 7.19 (d, J = 3.7 Hz, 1H), 5.02 (d, J = 13.0 Hz, 1H), 4.86 (d, J = 13.1 Hz, 1H), 4.56 (d, J = 10.2 Hz, 1H), 4.19 (dd, J = 11.8, 2.1 Hz, 1H), 3.88-3.77 (m, 1H), 3.37-3.26 (m, 1H), 3.03 (dd, J = 13.2, 10.7 Hz, 1H), 2.69 (s, 3H), 2.57 (s, 3H), 2.55 (s, 3H), 19F NMR (376 MHz, CD₂Cl₂) δ ppm −133.15 (s), −139.04 (s). | 483.2 |
| 364 | ¹H NMR (400 MHz, CD₂Cl₂) δ ppm 11.45 (s, 1H), 7.34 (d, J = 6.8 Hz, 1H), 6.61 (s, 1H), 6.35 (d, J = 8.2 Hz, 1H), 4.99 (d, J = 13.7 Hz, 1H), 4.82 (d, J = 12.8 Hz, 1H), 4.41 (d, J = 7.8 Hz, 1H), 4.15 (d, J = 11.3 Hz, 1H), 3.81-3.72 (m, 1H), 3.31-3.20 (m, 1H), 3.06-2.95 (m, 1H), 2.65 (s, 3H), 2.62 (s, 3H), 2.60 (s, 6H). 19F NMR (376 MHz, CD₂Cl₂) δ ppm −73.46 (s) | 483.1 |
| 365 | ¹H NMR (400 MHz, CDCl₃) δ ppm 7.42 (t, J = 12.8 Hz, 2H), 4.77 (dd, J = 8.0, 3.4 Hz, 1H), 3.92-3.73 (m, 2H), 3.64-3.41 (m, 2H), 2.72 (t, J = 11.3 Hz, 6H), 2.57 (s, 6H), 2.39-2.30 (m, 1H), 2.28-2.18 (m, 1H), 2.08 (qd, J = 8.7, 4.6 Hz, 1H), 1.18 (s, 1H), 1.06-1.01 (m, 2H), 0.93 (qd, J = 5.5, 1.2 Hz, 2H). | 485.2 |
| 366 | ¹H NMR (400 MHz, CDCl₃) δ ppm 7.44 (t, J = 5.8 Hz, 2H), 4.47 (dd, J = 11.4, 1.9 Hz, 1H), 4.18 (dt, J = 6.0, 3.3 Hz, 1H), 3.79-3.66 (m, 1H), 3.49 (tt, J = 7.3, 3.8 Hz, 1H), 3.37 (ddd, J = 15.8, 11.8, 3.7 Hz, 1H), 2.79-2.65 (m, 6H), 2.58 (s, 6H), 2.30 (d, J = 13.2 Hz, 1H), 2.07 (ddd, J = 11.6, 9.9, 4.2 Hz, 3H), 1.20 (d, J = 12.5 Hz, 1H), 1.06-0.96 (m, 2H), 0.92 (td, J = 7.1, 4.9 Hz, 2H). | 485.3 |
| 367 | ¹H NMR (400 MHz, CDCl₃) δ ppm 7.70-7.56 (m, 5H), 7.55-7.47 (m, 8H), 7.00 (s, 3H), 6.95 (s, 3H), 5.07 (s, 3H), 4.33 (s, 3H), 3.91 (d, J = 6.4 Hz, 4H), 3.66-3.58 (m, 3H), 3.51 (dd, J = 7.4, 3.6 Hz, 3H), 3.13-3.02 (m, 3H), 2.77 (s, 4H), 2.77 (s, 4H), 2.69 (d, J = 1.9 Hz, 13H), 2.60 (s, 10H), 1.27 (d, J = 6.4 Hz, 11H), 1.04 (d, J = 4.2 Hz, 7H), 1.00-0.89 (m, 7H). | 493.0 |
| 368 | ¹H NMR (400 MHz, CDCl₃) δ ppm 8.43 (d, J = 4.4 Hz, 1H), 7.58 (t, J = 7.9 Hz, 1H), 7.54 (s, 2H), 7.31-7.28 (m, 1H), 7.25-7.22 (m, 1H), 6.95 (s, 1H), 4.68 (dd, J = 10.9, 2.5 Hz, 1H), 4.46 (d, J = 12.5 Hz, 1H), 4.29 (d, J = 12.4 Hz, 1H), 3.94-3.86 (m, | 478.9 |

TABLE 8C-continued

Analytical data for compounds of Table 8B

| Ex # | NMR | M + H |
|---|---|---|
|  | 1H), 3.57 (td, J = 7.3, 3.7 Hz, 1H), 2.99 (dd, J = 12.7, 11.0 Hz, 1H), 2.77 (dd, J = 12.6, 10.7 Hz, 1H), 2.70 (s, 3H), 1.34 (d, J = 6.2 Hz, 3H), 1.12 (td, J = 7.3, 4.4 Hz, 2H), 1.04-0.99 (m, 2H). |  |
| 369 | $^1$H NMR (400 MHz, CDCl$_3$) δ 7.72 (dd, J = 14.8, 8.1 Hz, 1H), 7.51 (d, J = 9.1 Hz, 2H), 7.11-6.89 (m, 2H), 5.06 (s, 1H), 4.75 (d, J = 69.4 Hz, 2H), 3.86 (d, J = 64.9 Hz, 2H), 3.49 (s, 1H), 3.21 (s, 1H), 2.72 (s, 3H), 2.60 (s, 3H), 1.25 (d, J = 6.3 Hz, 3H), 1.01 (s, 2H), 0.93 (dd, J = 6.7, 3.1 Hz, 2H). | 478.1 |
| 370 | $^1$H NMR (400 MHz, CDCl3) δ 8.41 (s, 1H), 7.69 (dd, J = 14.8, 7.8 Hz, 1H), 7.50 (dd, J = 27.7, 12.3 Hz, 2H), 7.03 (dt, J = 17.4, 8.2 Hz, 2H), 5.07 (s, 1H), 4.83 (t, J = 28.4 Hz, 1H), 4.70 (d, J = 12.6 Hz, 1H), 4.06-3.72 (m, 1H), 3.58-3.17 (m, 2H), 2.74 (s, 3H), 1.26 (d, J = 6.3 Hz, 3H), 1.01 (s, 2H), 0.94 (d, J = 6.6 Hz, 2H). | 464.0 |
| 371 | $^1$H NMR (400 MHz, CDCl$_3$) δ 8.47-8.35 (m, 1H), 7.68 (dd, J = 14.5, 7.4 Hz, 1H), 7.53 (d, J = 5.3 Hz, 2H), 7.13-6.92 (m, 2H), 5.04 (s, 2H), 4.60 (d, J = 10.6 Hz, 1H), 3.91-3.76 (m, 1H), 3.57 (ddd, J = 10.9, 7.3, 3.7 Hz, 1H), 3.10 (dd, J = 13.4, 11.0 Hz, 1H), 2.86 (dd, J = 13.4, 10.7 Hz, 1H), 2.74 (s, 3H), 1.33 (d, J = 6.2 Hz, 3H), 1.17-1.07 (m, 2H), 1.06-0.96 (m, 2H). | 464.0 |
| 372 | $^1$H NMR (400 MHz, CDCl$_3$) δ ppm 7.65 (t, J = 7.8 Hz, 1H), 7.53 (t, J = 4.1 Hz, 2H), 7.30 (t, J = 6.0 Hz, 1H), 7.24 (t, J = 2.0 Hz, 1H), 4.97 (s, 2H), 4.60 (d, J = 8.7 Hz, 1H), 3.89-3.76 (m, 1H), 3.57 (ddd, J = 11.1, 7.3, 3.9 Hz, 1H), 3.07 (dd, J = 13.3, 11.0 Hz, 1H), 2.84 (dd, J = 13.4, 10.7 Hz, 1H), 2.71 (s, 3H), 2.59 (s, 3H), 1.32 (d, J = 6.2 Hz, 3H), 1.15-1.07 (m, 2H), 1.01 (dt, J = 12.3, 6.3 Hz, 2H). | 494.0 |
| 373 | $^1$H NMR (400 MHz, CDCl$_3$) δ ppm 7.65 (t, J = 7.8 Hz, 1H), 7.53 (t, J = 4.5 Hz, 2H), 7.33-7.28 (m, 1H), 7.24 (d, J = 1.9 Hz, 1H), 4.97 (s, 2H), 4.60 (d, J = 8.6 Hz, 1H), 3.88-3.77 (m, 1H), 3.62-3.53 (m, 1H), 3.07 (dd, J = 13.3, 11.0 Hz, 1H), 2.84 (dd, J = 13.3, 10.7 Hz, 1H), 2.71 (s, 3H), 2.59 (s, 3H), 1.32 (d, J = 6.2 Hz, 3H), 1.16-1.08 (m, 2H), 1.01 (q, J = 6.7 Hz, 2H). | 494.0 |
| 374 | $^1$H NMR (400 MHz, CDCl$_3$) δ ppm 8.41 (s, 1H), 7.62 (s, 1H), 7.58-7.50 (m, 2H), 7.38-7.27 (m, 2H), 5.04 (s, 2H), 4.60 (d, J = 9.1 Hz, 1H), 3.83 (s, 1H), 3.58 (s, 1H), 3.09 (dd, J = 13.4, 11.0 Hz, 1H), 2.86 (dd, J = 13.3, 10.7 Hz, 1H), 2.74 (s, 3H), 1.33 (d, J = 6.2 Hz, 3H), 1.18-1.07 (m, 2H), 1.06-0.95 (m, 2H). | 481.0 |
| 375 | $^1$H NMR (400 MHz, CDCl$_3$) δ ppm 8.41 (s, 1H), 7.62 (s, 1H), 7.53 (d, J = 5.8 Hz, 2H), 7.30 (dd, J = 15.3, 7.4 Hz, 2H), 5.04 (s, 2H), 4.60 (d, J = 9.4 Hz, 1H), 3.83 (s, 1H), 3.58 (s, 1H), 3.10 (dd, J = 13.4, 11.0 Hz, 1H), 2.86 (dd, J = 13.4, 10.7 Hz, 1H), 2.74 (s, 3H), 1.33 (d, J = 6.2 Hz, 3H), 1.12 (dt, J = 8.3, 4.3 Hz, 2H), 1.06-0.98 (m, 2H). | 481.0 |
| 376 | $^1$H NMR (400 MHz, Chloroform-d) δ ppm 7.70 (1H, s), 7.68-7.62 (1H, m), 7.49 (2H, s), 7.05 (1H, t, J = 8.4 Hz), 6.96 (1H, td, J = 9.4, 2.4 Hz), 4.61 (1H, d, J = 11.2 Hz), 3.85 (1H, dd, J = 10.8, 6.0 Hz), 3.54 (1H, tt, J = 7.2, 3.8 Hz), 2.76 (3H, s), 3.39-3.33 (1H, m), 2.68 (3H, s), 2.35 (1H, d, J = 13.1 Hz), 2.15 (1H, d, J = 13.1 Hz), 1.93 (1H, q, J = 12.2 Hz), 1.70-1.61 (1H, m), 1.33 (3H, d, J = 6.2 Hz), 1.09 (2H, t, J = 3.5 Hz), 0.99 (2H, t, J = 6.6 Hz). 19F NMR (376 MHz, Chloroform-d) δ ppm −109.3, −109.3, −109.2, −109.2, −109.2, −109.2, −109.2, −107.7, −107.7, −107.7, −107.7. | 456.20 |
| 377 | $^1$H NMR (400 MHz, CDCl$_3$) δ ppm 8.33 (d, J = 7.0 Hz, 1H), 7.56-7.42 (m, 3H), 6.69 (d, J = 21.2 Hz, 1H), 4.60 (dd, J = 10.8, 2.6 Hz, 1H), 4.37 (d, J = 12.6 Hz, 1H), 4.19 (d, J = 12.3 Hz, 1H), 3.82 (ddd, J = 10.4, 6.4, 2.6 Hz, 1H), 3.52 (tt, J = 7.3, 3.8 Hz, 1H), 2.95-2.75 (m, 1H), 2.70-2.57 (m, 4H), 2.52-2.47 (m, 6H), 1.27 (d, J = 6.2 Hz, 3H), 1.07 (td, J = 7.3, 4.6 Hz, 2H), 0.98-0.92 (m, 2H). | 485.0 |
| 378 | $^1$H NMR (400 MHz, CDCl$_3$) δ 7.47 (s, 2H), 6.73 (s, 1H), 4.61 (dd, J = 10.8, 2.6 Hz, 1H), 4.34 (d, J = 12.6 Hz, 1H), 4.16 (d, J = 12.5 Hz, 1H), 3.88-3.78 (m, 1H), 3.52 (ddd, J = 11.1, 7.4, 3.8 Hz, 1H), 2.88-2.79 (m, 1H), 2.65-2.60 (m, 1H), 2.58 (s, 6H), 2.50 (s, 5H), 1.26 (d, J = 6.2 Hz, 3H), 1.18 (s, 1H), 1.09-1.04 (m, 2H), 0.98-0.93 (m, 2H). | 499.1 |
| 379 | $^1$H NMR (400 MHz, CDCl$_3$) δ ppm 7.47 (s, 2H), 6.73 (s, 1H), 4.61 (dd, J = 10.8, 2.6 Hz, 1H), 4.34 (d, J = 12.6 Hz, 1H), 4.16 (d, J = 12.5 Hz, 1H), 3.88-3.78 (m, 1H), 3.52 (ddd, J = 11.1, 7.4, 3.8 Hz, 1H), 2.88-2.79 (m, 1H), 2.65-2.60 (m, 1H), 2.58 (s, 6H), 2.50 (s, 5H), 1.26 (d, J = 6.2 Hz, 3H), 1.18 (s, 1H), 1.09-1.04 (m, 2H), 0.98-0.93 (m, 2H). | 499.1 |
| 380 | $^1$H NMR (400 MHz, Chloroform-d) δ ppm 9.58 (s, 1H), 8.78 (d, J = 8.0, 2.1 Hz, 1H), 7.81 (d, J = 8.2 Hz, 1H), 7.54 (s, 1H), 7.48 (s, 1H), 7.01 (s, 1H), 4.64 (dd, J = 10.4, 2.8 Hz, 1H), 4.52-4.37 (m, 1H), 4.22 (d, J = 12.7 Hz, 1H), 4.17-4.06 (m, 1H), 3.87 (td, J = 11.6, 2.8 Hz, 1H), 3.58 (tt, J = 7.4, 3.8 Hz, 1H), 3.20 (td, J = 12.1, 3.6 Hz, 1H), 3.10 (dd, J = 12.8, 10.4 Hz, 1H), 2.67 (s, 3H), 2.64 (s, 3H), 1.09 (td, J = 4.7, 2.9 Hz, 2H), 1.06-0.94 (m, 2H). | 476.2 |
| 381 | $^1$H NMR (400 MHz, DMSO-d6) δ ppm 7.84 (s, 1H), 7.72 (t, J = 7.9 Hz, 1H), 7.64 (dd, J = 9.8, 2.0 Hz, 1H), 7.56-7.38 (m, 2H), 4.73 (d, J = 13.2 Hz, 1H), 4.61 (d, J = 13.3 Hz, 1H), 4.51 (dd, J = 10.5, 2.7 Hz, 1H), 4.01 (d, J = 11.5 Hz, 1H), 3.76-3.60 (m, 2H), 3.28-3.15 (m, 2H), 2.65 (s, 3H), 2.51 (s, 3H), 1.08-0.98 (m, 2H), 0.98-0.84 (m, 2H). | 496.2 |
| 382 | $^1$H NMR (400 MHz, CD$_2$Cl$_2$) δ ppm 7.59 (t, J = 7.9 Hz, 1H), 7.52 (s, 1H), 7.46 (s, 1H), 7.29 (dd, J = 8.4, 2.1 Hz, 1H), 7.24 (dd, J = 9.3, 2.0 Hz, 1H), 6.97 (s, 1H), 4.63 (dd, J = 10.3, 2.8 Hz, 1H), 4.44-4.27 (m, 1H), 4.20-4.12 (m, 1H), 4.12-4.05 (m, 1H), 3.85 (td, J = 11.5, 2.8 Hz, 1H), 3.57 (dq, J = 7.4, 3.7 Hz, 1H), 3.15 (td, J = 12.1, 3.7 Hz, 1H), 3.05 (dd, J = 12.8, 10.3 Hz, 1H), 2.65 (s, 3H), 2.56 (s, 3H), 1.14-1.04 (m, 2H), 1.02-0.94 (m, 2H). | 479.1 |
| 383 | $^1$H NMR (400 MHz, CD$_2$Cl$_2$) δ ppm 7.59 (t, J = 7.8 Hz, 1H), 7.52 (s, 1H), 7.46 (s, 1H), 7.29 (dd, J = 8.9, 1.6 Hz, 1H), 7.24 (dd, J = 9.5, 2.0 Hz, 1H), 6.97 (s, 1H), 4.63 (dd, J = 10.3, 2.8 Hz, 1H), 4.38 (d, J = 12.8 Hz, 1H), 4.15 (d, J = 12.9 Hz, 1H), 4.09 (d, J = 12.0 Hz, 1H), 3.85 (td, J = 11.5, 2.8 Hz, 1H), 3.57 (tt, J = 7.2, 3.7 Hz, 1H), 3.15 (td, J = 12.0, 3.5 Hz, 1H), 3.05 (dd, J = 12.8, 10.3 Hz, 1H), 2.65 (s, 3H), 2.56 (s, 3H), 1.14-1.03 (m, 2H), 1.02-0.92 (m, 2H). | 479.2 |
| 384 | $^1$H NMR (400 MHz, CD$_2$Cl$_2$) δ ppm 7.59 (t, J = 7.8 Hz, 1H), 7.52 (s, 1H), 7.46 (s, 1H), 7.29 (dd, J = 8.9, 1.6 Hz, 1H), 7.24 (dd, J = 9.5, 2.0 Hz, 1H), 6.97 (s, 1H), 4.63 (dd, J = 10.3, 2.8 Hz, 1H), 4.38 (d, J = 12.8 Hz, 1H), 4.15 (d, J = 12.9 Hz, 1H), 4.09 (d, J = 12.0 Hz, 1H), 3.85 (td, J = 11.5, 2.8 Hz, 1H), 3.57 (tt, J = 7.2, 3.7 Hz, 1H), 3.15 (td, J = 12.0, 3.5 Hz, 1H), 3.05 (dd, J = 12.8, 10.3 Hz, 1H), 2.65 (s, 3H), 2.56 (s, 3H), 1.14-1.03 (m, 2H), 1.02-0.92 (m, 2H). | 496.2 |
| 385 | $^1$H NMR (400 MHz, CD$_2$Cl$_2$) δ ppm 9.58 (d, J = 1.6 Hz, 1H), 8.78 (d, J = 8.1, 2.0 Hz, 1H), 7.81 (d, J = 8.2 Hz, 1H), 7.54 (s, 1H), 7.48 (s, 1H), 7.01 (s, 1H), 4.64 (dd, J = 10.4, 2.8 Hz, 1H), 4.44 (dd, J = 12.5, 2.8 Hz, 1H), 4.22 (d, J = 12.7 Hz, 1H), 4.11 (d, J = 3.4 Hz, 1H), 3.87 (td, J = 11.6, 2.9 Hz, 1H), 3.58 (tt, J = 7.5, 3.8 Hz, 1H), 3.20 (td, J = 12.1, 3.6 Hz, 1H), 3.10 (dd, J = 12.8, 10.4 Hz, 1H), 2.67 (s, 3H), 2.64 (s, 3H), 1.14-1.03 (m, 2H), 1.03-0.94 (m, 2H). | 496.2 |
| 386 | $^1$H NMR (400 MHz, Chloroform-d) δ ppm 8.72 (1H, s), 7.57 (1H, s), 7.48 (2H, s), 4.56 (1H, d, J = 11.2 Hz), 4.27-4.23 (1H, m), 3.85-3.77 (1H, m), 3.56 (1H, m), 3.30-3.21 (1H, m), 2.78 (3H, | 470.2 |

TABLE 8C-continued

Analytical data for compounds of Table 8B

| Ex # | NMR | M + H |
|---|---|---|
| | s), 2.61 (6H, s), 2.31 (1H, d, J = 13.2 Hz), 2.04-1.92 (3H, m), 1.12-1.06 (2H, m), 1.03-0.94 (2H, m). 19F NMR (376 MHz, Chloroform-d) δ ppm −73.0 | |
| 387 | $^1$H NMR (400 MHz, CD2Cl2) δ ppm 9.70 (s, 1H), 8.91 (d, J = 8.4 Hz, 1H), 7.88 (d, J = 8.2 Hz, 1H), 7.33 (d, J = 4.5 Hz, 1H), 6.65 (s, 1H), 6.34 (d, J = 7.2 Hz, 1H), 5.11-4.99 (m, 1H), 4.90 (d, J = 13.5 Hz, 1H), 4.42 (d, J = 8.7 Hz, 1H), 4.20 (d, J = 12.1 Hz, 1H), 3.82 (t, J = 11.2 Hz, 1H), 3.38-3.26 (m, 1H), 3.06 (dd, J = 13.7, 9.8 Hz, 1H), 2.72 (s, 3H), 2.67 (s, 3H). one exchangeable proton is not visible. 19F NMR (376 MHz, CD2Cl2) δ −68.40. | 483.10 |
| 388 | $^1$H NMR (400 MHz, CD$_2$Cl$_2$) δ ppm 8.47 (s, 1H), 7.55 (dd, J = 8.9, 5.9 Hz, 1H), 7.34 (dd, J = 8.8, 5.9 Hz, 1H), 7.28 (s, 1H), 7.20 (s, 1H), 5.02 (dd, J = 13.6, 0.8 Hz, 1H), 4.85 (d, J = 13.6 Hz, 1H), 4.56 (d, J = 8.3 Hz, 1H), 4.18 (dd, J = 11.6, 2.5 Hz, 1H), 3.87-3.79 (m, 1H), 3.36-3.25 (m, 1H), 3.03 (dd, J = 13.4, 10.6 Hz, 1H), 2.68 (s, 3H), 2.57 (s, 3H), 2.55 (s, 3H). 19F NMR (376 MHz, CD$_2$Cl$_2$) δ ppm −115.09 (s), −122.08 (s). | 448.2 |
| 389 | $^1$H NMR (400 MHz, DMSO-d6) δ ppm 8.87 (1H, s), 7.85 (1H, s), 7.66-7.72 (2H, m), 7.37-7.40 (2H, m), 7.25 (1H, t, J = 8.4 Hz), 4.48 (1H, d, J = 11.0 Hz), 4.08 (1H, d, J = 11.2 Hz), 3.61-3.71 (2H, m), 2.74 (3H, s), 2.21 (1H, d, J = 13.0 Hz), 1.85-1.97 (3H, m), 0.97 (2H, d, J = 4.2 Hz), 0.89 (2H, d, J = 7.3 Hz). | 482.2 |
| 390 | $^1$H NMR (400 MHz, CD$_2$Cl$_2$) δ ppm 8.41 (s, 2H), 8.39 (s, 1H), 7.23 (s, 1H), 7.14 (d, J = 4.0 Hz, 1H), 4.56 (dd, J = 11.3, 1.1 Hz, 1H), 4.39-4.32 (m, 1H), 3.90-3.79 (m, 1H), 3.64-3.51 (m, 1H), 2.81 (s, 3H), 2.79 (s, 3H), 2.52 (s, 3H), 2.48-2.40 (m, 1H), 2.24-2.13 (m, 2H), 2.01-1.88 (m, 1H). 19F NMR (376 MHz, CD$_2$Cl$_2$) δ ppm −113.77 (s), −113.80 (s). | 482.2 |
| 391 | $^1$H NMR (400 MHz, CD$_2$Cl$_2$) δ ppm 8.42 (d, J = 5.0 Hz, 1H), 8.35 (d, J = 8.2 Hz, 2H), 7.23 (s, 1H), 7.14 (d, J = 4.9 Hz, 1H), 4.69-4.57 (m, 2H), 4.40-4.33 (m, 1H), 3.99-3.89 (m, 1H), 2.83 (s, 3H), 2.82 (s, 3H), 2.52 (s, 3H), 2.34-2.24 (m, 1H), 2.23-2.16 (m, 1H), 2.12-2.01 (m, 1H), 2.01-1.93 (m, 1H), 19F NMR (376 MHz, CD$_2$Cl$_2$) δ ppm −113.54 (s), −113.56 (s). | 483.10 |
| 392 | $^1$H NMR (400 MHz, Chloroform-d): δ ppm 7.54 (1H, s), 7.48 (2H, s), 4.55 (1H, d, J = 11.2 Hz), 4.25 (1H, d, J = 11.4 Hz), 3.78-3.84 (1H, m), 3.53-3.59 (1H, m), 3.22 (1H, s), 2.73 (6H, d, J = 2.2 Hz), 2.61 (6H, s), 2.30 (1H, d, J = 13.1 Hz), 1.95-2.02 (3H, m), 1.10 (2H, t, J = 3.5 Hz), 0.99 (2H, t, J = 6.7 Hz). | 484.2 |
| 393 | $^1$H NMR (400 MHz, CD$_2$Cl$_2$) δ ppm 8.47 (d, J = 4.9 Hz, 1H), 7.55 (dd, J = 8.9, 5.9 Hz, 1H), 7.34 (dd, J = 8.8, 5.9 Hz, 1H), 7.27 (s, 1H), 7.20 (d, J = 4.4 Hz, 1H), 5.02 (d, J = 13.5 Hz, 1H), 4.85 (d, J = 13.4 Hz, 1H), 4.56 (dd, J = 10.3, 2.0 Hz, 1H), 4.18 (dd, J = 11.5, 2.4 Hz, 1H), 3.83 (td, J = 11.7, 2.7 Hz, 1H), 3.31 (td, J = 13.4, 3.5 Hz, 1H), 3.03 (dd, J = 13.4, 10.6 Hz, 1H), 2.68 (s, 3H), 2.57 (s, 3H), 2.55 (s, 3H). 19F NMR (376 MHz, CD$_2$Cl$_2$) δ ppm −115.10 (s), −122.08 (s). | 462.2 |
| 394 | $^1$H NMR (400 MHz, Chloroform-d) δ ppm 7.62 (t, J = 7.8 Hz, 1H), 7.48 (s, 1H), 7.42 (s, 1H), 7.31 (d, J = 8.5 Hz, 1H), 7.26 (d, J = 9.8 Hz, 1H), 4.84 (d, J = 13.4 Hz, 1H), 4.77 (d, J = 13.5 Hz, 1H), 3.66-3.50 (m, 1H), 3.41 (d, J = 11.9 Hz, 1H), 3.35-3.08 (m, 2H), 3.10-2.95 (m, 1H), 2.65 (s, 3H), 2.54 (d, J = 2.5 Hz, 3H), 2.36 (t, J = 11.9 Hz, 1H), 2.16 (s, 3H), 1.08 (q, J = 3.5 Hz, 2H), 0.98 (d, J = 6.8 Hz, 2H). | 468.20 |
| 395 | $^1$H NMR (400 MHz, Chloroform-d) δ ppm 7.67-7.58 (m, 1H), 7.48 (s, 1H), 7.42 (s, 1H), 7.31 (d, J = 8.4 Hz, 1H), 7.26 (d, J = 9.8 Hz, 1H), 4.91-4.80 (m, 1H), 4.81-4.68 (m, 1H), 3.57 (tq, J = 7.5, 4.1 Hz, 1H), 3.48-3.36 (m, 1H), 3.32-3.20 (m, 1H), 3.20-3.11 (m, 1H), 3.10-2.97 (m, 1H), 2.65 (s, 3H), | 488.20 |
| | 2.54 (d, J = 2.8 Hz, 3H), 2.42-2.31 (m, 1H), 2.16 (s, 3H), 1.14-1.05 (m, 2H), 1.02-0.92 (m, 2H). | |
| 396 | $^1$H NMR (400 MHz, CD$_2$Cl$_2$δ ppm 8.81 (s, 1H), 8.41 (s, 1H), 7.50-7.45 (m, 1H), 7.43-7.37 (m, 1H), 7.23 (s, 1H), 7.13 (d, J = 4.6 Hz, 1H), 4.55 (d, J = 11.5 Hz, 1H), 4.34 (dd, J = 10.6, 3.8 Hz, 1H), 3.84 (td, J = 11.7, 3.2 Hz, 1H), 3.66-3.57 (m, 1H), 2.86 (s, 3H), 2.51 (s, 3H), 2.47-2.40 (m, 1H), 2.25-2.13 (m, 2H), 2.01-1.90 (m, 1H). 19F NMR (376 MHz, CD$_2$Cl$_2$) δ ppm −133.01 (s), −138.66 (s). | 482.20 |
| 397 | $^1$H NMR (400 MHz, CD2Cl2) δ ppm 8.41 (d, J = 5.1 Hz, 1H), 7.51-7.44 (m, 1H), 7.44-7.36 (m, 1H), 7.22 (s, 1H), 7.13 (d, J = 4.7 Hz, 1H), 4.54 (dd, J = 11.6, 1.2 Hz, 1H), 4.37-4.30 (m, 1H), 3.88-3.77 (m, 1H), 3.63-3.52 (m, 1H), 2.80 (s, 3H), 2.70 (s, 3H), 2.51 (s, 3H), 2.46-2.39 (m, 1H), 2.23-2.11 (m, 2H), 2.00-1.89 (m, 1H) | 482.20 |
| 398 | $^1$H NMR (400 MHz, CDCl$_3$) δ ppm 7.66 (dd, J = 14.9, 8.2 Hz, 1H), 7.52 (d, J = 6.9 Hz, 2H), 7.06-6.92 (m, 2H), 6.90 (s, 1H), 5.06 (t, J = 3.6 Hz, 1H), 4.34 (dd, J = 12.9, 3.3 Hz, 1H), 4.07-3.87 (m, 2H), 3.62 (dd, J = 12.9, 3.8 Hz, 1H), 3.51 (ddd, J = 11.0, 7.4, 3.8 Hz, 1H), 3.06 (dt, J = 22.0, 11.0 Hz, 1H), 2.63 (d, J = 32.2 Hz, 6H), 1.26 (d, J = 6.3 Hz, 3H), 1.07-1.00 (m, 2H), 0.98-0.88 (m, 2H). | 477.1 |
| 399 | $^1$H NMR (400 MHz, Chloroform-d) δ ppm 8.48-8.46 (1H, m), 7.82 (1H, s), 7.71-7.67 (1H, m), 7.33 (2H, m), 7.08-7.03 (1H, m), 7.02-6.96 (1H, m), 4.96-4.92 (1H, m), 3.98 (2H, m), 3.56-3.53 (1H, m), 2.78 (3H, s), 2.70 (3H, s), 2.66-2.60 (4H, m), 2.30-2.17 (3H, m). | 446.2 |
| 400 | $^1$H NMR (400 MHz, Chloroform-d) δ ppm 8.48-8.46 (1H, m), 7.82 (1H, s), 7.71-7.67 (1H, m), 7.33 (2H, m), 7.08-7.03 (1H, m), 7.02-6.96 (1H, m), 4.96-4.92 (1H, m), 3.98 (2H, m), 3.56-3.53 (1H, m), 2.78 (3H, s), 2.70 (3H, s), 2.66-2.60 (4H, m), 2.30-2.17 (3H, m). | 446.2 |
| 401 | | 463.1 |
| 402 | | 478.0 |
| 403 | $^1$H NMR (400 MHz, CDCl$_3$) δ ppm 7.66 (dd, J = 14.9, 8.2 Hz, 1H), 7.52 (d, J = 6.9 Hz, 2H), 7.06-6.92 (m, 2H), 6.90 (s, 1H), 5.06 (t, J = 3.6 Hz, 1H), 4.34 (dd, J = 12.9, 3.3 Hz, 1H), 4.07-3.87 (m, 2H), 3.62 (dd, J = 12.9, 3.8 Hz, 1H), 3.51 (ddd, J = 11.0, 7.4, 3.8 Hz, 1H), 3.06 (dt, J = 22.0, 11.0 Hz, 1H), 2.63 (d, J = 32.2 Hz, 6H), 1.26 (d, J = 6.3 Hz, 3H), 1.07-1.00 (m, 2H), 0.98-0.88 (m, 2H). | 477.1 |
| 404 | $^1$H NMR (400 MHz, CDCl$_3$) δ ppm 8.38 (s, 1H), 7.66-7.36 (m, 2H), 5.06 (s, 1H), 4.70 (dt, J = 100.5, 50.4 Hz, 2H), 4.05-3.68 (m, 2H), 3.49 (dq, J = 7.3, 3.8 Hz, 1H), 3.27 (d, J = 87.1 Hz, 1H), 2.70 (s, 3H), 2.59 (d, J = 10.7 Hz, 6H), 1.24 (s, 3H), 1.02 (dd, J = 8.4, 4.9 Hz, 2H), 0.93 (t, J = 16.8 Hz, 2H). | 486.0 |
| 405 | $^1$H NMR (400 MHz, CDCl$_3$) δ ppm 8.38 (s, 1H), 7.54 (d, J = 8.6 Hz, 2H), 5.06 (d, J = 44.1 Hz, 2H), 4.57 (dd, J = 10.9, 2.4 Hz, 1H), 3.80 (ddd, J = 10.6, 6.3, 2.5 Hz, 1H), 3.65-3.52 (m, 1H), 3.05 (s, 1H), 2.81 (dd, J = 13.2, 10.8 Hz, 1H), 2.71 (s, 3H), 2.58 (s, 6H), 1.33 (d, J = 4.2 Hz, 3H), 1.13 (s, 2H), 0.99 (d, J = 27.6, 6.8 Hz, 2H). | 486.0 |
| 406 | $^1$H NMR (400 MHz, CDCl$_3$) δ ppm 8.75 (d, J = 7.1 Hz, 1H), 7.56 (d, J = 3.9 Hz, 1H), 7.47 (d, J = 15.4 Hz, 1H), 4.86-4.13 (m, 2H), 3.88-3.75 (m, 1H), 3.51 (t, J = 33.6 Hz, 2H), 2.81 (d, J = 5.2 Hz, 3H), 2.59 (s, 7H), 2.32 (d, J = 13.7 Hz, 1H), 2.08 (dd, J = 20.6, 8.9 Hz, 2H), 1.03 (d, J = 5.0 Hz, 4H). | 471.0 |
| 407 | $^1$H NMR (400 MHz, CDCl$_3$) δ ppm 8.75 (d, J = 7.1 Hz, 1H), 7.56 (d, J = 3.9 Hz, 1H), 7.47 (d, J = 15.4 Hz, 1H), 4.86-4.13 (m, 2H), 3.88-3.75 (m, 1H), 3.51 (t, J = 33.6 Hz, 2H), 2.81 (d, J = 5.2 Hz, 3H), 2.59 (s, 7H), 2.32 (d, J = 13.7 Hz, | 471.0 |

TABLE 8C-continued

Analytical data for compounds of Table 8B

| Ex # | NMR | M + H |
|---|---|---|
| | 1H), 2.08 (dd, J = 20.6, 8.9 Hz, 2H), 1.03 (d, J = 5.0 Hz, 4H). | |
| 408 | ¹H NMR (400 MHz, CDCl₃) δ ppm 7.46 (s, 2H), 5.05 (t, J = 3.5 Hz, 1H), 4.86 (s, 1H), 4.60 (s, 1H), 3.90 (s, 2H), 3.49 (ddd, J = 11.1, 7.3, 3.8 Hz, 1H), 3.15 (s, 1H), 2.70 (d, J = 14.3 Hz, 3H), 2.63 (s, 3H), 2.60 (s, 6H), 1.26-1.22 (m, 3H), 1.05-0.99 (m, 2H), 0.95 (d, J = 14.3 Hz, 2H). | 500.0 |
| 409 | ¹H NMR (400 MHz, CDCl₃) δ ppm 7.46 (s, 2H), 5.05 (t, J = 3.4 Hz, 1H), 4.87 (s, 1H), 4.60 (s, 1H), 3.89 (s, 2H), 3.49 (ddd, J = 11.1, 7.3, 3.8 Hz, 1H), 3.14 (s, 1H), 2.66 (d, J = 10.5 Hz, 3H), 2.63 (s, 3H), 2.60 (s, 6H), 1.23 (d, J = 6.2 Hz, 3H), 1.05-0.99 (m, 2H), 0.94 (s, 2H). | 500.0 |
| 410 | ¹H NMR (400 MHz, CDCl₃) δ ppm 7.58-7.50 (m, 2H), 5.09-4.89 (m, 2H), 4.57 (dd, J = 10.9, 2.6 Hz, 1H), 3.80 (ddd, J = 10.6, 6.3, 2.6 Hz, 1H), 3.58 (tt, J = 7.3, 3.8 Hz, 1H), 3.07-2.99 (m, 1H), 2.79 (dd, J = 13.3, 10.7 Hz, 1H), 2.68 (s, 3H), 2.63 (s, 3H), 2.58 (s, 6H), 1.32 (d, J = 6.2 Hz, 3H), 1.13 (s, 3H), 1.05-0.98 (m, 2H). | 500.0 |
| 411 | ¹H NMR (400 MHz, CDCl₃) δ ppm 7.57-7.51 (m, 2H), 4.98 (d, J = 46.1 Hz, 2H), 4.57 (dd, J = 10.9, 2.6 Hz, 1H), 3.80 (ddd, J = 10.5, 6.2, 2.5 Hz, 1H), 3.58 (tt, J = 7.3, 3.8 Hz, 1H), 3.07-2.98 (m, 1H), 2.79 (dd, J = 13.3, 10.7 Hz, 1H), 2.68 (s, 3H), 2.63 (s, 3H), 2.58 (s, 6H), 1.32 (d, J = 6.1 Hz, 3H), 1.10 (d, J = 16.9 Hz, 2H), 1.05-0.98 (m, 2H). | 500.0 |
| 412 | | 513.0 |
| 413 | | 513.0 |
| 414 | | 478.2 |
| 415 | | 463.1 |
| 416 | | 462.2 |
| 417 | | 462.2 |
| 418 | ¹H NMR (400 MHz, CDCl₃) δ 7.72 (dd, J = 14.8, 8.1 Hz, 1H), 7.51 (d, J = 9.1 Hz, 2H), 7.11-6.89 (m, 2H), 5.06 (s, 1H), 4.75 (d, J = 69.4 Hz, 2H), 3.86 (d, J = 64.9 Hz, 2H), 3.49 (s, 1H), 3.21 (s, 1H), 2.72 (s, 3H), 2.60 (s, 3H), 1.25 (d, J = 6.3 Hz, 3H), 1.01 (s, 2H), 0.93 (dd, J = 6.7, 3.1 Hz, 2H). | 478.1 |
| 419 | ¹H NMR (400 MHz, CDCl₃) δ ppm 8.42 (s, 1H), 7.66-7.58(m, 1H), 7.51(d, J = 8.2 Hz, 2H), 7.08-6.94(m, 2H), 6.90(s, 1H), 5.07 (t, J = 3.7 Hz, 1H), 4.38 (dd, J = 12.8, 3.4 Hz, 1H), 4.03-3.89 (m, 2H), 3.66 (dd, J = 13.0, 3.9 Hz, 1H), 3.51 (td, J = 7.3, 3.7 Hz, 1H), 3.12 (dd, J = 12.5, 8.6 Hz, 1H), 2.70 (s, 3H), 1.27 (d, J = 6.3 Hz, 3H), 1.07-1.01 (m, 2H), 0.99-0.91 (m, 2H). | 463.0 |
| 420 | | 464.0 |
| 422 | | 513.0 |
| 424 | ¹H NMR (400 MHz, CDCl₃) δ ppm 7.66 (t, J = 7.8 Hz, 1H), 7.52 (s, 2H), 7.37-7.27 (m, 2H), 5.06 (s, 1H), 4.76 (d, J = 57.5 Hz, 2H), 3.86 (d, J = 65.7 Hz, 2H), 3.50 (s, 1H), 3.21 (s, 1H), 2.72 (s, 3H), 2.59 (s, 3H), 1.25 (d, J = 6.2 Hz, 3H), 1.02 (s, 2H), 0.95 (s, 2H). | 494.0 |
| 425 | ¹H NMR (400 MHz, CDCl₃) δ ppm 7.65 (t, J = 7.8 Hz, 1H), 7.53 (t, J = 4.1 Hz, 2H), 7.30 (t, J = 6.0 Hz, 1H), 7.24 (d, J = 2.0 Hz, 1H), 4.97 (s, 2H), 4.60 (d, J = 8.7 Hz, 1H), 3.89-3.76 (m, 1H), 3.57 (ddd, J = 11.1, 7.3, 3.9 Hz, 1H), 3.07 (dd, J = 13.3, 11.0 Hz, 1H), 2.84 (dd, J = 13.4, 10.7 Hz, 1H), 2.71 (s, 3H), 2.59 (s, 3H), 1.32 (d, J = 6.2 Hz, 3H), 1.15-1.07 (m, 1H), 1.01 (dt, J = 12.3, 6.3 Hz, 2H). | 494.0 |
| 426 | ¹H NMR (400 MHz, CDCl₃) δ 7.71 (dd, J = 14.9, 7.8 Hz, 1H), 7.54 (t, J = 4.8 Hz, 2H), 7.10-6.87 (m, 2H), 5.03 (d, J = 37.5 Hz, 2H), 4.60 (d, J = 8.5 Hz, 1H), 3.92-3.72 (m, 1H), 3.57 (ddd, J = 10.9, 7.2, 3.7 Hz, 1H), 3.08 (dd, J = 13.4, 11.0 Hz, 1H), 2.84 (dd, J = 13.3, 10.7 Hz, 1H), 2.71 (s, 3H), 2.59 (s, 3H), 1.33 (d, J = 6.2 Hz, 3H), 1.16-1.08 (m, 2H), 1.01 (q, J = 6.8 Hz, 2H). | 478.1 |
| 427 | ¹H NMR (400 MHz, CDCl₃) δ 7.71 (dd, J = 15.0, 7.9 Hz, 1H), 7.54 (t, J = 5.2 Hz, 2H), 7.07-6.93 (m, 2H), 5.03 (d, J = 37.1 Hz, 3H), 4.60 (d, J = 8.6 Hz, 1H), 3.91-3.74 (m, 1H), 3.65-3.47 (m, 1H), 3.08 (dd, J = 13.3, 11.0 Hz, 1H), 2.84 (dd, J = 13.4, 10.7 Hz, 1H), 2.71 (s, 3H), 2.59 (s, 3H), 1.33 (d, J = 6.2 Hz, 3H), 1.16-1.07 (m, 2H), 1.06-0.97 (m, 2H). | 478.1 |

Synthesis of Intermediates

Method 11

Intermediate 1: 5,7-dichloro-2,3-dimethylpyrido[3,4-b]pyrazine

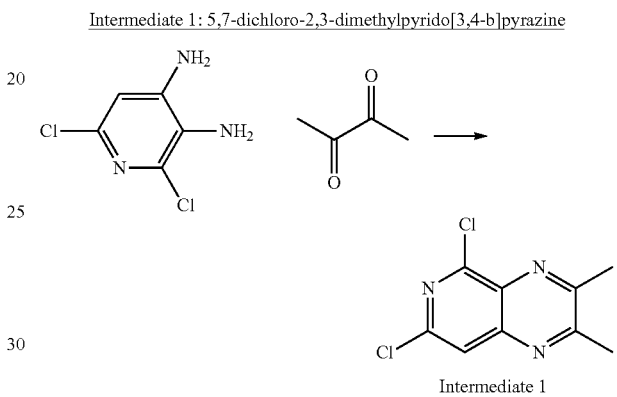

Intermediate 1

A 500 mL round bottom flask was charged with 3,4-diamino-2,6-dichloropyridine (27 g, 152 mmol) and 2,3-butanedione (15.99 mL, 182 mmol). EtOH (152 mL) was added to the flask and the mixture was heated to 70° C. After 5 h, the mixture was filtered through a fritted funnel and the eluent was concentrated to about 75 mL under reduced pressure. H₂O (150 mL) was added to the solution and the resulting solid was filtered off. The combined solid from both filtrations was washed with H₂O 3 times and was allowed to dry on the filter under air to afford 5,7-dichloro-2,3-dimethylpyrido[3,4-b]pyrazine as a light brown solid (34.5 g, 152 mmol). LC/MS (ESI⁺) m/z=228.0 [M+H]⁺ ¹H NMR (500 MHz, Chloroform-d) δ ppm 7.82 (s, 1H), 2.83 (s, 3H), 2.80 (s, 3H).

Method 12

Intermediate 2: 6,8-dichloro-2,3-dimethylpyrido[2,3-b]pyrazine

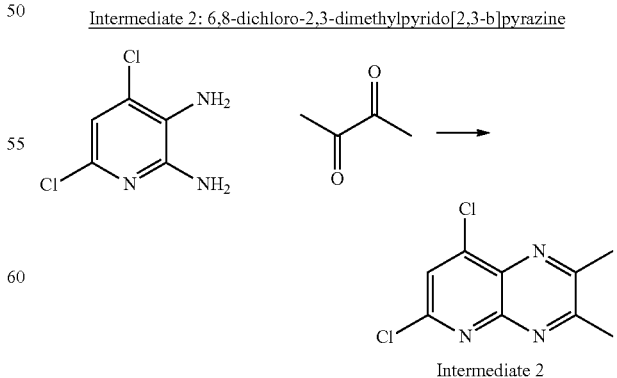

Intermediate 2

4,6-dichloropyridine-2,3-diamine (30 g, 169 mmol) and butane-2,3-dione (16.12 mL, 185 mmol) were combined in a 1 L round bottom flask. EtOH (600 mL) was added and the mixture was heated to 80° C. for 5 h. After cooling, the solvent was removed under reduced pressure. The resulting solid was triturated with diethyl ether and was filtered to afford 6,8-dichloro-2,3-dimethylpyrido[2,3-b]pyrazine as a light brown solid (36.5 g, 160 mmol). LC/MS (ESI⁺) m/z=228.0 [M+H]⁺ ¹H NMR (400 MHz, DMSO-d6): δ ppm 8.21 (s, 1H), 2.76 (s, 6H)

Method 13

Intermediate 3: 2,4-dichloro-6,7-dimethylpteridine

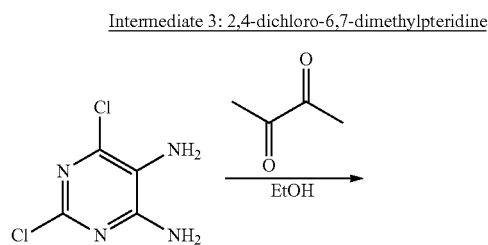

Intermediate 3

In a 100 mL round bottom flask 2,6-dichloropyrimidine-4,5-diamine (5 g, 27.9 mmol) and butane-2,3-dione (2.91 mL, 33.5 mmol) were combined in EtOH (27.9 mL) and the mixture was stirred at 30° C. for 18 h. After cooling, the solvent was removed under reduced pressure. The resulting solid was triturated with diethyl ether and filtered to afford 2,4-dichloro-6,7-dimethylpteridine (6.02 g, 26.3 mmol) as a light brown solid. LC/MS (ESI⁺) m/z=229.0 [M+H]₊ ¹H NMR (500 MHz, Chloroform-d) δ ppm 2.88 (s, 3H), 2.87 (s, 3H).

Method 14

Intermediate 4: 5,7-dichloro-2-methylpyrido[3,4-b]pyrazine

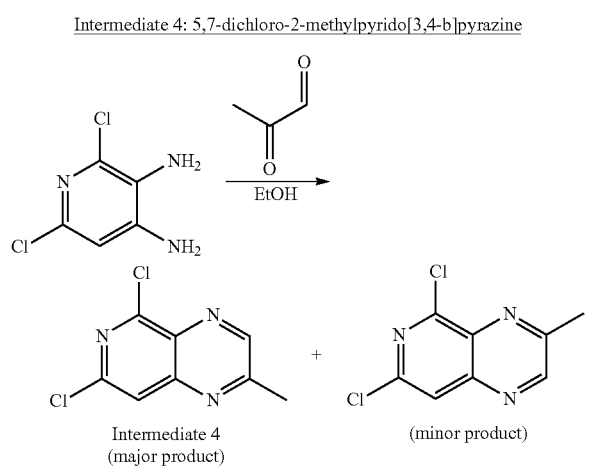

Intermediate 4 (major product)     (minor product)

Reaction was set up in two batches using 20 g and 25 g of 2,6-dichloropyridine-3,4-diamine (45 g, 252 mmol total). To a 50 mL round bottom flask were added 2,6-dichloropyridine-3,4-diamine (25 g, 140 mmol) and 2-oxopropanal (30.4 g, 169 mmol) in EtOH (250 mL). The reaction mixture was heated at 85° C. for 2 h. The reaction flask was cooled to room temperature. The mixture was diluted with H₂O and the resulting solids were filtered and washed with H₂O. The solid material was dissolved in DCM, dried over Na₂SO₄, filtered and concentrated under reduced pressure to furnish the reaction crude. This crude material was combined with 2,6-dichloropyridine-3,4-diamine from the second batch and both absorbed onto a plug of silica gel and purified by chromatography through a silica gel column, eluting with a gradient of 100% DCM, to provide 5,7-dichloro-2-methylpyrido[3,4-b]pyrazine (25.57 g, 119 mmol) as an off-white solid and 7.8 g of mixture of 2 isomers. Major isomer: LC/MS (ESI+) m/z=213.9[M+H]⁺ ¹H NMR (400 MHz, DMSO-d6): δ ppm 9.06 (s, 1H), 8.11 (s, 1H), 2.79 (s, 3H). Minor isomer: LC/MS (ESI+) m/z=214.0[M+H]⁺ ¹H NMR (400 MHz, DMSO-d6): δ ppm 9.16 (s, 1H), 8.20 (s, 1H), 2.79 (s, 3H).

Method 15

Intermediate 5: 5,7-dichloro-2,3-dimethyl-1,8-naphthyridine and

Intermediate 6: 2,4-dichloro-7-ethyl-1,8-naphthyridine

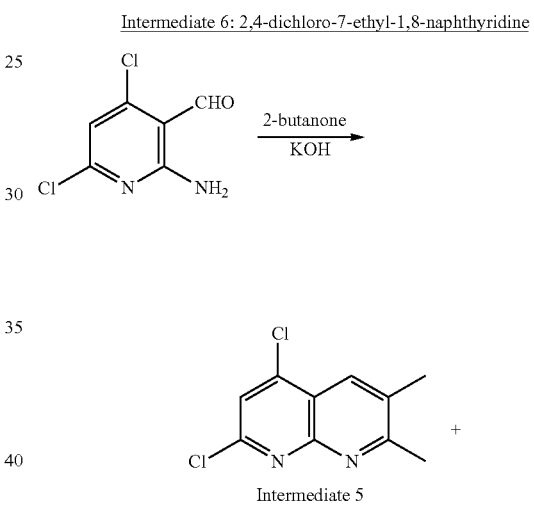

Intermediate 5

Intermediate 6

A screw-capped vial was charged with 2-amino-4,6-dichloronicotinaldehyde (0.5 g, 2.62 mmol) and methyl ethyl ketone (2.62 mL). To this solution was added KOH (0.147 g, 2.62 mmol). The reaction was stirred overnight at room temperature. H₂O was added and the aqueous phase was neutralized to a pH of 7 using 1N aqueous HCl. The aqueous phase was extracted with DCM. The organic phase was separated using a phase separator and was concentrated under reduced pressure. The crude material was purified by silica gel chromatography (0-10% MeOH (+1% NH₃) in DCM) to afford 5,7-dichloro-2,3-dimethyl-1,8-naphthyridine (0.284 g, 1.25 mmol, 47.7%). LC/MS (ESI⁺) m/z=227.0 [M+H]⁺ and 2,4-dichloro-7-ethyl-1,8-naphthyridine (0.18 g, 0.79 mmol) LC/MS (ESI⁺) m/z=227.0 [M+H]⁺.

Method 16

Intermediate 7: 5,7-dichloro-2-methyl-1,6-naphthyridine

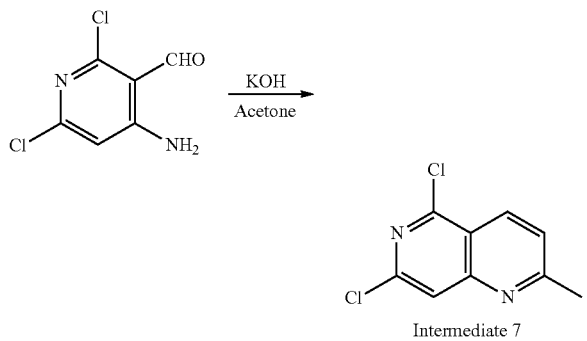

Intermediate 7

To a 50 mL vial were added 4-amino-2,6-dichloronicotinaldehyde (1.91 g, 10 mmol, JW Pharmlab) and KOH (0.84 g, 15.0 mmol) in acetone (10 mL). The reaction was stirred at rt for 30 min and a precipitate formed. The reaction mixture was diluted with EtOAc, dried, and concentrated. The crude material was purified via chromatography (0-30% EtOAc in DCM) to yield 1.65 g (71%) of 5,7-dichloro-2-methyl-1,6-naphthyridine as an off-white solid.

Method 17

Intermediate 8: 2,4-dichloro-7-methyl-1,8-napthyridine

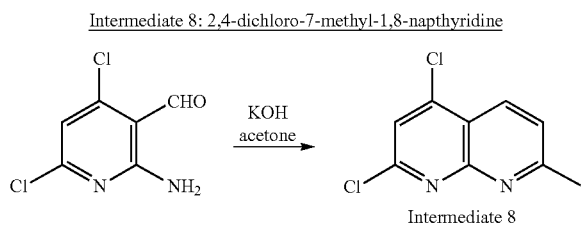

Intermediate 8

To a 50 mL vial were added 2-amino-4,6-dichloronicotinaldehyde (0.3507 g, 1.836 mmol) and acetone (1.836 mL). To this solution was added KOH (0.155 g, 2.75 mmol). The reaction was stirred at room temperature for 30 minutes. $H_2O$ was added and the aqueous phase was extracted with DCM. The organic phase was separated using a phase separator and was concentrated under reduced pressure to afford 2,4-dichloro-7-methyl-1,8-naphthyridine (0.317 g, 1.49 mmol). LC/MS (ESI$^+$) m/z=213.0 [M+H]$^+$ Method 18

Intermediate 9: 7-chloro-5-(4-chloro-2-fluorophenyl)-2-methyl-1,6-napthyridine

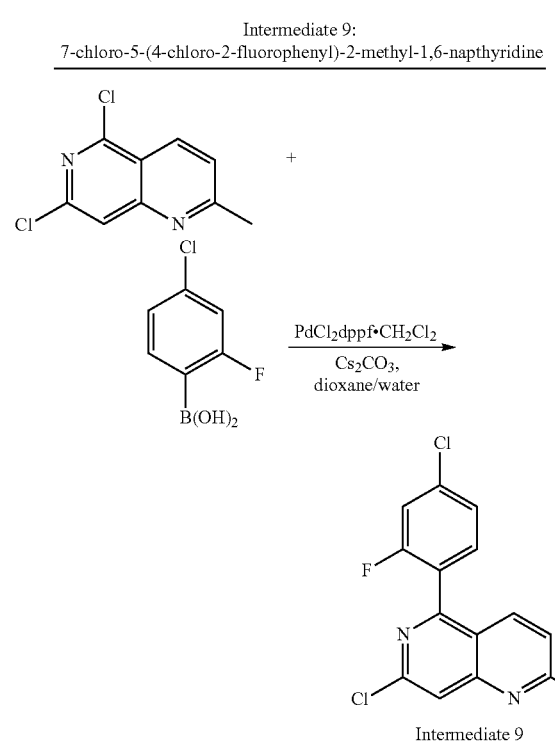

Intermediate 9

5,7-dichloro-2-methyl-1,6-naphthyridine (Intermediate 7, 0.852 g, 4 mmol), (1,1'-bis(diphenyl-phosphino)ferrocene)dichloropalladium (0.146 g, 0.200 mmol), (4-chloro-2-fluorophenyl)-boranediol (0.697 g, 4.00 mmol) and $Cs_2CO_3$ (3.91 g, 12.00 mmol) were combined in a 50 mL vial. The vial was evacuated and filled with $N_2$, and 1,4-dioxane (10 mL) and $H_2O$ (3 mL) were added. The reaction was stirred at 60° C. for 30 min, cooled to rt, and partitioned between DCM and $H_2O$. The mixture was passed through a phase separation cartridge, concentrated, and purified via silica gel chromatography (0-50% EtOAc in heptane) to yield 7-chloro-5-(4-chloro-2-fluorophenyl)-2-methyl-1,6-naphthyridine (710 mg, 2.3 mmol, 58%).

TABLE 9

| Intermediates 10-58 were prepared following the procedure described in Method 18, as follows: | | | | |
|---|---|---|---|---|
| Int # | Structure | Name | Starting Material 1 | Starting Material 2 |
| 10 | ![structure] | 6-chloro-4-(4-chloro-2-fluorophenyl)-2-methyl-2,3-dihydro-1H-pyrrolo[3,4-c]pyridin-1-one | 6-chloro-4-(4-chloro-2-fluorophenyl)-2,3-dihydro-1H-pyrrolo[3,4-c]pyridin-1-one (Enamine, Monmouth Jct., NJ, USA) | (4-chloro-2-fluorophenyl) boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 11 | 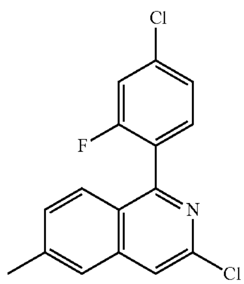 [SMILES: Cc1ccc2c(-c3ccc(Cl)cc3F)nc(Cl)cc2c1] | 3-chloro-1-(4-chloro-2-fluorophenyl)-6-methylisoquinoline | 1,3-dichloro-6-methylisoquinoline (Enamine, Monmouth Jct., NJ, USA) | (4-chloro-2-fluorophenyl) boronic acid |
| 12 | 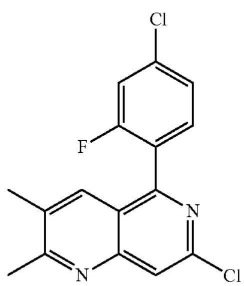 [SMILES: Cc1cc2c(-c3ccc(Cl)cc3F)nc(Cl)cc2nc1C] | 7-chloro-5-(4-chloro-2-fluorophenyl)-2,3-dimethyl-1,6-naphthyridine | 5,7-dichloro-2,3-dimethyl-1,6-naphthyridine (PharmaBlock Hatfield, PA, USA) | (4-chloro-2-fluorophenyl) boronic acid |
| 13 | 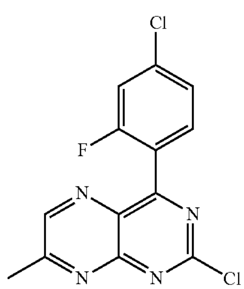 [SMILES: Cc1cnc2c(-c3ccc(Cl)cc3F)nc(Cl)nc2n1] | 2-chloro-4-(4-chloro-2-fluorophenyl)-7-methylpteridine | 2,4-dichloro-7-methylpteridine (PharmaBlock Hatfield, PA, USA) | (4-chloro-2-fluorophenyl) boronic acid |
| 14 | 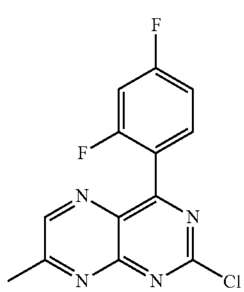 [SMILES: Cc1cnc2c(-c3ccc(F)cc3F)nc(Cl)nc2n1] | 2-chloro-4-(2,4-difluorophenyl)-7-methylpteridine | 2,4-dichloro-7-methylpteridine (PharmaBlock Hatfield, PA, USA) | (2,4-difluorophenyl) boronic acid |
| 15 | 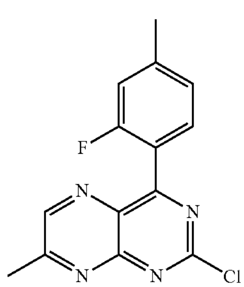 [SMILES: Cc1ccc(-c2nc(Cl)nc3nc(C)cnc23)c(F)c1] | 2-chloro-4-(2-fluoro-4-methylphenyl)-7-methylpteridine | 2,4-dichloro-7-methylpteridine (PharmaBlock Hatfield, PA, USA) | (2-fluoro-4-methylphenyl) boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 16 | 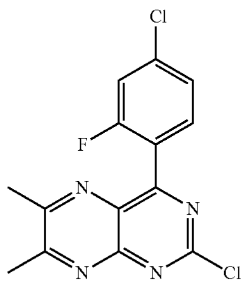 | 2-chloro-4-(4-chloro-2-fluorophenyl)-6,7-dimethylpteridine | 2,4-dichloro-6,7-dimethylpteridine (Intermediate 3) | (4-chloro-2-fluorophenyl) boronic acid |
| 17 | 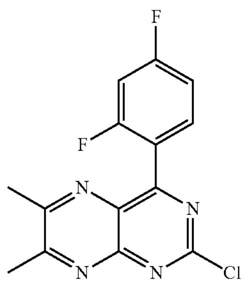 [SMILES: Cc1nc2nc(Cl)nc(-c3ccc(F)cc3F)c2nc1C] | 2-chloro-4-(2,4-difluorophenyl)-6,7-dimethylpteridine | 2,4-dichloro-6,7-dimethylpteridine (Intermediate 3) | (2,4-difluorophenyl) boronic acid |
| 18 | 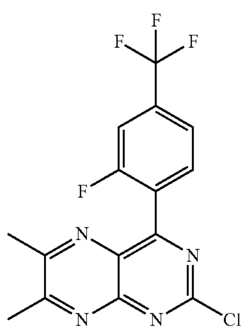 [SMILES: Cc1nc2nc(Cl)nc(-c3ccc(C(F)(F)F)cc3F)c2nc1C] | 2-chloro-4-(2-fluoro-4-(trifluoromethyl)phenyl)-6,7-dimethylpteridine | 2,4-dichloro-6,7-dimethylpteridine (Intermediate 3) | (2-fluoro-4-(trifluoromethyl)phenyl)boronic acid |
| 19 | 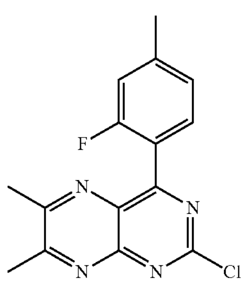 [SMILES: Cc1ccc(-c2nc(Cl)nc3nc(C)c(C)nc23)c(F)c1] | 2-chloro-4-(2-fluoro-4-methylphenyl)-6,7-dimethylpteridine | 2,4-dichloro-6,7-dimethylpteridine (Intermediate 3) | (2-fluoro-4-methylphenyl) boronic acid |
| 20 | 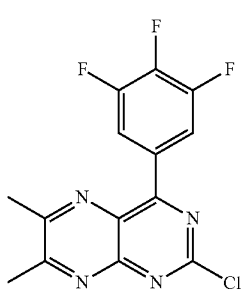 [SMILES: Cc1nc2nc(Cl)nc(-c3cc(F)c(F)c(F)c3)c2nc1C] | 2-chloro-6,7-dimethyl-4-(3,4,5-trifluorophenyl)pteridine | 2,4-dichloro-6,7-dimethylpteridine (Intermediate 3) | (3,4,5-trifluorophenyl) boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 21 | 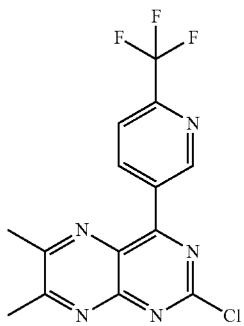 [SMILES: Cc1nc2nc(Cl)nc(-c3ccc(C(F)(F)F)nc3)c2nc1C] | 2-chloro-6,7-dimethyl-4-(6-(trifluoromethyl)pyridin-3-yl)pteridine | 2,4-dichloro-6,7-dimethylpteridine (Intermediate 3) | (6-(trifluoromethyl)pyridin-3-yl)boronic acid |
| 22 | 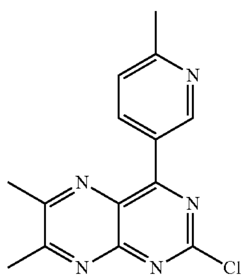 [SMILES: Cc1ccc(-c2nc(Cl)nc3nc(C)c(C)nc23)cn1] | 2-chloro-6,7-dimethyl-4-(6-methylpyridin-3-yl)pteridine | 2,4-dichloro-6,7-dimethylpteridine (Intermediate 3) | (6-methylpyridin-3-yl)boronic acid |
| 23 | 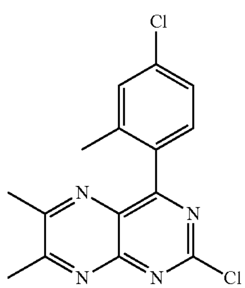 [SMILES: Cc1cc(Cl)ccc1-c1nc(Cl)nc2nc(C)c(C)nc12] | 2-chloro-4-(4-chloro-2-methylphenyl)-6,7-dimethylpteridine | 2,4-dichloro-6,7-dimethylpteridine (Intermediate 3) | (4-chloro-2-methylphenyl)boronic acid |
| 24 | 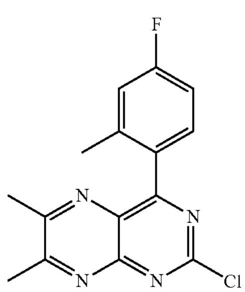 [SMILES: Cc1cc(F)ccc1-c1nc(Cl)nc2nc(C)c(C)nc12] | 2-chloro-4-(4-fluoro-2-methylphenyl)-6,7-dimethylpteridine | 2,4-dichloro-6,7-dimethylpteridine (Intermediate 3) | (4-fluoro-2-methylphenyl)boronic acid |
| 25 | 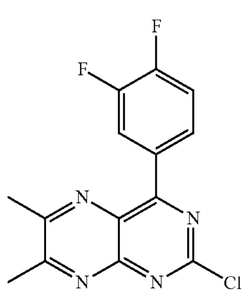 [SMILES: Cc1nc2nc(Cl)nc(-c3ccc(F)c(F)c3)c2nc1C] | 2-chloro-4-(3,4-difluorophenyl)-6,7-dimethylpteridine | 2,4-dichloro-6,7-dimethylpteridine (Intermediate 3) | (3,4-difluorophenyl)boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 26 | 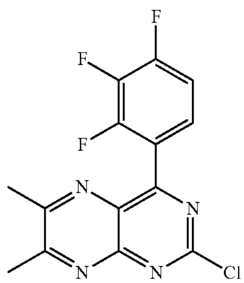 [SMILES: Cc1nc2nc(Cl)nc(-c3ccc(F)c(F)c3F)c2nc1C] | 2-chloro-6,7-dimethyl-4-(2,3,4-trifluorophenyl)pteridine | 2,4-dichloro-6,7-dimethylpteridine (Intermediate 3) | (2,3,4-trifluorophenyl)boronic acid |
| 27 | 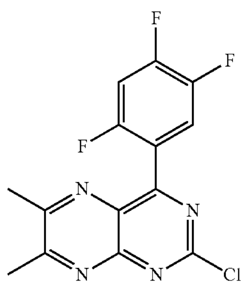 [SMILES: Cc1nc2nc(Cl)nc(-c3cc(F)c(F)cc3F)c2nc1C] | 2-chloro-6,7-dimethyl-4-(2,4,5-trifluorophenyl)pteridine | 2,4-dichloro-6,7-dimethylpteridine (Intermediate 3) | (2,4,5-trifluorophenyl)boronic acid |
| 28 | 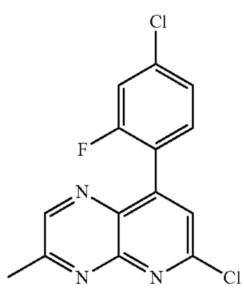 [SMILES: Cc1cnc2c(-c3ccc(Cl)cc3F)cc(Cl)nc2n1] | 6-chloro-8-(4-chloro-2-fluorophenyl)-3-methylpyrido[2,3-b]pyrazine | 6,8-dichloro-3-methylpyrido[2,3-b]pyrazine (PharmaBlock Hatfield, PA, USA) | (4-chloro-2-fluorophenyl)boronic acid |
| 29 | 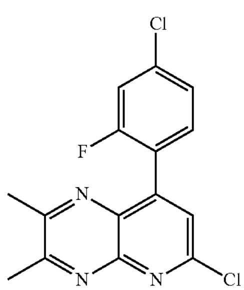 [SMILES: Cc1nc2nc(Cl)cc(-c3ccc(Cl)cc3F)c2nc1C] | 6-chloro-8-(4-chloro-2-fluorophenyl)-2,3-dimethylpyrido[2,3-b]pyrazine | 6,8-dichloro-2,3-dimethylpyrido[2,3-b]pyrazine (Intermediate 2) | (4-chloro-2-fluorophenyl)boronic acid |
| 30 | 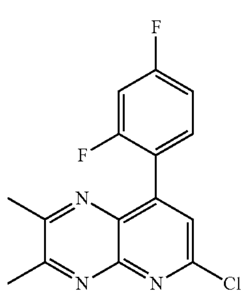 [SMILES: Cc1nc2nc(Cl)cc(-c3ccc(F)cc3F)c2nc1C] | 6-chloro-8-(2,4-difluorophenyl)-2,3-dimethylpyrido[2,3-b]pyrazine | 6,8-dichloro-2,3-dimethylpyrido[2,3-b]pyrazine (Intermediate 2) | (2,4-difluorophenyl)boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 31 | 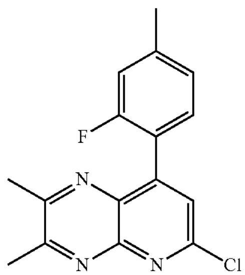 [SMILES: Cc1ccc(-c2cc(Cl)nc3nc(C)c(C)nc23)c(F)c1] | 6-chloro-8-(2-fluoro-4-methylphenyl)-2,3-dimethylpyrido[2,3-b]pyrazine | 6,8-dichloro-2,3-dimethylpyrido[2,3-b]pyrazine (Intermediate 2) | (2-fluoro-4-methylphenyl) boronic acid |
| 32 | 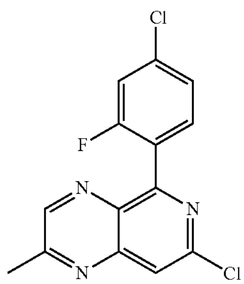 [SMILES: Cc1cnc2c(-c3ccc(Cl)cc3F)nc(Cl)cc2n1] | 7-chloro-5-(4-chloro-2-fluorophenyl)-2-methylpyrido[3,4-b]pyrazine | 5,7-dichloro-2-methylpyrido[3,4-b]pyrazine (Intermediate 4) | (4-chloro-2-fluorophenyl) boronic acid |
| 33 | 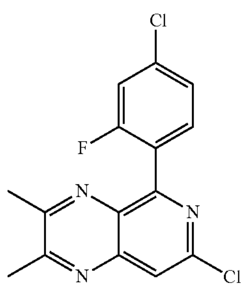 [SMILES: Cc1nc2cc(Cl)nc(-c3ccc(Cl)cc3F)c2nc1C] | 7-chloro-5-(4-chloro-2-fluorophenyl)-2,3-dimethylpyrido[3,4-b]pyrazine | 5,7-dichloro-2,3-dimethylpyrido[3,4-b]pyrazine (Intermediate 1) | (4-chloro-2-fluorophenyl) boronic acid |
| 34 | 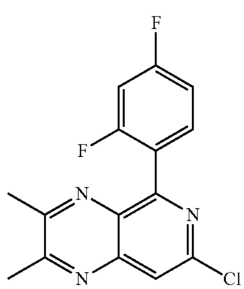 [SMILES: Cc1nc2cc(Cl)nc(-c3ccc(F)cc3F)c2nc1C] | 7-chloro-5-(2,4-difluorophenyl)-2,3-dimethylpyrido[3,4-b]pyrazine | 5,7-dichloro-2,3-dimethylpyrido[3,4-b]pyrazine (Intermediate 1) | (2,4-difluorophenyl) boronic acid |
| 35 | 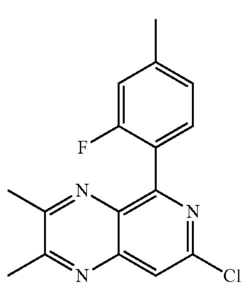 [SMILES: Cc1ccc(-c2nc(Cl)cc3nc(C)c(C)nc23)c(F)c1] | 7-chloro-5-(2-fluoro-4-methylphenyl)-2,3-dimethylpyrido[3,4-b]pyrazine | 5,7-dichloro-2,3-dimethylpyrido[3,4-b]pyrazine (Intermediate 1) | (2-fluoro-4-methylphenyl) boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 36 | 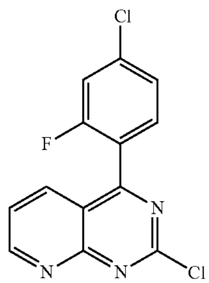 [SMILES: Fc1cc(Cl)ccc1-c1nc(Cl)nc2ncccc12] | 2-chloro-4-(4-chloro-2-fluorophenyl)pyrido[2,3-d]pyrimidine | 2,4-dichloropyrido[2,3-d]pyrimidine (Combi-Blocks, San Diego, CA, USA) | (4-chloro-2-fluorophenyl)boronic acid |
| 37 | 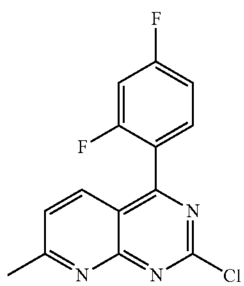 [SMILES: Cc1ccc2c(-c3ccc(F)cc3F)nc(Cl)nc2n1] | 2-chloro-4-(4-chloro-2-fluorophenyl)-7-methylpyrido[2,3-d]pyrimidine | 2,4-dichloro-7-methylpyrido[2,3-d]pyrimidine (PharmaBlock, Hatfield, PA, USA) | (4-chloro-2-fluorophenyl)boronic acid |
| 38 | 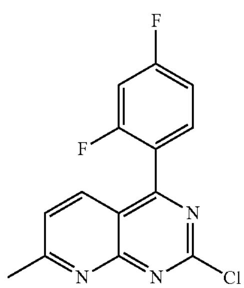 [SMILES: Cc1ccc2c(-c3ccc(F)cc3F)nc(Cl)nc2n1] | 2-chloro-4-(2,4-difluorophenyl)-7-methylpyrido[2,3-d]pyrimidine | 2,4-dichloro-7-methylpyrido[2,3-d]pyrimidine (PharmaBlock, Hatfield, PA, USA) | (2,4-difluorophenyl)boronic acid |
| 39 | 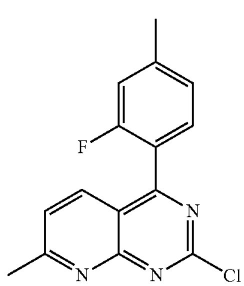 [SMILES: Cc1ccc(-c2nc(Cl)nc3nc(C)ccc23)c(F)c1] | 2-chloro-4-(2-fluoro-4-methylphenyl)-7-methylpyrido[2,3-d]pyrimidine | 2,4-dichloro-7-methylpyrido[2,3-d]pyrimidine (PharmaBlock, Hatfield, PA, USA) | (2-fluoro-4-methylphenyl)boronic acid |
| 40 | 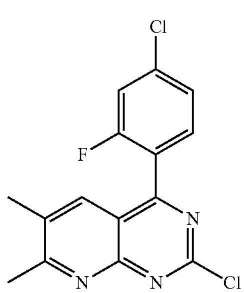 [SMILES: Cc1cc2c(-c3ccc(Cl)cc3F)nc(Cl)nc2nc1C] | 2-chloro-4-(4-chloro-2-fluorophenyl)-6,7-dimethylpyrido[2,3-d]pyrimidine | 2,4-dichloro-6,7-dimethylpyrido[2,3-d]pyrimidine (PharmaBlock, Hatfield, PA, USA) | (4-chloro-2-fluorophenyl)boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 41 | 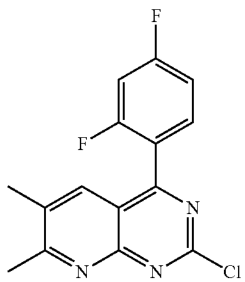 [SMILES: Cc1cc2c(-c3ccc(F)cc3F)nc(Cl)nc2nc1C] | 2-chloro-4-(2,4-difluorophenyl)-6,7-dimethylpyrido[2,3-d]pyrimidine | 2,4-dichloro-6,7-dimethylpyrido[2,3-d]pyrimidine (PharmaBlock, Hatfield, PA, USA) | (2,4-difluorophenyl) boronic acid |
| 42 | 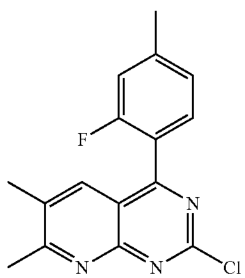 [SMILES: Cc1ccc(-c2nc(Cl)nc3nc(C)c(C)cc23)c(F)c1] | 2-chloro-4-(2-fluoro-4-methylphenyl)-6,7-dimethylpyrido[2,3-d]pyrimidine | 2,4-dichloro-6,7-dimethylpyrido[2,3-d]pyrimidine (PharmaBlock, Hatfield, PA, USA) | (2-fluoro-4-methylphenyl) boronic acid |
| 43 | 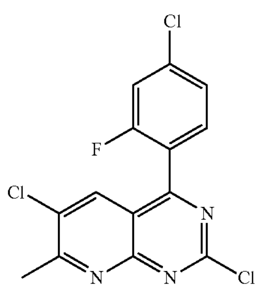 [SMILES: Cc1nc2nc(Cl)nc(-c3ccc(Cl)cc3F)c2cc1Cl] | 2,6-dichloro-4-(4-chloro-2-fluorophenyl)-7-methylpyrido[2,3-d]pyrimidine | 2,4,6-trichloro-7-methylpyrido[2,3-d]pyrimidine (PharmaBlock, Hatfield, PA, USA) | (4-chloro-2-fluorophenyl) boronic acid |
| 44 | 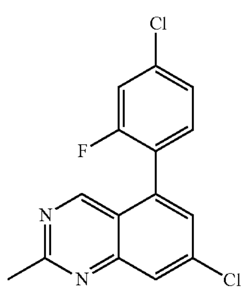 [SMILES: Cc1ncc2c(-c3ccc(Cl)cc3F)cc(Cl)cc2n1] | 7-chloro-5-(4-chloro-2-fluorophenyl)-2-methylquinazoline | 5,7-dichloro-2-methylquinazoline (PharmaBlock, Hatfield, PA, USA) | (4-chloro-2-fluorophenyl) boronic acid |
| 45 | 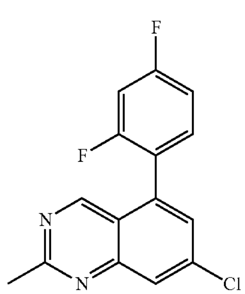 [SMILES: Cc1ncc2c(-c3ccc(F)cc3F)cc(Cl)cc2n1] | 7-chloro-5-(2,4-difluorophenyl)-2-methylquinazoline | 5,7-dichloro-2-methylquinazoline (PharmaBlock, Hatfield, PA, USA) | (2,4-difluorophenyl) boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 46 | 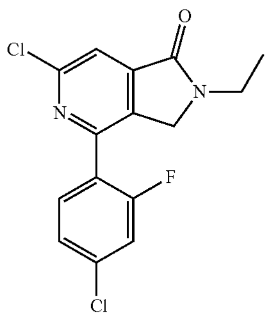 [SMILES: CCN1Cc2c(cc(Cl)nc2-c2ccc(Cl)cc2F)C1=O] | 6-chloro-4-(4-chloro-2-fluorophenyl)-2-ethyl-2,3-dihydro-1H-pyrrolo[3,4-c]pyridin-1-one | 4,6-dichloro-2-ethyl-2,3-dihydro-1H-pyrrolo[3,4-c]pyridin-1-one (Enamine, Monmouth Jct., NJ, USA) | (4-chloro-2-fluorophenyl) boronic acid |
| 47 | 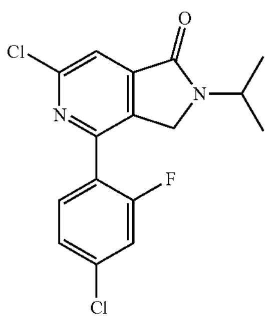 [SMILES: CC(C)N1Cc2c(cc(Cl)nc2-c2ccc(Cl)cc2F)C1=O] | 6-chloro-4-(4-chloro-2-fluorophenyl)-2-isopropyl-2,3-dihydro-1H-pyrrolo[3,4-c]pyridin-1-one | 4,6-dichloro-2-isopropyl-2,3-dihydro-1H-pyrrolo[3,4-c]pyridin-1-one (Enamine, Monmouth Jct., NJ, USA) | (4-chloro-2-fluorophenyl) boronic acid |
| 48 | 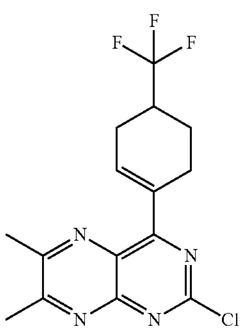 [SMILES: Cc1nc2nc(Cl)nc(C3=CCC(C(F)(F)F)CC3)c2nc1C] | 2-chloro-6,7-dimethyl-4-(4-(trifluoromethyl)cyclohex-1-en-1-yl)pteridine | 2,4-dichloro-6,7-dimethylpteridine (Intermediate 3) | (4-(trifluoromethyl)cyclohex-1-en-1-yl)boronic acid |
| 49 | 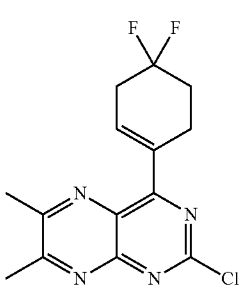 [SMILES: Cc1nc2nc(Cl)nc(C3=CCC(F)(F)CC3)c2nc1C] | 2-chloro-4-(4,4-difluorocyclohex-1-en-1-yl)-6,7-dimethylpteridine | 2,4-dichloro-6,7-dimethylpteridine (Intermediate 3) | (4,4-difluorocyclohex-1-en-1-yl)boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 50 | 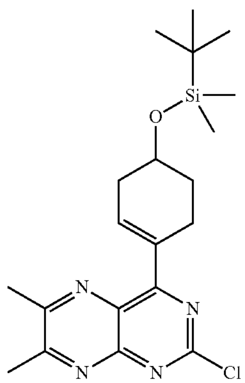 | 4-(4-((tert-butyldimethylsilyl)oxy)cyclohex-1-en-1-yl)-2-chloro-6,7-dimethylpteridine | 2,4-dichloro-6,7-dimethylpteridine (Intermediate 3) | (4-((tert-butyldimethylsilyl)oxy)cyclohex-1-en-1-yl)boronic acid |
| 51 | 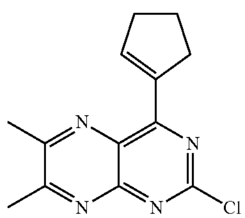 [SMILES: Cc1nc2nc(Cl)nc(C3=CCCC3)c2nc1C] | 2-chloro-4-(cyclopent-1-en-1-yl)-6,7-dimethylpteridine | 2,4-dichloro-6,7-dimethylpteridine (Intermediate 3) | cyclopent-1-en-1-ylboronic acid |
| 52 | 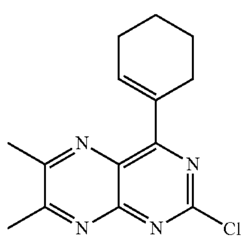 [SMILES: Cc1nc2nc(Cl)nc(C3=CCCCC3)c2nc1C] | 2-chloro-4-(cyclohex-1-en-1-yl)-6,7-dimethylpteridine | 2,4-dichloro-6,7-dimethylpteridine (Intermediate 3) | cyclohex-1-en-1-ylboronic acid |
| 53 | 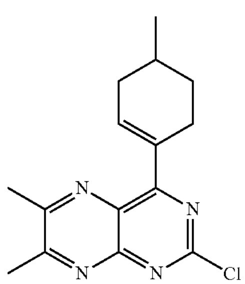 [SMILES: Cc1nc2nc(Cl)nc(C3=CCC(C)CC3)c2nc1C] | 2-chloro-6,7-dimethyl-4-(4-methylcyclohex-1-en-1-yl)pteridine | 2,4-dichloro-6,7-dimethylpteridine (Intermediate 3) | (4-methylcyclohex-1-en-1-yl)boronic acid |
| 54 | 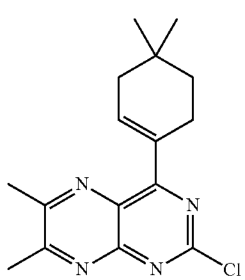 [SMILES: Cc1nc2nc(Cl)nc(C3=CCC(C)(C)CC3)c2nc1C] | 2-chloro-4-(4,4-dimethylcyclohex-1-en-1-yl)-6,7-dimethylpteridine | 2,4-dichloro-6,7-dimethylpteridine (Intermediate 3) | (4,4-dimethylcyclohex-1-en-1-yl)boronic acid |

TABLE 9-continued

Intermediates 10-58 were prepared following the procedure described in Method 18, as follows:

| Int # | Structure | Name | Starting Material 1 | Starting Material 2 |
|---|---|---|---|---|
| 55 | 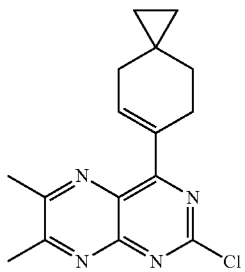 [SMILES: Cc1nc2nc(Cl)nc(C3=CCC4(CC3)CC4)c2nc1C] | 2-chloro-6,7-dimethyl-4-(spiro[2.5]oct-5-en-6-yl)pteridine | 2,4-dichloro-6,7-dimethylpteridine (Intermediate 3) | spiro[2.5]oct-5-en-6-ylboronic acid |
| 56 | 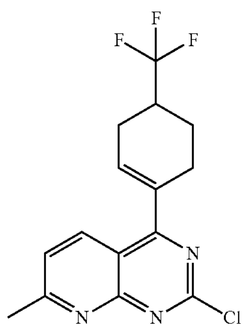 [SMILES: Cc1ccc2c(C3=CCC(C(F)(F)F)CC3)nc(Cl)nc2n1] | 2-chloro-7-methyl-4-(4-(trifluoromethyl)cyclohex-1-en-1-yl)pyrido[2,3-d]pyrimidine | 2,4-dichloro-7-methylpyrido[2,3-d]pyrimidine (PharmaBlock, Hatfield, PA, USA) | (4-(trifluoromethyl)cyclohex-1-en-1-yl)boronic acid |
| 57 | 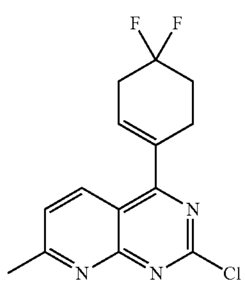 [SMILES: Cc1ccc2c(C3=CCC(F)(F)CC3)nc(Cl)nc2n1] | 2-chloro-4-(4,4-difluorocyclohex-1-en-1-yl)-7-methylpyrido[2,3-d]pyrimidine | 2,4-dichloro-7-methylpyrido[2,3-d]pyrimidine (PharmaBlock, Hatfield, PA, USA) | (4,4-difluorocyclohex-1-en-1-yl)boronic acid |
| 58 | 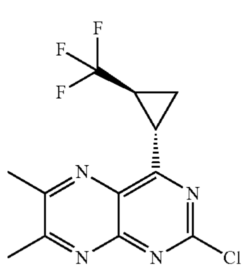 [SMILES: Cc1nc2nc(Cl)nc([C@H]3C[C@@H]3C(F)(F)F)c2nc1C] | 2-chloro-6,7-dimethyl-4-((1S,2S)-2-(trifluoromethyl)cyclopropyl)pteridine | 2,4-dichloro-6,7-dimethylpteridine (Intermediate 3) | ((1S,2S)-2-(trifluoromethyl)cyclopropyl)boronic acid |

Method 19
Intermediate 59: 2-chloro-6,7-dimethyl-4-((trans)-3-(trifluoromethyl)cyclobutyl)pteridine and Intermediate 60:
2-chloro-6,7-dimethyl-4-((cis)-3-(trifluoromethyl)cyclobutyl)pteridine

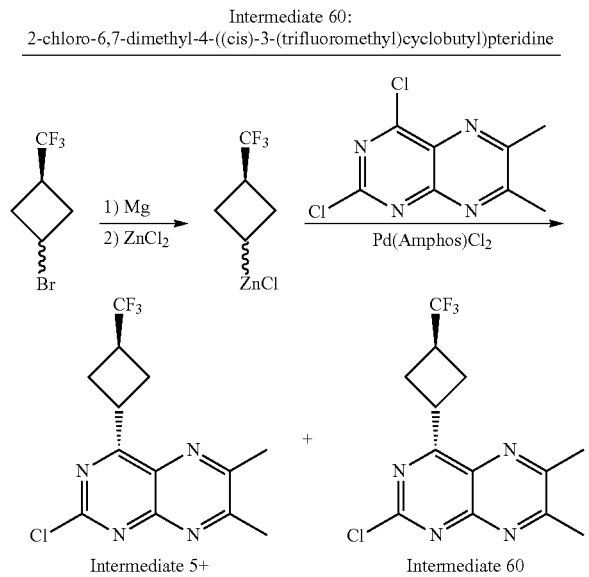

Step 1: (3-(trifluoromethyl)cyclobutyl)zinc(II) chloride. Magnesium (0.190 g, 7.82 mmol) was cleaned with a crystal of iodine then suspended in dry THF (3 mL) under $N_2$. 1-bromo-3-(trifluoromethyl)cyclobutane (1.25 g, 6.16 mmol) was added and the mixture stirred at rt. The mixture was stirred at ambient temperature for ~60 minutes and became a milky suspension. Zinc chloride solution in 2-MeTHF (2.92 mL, 5.54 mmol) was added dropwise and the mixture was stirred for 30 minutes. A white precipitate formed. The mixture was centrifuged for 10 min and the resulting dark yellow supernatant solution was used without further manipulation.

Step 2: 2-chloro-6,7-dimethyl-4-(3-(trifluoromethyl)cyclobutyl)pteridine. To a 40 mL vial was added bis(di-tert-butyl(4-dimethylaminophenyl)phosphine)-dichloropalladium(ii) (0.354 g, 0.500 mmol) and 2,4-dichloro-6,7-dimethylpteridine (Intermediate 3) (1.145 g, 5.00 mmol, Syngene) under $N_2$, 2.0 mL THF was added at rt, followed by ((1R,3R)-3-(trifluoromethyl)cyclobutyl)zinc(II) bromide in THF (1.0 eq). The solution turned purple and was stirred at 45 for 40 min. The reaction was concentrated, diluted with DCM (20 mL), quenched with $H_2O$ (10 mL) and HCl (2N, 3 mL) and extracted with DCM. The DCM extracts were combined, washed with brine, dried over $MgSO_4$ and concentrated. The residue was purified via silica gel chromatography (0%-40% EtOAc/EtOH in 10% DCM in Heptane) to afford 2-chloro-6,7-dimethyl-4-(3-(trifluoromethyl)cyclobutyl)pteridine (1.51 g, 4.77 mmol, 95% yield) as a yellow solid (~2.5/1 ratio of the cis/trans isomer). The compound was repurified via silica gel chromatography (0%-80% EtOAc in 10% DCM in Heptane) to afford:

Peak 1: 2-chloro-6,7-dimethyl-4-(trans-3-(trifluoromethyl)cyclobutyl)-pteridine (0.864 g, 2.73 mmol, 54.6% yield) as a yellow solid. $^1H$ NMR (500 MHz, Chloroform-d) δ ppm 4.89-4.98 (m, 1H), 3.08-3.29 (m, 1H), 2.66-2.88 (m, 10H), $^{19}F$ NMR (Chloroform-d, 471 MHz) δ ppm −74.03 (s); m/z (ESI, +ve ion): 317.0 $(M+H)^+$ Peak 2: 2-chloro-6,7-dimethyl-4-(cis-3-(trifluoromethyl)cyclobutyl)pteridine, 19% as a yellow solid. $^1H$ NMR (500 MHz, Chloroform-d) δ ppm 4.56-4.68 (m, 1H), 3.10-3.17 (m, 1H), 2.63-2.78 (m, 10H), $^{19}F$ NMR (Chloroform-d, 471 MHz) δ ppm −73.38 (s); m/z (ESI, +ve ion): 317.0 $(M+H)^+$

TABLE 10

Intermediates 61-70 and 110-113 were prepared following the procedure described in Method 19, as follows:

| Int # | Structure | Name | Starting Material 1 | Starting Material 2 |
|---|---|---|---|---|
| 61 | 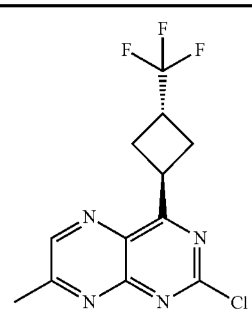 | 2-chloro-7-methyl-4-(trans-3-(trifluoromethyl)cyclobutyl)pteridine | 2,4-dichloro-7-methylpteridine (PharmaBlock Hatfield, PA, USA) | 1-bromo-3-(trifluoromethyl)cyclobutane |
| 62 | 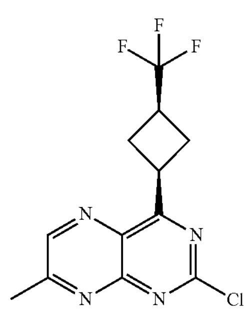 [SMILES: Cc1cnc2c(n1)nc(Cl)nc2[C@H]1C[C@@H](C(F)(F)F)C1] | 2-chloro-7-methyl-4-(cis-3-(trifluoromethyl)cyclobutyl)pteridine | 2,4-dichloro-7-methylpteridine (PharmaBlock Hatfield, PA, USA) | 1-bromo-3-(trifluoromethyl)cyclobutane |

TABLE 10-continued

Intermediates 61-70 and 110-113 were prepared following the procedure described in Method 19, as follows:

| Int # | Structure | Name | Starting Material 1 | Starting Material 2 |
|---|---|---|---|---|
| 63 | 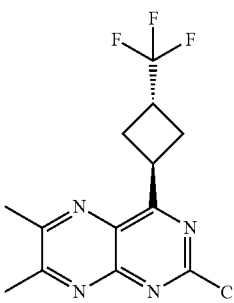 | 7-chloro-2,3-dimethyl-5-(trans-3-(trifluoromethyl)cyclobutyl)pyrido[3,4-b]pyrazine | 5,7-dichloro-2,3-dimethylpyrido[3,4-b]pyrazine (Intermediate 1) | 1-bromo-3-(trifluoromethyl)cyclobutane |
| 64 | 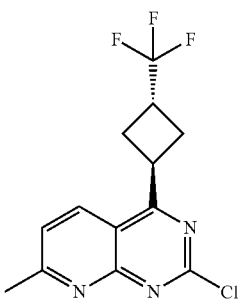 [SMILES: Cc1ccc2c(n1)nc(Cl)nc2[C@H]1C[C@H](C(F)(F)F)C1] | 2-chloro-7-methyl-4-(trans-3-(trifluoromethyl)cyclobutyl)pyrido[2,3-d]pyrimidine | 2,4-dichloro-7-methylpyrido[2,3-d]pyrimidine (PharmaBlock Hatfield, PA, USA) | 1-bromo-3-(trifluoromethyl)cyclobutane |
| 65 | 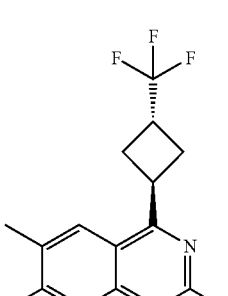 | 2-chloro-6,7-dimethyl-4-(trans-3-(trifluoromethyl)cyclobutyl)pyrido[2,3-d]pyrimidine | 2,4-dichloro-6,7-dimethylpyrido[2,3-d]pyrimidine (PharmaBlock Hatfield, PA, USA) | 1-bromo-3-(trifluoromethyl)cyclobutane |
| 66 | 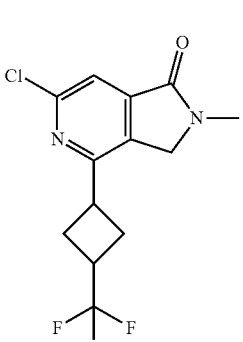 | 6-chloro-2-methyl-4-(3-(trifluoromethyl)cyclobutyl)-2,3-dihydro-1H-pyrrolo[3,4-c]pyridin-1-one | 4,6-dichloro-2-methyl-2,3-dihydro-1H-pyrrolo[3,4-c]pyridin-1-one (Enamine, Monmouth Jct., NJ, USA) | 1-bromo-3-(trifluoromethyl)cyclobutane |

TABLE 10-continued

Intermediates 61-70 and 110-113 were prepared following the procedure described in Method 19, as follows:

| Int # | Structure | Name | Starting Material 1 | Starting Material 2 |
|---|---|---|---|---|
| 67 | 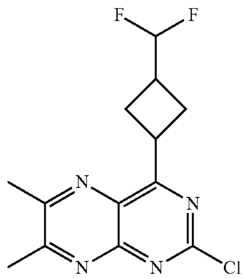 [SMILES: Cc1nc2nc(Cl)nc(C3CC(C(F)F)C3)c2nc1C] | 2-chloro-4-(3-(difluoromethyl)cyclobutyl)-6,7-dimethylpteridine | 2,4-dichloro-6,7-dimethylpteridine (Intermediate 3) | 1-bromo-3-(difluoromethyl)cyclobutane |
| 68 | 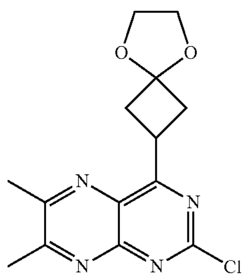 [SMILES: Cc1nc2nc(Cl)nc(C3CC4(C3)OCCO4)c2nc1C] | 2-chloro-6,7-dimethyl-4-(5,8-dioxaspiro[3.4]octan-2-yl)pteridine | 2,4-dichloro-6,7-dimethylpteridine (Intermediate 3) | 2-bromo-5,8-dioxaspiro[3.4]octane |
| 69 | 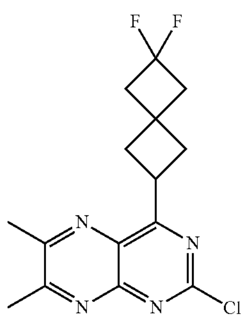 [SMILES: Cc1nc2nc(Cl)nc(C3CC4(C3)CC(F)(F)C4)c2nc1C] | 2-chloro-4-(6,6-difluorospiro[3.3]heptan-2-yl)-6,7-dimethylpteridine | 2,4-dichloro-6,7-dimethylpteridine (Intermediate 3) | 6-bromo-2,2-difluorospiro[3.3]heptane |
| 70 | 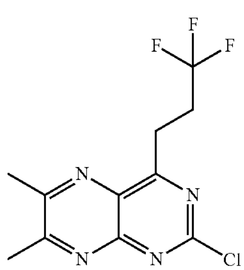 [SMILES: Cc1nc2nc(Cl)nc(CCC(F)(F)F)c2nc1C] | 2-chloro-6,7-dimethyl-4-(3,3,3-trifluoropropyl)pteridine | 2,4-dichloro-6,7-dimethylpteridine (Intermediate 3) | (3,3,3-trifluoropropyl)zinc(II) bromide |
| 110 | 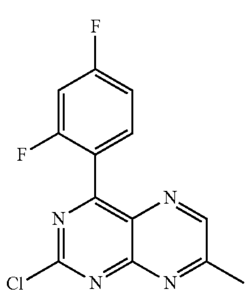 [SMILES: Cc1cnc2c(-c3ccc(F)cc3F)nc(Cl)nc2n1] | 7-chloro-5-(2,4-difluorophenyl)-2-methylpyrido[3,4-b]pyrazine | 5,7-dichloro-2-methylpyrido[3,4-b]pyrazine | 2,4-difluoro-1-iodobenzene |

TABLE 10-continued

Intermediates 61-70 and 110-113 were prepared following the procedure described in Method 19, as follows:

| Int # | Structure | Name | Starting Material 1 | Starting Material 2 |
|---|---|---|---|---|
| 111 | 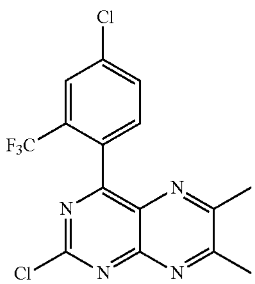 [SMILES: Cc1nc2nc(Cl)nc(-c3ccc(Cl)cc3C(F)(F)F)c2nc1C] | 2-chloro-4-[4-chloro-2-(trifluoromethyl)phenyl]-6,7-dimethyl-pteridine | 2,4-dichloro-7-methylpteridine | 4-chloro-1-iodo-2-(trifluoromethyl)benzene |
| 112 | 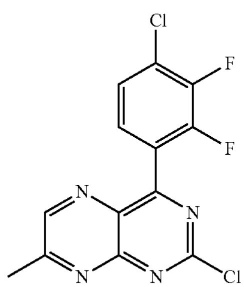 [SMILES: Cc1cnc2c(-c3ccc(Cl)c(F)c3F)nc(Cl)nc2n1] | 2-chloro-4-(4-chloro-2,3-difluoro-phenyl)-7-methyl-pteridine | 2,4-dichloro-7-methyl-pteridine | 1,2-dichloro-3-fluoro-4-iodobenzene |
| 113 | 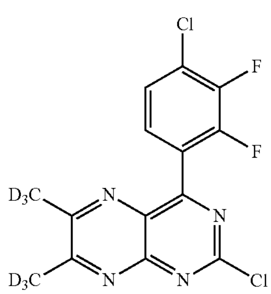 [SMILES: [2H]C([2H])([2H])c1nc2nc(Cl)nc(-c3ccc(Cl)c(F)c3F)c2nc1C([2H])([2H])[2H]] | 2-chloro-4-(4-chloro-2,3-difluoro-phenyl)-6,7-bis(trideuteriomethyl)pteridine | 2,4-dichloro-6,7-bis(trideuteriomethyl)pteridine | 1,2-dichloro-3-fluoro-4-iodobenzene |

Method 20

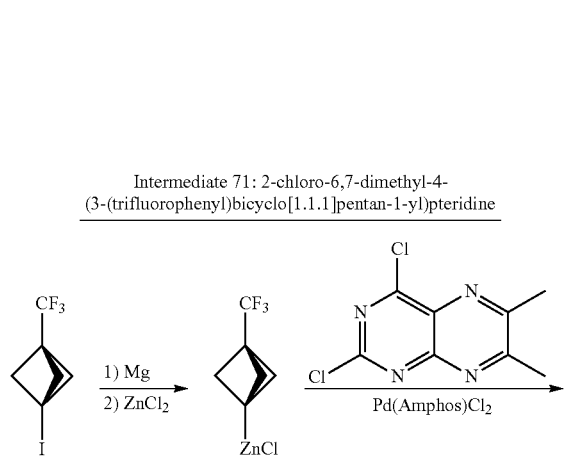

Intermediate 71: 2-chloro-6,7-dimethyl-4-(3-(trifluorophenyl)bicyclo[1.1.1]pentan-1-yl)pteridine

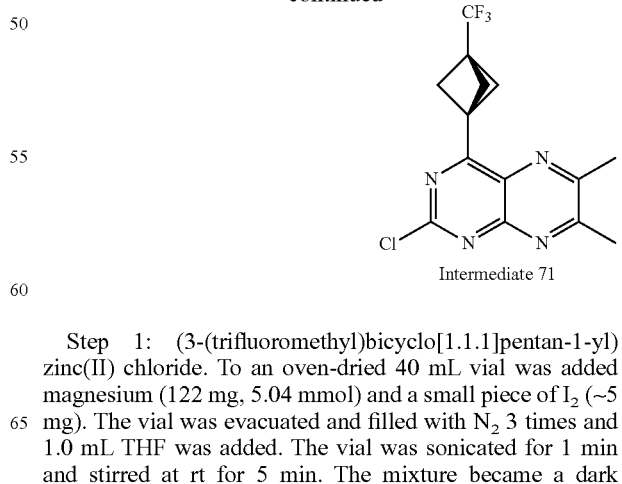

Intermediate 71

Step 1: (3-(trifluoromethyl)bicyclo[1.1.1]pentan-1-yl)zinc(II) chloride. To an oven-dried 40 mL vial was added magnesium (122 mg, 5.04 mmol) and a small piece of $I_2$ (~5 mg). The vial was evacuated and filled with $N_2$ 3 times and 1.0 mL THF was added. The vial was sonicated for 1 min and stirred at rt for 5 min. The mixture became a dark red/purple suspension. Then 1-iodo-3-(trifluoromethyl)bicyclo[1.1.1]pentane (1200 mg, 4.58 mmol) in 1 mL THF was added dropwise at room temperature. The purple I$_2$ color disappeared quickly, but no further exotherm was noticed. The vial was sealed and heated at 74° C. The mixture quickly turned clear and gradually became cloudy again. The mixture was heated for another 30 min until minimal Mg was left. An aliquot of the mixture was taken and subject to H and F NMR analysis, which showed >90% conv. to the Grignard reagent [Product: $^{19}$F NMR (Chloroform-d, 471 MHz) δ −73.99 (s, 1F); Substrate: $^{19}$F NMR (Chloroform-d, 471 MHz) δ −71.81 (s, 1F)]. The reaction mixture was cooled to room temperature. Zinc chloride solution in 2-MeTHF (2290 μL, 4.58 mmol) was added dropwise with an ice-H$_2$O bath. The mixture was warmed to rt and stirred for 30 minutes. A white precipitate formed, and the mixture was left to settle overnight. The clear supernatant solution was used without further manipulation. Titration with I$_2$ confirmed organozinc formation (12.3 mg I$_2$, 0.115 mL solution, 0.42 M solution in THF). Approximately 6.5 mL was able to be taken out (2.7 mmol, 59% yield).

Step 2: 2-chloro-6,7-dimethyl-4-(3-(trifluoromethyl)bicyclo[1.1.1]pentan-1-yl)pteridine. To a 40 mL vial was added bis(di-tert-butyl(4-dimethylaminophenyl)phosphine)-dichloro-palladium(ii) (49.6 mg, 0.070 mmol) and 2,4-dichloro-6,7-dimethylpteridine (Intermediate 3) (160 mg, 0.700 mmol, Syngene). The vial was evacuated and filled with N$_2$ 3 times. 0.5 mL THF was added at rt, followed with (3-(trifluoromethyl)bicyclo[1.1.1]pentan-1-yl)zinc(II) chloride (1.0 eq). The solution gradually turned purple and was stirred at 45° C. After 40 min, reaction reached ~90% conv. No change was observed after 2 h. The reaction was concentrated, diluted with DCM (8 mL), quenched with H$_2$O (4 mL) and HCl (2N, 0.4 mL), and extracted with DCM (10 mL×3). The DCM extracts were separated with a phase separator, concentrated, and purified with column chromatography (RediSep 12 g, 0%-40% EA/EtOH=3/1 blend in 10% DCM in Heptane) to afford 2-chloro-6,7-dimethyl-4-(3-(trifluoromethyl)bicyclo[1.1.1]pentan-1-yl)pteridine (174 mg, 0.529 mmol, 76% yield) as a yellow solid. $^1$H NMR (500 MHz, Chloroform-d) δ ppm 2.82 (m, 6H), 2.69 (s, 6H). $^{19}$F NMR (471 MHz, Chloroform-d) δ ppm −73.11 (s). m/z (ESI, +ve ion): 329.0 (M+H)$^+$.

TABLE 11

Intermediates 72 and 114-116 were prepared following the procedure described in Method 20, as follows:

| Int # | Structure | Name | Starting Material |
|---|---|---|---|
| 72 | 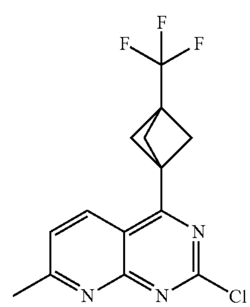 [SMILES: Cc1ccc2c(C34CC(C(F)(F)F)(C3)C4)nc(Cl)nc2n1] | 2-chloro-7-methyl-4-(3-(trifluoromethyl)bicyclo[1.1.1]pentan-1-yl)pyrido[2,3-d]pyrimidine | 2,4-dichloro-7-methylpyrido[2,3-d]pyrimidine (PharmaBlock Hatfield, PA, USA) |
| 114 | 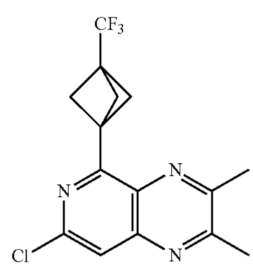 [SMILES: Cc1nc2cc(Cl)nc(C34CC(C(F)(F)F)(C3)C4)c2nc1C] | 7-chloro-2,3-dimethyl-5-(3-(trifluoromethyl)bicyclo[1.1.1]pentan-1-yl)pyrido[3,4-b]pyrazine | 5,7-dichloro-2,3-dimethyl-pyrido[3,4-b]pyrazine |
| 115 | 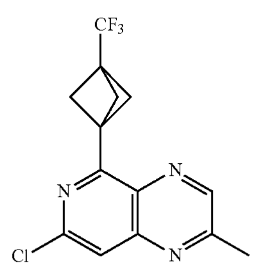 [SMILES: Cc1cnc2c(C34CC(C(F)(F)F)(C3)C4)nc(Cl)cc2n1] | 7-chloro-2-methyl-5-[3-(trifluoromethyl)-1-bicyclo[1.1.1]pentanyl]pyrido[3,4-b]pyrazine | 5,7-dichloro-2-methyl-pyrido[3,4-b]pyrazine |

TABLE 11-continued

Intermediates 72 and 114-116 were prepared following the procedure described in Method 20, as follows:

| Int # | Structure | Name | Starting Material |
|---|---|---|---|
| 116 | (structure shown) | 7-chloro-2-methyl-5-[3-(trifluoromethyl)-1-bicyclo[1.1.1]pentanyl]-1,6-naphthyridine | 5,7-dichloro-2-methyl-1,6-naphthyridine |

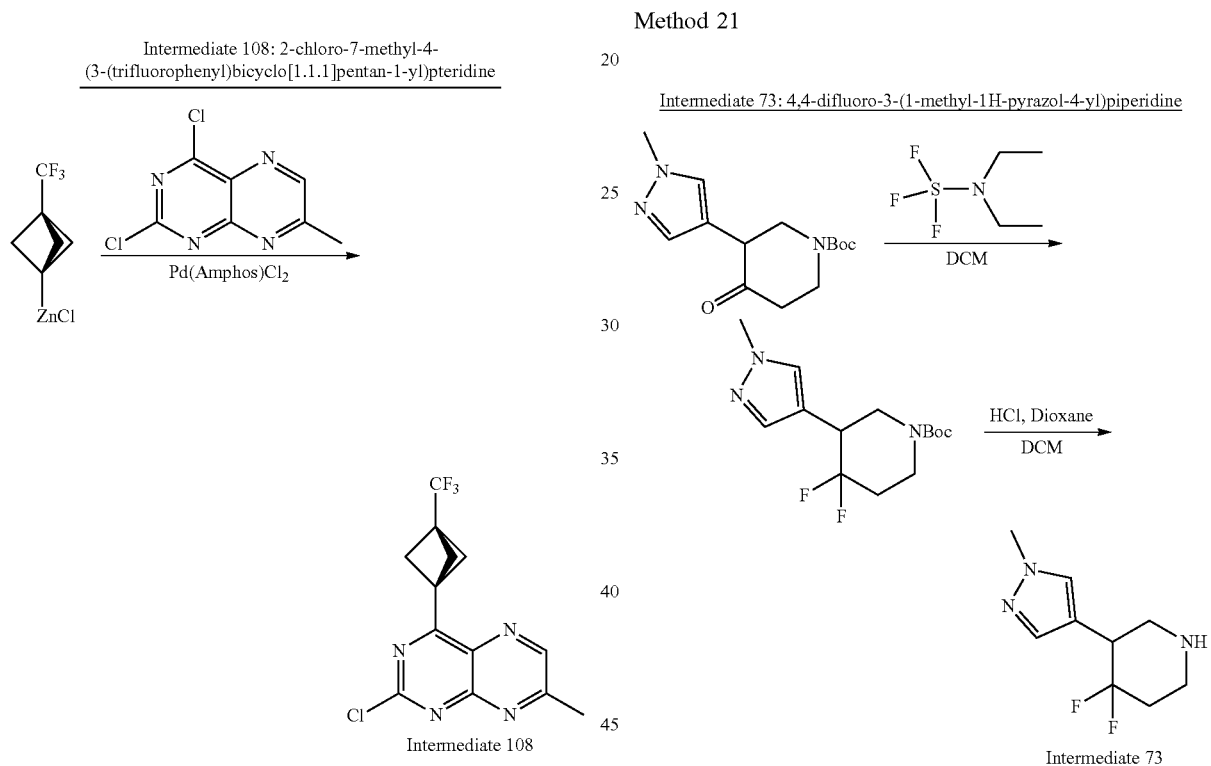

Intermediate 108: 2-chloro-7-methyl-4-(3-(trifluorophenyl)bicyclo[1.1.1]pentan-1-yl)pteridine Intermediate 108

Method 21

Intermediate 73: 4,4-difluoro-3-(1-methyl-1H-pyrazol-4-yl)piperidine

Intermediate 73

Intermediate 108 was prepared substantially as described in Method 20. To a 40 mL vial was added bis(di-tert-butyl(4-dimethylaminophenyl)phosphine)-dichloro-palladium(ii) (99 mg, 0.140 mmol) and 2,4-dichloro-7-dimethylpteridine (300 mg, 1.395 mmol, WuXi). The vial was evacuated and filled with $N_2$ 3 times. 3.5 mL THF was added at rt, followed with (3-(trifluoromethyl)bicyclo[1.1.1]pentan-1-yl)zinc(II) chloride (3671 μL, 1.395 mmol, 1.0 equiv., see Method 20, step 1). The solution gradually turned purple and was stirred at 45° C. overnight. The reaction was quenched with $NH_4Cl$ and EtOAc and extracted into EtOAc. The combined organic extracts were dried over MgSO4, filtered and concentrated to give the crude product. The crude material was purified by column chromatography to yield the desired product. m/z (ESI, +ve ion): 315.0 $(M+H)^+$.

Step 1: Tert-butyl 4,4-difluoro-3-(1-methyl-1H-pyrazol-4-yl)piperidine-1-carboxylate. To a 100-mL round-bottomed flask was added tert-butyl 3-(1-methyl-1H-pyrazol-4-yl)-4-oxopiperidine-1-carboxylate (1 g, 1.647 mmol)) in DCM (40 mL) and DAST (2.2 mL, 16.47 mmol) at 0° C. The reaction mixture was warmed to room temperature, stirred for 48 h, quenched with 10% sodium bicarbonate (50 mL) and extracted with DCM (30 mL). The organic extract was dried over $Na_2SO_4$. The solution was filtered and concentrated in vacuo to give the crude material as an orange oil. The crude material was purified by silica gel chromatography eluting with 50% EtOAc in hexane, to provide tert-butyl 4,4-difluoro-3-(1-methyl-1H-pyrazol-4-yl)piperidine-1-carboxylate (500 mg, 1.1 mmol, 64.5% yield) as yellow oil.

Step 2: 4,4-difluoro-3-(1-methyl-1H-pyrazol-4-yl)piperidine hydrochloride. To a 10-mL round-bottomed flask was added tert-butyl 4,4-difluoro-3-(1-methyl-1H-pyrazol-4-yl)piperidine-1-carboxylate (60 mg, 0.199 mmol)) in DCM (4 mL). The mixture was cooled to 0° C. and HCl in dioxane (0.5 mL, 2.000 mmol) was added. The reaction mixture was warmed to room temperature, stirred for 2 h, then concentrated in vacuo to give the crude product which was washed with diethyl ether to provide 4,4-difluoro-3-(1-methyl-1H-pyrazol-4-yl)piperidine hydrochloride (25 mg, 0.124 mmol, 62.4% yield) as white solid (hygroscopic). $^1$H NMR (400 MHz, DMSO-d6): δ ppm 9.36 (d, J=25.1 Hz, 2H), 7.73 (s, 1H), 7.41 (s, 1H), 3.82 (s, 4H), 3.57 (s, 2H), 3.18 (d, J=5.1 Hz, 1H), 2.39 (d, J=11.9 Hz, 2H).

Method 22

Intermediate 74: 2-(1-methyl-1H-pyrazol-4-yl)tetrahydro-2H-pyran-4-yl)zinc(II)bromide

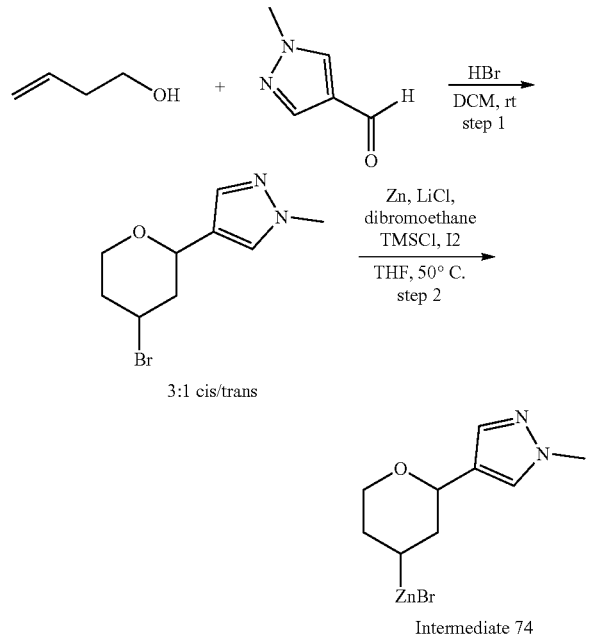

Step 1: 4-(4-bromotetrahydro-2H-pyran-2-yl)-1-methyl-1H-pyrazole. To a 100 mL flask was charged 1-methyl-1H-pyrazole-4-carbaldehyde (1.03 g, 9.35 mmol), 3-buten-1-ol (0.708 g, 0.842 mL, 9.82 mmol) and DCM (18.7 mL). To the flask was added hydrogen bromide-acetic acid (6.88 g, 5.08 mL, 28.1 mmol) in one portion. After 1 h, the crude reaction was carefully quenched with saturated NaHCO$_3$ solution and washed with EtOAc. The combined organic layer was dried over Na$_2$SO$_4$ and was filtered, and concentrated. The resulting crude material was purified by silica gel chromatography, eluting with 0% to 40% EtOAc/EtOH (3:1) in heptane, to provide 4-(4-bromotetrahydro-2H-pyran-2-yl)-1-methyl-1H-pyrazole (1.31 g, 5.33 mmol, 57% yield) as a light yellow oil as an ~3:1 mixture of cis/trans diastereomers. A second silica gel column provided the pure cis (0.85 g) and trans (0.27) isomers. If desired, the major (cis) diastereomers can be separated by SFC (Chiralpak AY-H 2×25 cm, 5 μm columns; mobile phase=10% EtOH, F=60 mL/min).

Major diastereomer (cis isomers): $^1$H NMR (500 MHz, Chloroform-d) δ ppm 7.46 (s, 1H), 7.36 (s, 1H), 4.36 (dd, J=11.3, 2.1 Hz, 1H), 4.25 (tt, J=11.9, 4.5 Hz, 1H), 4.08 (ddd, J=12.0, 4.8, 1.8 Hz, 1H), 3.89 (s, 3H), 3.58 (td, J=12.1, 2.3 Hz, 1H), 2.52 (ddt, J=12.9, 4.3, 2.1, 2.1 Hz, 1H), 2.12-2.26 (m, 3H). m/z (ESI, +ve ion): 245.0 [M+H]$^+$.

Minor diastereomer (trans isomers): $^1$H NMR (500 MHz, Chloroform-d) δ ppm 7.46 (s, 1H), 7.35 (s, 1H), 4.93 (dd, J=10.0, 2.9 Hz, 1H), 4.79 (quin, J=3.1 Hz, 1H), 4.12 (td, J=11.6, 2.1 Hz, 1H), 3.92-3.99 (m, 1H), 3.89 (s, 3H), 2.16-2.29 (m, 3H), 1.93-2.02 (m, 1H). m/z (ESI, +ve ion): 245.0 [M+H]$^+$.

Step 2: (2-(1-methyl-1H-pyrazol-4-yl)tetrahydro-2H-pyran-4-yl)zinc(II) bromide. To an oven-dried 50 mL flask was added Zn (0.320 g, 4.90 mmol), which was evacuated and backfilled with N$_2$ 3 times and the flask was capped with a rubber septum. Then a thermocouple probe was inserted and lithium chloride solution 0.5 M in anhydrous THF (3.26 mL, 1.632 mmol) was added. 1,2-dibromoethane (0.015 g, 7.03 μL, 0.082 mmol) was then added and the mixture was heated to an internal temp of 50° C. and held for 20 min. The flask was removed from the heating block and cooled to room temperature. Chlorotrimethylsilane (8.86 mg, 10.36 μL, 0.082 mmol) was added and the mixture was heated to an internal temperature of 50° C. and the temperature was held for 20 min. The flask was removed from the heating block and cooled to room temperature. Diiodine (8.28 mg, 0.033 mmol) was added as a solution in THF 0.1 mL, and the mixture was heated to an internal temperature of 50° C. and the temperature held for 20 min. While still hot, 4-bromo-tetrahydro-2H-pyran-2-yl)-1-methyl-1H-pyrazole (3:1 cis/trans mixture, 0.4 g, 1.632 mmol) was added as a THF solution (1.5 mL) and the resulting mixture was stirred at 50° C. overnight. The reaction solution was cooled to room temperature as the zinc powder was allowed to settle to provide a yellow solution of (2-(1-methyl-1H-pyrazol-4-yl)tetrahydro-2H-pyran-4-yl)zinc(II) bromide.

TABLE 12

Intermediates 75-77 were prepared following the procedure described in Method 22, as follows:

| Int # | Structure | Name | Starting Material |
|---|---|---|---|
| 75 | 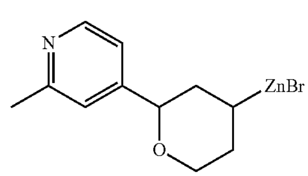 | (2-(2-methylpyridin-4-yl)tetrahydro-2H-pyran-4-yl)zinc(II) bromide | 2-methylisonicotin-aldehyde |

TABLE 12-continued

Intermediates 75-77 were prepared following the procedure described in Method 22, as follows:

| Int # | Structure | Name | Starting Material |
|---|---|---|---|
| 76 | (structure) | (2-(2-methoxypyridin-4-yl)tetrahydro-2H-pyran-4-yl)zinc(II) bromide | 2-methoxyisonicotin-aldehyde |
| 77 | (structure) | (2-(2-methylpyrimidin-5-yl)tetrahydro-2H-pyran-4-yl)zinc(II) bromide | 2-methylpyrimidine-5-carbaldehyde |
| 78 | (structure) | (2-methyl-6-(1-methyl-1H-pyrazol-4-yl)tetrahydro-2H-pyran-4-yl)zinc(II) bromide | 1-methyl-1H-pyrazole-4-carbaldehyde |

Method 23

Intermediate 79: 1-methyl-4-(4-(4,4,5,5-tetramethyl-1,3,2-dioxaborolan-2-yl)-5,6-dihydro-2H-pyran-4-yl)-1H-pyrazole

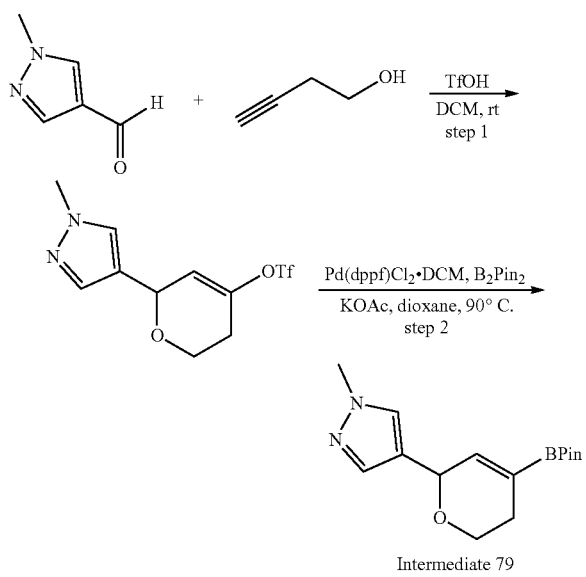

Step 1: To a 20 mL scintillation vial was charged 1-methyl-1H-pyrazole-4-carbaldehyde (200 mg, 1.816 mmol), which was purged with $N_2$. Then (2-hydroxyethyl) acetylene (191 mg, 206 μl, 2.72 mmol) and DCM (3.6 mL) were added. To the vial was added trifluoromethane sulfonic acid (327 mg, 194 μl, 2.180 mmol) slowly at 0° C. The reaction was warmed to room temperature after 5 min. After 5 h, additional trifluoromethane sulfonic acid (327 mg, 194 μl, 2.180 mmol) was added. After another 18 h, the crude reaction was carefully quenched with saturated $NaHCO_3$ solution and washed with DCM. The combined organic layers were dried over $Na_2SO_4$, filtered, and concentrated. The resulting crude material was absorbed onto a plug of silica gel and purified by chromatography through a Redi-Sep pre-packed silica gel column (40 g), eluting with 0% to 70% EtOAc in heptane, to provide 6-(1-methyl-1H-pyrazol-4-yl)-3,6-dihydro-2H-pyran-4-yl trifluoromethanesulfonate (227 mg, 0.727 mmol, 40% yield) as a light yellow oil. m/z (ESI, +ve ion): 313.0 [M+H]$^+$. $^1$H NMR (500 MHz, Chloroform-d) δ ppm 7.49 (s, 1H), 7.37 (s, 1H), 5.96 (dt, J=2.6, 1.4 Hz, 1H), 5.34 (q, J=2.6 Hz, 1H), 3.98-4.04 (m, 1H), 3.92 (s, 3H), 3.85 (ddd, J=11.5, 6.4, 5.2 Hz, 1H), 2.45-2.60 (m, 2H).

Step 2: 1-methyl-4-(4-(4,4,5,5-tetramethyl-1,3,2-dioxaborolan-2-yl)-5,6-dihydro-2H-pyran-2-yl)-1H-pyrazole. To a 20 mL scintillation vial was charged 6-(1-methyl-1H-pyrazol-4-yl)-3,6-dihydro-2H-pyran-4-yl trifluoromethanesulfonate (227 mg, 0.727 mmol), [1,1'-bis(diphenylphosphino)ferrocene]-dichloropalladium(ii), complex with DCM (59.4 mg, 0.073 mmol), bis(pinacolato)diboron (277 mg, 1.09 mmol) and potassium acetate (285 mg, 2.91 mmol). The flask was purged with $N_2$ and 1,4-dioxane (2.9 mL) was added. The reaction was heated to 90° C. for 2 h and the reaction was cooled to room temperature. The reaction mixture was diluted with EtOAc and filtered through a plug of silica gel. The crude material purified by silica gel chromatography eluting with 0% to 100% EtOAc in heptane, to provide 1-methyl-4-(4-(4,4,5,5-tetramethyl-1,3,2-dioxaborolan-2-yl)-5,6-dihydro-2H-pyran-2-yl)-1H-pyrazole (87 mg, 0.30 mmol, 41% yield) as a red oil. m/z (ESI, +ve ion): 291.2 [M+H]$^+$. $^1$H NMR (500 MHz, Chloroform-d) δ ppm 7.48 (s, 1H), 7.36 (s, 1H), 6.61 (q, J=1.9 Hz, 1H), 5.20 (q, J=2.6 Hz, 1H), 3.89-3.93 (m, 1H), 3.89 (s, 3H), 3.71-3.78 (m, 1H), 2.28-2.39 (m, 1H), 2.17-2.27 (m, 1H), 1.30 (s, 12H).

TABLE 13

Intermediates 80-82 were prepared following the procedure described in Method 23, as follows:

| Int # | Structure | Name | Starting Material |
|---|---|---|---|
| 80 | 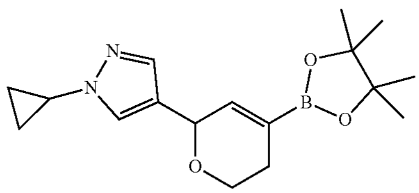 [SMILES: CC1(C)OB(C2=CC(c3cnn(C4CC4)c3)OCC2)OC1(C)C] | 1-cyclopropyl-4-(4-(4,4,5,5-tetramethyl-1,3,2-dioxaborolan-2-yl)-5,6-dihydro-2H-pyran-2-yl)-1H-pyrazole | 1-cyclopropyl-1H-pyrazole-4-carbaldehyde |
| 81 | 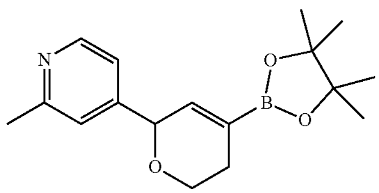 | 2-methyl-4-(4-(4,4,5,5-tetramethyl-1,3,2-dioxaborolan-2-yl)-5,6-dihydro-2H-pyran-2-yl)pyridine | 2-methylisonicotin-aldehyde |
| 82 | 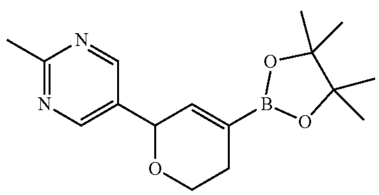 | 2-methyl-5-(4-(4,4,5,5-tetramethyl-1,3,2-dioxaborolan-2-yl)-5,6-dihydro-2H-pyran-2-yl)pyrimidine | 2-methyl-pyrimidine-5-carbaldehyde |

Method 24

Intermediate 83: 2-chloro-4-(3-methoxyazetidin-1-yl)-6,7-dimethylpteridine

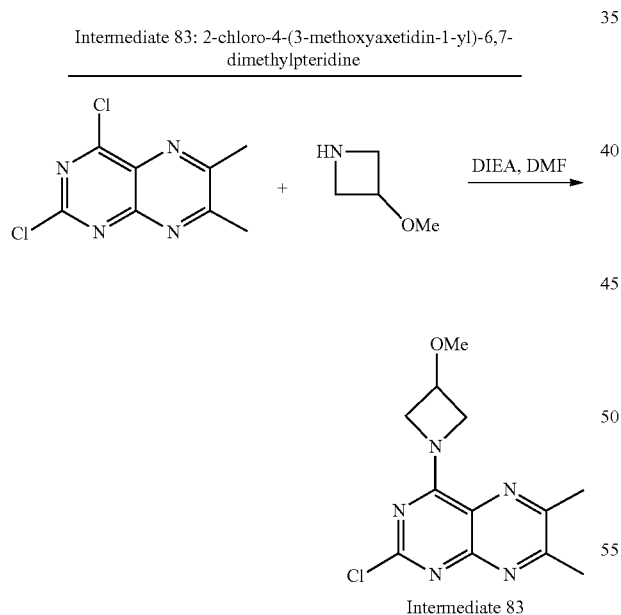

Intermediate 83

To a 10 mL vial containing 3-methoxyazetidine (0.026 g, 0.3 mmol) in DMF (1 mL) was added 2,4-dichloro-6,7-dimethylpteridine (Intermediate 3) (0.069 g, 0.3 mmol) and diisopropylethylamine (0.209 mL, 1.200 mmol). The mixture was heated at 95° C. for 7 h then cooled to rt. Conversion to the desired product (LCMS analysis) was high and the mixture was used without purification.

TABLE 14

Intermediates 84-92 were prepared following the procedure described in Method 24, as follow:

| Int. # | Structure | Name | Starting Material 1 | Starting Material 2 |
|---|---|---|---|---|
| 84 | 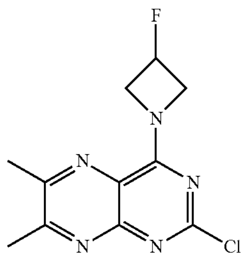 [SMILES: Cc1nc2nc(Cl)nc(N3CC(F)C3)c2nc1C] | 2-chloro-4-(3-fluoroazetidin-1-yl)-6,7-dimethylpteridine | 2,4-dichloro-6,7-dimethylpteridine (Intermediate 3) | 3-fluoroazetidine |
| 85 | 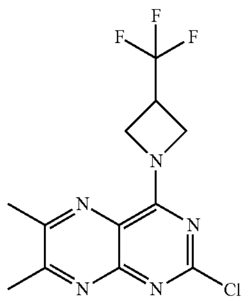 [SMILES: Cc1nc2nc(Cl)nc(N3CC(C(F)(F)F)C3)c2nc1C] | 2-chloro-6,7-dimethyl-4-(3-(trifluoromethyl)azetidin-1-yl)pteridine | 2,4-dichloro-6,7-dimethylpteridine (Intermediate 3) | 3-(trifluoromethyl)azetidine |
| 86 | 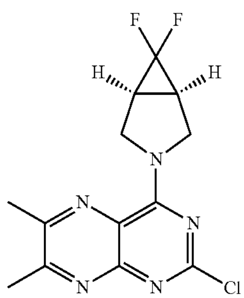 [SMILES: Cc1nc2nc(Cl)nc(N3C[C@@H]4[C@H](C3)C4(F)F)c2nc1C] | 2-chloro-4-((1R,5S)-6,6-difluoro-3-azabicyclo[3.1.0]hexan-3-yl)-6,7-dimethylpteridine | 2,4-dichloro-6,7-dimethylpteridine (Intermediate 3) | (1R,5S)-6,6-difluoro-3-azabicyclo[3.1.0]hexane |
| 87 | 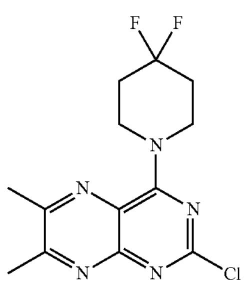 [SMILES: Cc1nc2nc(Cl)nc(N3CCC(F)(F)CC3)c2nc1C] | 2-chloro-4-(4,4-difluoropiperidin-1-yl)-6,7-dimethylpteridine | 2,4-dichloro-6,7-dimethylpteridine (Intermediate 3) | 4,4-difluoropiperidine |
| 88 | 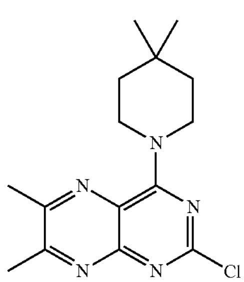 [SMILES: Cc1nc2nc(Cl)nc(N3CCC(C)(C)CC3)c2nc1C] | 2-chloro-4-(4,4-dimethylpiperidin-1-yl)-6,7-dimethylpteridine | 2,4-dichloro-6,7-dimethylpteridine (Intermediate 3) | 4,4-dimethylpiperidine |

TABLE 14-continued

Intermediates 84-92 were prepared following the procedure described in Method 24, as follow:

| Int. # | Structure | Name | Starting Material 1 | Starting Material 2 |
|---|---|---|---|---|
| 89 | 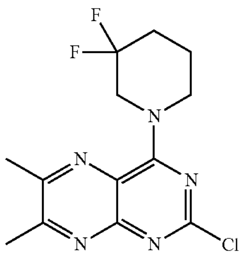 [SMILES: Cc1nc2nc(Cl)nc(N3CCCC(F)(F)C3)c2nc1C] | 2-chloro-4-(3,3-difluoropiperidin-1-yl)-6,7-dimethylpteridine | 2,4-dichloro-6,7-dimethylpteridine (Intermediate 3) | 3,3-difluoro-piperidine |
| 90 | 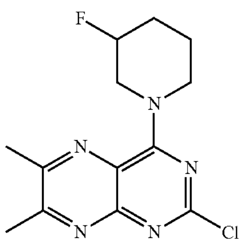 [SMILES: Cc1nc2nc(Cl)nc(N3CCCC(F)C3)c2nc1C] | 2-chloro-4-(3-fluoropiperidin-1-yl)-6,7-dimethylpteridine | 2,4-dichloro-6,7-dimethylpteridine (Intermediate 3) | 3-fluoro-piperidine |
| 91 | 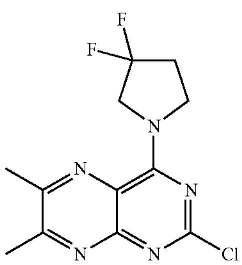 [SMILES: Cc1nc2nc(Cl)nc(N3CCC(F)(F)C3)c2nc1C] | 2-chloro-4-(3,3-difluoropyrrolidin-1-yl)-6,7-dimethylpteridine | 2,4-dichloro-6,7-dimethylpteridine (Intermediate 3) | 3,3-difluoro-pyrrolidine |
| 92 | 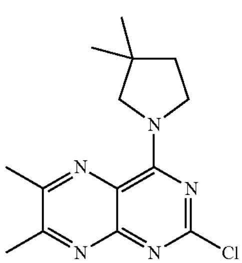 [SMILES: Cc1nc2nc(Cl)nc(N3CCC(C)(C)C3)c2nc1C] | 2-chloro-4-(3,3-dimethylpyrrolidin-1-yl)-6,7-dimethylpteridine | 2,4-dichloro-6,7-dimethylpteridine (Intermediate 3) | 3,3-dimethyl-pyrrolidine |

Method 25

Intermediate 93: 2-chloro-4-((3,3-difluorocyclobutyl)methoxy)-6,7-dimethylpyrido[2,3-d]pyrimidine

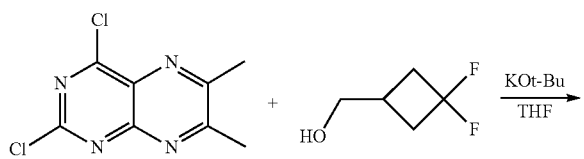

-continued

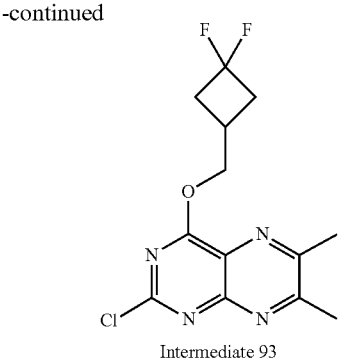

Intermediate 93

To a 10 mL vial was added 2,4-dichloro-6,7-dimethylpyrido[2,3-d]pyrimidine (49.8 mg, 0.218 mmol) and (3,3-difluorocyclobutyl)methanol (32.0 mg, 0.262 mmol) in tetrahydrofuran (1091 µL). The mixture was cooled to 0° C. and potassium t-butoxide (262 µL, 0.262 mmol) solution was added. After stirring for 1 h the solution was quenched with H₂O (10 mL) extracted with EtOAc and the organic layer dried over Na₂SO₄ and concentrated under vacuum. The crude product, 2-chloro-4-((3,3-difluorocyclobutyl) methoxy)-6,7-dimethylpyrido[2,3-d]pyrimidine, was used in subsequent steps without further purification.

TABLE 15

Intermediates 94-96 were prepared following the procedure described in Method 25, as follows:

| Int # | Structure | Name | Starting Material 1 | Starting Material 2 |
|---|---|---|---|---|
| 94 | 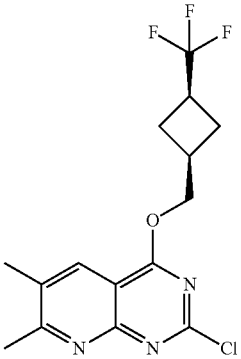 [SMILES: Cc1cc2c(OC[C@H]3C[C@@H](C(F)(F)F)C3)nc(Cl)nc2nc1C] | 2-chloro-6,7-dimethyl-4-(((cis)-3-(trifluoromethyl)cyclobutyl)methoxy)pyrido[2,3-d]pyrimidine | 2,4-dichloro-6,7-dimethylpyrido[2,3-d]pyrimidine (PharmaBlock Hatfield, PA, USA) | ((cis)-3-(trifluoromethyl)cyclobutyl)methanol |
| 95 | 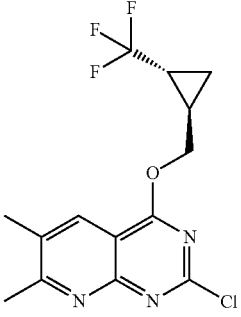 [SMILES: Cc1cc2c(OC[C@@H]3C[C@H]3C(F)(F)F)nc(Cl)nc2nc1C] | 2-chloro-6,7-dimethyl-4-(((1R,2R)-2-(trifluoromethyl)cyclopropyl)methoxy)pyrido[2,3-d]pyrimidine | 2,4-dichloro-6,7-dimethylpyrido[2,3-d]pyrimidine (PharmaBlock Hatfield, PA, USA) | ((1R,2R)-2-(trifluoromethyl)cyclopropyl)methanol |
| 96 | 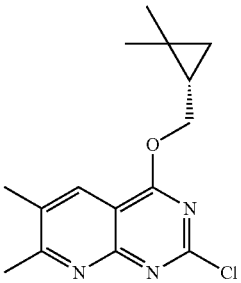 [SMILES: Cc1cc2c(OC[C@H]3CC3(C)C)nc(Cl)nc2nc1C] | (S)-2-chloro-4-((2,2-dimethylcyclopropyl)methoxy)-6,7-dimethylpyrido[2,3-d]pyrimidine | 2,4-dichloro-6,7-dimethylpyrido[2,3-d]pyrimidine (PharmaBlock Hatfield, PA, USA) | (S)-(2,2-dimethylcyclopropyl)methanol |

Method 26

Intermediate 97: (S)-4-(4-chloro-6-7-dimethyl-1,8napthyridin-2-yl)-2-(1-methyl-1H-pyrazol-4-yl)morpholine

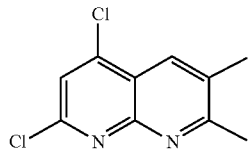

+

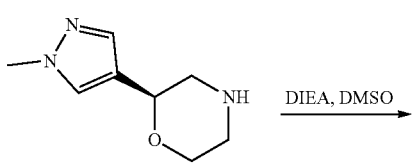   DIEA, DMSO →

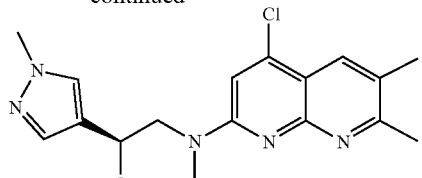

Intermediate 97

To a solution of 5,7-dichloro-2,3-dimethyl-1,8-naphthyridine (Intermediate 5, 0.234 g, 1.030 mmol) and DIEA 0.266 g, 0.359 mL, 2.061 mmol) in DMSO (3.4 mL) was added (S)-2-(1-methyl-1H-pyrazol-4-yl)morpholine (Enamine, Monmouth Jct., NJ, USA) (0.207 g, 1.237 mmol). The reaction mixture was stirred at 100° C. for 7 h. After cooling, the mixture was diluted with $H_2O$ and extracted with DCM. The organic phase was separated, concentrated under vacuum and purified by silica gel chromatography (0-10% MeOH (+1% $NH_3$) in DCM) to afford the title compound (S)-4-(4-chloro-6,7-dimethyl-1,8-naphthyridin-2-yl)-2-(1-methyl-1H-pyrazol-4-yl)morpholine (0.121 g, 0.339 mmol, 33.0%) m/z (ESI, +ive ion): 358.0 $(M+H)^+$, and the regioisomeric byproduct (S)-4-(2-chloro-6,7-dimethyl-1,8-naphthyridin-4-yl)-2-(1-methyl-1H-pyrazol-4-yl)morpholine (0.0183 g, 0.051 mmol, 4.9% yield).

TABLE 16

Intermediates 98-102 were prepared following the procedure described in Method 26, as follows:

| Int. # | Structure | Name | Starting Material |
|---|---|---|---|
| 98 | 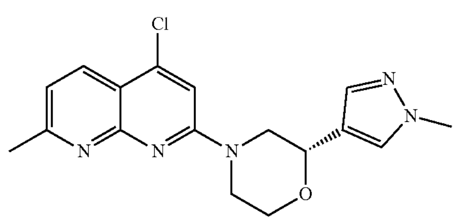 | (S)-4-(4-chloro-7-methyl-1,8-naphthyridin-2-yl)-2-(1-methyl-1H-pyrazol-4-yl)morpholine | 2,4-dichloro-7-methyl-1,8-naphthyridine (Intermediate 8) |
| 99 | 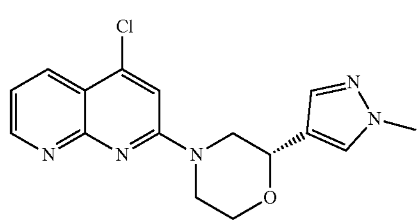 [SMILES: Cn1cc([C@H]2CN(c3cc(Cl)c4cccnc4n3)CCO2)cn1] | (S)-4-(4-chloro-1,8-naphthyridin-2-yl)-2-(1-methyl-1H-pyrazol-4-yl)morpholine | 2,4-dichloro-1,8-naphthyridine (Combi-Blocks, San Diego, CA, USA) |
| 100 | 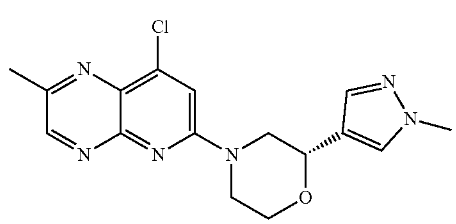 | (S)-4-(8-chloro-2-methylpyrido[2,3-b]pyrazin-6-yl)-2-(1-methyl-1H-pyrazol-4-yl)morpholine | 6,8-dichloro-2-methylpyrido[2,3-b]pyrazine (WuXi Apptech, Shanghai, China) |

TABLE 16-continued

Intermediates 98-102 were prepared following the procedure described in Method 26, as follows:

| Int. # | Structure | Name | Starting Material |
|---|---|---|---|
| 101 | 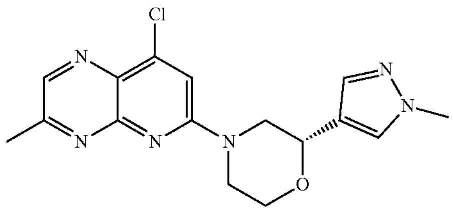 | (S)-4-(8-chloro-3-methylpyrido[2,3-b]pyrazin-6-yl)-2-(1-methyl-1H-pyrazol-4-yl)morpholine | 6,8-dichloro-3-methylpyrido[2,3-b]pyrazine (PharmaBlock Hatfield, PA, USA) |
| 102 | 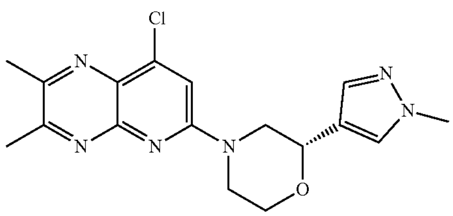 | (S)-4-(8-chloro-2,3-dimethylpyrido[2,3-b]pyrazin-6-yl)-2-(1-methyl-1H-pyrazol-4-yl)morpholine | 6,8-dichloro-2,3-dimethylpyrido[2,3-b]pyrazine (Intermediate 2) |

Method 27

Intermediate 103: (S)-4-(8-chloro-2,3-dimethylquinoxalin-6-yl)-2-(2-methylpyridin-4-yl)morpholine

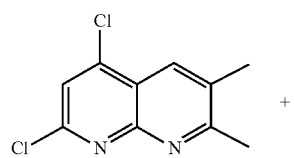

+

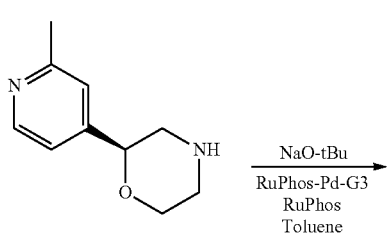

NaO-tBu
RuPhos-Pd-G3
RuPhos
Toluene
→

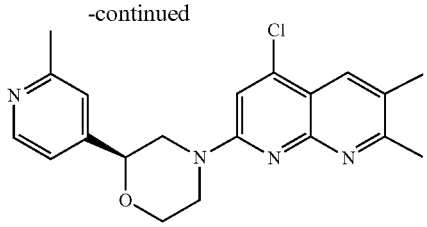

Intermediate 103

To a 25-mL reaction vial was added 7-bromo-5-chloro-2,3-dimethylquinoxaline (0.200 g, 0.737 mmol) and (S)-2-(2-methylpyridin-4-yl)morpholine (0.131 g, 0.737 mmol) in toluene (8 mL) followed by sodium tert-butoxide (0.106 g, 1.105 mmol). The reaction mixture was degassed with nitrogen for 5 min, then RuPhos-Pd-G3 (0.062 g, 0.074 mmol) and RuPhos (0.034 g, 0.074 mmol) were added, then the reaction mixture was heated at 80° C. for 2 h. The reaction mixture was diluted with $H_2O$ (7 mL) and extracted with EtOAc (2×10 mL), the organic extracts were dried over $Na_2SO_4$ and the organic extracts were concentrated to give the crude material. Purification by silica gel chromatography (30% to 100% EtOAc in hexane) provided (S)-4-(8-chloro-2,3-dimethylquinoxalin-6-yl)-2-(2-methylpyridin-4-yl)morpholine (0.170 g, 0.461 mmol, 62.6% yield) as orange solid. m/z (ESI, +ive ion): 351.0 (M+H)+.

TABLE 17

Intermediate 104 was prepared following the procedure described in Method 27, as follows:

| Int. # | Structure | Name | Starting Material 1 | Starting Material 2 |
|---|---|---|---|---|
| 104 | 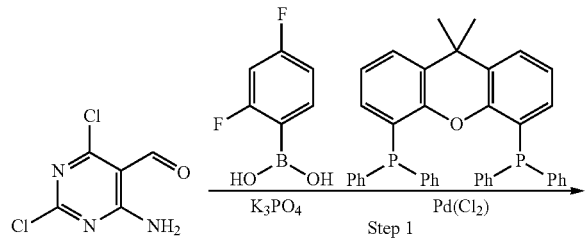 | (S)-4-(8-chloro-2,3-dimethyl-quinoxalin-6-yl)-2-(1-methyl-1H-pyrazol-4-yl)morpholine | 7-bromo-5-chloro-2,3-dimethyl-quinoxaline (WuXi Apptech, Shanghai, China) | (S)-2-(1-methyl-1H-pyrazol-4-yl)morpholine (Enamine, Monmouth Jct., NJ, USA) |

Method 28

Intermediate 105: (S)-4-amino-6-(2,4-difluorophenyl)-2-(2-(1-methyl-1H-pyrazol-4-yl)morpholino)pyrimidine-5-carbaldehyde

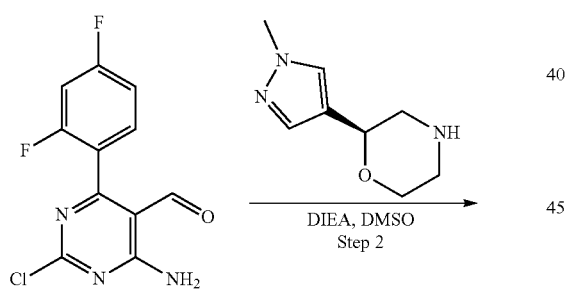

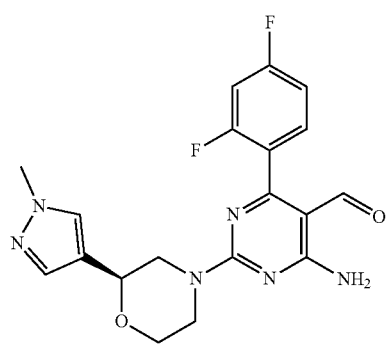

Intermediate 105

Step 1: 4-amino-2-chloro-6-(4-chloro-2-fluorophenyl)pyrimidine-5-carbaldehyde. In a 100 mL round bottom flask were added dichloro[9,9-dimethyl-4,5-bis(diphenylphosphino)xanthene]palladium(ii) (0.150 g, 0.198 mmol), (4-chloro-2-fluorophenyl)boronic acid (1.73 g, 9.90 mmol), 4-amino-2,6-dichloropyrimidine-5-carbaldehyde (1.9 g, 9.90 mmol) followed by 2-methyltetrahydrofuran (24.7 mL) and potassium phosphate (5.57 ml, 22.27 mmol). The vial was flushed under nitrogen (3×) and the reaction was stirred at 70° C. for 2 h. The reaction mixture was cooled to rt, water was added, and the precipitate was filtered and washed several times with water and diethyl ether. The crude 4-amino-2-chloro-6-(4-chloro-2-fluorophenyl)pyrimidine-5-carbaldehyde (1.3 g, 4.54 mmol, 45.9% yield) was used as such in the next step without further purification. m/z (ESI, +ive ion): 270.1 (M+H)+.

Step 2: (S)-4-amino-6-(2,4-difluorophenyl)-2-(2-(1-methyl-1H-pyrazol-4-yl)morpholino)pyrimidine-5-carbaldehyde. To a solution of 4-amino-2-chloro-6-(2,4-difluorophenyl)pyrimidine-5-carbaldehyde (0.2 g, 0.742 mmol) and DIEA (0.192 g, 0.258 mL, 1.48 mmol) in DMSO (2.47 mL) was added (S)-2-(1-methyl-1H-pyrazol-4-yl)morpholine (Enamine, Monmouth Jct., NJ, USA)(0.149 g, 0.890 mmol). The reaction mixture was stirred at 80° C. for 1 h, cooled to rt and water was added. The precipitate was filtered, washed several times with water and then with a small amount of diethyl ether. The resulting solid was dried under vacuum. The crude (S)-4-amino-6-(2,4-difluorophenyl)-2-(2-(1-methyl-1H-pyrazol-4-yl)morpholino)pyrimidine-5-carbaldehyde (0.177 g, 0.441 mmol, 59.5% yield) was used without further purification. m/z (ESI, +ive ion): 401.0 (M+H)+.

TABLE 18

Intermediate 106 and 107 was prepared following the procedure described in Method 28, as follows:

| Int. # | Structure | Name | Starting Material (Step 2) |
|---|---|---|---|
| 106 | (structure) | (S)-4-amino-6-(2,4-difluorophenyl)-2-(2-(2-methylpyridin-4-yl)morpholino)pyrimidine-5-carbaldehyde | (S)-2-(2-methylpyridin-4-yl)morpholine (Intermed Ltd. Kiev, Ukraine) |
| 107 | (structure) | (S)-4-amino-2-(2-(1-cyclopropyl-1H-pyrazol-4-yl)morpholino)-6-(2,4-difluorophenyl)pyrimidine-5-carbaldehyde | (S)-2-(1-cyclopropyl-1H-pyrazol-4-yl)morpholine (Azepine Ltd. Hampshire, UK) |

Method 29

Intermediate 117: 2,4-dichloro-7-methylpteridine

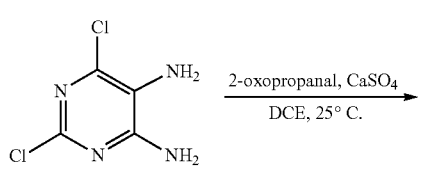

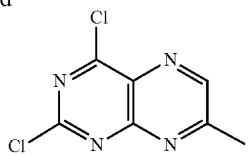

To a suspension of 2,6-dichloropyrimidine-4,5-diamine (5.00 g, 27.9 mmol) in DCE (250 mL) was added calcium sulfate (10.0 g, 73.5 mmol) followed by a dropwise addition of 2-oxopropanal (40% in water, 5.0 ml, 32.1 mmol). The reaction was stirred at 25° C. overnight then filtered through a plug of celite and evaporated under reduced pressure to afford the desired material as a light-yellow solid. (5.3 g, 88%). MS (m/z+): 215.0 [M+1]$^+$, $^1$H NMR (400 MHz, chloroform-d): 8.93 (1H, s), 2.91 (3H, s).

TABLE 19

Intermediate 118 was prepared following the procedure described in Method 29, as follows:

| Int # | Structure | Name | Starting Material 1 | Starting Material 2 |
|---|---|---|---|---|
| 118 | (structure) | 2,4-dichloro-6,7-bis(methyl-d3)pteridine | 2,6-dichloropyrimidine-4,5-diamine | biacetyl-d6 |

Method 30

Intermediate 119: 4-((2R,4S)-4-bromotetrahydro-2H-pyran-2-yl)-1-cyclopropyl-1H-pyrazol

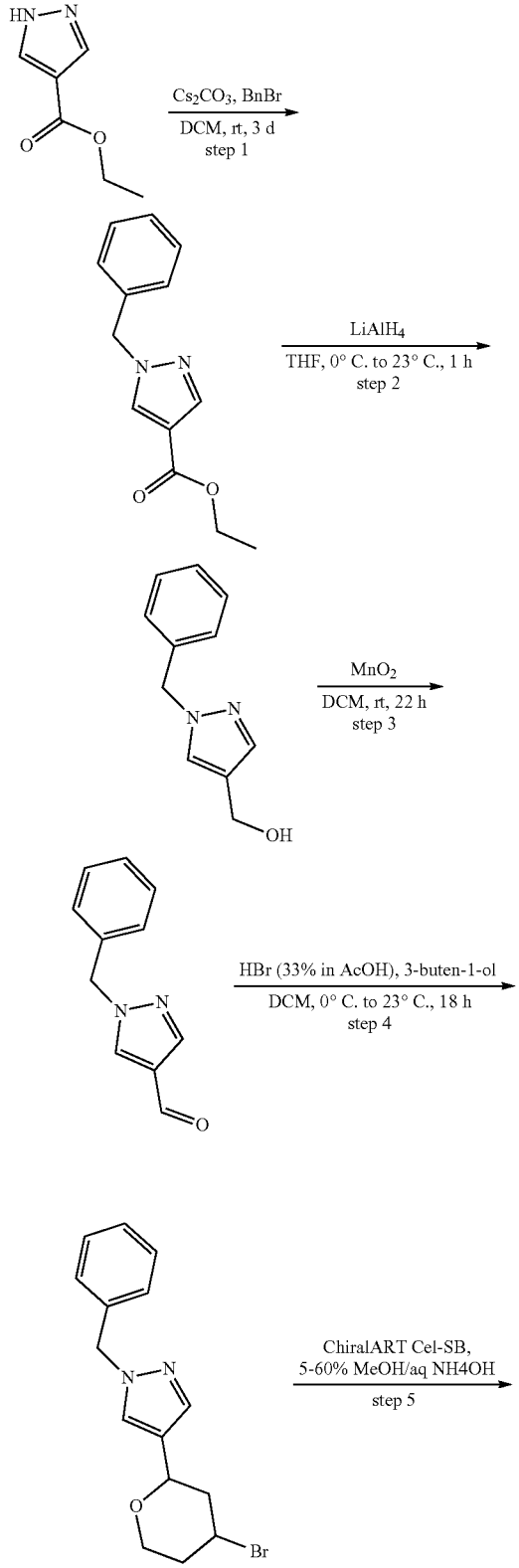

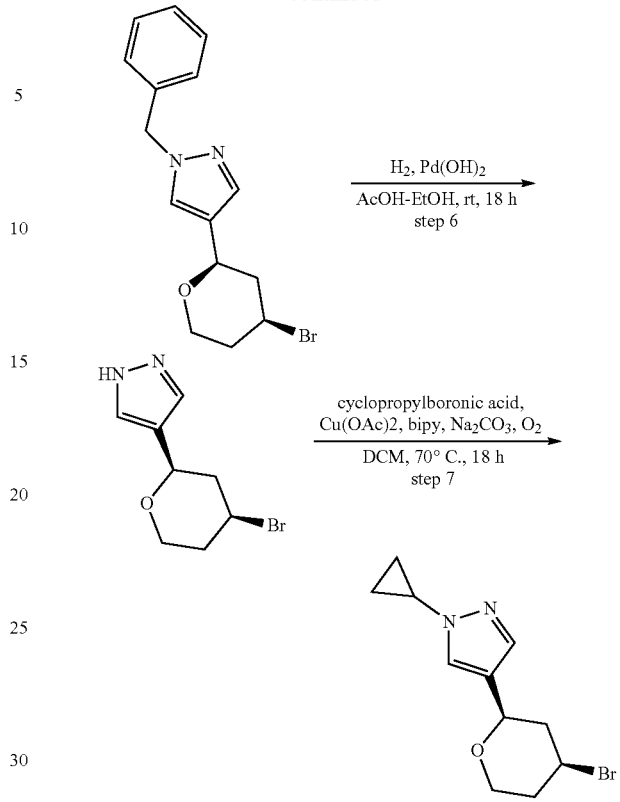

Step 1: Ethyl 1-benzyl-1H-pyrazole-4-carboxylate. To a solution of ethyl 1H-pyrazole-4-carboxylate (11.0 g, 78.5 mmol) in DMF (105 mL) was added cesium carbonate (51.2 g, 157 mmol), followed by benzyl bromide (9.3 mL, 78.4 mmol). The reaction was stirred at r.t. for 3 days. Water was added, and the product was extracted with EtOAc. The combined organic layers were washed several times with $H_2O$, then brine, dried over $Na_2SO_4$, filtered, and concentrated in vacuo to provide ethyl 1-benzyl-1H-pyrazole-4-carboxylate as a colorless syrup (16.7 g, 75.3 mmol, 96% yield). $^1$H NMR (400 MHz, Chloroform-d) δ ppm 7.94 (s, 1H), 7.85 (s, 1H), 7.43-7.30 (m, 3H), 7.26-7.22 (m, 2H), 5.30 (s, 2H), 4.27 (q, J=7.1 Hz, 2H), 1.32 (t, J=7.1 Hz, 3H). LC/MS (ESI$^+$) m/z=231.1 [M+H]$^+$.

Step 2: (1-benzyl-1H-pyrazol-4-yl)methanol. To a solution of ethyl 1-benzyl-1H-pyrazole-4-carboxylate (6.37 g, 27.7 mmol) in THF (69 mL) at 0° C. was added lithium aluminum hydride (2M in THF, 28 mL, 56.0 mmol) slowly. The solution was warmed to r.t. and stirred for 1 hour. The reaction was cooled to 0° C., and water (2.2 mL) was added dropwise, followed by 1M NaOH (6.0 mL) and water (2.2 mL). The solid was filtered through celite, and the filter cake was rinsed with EtOAc. The filtrate was concentrated in vacuo to provide (1-benzyl-1H-pyrazol-4-yl)methanol (4.43 g, 22.8 mmol, 85% yield) as a colorless syrup. $^1$H NMR (400 MHz, Chloroform-d) δ ppm 7.54 (s, 1H), 7.41-7.28 (m, 4H), 7.25-7.19 (m, 2H), 5.28 (s, 2H), 4.57 (s, 2H). LC/MS (ESI$^+$) m/z=189.1 [M+H]$^+$.

Step 3: 1-benzyl-1H-pyrazole-4-carbaldehyde. To a solution of (1-benzyl-1H-pyrazol-4-yl)methanol (4.43 g, 22.8 mmol) in DCM (40 mL) was added activated manganese (IV) oxide (20.7 g, 235 mmol) portionwise. The mixture stirred overnight at r.t. The solid was filtered through celite and rinsed with DCM. The filtrate was concentrated in vacuo, and the crude material was purified by silica gel chromatography eluting with 0-40% EtOAc in hexanes to provide 1-benzyl-1H-pyrazole-4-carbaldehyde-1 (3.41 g, 18.3 mmol, 76% yield) as a colorless syrup. $^1$H NMR (400 MHz, Chloroform-d) δ ppm 9.84 (s, 1H), 8.00 (s, 1H), 7.87 (s, 1H), 7.44-7.32 (m, 3H), 7.31-7.21 (m, 2H), 5.34 (s, 2H). LC/MS (ESI$^+$) m/z=187.1 [M+H]$^+$.

Step 4: 1-benzyl-4-(4-bromotetrahydro-2H-pyran-2-yl)-1H-pyrazole. To a solution of 1-benzyl-1H-pyrazole-4-carbaldehyde (3.05 g, 16.4 mmol) and 3-buten-1-ol (1.5 mL, 17.0 mmol) in DCM (41 mL) at 0° C. was added hydrobromic acid, 33% in acetic acid (8.1 mL, 49.1 mmol) dropwise. The solution was slowly warmed to r.t. overnight. The solution was then cooled to 0° C. and slowly quenched with saturated NaHCO$_3$ solution. The product was extracted with DCM. The combined organic layers were washed with brine, dried over Na$_2$SO$_4$, filtered, and concentrated in vacuo. The crude material was purified by silica gel chromatography eluting with 0-35% EtOAc in hexanes to provide 1-benzyl-4-(4-bromotetrahydro-2H-pyran-2-yl)-1H-pyrazole (4.13 g, 12.9 mmol, 75% yield) as a 1:1 mixture of cis/trans diastereomers. ($^1$H NMR reported as a 1:1 mixture of cis and trans.) $^1$H NMR (400 MHz, Chloroform-d) δ ppm 7.50 (s, 2H), 7.39-7.27 (m, 8H), 7.24-7.19 (m, 4H), 5.26 (s, 4H), 4.90 (dd, J=9.8, 3.1 Hz, 1H), 4.76 (t, J=3.4 Hz, 1H), 4.33 (dd, J=11.4, 2.0 Hz, 1H), 4.21 (tt, J=11.8, 4.5 Hz, 1H), 4.13-4.01 (m, 2H), 3.92 (dd, J=12.3, 4.7 Hz, 1H), 3.54 (td, J=12.1, 2.3 Hz, 1H), 2.48 (dt, J=14.0, 2.8 Hz, 1H), 2.25-2.18 (m, 2H), 2.18-2.12 (m, 3H), 2.11-2.03 (m, 1H), 1.99-1.87 (m, 1H). LC/MS (ESI$^+$) m/z=320.9 [M+H]$^+$.

Step 5: 1-benzyl-4-((2R,4S)-4-bromotetrahydro-2H-pyran-2-yl)-1H-pyrazole. The racemic product was purified by chiral SFC on a ChiralART Cel-SB column, 5 to 60% MeOH in aqueous NH$_4$OH solution to provide 1-benzyl-4-((2R,4S)-4-bromotetrahydro-2H-pyran-2-yl)-1H-pyrazole. $^1$H NMR (400 MHz, Chloroform-d) δ ppm 7.50 (s, 1H), 7.44-7.28 (m, 4H), 7.22 (d, J=7.1 Hz, 2H), 5.26 (s, 2H), 4.33 (dd, J=11.4, 2.2 Hz, 1H), 4.26-4.13 (m, 1H), 4.12-3.95 (m, 1H), 3.54 (tt, J=12.1, 2.2 Hz, 1H), 2.48 (ddd, J=13.1, 4.5, 2.2 Hz, 1H), 2.27-2.18 (m, 1H), 2.11 (qd, J=11.9, 5.1 Hz, 2H). LC/MS (ESI+) m/z=321.0 [M+H]$^+$.

Step 6: 4-((2R,4S)-4-bromotetrahydro-2H-pyran-2-yl)-1H-pyrazole. A solution 1-benzyl-4-((2R,4S)-4-bromotetrahydro-2H-pyran-2-yl)-1H-pyrazole (400 mg, 1.25 mmol) in EtOH (6.5 mL) and acetic acid (2.2 mL) was purged with argon via balloon and outlet for 10 minutes. Palladium hydroxide on carbon (70 mg, 0.25 mmol) was added quickly, and the solution was purged with argon via balloon and outlet for another 10 minutes. The argon balloon was replaced with a hydrogen balloon, and the reaction stirred at r.t. overnight. The catalyst was removed by filtration over celite and washed with ethanol several times. The filtrate was concentrated in vacuo. The crude material was purified by silica gel chromatography eluting with 30-100% EtOAc in hexanes to provide 4-((2R,4S)-4-bromotetrahydro-2H-pyran-2-yl)-1H-pyrazole (160 mg, 0.692 mmol, 56% yield) as a white solid. $^1$H NMR (400 MHz, DMSO-d6) δ ppm 12.70 (s, 1H), 7.68 (s, 1H), 7.44 (s, 1H), 4.50 (td, J=12.0, 5.9 Hz, 1H), 4.37 (dd, J=11.1, 2.1 Hz, 1H), 3.91 (dd, J=11.8, 4.8 Hz, 1H), 3.51 (td, J=12.0, 2.1 Hz, 1H), 2.43 (dt, J=13.0, 2.6 Hz, 1H), 2.26-2.12 (m, 1H), 2.07-1.87 (m, 2H). LC/MS (ESI+) m/z=230.0 [M+H]$^+$.

Step 7: 4-((2R,4S)-4-bromotetrahydro-2H-pyran-2-yl)-1-cyclopropyl-1H-pyrazole. To a solution of 4-((2R,4S)-4-bromotetrahydro-2H-pyran-2-yl)-1H-pyrazole (150 mg, 0.649 mmol) and cyclopropylboronic acid (112 mg, 1.30 mmol) in dichloroethane (4.3 mL) at 70° C. was added a mixture of copper(II) acetate (119 mg, 0.649 mmol) and 2,2'-dipyridyl (101 mg, 0.649 mmol) in one portion. The mixture was stirred at 70° C. overnight under oxygen atmosphere. The mixture was cooled to r.t., and saturated NaHCO$_3$ was added. The product was extracted with DCM, and the combined organic layers were washed with brine, dried over Na$_2$SO$_4$, filtered, and concentrated in vacuo. The crude product was purified by silica gel chromatography eluting with 10-60% EtOAc in hexanes to provide 4-((2R, 4S)-4-bromotetrahydro-2H-pyran-2-yl)-1-cyclopropyl-1H-pyrazole (160 mg, 0.561 mmol, 86% yield) as a yellow oil. $^1$H NMR (400 MHz, DMSO-d6) δ ppm 7.73 (s, 1H), 7.36 (s, 1H), 4.49 (tt, J=11.9, 4.4 Hz, 1H), 4.32 (dd, J=11.2, 2.0 Hz, 1H), 3.90 (ddd, J=11.8, 5.0, 1.8 Hz, 1H), 3.65 (tt, J=7.4, 3.9 Hz, 1H), 3.49 (td, J=12.0, 2.1 Hz, 1H), 2.41 (ddt, J=12.6, 4.3, 2.1 Hz, 1H), 2.17 (ddd, J=12.7, 4.5, 2.2 Hz, 1H), 2.05-1.86 (m, 2H), 1.05-0.95 (m, 2H), 0.95-0.87 (m, 2H). LC/MS (ESI+) m/z=270.8 [M+H]$^+$.

Method 31

Intermediate 120: 4-((2R, 4S, 6R)-4-bromo-6-methyltetrahydro-2H-pyran-2-yl)-1-cyclopropyl-1H-pyrazole

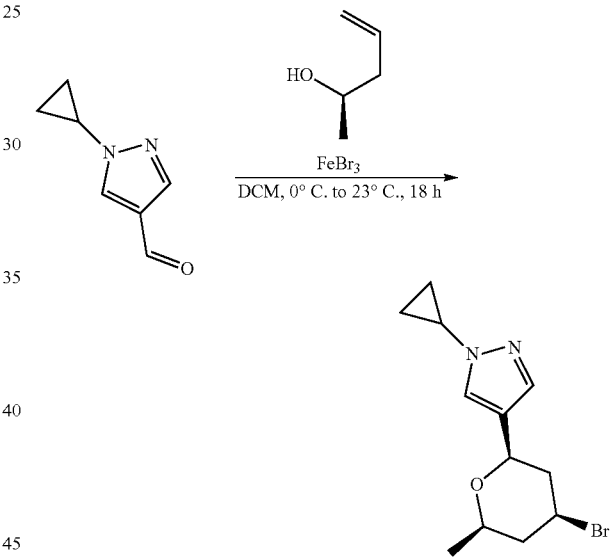

To iron (iii) bromide (3.20 g, 10.8 mmol) in a flame-dried 40 mL pressure vial equipped with a stir bar under argon was added a solution of 1-cyclopropylpyrazole-4-carbaldehyde (1.23 g, 9.03 mmol) and (2R)-pent-4-en-2-ol (778 mg, 9.03 mmol) in DCM (17 mL) under N$_2$ at 0° C. The reaction mixture was warmed to r.t. and stirred overnight. Water was added (20 mL), and the mixture was stirred for 30 mins. The product was extracted with DCM, and the combined organic layers were washed with brine, dried over Na$_2$SO$_4$, filtered, and concentrated in vacuo. The crude material was purified by silica gel chromatography eluting with 0-30% EtOAc in hexanes, followed by reverse phase chromatography eluting with 5-95% MeCN in H$_2$O to provide 4-[(2R,4S,6R)-4-bromo-6-methyl-tetrahydropyran-2-yl]-1-cyclopropyl-pyrazole (612 mg, 2.10 mmol, 23% yield) as a clear syrup. $^1$H NMR (400 MHz, Chloroform-d) δ ppm 7.66-7.34 (m, 2H), 4.36 (dd, J=11.4, 2.0 Hz, 1H), 4.22 (tt, J=12.1, 4.5 Hz, 1H), 3.60 (ddd, J=11.0, 6.2, 1.9 Hz, 1H), 3.54 (tt, J=7.3, 3.9 Hz, 1H), 2.45 (ddt, J=13.0, 4.4, 2.0 Hz, 1H), 2.28 (ddt, J=12.9, 4.1, 2.0 Hz, 1H), 2.06 (q, J=12.0 Hz, 1H), 1.78 (td, J=12.5, 11.0 Hz, 1H), 1.25 (d, J=6.2 Hz, 3H), 1.13-1.05 (m, 2H), 1.04-0.94 (m, 2H). LC/MS (ESI⁺) m/z=285.0 [M+H]⁺

Method 32

Intermediate 121: 4-((2R,4S)-4-bromotetrahydro-2H-pyran-2-yl)-1-methyl-1H-pyrazole

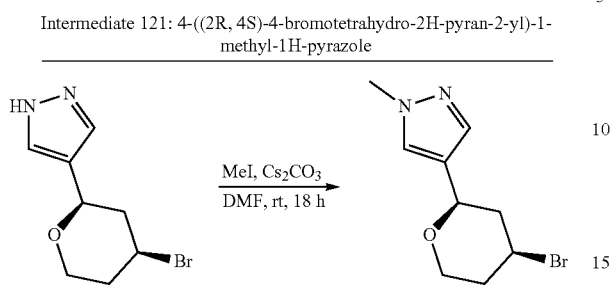

To a solution of 4-((2R,4S)-4-bromotetrahydro-2H-pyran-2-yl)-1H-pyrazole (25 mg, 0.108 mmol) in DMF (2.2 mL) was added cesium carbonate (88 mg, 0.270 mmol), followed by methyl iodide (0.0081 mL, 0.130 mmol). The reaction was stirred at r.t. overnight. Water was added, and the product was extracted with EtOAc. The combined organic layers were washed several times with H₂O, then brine, dried over Na₂SO₄, filtered, and concentrated in vacuo. The crude material was purified by silica gel chromatography eluting with 0-5% MeOH in DCM to provide 4-((2R,4S)-4-bromo-tetrahydro-2H-pyran-2-yl)-1-methyl-1H-pyrazole (18 mg, 0.0734 mmol, 68% yield) as a colorless solid. ¹H NMR (400 MHz, DMSO-d₆) δ ppm 7.64 (s, 1H), 7.36 (s, 1H), 4.50 (tt, J=12.0, 4.6 Hz, 1H), 4.33 (d, J=11.3 Hz, 1H), 3.90 (dd, J=11.8, 4.8 Hz, 1H), 3.78 (s, 3H), 3.50 (td, J=11.8, 2.0 Hz, 1H), 2.41 (d, J=12.5 Hz, 1H), 2.17 (dd, J=9.9, 6.4 Hz, 1H), 2.04-1.85 (m, 2H). LC/MS (ESI⁺) m/z=245.0 [M+H]⁺. The absolute configuration of the starting material 4-((2R,4S)-4-bromotetrahydro-2H-pyran-2-yl)-1H-pyrazole was elucidated by X-ray crystallography.

Method 33

Intermediate 122: 2-(methylpyridine-4-yl)morpholine

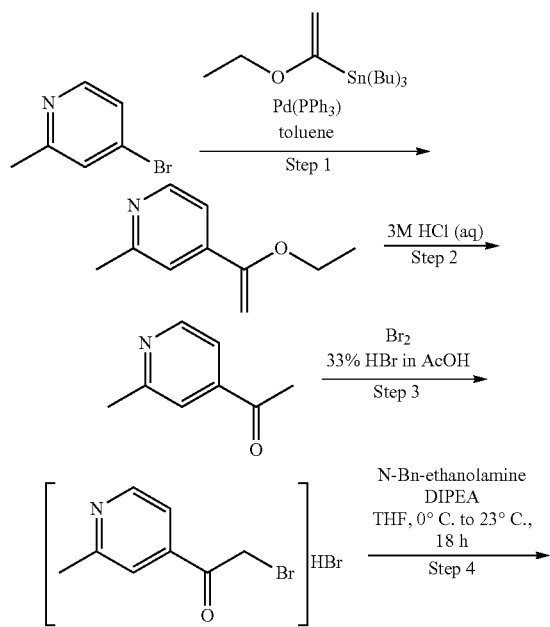

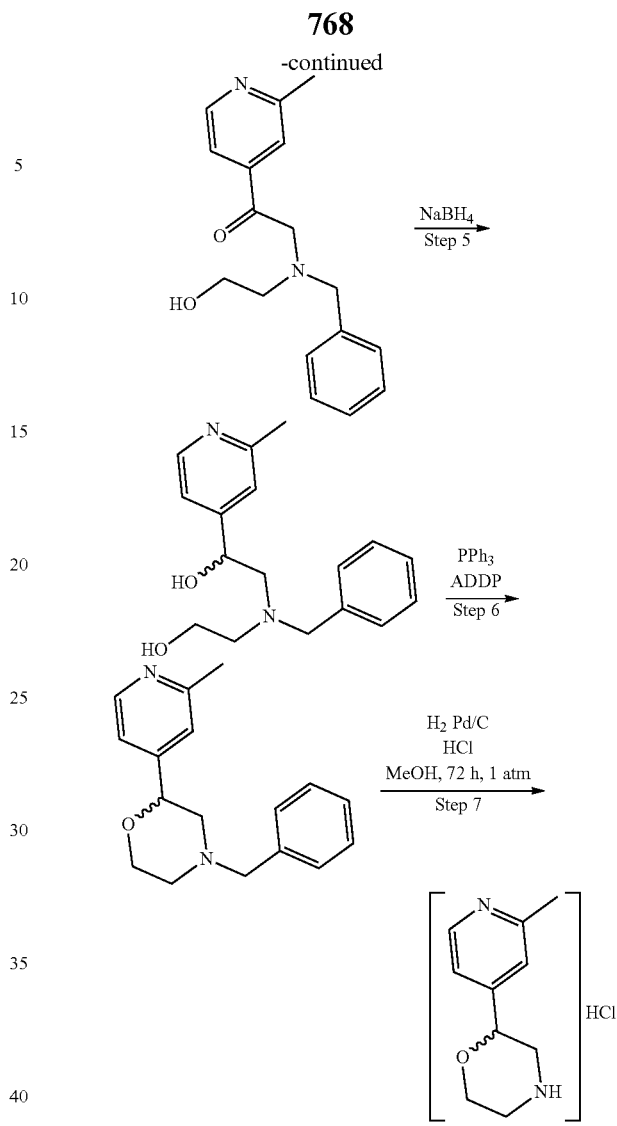

Step 1: 4-(1-ethoxyvinyl)-2-methylpyridine. A 250 mL pressure vessel was charged with 4-bromo-2-methylpyridine (6.90 mL, 58.1 mmol), 1-ethoxyvinyltributyltin (21.6 mL, 63.9 mmol, 1.1 equiv.) and toluene (100 mL) was purged N₂ gas at rt for 10 min. Tetrakis(triphenylphosphine)palladium (2.04 g, 2.91 mmol, 5 mol%) was added under N₂ atmosphere and the reaction mixture was purged with N₂ gas for 5 min at rt. The reaction vessel was sealed and stirred at 110° C. for 16 h. When the reaction was judged complete by LCMS, the reaction mixture was cooled to rt and KF (3.72 g, 1.1 equiv.), Na₂CO₃ (6.78 g, 1.1 equiv.) and silica (30 g) were added. The reaction mixture was stirred for 10 min and filtered through a pad of celite. The celite bed was washed with hexane (50 mL) and the combined filtrate was concentrated under reduced pressure. The crude residue was purified by column chromatography using silica gel, eluting with 0-5% EtOAc in hexane to afford 4-(1-ethoxyvinyl)-2-methylpyridine as a colorless oil (7.46 g, 79%). ¹H NMR (400 MHz, DMSO-d6): δ_H 8.41 (d, J=5.2 Hz, 1H), 7.35 (s, 1H), 8.41 (d, J=4.7 Hz, 1H), 5.01 (s, 1H), 4.46 (s, 1H), 3.91 (q, J=6.9 Hz, 2H), 2.47 (s, 3H), 1.35 (t, J=6.9 Hz, 3H). ESI-MS (m/z+): 164.2 [M+H]⁺, LC-RT: 0.505 min.

Step 2: 1-(2-methylpyridin-4-yl)ethan-1-one. A suspension of 5-(1-ethoxyvinyl)-2-methylpyridine (7.46 g, 45.7 mmol) in 3M HCl (30.5 mL, 91.4 mmol, 2 equiv.) was stirred at rt for 30 min. When the reaction was judged to be complete by LCMS, the reaction mixture was diluted with water (60 mL), basified to pH 11 with 5M NaOH and extracted with EtOAc (3×60 mL). The organic layer was dried (Na$_2$SO$_4$), filtered and concentrated under reduced pressure to afford 1-(2-methylpyridin-4-yl)ethan-1-one as a colorless oil (5.35 g, 82%). $^1$H NMR (400 MHz, DMSO-d6): $\delta_H$ 8.65 (d, J=5.0 Hz, 1H), 7.69 (s, 1H), 7.60 (d, J=4.2 Hz, 1H), 2.49 (s, 3H), 2.57 (s, 3H). ESI-MS (m/z+): 136.10 [M+H]$^+$, LC-RT: 0.202 min.

Step 3: 2-bromo-1-(2-methylpyridin-4-yl)ethan-1-one. A 100 mL round bottom flask was charged with 1-(2-methylpyridin-4-yl)ethan-1-one (5.00 g, 37.0 mmol) and HBr (33% in AcOH, 21 mL). The reaction mixture was cooled to 0° C. using an ice/water bath and a solution of bromine (1.9 mL, 37.0 mmol, 1.0 equiv.) in HBr (33% in AcOH, 7 ml) was added dropwise. The reaction mixture was stirred at 40° C. for 1 h and then further stirred at 80° C. for 1 h. When the reaction was judged complete by LCMS, the reaction mixture was cooled to rt, poured in Et$_2$O (100 mL) and stirred at rt for 30 min. The precipitate was filtered, washed with Et$_2$O (50 mL) and dried under reduced pressure to afford 2-bromo-1-(2-methylpyridin-4-yl)ethan-1-one (HBr salt) as a yellow solid (10.7 g, 96%). ESI-MS (m/z+): 274.0 [M+H]$^+$, LC-RT: 1.459 min.

Step 4: 2-(benzyl(2-hydroxyethyl)amino)-1-(2-methylpyridin-4-yl)ethan-1-one. To a solution of 2-bromo-1-(2-methylpyridin-4-yl)ethan-1-one acetate (10.7 g, 39.0 mmol) in THF (182 mL) at 0° C. was slowly added N-benzylethanolamine (5.54 mL, 39.0 mmol, 1.0 equiv.) followed by DIPEA (13.6 mL, 78.1 mmol). The reaction was slowly warmed to r.t. overnight, after which a precipitate formed. The solvent was removed in vacuo. Water was then added to the reaction mixture and the aqueous phase was extracted with EtOAc (3×100 mL). The combined organic phases were dried over Na$_2$SO$_4$, filtered, and concentrated in vacuo to provide 2-(benzyl(2-hydroxyethyl)amino)-1-(2-methylpyridin-4-yl)ethan-1-one (11.1 g, 100%) as a yellow solid. ESI-MS (m/z+): 285.10 [M+H]$^+$, LC-RT: 0.642 min.

Step 5: 2-(benzyl(2-hydroxyethyl)amino)-1-(2-methylpyridin-4-yl)ethan-1-one. A 500 mL round bottom flask was charged with 2-(benzyl(2-hydroxyethyl)amino)-1-(2-methylpyridin-4-yl)ethan-1-one (11.10 g, 39.0 mmol, 1 equiv.) in methanol (390 mL) and was cooled to 0° C. Sodium borohydride (2.95 g, 78.1 mmol, 2.0 equiv.) was added portion wise then the reaction was gradually warmed to r.t. over 12 h. When the reaction was judged to be complete by LCMS, the solution was cooled to 0° C., and water (250 mL) was added. The product was extracted with EtOAc (3×100 mL), and the combined organic layers were washed with brine, dried over Na$_2$SO$_4$, filtered, and concentrated in vacuo to give the pure product 2-(benzyl(2-hydroxyethyl)amino)-1-(2-methylpyridin-4-yl)ethan-1-ol (8.45 g, 29.5 mmol, 75.6%) as a clear oil. ESI-MS (m/z+): 287.20 [M+H]$^+$, LC-RT: 0.215 min.

Step 6: 2-(2-methylpyridin-4-yl)morpholine hydrochloride. A flame-dried 50 mL round bottom flask under nitrogen was charged with 4-benzyl-2-(2-methyl-4-pyridyl)morpholine (1.00 eq, 1.35 g, 5.03 mmol), Pd/C (0.252 eq, 135 mg, 1.27 mmol) and HCl (4M in dioxanes, 1.00 eq, 5.03 mmol). The reaction vial was purged with N$_2$ then the reaction mixture was bubbled with H$_2$ for 2 min. The needle was removed from the solution and the reaction was stirred at r.t. under positive pressure of H$_2$ (balloon) overnight. Complete conversion was observed by TLC and LCMS. The reaction mixture was filtrated on a pad of Celite and the solvent was removed in vacuo to yield the desired 2-(2-methyl-4-pyridyl)morpholine hydrochloride (1.01 g, 4.70 mmol, 93.51%). ESI-MS (m/z+): 179.1 [M+H]+, LC-RT: 0.240 min. $^1$H NMR (DMSO-d6, 400 MHz): $\delta_H$ 8.53 (1H, d, J=5.4 Hz), 7.45 (1H, s), 7.36 (1H, d, J=5.3 Hz), 4.94 (1H, d, J=11.0 Hz), 4.13 (1H, d, J=12.7 Hz), 4.00 (1H, t, J=12.3 Hz), 3.52 (1H, d, J=12.7 Hz), 3.06 (1H, t, J=12.4 Hz), 2.90 (1H, t, J=11.9 Hz), 2.54 (3H, s).

Method 34

Intermediate 123: 2-(1-cyclopropyl-1H-pyrazol-4-yl)-6-methylmorpholine

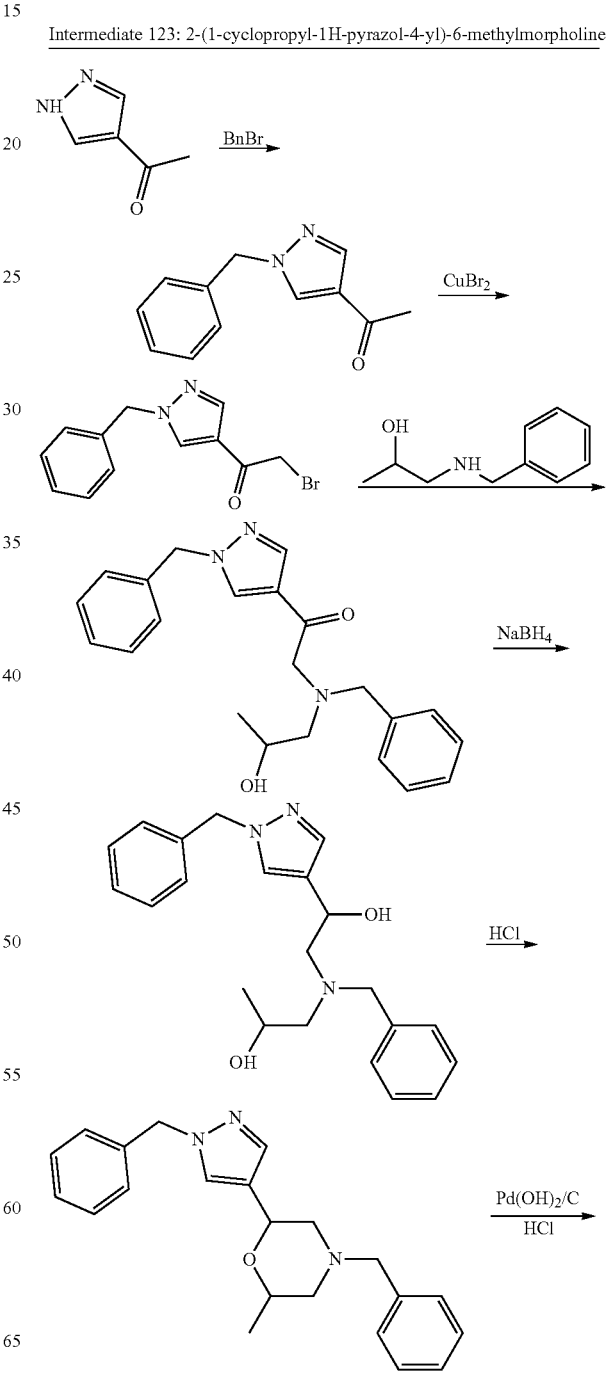

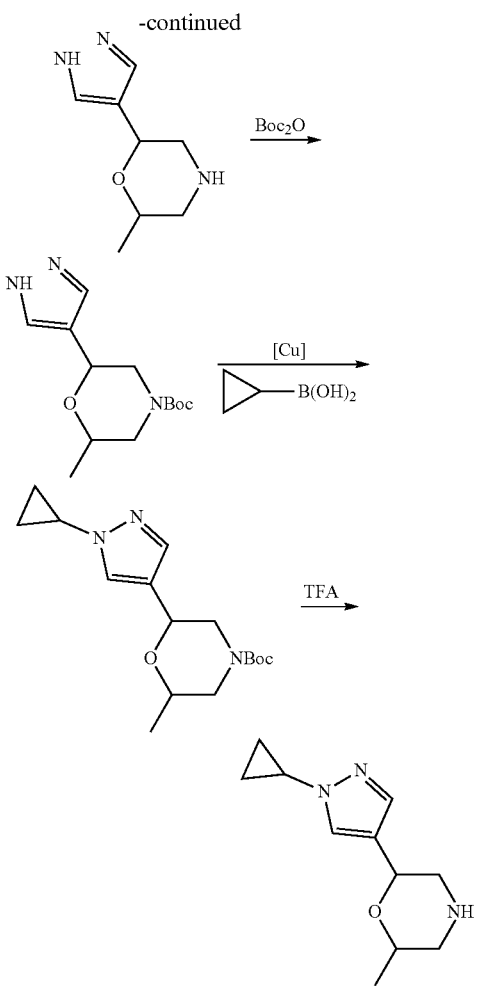

Step 1: To a stirred solution of 1-(1H-pyrazol-4-yl) ethan-1-one (10 g, 0.1 mol) and Cs$_2$CO$_3$ (48.3 g, 0.15 mol) in DMF (100 mL) was added (bromomethyl)benzene (20.3 g, 0.12 mol) drop wise at room temperature under N$_2$. The reaction was stirred at 80° C. for 1 h. The mixture was poured into water (500 mL) and extracted with EA (100 mL×3). The organic phase was washed with brine (100 mL×2), dried over Na$_2$SO$_4$ and filtered. The filtration was concentrated under vacuum, the residue was purified by column chromatography on silica gel (PE: EA=5:1) to afford 1-(1-benzyl-1H-pyrazol-4-yl) ethan-1-one (16.0 g) as a light yellow solid. LCMS: (M+H)$^+$=201.1; purity=97.36% (UV 254 nm); retention time=1.542 min.

Step 2: To a solution of 1-(1-benzyl-1H-pyrazol-4-y) ethan-1-one (3.9 g, 19.47 mmol) in 1,4-dioxane(40 mL) was added CuBr$_2$(7.23 g, 32.37 mmol) at rt. After addition, the reaction mixture was stirred at 85° C. for 7 h. The reaction mixture was poured into water (160 mL) and extracted with EA (80 mL×3). The combined organic layers were dried over anhydrous Na$_2$SO$_4$, filtered and concentrated. The crude product was purified by silica gel column (PE/EA, 1:10 to 1:5) to give 1-(1-benzyl-1H-pyrazol-4-yl)-2-bromoethan-1-one (2.9 g, 10.39 mmol) as a white solid. LCMS: (M+H)$^+$=280; Retention time=1.75 min.

Step 3: To a solution of compound 1-(1-benzyl-1H-pyrazol-4-yl)-2-bromoethan-1-one (2.9 g, 10.39 mmol) in THF (20 mL) at room temperature was slowly added 1-(benzylamino)propan-2-ol (1.89 g, 11.44 mmol) under N$_2$. The reaction mixture was stirred at 35° C. for 3 hour to give a yellow solution. Water (20 mL) was added drop wise to quench the reaction. The reaction mixture was extracted with EA (50 mL×3). The combined organic layer was dried over anhydrous Na$_2$SO$_4$, filtered and concentrated under reduced pressure. The combined crude material was absorbed onto a plug of silica gel and purified by chromatography through a silica gel column eluting with a silica gel column (PE/EA, 1:10 to 1:2) provide compound 2-(benzyl (2-hydroxypropyl)amino)-1-(1-benzyl-1H-pyrazol-4-yl) ethan-1-one (2.81 g, 7.73 mmol). LCMS: (M+H)$^+$=364; Retention time=1.34 min.

Step 4: To a solution of compound 2-(benzyl(2-hydroxypropyl)amino)-1-(1-benzyl-1H-pyrazol-4-yl)ethan-1-one (2.8 g, 7.70 mmol) in methanol (28 mL) at 0° C. was added sodium tetrahydroborate (0.58 g, 15.40 mmol) portion wise. The reaction mixture was stirred at 0° C. for 30 min and then at room temperature for 2 h. Ice-cooled water (20 mL) was added drop wise to quench the reaction. The reaction mixture was extracted with EA (50 mL×3). The combined organic layers were dried over anhydrous Na$_2$SO$_4$, filtered and concentrated to give 1-(benzyl(2-(1-benzyl-1H-pyrazol-4-yl)-2-hydroxyethyl)amino)propan-2-ol (2.8 g, 7.66 mmol) as a yellow liquid compound, which was used directly for next step without further purification. LCMS: (M+H)$^+$=366; Retention time=1.42 min.

Step 5: To a solution of compound 1-(benzyl(2-(1-benzyl-1H-pyrazol-4-yl)-2-hydroxyethyl)amino)propan-2-ol (2.8 g, 7.66 mmol) in 1,4-dioxane (15 mL) at room temperature was slowly added 6M HCl (15 ml). The reaction mixture was stirred at 110° C. for 4 h. 15% KOH was added drop wise to quench the reaction, adjust pH 8-9. The reaction mixture was extracted with EA (100 mL×3). The combined organic layers were dried over anhydrous Na$_2$SO$_4$, filtered and concentrated to give 4-benzyl-2-(1-benzyl-1H-pyrazol-4-yl)-6-methylmorpholine (2.39 g, 6.88 mmol) as a yellow liquid compound, which was used directly for next step without further purification. LCMS: (M+H)$^+$=348; Retention time=1.40 min.

Step 6: To a solution of 4-benzyl-2-(1-benzyl-1H-pyrazol-4-yl)-6-methylmorpholine (2.39 g, 6.88 mmol) in methanol (12 mL) and 2.4 mL HCl(6 M) was added Pd(OH)$_2$/C(0.48 g), the reaction mixture was stirred at 30° C. for 16 h. The reaction mixture was filtered and the filtrate was concentrated under vacuum, the residue was adjusted ph to 9-10 by Na$_2$CO$_3$ aq. The aqueous phase was directly used in next step. LCMS: (M+H)$_+$=168; Retention time=0.37 min.

Step 7: To a solution of step 6 in water/1,4-dioxane(10 mL/10 mL) was added Na$_2$CO$_3$ (0.88 g, 8.30 mml) and BoC$_2$O (1.58 g, 7.24 mmol). The reaction mixture was stirred at room temperature for 1 h. The reaction mixture was poured into water (20 mL) and extracted with EA (50 ml×3). The combined organic layers were dried over anhydrous Na$_2$SO$_4$, filtered and concentrated to give tert-butyl 2-methyl-6-(1H-pyrazol-4-yl)morpholine-4-carboxylate crude. The crude product was directly used in next step. LCMS: (M+H)$^+$=268; Retention time=1.57 min.

Step 8: To a solution of tert-butyl 2-methyl-6-(1H-pyrazol-4-yl)morpholine-4-carboxylate (1.77 g, 6.62 mmol) in DMF(35 mL) was added to cyclopropylboronic acid (1.71 g, 19.9 mmo1), Cu(OAc)$_2$ (1.32 g, 7.27 mmol), Na$_2$CO$_3$(1.40 g, 13.2 mmol), 2,2'-Dipyridyl(1.14 g, 7.30 mmol) at room temperature. The reaction mixture was stirred at 80° C. for 10 h.The mixture was poured into water (100 mL) and extracted with EA (60 mL×3). The organic phase was washed with brine (60 mL×2), dried over Na$_2$SO$_4$ and filtered. The filtrate was concentrated under vacuum, The crude product was purified by silica gel column (PE/EA, 1:10 to 1:5) to give tert-butyl 2-(1-cyclopropyl-1H-pyrazol-4-yl)-6-methylmorpholine-4-carboxylate (1.6 g, 5.20 mmol) as a yellow liquid. LCMS: (M+H)+=308; Retention time=1.51 min.

Step 9: To a solution of tert-butyl 2-(1-cyclopropyl-1H-pyrazol-4-yl)-6-methylmorpholine-4-carboxylate (1.6 g, 5.20 mmol) in dichloromethane (10 mL) was added TFA (3 mL), The reaction mixture was stirred at room temperature for 1 h. The filtrate was concentrated under vacuum to give 2-(1-cyclopropyl-1H-pyrazol-4-yl)-6-methylmorpholine (1.02 g, 4.93 mmol) as a yellow liquid. LCMS: (M+H)+=208; Retention time=1.14 min.
Method 35

Intermediate 124: 2-chloro-4-(4-chloro-2,3-difluoro-phenyl)-6,7-dimethyl-pteridine

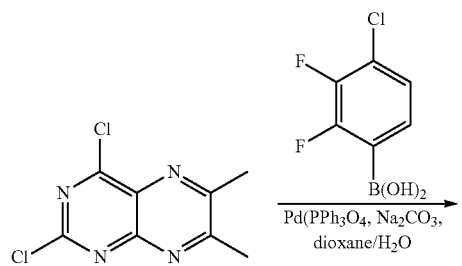

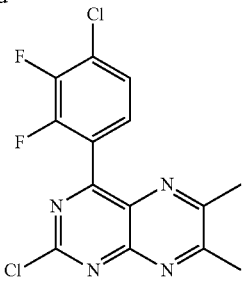

To a 20 mL microwave vial was added 2,4-dichloro-6,7-dimethyl-pteridine (500 mg, 2.18 mmol), (4-chloro-2,3-difluoro-phenyl)boronic acid (420 mg, 2.18 mmol), sodium carbonate (694 mg, 6.55 mmol), 1,4-dioxane (10 mL) and water (3 mL). The reaction mixture was degassed with nitrogen for 10 min. Pd(PPh$_3$)$_4$ (126 mg, 0.109 mmol) was added and the reaction mixture was heated at 40° C. for 3.5 h. The mixture was cooled to r.t., diluted with DCM (50 mL) and water (10 mL). The aqueous layer was extracted with DCM (2×20 mL). Combined organic layers were washed with brine (10 mL), dried over Na$_2$SO$_4$, and concentrated in vacuo. The crude residue was purified by silica gel chromatography (40 g SilicaSep column) using EtOAc and hexanes (50-60%) to obtain 2-chloro-4-(4-chloro-2,3-difluoro-phenyl)-6,7-dimethyl-pteridine (176 mg, 0.516 mmol, 24%) as a brown solid. ESI-MS (m/z+): 342.0 [M+H]$^+$, LC-RT: 3.579 min. $^1$H NMR (400 MHz, CDCl$_3$) δ ppm 7.53-7.46 (m, 1H), 7.43-7.35 (m, 1H), 2.86 (s, 3H), 2.75 (s, 3H). $^{19}$F NMR (376 MHz, CDCl$_3$) δ ppm −130.92 (s), −137.18 (s).

TABLE 20

Intermediate 125 was prepared following the procedure described in Method 35 using the starting materials indicated:

| Int # | Structure | Name | Starting Material 1 | Starting Material 2 |
| --- | --- | --- | --- | --- |
| 125 | 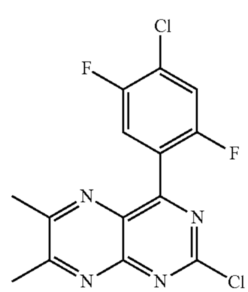 [SMILES: Cc1nc2nc(Cl)nc(-c3cc(F)c(Cl)cc3F)c2nc1C] | 2-chloro-4-(4-chloro-2,5-difluoro-phenyl)-6,7-dimethyl-pteridine | 2,4-dichloro-6,7-dimethyl-pteridine (intermediate 3) | (4-chloro-2,5-difluoro-phenyl)boronic acid |

Method 36

Intermediate 126: 2-chloro-6,7-dimethyl-4-(6-triflouromethyl)pyridin-3-yl)pteridine

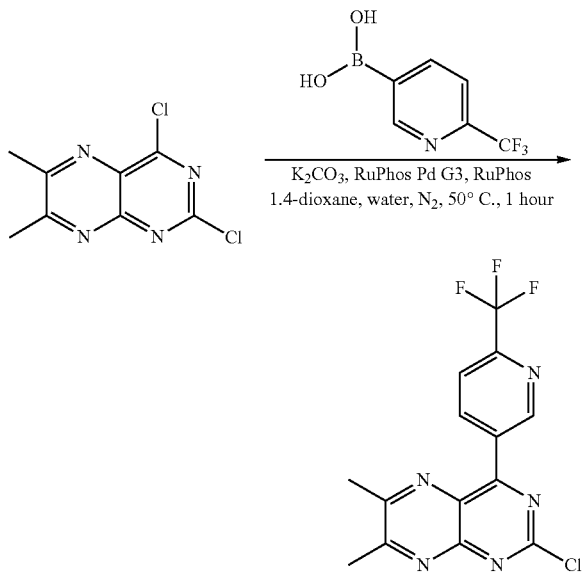

To a 20 mL sealed tube was added 2,4-dichloro-6,7-dimethylpteridine (2 eq, 1.2 g, 5.24 mmol) and 2-trifluoromethyl-pyridine-5-boronic acid (1 eq, 500 mg, 2.62 mmol), 1,4-dioxane (24.0 mL) and water (4.0 mL). Potassium carbonate (6 eq, 2.18 g, 15.8 mmol) was added and the reaction mixture was degassed with nitrogen for 10 min. RuPhos Pd G3 (0.1 eq, 200 mg, 283 µmol) was added and the reaction mixture was heated at 50° C. for 1 h. The mixture was cooled down to r.t., diluted with water (50.0 mL) and extracted with EtOAc (3×100 mL). The organic extracts were dried over Na$_2$SO$_4$, filtered and concentrated in vacuo. The crude material was purified by silica gel chromatography (120 g cartridge) using hexanes and EtOAc (50-60%) to afford 2-chloro-6,7-dimethyl-4-(6-(trifluoromethyl)pyridin-3-yl)teridine as a brown solid (867 mg, 65% yield). $^1$H NMR (400 MHz, CDCl$_3$) δ ppm 9.88 (s, 1H), 8.94 (d, J=8.3 Hz, 1H), 7.91 (d, J=8.2 Hz, 1H), 2.89 (s, 3H), 2.83 (s, 3H). $^{19}$F NMR (376 MHz, Chloroform-d) δ ppm –68.2 (s). m/z (ESI+): 340.0 [M+H]$^+$.

Method 43

Intermediate 109: (S)-2-(1-cyclopropyl-1H-pyrazol-4-yl)morpholine

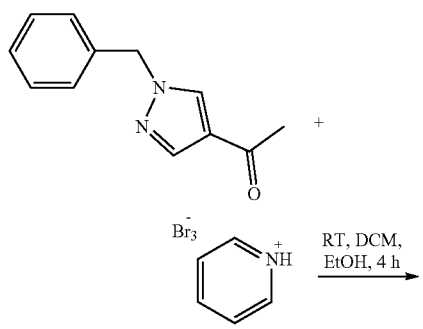

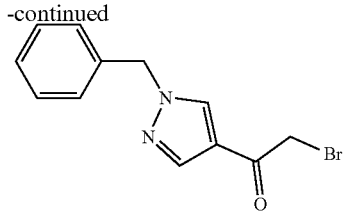

Step 1: To a 3-L round-bottomed flask was added 1-(1-benzyl-1H-pyrazol-4-yl)ethan-1-one (70.0 g, 350 mmol) in dichloromethane (2000 mL) and ethanol (550 mL) and pyridinium tribromide (117 g, 367 mmol) were added portion-wise at RT. The reaction mixture was stirred at RT for 4 h, then the reaction mixture was diluted with 1N sodium sulfate solution (1.5 Lit) and extracted with CH$_2$CL$_2$ (2×1500 mL), and the organic extracts were dried over Na$_2$SO$_4$. The solution was filtered and concentrated in vacuo to give the crude product as an off-white solid. This crude product was directly used for the next step. $^1$H NMR (400 MHz, DMSO-d6): δ ppm 8.65 (s, 1H), 8.05 (s, 1H), 7.28-7.38 (m, 5H), 5.39 (s, 2H), 4.60 (s, 2H).

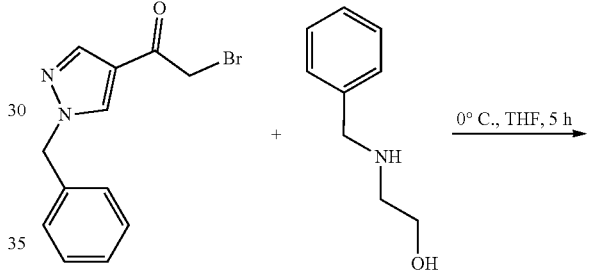

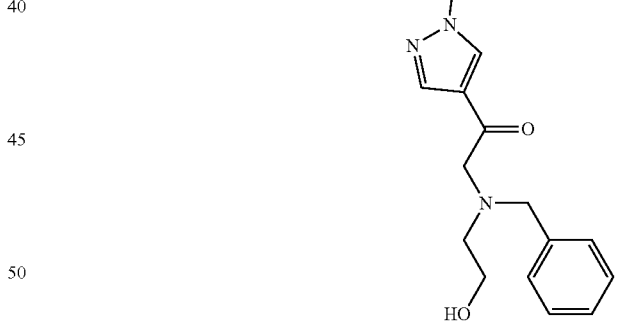

Step 2: To a 3-L round-bottomed flask was added 1-(1-benzyl-1H-pyrazol-4-yl)-2-bromoethan-1-one (203.0 g, 727 mmol) in tetrahydrofuran (2000 mL) and the reaction mixture was cooled to 0° C., then 2-(benzylamino)ethan-1-ol (176 g, 1164 mmol) was added and the reaction mixture was stirred at 0° C. for 30 min, then allowed to stir at RT for 5 h. The reaction mixture was diluted with water (1500 mL) and extracted with EtOAc (2×1500 mL), and the organic extracts were dried over Na$_2$SO$_4$. The solution was filtered and concentrated in vacuo to give the crude material 2-(benzyl(2-hydroxyethyl)amino)-1-(1-benzyl-1H-pyrazol-4-yl)ethan-1-one (240 g, 687 mmol, 94% yield) as a light yellow oil. This crude product was directly used for the next step. $^1$H NMR (400 MHz, DMSO-d6): δ ppm 8.57 (s, 1H), 7.97

(s, 1H), 7.20-7.31 (m, 10H), 5.36 (s, 2H), 4.44 (t, J=5.2 Hz, 1H), 3.68 (d, J=3.1 Hz, 2H), 3.46-3.50 (m, 4H), 2.60 (t, J=6.2 Hz, 2H).

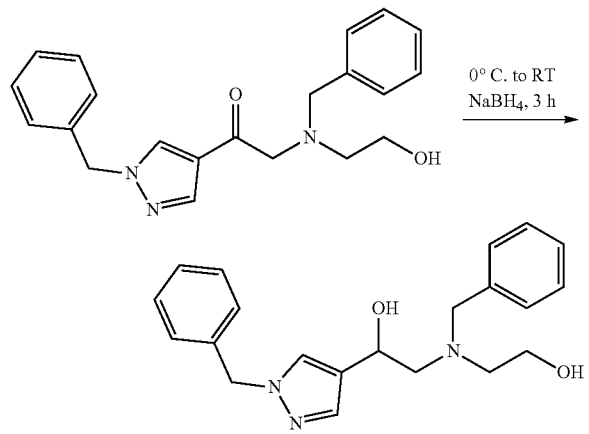

Step 3: To a 3-L round-bottomed flask was added 2-(benzyl(2-hydroxyethyl)amino)-1-(1-benzyl-1H-pyrazol-4-yl)ethan-1-one (240.0 g, 687 mmol) in methanol (2500 mL) and the reaction mixture was cooled to 0° C. Sodium borohydride (52.0 g, 1374 mmol) was added portion wise and the reaction mixture was stirred at 0° C., then allowed to warm to RT and stirred for 3 h. The solvent was evaporated under reduced pressure, the crude material was diluted with water (700 mL) and extracted with CH₂CL₂ (2×500 mL), and the organic extracts were dried over Na₂SO₄. The solution was filtered and concentrated in vacuo to give the crude material (2-(benzyl(2-hydroxyethyl)amino)-1-(1-benzyl-1H-pyrazol-4-yl)ethan-1-ol (236 g, 672 mmol, 98% yield) as a light colourless oil. The crude product was directly used for the next step. ¹H NMR (300 MHz, DMSO-d6): δ ppm 7.62 (s, 1H), 7.19-7.35 (m, 11H), 5.26 (s, 2H), 4.82 (d, J=3.8 Hz, 1H), 4.61-4.64 (m, 1H), 4.37 (t, J=5.4 Hz, 1H), 3.68 (d, J=3.5 Hz, 2H), 3.40-3.46 (m, 2H), 2.64 (m, 4H).

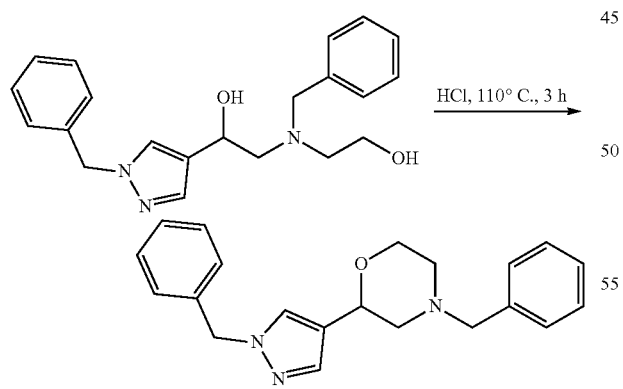

Step 4: To a 3-L round-bottomed flask was added 2-(benzyl(2-hydroxyethyl)amino)-1-(1-benzyl-1H-pyrazol-4-yl)ethan-1-ol (236.0 g, 672 mmol) in 6N HCl (2000 mL, 1.20E+04 mmol) at RT and the reaction mixture was heated at 110° C. for 3 h, then cooled to RT. The solvent was evaporated under reduced pressure to give the crude material. The crude material was dissolved in water (300 mL) and basified with 10% sodium bicarbonate solution up to pH 9 and extracted with ethyl acetate (2×800 mL), and the organic extracts were dried over Na₂SO₄. The solution was filtered and concentrated in vacuo to give the crude material. The crude material was absorbed onto a plug of silica gel and purified by chromatography through a pre-packed silica gel column (330 g), eluting with a gradient of 5% to 80% EtOAc in hexane, to provide 4-benzyl-2-(1-benzyl-1H-pyrazol-4-yl)morpholine (152 g, 456 mmol, 67.9% yield) as light brown oil. ¹H NMR (300 MHz, DMSO-d6): δ ppm 7.74 (s, 1 H), 7.19-7.39 (m, 11H), 5.25 (s, 2H), 4.43-4.46 (dd, J=11.1, 2.3 Hz, 1H), 3.78-3.81 (dd, J=11.7, 2.4 Hz, 1H), 3.49-3.61 (m, 3H), 2.79 (dd, J=12.2, 2.4 Hz, 1H), 2.57-2.65 (m, 1H), 2.05-2.17 (m, 2H).

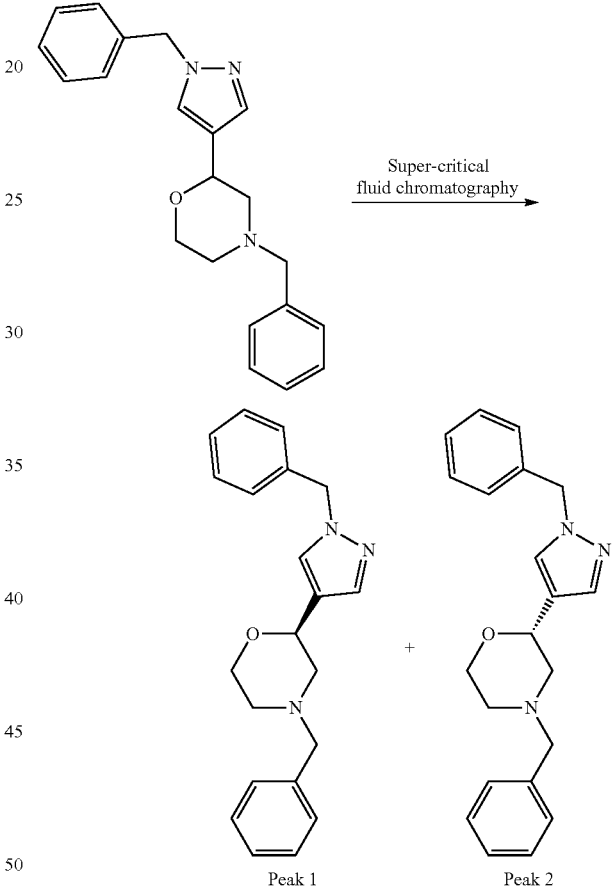

Step 5: Chiral Separation. The enantiomers were separated via supercritical fluid chromatography. (S)-4-benzyl-2-(1-benzyl-1H-pyrazol-4-yl)morpholine was collected as the first eluting product.

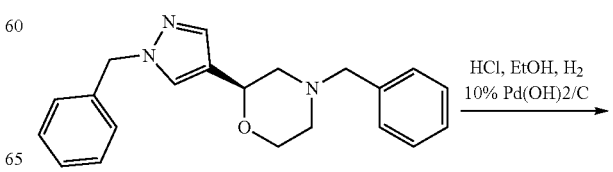

Step 6: To a 50-mL round-bottomed flask was added (S)-4-benzyl-2-(1-benzyl-1H-pyrazol-4-yl)morpholine (70 g, 210 mmol) in ethanol (7 mL) and HCl (12.76 mL, 420 mmol) and 10% Palladium hydroxide on carbon (36.9 g, 52.5 mmol) were added and the reaction mixture was stirred under 5 kg hydrogen gas atmosphere. The mixture was filtered through celite and washed with ethanol. The filtrate was concentrated to give (S)-2-(1H-pyrazol-4-yl)morpholine dihydrochloride (40 g, 177 mmol, 84% yield). $^1$H NMR (400 MHz, DMSO-d6): δ ppm 9.86 (s, 1H), 9.70 (s, 1H), 7.68 (d, J=2.8 Hz, 2H), 4.81 (dt, J=11.2, 2.7 Hz, 1H), 4.00 (dd, J=12.6, 4.0 Hz, 1H), 3.91 (tt, J=12.4, 2.7 Hz, 1H), 3.34 (d, J=12.6 Hz, 1H), 3.20 (d, J=12.6 Hz, 1H), 3.03 (dq, J=22.6, 11.3 Hz, 2H)

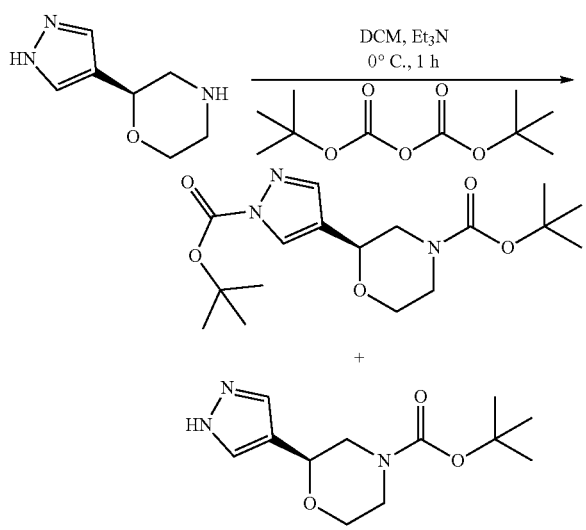

Step 7: To a 1-L round-bottomed flask was added (S)-2-(1H-pyrazol-4-yl)morpholine dihydrochloride (40.0 g, 177 mmol) in dichloromethane (800 mL) followed by triethylamine (99 mL, 708 mmol) dropwise at RT. The reaction mixture was cooled to 0° C. then Boc-anhydride (41.1 mL, 177 mmol) was added dropwise at 0° C. and the reaction mixture was stirred at 0° C. for 1 h. The reaction mixture was then diluted with saturated sodium bicarbonate (150 mL) and extracted with CH$_2$CL$_2$ (2×200 mL), and the organic extracts were dried over Na$_2$SO$_4$. The solution was filtered and concentrated in vacuo to give the crude material. The crude material was absorbed onto a plug of silica gel and purified by chromatography through a pre-packed silica gel column (80 g), eluting with a gradient of 5% to 100% EtOAc in hexane, to provide tert-butyl (S)-2-(1H-pyrazol-4-yl)morpholine-4-carboxylate (35.0 g, 138 mmol, 78% yield) as light brown oil, with tert-butyl (S)-2-(1-(tert-butoxycarbonyl)-1H-pyrazol-4-yl)morpholine-4-carboxylate (9.2 g, 26.0 mmol, 14.71% yield) as a light brown oil side product. $^1$H NMR (400 MHz, Methanol-d4): δ ppm 7.64 (d, J=36.8 Hz, 2H), 4.50 (dd, J=10.3, 2.8 Hz, 1H), 3.83-4.19 (m, 3H), 3.63 (td, J=11.4, 2.8 Hz, 1H), 3.06 (s, 2H), 1.48 (d, J=1.0 Hz, 9H).

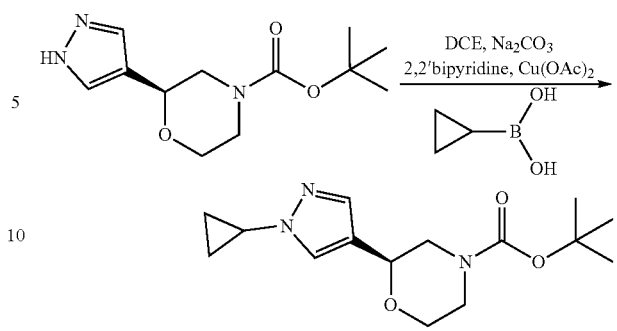

Step 8: To a 100-mL sealed tube was added tert-butyl (S)-2-(1H-pyrazol-4-yl)morpholine-4-carboxylate (2.50 g, 9.87 mmol) and cyclopropylboronic acid (1.865 g, 21.71 mmol) in 1,2-dichloroethane (40 mL) followed by sodium carbonate (2.301 g, 21.71 mmol), 2,2'-bipyridine (1.696 g, 10.86 mmol) and copper (II) acetate (1.972 g, 10.86 mmol). The reaction mixture was heated at 65° C. for 18 h, then cooled to RT and the solution was filtered through a celite bed and washed with DCM (200 mL), The organic layer was washed with 1 N HCl (50 mL),then the solvent was evaporated under reduced pressure to give the crude material. The crude material was absorbed onto a plug of silica gel and purified by chromatography through a pre-packed silica gel column (40 g), eluting with a gradient of 5% to 80% EtOAc in hexane, to provide tert-butyl (S)-2-(1-cyclopropyl-1H-pyrazol-4-yl)morpholine-4-carboxylate (1.65 g, 5.62 mmol, 57.0% yield) as colourless oil. $^1$H NMR (400 MHz, Methanol-d4): δ ppm 7.71 (s, 1H), 7.48 (d, J=0.8 Hz, 1H), 4.44 (dd, J=10.3, 2.9 Hz, 1H), 3.84-3.99 (m, 3H), 3.59-3.66 (m, 2H), 3.04 (s, 2H), 1.49 (s, 9H), 1.03-1.08 (m, 4H).

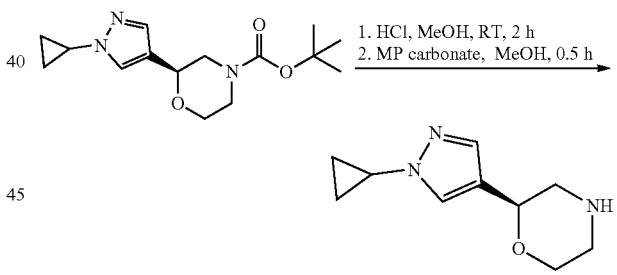

Step 9: To a 100-mL round-bottomed flask was added tert-butyl (S)-2-(1-cyclopropyl-1H-pyrazol-4-yl)morpholine-4-carboxylate (1.650 g, 5.62 mmol) in methanol (10 mL). HCl in methanol (14.06 mL, 56.2 mmol) was added dropwise at RT and the reaction mixture was stirred at RT for 2 h, then the solvent was evaporated under reduced pressure to give (S)-2-(1-cyclopropyl-1H-pyrazol-4-yl)morpholine hydrochloride (1.28 g, 5.57 mmol, 99% yield) as a colourless oil. The salt was then stirred in methanol, and MP carbonate was added. The mixture was left to stir at RT for 30 min, then was filtered and concentrated to yield the freebase (S)-2-(1-cyclopropyl-1H-pyrazol-4-yl)morpholine.

BIOLOGICAL EVALUATION

Provided in this section is the biological evaluation of the specific examples provided herein. See Examples A1-A4, Tables 19-22, and FIGS. 1-3.

Example A1.
In vitro Measurement of Triggering Receptor Expressed on Myeloid Cells 2 activity using cellular phosphorylation of Spleen Tyrosine Kinase ("Syk") Assays used for Examples 1-305

Pharmacological measurements of TREM2 signaling through DAP12 were made with TREM2 and DAP12 overexpressing HEK293 cells stable cell lines that had been single-cell cloned ("TREM2/DAP12-HEK"). The readout of the TREM2 signaling utilized Perkin Elmer AlphaScreen/AlphaLISA technology monitoring the phosphorylation levels of the Syk kinase. TREM2/DAP12-HEK cell lines were cultured in DMEM-F12 (Corning 10-092-CM) supplemented with 1X Penicillin/Streptomycin (Corning 30-002-CI), 1X GlutaMAX (Gibco 35050-061), and 10% Fetal Bovine Serum (Life Technologies 10099) referred to as "HEK Culture Medium". Suspensions of TREM2/DAP12-HEK cells were prepared in HEK Culture Medium and dispensed into 384-well poly-D-lysine coated microplates (Corning 354661) at a density of 20,000 cells/well using a Multidrop Combi peristaltic microplate dispenser (Thermo), 25 µL volume of cell suspension/well. Plates containing cells were then incubated for 20 hours in a humidified cell culture incubator at 37° C. with 5% $CO_2$ (Thermo). After incubation, culture medium was removed from all wells of each microplate and replaced with 20 µL of "Assay Buffer" comprised of DMEM-F12 (Corning 10-092-CM) supplemented with 1X Penicillin/Streptomycin (Corning 30-002-CI) and 0.1% Pluronic F-68 Polyol (MP Biomedical 092750049) using a Bravo 384-well pipette-based liquid handling system (Agilent). Assay Buffer contained diluted test articles (in 1% final DMSO concentration for compounds) or 100 nM anti-human/mouse TREM2 antibody (R&D Systems MAB17291) as a positive control, or 100 nM or rat IgG2B isotype Ab as a negative control (R&D Systems MAB0061). The plates were incubated with test articles and controls for 45 minutes at room temperature and then the medium was aspirated/removed from each well of the plates. A Multidrop Combi peristaltic liquid handler (Thermo) was used to dispense 15 µL/well of "Cell Lysis Immunoassay Buffer". The Cell Lysis Immunoassay Buffer contained M-PER Mammalian Protein Extraction Reagent (Pierce/ThermoFisher 78505), 1X Halt Phosphatase Inhibitor Cocktail (ThermoFisher #78427), 0.1875 nM anti-phospho-Syk (Tyr525/526) (C87C1) rabbit mAb (Cell Signaling Technologies catalog #2710), and 1.5 nM biotinylated Mouse anti-human Syk (4D10) antibody (BD Biosciences, catalog #624008). Plates were incubated for 1 hour at room temperature after the addition of the Cell Lysis Immunoassay Buffer. The Multidrop Combi liquid handler was used to dispense 15 µL of AlphaScreen Acceptor Bead Solution containing 7.5 µg/mL anti-rabbit IgG (Fc specific) AlphaLISA Acceptor Beads (Perkin Elmer AL104R) in 1X Immunoassay buffer (Perkin Elmer AL000F) to each well of the microplates. The plates were incubated for 2 hours at room temperature. Following the incubation with the AlphaLISA Acceptor Bead Solution, a Multidrop Combi liquid handler (Thermo) was used to dispense 15 µL of AlphaScreen Donor Bead Solution containing 30 µg/mL of AlphaScreen Streptavidin Donor beads (Perkin Elmer 6760002B) in 1X Immunoassay buffer (Perkin Elmer AL000F) to each well of the microplates. Microplates were incubated for 2 hours protected from light sources as the AlphaScreen reagents are light sensitive. Once the final incubation was completed, an AlphaScreen signal was acquired from the donor and acceptor beads using an Envision high throughput multi-modal microplate reader (Perkin Elmer) calibrated to the plate type with the AlphaScreen mirror and filter-set in 384-well mode, 680 nanometer excitation wavelength. The total measurement time per well was 550 milliseconds with a 180 millisecond excitation time.

After reading the AlphaScreen signal for each well of the microplates, on a plate-by-plate basis, each raw test article well value (x) was normalized to a Percent of Control ("POC") value using the following formula: POC=$((x - \mu_n)/(\mu_p - \mu_n))*100$ where $(\mu_n)$ is the mean negative control well signal for the given plate and $(\mu_p)$ is the mean positive control TREM2 antibody signal for the given plate. Each plate contained 12 of each type of control wells that were used to generate the mean values. For concentration response curve analysis with test articles tested at various concentrations, the % of activation values were analyzed with 4 Parameter Logistic or Sigmoidal Dose-Response Models using GeneData Screener (GeneData, AG) or GraphPad Prism 7 (Graphpad Software, Inc.). The potency of the test item was expressed as EC50 corresponding to the test item concentration able to activate the phospho-Syk AlphaScreen signal to 50% of the maximal response.

For pharmacological assessment of TREM2 signaling in cellular systems natively expressing TREM2, human monocyte-derived macrophages were utilized. $CD14^+$ monocytes positively selected from large-scale apheresis on healthy human donors (Lonza) were differentiated into macrophages in low-attachment bioprocess bags (Saint-Gobain Performance Plastics) for 9 days in RPMI-1640 medium (Gibco 11875093) supplemented with 10% Fetal Bovine Serum (Gibco 10082139), 10 mM HEPES (Gibco 15630080), 1X Penicillin-Streptomycin (Gibco 15140122), 1X Non-essential amino acids (Gibco 11140050), 1 mM Sodium Pyruvate (Gibco 11360070), 1X GlutaMAX (Gibco 35050-061), and 50 ng/mL M-CSF (Promocell C-60442A). After differentiation, macrophages were harvested and cryopreserved in BamBanker (Wako/GC LYMPHOTEC 302-14681/CS-02-001) in addition to undergoing quality control for expression of cell surface markers including TREM2 using flow cytometry. Batches utilized for phospho-Syk assays were approximately 80-90% $TREM2^+$ by flow cytometry.

After cryorecovering macrophages, live cell suspensions of 100,000 cells/mL in "Macrophage pSyk Assay Medium" were prepared, composed of RPMI-1640 with GlutaMAX medium (Gibco 61870036) supplemented with 10% Fetal Bovine Serum (Gibco 10082139), 10 mM HEPES (Gibco 15630080), 1X Penicillin-Streptomycin (Gibco 15140122), 1X Non-essential amino acids (Gibco 11140050), 1 mM Sodium Pyruvate (Gibco 11360070), and 10 ng/mL M-CSF (Promocell C-60442A). A Multidrop Combi peristatic liquid handling instrument (Thermo) was used to dispense 50 µL/well of cell suspension (5,000 cells/well) into poly-d-lysine coated 384-well plates (Corning 354661). After a 30 minute incubation at room temperature, plates were incubated in a humidified cell culture incubator at 37° C. with 5% $CO_2$ (Thermo) for 16 hours. To initiate the assay with test articles, medium in each well of the assay plates was aspirated and replaced with 20 µL Assay Buffer containing diluted test articles (in 1% final DMSO concentration for compounds) or Assay Buffer containing 1% DMSO for as a negative control. The remainder of the macrophage AlphaScreen phospho-Syk assay followed the procedure detailed above for the HEK cell lines.

After reading the AlphaScreen signal for each well of the microplates containing macrophages, on a plate-by-plate basis, each raw test article well value (x) was background subtracted from the mean negative control well signal for the given plate. Each plate contained 12-24 negative control wells that were used to generate the mean value for background subtraction. For concentration response curve analysis with the test articles tested at various concentrations, the values were analyzed with a 4 Parameter Logistic curve fit using GraphPad Prism 7 (Graphpad Software, Inc.). The potency of each test item was expressed as EC50 corresponding to the test item concentration able to activate the background subtracted phospho-Syk AlphaScreen signal to 50% of the maximal response.

The results presented in Table 19 have been generated with the in vitro assay described above for Examples 1-305. This assay may be used to test any of the compounds described herein to assess and characterize a compound's ability to act as an agonist of TREM2.

Compounds designated as "A" demonstrated an EC50 of ≤0.05 µM. Compounds designated as "B" demonstrated an EC50>0.05 µM and ≤0.5 µM. Compounds designated as "C" demonstrated an EC50>0.5 µM and ≤3.0 µM. Compounds designated as "D" demonstrated an EC50>3.0 µM and ≤100 µM. Compounds designated as "-" had not been tested as of the filing of the present application, but can be tested using the methods described herein.

Compounds designated as "++++" demonstrated an Emax>250. Compounds designated as "+++" demonstrated an Emax>150 and ≤250. Compounds designated as "++" demonstrated an Emax>100 and ≤150. Compounds designated as "+" demonstrated an Emax>45 and ≤100. Compounds designated as "-" had not been tested as of the filing of the present application, but can be tested using the methods described herein.

TABLE 19 hTREM2 EC50 Data (HEK293 Cells) for Examples 1-305 provided herein.

| Ex # | hTREM2 EC50 µM | hTREM2 Emax |
|---|---|---|
| 1 | A | ++++ |
| 2 | A | +++ |
| 3 | A | +++ |
| 4 | B | +++ |
| 5 | C | +++ |
| 6 | B | +++ |
| 7 | A | +++ |
| 8 | A | ++ |
| 9 | A | +++ |
| 10 | A | +++ |
| 11 | B | ++ |
| 12 | C | ++ |
| 13 | A | + |
| 14 | B | ++ |
| 15 | B | ++ |
| 16 | A | + |
| 17 | A | ++++ |
| 18 | A | +++ |
| 19 | A | +++ |
| 20 | C | +++ |
| 21 | A | ++++ |
| 22 | A | ++++ |
| 23 | A | ++++ |
| 24 | B | ++++ |
| 25 | A | ++++ |
| 26 | A | ++++ |
| 27 | C | ++ |
| 28 | C | +++ |
| 29 | D | − |
| 30 | C | ++ |
| 31 | A | +++ |
| 32 | A | +++ |
| 33 | A | ++++ |
| 34 | C | +++ |
| 35 | B | +++ |
| 36 | B | +++ |
| 37 | A | +++ |
| 38 | A | +++ |
| 39 | A | +++ |
| 40 | B | + |
| 41 | B | + |
| 42 | A | ++ |
| 43 | B | +++ |
| 44 | B | +++ |
| 45 | B | ++ |
| 46 | A | +++ |
| 47 | A | + |
| 48 | A | ++ |
| 49 | A | ++ |
| 50 | A | +++ |
| 51 | A | +++ |
| 52 | B | +++ |
| 53 | A | ++ |
| 54 | A | ++ |
| 55 | A | +++ |
| 56 | A | ++ |
| 57 | C | ++ |
| 58 | B | +++ |
| 59 | B | +++ |
| 60 | A | +++ |
| 61 | A | +++ |
| 62 | A | ++++ |
| 63 | A | +++ |
| 64 | A | +++ |
| 65 | A | +++ |
| 66 | C | ++ |
| 67 | B | + |
| 68 | D | − |
| 69 | C | + |
| 70 | C | + |
| 71 | D | ++ |
| 72 | C | + |
| 73 | B | ++++ |
| 74 | B | ++++ |
| 75 | B | ++++ |
| 76 | B | ++++ |
| 77 | A | +++ |
| 78 | B | +++ |
| 79 | A | ++++ |
| 80 | B | ++ |
| 81 | B | ++ |
| 82 | B | +++ |
| 83 | C | ++++ |
| 84 | A | +++ |
| 85 | A | +++ |
| 86 | A | ++++ |
| 87 | B | ++++ |
| 88 | A | ++++ |
| 89 | C | +++ |
| 90 | B | +++ |
| 91 | B | +++ |
| 92 | A | +++ |
| 93 | A | +++ |
| 94 | B | +++ |
| 95 | A | +++ |
| 96 | A | ++++ |
| 97 | C | + |
| 98 | B | ++ |
| 99 | A | + |
| 100 | B | ++ |
| 101 | D | − |
| 102 | A | + |
| 103 | A | ++++ |
| 104 | A | +++ |
| 105 | A | ++++ |
| 106 | B | +++ |
| 107 | A | +++ |
| 108 | B | + |
| 109 | D | − |
| 110 | C | + |

TABLE 19-continued hTREM2 EC50 Data (HEK293 Cells) for Examples 1-305 provided herein.

| Ex # | hTREM2 EC50 µM | hTREM2 Emax |
|---|---|---|
| 111 | C | + |
| 112 | A | +++ |
| 113 | A | ++ |
| 114 | A | +++ |
| 115 | A | ++ |
| 116 | A | +++ |
| 117 | D | − |
| 118 | C | + |
| 119 | B | ++ |
| 120 | B | ++++ |
| 121 | B | ++++ |
| 122 | C | +++ |
| 123 | A | +++ |
| 124 | A | ++++ |
| 125 | B | +++ |
| 126 | B | + |
| 127 | A | ++ |
| 128 | C | + |
| 129 | B | ++++ |
| 130 | A | + |
| 131 | B | +++ |
| 132 | A | ++ |
| 133 | A | +++ |
| 134 | B | + |
| 135 | B | + |
| 136 | A | +++ |
| 137 | A | +++ |
| 138 | A | +++ |
| 139 | A | +++ |
| 140 | B | ++ |
| 141 | B | ++ |
| 142 | D | ++ |
| 143 | B | +++ |
| 144 | B | ++ |
| 145 | A | + |
| 146 | C | ++ |
| 147 | D | ++++ |
| 148 | B | +++ |
| 149 | B | ++++ |
| 150 | B | ++++ |
| 151 | B | ++++ |
| 152 | A | ++++ |
| 153 | B | +++ |
| 154 | B | ++++ |
| 155 | C | ++ |
| 156 | B | +++ |
| 157 | A | ++++ |
| 158 | B | +++ |
| 159 | B | +++ |
| 160 | A | ++++ |
| 161 | A | +++ |
| 162 | A | ++++ |
| 163 | A | ++++ |
| 164 | A | ++++ |
| 165 | A | +++ |
| 166 | A | ++++ |
| 167 | B | ++++ |
| 168 | A | ++++ |
| 169 | A | +++ |
| 170 | A | ++++ |
| 171 | A | +++ |
| 172 | B | ++++ |
| 173 | A | +++ |
| 174 | B | +++ |
| 175 | C | ++ |
| 176 | A | +++ |
| 177 | C | +++ |
| 178 | A | ++++ |
| 179 | C | ++++ |
| 180 | B | +++ |
| 181 | A | +++ |
| 182 | A | +++ |
| 183 | A | ++++ |
| 184 | C | +++ |
| 185 | B | +++ |
| 186 | C | +++ |
| 187 | A | +++ |
| 188 | A | +++ |
| 189 | C | +++ |
| 190 | A | +++ |
| 191 | B | ++++ |
| 192 | A | ++++ |
| 193 | B | ++++ |
| 194 | C | ++++ |
| 195 | A | ++++ |
| 196 | A | +++ |
| 197 | A | ++++ |
| 198 | B | +++ |
| 199 | A | ++++ |
| 200 | C | +++ |
| 201 | A | +++ |
| 202 | C | ++ |
| 203 | A | +++ |
| 204 | C | ++++ |
| 205 | B | +++ |
| 206 | B | ++++ |
| 207 | A | +++ |
| 208 | A | +++ |
| 209 | B | +++ |
| 210 | B | ++++ |
| 211 | A | ++++ |
| 212 | C | ++++ |
| 213 | B | +++ |
| 214 | B | ++++ |
| 215 | A | +++ |
| 216 | A | +++ |
| 217 | B | +++ |
| 218 | A | +++ |
| 219 | B | ++++ |
| 220 | B | +++ |
| 221 | C | +++ |
| 222 | A | ++++ |
| 223 | B | ++++ |
| 224 | A | +++ |
| 225 | B | +++ |
| 226 | B | +++ |
| 227 | A | +++ |
| 228 | A | +++ |
| 229 | A | +++ |
| 230 | B | ++++ |
| 231 | A | +++ |
| 232 | A | ++ |
| 233 | D | +++ |
| 234 | C | +++ |
| 235 | D | + |
| 236 | D | +++ |
| 237 | D | +++ |
| 238 | D | + |
| 239 | D | +++ |
| 240 | D | ++++ |
| 241 | A | +++ |
| 242 | A | +++ |
| 243 | B | ++++ |
| 244 | C | +++ |
| 245 | D | ++++ |
| 246 | D | +++ |
| 247 | B | +++ |
| 248 | C | +++ |
| 249 | C | +++ |
| 250 | C | +++ |
| 251 | C | +++ |
| 252 | A | +++ |
| 253 | D | +++ |
| 254 | B | +++ |
| 255 | C | ++ |
| 256 | C | ++ |
| 257 | C | ++ |
| 258 | C | +++ |
| 259 | A | ++++ |
| 260 | C | +++ |

TABLE 19-continued hTREM2 EC50 Data (HEK293 Cells) for Examples 1-305 provided herein.

| Ex # | hTREM2 EC50 μM | hTREM2 Emax |
|---|---|---|
| 261 | C | +++ |
| 262 | D | − |
| 263 | C | +++ |
| 264 | C | ++++ |
| 265 | C | +++ |
| 266 | C | ++++ |
| 267 | C | ++ |
| 268 | C | ++++ |
| 269 | D | + |
| 270 | C | +++ |
| 271 | D | +++ |
| 272 | A | ++++ |
| 273 | A | +++ |
| 274 | D | ++ |
| 275 | D | + |
| 276 | B | ++++ |
| 277 | B | +++ |
| 278 | C | +++ |
| 279 | C | +++ |
| 280 | C | +++ |
| 281 | C | +++ |
| 282 | C | ++ |
| 283 | C | ++ |
| 284 | B | + |
| 285 | B | ++++ |
| 286 | A | +++ |
| 287 | C | +++ |
| 288 | A | ++ |
| 289 | D | ++ |
| 290 | B | +++ |
| 291 | B | ++++ |
| 292 | C | +++ |
| 293 | — | +++ |
| 294 | C | +++ |
| 295 | A | +++ |
| 296 | D | − |
| 297 | D | − |
| 298 | A | +++ |
| 299 | A | +++ |
| 300 | B | +++ |
| 301 | A | +++ |
| 302 | B | + |
| 303 | B | ++ |
| 304 | C | +++ |
| 305 | B | +++ |

Example A2.

In vitro Measurement of Triggering Receptor Expressed on Myeloid Cells 2 activity using cellular phosphorylation of Spleen Tyrosine Kinase ("Syk") Assays used for Examples 306-429

Measurement of TREM2 agonist potency was done using a HEK cell line expressing human TREM2 and DAP12 (HEK293T-hTREM2 cells). Binding of small molecules to, and activation of, TREM2 increases the phosphorylation of Syk. The resultant levels of Syk phosphorylation were measured using a commercial AlphaLisa reagent kit. To perform the assay, HEK-hTREM2 cells were plated at 14,000 cells per well in a 384 well plate, in 25 μL of complete growth media and incubated at 37° C., 5% $CO_2$ for 20-24 hours. Prior to the assay, test compounds were diluted in the 384 well plates in assay buffer and allowed to equilibrate for 30 minutes. Growth media was removed from cell plates by inversion on blotting paper, and 25 μL of test compounds in assay buffer was added to cells. Cells were incubated for 45 minutes at room temperature. After 45 minutes, assay buffer was removed and 10 μL of lysis buffer was added. Plates were shaken for 20 minutes at 350 RPM at room temperature. After complete lysis, AlphaLisa reagents were added to the lysate, and fluorescence intensity was measured using a Perkin Elmer Envision plate reader. Intensities were used to generate a standard curve, and % activation was calculated. Curve fitting was performed using Prism v9 software, log(agonist) vs response—variable slope (four parameters), and EC50s were calculated from the curve fit.

The results presented in Table 20 have been generated with the in vitro assay described above for Examples 306-429. This assay may be used to test any of the compounds described herein to assess and characterize a compound's ability to act as an agonist of TREM2.

Compounds designated as "A" demonstrated an EC50 of ≤0.05 μM. Compounds designated as "B" demonstrated an EC50>0.05 μM and ≤0.5 μM. Compounds designated as "C" demonstrated an EC50>0.5 μM and ≤3.0 μM. Compounds designated as "D" demonstrated an EC50>3.0 μM and ≤100 μM. Compounds designated as "-" had not been tested as of the filing of the present application, but can be tested using the methods described herein.

TABLE 20 hTREM2 EC50 Data (HEK293 Cells) for Examples 306-429 provided herein.

| Ex # | hTREM2 EC50 μM |
|---|---|
| 306 | B |
| 307 | B |
| 308 | B |
| 309 | B |
| 310 | B |
| 311 | B |
| 312 | A |
| 313 | A |
| 314 | A |
| 315 | A |
| 316 | B |
| 317 | A |
| 318 | A |
| 319 | A |
| 320 | — |
| 321 | B |
| 322 | A |
| 323 | A |
| 324 | B |
| 325 | A |
| 326 | A |
| 327 | A |
| 328 | A |
| 329 | — |
| 330 | A |
| 331 | C |
| 332 | A |
| 333 | C |
| 334 | A |
| 335 | A |
| 336 | B |
| 337 | A |
| 338 | C |
| 339 | B |
| 340 | B |
| 341 | A |
| 342 | A |
| 343 | B |
| 344 | A |
| 345 | — |
| 346 | A |
| 347 | A |
| 348 | A |
| 349 | A |
| 350 | C |
| 351 | — |
| 352 | A |
| 353 | B |
| 354 | A |

TABLE 20-continued hTREM2 EC50 Data (HEK293 Cells) for Examples 306-429 provided herein.

| Ex # | hTREM2 EC50 µM |
|---|---|
| 355 | B |
| 356 | A |
| 357 | A |
| 358 | A |
| 359 | A |
| 360 | A |
| 361 | B |
| 362 | A |
| 363 | A |
| 364 | A |
| 365 | B |
| 366 | A |
| 367 | B |
| 368 | B |
| 369 | A |
| 370 | B |
| 371 | A |
| 372 | A |
| 373 | A |
| 374 | A |
| 375 | A |
| 376 | C |
| 377 | B |
| 378 | B |
| 379 | B |
| 380 | A |
| 381 | A |
| 382 | A |
| 383 | B |
| 384 | A |
| 385 | B |
| 386 | A |
| 387 | A |
| 388 | B |
| 389 | A |
| 390 | — |
| 391 | A |
| 392 | A |
| 393 | B |
| 394 | A |
| 395 | A |
| 396 | B |
| 397 | A |
| 398 | A |
| 399 | A |
| 400 | A |
| 401 | A |
| 402 | A |
| 403 | B |
| 404 | A |
| 405 | B |
| 406 | C |
| 407 | A |
| 408 | A |
| 409 | B |
| 410 | A |
| 411 | A |
| 412 | B |
| 413 | A |
| 414 | A |
| 415 | B |
| 416 | B |
| 417 | B |
| 418 | — |
| 419 | B |
| 420 | A |
| 421 | C |
| 422 | A |
| 423 | B |
| 424 | A |
| 425 | A |
| 426 | A |
| 427 | A |
| 428 | B |
| 429 | C |

Example A3.

IP-10 expression in the brain and plasma of mice after administration of Example 192 and a TREM2 agonist antibody To test TREM2 target engagement in an acute dosing paradigm using the compound of Example 192 (5-(4-chloro-2-fluorophenyl)-2,3-dimethyl-7-((2R,4S)-2-(1-methyl-1H-pyrazol-4-yl)tetrahydro-2H-pyran-4-yl)pyrido[3,4-b]pyrazine), hTREM2-CV knock-in transgenic mice were dosed using oral gavage (PO) twice a day (0 and 10 h) followed by sample collection at 24 hours. 6 animals received the compound of Example 192 at 50 mg/kg, and 6 animals received vehicle only (2% Hydroxypropyl Methylcellulose, 1% Tween-80 in PBS). In the same experiment, an anti-hTREM2 Antibody Ab-1 was dosed intraperitoneally (IP) at 100 mg/kg (control was a non-binding matched IgG isotype control). Ab-1 is a murinized version of a human TREM2 agonist antibody, first described as an engineered variant of antibody 13E7 in PCT Application Publication WO2018/195506A1. Ab-1 has an HC according to SEQ ID NO:9, an LC according to SEQ ID NO:10, and exemplifies an anti-TREM2 antibody having the CDRs according to SEQ ID NOS:1-6. Twenty-four hours following the zero-hour dose, mice were humanely euthanized for blood collection prior to cardiac perfusion with PBS and brain harvest. Brains were micro dissected into right and left regions of interest (including the cortex and hippocampus) for independent processing of cytokine and mRNA expression profiles. Whole blood was collected into EDTA-containing vials to prevent coagulation, and centrifuged to isolate the plasma fraction before storage at −80° C. Right and left hemisphere cortices were flash frozen in liquid nitrogen and stored at −80° C. before lysis and homogenization.

Plasma and brain lysates were analyzed for IP-10 (CXCL10) and CCL2 (MCP1) expression using a Meso Scale Discovery (MSD) multi-array reader and V-PLEX kits per manufacturer's protocols. Both IP-10 and CCL2 are chemotactic cytokines involved in the regulation of monocyte infiltration, and both appear to be upregulated in response to TREM2 engagement in microglia.

Figure 2:
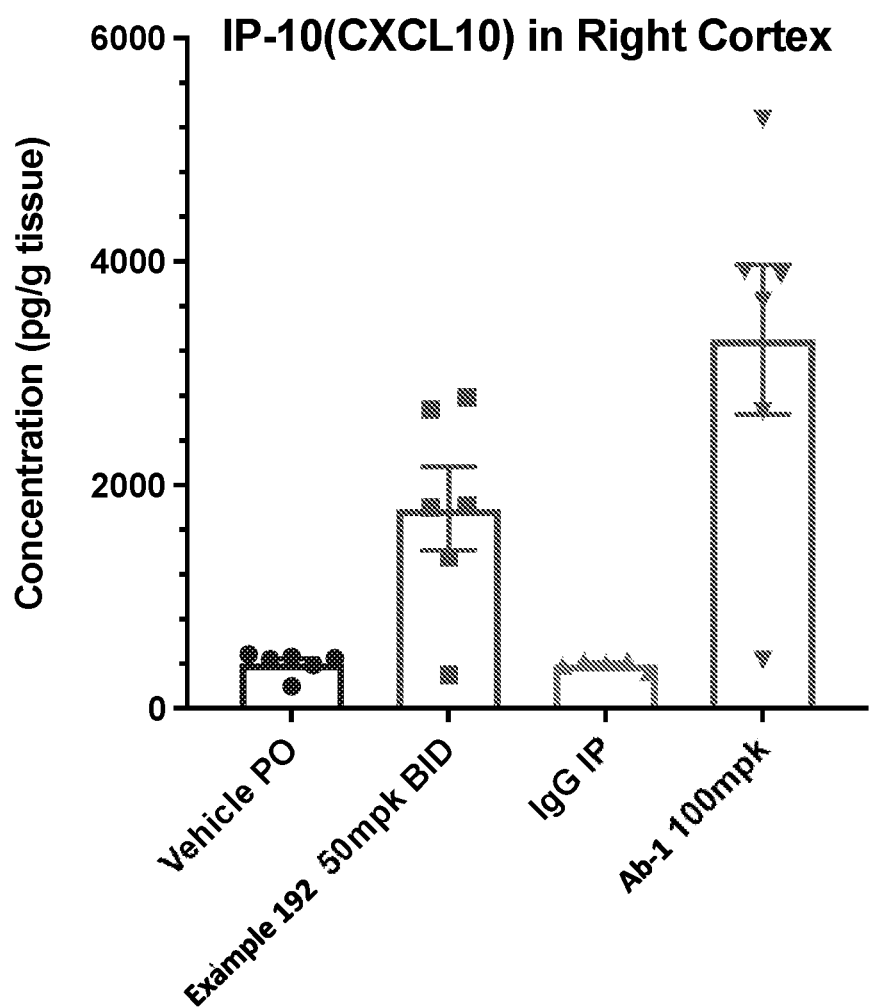
FIG. 2 is a graph showing the measured concentration of IP-10 (CXCL10) in the right cortex of mice 24 hours after administration of the compound of Example 192 or Antibody 13E7, as compared to controls. Error bars are shown as SEM.
Figure 3:
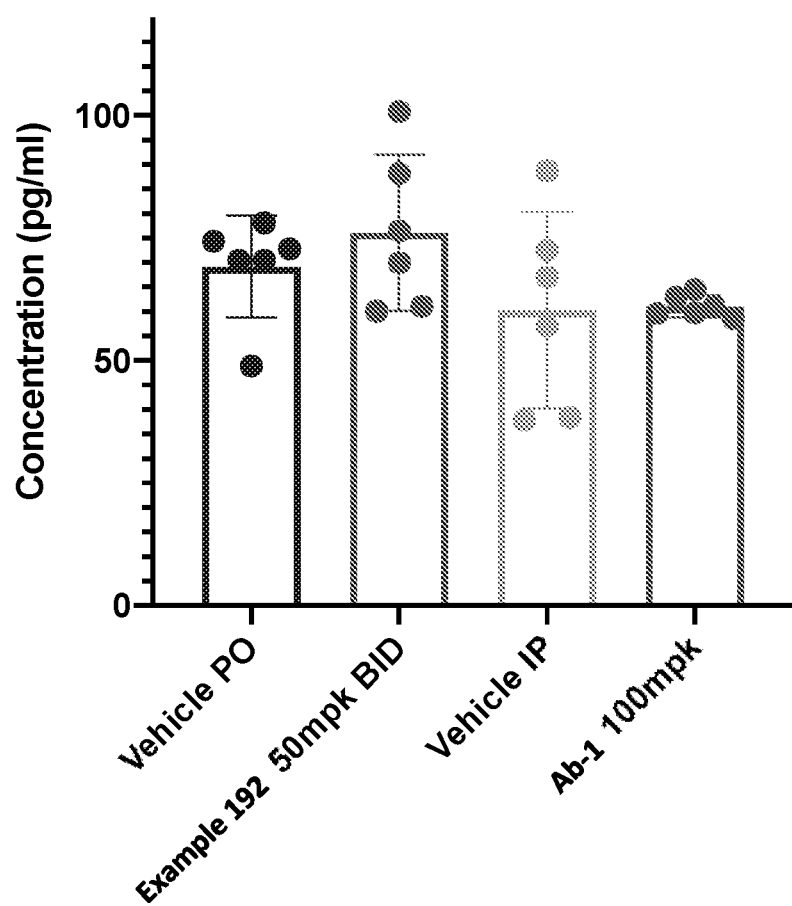
FIG. 3 is a graph showing the measured concentration of IP-10 (CXCL10) in plasma samples taken from mice 24 hours after administration of the compound of Example 192 or Antibody 13E7, as compared to controls. Error bars are shown as SEM.

Both the compound of Example 192 and Ab-1 induced upregulation of IP-10 and CCL2 in cortical lysates compared to vehicle-treated animals (FIGS. 1 and 2). The upregulation of IP-10 was more robust, and so IP-10 levels were analyzed in plasma from the same experiment. This analysis of peripheral IP-10 levels in the plasma fraction showed no apparent cytokine upregulation, indicating a brain compartment-specific effect of the compound of Example 192. These results indicate that CNS TREM2 is responsible for increased IP-10 (FIG. 3), ruling out a peripheral IP-10 increase and transfer to the brain. These results demonstrate TREM2 brain target engagement using the compound of Example 192 in vivo.

Example A4.

Nanostring analysis of gene expression profiles after administration of Example 192 and a TREM2 agonist antibody in a mouse model To assess the impact of TREM2 agonism on cellular processes and pathways, the right hemisphere hippocampi from the acute dosing of the compound of Example 192 and Ab-1, as described in Example A3, were analyzed for gene expression changes. Cells from frozen hippocampi were lysed, and RNA was isolated. Key gene expression profiles were analyzed using the nCounter Murine Neuroinflammation panel of 770 genes related to inflammation in the CNS. Results of individual gene expression changes relative to the mean of several housekeeper genes were grouped in pathways of interest and assigned a relative score using the nSolver analysis software.

Nanostring nSolver software includes a module for Cell Type Profiling that identifies genes linked to cell type in an experiment. Analysis using this module revealed an increase in microglia score (microglial-associated genes) with treatment with the compound of Example 192 and Ab-1, but no change in neuron or astrocyte scores, indicating microglial-specific effects of TREM2 agonism by both treatments, as expected with TREM2 activation. Table 21 reports the Cell Type Profiling scores for microglia, neuron and astrocyte genes, showing that microglia genes were upregulated by treatment with the compound of Example 192 and Ab-1. Pathway analysis was also performed. Genes associated with the adaptive immune response, innate immune response, microglia function, cytokine signalling, and cell cycle were all increased in hippocampi from animals treated with the compound of Example 192 and Ab-1. Table 22 reports the effects of the compound of Example 192 and Ab-1 on these genes, where the values reflect PC1 scores from principal component analysis of the gene set. These results support the finding of TREM2 target engagement on microglia using the compound of Example 192 and Ab-1.

TABLE 21

Cell Type Profiling Scores after treatment

| Gene Type | Treatment Group | | |
|---|---|---|---|
| | Vehicle | Ex 192 | Ab-1 |
| Microglia Score | 6.59 (0.108) | 6.82 (0.090) * | 7.01 (0.097) * |
| Neuron Score | 8.82 (0.108) | 8.81 (0.185) | 8.76 (0.063) |
| Astrocyte Score | 8.82 (0.044) | 8.86 (0.077) | 8.78 (0.044) |

Data shown is mean score (standard deviation).
* = p < 0.005 by Student's T-test, two-tailed.

TABLE 22

Cell Type Profiling Scores after treatment

| Pathway Score | Treatment Group | | |
|---|---|---|---|
| | Vehicle | Ex 192 | Ab-1 |
| Adaptive Immune Response | −1.01 (0.594) | 0.639 (0.929) * | 1.66 (0.400) * |
| Innate Immune Response | −0.984 (0.585) | 0.490 (0.674) * | 1.77 (0.418) * |
| Microglia Function | −1.04 (0.827) | 0.345 (0.908) * | 2.07 (0.424) * |
| Cytokine Signaling | −0.821 (0.564) | 0.180 (0.514) * | 1.75 (0.320) * |
| Cell Cycle | −0.789 (0.351) | 0.398 (0.414) * | 1.41 (0.462) * |

Data shown is mean score (standard deviation).
* = p < 0.005 by Student's T-test, two-tailed.

REFERENCES

Bianchin, M. M., H. M. Capella, D. L. Chaves, M. Steindel, E. C. Grisard, G. G. Ganev, J. P. da Silva Junior, S. Neto Evaldo, M. A. Poffo, R. Walz, C. G. Carlotti Junior and A. C. Sakamoto (2004). "Nasu-Hakola disease (polycystic lipomembranous osteodysplasia with sclerosing leukoencephalopathy—PLOSL): a dementia associated with bone cystic lesions. From clinical to genetic and molecular aspects." Cell Mol Neurobiol 24(1): 1-24.

Bianchin, M. M., K. C. Martin, A. C. de Souza, M. A. de Oliveira and C. R. Rieder (2010). "Nasu-Hakola disease and primary microglial dysfunction." Nat Rev Neurol 6(9): 2 p following 523.

Cantoni, C., B. Bollman, D. Licastro, M. Xie, R. Mikesell, R. Schmidt, C. M. Yuede, D. Galimberti, G. Olivecrona, R. S. Klein, A. H. Cross, K. Otero and L. Piccio (2015). "TREM2 regulates microglial cell activation in response to demyelination in vivo." Acta Neuropathol 129(3): 429-447.

Colonna, M. and O. Butovsky (2017). "Microglia Function in the Central Nervous System During Health and Neurodegeneration." Annu Rev Immunol 35: 441-468.

Cserep, C., B. Posfai, N. Lenart, R. Fekete, Z. I. Laszlo, Z. Lele, B. Orsolits, G. Molnar, S. Heindl, A. D. Schwarcz, K. Ujvari, Z. Kornyei, K. Toth, E. Szabadits, B. Sperlagh, M. Baranyi, L. Csiba, T. Hortobagyi, Z. Magloczky, B. Martinecz, G. Szabo, F. Erdelyi, R. Szipocs, M. M. Tamkun, B. Gesierich, M. Duering, I. Katona, A. Liesz, G. Tamas and A. Denes (2019). "Microglia monitor and protect neuronal function via specialized somatic purinergic junctions." Science 10.1126/science.aax6752: pp. 1-18.

Dardiotis, E., V. Siokas, E. Pantazi, M. Dardioti, D. Rikos, G. Xiromerisiou, A. Markou, D. Papadimitriou, M. Speletas and G. M. Hadjigeorgiou (2017). "A novel mutation in TREM2 gene causing Nasu-Hakola disease and review of the literature." Neurobiol Aging 53: 194.e13-194.e22.

Deming, Y., F. Filipello, F. Cignarella, C. Cantoni, S. Hsu, R. Mikesell, Z. Li, J. L. Del-Aguila, U. Dube, F. G. Farias, J. Bradley, J. Budde, L. Ibanez, M. V. Fernandez, K. Blennow, H. Zetterberg, A. Heslegrave, P. M. Johansson, J. Svensson, B. Nellgard, A. Lleo, D. Alcolea, J. Clarimon, L. Rami, J. L. Molinuevo, M. Suarez-Calvet, E. Morenas-Rodriguez, G. Kleinberger, M. Ewers, O. Harari, C. Haass, T. J. Brett, B. A. Benitez, C. M. Karch, L. Piccio and C. Cruchaga (2019). "The MS4A gene cluster is a key modulator of soluble TREM2 and Alzheimer's disease risk." Sci Transl Med 11(505) eaau2291: pp. 1-19.

Doens, D. and P. L. Fernandez (2014). "Microglia receptors and their implications in the response to amyloid beta for Alzheimer's disease pathogenesis." J Neuroinflammation 11: 48 (pp. 1-14).

Domingues, H. S., C. C. Portugal, R. Socodato and J. B. Relvas (2016). "Oligodendrocyte, Astrocyte, and Microglia Crosstalk in Myelin Development, Damage, and Repair." Front Cell Dev Biol 4: 71 (pp. 1-16).

Ewers, M., N. Franzmeier, M. Suarez-Calvet, E. Morenas-Rodriguez, M. A. A. Caballero, G. Kleinberger, L. Piccio, C. Cruchaga, Y. Deming, M. Dichgans, J. Q. Trojanowski, L. M. Shaw, M. W. Weiner, C. Haass and I. Alzheimer's Disease Neuroimaging (2019). "Increased soluble TREM2 in cerebrospinal fluid is associated with reduced cognitive and clinical decline in Alzheimer's disease." Sci Transl Med 11(507): eaav6221 (pp. 1-13).

Golde, T. E., W. J. Streit and P. Chakrabarty (2013). "Alzheimer's disease risk alleles in TREM2 illuminate innate immunity in Alzheimer's disease." Alzheimers Res Ther 5(3): 24(pp. 1-6).

Guerreiro, R., A. Wojtas, J. Bras, M. Carrasquillo, E. Rogaeva, E. Majounie, C. Cruchaga, C. Sassi, J. S. Kauwe, S. Younkin, L. Hazrati, J. Collinge, J. Pocock, T. Lashley, J. Williams, J. C. Lambert, P. Amouyel, A. Goate, R. Rademakers, K. Morgan, J. Powell, P. St George-Hyslop, A. Singleton and J. Hardy (2013). "TREM2 variants in Alzheimer's disease." N Engl J Med 10(368): 117-127.

Guerreiro R., E. Lohmann, J. M. Brás, J. R. Gibbs, J. D. Rohrer, N. Gurunlian, B. Dursun, B. Bilgic, H. Hanagasi, H. Gurvit, M. Emre, A. Singleton and J. Hardy (2013). "Using exome sequencing to reveal mutations in TREM2 presenting as a frontotemporal dementia-like syndrome without bone involvement." JAMA Neurol 70(1): 78-84.

Guo, Y., X. Wei, H. Yan, Y. Qin, S. Yan, J. Liu, Y. Zhao, F. Jiang, H. Lou (2019). "TREM2 deficiency aggravates α-synuclein-induced neurodegeneration and neuroinflammation in Parkinson's disease models." FASEB J 33(11): 12164-12174.

Hickman, S., S. Izzy, P. Sen, L. Morsett and J. El Khoury (2018). "Microglia in neurodegeneration." Nat Neurosci 21(10): 1359-1369.

Hickman, S. E. and J. El Khoury (2019). "Analysis of the Microglial Sensome." Methods Mol Biol 2034: 305-323.

Hickman, S. E., N. D. Kingery, T. K. Ohsumi, M. L. Borowsky, L. C. Wang, T. K. Means and J. El Khoury (2013). "The microglial sensome revealed by direct RNA sequencing." Nat Neurosci 16(12): 1896-1905.

Hollingworth, P., D. Harold, R. Sims, A. Gerrish, J. C. Lambert, M. M. Carrasquillo, R. Abraham, M. L. Hamshere, J. S. Pahwa, V. Moskvina, K. Dowzell, N. Jones, A. Stretton, C. Thomas, A. Richards, D. Ivanov, C. Widdowson, J. Chapman, S. Lovestone, J. Powell, P. Proitsi, M. K. Lupton, C. Brayne, D. C. Rubinsztein, M. Gill, B. Lawlor, A. Lynch, K. S. Brown, P. A. Passmore, D. Craig, B. McGuinness, S. Todd, C. Holmes, D. Mann, A. D. Smith, H. Beaumont, D. Warden, G. Wilcock, S. Love, P. G. Kehoe, N. M. Hooper, E. R. Vardy, J. Hardy, S. Mead, N. C. Fox, M. Rossor, J. Collinge, W. Maier, F. Jessen, E. Ruther, B. Schurmann, R. Heun, H. Kolsch, H. van den Bussche, I. Heuser, J. Kornhuber, J. Wiltfang, M. Dichgans, L. Frolich, H. Hampel, J. Gallacher, M. Hull, D. Rujescu, I. Giegling, A. M. Goate, J. S. Kauwe, C. Cruchaga, P. Nowotny, J. C. Morris, K. Mayo, K. Sleegers, K. Bettens, S. Engelborghs, P. P. De Deyn, C. Van Broeckhoven, G. Livingston, N. J. Bass, H. Gurling, A. McQuillin, R. Gwilliam, P. Deloukas, A. Al-Chalabi, C. E. Shaw, M. Tsolaki, A. B. Singleton, R. Guerreiro, T. W. Muhleisen, M. M. Nothen, S. Moebus, K. H. Jockel, N. Klopp, H. E. Wichmann, V. S. Pankratz, S. B. Sando, J. O. Aasly, M. Barcikowska, Z. K. Wszolek, D. W. Dickson, N. R. Graff-Radford, R. C. Petersen, I. Alzheimer's Disease Neuroimaging, C. M. van Duijn, M. M. Breteler, M. A. Ikram, A. L. DeStefano, A. L. Fitzpatrick, O. Lopez, L. J. Launer, S. Seshadri, C. consortium, C. Berr, D. Campion, J. Epelbaum, J. F. Dartigues, C. Tzourio, A. Alperovitch, M. Lathrop, E. consortium, T. M. Feulner, P. Friedrich, C. Riehle, M. Krawczak, S. Schreiber, M. Mayhaus, S. Nicolhaus, S. Wagenpfeil, S. Steinberg, H. Stefansson, K. Stefansson, J. Snaedal, S. Bjornsson, P. V. Jonsson, V. Chouraki, B. Genier-Boley, M. Hiltunen, H. Soininen, O. Combarros, D. Zelenika, M. Delepine, M. J. Bullido, F. Pasquier, I. Mateo, A. Frank-Garcia, E. Porcellini, O. Hanon, E. Coto, V. Alvarez, P. Bosco, G. Siciliano, M. Mancuso, F. Panza, V. Solfrizzi, B. Nacmias, S. Sorbi, P. Bossu, P. Piccardi, B. Arosio, G. Annoni, D. Seripa, A. Pilotto, E. Scarpini, D. Galimberti, A. Brice, D. Hannequin, F. Licastro, L. Jones, P. A. Holmans, T. Jonsson, M. Riemenschneider, K. Morgan, S. G. Younkin, M. J. Owen, M. O'Donovan, P. Amouyel and J. Williams (2011). "Common variants at ABCA7, MS4A6A/MS4A4E, EPHA1, CD33 and CD2AP are associated with Alzheimer's disease." Nat Genet 43(5): 429-435.

Hong, S., L. Dissing-Olesen and B. Stevens (2016). "New insights on the role of microglia in synaptic pruning in health and disease." Curr Opin Neurobiol 36: 128-134.

Huang, Q. Q. and R. M. Pope (2009). "The role of toll-like receptors in rheumatoid arthritis." Curr Rheumatol Rep 11(5): 357-364.

Ikegami, A., K. Haruwaka and H. Wake (2019). "Microglia: Lifelong modulator of neural circuits." Neuropathology 39(3): 173-180.

Jaitin, D. A., L. Adlung, C. A. Thaiss, A. Weiner, B. Li, H. Descamps, P. Lundgren, C. Bleriot, Z. Liu, A. Deczkowska, H. Keren-Shaul, E. David, N. Zmora, S. M. Eldar, N. Lubezky, O. Shibolet, D. A. Hill, M. A. Lazar, M. Colonna, F. Ginhoux, H. Shapiro, E. Elinav and I. Amit (2019). "Lipid-Associated Macrophages Control Metabolic Homeostasis in a Trem2-Dependent Manner " Cell 178(3): 686-698.e14.

Jay, T. R., V. E. von Saucken and G. E. Landreth (2017). "TREM2 in Neurodegenerative Diseases." Mol Neurodegener 12(1): 56 (pp. 1-33).

Jay, T. R., C. M. Miller, P. J. Cheng, L. C. Graham, S. Bemiller, M. L. Broihier, G. Xu, D. Margevicius, J. C. Karlo, G. L. Sousa, A. C. Cotleur, O. Butovsky, L. Bekris, S. M. Staugaitis, J. B. Leverenz, S. W. Pimplikar, G. E. Landreth, G. R. Howell, R. M. Ransohoff, B. T. Lamb (2015). "TREM2 deficiency eliminates TREM2+ inflammatory macrophages and ameliorates pathology in Alzheimer's disease mouse models." J Exp Med 212(3): 287-295.

Jonsson, T., H. Stefansson, S. Steinberg, I. Jonsdottir, P. V. Jonsson, J. Snaedal, S. Bjornsson, J. Huttenlocher, A. I. Levey, J. J. Lah, D. Rujescu, H. Hampel, I. Giegling, O. A. Andreassen, K. Engedal, I. Ulstein, S. Djurovic, C. Ibrahim-Verbaas, A. Hofman, M. A. Ikram, C. M. van Duijn, U. Thorsteinsdottir, A. Kong and K. Stefansson (2013). "Variant of TREM2 associated with the risk of Alzheimer's disease." N Engl J Med 368(2): 107-116.

Kang, S. S., A. Kurti, K. E. Baker, C. C. Liu, M. Colonna, J. D. Ulrich, D. M. Holtzman, G. Bu and J. D. Fryer (2018). "Behavioral and transcriptomic analysis of Trem2-null mice: not all knockout mice are created equal." Hum Mol Genet 27(2): 211-223.

Keren-Shaul, H., A. Spinrad, A. Weiner, O. Matcovitch-Natan, R. Dvir-Szternfeld, T. K. Ulland, E. David, K. Baruch, D. Lara-Astaiso, B. Toth, S. Itzkovitz, M. Colonna, M. Schwartz and I. Amit (2017). "A Unique Microglia Type Associated with Restricting Development of Alzheimer's Disease." Cell 169(7): 1276-1290.e17.

Kleinberger, G., Y. Yamanishi, M. Suarez-Calvet, E. Czirr, E. Lohmann, E. Cuyvers, H. Struyfs, N. Pettkus, A. Wenninger-Weinzierl, F. Mazaheri, S. Tahirovic, A. Lleo, D. Alcolea, J. Fortea, M. Willem, S. Lammich, J. L. Molinuevo, R. Sanchez-Valle, A. Antonell, A. Ramirez, M. T. Heneka, K. Sleegers, J. van der Zee, J. J. Martin, S. Engelborghs, A. Demirtas-Tatlidede, H. Zetterberg, C. Van Broeckhoven, H. Gurvit, T. Wyss-Coray, J. Hardy, M. Colonna and C. Haass (2014). "TREM2 mutations implicated in neurodegeneration impair cell surface transport and phagocytosis." Sci Transl Med 6(243): 243ra286 (pp. 1-13).

Kobayashi, M., H. Konishi, A. Sayo, T. Takai and H. Kiyama (2016). "TREM2/DAP12 Signal Elicits Proinflammatory Response in Microglia and Exacerbates Neuropathic Pain." J Neurosci 36(43): 11138-11150.

Kober, D. L. and T. J. Brett (2017). "TREM2-Ligand Interactions in Health and Disease." J Mol Biol 429(11): 1607-1629.

Lee, C. Y. D., A. Daggett, X. Gu, L. L. Jiang, P. Langfelder, X. Li, N. Wang, Y. Zhao, C. S. Park, Y. Cooper, I. Ferando, I. Mody, G. Coppola, H. Xu and X. W. Yang (2018). "Elevated TREM2 Gene Dosage Reprograms Microglia Responsivity and Ameliorates Pathological Phenotypes in Alzheimer's Disease Models." Neuron 97(5): 1032-1048.e5.

Leyns, C. E. G., M. Gratuze, S. Narasimhan, N. Jain, L. J. Koscal, H. Jiang, M. Manis, M. Colonna, V. M. Y. Lee, J. D. Ulrich and D. M. Holtzman (2019). "TREM2 function impedes tau seeding in neuritic plaques." Nat Neurosci 22(8): 1217-1222.

Li, Q. and B. A. Barres (2018). "Microglia and macrophages in brain homeostasis and disease." Nat Rev Immunol 18(4): 225-242.

Liddelow, S. A., K. A. Guttenplan, L. E. Clarke, F. C. Bennett, C. J. Bohlen, L. Schirmer, M. L. Bennett, A. E. Munch, W. S. Chung, T. C. Peterson, D. K. Wilton, A. Frouin, B. A. Napier, N. Panicker, M. Kumar, M. S. Buckwalter, D. H. Rowitch, V. L. Dawson, T. M. Dawson, B. Stevens and B. A. Barres (2017). "Neurotoxic reactive astrocytes are induced by activated microglia." Nature 541 (7638): 481-487.

Madry, C. and D. Attwell (2015). "Receptors, ion channels, and signaling mechanisms underlying microglial dynamics." J Biol Chem 290(20): 12443-12450.

Madry, H., J. Prudlo, A. Grgic and J. Freyschmidt (2007). "Nasu-Hakola disease (PLOSL): report of five cases and review of the literature." Clin Orthop Relat Res 454: 262-269.

Otero, K., M. Shinohara, H. Zhao, M. Cella, S. Gilfillan, A. Colucci, R. Faccio, F. P. Ross, S. L. Teitelbaum, H. Takayanagi and M. Colonna (2012). "TREM2 and beta-catenin regulate bone homeostasis by controlling the rate of osteoclastogenesis." J Immunol 188(6): 2612-2621.

Paloneva, J., J. Mandelin, A. Kiialainen, T. Bohling, J. Prudlo, P. Hakola, M. Haltia, Y. T. Konttinen and L. Peltonen (2003). "DAP12/TREM2 deficiency results in impaired osteoclast differentiation and osteoporotic features." J Exp Med 198(4): 669-675.

Paolicelli, R. C., G. Bolasco, F. Pagani, L. Maggi, M. Scianni, P. Panzanelli, M. Giustetto, T. A. Ferreira, E. Guiducci, L. Dumas, D. Ragozzino and C. T. Gross (2011). "Synaptic pruning by microglia is necessary for normal brain development." Science 333(6048): 1456-1458.

Parhizkar, S., T. Arzberger, M. Brendel, G. Kleinberger, M. Deussing, C. Focke, B. Nuscher, M. Xiong, A. Ghasemigharagoz, N. Katzmarski, S. Krasemann, S. F. Lichtenthaler, S. A. Muller, A. Colombo, L. S. Monasor, S. Tahirovic, J. Herms, M. Willem, N. Pettkus, O. Butovsky, P. Bartenstein, D. Edbauer, A. Rominger, A. Erturk, S. A. Grathwohl, J. J. Neher, D. M. Holtzman, M. Meyer-Luehmann and C. Haass (2019). "Loss of TREM2 function increases amyloid seeding but reduces plaque-associated ApoE." Nat Neurosci 22(2): 191-204.

Peng, Q., S. Malhotra, J. A. Torchia, W. G. Kerr, K. M. Coggeshall and M. B. Humphrey (2010). "TREM2- and DAP12-dependent activation of PI3K requires DAP10 and is inhibited by SHIP1." Sci Signal 3(122): ra38 (pp. 1-18).

Sellgren, C. M., J. Gracias, B. Watmuff, J. D. Biag, J. M. Thanos, P. B. Whittredge, T. Fu, K. Worringer, H. E. Brown, J. Wang, A. Kaykas, R. Karmacharya, C. P. Goold, S. D. Sheridan and R. H. Perlis (2019). "Increased synapse elimination by microglia in schizophrenia patient-derived models of synaptic pruning." Nat Neurosci 22(3): 374-385.

Shinozaki, Y., K. Shibata, K. Yoshida, E. Shigetomi, C. Gachet, K. Ikenaka, K. F. Tanaka and S. Koizumi (2017). "Transformation of Astrocytes to a Neuroprotective Phenotype by Microglia via P2Y1 Receptor Downregulation." Cell Rep 19(6): 1151-1164.

Shirotani, K., Y. Hori, R. Yoshizaki, E. Higuchi, M. Colonna, T. Saito, S. Hashimoto, T. Saito, T. C. Saido and N. Iwata (2019). "Aminophospholipids are signal-transducing TREM2 ligands on apoptotic cells." Sci Rep 9(1): 7508 (pp. 1-9).

Sims, R., S. J. van der Lee, A. C. Naj, C. Bellenguez, N. Badarinarayan, J. Jakobsdottir, B. W. Kunkle, A. Boland, R. Raybould, J. C. Bis, E. R. Martin, B. Grenier-Boley, S. Heilmann-Heimbach, V. Chouraki, A. B. Kuzma, K. Sleegers, M. Vronskaya, A. Ruiz, R. R. Graham, R. Olaso, P. Hoffmann, M. L. Grove, B. N. Vardarajan, M. Hiltunen, M. M. Nothen, C. C. White, K. L. Hamilton-Nelson, J. Epelbaum, W. Maier, S. H. Choi, G. W. Beecham, C. Dulary, S. Herms, A. V. Smith, C. C. Funk, C. Derbois, A. J. Forstner, S. Ahmad, H. Li, D. Bacq, D. Harold, C. L. Satizabal, O. Valladares, A. Squassina, R. Thomas, J. A. Brody, L. Qu, P. Sanchez-Juan, T. Morgan, F. J. Wolters, Y. Zhao, F. S. Garcia, N. Denning, M. Fornage, J. Malamon, M. C. D. Naranjo, E. Majounie, T. H. Mosley, B. Dombroski, D. Wallon, M. K. Lupton, J. Dupuis, P. Whitehead, L. Fratiglioni, C. Medway, X. Jian, S. Mukherjee, L. Keller, K. Brown, H. Lin, L. B. Cantwell, F. Panza, B. McGuinness, S. Moreno-Grau, J. D. Burgess, V. Solfrizzi, P. Proitsi, H. H. Adams, M. Allen, D. Seripa, P. Pastor, L. A. Cupples, N. D. Price, D Hannequin, A. Frank-Garcia, D. Levy, P. Chakrabarty, P. Caffarra, I. Giegling, A. S. Beiser, V. Giedraitis, H. Hampel, M. E. Garcia, X. Wang, L. Lannfelt, P. Mecocci, G. Eiriksdottir, P. K. Crane, F. Pasquier, V. Boccardi, I. Henandez, R. C. Barber, M. Scherer, L. Tarraga, P. M. Adams, M. Leber, Y. Chen, M. S. Albert, S. Riedel-Heller, V. Emilsson, D. Beekly, A. Braae, R. Schmidt, D. Blacker, C. Masullo, H. Schmidt, R. S. Doody, G. Spalletta, W. T. Longstreth, Jr., T. J. Fairchild, P. Bossu, O. L. Lopez, M. P. Frosch, E. Sacchinelli, B. Ghetti, Q. Yang, R. M. Huebinger, F. Jessen, S. Li, M. I. Kamboh, J. Morris, O. Sotolongo-Grau, M. J. Katz, C. Corcoran, M. Dunstan, A. Braddel, C. Thomas, A. Meggy, R. Marshall, A. Gerrish, J. Chapman, M. Aguilar, S. Taylor, M. Hill, M. D. Fairen, A. Hodges, B. Vellas, H. Soininen, I. Kloszewska, M. Daniilidou, J. Uphill, Y. Patel, J. T. Hughes, J. Lord, J. Turton, A. M. Hartmann, R. Cecchetti, C. Fenoglio, M. Serpente, M. Arcaro, C. Caltagirone, M. D. Orfei, A. Ciaramella, S. Pichler, M. Mayhaus, W. Gu, A. Lleo, J. Fortea, R. Blesa, I. S. Barber, K. Brookes, C. Cupidi, R. G. Maletta, D. Carrell, S. Sorbi, S. Moebus, M. Urbano, A. Pilotto, J. Kornhuber, P. Bosco, S. Todd, D. Craig, J. Johnston, M. Gill, B. Lawlor, A. Lynch, N. C. Fox, J. Hardy, A. Consortium, R. L. Albin, L. G. Apostolova, S. E. Arnold, S. Asthana, C. S. Atwood, C. T. Baldwin, L. L. Barnes, S. Barral, T. G. Beach, J. T. Becker, E. H. Bigio, T. D. Bird, B. F. Boeve, J. D. Bowen, A. Boxer, J. R. Burke, J. M. Burns, J. D. Buxbaum, N. J. Cairns, C. Cao, C. S. Carlson, C. M. Carlsson, R. M. Carney, M. M. Carrasquillo, S. L. Carroll, C. C. Diaz, H. C. Chui, D. G. Clark, D. H. Cribbs, E. A. Crocco, C. DeCarli, M. Dick, R. Duara, D. A. Evans, K. M. Faber, K. B. Fallon, D. W. Fardo, M. R. Farlow, S. Ferris, T. M. Foroud, D. R. Galasko, M. Gearing, D. H. Geschwind, J. R. Gilbert, N. R. Graff-Radford, R. C. Green, J. H. Growdon, R. L. Hamilton, L. E. Harrell, L. S. Honig, M. J. Huentelman, C. M. Hulette, B. T. Hyman, G. P. Jarvik, E. Abner, L. W. Jin, G. Jun, A. Karydas, J. A. Kaye, R. Kim, N. W. Kowall, J. H. Kramer, F. M. LaFerla, J. J. Lah, J. B. Leverenz, A. I. Levey, G. Li, A. P. Lieberman, K. L. Lunetta, C. G. Lyketsos, D. C. Marson, F. Martiniuk, D. C. Mash, E. Masliah, W. C. McCormick, S. M.

McCurry, A. N. McDavid, A. C. McKee, M. Mesulam, B. L. Miller, C. A. Miller, J. W. Miller, J. C. Morris, J. R. Murrell, A. J. Myers, S. O'Bryant, J. M. Olichney, V. S. Pankratz, J. E. Parisi, H. L. Paulson, W. Perry, E. Peskind, A. Pierce, W. W. Poon, H. Potter, J. F. Quinn, A. Raj, M. Raskind, B. Reisberg, C. Reitz, J. M. Ringman, E. D. Roberson, E. Rogaeva, H. J. Rosen, R. N. Rosenberg, M. A. Sager, A. J. Saykin, J. A. Schneider, L. S. Schneider, W. W. Seeley, A. G. Smith, J. A. Sonnen, S. Spina, R. A. Stern, R. H. Swerdlow, R. E. Tanzi, T. A. Thornton-Wells, J. Q. Trojanowski, J. C. Troncoso, V. M. Van Deerlin, L. J. Van Eldik, H. V. Vinters, J. P. Vonsattel, S. Weintraub, K. A. Welsh-Bohmer, K. C. Wilhelmsen, J. Williamson, T. S. Wingo, R. L. Woltjer, C. B. Wright, C. E. Yu, L. Yu, F. Garzia, F. Golamaully, G. Septier, S. Engelborghs, R. Vandenberghe, P. P. De Deyn, C. M. Fernadez, Y. A. Benito, H. Thonberg, C. Forsell, L. Lilius, A. Kinhult-Stahlbom, L. Kilander, R. Brundin, L. Concari, S. Helisalmi, A. M. Koivisto, A. Haapasalo, V. Dermecourt, N. Fievet, O. Hanon, C. Dufouil, A. Brice, K. Ritchie, B. Dubois, J. J. Himali, C. D. Keene, J. Tschanz, A. L. Fitzpatrick, W. A. Kukull, M. Norton, T. Aspelund, E. B. Larson, R. Munger, J. I. Rotter, R. B. Lipton, M. J. Bullido, A. Hofman, T. J. Montine, E. Coto, E. Boerwinkle, R. C. Petersen, V. Alvarez, F. Rivadeneira, E. M. Reiman, M. Gallo, C. J. O'Donnell, J. S. Reisch, A. C. Bruni, D. R. Royall, M. Dichgans, M. Sano, D. Galimberti, P. St George-Hyslop, E. Scarpini, D. W. Tsuang, M. Mancuso, U. Bonuccelli, A. R. Winslow, A. Daniele, C. K. Wu, C. A. E. Gerad/Perades, O. Peters, B. Nacmias, M. Riemenschneider, R. Heun, C. Brayne, D. C. Rubinsztein, J. Bras, R. Guerreiro, A. Al-Chalabi, C. E. Shaw, J. Collinge, D. Mann, M. Tsolaki, J. Clarimon, R. Sussams, S. Lovestone, M. C. O'Donovan, M. J. Owen, T. W. Behrens, S. Mead, A. M. Goate, A. G. Uitterlinden, C. Holmes, C. Cruchaga, M. Ingelsson, D. A. Bennett, J. Powell, T. E. Golde, C. Graff, P. L. De Jager, K. Morgan, N. Ertekin-Taner, O. Combarros, B. M. Psaty, P. Passmore, S. G. Younkin, C. Ben, V. Gudnason, D. Rujescu, D. W. Dickson, J. F. Dartigues, A. L. DeStefano, S. Ortega-Cubero, H. Hakonarson, D. Campion, M. Boada, J. K. Kauwe, L. A. Farrer, C. Van Broeckhoven, M. A. Ikram, L. Jones, J. L. Haines, C. Tzourio, L. J. Launer, V. Escott-Price, R. Mayeux, J. F. Deleuze, N. Amin, P. A. Holmans, M. A. Pericak-Vance, P. Amouyel, C. M. van Duijn, A. Ramirez, L. S. Wang, J. C. Lambert, S. Seshadri, J. Williams and G. D. Schellenberg (2017). "Rare coding variants in PLCG2, ABI3, and TREM2 implicate microglial-mediated innate immunity in Alzheimer's disease." Nat Genet 49(9): 1373-1384.

Suarez-Calvet, M., E. Morenas-Rodriguez, G. Kleinberger, K. Schlepckow, M. A. Araque Caballero, N. Franzmeier, A. Capell, K. Fellerer, B. Nuscher, E. Eren, J. Levin, Y. Deming, L. Piccio, C. M. Karch, C. Cruchaga, L. M. Shaw, J. Q. Trojanowski, M. Weiner, M. Ewers, C. Haass and I. Alzheimer's Disease Neuroimaging (2019). "Early increase of CSF sTREM2 in Alzheimer's disease is associated with tau related-neurodegeneration but not with amyloid-beta pathology." Mol Neurodegener 14(1): 1 (pp. 1-14).

Ulland, T. K., W. M. Song, S. C. Huang, J. D. Ulrich, A. Sergushichev, W. L. Beatty, A. A. Loboda, Y. Zhou, N. J. Cairns, A. Kambal, E. Loginicheva, S. Gilfillan, M. Cella, H. W. Virgin, E. R. Unanue, Y. Wang, M. N. Artyomov, D. M. Holtzman and M. Colonna (2017). "TREM2 Maintains Microglial Metabolic Fitness in Alzheimer's Disease." Cell 170(4): 649-663.e13.

Ulrich, J. D., D. M. Holtzman (2016). "TREM2 Function in Alzheimer's Disease and Neurodegeneration." ACS Chem Neurosci 20(7): 420-427.

Ulrich, J. D., T. K. Ulland, M. Colonna and D. M. Holtzman (2017). "Elucidating the Role of TREM2 in Alzheimer's Disease." Neuron 94(2): 237-248.

Wang, Y., M. Cella, K. Mallinson, J. D. Ulrich, K. L. Young, M. L. Robinette, S. Gilfillan, G. M. Krishnan, S. Sudhakar, B. H. Zinselmeyer, D. M. Holtzman, J. R. Cirrito and M. Colonna (2015). "TREM2 lipid sensing sustains the microglial response in an Alzheimer's disease model." Cell 160(6): 1061-1071.

Wu, R., X. Li, P. Xu, L. Huang, J. Cheng, X. Huang, J. Jiang, L. J. Wu and Y. Tang (2017). "TREM2 protects against cerebral ischemia/reperfusion injury." Mol Brain 10(1): 20 (pp. 1-13).

Yeh, F. L., Y. Wang, I. Tom , L. C. Gonzalez, M. Sheng (2016). "TREM2 Binds to Apolipoproteins, Including APOE and CLU/APOJ, and Thereby Facilitates Uptake of Amyloid-Beta by Microglia." Neuron 91(2): 328-340.

Yuan, P., C. Condello, C. D. Keene, Y. Wang, T. D. Bird, S. M. Paul, W. Luo, M. Colonna, D. Baddeley and J. Grutzendler (2016). "TREM2 Haplodeficiency in Mice and Humans Impairs the Microglia Barrier Function Leading to Decreased Amyloid Compaction and Severe Axonal Dystrophy." Neuron 90(4): 724-739.

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:

1. A compound selected from:

Ex. 1

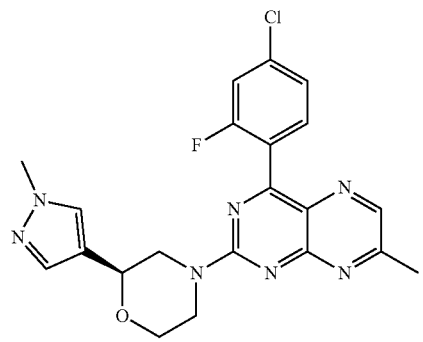 [SMILES: Cc1cnc2c(-c3ccc(Cl)cc3F)nc(N3CCO[C@@H](c4cnn(C)c4)C3)nc2n1]

Ex. 2

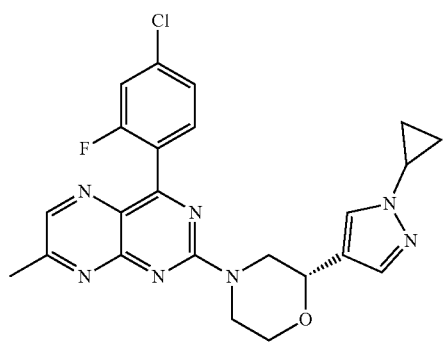

Ex. 3

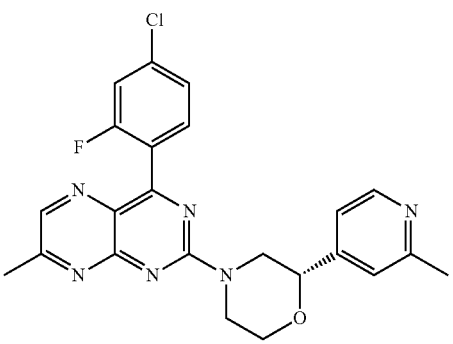

Ex. 7

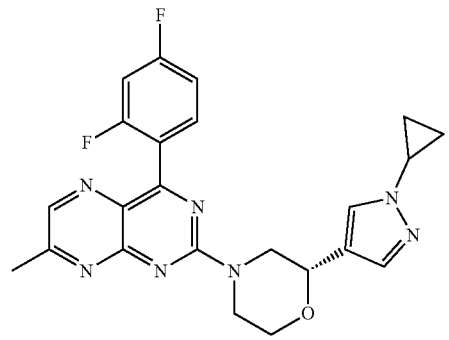

Ex. 8

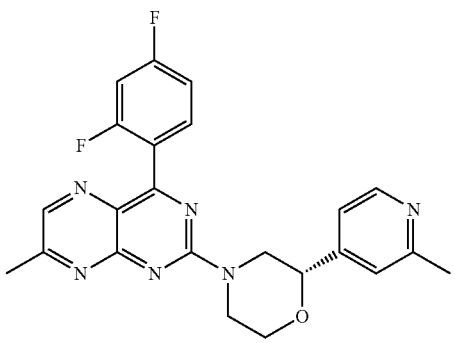

Ex. 9

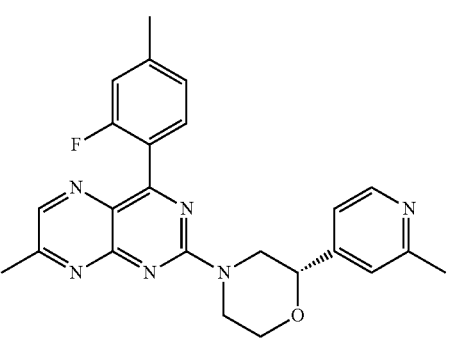

Ex. 10

| | |
|---|---|
| Ex. 13 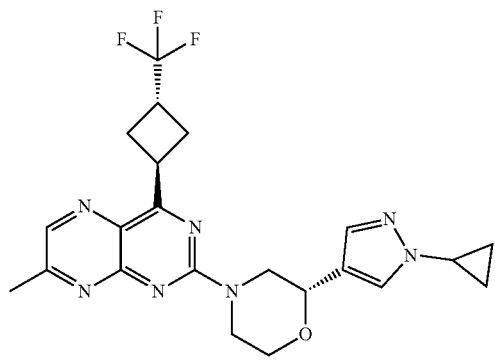 | Ex. 19 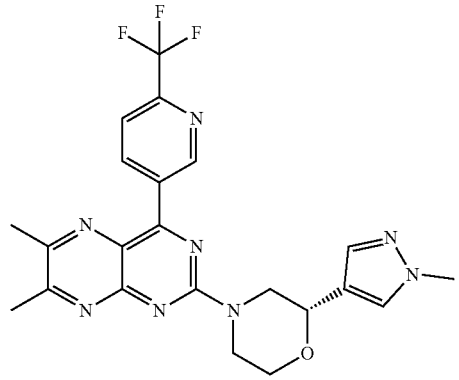 |
| Ex. 16 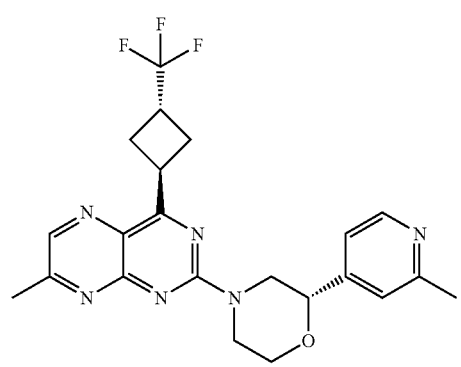 | Ex. 21 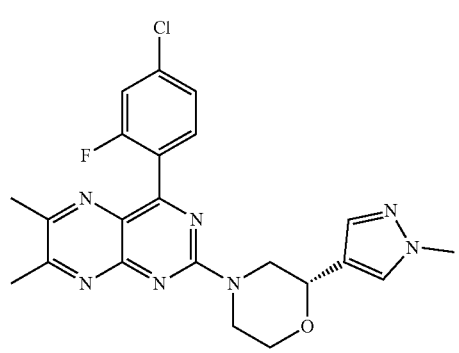 |
| Ex. 17 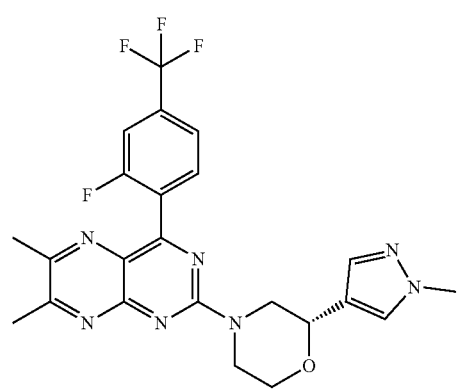 | Ex. 22 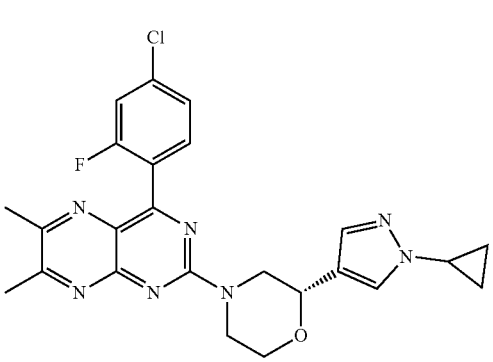 |
| Ex. 18 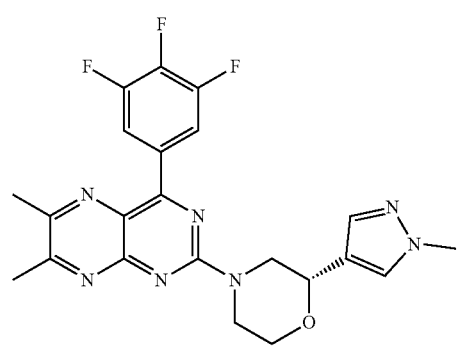 | Ex. 23 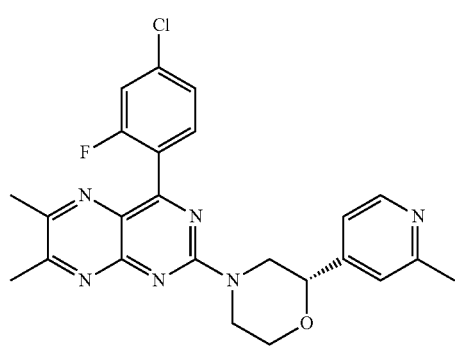 |

Ex. 25
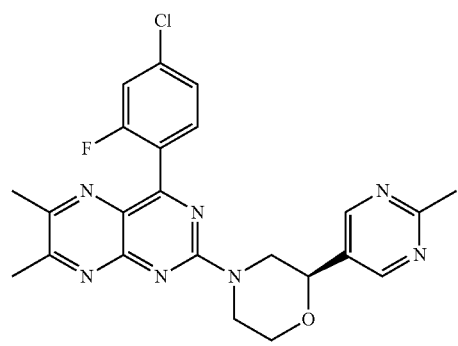
Ex. 33
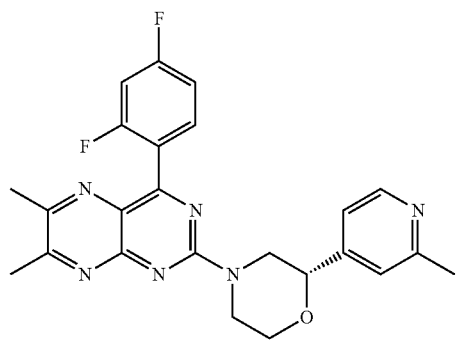
Ex. 26
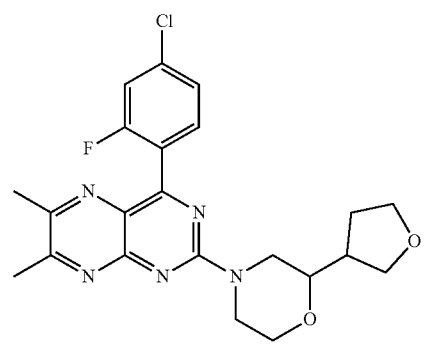
Ex. 37
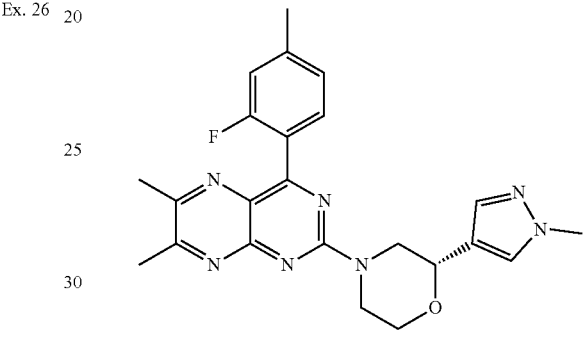
Ex. 31
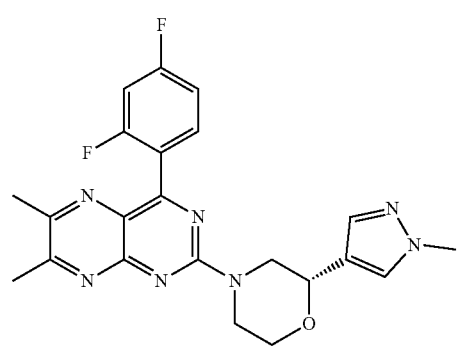
Ex. 38
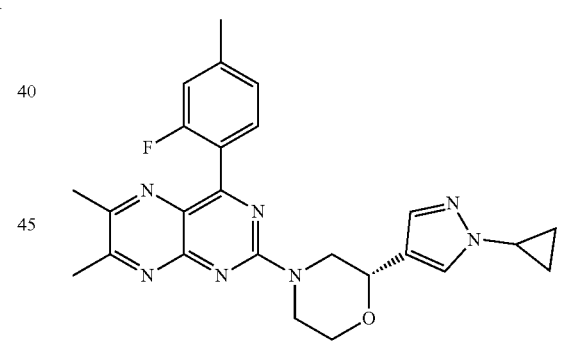
Ex. 32
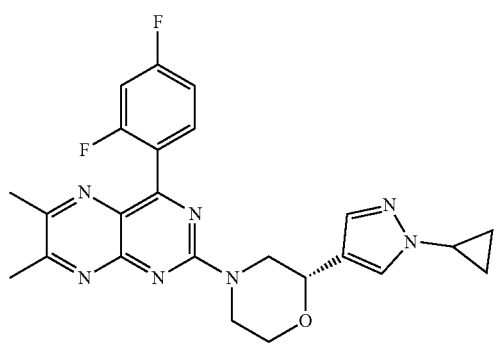
Ex. 39
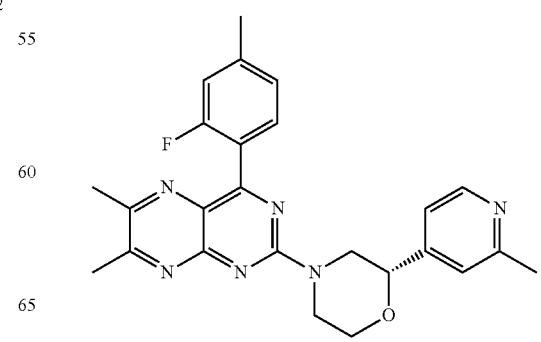

Ex. 42
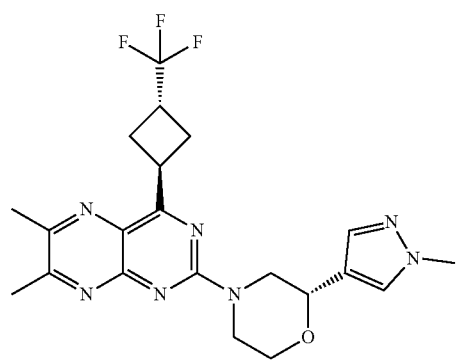
Ex. 49
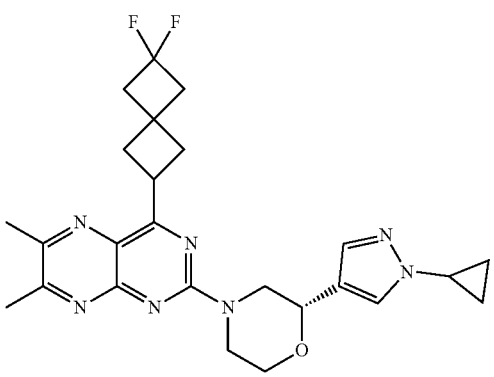
Ex. 46
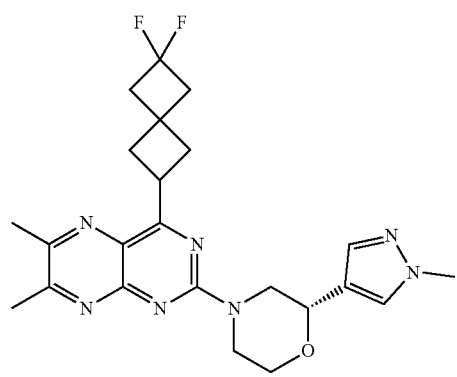
Ex. 50
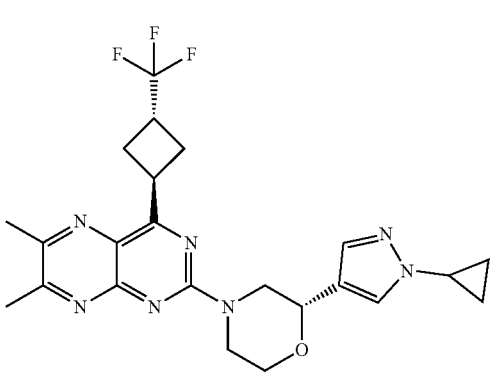
Ex. 47
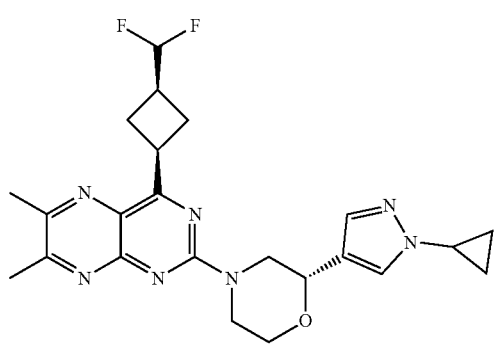
Ex. 51
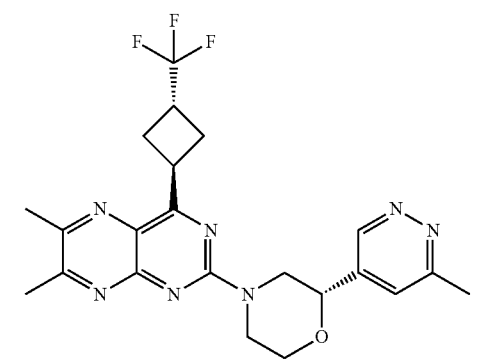
Ex. 48
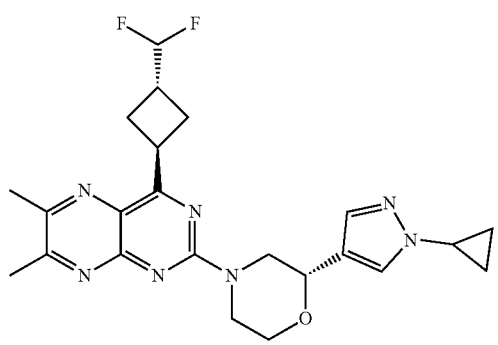
Ex. 53
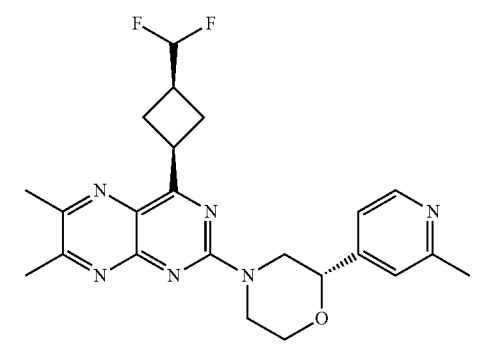

| | |
|---|---|
| Ex. 54 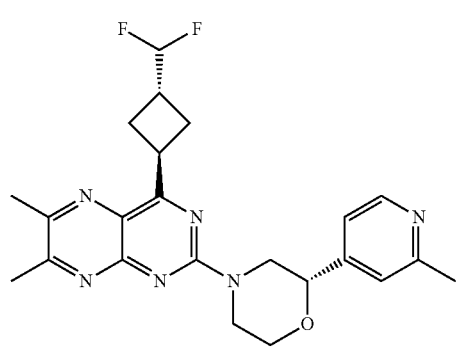 | Ex. 61 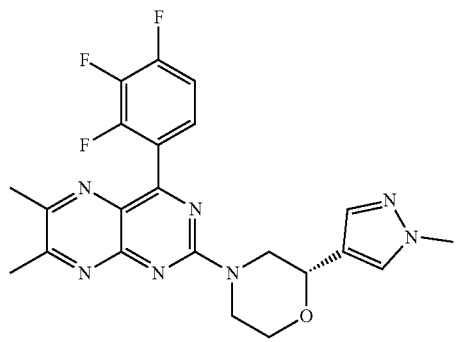 |
| Ex. 55 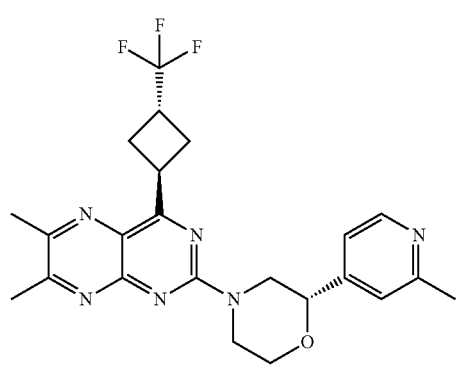 | Ex. 62 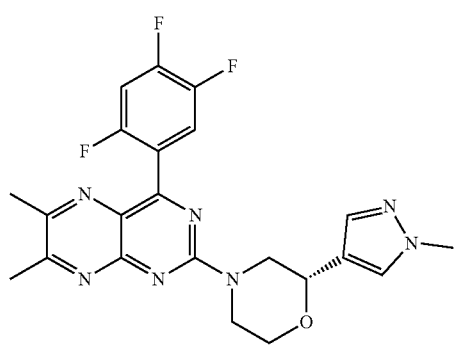 |
| Ex. 56 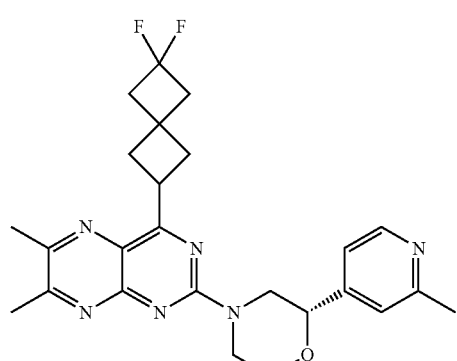 | Ex. 63 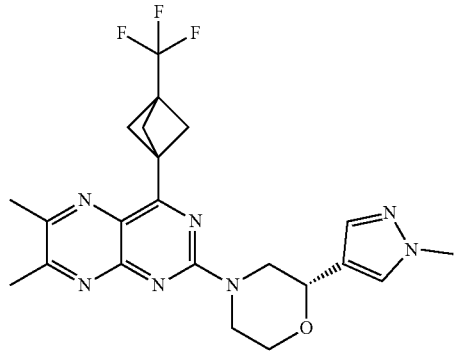 |
| Ex. 60 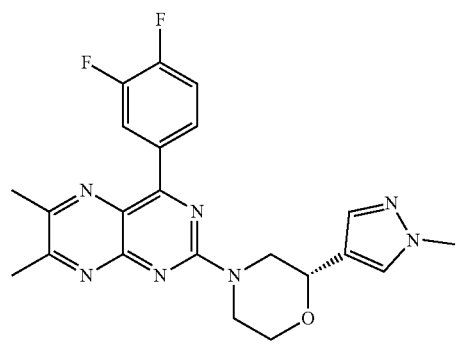 | Ex. 64 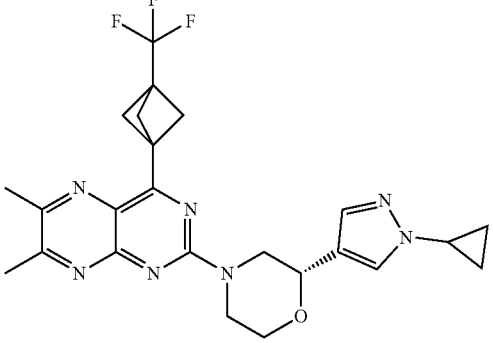 |

Ex. 65
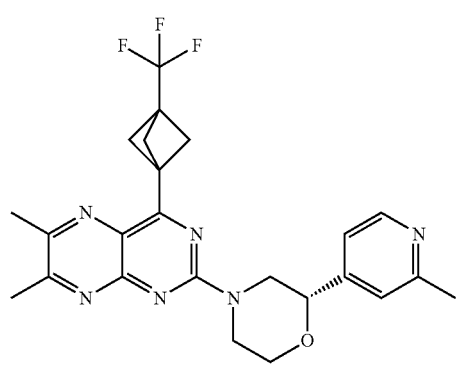
Ex. 133
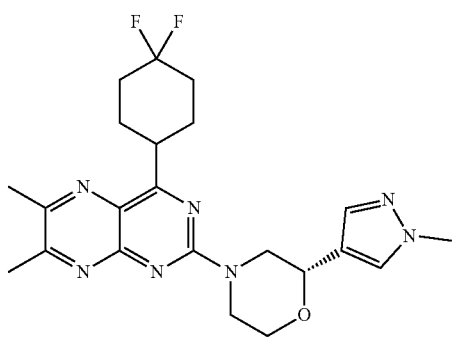
Ex. 127
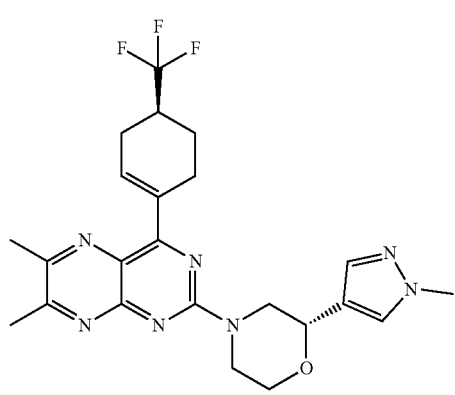
Ex. 136
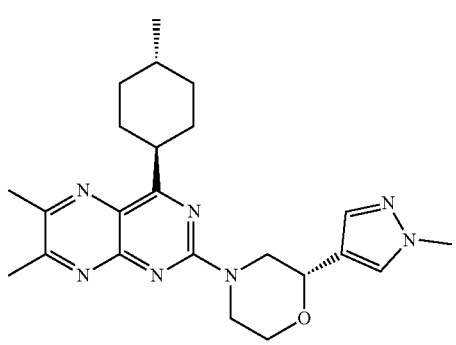
Ex. 130
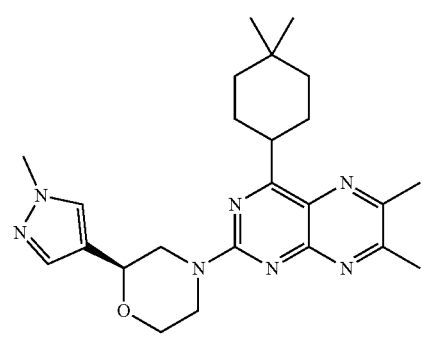
Ex. 137
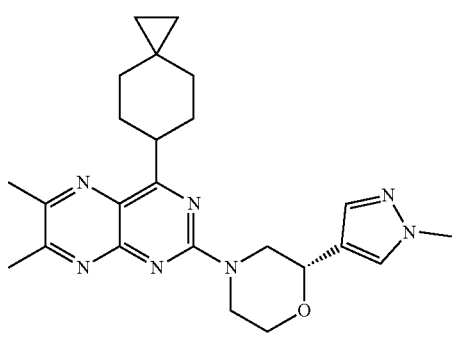
Ex. 132
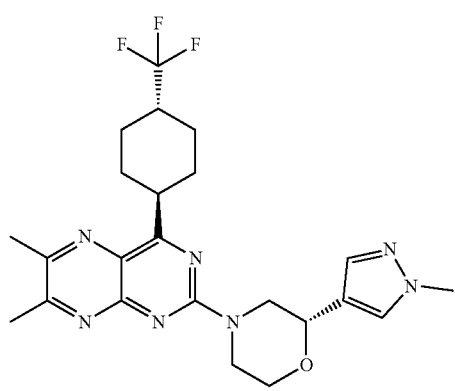
Ex. 138
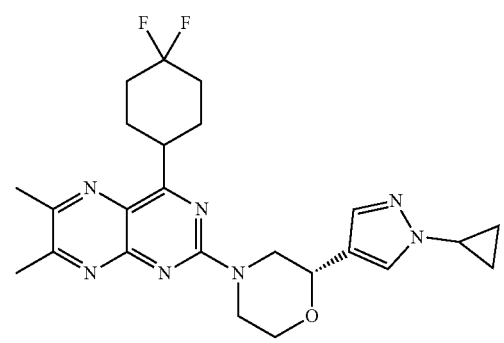

| | |
|---|---|
| Ex. 139 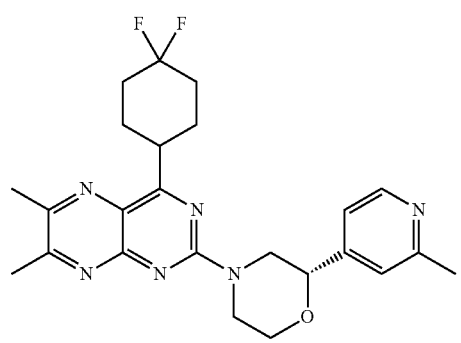 | Ex. 295 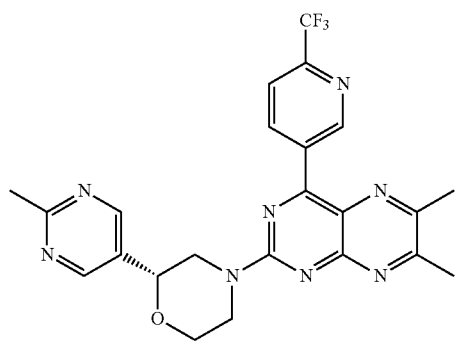 |
| Ex. 165 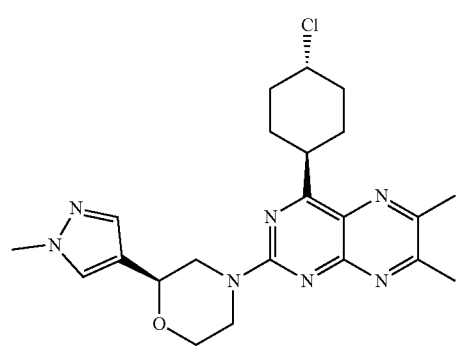 | Ex. 298 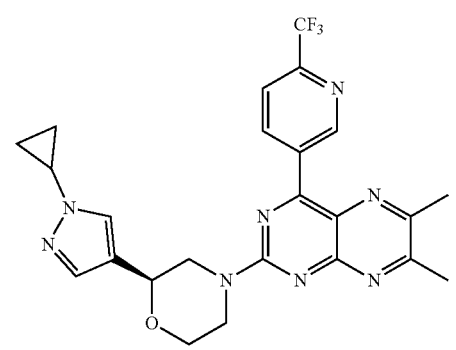 |
| Ex. 231 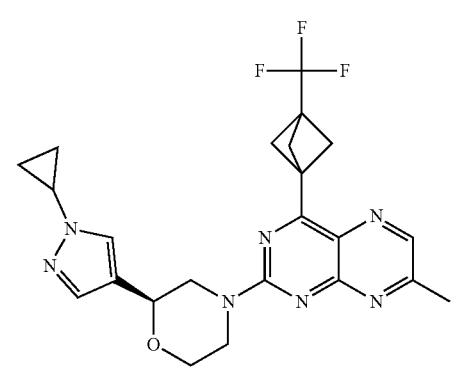 | Ex. 299 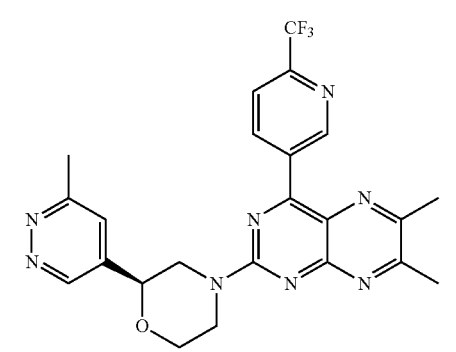 |
| Ex. 232 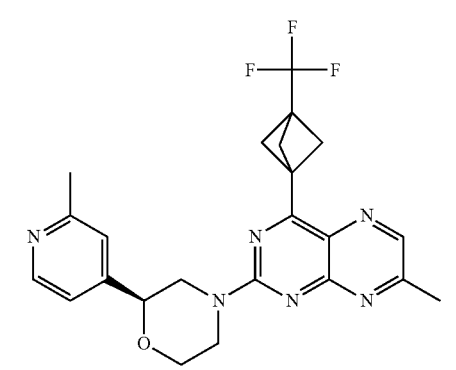 | Ex. 314 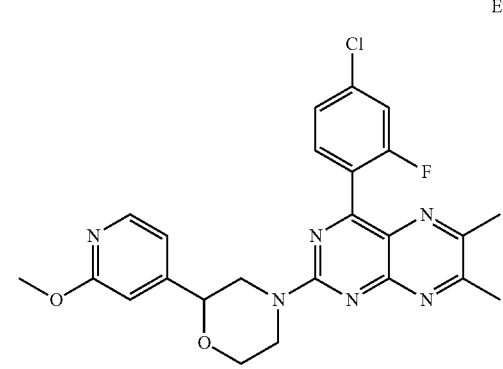 |

Ex. 318
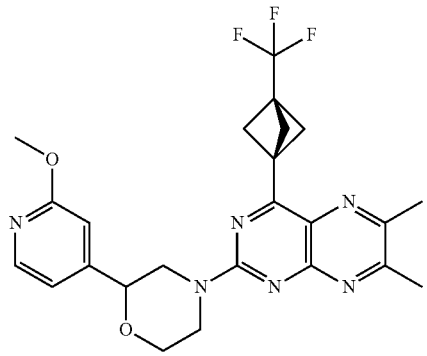 [SMILES: COc1cc(C2CN(c3nc4nc(C)c(C)nc4c([C@]45C[C@](C(F)(F)F)(C4)C5)n3)CCO2)ccn1]
Ex. 322
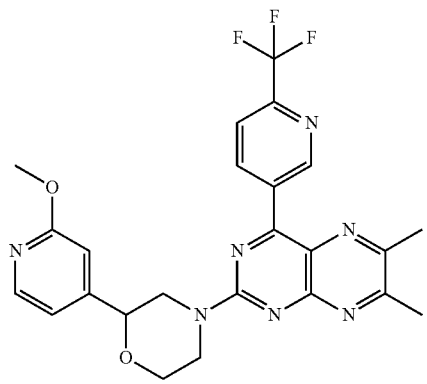 [SMILES: COc1cc(C2CN(c3nc(-c4ccc(C(F)(F)F)nc4)c4nc(C)c(C)nc4n3)CCO2)ccn1]
Ex. 335
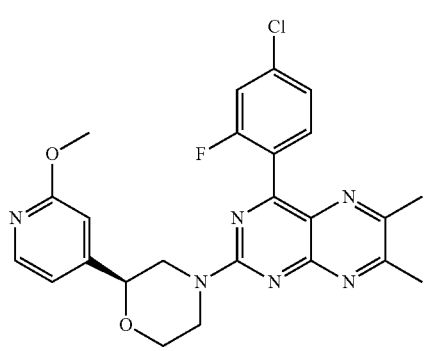 [SMILES: COc1cc([C@H]2CN(c3nc(-c4ccc(Cl)cc4F)c4nc(C)c(C)nc4n3)CCO2)ccn1]
Ex. 337
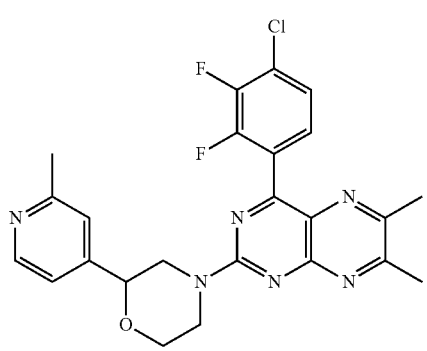
Ex. 352
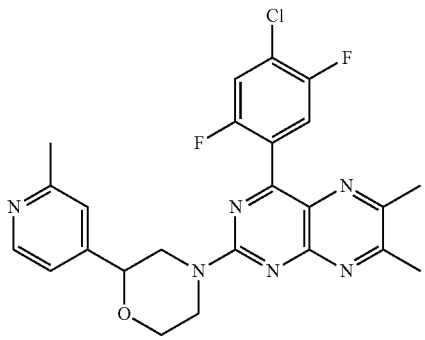 [SMILES: Cc1cc(C2CN(c3nc(-c4cc(F)c(Cl)cc4F)c4nc(C)c(C)nc4n3)CCO2)ccn1]
Ex. 354
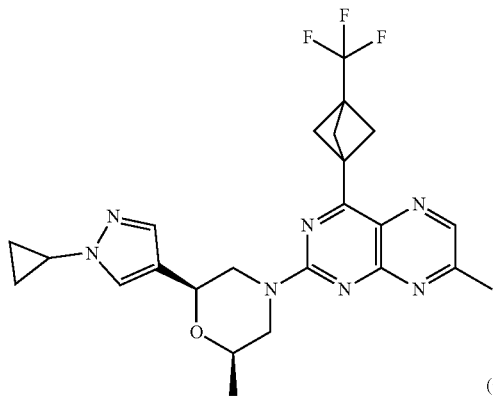
(+/-)
Ex. 356
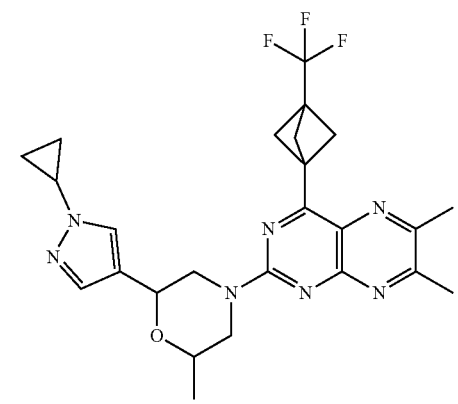
Ex. 359
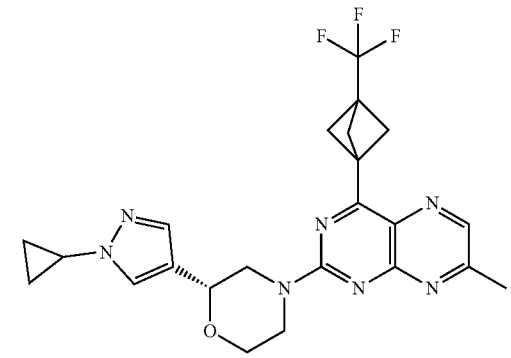

Ex. 363
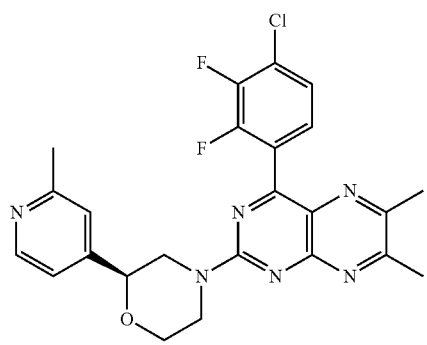
Ex. 364
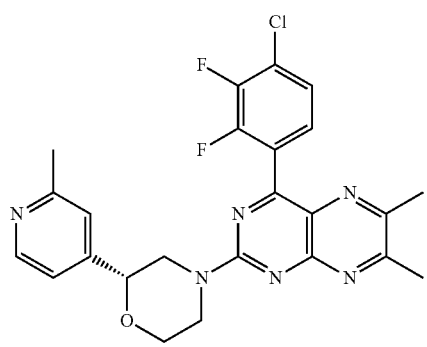
Ex. 369
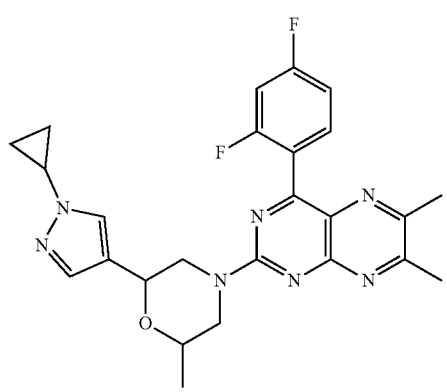
Ex. 371
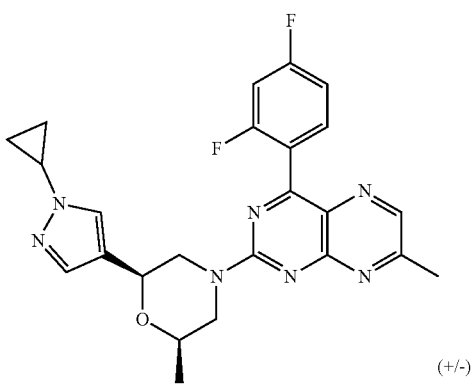
(+/-)
Ex. 372
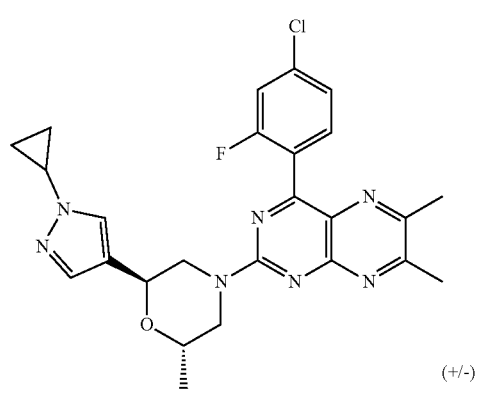
(+/-)
Ex. 373
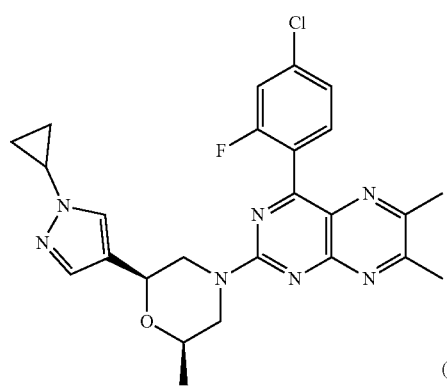
(+/-)
Ex. 374
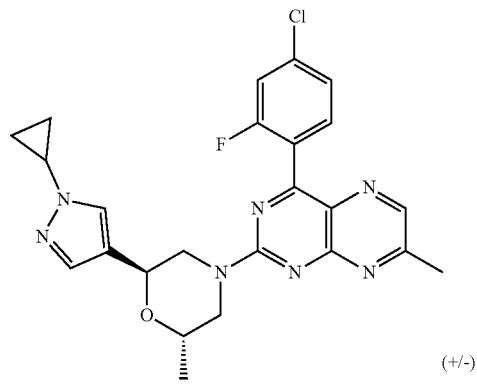
(+/-)
Ex. 375
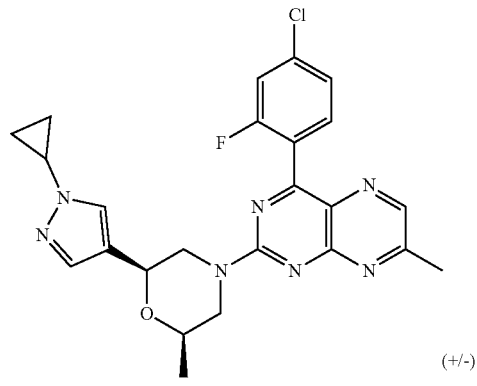
(+/-)

Ex. 381
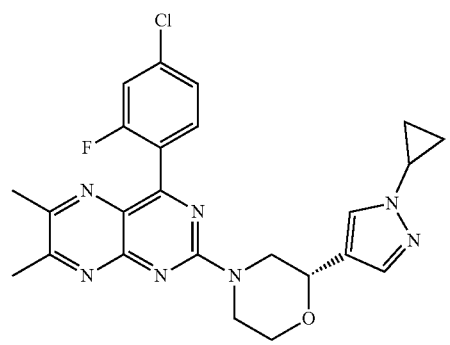
Ex. 408
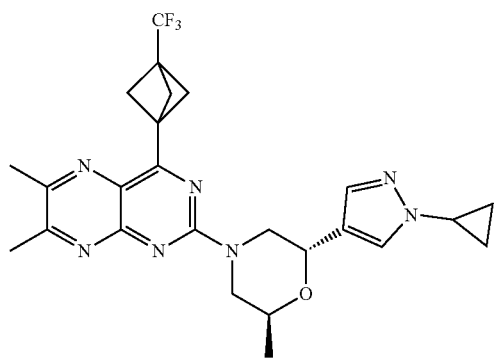
Ex. 387
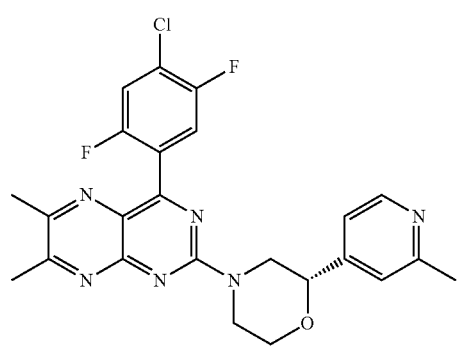
Ex. 410
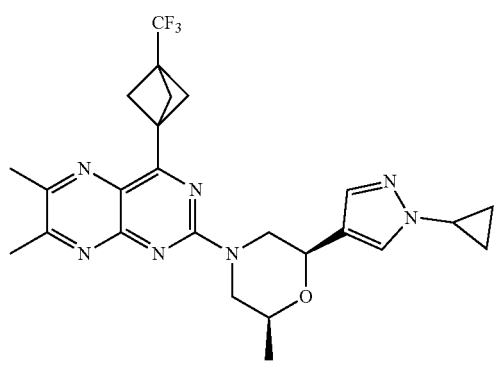
Ex. 391
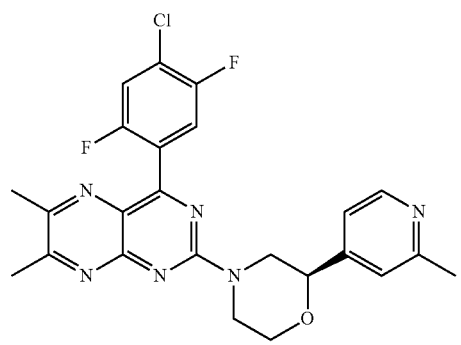
Ex. 411
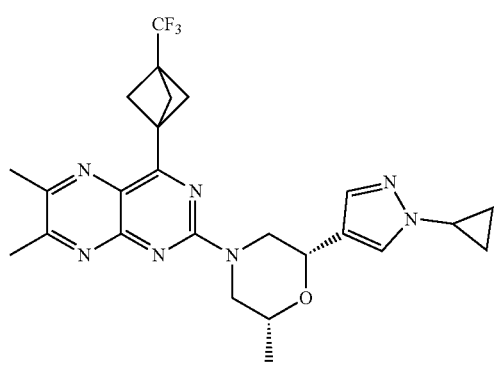
Ex. 404
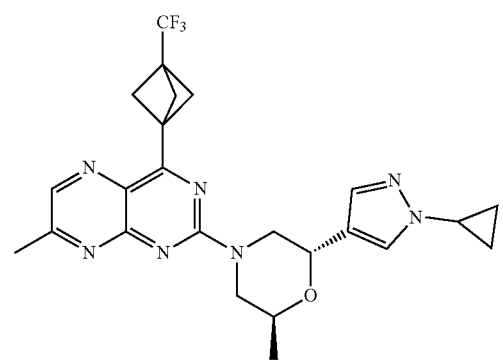
Ex. 420
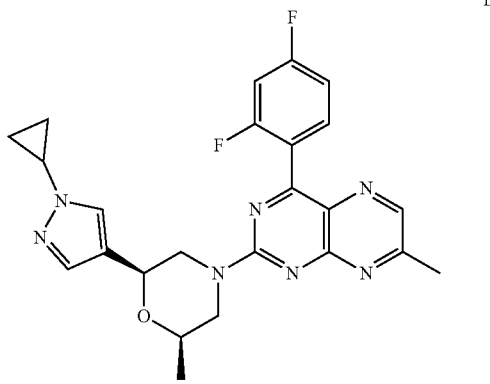

-continued

Ex. 422

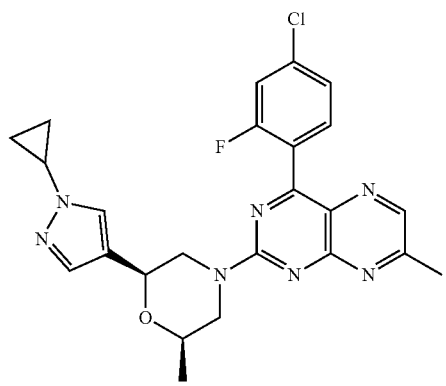

Ex. 424

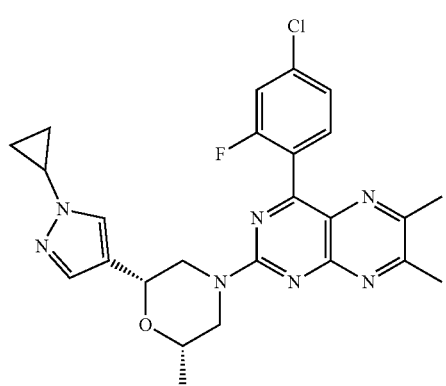

Ex. 425

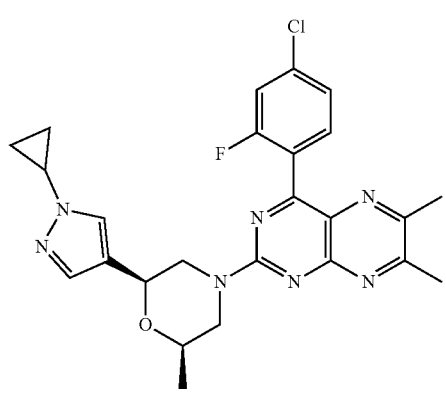

Ex. 426

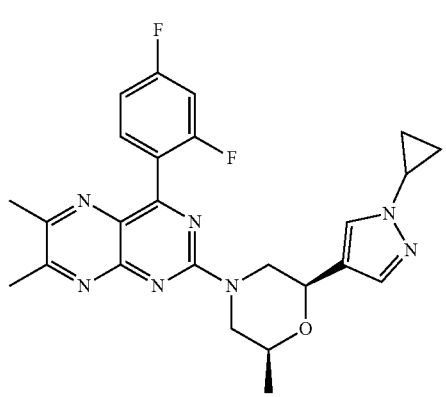

-continued

Ex. 427

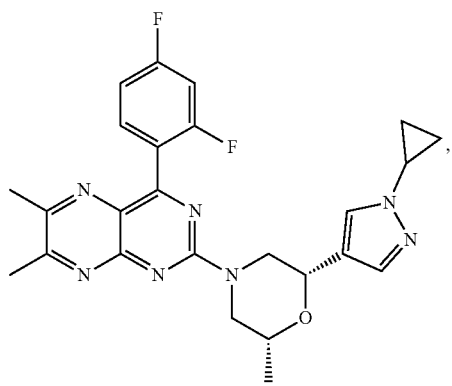

or a tautomer thereof, or a pharmaceutically acceptable salt of said compound or said tautomer.

2. The compound of claim 1, which is:

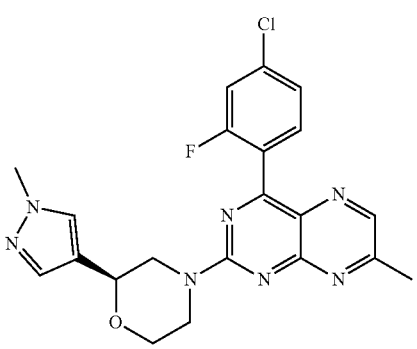 [SMILES: Cc1cnc2c(-c3ccc(Cl)cc3F)nc(N3CCO[C@@H](c4cnn(C)c4)C3)nc2n1]

Ex. 1, or a tautomer thereof, or a pharmaceutically acceptable salt of said compound or said tautomer.

3. The compound of claim 1, which is:

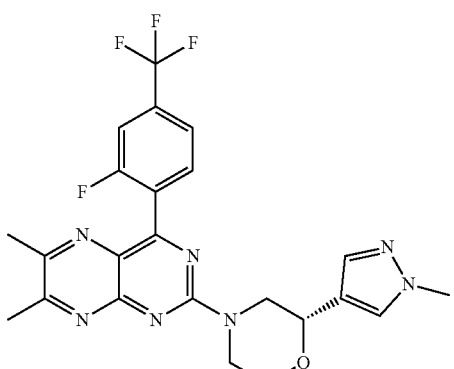

Ex. 17, or a tautomer thereof, or a pharmaceutically acceptable salt of said compound or said tautomer.

4. The compound of claim 1, which is:

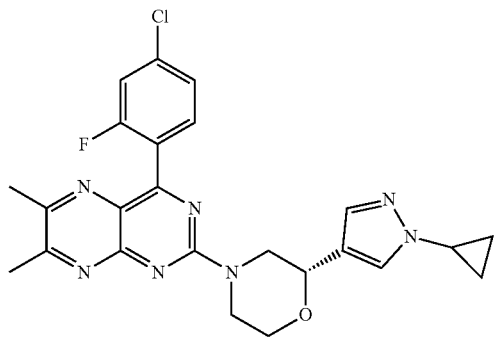

Ex. 22, or a tautomer thereof, or a pharmaceutically acceptable salt of said compound or said tautomer.

5. The compound of claim 1, which is:

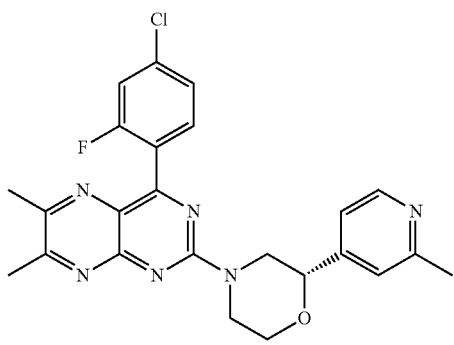

Ex. 23, or a tautomer thereof, or a pharmaceutically acceptable salt of said compound or said tautomer.

6. The compound of claim 1, which is:

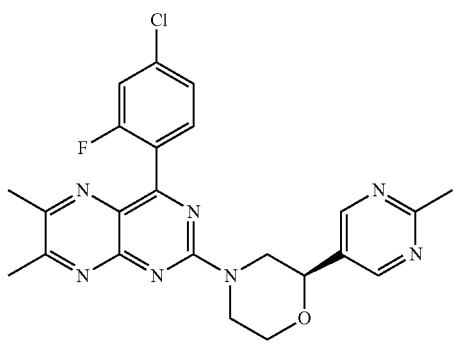

Ex. 25, or a tautomer thereof, or a pharmaceutically acceptable salt of said compound or said tautomer.

7. The compound of claim 1, which is:

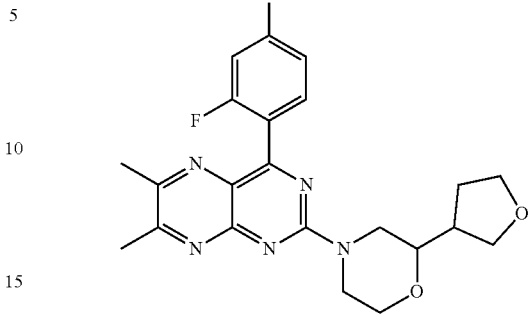

Ex. 26, or a tautomer thereof, or a pharmaceutically acceptable salt of said compound or said tautomer.

8. The compound of claim 1, which is:

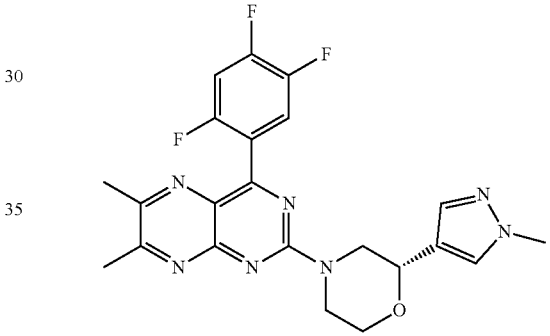

Ex. 62, or a tautomer thereof, or a pharmaceutically acceptable salt of said compound or said tautomer.

9. The compound of claim 1, which is:

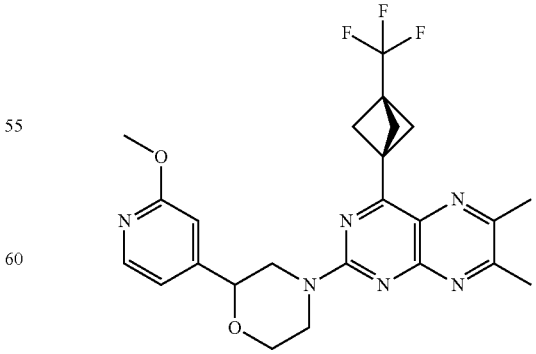

Ex. 318, or a tautomer thereof, or a pharmaceutically acceptable salt of said compound or said tautomer.

10. The compound of claim 1, which is:

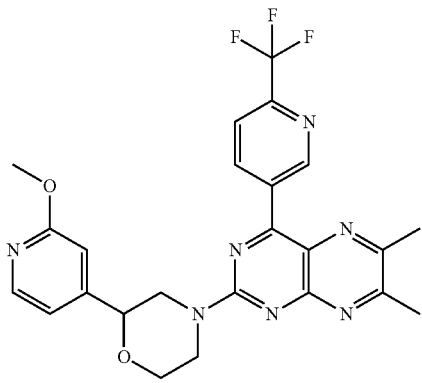

Ex. 322, or a tautomer thereof, or a pharmaceutically acceptable salt of said compound or said tautomer.

11. The compound of claim 1, which is:

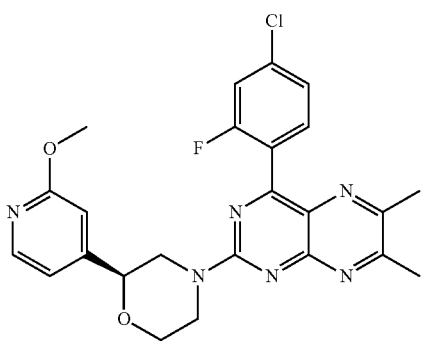

Ex. 335, or a tautomer thereof, or a pharmaceutically acceptable salt of said compound or said tautomer.

12. The compound of claim 1, which is:

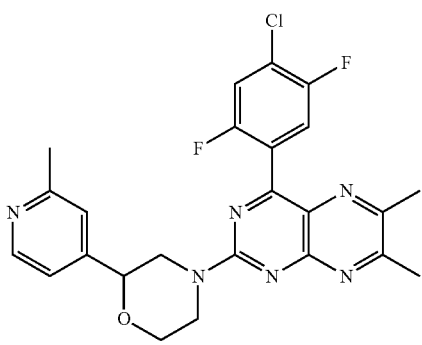

Ex. 352, or a tautomer thereof, or a pharmaceutically acceptable salt of said compound or said tautomer.

13. The compound of claim 1, which is:

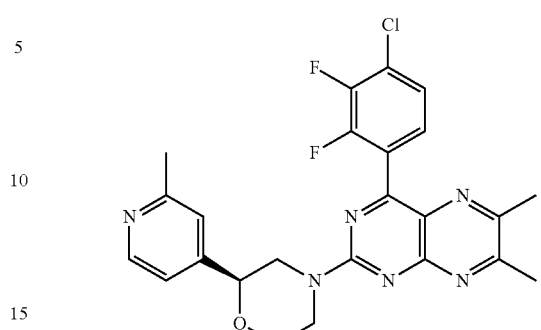

Ex. 363, or a tautomer thereof, or a pharmaceutically acceptable salt of said compound or said tautomer.

14. The compound of claim 1, which is:

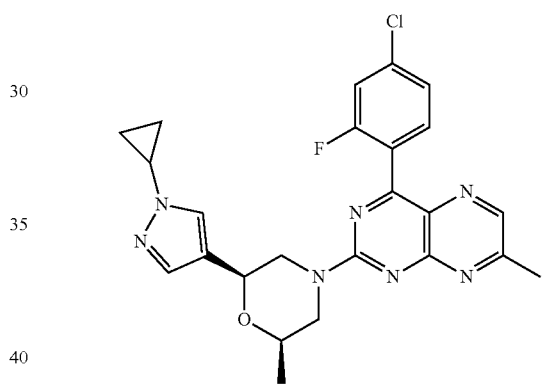

Ex. 422, or a tautomer thereof, or a pharmaceutically acceptable salt of said compound or said tautomer.

15. The compound of claim 1, which is:

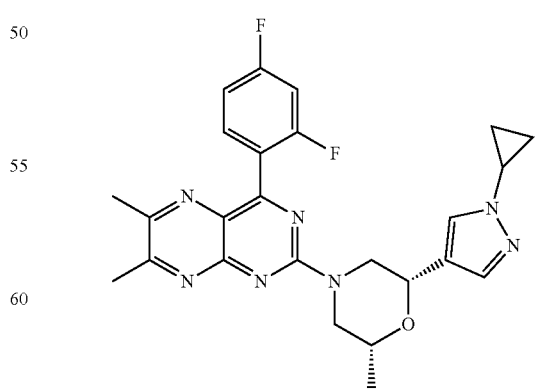

Ex. 427, or a tautomer thereof, or a pharmaceutically acceptable salt of said compound or said tautomer.

16. A pharmaceutical composition comprising a compound selected from:
Ex. 1
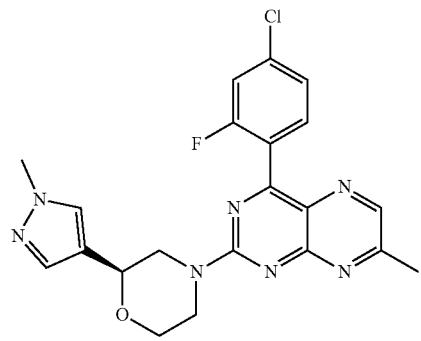
Ex. 2
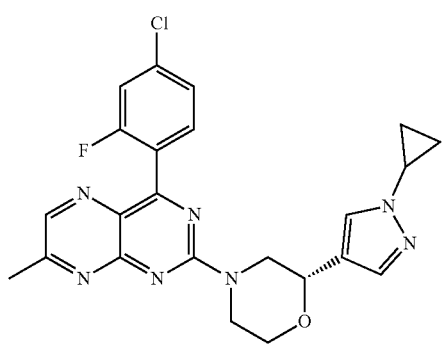
Ex. 3
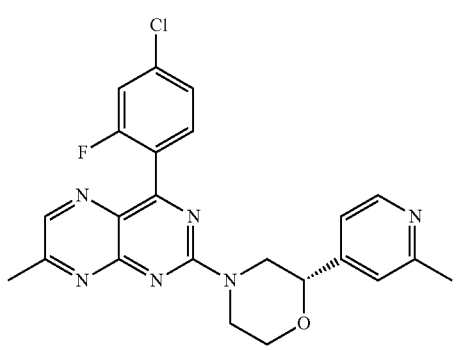
Ex. 7
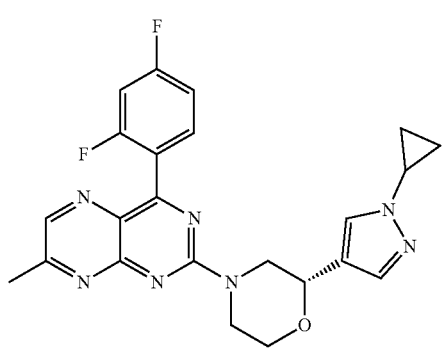
-continued
Ex. 8
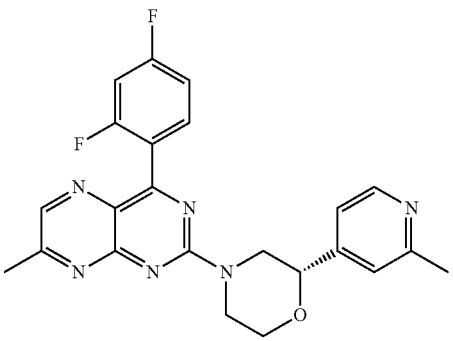
Ex. 9
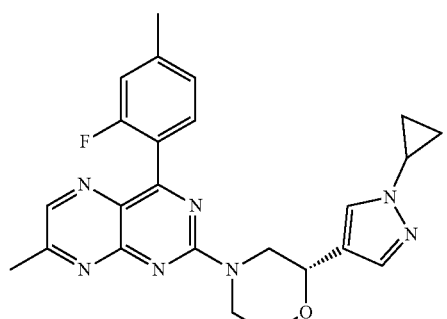
Ex. 10
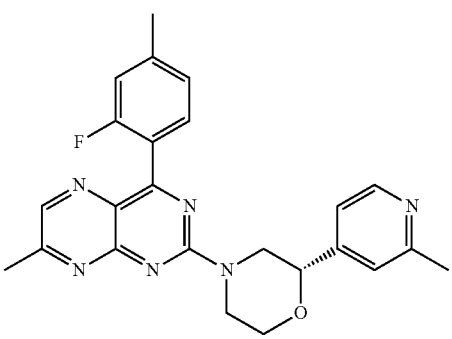
Ex. 13
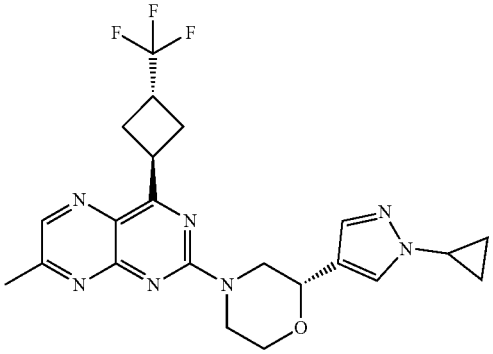

-continued
Ex. 16
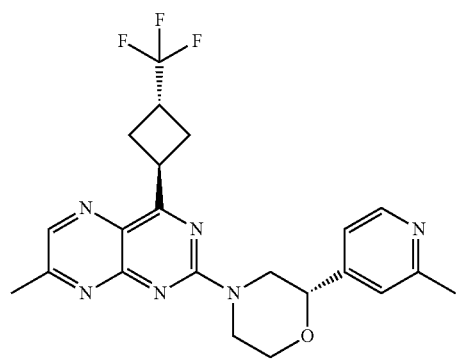
Ex. 17
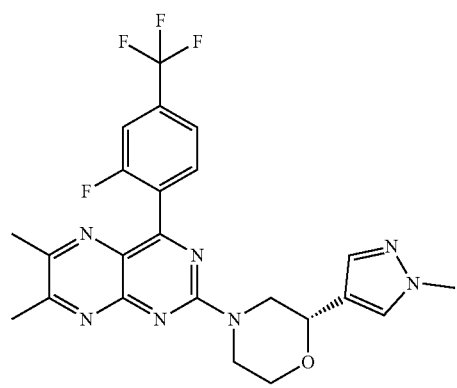
Ex. 18
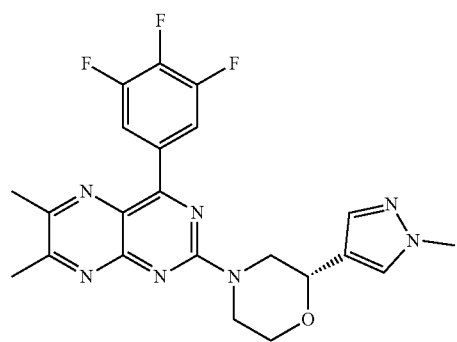
Ex. 19
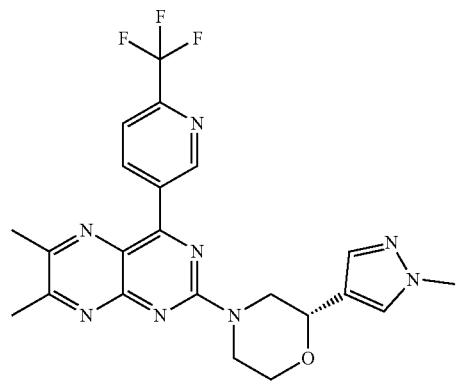
-continued
Ex. 21
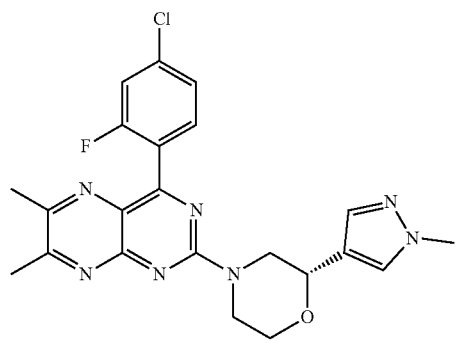
Ex. 22
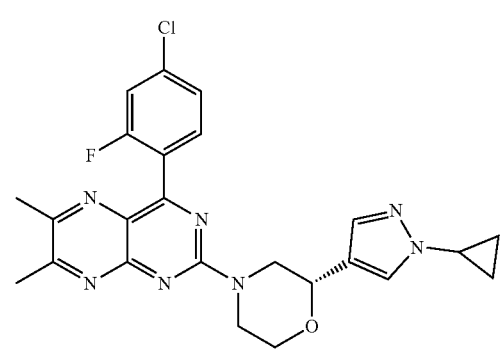
Ex. 23
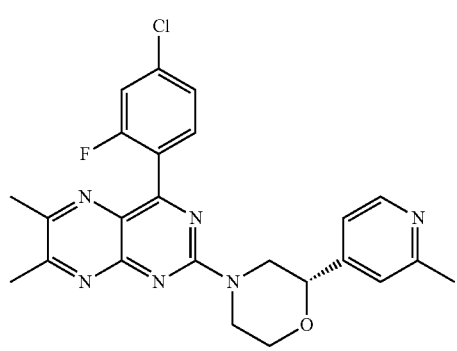
Ex. 25
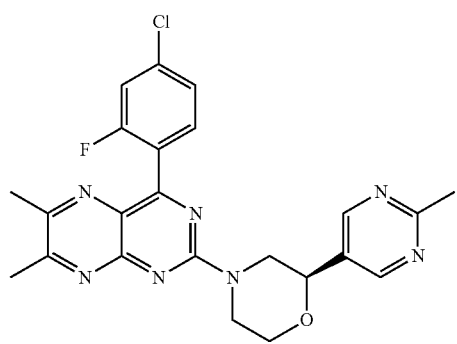

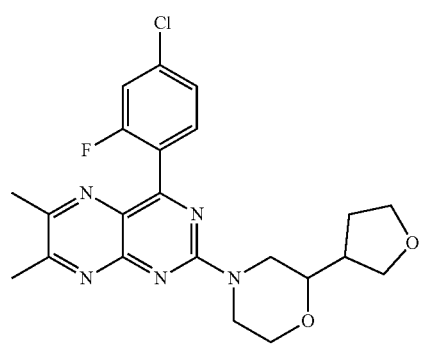
Ex. 26
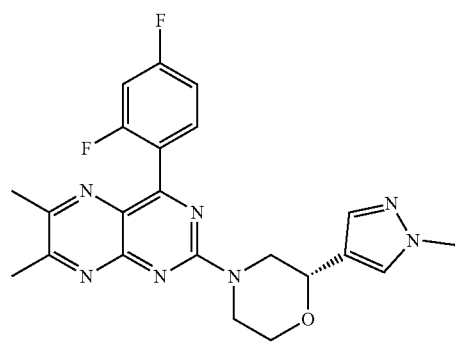
Ex. 31
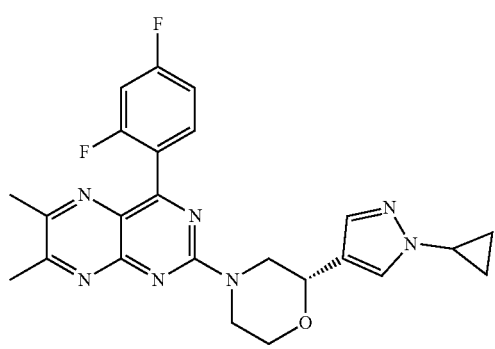
Ex. 32
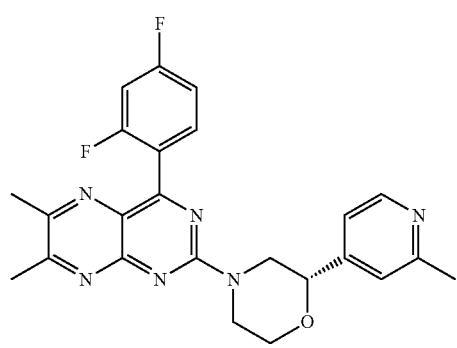
Ex. 33
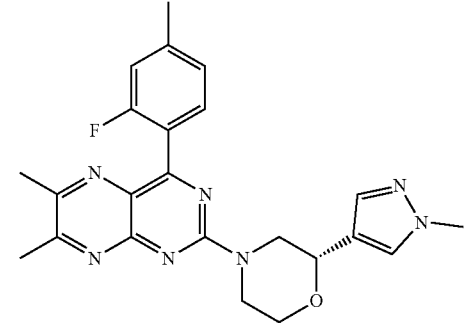
Ex. 37
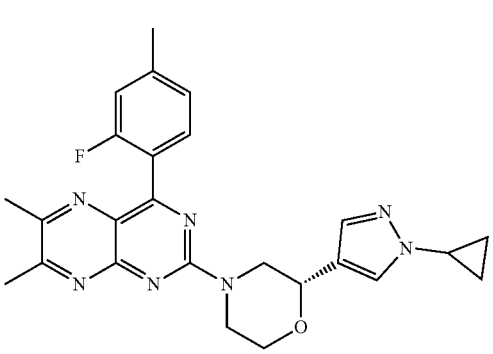
Ex. 38
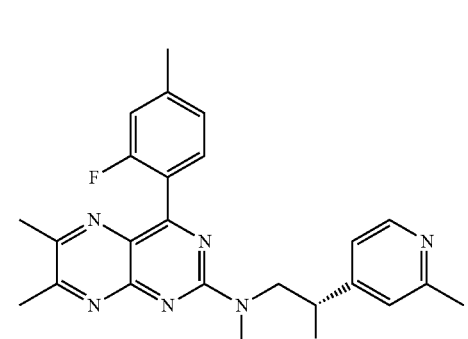
Ex. 39
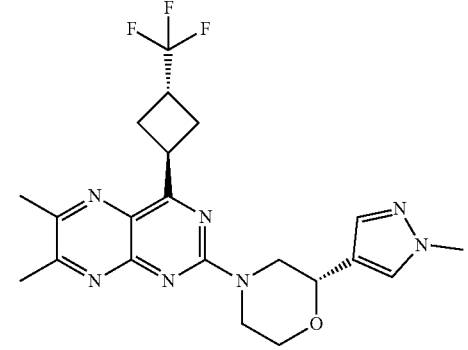
Ex. 42

| | |
|---|---|
| Ex. 46 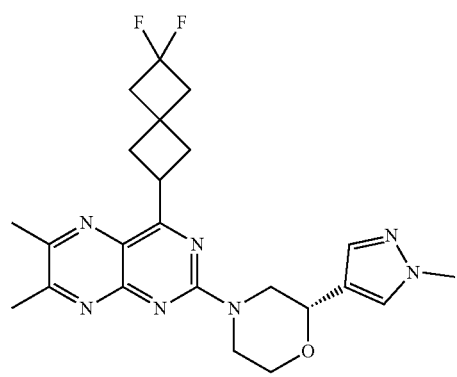 | Ex. 50 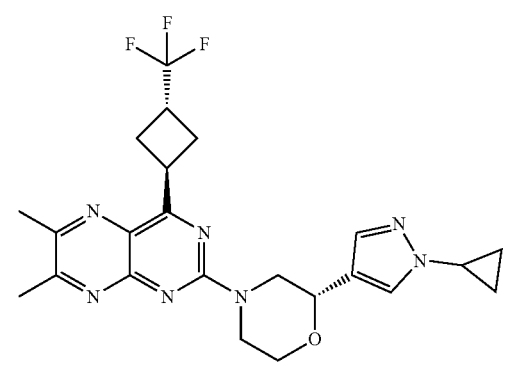 |
| Ex. 47 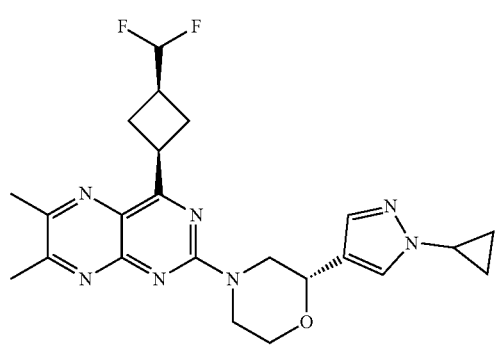 | Ex. 51 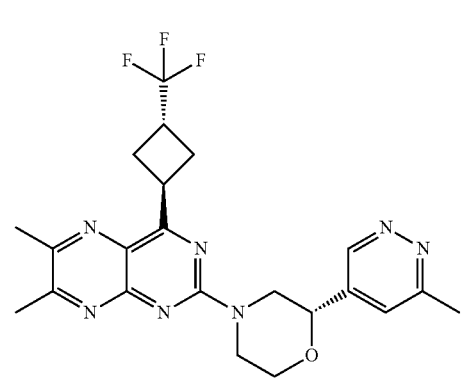 |
| Ex. 48 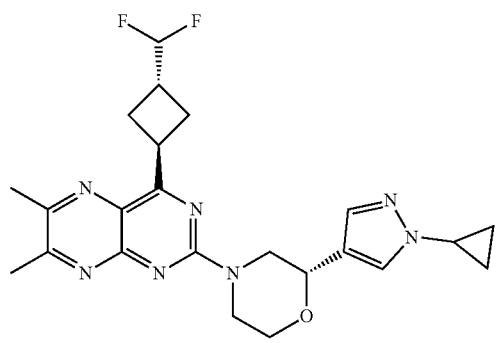 | Ex. 53 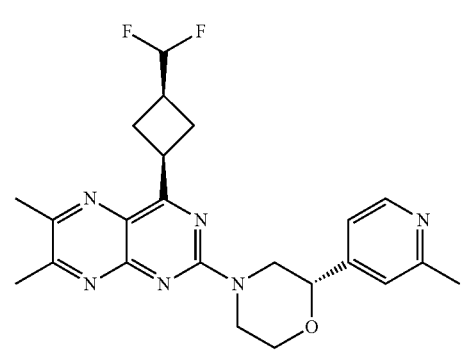 |
| Ex. 49 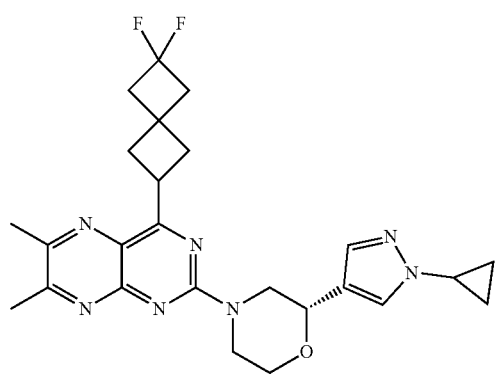 | Ex. 54 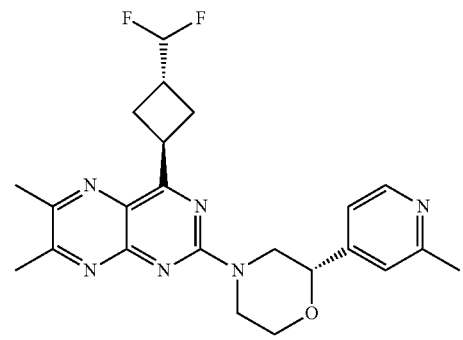 |

Ex. 55 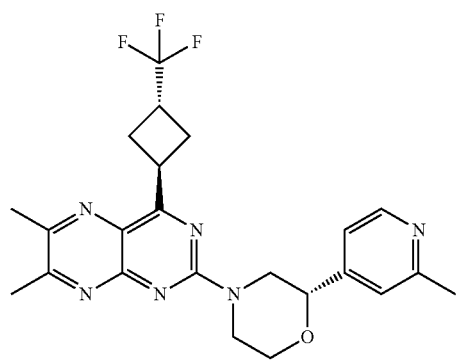
Ex. 56 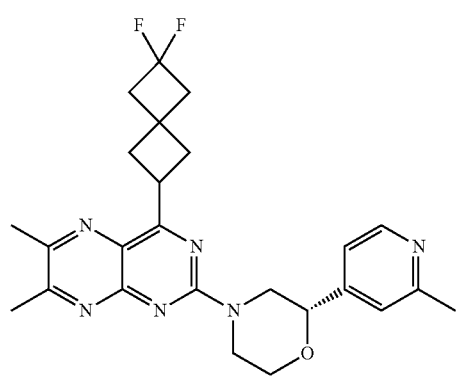
Ex. 60 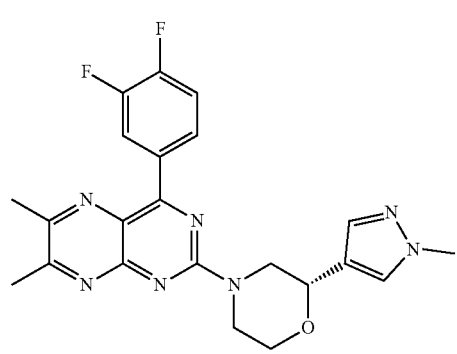
Ex. 61 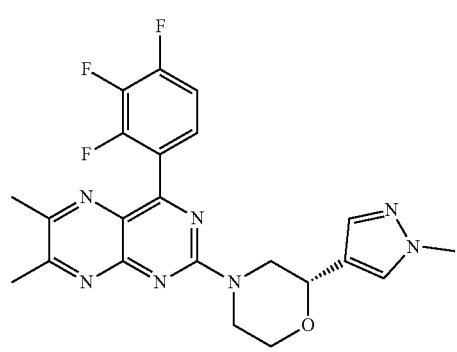
Ex. 62 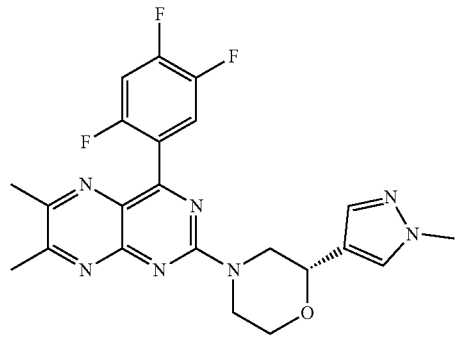
Ex. 63 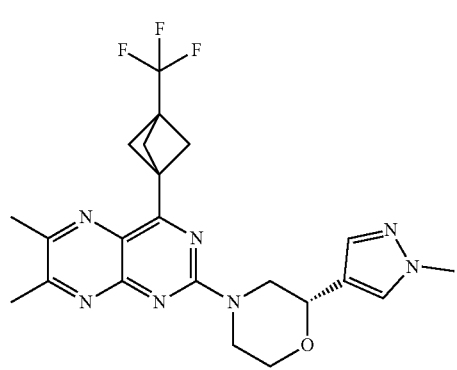
Ex. 64 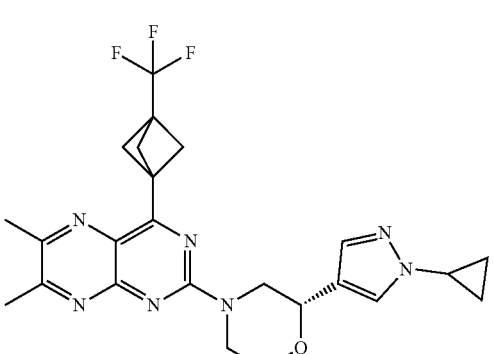
Ex. 65 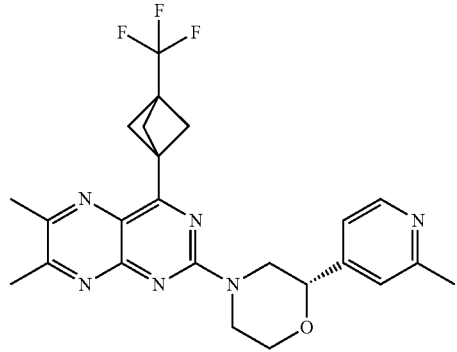

Ex. 127 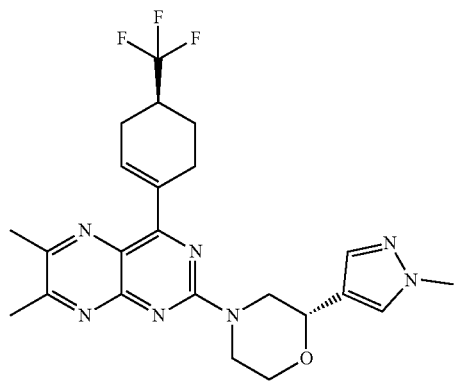
Ex. 130 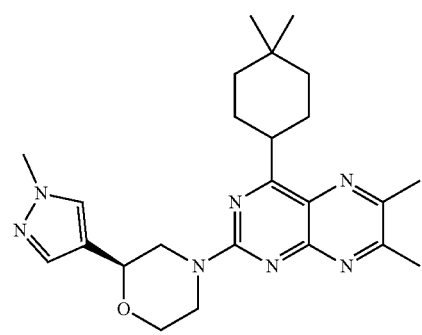
Ex. 132 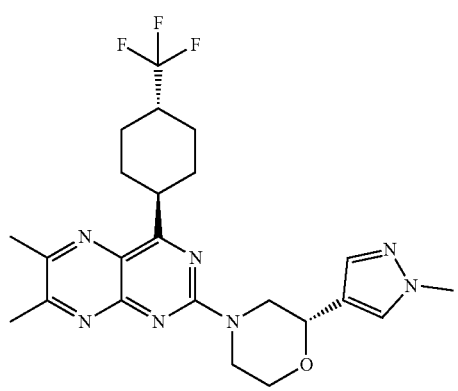
Ex. 133 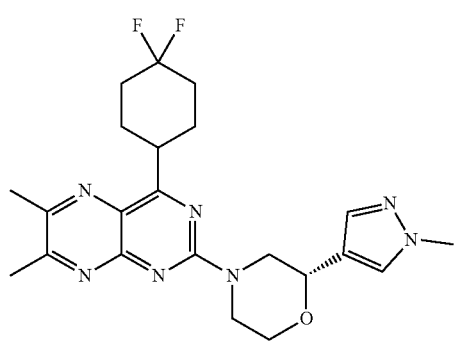
Ex. 136 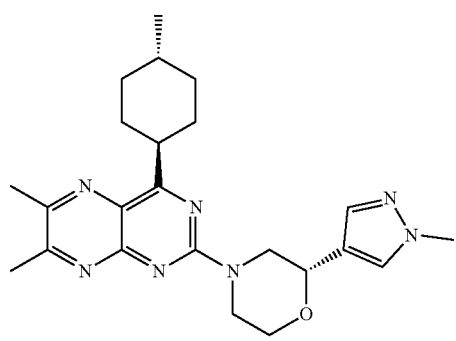
Ex. 137 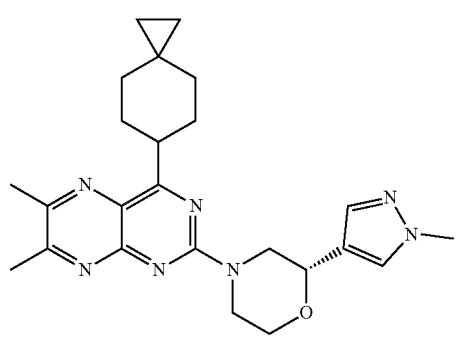
Ex. 138 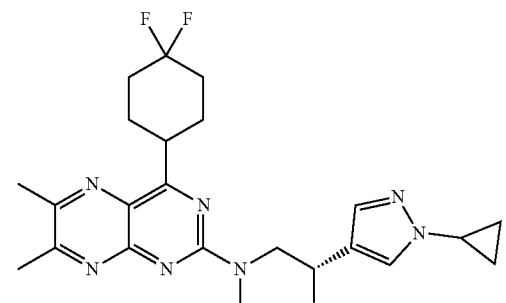
Ex. 139 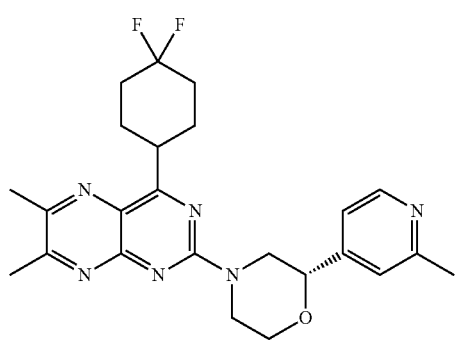

Ex. 165
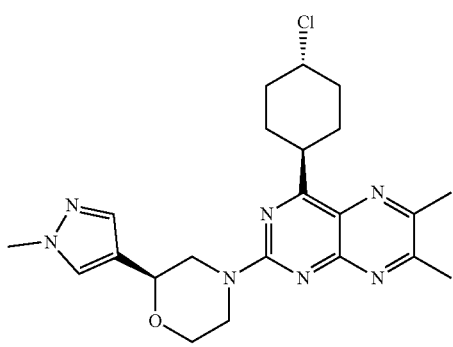
Ex. 231
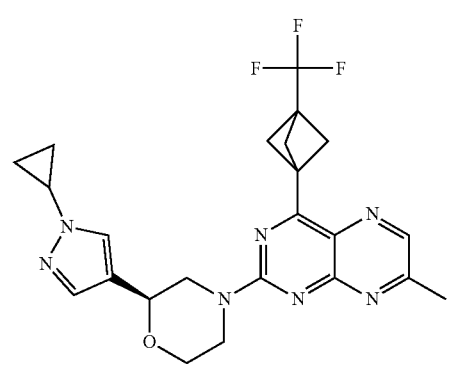
Ex. 232
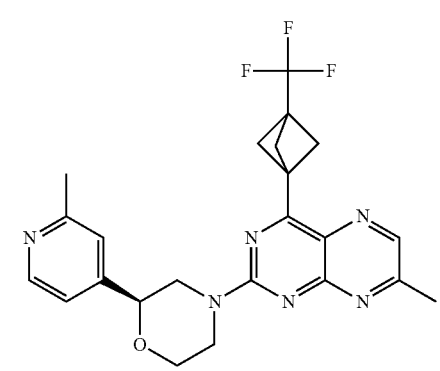
Ex. 295
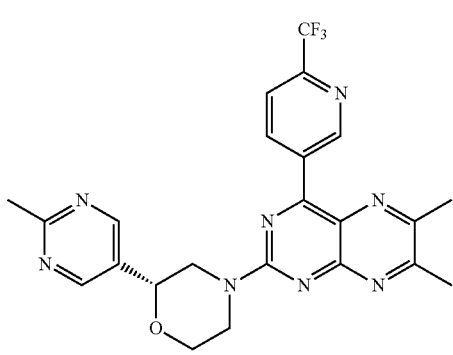
Ex. 298
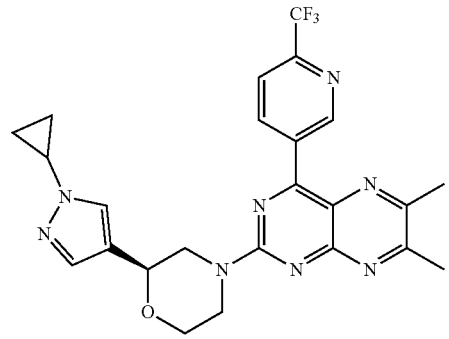
Ex. 299
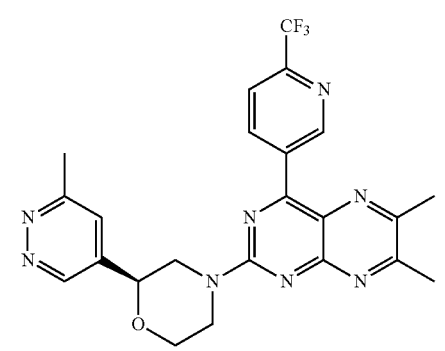
Ex. 314
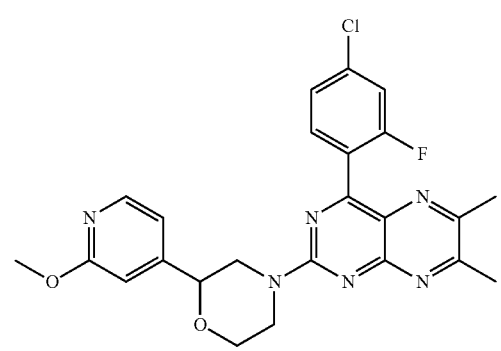
Ex. 318
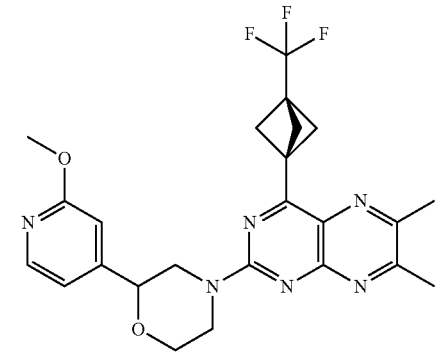 [SMILES: COc1cc(C2CN(c3nc4nc(C)c(C)nc4c([C@]45C[C@](C(F)(F)F)(C4)C5)n3)CCO2)ccn1]

Ex. 322
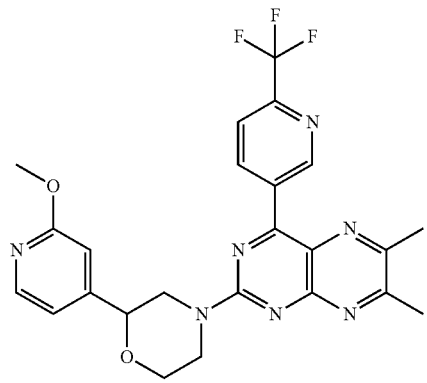 [SMILES: COc1cc(C2CN(c3nc(-c4ccc(C(F)(F)F)nc4)c4nc(C)c(C)nc4n3)CCO2)ccn1]
Ex. 335
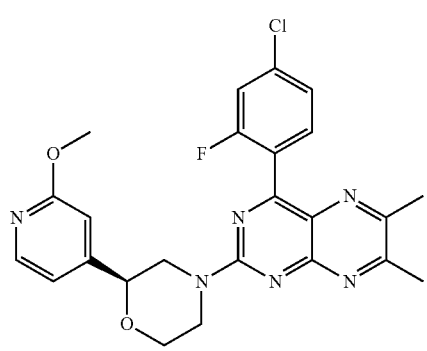 [SMILES: COc1cc([C@H]2CN(c3nc(-c4ccc(Cl)cc4F)c4nc(C)c(C)nc4n3)CCO2)ccn1]
Ex. 337
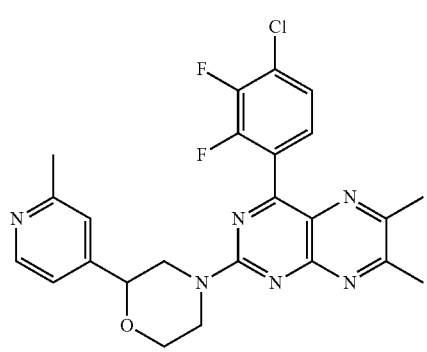
Ex. 352
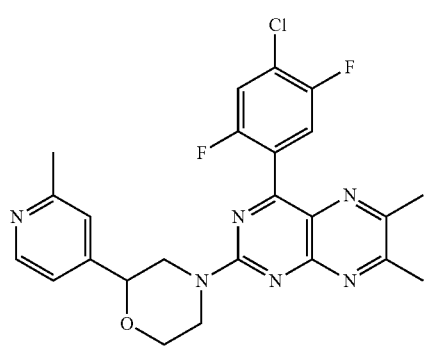
Ex. 354
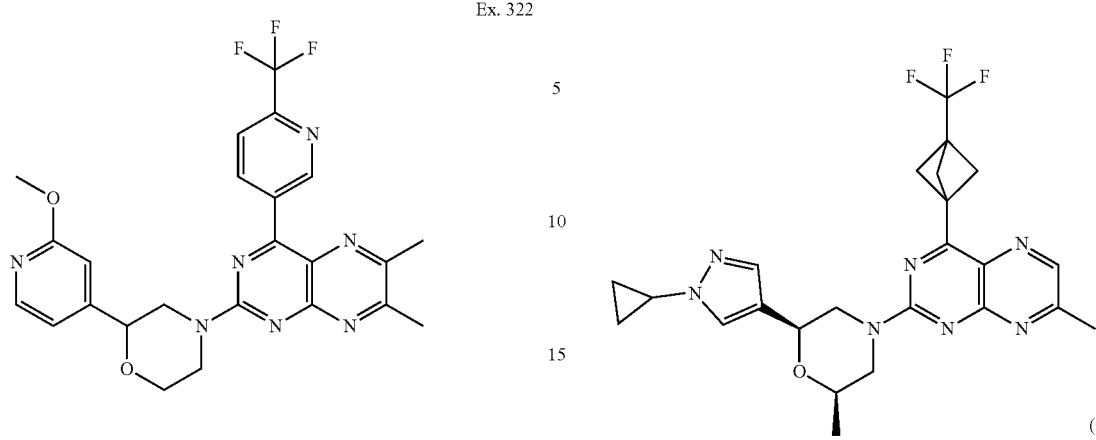
(+/-)
Ex. 356
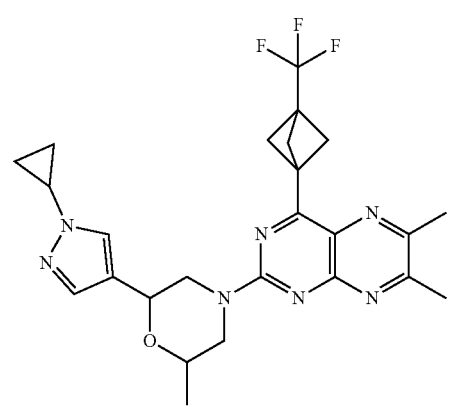
Ex. 359
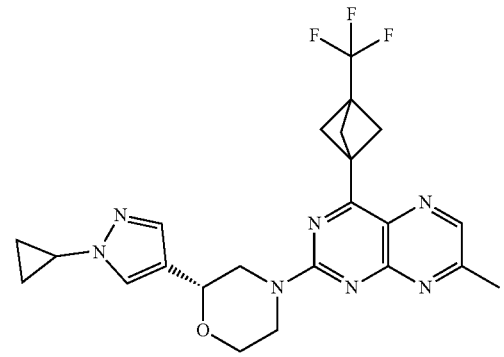
Ex. 363

-continued
Ex. 364
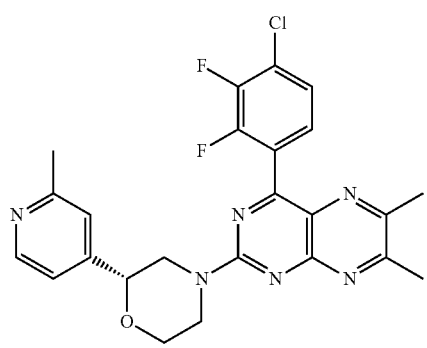
Ex. 373
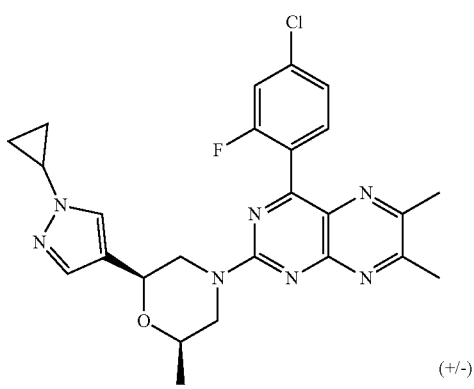
(+/-)
Ex. 369
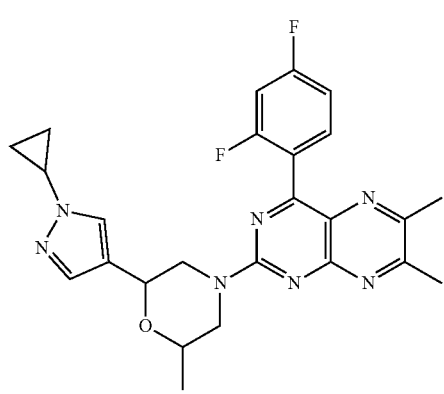
Ex. 374
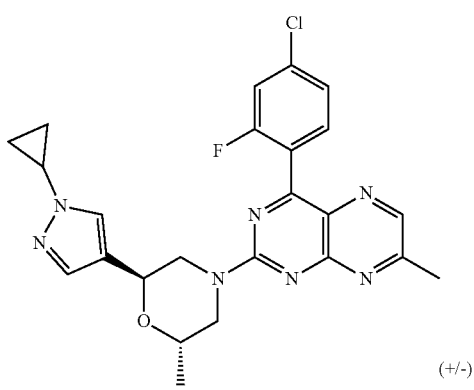
(+/-)
Ex. 371
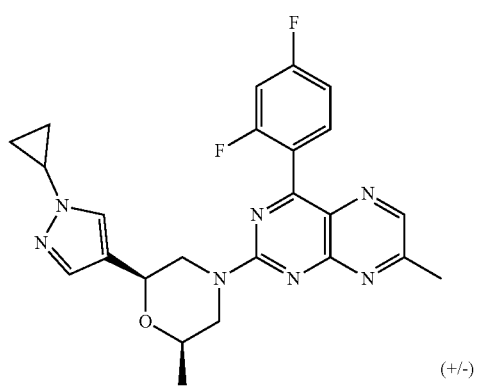
(+/-)
Ex. 375
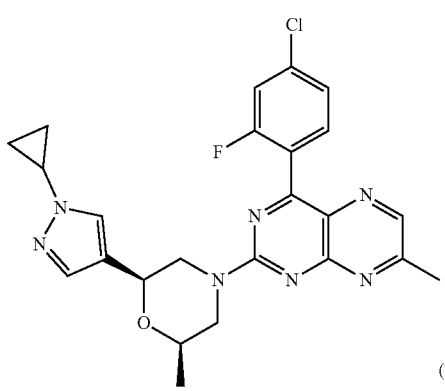
(+/-)
Ex. 372
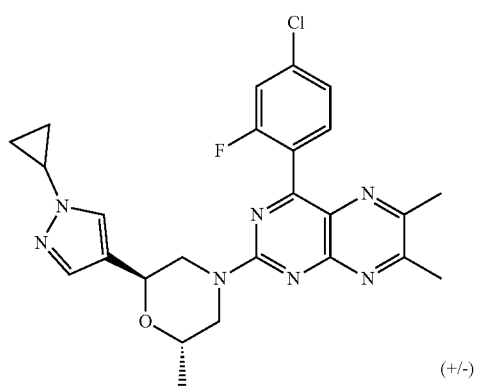
(+/-)
Ex. 381
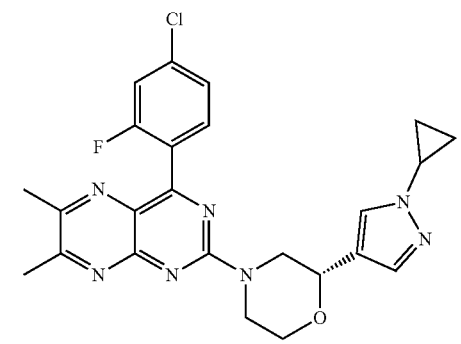

Ex. 387
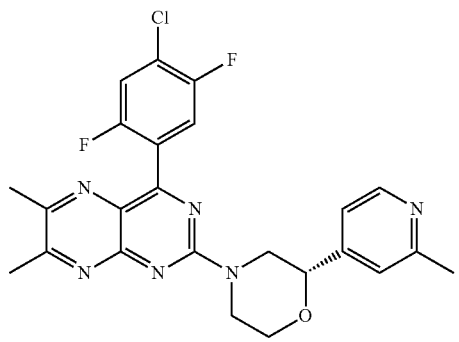
Ex. 391
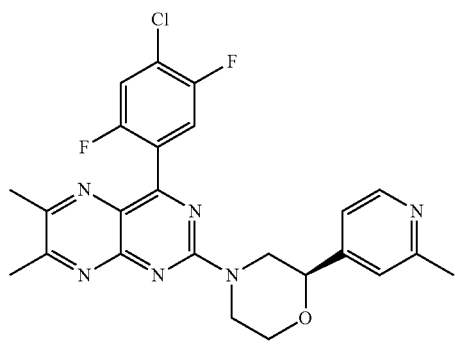
Ex. 404
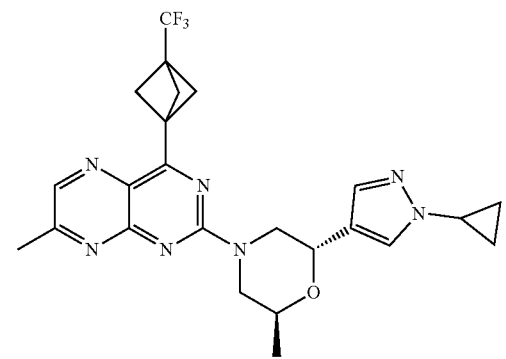
Ex. 408
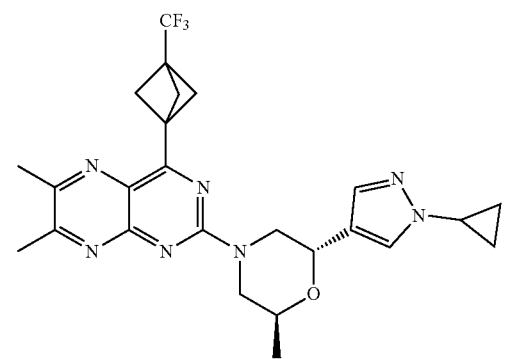
Ex. 410
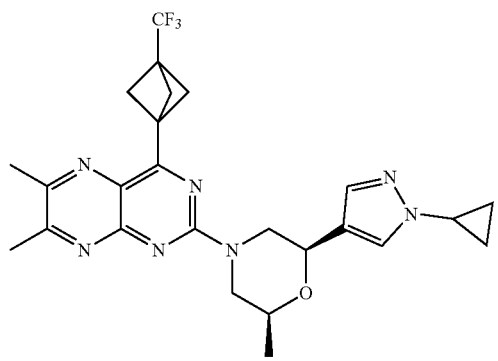
Ex. 411
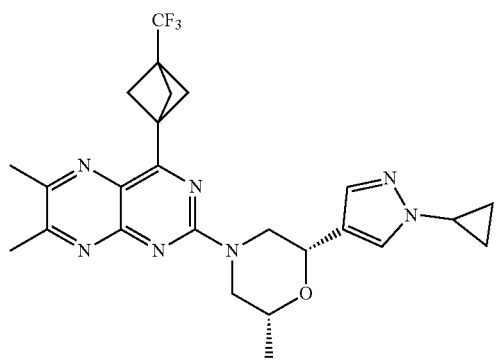
Ex. 420
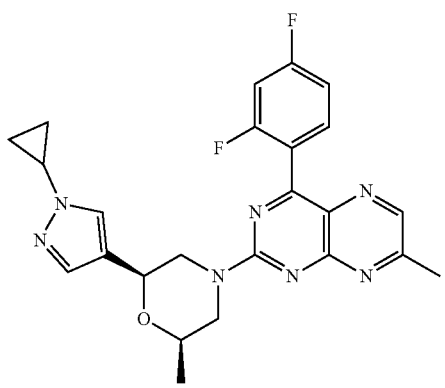
Ex. 422
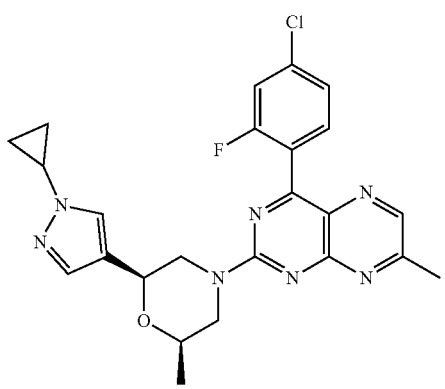

-continued

Ex. 424
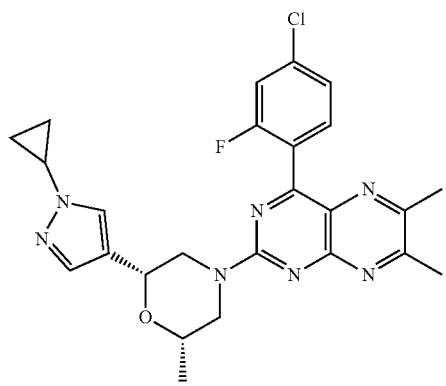

Ex. 425
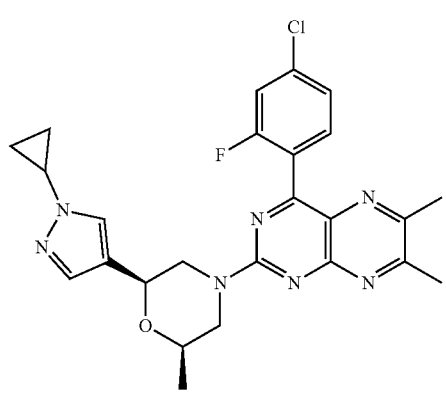

Ex. 426
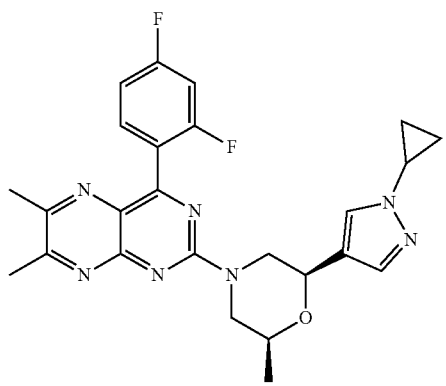

Ex. 427
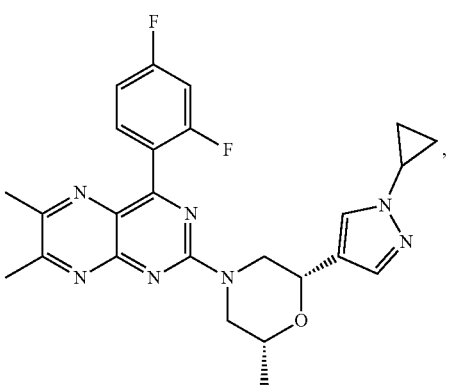

or a tautomer thereof, or a pharmaceutically acceptable salt of said compound or said tautomer, and a pharmaceutically acceptable excipient.

17. The pharmaceutical composition of claim 16, wherein the compound is

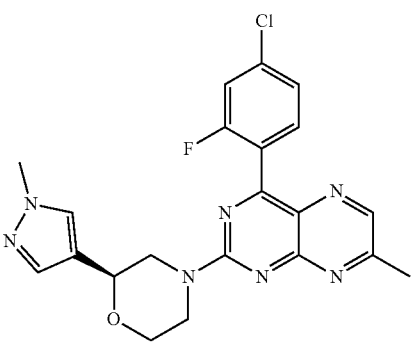

Ex. 1, or a tautomer thereof, or a pharmaceutically acceptable salt of said compound or said tautomer.

18. The pharmaceutical composition of claim 16, wherein the compound is

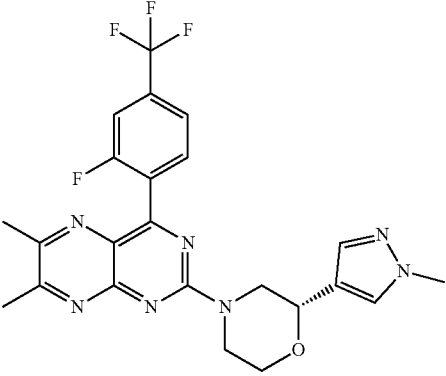

Ex. 17, or a tautomer thereof, or a pharmaceutically acceptable salt of said compound or said tautomer.

19. The pharmaceutical composition of claim 16, wherein the compound is

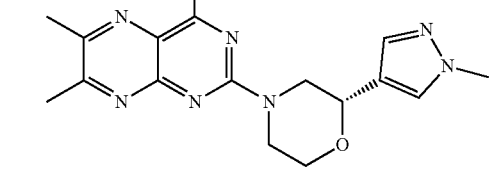

Ex. 22, or a tautomer thereof, or a pharmaceutically acceptable salt of said compound or said tautomer.

20. The pharmaceutical composition of claim 16, wherein the compound is

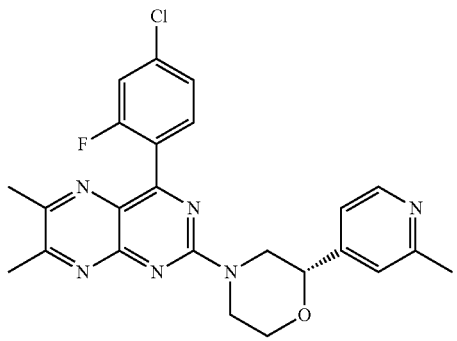

Ex. 23, or a tautomer thereof, or a pharmaceutically acceptable salt of said compound or said tautomer.

21. The pharmaceutical composition of claim 16, wherein the compound is

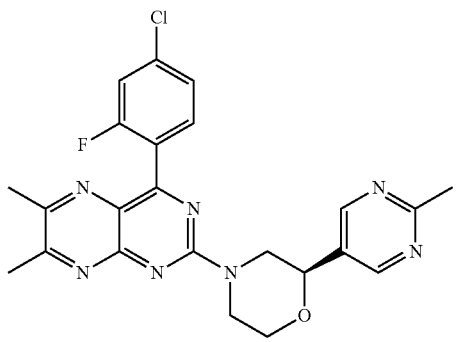

Ex. 25, or a tautomer thereof, or a pharmaceutically acceptable salt of said compound or said tautomer.

22. The pharmaceutical composition of claim 16, wherein the compound is

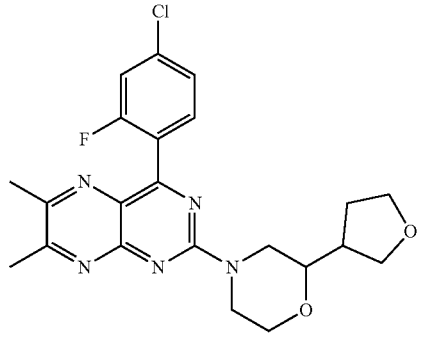

Ex. 26, or a tautomer thereof, or a pharmaceutically acceptable salt of said compound or said tautomer.

23. The pharmaceutical composition of claim 16, wherein the compound is

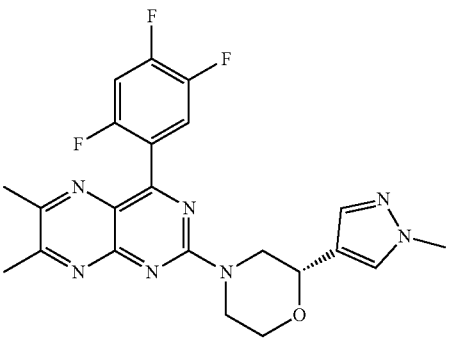

Ex. 62, or a tautomer thereof, or a pharmaceutically acceptable salt of said compound or said tautomer.

24. The pharmaceutical composition of claim 16, wherein the compound is

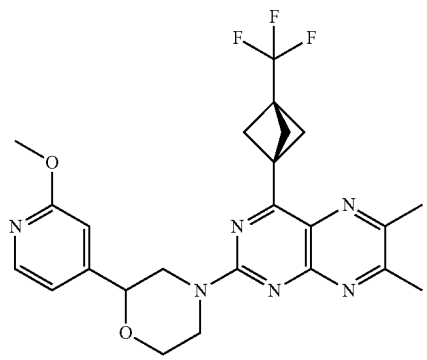

Ex. 318, or a tautomer thereof, or a pharmaceutically acceptable salt of said compound or said tautomer.

25. The pharmaceutical composition of claim 16, wherein the compound is

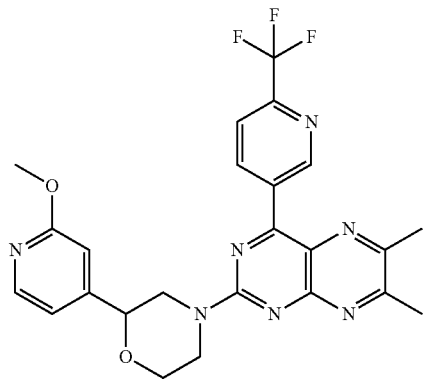

Ex. 322, or a tautomer thereof, or a pharmaceutically acceptable salt of said compound or said tautomer.

26. The pharmaceutical composition of claim 16, wherein the compound is

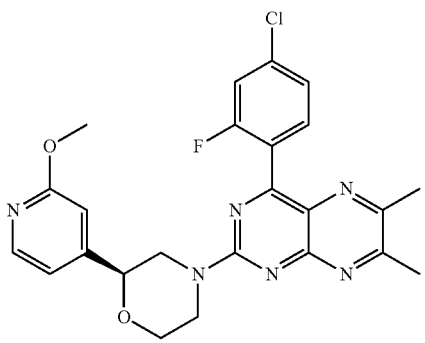

Ex. 335, or a tautomer thereof, or a pharmaceutically acceptable salt of said compound or said tautomer.

27. The pharmaceutical composition of claim 16, wherein the compound is

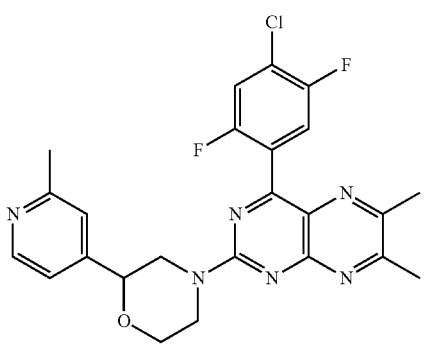 [SMILES: Cc1cc(C2CN(c3nc(-c4cc(F)c(Cl)cc4F)c4nc(C)c(C)nc4n3)CCO2)ccn1]

Ex. 352, or a tautomer thereof, or a pharmaceutically acceptable salt of said compound or said tautomer.

28. The pharmaceutical composition of claim 16, wherein the compound is

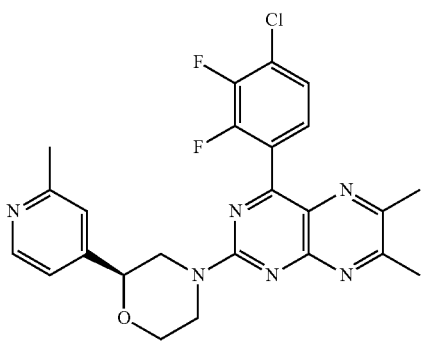 [SMILES: Cc1cc([C@H]2CN(c3nc(-c4ccc(Cl)c(F)c4F)c4nc(C)c(C)nc4n3)CCO2)ccn1]

Ex. 363, or a tautomer thereof, or a pharmaceutically acceptable salt of said compound or said tautomer.

29. The pharmaceutical composition of claim 16, wherein the compound is

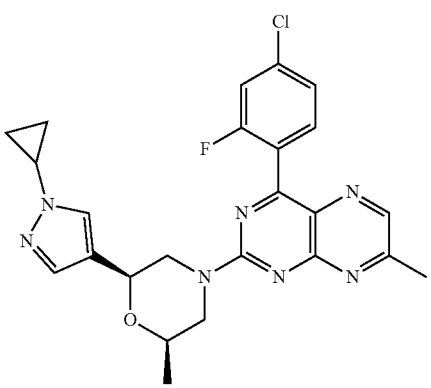 [SMILES: Cc1cnc2c(-c3ccc(Cl)cc3F)nc(N3C[C@@H](C)O[C@@H](c4cnn(C5CC5)c4)C3)nc2n1]

Ex. 422, or a tautomer thereof, or a pharmaceutically acceptable salt of said compound or said tautomer.

30. The pharmaceutical composition of claim 16, wherein the compound is

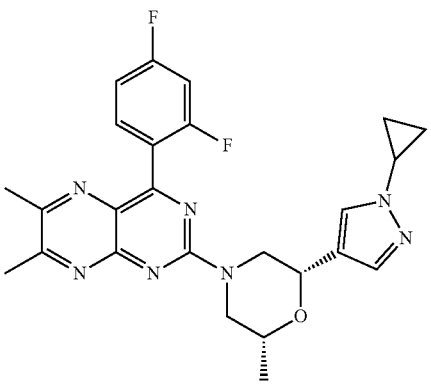 [SMILES: Cc1nc2nc(N3C[C@@H](C)O[C@@H](c4cnn(C5CC5)c4)C3)nc(-c3ccc(F)cc3F)c2nc1C]

Ex. 427, or a tautomer thereof, or a pharmaceutically acceptable salt of said compound or said tautomer.

* * * * *